US012692299B2

(12) United States Patent
Evans et al.

(10) Patent No.: US 12,692,299 B2
(45) Date of Patent: Jul. 28, 2026

(54) VARIANT ICOS LIGAND IMMUNOMODULATORY PROTEINS AND RELATED COMPOSITIONS AND METHODS

(71) Applicant: Alpine Immune Sciences, Inc., Seattle, WA (US)

(72) Inventors: Lawrence Evans, Seattle, WA (US); Michael Kornacker, Seattle, WA (US); Ryan Swanson, Seattle, WA (US)

(73) Assignee: Alpine Immune Sciences, Inc., Seattle, WA (US)

( * ) Notice: Subject to any disclaimer, the term of this patent is extended or adjusted under 35 U.S.C. 154(b) by 325 days.

(21) Appl. No.: 18/172,258

(22) Filed: Feb. 21, 2023

(65) Prior Publication Data

US 2023/0235012 A1     Jul. 27, 2023

Related U.S. Application Data

(63) Continuation of application No. 17/560,209, filed on Dec. 22, 2021, now Pat. No. 11,613,566, which is a continuation of application No. 16/757,344, filed as application No. PCT/US2018/056381 on Oct. 17, 2018, now abandoned.

(60) Provisional application No. 62/574,161, filed on Oct. 18, 2017.

(51) Int. Cl.
| | |
|---|---|
| *C12N 15/62* | (2006.01) |
| *A61K 35/54* | (2015.01) |
| *A61K 38/17* | (2006.01) |
| *A61K 40/11* | (2025.01) |
| *A61K 40/22* | (2025.01) |
| *A61K 40/31* | (2025.01) |
| *A61K 40/41* | (2025.01) |
| *A61K 40/42* | (2025.01) |
| *C07K 14/705* | (2006.01) |
| *C12N 5/071* | (2010.01) |
| *C12N 15/85* | (2006.01) |
| *C12P 21/02* | (2006.01) |

(52) U.S. Cl.
CPC ........ *C07K 14/70532* (2013.01); *A61K 35/54* (2013.01); *A61K 38/1774* (2013.01); *A61K 40/11* (2025.01); *A61K 40/22* (2025.01); *A61K 40/31* (2025.01); *A61K 40/418* (2025.01); *A61K 40/4205* (2025.01); *A61K 40/421* (2025.01); *A61K 40/4211* (2025.01); *C12N 5/0681* (2013.01); *C12N 15/85* (2013.01); *C12P 21/02* (2013.01); *A61K 2239/31* (2023.05); *C07K 2319/02* (2013.01); *C07K 2319/03* (2013.01); *C07K 2319/21* (2013.01); *C07K 2319/30* (2013.01); *C07K 2319/31* (2013.01); *C07K 2319/41* (2013.01); *C07K 2319/43* (2013.01)

(58) Field of Classification Search
None
See application file for complete search history.

(56) References Cited

U.S. PATENT DOCUMENTS

| | | |
|---|---|---|
| 5,168,062 A | 12/1992 | Stinski |
| 5,208,020 A | 5/1993 | Chari et al. |
| 5,385,839 A | 1/1995 | Stinski |
| 5,443,964 A | 8/1995 | Pickup et al. |
| 5,457,035 A | 10/1995 | Baum et al. |
| 5,500,362 A | 3/1996 | Robinson et al. |
| 5,538,848 A | 7/1996 | Livak et al. |
| 5,624,821 A | 4/1997 | Winter et al. |
| 5,648,260 A | 7/1997 | Winter et al. |
| 5,698,530 A | 12/1997 | Schlom et al. |
| 5,716,613 A | 2/1998 | Guber et al. |
| 5,716,826 A | 2/1998 | Guber et al. |
| 5,731,168 A | 3/1998 | Carter et al. |
| 5,767,071 A | 6/1998 | Palladino et al. |
| 5,780,426 A | 7/1998 | Palladino et al. |
| 5,821,337 A | 10/1998 | Carter et al. |
| 5,851,529 A | 12/1998 | Guber et al. |
| 5,891,432 A | 4/1999 | Hoo |
| 5,925,517 A | 7/1999 | Tyagi et al. |
| 5,998,205 A | 12/1999 | Hallenbeck et al. |
| 6,130,316 A | 10/2000 | Freeman et al. |
| 6,143,290 A | 11/2000 | Zhang et al. |
| 6,174,670 B1 | 1/2001 | Wittwer et al. |
| 6,194,551 B1 | 2/2001 | Idusogie et al. |
| 6,218,510 B1 | 4/2001 | Sharpe et al. |
| 6,294,660 B1 | 9/2001 | Sharpe et al. |
| 6,326,145 B1 | 12/2001 | Whitcombe et al. |
| 6,329,144 B1 | 12/2001 | Kubista et al. |
| 6,365,619 B1 | 4/2002 | Shi |
| 6,428,968 B1 | 8/2002 | Molnar-Kimber et al. |

(Continued)

FOREIGN PATENT DOCUMENTS

| | | |
|---|---|---|
| EP | 0757099 | 2/1997 |
| EP | 1385466 | 2/2004 |

(Continued)

OTHER PUBLICATIONS

"Database accession No. A0A2K5E9H6," Retrieved from UNIPROT, https://www.uniprot.org/uniprot/A0A2K5E9H6. Retrieved Sep. 13, 2019.

(Continued)

*Primary Examiner* — Michael D Pak
(74) *Attorney, Agent, or Firm* — Barnes & Thornburg, LLP

(57)     ABSTRACT

Provided herein are immunomodulatory proteins comprising ICOSL variants and nucleic acids encoding such proteins. The immunomodulatory proteins provide therapeutic utility for a variety of immunological and oncological conditions. Compositions and methods for making and using such proteins are provided.

6 Claims, 83 Drawing Sheets

Specification includes a Sequence Listing.

(56) References Cited

U.S. PATENT DOCUMENTS

| | | | |
|---|---|---|---|
| 6,596,535 | B1 | 7/2003 | Carter |
| 6,632,670 | B1 | 10/2003 | Wadsworth et al. |
| 6,635,427 | B2 | 10/2003 | Wittwer et al. |
| 6,635,472 | B1 | 10/2003 | Lauermann |
| 6,635,750 | B1 | 10/2003 | Coyle et al. |
| 6,641,809 | B1 | 11/2003 | Linsley et al. |
| 6,653,103 | B2 | 11/2003 | Peterson et al. |
| 6,689,871 | B1 | 2/2004 | Wolfe et al. |
| 6,723,316 | B2 | 4/2004 | Laquerre et al. |
| 6,730,512 | B2 | 5/2004 | Chang |
| 6,737,056 | B1 | 5/2004 | Presta |
| 6,855,317 | B2 | 2/2005 | Koelle et al. |
| 6,887,471 | B1 | 5/2005 | Linsley et al. |
| 6,897,045 | B2 | 5/2005 | Engelhardt et al. |
| 6,936,257 | B1 | 8/2005 | Bennett |
| 6,998,252 | B1 | 2/2006 | Moss et al. |
| 7,001,765 | B2 | 2/2006 | Maass et al. |
| 7,033,826 | B2 | 4/2006 | Perricaudet et al. |
| 7,094,875 | B2 | 8/2006 | Punnonen et al. |
| 7,125,717 | B2 | 10/2006 | Carter |
| 7,153,510 | B1 | 12/2006 | Rose |
| 7,172,893 | B2 | 2/2007 | Rabinowitz et al. |
| 7,238,526 | B2 | 7/2007 | Wilson et al. |
| 7,241,447 | B1 | 7/2007 | Engelhardt et al. |
| 7,247,615 | B2 | 7/2007 | Schlom et al. |
| 7,332,581 | B2 | 2/2008 | Presta |
| 7,368,116 | B2 | 5/2008 | Schlom et al. |
| 7,371,826 | B2 | 5/2008 | Presta |
| 7,378,087 | B2 | 5/2008 | Jefferies et al. |
| 7,521,532 | B2 | 4/2009 | Dunussi-Joannopoulos et al. |
| 7,537,924 | B2 | 5/2009 | Coffin |
| 7,550,296 | B2 | 6/2009 | Hermiston et al. |
| 7,588,767 | B2 | 9/2009 | Szalay et al. |
| 7,588,771 | B2 | 9/2009 | Szalay et al. |
| 7,612,170 | B2 | 11/2009 | Punnonen et al. |
| 7,619,078 | B2 | 11/2009 | Sharpe et al. |
| 7,662,398 | B2 | 2/2010 | Szalay et al. |
| 7,662,627 | B2 | 2/2010 | Johnson et al. |
| 7,709,214 | B2 | 5/2010 | Freeman et al. |
| 7,731,952 | B2 | 6/2010 | Mohr et al. |
| 7,731,974 | B2 | 6/2010 | Bell et al. |
| 7,754,221 | B2 | 7/2010 | Szalay et al. |
| 7,811,814 | B2 | 10/2010 | Bohn et al. |
| 7,897,146 | B2 | 3/2011 | Brown et al. |
| 7,906,111 | B2 | 3/2011 | Wilson et al. |
| 7,927,585 | B2 | 4/2011 | Snyder |
| 7,943,374 | B2 | 5/2011 | Hildinger |
| 7,968,340 | B2 | 6/2011 | Hallek et al. |
| 8,007,780 | B2 | 8/2011 | Arbetman et al. |
| 8,624,010 | B1 | 1/2014 | Yoshinaga |
| 8,709,417 | B2 | 4/2014 | Allison et al. |
| 8,911,726 | B2 | 12/2014 | Takahashi et al. |
| 8,956,619 | B2 | 2/2015 | Ostrand-Rosenberg |
| 9,029,315 | B2 | 5/2015 | Chen et al. |
| 9,103,831 | B2 | 8/2015 | O'Sullivan et al. |
| 9,375,475 | B2 | 6/2016 | Allison et al. |
| 9,453,227 | B2 | 9/2016 | Diamond et al. |
| 9,546,207 | B2 | 1/2017 | Kaempfer et al. |
| 9,834,604 | B2 | 12/2017 | Zhu et al. |
| 10,858,451 | B2 | 12/2020 | Bernett et al. |
| 10,882,914 | B2 | 1/2021 | Swanson et al. |
| 11,078,282 | B2 | 8/2021 | Swanson et al. |
| 11,319,359 | B2 | 5/2022 | Swanson et al. |
| 11,613,566 | B2 | 3/2023 | Evans et al. |
| 12,110,339 | B2 | 10/2024 | Swanson et al. |
| 2002/0009454 | A1 | 1/2002 | Boone et al. |
| 2002/0168714 | A1 | 11/2002 | Barbas et al. |
| 2003/0083246 | A1 | 5/2003 | Cohen et al. |
| 2003/0138881 | A1 | 7/2003 | Punnonen et al. |
| 2003/0158102 | A1 | 8/2003 | Chen et al. |
| 2004/0009604 | A1 | 1/2004 | Zhang et al. |
| 2004/0063094 | A1 | 4/2004 | Coffin et al. |
| 2004/0072283 | A1 | 4/2004 | Seed et al. |
| 2004/0146488 | A1 | 7/2004 | Hu et al. |
| 2005/0014934 | A1 | 1/2005 | Hinton et al. |
| 2005/0191296 | A1 | 9/2005 | Kaempfer et al. |
| 2005/0220818 | A1 | 10/2005 | Lorence |
| 2005/0260601 | A1 | 11/2005 | Whitt et al. |
| 2006/0024298 | A1 | 2/2006 | Lazar et al. |
| 2006/0039894 | A1 | 2/2006 | Mohr et al. |
| 2007/0098743 | A1 | 5/2007 | Bell et al. |
| 2007/0110720 | A1 | 5/2007 | Brown et al. |
| 2007/0202572 | A1 | 8/2007 | Szalay et al. |
| 2007/0212727 | A1 | 9/2007 | Szalay et al. |
| 2009/0010889 | A1 | 1/2009 | Brown et al. |
| 2009/0053244 | A1 | 2/2009 | Chen et al. |
| 2009/0098529 | A1 | 4/2009 | Chen et al. |
| 2009/0117034 | A1 | 5/2009 | Chen et al. |
| 2009/0136917 | A1 | 5/2009 | Szalay et al. |
| 2009/0155287 | A1 | 6/2009 | Chen et al. |
| 2009/0162288 | A1 | 6/2009 | Chen et al. |
| 2009/0215147 | A1 | 8/2009 | Zhang et al. |
| 2009/0252749 | A1 | 10/2009 | Leister et al. |
| 2009/0258031 | A1 | 10/2009 | Karrer et al. |
| 2009/0274728 | A1 | 11/2009 | Brown et al. |
| 2009/0285860 | A1 | 11/2009 | Martuza et al. |
| 2010/0062016 | A1 | 3/2010 | Szalay et al. |
| 2010/0092515 | A1 | 4/2010 | Conner et al. |
| 2010/0113567 | A1 | 5/2010 | Barber |
| 2010/0172877 | A1 | 7/2010 | van den Pol et al. |
| 2010/0178276 | A1 | 7/2010 | Sadelain et al. |
| 2010/0178684 | A1 | 7/2010 | Woo et al. |
| 2010/0196325 | A1 | 8/2010 | Szalay et al. |
| 2010/0233078 | A1 | 9/2010 | Szalay et al. |
| 2010/0261660 | A1 | 10/2010 | Punnonen et al. |
| 2011/0064650 | A1 | 3/2011 | Szalay |
| 2011/0064763 | A1 | 3/2011 | Allen et al. |
| 2011/0158948 | A1 | 6/2011 | Brown et al. |
| 2011/0159023 | A1 | 6/2011 | Langermann |
| 2011/0177032 | A1 | 7/2011 | Martuza |
| 2011/0195068 | A1 | 8/2011 | Langermann et al. |
| 2011/0212530 | A1 | 9/2011 | Baltimore et al. |
| 2011/0293705 | A1 | 12/2011 | Irvine et al. |
| 2013/0071409 | A1 | 3/2013 | Riley et al. |
| 2013/0149305 | A1 | 6/2013 | Ostrand-Rosenberg |
| 2013/0287748 | A1 | 10/2013 | June et al. |
| 2014/0050708 | A1 | 2/2014 | Powell et al. |
| 2014/0099309 | A1 | 4/2014 | Powell et al. |
| 2014/0154216 | A1 | 6/2014 | Coffin |
| 2014/0170141 | A1 | 6/2014 | Toporik et al. |
| 2014/0186380 | A1 | 7/2014 | Gurney |
| 2014/0186401 | A1 | 7/2014 | Diamond et al. |
| 2014/0227237 | A1 | 8/2014 | June et al. |
| 2014/0308299 | A1 | 10/2014 | Allison et al. |
| 2014/0322129 | A1 | 10/2014 | Leong et al. |
| 2014/0348832 | A1 | 11/2014 | Zhu et al. |
| 2015/0104451 | A1 | 4/2015 | Orban |
| 2015/0232532 | A1 | 8/2015 | Ostrand-Rosenberg |
| 2015/0266958 | A1 | 9/2015 | Hermans et al. |
| 2015/0359909 | A1 | 12/2015 | O'Sullivan et al. |
| 2016/0017018 | A1 | 1/2016 | Wang et al. |
| 2016/0017041 | A1 | 1/2016 | Violette et al. |
| 2016/0145344 | A1 | 5/2016 | Akbari |
| 2016/0158318 | A1 | 6/2016 | Cohen et al. |
| 2016/0244524 | A1 | 8/2016 | Allison et al. |
| 2016/0264643 | A1 | 9/2016 | Lazar et al. |
| 2016/0271218 | A1 | 9/2016 | Biro |
| 2016/0272707 | A1 | 9/2016 | Levine et al. |
| 2016/0339066 | A1 | 11/2016 | Szalay et al. |
| 2016/0340422 | A1 | 11/2016 | Chen et al. |
| 2017/0028040 | A1 | 2/2017 | Lan et al. |
| 2017/0042972 | A1 | 2/2017 | Karyekar |
| 2017/0320959 | A1 | 11/2017 | Swanson et al. |
| 2017/0369549 | A1 | 12/2017 | Peach et al. |
| 2018/0244749 | A1 | 8/2018 | Swanson et al. |
| 2018/0256644 | A1 | 9/2018 | Swanson et al. |
| 2018/0319861 | A1 | 11/2018 | Lan et al. |
| 2020/0040059 | A1 | 2/2020 | Swanson et al. |
| 2020/0283500 | A1 | 9/2020 | Evans et al. |
| 2021/0139606 | A1 | 5/2021 | Kontermann et al. |
| 2021/0188995 | A1 | 6/2021 | Swanson et al. |
| 2021/0363219 | A1 | 11/2021 | Swanson et al. |
| 2022/0112265 | A1 | 4/2022 | Evans et al. |
| 2022/0218785 | A1 | 7/2022 | Swanson et al. |

(56) References Cited

U.S. PATENT DOCUMENTS

| | | | |
|---|---|---|---|
| 2022/0242930 A1 | 8/2022 | Swanson et al. | |
| 2023/0101432 A1 | 3/2023 | Swanson | |
| 2023/0235012 A1 | 7/2023 | Evans et al. | |

FOREIGN PATENT DOCUMENTS

| | | |
|---|---|---|
| EP | 1391213 | 2/2004 |
| EP | 1520175 | 4/2005 |
| EP | 1606411 | 12/2005 |
| EP | 1870459 | 12/2007 |
| EP | 2194066 | 6/2010 |
| EP | 3020816 | 5/2016 |
| EP | 3461846 A1 | 4/2019 |
| JP | H09202800 A | 8/1997 |
| JP | 2014522846 A | 9/2014 |
| JP | 2018512856 A | 5/2018 |
| WO | WO-1993/010151 | 5/1993 |
| WO | WO-1994/011026 | 5/1994 |
| WO | WO-1994/029351 | 12/1994 |
| WO | WO-1998/050431 | 11/1998 |
| WO | WO-1999/038955 | 8/1999 |
| WO | WO-1999/051642 | 10/1999 |
| WO | WO-2000/042072 | 7/2000 |
| WO | WO-2001/030843 | 5/2001 |
| WO | WO-2002/000717 | 1/2002 |
| WO | 2004030636 A2 | 4/2004 |
| WO | WO-2004/029197 | 4/2004 |
| WO | WO-2004/056312 | 7/2004 |
| WO | WO-2005/063816 | 7/2005 |
| WO | WO-2005/100402 | 10/2005 |
| WO | WO-2006/019447 | 2/2006 |
| WO | WO-2006/029879 | 3/2006 |
| WO | 2007011941 A2 | 1/2007 |
| WO | WO-2007/005874 | 1/2007 |
| WO | WO-2007/052029 | 5/2007 |
| WO | WO-2008/011636 | 1/2008 |
| WO | WO-2008/092117 | 7/2008 |
| WO | WO-2008/155134 | 12/2008 |
| WO | WO-2009/029342 | 3/2009 |
| WO | WO-2009/041613 | 4/2009 |
| WO | WO-2009/067800 | 6/2009 |
| WO | WO-2009/076524 | 6/2009 |
| WO | WO-2009/105671 | 8/2009 |
| WO | 2010027827 A2 | 3/2010 |
| WO | 2010027828 A2 | 3/2010 |
| WO | WO-2010/077634 | 7/2010 |
| WO | WO-2011/020024 | 2/2011 |
| WO | WO-2011/056983 | 5/2011 |
| WO | WO-2011/066389 | 6/2011 |
| WO | WO-2011/097477 | 8/2011 |
| WO | WO-2011/113019 | 9/2011 |
| WO | WO-2011/133886 | 10/2011 |
| WO | WO-2012/079000 | 6/2012 |
| WO | WO-2012/125850 | 9/2012 |
| WO | WO-2012/140627 | 10/2012 |
| WO | WO-2012/141984 | 10/2012 |
| WO | WO-2012/149364 | 11/2012 |
| WO | WO-2013/003761 | 1/2013 |
| WO | WO-2013/079174 | 6/2013 |
| WO | WO-2013/130683 | 9/2013 |
| WO | WO-2013/149167 | 10/2013 |
| WO | WO-2013/169338 | 11/2013 |
| WO | WO-2014/089113 | 6/2014 |
| WO | 2014173975 A1 | 10/2014 |
| WO | WO-2014/198002 | 12/2014 |
| WO | WO-2014/207063 | 12/2014 |
| WO | WO-2015/009606 | 1/2015 |
| WO | WO-2015/107026 | 7/2015 |
| WO | 2015120363 A1 | 8/2015 |
| WO | WO 2015/120363 | 8/2015 |
| WO | WO-2015/149077 | 10/2015 |
| WO | WO-2016/008976 | 1/2016 |
| WO | WO-2016/011083 | 1/2016 |
| WO | WO-2016/191643 | 1/2016 |
| WO | 2016022468 A1 | 2/2016 |
| WO | 2016022994 A2 | 2/2016 |
| WO | WO-2016/022994 | 2/2016 |
| WO | WO 2016/034678 | 3/2016 |
| WO | WO-2016/073704 | 5/2016 |
| WO | WO-2016/118577 | 7/2016 |
| WO | 2016154684 A1 | 10/2016 |
| WO | WO 2016/154684 | 10/2016 |
| WO | WO-2016/164428 | 10/2016 |
| WO | WO-2016/168771 | 10/2016 |
| WO | 2017023749 A1 | 2/2017 |
| WO | WO 2017/019846 | 2/2017 |
| WO | WO-2017/023779 | 2/2017 |
| WO | WO-2017/034916 | 3/2017 |
| WO | WO-2017/048878 | 3/2017 |
| WO | WO-2017/055547 | 4/2017 |
| WO | 2017106061 A1 | 6/2017 |
| WO | WO-2017/181148 | 10/2017 |
| WO | WO-2017/181152 | 10/2017 |
| WO | WO-2017/201131 | 11/2017 |
| WO | WO-2018/022945 | 2/2018 |
| WO | WO-2018/022946 | 2/2018 |
| WO | WO-2018/075978 | 4/2018 |
| WO | 2018170021 A1 | 9/2018 |
| WO | WO-2019/079520 | 4/2019 |
| WO | 2019136179 | 7/2019 |
| WO | WO-2019/241758 | 12/2019 |
| WO | WO-2020/214867 | 10/2020 |

OTHER PUBLICATIONS

"Database accession No. AER57743 Human B7Rp1 extracellular domain (ECD)" Dated Apr. 19, 2007.

"Database accession No. BDH56778," Retrieved from GENESEQ, Retrieved on Sep. 13, 2019.

"Database accession No. BDV07959," Retrieved from GENESEQ, Retrieved on Sep. 12, 2019.

"Database accession No. A0A2J8M811," Retrieved from UNIPROT, https://www.uniprot.org /uniprot/A0A2J8M811. Retrieved on Mar. 5, 2020.

"Database accession No. H9Z6Y0," version 15. Retrieved from UNISAVE, http://www.ebi.ac.uk/uniprot/unisave/app/#/content/H9Z6Y0/15. Retrieved on Jun. 20, 2017.

"Database accession No. L8Y5K4," version 13. Retrieved from UNISAVE, http://www.ebi.ac.uk/uniprot/unisave/app/#/content/L8Y5K4/13. Retrieved on Sep. 28, 2017.

"Database accession No. NP_56074.1," version 1. Retrieved from NCBI, https://www.ncbi.nlm.nih.gov /protein /NP_056074.1, Retrieved on Mar. 3, 2020.

Adler S. et al., "Evaluation of Histologic, Serologic, and Clinical Changes in Response to Abatacept Treatment of Primary Sjögren's Syndrome: A Pilot Study" Arthritis Care and Research vol. 65, No. 11, Nov. 2013, pp. 1862-1868.

Alpine Immune Sciences, Inc., "Alpine Immune Sciences Announces Preclinical Data Showing Novel Immuno-Oncology Costimulatory Molecules Generated from vIgD Platform Fused with Trastuzumab Enhanced Immune Responses Against HER2-Positive Tumor Cells ," Data Presented at 2017 San Antonio Breast Cancer Symposium, Published Dec. 6, 2017, available online at: http://www.businesswire.com/news/home/20171206005074/en/Alpine-Immune-Sciences-Announces-Preclinical-Data-Showing.

Amatore et al., "Inducible Co-Stimulator (ICOS) as a Potential Therapeutic Target for Anti-Cancer Therapy," Expert Opin Ther Targets. (2018) 22(4): 343-351.

Auffermann-Gretzinger et al., "Rapid establishment of dendritic cell chimerism in allogeneic hematopoietic cell transplant recipients," Blood. (2002) 99(4): 1442-1448.

Baban et al., "Bacteria as vectors for gene therapy of cancer," Bioeng Bugs. (2010) 1(6):385-394.

Banovic et al., "Graft-versus-host disease prevents the maturation of plasmacytoid dendritic cells," J Immunol. (2009) 182(2): 912-920.

Benson et al., "GenBank," Nucleic Acids Res (2013) 41(Database issue):D36-D42.

Bowman S.J., et al., "Randomized Controlled Trial of Rituximab and Cost-Effectiveness Analysis in Treating Fatigue and Oral Dry-

(56)          References Cited

OTHER PUBLICATIONS ness in Primary Sj€ogren's Syndrome" Arthiritis and Rheumatology vol. 69, No. 7, Jul. 2017, pp. 1440-1450.

Brown et al., "Structure-based mutagenesis of the human immuno-deficiency virus type 1 DNA attachment site: effects on integration and cDNA synthesis," J Virol. (1999) 73(11):9011-9020.

Bruggemann et al., "Comparison of the effector functions of human immunoglobulins using a matched set of chimeric antibodies," J Exp Med. (1987) 166(5):1351-1361.

Buchschacher et al., "Human immunodeficiency virus vectors for inducible expression of foreign genes," J Virol. (1992) 66(5):2731-2739.

Burmeister et al., ICOS controls the pool size of effector-memory and regulatory T cells. J Immunol.(2008) 180:774-82.

Busch et al., "Dimers, leucine zippers and DNA-binding domains," Trends Genet. (1990) 6(2): 36-40.

Cai, B. et al., "C-terminal lysine processing of human immuno-globulin G2 heavy chain in vivo" 2011 Biotechnol Bioeng 108:404-412.

Canfield S.M., "The Binding Affinity of Human IgG for its High Affinity Fc Recepor is Determined by Multiple Amino Acids in the CH2 Domain and is Modulated by the Hinge Region" J. Exp. Med. vol. 173, Jun. 1991, pp. 483-1491.

Carsons S.E., et al., "Treatment Guidelines for Rheumatologic Manifestations of Sjorgen's Syndrome: Use of Biologic Agents, Management of Fatigue, and Inflammatory Musculoskeletal Pain" Arthritic Care and Research vol. 69, No. 4, Apr. 2017, pp. 517527.

Chang et al., "The discovery of small molecule carbamates as potent dual alpha(4)beta(1)/alpha(4)beta(7) integrin antagonists," Bioorg Med Chem Lett. Jan. 21, 2002;12(2):159-63.

Chari et al., "Immunoconjugates containing novel maytansinoids: promising anticancer drugs," Cancer Res. (1992) 52(1):127-131.

Chattopadhyay et al., "Structural basis of inducible costimulator ligand costimulatory function: determination of the cell surface oligomeric state and functional mapping of the receptor binding site of the protein," J Immunol. Sep. 15, 2006;177(6):3920-9.

Clynes et al., "Fc receptors are required in passive and active immunity to melanoma," Proc Natl Acad Sci U S A. (1998) 95(2):652-656.

Coates L.C., et al., "Group for Research and Assessment of Pso-riasis and Psoriatic Arthritis/Outcome Measures in Rheumatology Consensus-Based Recommendations and Research Agenda for Use of Composite Measures and Treatment Targets in Psoriatic Arthri-tis" Arthritis and Rheumatology, vol. 70, No. 3, Mar. 2018, pp. 345-355.

Colby et al., "Engineering antibody affinity by yeast surface dis-play," Methods Enzymol. 2004;388:348-58.

Colcher et al., "Use of monoclonal antibodies as radiopharmaceuticals for the localization of human carcinoma xenografts in athymic mice," Methods Enzymol. (1986); 121: 802-16.

Condomines et al., "Tumor-Targeted Human T Cells Expressing CD28-Based Chimeric Antigen Receptors Circumvent CTLA-4 Inhibition," PLoS One (2015) 10(6):e0130518.

Cornetta et al., "No retroviremia or pathology in long-term follow-up of monkeys exposed to a murine amphotropic retrovirus," Hum Gene Ther. (1991) Fall;2(3):215-9.

Covassin et al., "Human peripheral blood CD4 T cell-engrafted non-obese diabetic-scid IL2rγ(null) H2-Ab1 (tm1Gru) Tg (human leucocyte antigen D-related 4) mice: a mouse model of human allogeneic graft-versus-host disease," Clin Exp Immunol. 2011 166(2): 269-280.

Cragg et al., "Antibody specificity controls in vivo effector mecha-nisms of anti-CD20 reagents," Blood. (2004) 103(7):2738-2743.

Cragg et al., "Complement-mediated lysis by anti-CD20 mAb correlates with segregation into lipid rafts," Blood. (2003) 101(3):1045-1052.

Cunha JS, Gilek-Seibert K. "Systemic Lupus Erythematosus: A Review of the Clinical Approach to Diagnosis and Update on Current Targeted Therapies" R I Med J (2013). 2016;99(12):23-27. Published Dec. 1, 2016.

Cutler et al., in *Thomas' Hematopoietic Cell Transplantation*, F. Appelbaum, S. J. Forman, R. S. Negrin, K. G. Blume, Eds. (Blackwell Publishing Ltd, 2009), chap. 86, pp. 1287-1303.

David et al., "Protein iodination with solid state lactoperoxidase," Biochemistry. Feb. 26, 1974;13(5):1014-21.

Deeg et al., "The clinical spectrum of acute graft-versus-host disease," Semin Hematol. (2006) 43(1): 24-31.

Deisenhofer et al., "Crystallographic refinement and atomic models of a human Fc fragment and its complex with fragment B of protein A from *Staphylococcus aureus* at 2.9- and 2.8-A resolution," Bio-chemistry. Apr. 28, 1981;20(9):2361-70.

Del Papa N. et al., "Management of primary Sjgren's syndrome: recent developments and new classificiation criteria" Ther Adv Musculoskel Dis 2018, vol. 10(2) 39-54.

Despoix et al., "Mouse CD146/MCAM is a marker of natural killer cell maturation", Eur J Immunol. (2008) 38(10): 2855-2864.

Dick, L. et al., "C-terminal lysine variants in fully human mono-clonal antibodies: investigation of test methods and possible causes" 2008 Biotechnol Bioeng 100:1132-1143.

Dillon et al., "A Dual ICOS/CD28 Antagonist ICOSL Variant lg Domain (vlgDTM) Potently Suppresses Mouse Collagen-Induced Arthritis and Human Xenograft GVHD ," Abstract for 2017 ACR/ARHP Annual Meeting. Arthritis Rheumatol (2017) 69(suppl 10) Abstract No. 1328 (Nov. 3-8, 2017) Published Sep. 2017.

Dillon et al., "A Dual ICOS/CD28 Antagonist ICOSL Variant lg Domain (vlgDTM) Potently Suppresses Mouse Collagen-Induced Arthritis and Human Xenograft GVHD ," Presentation for 2017 ACR/ARHP Annual Meeting (Nov. 3-8, 2017).

Dillon et al., "Therapeutic Candidate ALPN-101, a Dual ICOS/CD28 Antagonist, Potently Suppresses Human/NSG Mouse Xeno-graft Graft vs. Host Disease (GvHD) in a Dose Ranging Study and Reduces Disease Activity in a Mouse Model of Hemophagocytic Lymphohistiocytosis (HLH)" Abstract ASH Dec. 1-4, 2018 Pub-lished Nov. 1, 2018.

Dillon et al., "Therapeutic Candidate ALPN-101, a Dual ICOS/CD28 Antagonist, Potently Suppresses Human/NSG Mouse Xeno-graft Graft vs. Host Disease (GvHD) in a Dose Ranging Study and Reduces Disease Activity in a Mouse Model of Hemophagocytic Lymphohistiocytosis (HLH)" Presentation ASH Dec. 1-4, 2018.

Dillon et al., "A Dual ICOS/CD28 Antagonist ICOSL Variant lg Domain (vlgDTM) Potently Suppresses Human Mixed Lymphocyte Reactions and Human/NSG Mouse Xenograft Graft vs. Host Dis-ease (GvHD)," Abstract for 2018 BMT Tandem Meetings, Salt Lake City, (Feb. 21-25, 2018) Published Jan. 2018.

Dillon et al., "A Dual ICOS/CD28 Antagonist ICOSL Variant lg Domain (vlgDTM) Potently Suppresses Human Mixed Lymphocyte Reactions and Human/NSG Mouse Xenograft Graft vs. Host Dis-ease (GvHD)" Presentation for BMT Tandem Meetings (ASBMT) , Salt Lake City, UT, Feb. 21-25, 2018, 1 page.

Dillon et al., "Therapeutic Candidate ALPN-101, a Dual ICOS/CD28 Antagonist, Demonstrates In Vivo Efficacy in an Experimen-tal Autoimmune Encephalomyelitis (EAE) Model" Abstract for the American Neurological Association Annual Meeting (ANA2018) Atlanta, Georgia, Oct. 20-23, 2018, 1 page Published Oct. 2018.

Dillon et al., "Therapeutic Candidate ALPN-101, a Dual ICOS/CD28 Antagonist, Demonstrates In Vivo Efficacy in an Experimen-tal Autoimmune Encephalomyelitis (EAE) Model" Presentation for the American Neurological Association Annual Meeting (ANA2018) Atlanta, Georgia, Oct. 20-23, 2018, 1 page.

Duncan et al., "The binding site for C1q on IgG," Nature. Apr. 21, 1988;332(6166):738-40.

Duncan, A.R., et al., "Localization of the binding site for the human high-affinity Fc receptor on IgG" 1988 Nature 332:563.

Ehx et al., "Xenogeneic Graft-Versus-Host Disease in Humanized NSG and NSG-HLA-A2/HHD Mice", Front Immunol. (2018) 9:1943.

Elyoussfi S., et al., "Tailored treatment options for patients with psoriatic arthritis and psoriasis: review of established and new biologic and small molecule therapies" Rheumatol Int (2016) 36:603-612.

Engelman et al., "Multiple effects of mutations in human immuno-deficiency virus type 1 integrase on viral replication," J Virol. 1995 69(5):2729-2736.

(56) References Cited

OTHER PUBLICATIONS

Ettinger R., et al., "Disrupted splenic architecture, but normal lymph node development in mice expressing a soluble lymphotoxin-b receptor-lgG1 fusion protein" Proc. Natl. Acad. Sci. USA, vol. 93, pp. 13102-13107, Nov. 1996 Immunologu.

Evans et al., "Generation of Novel Immuno-Oncology Biologics via Directed Evolution of Variant lgSF Domains," Poster Presentation for Immune Checkpoint Inhibitors, Boston, MA (Mar. 14-16, 2017) 1 page.

Evans et al., "Novel immunomodulatory proteins generated via directed evolution of variant lgSF domains," Abstract for AAI Immunology 2017, Washington D.C. (May 12-16, 2017) 1 page Published April A852017.

Evans et al., "Novel immunomodulatory proteins generated via directed evolution of variant lgSF domains," Poster for AAI Immunology 2017, Washington D.C. (May 12-16, 2017) 1 page.

Evans et al., "Therapeutic T Cell Activation Using Engineered Variant lgSF Domains," Abstract for Society for Immunotherapy of Cancer, National Harbor, MD, (Nov. 9-13, 2016) 1 page Published Nov. 8, 2016.

Evans et al., "Therapeutic T Cell Activation Using Engineered Variant lgSF Domains," Poster presented at Society for Immunotherapy of Cancer, National Harbor, MD, (Nov. 9-13, 2016) 1 page.

Ferrara et al., "Regenerating islet-derived 3-alpha is a biomarker of gastrointestinal graft-versus-host disease," Blood. (2011) 118(25): 6702-6708.

Ferro F., et al., "One year in review 2017: primary Sogren's syndrome" Clin Exp Rheumatol 2017; 35: 179-191.

Forcade et al., "An activated Th17-prone T cell subset involved in chronic graft-versus-host disease sensitive to pharmacological inhibition," JCI Insight. (2017) 2(12): e92111.

Ford et al., "Targeting co-stimulatory pathways: transplantation and autoimmunity," Nat Rev Nephrol. (2014) 10(1):14-24.

Fowler et al., "R707, a fully human antibody directed against CC-chemokine receptor 7, attenuates xenogeneic acute graft-versus-host disease", Am J Transplant. (2019) 19(7): 1941-1954.

Fraker et al., "Protein and cell membrane iodinations with a sparingly soluble chloroamide, 1,3,4,6-tetrachloro-3a,6a-diphrenylglycoluril," Biochem Biophys Res Commun. Feb. 28, 1978;80(4):849-57.

Freeman et al., "Engagement of the PD-1 immunoinhibitory receptor by a novel B7 family member leads to negative regulation of lymphocyte activation," J Exp Med (2000) 192(7):1027-1034.

Garcia-Aragoncillo et al., "Design of virotherapy for effective tumor treatment," Curr Opin Mol Ther. Aug. 2010;12(4):403-11.

Gazzano-Santoro et al., "A non-radioactive complement-dependent cytotoxicity assay for anti-CD20 monoclonal antibody," J Immunol Methods. Mar. 28, 1997;202(2):163-71.

Gentz et al., "Parallel association of Fos and Jun leucine zippers juxtaposes DNA binding domains," Science. (1989) 243(4899): 1695-1699.

Gherardi et al., "Recombinant poxviruses as mucosal vaccine vectors," J Gen Virol. (2005) 86(Pt 11):2925-2936.

Gordon, C, et al., "The British Society for Rheumatology guideline for the management of systemic lupus erythematosus in adults" Rheumatology 2018; 57:e1-e45 advanced publication Oct. 6, 2017.

Guerra et al., "Host response to the attenuated poxvirus vector NYVAC: upregulation of apoptotic genes and NF-kappaB-responsive genes in infected Hela cells," J Virol. (2006) 80(2): 985-98.

Hahn H.H. et al., "American College of Rheumatology Guidelines for Screening, Case Definition, Treatment and Management of Lupus Nephritis" Arthritis Care Res. (Hoboken). Jun. 2012; 64(6): 797-808.

Hallden et al., "Oncolytic virotherapy with modified adenoviruses and novel therapeutic targets," Expert Opin Ther Targets. Oct. 2012;16(10):945-58.

Harris et al., "CD80 costimulation is essential for the induction of airway eosinophilia," J Exp Med. Jan. 6, 1997;185(1):177-82.

Harris, R. J. "Processing of C-terminal lysine and arginine residues of proteins isolated from mammalian cell culture" 1995 J Chromatogr A 705:129-34.

Hartwell et al., "An early-biomarker algorithm predicts lethal graft-versus-host disease and survival," JCI Insight. (2017) 2(3): e89798.

Hellstrom et al., "Antitumor effects of L6, an lgG2a antibody that reacts with most human carcinomas," Proc Natl Acad Sci U S A. (1986) 83(18):7059-7063.

Hellstrom et al., "Strong antitumor activities of lgG3 antibodies to a human melanoma-associated ganglioside," Proc Natl Acad Sci U S A. (1985) 82(5):1499-1502.

Hinman et al., "Preparation and characterization of monoclonal antibody conjugates of the calicheamicins: a novel and potent family of antitumor antibiotics," Cancer Res. (1993) 53(14):3336-3342.

Holdgate N et al., "Recent advances in primary Sjogren's syndrome" [version 1; referees: 3 approved] F1000Research 2016, 5(F1000 Faculty Rev): 1412 Last updated: Jun. 17, 2016.

Hoseini et al., "A potent tetravalent T-cell-engaging bispecific antibody against CD33 in acute myeloid leukemia", Blood Adv. Jun. 12, 2018;2(11):1250-1258.

Hu et al., "Yaba-like disease virus: an alternative replicating poxvirus vector for cancer gene therapy," J Virol. (2001) 75(21):10300-10308.

Hunter et al., "Preparation of iodine-131 labelled human growth hormone of high specific activity," Nature. May 5, 1962;194:495-6.

Idusogie et al., "Mapping of the C1q binding site on rituxan, a chimeric antibody with a human lgG1 Fc," J Immunol. (2000) 164(8):4178-4184.

Johann et al., "GLVR1, a receptor for gibbon ape leukemia virus, is homologous to a phosphate permease of Neurospora crassa and is expressed at high levels in the brain and thymus," J Virol. (1992) 66(3):1635-1640.

Kabat et al., "Sequences of Proteins of Immunological Interest," Fifth Edition, U.S. Department of Health and Human Services, NIH Publication No. 91-3242 (1991), 83 pages.

Kawalec P, et al., "Comparative effectiveness of abatacept, apremilast, secukinumab and ustekinumab treatment of psoriatic arthritis: a systematic review and network meta-analysis" Rheumatology International (2018) 38:189-201.

Kirn et al., "Targeted and armed oncolytic poxviruses: a novel multi-mechanistic therapeutic class for cancer," Nat Rev Cancer. Jan. 2009;9(1):64-71.

Kolberg, "Gene-transfer virus contaminant linked to monkey's cancer," J NIH Res. (1992) 4:43-44.

Koura et al., "In vivo T cell costimulation blockade with abatacept for acute graft-versus-host disease prevention: a first-in-disease trial", Biol Blood Marrow Transplant. (2013) 19(11): 1638-1649.

Koyama et al., "Plasmacytoid dendritic cells prime alloreactive T cells to mediate graft-versus-host disease as antigen-presenting cells," Blood. (2009) 113(9): 2088-2095.

La Paglia G.M.C. et al., "One year in review 2017: systemic lupus erythematosus" Clin Exp Rheumatol 2017; 35:551-561.

Labrijn et al., "Therapeutic lgG4 antibodies engage in Fab-arm exchange with endogenous human lgG4 in vivo," Nat Biotechnol. Aug. 2009;27(8):767-71.

Laouar et al., "STAT3 is required for Flt3L-dependent dendritic cell differentiation," Immunity. (2003) 19(6): 903-912.

Larsen et al., "Rational development of LEA29Y (belatacept), a high-affinity variant of CTLA4-lg with potent immunosuppressive properties," Am J Transplant. Mar. 2005;5(3):443-53.

Levin et al., "Novel Immunomodulatory Proteins Generated Via Directed Evolution of Variant lgSF Domains," Abstract for Keystone Symposia: Immune Regulation in Autoimmunity and Cancer, Whistler, British Columbia, Canada (Mar. 26-30, 2017), 1 page Available to Attendees Feb. 26, 2017.

Levin et al., "Novel Immunomodulatory Proteins Generated Via Directed Evolution of Variant lgSF Domains," Poster presentation for Keystone Symposia: Immune Regulation in Autoimmunity and Cancer, Whistler, British Columbia, Canada (Mar. 26-30, 2017), 1 page.

(56)                References Cited

OTHER PUBLICATIONS

Levin et al., "Novel Variant lg Domain (vlgD) Proteins Generated Via Directed Evolution of IgSF Domains Have Therapeutic Efficacy in Animal Models of Graft Versus Host Disease," Abstract for ASH 2017 Nov. 1, 2017 (Dec. 9-12, 2017).

Levin et al., "Novel Variant lg Domain (vlgD) Proteins Generated Via Directed Evolution of IgSF Domains Have Therapeutic Efficacy in Animal Models of Graft Versus Host Disease," Poster for ASH 2017 (Dec. 9-12, 2017).

Levin et al., "Tumor-Localizing NKp30/ICOSL vlgD Fusion Proteins Direct Effective Dual CD28/ICOS T cell Costimulation to B7-H6+ Tumor Cells in vitro and Tumors in vivo" Abstract 2018 SITC (Nov. 7-11, 2018) Published Nov. 6, 2018.

Levin et al., "Tumor-Localizing NKp30/ICOSL vlgD Fusion Proteins Direct Effective Dual CD28/ICOS T cell Costimulation to B7-H6+ Tumor Cells in vitro and Tumors in vivo" Poster 2018 SITC (Nov. 7-11, 2018) Published Nov. 6, 2018.

Levin et al., "Tumor-localizing NKp30/ICOSL vlgD fusion proteins direct effective dual CD28/ICOS T cell costimulation to B7-H6+ tumor cells in vitro and tumors in vivo" Abstract SITC 2018.

Levin et al., "Novel Immunomodulatory Proteins Generated Via Directed Evolution of Variant IgSF Domains" Keystone Symposia on Molecular and Cellular Biology, Lymphocytes and their Roles in Cancer, Keystone, CO, Feb. 11-15, 2018, 1 page, presentation.

Levin, S.D., et al., "Novel Immunomodulatory proteins generated via directed evolution of variant IgSF domains." Front Immunol., (2020) 10:3086.

Lewis et al., "Novel immunomodulatory proteins generated via directed evolution of variant IgSF domains," Abstract for Poster Presentation at the Federation of Clinical Immunology Societies Meeting, Chicago IL (Jun. 14, 2017) 2 pages Published after Apr. 7, 2017.

Lewis et al., "Novel immunomodulatory proteins generated via directed evolution of variant IgSF domains," Poster Presentation at the Federation of Clinical Immunology Societies Meeting, Chicago IL (Jun. 14, 2017).

Li et al., "Comparison of anti-CD3 and anti-CD28-coated beads with soluble anti-CD3 for expanding human T cells: differing impact on CD8 T cell phenotype and responsiveness to restimulation," J Transl Med. (2010) 8:104.

Li et al., "Proteomics analysis reveals a Th17-prone cell population in presymptomatic graft-versus-host disease," JCI Insight. (2016) 1(6): e86660.

Li et al., "Structure of the human activating natural cytotoxicity receptor NKp30 bound to its tumor cell ligand B7-H6," J Exp Med (2011) 208(4): 703-714.

Lin et al., "Specific and dual antagonists of alpha(4)beta(1) and alpha(4)beta(7) integrins," Bioorg Med Chem Lett. Jan. 21, 2002;12(2):133-6.

Linsley et al., "Human B7-1 (CD80) and B7-2 (CD86) bind with similar avidities but distinct kinetics to CD28 and CTLA-4 receptors," Immunity. (1994) 1(9): 793-801.

Liu et al., "Eradication of large colon tumor xenografts by targeted delivery of maytansinoids," Proc Natl Acad Sci U S A. (1996) 93(16):8618-8623.

Lode et al., "Targeted therapy with a novel enediyene antibiotic calicheamicin theta(I)1 effectively suppresses growth and dissemination of liver metastases in a syngeneic model of murine neuroblastoma," Cancer Res. (1998) 58(14):2925-2928.

Lundqvist et al., "31st Annual Meeting and Associated Programs of the Society for Immunotherapy of Cancer (SITC 2016): part one," J Immunother Cancer, (2016) 4(Suppl 1):82.

Lundqvist et al., "31st Annual Meeting and Associated Programs of the Society for Immunotherapy of Cancer (SITC 2016): part two," J Immunother Cancer, (2016) 4(Suppl 1):82.

Mahmood F. et al., "Current concepts and unmet needs in psoriatic arthritis" Clinical Rheumatology vol. 37, pp. 297-305 (2018).

Mandler et al., "Immunoconjugates of geldanamycin and anti-HER2 monoclonal antibodies: antiproliferative activity on human breast carcinoma cell lines," J Natl Cancer Inst. Oct. 4, 2000;92(19):1573-81.

Mandler et al., "Modifications in synthesis strategy improve the yield and efficacy of geldanamycin-herceptin immunoconjugates," Bioconjug Chem. Jul.-Aug. 2002;13(4):786-91.

Mandler et al., "Synthesis and evaluation of antiproliferative activity of a geldanamycin-Herceptin immunoconjugate," Bioorg Med Chem Lett. May 15, 2000;10(10):1025-8.

Markey et al., "Conventional dendritic cells are the critical donor APC presenting alloantigen after experimental bone marrow transplantation", Blood. 2009 113(22): 5644-5649.

Markey et al., "Flt-3L Expansion of Recipient CD8α + Dendritic Cells Deletes Alloreactive Donor T Cells and Represents an Alternative to Posttransplant Cyclophosphamide for the Prevention of GVHD", Clin Cancer Res. (2018) 24(7): 1604-1616.

Markey et al., "Recipient plasmacytoid DCs are not required to prime allogeneic T-cell responses after BMT," Blood. (2009) 113(23): 6038-6039.

Martin et al., "Increasingly frequent diagnosis of acute gastrointestinal graft-versus-host disease after allogeneic hematopoietic cell transplantation," Biol Blood Marrow Transplant. (2004) 10(5): 320-327.

Matte et al., "Donor APCs are required for maximal GVHD but not for GVL", Nat Med. (2004) 10(9): 987-992.

Maute et al., "Engineering high-affinity PD-1 variants for optimized immunotherapy and immuno-PET imaging," Proc Natl Acad Sci U S A. (2015) 112(47): E6506-14.

Mayr et al., "Passage history, properties, and applicability of the attenuated vaccinia virus strain MVA," Infection. (1975);3:6-14. (English translation of abstract provided).

Mcdonald et al., "Plasma biomarkers of acute GVHD and nonrelapse mortality: predictive value of measurements before GVHD onset and treatment," Blood. (2015) 126(1): 113-120.

Mcloughlin et al., "TNFerade, an adenovector carrying the transgene for human tumor necrosis factor alpha, for patients with advanced solid tumors: surgical experience and long-term follow-up," Ann Surg Oncol. Oct. 2005;12(10):825-30.

Mcwilliams et al., "Mutations in the 5' end of the human immunodeficiency virus type 1 polypurine tract affect RNase H cleavage specificity and virus titer," J Virol. (2003) 77(20):11150-11157.

Meiners PM et al., "Abatacept treatment reduces disease activity in early primary Sjögren's syndrome (open-label proof of concept ASAP study)" Ann Rheum Dis. 2014;73(7):1393-1396.

Merchant et al., "An efficient route to human bispecific IgG," Nat Biotechnol. (1998) 16(7): 677-681.

Mercier et al., "A chimeric adenovirus vector encoding reovirus attachment protein sigma1 targets cells expressing junctional adhesion molecule 1," Proc Natl Acad Sci U S A. (2004) 101(16): 6188-6193.

Miller et al., "Construction and properties of retrovirus packaging cells based on gibbon ape leukemia virus," J Virol. (1991) 65(5):2220-2224.

Miller et al., "Construction and screening of antigen targeted immune yeast surface display antibody libraries," Curr Protoc Cytom. Jul. 2008;Chapter 4:Unit4.7.

Miller et al., "Gene transfer by retrovirus vectors occurs only in cells that are actively replicating at the time of infection," Mol Cell Biol. (1990) 10(8):4239-4242.

Miller, "Protein-protein recognition and the association of immunoglobulin constant domains," J Mol Biol. Dec. 20, 1990;216(4):965-73.

Milone et al., "Chimeric receptors containing CD137 signal transduction domains mediate enhanced survival of T cells and increased antileukemic efficacy in vivo," Mol Ther. (2009) 17(8):1453-64.

Miyoshi et al. "Development of a self-inactivating lentivirus vector," J Virol. (1998) 72(10):8150-8157.

Mizuhara et al., "T cell activation-associated hepatic injury: mediation by tumor necrosis factors and protection by interleukin 6," J Exp Med. 1994 179(5): 1529-1537.

(56)        References Cited

OTHER PUBLICATIONS

Mochizuki et al., "Delta-like ligand 4 identifies a previously uncharacter-ized population of inflammatory dendritic cells that plays important roles in eliciting allogeneic T cell responses in mice," J Immunol. (2013) 190(7): 3772-82.

Molin et al., "Two novel adenovirus vector systems permitting regulated protein expression in gene transfer experiments," J Virol. (1998) 72(10):8358-8361.

Mollweide et al., "Only therapeutic ICOS:ICOSL blockade allevi-ates acute graft versus host disease", Klin Padiatr. (2009) 221(6):344-50.

Morton et al., "Differential effects of CTLA-4 substitutions on the binding of human CD80 (B7-1) and CD86 (B7-2)," J Immunol. (1996) 156(3):1047-1054.

Narumi et al., "Adenovirus vector-mediated perforin expression driven by a glucocorticoid-inducible promoter inhibits tumor growth in vivo," Am J Respir Cell Mol Biol. (1998) 19(6):936-941.

Nightingale et al., "Transient gene expression by nonintegrating lentiviral vectors," Mol Ther. (2006) 13(6):1121-1132.

Nygren, "Conjugation of horseradish peroxidase to Fab fragments with different homobifunctional and heterobifunctional cross-linking reagents. A comparative study," J Histochem Cytochem. May 1982;30(5):407-12.

Omer AK et al., "Late Acute Graft Versus Host Disease After Allogeneic Hematopoietic Stem Cell Transplantation" Biol Blood Marrow Transplant. May 2016; 22(5): 879-883.

Paczesny et al., "A biomarker panel for acute graft-versus-host disease," Blood. (2009) 113(2): 273-278.

Paczesny et al., "Elafin is a biomarker of graft-versus-host disease of the skin," Sci Transl Med. (2010) 2(13): 13ra2.

Paczesny, "Biomarkers for post transplantation outcomes," Blood. (2018) 131(20): 2193-2204.

Pain et al., "Preparation of protein A-peroxidase monoconjugate using a heterobifunctional reagent, and its use in enzyme immunoas-says," J Immunol Methods. (1981);40(2):219-30.

Patton et al., "Evaluation of the efficiency of human immune system reconstitution in NSG mice and NSG mice containing a human HLA.A2 transgene using hematopoietic stem cells purified from different sources", J Immunol Methods. (2015) 422: 13-21.

Patyar et al., "Bacteria in cancer therapy: a novel experimental strategy," J Biomed Sci. (2010) 17(1):21.

Paulos et al., "The inducible costimulator (ICOS) is critical for the development of human T(H)17 cells", Sci Transl Med. (2010) 2(55): 55ra78.

Peach et al., "Both extracellular immunoglobin-like domains of CD80 contain residues critical for binding T cell surface receptors CTLA-4 and CD28," J Biol Chem. (1995) 270(36):21181-7.

Peach et al., "Complementarity determining region 1 (CDR1)- and CDR3-analogous regions in CTLA-4 and CD28 determine the binding to B7-1," J Exp Med (1994) 180(6):2049-2058.

Penix et al., "Two essential regulatory elements in the human interferon gamma promoter confer activation specific expression in T cells," J Exp Med. (1993) 178(5):1483-1496.

Peper et al., "An impedance-based cytotoxicity assay for real-time and label-free assessment of T-cell-mediated killing of adherent cells," J Immunol Methods. Mar. 2014;405:192-8.

Pérez De La Lastra et al., "Epitope mapping of 10 monoclonal antibodies against the pig analogue of human membrane cofactor protein (MCP)," Immunology. (1999) 96(4):663-70.

Petkova et al., "Enhanced half-life of genetically engineered human IgG1 antibodies in a humanized FcRn mouse model: potential application in humorally mediated autoimmune disease," Int Immunol. (2006) 18(12):1759-1769.

Peyrin-Biroulet L. et al., "Defining Disease Severity in Inflamma-tory Bowel Diseases: Current and Future Directions" Clinical Gastroenterology and Hepatology 2016; 14:348-354.

Pfeifer et al., "Gene therapy: promises and problems," Annu Rev Genomics Hum Genet. (2001);2:177-211.

Philpott et al., "Use of nonintegrating lentiviral vectors for gene therapy," Hum Gene Ther. (2007) 18(6): 483-9.

Powell et al., "Sequence and structural determinants required for priming of plus-strand DNA synthesis by the human immunodefi-ciency virus type 1 polypurine tract," J Virol. (1996) 70(8):5288-5296.

Qin et al., "Incorporation of a hinge domain improves the expansion of chimeric antigen receptor T cells," J Hematol Oncol. (2017) 10(1):68.

Qureshi et al., "Trans-endocytosis of CD80 and CD86: a molecular basis for the cell- extrinsic function of CTLA-4," Science (2011) 332(6029):600-603.

Rajpal A. et al., "Introduction: Antibody Structure and Function" Therapeutic Fc-Fusion Proteins, First Edition. Edited by Steven M. Chamow, Thomas Ryll, Henry B. Lowman, and Deborah Farson. 2014 by Wiley-VCH Verlag GmbH & Co. KGaA.

Ramadan et al., "From proteomics to discovery of first-in-class ST2 inhibitors active in vivo," JCI Insight. (2018) 3(14): e99208.

Ravetch et al., "Fc receptors," Annu Rev Immunol. (1991) 9:457-492.

Reizis et al., "Plasmacytoid Dendritic Cells: Development, Regu-lation, and Function," Immunity. (2019) 50(1): 37-50.

Ren et al., "The search for drug-targetable diagnostic, prognostic and predictive biomarkers in chronic graft-versus-host disease," Expert Rev Clin Immunol. (2018) 14(5): 389-404.

Rentero et al., "Screening of Large Molecule Diversities by Phage Display," Chimia (Aarau) (2011) 65(11): 843-845.

Rickel et al., "ICOSL Anti-HER2 V-mAbs: Localizing Engineered ICOSL Costimulatory Agonists to HER2+ tumors through Trastuzumab," Abstract for San Antonio Breast Cancer Symposium, San Antonio, TX (Dec. 5-9, 2017) 1 page Published Nov. 5, 2017.

Rickel et al., "ICOSL Anti-HER2 V-mAbs: Localizing Engineered ICOSL Costimulatory Agonists to HER2+ tumors through Trastuzumab," Presentation for San Antonio Breast Cancer Sym-posium, San Antonio, TX (Dec. 5-9, 2017) 1 page.

Ridgway et al., "'Knobs-into-holes' engineering of antibody CH3 domains for heavy chain heterodimerization," Protein Eng. Jul. 1996;9(7):617-21.

Rixon et al., "Novel Immunomodulatory Proteins Generated Via Directed Evolution of Variant lgSF Domains" PEGS: The Essential Protein Engineering Summit, Boston, MA, Apr. 30-May 1, 2018, 1 page. Abstract.

Rixon et al., "Novel Immunomodulatory Proteins Generated Via Directed Evolution of Variant lgSF Domains" PEGS: The Essential Protein Engineering Summit, Boston, MA, Apr. 30-May 1, 2018, 1 page. Presentation.

Roopenian D.C. et al., "FcRn: the neonatal Fc receptor comes of age" Nautre Review Immunologu, vol. 7, Sep. 2007 pp. 715-725.

Rosenberg et al., "Use of tumor-infiltrating lymphocytes and interleukin-2 in the immunotherapy of patients with metastatic melanoma. A preliminary report," N Engl J Med. (1988) 319(25):1676-1680.

Rowland et al., "Drug localisation and growth inhibition studies of vindesine-monoclonal anti-CEA conjugates in a human tumour xenograft," Cancer Immunol Immunother. (1986);21(3):183-7.

Sadelain, M. et al., "The basic principles of chimeric antigen receptor design." Cancer Discov., Apr. 2013, vol. 3, No. 4, pp. 388-398.

Schildberg et al., "Coinhibitory Pathways in the B7-CD28 Ligand-Receptor Family," Immunity. (2016) 44(5): 955-72.

Sciascia S. et al., "Recent advances in the management of systemic lupus erythematosus" [version 1; referees approved:2] F1000Research 2018, 7(F1000 Faculty Rev): 970 Last updated: Jun. 29, 2018.

Seow et al., "Biological gene delivery vehicles: beyond viral vectors," Mol Ther. (2009) 17(5):767-777.

Shields et al., "High resolution mapping of the binding site on human IgG1 for Fc gamma Rl, Fc gamma Rll, Fc gamma Rlll, and FcRn and design of lgG1 variants with improved binding to the Fc gamma R," J Biol Chem. (2001) 276(9):6591-6604.

Shlomchik et al., "Prevention of graft versus host disease by inactivation of host antigen-presenting cells," Science. (1999) 285(5426): 412-415.

Sommerfelt et al., "Receptor interference groups of 20 retroviruses plating on human cells," Virology. (1990) 176(1): 58-69.

(56) References Cited

OTHER PUBLICATIONS

Srivastava et al., "Engineering CAR-T cells: Design Concepts," Trends in Immunology (2015) 36(8):494-502.

Sturmhoefel et al., "Potent Activity of Soluble B7-lgG Fusion Proteins in Therapy of Established Tumors and as Vaccine Adjuvant," Cancer Res. (1999) 59(19): 4964-4972.

Tan LK et al., "Influence of the hinge region on complement activation, C1q binding, and segmental flexibility in chimeric human immunoglobulins" Proc. Natl. Acad. Sci. USA vol. 87, pp. 162-166, Jan. 1990 Immunology.

Tangney et al., "The use of Listeria monocytogenes as a DNA delivery vector for cancer gene therapy," Bioeng Bugs. (2010) 1(4):284-287.

Tareen et al., "Design of a novel integration-deficient lentivector technology that incorporates genetic and posttranslational elements to target human dendritic cells," Mol Ther. (2014) 22(3):575-587.

Tartaglia et al., "Highly attenuated poxvirus vectors," AIDS Res Hum Retroviruses. (1992) 8(8):1445-1447.

Taylor et al., "Targeting of inducible costimulator (ICOS) expressed on alloreactive T cells down-regulates graft-versus-host disease (GVHD) and facilitates engraftment of allogeneic bone marrow (BM)", Blood. (2005) 105(8): 3372-3380.

Teshima et al., "Response: Recipient plasmacytoid dendritic cells and graft-versus-host disease", Blood. (2009) 114(6): 1280.

Tewar M Draft Psoriatic Arthritis Guideline Presented at ACR 2017 Nov. 17, 2017.

Thompson et al., "cis-acting sequences required for inducible interleukin-2 enhancer function bind a novel Ets-related protein, Elf-1," Mol Cell Biol. (1992) 12(3):1043-1053.

Tiegs et al., "A T cell-dependent experimental liver injury in mice inducible by concanavalin A." J Clin Invest. (1992) 90(1): 196-203.

Todd et al., "Transcription of the interleukin 4 gene is regulated by multiple promoter elements," J Exp Med. (1993) 177(6):1663-1674.

Toyabe et al., "Requirement of IL-4 and liver NK1+ T cells for concanavalin A-induced hepatic injury in mice," J Immunol (1997) 159:1537-1542.

Trentin F et al., "Effectiveness, Tolerability, and Safety of Belimumab in Patients with Refractory SLE: a Review of Observational Clinical-Practice-Based Studies" Clinical Reviews in Allergy & Immunology (2018) 54:331-343.

Tsuboi H et al., "Effectiveness of abatacept for patients with Sjogren's syndrome associated with rheumatoid arthritis. An open label, multicenter, one-year, prospective study: ROSE (Rheumatoid Arthritis with Orencia Trial toward Sjogren's syndrome Endocrinopathy) trial" Mod Rheumatol, 2016; 26(6):891-899.

Uniprot H9Z6Y0 ICOS ligand Retrieved from https://www.uniprot.org/uniprot/H9Z6Y0. Retrieve on Jul. 10, 2020.

Uniprot L8Y5K4 ICOS Ligand Retrieved from https://www.uniprot.org/uniprot/L8Y5K4. Retrieved on Jul. 10, 2020.

Uzzaman et al., "Classification of hypersensitivity reactions," Allergy Asthma Proc. (2012) 33: S96-S99.

Van Der Lugt et al., "ST2 as a marker for risk of therapy-resistant graft-versus-host disease and death," N Engl J Med. (2013) 369(6): 529-539.

Van Pijkeren et al., "A novel Listeria monocytogenes-based DNA delivery system for cancer gene therapy," Hum Gene Ther. Apr. 2010;21(4):405-16.

Vitetta et al., "Redesigning nature's poisons to create anti-tumor reagents," Science. Nov. 20, 1987;238(4830):1098-104.

Wang et al., "In vitro characterization of the anti-PD-1 antibody nivolumab, BMS-936558, and in vivo toxicology in non-human primates," Cancer Immunol Res. (2014) 2(9):846-856.

Wang et al., "Molecular modeling and functional mapping of B7-H1 and B7-DC uncouple costimulatory function from PD-1 interaction," J Exp Med. 2003 197(9):1083-91.

Watkins et al., "CD28 blockade controls T cell activation to prevent graft-versus-host disease in primates", J Clin Invest. (2018) 128(9): 3991-4007.

Wikenheiser et al., "ICOS Co-Stimulation: Friend or Foe?," Front Immunol (2016) (7):304, 16 pgs.

Wilson et al., "Formation of infectious hybrid virions with gibbon ape leukemia virus and human T-cell leukemia virus retroviral envelope glycoproteins and the gag and pol proteins of Moloney murine leukemia virus," J Virol. (1989) 63(5):2374-2378.

Wu et al., "CTLA-4-B7 Interaction Is Sufficient to Costimulate T Cell Clonal Expansion," J. Exp. Med. (1997) 185(7):1327-1335.

Wu et al., "IL-24 modulates IFN-gamma expression in patients with tuberculosis," Immunol Lett. (2008) 117(1):57-62.

Yao et al., "B7-h2 is a costimulatory ligand for CD28 in human," Immunity. (2011) 34(5):729-40.

Yu et al., "The role of B7-CD28 co-stimulation in tumor rejection," Int Imm (1998) 10(6):791-797.

Zeiser et al., "Acute Graft-versus-Host Disease—Biologic Process, Prevention, and Therapy", N Engl J Med. Nov. 30, 2017;377(22):2167-2179.

Zhang et al., "An NKp30-Based Chimeric Anitgen Receptor Promotes T Cell Effector Functions and Antitumor Efficacy In Vivo," J Immunol (2012) 189:2290-2299.

Zhang et al., "Preterminal host dendritic cells in irradiated mice prime CD8+ T cell-mediated acute graft-versus-host disease," J Clin Invest. (2002) 109(10): 1335-1344.

Zhang et al., "ST2 blockade reduces sST2-producing T cells while maintaining protective mST2-expressing T cells during graft-versus-host disease", Sci Transl Med. (2015) 7(308): 308ra160.

Zhang et al., "Introduction to the Data Analysis of the Roche xCELLigence® System with RTCA Package," Bioconductor. May, 3, 2016, bioconductor.org/packages/devel/bioc/vignettes/RTCA/inst/doc/aboutRTCA.pdf, accessed Sep. 9, 2016, 11 pages.

Zhao et al., "Structural Design of Engineered Costimulation Determines Tumor Rejection Kinetics and Persistence of CAR T Cells," Cancer Cell (2015) 28(4):415-428.

Zhao et al., "TIGIT overexpression diminishes the function of CD4 T cells and ameliorates the severity of rheumatoid arthritis in mouse models," Exp Cell Res. Jan. 1, 2016;340(1):132-8.

Zimin et al., "A new rhesus macaque assembly and annotation for next-generation sequencing analyses," Biol Direct. Oct. 14, 2014;9(1):20.

Zufferey et al., "Self-inactivating lentivirus vector for safe and efficient in vivo gene delivery," J Virol. (1998) 72(12):9873-9880.

Piantoni et al., "Effector Tcells are expanded in systemic lup erythematos patients with high disease activity and damage indexes," Lup. (2018) 27(1): 143149.

Ruperto et al., Abatacept in children with juvenile idiopathic arthritis: a randomised, double-blind, placebo- controlled withdrawal trial. Lancet. (2008) 372:383-391.

Scarsi et al., "Baseline Nos. of circulating CD28negative T cells may predict clinical response to abatacept in patients with rheumatoid arthritis," J Rheumatol. (2011) 38(10): 210511.

Schmidt et al., "CD4+ CD7 CD28 T cells are expanded in rheumatoid arthritis and are characterized by autoreactivity," J Clin Invest. (1996) 97(9): 2027-2037.

Scholten et al., "Promiscuous behavior of HPV16E6 specific T cell receptor beta chains hampers functional expression in TCR transgenic T cells, which can be restored in part by genetic modification," Cell Oncol. (2010) 32:43-56.

Shendure et al., "Advanced sequencing technologies: methods and goals," Nat Rev Genet. (2004) 5(5): 33544.

Strohl, "Optimization of Fc-mediated effector functions of monoclonal antibodies," Curr Opin Biotechnol. (2009) Dec. 20(6):685-91.

Topalian et al., "Safety, activity, and immune correlates of anti-PD-1 antibody in cancer," N engl J Med (2012) 366:2443-2454.

Van Der Merwe et al.. "CD80 (B7-1) binds both CD28 and CTLA-4 with a low affinity and very fast kinetics," J exp Med (1997) 185:393-403.

Vincenti et al., "Costimulation blockade with belatacept in renal transplantation," N Engl J Med. (2005) 353:770-81.

Weber et al., "ICOS maintains the T follicular helper cell phenotype by down-regulating Kruppel-like factor 2," J Exp Med. (2015) 212:217-33.

Wekerle et al., "Belatacept: from rational design to clinical application," Transplant International (2012) 25:139-150.

(56)         References Cited

OTHER PUBLICATIONS

Wolchok et al., "Development of ipilimumab: a novel immunotherapeutic approach for the treatment of advanced melanoma," Ann N Y Acad Sci. (2013) 1291:1-13.

Xu et al., "Affinity and cross-reactivity engineering of CTLA4-Ig to modulate T cell costimulation," J Immunol (2012) 189(9):4470-4477.

Yang et al., "Clinical significance of inducible costimulator and CD28 coexpression on peripheral T subsets in patients with systemic lup erythematos," Chin J Microbiol Immunol, 2005, 25:248251 (English abstract).

Yoshinaga et al., Cell co-stimulation through B7RP-1 and ICOS. Nature. (1999) 402:827-832.

Zabinska et al., "CD3(+)CD8(+)CD28() T Lymphocytes in Patients with Lup Nephritis," J Immunol Res. (2016) 2016: 1058165.

Zhao et al., "A Bispecific Protein Capable of Engaging CTLA-4 andMHCII Protects Non-Obese Diabetic Mice from Autoimmune Diabetes," PLOS One (2013) 8(5): e63530-e63530.

Zhou et al., "Endogeno programmed death ligand1 restrains the development and onset of Sjogren's syndrome in nonobese diabetic mice," Scientific Reports. (2016) vol. 6; Article No. 39105.

Database accession No. XP_002787562.1 (Apr. 30, 2010); Retrieved from NCBI, https://www.ncbi.nlm.nih.gov/protein/XP_002787562.1, Retrieved May 12, 2024.

Database Accession No. BEK41690 "Human ICOSL variant protein fragment (ICOSL v24 Eco), Seq 132", GENESEQ, Nov. 30, 2017 (Nov. 30, 2017), XP002790439, Abstract.

"Database accession No. ADM18706." Retrieved from IBIS, http://ibis/exam/dbfetch.jsp?id=GSP:ADM18706. Retrieved on Oct. 10, 2017.

"Database accession No. ADM18913." Retrieved from IBIS, http://ibis/exam/dbfetch.jsp?id=GSP:ADM18913. Retrieved on Oct. 10, 2017.

"Database accession No. BCD07227." Retrieved from IBIS, http://ibis/exam/dbfetch.jsp?id=GSP:BCD07227. Retrieved on Oct. 10, 2017.

"Database accession No. BCD07228." Retrieved from IBIS, http://ibis/exam/dbfetch.jsp?id=GSP:BCD07228. Retrieved on Oct. 10, 2017.

Adom, Djamilatou, et al. "ICOSL+ plasmacytoid dendritic cells as inducer of graft-versus-host disease, responsive to a dual ICOS/CD28 antagonist." Science translational medicine 12.564 (2020): eaay4799.

Behr et al., "Trastuzumab and breast cancer," N Engl J Med. (2001) 345:995-996.

Biasini et al., "SWISS-MODEL: modelling protein tertiary and quaternary structure using evolutionary information," Nucleic Acids Res (2014) 42:W252-258.

Boder et al.. "Optimal screening of surface-displayed polypeptide libraries," Biotechnol Prog. (1998) 14:55-62.

Bork, P. "Powers and pitfalls in sequence analysis: the 70% hurdle," Genome Res. (2000) 10(4):398-400.

Bowie et al., "Deciphering the message in protein sequences: tolerance to amino acid substitutions," Science. (1990) 247(4948): 1306-10.

Brandt et al., The B7 family member B7-H6 is a tumor cell ligand for the activating natural killer cell receptor NKp30 in humans. J Exp Med. (2009) 206:1495-1503.

Burgess et al., "Possible dissociation of the heparin-binding and mitogenic activities of heparin-binding (acidic fibroblast) growth factor-1 from its receptor-binding activities by site-directed mutagenesis of a single lysine residue," J Cell Biol. (1990) 111(5 Pt 1):2129-38.

Carter et al., "Cytotoxic T-lymphocyte antigen-4 and programmed death-1 function as negative regulators of lymphocyte activation," Immunol Res (2003) 28:49-59.

Carter et al., "Humanization of an anti-p185HER2 antibody for human cancer therapy," Proc Natl Acad Sci USA (1992) 89:4285-4289.

Chao et al., "Isolating and engineering human antibodies using yeast surface display," Nat Protoc. (2006) 1:755-768.

Chaudhri et al., "PD-L1 Binds to B7-1 Only In Cis on the Same Cell Surface," Cancer Immunol Res (2018) 6 (8):921-929.

Cogswell et al., "An Analytical Comparison of Dako 28-8 PharmDx Assay and an E1L3N Laboratory-Developed Test in the Immunohistochemical Detection of Programmed Death-Ligand 1," Mol Diagn Ther (2017) 21(1): 85-93.

Conti et al., "Induction of pro-inflammatory cytokines (IL-1 and IL-6) and lung inflammation by Coronavirus-19 (COVI-19 or SARS-CoV-2): anti-inflammatory strategies," J Biol Regul Homeost Agents. (2020) 34(2):327-331.

Derer et al., Complement in antibody-based tumor therapy. Crit Rev Immunol. (2014) 34:199-214.

Dull et al., "A Third-Generation Lentivirus Vector with a Conditional Packaging System," J Virology (1998) 72(11): 8463-8471.

Ellis et al., "Interactions of CD80 and CD86 with CD28 and CTLA4, "J Immunol (1996) 156:2700-2709.

Esensten et al., CD28 costimulation: from mechanism to therapy. Immunity. (2016) 44:973-988.

Garin et al., "Strong increase in the percentage of the CD8bright+ CD28 Tcells and delayed engraftment associated with cyclosporineinduced autologo GVHD," Eur J Haematol. (1996) 56(3): 11923.

Ghiotto, M., et al."PD-L 1 and PD-L2 differ in their molecular mechanisms of interaction with PD-1", International Immunology, 2010, vol. 22, No. 8, pp. 651-660.

Greenspan et al., "Defining epitopes: It's not as easy as it seems," Nat Biotechnol. (1999) 17(10): 936-7.

Gregoire-Gauthier et al., "Use of immunoglobulins in the prevention of GvHD in a xenogeneic NOD/SCID/gammac- mouse model," Bone Marrow Transplant (2012) 47:439-450.

Haile et al., "A Soluble Form of CD80 Enhances Antitumor Immunity by Neutralizing Programmed Death Ligand-1and Simultaneously Providing Costimulation," Cancer Immunol Res (2014) 2(7): 610-615.

Halaby et al., "The immunoglobulin superfamily: an insight on its tissular, species, and functional diversity," J Mol Evol (1998) 46:389-400.

Jenkins et al., "CD28 delivers a costimulatory signal involved in antigen-specific IL-2 production by human T cells," J Immunol. (1991) 147:2461-6.

Klarquist et al., "The bm12 Inducible Model of Systemic Lup Erythematos (SLE) in C57BL/6 Mice," J Vis Exp. (2015) (105): e53319.

Kremer et al., "Treatment of rheumatoid arthritis by selective inhibition of T-cell activation with fusion protein CTLA4lg," N Engl J Med (2003) 349(20): 1907-1915.

Lazar et al., "Transforming growth factor alpha: mutation of aspartic acid 47 and leucine 48 results in different biological activities," Mol Cell Biol. (1988) 8(3): 1247-52.

Lazetic et al., "Chimeric co-stimulatory molecules that selectively act through CD28 or CTLA-4 on human T cells," J Biol Chem (2002)11;277(41):38660-38668.

Li, Minghui, et al. "Immunomodulation and pharmacological strategies in the treatment of graft-versus-host disease." Expert opinion on pharmacotherapy 9.13 (2008): 2305-2316.

Lin et al., "The PD-1/PD-L1 complex resembles the antigen-binding Fv domains of antibodies and T cell receptors," Proc Natl Acad Sci U S A. (2008) 105(8):3011-3016.

Lipson et al., "Antagonists of PD-1 and PD-L1 in Cancer Treatment," Semin Oncol. Aug. 2015;42(4):587-600.

Lobo et al., "Pharmacodynamic modeling of chemotherapeutic effects: application of a transit compartment model to characterize methotrexate effects in vitro." AAPS PharmSci (2002) 4(4):42, 11 pages.

Mease et al., "Efficacy and safety of abatacept, a T-cell modulator, in a randomised, double-blind, placebo-controlled, phase III study in psoriatic arthritis," Ann Rheum Dis. (2017) 76:1550-8.

Mou et al., "CD28 negative T cells: is their loss our gain?," Am J Transplant. (2014) 14(11): 24606.

Nowrousian, "Nextgeneration sequencing techniques for eukaryotic microorganisms: sequencingbased solutions to biological problems," Eukaryot Cell. (2010) 9(9): 130010.

(56)            References Cited

OTHER PUBLICATIONS

Ochoa et al., "Antibody-dependent cell cytotoxicity: immunotherapy strategies enhancing effector NK cells," Immunol Cell Biol. (2017) 95:347-55.

Parslow et al., "Antibody-drug conjugates for cancer therapy," Biomedicines. (2016) 4:E32.

1st Gen. CD19 CAR-T
1st Gen. CD19 CAR-T+CD80
1st Gen. CD19 CAR-T+ ICOSL
1st Gen. CD19 CART+CD80-TIP
1st Gen. CD19 CARTICOSL-TIP

Normalized Cell Index

Time (in Hour)

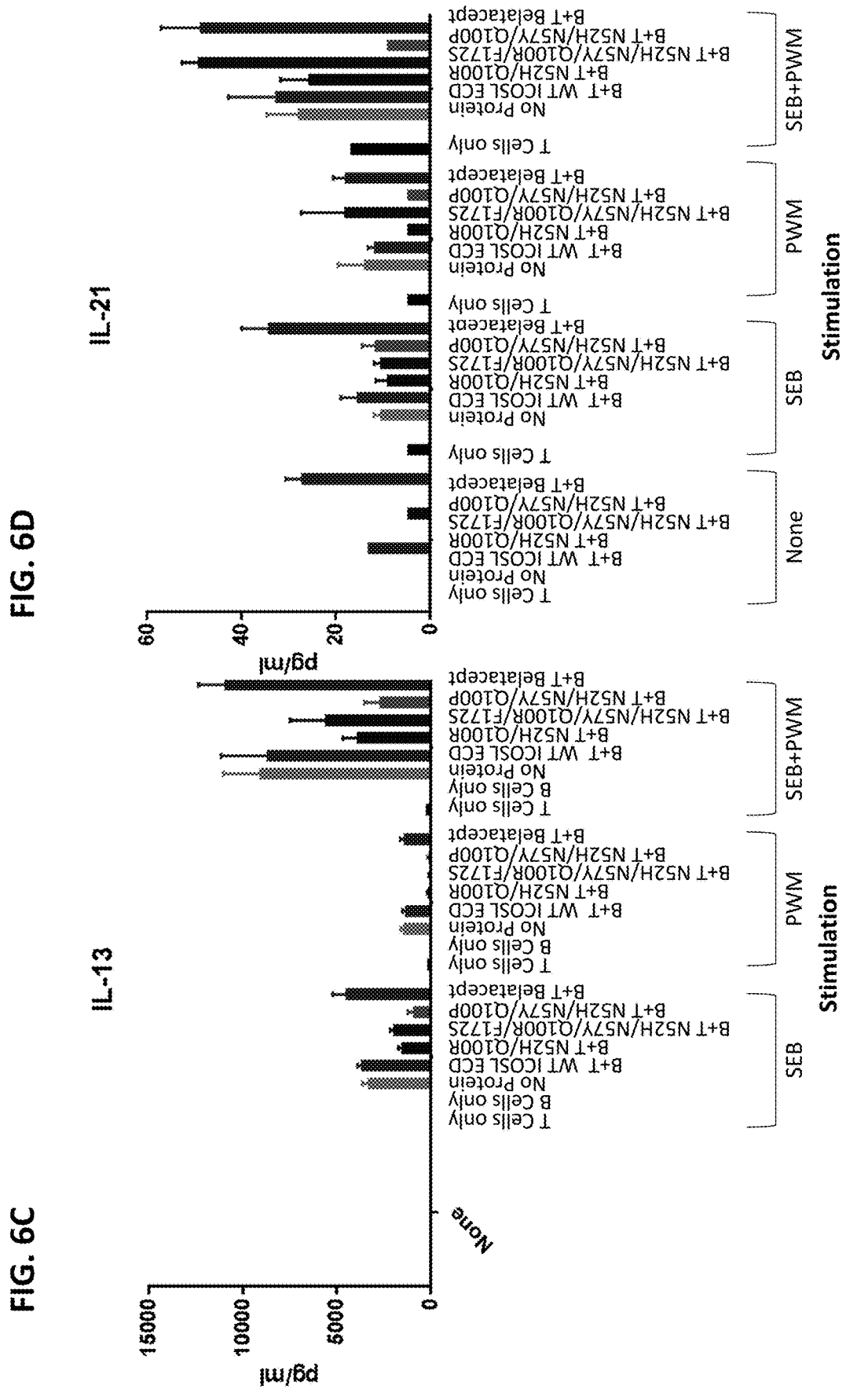

% Body Weight Loss

- ● Saline
- ■ WT-Fc
- ★ N52H/I143T
- ✕ N52H/N57Y/Q100P
- ◆ CTLA-4-Ig L104E/A29Y (Belatacept)

Mean % Body Weight Loss +/- SEM

Study Days

% Human T cells in Blood on Day 14

HuPBMC→NSG GVHD (Survival)
- Saline (0/9)
- WT ICOSL (0/9)
- N52H/N57Y/Q100R/C198R (7/9)
- N52H/N57Y/Q100R/F172S (9/9)
- N52H/Q100R (0/9)
- N52H/N57Y/Q100P (8/9)
- Belatacept (6/9)

Mean DAI Score

Day last dose (d. 37)

WT

ICOSL

Belatacept

N52H/N57Y/Q100R/C198R antibody and vIgD conjugate (V-Mab)

Tumor targeting vIgD

Stack Molecule

Soluble vIgD (e.g. vIgD-Fc)

ICOSL variant truncation #4 (SEQ ID NO: 602) with N52H/N57Y/Q100R/F172S

ICOSL variant truncation #5 (SEQ ID NO: 603) with N52H/N57Y/Q100R/F172S

ICOSL variant truncation #8 with mutations N207G/L208G (SEQ ID NO: 623) and with N52H/N57Y/Q100R/F172S ICOSL variant ECD with mutations N207G/L208G (SEQ ID NO: 628) with N52H/N57Y/Q100R/F172S ICOSL variant IgV (SEQ ID NO: 545) with N52H/N57Y/Q100R/F172S CIA Paw Scores Over Time % Change in Body Weight Over Time Fc Control Wildtype ICOSL-Fc CTLA-4 Fc ICOSL IgV -Fc (N52H/ N57Y/Q100R)

Total T Cells, Absolute Count

Ratio of Human T Cells to Mouse Cells

%CD28+ of huCD8+ T Cells

%CD28+ of huCD4+ T Cells

| Study | Dose (μg) | Cmax (μg/mL) | T1/2 (day) | AUC (day*μg/mL) |
|---|---|---|---|---|
| GVHD5 | 100 | 12.94 | 4.02 | 18.97 |
| Normal Mice | 100 | 12.30 | 0.84 | 30.04 |

SEQUENCE LISTING

```
Sequence total quantity: 933
SEQ ID NO: 1              moltype = AA  length = 288
FEATURE                  Location/Qualifiers
REGION                   1..288
                         note = MISC_FEATURE - CD80(B7-1)
source                   1..288
                         mol_type = protein
                         organism = Homo sapiens
SEQUENCE: 1
MGHTRRQGTS PSKCPYLNFF QLLVLAGLSH FCSGVIHVTK EVKEVATLSC GHNVSVEELA   60
QTRIYWQKEK KMVLTMMSGD MNIWPEYKNR TIFDITNNLS IVILALRPSD EGTYECVVLK  120
YEKDAFKREH LAEVTLSVKA DFPTPSISDF EIPTSNIRRI ICSTSGGFPE PHLSWLENGE  180
ELNAINTTVS QDPETELYAV SSKLDFNMTT NHSFMCLIKY GHLRVNQTFN WNTTKQEHFP  240
DNLLPSWAIT LISVNGIFVI CCLTYCFAPR CRERRRNERL RRESVRPV              288

SEQ ID NO: 2              moltype = AA  length = 329
FEATURE                  Location/Qualifiers
REGION                   1..329
                         note = MISC_FEATURE - CD86(B7-2)
source                   1..329
                         mol_type = protein
                         organism = Homo sapiens
SEQUENCE: 2
MDPQCTMGLS NILFVMAFLL SGAAPLKIQA YFNETADLPC QFANSQNQSL SELVVFWQDQ   60
ENLVLNEVYL GKEKFDSVHS KYMGRTSFDS DSWTLRLHNL QIKDKGLYQC IIHHKKPTGM  120
IRIHQMNSEL SVLANFSQPE IVPISNITEN VYINLTCSSI HGYPEPKKMS VLLRTKNSTI  180
EYDGVMQKSQ DNVTELYDVS ISLSVSFPDV TSNMTIFCIL ETDKTRLLSS PFSIELEDPQ  240
PPPDHIPWIT AVLPTVIICV MVFCLILWKW KKKKRPRNSY KCGTNTMERE ESEQTKKREK  300
IHIPERSDEA QRVFKSSKTS SCDKSDTCF                                   329

SEQ ID NO: 3              moltype = AA  length = 290
FEATURE                  Location/Qualifiers
REGION                   1..290
                         note = MISC_FEATURE - CD274 (PD-L1, B7-H1)
source                   1..290
```

```
                            mol_type = protein
                            organism = Homo sapiens
SEQUENCE: 3
MRIFAVFIFM  TYWHLLNAFT  VTVPKDLYVV  EYGSNMTIEC  KFPVEKQLDL  AALIVYWEME   60
DKNIIQFVHG  EEDLKVQHSS  YRQRARLLKD  QLSLGNAALQ  ITDVKLQDAG  VYRCMISYGG  120
ADYKRITVKV  NAPYNKINQR  ILVVDPVTSE  HELTCQAEGY  PKAEVIWTSS  DHQVLSGKTT  180
TTNSKREEKL  FNVTSTLRIN  TTTNEIFYCT  FRRLDPEENH  TAELVIPELP  LAHPPNERTH  240
LVILGAILLC  LGVALTFIFR  LRKGRMMDVK  KCGIQDTNSK  KQSDTHLEET             290

SEQ ID NO: 4                moltype = AA  length = 273
FEATURE                     Location/Qualifiers
REGION                      1..273
                            note = MISC_FEATURE - PDCD1LG2(PD-L2, CD273)
source                      1..273
                            mol_type = protein
                            organism = Homo sapiens
SEQUENCE: 4
MIFLLLMLSL  ELQLHQIAAL  FTVTVPKELY  IIEHGSNVTL  ECNFDTGSHV  NLGAITASLQ   60
KVENDTSPHR  ERATLLEEQL  PLGKASFHIP  QVQVRDEGQY  QCIIIYGVAW  DYKYLTLKVK  120
ASYRKINTHI  LKVPETDEVE  LTCQATGYPL  AEVSWPNVSV  PANTSHSRTP  EGLYQVTSVL  180
RLKPPPGRNF  SCVFWNTHVR  ELTLASIDLQ  SQMEPRTHPT  WLLHIFIPFC  IIAFIFIATV  240
IALRKQLCQK  LYSSKDTTKR  PVTTTKREVN  SAI                                 273

SEQ ID NO: 5                moltype = AA  length = 302
FEATURE                     Location/Qualifiers
REGION                      1..302
                            note = MISC_FEATURE - ICOSLG(B7RP1, CD275, ICOSL, B7-H2)
source                      1..302
                            mol_type = protein
                            organism = Homo sapiens
SEQUENCE: 5
MRLGSPGLLF  LLFSSLRADT  QEKEVRAMVG  SDVELSCACP  EGSRFDLNDV  YVYWQTSESK   60
TVVTYHIPQN  SSLENVDSRY  RNRALMSPAG  MLRGDFSLRL  FNVTPQDEQK  FHCLVLSQSL  120
GFQEVLSVEV  TLHVAANFSV  PVVSAPHSPS  QDELTFTCTS  INGYPRPNVY  WINKTDNSLL  180
DQALQNDTVF  LNMRGLYDVV  SVLRIARTPS  VNIGCCIENV  LLQQNLTVGS  QTGNDIGERD  240
KITENPVSTG  EKNAATWSIL  AVLCLLVVVA  VAIGWVCRDR  CLQHSYAGAW  AVSPETELTG  300
HV                                                                      302

SEQ ID NO: 6                moltype = AA  length = 534
FEATURE                     Location/Qualifiers
REGION                      1..534
                            note = MISC_FEATURE - CD276(B7-H3)
source                      1..534
                            mol_type = protein
                            organism = Homo sapiens
SEQUENCE: 6
MLRRRGSPGM  GVHVGAALGA  LWFCLTGALE  VQVPEDPVVA  LVGTDATLCC  SFSPEPGFSL   60
AQLNLIWQLT  DTKQLVHSFA  EGQDQGSAYA  NRTALFPDLL  AQGNASLRLQ  RVRVADEGSF  120
TCFVSIRDFG  SAAVSLQVAA  PYSKPSMTLE  PNKDLRPGDT  VTITCSSYQG  YPEAEVFWQD  180
GQGVPLTGNV  TTSQMANEQG  LFDVHSILRV  VLGANGTYSC  LVRNPVLQQD  AHSSVTITPQ  240
RSPTGAVEVQ  VPEDPVVALV  GTDATLRCSF  SPEPGFSLAQ  LNLIWQLTDT  KQLVHSFTEG  300
RDQGSAYANR  TALFPDLLAQ  GNASLRLQRV  RVADEGSFTC  FVSIRDFGSA  AVSLQVAAPY  360
SKPSMTLEPN  KDLRPGDTVT  ITCSSYRGYP  EAEVFWQDGQ  GVPLTGNVTT  SQMANEQGLF  420
DVHSVLRVVL  GANGTYSCLV  RNPVLQQDAH  GSVTITGQPM  TFPPEALWVT  VGLSVCLIAL  480
LVALAFVCWR  KIKQSCEEEN  AGAEDQDGEG  EGSKTALQPL  KHSDSKEDDG  QEIA        534

SEQ ID NO: 7                moltype = AA  length = 282
FEATURE                     Location/Qualifiers
REGION                      1..282
                            note = MISC_FEATURE - VTCN1(B7-H4)
source                      1..282
                            mol_type = protein
                            organism = Homo sapiens
SEQUENCE: 7
MASLGQILFW  SIISIIIILA  GAIALIIGFG  ISGRHSITVT  TVASAGNIGE  DGILSCTFEP   60
DIKLSDIVIQ  WLKEGVLGLV  HEFKEGKDEL  SEQDEMFRGR  TAVFADQVIV  GNASLRLKNV  120
QLTDAGTYKC  YIITSKGKGN  ANLEYKTGAF  SMPEVNVDYN  ASSETLRCEA  PRWFPQPTVV  180
WASQVDQGAN  FSEVSNTSFE  LNSENVTMKV  VSVLYNVTIN  NTYSCMIEND  IAKATGDIKV  240
TESEIKRRSH  LQLLNSKASL  CVSSFFAISW  ALLPLSPYLM  LK                      282

SEQ ID NO: 8                moltype = AA  length = 220
FEATURE                     Location/Qualifiers
REGION                      1..220
                            note = MISC_FEATURE - CD28
source                      1..220
                            mol_type = protein
                            organism = Homo sapiens
SEQUENCE: 8
MLRLLLALNL  FPSIQVTGNK  ILVKQSPMLV  AYDNAVNLSC  KYSYNLFSRE  FRASLHKGLD   60
```

-continued

```
SAVEVCVVYG NYSQQLQVYS KTGFNCDGKL GNESVTFYLQ NLYVNQTDIY FCKIEVMYPP   120
PYLDNEKSNG TIIHVKGKHL CPSPLFPGPS KPFWVLVVVG GVLACYSLLV TVAFIIFWVR   180
SKRSRLLHSD YMNMTPRRPG PTRKHYQPYA PPRDFAAYRS                        220

SEQ ID NO: 9              moltype = AA   length = 223
FEATURE                  Location/Qualifiers
REGION                   1..223
                         note = MISC_FEATURE - CTLA4
source                   1..223
                         mol_type = protein
                         organism = Homo sapiens
SEQUENCE: 9
MACLGFQRHK AQLNLATRTW PCTLLFFLLF IPVFCKAMHV AQPAVVLASS RGIASFVCEY   60
ASPGKATEVR VTVLRQADSQ VTEVCAATYM MGNELTFLDD SICTGTSSGN QVNLTIQGLR   120
AMDTGLYICK VELMYPPPYY LGIGNGTQIY VIDPEPCPDS DFLLWILAAV SSGLFFYSFL   180
LTAVSLSKML KKRSPLTTGV YVKMPPTEPE CEKQFQPYFI PIN                    223

SEQ ID NO: 10             moltype = AA   length = 288
FEATURE                  Location/Qualifiers
REGION                   1..288
                         note = MISC_FEATURE - PDCD1(PD-1)
source                   1..288
                         mol_type = protein
                         organism = Homo sapiens
SEQUENCE: 10
MQIPQAPWPV VWAVLQLGWR PGWFLDSPDR PWNPPTFSPA LLVVTEGDNA TFTCSFSNTS   60
ESFVLNWYRM SPSNQTDKLA AFPEDRSQPG QDCRFRVTQL PNGRDFHMSV VRARRNDSGT   120
YLCGAISLAP KAQIKESLRA ELRVTERRAE VPTAHPSPSP RPAGQFQTLV VGVVGGLLGS   180
LVLLVWVLAV ICSRAARGTI GARRTGQPLK EDPSAVPVFS VDYGELDFQW REKTPEPPVP   240
CVPEQTEYAT IVFPSGMGTS SPARRGSADG PRSAQPLRPE DGHCSWPL               288

SEQ ID NO: 11             moltype = AA   length = 199
FEATURE                  Location/Qualifiers
REGION                   1..199
                         note = MISC_FEATURE - ICOS
source                   1..199
                         mol_type = protein
                         organism = Homo sapiens
SEQUENCE: 11
MKSGLWYFFL FCLRIKVLTG EINGSANYEM FIFHNGGVQI LCKYPDIVQQ FKMQLLKGGQ   60
ILCDLTKTKG SGNTVSIKSL KFCHSQLSNN SVSFFLYNLD HSHANYYFCN LSIFDPPPFK   120
VTLTGGYLHI YESQLCCQLK FWLPIGCAAF VVVCILGCIL ICWLTKKKYS SSVHDPNGEY   180
MFMRAVNTAK KSRLTDVTL                                              199

SEQ ID NO: 12             moltype = AA   length = 289
FEATURE                  Location/Qualifiers
REGION                   1..289
                         note = MISC_FEATURE - BTLA(CD272)
source                   1..289
                         mol_type = protein
                         organism = Homo sapiens
SEQUENCE: 12
MKTLPAMLGT GKLFWVFFLI PYLDIWNIHG KESCDVQLYI KRQSEHSILA GDPFELECPV   60
KYCANRPHVT WCKLNGTTCV KLEDRQTSWK EEKNISFFIL HFEPVLPNDN GSYRCSANFQ   120
SNLIESHSTT LYVTDVKSAS ERPSKDEMAS RPWLLYRLLP LGGLPLLITT CFCLFCCLRR   180
HQGKQNELSD TAGREINLVD AHLKSEQTEA STRQNSQVLL SETGIYDNDP DLCFRMQEGS   240
EVYSNPCLEE NKPGIVYASL NHSVIGPNSR LARNVKEAPT EYASICVRS             289

SEQ ID NO: 13             moltype = AA   length = 458
FEATURE                  Location/Qualifiers
REGION                   1..458
                         note = MISC_FEATURE - CD4
source                   1..458
                         mol_type = protein
                         organism = Homo sapiens
SEQUENCE: 13
MNRGVPFRHL LLVLQLALLP AATQGKKVVL GKKGDTVELT CTASQKKSIQ FHWKNSNQIK   60
ILGNQGSFLT KGPSKLNDRA DSRRSLWDQG NFPLIIKNLK IEDSDTYICE VEDQKEEVQL   120
LVFGLTANSD THLLQGQSLT LTLESPPGSS PSVQCRSPRG KNIQGGKTLS VSQLELQDSG   180
TWTCTVLQNQ KKVEFKIDIV VLAFQKASSI VYKKEGEQVE FSFPLAFTVE KLTGSGELWW   240
QAERASSSKS WITFDLKNKE VSVKRVTQDP KLQMGKKLPL HLTLPQALPQ YAGSGNLTLA   300
LEAKTGKLHQ EVNLVVMRAT QLQKNLTCEV WGPTSPKLML SLKLENKEAK VSKREKAVWV   360
LNPEAGMWQC LLSDSGQVLL ESNIKVLPTW STPVQPMALI VLGGVAGLLL FIGLGIFFCV   420
RCRHRRRQAE RMSQIKRLLS EKKTCQCPHR FQKTCSPI                         458

SEQ ID NO: 14             moltype = AA   length = 235
FEATURE                  Location/Qualifiers
REGION                   1..235
                         note = MISC_FEATURE - CD8A(CD8-alpha)
```

```
source                          1..235
                                mol_type = protein
                                organism = Homo sapiens
SEQUENCE: 14
MALPVTALLL PLALLLHAAR PSQFRVSPLD RTWNLGETVE LKCQVLLSNP TSGCSWLFQP    60
RGAAASPTFL LYLSQNKPKA AEGLDTQRFS GKRLGDTFVL TLSDFRRENE GYYFCSALSN   120
SIMYFSHFVP VFLPAKPTTT PAPRPPTPAP TIASQPLSLR PEACRPAAGG AVHTRGLDFA   180
CDIYIWAPLA GTCGVLLLSL VITLYCNHRN RRRVCKCPRP VVKSGDKPSL SARYV        235

SEQ ID NO: 15                   moltype = AA   length = 210
FEATURE                         Location/Qualifiers
REGION                          1..210
                                note = MISC_FEATURE - CD8B(CD8-beta)
source                          1..210
                                mol_type = protein
                                organism = Homo sapiens
SEQUENCE: 15
MRPRLWLLLA AQLTVLHGNS VLQQTPAYIK VQTNKMVMLS CEAKISLSNM RIYWLRQRQA    60
PSSDSHHEFL ALWDSAKGTI HGEEVEQEKI AVFRDASRFI LNLTSVKPED SGIYFCMIVG   120
SPELTFGKGT QLSVVDFLPT TAQPTKKSTL KKRVCRLPRP ETQKGPLCSP ITLGLLVAGV   180
LVLLVSLGVA IHLCCRRRRA RLRFMKQFYK                                    210

SEQ ID NO: 16                   moltype = AA   length = 525
FEATURE                         Location/Qualifiers
REGION                          1..525
                                note = MISC_FEATURE - LAG3
source                          1..525
                                mol_type = protein
                                organism = Homo sapiens
SEQUENCE: 16
MWEAQFLGLL FLQPLWVAPV KPLQPGAEVP VVWAQEGAPA QLPCSPTIPL QDLSLLRRAG    60
VTWQHQPDSG PPAAAPGHPL APGPHPAAPS SWGPRPRRYT VLSVGPGGLR SGRLPLQPRV   120
QLDERGRQRG DFSLWLRPAR RADAGEYRAA VHLRDRALSC RLRLRLGQAS MTASPPGSLR   180
ASDWVILNCS FSRPDRPASV HWFRNRGQGR VPVRESPHHH LAESFLFLPQ VSPMDSGPWG   240
CILTYRDGFN VSIMYNLTVL GLEPPTPLTV YAGAGSRVGL PCRLPAGVGT RSFLTAKWTP   300
PGGGPDLLVT GDNGDFTLRL EDVSQAQAGT YTCHIHLQEQ QLNATVTLAI ITVTPKSFGS   360
PGSLGKLLCE VTPVSGQERF VWSSLDTPSQ RSFSGPWLEA QEAQLLSQPW QCQLYQGERL   420
LGAAVYFTEL SSPGAQRSGR APGALPAGHL LLFLILGVLS LLLLLVTGAFG FHLWRRQWRP   480
RRFSALEQGI HPPQAQSKIE ELEQEPEPEP EPEPEPEPEP EPEQL                   525

SEQ ID NO: 17                   moltype = AA   length = 301
FEATURE                         Location/Qualifiers
REGION                          1..301
                                note = MISC_FEATURE - HAVCR2(TIM-3)
source                          1..301
                                mol_type = protein
                                organism = Homo sapiens
SEQUENCE: 17
MFSHLPFDCV LLLLLLLLTR SSEVEYRAEV GQNAYLPCFY TPAAPGNLVP VCWGKGACPV    60
FECGNVVLRT DERDVNYWTS RYWLNGDFRK GDVSLTIENV TLADSGIYCC RIQIPGIMND   120
EKFNLKLVIK PAKVTPAPTR QRDFTAAFPR MLTTRGHGPA ETQTLGSLPD INLTQISTLA   180
NELRDSRLAN DLRDSGATIR IGIYIGAGIC AGLALALIFG ALIFKWYSHS KEKIQNLSLI   240
SLANLPPSGL ANAVAEGIRS EENIYTIEEN VYEVEEPNEY YCYVSSRQQP SQPLGCRFAM   300
P                                                                   301

SEQ ID NO: 18                   moltype = AA   length = 526
FEATURE                         Location/Qualifiers
REGION                          1..526
                                note = MISC_FEATURE - CEACAM1
source                          1..526
                                mol_type = protein
                                organism = Homo sapiens
SEQUENCE: 18
MGHLSAPLHR VRVPWQGLLL TASLLTFWNP PTTAQLTTES MPFNVAEGKE VLLLVHNLPQ    60
QLFGYSWYKG ERVDGNRQIV GYAIGTQQAT PGPANSGRET IYPNASLLIQ NVTQNDTGFY   120
TLQVIKSDLV NEEATGQFHV YPELPKPSIS SNNSNPVEDK DAVAFTCEPE TQDTTYLWWI   180
NNQSLPVSPR LQLSNGNRTL TLLSVTRNDT GPYECEIQNP VSANRSDPVT LNVTYGPDTP   240
TISPSDTYYR PGANLSLSCY AASNPPAQYS WLINGTFQQS TQELFIPNIT VNNSGSYTCH   300
ANNSVTGCNR TTVKTIIVTE LSPVVAKPQI KASKTTVTGD KDSVNLTCST NDTGISIRWF   360
FKNQSLPSSE RMKLSQGNTT LSINPVKRED AGTYWCEVFN PISKNQSDPI MLNVNYNALP   420
QENGLSPGAI AGIVIGVVAL VALIAVALAC FLHFGKTGRA SDQRDLTEHK PSVSNHTQDH   480
SNDPPNKMNE VTYSTLNFEA QQPTQPTSAS PSLTATEIIY SEVKKQ                  526

SEQ ID NO: 19                   moltype = AA   length = 244
FEATURE                         Location/Qualifiers
REGION                          1..244
                                note = MISC_FEATURE - TIGIT
source                          1..244
                                mol_type = protein
```

```
                         organism = Homo sapiens
SEQUENCE: 19
MRWCLLLIWA QGLRQAPLAS GMMTGTIETT GNISAEKGGS IILQCHLSST TAQVTQVNWE   60
QQDQLLAICN ADLGWHISPS FKDRVAPGPG LGLTLQSLTV NDTGEYFCIY HTYPDGTYTG  120
RIFLEVLESS VAEHGARFQI PLLGAMAATL VVICTAVIVV VALTRKKKAL RIHSVEGDLR  180
RKSAGQEEWS PSAPSPPGSC VQAEAAPAGL CGEQRGEDCA ELHDYFNVLS YRSLGNCSFF  240
TETG                                                              244

SEQ ID NO: 20              moltype = AA  length = 417
FEATURE                    Location/Qualifiers
REGION                     1..417
                           note = MISC_FEATURE - PVR(CD155)
source                     1..417
                           mol_type = protein
                           organism = Homo sapiens SEQUENCE: 20
MARAMAAAWP LLLVALLVLS WPPPGTGDVV VQAPTQVPGF LGDSVTLPCY LQVPNMEVTH   60
VSQLTWARHG ESGSMAVFHQ TQGPSYSESK RLEFVAARLG AELRNASLRM FGLRVEDEGN  120
YTCLFVTFPQ GSRSVDIWLR VLAKPQNTAE VQKVQLTGEP VPMARCVSTG GRPPAQITWH  180
SDLGGMPNTS QVPGFLSGTV TVTSLWILVP SSQVDGKNVT CKVEHESFEK PQLLTVNLTV  240
YYPPEVSISG YDNNWYLGQN EATLTCDARS NPEPTGYNWS TTMGPLPPFA VAQGAQLLIR  300
PVDKPINTTL ICNVTNALGA RQAELTVQVK EGPPSEHSGI SRNAIIFLVL GILVFLILLG  360
IGIYFYWSKC SREVLWHCHL CPSSTEHASA SANGHVSYSA VSRENSSSQD PQTEGTR     417

SEQ ID NO: 21              moltype = AA  length = 538
FEATURE                    Location/Qualifiers
REGION                     1..538
                           note = MISC_FEATURE - PVRL2(CD112)
source                     1..538
                           mol_type = protein
                           organism = Homo sapiens SEQUENCE: 21
MARAAALLPS RSPPTPLLWP LLLLLLLETG AQDVRVQVLP EVRGQLGGTV ELPCHLLPPV   60
PGLYISLVTW QRPDAPANHQ NVAAFHPKMG PSFPSPKPGS ERLSFVSAKQ STGQDTEAEL  120
QDATLALHGL TVEDEGNYTC EFATFPKGSV RGMTWLRVIA KPKNQAEAQK VTFSQDPTTV  180
ALCISKEGRP PARISWLSSL DWEAKETQVS GTLAGTVTVT SRFTLVPSGR ADGVTVTCKV  240
EHESFEEPAL IPVTLSVRYP PEVSISGYDD NWYLGRTDAT LSCDVRSNPE PTGYDWSTTS  300
GTFPTSAVAQ GSQLVIHAVD SLFNTTFVCT VTNAVGMGRA EQVIFVRETP NTAGAGATGG  360
IIGGIIAAII ATAVAATGIL ICRQQRKEQT LQGAEEDEDL EGPPSYKPPT PKAKLEAQEM  420
PSQLFTLGAS EHSPLKTPYF DAGASCTEQE MPRYHELPTL EERSGPLHPG ATSLGSPIPV  480
PPGPPAVEDV SLDLEDEEGE EEEEYLDKIN PIYDALSYSS PSDSYQGKGF VMSRAMYV    538

SEQ ID NO: 22              moltype = AA  length = 336
FEATURE                    Location/Qualifiers
REGION                     1..336
                           note = MISC_FEATURE - CD226
source                     1..336
                           mol_type = protein
                           organism = Homo sapiens SEQUENCE: 22
MDYPTLLLAL LHVYRALCEE VLWHTSVPFA ENMSLECVYP SMGILTQVEW FKIGTQQDSI   60
AIFSPTHGMV IRKPYAERVY FLNSTMASNN MTLFFRNASE DDVGYYSCSL YTYPQGTWQK  120
VIQVVQSDSF EAAVPSNSHI VSEPGKNVTL TCQPQMTWPV QAVRWEKIQP RQIDLLTYCN  180
LVHGRNFTSK FPRQIVSNCS HGRWSVIVIP DVTVSDSGLY RCYLQASAGE NETFVMRLTV  240
AEGKTDNQYT LFVAGGTVLL LLFVISITTI IVIFLNRRRR RERRDLFTES WDTQKAPNNY  300
RSPISTSQPT NQSMDDTRED IYVNYPTFSR RPKTRV                            336

SEQ ID NO: 23              moltype = AA  length = 351
FEATURE                    Location/Qualifiers
REGION                     1..351
                           note = MISC_FEATURE - CD2
source                     1..351
                           mol_type = protein
                           organism = Homo sapiens SEQUENCE: 23
MSFPCKFVAS FLLIFNVSSK GAVSKEITNA LETWGALGQD INLDIPSFQM SDDIDDIKWE   60
KTSDKKKIAQ FRKEKETFKE KDTYKLFKNG TLKIKHLKTD DQDIYKVSIY DTKGKNVLEK  120
IFDLKIQERV SKPKISWTCI NTTLTCEVMN GTDPELNLYQ DGKHLKLSQR VITHKWTTSL  180
SAKFKCTAGN KVSKESSVEP VSCPEKGLDI YLIIGICGGG SLLMVFVALL VFYITKRKKQ  240
RSRRNDEELE TRAHRVATEE RGRKPHQIPA STPQNPATSQ HPPPPPGHRS QAPSHRPPPP  300
GHRVQHQPQK RPPAPSGTQV HQQKGPPLPR PRVQPKPPHG AAENSLSPSS N           351

SEQ ID NO: 24              moltype = AA  length = 180
FEATURE                    Location/Qualifiers
REGION                     1..180
                           note = MISC_FEATURE - CD160
source                     1..180
                           mol_type = protein
                           organism = Homo sapiens
```

-continued

```
SEQUENCE: 24
MLLEPGRGCC ALAILLAIVD IQSGGCINIT SSASQEGTRL NLICTVWHKK EEAEGFVVFL  60
CKDRSGDCSP ETSLKQLRLK RDPGIDGVGE ISSQLMFTIS QVTPLHSGTY QCCARSQKSG  120
IRLQGHFFSI LFTETGNYTV TGLKQRQHLE FSHNEGTLSS GFLQEKVWVM LVTSLVALQA  180

SEQ ID NO: 25          moltype = AA  length = 278
FEATURE                Location/Qualifiers
REGION                 1..278
                       note = MISC_FEATURE - CD200
source                 1..278
                       mol_type = protein
                       organism = Homo sapiens
SEQUENCE: 25
MERLVIRMPF SHLSTYSLVW VMAAVVLCTA QVQVVTQDER EQLYTPASLK CSLQNAQEAL  60
IVTWQKKKAV SPENMVTFSE NHGVVIQPAY KDKINITQLG LQNSTITFWN ITLEDEGCYM  120
CLFNTFGFGK ISGTACLTVY VQPIVSLHYK FSEDHLNITC SATARPAPMV FWKVPRSGIE  180
NSTVTLSHPN GTTSVTSILH IKDPKNQVGK EVICQVLHLG TVTDFKQTVN KGYWFSVPLL  240
LSIVSLVILL VLISILLYWK RHRNQDRGEL SQGVQKMT                          278

SEQ ID NO: 26          moltype = AA  length = 325
FEATURE                Location/Qualifiers
REGION                 1..325
                       note = MISC_FEATURE - CD200R1(CD200R)
source                 1..325
                       mol_type = protein
                       organism = Homo sapiens
SEQUENCE: 26
MLCPWRTANL GLLLILTIFL VAASSSLCMD EKQITQNYSK VLAEVNTSWP VKMATNAVLC  60
CPPIALRNLI IITWEIILRG QPSCTKAYRK ETNETKETNC TDERITWVSR PDQNSDLQIR  120
PVAITHDGYY RCIMVTPDGN FHRGYHLQVL VTPEVTLFQN RNRTAVCKAV AGKPAAQISW  180
IPEGDCATKQ EYWSNGTVTV KSTCHWEVHN VSTVTCHVSH LTGNKSLYIE LLPVPGAKKS  240
AKLYIPYIIL TIIILTIVGF IWLLKVNGCR KYKLNKTEST PVVEEDEMQP YASYTEKNNP  300
LYDTTNKVKA SEALQSEVDT DLHTL                                        325

SEQ ID NO: 27          moltype = AA  length = 201
FEATURE                Location/Qualifiers
REGION                 1..201
                       note = MISC_FEATURE - NC R3 (NKp30)
source                 1..201
                       mol_type = protein
                       organism = Homo sapiens
SEQUENCE: 27
MAWMLLLILI MVHPGSCALW VSQPPEIRTL EGSSAFLPCS FNASQGRLAI GSVTWFRDEV  60
VPGKEVRNGT PEFRGRLAPL ASSRFLHDHQ AELHIRDVRG HDASIYVCRV EVLGLGVGTG  120
NGTRLVVEKE HPQLGAGTVL LLRAGFYAVS FLSVAVGSTV YYQGKCLTWK GPRRQLPAVV  180
PAPLPPPCGS SAHLLPPVPG G                                            201

SEQ ID NO: 28          moltype = AA  length = 208
FEATURE                Location/Qualifiers
REGION                 1..208
                       note = MISC_FEATURE - CD80(B7-1) ECD
source                 1..208
                       mol_type = protein
                       organism = Homo sapiens
SEQUENCE: 28
VIHVTKEVKE VATLSCGHNV SVEELAQTRI YWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 29          moltype = AA  length = 224
FEATURE                Location/Qualifiers
REGION                 1..224
                       note = MISC_FEATURE - CD86(B7-2) ECD
source                 1..224
                       mol_type = protein
                       organism = Homo sapiens
SEQUENCE: 29
APLKIQAYFN ETADLPCQFA NSQNQSLSEL VVFWQDQENL VLNEVYLGKE KFDSVHSKYM  60
GRTSFDSDSW TLRLHNLQIK DKGLYQCIIH HKKPTGMIRI HQMNSELSVL ANFSQPEIVP  120
ISNITENVYI NLTCSSIHGY PEPKKMSVLL RTKNSTIEYD GVMQKSQDNV TELYDVSISL  180
SVSFPDVTSN MTIFCILETD KTRLLSSPFS IELEDPQPPP DHIP                   224

SEQ ID NO: 30          moltype = AA  length = 220
FEATURE                Location/Qualifiers
REGION                 1..220
                       note = MISC_FEATURE - CD274 (PD-L1, B7-H1) ECD
source                 1..220
                       mol_type = protein
```

-continued

```
                      organism = Homo sapiens
SEQUENCE: 30
FTVTVPKDLY VVEYGSNMTI ECKFPVEKQL DLAALIVYWE MEDKNIIQFV HGEEDLKVQH   60
SSYRQRARLL KDQLSLGNAA LQITDVKLQD AGVYRCMISY GGADYKRITV KVNAPYNKIN  120
QRILVVDPVT SEHELTCQAE GYPKAEVIWT SSDHQVLSGK TTTTNSKREE KLFNVTSTLR  180
INTTTNEIFY CTFRRLDPEE NHTAELVIPE LPLAHPPNER                       220

SEQ ID NO: 31              moltype = AA  length = 201
FEATURE                    Location/Qualifiers
REGION                     1..201
                           note = MISC_FEATURE - PDCD1LG2(PD-L2, CD273) ECD
source                     1..201
                           mol_type = protein
                           organism = Homo sapiens
SEQUENCE: 31
LFTVTVPKEL YIIEHGSNVT LECNFDTGSH VNLGAITASL QKVENDTSPH RERATLLEEQ   60
LPLGKASFHI PQVQVRDEGQ YQCIIIYGVA WDYKYLTLKV KASYRKINTH ILKVPETDEV  120
ELTCQATGYP LAEVSWPNVS VPANTSHSRT PEGLYQVTSV LRLKPPPGRN FSCVFWNTHV  180
RELTLASIDL QSQMEPRTHP T                                           201

SEQ ID NO: 32              moltype = AA  length = 238
FEATURE                    Location/Qualifiers
REGION                     1..238
                           note = MISC_FEATURE - ICOSLG(B7RP1, CD275, ICOSL, B7-H2) ECD
source                     1..238
                           mol_type = protein
                           organism = Homo sapiens
SEQUENCE: 32
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 33              moltype = AA  length = 438
FEATURE                    Location/Qualifiers
REGION                     1..438
                           note = MISC_FEATURE - CD276(B7-H3) ECD
source                     1..438
                           mol_type = protein
                           organism = Homo sapiens
SEQUENCE: 33
LEVQVPEDPV VALVGTDATL CCSFSPEPGF SLAQLNLIWQ LTDTKQLVHS FAEGQDQGSA   60
YANRTALFPD LLAQGNASLR LQRVRVADEG SFTCFVSIRD FGSAAVSLQV AAPYSKPSMT  120
LEPNKDLRPG DTVTITCSSY QGYPEAEVFW QDGQGVPLTG NVTTSQMANE QGLFDVHSIL  180
RVVLGANGTY SCLVRNPVLQ QDAHSSVTIT PQRSPTGAVE VQVPEDPVVA LVGTDATLRC  240
SFSPEPGFSL AQLNLIWQLT DTKQLVHSFT EGRDQGSAYA NRTALFPDLL AQGNASLRLQ  300
RVRVADEGSF TCFVSIRDFG SAAVSLQVAA PYSKPSMTLE PNKDLRPGDT VTITCSSYRG  360
YPEAEVFWQD GQGVPLTGNV TTSQMANEQG LFDVHSVLRV VLGANGTYSC LVRNPVLQQD  420
AHGSVTITGQ PMTFPPEA                                               438

SEQ ID NO: 34              moltype = AA  length = 235
FEATURE                    Location/Qualifiers
REGION                     1..235
                           note = MISC_FEATURE - VTCN1(B7-H4) ECD
source                     1..235
                           mol_type = protein
                           organism = Homo sapiens
SEQUENCE: 34
LIIGFGISGR HSITVTTVAS AGNIGEDGIL SCTFEPDIKL SDIVIQWLKE GVLGLVHEFK   60
EGKDELSEQD EMFRGRTAVF ADQVIVGNAS LRLKNVQLTD AGTYKCYIIT SKGKGNANLE  120
YKTGAFSMPE VNVDYNASSE TLRCEAPRWF PQPTVWASQ VDQGANFSEV SNTSFELNSE  180
NVTMKVVSVL YNVTINNTYS CMIENDIAKA TGDIKVTESE IKRRSHLQLL NSKAS       235

SEQ ID NO: 35              moltype = AA  length = 134
FEATURE                    Location/Qualifiers
REGION                     1..134
                           note = MISC_FEATURE - CD28 ECD
source                     1..134
                           mol_type = protein
                           organism = Homo sapiens
SEQUENCE: 35
NKILVKQSPM LVAYDNAVNL SCKYSYNLFS REFRASLHKG LDSAVEVCVV YGNYSQQLQV   60
YSKTGFNCDG KLGNESVTFY LQNLYVNQTD IYFCKIEVMY PPPYLDNEKS NGTIIHVKGK  120
HLCPSPLFPG PSKP                                                   134

SEQ ID NO: 36              moltype = AA  length = 126
FEATURE                    Location/Qualifiers
REGION                     1..126
                           note = MISC_FEATURE - CTLA4 ECD
```

-continued

```
source                   1..126
                         mol_type = protein
                         organism = Homo sapiens
SEQUENCE: 36
KAMHVAQPAV VLASSRGIAS FVCEYASPGK ATEVRVTVLR QADSQVTEVC AATYMMGNEL  60
TFLDDSICTG TSSGNQVNLT IQGLRAMDTG LYICKVELMY PPPYYLGIGN GTQIYVIDPE  120
PCPDSD                                                             126

SEQ ID NO: 37           moltype = AA  length = 150
FEATURE                 Location/Qualifiers
REGION                  1..150
                        note = MISC_FEATURE - PDCD1(PD-1) ECD
source                  1..150
                        mol_type = protein
                        organism = Homo sapiens
SEQUENCE: 37
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV                                   150

SEQ ID NO: 38           moltype = AA  length = 120
FEATURE                 Location/Qualifiers
REGION                  1..120
                        note = MISC_FEATURE - ICOS ECD
source                  1..120
                        mol_type = protein
                        organism = Homo sapiens
SEQUENCE: 38
EINGSANYEM FIFHNGGVQI LCKYPDIVQQ FKMQLLKGGQ ILCDLTKTKG SGNTVSIKSL  60
KFCHSQLSNN SVSFFLYNLD HSHANYYFCN LSIFDPPPFK VTLTGGYLHI YESQLCCQLK  120

SEQ ID NO: 39           moltype = AA  length = 127
FEATURE                 Location/Qualifiers
REGION                  1..127
                        note = MISC_FEATURE - BTLA(CD272) ECD
source                  1..127
                        mol_type = protein
                        organism = Homo sapiens
SEQUENCE: 39
KESCDVQLYI KRQSEHSILA GDPFELECPV KYCANRPHVT WCKLNGTTCV KLEDRQTSWK  60
EEKNISFFIL HFEPVLPNDN GSYRCSANFQ SNLIESHSTT LYVTDVKSAS ERPSKDEMAS  120
RPWLLYR                                                            127

SEQ ID NO: 40           moltype = AA  length = 371
FEATURE                 Location/Qualifiers
REGION                  1..371
                        note = MISC_FEATURE - CD4 ECD
source                  1..371
                        mol_type = protein
                        organism = Homo sapiens
SEQUENCE: 40
KKVVLGKKGD TVELTCTASQ KKSIQFHWKN SNQIKILGNQ GSFLTKGPSK LNDRADSRRS  60
LWDQGNFPLI IKNLKIEDSD TYICEVEDQK EEVQLLVFGL TANSDTHLLQ GQSLTLTLES  120
PPGSSPSVQC RSPRGKNIQG GKTLSVSQLE LQDSGTWTCT VLQNQKKVEF KIDIVVLAFQ  180
KASSIVYKKE GEQVEFSFPL AFTVEKLTGS GELWWQAERA SSSKSWITFD LKNKEVSVKR  240
VTQDPKLQMG KKLPLHLTLP QALPQYAGSG NLTLALEAKT GKLHQEVNLV VMRATQLQKN  300
LTCEVWGPTS PKLMLSLKLE NKEAKVSKRE KAVWVLNPEA GMWQCLLSDS GQVLLESNIK  360
VLPTWSTPVQ P                                                       371

SEQ ID NO: 41           moltype = AA  length = 161
FEATURE                 Location/Qualifiers
REGION                  1..161
                        note = MISC_FEATURE - CD8A(CD8-alpha) ECD
source                  1..161
                        mol_type = protein
                        organism = Homo sapiens
SEQUENCE: 41
SQFRVSPLDR TWNLGETVEL KCQVLLSNPT SGCSWLFQPR GAAASPTFLL YLSQNKPKAA  60
EGLDTQRFSG KRLGDTFVLT LSDFRRENEG YYFCSALSNS IMYFSHFVPV FLPAKPTTTP  120
APRPPTPAPT IASQPLSLRP EACRPAAGGA VHTRGLDFAC D                      161

SEQ ID NO: 42           moltype = AA  length = 149
FEATURE                 Location/Qualifiers
REGION                  1..149
                        note = MISC_FEATURE - CD8B(CD8-beta) ECD
source                  1..149
                        mol_type = protein
                        organism = Homo sapiens
SEQUENCE: 42
```

-continued

```
LQQTPAYIKV QTNKMVMLSC EAKISLSNMR IYWLRQRQAP SSDSHHEFLA LWDSAKGTIH     60
GEEVEQEKIA VFRDASRFIL NLTSVKPEDS GIYFCMIVGS PELTFGKGTQ LSVVDFLPTT    120
AQPTKKSTLK KRVCRLPRPE TQKGPLCSP                                      149

SEQ ID NO: 43            moltype = AA  length = 422
FEATURE                  Location/Qualifiers
REGION                   1..422
                         note = MISC_FEATURE - LAG3 ECD
source                   1..422
                         mol_type = protein
                         organism = Homo sapiens
SEQUENCE: 43
VPVVWAQEGA PAQLPCSPTI PLQDLSLLRR AGVTWQHQPD SGPPAAAPGH PLAPGPHPAA     60
PSSWGPRPRR YTVLSVGPGG LRSGRLPLQP RVQLDERGRQ RGDFSLWLRP ARRADAGEYR    120
AAVHLRDRAL SCRLRLRLGQ ASMTASPPGS LRASDWVILN CSFSRPDRPA SVHWFRNRGQ    180
GRVPVRESPH HHLAESFLFL PQVSPMDSGP WGCILTYRDG FNVSIMYNLT VLGLEPPTPL    240
TVYAGAGSRV GLPCRLPAGV GTRSFLTAKW TPPGGGPDLL VTGDNGDFTL RLEDVSQAQA    300
GTYTCHIHLQ EQQLNATVTL AIITVTPKSF GSPGSLGKLL CEVTPVSGQE RFVWSSLDTP    360
SQRSFSGPWL EAQEAQLLSQ PWQCQLYQGE RLLGAAVYFT ELSSSPGAQRS GRAPGALPAG    420
HL                                                                  422

SEQ ID NO: 44            moltype = AA  length = 181
FEATURE                  Location/Qualifiers
REGION                   1..181
                         note = MISC_FEATURE - HAVCR2(TIM-3) ECD
source                   1..181
                         mol_type = protein
                         organism = Homo sapiens
SEQUENCE: 44
SEVEYRAEVG QNAYLPCFYT PAAPGNLVPV CWGKGACPVF ECGNVVLRTD ERDVNYWTSR     60
YWLNGDFRKG DVSLTIENVT LADSGIYCCR IQIPGIMNDE KFNLKLVIKP AKVTPAPTRQ    120
RDFTAAFPRM LTTRGHGPAE TQTLGSLPDI NLTQISTLAN ELRDSRLAND LRDSGATIRI    180
G                                                                   181

SEQ ID NO: 45            moltype = AA  length = 394
FEATURE                  Location/Qualifiers
REGION                   1..394
                         note = MISC_FEATURE - CEACAM1 ECD
source                   1..394
                         mol_type = protein
                         organism = Homo sapiens
SEQUENCE: 45
QLTTESMPFN VAEGKEVLLL VHNLPQQLFG YSWYKGERVD GNRQIVGYAI GTQQATPGPA     60
NSGRETIYPN ASLLIQNVTQ NDTGFYTLQV IKSDLVNEEA TGQFHVYPEL PKPSISSNNS    120
NPVEDKDAVA FTCEPETQDT TYLWWINNQS LPVSPRLQLS NGNRTLTLLS VTRNDTGPYE    180
CEIQNPVSAN RSDPVTLNVT YGPDTPTISP SDTYYRPGAN LSLSCYAASN PPAQYSWLIN    240
GTFQQSTQEL FIPNITVNNS GSYTCHANNS VTGCNRTTVK TIIVTELSPV VAKPQIKASK    300
TTVTGDKDSV NLTCSTNDTG ISIRWFFKNQ SLPSSERMKL SQGNTTLSIN PVKREDAGTY    360
WCEVFNPISK NQSDPIMLNV NYNALPQENG LSPG                                394

SEQ ID NO: 46            moltype = AA  length = 120
FEATURE                  Location/Qualifiers
REGION                   1..120
                         note = MISC_FEATURE - TIGIT ECD
source                   1..120
                         mol_type = protein
                         organism = Homo sapiens
SEQUENCE: 46
MMTGTIETTG NISAEKGGSI ILQCHLSSTT AQVTQVNWEQ QDQLLAICNA DLGWHISPSF     60
KDRVAPGPGL GLTLQSLTVN DTGEYFCIYH TYPDGTYTGR IFLEVLESSV AEHGARFQIP    120

SEQ ID NO: 47            moltype = AA  length = 323
FEATURE                  Location/Qualifiers
REGION                   1..323
                         note = MISC_FEATURE - PVR(CD155) ECD
source                   1..323
                         mol_type = protein
                         organism = Homo sapiens
SEQUENCE: 47
WPPPGTGDVV VQAPTQVPGF LGDSVTLPCY LQVPNMEVTH VSQLTWARHG ESGSMAVFHQ     60
TQGPSYSESK RLEFVAARLG AELRNASLRM FGLRVEDEGN YTCLFVTFPQ GSRSVDIWLR    120
VLAKPQNTAE VQKVQLTGEP VPMARCVSTG RPPAQITWH SDLGGMPNTS QVPGFLSGTV    180
TVTSLWILVP SSQVDGKNVT CKVEHESFEK PQLLTVNLTV YPPPEVSISG YDNNWYLGQN    240
EATLTCDARS NPEPTGYNWS TTMGPLPPFA VAQGAQLLIR PVDKPINTTL ICNVTNALGA    300
RQAELTVQVK EGPPSEHSGI SRN                                            323

SEQ ID NO: 48            moltype = AA  length = 329
FEATURE                  Location/Qualifiers
REGION                   1..329
```

-continued

```
                              note = MISC_FEATURE - PVRL2(CD112) ECD
source                        1..329
                              mol_type = protein
                              organism = Homo sapiens
SEQUENCE: 48
QDVRVQVLPE VRGQLGGTVE LPCHLLPPVP GLYISLVTWQ RPDAPANHQN VAAFHPKMGP    60
SFPSPKPGSE RLSFVSAKQS TGQDTEAELQ DATLALHGLT VEDEGNYTCE FATFPKGSVR   120
GMTWLRVIAK PKNQAEAQKV TFSQDPTTVA LCISKEGRPP ARISWLSSLD WEAKETQVSG   180
TLAGTVTVTS RFTLVPSGRA DGVTVTCKVE HESFEEPALI PVTLSVRYPP EVSISGYDDN   240
WYLGRTDATL SCDVRSNPEP TGYDWSTTSG TFPTSAVAQG SQLVIHAVDS LFNTTFVCTV   300
TNAVGMGRAE QVIFVRETPN TAGAGATGG                                     329

SEQ ID NO: 49           moltype = AA  length = 236
FEATURE                 Location/Qualifiers
REGION                  1..236
                        note = MISC_FEATURE - CD226 ECD
source                  1..236
                        mol_type = protein
                        organism = Homo sapiens
SEQUENCE: 49
EEVLWHTSVP FAENMSLECV YPSMGILTQV EWFKIGTQQD SIAIFSPTHG MVIRKPYAER    60
VYFLNSTMAS NNMTLFFRNA SEDDVGYYSC SLYTYPQGTW QKVIQVVQSD SFEAAVPSNS   120
HIVSEPGKNV TLTCQPQMTW PVQAVRWEKI QPRQIDLLTY CNLVHGRNFT SKFPRQIVSN   180
CSHGRWSVIV IPDVTVSDSG LYRCYLQASA GENETFVMRL TVAEGKTDNQ YTLFVA       236

SEQ ID NO: 50           moltype = AA  length = 185
FEATURE                 Location/Qualifiers
REGION                  1..185
                        note = MISC_FEATURE - CD2 ECD
source                  1..185
                        mol_type = protein
                        organism = Homo sapiens
SEQUENCE: 50
KEITNALETW GALGQDINLD IPSFQMSDDI DDIKWEKTSD KKKIAQFRKE KETFKEKDTY    60
KLFKNGTLKI KHLKTDDQDI YKVSIYDTKG KNVLEKIFDL KIQERVSKPK ISWTCINTTL   120
TCEVMNGTDP ELNLYQDGKH LKLSQRVITH KWTTSLSAKF KCTAGNKVSK ESSVEPVSCP   180
EKGLD                                                               185

SEQ ID NO: 51           moltype = AA  length = 133
FEATURE                 Location/Qualifiers
REGION                  1..133
                        note = MISC_FEATURE - CD160 ECD
source                  1..133
                        mol_type = protein
                        organism = Homo sapiens
SEQUENCE: 51
INITSSASQE GTRLNLICTV WHKKEEAEGF VVFLCKDRSG DCSPETSLKQ LRLKRDPGID    60
GVGEISSQLM FTISQVTPLH SGTYQCCARS QKSGIRLQGH FFSILFTETG NYTVTGLKQR   120
QHLEFSHNEG TLS                                                      133

SEQ ID NO: 52           moltype = AA  length = 202
FEATURE                 Location/Qualifiers
REGION                  1..202
                        note = MISC_FEATURE - CD200 ECD
source                  1..202
                        mol_type = protein
                        organism = Homo sapiens
SEQUENCE: 52
QVQVVTQDER EQLYTPASLK CSLQNAQEAL IVTWQKKKAV SPENMVTFSE NHGVVIQPAY    60
KDKINITQLG LQNSTITFWN ITLEDEGCYM CLFNTFGFGK ISGTACLTVY VQPIVSLHYK   120
FSEDHLNITC SATARPAPMV FWKVPRSGIE NSTVTLSHPN GTTSVTSILH IKDPKNQVGK   180
EVICQVLHLG TVTDFKQTVN KG                                            202

SEQ ID NO: 53           moltype = AA  length = 215
FEATURE                 Location/Qualifiers
REGION                  1..215
                        note = MISC_FEATURE - CD200R1(CD200R) ECD
source                  1..215
                        mol_type = protein
                        organism = Homo sapiens
SEQUENCE: 53
MDEKQITQNY SKVLAEVNTS WPVKMATNAV LCCPPIALRN LIIITWEIIL RGQPSCTKAY    60
RKETNETKET NCTDERITWV SRPDQNSDLQ IRPVAITHDG YYRCIMVTPD GNFHRGYHLQ   120
VLVTPEVTLF QNRNRTAVCK AVAGKPAAQI SWIPEGDCAT KQEYWSNGTV TVKSTCHWEV   180
HNVSTVTCHV SHLTGNKSLY IELLPVPGAK KSAKL                              215

SEQ ID NO: 54           moltype = AA  length = 117
FEATURE                 Location/Qualifiers
REGION                  1..117
```

-continued

```
                              note = MISC_FEATURE - NC R3 (NKp30) ECD
source                        1..117
                              mol_type = protein
                              organism = Homo sapiens
SEQUENCE: 54
LWVSQPPEIR TLEGSSAFLP CSFNASQGRL AIGSVTWFRD EVVPGKEVRN GTPEFRGRLA  60
PLASSRFLHD HQAELHIRDV RGHDASIYVC RVEVLGLGVG TGNGTRLVVE KEHPQLG     117

SEQ ID NO: 55                 moltype = AA  length = 208
FEATURE                       Location/Qualifiers
REGION                        1..208
                              note = CD80 v1 ECD
source                        1..208
                              mol_type = protein
                              organism = synthetic construct
SEQUENCE: 55
VIHVTKEVKE VATLSCGHNV SVEELAQTRI YWQKEKKMVL TMMSGDMNIW PEYKNRTIFD  60
ITNNLSIVIQ ALRPSDEGTY ECVVLKYEKD GFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 56                 moltype = AA  length = 208
FEATURE                       Location/Qualifiers
REGION                        1..208
                              note = CD80 v2 ECD
source                        1..208
                              mol_type = protein
                              organism = synthetic construct
SEQUENCE: 56
VIHVTKEVKE VATLSCGHNV SVEELAQTRI YWQKEKKMVL TMMSGDMNIW PEYKNRTIFD  60
ITNNLSIVIQ ALRPSDEGTY ECVVLKYEKD GFKREHLAEV TLSVKADFPT PSISDFEIPT  120
SNIRRIICSA SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 57                 moltype = AA  length = 208
FEATURE                       Location/Qualifiers
REGION                        1..208
                              note = CD80 v3 ECD
source                        1..208
                              mol_type = protein
                              organism = synthetic construct
SEQUENCE: 57
VIHVTKEVKE VATLSCGHNV SVEELAQTRI YWQKEKKMVL TMMSGDMNIW PEYKNRTIFD  60
ITNNLSIVIQ ALRPSDEGTY ECVVLKYEKD GFKREHLAEV TLSVKADFPT PSISDFEAPS  120
SNIRRIICSA SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 58                 moltype = AA  length = 208
FEATURE                       Location/Qualifiers
REGION                        1..208
                              note = CD80 v4 ECD
source                        1..208
                              mol_type = protein
                              organism = synthetic construct
SEQUENCE: 58
VIHMTKEVKE VATLSCGHNV SVEELAQTRI YWQKEKKMVL TMMSGDMNIW PEYKNRTIFD  60
ITNNLSIVIQ ALRPSDEGTY ECVVLKYEKD GFKREHLAEV TLSVKADFPT PSISDFEIPS  120
SNIRRIICSA SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 59                 moltype = AA  length = 208
FEATURE                       Location/Qualifiers
REGION                        1..208
                              note = CD80 v5 ECD
source                        1..208
                              mol_type = protein
                              organism = synthetic construct
SEQUENCE: 59
VIHVTKEVKE VATLSCGHNV SVEELAQTRI YWQKEKKMVL TMMSGDMNIW PEYKNRTIFD  60
ITNNLSIVIQ ALRPSDEGTY ECVVLKYEKD GFKREHLAEV TLSVKADFPT PSISDFEIPS  120
SNIRRIICSA SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 60                 moltype = AA  length = 208
FEATURE                       Location/Qualifiers
REGION                        1..208
                              note = CD80 v6 ECD
source                        1..208
                              mol_type = protein
```

```
                        organism = synthetic construct
SEQUENCE: 60
VIHVTKEVKE VATLSCGHNL SVEELAQTRI YWQKEKKMVL TMMSGDMNIW PEYKNRTIFD   60
ITNNLSIVIQ ALRPSDEGTY ECVVLKYEKD SFKREHLAEV TLSVKADFPT PSISDFEIPS  120
SNIRRIICSA SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 61           moltype = AA  length = 208
FEATURE                 Location/Qualifiers
REGION                  1..208
                        note = CD80 v7 ECD
source                  1..208
                        mol_type = protein
                        organism = synthetic construct
SEQUENCE: 61
VIHVTKEVKE VATLSCGHNV SVEELAQTRI YWQKEKKMVL TMMPGDMNIW PEYKNRTIFD   60
ITNNLSIVIQ ALRPSDEGTY ECVVLKYEKD GFKREHLAEV TLSVKADFPT PSISDFEIPT  120
SNIRRIICSA SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 62           moltype = AA  length = 208
FEATURE                 Location/Qualifiers
REGION                  1..208
                        note = CD80 v8 ECD
source                  1..208
                        mol_type = protein
                        organism = synthetic construct
SEQUENCE: 62
VIHVTKEVKE VATLSCGHNV SVEELAQTRI YWQKEKKMVL TMMSGDMNIW PEYKNRTIFD   60
ITNNLSIVIQ ALRPSDEGTY ECVVLKYEKD GFKREHLAEV TLSVKADFPT PSISDFGIPS  120
SNIRRIICSA SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 63           moltype = AA  length = 208
FEATURE                 Location/Qualifiers
REGION                  1..208
                        note = CD80 v9 ECD
source                  1..208
                        mol_type = protein
                        organism = synthetic construct
SEQUENCE: 63
VIHVTKEVKE VATLSCGHNV SVEELAQTRI YWQKEKKMVL TMMSGDMNIW PEYKNRTIFD   60
ITNNLSIVIL ALRPSDEGTY ECVVLKYEKD GFKREHLAEV TLSVKADFPT PSISDFEIPS  120
SNIRRIICSA SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 64           moltype = AA  length = 208
FEATURE                 Location/Qualifiers
REGION                  1..208
                        note = CD80 v10 ECD
source                  1..208
                        mol_type = protein
                        organism = synthetic construct
SEQUENCE: 64
VIHVTKEVKE VATLSCGHNV SVEELAQTRI YWQKEKKMVL TMMSGDMNIW PEYKNRTIFD   60
ITNNLSIVIR ALRPSDEGTY ECVVLKYEKD GFKREHLAEV TLSVKADFPT PSISDFEIPS  120
SNIRRIICSA SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 65           moltype = AA  length = 208
FEATURE                 Location/Qualifiers
REGION                  1..208
                        note = CD80 v11 ECD
source                  1..208
                        mol_type = protein
                        organism = synthetic construct
SEQUENCE: 65
VIHVTKEVKE VATLSCGHNV SVEELAQTRI YWQKEKKMVL TMMSGDMNIW PEYKNRTIFD   60
ITNNLSIVIQ ALRPSDEGTY ACVVLKYEKD GFKREHLAEV TLSVKADFPT PSISDFEIPS  120
SNIRRITCSA SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 66           moltype = AA  length = 208
FEATURE                 Location/Qualifiers
REGION                  1..208
                        note = CD80 v12 ECD
source                  1..208
                        mol_type = protein
                        organism = synthetic construct
```

```
SEQUENCE: 66
VIHVTKEVKE VATLSCGHNV SVEELAQTRI YWQKEKKMVL TMMSGDMNIW PEYKNRTIFD    60
ITNNLSIVIQ ALRPSDEGTY ECVVLKNEKD GFKREHLAEV TLSVKADFPT PSISDFEIPT   120
SNIRRIICSA SGGFPEPHLS WLENGEELNA INTTVSQDPE TELYAVSSKL DFNMTTNHSF   180
MCLIKYGHLR VNQTFNWNTT KQEHFPDN                                     208

SEQ ID NO: 67            moltype = AA   length = 208
FEATURE                  Location/Qualifiers
REGION                   1..208
                         note = CD80 v13 ECD
source                   1..208
                         mol_type = protein
                         organism = synthetic construct
SEQUENCE: 67
VIHVTKEVKE VATLSCGHNV SVEELAQSRI YWQKEKKMVL TMMSGDMNIW PEYKNRTIFD    60
ITNNLSIVIQ ALRPSDEGTY ECVVLKYEKD GFKRKHLAEV TLSVKADFPT PSISDFEIPS   120
SNIRRIICSA SGGFPEPHLS WLENGEELNA INTTVSQDPE TELYAVSSKL DFNMTTNHSF   180
MCLIKYGHLR VNQTFNWNTT KQEHFPDN                                     208

SEQ ID NO: 68            moltype = AA   length = 208
FEATURE                  Location/Qualifiers
REGION                   1..208
                         note = CD80 v14 ECD
source                   1..208
                         mol_type = protein
                         organism = synthetic construct
SEQUENCE: 68
VIHVTKEVKE VATLSCGHNV SVEELAQTRI YWQKEKKMVL TMMSGDMNIW PEYKNRTIFD    60
ITSNLSIVIQ ALRPSDEGTY ECVVLKYEKD GFKREHLAEV TLSVKADFPT PSISDFEIPS   120
SNIRRIICSA SGGFPEPHLS WLENGEELNA INTTVSQDPE TELYAVSSKL DFNMTTNHSF   180
MCLIKYGHLR VNQTFNWNTT KQEHFPDN                                     208

SEQ ID NO: 69            moltype = AA   length = 208
FEATURE                  Location/Qualifiers
REGION                   1..208
                         note = CD80 v15 ECD
source                   1..208
                         mol_type = protein
                         organism = synthetic construct
SEQUENCE: 69
VIHVTKEVKE VATLSCGHNV SVEELAQTRI YWQKEEKMVL TMMSGDMNIW PEYKNRTIFD    60
ITNNLSTVIQ ALRPSDEGTY ECVVLKYEKD GFKREHLAEV TLSVKADFPT PSISDFEIPS   120
SNIRRIICSA SGGFPEPHLS WLENGEELNA ITTTVSQDPE TELYAVSSKL DFNMTTNHSF   180
MCLIKYGHLR VNQTFNWNTT KQEHFPDN                                     208

SEQ ID NO: 70            moltype = AA   length = 208
FEATURE                  Location/Qualifiers
REGION                   1..208
                         note = CD80 v16 ECD
source                   1..208
                         mol_type = protein
                         organism = synthetic construct
SEQUENCE: 70
VIHVTKEVKE VATLSCGHNV SVEELAQTRI YWQKEKKMVL TMMSGDMNIW PGYKNRTIFD    60
ITNNLSIVIQ ALRPSDEGTY ECVVLKYEKD GFKREHLAEV TLSVKADFPT PSISDFEIPS   120
SNIRRIICSA SGGFPEPHLS WLENGEELNA INTTVSQDPE TELYAVSSKL DFNMTTNHSF   180
MCLIKYGHLR VNQTFNWNTT KQEHFPDN                                     208

SEQ ID NO: 71            moltype = AA   length = 208
FEATURE                  Location/Qualifiers
REGION                   1..208
                         note = CD80 v17 ECD
source                   1..208
                         mol_type = protein
                         organism = synthetic construct
SEQUENCE: 71
VIHVTKEVKE VATLSCGHNV SVEELAQTRI YWQKEKMVL TMMSGDMNIW PEYKNRTISD    60
ITNNLSIVIQ ALRPSDEGTY ECVVLKYEKD GFKREHLAEV TLSVKADFPT PSISDFEIPS   120
SNIRRIICSA SGGFPEPHLS WLENGEELNA INTTVSQDPE TELYAVSSKL DFNMTTNHSF   180
MCLIKYGHLR VNQTFNWNTT KQEHFPDN                                     208

SEQ ID NO: 72            moltype = AA   length = 208
FEATURE                  Location/Qualifiers
REGION                   1..208
                         note = CD80 v18 ECD
source                   1..208
                         mol_type = protein
                         organism = synthetic construct
SEQUENCE: 72
```

-continued

```
VIHVTKEVKE VATLSCGHNV SVEELAQTRI YWQKEKKMVL TMMSGDMNIW PEYKNRTIFD   60
ITNNLSIVIL ALRPSDEGTY ECVVLKYEKD GFKREHLAEV TLPVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 73              moltype = AA   length = 208
FEATURE                    Location/Qualifiers
REGION                     1..208
                           note = CD80 v19 ECD
source                     1..208
                           mol_type = protein
                           organism = synthetic construct
SEQUENCE: 73
VIHVTKEVKE VATLSCGHNV SVEELAQTRI YWQKEKKMVL TMMSGDMNIW PEYKNRTIFD   60
ITNNLSIVIL ALRPSDEGTY ECVVLKYEED AFKREHLAEV TLSVKADFPT PSISDFEIPT  120
SNIRRIICSA SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 74              moltype = AA   length = 208
FEATURE                    Location/Qualifiers
REGION                     1..208
                           note = CD80 v20 ECD
source                     1..208
                           mol_type = protein
                           organism = synthetic construct
SEQUENCE: 74
VIHVTKEVKE VATLSCGHNV SVEELAQTRI YWQKEKKMVL TMMSGDMNIW PEYKNRTIFD   60
ITNNLSIVIL ALRPSDEGTY ECVVLKYEKD GFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 75              moltype = AA   length = 208
FEATURE                    Location/Qualifiers
REGION                     1..208
                           note = CD80 v21 ECD
source                     1..208
                           mol_type = protein
                           organism = synthetic construct
SEQUENCE: 75
VIHVTKEVKE VATLSCGHNV SVEELAQTRI YWQKEKKMVL TMMSGDMNIW PEYKNRTIFV   60
ITNNLSIVIL ALRPSDEGTY ECVVLKYEKD GFKREHLAEV TLSVKADFPT PSISDFEIPS  120
SNIRRIICSA SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 76              moltype = AA   length = 208
FEATURE                    Location/Qualifiers
REGION                     1..208
                           note = CD80 v22 ECD
source                     1..208
                           mol_type = protein
                           organism = synthetic construct
SEQUENCE: 76
VIHVTKEVKE VATLSCGHNV SVEELAQTRI YWQKEKKMVL TMMSGDMNIW PEYMNRTIFD   60
ITNNLSIVIL ALRPSDEGTY ECVVLKYEKD GFKREHLAEV TLSVKADFPT PSISDFEIPS  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 77              moltype = AA   length = 208
FEATURE                    Location/Qualifiers
REGION                     1..208
                           note = CD80 v23 ECD
source                     1..208
                           mol_type = protein
                           organism = synthetic construct
SEQUENCE: 77
VIHVTKEVKE VATLSCGHNV SVEELAQTRI YWQKEKKTVL TMMSGDMNIW PEYKNRTIFD   60
ITNNLSIVIQ ALRPSDGGTY ECVVLKYEKD GFKREHLAEV TLSVKADFPT PSISDFEIPS  120
SNIRRIICSA SGGFPEPHLS WLENGEELNA ITTTVSQDPE TELYAVSSKL DFNMTTNHSF  180
MCLIKYGHLR VNQTFNWNTT KQEHFPDN                                    208

SEQ ID NO: 78              moltype = AA   length = 208
FEATURE                    Location/Qualifiers
REGION                     1..208
                           note = CD80 v24 ECD
source                     1..208
                           mol_type = protein
                           organism = synthetic construct
SEQUENCE: 78
VIHVTKEVKE VATLSCGHNV SVEELAQTHI YWQKEKKMVL TMMSGDMNIW PGYKNRTIFD   60
```

```
ITNNLSIVIR ALRPSDEGTY ECVVLKYGKD GFKREHLAEV TLSVKADFPT PSISDFEIPT   120
SNIRRIICSA SGGFPEPHLS WLENGEELNA INTTVSQDPE TELYAVSSKL DFNMTTNHSF   180
MCLIKYGHLR VNQTFNWNTT KQEHFPDN                                      208

SEQ ID NO: 79            moltype = AA  length = 208
FEATURE                  Location/Qualifiers
REGION                   1..208
                         note = CD80 v25 ECD
source                   1..208
                         mol_type = protein
                         organism = synthetic construct
SEQUENCE: 79
VIHVTKEVKE VATLSCGHNV SVEELAQTRI HWQKEKKMVL GMMSGDMNIW PEYKNRTIFD   60
ITNNLSIVIQ ALRPSDEGTY ECVVLKYEKD GFKREHLAEV TLSVKADFPT PSISDFEIPS   120
SNIRRIICSA SGGFPEPHLS WLENGEELNA INTTVSQDPE TELYAVSSKL DFNMTTNHSF   180
MCLIKYGHLR VNQTFNWNTT KQEHFPDN                                      208

SEQ ID NO: 80            moltype = AA  length = 208
FEATURE                  Location/Qualifiers
REGION                   1..208
                         note = CD80 v26 ECD
source                   1..208
                         mol_type = protein
                         organism = synthetic construct
SEQUENCE: 80
VIHVTKEVKE VATLSCGHNV SVEELAQTRI YWQKEKKMVL TMMSGDMNIW PEYKNRTIFD   60
ITNNLSIAIL ALRPSDEGTY ECVVLKYEKD AFKREHLAEV TLSVKADFPA PSISDFEIPT   120
SNIRRIICST SGGFPEPHLS WLENGEELNA INTTVSQDPE TELYAVSSKL DFNMTTNHSF   180
MCLIKYGHLR VNQTFNWNTT KQEHFPDN                                      208

SEQ ID NO: 81            moltype = AA  length = 208
FEATURE                  Location/Qualifiers
REGION                   1..208
                         note = CD80 v27 ECD
source                   1..208
                         mol_type = protein
                         organism = synthetic construct
SEQUENCE: 81
VIHVTKEVKE VATLSCGHNV SVEELAQTRI YWQKEKKMVL TMMSGDMNIW PEYKNRTIFD   60
ITNNLHIVIL ALRPSDEGTY ECVVLKYEKG AFKREHLAEV TLSVKADFPA PSISDLEIPT   120
SNIRRIICST SGGFPEPHLS WLENGEELNA INTTVSQDPE TELYAVSSKL DFNMTTNHSF   180
MCLIKYGHLR VNQTFNWNTT KQEHFPDN                                      208

SEQ ID NO: 82            moltype = AA  length = 208
FEATURE                  Location/Qualifiers
REGION                   1..208
                         note = CD80 v28 ECD
source                   1..208
                         mol_type = protein
                         organism = synthetic construct
SEQUENCE: 82
VIHVTKEVKE VATLSCGHNV SVEELAQTHI YWQKEKKMVL TMMSGDMNIW PGYKNRTIFD   60
ITNNLSIVIL ALRPSDEGTY ECVVLKYEKD AFKREHLAEV TLSVKADFPT PSISDFEIPS   120
SNIRRIICSA SGGFPEPHLS WLENGEELNA INTTVSQDPE TELYAVSSKL DFNMTTNHSF   180
MCLIKYGHLR VNQTFNWNTT KQEHFPDN                                      208

SEQ ID NO: 83            moltype = AA  length = 208
FEATURE                  Location/Qualifiers
REGION                   1..208
                         note = CD80 v29 ECD
source                   1..208
                         mol_type = protein
                         organism = synthetic construct
SEQUENCE: 83
VIHVTKEVKE VATLSCGHNV SVEELAQTRI YWQKEKKMVL TMMSGDMNIW PEYKNRTIFD   60
ITNNLSIVIL ALRPSDEGTY ECVVLKYEKD GFKREHLAEV TSSVKADFPT PSISDFEIPT   120
SNIRRIICST SGGFPEPHLS WLENGEELNA INTTVSQDPE TELYAVSSKL DFNMTTNHSF   180
MCLIKYGHLR VNQTFNWNTT KQEHFPDN                                      208

SEQ ID NO: 84            moltype = AA  length = 208
FEATURE                  Location/Qualifiers
REGION                   1..208
                         note = CD80 v30 ECD
source                   1..208
                         mol_type = protein
                         organism = synthetic construct
SEQUENCE: 84
VIHVTKEVKE VATLSCGHNV SVEELAQTRI YWQKEKKMVL TMMSGDMNIW PEYKNRTIFD   60
ITNNLSTVIQ ALRPSDEGTY ECVVLKYEKD GFKREHLAEV TLSVKADFPT PSISDFEIPS   120
```

-continued

```
SNIRRIICST SGGFPEPHLS WLENGEELNA INTTVSQDPE TELYAVSSKL DFNMTTNHSF    180
MCLIKYGHLR VNQTFNWNTT KQEHFPDN                                       208

SEQ ID NO: 85          moltype = AA   length = 208
FEATURE                Location/Qualifiers
REGION                 1..208
                       note = CD80 v31 ECD
source                 1..208
                       mol_type = protein
                       organism = synthetic construct
SEQUENCE: 85
VIHVTKEVKE VATLSCGHNV SVEELAQTRI YWQKEKKMVL TMMSGDMNIW PEYKNRTIFD    60
ITNNLSIVIQ ALRPSDEGTY ECVVLKYEKD GFKREHLAEV TLSVKADFPA PSISDFEIPS    120
SNIRRIICSA SGGFPEPHLS WLENGEELNA INTTVSQDPE TELYAVSSKL DFNMTTNHSF    180
MCLIKYGHLR VNQTFNWNTT KQEHFPDN                                       208

SEQ ID NO: 86          moltype = AA   length = 208
FEATURE                Location/Qualifiers
REGION                 1..208
                       note = CD80 v32 ECD
source                 1..208
                       mol_type = protein
                       organism = synthetic construct
SEQUENCE: 86
VIHVTKEVKE VATLSCGHNV SVEELAQTRI YWQKEKKVVL DMISGDMNIG PEYKNRTIFD    60
ITNNLSIVIL ALRPSGEGTY ECAVLKYEED AFKREHLAEV TLSVKADFPT PSISDFEIPS    120
SNIRRIICSA SGGFPEPHLS WLENGEELNA INTTVSQDPE TELYAVSSKL DFNMTTNHSF    180
MCLIKYGHLR VNQTFNWNTT KQEHFPDN                                       208

SEQ ID NO: 87          moltype = AA   length = 208
FEATURE                Location/Qualifiers
REGION                 1..208
                       note = CD80 v33 ECD
source                 1..208
                       mol_type = protein
                       organism = synthetic construct
SEQUENCE: 87
VIHVTKEVKE VATLSCGHNV SAEELAQTRI YWQKEKKMVL TMMSGDMNIW PEYKNRTIFD    60
ITNNLSIVIQ ALRPSDEGTY ECVVLKYEKD AFKREHLAEV TLSVKADFPT PSISDFEIPT    120
PNIRRIICST SGGFPEPHLS WLENGEELNA INTTVSQDPE TELYAVSSKL DFNMTTNHSF    180
MCLIKYGHLR VNQTFNWNTT KQEHFPDN                                       208

SEQ ID NO: 88          moltype = AA   length = 208
FEATURE                Location/Qualifiers
REGION                 1..208
                       note = CD80 v34 ECD
source                 1..208
                       mol_type = protein
                       organism = synthetic construct
SEQUENCE: 88
VIHVTKEVKE VVTLFCGHNV SVEELAQTRI HWQKEKKMVL GMMSGDMNIW PEYKNRTIFD    60
ITNNLSIVIL ALRPSDEGTY ECVVLKYEKD AFKREHLAEV TLSVKADFPT PSISDFEIPT    120
SNIRRIICSA SGGFPELHLS WLENGEELNA ITTTVSQDPE TELYAVSSKL DFNMTTNHSF    180
MCLIKYGHLR VNQTFNWNTT KQEHFPDN                                       208

SEQ ID NO: 89          moltype = AA   length = 208
FEATURE                Location/Qualifiers
REGION                 1..208
                       note = CD80 v35 ECD
source                 1..208
                       mol_type = protein
                       organism = synthetic construct
SEQUENCE: 89
VIHVTKEVKE VATLSCGHNV SVEELAQTRI YWQKEKKMVL TMMSGDMNIW PEYKNRTIFD    60
ITNNLSFVIR ALRPSDEGTY ECVVLKYGKD GFKREHLAEV TLSVKADFPT PSISDFEIPS    120
SNIRRIICSA SGGFPEPHLS WLENGEELNA INTTVSQDPE TELYAVSSKL DFNMTTNHSF    180
MCLIKYGHLR VNQTFNWNTT KQEHFPDN                                       208

SEQ ID NO: 90          moltype = AA   length = 208
FEATURE                Location/Qualifiers
REGION                 1..208
                       note = CD80 v36 ECD
source                 1..208
                       mol_type = protein
                       organism = synthetic construct
SEQUENCE: 90
VIHVTKEVKE VATLSCGHNV SVEGPAQTRI YWQKEKKMVL TMMSGDMNIW PEYKNRTIFD    60
ITNNLSIVIQ ALRPSDEGTY ECVVLKYEKD AFKREHLAEV TLSVKADFPT PSISDFEIPS    120
SNIRRIICST SGGFPEPHLS WLENGEELNA INTTVSQDPE TELYAVSSKL DFNMTTNHSF    180
```

-continued

```
MCLIKYGHLR VNQTFNWNTT KQEHFPDN                                          208

SEQ ID NO: 91            moltype = AA   length = 208
FEATURE                  Location/Qualifiers
REGION                   1..208
                         note = CD80 v37 ECD
source                   1..208
                         mol_type = protein
                         organism = synthetic construct
SEQUENCE: 91
VIHVTKEVKE VATLSCGHNV SVEELAQTRI YWQKEKKMVL TMMSGDMNIW PEYKNRTIFD       60
ITNNLSIVIL ALRPSDEGTY ECVVLKYEKD GLKREHLAEV TLSVKADLPT PSISDFEIPS       120
SNIRRIICST SGGFPEPHLS WLENGEELNA INTTVSQDPE TELYAVSSKL DFNMTTNHSF       180
MCLIKYGHLR VNQTFNWNTT KQEHFPDN                                          208

SEQ ID NO: 92            moltype = AA   length = 208
FEATURE                  Location/Qualifiers
REGION                   1..208
                         note = CD80 v38 ECD
source                   1..208
                         mol_type = protein
                         organism = synthetic construct
SEQUENCE: 92
VIHVTKEVKE VATLSCGHNV SVEELAQTDI LWHKEGKIVL AMRSGDTNIW PEYKNRTIFD       60
ITNNLSIVIL ALRPSDEGTY VCVVRKYEND TPVLEHLAEV TLSVKADFPT PSISDFETPT       120
SNIRRIICST SGGFPEPHLS WLENGEELSA INTTVSQDPE TELYAVSSKL DFNMTTNHSF       180
MCLIKYGHLR VNQTFNWNTT KQEHFPDN                                          208

SEQ ID NO: 93            moltype = AA   length = 208
FEATURE                  Location/Qualifiers
REGION                   1..208
                         note = CD80 v39 ECD
source                   1..208
                         mol_type = protein
                         organism = synthetic construct
SEQUENCE: 93
VIHVTKEVKE VATLSCGHNV SVEELAQTDI LWHKEGKIVL AMRSGDTNIW PEYKNRTIFD       60
ITNNLSIVIL ALRPSDEGTY VCVVRKYEND TPVLEHLAEV TLSVKADFPT PSISDFEIPT       120
SNIRRIICST SGGFPEPHLS WLESGEELSA INTTVSQDPE TELYAVSSKL DFNMTTNHSF       180
MCLIKYGHLR VNQTFNWNTT KQEHFPDN                                          208

SEQ ID NO: 94            moltype = AA   length = 208
FEATURE                  Location/Qualifiers
REGION                   1..208
                         note = CD80 v40 ECD
source                   1..208
                         mol_type = protein
                         organism = synthetic construct
SEQUENCE: 94
VIHVTKEVKE VATLSCGHNV SVEELAQTDI LWHKEGKIVL ATRSGDTNIW PEYKNRTIFD       60
ITNNLSIVIL ALRPSDEGTY VCVVRKYEND TPVLEHLAEV TLSVKADFPT PSISDFEIPT       120
SNIRRIICST SGGFPEPHLS WLENGEESSA INTTVSQDPE TELYAVSSKL DFNMTTNHSF       180
MCLIKYGHLR VNQTFNWNTT KQEHFPDN                                          208

SEQ ID NO: 95            moltype = AA   length = 208
FEATURE                  Location/Qualifiers
REGION                   1..208
                         note = CD80 v41 ECD
source                   1..208
                         mol_type = protein
                         organism = synthetic construct
SEQUENCE: 95
VIHVTKEVKE VATLSCGHNV SVEGLAQTDI LWHKEGKIVL AMRSGDTNIW PEYKNRTILD       60
ITNNLSIVIL ALRPSDEGTY VCVVRKYEND TPVLERLAEV TLSVKADFPT PSISDFEIPT       120
SNIRRIICST SGGFPEPHLS WLENGEELSA INTTVSQDPE TELYAVSSKL DFNMTTNHSF       180
MSLIKYGHLR VNQTFNWNTT KQEHFPDN                                          208

SEQ ID NO: 96            moltype = AA   length = 208
FEATURE                  Location/Qualifiers
REGION                   1..208
                         note = CD80 v42 ECD
source                   1..208
                         mol_type = protein
                         organism = synthetic construct
SEQUENCE: 96
VIHVTKEVKE VATLSCGHNV SVEELAQTDI LWHKEGKIVL AMRSGDTNIW PEYKNRTIFD       60
ITNNLSIVIL ALRPSDEGTY VCVVRKYEND TPVLEHLAEV TLSVKADFPT PSISDFEIPT       120
SNIRRIICST SGGFPEPHLS WLENGEELSA INTTVSQDPE TELYAVSSKL DFNMTTNHSF       180
MCLIKYGHLR VNQTFNWNTT KQEHFPDN                                          208
```

-continued

```
SEQ ID NO: 97          moltype = AA  length = 208
FEATURE                Location/Qualifiers
REGION                 1..208
                       note = CD80 v43 ECD
source                 1..208
                       mol_type = protein
                       organism = synthetic construct
SEQUENCE: 97
VIHVTKEVKE VATLSCGHNV SVEELAQTVI YWQKEKKMVL TMQSGDMNIW PEYKNRTIFD   60
ITNNLSIVIL ALRPSDEGTY RCVVIKYERL ENQGEHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 98          moltype = AA  length = 208
FEATURE                Location/Qualifiers
REGION                 1..208
                       note = CD80 v44 ECD
source                 1..208
                       mol_type = protein
                       organism = synthetic construct
SEQUENCE: 98
VIHVTKEVKE VATLSCGHNV SVEELAQTRI YWQKEKKMVL IMMSGDMNIW PEYKNRTIFD   60
ITNNLSIVIL ALRPSDEGTY ECVVLKYEKD GFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 99          moltype = AA  length = 208
FEATURE                Location/Qualifiers
REGION                 1..208
                       note = CD80 v45 ECD
source                 1..208
                       mol_type = protein
                       organism = synthetic construct
SEQUENCE: 99
VIHVTKEVKE VATLSCGHNV SVEELAQTRI YWQKEKKMVL TMMSGDMNIW PEYKNRTIFD   60
ITNNLSIVIL ALRPSDEGTY ECVVLKYERK GYRREHLAEV TLSVKADFPT PSISDFEIPT  120
SSIRRIICST SGGFPEPHLS WLENGEELNA INTTVSQDPE TELYAVSSKL DFNMTTSHSF  180
MCLIKYGHLR VNQTFNWNTT KQEHFPDN                                    208

SEQ ID NO: 100         moltype = AA  length = 208
FEATURE                Location/Qualifiers
REGION                 1..208
                       note = CD80 v46 ECD
source                 1..208
                       mol_type = protein
                       organism = synthetic construct
SEQUENCE: 100
VIHVTKEVKE VATLSCGHNV SVEELAQTRI YWQKEKKMVL TMMSGDMNIW PEYKNRTIFD   60
ITNNLSIVIL ALRPSDEGTY ECVVLKYERK GYRREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 101         moltype = AA  length = 208
FEATURE                Location/Qualifiers
REGION                 1..208
                       note = CD80 v47 ECD
source                 1..208
                       mol_type = protein
                       organism = synthetic construct
SEQUENCE: 101
VIHVTKEVKE VATLSCGHNV SVEELAQTRI YWQKEGQIVL TMMSGDMNIW PEYKNRTILD   60
ITNNLSIVIL ALRPSDEGTY VCVVRKYEND TPVLEHLAGV TLSVKADFPT PSISDFEIPT  120
SNIRRIICSA SGGFPEPHLS WLENGEELSA INTTVSQDPE TELYAVSSKL DFNMTTNHSF  180
MCLIKYGHLR VNQTFNWNTT KQEHFPDN                                    208

SEQ ID NO: 102         moltype = AA  length = 208
FEATURE                Location/Qualifiers
REGION                 1..208
                       note = CD80 v48 ECD
source                 1..208
                       mol_type = protein
                       organism = synthetic construct
SEQUENCE: 102
VIHVTKEVKE VATLSCGHNV SVEELAQTRI YWQKEKKMVL TMMSGDMNIW PEYKNRTIFD   60
ITNNLSIVIL ALRPSDEGTY ECVVLKYDRK GYRREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208
```

-continued

```
SEQ ID NO: 103          moltype = AA   length = 208
FEATURE                 Location/Qualifiers
REGION                  1..208
                        note = CD80 v49 ECD
source                  1..208
                        mol_type = protein
                        organism = synthetic construct
SEQUENCE: 103
VIHVTKEVKE VATLSCGHNV SVEELAQTRI YWQKEGQIVM TMMSGDMNIW PEYKNRTIFD   60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 104          moltype = AA   length = 208
FEATURE                 Location/Qualifiers
REGION                  1..208
                        note = CD80 v50 ECD
source                  1..208
                        mol_type = protein
                        organism = synthetic construct
SEQUENCE: 104
VIHVTKEVKE VATLSCGHNV SVEELAQTRI YWQKEGKMVL TMMSGDMNIW PEYKNRTIFD   60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 105          moltype = AA   length = 208
FEATURE                 Location/Qualifiers
REGION                  1..208
                        note = CD80 v51 ECD
source                  1..208
                        mol_type = protein
                        organism = synthetic construct
SEQUENCE: 105
VIHVTKEVKE VATLSCGHNV SVEELAQTHI HWQKEKKMVL GMMSGDMNIW PEYKNRTIFD   60
ITNNLSIVIL ALRPSDEGTY ECVVLKNGEN GFKREHLAEV TLSVKADFST PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 106          moltype = AA   length = 208
FEATURE                 Location/Qualifiers
REGION                  1..208
                        note = CD80 v52 ECD
source                  1..208
                        mol_type = protein
                        organism = synthetic construct
SEQUENCE: 106
VIHVTKEVKE VTTLSCGLNV SVEELAQTRI YWQKEKKMVL TMVSGDMNIW PEYKNRTILD   60
ITNNLSIVIL ALRPSDKGTY ECVVLKYEKD AFKREHLAEV TLSVKADFST PSISDFETPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 107          moltype = AA   length = 208
FEATURE                 Location/Qualifiers
REGION                  1..208
                        note = CD80 v53 ECD
source                  1..208
                        mol_type = protein
                        organism = synthetic construct
SEQUENCE: 107
VIHVTKEVKE VATLSCGHNV SVEELAQTVI FWQKEGKLVL TMQSGDMNIW PEYKNRTIFD   60
ITNNLSIVIL ALRPSDEGTY RCIVIKYERL ENQGEHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 108          moltype = AA   length = 208
FEATURE                 Location/Qualifiers
REGION                  1..208
                        note = CD80 v54 ECD
source                  1..208
                        mol_type = protein
                        organism = synthetic construct
SEQUENCE: 108
VIHVTKEVKE VATLSCGHNV SVEELAQTRI YWQKEKKMVL TMMSGDMNIW PEYKNRTIFD   60
ITNNLSIMIP APRPSDEGTY ECVVLEYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 109          moltype = AA   length = 238
```

-continued

```
FEATURE                 Location/Qualifiers
REGION                  1..238
                        note = ICOSL v1 ECD
source                  1..238
                        mol_type = protein
                        organism = synthetic construct
SEQUENCE: 109
DTQEKEVRAM VGSDVELSCA CPEGSRFDLN DVYVYWQTSE SKTVVTYHIP QSSSLENVDS      60
RYRNRALMSP AGMLRGDFSL RLFNVTPQDE QKFHCLVLSQ SLGFQEVLSV EVTLHVAANF     120
SVPVVSAPHS PSQDELTFTC TSINGYPRPN VYWINKTDNS LLDQALQNDT VFLNMRGLYD     180
VVSVLRIART PSVNIGCCIE NVLLQQNLTV GSQTGNDIGE RDKITENPVS TGEKNAAT       238

SEQ ID NO: 110          moltype = AA  length = 238
FEATURE                 Location/Qualifiers
REGION                  1..238
                        note = ICOSL v2 ECD
source                  1..238
                        mol_type = protein
                        organism = synthetic construct
SEQUENCE: 110
DTQEKEVRAM VGSDVELSCA CPEGSRFDLN DVYVYWQTSE SKTVVTYHIP QHSSLENVDS      60
RYRNRALMSP AGMLRGDFSL RLFNVTPQDE QKFHCLVLSQ SLGFQEVLSV EVTLHVAANF     120
SVPVVSAPHS PSQDELTFTC TSINGYPRPN VYWINKTDNS LLDQALQNDT VFLNMRGLYD     180
VVSVLRIART PSVNIGCCIE NVLLQQNLTV GSQTGNDIGE RDKITENPVS TGEKNAAT       238

SEQ ID NO: 111          moltype = AA  length = 238
FEATURE                 Location/Qualifiers
REGION                  1..238
                        note = ICOSL v3 ECD
source                  1..238
                        mol_type = protein
                        organism = synthetic construct
SEQUENCE: 111
DTQEKEVRAM VGSDVELSCA CPEGSRFDLN DVYVYWQTSE SKTVVTYHIP QDSSLENVDS      60
RYRNRALMSP AGMLRGDFSL RLFNVTPQDE QKFHCLVLSQ SLGFQEVLSV EVTLHVAANF     120
SVPVVSAPHS PSQDELTFTC TSINGYPRPN VYWINKTDNS LLDQALQNDT VFLNMRGLYD     180
VVSVLRIART PSVNIGCCIE NVLLQQNLTV GSQTGNDIGE RDKITENPVS TGEKNAAT       238

SEQ ID NO: 112          moltype = AA  length = 238
FEATURE                 Location/Qualifiers
REGION                  1..238
                        note = ICOSL v4 ECD
source                  1..238
                        mol_type = protein
                        organism = synthetic construct
SEQUENCE: 112
DTQEKEVRAM VGSDVELSCA CPEGSRFDLN DVYVYWQTSE SKTVVTYHIP QYSSLEYVDS      60
RYRNRALMSP AGMLRGDFSL RLFNVTPQDE QKFHCLVLSQ SLGFQEVLSV EVTLHVAANF     120
SVPVVSAPHS PSQDELTLTC TSINGYPRPN VYWINKTDNS LLDQALQNDT VFLNMRGLYD     180
VVSVLRIART PSVNIGCCIE NVPLQQNLTV GSQTGNDIGE RDKITENPVS TGEKNAAT       238

SEQ ID NO: 113          moltype = AA  length = 238
FEATURE                 Location/Qualifiers
REGION                  1..238
                        note = ICOSL v5 ECD
source                  1..238
                        mol_type = protein
                        organism = synthetic construct
SEQUENCE: 113
DTQEKEVRAM VGSDVELSCA CPEGSRFDLN DVYVYWQTSE SKTVVTYHIP QHSSLEYVDS      60
RYRNRALMSP AGMLRGDFSL RLFNVTPQDE QKFHCLVLSP SLGFQEVLSV EVTLHVAANF     120
SVPVVSAPHS PSQDELTFTC TSINGYPRPN VYWINKTDNS LLDQALQNDT VFLNMRGLYD     180
VVSVLRIART PSVNIGCCIE NVLLQQNLTV GSQTGNDIGE RDKITENPVS TGEKNAAT       238

SEQ ID NO: 114          moltype = AA  length = 238
FEATURE                 Location/Qualifiers
REGION                  1..238
                        note = ICOSL v6 ECD
source                  1..238
                        mol_type = protein
                        organism = synthetic construct
SEQUENCE: 114
DTQEKEVRAM VGSDVELSCA CPEGSRFDLN DVYVYWQTSE SKTVVTYHIP QSSSLENVDS      60
RYRNRALMSP AGMLRGDFSL RLFNVTPQDE QKFHCLVLSQ SLGFQEVLSV EVTLHVAANF     120
SVPVVSAPHS PSQDELTFTC TSINGCPRPN VCWINKTDNS LLDQALQNDT VFLNMRGLYD     180
VVSVLRIART PSVNIGCCIE NVLLQQNLTV GSQTGNDIGE RDKITENPVS TGEKNAAT       238

SEQ ID NO: 115          moltype = AA  length = 238
FEATURE                 Location/Qualifiers
```

```
REGION                    1..238
                          note = ICOSL v7 ECD
source                    1..238
                          mol_type = protein
                          organism = synthetic construct
SEQUENCE: 115
DTQEKEVRAM VGSDVELSCA CPEGSRFDLN DVYVYWQTSE SKTVVTYHIP QHSSLENVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCRIE NVLLQQNLTV GSQTGNDIGE RDKITENPVS TGEKNAAT    238

SEQ ID NO: 116           moltype = AA  length = 238
FEATURE                  Location/Qualifiers
REGION                   1..238
                         note = ICOSL v8 ECD
source                   1..238
                         mol_type = protein
                         organism = synthetic construct
SEQUENCE: 116
DTQEKEVRAM VGSDVELSCA CPEGSRFDLN DVYVYWQTSE SKTVVTYHIP QHSSLENVDS   60
RYRNRALMSP AGMLRGDFSL RLFNVTPQDE QKFHCLVLSQ SLGFQEVLSV EVTLHVAANF  120
SVPVVSAPHS PSQDELTFTD TSINGYPRPN VYWINKTDNS LLDQALQNDT VFLNMRGLYD  180
VVSVLRIART PSVNIGCCIE NVLLQQNLTV GSQTGNDIGE RDKIAENPVS TGEKNAAT    238

SEQ ID NO: 117           moltype = AA  length = 238
FEATURE                  Location/Qualifiers
REGION                   1..238
                         note = ICOSL v9 ECD
source                   1..238
                         mol_type = protein
                         organism = synthetic construct
SEQUENCE: 117
DTQEKEVRAM VGSDVELSCA CPEGSRFDLN DVYVYWQTSE SKTVVTYHIP QHSSLENVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCRIE NVLLQQNLTV GSQTGNDIGE RDKIAENPVS TGEKNAAT    238

SEQ ID NO: 118           moltype = AA  length = 238
FEATURE                  Location/Qualifiers
REGION                   1..238
                         note = ICOSL v10 ECD
source                   1..238
                         mol_type = protein
                         organism = synthetic construct
SEQUENCE: 118
DTQEKEVRAM VGSDVELSCA CPEGSRFDLN DVYVYWQTSE SKTVVTYHIP QHSSLENVDS   60
RYRNRALMSP AGMLRGDFSL RLFNVTPQDE QRFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 119           moltype = AA  length = 238
FEATURE                  Location/Qualifiers
REGION                   1..238
                         note = ICOSL v11 ECD
source                   1..238
                         mol_type = protein
                         organism = synthetic construct
SEQUENCE: 119
DTQEKEVRAM VGSDVELSCA CPEGSRFDLN DVYVYWQTSE SKTVVTYHIP QHSSLENVDS   60
RYRNRALMSP AGMLRGDFSL RLFNVTPQDE QKFHCLVLGQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 120           moltype = AA  length = 238
FEATURE                  Location/Qualifiers
REGION                   1..238
                         note = ICOSL v12 ECD
source                   1..238
                         mol_type = protein
                         organism = synthetic construct
SEQUENCE: 120
DTQEKEVRAM VGSDVELSCA CPEGSRFDLN DVYVYWQTSE SKTVVTYHIP QYSSLENVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 121           moltype = AA  length = 238
FEATURE                  Location/Qualifiers
REGION                   1..238
```

```
                              note = ICOSL v13 ECD
source                        1..238
                              mol_type = protein
                              organism = synthetic construct
SEQUENCE: 121
DTQEKEVRAM VGSDVELSCA CPEGSRFDLN DVYVYWQTSE SKTVVTYHIP QNSSLEYVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 122              moltype = AA  length = 238
FEATURE                    Location/Qualifiers
REGION                     1..238
                           note = ICOSL v14 ECD
source                     1..238
                           mol_type = protein
                           organism = synthetic construct
SEQUENCE: 122
DTQEKEVRAM VGSDVELSCA CPEGSRFDLN DVYVYWQTSE SKTVVTYHIP QNSSLEYVDS   60
RYRNRALMSP AGMLRGDFSL RLFNVTPQDE QKFHCLVLSP SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 123              moltype = AA  length = 238
FEATURE                    Location/Qualifiers
REGION                     1..238
                           note = ICOSL v15 ECD
source                     1..238
                           mol_type = protein
                           organism = synthetic construct
SEQUENCE: 123
DTQEKEVRAM VGSDVELSCA CPEGSRFDLN DVYVYWQTSE SKTVVTYHIP QSSSLENVDS   60
RYRNRALMSP AGMLRGDFSL RLFNVTPQDE QKFHCLVLSQ SLGFQEVLSV EVTLHVAANF  120
SVPVVSAPHG PSQDELTFTC TSINGYPRPN VCWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 124              moltype = AA  length = 238
FEATURE                    Location/Qualifiers
REGION                     1..238
                           note = ICOSL v16 ECD
source                     1..238
                           mol_type = protein
                           organism = synthetic construct
SEQUENCE: 124
DTQEKEVRAM VGSDVELSCA CPEGSRFDLN DVYVYWQTSE SKTVVTYHIP QSSSLENVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VCWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 125              moltype = AA  length = 238
FEATURE                    Location/Qualifiers
REGION                     1..238
                           note = ICOSL v17 ECD
source                     1..238
                           mol_type = protein
                           organism = synthetic construct
SEQUENCE: 125
DTQEKEVRAM VGSDVELSCA CPEGSRFDLN DVYVYWQTSE SKTVVTYHIP QSSSLENVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCRIE NVLLQQNLTV GSQTGNDIGE RDKITENPVS TGEKNAAT    238

SEQ ID NO: 126              moltype = AA  length = 238
FEATURE                    Location/Qualifiers
REGION                     1..238
                           note = ICOSL v18 ECD
source                     1..238
                           mol_type = protein
                           organism = synthetic construct
SEQUENCE: 126
DTQEKEVRAM VGSDVELSCA CPEGSRFDLN DVYVYWQTSE SKTVVTYHIP QYSSLEYVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VCWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 127              moltype = AA  length = 238
FEATURE                    Location/Qualifiers
REGION                     1..238
                           note = ICOSL v19 ECD
```

-continued

```
source                  1..238
                        mol_type = protein
                        organism = synthetic construct
    SEQUENCE: 127
DTQEKEVRAM VGSDVELSCA CPEGSRFDLN DVYVYWQTSE SKTVVTYHIP QYSSLEYVDS  60
RYRNRALMSP AGMLRGDFSL RLFNVTPQDE QKFHCLVLSQ SLGFQEVLSV EVTLHVAANF  120
SVPVVSAPPS PSQDELTFTC TSINGYPRPN VYWINKTDNS LLDQALQNDT VFLNMRGLYD  180
VVSVLRIART PSVNIGCRIE NVLLQQNLTV GSQTGNDIGE RDKITENPVS TGEKNAAT    238

SEQ ID NO: 128          moltype = AA  length = 238
FEATURE                 Location/Qualifiers
REGION                  1..238
                        note = ICOSL v20 ECD
source                  1..238
                        mol_type = protein
                        organism = synthetic construct
    SEQUENCE: 128
DTQEKEVRAM VGSDVELSCA CPEGSRFDLN DVYVYWQTSE SKTVVTYHIP QHSSLENVDS  60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS PLDQALQNDT VFLNMRGLYD  180
VVSVLRIART PSVNIGCRIE NVLLQQNLTV GSQTGNDIGE RDKITENPVS TGEKNAAT    238

SEQ ID NO: 129          moltype = AA  length = 238
FEATURE                 Location/Qualifiers
REGION                  1..238
                        note = ICOSL v21 ECD
source                  1..238
                        mol_type = protein
                        organism = synthetic construct
    SEQUENCE: 129
DTQEKEVRAM VGSDVELSCA CPEGSRFDLN DVYVYWQTSE SKTVVTYHIP QSSSLENVDS  60
RYRNRALMSP AGMLRGDFSL RLFNVTPQDE QKFHCLVLSQ SLGFQEVLSV EVELHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 130          moltype = AA  length = 238
FEATURE                 Location/Qualifiers
REGION                  1..238
                        note = ICOSL v22 ECD
source                  1..238
                        mol_type = protein
                        organism = synthetic construct
    SEQUENCE: 130
DTQEKEVRAM VGSDVELSCA CPEGSRFDLN DVYVYWQTSE SKTVVTYHIP QNSALENVDS  60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 131          moltype = AA  length = 238
FEATURE                 Location/Qualifiers
REGION                  1..238
                        note = ICOSL v23 ECD
source                  1..238
                        mol_type = protein
                        organism = synthetic construct
    SEQUENCE: 131
DTQEKEVRAM VGSDVELSCA CPEGSRFDLN DVYVYWQTSE SKTVVTYHIP QDSPLENVDS  60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 132          moltype = AA  length = 238
FEATURE                 Location/Qualifiers
REGION                  1..238
                        note = ICOSL v24 ECD
source                  1..238
                        mol_type = protein
                        organism = synthetic construct
    SEQUENCE: 132
DTQEKEVRAM VGSDVELSCA CPEGSRFDLN DVYVYWQTSE SKTVVTYHIP QKSSLENVDS  60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNPTV GSQTGNDIGE RDKITENPVS TGEKNAAT    238

SEQ ID NO: 133          moltype = AA  length = 238
FEATURE                 Location/Qualifiers
REGION                  1..238
                        note = ICOSL v25 ECD
source                  1..238
```

-continued

```
                              mol_type = protein
                              organism = synthetic construct
SEQUENCE: 133
DTQEKEVRAM VGSDVELSCA CPEGSRFDLN DVYVYWQTSE SKTVVTYHIP QSSSLENVDS    60
RYRNRALMSP AGMLRGDFSL RLFNVTPQDE QKFHCLVLSQ SLGFQEVLSV EVTLHVAANF   120
SVPVVSAPHS PSQDELTFTC TSINGYPRPN VHWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 134           moltype = AA  length = 238
FEATURE                  Location/Qualifiers
REGION                   1..238
                         note = ICOSL v26 ECD
source                   1..238
                         mol_type = protein
                         organism = synthetic construct
SEQUENCE: 134
DTQEKEVRAM VGSDVELSCA CPEGSRFDLN DVYVYWQTSE SKTVVTYHIP QDSSLENVDS    60
RYRNRALMSP AGMLRGDFSL RLFNVTPQDE QKFHCLVLSQ SLGFQEVLSV EVTLHVAANF   120
SVPVVSAPHS PSQDELTFTC TSINGYPRPN AYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 135           moltype = AA  length = 238
FEATURE                  Location/Qualifiers
REGION                   1..238
                         note = ICOSL v27 ECD
source                   1..238
                         mol_type = protein
                         organism = synthetic construct
SEQUENCE: 135
DTQEKEVRAM VGSDVELSCA CPEGSRFDLN DVYVYWQTSE SKTVVTYHIP QHSSLENVDS    60
RYRNRALMSP AGMLRGDFSL RLFNVTPQDE QKFHCLVLSQ SLGFQEVLSV EVTLHVAANF   120
SVPVVSAPHS PSQDELTFTC TSTNGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 136           moltype = AA  length = 238
FEATURE                  Location/Qualifiers
REGION                   1..238
                         note = ICOSL v28 ECD
source                   1..238
                         mol_type = protein
                         organism = synthetic construct
SEQUENCE: 136
DTQEKEVRAM VGSDVELSCA CPEGSRFDLN DVYVYWQTSE SKTVVTYHIP QSSSLENVDS    60
RYRNRALMSP AGMLRGDFSP RLFNVTPQDE QKFHCLVLSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 137           moltype = AA  length = 238
FEATURE                  Location/Qualifiers
REGION                   1..238
                         note = ICOSL v29 ECD
source                   1..238
                         mol_type = protein
                         organism = synthetic construct
SEQUENCE: 137
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSQ SLGFQEVLSV EVTLHVAANS   120
SVPVVSAPHS PSQDELTFTC TSINGYPRPN VHWINKTDNS LLDQALQNDT VFLNMRGLYD   180
VVSVLRIART PSVNIGCCIE SVLLQQNLTV GSQTGNDIGE RDKITENPVS TGEKNAAT     238

SEQ ID NO: 138           moltype = AA  length = 238
FEATURE                  Location/Qualifiers
REGION                   1..238
                         note = ICOSL v30 ECD
source                   1..238
                         mol_type = protein
                         organism = synthetic construct
SEQUENCE: 138
DTQEKEVRAM VGSDVELSCA CPEGSRFDLN DVYVYWQTSE SKTVVTYHIP QSSSLENVDS    60
RYRNRALMSP AGMLQGDFSL RLFNVTPQDE QKFHCLVLSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVPLQQNLTV GSQTGNDIGE RDKITENPVS TGEKNAAT     238

SEQ ID NO: 139           moltype = AA  length = 238
FEATURE                  Location/Qualifiers
REGION                   1..238
                         note = ICOSL v31 ECD
source                   1..238
                         mol_type = protein
```

-continued

```
                          organism = synthetic construct
SEQUENCE: 139
DTQEKEVRAM VGSDVELSCA CPEGSRFDLN DVYVYWQTSE SKTVVTYHIP QSSSLENVDS  60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTGNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 140          moltype = AA  length = 238
FEATURE                 Location/Qualifiers
REGION                  1..238
                        note = ICOSL v32 ECD
source                  1..238
                        mol_type = protein
                        organism = synthetic construct
SEQUENCE: 140
DTQEKEVRAM VGSDVELSCA CPEGSRFDLN DVYVYWQTSE SKTVVTYHIP QDSSLENVDS  60
RYRNRALMSP AGMLRGDFSL RLFNVTPQDE QKFHCLVLSQ SLGFQEVLSV EVTLHVAANF  120
SVPVVSAPHS PSHDELTFTC TSINGYPRPN VYWINKTGNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 141          moltype = AA  length = 238
FEATURE                 Location/Qualifiers
REGION                  1..238
                        note = ICOSL v33 ECD
source                  1..238
                        mol_type = protein
                        organism = synthetic construct
SEQUENCE: 141
DTQEKEVRAM VGSDVELSCA CPEGSRFDLN DVYVYWQTSE SKTVVTYHIP QSSSLEYVDS  60
RYRNRALMSP AGMLRGDFSL RLFNVTPQDE QKFDCVFSR SLGFQEVLSV EVTLHVAANF   120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 142          moltype = AA  length = 238
FEATURE                 Location/Qualifiers
REGION                  1..238
                        note = ICOSL v34 ECD
source                  1..238
                        mol_type = protein
                        organism = synthetic construct
SEQUENCE: 142
DTQEKEVRAM VGSDVELSCA CPEGSRFDLN DVYVYWQTSE SKTVVTYHIP QSSSLEYVDS  60
RYRNRALMSP AGMLRGDFSL RLFNVTPQDE QKFDCVFSR SLEFQEVLSV EVTLHVAANS   120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 143          moltype = AA  length = 117
FEATURE                 Location/Qualifiers
REGION                  1..117
                        note = NKp30 v1 ECD
source                  1..117
                        mol_type = protein
                        organism = synthetic construct
SEQUENCE: 143
LWVSQPPEIR TLEGSSAFLP CSFNASQGRV AIGSVTWFRD EVVPGKEVRN GTPEFRGRLV  60
PLAPSRFLHD HQAELHIRDV RGHDAGIYVC RVEVLGLGVG TGNGTRLVVE KEHPQLG     117

SEQ ID NO: 144          moltype = AA  length = 117
FEATURE                 Location/Qualifiers
REGION                  1..117
                        note = NKp30 v2 ECD
source                  1..117
                        mol_type = protein
                        organism = synthetic construct
SEQUENCE: 144
LWVSQPPEIR TLEGSSAFLP CSFNASQGRV AIGSVTWFRD EVVPGKEVRN GTPEFRGRLA  60
PLASSRFLHD HQAELHIRDV RGHDASIYVC RVEVLGLGVG TGNGTRLVVE KEHPQLG     117

SEQ ID NO: 145          moltype = AA  length = 117
FEATURE                 Location/Qualifiers
REGION                  1..117
                        note = NKp30 v3 ECD
source                  1..117
                        mol_type = protein
                        organism = synthetic construct
SEQUENCE: 145
LWVSQPPEIR TLEGSSAFLP CSFNASQGRL AIGSVTWFRD EVVPGKEVRN GTPEFRGRLV  60
PLASSRFLHD HQAELHIRDV RGHDASIYVC RVEVLGLGVG TGNGTRLVVE KEHPQLG     117
```

-continued

```
SEQ ID NO: 146         moltype = AA   length = 117
FEATURE                Location/Qualifiers
REGION                 1..117
                       note = NKp30 v4 ECD
source                 1..117
                       mol_type = protein
                       organism = synthetic construct
SEQUENCE: 146
LWVSQPPEIR TLEGSSAFLP CSFNASQGRL AIGSVTWFRD EVVPGKEVRN GTPEFRGRLA 60
PLAPSRFLHD HQAELHIRDV RGHDASIYVC RVEVLGLGVG TGNGTRLVVE KEHPQLG     117

SEQ ID NO: 147         moltype = AA   length = 117
FEATURE                Location/Qualifiers
REGION                 1..117
                       note = NKp30 v5 ECD
source                 1..117
                       mol_type = protein
                       organism = synthetic construct
SEQUENCE: 147
LWVSQPPEIR TLEGSSAFLP CSFNASQGRL AIGSVTWFRD EVVPGKEVRN GTPEFRGRLA 60
PLASSRFLHD HQAELHIRDV RGHDAGIYVC RVEVLGLGVG TGNGTRLVVE KEHPQLG     117

SEQ ID NO: 148         moltype = AA   length = 224
FEATURE                Location/Qualifiers
REGION                 1..224
                       note = CD86 v1 ECD
source                 1..224
                       mol_type = protein
                       organism = synthetic construct
SEQUENCE: 148
APLKIQAYFN ETADLPCQFA NSQNQSLSEL VVFWHDQENL VLNEVYLGKE KFDSVHSKYM 60
GRTSFDSDSW TLRLHNLQIK DKGLYQCIIL HKKPTGMIRI HHMNSELSVL ANFSQPEIVP 120
ISNITENVYI NLTCSSIHGY PEPKKMSVLL RTKNSTIEYD GVMQKSQDNV TELYDVSISL 180
SVSFPDVTSN MTIFCILETD KTRLLSSPFS IELEDPQPPP DHIP                 224

SEQ ID NO: 149         moltype = AA   length = 224
FEATURE                Location/Qualifiers
REGION                 1..224
                       note = CD86 v2 ECD
source                 1..224
                       mol_type = protein
                       organism = synthetic construct
SEQUENCE: 149
APLKIQAYFN ETADLPCQFA NSQNQSLSEL VVFWHDQENL VLNEVYLGKE KFDSVHSKYM 60
GRTSFDSDSW TLRLHNLQIK DKGLYQCIIH HKKPTGMIRI HQMNSELSVL ANFSQPEIVP 120
ISNITENVYI NLTCSSIHGY PEPKKMSVLL RTKNSTIEYD GVMQKSQDNV TELYDVSISL 180
SVSFPDVTSN MTIFCILETD KTRLLSSPFS IELEDPQPPP DHIP                 224

SEQ ID NO: 150         moltype = AA   length = 224
FEATURE                Location/Qualifiers
REGION                 1..224
                       note = CD86 v3 ECD
source                 1..224
                       mol_type = protein
                       organism = synthetic construct
SEQUENCE: 150
APLKIQAYFN ETADLPCQFA NSQNQSLSEL VVFWQDQENL VLNEVYLGKE KFDSVHSKYM 60
GRTSFDSDSW TLRLHNLQIK DKGLYQCIIL HKKPTGMIRI HQMNSELSVL ANFSQPEIVP 120
ISNITENVYI NLTCSSIHGY PEPKKMSVLL RTKNSTIEYD GVMQKSQDNV TELYDVSISL 180
SVSFPDVTSN MTIFCILETD KTRLLSSPFS IELEDPQPPP DHIP                 224

SEQ ID NO: 151         moltype = AA   length = 224
FEATURE                Location/Qualifiers
REGION                 1..224
                       note = CD86 v4 ECD
source                 1..224
                       mol_type = protein
                       organism = synthetic construct
SEQUENCE: 151
APLKIQAYFN ETADLPCQFA NSQNQSLSEL VVFWQDQENL VLNEVYLGKE KFDSVHSKYM 60
GRTSFDSDSW TLRLHNLQIK DKGLYQCIIH HKKPTGMIRI HHMNSELSVL ANFSQPEIVP 120
ISNITENVYI NLTCSSIHGY PEPKKMSVLL RTKNSTIEYD GVMQKSQDNV TELYDVSISL 180
SVSFPDVTSN MTIFCILETD KTRLLSSPFS IELEDPQPPP DHIP                 224

SEQ ID NO: 152         moltype = AA   length = 101
FEATURE                Location/Qualifiers
source                 1..101
                       mol_type = protein
                       organism = Homo sapiens
```

-continued

```
SEQUENCE: 152
VIHVTKEVKE VATLSCGHNV SVEELAQTRI YWQKEKKMVL TMMSGDMNIW PEYKNRTIFD   60
ITNNLSIVIL ALRPSDEGTY ECVVLKYEKD AFKREHLAEV T                       101

SEQ ID NO: 153             moltype = AA   length = 101
FEATURE                    Location/Qualifiers
REGION                     1..101
                           note = CD80 v1 IgV
source                     1..101
                           mol_type = protein
                           organism = synthetic construct
SEQUENCE: 153
VIHVTKEVKE VATLSCGHNV SVEELAQTRI YWQKEKKMVL TMMSGDMNIW PEYKNRTIFD   60
ITNNLSIVIQ ALRPSDEGTY ECVVLKYEKD GFKREHLAEV T                       101

SEQ ID NO: 154             moltype = AA   length = 101
FEATURE                    Location/Qualifiers
REGION                     1..101
                           note = CD80 v4 IgV
source                     1..101
                           mol_type = protein
                           organism = synthetic construct
SEQUENCE: 154
VIHMTKEVKE VATLSCGHNV SVEELAQTRI YWQKEKKMVL TMMSGDMNIW PEYKNRTIFD   60
ITNNLSIVIQ ALRPSDEGTY ECVVLKYEKD GFKREHLAEV T                       101

SEQ ID NO: 155             moltype = AA   length = 101
FEATURE                    Location/Qualifiers
REGION                     1..101
                           note = CD80 v6 IgV
source                     1..101
                           mol_type = protein
                           organism = synthetic construct
SEQUENCE: 155
VIHVTKEVKE VATLSCGHNL SVEELAQTRI YWQKEKKMVL TMMSGDMNIW PEYKNRTIFD   60
ITNNLSIVIQ ALRPSDEGTY ECVVLKYEKD SFKREHLAEV T                       101

SEQ ID NO: 156             moltype = AA   length = 101
FEATURE                    Location/Qualifiers
REGION                     1..101
                           note = CD80 v7 IgV
source                     1..101
                           mol_type = protein
                           organism = synthetic construct
SEQUENCE: 156
VIHVTKEVKE VATLSCGHNV SVEELAQTRI YWQKEKKMVL TMMPGDMNIW PEYKNRTIFD   60
ITNNLSIVIQ ALRPSDEGTY ECVVLKYEKD GFKREHLAEV T                       101

SEQ ID NO: 157             moltype = AA   length = 101
FEATURE                    Location/Qualifiers
REGION                     1..101
                           note = CD80 v9 IgV
source                     1..101
                           mol_type = protein
                           organism = synthetic construct
SEQUENCE: 157
VIHVTKEVKE VATLSCGHNV SVEELAQTRI YWQKEKKMVL TMMSGDMNIW PEYKNRTIFD   60
ITNNLSIVIL ALRPSDEGTY ECVVLKYEKD GFKREHLAEV T                       101

SEQ ID NO: 158             moltype = AA   length = 101
FEATURE                    Location/Qualifiers
REGION                     1..101
                           note = CD80 v10 IgV
source                     1..101
                           mol_type = protein
                           organism = synthetic construct
SEQUENCE: 158
VIHVTKEVKE VATLSCGHNV SVEELAQTRI YWQKEKKMVL TMMSGDMNIW PEYKNRTIFD   60
ITNNLSIVIR ALRPSDEGTY ECVVLKYEKD GFKREHLAEV T                       101

SEQ ID NO: 159             moltype = AA   length = 101
FEATURE                    Location/Qualifiers
REGION                     1..101
                           note = CD80 v11 IgV
source                     1..101
                           mol_type = protein
                           organism = synthetic construct
SEQUENCE: 159
VIHVTKEVKE VATLSCGHNV SVEELAQTRI YWQKEKKMVL TMMSGDMNIW PEYKNRTIFD   60
```

-continued

```
ITNNLSIVIQ ALRPSDEGTY ACVVLKYEKD GFKREHLAEV T                         101

SEQ ID NO: 160           moltype = AA  length = 101
FEATURE                  Location/Qualifiers
REGION                   1..101
                         note = CD80 v12 IgV
source                   1..101
                         mol_type = protein
                         organism = synthetic construct
SEQUENCE: 160
VIHVTKEVKE VATLSCGHNV SVEELAQTRI YWQKEKKMVL TMMSGDMNIW PEYKNRTIFD      60
ITNNLSIVIQ ALRPSDEGTY ECVVLKNEKD GFKREHLAEV T                         101

SEQ ID NO: 161           moltype = AA  length = 101
FEATURE                  Location/Qualifiers
REGION                   1..101
                         note = CD80 v13 IgV
source                   1..101
                         mol_type = protein
                         organism = synthetic construct
SEQUENCE: 161
VIHVTKEVKE VATLSCGHNV SVEELAQSRI YWQKEKKMVL TMMSGDMNIW PEYKNRTIFD      60
ITNNLSIVIQ ALRPSDEGTY ECVVLKYEKD GFKRKHLAEV T                         101

SEQ ID NO: 162           moltype = AA  length = 101
FEATURE                  Location/Qualifiers
REGION                   1..101
                         note = CD80 v14 IgV
source                   1..101
                         mol_type = protein
                         organism = synthetic construct
SEQUENCE: 162
VIHVTKEVKE VATLSCGHNV SVEELAQTRI YWQKEKKMVL TMMSGDMNIW PEYKNRTIFD      60
ITSNLSIVIQ ALRPSDEGTY ECVVLKYEKD GFKREHLAEV T                         101

SEQ ID NO: 163           moltype = AA  length = 101
FEATURE                  Location/Qualifiers
REGION                   1..101
                         note = CD80 v15 IgV
source                   1..101
                         mol_type = protein
                         organism = synthetic construct
SEQUENCE: 163
VIHVTKEVKE VATLSCGHNV SVEELAQTRI YWQKEEKMVL TMMSGDMNIW PEYKNRTIFD      60
ITNNLSTVIQ ALRPSDEGTY ECVVLKYEKD GFKREHLAEV T                         101

SEQ ID NO: 164           moltype = AA  length = 101
FEATURE                  Location/Qualifiers
REGION                   1..101
                         note = CD80 v16 IgV
source                   1..101
                         mol_type = protein
                         organism = synthetic construct
SEQUENCE: 164
VIHVTKEVKE VATLSCGHNV SVEELAQTRI YWQKEKKMVL TMMSGDMNIW PGYKNRTIFD      60
ITNNLSIVIQ ALRPSDEGTY ECVVLKYEKD GFKREHLAEV T                         101

SEQ ID NO: 165           moltype = AA  length = 101
FEATURE                  Location/Qualifiers
REGION                   1..101
                         note = CD80 v17 IgV
source                   1..101
                         mol_type = protein
                         organism = synthetic construct
SEQUENCE: 165
VIHVTKEVKE VATLSCGHNV SVEELAQTRI YWQKEKEMVL TMMSGDMNIW PEYKNRTISD      60
ITNNLSIVIQ ALRPSDEGTY ECVVLKYEKD GFKREHLAEV T                         101

SEQ ID NO: 166           moltype = AA  length = 101
FEATURE                  Location/Qualifiers
REGION                   1..101
                         note = CD80 v19 IgV
source                   1..101
                         mol_type = protein
                         organism = synthetic construct
SEQUENCE: 166
VIHVTKEVKE VATLSCGHNV SVEELAQTRI YWQKEKKMVL TMMSGDMNIW PEYKNRTIFD      60
ITNNLSIVIL ALRPSDEGTY ECVVLKYEED AFKREHLAEV T                         101
```

```
SEQ ID NO: 167              moltype = AA  length = 101
FEATURE                     Location/Qualifiers
REGION                      1..101
                            note = CD80 v21 IgV
source                      1..101
                            mol_type = protein
                            organism = synthetic construct
SEQUENCE: 167
VIHVTKEVKE VATLSCGHNV SVEELAQTRI YWQKEKKMVL TMMSGDMNIW PEYKNRTIFV   60
ITNNLSIVIL ALRPSDEGTY ECVVLKYEKD GFKREHLAEV T                       101

SEQ ID NO: 168              moltype = AA  length = 101
FEATURE                     Location/Qualifiers
REGION                      1..101
                            note = CD80 v22 IgV
source                      1..101
                            mol_type = protein
                            organism = synthetic construct
SEQUENCE: 168
VIHVTKEVKE VATLSCGHNV SVEELAQTRI YWQKEKKMVL TMMSGDMNIW PEYMNRTIFD   60
ITNNLSIVIL ALRPSDEGTY ECVVLKYEKD GFKREHLAEV T                       101

SEQ ID NO: 169              moltype = AA  length = 101
FEATURE                     Location/Qualifiers
REGION                      1..101
                            note = CD80 v23 IgV
source                      1..101
                            mol_type = protein
                            organism = synthetic construct
SEQUENCE: 169
VIHVTKEVKE VATLSCGHNV SVEELAQTRI YWQKEKKTVL TMMSGDMNIW PEYKNRTIFD   60
ITNNLSIVIQ ALRPSDGGTY ECVVLKYEKD GFKREHLAEV T                       101

SEQ ID NO: 170              moltype = AA  length = 101
FEATURE                     Location/Qualifiers
REGION                      1..101
                            note = CD80 v24 IgV
source                      1..101
                            mol_type = protein
                            organism = synthetic construct
SEQUENCE: 170
VIHVTKEVKE VATLSCGHNV SVEELAQTHI YWQKEKKMVL TMMSGDMNIW PGYKNRTIFD   60
ITNNLSIVIR ALRPSDEGTY ECVVLKYGKD GFKREHLAEV T                       101

SEQ ID NO: 171              moltype = AA  length = 101
FEATURE                     Location/Qualifiers
REGION                      1..101
                            note = CD80 v25 IgV
source                      1..101
                            mol_type = protein
                            organism = synthetic construct
SEQUENCE: 171
VIHVTKEVKE VATLSCGHNV SVEELAQTRI HWQKEKKMVL GMMSGDMNIW PEYKNRTIFD   60
ITNNLSIVIQ ALRPSDEGTY ECVVLKYEKD GFKREHLAEV T                       101

SEQ ID NO: 172              moltype = AA  length = 101
FEATURE                     Location/Qualifiers
REGION                      1..101
                            note = CD80 v26 IgV
source                      1..101
                            mol_type = protein
                            organism = synthetic construct
SEQUENCE: 172
VIHVTKEVKE VATLSCGHNV SVEELAQTRI YWQKEKKMVL TMMSGDMNIW PEYKNRTIFD   60
ITNNLSIAIL ALRPSDEGTY ECVVLKYEKD AFKREHLAEV T                       101

SEQ ID NO: 173              moltype = AA  length = 101
FEATURE                     Location/Qualifiers
REGION                      1..101
                            note = CD80 v27 IgV
source                      1..101
                            mol_type = protein
                            organism = synthetic construct
SEQUENCE: 173
VIHVTKEVKE VATLSCGHNV SVEELAQTRI YWQKEKKMVL TMMSGDMNIW PEYKNRTIFD   60
ITNNLHIVIL ALRPSDEGTY ECVVLKYEKG AFKREHLAEV T                       101

SEQ ID NO: 174              moltype = AA  length = 101
FEATURE                     Location/Qualifiers
```

-continued

```
REGION                  1..101
                        note = CD80 v28 IgV
source                  1..101
                        mol_type = protein
                        organism = synthetic construct
SEQUENCE: 174
VIHVTKEVKE VATLSCGHNV SVEELAQTHI YWQKEKKMVL TMMSGDMNIW PGYKNRTIFD   60
ITNNLSIVIL ALRPSDEGTY ECVVLKYEKD AFKREHLAEV T                      101

SEQ ID NO: 175          moltype = AA  length = 101
FEATURE                 Location/Qualifiers
REGION                  1..101
                        note = CD80 v30 IgV
source                  1..101
                        mol_type = protein
                        organism = synthetic construct
SEQUENCE: 175
VIHVTKEVKE VATLSCGHNV SVEELAQTRI YWQKEKKMVL TMMSGDMNIW PEYKNRTIFD   60
ITNNLSTVIQ ALRPSDEGTY ECVVLKYEKD GFKREHLAEV T                      101

SEQ ID NO: 176          moltype = AA  length = 101
FEATURE                 Location/Qualifiers
REGION                  1..101
                        note = CD80 v32 IgV
source                  1..101
                        mol_type = protein
                        organism = synthetic construct
SEQUENCE: 176
VIHVTKEVKE VATLSCGHNV SVEELAQTRI YWQKEKKVVL DMISGDMNIG PEYKNRTIFD   60
ITNNLSIVIL ALRPSGEGTY ECAVLKYEED AFKREHLAEV T                      101

SEQ ID NO: 177          moltype = AA  length = 101
FEATURE                 Location/Qualifiers
REGION                  1..101
                        note = CD80 v33 IgV
source                  1..101
                        mol_type = protein
                        organism = synthetic construct
SEQUENCE: 177
VIHVTKEVKE VATLSCGHNV SAEELAQTRI YWQKEKKMVL TMMSGDMNIW PEYKNRTIFD   60
ITNNLSIVIQ ALRPSDEGTY ECVVLKYEKD AFKREHLAEV T                      101

SEQ ID NO: 178          moltype = AA  length = 101
FEATURE                 Location/Qualifiers
REGION                  1..101
                        note = CD80 v34 IgV
source                  1..101
                        mol_type = protein
                        organism = synthetic construct
SEQUENCE: 178
VIHVTKEVKE VVTLFCGHNV SVEELAQTRI HWQKEKKMVL GMMSGDMNIW PEYKNRTIFD   60
ITNNLSIVIL ALRPSDEGTY ECVVLKYEKD AFKREHLAEV T                      101

SEQ ID NO: 179          moltype = AA  length = 101
FEATURE                 Location/Qualifiers
REGION                  1..101
                        note = CD80 v35 IgV
source                  1..101
                        mol_type = protein
                        organism = synthetic construct
SEQUENCE: 179
VIHVTKEVKE VATLSCGHNV SVEELAQTRI YWQKEKKMVL TMMSGDMNIW PEYKNRTIFD   60
ITNNLSFVIR ALRPSDEGTY ECVVLKYGKD GFKREHLAEV T                      101

SEQ ID NO: 180          moltype = AA  length = 101
FEATURE                 Location/Qualifiers
REGION                  1..101
                        note = CD80 v36 IgV
source                  1..101
                        mol_type = protein
                        organism = synthetic construct
SEQUENCE: 180
VIHVTKEVKE VATLSCGHNV SVEGPAQTRI YWQKEKKMVL TMMSGDMNIW PEYKNRTIFD   60
ITNNLSIVIQ ALRPSDEGTY ECVVLKYEKD AFKREHLAEV T                      101

SEQ ID NO: 181          moltype = AA  length = 101
FEATURE                 Location/Qualifiers
REGION                  1..101
                        note = CD80 v37 IgV
```

-continued

```
source                    1..101
                          mol_type = protein
                          organism = synthetic construct
SEQUENCE: 181
VIHVTKEVKE VATLSCGHNV SVEELAQTRI YWQKEKKMVL TMMSGDMNIW PEYKNRTIFD    60
ITNNLSIVIL ALRPSDEGTY ECVVLKYEKD GLKREHLAEV T                       101

SEQ ID NO: 182           moltype = AA  length = 101
FEATURE                  Location/Qualifiers
REGION                   1..101
                         note = CD80 v38 IgV
source                   1..101
                         mol_type = protein
                         organism = synthetic construct
SEQUENCE: 182
VIHVTKEVKE VATLSCGHNV SVEELAQTDI LWHKEGKIVL AMRSGDTNIW PEYKNRTIFD    60
ITNNLSIVIL ALRPSDEGTY VCVVRKYEND TPVLEHLAEV T                       101

SEQ ID NO: 183           moltype = AA  length = 101
FEATURE                  Location/Qualifiers
REGION                   1..101
                         note = CD80 v40 IgV
source                   1..101
                         mol_type = protein
                         organism = synthetic construct
SEQUENCE: 183
VIHVTKEVKE VATLSCGHNV SVEELAQTDI LWHKEGKIVL ATRSGDTNIW PEYKNRTIFD    60
ITNNLSIVIL ALRPSDEGTY VCVVRKYEND TPVLEHLAEV T                       101

SEQ ID NO: 184           moltype = AA  length = 101
FEATURE                  Location/Qualifiers
REGION                   1..101
                         note = CD80 v41 IgV
source                   1..101
                         mol_type = protein
                         organism = synthetic construct
SEQUENCE: 184
VIHVTKEVKE VATLSCGHNV SVEGLAQTDI LWHKEGKIVL AMRSGDTNIW PEYKNRTILD    60
ITNNLSIVIL ALRPSDEGTY VCVVRKYEND TPVLERLAEV T                       101

SEQ ID NO: 185           moltype = AA  length = 101
FEATURE                  Location/Qualifiers
REGION                   1..101
                         note = CD80 v43 IgV
source                   1..101
                         mol_type = protein
                         organism = synthetic construct
SEQUENCE: 185
VIHVTKEVKE VATLSCGHNV SVEELAQTVI YWQKEKKMVL TMQSGDMNIW PEYKNRTIFD    60
ITNNLSIVIL ALRPSDEGTY RCVVIKYERL ENQGEHLAEV T                       101

SEQ ID NO: 186           moltype = AA  length = 101
FEATURE                  Location/Qualifiers
REGION                   1..101
                         note = CD80 v44 IgV
source                   1..101
                         mol_type = protein
                         organism = synthetic construct
SEQUENCE: 186
VIHVTKEVKE VATLSCGHNV SVEELAQTRI YWQKEKKMVL IMMSGDMNIW PEYKNRTIFD    60
ITNNLSIVIL ALRPSDEGTY ECVVLKYEKD GFKREHLAEV T                       101

SEQ ID NO: 187           moltype = AA  length = 101
FEATURE                  Location/Qualifiers
REGION                   1..101
                         note = CD80 v45 IgV
source                   1..101
                         mol_type = protein
                         organism = synthetic construct
SEQUENCE: 187
VIHVTKEVKE VATLSCGHNV SVEELAQTRI YWQKEKKMVL TMMSGDMNIW PEYKNRTIFD    60
ITNNLSIVIL ALRPSDEGTY ECVVLKYERK GYRREHLAEV T                       101

SEQ ID NO: 188           moltype = AA  length = 101
FEATURE                  Location/Qualifiers
REGION                   1..101
                         note = CD80 v47 IgV
source                   1..101
                         mol_type = protein
```

-continued

```
                                organism = synthetic construct
SEQUENCE: 188
VIHVTKEVKE VATLSCGHNV SVEELAQTRI YWQKEGQIVL TMMSGDMNIW PEYKNRTILD    60
ITNNLSIVIL ALRPSDEGTY VCVVRKYEND TPVLEHLAGV T                        101

SEQ ID NO: 189         moltype = AA  length = 101
FEATURE                Location/Qualifiers
REGION                 1..101
                       note = CD80 v48 IgV
source                 1..101
                       mol_type = protein
                       organism = synthetic construct
SEQUENCE: 189
VIHVTKEVKE VATLSCGHNV SVEELAQTRI YWQKEKKMVL TMMSGDMNIW PEYKNRTIFD    60
ITNNLSIVIL ALRPSDEGTY ECVVLKYDRK GYRREHLAEV T                        101

SEQ ID NO: 190         moltype = AA  length = 101
FEATURE                Location/Qualifiers
REGION                 1..101
                       note = CD80 v49 IgV
source                 1..101
                       mol_type = protein
                       organism = synthetic construct
SEQUENCE: 190
VIHVTKEVKE VATLSCGHNV SVEELAQTRI YWQKEGQIVM TMMSGDMNIW PEYKNRTIFD    60
ITNNLSIVIL ALRPSDEGTY ECVVLKYEKD AFKREHLAEV T                        101

SEQ ID NO: 191         moltype = AA  length = 101
FEATURE                Location/Qualifiers
REGION                 1..101
                       note = CD80 v50 IgV
source                 1..101
                       mol_type = protein
                       organism = synthetic construct
SEQUENCE: 191
VIHVTKEVKE VATLSCGHNV SVEELAQTRI YWQKEGKMVL TMMSGDMNIW PEYKNRTIFD    60
ITNNLSIVIL ALRPSDEGTY ECVVLKYEKD AFKREHLAEV T                        101

SEQ ID NO: 192         moltype = AA  length = 101
FEATURE                Location/Qualifiers
REGION                 1..101
                       note = CD80 v51 IgV
source                 1..101
                       mol_type = protein
                       organism = synthetic construct
SEQUENCE: 192
VIHVTKEVKE VATLSCGHNV SVEELAQTHI HWQKEKKMVL GMMSGDMNIW PEYKNRTIFD    60
ITNNLSIVIL ALRPSDEGTY ECVVLKNGEN GFKREHLAEV T                        101

SEQ ID NO: 193         moltype = AA  length = 101
FEATURE                Location/Qualifiers
REGION                 1..101
                       note = CD80 v52 IgV
source                 1..101
                       mol_type = protein
                       organism = synthetic construct
SEQUENCE: 193
VIHVTKEVKE VTTLSCGLNV SVEELAQTRI YWQKEKKMVL TMVSGDMNIW PEYKNRTILD    60
ITNNLSIVIL ALRPSDKGTY ECVVLKYEKD AFKREHLAEV T                        101

SEQ ID NO: 194         moltype = AA  length = 101
FEATURE                Location/Qualifiers
REGION                 1..101
                       note = CD80 v53 IgV
source                 1..101
                       mol_type = protein
                       organism = synthetic construct
SEQUENCE: 194
VIHVTKEVKE VATLSCGHNV SVEELAQTVI FWQKEGKLVL TMQSGDMNIW PEYKNRTIFD    60
ITNNLSIVIL ALRPSDEGTY RCIVIKYERL ENQGEHLAEV T                        101

SEQ ID NO: 195         moltype = AA  length = 101
FEATURE                Location/Qualifiers
REGION                 1..101
                       note = CD80 v54 IgV
source                 1..101
                       mol_type = protein
                       organism = synthetic construct
SEQUENCE: 195
```

```
VIHVTKEVKE VATLSCGHNV SVEELAQTRI YWQKEKKMVL TMMSGDMNIW PEYKNRTIFD  60
ITNNLSIMIP APRPSDEGTY ECVVLEYEKD AFKREHLAEV T                     101

SEQ ID NO: 196          moltype = AA  length = 111
FEATURE                 Location/Qualifiers
REGION                  1..111
                        note = ICOSL WT IgV
source                  1..111
                        mol_type = protein
                        organism = synthetic construct
SEQUENCE: 196
DTQEKEVRAM VGSDVELSCA CPEGSRFDLN DVYVYWQTSE SKTVVTYHIP QNSSLENVDS  60
RYRNRALMSP AGMLRGDFSL RLFNVTPQDE QKFHCLVLSQ SLGFQEVLSV E          111

SEQ ID NO: 197          moltype = AA  length = 111
FEATURE                 Location/Qualifiers
REGION                  1..111
                        note = ICOSL v1 IgV
source                  1..111
                        mol_type = protein
                        organism = synthetic construct
SEQUENCE: 197
DTQEKEVRAM VGSDVELSCA CPEGSRFDLN DVYVYWQTSE SKTVVTYHIP QSSSLENVDS  60
RYRNRALMSP AGMLRGDFSL RLFNVTPQDE QKFHCLVLSQ SLGFQEVLSV E          111

SEQ ID NO: 198          moltype = AA  length = 111
FEATURE                 Location/Qualifiers
REGION                  1..111
                        note = ICOSL v2 IgV
source                  1..111
                        mol_type = protein
                        organism = synthetic construct
SEQUENCE: 198
DTQEKEVRAM VGSDVELSCA CPEGSRFDLN DVYVYWQTSE SKTVVTYHIP QHSSLENVDS  60
RYRNRALMSP AGMLRGDFSL RLFNVTPQDE QKFHCLVLSQ SLGFQEVLSV E          111

SEQ ID NO: 199          moltype = AA  length = 111
FEATURE                 Location/Qualifiers
REGION                  1..111
                        note = ICOSL v3 IgV
source                  1..111
                        mol_type = protein
                        organism = synthetic construct
SEQUENCE: 199
DTQEKEVRAM VGSDVELSCA CPEGSRFDLN DVYVYWQTSE SKTVVTYHIP QDSSLENVDS  60
RYRNRALMSP AGMLRGDFSL RLFNVTPQDE QKFHCLVLSQ SLGFQEVLSV E          111

SEQ ID NO: 200          moltype = AA  length = 111
FEATURE                 Location/Qualifiers
REGION                  1..111
                        note = ICOSL v4 IgV
source                  1..111
                        mol_type = protein
                        organism = synthetic construct
SEQUENCE: 200
DTQEKEVRAM VGSDVELSCA CPEGSRFDLN DVYVYWQTSE SKTVVTYHIP QYSSLEYVDS  60
RYRNRALMSP AGMLRGDFSL RLFNVTPQDE QKFHCLVLSQ SLGFQEVLSV E          111

SEQ ID NO: 201          moltype = AA  length = 111
FEATURE                 Location/Qualifiers
REGION                  1..111
                        note = ICOSL v5 IgV
source                  1..111
                        mol_type = protein
                        organism = synthetic construct
SEQUENCE: 201
DTQEKEVRAM VGSDVELSCA CPEGSRFDLN DVYVYWQTSE SKTVVTYHIP QHSSLEYVDS  60
RYRNRALMSP AGMLRGDFSL RLFNVTPQDE QKFHCLVLSP SLGFQEVLSV E          111

SEQ ID NO: 202          moltype = AA  length = 111
FEATURE                 Location/Qualifiers
REGION                  1..111
                        note = ICOSL v10 IgV
source                  1..111
                        mol_type = protein
                        organism = synthetic construct
SEQUENCE: 202
DTQEKEVRAM VGSDVELSCA CPEGSRFDLN DVYVYWQTSE SKTVVTYHIP QHSSLENVDS  60
RYRNRALMSP AGMLRGDFSL RLFNVTPQDE QRFHCLVLSQ SLGFQEVLSV E          111
```

-continued

```
SEQ ID NO: 203           moltype = AA  length = 111
FEATURE                  Location/Qualifiers
REGION                   1..111
                         note = ICOSL v11 IgV
source                   1..111
                         mol_type = protein
                         organism = synthetic construct
SEQUENCE: 203
DTQEKEVRAM VGSDVELSCA CPEGSRFDLN DVYVYWQTSE SKTVVTYHIP QHSSLENVDS  60
RYRNRALMSP AGMLRGDFSL RLFNVTPQDE QKFHCLVLGQ SLGFQEVLSV E          111

SEQ ID NO: 204           moltype = AA  length = 111
FEATURE                  Location/Qualifiers
REGION                   1..111
                         note = ICOSL v12 IgV
source                   1..111
                         mol_type = protein
                         organism = synthetic construct
SEQUENCE: 204
DTQEKEVRAM VGSDVELSCA CPEGSRFDLN DVYVYWQTSE SKTVVTYHIP QYSSLENVDS  60
RYRNRALMSP AGMLRGDFSL RLFNVTPQDE QKFHCLVLSQ SLGFQEVLSV E          111

SEQ ID NO: 205           moltype = AA  length = 111
FEATURE                  Location/Qualifiers
REGION                   1..111
                         note = ICOSL v13 IgV
source                   1..111
                         mol_type = protein
                         organism = synthetic construct
SEQUENCE: 205
DTQEKEVRAM VGSDVELSCA CPEGSRFDLN DVYVYWQTSE SKTVVTYHIP QNSSLEYVDS  60
RYRNRALMSP AGMLRGDFSL RLFNVTPQDE QKFHCLVLSQ SLGFQEVLSV E          111

SEQ ID NO: 206           moltype = AA  length = 111
FEATURE                  Location/Qualifiers
REGION                   1..111
                         note = ICOSL v14 IgV
source                   1..111
                         mol_type = protein
                         organism = synthetic construct
SEQUENCE: 206
DTQEKEVRAM VGSDVELSCA CPEGSRFDLN DVYVYWQTSE SKTVVTYHIP QNSSLEYVDS  60
RYRNRALMSP AGMLRGDFSL RLFNVTPQDE QKFHCLVLSP SLGFQEVLSV E          111

SEQ ID NO: 207           moltype = AA  length = 111
FEATURE                  Location/Qualifiers
REGION                   1..111
                         note = ICOSL v22 IgV
source                   1..111
                         mol_type = protein
                         organism = synthetic construct
SEQUENCE: 207
DTQEKEVRAM VGSDVELSCA CPEGSRFDLN DVYVYWQTSE SKTVVTYHIP QNSALENVDS  60
RYRNRALMSP AGMLRGDFSL RLFNVTPQDE QKFHCLVLSQ SLGFQEVLSV E          111

SEQ ID NO: 208           moltype = AA  length = 111
FEATURE                  Location/Qualifiers
REGION                   1..111
                         note = ICOSL v23 IgV
source                   1..111
                         mol_type = protein
                         organism = synthetic construct
SEQUENCE: 208
DTQEKEVRAM VGSDVELSCA CPEGSRFDLN DVYVYWQTSE SKTVVTYHIP QDSPLENVDS  60
RYRNRALMSP AGMLRGDFSL RLFNVTPQDE QKFHCLVLSQ SLGFQEVLSV E          111

SEQ ID NO: 209           moltype = AA  length = 111
FEATURE                  Location/Qualifiers
REGION                   1..111
                         note = ICOSL v24 IgV
source                   1..111
                         mol_type = protein
                         organism = synthetic construct
SEQUENCE: 209
DTQEKEVRAM VGSDVELSCA CPEGSRFDLN DVYVYWQTSE SKTVVTYHIP QKSSLENVDS  60
RYRNRALMSP AGMLRGDFSL RLFNVTPQDE QKFHCLVLSQ SLGFQEVLSV E          111

SEQ ID NO: 210           moltype = AA  length = 111
```

-continued

```
FEATURE                  Location/Qualifiers
REGION                   1..111
                         note = ICOSL v28 IgV
source                   1..111
                         mol_type = protein
                         organism = synthetic construct
SEQUENCE: 210
DTQEKEVRAM VGSDVELSCA CPEGSRFDLN DVYVYWQTSE SKTVVTYHIP QSSSLENVDS  60
RYRNRALMSP AGMLRGDFSP RLFNVTPQDE QKFHCLVLSQ SLGFQEVLSV E           111

SEQ ID NO: 211           moltype = AA  length = 111
FEATURE                  Location/Qualifiers
REGION                   1..111
                         note = ICOSL v30 IgV
source                   1..111
                         mol_type = protein
                         organism = synthetic construct
SEQUENCE: 211
DTQEKEVRAM VGSDVELSCA CPEGSRFDLN DVYVYWQTSE SKTVVTYHIP QSSSLENVDS  60
RYRNRALMSP AGMLQGDFSL RLFNVTPQDE QKFHCLVLSQ SLGFQEVLSV E           111

SEQ ID NO: 212           moltype = AA  length = 111
FEATURE                  Location/Qualifiers
REGION                   1..111
                         note = ICOSL v33 IgV
source                   1..111
                         mol_type = protein
                         organism = synthetic construct
SEQUENCE: 212
DTQEKEVRAM VGSDVELSCA CPEGSRFDLN DVYVYWQTSE SKTVVTYHIP QSSSLEYVDS  60
RYRNRALMSP AGMLRGDFSL RLFNVTPQDE QKFDCFVFSR SLGFQEVLSV E           111

SEQ ID NO: 213           moltype = AA  length = 111
FEATURE                  Location/Qualifiers
REGION                   1..111
                         note = ICOSL v34 IgV
source                   1..111
                         mol_type = protein
                         organism = synthetic construct
SEQUENCE: 213
DTQEKEVRAM VGSDVELSCA CPEGSRFDLN DVYVYWQTSE SKTVVTYHIP QSSSLEYVDS  60
RYRNRALMSP AGMLRGDFSL RLFNVTPQDE QKFDCFVFSR SLEFQEVLSV E           111

SEQ ID NO: 214           moltype = AA  length = 108
FEATURE                  Location/Qualifiers
REGION                   1..108
                         note = MISC_FEATURE - NKp30 WT IgC-like
source                   1..108
                         mol_type = protein
                         organism = Homo sapiens
SEQUENCE: 214
LWVSQPPEIR TLEGSSAFLP CSFNASQGRL AIGSVTWFRD EVVPGKEVRN GTPEFRGRLA  60
PLASSRFLHD HQAELHIRDV RGHDASIYVC RVEVLGLGVG TGNGTRLV               108

SEQ ID NO: 215           moltype = AA  length = 108
FEATURE                  Location/Qualifiers
REGION                   1..108
                         note = NKp30 v1 IgC-like
source                   1..108
                         mol_type = protein
                         organism = synthetic construct
SEQUENCE: 215
LWVSQPPEIR TLEGSSAFLP CSFNASQGRV AIGSVTWFRD EVVPGKEVRN GTPEFRGRLV  60
PLAPSRFLHD HQAELHIRDV RGHDAGIYVC RVEVLGLGVG TGNGTRLV               108

SEQ ID NO: 216           moltype = AA  length = 108
FEATURE                  Location/Qualifiers
REGION                   1..108
                         note = NKp30 v2 IgC-like
source                   1..108
                         mol_type = protein
                         organism = synthetic construct
SEQUENCE: 216
LWVSQPPEIR TLEGSSAFLP CSFNASQGRV AIGSVTWFRD EVVPGKEVRN GTPEFRGRLA  60
PLASSRFLHD HQAELHIRDV RGHDASIYVC RVEVLGLGVG TGNGTRLV               108

SEQ ID NO: 217           moltype = AA  length = 108
FEATURE                  Location/Qualifiers
REGION                   1..108
```

-continued

```
                              note = NKp30 v3 IgC-like
source                        1..108
                              mol_type = protein
                              organism = synthetic construct
SEQUENCE: 217
LWVSQPPEIR TLEGSSAFLP CSFNASQGRL AIGSVTWFRD EVVPGKEVRN GTPEFRGRLV   60
PLASSRFLHD HQAELHIRDV RGHDASIYVC RVEVLGLGVG TGNGTRLV                 108

SEQ ID NO: 218                moltype = AA  length = 108
FEATURE                       Location/Qualifiers
REGION                        1..108
                              note = NKp30 v4 IgC-like
source                        1..108
                              mol_type = protein
                              organism = synthetic construct
SEQUENCE: 218
LWVSQPPEIR TLEGSSAFLP CSFNASQGRL AIGSVTWFRD EVVPGKEVRN GTPEFRGRLA   60
PLAPSRFLHD HQAELHIRDV RGHDASIYVC RVEVLGLGVG TGNGTRLV                 108

SEQ ID NO: 219                moltype = AA  length = 108
FEATURE                       Location/Qualifiers
REGION                        1..108
                              note = NKp30 v5 IgC-like
source                        1..108
                              mol_type = protein
                              organism = synthetic construct
SEQUENCE: 219
LWVSQPPEIR TLEGSSAFLP CSFNASQGRL AIGSVTWFRD EVVPGKEVRN GTPEFRGRLA   60
PLASSRFLHD HQAELHIRDV RGHDAGIYVC RVEVLGLGVG TGNGTRLV                 108

SEQ ID NO: 220                moltype = AA  length = 99
FEATURE                       Location/Qualifiers
REGION                        1..99
                              note = MISC_FEATURE - CD86 WT IgV
source                        1..99
                              mol_type = protein
                              organism = Homo sapiens
SEQUENCE: 220
NETADLPCQF ANSQNQSLSE LVVFWQDQEN LVLNEVYLGK EKFDSVHSKY MGRTSFDSDS   60
WTLRLHNLQI KDKGLYQCII HHKKPTGMIR IHQMNSELS                          99

SEQ ID NO: 221                moltype = AA  length = 99
FEATURE                       Location/Qualifiers
REGION                        1..99
                              note = CD86 v1 IgV
source                        1..99
                              mol_type = protein
                              organism = synthetic construct
SEQUENCE: 221
NETADLPCQF ANSQNQSLSE LVVFWHDQEN LVLNEVYLGK EKFDSVHSKY MGRTSFDSDS   60
WTLRLHNLQI KDKGLYQCII LHKKPTGMIR IHHMNSELS                          99

SEQ ID NO: 222                moltype = AA  length = 99
FEATURE                       Location/Qualifiers
REGION                        1..99
                              note = CD86 v2 IgV
source                        1..99
                              mol_type = protein
                              organism = synthetic construct
SEQUENCE: 222
NETADLPCQF ANSQNQSLSE LVVFWHDQEN LVLNEVYLGK EKFDSVHSKY MGRTSFDSDS   60
WTLRLHNLQI KDKGLYQCII HHKKPTGMIR IHQMNSELS                          99

SEQ ID NO: 223                moltype = AA  length = 99
FEATURE                       Location/Qualifiers
REGION                        1..99
                              note = CD86 v3 IgV
source                        1..99
                              mol_type = protein
                              organism = synthetic construct
SEQUENCE: 223
NETADLPCQF ANSQNQSLSE LVVFWQDQEN LVLNEVYLGK EKFDSVHSKY MGRTSFDSDS   60
WTLRLHNLQI KDKGLYQCII LHKKPTGMIR IHQMNSELS                          99

SEQ ID NO: 224                moltype = AA  length = 99
FEATURE                       Location/Qualifiers
REGION                        1..99
                              note = CD86 v4 IgV
source                        1..99
```

-continued

```
                            mol_type = protein
                            organism = synthetic construct
SEQUENCE: 224
NETADLPCQF ANSQNQSLSE LVVFWQDQEN LVLNEVYLGK EKFDSVHSKY MGRTSFDSDS    60
WTLRLHNLQI KDKGLYQCII HHKKPTGMIR IHHMNSELS                           99

SEQ ID NO: 225            moltype = AA  length = 19
FEATURE                   Location/Qualifiers
REGION                    1..19
                          note = MISC_FEATURE - VH signal peptide
source                    1..19
                          mol_type = protein
                          organism = Homo sapiens
SEQUENCE: 225
MGSTAILALL LAVLQGVSA                                                 19

SEQ ID NO: 226            moltype = AA  length = 232
FEATURE                   Location/Qualifiers
REGION                    1..232
                          note = MISC_FEATURE - IgG1 Fc
source                    1..232
                          mol_type = protein
                          organism = Homo sapiens
SEQUENCE: 226
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR EEMTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 227            moltype = AA  length = 235
FEATURE                   Location/Qualifiers
REGION                    1..235
                          note = MISC_FEATURE - IgG2 Fc
source                    1..235
                          mol_type = protein
                          organism = Homo sapiens
SEQUENCE: 227
TKVDKTVERK CCVECPPCPA PPVAGPSVFL FPPKPKDTLM ISRTPEVTCV VVDVSHEDPE    60
VQFNWYVDGV EVHNAKTKPR EEQFNSTFRV VSVLTVVHQD WLNGKEYKCK VSNKGLPAPI   120
EKTISKTKGQ PREPQVYTLP PSREEMTKNQ VSLTCLVKGF YPSDIAVEWE SNGQPENNYK   180
TTPPMLDSDG SFFLYSKLTV DKSRWQQGNV FSCSVMHEAL HNHYTQKSLS LSPGK        235

SEQ ID NO: 228            moltype = AA  length = 15
FEATURE                   Location/Qualifiers
REGION                    1..15
                          note = IgV-IgV linker
source                    1..15
                          mol_type = protein
                          organism = synthetic construct
SEQUENCE: 228
GGGGSGGGGS GGGGS                                                    15

SEQ ID NO: 229            moltype = AA  length = 10
FEATURE                   Location/Qualifiers
REGION                    1..10
                          note = IgV-Fc linker 1
source                    1..10
                          mol_type = protein
                          organism = synthetic construct
SEQUENCE: 229
GGGGSGGGGS                                                          10

SEQ ID NO: 230            moltype = AA  length = 13
FEATURE                   Location/Qualifiers
REGION                    1..13
                          note = IgV-Fc linker 2
source                    1..13
                          mol_type = protein
                          organism = synthetic construct
SEQUENCE: 230
GGGGSGGGGS AAA                                                      13

SEQ ID NO: 231            moltype = AA  length = 15
FEATURE                   Location/Qualifiers
REGION                    1..15
                          note = CD80 WT linker 1
source                    1..15
                          mol_type = protein
                          organism = synthetic construct
```

-continued

```
SEQUENCE: 231
KADFPTPSIS DFEIP                                                         15

SEQ ID NO: 232        moltype = AA  length = 10
FEATURE               Location/Qualifiers
REGION                1..10
                      note = CD80 WT linker 2
source                1..10
                      mol_type = protein
                      organism = synthetic construct
SEQUENCE: 232
TTKQEHFPDN                                                              10

SEQ ID NO: 233        moltype = AA  length = 11
FEATURE               Location/Qualifiers
REGION                1..11
                      note = ICOSL WT linker 1
source                1..11
                      mol_type = protein
                      organism = synthetic construct
SEQUENCE: 233
VTLHVAANFS V                                                            11

SEQ ID NO: 234        moltype = AA  length = 29
FEATURE               Location/Qualifiers
REGION                1..29
                      note = ICOSL WT linker 2
source                1..29
                      mol_type = protein
                      organism = synthetic construct
SEQUENCE: 234
VGSQTGNDIG ERDKITENPV STGEKNAAT                                         29

SEQ ID NO: 235        moltype = AA  length = 9
FEATURE               Location/Qualifiers
REGION                1..9
                      note = NKp30 WT linker 1
source                1..9
                      mol_type = protein
                      organism = synthetic construct
SEQUENCE: 235
VEKEHPQLG                                                                9

SEQ ID NO: 236        moltype = AA  length = 9
FEATURE               Location/Qualifiers
REGION                1..9
                      note = CD86 WT linker 1
source                1..9
                      mol_type = protein
                      organism = synthetic construct
SEQUENCE: 236
APLKIQAYF                                                                9

SEQ ID NO: 237        moltype = AA  length = 18
FEATURE               Location/Qualifiers
REGION                1..18
                      note = CD86 WT linker 2
source                1..18
                      mol_type = protein
                      organism = synthetic construct
SEQUENCE: 237
VLANFSQPEI VPISNITE                                                     18

SEQ ID NO: 238        moltype = AA  length = 22
FEATURE               Location/Qualifiers
REGION                1..22
                      note = CD86 WT linker 3
source                1..22
                      mol_type = protein
                      organism = synthetic construct
SEQUENCE: 238
RLLSSPFSIE LEDPQPPPDH IP                                                22

SEQ ID NO: 239        moltype = AA  length = 238
FEATURE               Location/Qualifiers
REGION                1..238
                      note = ICOSL v35 ECD
source                1..238
                      mol_type = protein
```

-continued

```
                        organism = synthetic construct
SEQUENCE: 239
DTQEKEVRAM VGSDVELSCA CPEGSRFDLN DVYVYWQTSE SKTVVTYHIP QSSSLENVDS  60
RYRNRALMSP AGMLRGDFSL RLFNVTPQDE QKFHCLVLSQ SLEFQEVLSV EVTLHVAANF 120
SVPVVSAPHS PSQDELTFTC TSINGYPRPN VYWINKTDNS LLDQALQNDT VFLNMRGLYD 180
VVSVLRIART PSVNIGCCIE NVLLQQNLTV GSQTGNDIGE RDKITENPVS TGEKNAAT    238

SEQ ID NO: 240          moltype = AA   length = 111
FEATURE                 Location/Qualifiers
REGION                  1..111
                        note = ICOSL v35 IgV
source                  1..111
                        mol_type = protein
                        organism = synthetic construct
SEQUENCE: 240
DTQEKEVRAM VGSDVELSCA CPEGSRFDLN DVYVYWQTSE SKTVVTYHIP QSSSLENVDS  60
RYRNRALMSP AGMLRGDFSL RLFNVTPQDE QKFHCLVLSQ SLEFQEVLSV E          111

SEQ ID NO: 241          moltype = AA   length = 254
FEATURE                 Location/Qualifiers
REGION                  1..254
                        note = CD80-TIP I67T/L70Q/A91G/T120S
source                  1..254
                        mol_type = protein
                        organism = synthetic construct
SEQUENCE: 241
VIHVTKEVKE VATLSCGHNV SVEELAQTRI YWQKEKKMVL TMMSGDMNIW PEYKNRTIFD  60
ITNNLSTVIQ ALRPSDEGTY ECVVLKYEKD GFKREHLAEV TLSVKADFPT PSISDFEIPS 120
SNIRRIICST SGGFPEPHLS WLENGEELNA INTTVSQDPE TELYAVSSKL DFNMTTNHSF 180
MCLIKYGHLR VNQTFNWNTT KQEHFPDNLL PSWAITLISV NGIFVICCLT YCFAPRCRER 240
RRNERLRRES VRPV                                                   254

SEQ ID NO: 242          moltype = DNA   length = 867
FEATURE                 Location/Qualifiers
misc_feature            1..867
                        note = CD80-TIP I67T/L70Q/A91G/T120S
source                  1..867
                        mol_type = other DNA
                        organism = synthetic construct
SEQUENCE: 242
atgggccaca cacggaggca gggaacatca ccatccaagt gtccatacct caatttcttt  60
cagctcttgg tgctggctgg tctttctcac ttctgttcag gtgttatcca cgtgaccaag 120
gaagtgaaag aagtggcaac gctgtcctgt ggtcacaatg tttctgttga agagctggca 180
caaactcgca tctactggca aaaggagaag aaaatggtgc tgactatgat gtctggggac 240
atgaatatat ggcccgagta caagaaccgg accatctttg atatcactaa taacctctcc 300
acagtgatcc aagctctgcg cccatctgac gagggcacat acgagtgtgt tgttctgaag 360
tatgaaaaag acggcttcaa gcgggaacac ctggctgaag tgacgttatc agtcaaagct 420
gacttcccta cacctagtat atctgacttt gaaattccat cttctaatat tagaaggata 480
atttgctcaa cctctggagg ttttccagag cctcacctct cctggttgga aaatggagaa 540
gaattaaatg ccatcaacac aacagtttcc caagatcctg aaactgagct ctatgctgtt 600
agcagcaaac tggatttcaa tatgacaacc aaccacagt catgtgtct catcaagtat 660
ggacatttaa gagtgaatca gaccttcaac tggaatacaa ccaagcaaga gcattttcct 720
gataacctgc tcccatcctg ggccattacc ttaatctcag taaatggaat ttttgtgata 780
tgctgcctga cctactgctt tgccccaaga tgcagagaga gaaggaggaa tgagagattg 840
agaagggaaa gtgtacgccc tgtataa                                    867

SEQ ID NO: 243          moltype = AA   length = 284
FEATURE                 Location/Qualifiers
REGION                  1..284
                        note = ICOSL-TIP N52H/I143T
source                  1..284
                        mol_type = protein
                        organism = synthetic construct
SEQUENCE: 243
DTQEKEVRAM VGSDVELSCA CPEGSRFDLN DVYVYWQTSE SKTVVTYHIP QHSSLENVDS  60
RYRNRALMSP AGMLRGDFSL RLFNVTPQDE QKFHCLVLSQ SLGFQEVLSV EVTLHVAANF 120
SVPVVSAPHS PSQDELTFTC TSTNGYPRPN VYWINKTDNS LLDQALQNDT VFLNMRGLYD 180
VVSVLRIART PSVNIGCCIE NVLLQQNLTV GSQTGNDIGE RDKITENPVS TGEKNAATWS 240
ILAVLCLLVV VAVAIGWVCR DRCLQHSYAG AWAVSPETEL TGHV                  284

SEQ ID NO: 244          moltype = DNA   length = 909
FEATURE                 Location/Qualifiers
misc_feature            1..909
                        note = ICOSL-TIP N52H/I143T
source                  1..909
                        mol_type = other DNA
                        organism = synthetic construct
SEQUENCE: 244
atgcggctgg gcagtcctgg actgctcttc ctgctcttca gcagccttcg agctgatact  60
```

-continued

```
caggagaagg aagtcagagc gatggtaggc agcgacgtgg agctcagctg cgcttgccct  120
gaaggaagcc gttttgattt aaatgatgtt tacgtatatt ggcaaaccag tgagtcgaaa  180
accgtggtga cctaccacat cccacagcac agctccttgg aaaacgtgga cagccgctac  240
cggaaccgag ccctgatgtc accggccggc atgctgcggg gcgacttctc cctgcgcttg  300
ttcaacgtca cccccccagga cgagcagaag tttcactgcc tggtgttgag ccaatccctg  360
ggattccagg aggtttttgag cgttgaggtt acactgcatg tggcagcaaa cttcagcgtg  420
cccgtcgtca gcgcccccca cagccctcc caggatgagc tcaccttcac gtgtacatcc  480
accaacggct accccaggcc caacgtgtac tggatcaata gacggacaa cagcctgctg  540
gaccaggctc tgcagaatga caccgtcttc ttgaacatgg ggggcttgta tgacgtggtc  600
agcgtgctga ggatcgcacg gacccccagc gtgaacattg gctgctgcat agagaacgtg  660
cttctgcagc agaacctgac tgtcggcagc cagacaggaa atgacatcgg agagagagac  720
aagatcacag agaatccagt cagtaccggc gagaaaaacg cggccacgtg gagcatcctg  780
gctgtcctgt gcctgctt gt ggtcgtggcg gtggccatag gctgggtgtg cagggaccga  840
tgcctccaac acagctatgc aggtgcctgg gctgtgagtc cggagacaga gctcactggc  900
cacgtttga                                                           909
```

SEQ ID NO: 245       moltype = AA   length = 248
FEATURE              Location/Qualifiers
REGION               1..248
                     note = Anti-CD19 scFv
source               1..248
                     mol_type = protein
                     organism = synthetic construct
SEQUENCE: 245
```
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSSAAA                                                            248
```

SEQ ID NO: 246       moltype = AA   length = 71
FEATURE              Location/Qualifiers
REGION               1..71
                     note = CD8-derived hinge and transmembrane domain
source               1..71
                     mol_type = protein
                     organism = synthetic construct
SEQUENCE: 246
```
KPTTTPAPRP PTPAPTIASQ PLSLRPEASR PAAGGAVHTR GLDFASDIYI WAPLAGTCGV  60
LLLSLVITLY C                                                        71
```

SEQ ID NO: 247       moltype = AA   length = 112
FEATURE              Location/Qualifiers
REGION               1..112
                     note = CD3zeta intracellular signaling domain
source               1..112
                     mol_type = protein
                     organism = synthetic construct
SEQUENCE: 247
```
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR           112
```

SEQ ID NO: 248       moltype = DNA   length = 1356
FEATURE              Location/Qualifiers
misc_feature         1..1356
                     note = AntiCD19x8z chimeric antigen receptor
misc_feature         1..1356
                     note = antiCD19x8z chimeric antigen receptornucleotide
source               1..1356
                     mol_type = other DNA
                     organism = synthetic construct
SEQUENCE: 248
```
atggccttac cagtgaccgc cttgctcctg ccgctggcct tgctgctcca cgccgccagg   60
ccggacatcc agatgacaca gactacatcc tccctgctg cctctctggg agacagagtc   120
accatcagtt gcagggcaag tcaggacatt agtaaatatt taaattggta tcagcagaaa   180
ccagatggaa ctgttaaact cctgatctac catacatcaa gattacactc aggagtccca   240
tcaaggttca gtggcagtgg gtctgggaca gattattctc tcaccattag caacctggag   300
caagaagata ttgccactta cttttgccaa cagggtaata cgcttccgta cacgttcgga   360
gggggacta agttggaaat aacaggctcc acctctggat ccggcaagcc cggatctgga   420
gagggatcca ccaagggcga ggtgaaactg caggagtcag gacctggcct ggtggcgccc   480
tcacagagcc tgtccgtcac atgcactgtc tcagggtct cattacccga ctatggtgta   540
agctggattc gccagcctcc acgaaagggt ctggagtggc tggagtaat atgggggagt   600
gaaaccacat actataattc agctctcaaa tccagactga ccatcatcaa ggacaactcc   660
aagagccaag ttttcttaaa aatgaacagt ctgcaaactg atgacacagc catttactac   720
tgtgccaaac attattacta cggtggtagc tatgctatgg actactgggg tcaaggaacc   780
tcagtcaccg tctcctcagc ggcgcaaag cccaccacga cgcagcgcc gcgaccacca   840
acaccggcgc ccaccatcgc gtcgcagccc ctgtccctgc gcccagaggc gagcggggcca   900
gcggcggggg gcgcagtgca cacgaggggg ctggacttcg ccagtgatat ctacatctgg   960
gcgcccctgg ccgggacttg tggggtcctt ctcctgtcac tggttatcac cctttactgc  1020
```

-continued

```
agagtgaagt tcagcaggag cgcagacgcc cccgcgtacc agcagggcca gaaccagctc   1080
tataacgagc tcaatctagg acgaagagag gagtacgatg ttttggacaa gagacgtggc   1140
cgggaccctg agatgggggg aaagccgaga aggaagaacc ctcaggaagg cctgtacaat   1200
gaactgcaga aagataagat ggcggaggcc tacagtgaga ttgggatgaa aggcgagcgc   1260
cggaggggca aggggcacga tggcctttac caggtctca gtacagccac caaggacacc    1320
tacgacgccc ttcacatgca ggccctgccc cctcgc                            1356

SEQ ID NO: 249            moltype = DNA   length = 63
FEATURE                   Location/Qualifiers
misc_feature             1..63
                          note = T2A
source                   1..63
                          mol_type = other DNA
                          organism = synthetic construct
SEQUENCE: 249
ggcagtggcg agggcagagg aagtctgcta acatgcggtg acgtcgagga gaatcctggc   60
cca                                                                63

SEQ ID NO: 250            moltype = AA   length = 21
FEATURE                   Location/Qualifiers
REGION                   1..21
                          note = T2A
source                   1..21
                          mol_type = protein
                          organism = synthetic construct
SEQUENCE: 250
GSGEGRGSLL TCGDVEENPG P                                            21

SEQ ID NO: 251            moltype = DNA   length = 867
FEATURE                   Location/Qualifiers
misc_feature             1..867
                          note = CD80
source                   1..867
                          mol_type = unassigned DNA
                          organism = Homo sapiens
SEQUENCE: 251
atgggccaca cacggaggca gggaacatca ccatccaagt gtccatacct caatttcttt   60
cagctcttgg tgctggctgg tctttctcac ttctgttcag gtgttatcca cgtgaccaag   120
gaagtgaaag aagtggcaac gctgtcctgt ggtcacaatg tttctgttga agagctgtca   180
caaactcgca tctactggca aaaggagaag aaaatggtgc tgactatgat gtctggggac   240
atgaatatat ggcccgagta caagaaccgg accatctttg atatcactaa taacctctcc   300
attgtgatcc tggctctgcg cccatctgac gagggcacat acgagtgtgt tgttctgaag   360
tatgaaaaag acgctttcaa gcgggaacac ctggctgaag tgacgttatc agtcaaagct   420
gacttcccta cacctagtat atctgacttt gaaattccaa cttctaatat tagaaggata   480
atttgctcaa cctctggagg ttttccagag cctcacctct cctggttgga aaatggagaa   540
gaattaaatg ccatcaacac aacagtttcc caagatcctg aaactgagct ctatgctgtt   600
agcagcaaac tggatttcaa tatgacaacc aaccacagct tcatgtgtct catcaagtat   660
ggacatttaa gagtgaatca gaccttcaac tggaatacaa ccaagcaaga gcattttcct   720
gataacctgc tcccatcctg ggccattacc ttaatctcag taaatggaat ttttgtgata   780
tgctgcctga cctactgctt tgccccaaga tgcagagaga gaaggaggaa tgagagattg   840
agaagggaaa gtgtacgccc tgtataa                                      867

SEQ ID NO: 252            moltype = DNA   length = 909
FEATURE                   Location/Qualifiers
misc_feature             1..909
                          note = ICOSL
source                   1..909
                          mol_type = unassigned DNA
                          organism = Homo sapiens
SEQUENCE: 252
atgcggctgg gcagtcctgg actgctcttc ctgctcttca gcagccttcg agctgatact   60
caggagaagg aagtcagagc gatggtaggc agcgacgtgg agctcagctg cgcttgccct   120
gaaggaagcc gttttgattt aaatgatgtt tacgtatatt ggcaaaccag tgagtcgaaa   180
accgtggtga cctaccacat cccacagaac agctccttgg aaaacgtgga cagccgctac   240
cggaaccgag ccctgatgtc accggccggc atgctgcggg cgacttctc cctgcgcttg    300
ttcaacgtca cccccagga cgagcagaag tttcactgcc tggtgttgag ccaatccctg    360
ggattccagg aggttttgag cgttgaggtt acactgcatg tggcagcaaa cttcagcgtg   420
cccgtcgtca gcgcccccca cagccctcc caggatgagc tcacccttac gtgtacatcc   480
ataaacggct accccaggcc caacgtgtac tggatcaata agcggacaa cagcctgcctg  540
gaccaggctc tgcagaatga caccgtcttc ttgaacatgc ggggcttgta tgacgtggtc   600
agcgtgctga ggatcgcacg gacccccagc gtgaacattg ctgctgcat agagaacgtg    660
cttctgcagc agaacctgac tgtcggcagc cagacaggaa atgacatcgg agagagagac   720
aagatcacag agaatccagt cagtaccggc gagaaaacg cggccacgtg gagcatcctg     780
gctgtcctgt gcctgcttgt ggtcgtggcg gtggccatag ctgggtgtg cagggaccga   840
tgcctccaac acagctatgc aggtgcctgg ctgtgagtc cggagacaga gctcactggc    900
cacgtttga                                                          909

SEQ ID NO: 253            moltype = AA   length = 254
FEATURE                   Location/Qualifiers
```

-continued

```
REGION                        1..254
                              note = MISC_FEATURE - Mature CD80(B7-1)
source                        1..254
                              mol_type = protein
                              organism = Homo sapiens
SEQUENCE: 253
VIHVTKEVKE VATLSCGHNV SVEELAQTRI YWQKEKKMVL TMMSGDMNIW PEYKNRTIFD   60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDNLL PSWAITLISV NGIFVICCLT YCFAPRCRER  240
RRNERLRRES VRPV                                                    254

SEQ ID NO: 254                moltype = AA  length = 306
FEATURE                       Location/Qualifiers
REGION                        1..306
                              note = MISC_FEATURE - Mature CD86(B7-2)
source                        1..306
                              mol_type = protein
                              organism = Homo sapiens
SEQUENCE: 254
APLKIQAYFN ETADLPCQFA NSQNQSLSEL VVFWQDQENL VLNEVYLGKE KFDSVHSKYM   60
GRTSFDSDSW TLRLHNLQIK DKGLYQCIIH HKKPTGMIRI HQMNSELSVL ANFSQPEIVP  120
ISNITENVYI NLTCSSIHGY PEPKKMSVLL RTKNSTIEYD GVMQKSQDNV TELYDVSISL  180
SVSFPDVTSN MTIFCILETD KTRLLSSPFS IELEDPQPPP DHIPWITAVL PTVIICVMVF  240
CLILWKWKKK KRPRNSYKCG TNTMEREESE QTKKREKIHI PERSDEAQRV FKSSKTSSCD  300
KSDTCF                                                             306

SEQ ID NO: 255                moltype = AA  length = 272
FEATURE                       Location/Qualifiers
REGION                        1..272
                              note = MISC_FEATURE - Mature CD274 (PD-L1, B7-H1)
source                        1..272
                              mol_type = protein
                              organism = Homo sapiens
SEQUENCE: 255
FTVTVPKDLY VVEYGSNMTI ECKFPVEKQL DLAALIVYWE MEDKNIIQFV HGEEDLKVQH   60
SSYRQRARLL KDQLSLGNAA LQITDVKLQD AGVYRCMISY GGADYKRITV KVNAPYNKIN  120
QRILVVDPVT SEHELTCQAE GYPKAEVIWT SSDHQVLSGK TTTTNSKREE KLFNVTSTLR  180
INTTTNEIFY CTFRRLDPEE NHTAELVIPE LPLAHPPNER THLVILGAIL LCLGVALTFI  240
FRLRKGRMMD VKKCGIQDTN SKKQSDTHLE ET                                272

SEQ ID NO: 256                moltype = AA  length = 254
FEATURE                       Location/Qualifiers
REGION                        1..254
                              note = MISC_FEATURE - Mature PDCD1LG2(PD-L2, CD273)
source                        1..254
                              mol_type = protein
                              organism = Homo sapiens
SEQUENCE: 256
LFTVTVPKEL YIIEHGSNVT LECNFDTGSH VNLGAITASL QKVENDTSPH RERATLLEEQ   60
LPLGKASFHI PQVQVRDEGQ YQCIIIYGVA WDYKYLTLKV KASYRKINTH ILKVPETDEV  120
ELTCQATGYP LAEVSWPNVS VPANTSHSRT PEGLYQVTSV LRLKPPPGRN FSCVFWNTHV  180
RELTLASIDL QSQMEPRTHP TWLLHIFIPF CIIAFIFIAT VIALRKQLCQ KLYSSKDTTK  240
RPVTTTKREV NSAI                                                    254

SEQ ID NO: 257                moltype = AA  length = 284
FEATURE                       Location/Qualifiers
REGION                        1..284
                              note = MISC_FEATURE - Mature ICOSLG(B7RP1, CD275, ICOSL,
                              B7-H2)
source                        1..284
                              mol_type = protein
                              organism = Homo sapiens
SEQUENCE: 257
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAATWS  240
ILAVLCLLVV VAVAIGWVCR DRCLQHSYAG AWAVSPETEL TGHV                   284

SEQ ID NO: 258                moltype = AA  length = 506
FEATURE                       Location/Qualifiers
REGION                        1..506
                              note = MISC_FEATURE - Mature CD276(B7-H3)
source                        1..506
                              mol_type = protein
                              organism = Homo sapiens
SEQUENCE: 258
LEVQVPEDPV VALVGTDATL CCSFSPEPGF SLAQLNLIWQ LTDTKQLVHS FAEGQDQGSA   60
```

-continued

```
YANRTALFPD LLAQGNASLR LQRVRVADEG SFTCFVSIRD FGSAAVSLQV AAPYSKPSMT    120
LEPNKDLRPG DTVTITCSSY QGYPEAEVFW QDGQGVPLTG NVTTSQMANE QGLFDVHSIL    180
RVVLGANGTY SCLVRNPVLQ QDAHSSVTIT PQRSPTGAVE VQVPEDPVVA LVGTDATLRC    240
SFSPEPGFSL AQLNLIWQLT DTKQLVHSFT EGRDQGSAYA NRTALFPDLL AQGNASLRLQ    300
RVRVADEGSF TCFVSIRDFG SAAVSLQVAA PYSKPSMTLE PNKDLRPGDT VTITCSSYRG    360
YPEAEVFWQD GQGVPLTGNV TTSQMANEQG LFDVHSVLRV VLGANGTYSC LVRNPVLQQD    420
AHGSVTITGQ PMTFPPEALW VTVGLSVCLI ALLVALAFVC WRKIKQSCEE ENAGAEDQDG    480
EGEGSKTALQ PLKHSDSKED DGQEIA                                        506

SEQ ID NO: 259          moltype = AA  length = 258
FEATURE                 Location/Qualifiers
REGION                  1..258
                        note = MISC_FEATURE - Mature VTCN1(B7-H4)
source                  1..258
                        mol_type = protein
                        organism = Homo sapiens
SEQUENCE: 259
LIIGFGISGR HSITVTTVAS AGNIGEDGIL SCTFEPDIKL SDIVIQWLKE GVLGLVHEFK     60
EGKDELSEQD EMFRGRTAVF ADQVIVGNAS LRLKNVQLTD AGTYKCYIIT SKGKGNANLE    120
YKTGAFSMPE VNVDYNASSE TLRCEAPRWF PQPTVVWASQ VDQGANFSEV SNTSFELNSE    180
NVTMKVVSVL YNVTINNTYS CMIENDIAKA TGDIKVTESE IKRRSHLQLL NSKASLCVSS    240
FFAISWALLP LSPYLMLK                                                 258

SEQ ID NO: 260          moltype = AA  length = 202
FEATURE                 Location/Qualifiers
REGION                  1..202
                        note = MISC_FEATURE - Mature CD28
source                  1..202
                        mol_type = protein
                        organism = Homo sapiens
SEQUENCE: 260
NKILVKQSPM LVAYDNAVNL SCKYSYNLFS REFRASLHKG LDSAVEVCVV YGNYSQQLQV     60
YSKTGFNCDG KLGNESVTFY LQNLYVNQTD IYFCKIEVMY PPPYLDNEKS NGTIIHVKGK    120
HLCPSPLFPG PSKPFWVLVV VGGVLACYSL LVTVAFIIFW VRSKRSRLLH SDYMNMTPRR    180
PGPTRKHYQP YAPPRDFAAY RS                                            202

SEQ ID NO: 261          moltype = AA  length = 188
FEATURE                 Location/Qualifiers
REGION                  1..188
                        note = MISC_FEATURE - Mature CTLA4
source                  1..188
                        mol_type = protein
                        organism = Homo sapiens
SEQUENCE: 261
KAMHVAQPAV VLASSRGIAS FVCEYASPGK ATEVRVTVLR QADSQVTEVC AATYMMGNEL     60
TFLDDSICTG TSSGNQVNLT IQGLRAMDTG LYICKVELMY PPPYYLGIGN GTQIYVIDPE    120
PCPDSDFLLW ILAAVSSGLF FYSFLLTAVS LSKMLKKRSP LTTGVYVKMP PTEPECEKQF    180
QPYFIPIN                                                           188

SEQ ID NO: 262          moltype = AA  length = 268
FEATURE                 Location/Qualifiers
REGION                  1..268
                        note = MISC_FEATURE - Mature PDCD1(PD-1)
source                  1..268
                        mol_type = protein
                        organism = Homo sapiens
SEQUENCE: 262
PGWFLDSPDR PWNPPTFSPA LLVVTEGDNA TFTCSFSNTS ESFVLNWYRM SPSNQTDKLA     60
AFPEDRSQPG QDCRFRVTQL PNGRDFHMSV VRARRNDSGT YLCGAISLAP KAQIKESLRA    120
ELRVTERRAE VPTAHPSPSP RPAGQFQTLV VGVVGGLLGS LVLLVWVLAV ICSRAARGTI    180
GARRTGQPLK EDPSAVPVFS VDYGELDFQW REKTPEPPVP CVPEQTEYAT IVFPSGMGTS    240
SPARRGSADG PRSAQPLRPE DGHCSWPL                                      268

SEQ ID NO: 263          moltype = AA  length = 179
FEATURE                 Location/Qualifiers
REGION                  1..179
                        note = MISC_FEATURE - Mature ICOS
source                  1..179
                        mol_type = protein
                        organism = Homo sapiens
SEQUENCE: 263
EINGSANYEM FIFHNGGVQI LCKYPDIVQQ FKMQLLKGGQ ILCDLTKTKG SGNTVSIKSL     60
KFCHSQLSNN SVSFFLYNLD HSHANYYFCN LSIFDPPPFK VTLTGGYLHI YESQLCCQLK    120
FWLPIGCAAF VVVCILGCIL ICWLTKKKYS SSVHDPNGEY MFMRAVNTAK KSRLTDVTL    179

SEQ ID NO: 264          moltype = AA  length = 259
FEATURE                 Location/Qualifiers
REGION                  1..259
                        note = MISC_FEATURE - Mature BTLA(CD272)
```

-continued

```
source                   1..259
                         mol_type = protein
                         organism = Homo sapiens
SEQUENCE: 264
KESCDVQLYI KRQSEHSILA GDPFELECPV KYCANRPHVT WCKLNGTTCV KLEDRQTSWK    60
EEKNISFFIL HFEPVLPNDN GSYRCSANFQ SNLIESHSTT LYVTDVKSAS ERPSKDEMAS   120
RPWLLYRLLP LGGGLPLLITT CFCLFCCLRR HQGKQNELSD TAGREINLVD AHLKSEQTEA   180
STRQNSQVLL SETGIYDNDP DLCFRMQEGS EVYSNPCLEE NKPGIVYASL NHSVIGPNSR   240
LARNVKEAPT EYASICVRS                                                259

SEQ ID NO: 265           moltype = AA  length = 433
FEATURE                  Location/Qualifiers
REGION                   1..433
                         note = MISC_FEATURE - Mature CD4
source                   1..433
                         mol_type = protein
                         organism = Homo sapiens
SEQUENCE: 265
KKVVLGKKGD TVELTCTASQ KKSIQFHWKN SNQIKILGNQ GSFLTKGPSK LNDRADSRRS    60
LWDQGNFPLI IKNLKIEDSD TYICEVEDQK EEVQLLVFGL TANSDTHLLQ GQSLTLTLES   120
PPGSSPSVQC RSPRGKNIQG GKTLSVSQLE LQDSGTWTCT VLQNQKKVEF KIDIVVLAFQ   180
KASSIVYKKE GEQVEFSFPL AFTVEKLTGS GELWWQAERA SSSKSWITFD LKNKEVSVKR   240
VTQDPKLQMG KKLPLHLTLP QALPQYAGSG NLTLALEAKT GKLHQEVNLV VMRATQLQKN   300
LTCEVWGPTS PKLMLSLKLE NKEAKVSKRE KAVWVLNPEA GMWQCLLSDS GQVLLESNIK   360
VLPTWSTPVQ PMALIVLGGV AGLLLFIGLG IFFCVRCRHR RRQAERMSQI KRLLSEKKTC   420
QCPHRFQKTC SPI                                                      433

SEQ ID NO: 266           moltype = AA  length = 214
FEATURE                  Location/Qualifiers
REGION                   1..214
                         note = MISC_FEATURE - Mature CD8A(CD8-alpha)
source                   1..214
                         mol_type = protein
                         organism = Homo sapiens
SEQUENCE: 266
SQFRVSPLDR TWNLGETVEL KCQVLLSNPT SGCSWLFQPR GAAASPTFLL YLSQNKPKAA    60
EGLDTQRFSG KRLGDTFVLT LSDFRRENEG YYFCSALSNS IMYFSHFVPV FLPAKPTTTP   120
APRPPTPAPT IASQPLSLRP EACRPAAGGA VHTRGLDFAC DIYIWAPLAG TCGVLLLSLV   180
ITLYCNHRNR RRVCKCPRPV VKSGDKPSLS ARYV                               214

SEQ ID NO: 267           moltype = AA  length = 189
FEATURE                  Location/Qualifiers
REGION                   1..189
                         note = MISC_FEATURE - Mature CD8B(CD8-beta)
source                   1..189
                         mol_type = protein
                         organism = Homo sapiens
SEQUENCE: 267
LQQTPAYIKV QTNKMVMLSC EAKISLSNMR IYWLRQRQAP SSDSHHEFLA LWDSAKGTIH    60
GEEVEQEKIA VFRDASRFIL NLTSVKPEDS GIYFCMIVGS PELTFGKGTQ LSVVDFLPTT   120
AQPTKKSTLK KRVCRLPRPE TQKGPLCSPI TLGLLVAGVL VLLVSLGVAI HLCCRRRRAR   180
LRFMKQFYK                                                           189

SEQ ID NO: 268           moltype = AA  length = 497
FEATURE                  Location/Qualifiers
REGION                   1..497
                         note = MISC_FEATURE - Mature LAG3
source                   1..497
                         mol_type = protein
                         organism = Homo sapiens
SEQUENCE: 268
VPVVWAQEGA PAQLPCSPTI PLQDLSLLRR AGVTWQHQPD SGPPAAAPGH PLAPGPHPAA    60
PSSWGPRPRR YTVLSVGPGG LRSGRLPLQP RVQLDERGRQ RGDFSLWLRP ARRADAGEYR   120
AAVHLRDRAL SCRLRLRLGQ ASMTASPPGS LRASDWVILN CSFSRPDRPA SVHWFRNRGQ   180
GRVPVRESPH HHLAESFLFL PQVSPMDSGP WGCILTYRDG FNVSIMYNLT VLGLEPPTPL   240
TVYAGAGSRV GLPCRLPAGV GTRSFLTAKW TPPGGGPDLL VTGDNGDFTL RLEDVSQAQA   300
GTYTCHIHLQ EQQLNATVTL AIITVTPKSF GSPGSLGKLL CEVTPVSGQE RFVWSSLDTP   360
SQRSFSGPWL EAQEAQLLSQ PWQCQLYQGE RLLGAAVYFT ELSSPGAQRS GRAPGALPAG   420
HLLLFLILGV LSLLLLVTGA FGFHLWRRQW RPRRFSALEQ GIHPPQAQSK IEELEQEPEP   480
EPEPEPEPEP EPEPEQL                                                  497

SEQ ID NO: 269           moltype = AA  length = 280
FEATURE                  Location/Qualifiers
REGION                   1..280
                         note = MISC_FEATURE - Mature HAVCR2(TIM-3)
source                   1..280
                         mol_type = protein
                         organism = Homo sapiens
SEQUENCE: 269
```

```
SEVEYRAEVG QNAYLPCFYT PAAPGNLVPV CWGKGACPVF ECGNVVLRTD ERDVNYWTSR  60
YWLNGDFRKG DVSLTIENVT LADSGIYCCR IQIPGIMNDE KFNLKLVIKP AKVTPAPTRQ  120
RDFTAAFPRM LTTRGHGPAE TQTLGSLPDI NLTQISTLAN ELRDSRLAND LRDSGATIRI  180
GIYIGAGICA GLALALIFGA LIFKWYSHSK EKIQNLSLIS LANLPPSGLA NAVAEGIRSE  240
ENIYTIEENV YEVEEPNEYY CYVSSRQQPS QPLGCRFAMP                         280

SEQ ID NO: 270          moltype = AA  length = 492
FEATURE                 Location/Qualifiers
REGION                  1..492
                        note = MISC_FEATURE - Mature CEACAM1
source                  1..492
                        mol_type = protein
                        organism = Homo sapiens
SEQUENCE: 270
QLTTESMPFN VAEGKEVLLL VHNLPQQLFG YSWYKGERVD GNRQIVGYAI GTQQATPGPA  60
NSGRETIYPN ASLLIQNVTQ NDTGFYTLQV IKSDLVNEEA TGQFHVYPEL PKPSISSNNS  120
NPVEDKDAVA FTCEPETQDT TYLWWINNQS LPVSPRLQLS NGNRTLTLLS VTRNDTGPYE  180
CEIQNPVSAN RSDPVTLNVT YGPDTPTISP SDTYYRPGAN LSLSCYAASN PPAQYSWLIN  240
GTFQQSTQEL FIPNITVNNS GSYTCHANNS VTGCNRTTVK TIIVTELSPV VAKPQIKASK  300
TTVTGDKDSV NLTCSTNDTG ISIRWFFKNQ SLPSSERMKL SQGNTTLSIN PVKREDAGTY  360
WCEVFNPISK NQSDPIMLNV NYNALPQENG LSPGAIAGIV IGVVALVALI AVALACFLHF  420
GKTGRASDQR DLTEHKPSVS NHTQDHSNDP PNKMNEVTYS TLNFEAQQPT QPTSASPSLT  480
ATEIIYSEVK KQ                                                      492

SEQ ID NO: 271          moltype = AA  length = 222
FEATURE                 Location/Qualifiers
REGION                  1..222
                        note = MISC_FEATURE - Mature TIGIT
source                  1..222
                        mol_type = protein
                        organism = Homo sapiens
SEQUENCE: 271
MTGTIETTGN ISAEKGGSII LQCHLSSTTA QVTQVNWEQQ DQLLAICNAD LGWHISPSFK  60
DRVAPGPGLG LTLQSLTVND TGEYFCIYHT YPDGTYTGRI FLEVLESSVA EHGARFQIPL  120
LGAMAATLVV ICTAVIVVVA LTRKKKALRI HSVEGDLRRK SAGQEEWSPS APSPPGSCVQ  180
AEAAPAGLCG EQRGEDCAEL HDYFNVLSYR SLGNCSFFTE TG                     222

SEQ ID NO: 272          moltype = AA  length = 397
FEATURE                 Location/Qualifiers
REGION                  1..397
                        note = MISC_FEATURE - Mature PVR(CD155)
source                  1..397
                        mol_type = protein
                        organism = Homo sapiens
SEQUENCE: 272
WPPPGTGDVV VQAPTQVPGF LGDSVTLPCY LQVPNMEVTH VSQLTWARHG ESGSMAVFHQ  60
TQGPSYSESK RLEFVAARLG AELRNASLRM FGLRVEDEGN YTCLFVTFPQ GSRSVDIWLR  120
VLAKPQNTAE VQKVQLTGEP VPMARCVSTG GRPPAQITWH SDLGGMPNTS QVPGFLSGTV  180
TVTSLWILVP SSQVDGKNVT CKVEHESFEK PQLLTVNLTV YPPPEVSISG YDNNWYLGQN  240
EATLTCDARS NPEPTGYNWS TTMGPLPPFA VAQGAQLLIR PVDKPINTTL ICNVTNALGA  300
RQAELTVQVK EGPPSEHSGI SRNAIIFLVL GILVFLILLG IGIYFYWSKC SREVLWHCHL  360
CPSSTEHASA SANGHVSYSA VSRENSSSQD PQTEGTR                           397

SEQ ID NO: 273          moltype = AA  length = 507
FEATURE                 Location/Qualifiers
REGION                  1..507
                        note = MISC_FEATURE - Mature PVRL2(CD112)
source                  1..507
                        mol_type = protein
                        organism = Homo sapiens
SEQUENCE: 273
QDVRVQVLPE VRGQLGGTVE LPCHLLPPVP GLYISLVTWQ RPDAPANHQN VAAFHPKMGP  60
SFPSPKPGSE RLSFVSAKQS TGQDTEAELQ DATLALHGLT VEDEGNYTCE FATFPKGSVR  120
GMTWLRVIAK PKNQAEAQKV TFSQDPTTVA LCISKEGRPP ARISWLSSLD WEAKETQVSG  180
TLAGTVTVTS RFTLVPSGRA DGVTVTCKVE HESFEEPALI PVTLSVRYPP EVSISGYDDN  240
WYLGRTDATL SCDVRSNPEP TGYDWSTTSG TFPTSAVAQG SQLVIHAVDS LFNTTFVCTV  300
TNAVGMRAEQ VIFVRETPN TAGAGATGGI IGGIIAAIIA TAVAATGILI CRQQRKEQTL  360
QGAEEDEDLE GPPSYKPPTP KAKLEAQEMP SQLFTLGASE HSPLKTPYFD AGASCTEQEM  420
PRYHELPTLE ERSGPLHPGA TSLGSPIPVP PGPPAVEDVS LDLEDEEGEE EEEYLDKINP  480
IYDALSYSSP SDSYQGKGFV MSRAMYV                                      507

SEQ ID NO: 274          moltype = AA  length = 318
FEATURE                 Location/Qualifiers
REGION                  1..318
                        note = MISC_FEATURE - Mature CD226
source                  1..318
                        mol_type = protein
                        organism = Homo sapiens
SEQUENCE: 274
```

-continued

```
EEVLWHTSVP FAENMSLECV YPSMGILTQV EWFKIGTQQD SIAIFSPTHG MVIRKPYAER    60
VYFLNSTMAS NNMTLFFRNA SEDDVGYYSC SLYTYPQGTW QKVIQVVQSD SFEAAVPSNS   120
HIVSEPGKNV TLTCQPQMTW PVQAVRWEKI QPRQIDLLTY CNLVHGRNFT SKFPRQIVSN   180
CSHGRWSVIV IPDVTVSDSG LYRCYLQASA GENETFVMRL TVAEGKTDNQ YTLFVAGGTV   240
LLLLFVISIT TIIVIFLNRR RRRERRDLFT ESWDTQKAPN NYRSPISTSQ PTNQSMDDTR   300
EDIYVNYPTF SRRPKTRV                                                 318

SEQ ID NO: 275          moltype = AA  length = 327
FEATURE                 Location/Qualifiers
REGION                  1..327
                        note = MISC_FEATURE - Mature CD2
source                  1..327
                        mol_type = protein
                        organism = Homo sapiens
SEQUENCE: 275
KEITNALETW GALGQDINLD IPSFQMSDDI DDIKWEKTSD KKKIAQFRKE KETFKEKDTY    60
KLFKNGTLKI KHLKTDDQDI YKVSIYDTKG KNVLEKIFDL KIQERVSKPK ISWTCINTTL   120
TCEVMNGTDP ELNLYQDGKH LKLSQRVITH KWTTSLSAKF KCTAGNKVSK ESSVEPVSCP   180
EKGLDIYLII GICGGGSLLM VFVALLVFYI TKRKKQRSRR NDEELETRAH RVATEERGRK   240
PHQIPASTPQ NPATSQHPPP PPGHRSQAPS HRPPPPGHRV QHQPQKRPPA PSGTQVHQQK   300
GPPLPRPRVQ PKPPHGAAEN SLSPSSN                                       327

SEQ ID NO: 276          moltype = AA  length = 154
FEATURE                 Location/Qualifiers
REGION                  1..154
                        note = MISC_FEATURE - Mature CD160
source                  1..154
                        mol_type = protein
                        organism = Homo sapiens
SEQUENCE: 276
INITSSASQE GTRLNLICTV WHKKEEAEGF VVFLCKDRSG DCSPETSLKQ LRLKRDPGID    60
GVGEISSQLM FTISQVTPLH SGTYQCCARS QKSGIRLQGH FFSILFTETG NYTVTGLKQR   120
QHLEFSHNEG TLSSGFLQEK VWVMLVTSLV ALQA                               154

SEQ ID NO: 277          moltype = AA  length = 248
FEATURE                 Location/Qualifiers
REGION                  1..248
                        note = MISC_FEATURE - Mature CD200
source                  1..248
                        mol_type = protein
                        organism = Homo sapiens
SEQUENCE: 277
QVQVVTQDER EQLYTPASLK CSLQNAQEAL IVTWQKKKAV SPENMVTFSE NHGVVIQPAY    60
KDKINITQLG LQNSTITFWN ITLEDEGCYM CLFNTFGFGK ISGTACLTVY VQPIVSLHYK   120
FSEDHLNITC SATARPAPMV FWKVPRSGIE NSTVTLSHPN GTTSVTSILH IKDPKNQVGK   180
EVICQVLHLG TVTDFKQTVN KGYWFSVPLL LSIVSLVILL VLISILLYWK RHRNQDRGEL   240
SQGVQKMT                                                            248

SEQ ID NO: 278          moltype = AA  length = 297
FEATURE                 Location/Qualifiers
REGION                  1..297
                        note = MISC_FEATURE - Mature CD200R1(CD200R)
source                  1..297
                        mol_type = protein
                        organism = Homo sapiens
SEQUENCE: 278
MDEKQITQNY SKVLAEVNTS WPVKMATNAV LCCPPIALRN LIIITWEIIL RGQPSCTKAY    60
RKETNETKET NCTDERITWV SRPDQNSDLQ IRPVAITHDG YYRCIMVTPD GNFHRGYHLQ   120
VLVTPEVTLF QNRNRTAVCK AVAGKPAAQI SWIPEGDCAT KQEYWSNGTV TVKSTCHWEV   180
HNVSTVTCHV SHLTGNKSLY IELLPVPGAK KSAKLYIPYI ILTIIILTIV GFIWLLKVNG   240
CRKYKLNKTE STPVVEEDEM QPYASYTEKN NPLYDTTNKV KASEALQSEV DTDLHTL      297

SEQ ID NO: 279          moltype = AA  length = 183
FEATURE                 Location/Qualifiers
REGION                  1..183
                        note = MISC_FEATURE - Mature NC R3 (NKp30)
source                  1..183
                        mol_type = protein
                        organism = Homo sapiens
SEQUENCE: 279
LWVSQPPEIR TLEGSSAFLP CSFNASQGRL AIGSVTWFRD EVVPGKEVRN GTPEFRGRLA    60
PLASSRFLHD HQAELHIRDV RGHDASIYVC RVEVLGLGVG TGNGTRLVVE KEHPQLGAGT   120
VLLLRAGFYA VSFLSVAVGS TVYYQGKCLT WKGPRRQLPA VVPAPLPPPC GSSAHLLPPV   180
PGG                                                                 183

SEQ ID NO: 280          moltype = AA  length = 238
FEATURE                 Location/Qualifiers
REGION                  1..238
                        note = ICOSL v36 ECD
```

-continued

```
source                1..238
                      mol_type = protein
                      organism = synthetic construct
SEQUENCE: 280
DTQEKEVRAM VGSDVELSCA CPEGSRFDLN DVYVYWQTSE SKTVVTYHIP QHSSLENVDS    60
RYRNRALMSP AGMLRGDLSL RLFNVTPQDE QKFHCLVLSR SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 281          moltype = AA   length = 238
FEATURE                 Location/Qualifiers
REGION                  1..238
                        note = ICOSL v37 ECD
source                  1..238
                        mol_type = protein
                        organism = synthetic construct
SEQUENCE: 281
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 282          moltype = AA   length = 238
FEATURE                 Location/Qualifiers
REGION                  1..238
                        note = ICOSL v38 ECD
source                  1..238
                        mol_type = protein
                        organism = synthetic construct
SEQUENCE: 282
DTQEKEVRAM VGSDVELSCA CPEGSRFDLN DVYVYWQTSE SKTVVTYHIP QHSSLEYVDS    60
RYRNRALMSP AGMLQGDFSL RLFNVTPQDE QKFHCLVLSR SLGFQEVLSD EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 283          moltype = AA   length = 238
FEATURE                 Location/Qualifiers
REGION                  1..238
                        note = ICOSL v39 ECD
source                  1..238
                        mol_type = protein
                        organism = synthetic construct
SEQUENCE: 283
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 284          moltype = AA   length = 238
FEATURE                 Location/Qualifiers
REGION                  1..238
                        note = ICOSL v40 ECD
source                  1..238
                        mol_type = protein
                        organism = synthetic construct
SEQUENCE: 284
DTQEKEVRAM VGSDVELSCA CPEGSRFDLN DVYVYWQTSE SKTVVTYHIP QHSSLEYVDS    60
RYRNRALMSP AGMQRGDFSL RLFNVTPQDE QKFHCLVLSR SLGFQEVLSD EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 285          moltype = AA   length = 238
FEATURE                 Location/Qualifiers
REGION                  1..238
                        note = ICOSL v41 ECD
source                  1..238
                        mol_type = protein
                        organism = synthetic construct
SEQUENCE: 285
DTQEKEVRAM VGSDVELSCA CPEGSRFDLN DVYVYWQTSE SKTVVTYHIP QHSSLENVDS    60
RYRNRALMSP AGMLRGDFSL RLFNVTPQDE QKFHCLVLSR SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 286          moltype = AA   length = 238
FEATURE                 Location/Qualifiers
REGION                  1..238
                        note = ICOSL v42 ECD
source                  1..238
```

-continued

```
                            mol_type = protein
                            organism = synthetic construct
SEQUENCE: 286
DTQEKEVRAM VGSDVELSCA CPEGSRFDLN DVYVYWQTSE SKTVVTYHIP QHSSLENVDS    60
RYRNRALMSP AGMLRGDFSL RLFNVTPQDE QKFHCLVLSQ SLGFQEVLSV EVTLHVAANF   120
GVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 287            moltype = AA   length = 238
FEATURE                   Location/Qualifiers
REGION                    1..238
                          note = ICOSL v43 ECD
source                    1..238
                          mol_type = protein
                          organism = synthetic construct
SEQUENCE: 287
DTQEKEVRAM VGSDVELSCV CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLGV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 288            moltype = AA   length = 238
FEATURE                   Location/Qualifiers
REGION                    1..238
                          note = ICOSL v44 ECD
source                    1..238
                          mol_type = protein
                          organism = synthetic construct
SEQUENCE: 288
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSP SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 289            moltype = AA   length = 238
FEATURE                   Location/Qualifiers
REGION                    1..238
                          note = ICOSL v45 ECD
source                    1..238
                          mol_type = protein
                          organism = synthetic construct
SEQUENCE: 289
DTQEKEVRAM VGSDVELSCA CPEGSRFDLN DVYVYWQTSE SKTVVTYHIP QHSSLEYVDS    60
SYRNRALMSP AGMLRGDFSL RLFNVTPQDE QKFHCLVLSR SLGFQEVLSD EVTLHVAANF   120
SVPVVSAPHS PSQDELTFTC TSINGYPRPN VYWINKTDNS LLDQALQNDT VFSNMRGLYD   180
VVSVLRIART PSVNIGCCIE NVLLQQNLTV GSQTGNDIGE RDKITENPVS TGEKNAAT     238

SEQ ID NO: 290            moltype = AA   length = 238
FEATURE                   Location/Qualifiers
REGION                    1..238
                          note = ICOSL v46 ECD
source                    1..238
                          mol_type = protein
                          organism = synthetic construct
SEQUENCE: 290
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSV EVTLHVAANF   120
SAPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 291            moltype = AA   length = 238
FEATURE                   Location/Qualifiers
REGION                    1..238
                          note = ICOSL v47 ECD
source                    1..238
                          mol_type = protein
                          organism = synthetic construct
SEQUENCE: 291
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSV EVTLHVAANF   120
SVPVVSAPHS PSQDELTFTC TSINGYPRPN VYWINKTDNS LLDQALQNDT VSLNMRGLYD   180
VVSVLRIART PSVNIGCCIE NVLLQQNLTV GSQTGNDIGE RDKITENPVS TGEKNAAT     238

SEQ ID NO: 292            moltype = AA   length = 238
FEATURE                   Location/Qualifiers
REGION                    1..238
                          note = ICOSL v48 ECD
source                    1..238
                          mol_type = protein
```

-continued

```
                         organism = synthetic construct
SEQUENCE: 292
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 293           moltype = AA  length = 238
FEATURE                  Location/Qualifiers
REGION                   1..238
                         note = ICOSL v49 ECD
source                   1..238
                         mol_type = protein
                         organism = synthetic construct
SEQUENCE: 293
DTQEKEVRAM VGSDVELSCA CPEGSRFDLN DVYVYWQTSE SKTVVTYHIP QSSSLENVDS    60
RYRNRALMSP AGMLRGDFSL RLFNVTPQDE QKFHCLVLSQ SLGFQEVLSV EVTLHVAANS   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 294           moltype = AA  length = 238
FEATURE                  Location/Qualifiers
REGION                   1..238
                         note = ICOSL v50 ECD
source                   1..238
                         mol_type = protein
                         organism = synthetic construct
SEQUENCE: 294
DTQEKEVRAM VGSDVELSCA CPEGSRFDLN DVYVYWQTSE SKTVVTYHIP QSSSLENVDS    60
RYRNRALMSP AGMLRGDFSL RLFNVTPQDE QKFHCLALSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 295           moltype = AA  length = 238
FEATURE                  Location/Qualifiers
REGION                   1..238
                         note = ICOSL v51 ECD
source                   1..238
                         mol_type = protein
                         organism = synthetic construct
SEQUENCE: 295
DTQEKEVRAM VGSDVELSCA CPEGSRFDLN DVYVYWQTSE SKTVVTYHIP QSSSLENVDS    60
RYRNRALMSP ARMLRGDFSL RLFNVTPQDE QKFHCLVLSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 296           moltype = AA  length = 238
FEATURE                  Location/Qualifiers
REGION                   1..238
                         note = ICOSL v52 ECD
source                   1..238
                         mol_type = protein
                         organism = synthetic construct
SEQUENCE: 296
DTQEKEVRAM VGSDVELSCA CPEGSRFDLN DVYVYWQTSE SKTVVTYHIP QSSSLENVDS    60
RYRNRALMSP TGMLRGDFSL RLFNVTPQDE QKFHCLVLSQ SLGFQEVLSV EVTLHVTANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 297           moltype = AA  length = 238
FEATURE                  Location/Qualifiers
REGION                   1..238
                         note = ICOSL v53 ECD
source                   1..238
                         mol_type = protein
                         organism = synthetic construct
SEQUENCE: 297
DTQEKEVRAM VGSDVELSCA CPEGSRFDLN DVYVYWQTSE SKTVVTYHIP QSSSLENVDS    60
RYRNRALMSP AGMLRGDFSL RLFNVTPQDE QKFHCLVLSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGG RDKITENPVS TGEKNAAT     238

SEQ ID NO: 298           moltype = AA  length = 238
FEATURE                  Location/Qualifiers
REGION                   1..238
                         note = ICOSL v54 ECD
source                   1..238
                         mol_type = protein
                         organism = synthetic construct
```

-continued

```
SEQUENCE: 298
DTQEKEVRAM VGSDVELSCA CPEGSRFDLN DVYVYWQTSE SKTVVTHHIP QSSSLENVDS    60
RYRNRALMSP AGMLRGDFSL RLFNVTPQDE QKFHCLVLSQ SLGFQEALSV EVTLHVAANS   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 299          moltype = AA   length = 238
FEATURE                 Location/Qualifiers
REGION                  1..238
                        note = ICOSL v55 ECD
source                  1..238
                        mol_type = protein
                        organism = synthetic construct
SEQUENCE: 299
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD EVTLHVAANF   120
SVPVVSAPHS PFQDELTFTC TSINGYPRPN VYWINKTDNS LLDQALQNDT VFLNTRGLYD   180
VVSVLRIART PSVNIGCCIE NVLLQQNLTV GSQTGNDIGE RDKITENPVS TGEKNAAT     238

SEQ ID NO: 300          moltype = AA   length = 238
FEATURE                 Location/Qualifiers
REGION                  1..238
                        note = ICOSL v56 ECD
source                  1..238
                        mol_type = protein
                        organism = synthetic construct
SEQUENCE: 300
DTQEKEVRAM VGSDVVLSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD EVTLRVAANF   120
SVPVVSAPHS PSQDELTFTC TSINGYPRPN VCWINMTDNS LLDQALQNDT VFLNMRGLYD   180
VVSVLRIART PSVNIGCRIE NVLLQQNLTV GSQTGNDIGE RDKITENPVS TGEKNAAT     238

SEQ ID NO: 301          moltype = AA   length = 238
FEATURE                 Location/Qualifiers
REGION                  1..238
                        note = ICOSL v57 ECD
source                  1..238
                        mol_type = protein
                        organism = synthetic construct
SEQUENCE: 301
DTQEKEVRAM VGSDVELSCA CPEGSRFDLN DVYVYWRTSE SKTVVTYHIP QHSSLEYVDS    60
RYRNRALMSP AGMLRGDFSL RLFNVTPQDE QKFHCLVLSR SLGFQEVLSN EVTLHVAANF   120
SVPVVSAPHS PSQDELTFTC TFINGYPRPN VYWINKTDNS LLDQALQNDT VFLNMRGLYD   180
VVSVLRIART PSVNIGCRIE NVLLQQNLTV GSQTGNVIGE GDKITENPVS TGEKNAAT     238

SEQ ID NO: 302          moltype = AA   length = 238
FEATURE                 Location/Qualifiers
REGION                  1..238
                        note = ICOSL v58 ECD
source                  1..238
                        mol_type = protein
                        organism = synthetic construct
SEQUENCE: 302
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD EVTLHVAANF   120
SVPVVSAPHS PSQDELTFTC TSINGYPRPN VYWINKTDNS LLDQALQNDT VFLNMRGLYD   180
VVSVLRIART PSVNIGCRIE NVLLQQNLTV GSQTGNDIGE RDKITENPVS TGEKNAAT     238

SEQ ID NO: 303          moltype = AA   length = 238
FEATURE                 Location/Qualifiers
REGION                  1..238
                        note = ICOSL v59 ECD
source                  1..238
                        mol_type = protein
                        organism = synthetic construct
SEQUENCE: 303
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD EVTLHAAANF   120
SVPVVSAPHS PSQDELTFTC TSINGYPRPN VYWINKTDNS MLDQALQNDT VSLNMRGLYD   180
VVSVLRIART PGVNIGCRIE NVLLQQNLTV GSQTGNDIGE RDKITENPVS TGEKNAAT     238

SEQ ID NO: 304          moltype = AA   length = 238
FEATURE                 Location/Qualifiers
REGION                  1..238
                        note = ICOSL v60 ECD
source                  1..238
                        mol_type = protein
                        organism = synthetic construct
SEQUENCE: 304
```

-continued

```
DTQEKEVRAM VGSDVELSCA CPEGSRSDLN DVYVYWQTSE SKTVVTYHIP QHSSLEYVDS    60
RYRNRALMSP AGMLRGDFSL RLFNVTPQDE QKFHCLVLSQ SLGFQEVLSN EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 305          moltype = AA   length = 238
FEATURE                 Location/Qualifiers
REGION                  1..238
                        note = ICOSL v61 ECD
source                  1..238
                        mol_type = protein
                        organism = synthetic construct
SEQUENCE: 305
DTQEKEVRAM VGSDVELSCA CPEGSRFDLN DVYVYWQTSE SKTVVTYHIP QSSSLENVDS    60
RYRNRALMSP AGMLRGDFSL RLFNVTPQDE QKFECIVLSQ SLGFQEVLNV EVTLHVAANF   120
SVPVVSAPHS PSQDELTFTC TSINGYPRPN VYWINKTDNS LLDQAQQNDT VFLNMRGLYD   180
VVSVLRIART PSVNIGCCIE NVLLQQNLTV GSQTGNDIGE RDKITENPVS TGEKNAAT     238

SEQ ID NO: 306          moltype = AA   length = 238
FEATURE                 Location/Qualifiers
REGION                  1..238
                        note = ICOSL v62 ECD
source                  1..238
                        mol_type = protein
                        organism = synthetic construct
SEQUENCE: 306
DTQEKEVRAM VGSDVELRCA CPEGSRFDLN DVYVYWQTSE SKTVVTYHIP QSSSLENVDS    60
RYRNRALMSP AGMLRGDFSL RLFNVTPQDE QKLHCLVLSQ SLGFQEVLSV EVTLHVAANF   120
SVPVVSAPHS PSQDELTFTC TSVNGYPRPN VYWINKTDNS LLDQALQNDT VFLNMRGLYD   180
VVSVLRIART PSVNIGCCIE NVLLQQNLTV GSQTGNDIGE GDKITENPVS TGEKNAAT     238

SEQ ID NO: 307          moltype = AA   length = 238
FEATURE                 Location/Qualifiers
REGION                  1..238
                        note = ICOSL v63 ECD
source                  1..238
                        mol_type = protein
                        organism = synthetic construct
SEQUENCE: 307
DTQEKEVRAM VGSDVELSCT CPEGSRFDLN DVYVYWQTSE SKTVVTYHIP QDSSLENVDS    60
RYRNRALMSP AGMLRGDFSL RLFNVTPQDE QKFHCLVLSQ SLGFQEVLSV EVTLHVAANF   120
SVPVVSAPHS PSQDELTFTC TSINGCPRPN VYWINKTDNS LLDLALQNDT VFLNMRGLYD   180
VVSVLRIART PSVNIGCCIE NVLLQQNLTV GSQTGNDIGE RDKITENPVS TGEKNAAT     238

SEQ ID NO: 308          moltype = AA   length = 238
FEATURE                 Location/Qualifiers
REGION                  1..238
                        note = ICOSL v64 ECD
source                  1..238
                        mol_type = protein
                        organism = synthetic construct
SEQUENCE: 308
DTQEKEVRAM EGSDVELSCA CPEGSRFDLD DVYVYWQTSE SKTVVTYHIP QHSSLEYVDS    60
RYRNRALMSP AGMLRGDFSL RLFNVTPQDE QKFECIVFSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVDIGCCIE NVLLQQNLTA GSQTGNDTGE RDKITENPVS TGEKNAAT     238

SEQ ID NO: 309          moltype = AA   length = 238
FEATURE                 Location/Qualifiers
REGION                  1..238
                        note = ICOSL v65 ECD
source                  1..238
                        mol_type = protein
                        organism = synthetic construct
SEQUENCE: 309
DTQEKEVRAM VGSDVELSCA CPEGSRFDLN DVYVYWQTSE SKTVVTYHIP QSSSLENVDS    60
RYRNRALMSP AGMLRGDFSL RLFNVTPQDE QKFECIVLSQ SLGFQEVLSV EVTLHVAANF   120
SMPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 310          moltype = AA   length = 238
FEATURE                 Location/Qualifiers
REGION                  1..238
                        note = ICOSL v66 ECD
source                  1..238
                        mol_type = protein
                        organism = synthetic construct
SEQUENCE: 310
DTQEKEVRAM VGSDVELSCA CPEGSRFDLN DVYVYWQTSE SKTVVTYHIP QHSSLEYVDS    60
```

```
RYRNRALMSP AGMLRGDFSL RLFNVTPQDE QKFECIVLSQ SLGFQEVLSV EVTLHVAANI 120
SVPVVTAPHS PSQDELTFTC TSINGYPRPN VYRINKTDNS LLDQALQNDT VFLNMRGLYD 180
VVSVLRIART PSVNIGCCIE NVLLQQNLTV GSQTGNDNGE RDKITENPVS TGEKNAAT    238

SEQ ID NO: 311          moltype = AA  length = 238
FEATURE                 Location/Qualifiers
REGION                  1..238
                        note = ICOSL v67 ECD
source                  1..238
                        mol_type = protein
                        organism = synthetic construct
SEQUENCE: 311
DTQEKEVRAV VGSDVELRCA CPEGSRFDLD DVYVYWQTSE SKTVVTYHIP QSSSLENVDS 60
RYRNRALMSP AGMLRGDFSL RLFNVTPQDE QKFHCLVLSQ SLGFQEVLSV EVTLHVAANF 120
SVPVVRAPHS PSQDELTFSC TSINGYPRPN VYWINKTDNS LLDQALQNDT VFLNMRGLYD 180
VVSVLRIART PSVNIGCCIE NVFLQQNLTV GSQTGNDIGE RDKITENPVS TGEKNAAT    238

SEQ ID NO: 312          moltype = AA  length = 238
FEATURE                 Location/Qualifiers
REGION                  1..238
                        note = ICOSL v68 ECD
source                  1..238
                        mol_type = protein
                        organism = synthetic construct
SEQUENCE: 312
DTQEKEVRAM VGSDVELSCA CPEGGRFDLD DVYVYWQTSE SKTVVTYHIP QSSSLENVDS 60
RYRNRALMSP AGMLRGDFSL RLFNVTPQDE QKFHCLVLSQ SLGFQEVLSV EVTLHVAANS 120
SVPVVSAPHS PSQDELTFTC TSINGYPRPN VYWINKTDNS LLDQALQNDT VFLNMRGLYD 180
VVSVLRIART PSVNIGCCIE NVLLQQNLTV GSQTGNDIGE RDKITEKPVS TGEKNAAT    238

SEQ ID NO: 313          moltype = AA  length = 238
FEATURE                 Location/Qualifiers
REGION                  1..238
                        note = ICOSL v69 ECD
source                  1..238
                        mol_type = protein
                        organism = synthetic construct
SEQUENCE: 313
DTQEKEVRAM VGSDVELSCA CPEGSRFDLD DVYVYWQTSE SKTVVTYHIP QSSSLENVDS 60
RYRNRAPMSP AGMLRGDFSL RLFNVTPQDE QKFHCLVLSK SLGFQEVLSV EVTLHVAANF 120
SVPVVSAPHS PSQDELTFTC TSINGYPRPN VYWINKTDNS LLDQALQNDT VFLNMRGLYD 180
VVSVLRIART PSVNIGCCIE NVLLQQNLTV GSQTGNGIGE KDKISENPVS TGEKNAAT    238

SEQ ID NO: 314          moltype = AA  length = 238
FEATURE                 Location/Qualifiers
REGION                  1..238
                        note = ICOSL v70 ECD
source                  1..238
                        mol_type = protein
                        organism = synthetic construct
SEQUENCE: 314
DTQEKEVRAM VGSDVELSCA CPEGSRFDLN DVYVYWQTSE SKTVVTYHIP QHSSLEYVDS 60
RYRNRALMSP AGMLRGDFSL RLFNVTPQDE QKFHCLVLSR SLGFQEVLSD EVTLHVTANF 120
SVPVVSAPHS PSQDELTFTC TSINGYPRPN VYWINKTDNS LLDQALQNDT VFLNMRGLYD 180
VVSVLRIARS PSVNIGCRIE NVLLQQNLTV GSQTGNDIGE RDKITENPVS TGEKNAAT    238

SEQ ID NO: 315          moltype = AA  length = 238
FEATURE                 Location/Qualifiers
REGION                  1..238
                        note = ICOSL v71 ECD
source                  1..238
                        mol_type = protein
                        organism = synthetic construct
SEQUENCE: 315
DTQEKEVRAM VGSDVELSCA CPEGSRFDLN DVYVYWQTSE SKTVVTYHIP QHSSLEYVDS 60
RYRNRALMSP AGMLRGDFSL RLFNVTPQDE QKFHCLVLSR SLGFQEVLSD EVTLHVAANF 120
SVPVVSAPHS PSQDELTFTC TSINGYPRPN VYWINKTDNS LLDQALQNDT VSLNMRGLYD 180
VVSVLRIART PSVNIGCRIE NVLLQQNLTV GSQTGNDIGE RDKITENPVS TGEKNAAT    238

SEQ ID NO: 316          moltype = AA  length = 238
FEATURE                 Location/Qualifiers
REGION                  1..238
                        note = ICOSL v72 ECD
source                  1..238
                        mol_type = protein
                        organism = synthetic construct
SEQUENCE: 316
DTQEKEVRAM VGSDVELSCA CPEGGRCDLN DVYVYWQTSE SKTVVTYHIP QHSSLEYVDS 60
RYRNRALMSP AGMLRGDFSL RLFNVTPQDE QKFHCLVLSR SLGFQEVLSD EVTLHVAANF 120
```

-continued

```
SVPVVSAPHS PSQDKLTFTC TSINGYPRPN VYWINKTDNS LLDQALQNDT VFSNMRGLYD    180
VVSVLRIART PSVNIGCRIE NVLLQQNLTV GSQTGNDIGE RDKITENPVS TGEKNAAT      238

SEQ ID NO: 317          moltype = AA   length = 238
FEATURE                 Location/Qualifiers
REGION                  1..238
                        note = ICOSL v73 ECD
source                  1..238
                        mol_type = protein
                        organism = synthetic construct
SEQUENCE: 317
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSQ SLGFQEVLSA EVTLHVAANF    120
SVPVVSAPHS PSQDELTFTC TSINGYPRPN VYWINKTDNS LLDQALQNDT VFLNMRGLYD    180
VVSVLRIART PSVNIGCRIE NVLLQQNLTV GSQTGNDIGE IDKITENPVS TGEKNAAT      238

SEQ ID NO: 318          moltype = AA   length = 238
FEATURE                 Location/Qualifiers
REGION                  1..238
                        note = ICOSL v74 ECD
source                  1..238
                        mol_type = protein
                        organism = synthetic construct
SEQUENCE: 318
DTQEKEVRAI VGGDVELSCA CPEGSRFDLN DVYVYWQTSE SKTVVTYHIP QHSSLEYVDS    60
RYRNRALMSP AGMLRGGFSL RLFNVTPQDE QKFHCLVLSA SLGFQEVLSA EVTLHVAANF    120
SVPVVSAPPS PSQDELTFTC TSVNGYPRPN VYWINKTDNS LLDQALQNDT VSLNMRGLYD    180
VVSVLRIART PSMNIGCRIE NVLLQQNLTV GSQTGNDIGE RDKITENPVS TGEKNAAT      238

SEQ ID NO: 319          moltype = AA   length = 238
FEATURE                 Location/Qualifiers
REGION                  1..238
                        note = ICOSL v75 ECD
source                  1..238
                        mol_type = protein
                        organism = synthetic construct
SEQUENCE: 319
DTQEKEVRAM VGSDVELSCA CPEGSRFDLN DVYVYWQTSE SKTVVTYHIP QHSSLEYVDS    60
CFRNRALMSP AGMLRGDFSL RLFNVTPQDE QKFHCLVLSR SLGFQEVLSN EVTLHVAANS    120
SVPVVSAPHS PSQDELTFTC TSINGYPRPN VYWINKTDNS LLDQALQNDT VFLNMRGLYD    180
VVSVLRIART PSVNIGCRIE NVLLQQNLTV GSQTGNDIGE RDKITENPVS TGEKNAAT      238

SEQ ID NO: 320          moltype = AA   length = 238
FEATURE                 Location/Qualifiers
REGION                  1..238
                        note = ICOSL v76 ECD
source                  1..238
                        mol_type = protein
                        organism = synthetic construct
SEQUENCE: 320
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD EVTLRVAANF    120
SVPVVSAPHS PSQDELTFTC TSINGYPRPN VYWINKTDNS LLDQALQNDT VFLNMRGLYD    180
VVSVLRIART PSVNIGCRIE NVLLQQNLTV GSQTGNDIGE RDKITENPVS TGEKNAAT      238

SEQ ID NO: 321          moltype = AA   length = 238
FEATURE                 Location/Qualifiers
REGION                  1..238
                        note = ICOSL v77 ECD
source                  1..238
                        mol_type = protein
                        organism = synthetic construct
SEQUENCE: 321
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD EVTLHVAANF    120
SVPVVSAPHS PSQDELTFTC TSIDGYPRPN VYWINKTDNS LLDQALQNDT VSLNMRGLYD    180
VVSVLRIART PSVNIGCRIE NVLLQQNLTV GSQTGNDIGE RDKITENPVS TGEKNAAT      238

SEQ ID NO: 322          moltype = AA   length = 238
FEATURE                 Location/Qualifiers
REGION                  1..238
                        note = ICOSL v78 ECD
source                  1..238
                        mol_type = protein
                        organism = synthetic construct
SEQUENCE: 322
DTQEKEVRAM VGSDVELSCA CPEGSRFDLN DVYVYWQTSE SKTVVTYHIP QSSSLENVDS    60
RYRNRALMSP AGMLRGDFSL RLFNVTPQDE QKFECLVFSR SLGFQEVLSV EVTLHVAANF    120
SVPVVSAPHS PSQDELTFTC TSINGYPRPN VYWINKTDNS LLDQALQNDT VFLNMRGLYD    180
```

-continued

```
VVSVLRIART PSVNIGCCIE NVLLQQNLTV GSQTGNDIGE RDKITENPVS TGEKNAAT      238

SEQ ID NO: 323            moltype = AA   length = 238
FEATURE                   Location/Qualifiers
REGION                    1..238
                          note = ICOSL v79 ECD
source                    1..238
                          mol_type = protein
                          organism = synthetic construct
SEQUENCE: 323
DTQEKEVRAM VGSDVELSCA CPEGSRFDLN DVVYWQTSE SKTVVTYHIP QSSSLENVDS       60
RYRNRALMSP AGMLRGDFSL RLFNVTPQDA QKFHCLVLSQ SLGFQEVLSV EVTLHVAANF     120
SVPVVSAPHS PSQDELTFTC TSINGYPRPN VYWINKTDNS LLDQALQNDT VFLNMRGLYD     180
VVSVLRIART PSVNIGCCIE NVLLQQNLTV GSQTGNDIGE RDKITENPVS TGEKNAAT      238

SEQ ID NO: 324            moltype = AA   length = 238
FEATURE                   Location/Qualifiers
REGION                    1..238
                          note = ICOSL v80 ECD
source                    1..238
                          mol_type = protein
                          organism = synthetic construct
SEQUENCE: 324
DTQEKEVRAM VGSDVELSCA CPEGSRFDLD DVVYWQTSE SETVVTYHIP QSSSLENVDS       60
RYRNRALMSP AGMLRGDFSL RLFNVTPQDE QKFHCLVLSQ SLGFQEVLSV EVTLHVAANF     120
SVPVVSAPHS PSQDELTFTC TSINGYPRPN VYWINKTDNS LLDQALQNDT VFLNMRGLYD     180
VVSVLRIART PSVNIGCCIE NVLLQQNLTV GSQTGNDIGE RDKITENPVS TGEKNAAT      238

SEQ ID NO: 325            moltype = AA   length = 238
FEATURE                   Location/Qualifiers
REGION                    1..238
                          note = ICOSL v81 ECD
source                    1..238
                          mol_type = protein
                          organism = synthetic construct
SEQUENCE: 325
DTQEKEVRAM VGSDVELSCA CPEGSRFDLN DVVYWQTSE SKTVVTYHIP QSSSLENVDS       60
RYRNRALMSP AGMLRGDFSL RLFNVTPQDE QKFHCLVLSQ SLGFQEVLSV EVTLHVAANS     120
SVPVVSAPHS PSQDELTFTC TSVNGYPRPN VYWINKTDNS LLDQALQNDT VFLNMRGLYD     180
VVSVLRIART PSVNIGCCIE NVLLQQNLTV GSQTGNDIGE RDKVTENPVS TGEKNAAT      238

SEQ ID NO: 326            moltype = AA   length = 111
FEATURE                   Location/Qualifiers
REGION                    1..111
                          note = ICOSL v36 IgV
source                    1..111
                          mol_type = protein
                          organism = synthetic construct
SEQUENCE: 326
DTQEKEVRAM VGSDVELSCA CPEGSRFDLN DVVYWQTSE SKTVVTYHIP QHSSLENVDS       60
RYRNRALMSP AGMLRGDLSL RLFNVTPQDE QKFHCLVLSR SLGFQEVLSV E             111

SEQ ID NO: 327            moltype = AA   length = 111
FEATURE                   Location/Qualifiers
REGION                    1..111
                          note = ICOSL v37IgV
source                    1..111
                          mol_type = protein
                          organism = synthetic construct
SEQUENCE: 327
DTQEKEVRAM VGSDVELSCA CPEGSRFDLN DVVYWQTSE SKTVVTYHIP QHSSLEYVDS       60
RYRNRALMSP AGMLRGDFSL RLFNVTPQDE QKFHCLVLSR SLGFQEVLSD E             111

SEQ ID NO: 328            moltype = AA   length = 111
FEATURE                   Location/Qualifiers
REGION                    1..111
                          note = ICOSL v38IgV
source                    1..111
                          mol_type = protein
                          organism = synthetic construct
SEQUENCE: 328
DTQEKEVRAM VGSDVELSCA CPEGSRFDLN DVVYWQTSE SKTVVTYHIP QHSSLEYVDS       60
RYRNRALMSP AGMLQGDFSL RLFNVTPQDE QKFHCLVLSR SLGFQEVLSD E             111

SEQ ID NO: 329            moltype = AA   length = 111
FEATURE                   Location/Qualifiers
REGION                    1..111
                          note = ICOSL v39IgV
source                    1..111
```

```
                              mol_type = protein
                              organism = synthetic construct
SEQUENCE: 329
DTQEKEVRAM VGSDVELSCA CPEGSRFDLN DVYVYWQTSE SKTVVTYHIP QHSSLEYVDS  60
RYRNRALMSP AGMLRGDFSL RLFNVTPQDE QKFHCLVLSR SLGFQEVLSV E            111

SEQ ID NO: 330          moltype = AA  length = 111
FEATURE                 Location/Qualifiers
REGION                  1..111
                        note = ICOSL v40IgV
source                  1..111
                        mol_type = protein
                        organism = synthetic construct
SEQUENCE: 330
DTQEKEVRAM VGSDVELSCA CPEGSRFDLN DVYVYWQTSE SKTVVTYHIP QHSSLEYVDS  60
RYRNRALMSP AGMQRGDFSL RLFNVTPQDE QKFHCLVLSR SLGFQEVLSD E            111

SEQ ID NO: 331          moltype = AA  length = 111
FEATURE                 Location/Qualifiers
REGION                  1..111
                        note = ICOSL v41IgV
source                  1..111
                        mol_type = protein
                        organism = synthetic construct
SEQUENCE: 331
DTQEKEVRAM VGSDVELSCA CPEGSRFDLN DVYVYWQTSE SKTVVTYHIP QHSSLENVDS  60
RYRNRALMSP AGMLRGDFSL RLFNVTPQDE QKFHCLVLSR SLGFQEVLSV E            111

SEQ ID NO: 332          moltype = AA  length = 111
FEATURE                 Location/Qualifiers
REGION                  1..111
                        note = ICOSL v43IgV
source                  1..111
                        mol_type = protein
                        organism = synthetic construct
SEQUENCE: 332
DTQEKEVRAM VGSDVELSCV CPEGSRFDLN DVYVYWQTSE SKTVVTYHIP QHSSLEYVDS  60
RYRNRALMSP AGMLRGDFSL RLFNVTPQDE QKFHCLVLSR SLGFQEVLGV E            111

SEQ ID NO: 333          moltype = AA  length = 111
FEATURE                 Location/Qualifiers
REGION                  1..111
                        note = ICOSL v44IgV
source                  1..111
                        mol_type = protein
                        organism = synthetic construct
SEQUENCE: 333
DTQEKEVRAM VGSDVELSCA CPEGSRFDLN DVYVYWQTSE SKTVVTYHIP QHSSLEYVDS  60
RYRNRALMSP AGMLRGDFSL RLFNVTPQDE QKFHCLVLSP SLGFQEVLSV E            111

SEQ ID NO: 334          moltype = AA  length = 111
FEATURE                 Location/Qualifiers
REGION                  1..111
                        note = ICOSL v48 IgV
source                  1..111
                        mol_type = protein
                        organism = synthetic construct
SEQUENCE: 334
DTQEKEVRAM VGSDVELSCA CPEGSRFDLN DVYVYWQTSE SKTVVTYHIP QHSSLEYVDS  60
RYRNRALMSP AGMLRGDFSL RLFNVTPQDE QKFHCLVLSQ SLGFQEVLSV E            111

SEQ ID NO: 335          moltype = AA  length = 111
FEATURE                 Location/Qualifiers
REGION                  1..111
                        note = ICOSL v50 IgV
source                  1..111
                        mol_type = protein
                        organism = synthetic construct
SEQUENCE: 335
DTQEKEVRAM VGSDVELSCA CPEGSRFDLN DVYVYWQTSE SKTVVTYHIP QSSSLENVDS  60
RYRNRALMSP AGMLRGDFSL RLFNVTPQDE QKFHCLALSQ SLGFQEVLSV E            111

SEQ ID NO: 336          moltype = AA  length = 111
FEATURE                 Location/Qualifiers
REGION                  1..111
                        note = ICOSL v51IgV
source                  1..111
                        mol_type = protein
                        organism = synthetic construct
```

-continued

```
SEQUENCE: 336
DTQEKEVRAM VGSDVELSCA CPEGSRFDLN DVYVYWQTSE SKTVVTYHIP QSSSLENVDS   60
RYRNRALMSP ARMLRGDFSL RLFNVTPQDE QKFHCLVLSQ SLGFQEVLSV E            111

SEQ ID NO: 337              moltype = AA  length = 111
FEATURE                     Location/Qualifiers
REGION                      1..111
                            note = ICOSL v60IgV
source                      1..111
                            mol_type = protein
                            organism = synthetic construct
SEQUENCE: 337
DTQEKEVRAM VGSDVELSCA CPEGSRSDLN DVYVYWQTSE SKTVVTYHIP QHSSLEYVDS   60
RYRNRALMSP AGMLRGDFSL RLFNVTPQDE QKFHCLVLSQ SLGFQEVLSN E            111

SEQ ID NO: 338              moltype = AA  length = 111
FEATURE                     Location/Qualifiers
REGION                      1..111
                            note = ICOSL v78IgV
source                      1..111
                            mol_type = protein
                            organism = synthetic construct
SEQUENCE: 338
DTQEKEVRAM VGSDVELSCA CPEGSRFDLN DVYVYWQTSE SKTVVTYHIP QSSSLENVDS   60
RYRNRALMSP AGMLRGDFSL RLFNVTPQDE QKFECLVFSR SLGFQEVLSV E            111

SEQ ID NO: 339              moltype = AA  length = 111
FEATURE                     Location/Qualifiers
REGION                      1..111
                            note = ICOSL v79 IgV
source                      1..111
                            mol_type = protein
                            organism = synthetic construct
SEQUENCE: 339
DTQEKEVRAM VGSDVELSCA CPEGSRFDLN DVYVYWQTSE SKTVVTYHIP QSSSLENVDS   60
RYRNRALMSP AGMLRGDFSL RLFNVTPQDA QKFHCLVLSQ SLGFQEVLSV E            111

SEQ ID NO: 340              moltype = AA  length = 111
FEATURE                     Location/Qualifiers
REGION                      1..111
                            note = ICOSL v80IgV
source                      1..111
                            mol_type = protein
                            organism = synthetic construct
SEQUENCE: 340
DTQEKEVRAM VGSDVELSCA CPEGSRFDLD DVYVYWQTSE SETVVTYHIP QSSSLENVDS   60
RYRNRALMSP AGMLRGDFSL RLFNVTPQDE QKFHCLVLSQ SLGFQEVLSV E            111

SEQ ID NO: 341              moltype = AA  length = 414
FEATURE                     Location/Qualifiers
REGION                      1..414
                            note = MISC_FEATURE - VSIG8
source                      1..414
                            mol_type = protein
                            organism = Homo sapiens
SEQUENCE: 341
MRVGGAFHLL LVCLSPALLS AVRINGDGQE VLYLAEGDNV RLGCPYVLDP EDYGPNGLDI   60
EWMQVNSDPA HHRENVFLSY QDKRINHGSL PHLQQRVRFA ASDPSQYDAS INLMNLQVSD  120
TATYECRVKK TTMATRKVIV TVQARPAVPM CWTEGHMTYG NDVVLKCYAS GGSQPLSYKW  180
AKISGHHYPY RAGSYTSQHS YHSELSYQES FHSSINQGLN NGDLVLKDIS RADDGLYQCT  240
VANNVGYSVC VVEVKVSDSR RIGVIIGIVL GSLLALGCLA VGIWGLVCCC CGGSGAGGAR  300
GAFGYGNGGG VGGGACGDLA SEIREDAVAP GCKASGRGSR VTHLLGYPTQ NVSRSLRRKY  360
APPPCGGPED VALAPCTAAA ACEAGPSPVY VKVKSAEPAD CAEGPVQCKN GLLV         414

SEQ ID NO: 342              moltype = AA  length = 393
FEATURE                     Location/Qualifiers
REGION                      1..393
                            note = MISC_FEATURE - Mature VSIG8
source                      1..393
                            mol_type = protein
                            organism = Homo sapiens
SEQUENCE: 342
VRINGDGQEV LYLAEGDNVR LGCPYVLDPE DYGPNGLDIE WMQVNSDPAH HRENVFLSYQ   60
DKRINHGSLP HLQQRVRFAA SDPSQYDASI NLMNLQVSDT ATYECRVKKT TMATRKVIVT  120
VQARPAVPMC WTEGHMTYGN DVVLKCYASG GSQPLSYKWA KISGHHYPYR AGSYTSQHSY  180
HSELSYQESF HSSINQGLNN GDLVLKDISR ADDGLYQCTV ANNVGYSVCV VEVKVSDSRR  240
IGVIIGIVLG SLLALGCLAV GIWGLVCCCC GGSGAGGARG AFGYGNGGGV GGGACGDLAS  300
EIREDAVAPG CKASGRGSRV THLLGYPTQN VSRSLRRKYA PPPCGGPEDV ALAPCTAAAA  360
CEAGPSPVYV KVKSAEPADC AEGPVQCKNG LLV                                393
```

-continued

```
SEQ ID NO: 343              moltype = AA  length = 242
FEATURE                     Location/Qualifiers
REGION                      1..242
                            note = MISC_FEATURE - VSIG8 ECD
source                      1..242
                            mol_type = protein
                            organism = Homo sapiens
SEQUENCE: 343
VRINGDGQEV LYLAEGDNVR LGCPYVLDPE DYGPNGLDIE WMQVNSDPAH HRENVFLSYQ  60
DKRINHGSLP HLQQRVRFAA SDPSQYDASI NLMNLQVSDT ATYECRVKKT TMATRKVIVT  120
VQARPAVPMC WTEGHMTYGN DVVLKCYASG GSQPLSYKWA KISGHHYPYR AGSYTSQHSY  180
HSELSYQESF HSSINQGLNN GDLVLKDISR ADDGLYQCTV ANNVGYSVCV VEVKVSDSRR  240
IG                                                                242

SEQ ID NO: 344              moltype = AA  length = 16
FEATURE                     Location/Qualifiers
REGION                      1..16
                            note = CD33 Signal Peptide
source                      1..16
                            mol_type = protein
                            organism = synthetic construct
SEQUENCE: 344
MPLLLLLPLL WAGALA                                                 16

SEQ ID NO: 345              moltype = AA  length = 22
FEATURE                     Location/Qualifiers
REGION                      1..22
                            note = IgGkappa light chain
source                      1..22
                            mol_type = protein
                            organism = synthetic construct
SEQUENCE: 345
MDMRVLAQLL GLLLLCFPGA RC                                          22

SEQ ID NO: 346              moltype = AA  length = 18
FEATURE                     Location/Qualifiers
REGION                      1..18
                            note = HSA signal peptide
source                      1..18
                            mol_type = protein
                            organism = synthetic construct
SEQUENCE: 346
MKWVTFISLL FLFSSAYS                                               18

SEQ ID NO: 347              moltype = AA  length = 22
FEATURE                     Location/Qualifiers
REGION                      1..22
                            note = Ig kappa light chain
source                      1..22
                            mol_type = protein
                            organism = synthetic construct
SEQUENCE: 347
MDMRAPAGIF GFLLVLFPGY RS                                          22

SEQ ID NO: 348              moltype = AA  length = 19
FEATURE                     Location/Qualifiers
REGION                      1..19
                            note = Human azurocidin preprotein signal sequence
source                      1..19
                            mol_type = protein
                            organism = synthetic construct
SEQUENCE: 348
MTRLTVLALL AGLLASSRA                                              19

SEQ ID NO: 349              moltype = AA  length = 19
FEATURE                     Location/Qualifiers
REGION                      1..19
                            note = IgG heavy chain signal peptide
source                      1..19
                            mol_type = protein
                            organism = synthetic construct
SEQUENCE: 349
MELGLSWIFL LAILKGVQC                                              19

SEQ ID NO: 350              moltype = AA  length = 19
FEATURE                     Location/Qualifiers
REGION                      1..19
                            note = IgG heavy chain signal peptide
```

-continued

```
source                  1..19
                        mol_type = protein
                        organism = synthetic construct
SEQUENCE: 350
MELGLRWVFL VAILEGVQC                                          19

SEQ ID NO: 351          moltype = AA  length = 19
FEATURE                 Location/Qualifiers
REGION                  1..19
                        note = IgG heavy chain signal peptide
source                  1..19
                        mol_type = protein
                        organism = synthetic construct
SEQUENCE: 351
MKHLWFFLLL VAAPRWVLS                                          19

SEQ ID NO: 352          moltype = AA  length = 19
FEATURE                 Location/Qualifiers
REGION                  1..19
                        note = IgG heavy chain signal peptide
source                  1..19
                        mol_type = protein
                        organism = synthetic construct
SEQUENCE: 352
MDWTWRILFL VAAATGAHS                                          19

SEQ ID NO: 353          moltype = AA  length = 19
FEATURE                 Location/Qualifiers
REGION                  1..19
                        note = IgG heavy chain signal peptide
source                  1..19
                        mol_type = protein
                        organism = synthetic construct
SEQUENCE: 353
MDWTWRFLFV VAAATGVQS                                          19

SEQ ID NO: 354          moltype = AA  length = 19
FEATURE                 Location/Qualifiers
REGION                  1..19
                        note = IgG heavy chain signal peptide
source                  1..19
                        mol_type = protein
                        organism = synthetic construct
SEQUENCE: 354
MEFGLSWLFL VAILKGVQC                                          19

SEQ ID NO: 355          moltype = AA  length = 19
FEATURE                 Location/Qualifiers
REGION                  1..19
                        note = IgG heavy chain signal peptide
source                  1..19
                        mol_type = protein
                        organism = synthetic construct
SEQUENCE: 355
MEFGLSWVFL VALFRGVQC                                          19

SEQ ID NO: 356          moltype = AA  length = 26
FEATURE                 Location/Qualifiers
REGION                  1..26
                        note = IgG heavy chain signal peptide
source                  1..26
                        mol_type = protein
                        organism = synthetic construct
SEQUENCE: 356
MDLLHKNMKH LWFFLLLVAA PRWVLS                                  26

SEQ ID NO: 357          moltype = AA  length = 22
FEATURE                 Location/Qualifiers
REGION                  1..22
                        note = IgG Kappa light chain signal sequences
source                  1..22
                        mol_type = protein
                        organism = synthetic construct
SEQUENCE: 357
MDMRVPAQLL GLLLLWLSGA RC                                      22

SEQ ID NO: 358          moltype = AA  length = 22
FEATURE                 Location/Qualifiers
REGION                  1..22
```

-continued

```
                              note = IgG Kappa light chain signal sequences
source                        1..22
                              mol_type = protein
                              organism = synthetic construct
SEQUENCE: 358
MKYLLPTAAA GLLLLAAQPA MA                                                22

SEQ ID NO: 359                moltype = AA  length = 17
FEATURE                       Location/Qualifiers
REGION                        1..17
                              note = Gaussia luciferase
source                        1..17
                              mol_type = protein
                              organism = synthetic construct
SEQUENCE: 359
MGVKVLFALI CIAVAEA                                                      17

SEQ ID NO: 360                moltype = AA  length = 18
FEATURE                       Location/Qualifiers
REGION                        1..18
                              note = Human albumin
source                        1..18
                              mol_type = protein
                              organism = synthetic construct
SEQUENCE: 360
MKWVTFISLL FLFSSAYS                                                     18

SEQ ID NO: 361                moltype = AA  length = 18
FEATURE                       Location/Qualifiers
REGION                        1..18
                              note = Human chymotrypsinogen
source                        1..18
                              mol_type = protein
                              organism = synthetic construct
SEQUENCE: 361
MAFLWLLSCW ALLGTTFG                                                     18

SEQ ID NO: 362                moltype = AA  length = 14
FEATURE                       Location/Qualifiers
REGION                        1..14
                              note = Human interleukin-2
source                        1..14
                              mol_type = protein
                              organism = synthetic construct
SEQUENCE: 362
MQLLSCIALI LALV                                                         14

SEQ ID NO: 363                moltype = AA  length = 15
FEATURE                       Location/Qualifiers
REGION                        1..15
                              note = Human trypsinogen-2
source                        1..15
                              mol_type = protein
                              organism = synthetic construct
SEQUENCE: 363
MNLLLILTFV AAAVA                                                        15

SEQ ID NO: 364                moltype = AA  length = 238
FEATURE                       Location/Qualifiers
REGION                        1..238
                              note = ICOSL v81 ECD
source                        1..238
                              mol_type = protein
                              organism = synthetic construct
SEQUENCE: 364
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD EVTLHVAANF    120
SVPVVSAPHS PSQDELTFTC TSINGYPRPN VYWINKTDNS LLDQALQNDT VFLNMRGLYD    180
VVSVLRIART PSVNIGCRIE NVLLQQNLTV GGQTGNDIGE RDKITENPVS TGEKNAAT      238

SEQ ID NO: 365                moltype = AA  length = 238
FEATURE                       Location/Qualifiers
REGION                        1..238
                              note = ICOSL v82 ECD
source                        1..238
                              mol_type = protein
                              organism = synthetic construct
SEQUENCE: 365
DTQEKEVRAM VGSDVELSCA CPEGSRFDLN DVYVYWQTSE SKTVVTYHIP QHSSLEYVDS    60
```

```
RYRNRALMSP AGMLRGDFSL RLFNVTPQDE QKFHCLVLSR SLGFQEVLSV EVTLHVAANF    120
SVPVVSAPHS PSQDELTFTC TSINGYPRPN VYWINKTDNS LLDQALQNDT VFLNMRGLYD    180
VVSVLRIART PSVNIGCRIE NVLLQQNLTV GSQTGNDIGE RDKITENPVS TGEKNAAT      238

SEQ ID NO: 366          moltype = AA   length = 238
FEATURE                 Location/Qualifiers
REGION                  1..238
                        note = ICOSL v83 ECD
source                  1..238
                        mol_type = protein
                        organism = synthetic construct
SEQUENCE: 366
DTQEKEVRAM VGSDVELSCA CPEGSRFDLN DVYVYWQTSE SKTVVTYHIP QSSSLENVDS    60
RYRNRALMSP AGMLRGDFSL RLFNVTPQDE QKFHCLVLSQ SLGFQEVLSV EVTLHVAANF    120
SVPVVSAPHS PSQDELTFTC TSINGYPRPN VYWINKTDNS LLDQALQNDT VFLNMRGLYD    180
VVSVLRIART PSVDIGCCIE NVLLQQNLTV GSQTGNDIGE RDKITENPVS TGEKNAAT      238

SEQ ID NO: 367          moltype = AA   length = 238
FEATURE                 Location/Qualifiers
REGION                  1..238
                        note = ICOSL v84 ECD
source                  1..238
                        mol_type = protein
                        organism = synthetic construct
SEQUENCE: 367
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SRGFQEVLSD EVTLRVAANF    120
SVPVVSAPHS PSQDELTFTC TSINGYPRPN VYWINKTDNS LLDQALQNDT VFLNMRGLYD    180
VVSVLRIART PSVNIGCRIE NVLLQQNLTV GSQTGNDIGE RDKITENPVS TGEKNAAT      238

SEQ ID NO: 368          moltype = AA   length = 238
FEATURE                 Location/Qualifiers
REGION                  1..238
                        note = ICOSL v85 ECD
source                  1..238
                        mol_type = protein
                        organism = synthetic construct
SEQUENCE: 368
DTQEKEVRAM VGSDVELSCA CPEGSRFDLN DVYVYWQTSE SKTVVTYHIP QSSPLENVDS    60
RYRNRALMSP AGMLRGDFSL RLFNVTPQDE QKFHCLVLSQ SLGFQEVLSV EVTLHVAANF    120
SVPVVSAPHS PSQDELTFTC TSINGYPRPN VYWINKTDNS LLDQALQNDT VFLNMRGLYD    180
VVSVLRIART PSVNIGCCIE NVLLQQNLTV GSQTGNDIGE RDKITENPVS TGEKNAAT      238

SEQ ID NO: 369          moltype = AA   length = 238
FEATURE                 Location/Qualifiers
REGION                  1..238
                        note = ICOSL v86 ECD
source                  1..238
                        mol_type = protein
                        organism = synthetic construct
SEQUENCE: 369
DTQEKEVRAM VGSDVELSCA CPEGSRFDLN DVYVYWQPSE SKTVVTYHIP QSSSLEDVDS    60
RYRNRALMSP AGMLRGDFSL RLFNVTPQDE QKFHCLVLSQ SLGFQEVLSV EVTLHVAANF    120
SVPVVSAPHS PSQDELTFTC TSINGYPRPN VYWINKTDNS LLDQALQNDT VFLNMRGLYD    180
VVSVLRIART PSVNIGCCIE NVLLQQNLTV GSQTGNDIGE RDKITENPVS TGEKNAAT      238

SEQ ID NO: 370          moltype = AA   length = 237
FEATURE                 Location/Qualifiers
REGION                  1..237
                        note = ICOSL v87 ECD
source                  1..237
                        mol_type = protein
                        organism = synthetic construct
SEQUENCE: 370
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSQ SLGFQEVLSV VTLHVAANFS    120
VPVVSAPHSP SQDELTFTCT SINGYPRPNV YWINKTDNSL LDQALQNDTV FLNMRGLYDV    180
VSVLRIARTP SVNIGCCIEN VLLQQNLTVG SQTGNDIGER DKITENPVST GEKNAAT       237

SEQ ID NO: 371          moltype = AA   length = 237
FEATURE                 Location/Qualifiers
REGION                  1..237
                        note = ICOSL v88 ECD
source                  1..237
                        mol_type = protein
                        organism = synthetic construct
SEQUENCE: 371
DTQEKEVRAM VGSDVELSCA CPEGSRFDLN DVVYWQTSES KTVVTYHIPQ NSSLENVDSR    60
YRNRALMSPA GMLRGDFSLR LFNVTPQDEQ KFHCLVLSQS LGFQEVLSVE VTLHVAANFS    120
```

-continued

```
VPVVSAPHSP SQDELTFTCT SINGYPRPNV YWINKTDNSL LDQALQNDTV FLNMRGLYDV    180
VSVLRIARTP SVNIGCCIEN VLLQQNLTVG SQTGNDIGER DKITENPVST GEKNAAT       237

SEQ ID NO: 372           moltype = AA   length = 237
FEATURE                  Location/Qualifiers
REGION                   1..237
                         note = ICOSL v89 ECD
source                   1..237
                         mol_type = protein
                         organism = synthetic construct
SEQUENCE: 372
DTQEKEVRAM VGSDVELSCA CPEGSRFDLN DVYVYWQTSE SKTVVTYHIP QHSSLENVDS    60
RYRNRALMSP AGMLRGDFSL RLFNVTPQDE QKFHCLVLSQ SLGFQEVLSV EVTLHVAANF    120
SVPVVSAPHS PSQDELTFTT SINGYPRPNV YWINKTDNSL LDQALQNDTV FLNMRGLYDV    180
VSVLRIARTP SVNIGCCIEN VLLQQNLTVG SQTGNDIGER DKIAENPVST GEKNAAT       237

SEQ ID NO: 373           moltype = AA   length = 238
FEATURE                  Location/Qualifiers
REGION                   1..238
                         note = ICOSL v90 ECD
source                   1..238
                         mol_type = protein
                         organism = synthetic construct
SEQUENCE: 373
DTQEKEVRAM VGSDVELSCA CPEGSRFDLN DVYVYWQTSE SKTVVTYHIP QHSSLENVDS    60
RYRNRALMSP AGMLRGDLSL RLFNVTPQDE QKFHCLVLSR SLGFQEVLSV EVTLHVAANF    120
SVPVVSAPHS PSQDELTFTC TSINGYPRPN VYWINKTDNS LLDQALQNDT VFLNMRGLYD    180
VVSVLRIART PSVNIGCRIE NVLLQQNLTV GSQTGNDIGE RDKITENPVS TGEKNAAT      238

SEQ ID NO: 374           moltype = AA   length = 238
FEATURE                  Location/Qualifiers
REGION                   1..238
                         note = ICOSL v91ECD
source                   1..238
                         mol_type = protein
                         organism = synthetic construct
SEQUENCE: 374
DTQEKEVRAM VGSDVELSCA CPEGSRFDLN DVYVYWQTSE SKTVVTYHIP QHSSLEYVDS    60
RYRNRALMSP AGMLQGDFSL RLFNVTPQDE QKFHCLVLSP SLGFQEVLSD EVTLHVAANF    120
SVPVVSAPHS PSQDELTFTC TSINGYPRPN VYWINKTDNS LLDQALQNDT VFLNMRGLYD    180
VVSVLRIART PSVNIGCCIE NVLLQQNLTV GSQTGNDIGE RDKITENPVS TGEKNAAT      238

SEQ ID NO: 375           moltype = AA   length = 238
FEATURE                  Location/Qualifiers
REGION                   1..238
                         note = ICOSL v92 ECD
source                   1..238
                         mol_type = protein
                         organism = synthetic construct
SEQUENCE: 375
DTQEKEVRAM VGSDVELSCA CPEGSRFDLN DVYVYWQTSE SKTVVTYHIP QHSSLEYVDS    60
RYRNRALMSP AGMQRGDFSL RLFNVTPQDE QKFHCLVLSQ SLGFQEVLSD EVTLHVAANF    120
SVPVVSAPHS PSQDELTFTC TSINGYPRPN VYWINKTDNS LLDQALQNDT VFLNMRGLYD    180
VVSVLRIART PGVNIGCCIE NVLLQQNLTV GSQTGNDIGE RDKITENPVS TGEKNAAT      238

SEQ ID NO: 376           moltype = AA   length = 238
FEATURE                  Location/Qualifiers
REGION                   1..238
                         note = ICOSL v93 ECD
source                   1..238
                         mol_type = protein
                         organism = synthetic construct
SEQUENCE: 376
DTQEKEVRAM VGSDVELSCA CPEGSRFDLN DVYVYWQTSE SKTVVTYHIP QHSSLENVDS    60
RYRNRALMSP AGMLRGDFSL RLFNVTPQDE QKFHCLVLSQ SLGFQEVLSV EVTLHVAANF    120
GVPVVSAPHS PSQDELTFTC TSINGYPRPN VYWINKTDNS LLDQALQNDT VFLNMRGLYD    180
VVSVLRIART PSVNIGCRIE NVLLQQNLTV GSQTGNDIGE RDKITENPVS TGEKNAAT      238

SEQ ID NO: 377           moltype = AA   length = 238
FEATURE                  Location/Qualifiers
REGION                   1..238
                         note = ICOSL v94 ECD
source                   1..238
                         mol_type = protein
                         organism = synthetic construct
SEQUENCE: 377
DTQEKEVRAM VGSDVELSCA CPEGSRFDLN DVYVYWQTSE SKTVVTYHIP QSSSLENVDS    60
RYRNRALMSP AGMLRGDFSL RLFNVTPQDE QKFHCLVLSQ SLGFQEVLSV EVTLHVAANS    120
SVPVVSAPHS PSQDELTFTC TSINGYPRPN VYWINKTDNS LLDQALQNDT VFLNMRGLYD    180
```

-continued

```
VVSVLRIART PSVNIGCCIE NVLLQQNLTV GSQTGNDIGE RDKITEKPVS TGEKNAAT      238

SEQ ID NO: 378              moltype = AA  length = 238
FEATURE                     Location/Qualifiers
REGION                      1..238
                            note = ICOSL v96 ECD
source                      1..238
                            mol_type = protein
                            organism = synthetic construct
SEQUENCE: 378
DTQEKEVRAM VGSDVELSCA CPEGSRFDLN DVYVYWQTSE SKTVVTYHIP QSSSLENVDS      60
RYRNRALMSP TGMLRGDFSL RLFNVTPQDE QKFHCLVLSQ SLGFQEVLSV EVTLHVTANF     120
SVPVVSAPHS PSQDELTFTC TSINGYPRPN VYWINKTDNS LLDQALQNDT VFLNMRGLYD     180
VVSVLRIARA PSVNIGCRIE NVLLQQNLTV GSQTGNDIGE RDKITENPVS TGEKNAAT      238

SEQ ID NO: 379              moltype = AA  length = 238
FEATURE                     Location/Qualifiers
REGION                      1..238
                            note = ICOSL v96 ECD
source                      1..238
                            mol_type = protein
                            organism = synthetic construct
SEQUENCE: 379
DTQEKEVRAM VGSDVELSCA CPEGSRFDLN DVYVYWQTSE SKAVVTYHIP QHSSLEYVDS      60
RYRNRALMSP AGMQRGDFSL RLFNVTPQGE QKFHCLVLSQ SLGFQEVLSD EVTLHVAANF     120
SVPVVSAPHS PSQDELTFTC TSINGYPRPN VYWINKTDNS LLDQALQNDT VSLNMRGLYD     180
VVSVLRIART PSVNIGCCIE NVLLQQNLTV GSQTGNDIGE RDKITENPVS TGEKNAAT      238

SEQ ID NO: 380              moltype = AA  length = 238
FEATURE                     Location/Qualifiers
REGION                      1..238
                            note = ICOSL v97 ECD
source                      1..238
                            mol_type = protein
                            organism = synthetic construct
SEQUENCE: 380
DTQEKEVRAM VGSDVELSCA CPEGSRFDLN DVYVYWQTSE SKTVVTYHIP QHSSLEYVDS      60
RYRNRALMSP AGMLRGDFSL RLFNVTPQDE QKFHCLVLSR SLGFQEVLSD EVTLHVAANF     120
SVPVVSAPHS PFQDELTFTC TSINGYPRPN VYWINKTDNS LLDQALQNDT VFLNTRGLYD     180
VVSVLRIART PSVNIGCCIE NVLLQQNLTV GSQTGNDIGE RDKITENPVS TGEKNAAT      238

SEQ ID NO: 381              moltype = AA  length = 238
FEATURE                     Location/Qualifiers
REGION                      1..238
                            note = ICOSL v98 ECD
source                      1..238
                            mol_type = protein
                            organism = synthetic construct
SEQUENCE: 381
DTQEKEVRAM VGSDVELSCA CPEGSRFDLN DVYVYWQTSE SKTVVTYHIP QHSSLEYVDS      60
RYRNRALMSP AGMLRGDFSL RLFNVTPQDE QKFHCLVLSD SLGFQEILSD EVTLHVAANF     120
SVPVVSAPHS PSQDELTFTC TSINGYPRPN VYWFNKTDNS LLDQALQNDT VFLNMRGLYD     180
VVSVLRIART PSVNIGCRIE NVLLQQNLTV GSQTGNDIGE GDKITENPVS TGEKNAAT      238

SEQ ID NO: 382              moltype = AA  length = 111
FEATURE                     Location/Qualifiers
REGION                      1..111
                            note = ICOSL v85IgV
source                      1..111
                            mol_type = protein
                            organism = synthetic construct
SEQUENCE: 382
DTQEKEVRAM VGSDVELSCA CPEGSRFDLN DVYVYWQTSE SKTVVTYHIP QSSPLENVDS      60
RYRNRALMSP AGMLRGDFSL RLFNVTPQDE QKFHCLVLSQ SLGFQEVLSV E             111

SEQ ID NO: 383              moltype = AA  length = 111
FEATURE                     Location/Qualifiers
REGION                      1..111
                            note = ICOSL v86IgV
source                      1..111
                            mol_type = protein
                            organism = synthetic construct
SEQUENCE: 383
DTQEKEVRAM VGSDVELSCA CPEGSRFDLN DVYVYWQPSE SKTVVTYHIP QSSSLEDVDS      60
RYRNRALMSP AGMLRGDFSL RLFNVTPQDE QKFHCLVLSQ SLGFQEVLSV E             111

SEQ ID NO: 384              moltype = AA  length = 110
FEATURE                     Location/Qualifiers
REGION                      1..110
```

-continued

```
                          note = ICOSL v87IgV
source                    1..110
                          mol_type = protein
                          organism = synthetic construct
SEQUENCE: 384
DTQEKEVRAM VGSDVELSCA CPEGSRFDLN DVVYWQTSE SKTVVTYHIP QNSSLENVDS   60
RYRNRALMSP AGMLRGDFSL RLFNVTPQDE QKFHCLVLSQ SLGFQEVLSV            110

SEQ ID NO: 385            moltype = AA  length = 110
FEATURE                   Location/Qualifiers
REGION                    1..110
                          note = ICOSL v88IgV
source                    1..110
                          mol_type = protein
                          organism = synthetic construct
SEQUENCE: 385
DTQEKEVRAM VGSDVELSCA CPEGSRFDLN DVVYWQTSES KTVVTYHIPQ NSSLENVDSR   60
YRNRALMSPA GMLRGDFSLR LFNVTPQDEQ KFHCLVLSQS LGFQEVLSVE            110

SEQ ID NO: 386            moltype = AA  length = 111
FEATURE                   Location/Qualifiers
REGION                    1..111
                          note = ICOSL v91IgV
source                    1..111
                          mol_type = protein
                          organism = synthetic construct
SEQUENCE: 386
DTQEKEVRAM VGSDVELSCA CPEGSRFDLN DVVYWQTSE SKTVVTYHIP QHSSLEYVDS   60
RYRNRALMSP AGMLQGDFSL RLFNVTPQDE QKFHCLVLSP SLGFQEVLSD E          111

SEQ ID NO: 387            moltype = AA  length = 238
FEATURE                   Location/Qualifiers
REGION                    1..238
                          note = ICOSL v99 ECD
source                    1..238
                          mol_type = protein
                          organism = synthetic construct
SEQUENCE: 387
DTQEKEVRAM VGSDVELSCA CPEGSRFDLN DVVYWQTSE SKTVVTYHIP QNSSLENVDS   60
RYRNRALMSP AGMLRGDFSL RLFQVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 388            moltype = AA  length = 238
FEATURE                   Location/Qualifiers
REGION                    1..238
                          note = ICOSL v100 ECD
source                    1..238
                          mol_type = protein
                          organism = synthetic construct
SEQUENCE: 388
DTQEKEVRAM VGSDVELSCA CPEGSRFDLN DVVYWQTSE SKTVVTYHIP QNSSLENVDS   60
RYRNRALMSP AGMLRGDFSL RLFNVTPQDE QKFHCLVLSQ SLGFQEVLSV EVTLHVAAQF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 389            moltype = AA  length = 238
FEATURE                   Location/Qualifiers
REGION                    1..238
                          note = ICOSL v101 ECD
source                    1..238
                          mol_type = protein
                          organism = synthetic construct
SEQUENCE: 389
DTQEKEVRAM VGSDVELSCA CPEGSRFDLN DVVYWQTSE SKTVVTYHIP QNSSLENVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQQDT VFLNMRGLYD  180
VVSVLRIART PSVNIGCCIE NVLLQQNLTV GSQTGNDIGE RDKITENPVS TGEKNAAT    238

SEQ ID NO: 390            moltype = AA  length = 238
FEATURE                   Location/Qualifiers
REGION                    1..238
                          note = ICOSL v102 ECD
source                    1..238
                          mol_type = protein
                          organism = synthetic construct
SEQUENCE: 390
DTQEKEVRAM VGSDVELSCA CPEGSRFDLN DVVYWQTSE SKTVVTYHIP QNSSLENVDS   60
RYRNRALMSP AGMLRGDFSL RLFNVTPQDE QKFHCLVLSQ SLGFQEVLSV EVTLHVAANF  120
```

-continued

```
SVPVVSAPHS PSQDELTFTC TSINGYPRPN VYWINKTDNS LLDQALQNDT VFLNMRGLYD  180
VVSVLRIART PSVNIGCCIE NVLLQQQLTV GSQTGNDIGE RDKITENPVS TGEKNAAT    238

SEQ ID NO: 391              moltype = AA  length = 238
FEATURE                    Location/Qualifiers
REGION                     1..238
                           note = ICOSL v103 ECD
VARIANT                    207
                           note = X = N or Q
source                     1..238
                           mol_type = protein
                           organism = synthetic construct
SEQUENCE: 391
DTQEKEVRAM VGSDVELSCA CPEGSRFDLN DVYVYWQTSE SKTVVTYHIP QQSSLENVDS  60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQXLTV GSQTGNDIGE RDKITENPVS TGEKNAAT    238

SEQ ID NO: 392              moltype = AA  length = 238
FEATURE                    Location/Qualifiers
REGION                     1..238
                           note = ICOSL v104 ECD
VARIANT                    168
                           note = X = N or Q
VARIANT                    207
                           note = X = N or Q
source                     1..238
                           mol_type = protein
                           organism = synthetic construct
SEQUENCE: 392
DTQEKEVRAM VGSDVELSCA CPEGSRFDLN DVYVYWQTSE SKTVVTYHIP QNSSLENVDS  60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQXDT VFLNMRGLYD  180
VVSVLRIART PSVNIGCCIE NVLLQQXLTV GSQTGNDIGE RDKITENPVS TGEKNAAT    238

SEQ ID NO: 393              moltype = AA  length = 238
FEATURE                    Location/Qualifiers
REGION                     1..238
                           note = ICOSL v105 ECD
source                     1..238
                           mol_type = protein
                           organism = synthetic construct
SEQUENCE: 393
DTQEKEVRAM VGSDVELSCA CPEGSRFDLN DVYVYWQTSE SKTVVTYHIP QQSSLENVDS  60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQQDT VFLNMRGLYD  180
VVSVLRIART PSVNIGCCIE NVLLQQNLTV GSQTGNDIGE RDKITENPVS TGEKNAAT    238

SEQ ID NO: 394              moltype = AA  length = 238
FEATURE                    Location/Qualifiers
REGION                     1..238
                           note = ICOSL v106 ECD
source                     1..238
                           mol_type = protein
                           organism = synthetic construct
SEQUENCE: 394
DTQEKEVRAM VGSDVELSCA CPEGSRFDLN DVYVYWQTSE SKTVVTYHIP QNSSLENVDS  60
RYRNRALMSP AGMLRGDFSL RLFQVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQQLTV GSQTGNDIGE RDKITENPVS TGEKNAAT    238

SEQ ID NO: 395              moltype = AA  length = 238
FEATURE                    Location/Qualifiers
REGION                     1..238
                           note = ICOSL v107 ECD
source                     1..238
                           mol_type = protein
                           organism = synthetic construct
SEQUENCE: 395
DTQEKEVRAM VGSDVELSCA CPEGSRFDLN DVYVYWQTSE SKTVVTYHIP QNSSLENVDS  60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWIQKTDNS LLDQALQNDT VFLNMRGLYD  180
VVSVLRIART PSVNIGCCIE NVLLQQQLTV GSQTGNDIGE RDKITENPVS TGEKNAAT    238

SEQ ID NO: 396              moltype = AA  length = 238
FEATURE                    Location/Qualifiers
REGION                     1..238
                           note = ICOSL v108 ECD
source                     1..238
```

-continued

```
                                mol_type = protein
                                organism = synthetic construct
SEQUENCE: 396
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSQ SLGFQEVLSV EVTLHVAAQF   120
SVPVVSAPHS PSQDELTFTC TSINGYPRPN VYWINKTDNS LLDQALQQDT VFLNMRGLYD   180
VVSVLRIART PSVNIGCCIE NVLLQQNLTV GSQTGNDIGE RDKITENPVS TGEKNAAT     238

SEQ ID NO: 397           moltype = AA   length = 238
FEATURE                  Location/Qualifiers
REGION                   1..238
                         note = ICOSL v109 ECD
source                   1..238
                         mol_type = protein
                         organism = synthetic construct
SEQUENCE: 397
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSQ SLGFQEVLSV EVTLHVAAQF   120
SVPVVSAPHS PSQDELTFTC TSINGYPRPN VYWINKTDNS LLDQALQNDT VFLNMRGLYD   180
VVSVLRIART PSVNIGCCIE NVLLQQQLTV GSQTGNDIGE RDKITENPVS TGEKNAAT     238

SEQ ID NO: 398           moltype = AA   length = 238
FEATURE                  Location/Qualifiers
REGION                   1..238
                         note = ICOSL v110 ECD
VARIANT                  155
                         note = X = N or Q
source                   1..238
                         mol_type = protein
                         organism = synthetic construct
SEQUENCE: 398
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSQ SLGFQEVLSV EVTLHVAAQF   120
SVPVVSAPHS PSQDELTFTC TSINGYPRPN VYWIXKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 399           moltype = AA   length = 238
FEATURE                  Location/Qualifiers
REGION                   1..238
                         note = ICOSL v111 ECD
source                   1..238
                         mol_type = protein
                         organism = synthetic construct
SEQUENCE: 399
DTQEKEVRAM VGSDVELSCA CPEGSRFDLN DVYVYWQTSE SKTVVTYHIP QQSSLENVDS    60
RYRNRALMSP AGMLRGDFSL RLFQVTPQDE QKFHCLVLSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 400           moltype = AA   length = 238
FEATURE                  Location/Qualifiers
REGION                   1..238
                         note = ICOSL v112 ECD
source                   1..238
                         mol_type = protein
                         organism = synthetic construct
SEQUENCE: 400
DTQEKEVRAM VGSDVELSCA CPEGSRFDLN DVYVYWQTSE SKTVVTYHIP QQSSLENVDS    60
RYRNRALMSP AGMLRGDFSL RLFNVTPQDE QKFHCLVLSQ SLGFQEVLSV EVTLHVAAQF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 401           moltype = AA   length = 238
FEATURE                  Location/Qualifiers
REGION                   1..238
                         note = ICOSL v113 ECD
source                   1..238
                         mol_type = protein
                         organism = synthetic construct
SEQUENCE: 401
DTQEKEVRAM VGSDVELSCA CPEGSRFDLN DVYVYWQTSE SKTVVTYHIP QNSSLENVDS    60
RYRNRALMSP AGMLRGDFSL RLFQVTPQDE QKFHCLVLSQ SLGFQEVLSV EVTLHVAAQF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 402           moltype = AA   length = 238
FEATURE                  Location/Qualifiers
REGION                   1..238
                         note = Artificial Sequence
```

-continued

```
source                  1..238
                        mol_type = protein
                        organism = synthetic construct
SEQUENCE: 402
DTQEKEVRAM VGSDVELSCA CPEGSRFDLN DVYVYWQTSE SKTVVTYHIP QQSSLENVDS  60
RYRNRALMSP AGMLRGDFSL RLFQVTPQDE QKFHCLVLSQ SLGFQEVLSV EVTLHVAANF 120
SVPVVSAPHS PSQDELTFTC TSINGYPRPN VYWINKTDNS LLDQALQQDT VFLNMRGLYD 180
VVSVLRIART PSVNIGCCIE NVLLQQNLTV GSQTGNDIGE RDKITENPVS TGEKNAAT   238

SEQ ID NO: 403         moltype = AA  length = 238
FEATURE                Location/Qualifiers
REGION                 1..238
                       note = ICOSL v115 ECD
source                 1..238
                       mol_type = protein
                       organism = synthetic construct
SEQUENCE: 403
DTQEKEVRAM VGSDVELSCA CPEGSRFDLN DVYVYWQTSE SKTVVTYHIP QQSSLENVDS  60
RYRNRALMSP AGMLRGDFSL RLFQVTPQDE QKFHCLVLSQ SLGFQEVLSV EVTLHVAANF 120
SVPVVSAPHS PSQDELTFTC TSINGYPRPN VYWINKTDNS LLDQALQNDT VFLNMRGLYD 180
VVSVLRIART PSVNIGCCIE NVLLQQQLTV GSQTGNDIGE RDKITENPVS TGEKNAAT   238

SEQ ID NO: 404         moltype = AA  length = 238
FEATURE                Location/Qualifiers
REGION                 1..238
                       note = ICOSL v116 ECD
source                 1..238
                       mol_type = protein
                       organism = synthetic construct
SEQUENCE: 404
DTQEKEVRAM VGSDVELSCA CPEGSRFDLN DVYVYWQTSE SKTVVTYHIP QNSSLENVDS  60
RYRNRALMSP AGMLRGDFSL RLFQVTPQDE QKFHCLVLSQ SLGFQEVLSV EVTLHVAANF 120
SVPVVSAPHS PSQDELTFTC TSINGYPRPN VYWIQKTDNS LLDQALQQDT VFLNMRGLYD 180
VVSVLRIART PSVNIGCCIE NVLLQQNLTV GSQTGNDIGE RDKITENPVS TGEKNAAT   238

SEQ ID NO: 405         moltype = AA  length = 238
FEATURE                Location/Qualifiers
REGION                 1..238
                       note = ICOSL v117 ECD
source                 1..238
                       mol_type = protein
                       organism = synthetic construct
SEQUENCE: 405
DTQEKEVRAM VGSDVELSCA CPEGSRFDLN DVYVYWQTSE SKTVVTYHIP QNSSLENVDS  60
RYRNRALMSP AGMLRGDFSL RLFQVTPQDE QKFHCLVLSQ SLGFQEVLSV EVTLHVAANF 120
SVPVVSAPHS PSQDELTFTC TSINGYPRPN VYWINKTDNS LLDQALQQDT VFLNMRGLYD 180
VVSVLRIART PSVNIGCCIE NVLLQQQLTV GSQTGNDIGE RDKITENPVS TGEKNAAT   238

SEQ ID NO: 406         moltype = AA  length = 238
FEATURE                Location/Qualifiers
REGION                 1..238
                       note = ICOSL v118 ECD
source                 1..238
                       mol_type = protein
                       organism = synthetic construct
SEQUENCE: 406
DTQEKEVRAM VGSDVELSCA CPEGSRFDLN DVYVYWQTSE SKTVVTYHIP QNSSLENVDS  60
RYRNRALMSP AGMLRGDFSL RLFQVTPQDE QKFHCLVLSQ SLGFQEVLSV EVTLHVAANF 120
SVPVVSAPHS PSQDELTFTC TSINGYPRPN VYWIHKTDNS LLDQALQNDT VFLNMRGLYD 180
VVSVLRIART PSVNIGCCIE NVLLQQQLTV GSQTGNDIGE RDKITENPVS TGEKNAAT   238

SEQ ID NO: 407         moltype = AA  length = 238
FEATURE                Location/Qualifiers
REGION                 1..238
                       note = ICOSL v119 ECD
source                 1..238
                       mol_type = protein
                       organism = synthetic construct
SEQUENCE: 407
DTQEKEVRAM VGSDVELSCA CPEGSRFDLN DVYVYWQTSE SKTVVTYHIP QNSSLENVDS  60
RYRNRALMSP AGMLRGDFSL RLFNVTPQDE QKFHCLVLSQ SLGFQEVLSV EVTLHVAANF 120
SVPVVSAPHS PSQDELTFTC TSINGYPRPN VYWIQKTDNS LLDQALQQDT VFLNMRGLYD 180
VVSVLRIART PSVNIGCCIE NVLLQQQLTV GSQTGNDIGE RDKITENPVS TGEKNAAT   238

SEQ ID NO: 408         moltype = AA  length = 238
FEATURE                Location/Qualifiers
REGION                 1..238
                       note = ICOSL v120 ECD
source                 1..238
```

-continued

```
                            mol_type = protein
                            organism = synthetic construct
SEQUENCE: 408
DTQEKEVRAM VGSDVELSCA CPEGSRFDLN DVYVYWQTSE SKTVVTYHIP QNSSLENVDS      60
RYRNRALMSP AGMLRGDFSL RLFNVTPQDE QKFHCLVLSQ SLGFQEVLSV EVTLHVAAQF     120
SVPVVSAPHS PSQDELTFTC TSINGYPRPN VYWIQKTDNS LLDQALQQDT VFLNMRGLYD     180
VVSVLRIART PSVNIGCCIE NVLLQQNLTV GSQTGNDIGE RDKITENPVS TGEKNAAT       238

SEQ ID NO: 409          moltype = AA  length = 238
FEATURE                 Location/Qualifiers
REGION                  1..238
                        note = ICOSL v121 ECD
source                  1..238
                        mol_type = protein
                        organism = synthetic construct
SEQUENCE: 409
DTQEKEVRAM VGSDVELSCA CPEGSRFDLN DVYVYWQTSE SKTVVTYHIP QNSSLENVDS      60
RYRNRALMSP AGMLRGDFSL RLFNVTPQDE QKFHCLVLSQ SLGFQEVLSV EVTLHVAAQF     120
SVPVVSAPHS PSQDELTFTC TSINGYPRPN VYWINKTDNS LLDQALQQDT VFLNMRGLYD     180
VVSVLRIART PSVNIGCCIE NVLLQQQLTV GSQTGNDIGE RDKITENPVS TGEKNAAT       238

SEQ ID NO: 410          moltype = AA  length = 238
FEATURE                 Location/Qualifiers
REGION                  1..238
                        note = ICOSL v122 ECD
source                  1..238
                        mol_type = protein
                        organism = synthetic construct
SEQUENCE: 410
DTQEKEVRAM VGSDVELSCA CPEGSRFDLN DVYVYWQTSE SKTVVTYHIP QNSSLENVDS      60
RYRNRALMSP AGMLRGDFSL RLFQVTPQDE QKFHCLVLSQ SLGFQEVLSV EVTLHVAAQF     120
SVPVVSAPHS PSQDELTFTC TSINGYPRPN VYWINKTDNS LLDQALQNDT VFLNMRGLYD     180
VVSVLRIART PSVNIGCCIE NVLLQQQLTV GSQTGNDIGE RDKITENPVS TGEKNAAT       238

SEQ ID NO: 411          moltype = AA  length = 238
FEATURE                 Location/Qualifiers
REGION                  1..238
                        note = ICOSL v123 ECD
source                  1..238
                        mol_type = protein
                        organism = synthetic construct
SEQUENCE: 411
DTQEKEVRAM VGSDVELSCA CPEGSRFDLN DVYVYWQTSE SKTVVTYHIP QNSSLENVDS      60
RYRNRALMSP AGMLRGDFSL RLFNVTPQDE QKFHCLVLSQ SLGFQEVLSV EVTLHVAAQF     120
SVPVVSAPHS PSQDELTFTC TSINGYPRPN VYWIHKTDNS LLDQALQNDT VFLNMRGLYD     180
VVSVLRIART PSVNIGCCIE NVLLQQQLTV GSQTGNDIGE RDKITENPVS TGEKNAAT       238

SEQ ID NO: 412          moltype = AA  length = 238
FEATURE                 Location/Qualifiers
REGION                  1..238
                        note = ICOSL v124 ECD
source                  1..238
                        mol_type = protein
                        organism = synthetic construct
SEQUENCE: 412
DTQEKEVRAM VGSDVELSCA CPEGSRFDLN DVYVYWQTSE SKTVVTYHIP QNSSLENVDS      60
RYRNRALMSP AGMLRGDFSL RLFQVTPQDE QKFHCLVLSQ SLGFQEVLSV EVTLHVAAQF     120
SVPVVSAPHS PSQDELTFTC TSINGYPRPN VYWIQKTDNS LLDQALQNDT VFLNMRGLYD     180
VVSVLRIART PSVNIGCCIE NVLLQQNLTV GSQTGNDIGE RDKITENPVS TGEKNAAT       238

SEQ ID NO: 413          moltype = AA  length = 238
FEATURE                 Location/Qualifiers
REGION                  1..238
                        note = ICOSL v125 ECD
source                  1..238
                        mol_type = protein
                        organism = synthetic construct
SEQUENCE: 413
DTQEKEVRAM VGSDVELSCA CPEGSRFDLN DVYVYWQTSE SKTVVTYHIP QQSSLENVDS      60
RYRNRALMSP AGMLRGDFSL RLFNVTPQDE QKFHCLVLSQ SLGFQEVLSV EVTLHVAAQF     120
SVPVVSAPHS PSQDELTFTC TSINGYPRPN VYWIQKTDNS LLDQALQNDT VFLNMRGLYD     180
VVSVLRIART PSVNIGCCIE NVLLQQNLTV GSQTGNDIGE RDKITENPVS TGEKNAAT       238

SEQ ID NO: 414          moltype = AA  length = 238
FEATURE                 Location/Qualifiers
REGION                  1..238
                        note = ICOSL v126 ECD
source                  1..238
                        mol_type = protein
```

-continued

```
                      organism = synthetic construct
SEQUENCE: 414
DTQEKEVRAM VGSDVELSCA CPEGSRFDLN DVYVYWQTSE SKTVVTYHIP QHSSLENVDS  60
RYRNRALMSP AGMLRGDFSL RLFQVTPQDE QKFHCLVLSQ SLGFQEVLSV EVTLHVAAQF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 415           moltype = AA  length = 238
FEATURE                  Location/Qualifiers
REGION                   1..238
                         note = ICOSL v127 ECD
VARIANT                  168
                         note = X = N or Q
VARIANT                  207
                         note = X = N or Q
source                   1..238
                         mol_type = protein
                         organism = synthetic construct
SEQUENCE: 415
DTQEKEVRAM VGSDVELSCA CPEGSRFDLN DVYVYWQTSE SKTVVTYHIP QHSSLENVDS  60
RYRNRALMSP AGMLRGDFSL RLFQVTPQDE QKFHCLVLSQ SLGFQEVLSV EVTLHVAANF  120
SVPVVSAPHS PSQDELTFTC TSINGYPRPN VYWINKTDNS LLDQALQXDT VFLNMRGLYD  180
VVSVLRIART PSVNIGCCIE NVLLQQXLTV GSQTGNDIGE RDKITENPVS TGEKNAAT    238

SEQ ID NO: 416           moltype = AA  length = 238
FEATURE                  Location/Qualifiers
REGION                   1..238
                         note = ICOSL v128 ECD
VARIANT                  155
                         note = X = N or Q
VARIANT                  168
                         note = X = N or Q
source                   1..238
                         mol_type = protein
                         organism = synthetic construct
SEQUENCE: 416
DTQEKEVRAM VGSDVELSCA CPEGSRFDLN DVYVYWQTSE SKTVVTYHIP QQSSLENVDS  60
RYRNRALMSP AGMLRGDFSL RLFQVTPQDE QKFHCLVLSQ SLGFQEVLSV EVTLHVAANF  120
SVPVVSAPHS PSQDELTFTC TSINGYPRPN VYWIXKTDNS LLDQALQXDT VFLNMRGLYD  180
VVSVLRIART PSVNIGCCIE NVLLQQNLTV GSQTGNDIGE RDKITENPVS TGEKNAAT    238

SEQ ID NO: 417           moltype = AA  length = 238
FEATURE                  Location/Qualifiers
REGION                   1..238
                         note = ICOSL v129 ECD
source                   1..238
                         mol_type = protein
                         organism = synthetic construct
SEQUENCE: 417
DTQEKEVRAM VGSDVELSCA CPEGSRFDLN DVYVYWQTSE SKTVVTYHIP QQSSLENVDS  60
RYRNRALMSP AGMLRGDFSL RLFQVTPQDE QKFHCLVLSQ SLGFQEVLSV EVTLHVAANF  120
SVPVVSAPHS PSQDELTFTC TSINGYPRPN VYWINKTDNS LLDQALQQDT VFLNMRGLYD  180
VVSVLRIART PSVNIGCCIE NVLLQQNLTV GSQTGNDIGE RDKITENPVS TGEKNAAT    238

SEQ ID NO: 418           moltype = AA  length = 238
FEATURE                  Location/Qualifiers
REGION                   1..238
                         note = ICOSL v131 ECD
source                   1..238
                         mol_type = protein
                         organism = synthetic construct
SEQUENCE: 418
DTQEKEVRAM VGSDVELSCA CPEGSRFDLN DVYVYWQTSE SKTVVTYHIP QNSSLENVDS  60
RYRNRALMSP AGMLRGDFSL RLFQVTPQDE QKFHCLVLSQ SLGFQEVLSV EVTLHVAAQF  120
SVPVVSAPHS PSQDELTFTC TSINGYPRPN VYWIQKTDNS LLDQALQQDT VFLNMRGLYD  180
VVSVLRIART PSVNIGCCIE NVLLQQNLTV GSQTGNDIGE RDKITENPVS TGEKNAAT    238

SEQ ID NO: 419           moltype = AA  length = 238
FEATURE                  Location/Qualifiers
REGION                   1..238
                         note = ICOSL v131 ECD
source                   1..238
                         mol_type = protein
                         organism = synthetic construct
SEQUENCE: 419
DTQEKEVRAM VGSDVELSCA CPEGSRFDLN DVYVYWQTSE SKTVVTYHIP QNSSLENVDS  60
RYRNRALMSP AGMLRGDFSL RLFQVTPQDE QKFHCLVLSQ SLGFQEVLSV EVTLHVAANF  120
SVPVVSAPHS PSQDELTFTC TSINGYPRPN VYWIQKTDNS LLDQALQQDT VFLNMRGLYD  180
VVSVLRIART PSVNIGCCIE NVLLQQQLTV GSQTGNDIGE RDKITENPVS TGEKNAAT    238
```

-continued

```
SEQ ID NO: 420          moltype = AA  length = 238
FEATURE                 Location/Qualifiers
REGION                  1..238
                        note = ICOSL v132 ECD
source                  1..238
                        mol_type = protein
                        organism = synthetic construct
SEQUENCE: 420
DTQEKEVRAM VGSDVELSCA CPEGSRFDLN DVYVYWQTSE SKTVVTYHIP QNSSLENVDS  60
RYRNRALMSP AGMLRGDFSL RLFQVTPQDE QKFHCLVLSQ SLGFQEVLSV EVTLHVAAQF  120
SVPVVSAPHS PSQDELTFTC TSINGYPRPN VYWIQKTDNS LLDQALQNDT VFLNMRGLYD  180
VVSVLRIART PSVNIGCCIE NVLLQQQLTV GSQTGNDIGE RDKITENPVS TGEKNAAT    238

SEQ ID NO: 421          moltype = AA  length = 238
FEATURE                 Location/Qualifiers
REGION                  1..238
                        note = ICOSL v133 ECD
source                  1..238
                        mol_type = protein
                        organism = synthetic construct
SEQUENCE: 421
DTQEKEVRAM VGSDVELSCA CPEGSRFDLN DVYVYWQTSE SKTVVTYHIP QQSSLENVDS  60
RYRNRALMSP AGMLRGDFSL RLFQVTPQDE QKFHCLVLSQ SLGFQEVLSV EVTLHVAAQF  120
SVPVVSAPHS PSQDELTFTC TSINGYPRPN VYWINKTDNS LLDQALQNDT VFLNMRGLYD  180
VVSVLRIART PSVNIGCCIE NVLLQQQLTV GSQTGNDIGE RDKITENPVS TGEKNAAT    238

SEQ ID NO: 422          moltype = AA  length = 238
FEATURE                 Location/Qualifiers
REGION                  1..238
                        note = ICOSL v134 ECD
source                  1..238
                        mol_type = protein
                        organism = synthetic construct
SEQUENCE: 422
DTQEKEVRAM VGSDVELSCA CPEGSRFDLN DVYVYWQTSE SKTVVTYHIP QQSSLENVDS  60
RYRNRALMSP AGMLRGDFSL RLFQVTPQDE QKFHCLVLSQ SLGFQEVLSV EVTLHVAAQF  120
SVPVVSAPHS PSQDELTFTC TSINGYPRPN VYWIQKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 423          moltype = AA  length = 238
FEATURE                 Location/Qualifiers
REGION                  1..238
                        note = ICOSL v135 ECD
source                  1..238
                        mol_type = protein
                        organism = synthetic construct
SEQUENCE: 423
DTQEKEVRAM VGSDVELSCA CPEGSRFDLN DVYVYWQTSE SKTVVTYHIP QQSSLENVDS  60
RYRNRALMSP AGMLRGDFSL RLFQVTPQDE QKFHCLVLSQ SLGFQEVLSV EVTLHVAAQF  120
SVPVVSAPHS PSQDELTFTC TSINGYPRPN VYWIQKTDNS LLDQALQNDT VFLNMRGLYD  180
VVSVLRIART PSVNIGCCIE NVLLQQQLTV GSQTGNDIGE RDKITENPVS TGEKNAAT    238

SEQ ID NO: 424          moltype = AA  length = 238
FEATURE                 Location/Qualifiers
REGION                  1..238
                        note = ICOSL v136 ECD
source                  1..238
                        mol_type = protein
                        organism = synthetic construct
SEQUENCE: 424
DTQEKEVRAM VGSDVELSCA CPEGSRFDLN DVYVYWQTSE SKTVVTYHIP QNSSLENVDS  60
RYRNRALMSP AGMLRGDFSL RLFQVTPQDE QKFHCLVLSQ SLGFQEVLSV EVTLHVAAQF  120
SVPVVSAPHS PSQDELTFTC TSINGYPRPN VYWIQKTDNS LLDQALQQDT VFLNMRGLYD  180
VVSVLRIART PSVNIGCCIE NVLLQQQLTV GSQTGNDIGE RDKITENPVS TGEKNAAT    238

SEQ ID NO: 425          moltype = AA  length = 111
FEATURE                 Location/Qualifiers
REGION                  1..111
                        note = ICOSL v99 IgV
source                  1..111
                        mol_type = protein
                        organism = synthetic construct
SEQUENCE: 425
DTQEKEVRAM VGSDVELSCA CPEGSRFDLN DVYVYWQTSE SKTVVTYHIP QNSSLENVDS  60
RYRNRALMSP AGMLRGDFSL RLFQVTPQDE QKFHCLVLSQ SLGFQEVLSV E           111

SEQ ID NO: 426          moltype = AA  length = 111
FEATURE                 Location/Qualifiers
```

```
REGION                   1..111
                         note = ICOSL v111 IgV
source                   1..111
                         mol_type = protein
                         organism = synthetic construct
SEQUENCE: 426
DTQEKEVRAM VGSDVELSCA CPEGSRFDLN DVVYVWQTSE SKTVVTYHIP QQSSLENVDS   60
RYRNRALMSP AGMLRGDFSL RLFQVTPQDE QKFHCLVLSQ SLGFQEVLSV E           111

SEQ ID NO: 427          moltype = AA  length = 238
FEATURE                 Location/Qualifiers
REGION                  1..238
                        note = ICOSL v137 ECD
source                  1..238
                        mol_type = protein
                        organism = synthetic construct
SEQUENCE: 427
DTQEKEVRAM VGSDVELSCA CPEGSRFDLN DVYVYVWQTSE SKTVVTYHIP QNSSLENVDS   60
RYRNRALMSP AGMLRGDFSL RLFNVTPQDE QKFHCLVLSR SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 428          moltype = AA  length = 238
FEATURE                 Location/Qualifiers
REGION                  1..238
                        note = ICOSL v138 ECD
source                  1..238
                        mol_type = protein
                        organism = synthetic construct
SEQUENCE: 428
DTQEKEVRAM VGSDVELSCA CPEGSRFDLN DVYVYVWQTSE SKTVVTYHIP QNSSLENVDS   60
RYRNRALMSP AGMLRGDFSL RLFNVTPQDE QKFHCLVLSQ SLGFQEVLSV EVTLHVAANF  120
SVPVVSAPHS PSQDELTLTC TSINGYPRPN VYWINKTDNS LLDQALQNDT VFLNMRGLYD  180
VVSVLRIART PSVNIGCCIE NVPLQQNLTV GSQTGNDIGE RDKITENPVS TGEKNAAT    238

SEQ ID NO: 429          moltype = AA  length = 238
FEATURE                 Location/Qualifiers
REGION                  1..238
                        note = ICOSL v139 ECD
source                  1..238
                        mol_type = protein
                        organism = synthetic construct
SEQUENCE: 429
DTQEKEVRAM VGSDVELSCA CPEGSRFDLN DVYVYVWQTSE SKTVVTYHIP QYSSLENVDS   60
RYRNRALMSP AGMLRGDFSL RLFNVTPQDE QKFHCLVLSQ SLGFQEVLSV EVTLHVAANF  120
SVPVVSAPHS PSQDELTLTC TSINGYPRPN VYWINKTDNS LLDQALQNDT VFLNMRGLYD  180
VVSVLRIART PSVNIGCCIE NVPLQQNLTV GSQTGNDIGE RDKITENPVS TGEKNAAT    238

SEQ ID NO: 430          moltype = AA  length = 238
FEATURE                 Location/Qualifiers
REGION                  1..238
                        note = ICOSL v140 ECD
source                  1..238
                        mol_type = protein
                        organism = synthetic construct
SEQUENCE: 430
DTQEKEVRAM VGSDVELSCA CPEGSRFDLN DVYVYVWQTSE SKTVVTYHIP QNSSLEYVDS   60
RYRNRALMSP AGMLRGDFSL RLFNVTPQDE QKFHCLVLSR SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCRIE NVLLQQNLTV GSQTGNDIGE RDKITENPVS TGEKNAAT    238

SEQ ID NO: 431          moltype = AA  length = 238
FEATURE                 Location/Qualifiers
REGION                  1..238
                        note = ICOSL v141 ECD
source                  1..238
                        mol_type = protein
                        organism = synthetic construct
SEQUENCE: 431
DTQEKEVRAM VGSDVELSCA CPEGSRFDLN DVYVYVWQTSE SKTVVTYHIP QNSSLEYVDS   60
RYRNRALMSP AGMLRGDFSL RLFNVTPQDE QKFHCLVLSQ SLGFQEVLSV EVTLHVAANF  120
SVPVVSAPHS PSQDELTLTC TSINGYPRPN VYWINKTDNS LLDQALQNDT VFLNMRGLYD  180
VVSVLRIART PSVNIGCCIE NVPLQQNLTV GSQTGNDIGE RDKITENPVS TGEKNAAT    238

SEQ ID NO: 432          moltype = AA  length = 238
FEATURE                 Location/Qualifiers
REGION                  1..238
                        note = ICOSL v142 ECD
source                  1..238
```

```
                              mol_type = protein
                              organism = synthetic construct
SEQUENCE: 432
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSR SLGFQEVLSV EVTLHVAANF   120
SVPVVSAPHS PSQDELTLTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 433          moltype = AA  length = 238
FEATURE                 Location/Qualifiers
REGION                  1..238
                        note = ICOSL v143 ECD
source                  1..238
                        mol_type = protein
                        organism = synthetic construct
SEQUENCE: 433
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVPLQQNLTV GSQTGNDIGE RDKITENPVS TGEKNAAT     238

SEQ ID NO: 434          moltype = AA  length = 111
FEATURE                 Location/Qualifiers
REGION                  1..111
                        note = ICOSL v137 IgV
source                  1..111
                        mol_type = protein
                        organism = synthetic construct
SEQUENCE: 434
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSR SLGFQEVLSV E            111

SEQ ID NO: 435          moltype = AA  length = 238
FEATURE                 Location/Qualifiers
REGION                  1..238
                        note = ICOSL v144 ECD
source                  1..238
                        mol_type = protein
                        organism = synthetic construct
SEQUENCE: 435
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSV EVTLRVAANF   120
SVPVVSAPHS PSQDELTFTC TSINGYPRPN VYWINKTDNS LLDQALQNDT VFLNMRGLYD   180
VVSVLRIART PSVNIGCRIE NVLLQQNLTV GSQTGNDIGE RDKITENPVS TGEKNAAT     238

SEQ ID NO: 436          moltype = AA  length = 238
FEATURE                 Location/Qualifiers
REGION                  1..238
                        note = ICOSL v145 ECD
source                  1..238
                        mol_type = protein
                        organism = synthetic construct
SEQUENCE: 436
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSV EVTLHVAANF   120
SVPVVSAPHS PSQDELTFTC TSINGYPRPN VYWINKTDNS LLDQALQNDT VSLNMRGLYD   180
VVSVLRIART PSVNIGCRIE NVLLQQNLTV GSQTGNDIGE RDKITENPVS TGEKNAAT     238

SEQ ID NO: 437          moltype = AA  length = 238
FEATURE                 Location/Qualifiers
REGION                  1..238
                        note = ICOSL v146 ECD
source                  1..238
                        mol_type = protein
                        organism = synthetic construct
SEQUENCE: 437
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSV EVTLRVAANF   120
SVPVVSAPHS PSQDELTFTC TSINGYPRPN VYWINKTDNS LLDQALQNDT VSLNMRGLYD   180
VVSVLRIART PSVNIGCRIE NVLLQQNLTV GSQTGNDIGE RDKITENPVS TGEKNAAT     238

SEQ ID NO: 438          moltype = AA  length = 238
FEATURE                 Location/Qualifiers
REGION                  1..238
                        note = ICOSL v147 ECD
source                  1..238
                        mol_type = protein
                        organism = synthetic construct
SEQUENCE: 438
```

-continued

```
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSV EVTLRVAANF   120
SVPVVSAPHS PSQDELTFTC TSVNGYPRPN VYWINKTDNS LLDQALQNDT VSLNMRGLYD   180
VVSVLRIART PSVNIGCRIE NVLLQQNLTV GSQTGNDIGE RDKITENPVS TGEKNAAT     238

SEQ ID NO: 439          moltype = AA  length = 238
FEATURE                 Location/Qualifiers
REGION                  1..238
                        note = ICOSL v148 ECD
source                  1..238
                        mol_type = protein
                        organism = synthetic construct
SEQUENCE: 439
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SRGFQEVLSV EVTLRVAANF   120
SVPVVSAPHS PSQDELTFTC TSINGYPRPN VYWINKTDNS LLDQALQNDT VSLNMRGLYD   180
VVSVLRIART PSVNIGCRIE NVLLQQNLTV GSQTGNDIGE RDKITENPVS TGEKNAAT     238

SEQ ID NO: 440          moltype = AA  length = 238
FEATURE                 Location/Qualifiers
REGION                  1..238
                        note = ICOSL v149 ECD
source                  1..238
                        mol_type = protein
                        organism = synthetic construct
SEQUENCE: 440
DTQEKEVRAM VGSDVELSCA CPEGSRFDLN DVYVYWQTSE SKTVVTYHIP QHSSLENVDS    60
RYRNRALMSP AGMLRGDFSL RLFNVTPQDE QKFHCLVLSQ SLGFQEVLSV EVTLHVAANF   120
SAPVVSAPHS PSQDELTFTC TSINGYPRPN VYWINKTDNS LLDQALQNDT VSLNMRGLYD   180
VVSVLRIART PSVNIGCRIE NVLLQQNLTV GSQTGNDIGE RDKITENPVS TGEKNAAT     238

SEQ ID NO: 441          moltype = AA  length = 238
FEATURE                 Location/Qualifiers
REGION                  1..238
                        note = ICOSL v150 ECD
source                  1..238
                        mol_type = protein
                        organism = synthetic construct
SEQUENCE: 441
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSV EVTLRVAANF   120
SVPVVSAPHS PSQDELTFTC TSINGYPRPN VYWINKTDNS LLDQALQNDT VSLNMRGLYD   180
VVSVLRIART PSVDIGCCIE NVLLQQNLTV GSQTGNDIGE RDKITENPVS TGEKNAAT     238

SEQ ID NO: 442          moltype = AA  length = 238
FEATURE                 Location/Qualifiers
REGION                  1..238
                        note = ICOSL v151 ECD
source                  1..238
                        mol_type = protein
                        organism = synthetic construct
SEQUENCE: 442
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSQ SLGFQEVLSV EVTLRVAANF   120
SVPVVSAPHS PSQDELTFTC TSINGYPRPN VYWINKTDNS LLDQALQNDT VSLNMRGLYD   180
VVSVLRIART PSVNIGCRIE NVLLQQNLTV GSQTGNDIGE RDKITENPVS TGEKNAAT     238

SEQ ID NO: 443          moltype = AA  length = 238
FEATURE                 Location/Qualifiers
REGION                  1..238
                        note = ICOSL v152 ECD
source                  1..238
                        mol_type = protein
                        organism = synthetic construct
SEQUENCE: 443
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSV EVTLRVAANF   120
SVPVVSAPHS PSQDELTFTC TSINGYPRPN VYWINKTDNS LLDQALQNDT VFLNMRGLYD   180
VVSVLRIART PSVNIGCRIE NVLLQQNLTV GSQTGNDIGE RDKITENPVS TGEKNAAT     238

SEQ ID NO: 444          moltype = AA  length = 238
FEATURE                 Location/Qualifiers
REGION                  1..238
                        note = ICOSL v153 ECD
source                  1..238
                        mol_type = protein
                        organism = synthetic construct
SEQUENCE: 444
DTQEKEVRAM VGSDVELSCA CPEGSRFDLN DVYVYWQTSE SKTVVTYHIP QHSSLEYVDS    60
```

-continued

```
RYRNRALMSP AGMLRGDFSL RLFNVTPQDE QKFHCLVLSQ SLGFQEVLSV EVTLRVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 445            moltype = AA  length = 238
FEATURE                   Location/Qualifiers
REGION                    1..238
                          note = ICOSL v154 ECD
source                    1..238
                          mol_type = protein
                          organism = synthetic construct
SEQUENCE: 445
DTQEKEVRAM VGSDVELSCA CPEGSRFDLN DVYVYWQTSE SKTVVTYHIP QHSSLEYVDS  60
RYRNRALMSP AGMLRGDFSL RLFNVTPQDE QKFHCLVLSR SLGFQEVLSV EVTLRVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 446            moltype = AA  length = 238
FEATURE                   Location/Qualifiers
REGION                    1..238
                          note = ICOSL v155 ECD
source                    1..238
                          mol_type = protein
                          organism = synthetic construct
SEQUENCE: 446
DTQEKEVRAM VGSDVELSCA CPEGSRFDLN DVYVYWQTSE SKTVVTYHIP QHSSLEYVDS  60
RYRNRALMSP AGMLRGDFSL RLFNVTPQDE QKFHCLVLSR SLGFQEVLSV EVTLRVAANF  120
SVPVVSAPHS PSQDELTFTC TSINGYPRPN VYWINKTDNS LLDQALQNDT VSLNMRGLYD  180
VVSVLRIART PSVNIGCCIE NVLLQQNLTV GSQTGNDIGE RDKVTENPVS TGEKNAAT    238

SEQ ID NO: 447            moltype = AA  length = 238
FEATURE                   Location/Qualifiers
REGION                    1..238
                          note = ICOSL v156 ECD
source                    1..238
                          mol_type = protein
                          organism = synthetic construct
SEQUENCE: 447
DTQEKEVRAM VGSDVELSCA CPEGSRFDLN DVYVYWQTSE SKTVVTYHIP QHSSLEYVDS  60
RYRNRALMSP AGMLRGDFSL RLFNVTPQDE QKFHCLVLSR SLGFQEVLSV EVTLRVAANF  120
SVPVVSAPHS PSQDELTFTC TSINGYPRPN VYWINKTDNS LLDQALQNDT VSLNMRGLYD  180
VVSVLRIART PSVNIGCCIE NVLLQQNLTV GSQTGNDIGE RDKITENPVS TGEKNAAT    238

SEQ ID NO: 448            moltype = AA  length = 238
FEATURE                   Location/Qualifiers
REGION                    1..238
                          note = ICOSL v157 ECD
source                    1..238
                          mol_type = protein
                          organism = synthetic construct
SEQUENCE: 448
DTQEKEVRAM VGSDVELSCA CPEGSRFDLN DVYVYWQTSE SKTVVTYHIP QHSSLEYVDS  60
RYRNRALMSP AGMLRGDFSL RLFNVTPQDE QKFHCLVLSR SLGFQEVLSV EVTLHVAANF  120
SVPVVSAPHS PSQDELTFTC TSINGYPRPN VYWINKTDNS LLDQALQNDT VSLNMRGLYD  180
VVSVLRIART PSVNIGCCIE NVLLQQNLTV GSQTGNDIGE RDKITENPVS TGEKNAAT    238

SEQ ID NO: 449            moltype = AA  length = 238
FEATURE                   Location/Qualifiers
REGION                    1..238
                          note = ICOSL v158 ECD
source                    1..238
                          mol_type = protein
                          organism = synthetic construct
SEQUENCE: 449
DTQEKEVRAM VGSDVELSCA CPEGSRFDLN DVYVYWQTSE SKTVVTYHIP QHSSLENVDS  60
RYRNRALMSP AGMLRGDFSL RLFNVTPQDE QKFHCLVLSR SLGFQEVLSV EVTLRVAANF  120
SVPVVSAPHS PSQDELTFTC TSTNGYPRPN VYWINKTDNS LLDQALQNDT VSLNMRGLYD  180
VVSVLRIART PSVNIGCCIE NVLLQQNLTV GSQTGNDIGE RDKITENPVS TGEKNAAT    238

SEQ ID NO: 450            moltype = AA  length = 238
FEATURE                   Location/Qualifiers
REGION                    1..238
                          note = ICOSL v159 ECD
source                    1..238
                          mol_type = protein
                          organism = synthetic construct
SEQUENCE: 450
DTQEKEVRAM VGSDVELSCA CPEGSRFDLN DVYVYWQTSE SKTVVTYHIP QHSSLEYVDS  60
RYRNRALMSP AGMLRGDFSL RLFNVTPQDE QKFHCLVLSP SLGFQEVLSV EVTLRVAANF  120
```

-continued

```
SVPVVSAPHS PSQDELTFTC TSINGYPRPN VYWINKTDNS LLDQALQNDT VSLNMRGLYD    180
VVSVLRIART PSVNIGCCIE NVLLQQNLTV GSQTGNDIGE RDKITENPVS TGEKNAAT      238

SEQ ID NO: 451          moltype = AA  length = 238
FEATURE                 Location/Qualifiers
REGION                  1..238
                        note = ICOSL v160 ECD
source                  1..238
                        mol_type = protein
                        organism = synthetic construct
SEQUENCE: 451
DTQEKEVRAM VGSDVELSCA CPEGSRFDLN DVYVYWQTSE SKTVVTYHIP QYSSLEYVDS    60
RYRNRALMSP AGMLRGDFSL RLFNVTPQDE QKFHCLVLSP SLGFQEVLSV EVTLHVAANF    120
SVPVVSAPHS PSQDELTFTC TSINGYPRPN VYWINKTDNS LLDQALQNDT VSLNMRGLYD    180
VVSVLRIART PSVNIGCCIE NVLLQQNLTV GSQTGNDIGE RDKITENPVS TGEKNAAT      238

SEQ ID NO: 452          moltype = AA  length = 238
FEATURE                 Location/Qualifiers
REGION                  1..238
                        note = ICOSL v161 ECD
source                  1..238
                        mol_type = protein
                        organism = synthetic construct
SEQUENCE: 452
DTQEKEVRAM VGSDVVLSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD EVTLRVAANF    120
SVPVVSAPHS PSQDELTFTC TSINGYPRPN VYWINKTDNS LLDQALQNDT VFLNMRGLYD    180
VVSVLRIART PSVNIGCRIE NVLLQQNLTV GSQTGNDIGE RDKITENPVS TGEKNAAT      238

SEQ ID NO: 453          moltype = AA  length = 238
FEATURE                 Location/Qualifiers
REGION                  1..238
                        note = ICOSL v162 ECD
source                  1..238
                        mol_type = protein
                        organism = synthetic construct
SEQUENCE: 453
DTQEKEVRAM VGSDVVLSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD EVTLRVAANF    120
SVPVVSAPHS PSQDELTFTC TSINGYPRPN VCWINMTDNS LLDQALQNDT VSLNMRGLYD    180
VVSVLRIART PSVNIGCRIE NVLLQQNLTV GSQTGNDIGE RDKITENPVS TGEKNAAT      238

SEQ ID NO: 454          moltype = AA  length = 238
FEATURE                 Location/Qualifiers
REGION                  1..238
                        note = ICOSL v163 ECD
source                  1..238
                        mol_type = protein
                        organism = synthetic construct
SEQUENCE: 454
DTQEKEVRAM VGSDVELSCA CPEGSRFDLD DVYVYWQTSE SETVVTYHIP QSSSLENVDS    60
RYRNRALMSP AGMLRGDFSL RLFNVTPQDE QKFHCLVLSQ SLGFQEVLSV EVTLRVAANF    120
SVPVVSAPHS PSQDELTFTC TSINGYPRPN VYWINKTDNS LLDQALQNDT VFLNMRGLYD    180
VVSVLRIART PSVNIGCCIE NVLLQQNLTV GSQTGNDIGE RDKITENPVS TGEKNAAT      238

SEQ ID NO: 455          moltype = AA  length = 238
FEATURE                 Location/Qualifiers
REGION                  1..238
                        note = ICOSL v164 ECD
source                  1..238
                        mol_type = protein
                        organism = synthetic construct
SEQUENCE: 455
DTQEKEVRAM VGSDVELSCA CPEGSRFDLD DVYVYWQTSE SETVVTYHIP QSSSLENVDS    60
RYRNRALMSP AGMLRGDFSL RLFNVTPQDE QKFHCLVLSQ SLGFQEVLSV EVTLRVAANF    120
SVPVVSAPHS PSQDELTFTC TSINGYPRPN VYWINKTDNS LLDQALQNDT VFLNMRGLYD    180
VVSVLRIART PSVNIGCCIE NVLLQQNLTV GSQTGNDIGE RDKITENPVS TGEKNAAT      238

SEQ ID NO: 456          moltype = AA  length = 238
FEATURE                 Location/Qualifiers
REGION                  1..238
                        note = ICOSL v165 ECD
source                  1..238
                        mol_type = protein
                        organism = synthetic construct
SEQUENCE: 456
DTQEKEVRAM VGSDVELSCA CPEGSRFDLD DVYVYWQTSE SETVVTYHIP QSSSLENVDS    60
RYRNRALMSP AGMLRGDFSL RLFNVTPQDE QKFHCLVLSQ SLGFQEVLSV EVTLRVAANF    120
SVPVVSAPHS PSQDELTFTC TSINGYPRPN VYWINKTDNS LLDQALQNDT VFLNMRGLYD    180
```

-continued

```
VVSVLRIART PSVNIGCRIE NVLLQQNLTV GSQTGNDIGE IDKITENPVS TGEKNAAT    238

SEQ ID NO: 457          moltype = AA  length = 238
FEATURE                 Location/Qualifiers
REGION                  1..238
                        note = ICOSL v166 ECD
source                  1..238
                        mol_type = protein
                        organism = synthetic construct
SEQUENCE: 457
DTQEKEVRAM VGSDVELSCA CPEGSRFDLD DVYVYWQTSE SETVVTYHIP QSSSLENVDS    60
RYRNRALMSP AGMLRGDFSL RLFNVTPQDE QKFHCLVLSQ SLGFQEVLSV EVTLRVAANF    120
SVPVVSAPHS PSQDELTFTC TSINGYPRPN VYWINKTDNS LLDQALQNDT VFLNMRGLYD    180
VVSVLRIART PSVNIGCRIE NVLLQQNLTV GSQTGNDIGE RDKITENPVS TGEKNAAT     238

SEQ ID NO: 458          moltype = AA  length = 238
FEATURE                 Location/Qualifiers
REGION                  1..238
                        note = ICOSL v167 ECD
source                  1..238
                        mol_type = protein
                        organism = synthetic construct
SEQUENCE: 458
DTQEKEVRAM VGSDVELSCA CPEGSRFDLD DVYVYWQTSE SETVVTYHIP QSSSLENVDS    60
RYRNRALMSP AGMLRGDFSL RLFNVTPQDE QKFHCLVLSQ SLGFQEVLSV EVTLRVAANF    120
SVPVVSAPHS PSQDELTFTC TSINGYPRPN VYWINKTDNS LLDQALQNDT VSLNMRGLYD    180
VVSVLRIART PSVDIGCCIE NVLLQQNLTV GSQTGNDIGE RDKITENPVS TGEKNAAT     238

SEQ ID NO: 459          moltype = AA  length = 238
FEATURE                 Location/Qualifiers
REGION                  1..238
                        note = ICOSL v168 ECD
source                  1..238
                        mol_type = protein
                        organism = synthetic construct
SEQUENCE: 459
DTQEKEVRAM VGSDVELSCA CPEGSRFDLN DVYVYWQTSE SKTVVTYHIP QSSSLENVDS    60
RYRNRALMSP AGMLRGDFSL RLFNVTPQDE QKFHCLVLSQ SLGFQEVLSV EVTLRVAANS    120
SVPVVSAPHS PSQDELTFTC TSVNGYPRPN VYWINKTDNS LLDQALQNDT VFLNMRGLYD    180
VVSVLRIART PSVNIGCRIE NVLLQQNLTV GSQTGNDIGE RDKITENPVS TGEKNAAT     238

SEQ ID NO: 460          moltype = AA  length = 238
FEATURE                 Location/Qualifiers
REGION                  1..238
                        note = ICOSL v169 ECD
source                  1..238
                        mol_type = protein
                        organism = synthetic construct
SEQUENCE: 460
DTQEKEVRAM VGSDVELSCA CPEGSRFDLN DVYVYWQTSE SKTVVTYHIP QSSSLENVDS    60
RYRNRALMSP AGMLRGDFSL RLFNVTPQDE QKFHCLVLSQ SLGFQEVLSV EVTLRVAANF    120
SVPVVSAPHS PSQDELTFTC TSINGYPRPN VYWINKTDNS LLDQALQNDT VSLNMRGLYD    180
VVSVLRIART PSVNIGCRIE NVLLQQNLTV GSQTGNDIGE RDKITENPVS TGEKNAAT     238

SEQ ID NO: 461          moltype = AA  length = 238
FEATURE                 Location/Qualifiers
REGION                  1..238
                        note = ICOSL v170 ECD
source                  1..238
                        mol_type = protein
                        organism = synthetic construct
SEQUENCE: 461
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSP SLGFQEVLSV EVTLHVAANF    120
SVPVVSAPHS PSQDELTFTC TSINGYPRPN VYWINKTDNS LLDQALQNDT VFLNMRGLYD    180
VVSVLRIART PSVNIGCRIE NVLLQQNLTV GSQTGNDIGE RDKITENPVS TGEKNAAT     238

SEQ ID NO: 462          moltype = AA  length = 238
FEATURE                 Location/Qualifiers
REGION                  1..238
                        note = ICOSL v171 ECD
source                  1..238
                        mol_type = protein
                        organism = synthetic construct
SEQUENCE: 462
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSP SLGFQEVLSV EVTLRVAANF    120
SVPVVSAPHS PSQDELTFTC TSINGYPRPN VYWINKTDNS LLDQALQNDT VSLNMRGLYD    180
VVSVLRIART PSVNIGCRIE NVLLQQNLTV GSQTGNDIGE RDKITENPVS TGEKNAAT     238
```

-continued

```
SEQ ID NO: 463            moltype = AA  length = 238
FEATURE                   Location/Qualifiers
REGION                    1..238
                          note = ICOSL v172 ECD
source                    1..238
                          mol_type = protein
                          organism = synthetic construct
SEQUENCE: 463
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSP SLGFQEVLSV EVTLHVAANF  120
SVPVVSAPHS PSQDELTFTC TSINGYPRPN VYWINKTDNS LLDQALQNDT VSLNMRGLYD  180
VVSVLRIART PSVNIGCRIE NVLLQQNLTV GSQTGNDIGE RDKITENPVS TGEKNAAT    238

SEQ ID NO: 464            moltype = AA  length = 238
FEATURE                   Location/Qualifiers
REGION                    1..238
                          note = ICOSL v173 ECD
source                    1..238
                          mol_type = protein
                          organism = synthetic construct
SEQUENCE: 464
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSP SLGFQEVLSV EVTLRVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 465            moltype = AA  length = 238
FEATURE                   Location/Qualifiers
REGION                    1..238
                          note = ICOSL v174 ECD
source                    1..238
                          mol_type = protein
                          organism = synthetic construct
SEQUENCE: 465
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSP SLGFQEVLSV EVTLRVAANF  120
SVPVVSAPHS PSQDELTFTC TSINGYPRPN VYWINKTDNS LLDQALQNDT VFLNMRGLYD  180
VVSVLRIART PSVNIGCRIE NVLLQQNLTV GSQTGNDIGE RDKITENPVS TGEKNAAT    238

SEQ ID NO: 466            moltype = AA  length = 238
FEATURE                   Location/Qualifiers
REGION                    1..238
                          note = ICOSL v175 ECD
source                    1..238
                          mol_type = protein
                          organism = synthetic construct
SEQUENCE: 466
DTQEKEVRAM VGSDVELSCA CPEGSRFDLN DVYVYWQTSE SKTVVTYHIP QHSSLENVDS   60
RYRNRALMSP AGMLRGDFSL RLFNVTPQDE QKFHCLVLSR SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCRIE NVLLQQNLTV GSQTGNDIGE RDKITENPVS TGEKNAAT    238

SEQ ID NO: 467            moltype = AA  length = 238
FEATURE                   Location/Qualifiers
REGION                    1..238
                          note = ICOSL v176 ECD
source                    1..238
                          mol_type = protein
                          organism = synthetic construct
SEQUENCE: 467
DTQEKEVRAM VGSDVELSCA CPEGSRFDLN DVYVYWQTSE SKTVVTYHIP QHSSLENVDS   60
RYRNRALMSP AGMLRGDFSL RLFNVTPQDE QKFHCLVLSR SLGFQEVLSV EVTLRVAANF  120
SVPVVSAPHS PSQDELTFTC TSINGYPRPN VYWINKTDNS LLDQALQNDT VSLNMRGLYD  180
VVSVLRIART PSVNIGCCIE NVLLQQNLTV GSQTGNDIGE RDKITENPVS TGEKNAAT    238

SEQ ID NO: 468            moltype = AA  length = 238
FEATURE                   Location/Qualifiers
REGION                    1..238
                          note = ICOSL v177 ECD
VARIANT                   115
                          note = X is H or Q
source                    1..238
                          mol_type = protein
                          organism = synthetic construct
SEQUENCE: 468
DTQEKEVRAM VGSDVELSCA CPEGSRFDLN DVYVYWQTSE SKTVVTYHIP QHSSLENVDS   60
RYRNRALMSP AGMLRGDFSL RLFNVTPQDE QKFHCLVLSR SLGFQEVLSV EVTLXVAANF  120
SVPVVSAPHS PSQDELTFTC TSINGYPRPN VYWINKTDNS LLDQALQNDT VSLNMRGLYD  180
```

-continued

```
VVSVLRIART PSVNIGCRIE NVLLQQNLTV GSQTGNDIGE RDKITENPVS TGEKNAAT         238

SEQ ID NO: 469          moltype = AA   length = 238
FEATURE                 Location/Qualifiers
REGION                  1..238
                        note = ICOSL v178 ECD
source                  1..238
                        mol_type = protein
                        organism = synthetic construct
SEQUENCE: 469
DTQEKEVRAM VGSDVELSCA CPEGSRFDLN DVVYWQTSE SKTVVTYHIP QHSSLENVDS         60
RYRNRALMSP AGMLRGDFSL RLFNVTPQDE QKFHCLVLSR SLGFQEVLSV EVTLRVAANF        120
SVPVVSAPHS PSQDELTFTC TSINGYPRPN VYWINKTDNS LLDQALQNDT VSLNMRGLYD        180
VVSVLRIART PSVNIGCRIE NVLLQQNLTV GSQTGNDIGE RDKITENPVS TGEKNAAT         238

SEQ ID NO: 470          moltype = AA   length = 238
FEATURE                 Location/Qualifiers
REGION                  1..238
                        note = ICOSL v179 ECD
source                  1..238
                        mol_type = protein
                        organism = synthetic construct
SEQUENCE: 470
DTQEKEVRAM VGSDVELSCA CPEGSRFDLN DVVYWQTSE SKTVVTYHIP QHSSLEYVDS         60
RYRNRALMSP AGMLRGDFSL RLFNVTPQDE QKFHCLVLSR SLGFQEVLSV EVTLHVAANF        120
SVPVVSAPHS PSQDELTFTC TSINGYPRPN VYWINKTDNS LLDQALQNDT VSLNMRGLYD        180
VVSVLRIART PSVNIGCRIE NVLLQQNLTV GSQTGNDIGE RDKITENPVS TGEKNAAT         238

SEQ ID NO: 471          moltype = AA   length = 18
FEATURE                 Location/Qualifiers
REGION                  1..18
                        note = CD80 WT linker 1 (including first 3 aa)
source                  1..18
                        mol_type = protein
                        organism = synthetic construct
SEQUENCE: 471
LSVKADFPTP SISDFEIP                                                      18

SEQ ID NO: 472          moltype = AA   length = 232
FEATURE                 Location/Qualifiers
REGION                  1..232
                        note = Knob Fc
source                  1..232
                        mol_type = protein
                        organism = synthetic construct
SEQUENCE: 472
EPKSSDKTHT CPPCPAPEAE GAPSVFLFPP KPKDTLMISR TPEVTCVVVD VSHEDPEVKF        60
NWYVDGVEVH NAKTKPREEQ YNSTYRVVSV LTVLHQDWLN GKEYKCKVSN KALPAPIEKT        120
ISKAKGQPRE PQVYTLPPCR EEMTKNQVSL WCLVKGFYPS DIAVEWESNG QPENNYKTTP        180
PVLDSDGSFF LYSKLTVDKS RWQQGNVFSC SVMHEALHNH YTQKSLSLSP GK               232

SEQ ID NO: 473          moltype = AA   length = 232
FEATURE                 Location/Qualifiers
REGION                  1..232
                        note = Hole Fc
source                  1..232
                        mol_type = protein
                        organism = synthetic construct
SEQUENCE: 473
EPKSSDKTHT CPPCPAPEAE GAPSVFLFPP KPKDTLMISR TPEVTCVVVD VSHEDPEVKF        60
NWYVDGVEVH NAKTKPREEQ YNSTYRVVSV LTVLHQDWLN GKEYKCKVSN KALPAPIEKT        120
ISKAKGQPRE PQVCTLPPSR EEMTKNQVSL SCAVKGFYPS DIAVEWESNG QPENNYKTTP        180
PVLDSDGSFF LVSKLTVDKS RWQQGNVFSC SVMHEALHNH YTQKSLSLSP GK               232

SEQ ID NO: 474          moltype = AA   length = 232
FEATURE                 Location/Qualifiers
REGION                  1..232
                        note = Fc region
source                  1..232
                        mol_type = protein
                        organism = synthetic construct
SEQUENCE: 474
EPKSSDKTHT CPPCPAPEAE GAPSVFLFPP KPKDTLMISR TPEVTCVVVD VSHEDPEVKF        60
NWYVDGVEVH NAKTKPREEQ YNSTYRVVSV LTVLHQDWLN GKEYKCKVSN KALPAPIEKT        120
ISKAKGQPRE PQVYTLPPSR DELTKNQVSL TCLVKGFYPS DIAVEWESNG QPENNYKTTP        180
PVLDSDGSFF LYSKLTVDKS RWQQGNVFSC SVMHEALHNH YTQKSLSLSP GK               232

SEQ ID NO: 475          moltype = AA   length = 8
FEATURE                 Location/Qualifiers
```

-continued

```
REGION                  1..8
                        note = Stuffer
source                  1..8
                        mol_type = protein
                        organism = synthetic construct
SEQUENCE: 475
HMSSVSAQ                                                            8

SEQ ID NO: 476          moltype = AA   length = 232
FEATURE                 Location/Qualifiers
REGION                  1..232
                        note = Fc (C5S (C220S), R77C, (R292C),N82G (N297G), V87C
                        (V302C))
source                  1..232
                        mol_type = protein
                        organism = synthetic construct
SEQUENCE: 476
EPKSSDKTHT CPPCPAPELL GGPSVFLFPP KPKDTLMISR TPEVTCVVVD VSHEDPEVKF   60
NWYVDGVEVH NAKTKPCEEQ YGSTYRCVSV LTVLHQDWLN GKEYKCKVSN KALPAPIEKT   120
ISKAKGQPRE PQVYTLPPSR EEMTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 477          moltype = AA   length = 232
FEATURE                 Location/Qualifiers
REGION                  1..232
                        note = Fc with C220S/L234A/L235E/G237A
source                  1..232
                        mol_type = protein
                        organism = synthetic construct
SEQUENCE: 477
EPKSSDKTHT CPPCPAPEAE GAPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT   120
ISKAKGQPRE PQVYTLPPSR EEMTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 478          moltype = AA   length = 231
FEATURE                 Location/Qualifiers
REGION                  1..231
                        note = Fc with C220S/E233P/L234V/L235A/G236del/S267K
source                  1..231
                        mol_type = protein
                        organism = synthetic construct
SEQUENCE: 478
EPKSSDKTHT CPPCPAPPVA GPSVFLFPPK PKDTLMISRT PEVTCVVVDV KHEDPEVKFN   60
WYVDGVEVHN AKTKPREEQY NSTYRVVSVL TVLHQDWLNG KEYKCKVSNK ALPAPIEKTI   120
SKAKGQPREP QVYTLPPSRE EMTKNQVSLT CLVKGFYPSD IAVEWESNGQ PENNYKTTPP   180
VLDSDGSFFL YSKLTVDKSR WQQGNVFSCS VMHEALHNHY TQKSLSLSPG K            231

SEQ ID NO: 479          moltype = AA   length = 431
FEATURE                 Location/Qualifiers
REGION                  1..431
                        note = antiCD19z chimeric antigen receptor
source                  1..431
                        mol_type = protein
                        organism = synthetic construct
SEQUENCE: 479
DIQMTQTTSS LSASLGDRVT ISCRASQDIS KYLNWYQQKP DGTVKLLIYH TSRLHSGVPS   60
RFSGSGSGTD YSLTISNLEQ EDIATYFCQQ GNTLPYTFGG GTKLEITGST SGSGKPGSGE   120
GSTKGEVKLQ ESGPGLVAPS QSLSVTCTVS GVSLPDYGVS WIRQPPRKGL EWLGVIWGSE   180
TTYYNSALKS RLTIIKDNSK SQVFLKMNSL QTDDTAIYYC AKHYYYGGSY AMDYWGQGTS   240
VTVSSAAAKP TTTPAPRPPT PAPTIASQPL SLRPEASRPA AGGAVHTRGL DFASDIYIWA   300
PLAGTCGVLL LSLVITLYCR VKFSRSADAP AYQQGQNQLY NELNLGRREE YDVLDKRRGR   360
DPEMGGKPRR KNPQEGLYNE LQKDKMAEAY SEIGMKGERR RGKGHDGLYQ GLSTATKDTY   420
DALHMQALPP R                                                       431

SEQ ID NO: 480          moltype = AA   length = 21
FEATURE                 Location/Qualifiers
REGION                  1..21
                        note = CD8-derived signal sequence
source                  1..21
                        mol_type = protein
                        organism = synthetic construct
SEQUENCE: 480
MALPVTALLL PLALLLHAAR P                                             21

SEQ ID NO: 481          moltype = AA   length = 23
FEATURE                 Location/Qualifiers
REGION                  1..23
                        note = CD8-derived signal sequence
```

```
source                       1..23
                             mol_type = protein
                             organism = synthetic construct
SEQUENCE: 481
MALPVTALLL PLALLLHAAR PGS                                            23

SEQ ID NO: 482               moltype = AA  length = 245
FEATURE                      Location/Qualifiers
REGION                       1..245
                             note = anti-CD19 scFv
source                       1..245
                             mol_type = protein
                             organism = synthetic construct
SEQUENCE: 482
DIQMTQTTSS LSASLGDRVT ISCRASQDIS KYLNWYQQKP DGTVKLLIYH TSRLHSGVPS    60
RFSGSGSGTD YSLTISNLEQ EDIATYFCQQ GNTLPYTFGG GTKLEITGST SGSGKPGSGE    120
GSTKGEVKLQ ESGPGLVAPS QSLSVTCTVS GVSLPDYGVS WIRQPPRKGL EWLGVIWGSE    180
TTYYNSALKS RLTIIKDNSK SQVFLKMNSL QTDDTAIYYC AKHYYYGGSY AMDYWGQGTS    240
VTVSS                                                               245

SEQ ID NO: 483               moltype = AA  length = 69
FEATURE                      Location/Qualifiers
REGION                       1..69
                             note = CD8-derived hinge and transmembrane domain
source                       1..69
                             mol_type = protein
                             organism = synthetic construct
SEQUENCE: 483
AKPTTTPAPR PPTPAPTIAS QPLSLRPEAC RPAAGGAVHT RGLDFACDIY IWAPLAGTCG    60
VLLLSLVIT                                                            69

SEQ ID NO: 484               moltype = AA  length = 42
FEATURE                      Location/Qualifiers
REGION                       1..42
                             note = 4-1BB-derived costimulatory domain
source                       1..42
                             mol_type = protein
                             organism = synthetic construct
SEQUENCE: 484
KRGRKKLLYI FKQPFMRPVQ TTQEEDGCSC RFPEEEEGGC EL                       42

SEQ ID NO: 485               moltype = AA  length = 40
FEATURE                      Location/Qualifiers
REGION                       1..40
                             note = CD28-derived costimulatory domain
source                       1..40
                             mol_type = protein
                             organism = synthetic construct
SEQUENCE: 485
SKRSRLLHSD YMNMTPRRPG PTRKHYQPYA PPRDFAAYRS                          40

SEQ ID NO: 486               moltype = AA  length = 41
FEATURE                      Location/Qualifiers
REGION                       1..41
                             note = CD28-derived costimulatory domain
source                       1..41
                             mol_type = protein
                             organism = synthetic construct
SEQUENCE: 486
RSKRSRLLHS DYMNMTPRRP GPTRKHYQPY APPRDFAAYR S                        41

SEQ ID NO: 487               moltype = AA  length = 44
FEATURE                      Location/Qualifiers
REGION                       1..44
                             note = CD28-derived costimulatory domain
source                       1..44
                             mol_type = protein
                             organism = synthetic construct
SEQUENCE: 487
FWVRSKRSRL LHSDYMNMTP RRPGPTRKHY QPYAPPRDFA AYRS                     44

SEQ ID NO: 488               moltype = AA  length = 20
FEATURE                      Location/Qualifiers
REGION                       1..20
                             note = T2A protein
source                       1..20
                             mol_type = protein
                             organism = synthetic construct
SEQUENCE: 488
```

```
SGEGRGSLLT CGDVEENPGP                                                    20

SEQ ID NO: 489          moltype = AA  length = 232
FEATURE                 Location/Qualifiers
REGION                  1..232
                        note = Blue fluorescent protein
source                  1..232
                        mol_type = protein
                        organism = synthetic construct
SEQUENCE: 489
SELIKENMHM KLYMEGTVDN HHFKCTSEGE GKPYEGTQTM RIKVVEGGPL PFAFDILATS    60
FLYGSKTFIN HTQGIPDFFK QSFPEGFTWE RVTTYEDGGV LTATQDTSLQ DGCLIYNVKI   120
RGVNFTSNGP VMQKKTLGWE AFTETLYPAD GGLEGRNDMA LKLVGGSHLI ANIKTTYRSK   180
KPAKNLKMPG VYYVDYRLER IKEANNETYV EQHEVAVARY CDLPSKLGHK LN           232

SEQ ID NO: 490          moltype = AA  length = 472
FEATURE                 Location/Qualifiers
REGION                  1..472
                        note = 2nd Gen CAR (without signal sequence or T2A or BFP)
source                  1..472
                        mol_type = protein
                        organism = synthetic construct
SEQUENCE: 490
DIQMTQTTSS LSASLGDRVT ISCRASQDIS KYLNWYQQKP DGTVKLLIYH TSRLHSGVPS    60
RFSGSGSGTD YSLTISNLEQ EDIATYFCQQ GNTLPYTFGG GTKLEITGST SGSGKPGSGE   120
GSTKGEVKLQ ESGPGLVAPS QSLSVTCTVS GVSLPDYGVS WIRQPPRKGL EWLGVIWGSE   180
TTYYNSALKS RLTIIKDNSK SQVFLKMNSL QTDDTAIYYC AKHYYYGGSY AMDYWGQGTS   240
VTVSSASAKP TTTPAPRPPT PAPTIASQPL SLRPEACRPA AGGAVHTRGL DFACDIYIWA   300
PLAGTCGVLL LSLVITMHKR GRKKLLYIFK QPFMRPVQTT QEEDGCSCRF PEEEEGGCEL   360
RVKFSRSADA PAYQQGQNQL YNELNLGRRE EYDVLDKRRG RDPEMGGKPR RKNPQEGLYN   420
ELQKDKMAEA YSEIGMKGER RRGKGHDGLY QGLSTATKDT YDALHMQALP PR           472

SEQ ID NO: 491          moltype = AA  length = 497
FEATURE                 Location/Qualifiers
REGION                  1..497
                        note = 2nd Gen CAR with T2A
source                  1..497
                        mol_type = protein
                        organism = synthetic construct
SEQUENCE: 491
DIQMTQTTSS LSASLGDRVT ISCRASQDIS KYLNWYQQKP DGTVKLLIYH TSRLHSGVPS    60
RFSGSGSGTD YSLTISNLEQ EDIATYFCQQ GNTLPYTFGG GTKLEITGST SGSGKPGSGE   120
GSTKGEVKLQ ESGPGLVAPS QSLSVTCTVS GVSLPDYGVS WIRQPPRKGL EWLGVIWGSE   180
TTYYNSALKS RLTIIKDNSK SQVFLKMNSL QTDDTAIYYC AKHYYYGGSY AMDYWGQGTS   240
VTVSSASAKP TTTPAPRPPT PAPTIASQPL SLRPEACRPA AGGAVHTRGL DFACDIYIWA   300
PLAGTCGVLL LSLVITMHKR GRKKLLYIFK QPFMRPVQTT QEEDGCSCRF PEEEEGGCEL   360
RVKFSRSADA PAYQQGQNQL YNELNLGRRE EYDVLDKRRG RDPEMGGKPR RKNPQEGLYN   420
ELQKDKMAEA YSEIGMKGER RRGKGHDGLY QGLSTATKDT YDALHMQALP PRGGRSGEGR   480
GSLLTCGDVE ENPGPSR                                                   497

SEQ ID NO: 492          moltype = AA  length = 471
FEATURE                 Location/Qualifiers
REGION                  1..471
                        note = 2nd Gen CAR with CD28-derived costimulatory domain
                        (withoutsignal sequence or T2A or BFP)
source                  1..471
                        mol_type = protein
                        organism = synthetic construct
SEQUENCE: 492
DIQMTQTTSS LSASLGDRVT ISCRASQDIS KYLNWYQQKP DGTVKLLIYH TSRLHSGVPS    60
RFSGSGSGTD YSLTISNLEQ EDIATYFCQQ GNTLPYTFGG GTKLEITGST SGSGKPGSGE   120
GSTKGEVKLQ ESGPGLVAPS QSLSVTCTVS GVSLPDYGVS WIRQPPRKGL EWLGVIWGSE   180
TTYYNSALKS RLTIIKDNSK SQVFLKMNSL QTDDTAIYYC AKHYYYGGSY AMDYWGQGTS   240
VTVSSASAKP TTTPAPRPPT PAPTIASQPL SLRPEACRPA AGGAVHTRGL DFACDIYIWA   300
PLAGTCGVLL LSLVITMHRS KRSRLLHSDY MNMTPRRPGP TRKHYQPYAP PRDFAAYRSR   360
VKFSRSADAP AYQQGQNQLY NELNLGRREE YDVLDKRRGR DPEMGGKPRR KNPQEGLYNE   420
LQKDKMAEAY SEIGMKGERR RGKGHDGLYQ GLSTATKDTY DALHMQALPP R            471

SEQ ID NO: 493          moltype = AA  length = 270
FEATURE                 Location/Qualifiers
REGION                  1..270
                        note = Nkp30 stack
source                  1..270
                        mol_type = protein
                        organism = synthetic construct
SEQUENCE: 493
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSP SLGFQEVLSV EVTLHVAANF   120
SVGGGGSGGG GSGGGGSLWV SQPPEIRTLE GSSAFLPCSF NASQGRVAIG SVTWFRDEVV   180
```

-continued

```
PGKEVRNGTP EFRGRLVPLA PSRFLHDHQA ELHIRDVRGH DAGIYVCRVE VLGLGVGTGN  240
GTRLVVEKEH PQLGGGGGSG GGGSAAAEPK                                   270

SEQ ID NO: 494              moltype = AA  length = 302
FEATURE                     Location/Qualifiers
REGION                      1..302
                            note = TIP v1
source                      1..302
                            mol_type = protein
                            organism = synthetic construct
SEQUENCE: 494
MRLGSPGLLF LLFSSLRADT QEKEVRAMVG SDVELSCACP EGSRFDLNDV YVYWQTSESK  60
TVVTYHIPQN SSLENVDSRY RNRALMSPAG MLRGDFSLRL FNVTPQDEQK FHCLVLSQSL  120
GFQEVLSVEV TLHVAANFSV PVVSAPHSPS QDELTFTCTS INGYPRPNVY WINKTDNSLL  180
DQALQNDTVF LNMRGLYDVV SVLRIARTPS VNIGCCIENV LLQQNLTVGS QTGNDIGERD  240
KITENPVSTG EKNAATWSIL AVLCLLVVVA VAIGWVCRDR CLQHSYAGAW AVSPETELTG  300
HV                                                                302

SEQ ID NO: 495              moltype = AA  length = 284
FEATURE                     Location/Qualifiers
REGION                      1..284
                            note = TIP v1 without Signal Peptide
source                      1..284
                            mol_type = protein
                            organism = synthetic construct
SEQUENCE: 495
DTQEKEVRAM VGSDVELSCA CPEGSRFDLN DVYVYWQTSE SKTVVTYHIP QNSSLENVDS  60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAATWS  240
ILAVLCLLVV VAVAIGWVCR DRCLQHSYAG AWAVSPETEL TGHV                  284

SEQ ID NO: 496              moltype = AA  length = 302
FEATURE                     Location/Qualifiers
REGION                      1..302
                            note = TIP v2
source                      1..302
                            mol_type = protein
                            organism = synthetic construct
SEQUENCE: 496
MRLGSPGLLF LLFSSLRADT QEKEVRAMVG SDVELSCACP EGSRFDLNDV YVYWQTSESK  60
TVVTYHIPQD SSLENVDSRY RNRALMSPAG MLRGDFSLRL FNVTPQDEQK FHCLVLSQSL  120
GFQEVLSVEV TLHVAANFSV PVVSAPHSPS QDELTFTCTS INGYPRPNVY WINKTDNSLL  180
DQALQNDTVF LNMRGLYDVV SVLRIARTPS VNIGCCIENV LLQQNLTVGS QTGNDIGERD  240
KITENPVSTG EKNAATWSIL AVLCLLVVVA VAIGWVCRDR CLQHSYAGAW AVSPETELTG  300
HV                                                                302

SEQ ID NO: 497              moltype = AA  length = 284
FEATURE                     Location/Qualifiers
REGION                      1..284
                            note = TIP v2 without Signal Peptide
source                      1..284
                            mol_type = protein
                            organism = synthetic construct
SEQUENCE: 497
DTQEKEVRAM VGSDVELSCA CPEGSRFDLN DVYVYWQTSE SKTVVTYHIP QDSSLENVDS  60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAATWS  240
ILAVLCLLVV VAVAIGWVCR DRCLQHSYAG AWAVSPETEL TGHV                  284

SEQ ID NO: 498              moltype = AA  length = 302
FEATURE                     Location/Qualifiers
REGION                      1..302
                            note = TIP v3
source                      1..302
                            mol_type = protein
                            organism = synthetic construct
SEQUENCE: 498
MRLGSPGLLF LLFSSLRADT QEKEVRAMVG SDVELSCACP EGSRFDLNDV YVYWQTSESK  60
TVVTYHIPQH SSLEYVDSRY RNRALMSPAG MLRGDFSLRL FNVTPQDEQK FHCLVLSPSL  120
GFQEVLSVEV TLHVAANFSV PVVSAPHSPS QDELTFTCTS INGYPRPNVY WINKTDNSLL  180
DQALQNDTVF LNMRGLYDVV SVLRIARTPS VNIGCCIENV LLQQNLTVGS QTGNDIGERD  240
KITENPVSTG EKNAATWSIL AVLCLLVVVA VAIGWVCRDR CLQHSYAGAW AVSPETELTG  300
HV                                                                302

SEQ ID NO: 499              moltype = AA  length = 284
FEATURE                     Location/Qualifiers
REGION                      1..284
```

```
                              note = TIP v3 without Signal Peptide
source                        1..284
                              mol_type = protein
                              organism = synthetic construct
SEQUENCE: 499
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSP SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAATWS   240
ILAVLCLLVV VAVAIGWVCR DRCLQHSYAG AWAVSPETEL TGHV                    284

SEQ ID NO: 500         moltype = AA  length = 302
FEATURE                Location/Qualifiers
REGION                 1..302
                       note = TIP v4
source                 1..302
                       mol_type = protein
                       organism = synthetic construct
SEQUENCE: 500
MRLGSPGLLF LLFSSLRADT QEKEVRAMVG SDVVLSCACP EGSRFDLNDV YVYWQTSESK   60
TVVTYHIPQH SSLEYVDSRY RNRALMSPAG MLRGDFSLRL FNVTPQDEQK FHCLVLSRSL   120
GFQEVLSDEV TLRVAANFSV PVVSAPHSPS QDELTFTCTS INGYPRPNVC WINMTDNSLL   180
DQALQNDTVF LNMRGLYDVV SVLRIARTPS VNIGCRIENV LLQQNLTVGS QTGNDIGERD   240
KITENPVSTG EKNAATWSIL AVLCLLVVVA VAIGWVCRDR CLQHSYAGAW AVSPETELTG   300
HV                                                                  302

SEQ ID NO: 501         moltype = AA  length = 284
FEATURE                Location/Qualifiers
REGION                 1..284
                       note = TIP v4 without Signal Peptide
source                 1..284
                       mol_type = protein
                       organism = synthetic construct
SEQUENCE: 501
DTQEKEVRAM VGSDVVLSCA CPEGSRFDLN DVYVYWQTSE SKTVVTYHIP QHSSLEYVDS   60
RYRNRALMSP AGMLRGDFSL RLFNVTPQDE QKFHCLVLSR SLGFQEVLSD EVTLRVAANF   120
SVPVVSAPHS PSQDELTFTC TSINGYPRPN VCWINMTDNS LLDQALQNDT VFLNMRGLYD   180
VVSVLRIART PSVNIGCRIE NVLLQQNLTV GSQTGNDIGE RDKITENPVS TGEKNAATWS   240
ILAVLCLLVV VAVAIGWVCR DRCLQHSYAG AWAVSPETEL TGHV                    284

SEQ ID NO: 502         moltype = AA  length = 302
FEATURE                Location/Qualifiers
REGION                 1..302
                       note = TIP v5
source                 1..302
                       mol_type = protein
                       organism = synthetic construct
SEQUENCE: 502
MRLGSPGLLF LLFSSLRADT QEKEVRAMVG SDVELSCACP EGSRFDLNDV YVYWQTSESK   60
TVVTYHIPQH SSLEYVDSRY RNRALMSPAG MLRGDFSLRL FNVTPQDEQK FHCLVLSRSL   120
GFQEVLSVEV TLHVAANFSV PVVSAPHSPS QDELTFTCTS INGYPRPNVY WINKTDNSLL   180
DQALQNDTVF LNMRGLYDVV SVLRIARTPS VNIGCCIENV LLQQNLTVGS QTGNDIGERD   240
KITENPVSTG EKNAATWSIL AVLCLLVVVA VAIGWVCRDR CLQHSYAGAW AVSPETELTG   300
HV                                                                  302

SEQ ID NO: 503         moltype = AA  length = 284
FEATURE                Location/Qualifiers
REGION                 1..284
                       note = TIP v5 without Signal Peptide
source                 1..284
                       mol_type = protein
                       organism = synthetic construct
SEQUENCE: 503
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSR SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAATWS   240
ILAVLCLLVV VAVAIGWVCR DRCLQHSYAG AWAVSPETEL TGHV                    284

SEQ ID NO: 504         moltype = AA  length = 116
FEATURE                Location/Qualifiers
REGION                 1..116
                       note = NKp30 v1 IgV-like
source                 1..116
                       mol_type = protein
                       organism = synthetic construct
SEQUENCE: 504
LWVSQPPEIR TLEGSSAFLP CSFNASQGRV AIGSVTWFRD EVVPGKEVRN GTPEFRGRLV   60
PLAPSRFLHD HQAELHIRDV RGHDAGIYVC RVEVLGLGVG TGNGTRLVVE KEHPQL       116
```

-continued

```
SEQ ID NO: 505              moltype = AA   length = 229
FEATURE                     Location/Qualifiers
REGION                      1..229
                            note = IgG4 Fc
source                      1..229
                            mol_type = protein
                            organism = synthetic construct
SEQUENCE: 505
ESKYGPPCPS CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK             229

SEQ ID NO: 506              moltype = AA   length = 229
FEATURE                     Location/Qualifiers
REGION                      1..229
                            note = IgG4 Fc S228P
source                      1..229
                            mol_type = protein
                            organism = synthetic construct
SEQUENCE: 506
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK             229

SEQ ID NO: 507              moltype = AA   length = 232
FEATURE                     Location/Qualifiers
REGION                      1..232
                            note = IgG1 Fc C220S
source                      1..232
                            mol_type = protein
                            organism = synthetic construct
SEQUENCE: 507
EPKSSDKTHT CPPCPAPELL GGPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 508              moltype = AA   length = 208
FEATURE                     Location/Qualifiers
REGION                      1..208
                            note = CD80 v55 ECD
source                      1..208
                            mol_type = protein
                            organism = synthetic construct
SEQUENCE: 508
VIHVTKEVKE VATLSCGHNV SVEELAQTRI YWQKEKKMVL TMMSGDMNIW PEYKNRTIFD   60
ITNNLSIVIQ ALRPSDEGTY ECVVLKYEKD GFKREHLAEV TLSVKADFPT PSISDFEIPT  120
SNIRRIICST SGGFPEPHLS WLEDGEELNA INTTVSQDPE TELYAVSSKL DFNMTTNHSF  180
MCLIKYGHLR VNQTFNWNTT KQEHFPDN                                    208

SEQ ID NO: 509              moltype = AA   length = 208
FEATURE                     Location/Qualifiers
REGION                      1..208
                            note = CD80 v56 ECD
source                      1..208
                            mol_type = protein
                            organism = synthetic construct
SEQUENCE: 509
VIHVTKEVKE VATLSCGHNV SVEELAQTRI YWQKEKKMVL TMMSGDMNIW PEYKNRTIFD   60
ITNNLSIVIQ ALRPSDEGTY ECVVLKYEKD GFKREHLAEV TLSVKADFPT PSISDFEAPS  120
SNIRRIICSA SGGFPEPHLS WLENGEELNA INTTVSQDPE TELYAVSSEL DFNMTTNHSF  180
MCLIKYGHLR VNQTFNWNTT KQEHFPDN                                    208

SEQ ID NO: 510              moltype = AA   length = 208
FEATURE                     Location/Qualifiers
REGION                      1..208
                            note = CD80 v57 ECD
source                      1..208
                            mol_type = protein
                            organism = synthetic construct
SEQUENCE: 510
VIHMTKEVKE VATLSCGHNV SVEELAQTRI YWQKEKKMVL TMMSGDMNIW PEYKNRTIFD   60
ITNNLSIVIQ ALRPSDEGTY ECVVLKYEKD GFKREHLAEV TLSVKADFPT PSISDFEVPS  120
SNIRRIICSA SGGFPEPHLS WLENGEELNA INTTVSQDPE TELYAVSSEL DFNMTTNHSF  180
MCLIKYGHLR VNQTFNWNTT KQEHFPDN                                    208
```

-continued

```
SEQ ID NO: 511                moltype = AA  length = 208
FEATURE                       Location/Qualifiers
REGION                        1..208
                              note = CD80 v58 ECD
source                        1..208
                              mol_type = protein
                              organism = synthetic construct
SEQUENCE: 511
VIHVTKEVKE VATLSCGHNV SVEELAQTRI YWQKEKKMVL TMMSGDMNIW PEYKNRTIFD   60
ITNNLSIVIQ ALRPSDEGTY ECVVLKYEKD GFKREHLAEV TLSVKADFPT PSISDFEVPS  120
SNIRRIICSA SGGFPEPHLS WLENGEELNA INTTVSQDPE TELYAVSSEL DFNMTTNHSF  180
MCLIKYGHLR VNQTFNWNTT KQEHFPDN                                     208

SEQ ID NO: 512                moltype = AA  length = 208
FEATURE                       Location/Qualifiers
REGION                        1..208
                              note = CD80 v59 ECD
source                        1..208
                              mol_type = protein
                              organism = synthetic construct
SEQUENCE: 512
VIHVTKEVKE VATLSCGHNV SVEELAQTRI YWQKEKKMVL TMMSGDMNIW PEYKNRTIFD   60
ITNNLSIVIQ ALRPSDEGTY ECVVLKYEKD GFKREHLAEV TLSVKADFPT PSISDFEVPS  120
SNIRRIICSA SGGFPEPHLS WLENGEELNA INTTVSQDPE TELYAVSSKL DFNMTTNHSF  180
MCLIKYGHLR VSQTFNWNTT KQEHFPDN                                     208

SEQ ID NO: 513                moltype = AA  length = 208
FEATURE                       Location/Qualifiers
REGION                        1..208
                              note = CD80 v60 ECD
source                        1..208
                              mol_type = protein
                              organism = synthetic construct
SEQUENCE: 513
VIHVTKEVKE VATLSCGHNL SVEELAQTRI YWQKEKKMVL TMMSGDMNIW PEYKNRTIFD   60
ITNNLSIVIQ ALRPSDEGTY ECVVLKYEKD GFKREHLAEV TLSVKADFPT PSISDFEVPS  120
SNIRRIICSA SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 514                moltype = AA  length = 208
FEATURE                       Location/Qualifiers
REGION                        1..208
                              note = CD80 v61 ECD
source                        1..208
                              mol_type = protein
                              organism = synthetic construct
SEQUENCE: 514
VIHVTKEVKE VATLSCGHNV SVEELAQTRI YWQKEKKMVL TMMSGDMNIW PEYKNRTIFD   60
ITNNLSIVIQ ALRPSDEGTY ECVVLKYEKD GFKREHLAEV TLSVKADFPT PSISDFGVPS  120
SNIRRIICSA SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 515                moltype = AA  length = 208
FEATURE                       Location/Qualifiers
REGION                        1..208
                              note = CD80 v62 ECD
source                        1..208
                              mol_type = protein
                              organism = synthetic construct
SEQUENCE: 515
VIHVTKEVKE VATLSCGHNV SVEELAQTRI YWQKEKKMVL TMMSGDMNIW PEYKNRTIFD   60
ITNNLSIVIL ALRPSDEGTY ECVVLKYEKD GFKREHLAEV TLSVKADFPT PSISDFEVPS  120
SNIRRIICSA SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 516                moltype = AA  length = 208
FEATURE                       Location/Qualifiers
REGION                        1..208
                              note = CD80 v63 ECD
source                        1..208
                              mol_type = protein
                              organism = synthetic construct
SEQUENCE: 516
VIHVTKEVKE VATLSCGHNV SVEELAQTRI YWQKEKKMVL TMMSGDMNIW PEYKNRTIFD   60
ITNNLSIVIR ALRPSDEGTY ECVVLKYEKD GFKREHLAEV TLSVKADFPT PSISDFEVPS  120
SNIRRIICSA SGGFPEPHLS WLENGEELNA INTTVSQDPE TELYAVSSKL DFNMTTNHSF  180
MCLIKYGHLR VNQTFNWNST KQEHFPDN                                     208

SEQ ID NO: 517                moltype = AA  length = 208
```

-continued

```
FEATURE                 Location/Qualifiers
REGION                  1..208
                        note = CD80 v64 ECD
source                  1..208
                        mol_type = protein
                        organism = synthetic construct
SEQUENCE: 517
VIHVTKEVKE VATLSCGHNV SVEELAQTRI YWQKEKKMVL TMMSGDMNIW PEYKNRTIFD   60
ITNNLSIVIQ ALRPSDEGTY ACVVLKYEKD GFKREHLAEV TLSVKADFPT PSISDFEVPS   120
SNIRRITCSA SGGFPEPHLS WLENGEELNA INTTVSQDPE TELYAVSSKL DFNMTTNHSF   180
MCLIKYGHLR VNQTFNWNTT KQEHFPDN                                     208

SEQ ID NO: 518          moltype = AA  length = 208
FEATURE                 Location/Qualifiers
REGION                  1..208
                        note = CD80 v65 ECD
source                  1..208
                        mol_type = protein
                        organism = synthetic construct
SEQUENCE: 518
VIHVTKEVKE VATLSCGHNV SVEELAQSRI YWQKEKKMVL TMMSGDMNIW PEYKNRTIFD   60
ITNNLSIVIQ ALRPSDEGTY ECVVLKYEKD GFKRKHLAEV TLSVKADFPT PSISDFEVPS   120
SNIRRVICSA SGGFPEPHLS WLENGEELNA INTTVSQDPE TELYAVSNKL DFNMTTNHSF   180
MCLIKYGHLR VNQTFNWNTT KQEHFPDN                                     208

SEQ ID NO: 519          moltype = AA  length = 208
FEATURE                 Location/Qualifiers
REGION                  1..208
                        note = CD80 v66 ECD
source                  1..208
                        mol_type = protein
                        organism = synthetic construct
SEQUENCE: 519
VIHVTKEVKE VATLSCGHNV SVEELAQTRI YWQKEKKMVL TMMSGDMNIW PEYKNRTIFD   60
ITSNLSIVIQ ALRPSDEGTY ECVVLKYEKD GFKREHLAEV TLSVKADFPT PSITDFEVPS   120
SNIRRIICSA SGGFPEPHLS WLENGEELNA INTTVSQDPE TELYAVSSKL DFNMTTNHSF   180
MCLIKYGDLR VNQTFNWNTT KQEHFPDN                                     208

SEQ ID NO: 520          moltype = AA  length = 208
FEATURE                 Location/Qualifiers
REGION                  1..208
                        note = CD80 v67 ECD
source                  1..208
                        mol_type = protein
                        organism = synthetic construct
SEQUENCE: 520
VIHVTKEVKE VATLSCGHNV SVEELAQTRI YWQKEEKMVL TMMSGDMNIW PEYKNRTIFD   60
ITNNLSTVIQ ALRPSDEGTY ECVVLKYEKD GFKREHLAEV TLSVKADFPT PSISDFEVPS   120
SNIRRIICSA SGGFPEPHLS WLENGEELNA ITTTVSQDPE TELYAVSSKL DFNMTTNHSF   180
MCLIKYGHLR VNQTFNWNTT KQEHFPDN                                     208

SEQ ID NO: 521          moltype = AA  length = 208
FEATURE                 Location/Qualifiers
REGION                  1..208
                        note = CD80 v68 ECD
source                  1..208
                        mol_type = protein
                        organism = synthetic construct
SEQUENCE: 521
VIHVTKEVKE VATLSCGHNV SVEELAQTRI YWQKEKKMVL TMMSGDMNIW PGYKNRTIFD   60
ITNNLSIVIQ ALRPSDEGTY ECVVLKYEKD GFKREHLAEV TLSVKANFPT PSISDFEVPS   120
SNIRRIICSA SGGFPEPHLS WLENGEELNA INTTVSQDPE TELYAVSSEL DFNMTTNHSF   180
MCLIKYGHLR VNQTFNWNTT KQEHFPDN                                     208

SEQ ID NO: 522          moltype = AA  length = 208
FEATURE                 Location/Qualifiers
REGION                  1..208
                        note = CD80 v69 ECD
source                  1..208
                        mol_type = protein
                        organism = synthetic construct
SEQUENCE: 522
VIHVTKEVKE VATLSCGHNV SVEELAQTRI YWQKEKEMVL TMMSGDMNIW PEYKNRTISD   60
ITNNLSIVIQ ALRPSDEGTY ECVVLKYEKD GFKREHLAEV TLSVKADFPT PSISDFEVPS   120
SNIRRIICSA SGGFPEPHLS WLENGEELNA INTTVSQDPE TELYAVSSKL DFNMTTNHSF   180
MCLIEYGHLR VNQTFNWNTT KQEHFPDN                                     208

SEQ ID NO: 523          moltype = AA  length = 208
FEATURE                 Location/Qualifiers
```

-continued

```
REGION                  1..208
                        note = CD80 v70 ECD
source                  1..208
                        mol_type = protein
                        organism = synthetic construct
SEQUENCE: 523
VIHVTKEVKE VATLSCGHNV SVEELAQTRI YWQKEKKMVL TMMSGDMNIW PEYKNRTIFV    60
ITNNLSIVIL ALRPSDEGTY ECVVLKYEKD GFKREHLAEV TLSVKADFPT PSISDFEVPS   120
SNIRRIICSA SGGFPEPHLS WLENGEELNA INTTVSQDPE TELYAVSSEL DFNMTTNHSF   180
MCLIKYGHLR VNQTFNWNTT KQEHFPDN                                      208

SEQ ID NO: 524          moltype = AA  length = 208
FEATURE                 Location/Qualifiers
REGION                  1..208
                        note = CD80 v71 ECD
source                  1..208
                        mol_type = protein
                        organism = synthetic construct
SEQUENCE: 524
VIHVTKEVKE VATLSCGHNV SVEELAQTRI YWQKEKKMVL TMMSGDMNIW PEYMNRTIFD    60
ITNNLSIVIQ ALRPSDEGTY ECVVLKYEKD GFKREHLAEV TLSVKADFPT PSISDFEIPT   120
SNIRRIICST SGGFPEPHLS WLENGEELNA INTTVSQDPE TELHAVSSKL DFNMTTNHSF   180
MCLIKYGDLR VNQTFNWNTT KQEHFPDN                                      208

SEQ ID NO: 525          moltype = AA  length = 208
FEATURE                 Location/Qualifiers
REGION                  1..208
                        note = CD80 v72 ECD
source                  1..208
                        mol_type = protein
                        organism = synthetic construct
SEQUENCE: 525
VIHVTKEVKE VATLSCGHNV SVEELAQTRI YWQKEKKTVL TMMSGDMNIW PEYKNRTIFD    60
ITNNLSIVIQ ALRPSDGGTY ECVVLKYEKD GFKREHLAEV TLSVKADFPT PSISDFEVPS   120
SNIRRIICSA SGGFPEPHLS WLENGEELNA INTTVSQDPE TELYAVSSKL DFNMTTNHSF   180
MCLIKYGHLR VNQTFNWNTT KQEHFPDN                                      208

SEQ ID NO: 526          moltype = AA  length = 208
FEATURE                 Location/Qualifiers
REGION                  1..208
                        note = CD80 v73 ECD
source                  1..208
                        mol_type = protein
                        organism = synthetic construct
SEQUENCE: 526
VIHVTKEVKE VATLSCGHNV SVEELAQTRI HWQKEKKMVL GMLSGDMNIW PEYKNRTIFD    60
ITNNLSIVIQ ALRPSDEGTY ECVVLKYEKD GFKREHLAEV TLSVKADFPT PSISDFEVPS   120
SNIRRVICSA SGGFPEPHLS WLENGEELNA INTTVSQDPE TELYAVSSKL DFNMTTNHSF   180
MCLIKYGHLR VNQTFNWNTT KQEHFPDN                                      208

SEQ ID NO: 527          moltype = AA  length = 208
FEATURE                 Location/Qualifiers
REGION                  1..208
                        note = CD80 v74 ECD
source                  1..208
                        mol_type = protein
                        organism = synthetic construct
SEQUENCE: 527
VIHVTKEVKE VATLSCGHNV SVEELAQTRI YWQKEKKMVL TMMSGDMNIW PEYKNRTIFD    60
ITNNHSIVIL ALRPSDEGTY ECVVLKYEKG AFKREHLAEV TLSVKADFPA PSISDLEIPT   120
SNIRRIICST SGGFPEPHLS WLENGEELNA INTTVSQDPE TELYAVSSKL DFNMTTNHSF   180
MCLIKYGHLR VNQTFNWNTT KQEHFPDN                                      208

SEQ ID NO: 528          moltype = AA  length = 208
FEATURE                 Location/Qualifiers
REGION                  1..208
                        note = CD80 v75 ECD
source                  1..208
                        mol_type = protein
                        organism = synthetic construct
SEQUENCE: 528
VIHVTKEVKE VATLSCGHNV SVEELAQTHI YWQKEKKMVL TMMSGDMNIW PGYKNRTIFD    60
ITNNLSIVIL ALRPSDEGTY ECVVLKYEKN AFKREHLAEV TLSVKADFPT PSISDFEVPS   120
SNIRRIICSA SGGFPEPHLS WLENGEELNA INTTVSQDPE TELYAVSSKL DFNMTTNHSF   180
MCLIKYGHLR VNQTFNWNTT KQEHFPDN                                      208

SEQ ID NO: 529          moltype = AA  length = 208
FEATURE                 Location/Qualifiers
REGION                  1..208
```

```
                              note = CD80 v76 ECD
source                        1..208
                              mol_type = protein
                              organism = synthetic construct
SEQUENCE: 529
VIHVTKEVKE VATLSCGHNV SVEELAQTHI YWQKEKKMVL TMMSGDMNIW PGYKNRTIFD    60
ITNNLSIVIL ALRPSDEGTY ECVVLKYEKN AFKREHLAEV TLSVKADFPT PSISDFEVPS   120
SNIRRIICSA SGGFPEPHLS WLENGEELNA INTTVSQDPE TELYAVSSKL DFNMTTNHSF   180
MCLIKYGHLR VNQTFNWNTT KQEHFPDN                                      208

SEQ ID NO: 530                moltype = AA  length = 208
FEATURE                       Location/Qualifiers
REGION                        1..208
                              note = CD80 v77 ECD
source                        1..208
                              mol_type = protein
                              organism = synthetic construct
SEQUENCE: 530
VIHVTKEVKE VATLSCGHNV SVEELAQTRI YWQKEKKMVL TMMSGDMNIW PEYKNRTIFD    60
ITNNLSTVIQ ALRPSDEGTY ECVVLKYEKD GFKREHLAEV TLSVKADFPT PSISDFEVPS   120
SNIRRIICST SGGFPEPHLS WLENGEELNA INTTVSQDPE TELYAVSSKL DFNMTTNHSF   180
MCLIKYGHLR VNQTFHWNTT KQEHFPDN                                      208

SEQ ID NO: 531                moltype = AA  length = 208
FEATURE                       Location/Qualifiers
REGION                        1..208
                              note = CD80 v78 ECD
source                        1..208
                              mol_type = protein
                              organism = synthetic construct
SEQUENCE: 531
VIHVTKEVKE VATLSCGHNV SVEELAQTRI YWQKEKKMVL TMMSGDMNIW PEYKNRTIFD    60
ITNNLSIVIQ ALRPSDEGTY ECVVLKYEKD GFKREHLAEV TLSVKADFPA PSISDFEVPS   120
SNIRRIICSA SGGFPEPHLS WLENGEELNA INTTVSQDPE TELYAVSSKL DFNMTTNHSF   180
MCLIKYGHLR VNQTFNWNTT KQEHFPDN                                      208

SEQ ID NO: 532                moltype = AA  length = 208
FEATURE                       Location/Qualifiers
REGION                        1..208
                              note = CD80 v79 ECD
source                        1..208
                              mol_type = protein
                              organism = synthetic construct
SEQUENCE: 532
VIHVTKEVKE VATLSCGHNV SVEELAQTRI YWQKEKKVVL DMISGDMNIG PEYKNRTIFD    60
ITNNLSIVIL ALRPSGEGTY ECAVLKYEED AFKREHLAEV TLSVKADFPT PSISDFEVPS   120
SNIRRVICSA SGGFPEPHLS WLENGEELNA INTTVSQDPE TELYAVSSKL DFNMTTNHSF   180
MCLIKYGHLR VNQTFNWNTT KQEHFPDN                                      208

SEQ ID NO: 533                moltype = AA  length = 208
FEATURE                       Location/Qualifiers
REGION                        1..208
                              note = CD80 v80 ECD
source                        1..208
                              mol_type = protein
                              organism = synthetic construct
SEQUENCE: 533
VIHVTKEVKE VVTLFCGHNV SVEELAQTRI HWQKEKKLVL GMLSGDMNIW PEYKNRTIFD    60
ITNNLSIVIL ALRPSDEGTY ECVVLKYEKN AFKREHLAEV TLSVKADFPT PSISDFEIPT   120
SNIRRIICSA SGGFPELHLS WLENGEELDA ITTTVSQDPE TELYAVSSKL DFNMTTNHSF   180
MCLIKYGHLR VNQTFNWNTT KQEHFPDN                                      208

SEQ ID NO: 534                moltype = AA  length = 208
FEATURE                       Location/Qualifiers
REGION                        1..208
                              note = CD80 v81 ECD
source                        1..208
                              mol_type = protein
                              organism = synthetic construct
SEQUENCE: 534
VIHVTKEVKE VATLSCGHNV SVEELAQTRI YWQKEKKMVL TMMSGDMNIW PEYKNRTIFD    60
ITNNLSFVIR ALRPSDEGTY ECVVLKYGKD GFKREHLAEV TLSVKADFPT PSISDFEVPS   120
SNIRRIICSA SGGFPEPHLS WLENGEELNA INTTVSQDPE TELYAVSSKL DFNMTTNHSF   180
MCLIKYGHLR VNQTFNWNTT KQEHFPDN                                      208

SEQ ID NO: 535                moltype = AA  length = 208
FEATURE                       Location/Qualifiers
REGION                        1..208
                              note = CD80 v82 ECD
```

-continued

```
source                    1..208
                          mol_type = protein
                          organism = synthetic construct
SEQUENCE: 535
VIHVTKEVKE VATLSCGHNV SVEGPAQTRI YWQKEKKMVL TMMSGDMNIW PEYKNRTIFD    60
ITNNLSIVIQ ALRPSDEGTY ECVVLKYEKD GFKREHLAEV TLSVKADFPT PSISDFEVPS   120
SNIRRIICST SGGFPEPHLS WLENGEELNA ITTTVSQDPE TELYAVSSKL DFNMTTNHSF   180
MCLIKYGHLR VNQTFNWNTT KQEHFPDN                                      208

SEQ ID NO: 536           moltype = AA  length = 208
FEATURE                  Location/Qualifiers
REGION                   1..208
                         note = CD80 v83 ECD
source                   1..208
                         mol_type = protein
                         organism = synthetic construct
SEQUENCE: 536
VIHVTKEVKE VATLSCGHNV SVEELAQTRI YWQKEKKMVL TMMSGDMNIW PEYKNRTIFD    60
ITNNLSIVIL ALRPSDEGTY ECVVLKYEKD GLKREHLAEV TLSVKADLPT PSISDFEVPS   120
SNIRRIICST SGGFPEPHLS WLENGEELNA INTTVSQDPE TELYAVSSKL DFNMTTNHSF   180
MCLIKYGHLR VNQTFNWNTT KQEHFPDN                                      208

SEQ ID NO: 537           moltype = AA  length = 208
FEATURE                  Location/Qualifiers
REGION                   1..208
                         note = CD80 v84 ECD
source                   1..208
                         mol_type = protein
                         organism = synthetic construct
SEQUENCE: 537
VIHVTKEVKE VATLSCGHNV SVEELAQTRI YWQKEKKMVL TMMSGDMNIW PEYKNRTIFD    60
ITNNLSIVIL ALRPSDEGTY ECVVLKYDRK GYRREHLAEV TLSVKADFPT PSISDFEIPT   120
SSIRRIICST SGGFPEPHLS WLENGEELNA INTTVSQDPE TELYAVSSKL DFNMTTSHSF   180
MCLIKYGHLR VNQTFNWNTT KQEHFPDN                                      208

SEQ ID NO: 538           moltype = AA  length = 208
FEATURE                  Location/Qualifiers
REGION                   1..208
                         note = CD80 v85 ECD
source                   1..208
                         mol_type = protein
                         organism = synthetic construct
SEQUENCE: 538
VIHVTKEVKE VATLSCGHNV SVEELAQTRI YWQKEKKMVL TMMSGDMNIW PEYKNRTIFD    60
ITNNLSIVIL ALRPSDEGTY ECVVLKYDRK GYRREHLAEV TLSVKADFPT PSISDFEIPT   120
SNIRRIICST SGGFPEPHLS WLENGEELNA INTTVSQDPE TELYAVSSKL DFNMTTNHSF   180
MCLIKYGHLR VNQTFNWNTT KQEHFPDN                                      208

SEQ ID NO: 539           moltype = AA  length = 208
FEATURE                  Location/Qualifiers
REGION                   1..208
                         note = CD80 v86 ECD
source                   1..208
                         mol_type = protein
                         organism = synthetic construct
SEQUENCE: 539
VIHVTKEVKE VATLSCGHNV SVEELAQTRI YWQKEGQIVM TMMSGDMNIW PEYKNRTILD    60
ITNNLSIVIL ALRPSDEGTY VCVVRKYEND TPVLEHLAGV TLSVKADFPT PSISDFEIPT   120
SNIRRIICSA SGGFPEPHLS WLENGEELSA INTTVSQDPE TELYAVSSKL DFNMTTNHSF   180
MCLIKYGHLR VNQTFNWNTT KQEHFPDN                                      208

SEQ ID NO: 540           moltype = AA  length = 208
FEATURE                  Location/Qualifiers
REGION                   1..208
                         note = CD80 v87 ECD
source                   1..208
                         mol_type = protein
                         organism = synthetic construct
SEQUENCE: 540
VIHVTKEVKE VATLSCGHNV SVEELAQTRI YWQKEGKMVM TMMSGDMNIW PEYKNRTIFD    60
ITNNLSIVIL ALRPSDEGTY ECVVLKYEKD AFKREHLAEV TLSVKADFPT PSISDFEIPT   120
SNIRRIICST SGGFPEPHLS WLENGEELNA INTTVSQDPE TELYAVSSKL DFNMTTNHSF   180
MCLIKYGHLR VNQTFNWNTT KQEHFPDN                                      208

SEQ ID NO: 541           moltype = AA  length = 101
FEATURE                  Location/Qualifiers
REGION                   1..101
                         note = CD80 v85 IgV
source                   1..101
```

```
                                mol_type = protein
                                organism = synthetic construct
SEQUENCE: 541
VIHVTKEVKE VATLSCGHNV SVEELAQTRI YWQKEKKMVL TMMSGDMNIW PEYKNRTIFD    60
ITNNLSIVIL ALRPSDEGTY ECVVLKYDRK GYRREHLAEV T                        101

SEQ ID NO: 542              moltype = AA  length = 101
FEATURE                     Location/Qualifiers
REGION                      1..101
                            note = CD80 v87 IgV
VARIANT                     94
                            note = X is R or Q
source                      1..101
                            mol_type = protein
                            organism = synthetic construct
SEQUENCE: 542
VIHVTKEVKE VATLSCGHNV SVEELAQTRI YWQKEGKMVM TMMSGDMNIW PEYKNRTIFD    60
ITNNLSIVIL ALRPSDEGTY ECVVLKYEKD AFKREHLAEV T                        101

SEQ ID NO: 543              moltype = AA  length = 107
FEATURE                     Location/Qualifiers
REGION                      1..107
                            note = CD80 v85 IgV
source                      1..107
                            mol_type = protein
                            organism = synthetic construct
SEQUENCE: 543
VIHVTKEVKE VATLSCGHNV SVEELAQTRI YWQKEKKMVL TMMSGDMNIW PEYKNRTIFD    60
ITNNLSIVIL ALRPSDEGTY ECVVLKYDRK GYRREHLAEV TLSVKAD                  107

SEQ ID NO: 544              moltype = AA  length = 107
FEATURE                     Location/Qualifiers
REGION                      1..107
                            note = CD80 v87 IgV
source                      1..107
                            mol_type = protein
                            organism = synthetic construct
SEQUENCE: 544
VIHVTKEVKE VATLSCGHNV SVEELAQTRI YWQKEGKMVM TMMSGDMNIW PEYKNRTIFD    60
ITNNLSIVIL ALRPSDEGTY ECVVLKYEKD AFKREHLAEV TLSVKAD                  107

SEQ ID NO: 545              moltype = AA  length = 122
FEATURE                     Location/Qualifiers
source                      1..122
                            mol_type = protein
                            organism = Homo sapiens
SEQUENCE: 545
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSQ SLGFQEVLSV EVTLHVAANF   120
SV                                                                  122

SEQ ID NO: 546              moltype = AA  length = 122
FEATURE                     Location/Qualifiers
REGION                      1..122
                            note = ICOSL v1 IgV
source                      1..122
                            mol_type = protein
                            organism = synthetic construct
SEQUENCE: 546
DTQEKEVRAM VGSDVELSCA CPEGSRFDLN DVYVYWQTSE SKTVVTYHIP QSSSLENVDS    60
RYRNRALMSP AGMLRGDFSL RLFNVTPQDE QKFHCLVLSQ SLGFQEVLSV EVTLHVAANF   120
SV                                                                  122

SEQ ID NO: 547              moltype = AA  length = 122
FEATURE                     Location/Qualifiers
REGION                      1..122
                            note = ICOSL v2 IgV
source                      1..122
                            mol_type = protein
                            organism = synthetic construct
SEQUENCE: 547
DTQEKEVRAM VGSDVELSCA CPEGSRFDLN DVYVYWQTSE SKTVVTYHIP QHSSLENVDS    60
RYRNRALMSP AGMLRGDFSL RLFNVTPQDE QKFHCLVLSQ SLGFQEVLSV EVTLHVAANF   120
SV                                                                  122

SEQ ID NO: 548              moltype = AA  length = 122
FEATURE                     Location/Qualifiers
REGION                      1..122
                            note = ICOSL v3 IgV
```

-continued

```
source                  1..122
                        mol_type = protein
                        organism = synthetic construct
SEQUENCE: 548
DTQEKEVRAM VGSDVELSCA CPEGSRFDLN DVYVYWQTSE SKTVVTYHIP QDSSLENVDS   60
RYRNRALMSP AGMLRGDFSL RLFNVTPQDE QKFHCLVLSQ SLGFQEVLSV EVTLHVAANF  120
SV                                                                122

SEQ ID NO: 549         moltype = AA  length = 122
FEATURE                Location/Qualifiers
REGION                 1..122
                       note = ICOSL v5 IgV
source                 1..122
                       mol_type = protein
                       organism = synthetic construct SEQUENCE: 549
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSP SLGFQEVLSV EVTLHVAANF  120
SV                                                                122

SEQ ID NO: 550         moltype = AA  length = 122
FEATURE                Location/Qualifiers
REGION                 1..122
                       note = ICOSL v10 IgV
source                 1..122
                       mol_type = protein
                       organism = synthetic construct
SEQUENCE: 550
DTQEKEVRAM VGSDVELSCA CPEGSRFDLN DVYVYWQTSE SKTVVTYHIP QHSSLENVDS   60
RYRNRALMSP AGMLRGDFSL RLFNVTPQDE QRFHCLVLSQ SLGFQEVLSV EVTLHVAANF  120
SV                                                                122

SEQ ID NO: 551         moltype = AA  length = 122
FEATURE                Location/Qualifiers
REGION                 1..122
                       note = ICOSL v11 IgV
source                 1..122
                       mol_type = protein
                       organism = synthetic construct
SEQUENCE: 551
DTQEKEVRAM VGSDVELSCA CPEGSRFDLN DVYVYWQTSE SKTVVTYHIP QHSSLENVDS   60
RYRNRALMSP AGMLRGDFSL RLFNVTPQDE QKFHCLVLGQ SLGFQEVLSV EVTLHVAANF  120
SV                                                                122

SEQ ID NO: 552         moltype = AA  length = 122
FEATURE                Location/Qualifiers
REGION                 1..122
                       note = ICOSL v12 IgV
source                 1..122
                       mol_type = protein
                       organism = synthetic construct
SEQUENCE: 552
DTQEKEVRAM VGSDVELSCA CPEGSRFDLN DVYVYWQTSE SKTVVTYHIP QYSSLENVDS   60
RYRNRALMSP AGMLRGDFSL RLFNVTPQDE QKFHCLVLSQ SLGFQEVLSV EVTLHVAANF  120
SV                                                                122

SEQ ID NO: 553         moltype = AA  length = 122
FEATURE                Location/Qualifiers
REGION                 1..122
                       note = ICOSL v13 IgV
source                 1..122
                       mol_type = protein
                       organism = synthetic construct
SEQUENCE: 553
DTQEKEVRAM VGSDVELSCA CPEGSRFDLN DVYVYWQTSE SKTVVTYHIP QNSSLEYVDS   60
RYRNRALMSP AGMLRGDFSL RLFNVTPQDE QKFHCLVLSQ SLGFQEVLSV EVTLHVAANF  120
SV                                                                122

SEQ ID NO: 554         moltype = AA  length = 122
FEATURE                Location/Qualifiers
REGION                 1..122
                       note = ICOSL v14 IgV
source                 1..122
                       mol_type = protein
                       organism = synthetic construct
SEQUENCE: 554
DTQEKEVRAM VGSDVELSCA CPEGSRFDLN DVYVYWQTSE SKTVVTYHIP QNSSLEYVDS   60
RYRNRALMSP AGMLRGDFSL RLFNVTPQDE QKFHCLVLSP SLGFQEVLSV EVTLHVAANF  120
SV                                                                122
```

-continued

```
SEQ ID NO: 555              moltype = AA   length = 122
FEATURE                     Location/Qualifiers
REGION                      1..122
                            note = ICOSL v21 IgV
source                      1..122
                            mol_type = protein
                            organism = synthetic construct
SEQUENCE: 555
DTQEKEVRAM VGSDVELSCA CPEGSRFDLN DVYVYWQTSE SKTVVTYHIP QSSSLENVDS  60
RYRNRALMSP AGMLRGDFSL RLFNVTPQDE QKFHCLVLSQ SLGFQEVLSV EVELHVAANF  120
SV                                                                 122

SEQ ID NO: 556              moltype = AA   length = 122
FEATURE                     Location/Qualifiers
REGION                      1..122
                            note = ICOSL v22 IgV
source                      1..122
                            mol_type = protein
                            organism = synthetic construct
SEQUENCE: 556
DTQEKEVRAM VGSDVELSCA CPEGSRFDLN DVYVYWQTSE SKTVVTYHIP QNSALENVDS  60
RYRNRALMSP AGMLRGDFSL RLFNVTPQDE QKFHCLVLSQ SLGFQEVLSV EVTLHVAANF  120
SV                                                                 122

SEQ ID NO: 557              moltype = AA   length = 122
FEATURE                     Location/Qualifiers
REGION                      1..122
                            note = ICOSL v23 IgV
source                      1..122
                            mol_type = protein
                            organism = synthetic construct
SEQUENCE: 557
DTQEKEVRAM VGSDVELSCA CPEGSRFDLN DVYVYWQTSE SKTVVTYHIP QDSPLENVDS  60
RYRNRALMSP AGMLRGDFSL RLFNVTPQDE QKFHCLVLSQ SLGFQEVLSV EVTLHVAANF  120
SV                                                                 122

SEQ ID NO: 558              moltype = AA   length = 122
FEATURE                     Location/Qualifiers
REGION                      1..122
                            note = ICOSL v28 IgV
source                      1..122
                            mol_type = protein
                            organism = synthetic construct
SEQUENCE: 558
DTQEKEVRAM VGSDVELSCA CPEGSRFDLN DVYVYWQTSE SKTVVTYHIP QSSSLENVDS  60
RYRNRALMSP AGMLRGDFSP RLFNVTPQDE QKFHCLVLSQ SLGFQEVLSV EVTLHVAANF  120
SV                                                                 122

SEQ ID NO: 559              moltype = AA   length = 122
FEATURE                     Location/Qualifiers
REGION                      1..122
                            note = ICOSL v33 IgV
source                      1..122
                            mol_type = protein
                            organism = synthetic construct
SEQUENCE: 559
DTQEKEVRAM VGSDVELSCA CPEGSRFDLN DVYVYWQTSE SKTVVTYHIP QSSSLEYVDS  60
RYRNRALMSP AGMLRGDFSL RLFNVTPQDE QKFDCFVFSR SLGFQEVLSV EVTLHVAANF  120
SV                                                                 122

SEQ ID NO: 560              moltype = AA   length = 122
FEATURE                     Location/Qualifiers
REGION                      1..122
                            note = ICOSL v34 IgV
source                      1..122
                            mol_type = protein
                            organism = synthetic construct
SEQUENCE: 560
DTQEKEVRAM VGSDVELSCA CPEGSRFDLN DVYVYWQTSE SKTVVTYHIP QSSSLEYVDS  60
RYRNRALMSP AGMLRGDFSL RLFNVTPQDE QKFDCFVFSR SLEFQEVLSV EVTLHVAANS  120
SV                                                                 122

SEQ ID NO: 561              moltype = AA   length = 122
FEATURE                     Location/Qualifiers
REGION                      1..122
                            note = ICOSL v35 IgV
source                      1..122
                            mol_type = protein
```

```
                           organism = synthetic construct
SEQUENCE: 561
DTQEKEVRAM VGSDVELSCA CPEGSRFDLN DVYVYWQTSE SKTVVTYHIP QSSSLENVDS    60
RYRNRALMSP AGMLRGDFSL RLFNVTPQDE QKFHCLVLSQ SLEFQEVLSV EVTLHVAANF   120
SV                                                                 122

SEQ ID NO: 562             moltype = AA  length = 122
FEATURE                    Location/Qualifiers
REGION                     1..122
                           note = ICOSL v36 IgV
source                     1..122
                           mol_type = protein
                           organism = synthetic construct
SEQUENCE: 562
DTQEKEVRAM VGSDVELSCA CPEGSRFDLN DVYVYWQTSE SKTVVTYHIP QHSSLENVDS    60
RYRNRALMSP AGMLRGDLSL RLFNVTPQDE QKFHCLVLSR SLGFQEVLSV EVTLHVAANF   120
SV                                                                 122

SEQ ID NO: 563             moltype = AA  length = 122
FEATURE                    Location/Qualifiers
REGION                     1..122
                           note = ICOSL v37 IgV
source                     1..122
                           mol_type = protein
                           organism = synthetic construct
SEQUENCE: 563
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD EVTLHVAANF   120
SV                                                                 122

SEQ ID NO: 564             moltype = AA  length = 122
FEATURE                    Location/Qualifiers
REGION                     1..122
                           note = ICOSL v38 IgV
source                     1..122
                           mol_type = protein
                           organism = synthetic construct
SEQUENCE: 564
DTQEKEVRAM VGSDVELSCA CPEGSRFDLN DVYVYWQTSE SKTVVTYHIP QHSSLEYVDS    60
RYRNRALMSP AGMLQGDFSL RLFNVTPQDE QKFHCLVLSR SLGFQEVLSD EVTLHVAANF   120
SV                                                                 122

SEQ ID NO: 565             moltype = AA  length = 122
FEATURE                    Location/Qualifiers
REGION                     1..122
                           note = ICOSL v39 IgV
source                     1..122
                           mol_type = protein
                           organism = synthetic construct
SEQUENCE: 565
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSV EVTLHVAANF   120
SV                                                                 122

SEQ ID NO: 566             moltype = AA  length = 122
FEATURE                    Location/Qualifiers
REGION                     1..122
                           note = ICOSL v40 IgV
source                     1..122
                           mol_type = protein
                           organism = synthetic construct
SEQUENCE: 566
DTQEKEVRAM VGSDVELSCA CPEGSRFDLN DVYVYWQTSE SKTVVTYHIP QHSSLEYVDS    60
RYRNRALMSP AGMQRGDFSL RLFNVTPQDE QKFHCLVLSR SLGFQEVLSD EVTLHVAANF   120
SV                                                                 122

SEQ ID NO: 567             moltype = AA  length = 122
FEATURE                    Location/Qualifiers
REGION                     1..122
                           note = ICOSL v41 IgV
source                     1..122
                           mol_type = protein
                           organism = synthetic construct
SEQUENCE: 567
DTQEKEVRAM VGSDVELSCA CPEGSRFDLN DVYVYWQTSE SKTVVTYHIP QHSSLENVDS    60
RYRNRALMSP AGMLRGDFSL RLFNVTPQDE QKFHCLVLSR SLGFQEVLSV EVTLHVAANF   120
SV                                                                 122

SEQ ID NO: 568             moltype = AA  length = 122
```

-continued

```
FEATURE            Location/Qualifiers
REGION             1..122
                   note = ICOSL v42 IgV
source             1..122
                   mol_type = protein
                   organism = synthetic construct
SEQUENCE: 568
DTQEKEVRAM VGSDVELSCA CPEGSRFDLN DVYVYWQTSE SKTVVTYHIP QHSSLENVDS   60
RYRNRALMSP AGMLRGDFSL RLFNVTPQDE QKFHCLVLSQ SLGFQEVLSV EVTLHVAANF  120
GV                                                                 122

SEQ ID NO: 569         moltype = AA  length = 122
FEATURE            Location/Qualifiers
REGION             1..122
                   note = ICOSL v43 IgV
source             1..122
                   mol_type = protein
                   organism = synthetic construct
SEQUENCE: 569
DTQEKEVRAM VGSDVELSCV CPEGSRFDLN DVYVYWQTSE SKTVVTYHIP QHSSLEYVDS   60
RYRNRALMSP AGMLRGDFSL RLFNVTPQDE QKFHCLVLSR SLGFQEVLGV EVTLHVAANF  120
SV                                                                 122

SEQ ID NO: 570         moltype = AA  length = 122
FEATURE            Location/Qualifiers
REGION             1..122
                   note = ICOSL v44 IgV
source             1..122
                   mol_type = protein
                   organism = synthetic construct
SEQUENCE: 570
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSP SLGFQEVLSV EVTLHVAANF  120
SV                                                                 122

SEQ ID NO: 571         moltype = AA  length = 122
FEATURE            Location/Qualifiers
REGION             1..122
                   note = ICOSL v46 IgV
source             1..122
                   mol_type = protein
                   organism = synthetic construct
SEQUENCE: 571
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSR SLGFQEVLSV EVTLHVAANF  120
SA                                                                 122

SEQ ID NO: 572         moltype = AA  length = 122
FEATURE            Location/Qualifiers
REGION             1..122
                   note = ICOSL v48 IgV
source             1..122
                   mol_type = protein
                   organism = synthetic construct
SEQUENCE: 572
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSQ SLGFQEVLSV EVTLHVAANF  120
SV                                                                 122

SEQ ID NO: 573         moltype = AA  length = 122
FEATURE            Location/Qualifiers
REGION             1..122
                   note = ICOSL v49 IgV
source             1..122
                   mol_type = protein
                   organism = synthetic construct
SEQUENCE: 573
DTQEKEVRAM VGSDVELSCA CPEGSRFDLN DVYVYWQTSE SKTVVTYHIP QSSSLENVDS   60
RYRNRALMSP AGMLRGDFSL RLFNVTPQDE QKFHCLVLSQ SLGFQEVLSV EVTLHVAANS  120
SV                                                                 122

SEQ ID NO: 574         moltype = AA  length = 122
FEATURE            Location/Qualifiers
REGION             1..122
                   note = ICOSL v50 IgV
source             1..122
                   mol_type = protein
                   organism = synthetic construct
SEQUENCE: 574
```

-continued

```
DTQEKEVRAM VGSDVELSCA CPEGSRFDLN DVYVYWQTSE SKTVVTYHIP QSSSLENVDS   60
RYRNRALMSP AGMLRGDFSL RLFNVTPQDE QKFHCLALSQ SLGFQEVLSV EVTLHVAANF  120
SV                                                                122

SEQ ID NO: 575          moltype = AA  length = 122
FEATURE                 Location/Qualifiers
REGION                  1..122
                        note = ICOSL v51 IgV
source                  1..122
                        mol_type = protein
                        organism = synthetic construct
SEQUENCE: 575
DTQEKEVRAM VGSDVELSCA CPEGSRFDLN DVYVYWQTSE SKTVVTYHIP QSSSLENVDS   60
RYRNRALMSP ARMLRGDFSL RLFNVTPQDE QKFHCLVLSQ SLGFQEVLSV EVTLHVAANF  120
SV                                                                122

SEQ ID NO: 576          moltype = AA  length = 122
FEATURE                 Location/Qualifiers
REGION                  1..122
                        note = ICOSL v52 IgV
source                  1..122
                        mol_type = protein
                        organism = synthetic construct
SEQUENCE: 576
DTQEKEVRAM VGSDVELSCA CPEGSRFDLN DVYVYWQTSE SKTVVTYHIP QSSSLENVDS   60
RYRNRALMSP TGMLRGDFSL RLFNVTPQDE QKFHCLVLSQ SLGFQEVLSV EVTLHVTANF  120
SV                                                                122

SEQ ID NO: 577          moltype = AA  length = 122
FEATURE                 Location/Qualifiers
REGION                  1..122
                        note = ICOSL v54 IgV
source                  1..122
                        mol_type = protein
                        organism = synthetic construct
SEQUENCE: 577
DTQEKEVRAM VGSDVELSCA CPEGSRFDLN DVYVYWQTSE SKTVVTHHIP QSSSLENVDS   60
RYRNRALMSP AGMLRGDFSL RLFNVTPQDE QKFHCLVLSQ SLGFQEALSV EVTLHVAANS  120
SV                                                                122

SEQ ID NO: 578          moltype = AA  length = 122
FEATURE                 Location/Qualifiers
REGION                  1..122
                        note = ICOSL v60 IgV
source                  1..122
                        mol_type = protein
                        organism = synthetic construct
SEQUENCE: 578
DTQEKEVRAM VGSDVELSCA CPEGSRSDLN DVYVYWQTSE SKTVVTYHIP QHSSLEYVDS   60
RYRNRALMSP AGMLRGDFSL RLFNVTPQDE QKFHCLVLSQ SLGFQEVLSN EVTLHVAANF  120
SV                                                                122

SEQ ID NO: 579          moltype = AA  length = 122
FEATURE                 Location/Qualifiers
REGION                  1..122
                        note = ICOSL v65 IgV
source                  1..122
                        mol_type = protein
                        organism = synthetic construct
SEQUENCE: 579
DTQEKEVRAM VGSDVELSCA CPEGSRFDLN DVYVYWQTSE SKTVVTYHIP QSSSLENVDS   60
RYRNRALMSP AGMLRGDFSL RLFNVTPQDE QKFECIVLSQ SLGFQEVLSV EVTLHVAANF  120
SM                                                                122

SEQ ID NO: 580          moltype = AA  length = 122
FEATURE                 Location/Qualifiers
REGION                  1..122
                        note = ICOSL v78 IgV
source                  1..122
                        mol_type = protein
                        organism = synthetic construct
SEQUENCE: 580
DTQEKEVRAM VGSDVELSCA CPEGSRFDLN DVYVYWQTSE SKTVVTYHIP QSSSLENVDS   60
RYRNRALMSP AGMLRGDFSL RLFNVTPQDE QKFECLVFSR SLGFQEVLSV EVTLHVAANF  120
SV                                                                122

SEQ ID NO: 581          moltype = AA  length = 122
FEATURE                 Location/Qualifiers
REGION                  1..122
```

```
                          note = ICOSL v79 IgV
source                    1..122
                          mol_type = protein
                          organism = synthetic construct
SEQUENCE: 581
DTQEKEVRAM VGSDVELSCA CPEGSRFDLN DVYVYWQTSE SKTVVTYHIP QSSSLENVDS   60
RYRNRALMSP AGMLRGDFSL RLFNVTPQDA QKFHCLVLSQ SLGFQEVLSV EVTLHVAANF  120
SV                                                                122

SEQ ID NO: 582            moltype = AA  length = 122
FEATURE                   Location/Qualifiers
REGION                    1..122
                          note = ICOSL v80 IgV
source                    1..122
                          mol_type = protein
                          organism = synthetic construct
SEQUENCE: 582
DTQEKEVRAM VGSDVELSCA CPEGSRFDLD DVYVYWQTSE SETVVTYHIP QSSSLENVDS   60
RYRNRALMSP AGMLRGDFSL RLFNVTPQDE QKFHCLVLSQ SLGFQEVLSV EVTLHVAANF  120
SV                                                                122

SEQ ID NO: 583            moltype = AA  length = 122
FEATURE                   Location/Qualifiers
REGION                    1..122
                          note = ICOSL v85 IgV
source                    1..122
                          mol_type = protein
                          organism = synthetic construct
SEQUENCE: 583
DTQEKEVRAM VGSDVELSCA CPEGSRFDLN DVYVYWQTSE SKTVVTYHIP QSSPLENVDS   60
RYRNRALMSP AGMLRGDFSL RLFNVTPQDE QKFHCLVLSQ SLGFQEVLSV EVTLHVAANF  120
SV                                                                122

SEQ ID NO: 584            moltype = AA  length = 122
FEATURE                   Location/Qualifiers
REGION                    1..122
                          note = ICOSL v86 IgV
source                    1..122
                          mol_type = protein
                          organism = synthetic construct
SEQUENCE: 584
DTQEKEVRAM VGSDVELSCA CPEGSRFDLN DVYVYWQPSE SKTVVTYHIP QSSSLEDVDS   60
RYRNRALMSP AGMLRGDFSL RLFNVTPQDE QKFHCLVLSQ SLGFQEVLSV EVTLHVAANF  120
SV                                                                122

SEQ ID NO: 585            moltype = AA  length = 121
FEATURE                   Location/Qualifiers
REGION                    1..121
                          note = ICOSL v87 IgV
source                    1..121
                          mol_type = protein
                          organism = synthetic construct
SEQUENCE: 585
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSQ SLGFQEVLSV VTLHVAANFS  120
V                                                                 121

SEQ ID NO: 586            moltype = AA  length = 121
FEATURE                   Location/Qualifiers
REGION                    1..121
                          note = ICOSL v88 IgV
source                    1..121
                          mol_type = protein
                          organism = synthetic construct
SEQUENCE: 586
DTQEKEVRAM VGSDVELSCA CPEGSRFDLN DVVVYWQTSES KTVVTYHIPQ NSSLENVDSR   60
YRNRALMSPA GMLRGDFSLR LFNVTPQDEQ KFHCLVLSQS LGFQEVLSVE VTLHVAANFS  120
V                                                                 121

SEQ ID NO: 587            moltype = AA  length = 122
FEATURE                   Location/Qualifiers
REGION                    1..122
                          note = ICOSL v91IgV
source                    1..122
                          mol_type = protein
                          organism = synthetic construct
SEQUENCE: 587
DTQEKEVRAM VGSDVELSCA CPEGSRFDLN DVYVYWQTSE SKTVVTYHIP QHSSLEYVDS   60
RYRNRALMSP AGMQRGDFSL RLFNVTPQDE QKFHCLVLSQ SLGFQEVLSD EVTLHVAANF  120
```

-continued

```
SV                                                                     122

SEQ ID NO: 588           moltype = AA   length = 122
FEATURE                  Location/Qualifiers
REGION                   1..122
                         note = ICOSL v99 IgV
source                   1..122
                         mol_type = protein
                         organism = synthetic construct
SEQUENCE: 588
DTQEKEVRAM VGSDVELSCA CPEGSRFDLN DVYVYWQTSE SKTVVTYHIP QNSSLENVDS    60
RYRNRALMSP AGMLRGDFSL RLFQVTPQDE QKFHCLVLSQ SLGFQEVLSV EVTLHVAANF   120
SV                                                                     122

SEQ ID NO: 589           moltype = AA   length = 122
FEATURE                  Location/Qualifiers
REGION                   1..122
                         note = ICOSL v100 IgV
source                   1..122
                         mol_type = protein
                         organism = synthetic construct
SEQUENCE: 589
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSQ SLGFQEVLSV EVTLHVAAQF   120
SV                                                                     122

SEQ ID NO: 590           moltype = AA   length = 122
FEATURE                  Location/Qualifiers
REGION                   1..122
                         note = ICOSL v111 IgV
source                   1..122
                         mol_type = protein
                         organism = synthetic construct
SEQUENCE: 590
DTQEKEVRAM VGSDVELSCA CPEGSRFDLN DVYVYWQTSE SKTVVTYHIP QQSSLENVDS    60
RYRNRALMSP AGMLRGDFSL RLFQVTPQDE QKFHCLVLSQ SLGFQEVLSV EVTLHVAANF   120
SV                                                                     122

SEQ ID NO: 591           moltype = AA   length = 122
FEATURE                  Location/Qualifiers
REGION                   1..122
                         note = ICOSL v112 IgV
source                   1..122
                         mol_type = protein
                         organism = synthetic construct
SEQUENCE: 591
DTQEKEVRAM VGSDVELSCA CPEGSRFDLN DVYVYWQTSE SKTVVTYHIP QQSSLENVDS    60
RYRNRALMSP AGMLRGDFSL RLFNVTPQDE QKFHCLVLSQ SLGFQEVLSV EVTLHVAAQF   120
SV                                                                     122

SEQ ID NO: 592           moltype = AA   length = 122
FEATURE                  Location/Qualifiers
REGION                   1..122
                         note = ICOSL v113 IgV
source                   1..122
                         mol_type = protein
                         organism = synthetic construct
SEQUENCE: 592
DTQEKEVRAM VGSDVELSCA CPEGSRFDLN DVYVYWQTSE SKTVVTYHIP QNSSLENVDS    60
RYRNRALMSP AGMLRGDFSL RLFQVTPQDE QKFHCLVLSQ SLGFQEVLSV EVTLHVAAQF   120
SV                                                                     122

SEQ ID NO: 593           moltype = AA   length = 122
FEATURE                  Location/Qualifiers
REGION                   1..122
                         note = ICOSL v126 IgV
source                   1..122
                         mol_type = protein
                         organism = synthetic construct
SEQUENCE: 593
DTQEKEVRAM VGSDVELSCA CPEGSRFDLN DVYVYWQTSE SKTVVTYHIP QHSSLENVDS    60
RYRNRALMSP AGMLRGDFSL RLFQVTPQDE QKFHCLVLSQ SLGFQEVLSV EVTLHVAAQF   120
SV                                                                     122

SEQ ID NO: 594           moltype = AA   length = 122
FEATURE                  Location/Qualifiers
REGION                   1..122
                         note = ICOSL v137 IgV
source                   1..122
```

-continued

```
                              mol_type = protein
                              organism = synthetic construct
SEQUENCE: 594
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSR SLGFQEVLSV EVTLHVAANF  120
SV                                                                 122

SEQ ID NO: 595          moltype = AA  length = 122
FEATURE                 Location/Qualifiers
REGION                  1..122
                        note = ICOSL v153 IgV
source                  1..122
                        mol_type = protein
                        organism = synthetic construct
SEQUENCE: 595
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSQ SLGFQEVLSV EVTLRVAANF  120
SV                                                                 122

SEQ ID NO: 596          moltype = AA  length = 122
FEATURE                 Location/Qualifiers
REGION                  1..122
                        note = ICOSL v154 IgV
source                  1..122
                        mol_type = protein
                        organism = synthetic construct
SEQUENCE: 596
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSR SLGFQEVLSV EVTLRVAANF  120
SV                                                                 122

SEQ ID NO: 597          moltype = AA  length = 122
FEATURE                 Location/Qualifiers
REGION                  1..122
                        note = ICOSL v163 IgV
source                  1..122
                        mol_type = protein
                        organism = synthetic construct
SEQUENCE: 597
DTQEKEVRAM VGSDVELSCA CPEGSRFDLD DVYVYWQTSE SETVVTYHIP QSSSLENVDS   60
RYRNRALMSP AGMLRGDFSL RLFNVTPQDE QKFHCLVLSQ SLGFQEVLSV EVTLRVAANF  120
SV                                                                 122

SEQ ID NO: 598          moltype = AA  length = 122
FEATURE                 Location/Qualifiers
REGION                  1..122
                        note = ICOSL v164 IgV
source                  1..122
                        mol_type = protein
                        organism = synthetic construct
SEQUENCE: 598
DTQEKEVRAM VGSDVELSCA CPEGSRFDLD DVYVYWQTSE SETVVTYHIP QSSSLENVDS   60
RYRNRALMSP AGMLRGDFSL RLFNVTPQDE QKFHCLVLSQ SLGFQEVLSV EVTLRVAANF  120
SV                                                                 122

SEQ ID NO: 599          moltype = AA  length = 122
FEATURE                 Location/Qualifiers
REGION                  1..122
                        note = ICOSL v173 IgV
source                  1..122
                        mol_type = protein
                        organism = synthetic construct
SEQUENCE: 599
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSP SLGFQEVLSV EVTLRVAANF  120
SV                                                                 122

SEQ ID NO: 600          moltype = AA  length = 208
FEATURE                 Location/Qualifiers
REGION                  1..208
                        note = ICOSL WT ECD Truncation 2
source                  1..208
                        mol_type = protein
                        organism = synthetic construct
SEQUENCE: 600
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNL                                     208
```

-continued

```
SEQ ID NO: 601              moltype = AA  length = 213
FEATURE                     Location/Qualifiers
REGION                      1..213
                            note = ICOSL WT ECD Truncation 3
source                      1..213
                            mol_type = protein
                            organism = synthetic construct
SEQUENCE: 601
DTQEKEVRAM VGSDVELSCA CPEGSRFDLN DVYVYWQTSE SKTVVTYHIP QNSSLENVDS  60
RYRNRALMSP AGMLRGDFSL RLFNVTPQDE QKFHCLVLSQ SLGFQEVLSV EVTLHVAANF 120
SVPVVSAPHS PSQDELTFTC TSINGYPRPN VYWINKTDNS LLDQALQNDT VFLNMRGLYD 180
VVSVLRIART PSVNIGCCIE NVLLQQNLTV GSQ                             213

SEQ ID NO: 602              moltype = AA  length = 207
FEATURE                     Location/Qualifiers
REGION                      1..207
                            note = ICOSL WT ECD Truncation 4
source                      1..207
                            mol_type = protein
                            organism = synthetic construct
SEQUENCE: 602
DTQEKEVRAM VGSDVELSCA CPEGSRFDLN DVYVYWQTSE SKTVVTYHIP QNSSLENVDS  60
RYRNRALMSP AGMLRGDFSL RLFNVTPQDE QKFHCLVLSQ SLGFQEVLSV EVTLHVAANF 120
SVPVVSAPHS PSQDELTFTC TSINGYPRPN VYWINKTDNS LLDQALQNDT VFLNMRGLYD 180
VVSVLRIART PSVNIGCCIE NVLLQQN                                    207

SEQ ID NO: 603              moltype = AA  length = 206
FEATURE                     Location/Qualifiers
REGION                      1..206
                            note = ICOSL WT ECD Truncation 5
source                      1..206
                            mol_type = protein
                            organism = synthetic construct
SEQUENCE: 603
DTQEKEVRAM VGSDVELSCA CPEGSRFDLN DVYVYWQTSE SKTVVTYHIP QNSSLENVDS  60
RYRNRALMSP AGMLRGDFSL RLFNVTPQDE QKFHCLVLSQ SLGFQEVLSV EVTLHVAANF 120
SVPVVSAPHS PSQDELTFTC TSINGYPRPN VYWINKTDNS LLDQALQNDT VFLNMRGLYD 180
VVSVLRIART PSVNIGCCIE NVLLQQ                                     206

SEQ ID NO: 604              moltype = AA  length = 204
FEATURE                     Location/Qualifiers
REGION                      1..204
                            note = ICOSL WT ECD Truncation 6
source                      1..204
                            mol_type = protein
                            organism = synthetic construct
SEQUENCE: 604
DTQEKEVRAM VGSDVELSCA CPEGSRFDLN DVYVYWQTSE SKTVVTYHIP QNSSLENVDS  60
RYRNRALMSP AGMLRGDFSL RLFNVTPQDE QKFHCLVLSQ SLGFQEVLSV EVTLHVAANF 120
SVPVVSAPHS PSQDELTFTC TSINGYPRPN VYWINKTDNS LLDQALQNDT VFLNMRGLYD 180
VVSVLRIART PSVNIGCCIE NVLL                                       204

SEQ ID NO: 605              moltype = AA  length = 201
FEATURE                     Location/Qualifiers
REGION                      1..201
                            note = ICOSL WT ECD Truncation 7
source                      1..201
                            mol_type = protein
                            organism = synthetic construct
SEQUENCE: 605
DTQEKEVRAM VGSDVELSCA CPEGSRFDLN DVYVYWQTSE SKTVVTYHIP QNSSLENVDS  60
RYRNRALMSP AGMLRGDFSL RLFNVTPQDE QKFHCLVLSQ SLGFQEVLSV EVTLHVAANF 120
SVPVVSAPHS PSQDELTFTC TSINGYPRPN VYWINKTDNS LLDQALQNDT VFLNMRGLYD 180
VVSVLRIART PSVNIGCCIE N                                          201

SEQ ID NO: 606              moltype = AA  length = 209
FEATURE                     Location/Qualifiers
REGION                      1..209
                            note = ICOSL WT ECD Truncation 8
source                      1..209
                            mol_type = protein
                            organism = synthetic construct
SEQUENCE: 606
DTQEKEVRAM VGSDVELSCA CPEGSRFDLN DVYVYWQTSE SKTVVTYHIP QNSSLENVDS  60
RYRNRALMSP AGMLRGDFSL RLFNVTPQDE QKFHCLVLSQ SLGFQEVLSV EVTLHVAANF 120
SVPVVSAPHS PSQDELTFTC TSINGYPRPN VYWINKTDNS LLDQALQNDT VFLNMRGLYD 180
VVSVLRIART PSVNIGCCIE NVLLQQNLT                                  209
```

-continued

```
SEQ ID NO: 607          moltype = AA   length = 208
FEATURE                 Location/Qualifiers
REGION                  1..208
                        note = ICOSL N207A ECD Truncation 2
source                  1..208
                        mol_type = protein
                        organism = synthetic construct
SEQUENCE: 607
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQAL                                    208

SEQ ID NO: 608          moltype = AA   length = 208
FEATURE                 Location/Qualifiers
REGION                  1..208
                        note = ICOSL N207G ECD Truncation 2
source                  1..208
                        mol_type = protein
                        organism = synthetic construct
SEQUENCE: 608
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQGL                                    208

SEQ ID NO: 609          moltype = AA   length = 208
FEATURE                 Location/Qualifiers
REGION                  1..208
                        note = ICOSL L208G ECD Truncation 2
source                  1..208
                        mol_type = protein
                        organism = synthetic construct
SEQUENCE: 609
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNG                                    208

SEQ ID NO: 610          moltype = AA   length = 213
FEATURE                 Location/Qualifiers
REGION                  1..213
                        note = ICOSL N207A ECD Truncation 3
source                  1..213
                        mol_type = protein
                        organism = synthetic construct
SEQUENCE: 610
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQALTV GSQ                              213

SEQ ID NO: 611          moltype = AA   length = 213
FEATURE                 Location/Qualifiers
REGION                  1..213
                        note = ICOSL N207G ECD Truncation 3
source                  1..213
                        mol_type = protein
                        organism = synthetic construct
SEQUENCE: 611
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQGLTV GSQ                              213

SEQ ID NO: 612          moltype = AA   length = 213
FEATURE                 Location/Qualifiers
REGION                  1..213
                        note = ICOSL L208G ECD Truncation 3
source                  1..213
                        mol_type = protein
                        organism = synthetic construct
SEQUENCE: 612
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNGTV GSQ                              213

SEQ ID NO: 613          moltype = AA   length = 207
```

-continued

```
FEATURE             Location/Qualifiers
REGION              1..207
                    note = ICOSL N207A ECD Truncation 4
source              1..207
                    mol_type = protein
                    organism = synthetic construct
SEQUENCE: 613
DTQEKEVRAM VGSDVELSCA CPEGSRFDLN DVYVYWQTSE SKTVVTYHIP QNSSLENVDS       60
RYRNRALMSP AGMLRGDFSL RLFNVTPQDE QKFHCLVLSQ SLGFQEVLSV EVTLHVAANF      120
SVPVVSAPHS PSQDELTFTC TSINGYPRPN VYWINKTDNS LLDQALQNDT VFLNMRGLYD      180
VVSVLRIART PSVNIGCCIE NVLLQQA                                         207

SEQ ID NO: 614       moltype = AA  length = 207
FEATURE             Location/Qualifiers
REGION              1..207
                    note = ICOSL N207G ECD Truncation 4
source              1..207
                    mol_type = protein
                    organism = synthetic construct
SEQUENCE: 614
DTQEKEVRAM VGSDVELSCA CPEGSRFDLN DVYVYWQTSE SKTVVTYHIP QNSSLENVDS       60
RYRNRALMSP AGMLRGDFSL RLFNVTPQDE QKFHCLVLSQ SLGFQEVLSV EVTLHVAANF      120
SVPVVSAPHS PSQDELTFTC TSINGYPRPN VYWINKTDNS LLDQALQNDT VFLNMRGLYD      180
VVSVLRIART PSVNIGCCIE NVLLQQG                                         207

SEQ ID NO: 615       moltype = AA  length = 209
FEATURE             Location/Qualifiers
REGION              1..209
                    note = ICOSL N207A ECD Truncation 8
source              1..209
                    mol_type = protein
                    organism = synthetic construct
SEQUENCE: 615
DTQEKEVRAM VGSDVELSCA CPEGSRFDLN DVYVYWQTSE SKTVVTYHIP QNSSLENVDS       60
RYRNRALMSP AGMLRGDFSL RLFNVTPQDE QKFHCLVLSQ SLGFQEVLSV EVTLHVAANF      120
SVPVVSAPHS PSQDELTFTC TSINGYPRPN VYWINKTDNS LLDQALQNDT VFLNMRGLYD      180
VVSVLRIART PSVNIGCCIE NVLLQQALT                                       209

SEQ ID NO: 616       moltype = AA  length = 209
FEATURE             Location/Qualifiers
REGION              1..209
                    note = ICOSL N207G ECD Truncation 8
source              1..209
                    mol_type = protein
                    organism = synthetic construct
SEQUENCE: 616
DTQEKEVRAM VGSDVELSCA CPEGSRFDLN DVYVYWQTSE SKTVVTYHIP QNSSLENVDS       60
RYRNRALMSP AGMLRGDFSL RLFNVTPQDE QKFHCLVLSQ SLGFQEVLSV EVTLHVAANF      120
SVPVVSAPHS PSQDELTFTC TSINGYPRPN VYWINKTDNS LLDQALQNDT VFLNMRGLYD      180
VVSVLRIART PSVNIGCCIE NVLLQQGLT                                       209

SEQ ID NO: 617       moltype = AA  length = 209
FEATURE             Location/Qualifiers
REGION              1..209
                    note = ICOSL L208G ECD Truncation 8
source              1..209
                    mol_type = protein
                    organism = synthetic construct
SEQUENCE: 617
DTQEKEVRAM VGSDVELSCA CPEGSRFDLN DVYVYWQTSE SKTVVTYHIP QNSSLENVDS       60
RYRNRALMSP AGMLRGDFSL RLFNVTPQDE QKFHCLVLSQ SLGFQEVLSV EVTLHVAANF      120
SVPVVSAPHS PSQDELTFTC TSINGYPRPN VYWINKTDNS LLDQALQNDT VFLNMRGLYD      180
VVSVLRIART PSVNIGCCIE NVLLQQNGT                                       209

SEQ ID NO: 618       moltype = AA  length = 208
FEATURE             Location/Qualifiers
REGION              1..208
                    note = ICOSL N207A/L208G ECD Truncation 2
source              1..208
                    mol_type = protein
                    organism = synthetic construct
SEQUENCE: 618
DTQEKEVRAM VGSDVELSCA CPEGSRFDLN DVYVYWQTSE SKTVVTYHIP QNSSLENVDS       60
RYRNRALMSP AGMLRGDFSL RLFNVTPQDE QKFHCLVLSQ SLGFQEVLSV EVTLHVAANF      120
SVPVVSAPHS PSQDELTFTC TSINGYPRPN VYWINKTDNS LLDQALQNDT VFLNMRGLYD      180
VVSVLRIART PSVNIGCCIE NVLLQQAG                                        208

SEQ ID NO: 619       moltype = AA  length = 208
FEATURE             Location/Qualifiers
```

-continued

```
REGION                  1..208
                        note = ICOSL N207G/L208G ECD Truncation 2
source                  1..208
                        mol_type = protein
                        organism = synthetic construct
SEQUENCE: 619
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQGG                                      208

SEQ ID NO: 620          moltype = AA  length = 213
FEATURE                 Location/Qualifiers
REGION                  1..213
                        note = ICOSL N207A/L208G ECD Truncation 3
source                  1..213
                        mol_type = protein
                        organism = synthetic construct
SEQUENCE: 620
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQAGTV GSQ                                213

SEQ ID NO: 621          moltype = AA  length = 213
FEATURE                 Location/Qualifiers
REGION                  1..213
                        note = ICOSL N207G/L208G ECD Truncation 3
source                  1..213
                        mol_type = protein
                        organism = synthetic construct
SEQUENCE: 621
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQGGTV GSQ                                213

SEQ ID NO: 622          moltype = AA  length = 209
FEATURE                 Location/Qualifiers
REGION                  1..209
                        note = ICOSL N207A/L208G ECD Truncation 8
source                  1..209
                        mol_type = protein
                        organism = synthetic construct
SEQUENCE: 622
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQAGT                                     209

SEQ ID NO: 623          moltype = AA  length = 209
FEATURE                 Location/Qualifiers
REGION                  1..209
                        note = ICOSL N207G/L208G ECD Truncation 8
source                  1..209
                        mol_type = protein
                        organism = synthetic construct
SEQUENCE: 623
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQGGT                                     209

SEQ ID NO: 624          moltype = AA  length = 238
FEATURE                 Location/Qualifiers
REGION                  1..238
                        note = ICOSL N207A Full ECD
source                  1..238
                        mol_type = protein
                        organism = synthetic construct
SEQUENCE: 624
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQALTV GSQTGNDIGE RDKITENPVS TGEKNAAT     238

SEQ ID NO: 625          moltype = AA  length = 238
FEATURE                 Location/Qualifiers
REGION                  1..238
```

-continued

```
                              note = ICOSL N207G Full ECD
source                        1..238
                              mol_type = protein
                              organism = synthetic construct
SEQUENCE: 625
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQGLTV GSQTGNDIGE RDKITENPVS TGEKNAAT     238

SEQ ID NO: 626                moltype = AA  length = 238
FEATURE                       Location/Qualifiers
REGION                        1..238
                              note = ICOSL L208G Full ECD
source                        1..238
                              mol_type = protein
                              organism = synthetic construct
SEQUENCE: 626
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNGTV GSQTGNDIGE RDKITENPVS TGEKNAAT     238

SEQ ID NO: 627                moltype = AA  length = 238
FEATURE                       Location/Qualifiers
REGION                        1..238
                              note = ICOSL N207A/L208G Full ECD
source                        1..238
                              mol_type = protein
                              organism = synthetic construct
SEQUENCE: 627
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQAGTV GSQTGNDIGE RDKITENPVS TGEKNAAT     238

SEQ ID NO: 628                moltype = AA  length = 238
FEATURE                       Location/Qualifiers
REGION                        1..238
                              note = ICOSL N207G/L208G Full ECD
source                        1..238
                              mol_type = protein
                              organism = synthetic construct
SEQUENCE: 628
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSQ SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQGGTV GSQTGNDIGE RDKITENPVS TGEKNAAT     238

SEQ ID NO: 629                moltype = AA  length = 5
FEATURE                       Location/Qualifiers
REGION                        1..5
                              note = EAAAK Linker
source                        1..5
                              mol_type = protein
                              organism = synthetic construct
SEQUENCE: 629
EAAAK                                                               5

SEQ ID NO: 630                moltype = AA  length = 15
FEATURE                       Location/Qualifiers
REGION                        1..15
                              note = 3x EAAAK Linker
source                        1..15
                              mol_type = protein
                              organism = synthetic construct
SEQUENCE: 630
EAAAKEAAAK EAAAK                                                    15

SEQ ID NO: 631                moltype = AA  length = 25
FEATURE                       Location/Qualifiers
REGION                        1..25
                              note = 5x EAAAK Linker
source                        1..25
                              mol_type = protein
                              organism = synthetic construct
SEQUENCE: 631
EAAAKEAAAK EAAAKEAAAK EAAAK                                         25
```

-continued

```
SEQ ID NO: 632              moltype = AA  length = 231
FEATURE                    Location/Qualifiers
REGION                     1..231
                           note = Fc (C5S (C220S), R77C, (R292C),N82G (N297G), V87C
                           (V302C),L232del (K447del))
source                     1..231
                           mol_type = protein
                           organism = synthetic construct
SEQUENCE: 632
EPKSSDKTHT CPPCPAPELL GGPSVFLFPP KPKDTLMISR TPEVTCVVVD VSHEDPEVKF   60
NWYVDGVEVH NAKTKPCEEQ YGSTYRCVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP G          231

SEQ ID NO: 633              moltype = AA  length = 231
FEATURE                    Location/Qualifiers
REGION                     1..231
                           note = Fc with C220S/L234A/L235E/G237A/K447del
source                     1..231
                           mol_type = protein
                           organism = synthetic construct
SEQUENCE: 633
EPKSSDKTHT CPPCPAPEAE GAPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP G          231

SEQ ID NO: 634              moltype = AA  length = 230
FEATURE                    Location/Qualifiers
REGION                     1..230
                           note = Fc with C220S/E233P/L234V/L235A/G236del/S267K/K447del
source                     1..230
                           mol_type = protein
                           organism = synthetic construct
SEQUENCE: 634
EPKSSDKTHT CPPCPAPPVA GPSVFLFPPK PKDTLMISRT PEVTCVVVDV KHEDPEVKFN   60
WYVDGVEVHN AKTKPREEQY NSTYRVVSVL TVLHQDWLNG KEYKCKVSNK ALPAPIEKTI  120
SKAKGQPREP QVYTLPPSRE EMTKNQVSLT CLVKGFYPSD IAVEWESNGQ PENNYKTTPP  180
VLDSDGSFFL YSKLTVDKSR WQQGNVFSCS VMHEALHNHY TQKSLSLSPG            230

SEQ ID NO: 635              moltype = AA  length = 7
FEATURE                    Location/Qualifiers
REGION                     1..7
                           note = Linker
source                     1..7
                           mol_type = protein
                           organism = synthetic construct
SEQUENCE: 635
GSGGGGS                                                             7

SEQ ID NO: 636              moltype = AA  length = 5
FEATURE                    Location/Qualifiers
REGION                     1..5
                           note = 4GS Linker
source                     1..5
                           mol_type = protein
                           organism = synthetic construct
SEQUENCE: 636
GGGGS                                                               5

SEQ ID NO: 637              moltype = AA  length = 231
FEATURE                    Location/Qualifiers
REGION                     1..231
                           note = Fc region
source                     1..231
                           mol_type = protein
                           organism = synthetic construct
SEQUENCE: 637
EPKSSDKTHT CPPCPAPEAE GAPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP G          231

SEQ ID NO: 638              moltype = AA  length = 238
FEATURE                    Location/Qualifiers
REGION                     1..238
                           note = ICOSL v180 ECD
source                     1..238
                           mol_type = protein
```

```
                          organism = synthetic construct
SEQUENCE: 638
DTQEKEVRAM VGSDVELSCA CPEGSRFDLN DVYVYWQTSE SKTVVTYHIP QASSLEFVDS    60
RYRNRALMSP AGMLRGDFSL RLFNVTPQDE QKFHCLVLSS SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 639            moltype = AA  length = 238
FEATURE                   Location/Qualifiers
REGION                    1..238
                          note = ICOSL v181 ECD
source                    1..238
                          mol_type = protein
                          organism = synthetic construct
SEQUENCE: 639
DTQEKEVRAM VGSDVELSCA CPEGSRFDLN DVYVYWQTSE SKTVVTYHIP QASSLEHVDS    60
RYRNRALMSP AGMLRGDFSL RLFNVTPQDE QKFHCLVLSS SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 640            moltype = AA  length = 238
FEATURE                   Location/Qualifiers
REGION                    1..238
                          note = ICOSL v182 ECD
source                    1..238
                          mol_type = protein
                          organism = synthetic construct
SEQUENCE: 640
DTQEKEVRAM VGSDVELSCA CPEGSRFDLN DVYVYWQTSE SKTVVTYHIP QASSLEYVDS    60
RYRNRALMSP AGMLRGDFSL RLFNVTPQDE QKFHCLVLSS SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 641            moltype = AA  length = 238
FEATURE                   Location/Qualifiers
REGION                    1..238
                          note = ICOSL v183 ECD
source                    1..238
                          mol_type = protein
                          organism = synthetic construct
SEQUENCE: 641
DTQEKEVRAM VGSDVELSCA CPEGSRFDLN DVYVYWQTSE SKTVVTYHIP QDSSLEAVDS    60
RYRNRALMSP AGMLRGDFSL RLFNVTPQDE QKFHCLVLSA SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 642            moltype = AA  length = 238
FEATURE                   Location/Qualifiers
REGION                    1..238
                          note = ICOSL v184 ECD
source                    1..238
                          mol_type = protein
                          organism = synthetic construct
SEQUENCE: 642
DTQEKEVRAM VGSDVELSCA CPEGSRFDLN DVYVYWQTSE SKTVVTYHIP QDSSLENVDS    60
RYRNRALMSP AGMLRGDFSL RLFNVTPQDE QKFHCLVLSS SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 643            moltype = AA  length = 238
FEATURE                   Location/Qualifiers
REGION                    1..238
                          note = ICOSL v185 ECD
source                    1..238
                          mol_type = protein
                          organism = synthetic construct
SEQUENCE: 643
DTQEKEVRAM VGSDVELSCA CPEGSRFDLN DVYVYWQTSE SKTVVTYHIP QGSSLENVDS    60
RYRNRALMSP AGMLRGDFSL RLFNVTPQDE QKFHCLVLSA SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 644            moltype = AA  length = 238
FEATURE                   Location/Qualifiers
REGION                    1..238
                          note = ICOSL v186 ECD
source                    1..238
                          mol_type = protein
                          organism = synthetic construct
```

```
SEQUENCE: 644
DTQEKEVRAM VGSDVELSCA CPEGSRFDLN DVYVYWQTSE SKTVVTYHIP QHSSLENVDS   60
RYRNRALMSP AGMLRGDFSL RLFNVTPQDE QKFHCLVLSA SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 645            moltype = AA  length = 238
FEATURE                   Location/Qualifiers
REGION                    1..238
                          note = ICOSL v187 ECD
source                    1..238
                          mol_type = protein
                          organism = synthetic construct
SEQUENCE: 645
DTQEKEVRAM VGSDVELSCA CPEGSRFDLN DVYVYWQTSE SKTVVTYHIP QMSSLEHVDS   60
RYRNRALMSP AGMLRGDFSL RLFNVTPQDE QKFHCLVLSS SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 646            moltype = AA  length = 238
FEATURE                   Location/Qualifiers
REGION                    1..238
                          note = ICOSL v188 ECD
source                    1..238
                          mol_type = protein
                          organism = synthetic construct
SEQUENCE: 646
DTQEKEVRAM VGSDVELSCA CPEGSRFDLN DVYVYWQTSE SKTVVTYHIP QMSSLEWVDS   60
RYRNRALMSP AGMLRGDFSL RLFNVTPQDE QKFHCLVLSP SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 647            moltype = AA  length = 238
FEATURE                   Location/Qualifiers
REGION                    1..238
                          note = ICOSL v189 ECD
source                    1..238
                          mol_type = protein
                          organism = synthetic construct
SEQUENCE: 647
DTQEKEVRAM VGSDVELSCA CPEGSRFDLN DVYVYWQTSE SKTVVTYHIP QQSSLEFVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 648            moltype = AA  length = 238
FEATURE                   Location/Qualifiers
REGION                    1..238
                          note = ICOSL v190 ECD
source                    1..238
                          mol_type = protein
                          organism = synthetic construct
SEQUENCE: 648
DTQEKEVRAM VGSDVELSCA CPEGSRFDLN DVYVYWQTSE SKTVVTYHIP QQSSLESVDS   60
RYRNRALMSP AGMLRGDFSL RLFNVTPQDE QKFHCLVLSV SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 649            moltype = AA  length = 238
FEATURE                   Location/Qualifiers
REGION                    1..238
                          note = ICOSL v191 ECD
source                    1..238
                          mol_type = protein
                          organism = synthetic construct
SEQUENCE: 649
DTQEKEVRAM VGSDVELSCA CPEGSRFDLN DVYVYWQTSE SKTVVTYHIP QRSSLELVDS   60
RYRNRALMSP AGMLRGDFSL RLFNVTPQDE QKFHCLVLSA SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 650            moltype = AA  length = 238
FEATURE                   Location/Qualifiers
REGION                    1..238
                          note = ICOSL v192 ECD
source                    1..238
                          mol_type = protein
                          organism = synthetic construct
SEQUENCE: 650
```

```
DTQEKEVRAM VGSDVELSCA CPEGSRFDLN DVYVYWQTSE SKTVVTYHIP QRSSLEYVDS    60
RYRNRALMSP AGMLRGDFSL RLFNVTPQDE QKFHCLVLSP SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 651            moltype = AA  length = 238
FEATURE                   Location/Qualifiers
REGION                    1..238
                          note = ICOSL v193 ECD
source                    1..238
                          mol_type = protein
                          organism = synthetic construct
SEQUENCE: 651
DTQEKEVRAM VGSDVELSCA CPEGSRFDLN DVYVYWQTSE SKTVVTYHIP QRSSLEYVDS    60
RYRNRALMSP AGMLRGDFSL RLFNVTPQDE QKFHCLVLSS SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 652            moltype = AA  length = 238
FEATURE                   Location/Qualifiers
REGION                    1..238
                          note = ICOSL v194 ECD
source                    1..238
                          mol_type = protein
                          organism = synthetic construct
SEQUENCE: 652
DTQEKEVRAM VGSDVELSCA CPEGSRFDLN DVYVYWQTSE SKTVVTYHIP QSSSLEAVDS    60
RYRNRALMSP AGMLRGDFSL RLFNVTPQDE QKFHCLVLSA SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 653            moltype = AA  length = 238
FEATURE                   Location/Qualifiers
REGION                    1..238
                          note = ICOSL v195 ECD
source                    1..238
                          mol_type = protein
                          organism = synthetic construct
SEQUENCE: 653
DTQEKEVRAM VGSDVELSCA CPEGSRFDLN DVYVYWQTSE SKTVVTYHIP QSSSLEHVDS    60
RYRNRALMSP AGMLRGDFSL RLFNVTPQDE QKFHCLVLSE SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 654            moltype = AA  length = 238
FEATURE                   Location/Qualifiers
REGION                    1..238
                          note = ICOSL v196 ECD
source                    1..238
                          mol_type = protein
                          organism = synthetic construct
SEQUENCE: 654
DTQEKEVRAM VGSDVELSCA CPEGSRFDLN DVYVYWQTSE SKTVVTYHIP QSSSLELVDS    60
RYRNRALMSP AGMLRGDFSL RLFNVTPQDE QKFHCLVLSS SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 655            moltype = AA  length = 238
FEATURE                   Location/Qualifiers
REGION                    1..238
                          note = ICOSL v197 ECD
source                    1..238
                          mol_type = protein
                          organism = synthetic construct
SEQUENCE: 655
DTQEKEVRAM VGSDVELSCA CPEGSRFDLN DVYVYWQTSE SKTVVTYHIP QSSSLEMVDS    60
RYRNRALMSP AGMLRGDFSL RLFNVTPQDE QKFHCLVLSS SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAAT     238

SEQ ID NO: 656            moltype = AA  length = 238
FEATURE                   Location/Qualifiers
REGION                    1..238
                          note = ICOSL v198 ECD
source                    1..238
                          mol_type = protein
                          organism = synthetic construct
SEQUENCE: 656
DTQEKEVRAM VGSDVELSCA CPEGSRFDLN DVYVYWQTSE SKTVVTYHIP QSSSLEYVDS    60
```

-continued

```
RYRNRALMSP AGMLRGDFSL RLFNVTPQDE QKFHCLVLSS SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT     238

SEQ ID NO: 657            moltype = AA  length = 238
FEATURE                   Location/Qualifiers
REGION                    1..238
                          note = ICOSL v199 ECD
source                    1..238
                          mol_type = protein
                          organism = synthetic construct
SEQUENCE: 657
DTQEKEVRAM VGSDVELSCA CPEGSRFDLN DVYVYWQTSE SKTVVTYHIP QSSSLEYVDS   60
RYRNRALMSP AGMLRGDFSL RLFNVTPQDE QKFHCLVLSM SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT     238

SEQ ID NO: 658            moltype = AA  length = 238
FEATURE                   Location/Qualifiers
REGION                    1..238
                          note = ICOSL v200 ECD
source                    1..238
                          mol_type = protein
                          organism = synthetic construct
SEQUENCE: 658
DTQEKEVRAM VGSDVELSCA CPEGSRFDLN DVYVYWQTSE SKTVVTYHIP QSSSLEYVDS   60
RYRNRALMSP AGMLRGDFSL RLFNVTPQDE QKFHCLVLSV SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT     238

SEQ ID NO: 659            moltype = AA  length = 238
FEATURE                   Location/Qualifiers
REGION                    1..238
                          note = ICOSL v201 ECD
source                    1..238
                          mol_type = protein
                          organism = synthetic construct
SEQUENCE: 659
DTQEKEVRAM VGSDVELSCA CPEGSRFDLN DVYVYWQTSE SKTVVTYHIP QTSSLEHVDS   60
RYRNRALMSP AGMLRGDFSL RLFNVTPQDE QKFHCLVLSS SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT     238

SEQ ID NO: 660            moltype = AA  length = 238
FEATURE                   Location/Qualifiers
REGION                    1..238
                          note = ICOSL v202 ECD
source                    1..238
                          mol_type = protein
                          organism = synthetic construct
SEQUENCE: 660
DTQEKEVRAM VGSDVELSCA CPEGSRFDLN DVYVYWQTSE SKTVVTYHIP QTSSLEHVDS   60
RYRNRALMSP AGMLRGDFSL RLFNVTPQDE QKFHCLVLSA SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT     238

SEQ ID NO: 661            moltype = AA  length = 238
FEATURE                   Location/Qualifiers
REGION                    1..238
                          note = ICOSL v203 ECD
source                    1..238
                          mol_type = protein
                          organism = synthetic construct
SEQUENCE: 661
DTQEKEVRAM VGSDVELSCA CPEGSRFDLN DVYVYWQTSE SKTVVTYHIP QTSSLEYVDS   60
RYRNRALMSP AGMLRGDFSL RLFNVTPQDE QKFHCLVLSA SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT     238

SEQ ID NO: 662            moltype = AA  length = 238
FEATURE                   Location/Qualifiers
REGION                    1..238
                          note = ICOSL v204 ECD
source                    1..238
                          mol_type = protein
                          organism = synthetic construct
SEQUENCE: 662
DTQEKEVRAM VGSDVELSCA CPEGSRFDLN DVYVYWQTSE SKTVVTYHIP QVSSLELVDS   60
RYRNRALMSP AGMLRGDFSL RLFNVTPQDE QKFHCLVLSA SLGFQEVLSV EVTLHVAANF  120
```

```
SVPVVSAPHS PSQDELTFTC TSINGYPRPN VYWINKTDNS LLDQALQNDT VFLNMRGLYD    180
VVSVLRIART PSVNIGCCIE NVLLQQNLTV GSQTGNDIGE RDKITENPVS TGEKNAAT       238

SEQ ID NO: 663          moltype = AA   length = 238
FEATURE                 Location/Qualifiers
REGION                  1..238
                        note = ICOSL v205 ECD
source                  1..238
                        mol_type = protein
                        organism = synthetic construct
SEQUENCE: 663
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSK SLGFQEVLSV EVTLHVAANF    120
SVPVVSAPHS PSQDELTFTC TSINGYPRPN VYWINKTDNS LLDQALQNDT VFLNMRGLYD    180
VVSVLRIART PSVNIGCCIE NVLLQQNLTV GSQTGNDIGE RDKITENPVS TGEKNAAT       238

SEQ ID NO: 664          moltype = AA   length = 238
FEATURE                 Location/Qualifiers
REGION                  1..238
                        note = ICOSL v206 ECD
source                  1..238
                        mol_type = protein
                        organism = synthetic construct
SEQUENCE: 664
DTQEKEVRAM VGSDVELSCA CPEGSRFDLN DVYVYWQTSE SKTVVTYHIP QKSSLEYVDS    60
RYRNRALMSP AGMLRGDFSL RLFNVTPQDE QKFHCLVLSR SLGFQEVLSV EVTLHVAANF    120
SVPVVSAPHS PSQDELTFTC TSINGYPRPN VYWINKTDNS LLDQALQNDT VFLNMRGLYD    180
VVSVLRIART PSVNIGCCIE NVLLQQNLTV GSQTGNDIGE RDKITENPVS TGEKNAAT       238

SEQ ID NO: 665          moltype = AA   length = 238
FEATURE                 Location/Qualifiers
REGION                  1..238
                        note = ICOSL v207 ECD
source                  1..238
                        mol_type = protein
                        organism = synthetic construct
SEQUENCE: 665
DTQEKEVRAM VGSDVELSCA CPEGSRFDLN DVYVYWQTSE SKTVVTYHIP QLSSLEHVDS    60
RYRNRALMSP AGMLRGDFSL RLFNVTPQDE QKFHCLVLSR SLGFQEVLSV EVTLHVAANF    120
SVPVVSAPHS PSQDELTFTC TSINGYPRPN VYWINKTDNS LLDQALQNDT VFLNMRGLYD    180
VVSVLRIART PSVNIGCCIE NVLLQQNLTV GSQTGNDIGE RDKITENPVS TGEKNAAT       238

SEQ ID NO: 666          moltype = AA   length = 238
FEATURE                 Location/Qualifiers
REGION                  1..238
                        note = ICOSL v208 ECD
source                  1..238
                        mol_type = protein
                        organism = synthetic construct
SEQUENCE: 666
DTQEKEVRAM VGSDVELSCA CPEGSRFDLN DVYVYWQTSE SKTVVTYHIP QRSSLEFVDS    60
RYRNRALMSP AGMLRGDFSL RLFNVTPQDE QKFHCLVLSN SLGFQEVLSV EVTLHVAANF    120
SVPVVSAPHS PSQDELTFTC TSINGYPRPN VYWINKTDNS LLDQALQNDT VFLNMRGLYD    180
VVSVLRIART PSVNIGCCIE NVLLQQNLTV GSQTGNDIGE RDKITENPVS TGEKNAAT       238

SEQ ID NO: 667          moltype = AA   length = 238
FEATURE                 Location/Qualifiers
REGION                  1..238
                        note = ICOSL v209 ECD
source                  1..238
                        mol_type = protein
                        organism = synthetic construct
SEQUENCE: 667
DTQEKEVRAM VGSDVELSCA CPEGSRFDLN DVYVYWQTSE SKTVVTYHIP QRSSLEFVDS    60
RYRNRALMSP AGMLRGDFSL RLFNVTPQDE QKFHCLVLSP SLGFQEVLSV EVTLHVAANF    120
SVPVVSAPHS PSQDELTFTC TSINGYPRPN VYWINKTDNS LLDQALQNDT VFLNMRGLYD    180
VVSVLRIART PSVNIGCCIE NVLLQQNLTV GSQTGNDIGE RDKITENPVS TGEKNAAT       238

SEQ ID NO: 668          moltype = AA   length = 238
FEATURE                 Location/Qualifiers
REGION                  1..238
                        note = N52R, N57F, Q100R
source                  1..238
                        mol_type = protein
                        organism = synthetic construct
SEQUENCE: 668
DTQEKEVRAM VGSDVELSCA CPEGSRFDLN DVYVYWQTSE SKTVVTYHIP QRSSLEFVDS    60
RYRNRALMSP AGMLRGDFSL RLFNVTPQDE QKFHCLVLSR SLGFQEVLSV EVTLHVAANF    120
SVPVVSAPHS PSQDELTFTC TSINGYPRPN VYWINKTDNS LLDQALQNDT VFLNMRGLYD    180
```

```
VVSVLRIART PSVNIGCCIE NVLLQQNLTV GSQTGNDIGE RDKITENPVS TGEKNAAT        238

SEQ ID NO: 669            moltype = AA   length = 238
FEATURE                   Location/Qualifiers
REGION                    1..238
                          note = ICOSL v211 ECD
source                    1..238
                          mol_type = protein
                          organism = synthetic construct
SEQUENCE: 669
DTQEKEVRAM VGSDVELSCA CPEGSRFDLN DVYVYWQTSE SKTVVTYHIP QRSSLEFVDS      60
RYRNRALMSP AGMLRGDFSL RLFNVTPQDE QKFHCLVLST SLGFQEVLSV EVTLHVAANF     120
SVPVVSAPHS PSQDELTFTC TSINGYPRPN VYWINKTDNS LLDQALQNDT VFLNMRGLYD     180
VVSVLRIART PSVNIGCCIE NVLLQQNLTV GSQTGNDIGE RDKITENPVS TGEKNAAT       238

SEQ ID NO: 670            moltype = AA   length = 238
FEATURE                   Location/Qualifiers
REGION                    1..238
                          note = ICOSL v212 ECD
source                    1..238
                          mol_type = protein
                          organism = synthetic construct
SEQUENCE: 670
DTQEKEVRAM VGSDVELSCA CPEGSRFDLN DVYVYWQTSE SKTVVTYHIP QRSSLEHVDS      60
RYRNRALMSP AGMLRGDFSL RLFNVTPQDE QKFHCLVLSK SLGFQEVLSV EVTLHVAANF     120
SVPVVSAPHS PSQDELTFTC TSINGYPRPN VYWINKTDNS LLDQALQNDT VFLNMRGLYD     180
VVSVLRIART PSVNIGCCIE NVLLQQNLTV GSQTGNDIGE RDKITENPVS TGEKNAAT       238

SEQ ID NO: 671            moltype = AA   length = 238
FEATURE                   Location/Qualifiers
REGION                    1..238
                          note = ICOSL v213 ECD
source                    1..238
                          mol_type = protein
                          organism = synthetic construct
SEQUENCE: 671
DTQEKEVRAM VGSDVELSCA CPEGSRFDLN DVYVYWQTSE SKTVVTYHIP QRSSLELVDS      60
RYRNRALMSP AGMLRGDFSL RLFNVTPQDE QKFHCLVLSS SLGFQEVLSV EVTLHVAANF     120
SVPVVSAPHS PSQDELTFTC TSINGYPRPN VYWINKTDNS LLDQALQNDT VFLNMRGLYD     180
VVSVLRIART PSVNIGCCIE NVLLQQNLTV GSQTGNDIGE RDKITENPVS TGEKNAAT       238

SEQ ID NO: 672            moltype = AA   length = 238
FEATURE                   Location/Qualifiers
REGION                    1..238
                          note = ICOSL v214 ECD
source                    1..238
                          mol_type = protein
                          organism = synthetic construct
SEQUENCE: 672
DTQEKEVRAM VGSDVELSCA CPEGSRFDLN DVYVYWQTSE SKTVVTYHIP QRSSLEWVDS      60
RYRNRALMSP AGMLRGDFSL RLFNVTPQDE QKFHCLVLSK SLGFQEVLSV EVTLHVAANF     120
SVPVVSAPHS PSQDELTFTC TSINGYPRPN VYWINKTDNS LLDQALQNDT VFLNMRGLYD     180
VVSVLRIART PSVNIGCCIE NVLLQQNLTV GSQTGNDIGE RDKITENPVS TGEKNAAT       238

SEQ ID NO: 673            moltype = AA   length = 238
FEATURE                   Location/Qualifiers
REGION                    1..238
                          note = ICOSL v215 ECD
source                    1..238
                          mol_type = protein
                          organism = synthetic construct
SEQUENCE: 673
DTQEKEVRAM VGSDVELSCA CPEGSRFDLN DVYVYWQTSE SKTVVTYHIP QRSSLEWVDS      60
RYRNRALMSP AGMLRGDFSL RLFNVTPQDE QKFHCLVLSQ SLGFQEVLSV EVTLHVAANF     120
SVPVVSAPHS PSQDELTFTC TSINGYPRPN VYWINKTDNS LLDQALQNDT VFLNMRGLYD     180
VVSVLRIART PSVNIGCCIE NVLLQQNLTV GSQTGNDIGE RDKITENPVS TGEKNAAT       238

SEQ ID NO: 674            moltype = AA   length = 238
FEATURE                   Location/Qualifiers
REGION                    1..238
                          note = ICOSL v216 ECD
source                    1..238
                          mol_type = protein
                          organism = synthetic construct
SEQUENCE: 674
DTQEKEVRAM VGSDVELSCA CPEGSRFDLN DVYVYWQTSE SKTVVTYHIP QRSSLEYVDS      60
RYRNRALMSP AGMLRGDFSL RLFNVTPQDE QKFHCLVLSR SLGFQEVLSV EVTLHVAANF     120
SVPVVSAPHS PSQDELTFTC TSINGYPRPN VYWINKTDNS LLDQALQNDT VFLNMRGLYD     180
VVSVLRIART PSVNIGCCIE NVLLQQNLTV GSQTGNDIGE RDKITENPVS TGEKNAAT       238
```

```
SEQ ID NO: 675              moltype = AA  length = 238
FEATURE                     Location/Qualifiers
REGION                      1..238
                            note = ICOSL v217 ECD
source                      1..238
                            mol_type = protein
                            organism = synthetic construct
SEQUENCE: 675
DTQEKEVRAM VGSDVELSCA CPEGSRFDLN DVYVYWQTSE SKTVVTYHIP QCSSLEEVDS   60
RYRNRALMSP AGMLRGDFSL RLFNVTPQDE QKFHCLVLSS SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 676              moltype = AA  length = 238
FEATURE                     Location/Qualifiers
REGION                      1..238
                            note = ICOSL v218 ECD
source                      1..238
                            mol_type = protein
                            organism = synthetic construct
SEQUENCE: 676
DTQEKEVRAM VGSDVELSCA CPEGSRFDLN DVYVYWQTSE SKTVVTYHIP QGSSLEPVDS   60
RYRNRALMSP AGMLRGDFSL RLFNVTPQDE QKFHCLVLSD SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 677              moltype = AA  length = 238
FEATURE                     Location/Qualifiers
REGION                      1..238
                            note = ICOSL v219 ECD
source                      1..238
                            mol_type = protein
                            organism = synthetic construct
SEQUENCE: 677
DTQEKEVRAM VGSDVELSCA CPEGSRFDLN DVYVYWQTSE SKTVVTYHIP QGSSLEVVDS   60
RYRNRALMSP AGMLRGDFSL RLFNVTPQDE QKFHCLVLSG SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 678              moltype = AA  length = 238
FEATURE                     Location/Qualifiers
REGION                      1..238
                            note = ICOSL v220 ECD
source                      1..238
                            mol_type = protein
                            organism = synthetic construct
SEQUENCE: 678
DTQEKEVRAM VGSDVELSCA CPEGSRFDLN DVYVYWQTSE SKTVVTYHIP QGSSLEVVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 679              moltype = AA  length = 238
FEATURE                     Location/Qualifiers
REGION                      1..238
                            note = ICOSL v221 ECD
source                      1..238
                            mol_type = protein
                            organism = synthetic construct
SEQUENCE: 679
DTQEKEVRAM VGSDVELSCA CPEGSRFDLN DVYVYWQTSE SKTVVTYHIP QLSSLEVVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 680              moltype = AA  length = 238
FEATURE                     Location/Qualifiers
REGION                      1..238
                            note = ICOSL v222 ECD
source                      1..238
                            mol_type = protein
                            organism = synthetic construct
SEQUENCE: 680
DTQEKEVRAM VGSDVELSCA CPEGSRFDLN DVYVYWQTSE SKTVVTYHIP QPSSLEPVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238
```

```
SEQ ID NO: 681            moltype = AA  length = 238
FEATURE                   Location/Qualifiers
REGION                    1..238
                          note = ICOSL v223 ECD
source                    1..238
                          mol_type = protein
                          organism = synthetic construct
SEQUENCE: 681
DTQEKEVRAM VGSDVELSCA CPEGSRFDLN DVYVYWQTSE SKTVVTYHIP QPSSLESVDS  60
RYRNRALMSP AGMLRGDFSL RLFNVTPQDE QKFHCLVLSG SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 682            moltype = AA  length = 238
FEATURE                   Location/Qualifiers
REGION                    1..238
                          note = ICOSL v224 ECD
source                    1..238
                          mol_type = protein
                          organism = synthetic construct
SEQUENCE: 682
DTQEKEVRAM VGSDVELSCA CPEGSRFDLN DVYVYWQTSE SKTVVTYHIP QSSSLELVDS  60
RYRNRALMSP AGMLRGDFSL RLFNVTPQDE QKFHCLVLSG SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 683            moltype = AA  length = 238
FEATURE                   Location/Qualifiers
REGION                    1..238
                          note = ICOSL v225 ECD
source                    1..238
                          mol_type = protein
                          organism = synthetic construct
SEQUENCE: 683
DTQEKEVRAM VGSDVELSCA CPEGSRFDLN DVYVYWQTSE SKTVVTYHIP QTSSLEKVDS  60
RYRNRALMSP AGMLRGDFSL RLFNVTPQDE QKFHCLVLSP SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 684            moltype = AA  length = 238
FEATURE                   Location/Qualifiers
REGION                    1..238
                          note = ICOSL v226 ECD
source                    1..238
                          mol_type = protein
                          organism = synthetic construct
SEQUENCE: 684
DTQEKEVRAM VGSDVELSCA CPEGSRFDLN DVYVYWQTSE SKTVVTYHIP QVSSLETVDS  60
RYRNRALMSP AGMLRGDFSL RLFNVTPQDE QKFHCLVLSL SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 685            moltype = AA  length = 238
FEATURE                   Location/Qualifiers
REGION                    1..238
                          note = ICOSL v227 ECD
source                    1..238
                          mol_type = protein
                          organism = synthetic construct
SEQUENCE: 685
DTQEKEVRAM VGSDVELSCA CPEGSRFDLN DVYVYWQTSE SKTVVTYHIP QNSSLEQVDS  60
RYRNRALMSP AGMLRGDFSL RLFNVTPQDE QKFHCLVLSP SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAAT    238

SEQ ID NO: 686            moltype = AA  length = 111
FEATURE                   Location/Qualifiers
REGION                    1..111
                          note = ICOSL v180 IgV
source                    1..111
                          mol_type = protein
                          organism = synthetic construct
SEQUENCE: 686
DTQEKEVRAM VGSDVELSCA CPEGSRFDLN DVYVYWQTSE SKTVVTYHIP QASSLEFVDS  60
RYRNRALMSP AGMLRGDFSL RLFNVTPQDE QKFHCLVLSS SLGFQEVLSV E           111

SEQ ID NO: 687            moltype = AA  length = 111
FEATURE                   Location/Qualifiers
REGION                    1..111
```

-continued

```
                              note = ICOSL v181 IgV
source                        1..111
                              mol_type = protein
                              organism = synthetic construct
SEQUENCE: 687
DTQEKEVRAM VGSDVELSCA CPEGSRFDLN DVYVYWQTSE SKTVVTYHIP QASSLEHVDS    60
RYRNRALMSP AGMLRGDFSL RLFNVTPQDE QKFHCLVLSS SLGFQEVLSV E            111

SEQ ID NO: 688               moltype = AA  length = 111
FEATURE                      Location/Qualifiers
REGION                       1..111
                             note = ICOSL v182 IgV
source                       1..111
                             mol_type = protein
                             organism = synthetic construct
SEQUENCE: 688
DTQEKEVRAM VGSDVELSCA CPEGSRFDLN DVYVYWQTSE SKTVVTYHIP QASSLEYVDS    60
RYRNRALMSP AGMLRGDFSL RLFNVTPQDE QKFHCLVLSA SLGFQEVLSV E            111

SEQ ID NO: 689               moltype = AA  length = 111
FEATURE                      Location/Qualifiers
REGION                       1..111
                             note = ICOSL v183 IgV
source                       1..111
                             mol_type = protein
                             organism = synthetic construct
SEQUENCE: 689
DTQEKEVRAM VGSDVELSCA CPEGSRFDLN DVYVYWQTSE SKTVVTYHIP QDSSLEAVDS    60
RYRNRALMSP AGMLRGDFSL RLFNVTPQDE QKFHCLVLSA SLGFQEVLSV E            111

SEQ ID NO: 690               moltype = AA  length = 111
FEATURE                      Location/Qualifiers
REGION                       1..111
                             note = ICOSL v184 IgV
source                       1..111
                             mol_type = protein
                             organism = synthetic construct
SEQUENCE: 690
DTQEKEVRAM VGSDVELSCA CPEGSRFDLN DVYVYWQTSE SKTVVTYHIP QDSSLENVDS    60
RYRNRALMSP AGMLRGDFSL RLFNVTPQDE QKFHCLVLSS SLGFQEVLSV E            111

SEQ ID NO: 691               moltype = AA  length = 111
FEATURE                      Location/Qualifiers
REGION                       1..111
                             note = ICOSL v185 IgV
source                       1..111
                             mol_type = protein
                             organism = synthetic construct
SEQUENCE: 691
DTQEKEVRAM VGSDVELSCA CPEGSRFDLN DVYVYWQTSE SKTVVTYHIP QGSSLENVDS    60
RYRNRALMSP AGMLRGDFSL RLFNVTPQDE QKFHCLVLSA SLGFQEVLSV E            111

SEQ ID NO: 692               moltype = AA  length = 111
FEATURE                      Location/Qualifiers
REGION                       1..111
                             note = ICOSL v186 IgV
source                       1..111
                             mol_type = protein
                             organism = synthetic construct
SEQUENCE: 692
DTQEKEVRAM VGSDVELSCA CPEGSRFDLN DVYVYWQTSE SKTVVTYHIP QHSSLENVDS    60
RYRNRALMSP AGMLRGDFSL RLFNVTPQDE QKFHCLVLSA SLGFQEVLSV E            111

SEQ ID NO: 693               moltype = AA  length = 111
FEATURE                      Location/Qualifiers
REGION                       1..111
                             note = ICOSL v187 IgV
source                       1..111
                             mol_type = protein
                             organism = synthetic construct
SEQUENCE: 693
DTQEKEVRAM VGSDVELSCA CPEGSRFDLN DVYVYWQTSE SKTVVTYHIP QMSSLEHVDS    60
RYRNRALMSP AGMLRGDFSL RLFNVTPQDE QKFHCLVLSS SLGFQEVLSV E            111

SEQ ID NO: 694               moltype = AA  length = 111
FEATURE                      Location/Qualifiers
REGION                       1..111
                             note = ICOSL v188 IgV
source                       1..111
```

-continued

```
                         mol_type = protein
                         organism = synthetic construct
SEQUENCE: 694
DTQEKEVRAM VGSDVELSCA CPEGSRFDLN DVYVYWQTSE SKTVVTYHIP QMSSLEWVDS  60
RYRNRALMSP AGMLRGDFSL RLFNVTPQDE QKFHCLVLSP SLGFQEVLSV E          111

SEQ ID NO: 695          moltype = AA  length = 111
FEATURE                 Location/Qualifiers
REGION                  1..111
                        note = ICOSL v189 IgV
source                  1..111
                        mol_type = protein
                        organism = synthetic construct
SEQUENCE: 695
DTQEKEVRAM VGSDVELSCA CPEGSRFDLN DVYVYWQTSE SKTVVTYHIP QQSSLEFVDS  60
RYRNRALMSP AGMLRGDFSL RLFNVTPQDE QKFHCLVLSQ SLGFQEVLSV E          111

SEQ ID NO: 696          moltype = AA  length = 111
FEATURE                 Location/Qualifiers
REGION                  1..111
                        note = ICOSL v190 IgV
source                  1..111
                        mol_type = protein
                        organism = synthetic construct
SEQUENCE: 696
DTQEKEVRAM VGSDVELSCA CPEGSRFDLN DVYVYWQTSE SKTVVTYHIP QQSSLESVDS  60
RYRNRALMSP AGMLRGDFSL RLFNVTPQDE QKFHCLVLSA SLGFQEVLSV E          111

SEQ ID NO: 697          moltype = AA  length = 111
FEATURE                 Location/Qualifiers
REGION                  1..111
                        note = ICOSL v191 IgV
source                  1..111
                        mol_type = protein
                        organism = synthetic construct
SEQUENCE: 697
DTQEKEVRAM VGSDVELSCA CPEGSRFDLN DVYVYWQTSE SKTVVTYHIP QRSSLELVDS  60
RYRNRALMSP AGMLRGDFSL RLFNVTPQDE QKFHCLVLSA SLGFQEVLSV E          111

SEQ ID NO: 698          moltype = AA  length = 111
FEATURE                 Location/Qualifiers
REGION                  1..111
                        note = ICOSL v192 IgV
source                  1..111
                        mol_type = protein
                        organism = synthetic construct
SEQUENCE: 698
DTQEKEVRAM VGSDVELSCA CPEGSRFDLN DVYVYWQTSE SKTVVTYHIP QRSSLEYVDS  60
RYRNRALMSP AGMLRGDFSL RLFNVTPQDE QKFHCLVLSP SLGFQEVLSV E          111

SEQ ID NO: 699          moltype = AA  length = 111
FEATURE                 Location/Qualifiers
REGION                  1..111
                        note = ICOSL v193 IgV
source                  1..111
                        mol_type = protein
                        organism = synthetic construct
SEQUENCE: 699
DTQEKEVRAM VGSDVELSCA CPEGSRFDLN DVYVYWQTSE SKTVVTYHIP QRSSLEYVDS  60
RYRNRALMSP AGMLRGDFSL RLFNVTPQDE QKFHCLVLSS SLGFQEVLSV E          111

SEQ ID NO: 700          moltype = AA  length = 111
FEATURE                 Location/Qualifiers
REGION                  1..111
                        note = ICOSL v194 IgV
source                  1..111
                        mol_type = protein
                        organism = synthetic construct
SEQUENCE: 700
DTQEKEVRAM VGSDVELSCA CPEGSRFDLN DVYVYWQTSE SKTVVTYHIP QSSSLEAVDS  60
RYRNRALMSP AGMLRGDFSL RLFNVTPQDE QKFHCLVLSA SLGFQEVLSV E          111

SEQ ID NO: 701          moltype = AA  length = 111
FEATURE                 Location/Qualifiers
REGION                  1..111
                        note = ICOSL v195 IgV
source                  1..111
                        mol_type = protein
                        organism = synthetic construct
```

```
SEQUENCE: 701
DTQEKEVRAM VGSDVELSCA CPEGSRFDLN DVYVYWQTSE SKTVVTYHIP QSSSLEHVDS    60
RYRNRALMSP AGMLRGDFSL RLFNVTPQDE QKFHCLVLSE SLGFQEVLSV E            111

SEQ ID NO: 702          moltype = AA   length = 111
FEATURE                 Location/Qualifiers
REGION                  1..111
                        note = ICOSL v196 IgV
source                  1..111
                        mol_type = protein
                        organism = synthetic construct
SEQUENCE: 702
DTQEKEVRAM VGSDVELSCA CPEGSRFDLN DVYVYWQTSE SKTVVTYHIP QSSSLELVDS    60
RYRNRALMSP AGMLRGDFSL RLFNVTPQDE QKFHCLVLSS SLGFQEVLSV E            111

SEQ ID NO: 703          moltype = AA   length = 111
FEATURE                 Location/Qualifiers
REGION                  1..111
                        note = ICOSL v197 IgV
source                  1..111
                        mol_type = protein
                        organism = synthetic construct
SEQUENCE: 703
DTQEKEVRAM VGSDVELSCA CPEGSRFDLN DVYVYWQTSE SKTVVTYHIP QSSSLEMVDS    60
RYRNRALMSP AGMLRGDFSL RLFNVTPQDE QKFHCLVLSS SLGFQEVLSV E            111

SEQ ID NO: 704          moltype = AA   length = 111
FEATURE                 Location/Qualifiers
REGION                  1..111
                        note = ICOSL v198 IgV
source                  1..111
                        mol_type = protein
                        organism = synthetic construct
SEQUENCE: 704
DTQEKEVRAM VGSDVELSCA CPEGSRFDLN DVYVYWQTSE SKTVVTYHIP QSSSLEYVDS    60
RYRNRALMSP AGMLRGDFSL RLFNVTPQDE QKFHCLVLSS SLGFQEVLSV E            111

SEQ ID NO: 705          moltype = AA   length = 111
FEATURE                 Location/Qualifiers
REGION                  1..111
                        note = ICOSL v199 IgV
source                  1..111
                        mol_type = protein
                        organism = synthetic construct
SEQUENCE: 705
DTQEKEVRAM VGSDVELSCA CPEGSRFDLN DVYVYWQTSE SKTVVTYHIP QSSSLEYVDS    60
RYRNRALMSP AGMLRGDFSL RLFNVTPQDE QKFHCLVLSM SLGFQEVLSV E            111

SEQ ID NO: 706          moltype = AA   length = 111
FEATURE                 Location/Qualifiers
REGION                  1..111
                        note = ICOSL v200 IgV
source                  1..111
                        mol_type = protein
                        organism = synthetic construct
SEQUENCE: 706
DTQEKEVRAM VGSDVELSCA CPEGSRFDLN DVYVYWQTSE SKTVVTYHIP QSSSLEYVDS    60
RYRNRALMSP AGMLRGDFSL RLFNVTPQDE QKFHCLVLSV SLGFQEVLSV E            111

SEQ ID NO: 707          moltype = AA   length = 111
FEATURE                 Location/Qualifiers
REGION                  1..111
                        note = ICOSL v201 IgV
source                  1..111
                        mol_type = protein
                        organism = synthetic construct
SEQUENCE: 707
DTQEKEVRAM VGSDVELSCA CPEGSRFDLN DVYVYWQTSE SKTVVTYHIP QTSSLEHVDS    60
RYRNRALMSP AGMLRGDFSL RLFNVTPQDE QKFHCLVLSS SLGFQEVLSV E            111

SEQ ID NO: 708          moltype = AA   length = 111
FEATURE                 Location/Qualifiers
REGION                  1..111
                        note = ICOSL v202 IgV
source                  1..111
                        mol_type = protein
                        organism = synthetic construct
SEQUENCE: 708
DTQEKEVRAM VGSDVELSCA CPEGSRFDLN DVYVYWQTSE SKTVVTYHIP QTSSLEHVDS    60
```

-continued

```
RYRNRALMSP AGMLRGDFSL RLFNVTPQDE QKFHCLVLSA SLGFQEVLSV E              111

SEQ ID NO: 709          moltype = AA  length = 111
FEATURE                 Location/Qualifiers
REGION                  1..111
                        note = ICOSL v203 IgV
source                  1..111
                        mol_type = protein
                        organism = synthetic construct
SEQUENCE: 709
DTQEKEVRAM VGSDVELSCA CPEGSRFDLN DVYVYWQTSE SKTVVTYHIP QTSSLEYVDS     60
RYRNRALMSP AGMLRGDFSL RLFNVTPQDE QKFHCLVLSA SLGFQEVLSV E              111

SEQ ID NO: 710          moltype = AA  length = 111
FEATURE                 Location/Qualifiers
REGION                  1..111
                        note = ICOSL v204 IgV
source                  1..111
                        mol_type = protein
                        organism = synthetic construct
SEQUENCE: 710
DTQEKEVRAM VGSDVELSCA CPEGSRFDLN DVYVYWQTSE SKTVVTYHIP QVSSLELVDS     60
RYRNRALMSP AGMLRGDFSL RLFNVTPQDE QKFHCLVLSA SLGFQEVLSV E              111

SEQ ID NO: 711          moltype = AA  length = 111
FEATURE                 Location/Qualifiers
REGION                  1..111
                        note = ICOSL v205 IgV
source                  1..111
                        mol_type = protein
                        organism = synthetic construct
SEQUENCE: 711
DTQEKEVRAM VGSDVELSCA CPEGSRFDLN DVYVYWQTSE SKTVVTYHIP QHSSLEYVDS     60
RYRNRALMSP AGMLRGDFSL RLFNVTPQDE QKFHCLVLSK SLGFQEVLSV E              111

SEQ ID NO: 712          moltype = AA  length = 111
FEATURE                 Location/Qualifiers
REGION                  1..111
                        note = ICOSL v206 IgV
source                  1..111
                        mol_type = protein
                        organism = synthetic construct
SEQUENCE: 712
DTQEKEVRAM VGSDVELSCA CPEGSRFDLN DVYVYWQTSE SKTVVTYHIP QKSSLEYVDS     60
RYRNRALMSP AGMLRGDFSL RLFNVTPQDE QKFHCLVLSR SLGFQEVLSV E              111

SEQ ID NO: 713          moltype = AA  length = 111
FEATURE                 Location/Qualifiers
REGION                  1..111
                        note = ICOSL v207 IgV
source                  1..111
                        mol_type = protein
                        organism = synthetic construct
SEQUENCE: 713
DTQEKEVRAM VGSDVELSCA CPEGSRFDLN DVYVYWQTSE SKTVVTYHIP QLSSLEHVDS     60
RYRNRALMSP AGMLRGDFSL RLFNVTPQDE QKFHCLVLSR SLGFQEVLSV E              111

SEQ ID NO: 714          moltype = AA  length = 111
FEATURE                 Location/Qualifiers
REGION                  1..111
                        note = ICOSL v208 IgV
source                  1..111
                        mol_type = protein
                        organism = synthetic construct
SEQUENCE: 714
DTQEKEVRAM VGSDVELSCA CPEGSRFDLN DVYVYWQTSE SKTVVTYHIP QRSSLEFVDS     60
RYRNRALMSP AGMLRGDFSL RLFNVTPQDE QKFHCLVLSN SLGFQEVLSV E              111

SEQ ID NO: 715          moltype = AA  length = 111
FEATURE                 Location/Qualifiers
REGION                  1..111
                        note = ICOSL v209 IgV
source                  1..111
                        mol_type = protein
                        organism = synthetic construct
SEQUENCE: 715
DTQEKEVRAM VGSDVELSCA CPEGSRFDLN DVYVYWQTSE SKTVVTYHIP QRSSLEFVDS     60
RYRNRALMSP AGMLRGDFSL RLFNVTPQDE QKFHCLVLSP SLGFQEVLSV E              111
```

-continued

```
SEQ ID NO: 716          moltype = AA  length = 111
FEATURE                 Location/Qualifiers
REGION                  1..111
                        note = ICOSL v210 IgV
source                  1..111
                        mol_type = protein
                        organism = synthetic construct
SEQUENCE: 716
DTQEKEVRAM VGSDVELSCA CPEGSRFDLN DVYVYWQTSE SKTVVTYHIP QRSSLEFVDS  60
RYRNRALMSP AGMLRGDFSL RLFNVTPQDE QKFHCLVLSR SLGFQEVLSV E          111

SEQ ID NO: 717          moltype = AA  length = 111
FEATURE                 Location/Qualifiers
REGION                  1..111
                        note = ICOSL v211 IgV
source                  1..111
                        mol_type = protein
                        organism = synthetic construct
SEQUENCE: 717
DTQEKEVRAM VGSDVELSCA CPEGSRFDLN DVYVYWQTSE SKTVVTYHIP QRSSLEFVDS  60
RYRNRALMSP AGMLRGDFSL RLFNVTPQDE QKFHCLVLST SLGFQEVLSV E          111

SEQ ID NO: 718          moltype = AA  length = 111
FEATURE                 Location/Qualifiers
REGION                  1..111
                        note = ICOSL v212 IgV
source                  1..111
                        mol_type = protein
                        organism = synthetic construct
SEQUENCE: 718
DTQEKEVRAM VGSDVELSCA CPEGSRFDLN DVYVYWQTSE SKTVVTYHIP QRSSLEHVDS  60
RYRNRALMSP AGMLRGDFSL RLFNVTPQDE QKFHCLVLSK SLGFQEVLSV E          111

SEQ ID NO: 719          moltype = AA  length = 111
FEATURE                 Location/Qualifiers
REGION                  1..111
                        note = ICOSL v213 IgV
source                  1..111
                        mol_type = protein
                        organism = synthetic construct
SEQUENCE: 719
DTQEKEVRAM VGSDVELSCA CPEGSRFDLN DVYVYWQTSE SKTVVTYHIP QRSSLELVDS  60
RYRNRALMSP AGMLRGDFSL RLFNVTPQDE QKFHCLVLSS SLGFQEVLSV E          111

SEQ ID NO: 720          moltype = AA  length = 111
FEATURE                 Location/Qualifiers
REGION                  1..111
                        note = ICOSL v214 IgV
source                  1..111
                        mol_type = protein
                        organism = synthetic construct
SEQUENCE: 720
DTQEKEVRAM VGSDVELSCA CPEGSRFDLN DVYVYWQTSE SKTVVTYHIP QRSSLEWVDS  60
RYRNRALMSP AGMLRGDFSL RLFNVTPQDE QKFHCLVLSK SLGFQEVLSV E          111

SEQ ID NO: 721          moltype = AA  length = 111
FEATURE                 Location/Qualifiers
REGION                  1..111
                        note = ICOSL v215 IgV
source                  1..111
                        mol_type = protein
                        organism = synthetic construct
SEQUENCE: 721
DTQEKEVRAM VGSDVELSCA CPEGSRFDLN DVYVYWQTSE SKTVVTYHIP QRSSLEWVDS  60
RYRNRALMSP AGMLRGDFSL RLFNVTPQDE QKFHCLVLSQ SLGFQEVLSV E          111

SEQ ID NO: 722          moltype = AA  length = 111
FEATURE                 Location/Qualifiers
REGION                  1..111
                        note = ICOSL v216 IgV
source                  1..111
                        mol_type = protein
                        organism = synthetic construct
SEQUENCE: 722
DTQEKEVRAM VGSDVELSCA CPEGSRFDLN DVYVYWQTSE SKTVVTYHIP QRSSLEYVDS  60
RYRNRALMSP AGMLRGDFSL RLFNVTPQDE QKFHCLVLSR SLGFQEVLSV E          111

SEQ ID NO: 723          moltype = AA  length = 111
FEATURE                 Location/Qualifiers
```

-continued

```
REGION                    1..111
                          note = ICOSL v217 IgV
source                    1..111
                          mol_type = protein
                          organism = synthetic construct
SEQUENCE: 723
DTQEKEVRAM VGSDVELSCA CPEGSRFDLN DVYVYWQTSE SKTVVTYHIP QCSSLEEVDS    60
RYRNRALMSP AGMLRGDFSL RLFNVTPQDE QKFHCLVLSS SLGFQEVLSV E            111

SEQ ID NO: 724            moltype = AA   length = 111
FEATURE                   Location/Qualifiers
REGION                    1..111
                          note = ICOSL v218 IgV
source                    1..111
                          mol_type = protein
                          organism = synthetic construct
SEQUENCE: 724
DTQEKEVRAM VGSDVELSCA CPEGSRFDLN DVYVYWQTSE SKTVVTYHIP QGSSLEPVDS    60
RYRNRALMSP AGMLRGDFSL RLFNVTPQDE QKFHCLVLSD SLGFQEVLSV E            111

SEQ ID NO: 725            moltype = AA   length = 111
FEATURE                   Location/Qualifiers
REGION                    1..111
                          note = ICOSL v219 IgV
source                    1..111
                          mol_type = protein
                          organism = synthetic construct
SEQUENCE: 725
DTQEKEVRAM VGSDVELSCA CPEGSRFDLN DVYVYWQTSE SKTVVTYHIP QGSSLEVVDS    60
RYRNRALMSP AGMLRGDFSL RLFNVTPQDE QKFHCLVLSG SLGFQEVLSV E            111

SEQ ID NO: 726            moltype = AA   length = 111
FEATURE                   Location/Qualifiers
REGION                    1..111
                          note = ICOSL v220 IgV
source                    1..111
                          mol_type = protein
                          organism = synthetic construct
SEQUENCE: 726
DTQEKEVRAM VGSDVELSCA CPEGSRFDLN DVYVYWQTSE SKTVVTYHIP QGSSLEVVDS    60
RYRNRALMSP AGMLRGDFSL RLFNVTPQDE QKFHCLVLSQ SLGFQEVLSV E            111

SEQ ID NO: 727            moltype = AA   length = 111
FEATURE                   Location/Qualifiers
REGION                    1..111
                          note = ICOSL v221 IgV
source                    1..111
                          mol_type = protein
                          organism = synthetic construct
SEQUENCE: 727
DTQEKEVRAM VGSDVELSCA CPEGSRFDLN DVYVYWQTSE SKTVVTYHIP QLSSLEVVDS    60
RYRNRALMSP AGMLRGDFSL RLFNVTPQDE QKFHCLVLSQ SLGFQEVLSV E            111

SEQ ID NO: 728            moltype = AA   length = 111
FEATURE                   Location/Qualifiers
REGION                    1..111
                          note = ICOSL v222 IgV
source                    1..111
                          mol_type = protein
                          organism = synthetic construct
SEQUENCE: 728
DTQEKEVRAM VGSDVELSCA CPEGSRFDLN DVYVYWQTSE SKTVVTYHIP QPSSLEPVDS    60
RYRNRALMSP AGMLRGDFSL RLFNVTPQDE QKFHCLVLSQ SLGFQEVLSV E            111

SEQ ID NO: 729            moltype = AA   length = 111
FEATURE                   Location/Qualifiers
REGION                    1..111
                          note = ICOSL v223 IgV
source                    1..111
                          mol_type = protein
                          organism = synthetic construct
SEQUENCE: 729
DTQEKEVRAM VGSDVELSCA CPEGSRFDLN DVYVYWQTSE SKTVVTYHIP QPSSLESVDS    60
RYRNRALMSP AGMLRGDFSL RLFNVTPQDE QKFHCLVLSG SLGFQEVLSV E            111

SEQ ID NO: 730            moltype = AA   length = 111
FEATURE                   Location/Qualifiers
REGION                    1..111
                          note = ICOSL v224 IgV
```

-continued

```
source                  1..111
                        mol_type = protein
                        organism = synthetic construct
SEQUENCE: 730
DTQEKEVRAM VGSDVELSCA CPEGSRFDLN DVYVYWQTSE SKTVVTYHIP QSSSLELVDS   60
RYRNRALMSP AGMLRGDFSL RLFNVTPQDE QKFHCLVLSG SLGFQEVLSV E            111

SEQ ID NO: 731          moltype = AA   length = 111
FEATURE                 Location/Qualifiers
REGION                  1..111
                        note = ICOSL v225 IgV
source                  1..111
                        mol_type = protein
                        organism = synthetic construct
SEQUENCE: 731
DTQEKEVRAM VGSDVELSCA CPEGSRFDLN DVYVYWQTSE SKTVVTYHIP QTSSLEKVDS   60
RYRNRALMSP AGMLRGDFSL RLFNVTPQDE QKFHCLVLSP SLGFQEVLSV E            111

SEQ ID NO: 732          moltype = AA   length = 111
FEATURE                 Location/Qualifiers
REGION                  1..111
                        note = ICOSL v226 IgV
source                  1..111
                        mol_type = protein
                        organism = synthetic construct
SEQUENCE: 732
DTQEKEVRAM VGSDVELSCA CPEGSRFDLN DVYVYWQTSE SKTVVTYHIP QVSSLETVDS   60
RYRNRALMSP AGMLRGDFSL RLFNVTPQDE QKFHCLVLSL SLGFQEVLSV E            111

SEQ ID NO: 733          moltype = AA   length = 111
FEATURE                 Location/Qualifiers
REGION                  1..111
                        note = ICOSL v227 IgV
source                  1..111
                        mol_type = protein
                        organism = synthetic construct
SEQUENCE: 733
DTQEKEVRAM VGSDVELSCA CPEGSRFDLN DVYVYWQTSE SKTVVTYHIP QNSSLEQVDS   60
RYRNRALMSP AGMLRGDFSL RLFNVTPQDE QKFHCLVLSP SLGFQEVLSV E            111

SEQ ID NO: 734          moltype = AA   length = 122
FEATURE                 Location/Qualifiers
REGION                  1..122
                        note = ICOSL v180 IgV
source                  1..122
                        mol_type = protein
                        organism = synthetic construct
SEQUENCE: 734
DTQEKEVRAM VGSDVELSCA CPEGSRFDLN DVYVYWQTSE SKTVVTYHIP QASSLEFVDS   60
RYRNRALMSP AGMLRGDFSL RLFNVTPQDE QKFHCLVLSS SLGFQEVLSV EVTLHVAANF  120
SV                                                                 122

SEQ ID NO: 735          moltype = AA   length = 122
FEATURE                 Location/Qualifiers
REGION                  1..122
                        note = ICOSL v181 IgV
source                  1..122
                        mol_type = protein
                        organism = synthetic construct
SEQUENCE: 735
DTQEKEVRAM VGSDVELSCA CPEGSRFDLN DVYVYWQTSE SKTVVTYHIP QASSLEHVDS   60
RYRNRALMSP AGMLRGDFSL RLFNVTPQDE QKFHCLVLSS SLGFQEVLSV EVTLHVAANF  120
SV                                                                 122

SEQ ID NO: 736          moltype = AA   length = 122
FEATURE                 Location/Qualifiers
REGION                  1..122
                        note = ICOSL v182 IgV
source                  1..122
                        mol_type = protein
                        organism = synthetic construct
SEQUENCE: 736
DTQEKEVRAM VGSDVELSCA CPEGSRFDLN DVYVYWQTSE SKTVVTYHIP QASSLEYVDS   60
RYRNRALMSP AGMLRGDFSL RLFNVTPQDE QKFHCLVLSA SLGFQEVLSV EVTLHVAANF  120
SV                                                                 122

SEQ ID NO: 737          moltype = AA   length = 122
FEATURE                 Location/Qualifiers
REGION                  1..122
```

-continued

```
                              note = ICOSL v183 IgV
source                        1..122
                              mol_type = protein
                              organism = synthetic construct
SEQUENCE: 737
DTQEKEVRAM VGSDVELSCA CPEGSRFDLN DVYVYWQTSE SKTVVTYHIP QDSSLEAVDS    60
RYRNRALMSP AGMLRGDFSL RLFNVTPQDE QKFHCLVLSA SLGFQEVLSV EVTLHVAANF   120
SV                                                                  122

SEQ ID NO: 738               moltype = AA  length = 122
FEATURE                      Location/Qualifiers
REGION                       1..122
                              note = ICOSL v184 IgV
source                        1..122
                              mol_type = protein
                              organism = synthetic construct
SEQUENCE: 738
DTQEKEVRAM VGSDVELSCA CPEGSRFDLN DVYVYWQTSE SKTVVTYHIP QDSSLENVDS    60
RYRNRALMSP AGMLRGDFSL RLFNVTPQDE QKFHCLVLSS SLGFQEVLSV EVTLHVAANF   120
SV                                                                  122

SEQ ID NO: 739               moltype = AA  length = 122
FEATURE                      Location/Qualifiers
REGION                       1..122
                              note = ICOSL v185 IgV
source                        1..122
                              mol_type = protein
                              organism = synthetic construct
SEQUENCE: 739
DTQEKEVRAM VGSDVELSCA CPEGSRFDLN DVYVYWQTSE SKTVVTYHIP QGSSLENVDS    60
RYRNRALMSP AGMLRGDFSL RLFNVTPQDE QKFHCLVLSA SLGFQEVLSV EVTLHVAANF   120
SV                                                                  122

SEQ ID NO: 740               moltype = AA  length = 122
FEATURE                      Location/Qualifiers
REGION                       1..122
                              note = ICOSL v186 IgV
source                        1..122
                              mol_type = protein
                              organism = synthetic construct
SEQUENCE: 740
DTQEKEVRAM VGSDVELSCA CPEGSRFDLN DVYVYWQTSE SKTVVTYHIP QHSSLENVDS    60
RYRNRALMSP AGMLRGDFSL RLFNVTPQDE QKFHCLVLSA SLGFQEVLSV EVTLHVAANF   120
SV                                                                  122

SEQ ID NO: 741               moltype = AA  length = 122
FEATURE                      Location/Qualifiers
REGION                       1..122
                              note = ICOSL v187 IgV
source                        1..122
                              mol_type = protein
                              organism = synthetic construct
SEQUENCE: 741
DTQEKEVRAM VGSDVELSCA CPEGSRFDLN DVYVYWQTSE SKTVVTYHIP QMSSLEHVDS    60
RYRNRALMSP AGMLRGDFSL RLFNVTPQDE QKFHCLVLSS SLGFQEVLSV EVTLHVAANF   120
SV                                                                  122

SEQ ID NO: 742               moltype = AA  length = 122
FEATURE                      Location/Qualifiers
REGION                       1..122
                              note = ICOSL v188 IgV
source                        1..122
                              mol_type = protein
                              organism = synthetic construct
SEQUENCE: 742
DTQEKEVRAM VGSDVELSCA CPEGSRFDLN DVYVYWQTSE SKTVVTYHIP QMSSLEWVDS    60
RYRNRALMSP AGMLRGDFSL RLFNVTPQDE QKFHCLVLSP SLGFQEVLSV EVTLHVAANF   120
SV                                                                  122

SEQ ID NO: 743               moltype = AA  length = 122
FEATURE                      Location/Qualifiers
REGION                       1..122
                              note = ICOSL v189 IgV
source                        1..122
                              mol_type = protein
                              organism = synthetic construct
SEQUENCE: 743
DTQEKEVRAM VGSDVELSCA CPEGSRFDLN DVYVYWQTSE SKTVVTYHIP QQSSLEFVDS    60
RYRNRALMSP AGMLRGDFSL RLFNVTPQDE QKFHCLVLSQ SLGFQEVLSV EVTLHVAANF   120
```

-continued

```
SV                                                              122

SEQ ID NO: 744          moltype = AA   length = 122
FEATURE                 Location/Qualifiers
REGION                  1..122
                        note = ICOSL v190 IgV
source                  1..122
                        mol_type = protein
                        organism = synthetic construct
SEQUENCE: 744
DTQEKEVRAM VGSDVELSCA CPEGSRFDLN DVYVYWQTSE SKTVVTYHIP QQSSLESVDS   60
RYRNRALMSP AGMLRGDFSL RLFNVTPQDE QKFHCLVLSA SLGFQEVLSV EVTLHVAANF  120
SV                                                              122

SEQ ID NO: 745          moltype = AA   length = 122
FEATURE                 Location/Qualifiers
REGION                  1..122
                        note = ICOSL v191 IgV
source                  1..122
                        mol_type = protein
                        organism = synthetic construct
SEQUENCE: 745
DTQEKEVRAM VGSDVELSCA CPEGSRFDLN DVYVYWQTSE SKTVVTYHIP QRSSLELVDS   60
RYRNRALMSP AGMLRGDFSL RLFNVTPQDE QKFHCLVLSA SLGFQEVLSV EVTLHVAANF  120
SV                                                              122

SEQ ID NO: 746          moltype = AA   length = 122
FEATURE                 Location/Qualifiers
REGION                  1..122
                        note = ICOSL v192 IgV
source                  1..122
                        mol_type = protein
                        organism = synthetic construct
SEQUENCE: 746
DTQEKEVRAM VGSDVELSCA CPEGSRFDLN DVYVYWQTSE SKTVVTYHIP QRSSLEYVDS   60
RYRNRALMSP AGMLRGDFSL RLFNVTPQDE QKFHCLVLSP SLGFQEVLSV EVTLHVAANF  120
SV                                                              122

SEQ ID NO: 747          moltype = AA   length = 122
FEATURE                 Location/Qualifiers
REGION                  1..122
                        note = ICOSL v193 IgV
source                  1..122
                        mol_type = protein
                        organism = synthetic construct
SEQUENCE: 747
DTQEKEVRAM VGSDVELSCA CPEGSRFDLN DVYVYWQTSE SKTVVTYHIP QRSSLEYVDS   60
RYRNRALMSP AGMLRGDFSL RLFNVTPQDE QKFHCLVLSS SLGFQEVLSV EVTLHVAANF  120
SV                                                              122

SEQ ID NO: 748          moltype = AA   length = 122
FEATURE                 Location/Qualifiers
REGION                  1..122
                        note = ICOSL v194 IgV
source                  1..122
                        mol_type = protein
                        organism = synthetic construct
SEQUENCE: 748
DTQEKEVRAM VGSDVELSCA CPEGSRFDLN DVYVYWQTSE SKTVVTYHIP QSSSLEAVDS   60
RYRNRALMSP AGMLRGDFSL RLFNVTPQDE QKFHCLVLSA SLGFQEVLSV EVTLHVAANF  120
SV                                                              122

SEQ ID NO: 749          moltype = AA   length = 122
FEATURE                 Location/Qualifiers
REGION                  1..122
                        note = ICOSL v195 IgV
source                  1..122
                        mol_type = protein
                        organism = synthetic construct
SEQUENCE: 749
DTQEKEVRAM VGSDVELSCA CPEGSRFDLN DVYVYWQTSE SKTVVTYHIP QSSSLEHVDS   60
RYRNRALMSP AGMLRGDFSL RLFNVTPQDE QKFHCLVLSE SLGFQEVLSV EVTLHVAANF  120
SV                                                              122

SEQ ID NO: 750          moltype = AA   length = 122
FEATURE                 Location/Qualifiers
REGION                  1..122
                        note = ICOSL v196 IgV
source                  1..122
```

-continued

```
                              mol_type = protein
                              organism = synthetic construct
SEQUENCE: 750
DTQEKEVRAM VGSDVELSCA CPEGSRFDLN DVYVYWQTSE SKTVVTYHIP QSSSLELVDS   60
RYRNRALMSP AGMLRGDFSL RLFNVTPQDE QKFHCLVLSS SLGFQEVLSV EVTLHVAANF  120
SV                                                               122

SEQ ID NO: 751          moltype = AA  length = 122
FEATURE                 Location/Qualifiers
REGION                  1..122
                        note = ICOSL v197 IgV
source                  1..122
                        mol_type = protein
                        organism = synthetic construct
SEQUENCE: 751
DTQEKEVRAM VGSDVELSCA CPEGSRFDLN DVYVYWQTSE SKTVVTYHIP QSSSLEMVDS   60
RYRNRALMSP AGMLRGDFSL RLFNVTPQDE QKFHCLVLSS SLGFQEVLSV EVTLHVAANF  120
SV                                                               122

SEQ ID NO: 752          moltype = AA  length = 122
FEATURE                 Location/Qualifiers
REGION                  1..122
                        note = ICOSL v198 IgV
source                  1..122
                        mol_type = protein
                        organism = synthetic construct
SEQUENCE: 752
DTQEKEVRAM VGSDVELSCA CPEGSRFDLN DVYVYWQTSE SKTVVTYHIP QSSSLEYVDS   60
RYRNRALMSP AGMLRGDFSL RLFNVTPQDE QKFHCLVLSS SLGFQEVLSV EVTLHVAANF  120
SV                                                               122

SEQ ID NO: 753          moltype = AA  length = 122
FEATURE                 Location/Qualifiers
REGION                  1..122
                        note = ICOSL v199 IgV
source                  1..122
                        mol_type = protein
                        organism = synthetic construct
SEQUENCE: 753
DTQEKEVRAM VGSDVELSCA CPEGSRFDLN DVYVYWQTSE SKTVVTYHIP QSSSLEYVDS   60
RYRNRALMSP AGMLRGDFSL RLFNVTPQDE QKFHCLVLSM SLGFQEVLSV EVTLHVAANF  120
SV                                                               122

SEQ ID NO: 754          moltype = AA  length = 122
FEATURE                 Location/Qualifiers
REGION                  1..122
                        note = ICOSL v200 IgV
source                  1..122
                        mol_type = protein
                        organism = synthetic construct
SEQUENCE: 754
DTQEKEVRAM VGSDVELSCA CPEGSRFDLN DVYVYWQTSE SKTVVTYHIP QSSSLEYVDS   60
RYRNRALMSP AGMLRGDFSL RLFNVTPQDE QKFHCLVLSV SLGFQEVLSV EVTLHVAANF  120
SV                                                               122

SEQ ID NO: 755          moltype = AA  length = 122
FEATURE                 Location/Qualifiers
REGION                  1..122
                        note = ICOSL v201 IgV
source                  1..122
                        mol_type = protein
                        organism = synthetic construct
SEQUENCE: 755
DTQEKEVRAM VGSDVELSCA CPEGSRFDLN DVYVYWQTSE SKTVVTYHIP QTSSLEHVDS   60
RYRNRALMSP AGMLRGDFSL RLFNVTPQDE QKFHCLVLSS SLGFQEVLSV EVTLHVAANF  120
SV                                                               122

SEQ ID NO: 756          moltype = AA  length = 122
FEATURE                 Location/Qualifiers
REGION                  1..122
                        note = ICOSL v202 IgV
source                  1..122
                        mol_type = protein
                        organism = synthetic construct
SEQUENCE: 756
DTQEKEVRAM VGSDVELSCA CPEGSRFDLN DVYVYWQTSE SKTVVTYHIP QTSSLEHVDS   60
RYRNRALMSP AGMLRGDFSL RLFNVTPQDE QKFHCLVLSA SLGFQEVLSV EVTLHVAANF  120
SV                                                               122
```

```
SEQ ID NO: 757              moltype = AA  length = 122
FEATURE                    Location/Qualifiers
REGION                     1..122
                           note = ICOSL v203 IgV
source                     1..122
                           mol_type = protein
                           organism = synthetic construct
SEQUENCE: 757
DTQEKEVRAM VGSDVELSCA CPEGSRFDLN DVYVYWQTSE SKTVVTYHIP QTSSLEYVDS   60
RYRNRALMSP AGMLRGDFSL RLFNVTPQDE QKFHCLVLSA SLGFQEVLSV EVTLHVAANF  120
SV                                                                122

SEQ ID NO: 758              moltype = AA  length = 122
FEATURE                    Location/Qualifiers
REGION                     1..122
                           note = ICOSL v204 IgV
source                     1..122
                           mol_type = protein
                           organism = synthetic construct
SEQUENCE: 758
DTQEKEVRAM VGSDVELSCA CPEGSRFDLN DVYVYWQTSE SKTVVTYHIP QVSSLELVDS   60
RYRNRALMSP AGMLRGDFSL RLFNVTPQDE QKFHCLVLSA SLGFQEVLSV EVTLHVAANF  120
SV                                                                122

SEQ ID NO: 759              moltype = AA  length = 122
FEATURE                    Location/Qualifiers
REGION                     1..122
                           note = ICOSL v205 IgV
source                     1..122
                           mol_type = protein
                           organism = synthetic construct
SEQUENCE: 759
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSK SLGFQEVLSV EVTLHVAANF  120
SV                                                                122

SEQ ID NO: 760              moltype = AA  length = 122
FEATURE                    Location/Qualifiers
REGION                     1..122
                           note = ICOSL v206 IgV
source                     1..122
                           mol_type = protein
                           organism = synthetic construct
SEQUENCE: 760
DTQEKEVRAM VGSDVELSCA CPEGSRFDLN DVYVYWQTSE SKTVVTYHIP QKSSLEYVDS   60
RYRNRALMSP AGMLRGDFSL RLFNVTPQDE QKFHCLVLSR SLGFQEVLSV EVTLHVAANF  120
SV                                                                122

SEQ ID NO: 761              moltype = AA  length = 122
FEATURE                    Location/Qualifiers
REGION                     1..122
                           note = ICOSL v207 IgV
source                     1..122
                           mol_type = protein
                           organism = synthetic construct
SEQUENCE: 761
DTQEKEVRAM VGSDVELSCA CPEGSRFDLN DVYVYWQTSE SKTVVTYHIP QLSSLEHVDS   60
RYRNRALMSP AGMLRGDFSL RLFNVTPQDE QKFHCLVLSR SLGFQEVLSV EVTLHVAANF  120
SV                                                                122

SEQ ID NO: 762              moltype = AA  length = 122
FEATURE                    Location/Qualifiers
REGION                     1..122
                           note = ICOSL v208 IgV
source                     1..122
                           mol_type = protein
                           organism = synthetic construct
SEQUENCE: 762
DTQEKEVRAM VGSDVELSCA CPEGSRFDLN DVYVYWQTSE SKTVVTYHIP QRSSLEFVDS   60
RYRNRALMSP AGMLRGDFSL RLFNVTPQDE QKFHCLVLSN SLGFQEVLSV EVTLHVAANF  120
SV                                                                122

SEQ ID NO: 763              moltype = AA  length = 122
FEATURE                    Location/Qualifiers
REGION                     1..122
                           note = ICOSL v209 IgV
source                     1..122
                           mol_type = protein
                           organism = synthetic construct
```

```
SEQUENCE: 763
DTQEKEVRAM VGSDVELSCA CPEGSRFDLN DVYVYWQTSE SKTVVTYHIP QRSSLEFVDS  60
RYRNRALMSP AGMLRGDFSL RLFNVTPQDE QKFHCLVLSP SLGFQEVLSV EVTLHVAANF  120
SV                                                                122

SEQ ID NO: 764           moltype = AA  length = 122
FEATURE                  Location/Qualifiers
REGION                   1..122
                         note = ICOSL v210 IgV
source                   1..122
                         mol_type = protein
                         organism = synthetic construct
SEQUENCE: 764
DTQEKEVRAM VGSDVELSCA CPEGSRFDLN DVYVYWQTSE SKTVVTYHIP QRSSLEFVDS  60
RYRNRALMSP AGMLRGDFSL RLFNVTPQDE QKFHCLVLSR SLGFQEVLSV EVTLHVAANF  120
SV                                                                122

SEQ ID NO: 765           moltype = AA  length = 122
FEATURE                  Location/Qualifiers
REGION                   1..122
                         note = ICOSL v211 IgV
source                   1..122
                         mol_type = protein
                         organism = synthetic construct
SEQUENCE: 765
DTQEKEVRAM VGSDVELSCA CPEGSRFDLN DVYVYWQTSE SKTVVTYHIP QRSSLEFVDS  60
RYRNRALMSP AGMLRGDFSL RLFNVTPQDE QKFHCLVLST SLGFQEVLSV EVTLHVAANF  120
SV                                                                122

SEQ ID NO: 766           moltype = AA  length = 122
FEATURE                  Location/Qualifiers
REGION                   1..122
                         note = ICOSL v212 IgV
source                   1..122
                         mol_type = protein
                         organism = synthetic construct
SEQUENCE: 766
DTQEKEVRAM VGSDVELSCA CPEGSRFDLN DVYVYWQTSE SKTVVTYHIP QRSSLEHVDS  60
RYRNRALMSP AGMLRGDFSL RLFNVTPQDE QKFHCLVLSK SLGFQEVLSV EVTLHVAANF  120
SV                                                                122

SEQ ID NO: 767           moltype = AA  length = 122
FEATURE                  Location/Qualifiers
REGION                   1..122
                         note = ICOSL v213 IgV
source                   1..122
                         mol_type = protein
                         organism = synthetic construct
SEQUENCE: 767
DTQEKEVRAM VGSDVELSCA CPEGSRFDLN DVYVYWQTSE SKTVVTYHIP QRSSLELVDS  60
RYRNRALMSP AGMLRGDFSL RLFNVTPQDE QKFHCLVLSS SLGFQEVLSV EVTLHVAANF  120
SV                                                                122

SEQ ID NO: 768           moltype = AA  length = 122
FEATURE                  Location/Qualifiers
REGION                   1..122
                         note = ICOSL v214 IgV
source                   1..122
                         mol_type = protein
                         organism = synthetic construct
SEQUENCE: 768
DTQEKEVRAM VGSDVELSCA CPEGSRFDLN DVYVYWQTSE SKTVVTYHIP QRSSLEWVDS  60
RYRNRALMSP AGMLRGDFSL RLFNVTPQDE QKFHCLVLSK SLGFQEVLSV EVTLHVAANF  120
SV                                                                122

SEQ ID NO: 769           moltype = AA  length = 122
FEATURE                  Location/Qualifiers
REGION                   1..122
                         note = ICOSL v215 IgV
source                   1..122
                         mol_type = protein
                         organism = synthetic construct
SEQUENCE: 769
DTQEKEVRAM VGSDVELSCA CPEGSRFDLN DVYVYWQTSE SKTVVTYHIP QRSSLEWVDS  60
RYRNRALMSP AGMLRGDFSL RLFNVTPQDE QKFHCLVLSQ SLGFQEVLSV EVTLHVAANF  120
SV                                                                122

SEQ ID NO: 770           moltype = AA  length = 122
FEATURE                  Location/Qualifiers
```

-continued

```
REGION                      1..122
                            note = ICOSL v216 IgV
source                      1..122
                            mol_type = protein
                            organism = synthetic construct
SEQUENCE: 770
DTQEKEVRAM VGSDVELSCA CPEGSRFDLN DVYVYWQTSE SKTVVTYHIP QRSSLEYVDS    60
RYRNRALMSP AGMLRGDFSL RLFNVTPQDE QKFHCLVLSR SLGFQEVLSV EVTLHVAANF   120
SV                                                                  122

SEQ ID NO: 771              moltype = AA   length = 122
FEATURE                     Location/Qualifiers
REGION                      1..122
                            note = ICOSL v217 IgV
source                      1..122
                            mol_type = protein
                            organism = synthetic construct
SEQUENCE: 771
DTQEKEVRAM VGSDVELSCA CPEGSRFDLN DVYVYWQTSE SKTVVTYHIP QCSSLEEVDS    60
RYRNRALMSP AGMLRGDFSL RLFNVTPQDE QKFHCLVLSS SLGFQEVLSV EVTLHVAANF   120
SV                                                                  122

SEQ ID NO: 772              moltype = AA   length = 122
FEATURE                     Location/Qualifiers
REGION                      1..122
                            note = ICOSL v218 IgV
source                      1..122
                            mol_type = protein
                            organism = synthetic construct
SEQUENCE: 772
DTQEKEVRAM VGSDVELSCA CPEGSRFDLN DVYVYWQTSE SKTVVTYHIP QGSSLEPVDS    60
RYRNRALMSP AGMLRGDFSL RLFNVTPQDE QKFHCLVLSD SLGFQEVLSV EVTLHVAANF   120
SV                                                                  122

SEQ ID NO: 773              moltype = AA   length = 122
FEATURE                     Location/Qualifiers
REGION                      1..122
                            note = ICOSL v219 IgV
source                      1..122
                            mol_type = protein
                            organism = synthetic construct
SEQUENCE: 773
DTQEKEVRAM VGSDVELSCA CPEGSRFDLN DVYVYWQTSE SKTVVTYHIP QGSSLEVVDS    60
RYRNRALMSP AGMLRGDFSL RLFNVTPQDE QKFHCLVLSG SLGFQEVLSV EVTLHVAANF   120
SV                                                                  122

SEQ ID NO: 774              moltype = AA   length = 122
FEATURE                     Location/Qualifiers
REGION                      1..122
                            note = ICOSL v220 IgV
source                      1..122
                            mol_type = protein
                            organism = synthetic construct
SEQUENCE: 774
DTQEKEVRAM VGSDVELSCA CPEGSRFDLN DVYVYWQTSE SKTVVTYHIP QGSSLEVVDS    60
RYRNRALMSP AGMLRGDFSL RLFNVTPQDE QKFHCLVLSQ SLGFQEVLSV EVTLHVAANF   120
SV                                                                  122

SEQ ID NO: 775              moltype = AA   length = 122
FEATURE                     Location/Qualifiers
REGION                      1..122
                            note = ICOSL v221 IgV
source                      1..122
                            mol_type = protein
                            organism = synthetic construct
SEQUENCE: 775
DTQEKEVRAM VGSDVELSCA CPEGSRFDLN DVYVYWQTSE SKTVVTYHIP QLSSLEVVDS    60
RYRNRALMSP AGMLRGDFSL RLFNVTPQDE QKFHCLVLSQ SLGFQEVLSV EVTLHVAANF   120
SV                                                                  122

SEQ ID NO: 776              moltype = AA   length = 122
FEATURE                     Location/Qualifiers
REGION                      1..122
                            note = ICOSL v222 IgV
source                      1..122
                            mol_type = protein
                            organism = synthetic construct
SEQUENCE: 776
DTQEKEVRAM VGSDVELSCA CPEGSRFDLN DVYVYWQTSE SKTVVTYHIP QPSSLEPVDS    60
```

-continued

```
RYRNRALMSP AGMLRGDFSL RLFNVTPQDE QKFHCLVLSQ SLGFQEVLSV EVTLHVAANF   120
SV                                                                  122

SEQ ID NO: 777          moltype = AA   length = 122
FEATURE                 Location/Qualifiers
REGION                  1..122
                        note = ICOSL v223 IgV
source                  1..122
                        mol_type = protein
                        organism = synthetic construct
SEQUENCE: 777
DTQEKEVRAM VGSDVELSCA CPEGSRFDLN DVYVYWQTSE SKTVVTYHIP QPSSLESVDS   60
RYRNRALMSP AGMLRGDFSL RLFNVTPQDE QKFHCLVLSG SLGFQEVLSV EVTLHVAANF   120
SV                                                                  122

SEQ ID NO: 778          moltype = AA   length = 122
FEATURE                 Location/Qualifiers
REGION                  1..122
                        note = ICOSL v224 IgV
source                  1..122
                        mol_type = protein
                        organism = synthetic construct
SEQUENCE: 778
DTQEKEVRAM VGSDVELSCA CPEGSRFDLN DVYVYWQTSE SKTVVTYHIP QSSSLELVDS   60
RYRNRALMSP AGMLRGDFSL RLFNVTPQDE QKFHCLVLSG SLGFQEVLSV EVTLHVAANF   120
SV                                                                  122

SEQ ID NO: 779          moltype = AA   length = 122
FEATURE                 Location/Qualifiers
REGION                  1..122
                        note = ICOSL v225 IgV
source                  1..122
                        mol_type = protein
                        organism = synthetic construct
SEQUENCE: 779
DTQEKEVRAM VGSDVELSCA CPEGSRFDLN DVYVYWQTSE SKTVVTYHIP QTSSLEKVDS   60
RYRNRALMSP AGMLRGDFSL RLFNVTPQDE QKFHCLVLSP SLGFQEVLSV EVTLHVAANF   120
SV                                                                  122

SEQ ID NO: 780          moltype = AA   length = 122
FEATURE                 Location/Qualifiers
REGION                  1..122
                        note = ICOSL v226 IgV
source                  1..122
                        mol_type = protein
                        organism = synthetic construct
SEQUENCE: 780
DTQEKEVRAM VGSDVELSCA CPEGSRFDLN DVYVYWQTSE SKTVVTYHIP QVSSLETVDS   60
RYRNRALMSP AGMLRGDFSL RLFNVTPQDE QKFHCLVLSL SLGFQEVLSV EVTLHVAANF   120
SV                                                                  122

SEQ ID NO: 781          moltype = AA   length = 122
FEATURE                 Location/Qualifiers
REGION                  1..122
                        note = ICOSL v227 IgV
source                  1..122
                        mol_type = protein
                        organism = synthetic construct
SEQUENCE: 781
DTQEKEVRAM VGSDVELSCA CPEGSRFDLN DVYVYWQTSE SKTVVTYHIP QNSSLEQVDS   60
RYRNRALMSP AGMLRGDFSL RLFNVTPQDE QKFHCLVLSP SLGFQEVLSV EVTLHVAANF   120
SV                                                                  122

SEQ ID NO: 782          moltype = AA   length = 111
FEATURE                 Location/Qualifiers
REGION                  1..111
                        note = ICOSL v4 IgV
source                  1..111
                        mol_type = protein
                        organism = synthetic construct
SEQUENCE: 782
DTQEKEVRAM VGSDVELSCA CPEGSRFDLN DVYVYWQTSE SKTVVTYHIP QYSSLEYVDS   60
RYRNRALMSP AGMLRGDFSL RLFNVTPQDE QKFHCLVLSQ SLGFQEVLSV E           111

SEQ ID NO: 783          moltype = AA   length = 122
FEATURE                 Location/Qualifiers
REGION                  1..122
                        note = ICOSL v4 IgV
source                  1..122
```

-continued

```
                            mol_type = protein
                            organism = synthetic construct
SEQUENCE: 783
DTQEKEVRAM VGSDVELSCA CPEGSRFDLN DVYVYWQTSE SKTVVTYHIP QYSSLEYVDS    60
RYRNRALMSP AGMLRGDFSL RLFNVTPQDE QKFHCLVLSQ SLGFQEVLSV EVTLHVAANF   120
SV                                                                 122

SEQ ID NO: 784          moltype = AA  length = 111
FEATURE                 Location/Qualifiers
REGION                  1..111
                        note = ICOSL v21 IgV
source                  1..111
                        mol_type = protein
                        organism = synthetic construct
SEQUENCE: 784
DTQEKEVRAM VGSDVELSCA CPEGSRFDLN DVYVYWQTSE SKTVVTYHIP QSSSLENVDS    60
RYRNRALMSP AGMLRGDFSL RLFNVTPQDE QKFHCLVLSQ SLGFQEVLSV E           111

SEQ ID NO: 785          moltype = AA  length = 111
FEATURE                 Location/Qualifiers
REGION                  1..111
                        note = ICOSL v24 IgV
source                  1..111
                        mol_type = protein
                        organism = synthetic construct
SEQUENCE: 785
DTQEKEVRAM VGSDVELSCA CPEGSRFDLN DVYVYWQTSE SKTVVTYHIP QKSSLENVDS    60
RYRNRALMSP AGMLRGDFSL RLFNVTPQDE QKFHCLVLSQ SLGFQEVLSV E           111

SEQ ID NO: 786          moltype = AA  length = 122
FEATURE                 Location/Qualifiers
REGION                  1..122
                        note = ICOSL v24 IgV
source                  1..122
                        mol_type = protein
                        organism = synthetic construct
SEQUENCE: 786
DTQEKEVRAM VGSDVELSCA CPEGSRFDLN DVYVYWQTSE SKTVVTYHIP QKSSLENVDS    60
RYRNRALMSP AGMLRGDFSL RLFNVTPQDE QKFHCLVLSQ SLGFQEVLSV EVTLHVAANF   120
SV                                                                 122

SEQ ID NO: 787          moltype = AA  length = 111
FEATURE                 Location/Qualifiers
REGION                  1..111
                        note = ICOSL v30 IgV
source                  1..111
                        mol_type = protein
                        organism = synthetic construct
SEQUENCE: 787
DTQEKEVRAM VGSDVELSCA CPEGSRFDLN DVYVYWQTSE SKTVVTYHIP QSSSLENVDS    60
RYRNRALMSP AGMLQGDFSL RLFNVTPQDE QKFHCLVLSQ SLGFQEVLSV E           111

SEQ ID NO: 788          moltype = AA  length = 122
FEATURE                 Location/Qualifiers
REGION                  1..122
                        note = ICOSL v30 IgV
source                  1..122
                        mol_type = protein
                        organism = synthetic construct
SEQUENCE: 788
DTQEKEVRAM VGSDVELSCA CPEGSRFDLN DVYVYWQTSE SKTVVTYHIP QSSSLENVDS    60
RYRNRALMSP AGMLQGDFSL RLFNVTPQDE QKFHCLVLSQ SLGFQEVLSV EVTLHVAANF   120
SV                                                                 122

SEQ ID NO: 789          moltype = AA  length = 111
FEATURE                 Location/Qualifiers
REGION                  1..111
                        note = ICOSL v34 IgV
source                  1..111
                        mol_type = protein
                        organism = synthetic construct
SEQUENCE: 789
DTQEKEVRAM VGSDVELSCA CPEGSRFDLN DVYVYWQTSE SKTVVTYHIP QSSSLEYVDS    60
RYRNRALMSP AGMLRGDFSL RLFNVTPQDE QKFDCFVFSR SLEFQEVLSV E           111

SEQ ID NO: 790          moltype = AA  length = 111
FEATURE                 Location/Qualifiers
REGION                  1..111
                        note = ICOSL v96 IgV
```

-continued

```
source                   1..111
                         mol_type = protein
                         organism = synthetic construct
SEQUENCE: 790
DTQEKEVRAM VGSDVELSCA CPEGSRFDLN DVYVYWQTSE SKAVVTYHIP QHSSLEYVDS    60
RYRNRALMSP AGMQRGDFSL RLFNVTPQGE QKFHCLVLSQ SLGFQEVLSD E             111

SEQ ID NO: 791          moltype = AA  length = 111
FEATURE                 Location/Qualifiers
REGION                  1..111
                        note = ICOSL v45 IgV
source                  1..111
                        mol_type = protein
                        organism = synthetic construct
SEQUENCE: 791
DTQEKEVRAM VGSDVELSCA CPEGSRFDLN DVYVYWQTSE SKTVVTYHIP QHSSLEYVDS    60
SYRNRALMSP AGMLRGDFSL RLFNVTPQDE QKFHCLVLSR SLGFQEVLSD E             111

SEQ ID NO: 792          moltype = AA  length = 122
FEATURE                 Location/Qualifiers
REGION                  1..122
                        note = ICOSL v45 IgV
source                  1..122
                        mol_type = protein
                        organism = synthetic construct
SEQUENCE: 792
DTQEKEVRAM VGSDVELSCA CPEGSRFDLN DVYVYWQTSE SKTVVTYHIP QHSSLEYVDS    60
SYRNRALMSP AGMLRGDFSL RLFNVTPQDE QKFHCLVLSR SLGFQEVLSD EVTLHVAANF   120
SV                                                                  122

SEQ ID NO: 793          moltype = AA  length = 111
FEATURE                 Location/Qualifiers
REGION                  1..111
                        note = ICOSL v52 IgV
source                  1..111
                        mol_type = protein
                        organism = synthetic construct
SEQUENCE: 793
DTQEKEVRAM VGSDVELSCA CPEGSRFDLN DVYVYWQTSE SKTVVTYHIP QSSSLENVDS    60
RYRNRALMSP TGMLRGDFSL RLFNVTPQDE QKFHCLVLSQ SLGFQEVLSV E             111

SEQ ID NO: 794          moltype = AA  length = 111
FEATURE                 Location/Qualifiers
REGION                  1..111
                        note = ICOSL v54 IgV
source                  1..111
                        mol_type = protein
                        organism = synthetic construct
SEQUENCE: 794
DTQEKEVRAM VGSDVELSCA CPEGSRFDLN DVYVYWQTSE SKTVVTHHIP QSSSLENVDS    60
RYRNRALMSP AGMLRGDFSL RLFNVTPQDE QKFHCLVLSQ SLGFQEALSV E             111

SEQ ID NO: 795          moltype = AA  length = 111
FEATURE                 Location/Qualifiers
REGION                  1..111
                        note = ICOSL v56 IgV
source                  1..111
                        mol_type = protein
                        organism = synthetic construct
SEQUENCE: 795
DTQEKEVRAM VGSDVVLSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD E             111

SEQ ID NO: 796          moltype = AA  length = 122
FEATURE                 Location/Qualifiers
REGION                  1..122
                        note = ICOSL v56 IgV
source                  1..122
                        mol_type = protein
                        organism = synthetic construct
SEQUENCE: 796
DTQEKEVRAM VGSDVVLSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD EVTLRVAANF   120
SV                                                                  122

SEQ ID NO: 797          moltype = AA  length = 111
FEATURE                 Location/Qualifiers
REGION                  1..111
                        note = ICOSL v57 IgV
```

-continued

```
source                   1..111
                         mol_type = protein
                         organism = synthetic construct
SEQUENCE: 797
DTQEKEVRAM VGSDVELSCA CPEGSRFDLN DVYVYWRTSE SKTVVTYHIP QHSSLEYVDS   60
RYRNRALMSP AGMLRGDFSL RLFNVTPQDE QKFHCLVLSR SLGFQEVLSN E            111

SEQ ID NO: 798          moltype = AA  length = 122
FEATURE                 Location/Qualifiers
REGION                  1..122
                        note = ICOSL v57 IgV
source                  1..122
                        mol_type = protein
                        organism = synthetic construct
SEQUENCE: 798
DTQEKEVRAM VGSDVELSCA CPEGSRFDLN DVYVYWRTSE SKTVVTYHIP QHSSLEYVDS   60
RYRNRALMSP AGMLRGDFSL RLFNVTPQDE QKFHCLVLSR SLGFQEVLSN EVTLHVAANF  120
SV                                                                 122

SEQ ID NO: 799          moltype = AA  length = 111
FEATURE                 Location/Qualifiers
REGION                  1..111
                        note = ICOSL v59 IgV
source                  1..111
                        mol_type = protein
                        organism = synthetic construct
SEQUENCE: 799
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSR SLGFQEVLSD E            111

SEQ ID NO: 800          moltype = AA  length = 122
FEATURE                 Location/Qualifiers
REGION                  1..122
                        note = ICOSL v59 IgV
source                  1..122
                        mol_type = protein
                        organism = synthetic construct
SEQUENCE: 800
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSR SLGFQEVLSD EVTLHAAANF  120
SV                                                                 122

SEQ ID NO: 801          moltype = AA  length = 111
FEATURE                 Location/Qualifiers
REGION                  1..111
                        note = ICOSL v61 IgV
source                  1..111
                        mol_type = protein
                        organism = synthetic construct
SEQUENCE: 801
DTQEKEVRAM VGSDVELSCA CPEGSRFDLN DVYVYWQTSE SKTVVTYHIP QSSSLENVDS   60
RYRNRALMSP AGMLRGDFSL RLFNVTPQDE QKFECIVLSQ SLGFQEVLNV E            111

SEQ ID NO: 802          moltype = AA  length = 122
FEATURE                 Location/Qualifiers
REGION                  1..122
                        note = ICOSL v61 IgV
source                  1..122
                        mol_type = protein
                        organism = synthetic construct
SEQUENCE: 802
DTQEKEVRAM VGSDVELSCA CPEGSRFDLN DVYVYWQTSE SKTVVTYHIP QSSSLENVDS   60
RYRNRALMSP AGMLRGDFSL RLFNVTPQDE QKFECIVLSQ SLGFQEVLNV EVTLHVAANF  120
SV                                                                 122

SEQ ID NO: 803          moltype = AA  length = 111
FEATURE                 Location/Qualifiers
REGION                  1..111
                        note = ICOSL v62 IgV
source                  1..111
                        mol_type = protein
                        organism = synthetic construct
SEQUENCE: 803
DTQEKEVRAM VGSDVELRCA CPEGSRFDLN DVYVYWQTSE SKTVVTYHIP QSSSLENVDS   60
RYRNRALMSP AGMLRGDFSL RLFNVTPQDE QKLHCLVLSQ SLGFQEVLSV E            111

SEQ ID NO: 804          moltype = AA  length = 122
FEATURE                 Location/Qualifiers
REGION                  1..122
```

-continued

```
                            note = ICOSL v62 IgV
source                      1..122
                            mol_type = protein
                            organism = synthetic construct
SEQUENCE: 804
DTQEKEVRAM VGSDVELRCA CPEGSRFDLN DVYVYWQTSE SKTVVTYHIP QSSSLENVDS   60
RYRNRALMSP AGMLRGDFSL RLFNVTPQDE QKLHCLVLSQ SLGFQEVLSV EVTLHVAANF  120
SV                                                                 122

SEQ ID NO: 805             moltype = AA  length = 111
FEATURE                    Location/Qualifiers
REGION                     1..111
                           note = ICOSL v63 IgV
source                     1..111
                           mol_type = protein
                           organism = synthetic construct
SEQUENCE: 805
DTQEKEVRAM VGSDVELSCT CPEGSRFDLN DVYVYWQTSE SKTVVTYHIP QDSSLENVDS   60
RYRNRALMSP AGMLRGDFSL RLFNVTPQDE QKFHCLVLSQ SLGFQEVLSV E           111

SEQ ID NO: 806             moltype = AA  length = 122
FEATURE                    Location/Qualifiers
REGION                     1..122
                           note = ICOSL v63 IgV
source                     1..122
                           mol_type = protein
                           organism = synthetic construct
SEQUENCE: 806
DTQEKEVRAM VGSDVELSCT CPEGSRFDLN DVYVYWQTSE SKTVVTYHIP QDSSLENVDS   60
RYRNRALMSP AGMLRGDFSL RLFNVTPQDE QKFHCLVLSQ SLGFQEVLSV EVTLHVAANF  120
SV                                                                 122

SEQ ID NO: 807             moltype = AA  length = 111
FEATURE                    Location/Qualifiers
REGION                     1..111
                           note = ICOSL v64 IgV
source                     1..111
                           mol_type = protein
                           organism = synthetic construct
SEQUENCE: 807
DTQEKEVRAM EGSDVELSCA CPEGSRFDLD DVYVYWQTSE SKTVVTYHIP QHSSLEYVDS   60
RYRNRALMSP AGMLRGDFSL RLFNVTPQDE QKFECIVFSQ SLGFQEVLSV E           111

SEQ ID NO: 808             moltype = AA  length = 122
FEATURE                    Location/Qualifiers
REGION                     1..122
                           note = ICOSL v64 IgV
source                     1..122
                           mol_type = protein
                           organism = synthetic construct
SEQUENCE: 808
DTQEKEVRAM EGSDVELSCA CPEGSRFDLD DVYVYWQTSE SKTVVTYHIP QHSSLEYVDS   60
RYRNRALMSP AGMLRGDFSL RLFNVTPQDE QKFECIVFSQ SLGFQEVLSV EVTLHVAANF  120
SV                                                                 122

SEQ ID NO: 809             moltype = AA  length = 111
FEATURE                    Location/Qualifiers
REGION                     1..111
                           note = ICOSL v65 IgV
source                     1..111
                           mol_type = protein
                           organism = synthetic construct
SEQUENCE: 809
DTQEKEVRAM VGSDVELSCA CPEGSRFDLN DVYVYWQTSE SKTVVTYHIP QSSSLENVDS   60
RYRNRALMSP AGMLRGDFSL RLFNVTPQDE QKFECIVLSQ SLGFQEVLSV E           111

SEQ ID NO: 810             moltype = AA  length = 111
FEATURE                    Location/Qualifiers
REGION                     1..111
                           note = ICOSL v66 IgV
source                     1..111
                           mol_type = protein
                           organism = synthetic construct
SEQUENCE: 810
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFECIVLSQ SLGFQEVLSV E           111

SEQ ID NO: 811             moltype = AA  length = 122
FEATURE                    Location/Qualifiers
```

-continued

```
REGION                    1..122
                          note = ICOSL v66 IgV
source                    1..122
                          mol_type = protein
                          organism = synthetic construct
SEQUENCE: 811
DTQEKEVRAM VGSDVELSCA CPEGSRFDLN DVYVYWQTSE SKTVVTYHIP QHSSLEYVDS  60
RYRNRALMSP AGMLRGDFSL RLFNVTPQDE QKFECIVLSQ SLGFQEVLSV EVTLHVAANI  120
SV                                                                 122

SEQ ID NO: 812            moltype = AA  length = 111
FEATURE                   Location/Qualifiers
REGION                    1..111
                          note = ICOSL v67 IgV
source                    1..111
                          mol_type = protein
                          organism = synthetic construct
SEQUENCE: 812
DTQEKEVRAV VGSDVELRCA CPEGSRFDLD DVYVYWQTSE SKTVVTYHIP QSSSLENVDS  60
RYRNRALMSP AGMLRGDFSL RLFNVTPQDE QKFHCLVLSQ SLGFQEVLSV E           111

SEQ ID NO: 813            moltype = AA  length = 122
FEATURE                   Location/Qualifiers
REGION                    1..122
                          note = ICOSL v67 IgV
source                    1..122
                          mol_type = protein
                          organism = synthetic construct
SEQUENCE: 813
DTQEKEVRAV VGSDVELRCA CPEGSRFDLD DVYVYWQTSE SKTVVTYHIP QSSSLENVDS  60
RYRNRALMSP AGMLRGDFSL RLFNVTPQDE QKFHCLVLSQ SLGFQEVLSV EVTLHVAANF  120
SV                                                                 122

SEQ ID NO: 814            moltype = AA  length = 111
FEATURE                   Location/Qualifiers
REGION                    1..111
                          note = ICOSL v68 IgV
source                    1..111
                          mol_type = protein
                          organism = synthetic construct
SEQUENCE: 814
DTQEKEVRAM VGSDVELSCA CPEGGRFDLD DVYVYWQTSE SKTVVTYHIP QSSSLENVDS  60
RYRNRALMSP AGMLRGDFSL RLFNVTPQDE QKFHCLVLSQ SLGFQEVLSV E           111

SEQ ID NO: 815            moltype = AA  length = 122
FEATURE                   Location/Qualifiers
REGION                    1..122
                          note = ICOSL v68 IgV
source                    1..122
                          mol_type = protein
                          organism = synthetic construct
SEQUENCE: 815
DTQEKEVRAM VGSDVELSCA CPEGGRFDLD DVYVYWQTSE SKTVVTYHIP QSSSLENVDS  60
RYRNRALMSP AGMLRGDFSL RLFNVTPQDE QKFHCLVLSQ SLGFQEVLSV EVTLHVAANS  120
SV                                                                 122

SEQ ID NO: 816            moltype = AA  length = 111
FEATURE                   Location/Qualifiers
REGION                    1..111
                          note = ICOSL v69 IgV
source                    1..111
                          mol_type = protein
                          organism = synthetic construct
SEQUENCE: 816
DTQEKEVRAM VGSDVELSCA CPEGSRFDLD DVYVYWQTSE SKTVVTYHIP QSSSLENVDS  60
RYRNRAPMSP AGMLRGDFSL RLFNVTPQDE QKFHCLVLSK SLGFQEVLSV E           111

SEQ ID NO: 817            moltype = AA  length = 122
FEATURE                   Location/Qualifiers
REGION                    1..122
                          note = ICOSL v69 IgV
source                    1..122
                          mol_type = protein
                          organism = synthetic construct
SEQUENCE: 817
DTQEKEVRAM VGSDVELSCA CPEGSRFDLD DVYVYWQTSE SKTVVTYHIP QSSSLENVDS  60
RYRNRAPMSP AGMLRGDFSL RLFNVTPQDE QKFHCLVLSK SLGFQEVLSV EVTLHVAANF  120
SV                                                                 122
```

```
SEQ ID NO: 818          moltype = AA  length = 122
FEATURE                 Location/Qualifiers
REGION                  1..122
                        note = ICOSL v70 IgV
source                  1..122
                        mol_type = protein
                        organism = synthetic construct
SEQUENCE: 818
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSR SLGFQEVLSD EVTLHVTANF  120
SV                                                                122

SEQ ID NO: 819          moltype = AA  length = 111
FEATURE                 Location/Qualifiers
REGION                  1..111
                        note = ICOSL v72 IgV
source                  1..111
                        mol_type = protein
                        organism = synthetic construct
SEQUENCE: 819
DTQEKEVRAM VGSDVELSCA CPEGGRCDLN DVYVYWQTSE SKTVVTYHIP QHSSLEYVDS   60
RYRNRALMSP AGMLRGDFSL RLFNVTPQDE QKFHCLVLSR SLGFQEVLSD E           111

SEQ ID NO: 820          moltype = AA  length = 122
FEATURE                 Location/Qualifiers
REGION                  1..122
                        note = ICOSL v72 IgV
source                  1..122
                        mol_type = protein
                        organism = synthetic construct
SEQUENCE: 820
DTQEKEVRAM VGSDVELSCA CPEGGRCDLN DVYVYWQTSE SKTVVTYHIP QHSSLEYVDS   60
RYRNRALMSP AGMLRGDFSL RLFNVTPQDE QKFHCLVLSR SLGFQEVLSD EVTLHVAANF  120
SV                                                                122

SEQ ID NO: 821          moltype = AA  length = 111
FEATURE                 Location/Qualifiers
REGION                  1..111
                        note = ICOSL v73 IgV
source                  1..111
                        mol_type = protein
                        organism = synthetic construct
SEQUENCE: 821
DTQEKEVRAI VGGDVELSCA CPEGSRFDLN DVYVYWQTSE SKTVVTYHIP QHSSLEYVDS   60
RYRNRALMSP AGMLRGGFSL RLFNVTPQDE QKFHCLVLSQ SLGFQEVLSA E           111

SEQ ID NO: 822          moltype = AA  length = 122
FEATURE                 Location/Qualifiers
REGION                  1..122
                        note = ICOSL v73 IgV
source                  1..122
                        mol_type = protein
                        organism = synthetic construct
SEQUENCE: 822
DTQEKEVRAI VGGDVELSCA CPEGSRFDLN DVYVYWQTSE SKTVVTYHIP QHSSLEYVDS   60
RYRNRALMSP AGMLRGGFSL RLFNVTPQDE QKFHCLVLSQ SLGFQEVLSA EVTLHVAANF  120
SV                                                                122

SEQ ID NO: 823          moltype = AA  length = 111
FEATURE                 Location/Qualifiers
REGION                  1..111
                        note = ICOSL v74 IgV
source                  1..111
                        mol_type = protein
                        organism = synthetic construct
SEQUENCE: 823
DTQEKEVRAI VGGDVELSCA CPEGSRFDLN DVYVYWQTSE SKTVVTYHIP QHSSLEYVDS   60
RYRNRALMSP AGMLRGGFSL RLFNVTPQDE QKFHCLVLSQ SLGFQEVLSA E           111

SEQ ID NO: 824          moltype = AA  length = 122
FEATURE                 Location/Qualifiers
REGION                  1..122
                        note = ICOSL v74 IgV
source                  1..122
                        mol_type = protein
                        organism = synthetic construct
SEQUENCE: 824
DTQEKEVRAI VGGDVELSCA CPEGSRFDLN DVYVYWQTSE SKTVVTYHIP QHSSLEYVDS   60
RYRNRALMSP AGMLRGGFSL RLFNVTPQDE QKFHCLVLSQ SLGFQEVLSA EVTLHVAANF  120
```

-continued

```
SV                                                                          122

SEQ ID NO: 825           moltype = AA   length = 111
FEATURE                  Location/Qualifiers
REGION                   1..111
                         note = ICOSL v75 IgV
source                   1..111
                         mol_type = protein
                         organism = synthetic construct
SEQUENCE: 825
DTQEKEVRAM VGSDVELSCA CPEGSRFDLN DVYVYWQTSE SKTVVTYHIP QHSSLEYVDS    60
CFRNRALMSP AGMLRGDFSL RLFNVTPQDE QKFHCLVLSR SLGFQEVLSN E            111

SEQ ID NO: 826           moltype = AA   length = 122
FEATURE                  Location/Qualifiers
REGION                   1..122
                         note = ICOSL v75 IgV
source                   1..122
                         mol_type = protein
                         organism = synthetic construct
SEQUENCE: 826
DTQEKEVRAM VGSDVELSCA CPEGSRFDLN DVYVYWQTSE SKTVVTYHIP QHSSLEYVDS    60
CFRNRALMSP AGMLRGDFSL RLFNVTPQDE QKFHCLVLSR SLGFQEVLSN EVTLHVAANS   120
SV                                                                          122

SEQ ID NO: 827           moltype = AA   length = 122
FEATURE                  Location/Qualifiers
REGION                   1..122
                         note = ICOSL v76 IgV
source                   1..122
                         mol_type = protein
                         organism = synthetic construct
SEQUENCE: 827
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD EVTLRVAANF   120
SV                                                                          122

SEQ ID NO: 828           moltype = AA   length = 111
FEATURE                  Location/Qualifiers
REGION                   1..111
                         note = ICOSL v81 IgV
source                   1..111
                         mol_type = protein
                         organism = synthetic construct
SEQUENCE: 828
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD E            111

SEQ ID NO: 829           moltype = AA   length = 122
FEATURE                  Location/Qualifiers
REGION                   1..122
                         note = ICOSL v81 IgV
source                   1..122
                         mol_type = protein
                         organism = synthetic construct
SEQUENCE: 829
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD EVTLHVAANF   120
SV                                                                          122

SEQ ID NO: 830           moltype = AA   length = 111
FEATURE                  Location/Qualifiers
REGION                   1..111
                         note = ICOSL v84 IgV
source                   1..111
                         mol_type = protein
                         organism = synthetic construct
SEQUENCE: 830
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SRGFQEVLSD E            111

SEQ ID NO: 831           moltype = AA   length = 122
FEATURE                  Location/Qualifiers
REGION                   1..122
                         note = ICOSL v84 IgV
source                   1..122
                         mol_type = protein
                         organism = synthetic construct
SEQUENCE: 831
```

-continued

```
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SRGFQEVLSD EVTLRVAANF   120
SV                                                                 122

SEQ ID NO: 832           moltype = AA  length = 111
FEATURE                  Location/Qualifiers
REGION                   1..111
                         note = ICOSL v92 IgV
source                   1..111
                         mol_type = protein
                         organism = synthetic construct
SEQUENCE: 832
DTQEKEVRAM VGSDVELSCA CPEGSRFDLN DVYVYWQTSE SKTVVTYHIP QHSSLEYVDS    60
RYRNRALMSP AGMQRGDFSL RLFNVTPQDE QKFHCLVLSQ SLGFQEVLSD E            111

SEQ ID NO: 833           moltype = AA  length = 122
FEATURE                  Location/Qualifiers
REGION                   1..122
                         note = ICOSL v92 IgV
source                   1..122
                         mol_type = protein
                         organism = synthetic construct
SEQUENCE: 833
DTQEKEVRAM VGSDVELSCA CPEGSRFDLN DVYVYWQTSE SKTVVTYHIP QHSSLEYVDS    60
RYRNRALMSP AGMQRGDFSL RLFNVTPQDE QKFHCLVLSQ SLGFQEVLSD EVTLHVAANF   120
SV                                                                 122

SEQ ID NO: 834           moltype = AA  length = 122
FEATURE                  Location/Qualifiers
REGION                   1..122
                         note = ICOSL v96 IgV
source                   1..122
                         mol_type = protein
                         organism = synthetic construct
SEQUENCE: 834
DTQEKEVRAM VGSDVELSCA CPEGSRFDLN DVYVYWQTSE SKAVVTYHIP QHSSLEYVDS    60
RYRNRALMSP AGMQRGDFSL RLFNVTPQGE QKFHCLVLSQ SLGFQEVLSD EVTLHVAANF   120
SV                                                                 122

SEQ ID NO: 835           moltype = AA  length = 111
FEATURE                  Location/Qualifiers
REGION                   1..111
                         note = ICOSL v98 IgV
source                   1..111
                         mol_type = protein
                         organism = synthetic construct
SEQUENCE: 835
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEILSD E            111

SEQ ID NO: 836           moltype = AA  length = 122
FEATURE                  Location/Qualifiers
REGION                   1..122
                         note = ICOSL v98 IgV
source                   1..122
                         mol_type = protein
                         organism = synthetic construct
SEQUENCE: 836
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEILSD EVTLHVAANF   120
SV                                                                 122

SEQ ID NO: 837           moltype = AA  length = 111
FEATURE                  Location/Qualifiers
REGION                   1..111
                         note = ICOSL v103 IgV
source                   1..111
                         mol_type = protein
                         organism = synthetic construct
SEQUENCE: 837
DTQEKEVRAM VGSDVELSCA CPEGSRFDLN DVYVYWQTSE SKTVVTYHIP QQSSLENVDS    60
RYRNRALMSP AGMLRGDFSL RLFNVTPQDE QKFHCLVLSQ SLGFQEVLSV E            111

SEQ ID NO: 838           moltype = AA  length = 122
FEATURE                  Location/Qualifiers
REGION                   1..122
                         note = ICOSL v103 IgV
source                   1..122
                         mol_type = protein
```

-continued

```
                             organism = synthetic construct
SEQUENCE: 838
DTQEKEVRAM VGSDVELSCA CPEGSRFDLN DVYVYWQTSE SKTVVTYHIP QQSSLENVDS    60
RYRNRALMSP AGMLRGDFSL RLFNVTPQDE QKFHCLVLSQ SLGFQEVLSV EVTLHVAANF   120
SV                                                                 122

SEQ ID NO: 839          moltype = AA  length = 111
FEATURE                 Location/Qualifiers
REGION                  1..111
                        note = ICOSL v126 IgV
source                  1..111
                        mol_type = protein
                        organism = synthetic construct
SEQUENCE: 839
DTQEKEVRAM VGSDVELSCA CPEGSRFDLN DVYVYWQTSE SKTVVTYHIP QHSSLENVDS    60
RYRNRALMSP AGMLRGDFSL RLFQVTPQDE QKFHCLVLSQ SLGFQEVLSV E           111

SEQ ID NO: 840          moltype = AA  length = 122
FEATURE                 Location/Qualifiers
REGION                  1..122
                        note = ICOSL v106 IgV
source                  1..122
                        mol_type = protein
                        organism = synthetic construct
SEQUENCE: 840
DTQEKEVRAM VGSDVELSCA CPEGSRFDLN DVYVYWQTSE SKTVVTYHIP QNSSLENVDS    60
RYRNRALMSP AGMLRGDFSL RLFQVTPQDE QKFHCLVLSQ SLGFQEVLSV EVTLHVAANF   120
SV                                                                 122

SEQ ID NO: 841          moltype = AA  length = 122
FEATURE                 Location/Qualifiers
REGION                  1..122
                        note = ICOSL v127 IgV
source                  1..122
                        mol_type = protein
                        organism = synthetic construct
SEQUENCE: 841
DTQEKEVRAM VGSDVELSCA CPEGSRFDLN DVYVYWQTSE SKTVVTYHIP QHSSLENVDS    60
RYRNRALMSP AGMLRGDFSL RLFQVTPQDE QKFHCLVLSQ SLGFQEVLSV EVTLHVAANF   120
SV                                                                 122

SEQ ID NO: 842          moltype = AA  length = 122
FEATURE                 Location/Qualifiers
REGION                  1..122
                        note = ICOSL v108 IgV
source                  1..122
                        mol_type = protein
                        organism = synthetic construct
SEQUENCE: 842
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSQ SLGFQEVLSV EVTLHVAAQF   120
SV                                                                 122

SEQ ID NO: 843          moltype = AA  length = 122
FEATURE                 Location/Qualifiers
REGION                  1..122
                        note = ICOSL v129 IgV
source                  1..122
                        mol_type = protein
                        organism = synthetic construct
SEQUENCE: 843
DTQEKEVRAM VGSDVELSCA CPEGSRFDLN DVYVYWQTSE SKTVVTYHIP QQSSLENVDS    60
RYRNRALMSP AGMLRGDFSL RLFQVTPQDE QKFHCLVLSQ SLGFQEVLSV EVTLHVAAQF   120
SV                                                                 122

SEQ ID NO: 844          moltype = AA  length = 111
FEATURE                 Location/Qualifiers
REGION                  1..111
                        note = ICOSL v140 IgV
source                  1..111
                        mol_type = protein
                        organism = synthetic construct
SEQUENCE: 844
DTQEKEVRAM VGSDVELSCA CPEGSRFDLN DVYVYWQTSE SKTVVTYHIP QNSSLEYVDS    60
RYRNRALMSP AGMLRGDFSL RLFNVTPQDE QKFHCLVLSR SLGFQEVLSV E           111

SEQ ID NO: 845          moltype = AA  length = 122
FEATURE                 Location/Qualifiers
REGION                  1..122
```

-continued

```
                             note = ICOSL v140 IgV
source                       1..122
                             mol_type = protein
                             organism = synthetic construct
SEQUENCE: 845
DTQEKEVRAM VGSDVELSCA CPEGSRFDLN DVYVYWQTSE SKTVVTYHIP QNSSLEYVDS   60
RYRNRALMSP AGMLRGDFSL RLFNVTPQDE QKFHCLVLSR SLGFQEVLSV EVTLHVAANF  120
SV                                                                122

SEQ ID NO: 846               moltype = AA  length = 111
FEATURE                      Location/Qualifiers
REGION                       1..111
                             note = ICOSL v142 IgV
source                       1..111
                             mol_type = protein
                             organism = synthetic construct
SEQUENCE: 846
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSR SLGFQEVLSV E           111

SEQ ID NO: 847               moltype = AA  length = 122
FEATURE                      Location/Qualifiers
REGION                       1..122
                             note = ICOSL v142 IgV
source                       1..122
                             mol_type = protein
                             organism = synthetic construct
SEQUENCE: 847
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSR SLGFQEVLSV EVTLHVAANF  120
SV                                                                122

SEQ ID NO: 848               moltype = AA  length = 122
FEATURE                      Location/Qualifiers
REGION                       1..122
                             note = ICOSL v177 IgV
VARIANT                      115
                             note = x is H or Q
source                       1..122
                             mol_type = protein
                             organism = synthetic construct
SEQUENCE: 848
DTQEKEVRAM VGSDVELSCA CPEGSRFDLN DVYVYWQTSE SKTVVTYHIP QHSSLENVDS   60
RYRNRALMSP AGMLRGDFSL RLFNVTPQDE QKFHCLVLSR SLGFQEVLSV EVTLXVAANF  120
SV                                                                122

SEQ ID NO: 849               moltype = AA  length = 111
FEATURE                      Location/Qualifiers
REGION                       1..111
                             note = ICOSL v148 IgV
source                       1..111
                             mol_type = protein
                             organism = synthetic construct
SEQUENCE: 849
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSR SRGFQEVLSV E           111

SEQ ID NO: 850               moltype = AA  length = 122
FEATURE                      Location/Qualifiers
REGION                       1..122
                             note = ICOSL v148 IgV
source                       1..122
                             mol_type = protein
                             organism = synthetic construct
SEQUENCE: 850
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSR SRGFQEVLSV EVTLRVAANF  120
SV                                                                122

SEQ ID NO: 851               moltype = AA  length = 122
FEATURE                      Location/Qualifiers
REGION                       1..122
                             note = ICOSL v149 IgV
source                       1..122
                             mol_type = protein
                             organism = synthetic construct
SEQUENCE: 851
DTQEKEVRAM VGSDVELSCA CPEGSRFDLN DVYVYWQTSE SKTVVTYHIP QHSSLENVDS   60
RYRNRALMSP AGMLRGDFSL RLFNVTPQDE QKFHCLVLSQ SLGFQEVLSV EVTLHVAANF  120
```

-continued

```
SA                                                               122

SEQ ID NO: 852          moltype = AA  length = 122
FEATURE                 Location/Qualifiers
REGION                  1..122
                        note = ICOSL v158 IgV
source                  1..122
                        mol_type = protein
                        organism = synthetic construct
SEQUENCE: 852
DTQEKEVRAM VGSDVELSCA CPEGSRFDLN DVYVYWQTSE SKTVVTYHIP QHSSLENVDS   60
RYRNRALMSP AGMLRGDFSL RLFNVTPQDE QKFHCLVLSR SLGFQEVLSV EVTLRVAANF  120
SV                                                               122

SEQ ID NO: 853          moltype = AA  length = 122
FEATURE                 Location/Qualifiers
REGION                  1..122
                        note = ICOSL v169 IgV
source                  1..122
                        mol_type = protein
                        organism = synthetic construct
SEQUENCE: 853
DTQEKEVRAM VGSDVELSCA CPEGSRFDLN DVYVYWQTSE SKTVVTYHIP QSSSLENVDS   60
RYRNRALMSP AGMLRGDFSL RLFNVTPQDE QKFHCLVLSQ SLGFQEVLSV EVTLRVAANF  120
SV                                                               122

SEQ ID NO: 854          moltype = AA  length = 111
FEATURE                 Location/Qualifiers
REGION                  1..111
                        note = ICOSL v160 IgV
source                  1..111
                        mol_type = protein
                        organism = synthetic construct
SEQUENCE: 854
DTQEKEVRAM VGSDVELSCA CPEGSRFDLN DVYVYWQTSE SKTVVTYHIP QYSSLEYVDS   60
RYRNRALMSP AGMLRGDFSL RLFNVTPQDE QKFHCLVLSP SLGFQEVLSV E          111

SEQ ID NO: 855          moltype = AA  length = 122
FEATURE                 Location/Qualifiers
REGION                  1..122
                        note = ICOSL v160 IgV
source                  1..122
                        mol_type = protein
                        organism = synthetic construct
SEQUENCE: 855
DTQEKEVRAM VGSDVELSCA CPEGSRFDLN DVYVYWQTSE SKTVVTYHIP QYSSLEYVDS   60
RYRNRALMSP AGMLRGDFSL RLFNVTPQDE QKFHCLVLSP SLGFQEVLSV EVTLHVAANF  120
SV                                                               122

SEQ ID NO: 856          moltype = AA  length = 111
FEATURE                 Location/Qualifiers
REGION                  1..111
                        note = ICOSL v164 IgV
source                  1..111
                        mol_type = protein
                        organism = synthetic construct
SEQUENCE: 856
DTQEKEVRAM VGSDVELSCA CPEGSRFDLD DVYVYWQTSE SETVVTYHIP QSSSLENVDS   60
RYRNRALMSP AGMLRGDFSL RLFNVTPQDE QKFHCLVLSQ SLGFQEVLSV E          111

SEQ ID NO: 857          moltype = AA  length = 122
FEATURE                 Location/Qualifiers
REGION                  1..122
                        note = ICOSL v168 IgV
source                  1..122
                        mol_type = protein
                        organism = synthetic construct
SEQUENCE: 857
DTQEKEVRAM VGSDVELSCA CPEGSRFDLN DVYVYWQTSE SKTVVTYHIP QSSSLENVDS   60
RYRNRALMSP AGMLRGDFSL RLFNVTPQDE QKFHCLVLSQ SLGFQEVLSV EVTLRVAANS  120
SV                                                               122

SEQ ID NO: 858          moltype = AA  length = 237
FEATURE                 Location/Qualifiers
REGION                  1..237
                        note = eGFP
source                  1..237
                        mol_type = protein
                        organism = synthetic construct
```

-continued

```
SEQUENCE: 858
SKGEELFTGV VPILVELDGD VNGHKFSVSG EGEGDATYGK LTLKFICTTG KLPVPWPTLV    60
TTLTYGVQCF SRYPDHMKQH DFFKSAMPEG YVQERTIFFK DDGNYKTRAE VKFEGDTLVN   120
RIELKGIDFK EDGNILGHKL EYNYNSHNVY IMADKQKNGI KVNFKIRHNI EDGSVQLADH   180
YQQNTPIGDG PVLLPDNHYL STQSALSKDP NEKRDHMVLL EFVTAAGITH GMDELYK      237

SEQ ID NO: 859          moltype = AA   length = 237
FEATURE                 Location/Qualifiers
REGION                  1..237
                        note = Green fluorescent protein
source                  1..237
                        mol_type = protein
                        organism = synthetic construct
SEQUENCE: 859
SKGEELFTGV VPILVELDGD VNGHKFSVSG EGEGDATYGK LTLKFICTTG KLPVPWPTLV    60
TTFSYGVQCF SRYPDHMKQH DFFKSAMPEG YVQERTIFFK DDGNYKTRAE VKFEGDTLVN   120
RIELKGIDFK EDGNILGHKL EYNYNSHNVY IMADKQKNGI KVNFKIRHNI EDGSVQLADH   180
YQQNTPIGDG PVLLPDNHYL STQSALSKDP NEKRDHMVLL EFVTAAGITH GMDELYK      237

SEQ ID NO: 860          moltype = AA   length = 20
FEATURE                 Location/Qualifiers
REGION                  1..20
                        note = T2A protein
source                  1..20
                        mol_type = protein
                        organism = synthetic construct
SEQUENCE: 860
SGEGRGSLLT CGDVEENPGP                                                20

SEQ ID NO: 861          moltype = AA   length = 21
FEATURE                 Location/Qualifiers
REGION                  1..21
                        note = T2A protein
source                  1..21
                        mol_type = protein
                        organism = synthetic construct
SEQUENCE: 861
GSGEGRGSLL TCGDVEENPG P                                              21

SEQ ID NO: 862          moltype = AA   length = 18
FEATURE                 Location/Qualifiers
REGION                  1..18
                        note = T2A protein
source                  1..18
                        mol_type = protein
                        organism = synthetic construct
SEQUENCE: 862
EGRGSLLTCG DVEENPGP                                                  18

SEQ ID NO: 863          moltype = AA   length = 22
FEATURE                 Location/Qualifiers
REGION                  1..22
                        note = P2A protein
source                  1..22
                        mol_type = protein
                        organism = synthetic construct
SEQUENCE: 863
GSGATNFSLL KQAGDVEENP GP                                             22

SEQ ID NO: 864          moltype = AA   length = 6
FEATURE                 Location/Qualifiers
REGION                  1..6
                        note = His tag
source                  1..6
                        mol_type = protein
                        organism = synthetic construct
SEQUENCE: 864
HHHHHH                                                                6

SEQ ID NO: 865          moltype = AA   length = 8
FEATURE                 Location/Qualifiers
REGION                  1..8
                        note = Flag tag
source                  1..8
                        mol_type = protein
                        organism = synthetic construct
SEQUENCE: 865
DYKDDDDK                                                              8
```

```
SEQ ID NO: 866           moltype = AA  length = 448
FEATURE                  Location/Qualifiers
REGION                   1..448
                         note = Atezolizumab Heavy Chain
source                   1..448
                         mol_type = protein
                         organism = synthetic construct
SEQUENCE: 866
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 867           moltype = AA  length = 214
FEATURE                  Location/Qualifiers
REGION                   1..214
                         note = Atezolizumab Light Chain
source                   1..214
                         mol_type = protein
                         organism = synthetic construct
SEQUENCE: 867
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 868           moltype = AA  length = 580
FEATURE                  Location/Qualifiers
REGION                   1..580
                         note = ICOSL WT IgV - Atezolizumab HC
source                   1..580
                         mol_type = protein
                         organism = synthetic construct
SEQUENCE: 868
DTQEKEVRAM VGSDVELSCA CPEGSRFDLN DVYVYWQTSE SKTVVTYHIP QNSSLENVDS  60
RYRNRALMSP AGMLRGDFSL RLFNVTPQDE QKFHCLVLSQ SLGFQEVLSV EVTLHVAANF  120
SVGGGGSGGG GSEVQLVESG GGLVQPGGSL RLSCAASGFT FSDSWIHWVR QAPGKGLEWV  180
AWISPYGGST YYADSVKGRF TISADTSKNT AYLQMNSLRA EDTAVYYCAR RHWPGGFDYW  240
GQGTLVTVSS ASTKGPSVFP LAPSSKSTSG GTAALGCLVK DYFPEPVTVS WNSGALTSGV  300
HTFPAVLQSS GLYSLSSVVT VPSSSLGTQT YICNVNHKPS NTKVDKKVEP KSCDKTHTCP  360
PCPAPELLGG PSVFLFPPKP KDTLMISRTP EVTCVVVDVS HEDPEVKFNW YVDGVEVHNA  420
KTKPREEQYA STYRVVSVLT VLHQDWLNGK EYKCKVSNKA LPAPIEKTIS KAKGQPREPQ  480
VYTLPPSREE MTKNQVSLTC LVKGFYPSDI AVEWESNGQP ENNYKTTPPV LDSDGSFFLY  540
SKLTVDKSRW QQGNVFSCSV MHEALHNHYT QKSLSLSPGK                        580

SEQ ID NO: 869           moltype = AA  length = 580
FEATURE                  Location/Qualifiers
REGION                   1..580
                         note = ICOSL v56 IgV - Atezolizumab HC
source                   1..580
                         mol_type = protein
                         organism = synthetic construct
SEQUENCE: 869
DTQEKEVRAM VGSDVVLSCA CPEGSRFDLN DVYVYWQTSE SKTVVTYHIP QHSSLEYVDS  60
RYRNRALMSP AGMLRGDFSL RLFNVTPQDE QKFHCLVLSR SLGFQEVLSD EVTLRVAANF  120
SVGGGGSGGG GSEVQLVESG GGLVQPGGSL RLSCAASGFT FSDSWIHWVR QAPGKGLEWV  180
AWISPYGGST YYADSVKGRF TISADTSKNT AYLQMNSLRA EDTAVYYCAR RHWPGGFDYW  240
GQGTLVTVSS ASTKGPSVFP LAPSSKSTSG GTAALGCLVK DYFPEPVTVS WNSGALTSGV  300
HTFPAVLQSS GLYSLSSVVT VPSSSLGTQT YICNVNHKPS NTKVDKKVEP KSCDKTHTCP  360
PCPAPELLGG PSVFLFPPKP KDTLMISRTP EVTCVVVDVS HEDPEVKFNW YVDGVEVHNA  420
KTKPREEQYA STYRVVSVLT VLHQDWLNGK EYKCKVSNKA LPAPIEKTIS KAKGQPREPQ  480
VYTLPPSREE MTKNQVSLTC LVKGFYPSDI AVEWESNGQP ENNYKTTPPV LDSDGSFFLY  540
SKLTVDKSRW QQGNVFSCSV MHEALHNHYT QKSLSLSPGK                        580

SEQ ID NO: 870           moltype = AA  length = 580
FEATURE                  Location/Qualifiers
REGION                   1..580
                         note = ICOSL v39 IgV - Atezolizumab HC
source                   1..580
                         mol_type = protein
                         organism = synthetic construct
SEQUENCE: 870
DTQEKEVRAM VGSDVELSCA CPEGSRFDLN DVYVYWQTSE SKTVVTYHIP QHSSLEYVDS  60
RYRNRALMSP AGMLRGDFSL RLFNVTPQDE QKFHCLVLSR SLGFQEVLSV EVTLHVAANF  120
SVGGGGSGGG GSEVQLVESG GGLVQPGGSL RLSCAASGFT FSDSWIHWVR QAPGKGLEWV  180
```

-continued

```
AWISPYGGST YYADSVKGRF TISADTSKNT AYLQMNSLRA EDTAVYYCAR RHWPGGFDYW    240
GQGTLVTVSS ASTKGPSVFP LAPSSKSTSG GTAALGCLVK DYFPEPVTVS WNSGALTSGV    300
HTFPAVLQSS GLYSLSSVVT VPSSSLGTQT YICNVNHKPS NTKVDKKVEP KSCDKTHTCP    360
PCPAPELLGG PSVFLFPPKP KDTLMISRTP EVTCVVVDVS HEDPEVKFNW YVDGVEVHNA    420
KTKPREEQYA STYRVVSVLT VLHQDWLNGK EYKCKVSNKA LPAPIEKTIS KAKGQPREPQ    480
VYTLPPSREE MTKNQVSLTC LVKGFYPSDI AVEWESNGQP ENNYKTTPPV LDSDGSFFLY    540
SKLTVDKSRW QQGNVFSCSV MHEALHNHYT QKSLSLSPGK                         580

SEQ ID NO: 871          moltype = AA   length = 346
FEATURE                 Location/Qualifiers
REGION                  1..346
                        note = ICOSL WT IgV - Atezolizumab LC
source                  1..346
                        mol_type = protein
                        organism = synthetic construct
SEQUENCE: 871
DTQEKEVRAM VGSDVELSCA CPEGSRFDLN DVYVYWQTSE SKTVVTYHIP QNSSLENVDS    60
RYRNRALMSP AGMLRGDFSL RLFNVTPQDE QKFHCLVLSQ SLGFQEVLSV EVTLHVAANF    120
SVGGGGSGGG GSDIQMTQSP SSLSASVGDR VTITCRASQD VSTAVAWYQQ KPGKAPKLLI    180
YSASFLYSGV PSRFSGSGSG TDFTLTISSL QPEDFATYYC QQYLYHPATF GQGTKVEIKR    240
TVAAPSVFIF PPSDEQLKSG TASVVCLLNN FYPREAKVQW KVDNALQSGN SQESVTEQDS    300
KDSTYSLSST LTLSKADYEK HKVYACEVTH QGLSSPVTKS FNRGEC                  346

SEQ ID NO: 872          moltype = AA   length = 346
FEATURE                 Location/Qualifiers
REGION                  1..346
                        note = ICOSL v56 IgV - Atezolizumab LC
source                  1..346
                        mol_type = protein
                        organism = synthetic construct
SEQUENCE: 872
DTQEKEVRAM VGSDVVLSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD EVTLRVAANF    120
SVGGGGSGGG GSDIQMTQSP SSLSASVGDR VTITCRASQD VSTAVAWYQQ KPGKAPKLLI    180
YSASFLYSGV PSRFSGSGSG TDFTLTISSL QPEDFATYYC QQYLYHPATF GQGTKVEIKR    240
TVAAPSVFIF PPSDEQLKSG TASVVCLLNN FYPREAKVQW KVDNALQSGN SQESVTEQDS    300
KDSTYSLSST LTLSKADYEK HKVYACEVTH QGLSSPVTKS FNRGEC                  346

SEQ ID NO: 873          moltype = AA   length = 346
FEATURE                 Location/Qualifiers
REGION                  1..346
                        note = ICOSL v39 IgV - Atezolizumab LC
source                  1..346
                        mol_type = protein
                        organism = synthetic construct
SEQUENCE: 873
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSV EVTLHVAANF    120
SVGGGGSGGG GSDIQMTQSP SSLSASVGDR VTITCRASQD VSTAVAWYQQ KPGKAPKLLI    180
YSASFLYSGV PSRFSGSGSG TDFTLTISSL QPEDFATYYC QQYLYHPATF GQGTKVEIKR    240
TVAAPSVFIF PPSDEQLKSG TASVVCLLNN FYPREAKVQW KVDNALQSGN SQESVTEQDS    300
KDSTYSLSST LTLSKADYEK HKVYACEVTH QGLSSPVTKS FNRGEC                  346

SEQ ID NO: 874          moltype = AA   length = 580
FEATURE                 Location/Qualifiers
REGION                  1..580
                        note = Atezolizumab HC - ICOSL WT IgV
source                  1..580
                        mol_type = protein
                        organism = synthetic construct
SEQUENCE: 874
EVQLVESGGG LVQPGGSLRL SCAASGFTFS DSWIHWVRQA PGKGLEWVAW ISPYGGSTYY    60
ADSVKGRFTI SADTSKNTAY LQMNSLRAED TAVYYCARRH WPGGFDYWGQ GTLVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CDKTHTCPPC PAPELLGGPS    240
VFLFPPKPKD TLMISRTPEV TCVVVDVSHE DPEVKFNWYV DGVEVHNAKT KPREEQYAST    300
YRVVSVLTVL HQDWLNGKEY KCKVSNKALP APIEKTISKA KGQPREPQVY TLPPSREEMT    360
KNQVSLTCLV KGFYPSDIAV EWESNGQPEN NYKTTPPVLD SDGSFFLYSK LTVDKSRWQQ    420
GNVFSCSVMH EALHNHYTQK SLSLSPGKGG GGSGGGGSDT QEKEVRAMVG SDVELSCACP    480
EGSRFDLNDV YVYWQTSESK TVVTYHIPQN SSLENVDSRY RNRALMSPAG MLRGDFSLRL    540
FNVTPQDEQK FHCLVLSQSL GFQEVLSVEV TLHVAANFSV                          580

SEQ ID NO: 875          moltype = AA   length = 580
FEATURE                 Location/Qualifiers
REGION                  1..580
                        note = Atezolizumab HC - ICOSL v56 IgV
source                  1..580
                        mol_type = protein
                        organism = synthetic construct
```

```
SEQUENCE: 875
EVQLVESGGG LVQPGGSLRL SCAASGFTFS DSWIHWVRQA PGKGLEWVAW ISPYGGSTYY    60
ADSVKGRFTI SADTSKNTAY LQMNSLRAED TAVYYCARRH WPGGFDYWGQ GTLVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CDKTHTCPPC PAPELLGGPS    240
VFLFPPKPKD TLMISRTPEV TCVVVDVSHE DPEVKFNWYV DGVEVHNAKT KPREEQYAST    300
YRVVSVLTVL HQDWLNGKEY KCKVSNKALP APIEKTISKA KGQPREPQVY TLPPSREEMT    360
KNQVSLTCLV KGFYPSDIAV EWESNGQPEN NYKTTPPVLD SDGSFFLYSK LTVDKSRWQQ    420
GNVFSCSVMH EALHNHYTQK SLSLSPGKGG GGSGGGGSDT QEKEVRAMVG SDVVLSCACP    480
EGSRFDLNDV YVYWQTSESK TVVTYHIPQH SSLEYVDSRY RNRALMSPAG MLRGDFSLRL    540
FNVTPQDEQK FHCLVLSRSL GFQEVLSDEV TLRVAANFSV                          580

SEQ ID NO: 876          moltype = AA   length = 580
FEATURE                 Location/Qualifiers
REGION                  1..580
                        note = Atezolizumab HC - ICOSL v39 IgV
source                  1..580
                        mol_type = protein
                        organism = synthetic construct
SEQUENCE: 876
EVQLVESGGG LVQPGGSLRL SCAASGFTFS DSWIHWVRQA PGKGLEWVAW ISPYGGSTYY    60
ADSVKGRFTI SADTSKNTAY LQMNSLRAED TAVYYCARRH WPGGFDYWGQ GTLVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CDKTHTCPPC PAPELLGGPS    240
VFLFPPKPKD TLMISRTPEV TCVVVDVSHE DPEVKFNWYV DGVEVHNAKT KPREEQYAST    300
YRVVSVLTVL HQDWLNGKEY KCKVSNKALP APIEKTISKA KGQPREPQVY TLPPSREEMT    360
KNQVSLTCLV KGFYPSDIAV EWESNGQPEN NYKTTPPVLD SDGSFFLYSK LTVDKSRWQQ    420
GNVFSCSVMH EALHNHYTQK SLSLSPGKGG GGSGGGGSDT QEKEVRAMVG SDVELSCACP    480
EGSRFDLNDV YVYWQTSESK TVVTYHIPQH SSLEYVDSRY RNRALMSPAG MLRGDFSLRL    540
FNVTPQDEQK FHCLVLSRSL GFQEVLSVEV TLHVAANFSV                          580

SEQ ID NO: 877          moltype = AA   length = 346
FEATURE                 Location/Qualifiers
REGION                  1..346
                        note = Atezolizumab LC - ICOSL WT IgV
source                  1..346
                        mol_type = protein
                        organism = synthetic construct
SEQUENCE: 877
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YLYHPATFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGECGGGGSG GGGSDTQEKE VRAMVGSDVV    240
LSCACPEGSR FDLNDVYVYW QTSESKTVVT YHIPQNSSLE NVDSRYRNRA LMSPAGMLRG    300
DFSLRLFNVT PQDEQKFHCL VLSQSLGFQE VLSVEVTLHV AANFSV                  346

SEQ ID NO: 878          moltype = AA   length = 346
FEATURE                 Location/Qualifiers
REGION                  1..346
                        note = Atezolizumab LC - ICOSL v56 IgV
source                  1..346
                        mol_type = protein
                        organism = synthetic construct
SEQUENCE: 878
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YLYHPATFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGECGGGGSG GGGSDTQEKE VRAMVGSDVV    240
LSCACPEGSR FDLNDVYVYW QTSESKTVVT YHIPQHSSLE YVDSRYRNRA LMSPAGMLRG    300
DFSLRLFNVT PQDEQKFHCL VLSRSLGFQE VLSDEVTLRV AANFSV                  346

SEQ ID NO: 879          moltype = AA   length = 346
FEATURE                 Location/Qualifiers
REGION                  1..346
                        note = Atezolizumab LC - ICOSL v39 IgV
source                  1..346
                        mol_type = protein
                        organism = synthetic construct
SEQUENCE: 879
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YLYHPATFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGECGGGGSG GGGSDTQEKE VRAMVGSDVE    240
LSCACPEGSR FDLNDVYVYW QTSESKTVVT YHIPQHSSLE YVDSRYRNRA LMSPAGMLRG    300
DFSLRLFNVT PQDEQKFHCL VLSRSLGFQE VLSVEVTLHV AANFSV                  346

SEQ ID NO: 880          moltype = AA   length = 696
FEATURE                 Location/Qualifiers
REGION                  1..696
```

-continued

```
                        note = ICOSL WT ECD - Atezolizumab HC
source                  1..696
                        mol_type = protein
                        organism = synthetic construct
SEQUENCE: 880
DTQEKEVRAM VGSDVELSCA CPEGSRFDLN DVYVYWQTSE SKTVVTYHIP QNSSLENVDS  60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAATGG  240
GGSGGGGSEV QLVESGGGLV QPGGSLRLSC AASGFTFSDS WIHWVRQAPG KGLEWVAWIS  300
PYGGSTYYAD SVKGRFTISA DTSKNTAYLQ MNSLRAEDTA VYYCARRHWP GGFDYWGQGT  360
LVTVSSASTK GPSVFPLAPS SKSTSGGTAA LGCLVKDYFP EPVTVSWNSG ALTSGVHTFP  420
AVLQSSGLYS LSSVVTVPSS SLGTQTYICN VNHKPSNTKV DKKVEPKSCD KTHTCPPCPA  480
PELLGGPSVF LFPPKPKDTL MISRTPEVTC VVVDVSHEDP EVKFNWYVDG VEVHNAKTKP  540
REEQYASTYR VVSVLTVLHQ DWLNGKEYKC KVSNKALPAP IEKTISKAKG QPREPQVYTL  600
PPSREEMTKN QVSLTCLVKG FYPSDIAVEW ESNGQPENNY KTTPPVLDSD GSFFLYSKLT  660
VDKSRWQQGN VFSCSVMHEA LHNHYTQKSL SLSPGK                            696

SEQ ID NO: 881          moltype = AA  length = 696
FEATURE                 Location/Qualifiers
REGION                  1..696
                        note = ICOSL v56 ECD - Atezolizumab HC
source                  1..696
                        mol_type = protein
                        organism = synthetic construct
SEQUENCE: 881
DTQEKEVRAM VGSDVVLSCA CPEGSRFDLN DVYVYWQTSE SKTVVTYHIP QHSSLEYVDS  60
RYRNRALMSP AGMLRGDFSL RLFNVTPQDE QKFHCLVLSR SLGFQEVLSD EVTLRVAANF  120
SVPVVSAPHS PSQDELTFTC TSINGYPRPN VCWINMTDNS LLDQALQNDT VFLNMRGLYD  180
VVSVLRCRIE NVLLQQNLTV GSQTGNDIGE RDKITENPVS TGEKNAATGG  240
GGSGGGGSEV QLVESGGGLV QPGGSLRLSC AASGFTFSDS WIHWVRQAPG KGLEWVAWIS  300
PYGGSTYYAD SVKGRFTISA DTSKNTAYLQ MNSLRAEDTA VYYCARRHWP GGFDYWGQGT  360
LVTVSSASTK GPSVFPLAPS SKSTSGGTAA LGCLVKDYFP EPVTVSWNSG ALTSGVHTFP  420
AVLQSSGLYS LSSVVTVPSS SLGTQTYICN VNHKPSNTKV DKKVEPKSCD KTHTCPPCPA  480
PELLGGPSVF LFPPKPKDTL MISRTPEVTC VVVDVSHEDP EVKFNWYVDG VEVHNAKTKP  540
REEQYASTYR VVSVLTVLHQ DWLNGKEYKC KVSNKALPAP IEKTISKAKG QPREPQVYTL  600
PPSREEMTKN QVSLTCLVKG FYPSDIAVEW ESNGQPENNY KTTPPVLDSD GSFFLYSKLT  660
VDKSRWQQGN VFSCSVMHEA LHNHYTQKSL SLSPGK                            696

SEQ ID NO: 882          moltype = AA  length = 696
FEATURE                 Location/Qualifiers
REGION                  1..696
                        note = ICOSL v39 ECD - Atezolizumab HC
source                  1..696
                        mol_type = protein
                        organism = synthetic construct
SEQUENCE: 882
DTQEKEVRAM VGSDVELSCA CPEGSRFDLN DVYVYWQTSE SKTVVTYHIP QHSSLEYVDS  60
RYRNRALMSP AGMLRGDFSL RLFNVTPQDE QKFHCLVLSR SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAATGG  240
GGSGGGGSEV QLVESGGGLV QPGGSLRLSC AASGFTFSDS WIHWVRQAPG KGLEWVAWIS  300
PYGGSTYYAD SVKGRFTISA DTSKNTAYLQ MNSLRAEDTA VYYCARRHWP GGFDYWGQGT  360
LVTVSSASTK GPSVFPLAPS SKSTSGGTAA LGCLVKDYFP EPVTVSWNSG ALTSGVHTFP  420
AVLQSSGLYS LSSVVTVPSS SLGTQTYICN VNHKPSNTKV DKKVEPKSCD KTHTCPPCPA  480
PELLGGPSVF LFPPKPKDTL MISRTPEVTC VVVDVSHEDP EVKFNWYVDG VEVHNAKTKP  540
REEQYASTYR VVSVLTVLHQ DWLNGKEYKC KVSNKALPAP IEKTISKAKG QPREPQVYTL  600
PPSREEMTKN QVSLTCLVKG FYPSDIAVEW ESNGQPENNY KTTPPVLDSD GSFFLYSKLT  660
VDKSRWQQGN VFSCSVMHEA LHNHYTQKSL SLSPGK                            696

SEQ ID NO: 883          moltype = AA  length = 462
FEATURE                 Location/Qualifiers
REGION                  1..462
                        note = ICOSL WT ECD - Atezolizumab LC
source                  1..462
                        mol_type = protein
                        organism = synthetic construct
SEQUENCE: 883
DTQEKEVRAM VGSDVELSCA CPEGSRFDLN DVYVYWQTSE SKTVVTYHIP QNSSLENVDS  60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VFLNMRGLYD  180
VVSVLRIART PSVNIGCCIE NVLLQQNLTV GSQTGNDIGE RDKITENPVS TGEKNAATGG  240
GGSGGGGSDI QMTQSPSSLS ASVGDRVTIT CRASQDVSTA VAWYQQKPGK APKLLIYSAS  300
FLYSGVPSRF SGSGSGTDFT LTISSLQPED FATYYCQQYL YHPATFGQGT KVEIKRTVAA  360
PSVFIFPPSD EQLKSGTASV VCLLNNFYPR EAKVQWKVDN ALQSGNSQES VTEQDSKDST  420
YSLSSTLTLS KADYEKHKVY ACEVTHQGLS SPVTKSFNRG EC                     462

SEQ ID NO: 884          moltype = AA  length = 462
FEATURE                 Location/Qualifiers
```

```
REGION                   1..462
                         note = ICOSL v56 ECD - Atezolizumab LC
source                   1..462
                         mol_type = protein
                         organism = synthetic construct
SEQUENCE: 884
DTQEKEVRAM VGSDVVLSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSD EVTLRVAANF   120
SVPVVSAPHS PSQDELTFTC TSINGYPRPN VCWINMTDNS LLDQALQNDT VFLNMRGLYD   180
VVSVLRIART PSVNIGCRIE NVLLQQNLTV GSQTGNDIGE RDKITENPVS TGEKNAATGG   240
GGSGGGGSDI QMTQSPSSLS ASVGDRVTIT CRASQDVSTA VAWYQQKPGK APKLLIYSAS   300
FLYSGVPSRF SGSGSGTDFT LTISSLQPED FATYYCQQYL YHPATFGQGT KVEIKRTVAA   360
PSVFIFPPSD EQLKSGTASV VCLLNNFYPR EAKVQWKVDN ALQSGNSQES VTEQDSKDST   420
YSLSSTLTLS KADYEKHKVY ACEVTHQGLS SPVTKSFNRG EC                      462

SEQ ID NO: 885           moltype = AA   length = 462
FEATURE                  Location/Qualifiers
REGION                   1..462
                         note = ICOSL v39 ECD - Atezolizumab LC
source                   1..462
                         mol_type = protein
                         organism = synthetic construct
SEQUENCE: 885
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSR SLGFQEVLSV EVTLHVAANF   120
SVPVVSAPHS PSQDELTFTC TSINGYPRPN VYWINKTDNS LLDQALQNDT VFLNMRGLYD   180
VVSVLRIART PSVNIGCCIE NVLLQQNLTV GSQTGNDIGE RDKITENPVS TGEKNAATGG   240
GGSGGGGSDI QMTQSPSSLS ASVGDRVTIT CRASQDVSTA VAWYQQKPGK APKLLIYSAS   300
FLYSGVPSRF SGSGSGTDFT LTISSLQPED FATYYCQQYL YHPATFGQGT KVEIKRTVAA   360
PSVFIFPPSD EQLKSGTASV VCLLNNFYPR EAKVQWKVDN ALQSGNSQES VTEQDSKDST   420
YSLSSTLTLS KADYEKHKVY ACEVTHQGLS SPVTKSFNRG EC                      462

SEQ ID NO: 886           moltype = AA   length = 696
FEATURE                  Location/Qualifiers
REGION                   1..696
                         note = Atezolizumab HC - ICOSL WT ECD
source                   1..696
                         mol_type = protein
                         organism = synthetic construct
SEQUENCE: 886
EVQLVESGGG LVQPGGSLRL SCAASGFTFS DSWIHWVRQA PGKGLEWVAW ISPYGGSTYY    60
ADSVKGRFTI SADTSKNTAY LQMNSLRAED TAVYYCARRH WPGGFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYAST   300
YRVVSVLTVL HQDWLNGKEY KCKVSNKALP APIEKTISKA KGQPREPQVY TLPPSREEMT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGKGG GGSGGGGSDT QEKEVRAMVG SDVELSCACP   480
EGSRFDLNDV YVYWQTSESK TVVTYHIPQN SSLENVDSRY RNRALMSPAG MLRGDFSLRL   540
FNVTPQDEQK FHCLVLSQSL GFQEVLSVEV TLHVAANFSV PVVSAPHSPS QDELTFTCTS   600
INGYPRPNVY WINKTDNSLL DQALQNDTVF LNMRGLYDVV SVLRIARTPS VNIGCCIENV   660
LLQQNLTVGS QTGNDIGERD KITENPVSTG EKNAAT                             696

SEQ ID NO: 887           moltype = AA   length = 696
FEATURE                  Location/Qualifiers
REGION                   1..696
                         note = Atezolizumab HC - ICOSL v56 ECD
source                   1..696
                         mol_type = protein
                         organism = synthetic construct
SEQUENCE: 887
EVQLVESGGG LVQPGGSLRL SCAASGFTFS DSWIHWVRQA PGKGLEWVAW ISPYGGSTYY    60
ADSVKGRFTI SADTSKNTAY LQMNSLRAED TAVYYCARRH WPGGFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYAST   300
YRVVSVLTVL HQDWLNGKEY KCKVSNKALP APIEKTISKA KGQPREPQVY TLPPSREEMT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGKGG GGSGGGGSDT QEKEVRAMVG SDVLSCACP    480
EGSRFDLNDV YVYWQTSESK TVVTYHIPQH SSLEYVDSRY RNRALMSPAG MLRGDFSLRL   540
FNVTPQDEQK FHCLVLSRSL GFQEVLSDEV TLRVAANFSV PVVSAPHSPS QDELTFTCTS   600
INGYPRPNVC WINMTDNSLL DQALQNDTVF LNMRGLYDVV SVLRIARTPS VNIGCRIENV   660
LLQQNLTVGS QTGNDIGERD KITENPVSTG EKNAAT                             696

SEQ ID NO: 888           moltype = AA   length = 696
FEATURE                  Location/Qualifiers
REGION                   1..696
                         note = Atezolizumab HC - ICOSL v39 ECD
source                   1..696
```

```
                              mol_type = protein
                              organism = synthetic construct
SEQUENCE: 888
EVQLVESGGG LVQPGGSLRL SCAASGFTFS DSWIHWVRQA PGKGLEWVAW ISPYGGSTYY    60
ADSVKGRFTI SADTSKNTAY LQMNSLRAED TAVYYCARRH WPGGFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYAST   300
YRVVSVLTVL HQDWLNGKEY KCKVSNKALP APIEKTISKA KGQPREPQVY TLPPSREEMT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGKGG GGSGGGGSDT QEKEVRAMVG SDVELSCACP   480
EGSRFDLNDV YVYWQTSESK TVVTYHIPQH SSLEYVDSRY RNRALMSPAG MLRGDFSLRL   540
FNVTPQDEQK FHCLVLSRSL GFQEVLSVEV TLHVAANFSV PVVSAPHSPS QDELTFTCTS   600
INGYPRPNVY WINKTDNSLL DQALQNDTVF LNMRGLYDVV SVLRIARTPS VNIGCCIENV   660
LLQQNLTVGS QTGNDIGERD KITENPVSTG EKNAAT                             696

SEQ ID NO: 889         moltype = AA  length = 462
FEATURE                Location/Qualifiers
REGION                 1..462
                       note = Atezolizumab LC - ICOSL WT ECD
source                 1..462
                       mol_type = protein
                       organism = synthetic construct
SEQUENCE: 889
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YLYHPATFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGGGGSG GGGSDTQEKE VRAMVGSDVE   240
LSCACPEGSR FDLNDVYVYW QTSESKTVVT YHIPQNSSLE NVDSRYRNRA LMSPAGMLRG   300
DFSLRLFNVT PQDEQKFHCL VLSQSLGFQE VLSVEVTLHV AANFSVPVVS APHSPSQDEL   360
TFTCTSINGY PRPNVYWINK TDNSLLDQAL QNDTVFLNMR GLYDVVSVLR IARTPSVNIG   420
CCIENVLLQQ NLTVGSQTGN DIGERDKITE NPVSTGEKNA AT                      462

SEQ ID NO: 890         moltype = AA  length = 462
FEATURE                Location/Qualifiers
REGION                 1..462
                       note = Atezolizumab LC - ICOSL v56 ECD
source                 1..462
                       mol_type = protein
                       organism = synthetic construct
SEQUENCE: 890
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YLYHPATFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGGGGSG GGGSDTQEKE VRAMVGSDVV   240
LSCACPEGSR FDLNDVYVYW QTSESKTVVT YHIPQHSSLE YVDSRYRNRA LMSPAGMLRG   300
DFSLRLFNVT PQDEQKFHCL VLSRSLGFQE VLSDEVTLHV AANFSVPVVS APHSPSQDEL   360
TFTCTSINGY PRPNVCWINM TDNSLLDQAL QNDTVFLNMR GLYDVVSVLR IARTPSVNIG   420
CRIENVLLQQ NLTVGSQTGN DIGERDKITE NPVSTGEKNA AT                      462

SEQ ID NO: 891         moltype = AA  length = 462
FEATURE                Location/Qualifiers
REGION                 1..462
                       note = Atezolizumab LC - ICOSL v39 ECD
source                 1..462
                       mol_type = protein
                       organism = synthetic construct
SEQUENCE: 891
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YLYHPATFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGGGGSG GGGSDTQEKE VRAMVGSDVE   240
LSCACPEGSR FDLNDVYVYW QTSESKTVVT YHIPQHSSLE YVDSRYRNRA LMSPAGMLRG   300
DFSLRLFNVT PQDEQKFHCL VLSRSLGFQE VLSVEVTLHV AANFSVPVVS APHSPSQDEL   360
TFTCTSINGY PRPNVYWINK TDNSLLDQAL QNDTVFLNMR GLYDVVSVLR IARTPSVNIG   420
CCIENVLLQQ NLTVGSQTGN DIGERDKITE NPVSTGEKNA AT                      462

SEQ ID NO: 892         moltype = AA  length = 582
FEATURE                Location/Qualifiers
REGION                 1..582
                       note = ICOSL v5 IgV - Atezolizumab HC
source                 1..582
                       mol_type = protein
                       organism = synthetic construct
SEQUENCE: 892
DTQEKEVRAM VGSDVELSCA CPEGSRFDLN DVVYVYWQTSE SKTVVTYHIP QHSSLEYVDS    60
RYRNRALMSP AGMLRGDFSL RLFNVTPQDE QKFHCLVLSP SLGFQEVLSV EVTLHVAANF   120
SVGSGGGGSG GGGSEVQLVE SGGGLVQPGG SLRLSCAASG FTFSDSWIHW VRQAPGKGLE   180
WVAWISPYGG STYYADSVKG RFTISADTSK NTAYLQMNSL RAEDTAVYYC ARRHWPGGFD   240
```

-continued

```
YWGQGTLVTV SSASTKGPSV FPLAPSSKST SGGTAALGCL VKDYFPEPVT VSWNSGALTS    300
GVHTFPAVLQ SSGLYSLSSV VTVPSSSLGT QTYICNVNHK PSNTKVDKKV EPKSCDKTHT    360
CPPCPAPELL GGPSVFLFPP KPKDTLMISR TPEVTCVVVD VSHEDPEVKF NWYVDGVEVH    420
NAKTKPREEQ YASTYRVVSV LTVLHQDWLN GKEYKCKVSN KALPAPIEKT ISKAKGQPRE    480
PQVYTLPPSR EEMTKNQVSL TCLVKGFYPS DIAVEWESNG QPENNYKTTP PVLDSDGSFF    540
LYSKLTVDKS RWQQGNVFSC SVMHEALHNH YTQKSLSLSP GK                       582

SEQ ID NO: 893            moltype = AA  length = 580
FEATURE                   Location/Qualifiers
REGION                    1..580
                          note = Atezolizumab HC - ICOSL v5 IgV
source                    1..580
                          mol_type = protein
                          organism = synthetic construct
SEQUENCE: 893
EVQLVESGGG LVQPGGSLRL SCAASGFTFS DSWIHWVRQA PGKGLEWVAW ISPYGGSTYY    60
ADSVKGRFTI SADTSKNTAY LQMNSLRAED TAVYYCARRH WPGGFDYWGQ GTLVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CDKTHTCPPC PAPELLGGPS    240
VFLFPPKPKD TLMISRTPEV TCVVVDVSHE DPEVKFNWYV DGVEVHNAKT KPREEQYAST    300
YRVVSVLTVL HQDWLNGKEY KCKVSNKALP APIEKTISKA KGQPREPQVY TLPPSREEMT    360
KNQVSLTCLV KGFYPSDIAV EWESNGQPEN NYKTTPPVLD SDGSFFLYSK LTVDKSRWQQ    420
GNVFSCSVMH EALHNHYTQK SLSLSPGKGG GGSGGGGSDT QEKEVRAMVG SDVELSCACP    480
EGSRFDLNDV YVYWQTSESK TVVTYHIPQH SSLEYVDSRY RNRALMSPAG MLRGDFSLRL    540
FNVTPQDEQK FHCLVLSPSL GFQEVLSVEV TLHVAANFSV                          580

SEQ ID NO: 894            moltype = AA  length = 348
FEATURE                   Location/Qualifiers
REGION                    1..348
                          note = ICOSL v5 IgV - Atezolizumab LC
source                    1..348
                          mol_type = protein
                          organism = synthetic construct
SEQUENCE: 894
DTQEKEVRAM VGSDVELSCA CPEGSRFDLN DVYVYWQTSE SKTVVTYHIP QHSSLEYVDS    60
RYRNRALMSP AGMLRGDFSL RLFNVTPQDE QKFHCLVLSP SLGFQEVLSV EVTLHVAANF    120
SVGSGGGGSG GGGSDIQMTQ SPSSLSASVG DRVTITCRAS QDVSTAVAWY QQKPGKAPKL    180
LIYSASFLYS GVPSRFSGSG SGTDFTLTIS SLQPEDFATY YCQQYLYHPA TFGQGTKVEI    240
KRTVAAPSVF IFPPSDEQLK SGTASVVCLL NNFYPREAKV QWKVDNALQS GNSQESVTEQ    300
DSKDSTYSLS STLTLSKADY EKHKVYACEV THQGLSSPVT KSFNRGEC                 348

SEQ ID NO: 895            moltype = AA  length = 346
FEATURE                   Location/Qualifiers
REGION                    1..346
                          note = Atezolizumab LC - ICOSL v5 IgV
source                    1..346
                          mol_type = protein
                          organism = synthetic construct
SEQUENCE: 895
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YLYHPATFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGECGGGGSG GGGSDTQEKE VRAMVGSDVE    240
LSCACPEGSR FDLNDVYVYW QTSESKTVVT YHIPQHSSLE YVDSRYRNRA LMSPAGMLRG    300
DFSLRLFNVT PQDEQKFHCL VLSPSLGFQE VLSVEVTLHV AANFSV                   346

SEQ ID NO: 896            moltype = AA  length = 239
FEATURE                   Location/Qualifiers
REGION                    1..239
                          note = eGFP
source                    1..239
                          mol_type = protein
                          organism = synthetic construct
SEQUENCE: 896
MVSKGEELFT GVVPILVELD GDVNGHKFSV SGEGEGDATY GKLTLKFICT TGKLPVPWPT    60
LVTTLTYGVQ CFSRYPDHMK QHDFFKSAMP EGYVQERTIF FKDDGNYKTR AEVKFEGDTL    120
VNRIELKGID FKEDGNILGH KLEYNYNSHN VYIMADKQKN GIKVNFKIRH NIEDGSVQLA    180
DHYQQNTPIG DGPVLLPDNH YLSTQSALSK DPNEKRDHMV LLEFVTAAGI TLGMDELYK     239

SEQ ID NO: 897            moltype = AA  length = 68
FEATURE                   Location/Qualifiers
REGION                    1..68
                          note = CD8 hinge and transmembrane domain
source                    1..68
                          mol_type = protein
                          organism = synthetic construct
SEQUENCE: 897
KPTTTPAPRP PTPAPTIASQ PLSLRPEACR PAAGGAVHTR GLDFACDIYI WAPLAGTCGV    60
LLLSLVIT                                                            68
```

-continued

```
SEQ ID NO: 898          moltype = AA   length = 431
FEATURE                 Location/Qualifiers
REGION                  1..431
                        note = antiCD19 chimeric antigen receptor CAR-2
source                  1..431
                        mol_type = protein
                        organism = synthetic construct
SEQUENCE: 898
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE 120
GSTKGEVKLQ ESGPGLVAPS QSLSVTCTVS GVSLPDYGVS WIRQPPRKGL EWLGVIWGSE 180
TTYYNSALKS RLTIIKDNSK SQVFLKMNSL QTDDTAIYYC AKHYYYGGSY AMDYWGQGTS 240
VTVSSASAKP TTTPAPRPPT PAPTIASQPL SLRPEASRPA AGGAVHTRGL DFASDIYIWA 300
PLAGTCGVLL LSLVITLYCR VKFSRSADAP AYQQGQNQLY NELNLGRREE YDVLDKRRGR 360
DPEMGGKPRR KNPQEGLYNE LQKDKMAEAY SEIGMKGERR RGKGHDGLYQ GLSTATKDTY 420
DALHMQALPP R                                                      431

SEQ ID NO: 899          moltype = AA   length = 707
FEATURE                 Location/Qualifiers
REGION                  1..707
                        note = antiCD19 chimeric antigen receptor CAR-2
source                  1..707
                        mol_type = protein
                        organism = synthetic construct
SEQUENCE: 899
MALPVTALLL PLALLLHAAR PDIQMTQTTS SLSASLGDRV TISCRASQDI SKYLNWYQQK  60
PDGTVKLLIY HTSRLHSGVP SRFSGSGSGT DYSLTISNLE QEDIATYFCQ QGNTLPYTFG 120
GGTKLEITGS TSGSGKPGSG EGSTKGEVKL QESGPGLVAP SQSLSVTCTV SGVSLPDYGV 180
SWIRQPPRKG LEWLGVIWGS ETTYYNSALK SRLTIIKDNS KSQVFLKMNS LQTDDTAIYY 240
CAKHYYYGGS YAMDYWGQGT SVTVSSASAK PTTTPAPRPP TPAPTIASQP LSLRPEASRP 300
AAGGAVHTRG LDFASDIYIW APLAGTCGVL LLSLVITLYC RVKFSRSADA PAYQQGQNQL 360
YNELNLGRRE EYDVLDKRRG RDPEMGGKPR RKNPQEGLYN ELQKDKMAEA YSEIGMKGER 420
RRGKGHDGLY QGLSTATKDT YDALHMQALP PRGSGEGRGS LLTCGDVEEN PGPSRSELIK 480
ENMHMKLYME GTVDNHHFKC TSEGEGKPYE GTQTMRIKVV EGGPLPFAFD ILATSFLYGS 540
KTFINHTQGI PDFFKQSFPE GFTWERVTTY EDGGVLTATQ DTSLQDGCLI YNVKIRGVNF 600
TSNGPVMQKK TLGWEAFTET LYPADGGLEG RNDMALKLVG GSHLIANIKT TYRSKKPAKN 660
LKMPGVYYVD YRLERIKEAN NETYVEQHEV AVARYCDLPS KLGHKLN            707

SEQ ID NO: 900          moltype = DNA  length = 8708
FEATURE                 Location/Qualifiers
misc_feature            1..8708
                        note = anti-CD19 chimeric antigen receptor CAR-2
source                  1..8708
                        mol_type = other DNA
                        organism = synthetic construct
SEQUENCE: 900
agcttaatgt agtcttatgc aatactcttg tagtcttgca acatggtaac gatgagttag   60
caacatgcct tacaaggaga gaaaaagcac cgtgcatgcc gattggtgga agtaaggtgg  120
tacgatcgtg ccttattagg aaggcaacag acgggtctga catggattgg acgaaccact  180
gaattgccgc attgcagaga tattgtattt aagtgcctag ctcgatacaa taaacgggtc  240
tctctggtta gaccagatct gagcctggga gctctctggc taactaggga acccactgct  300
taagcctcaa taaagcttgc cttgagtgct tcaagtagtg tgtgcccgtc tgttgtgtga  360
ctctggtaac tagagatccc tcagacccct ttagtcagtg tggaaaatct ctagcagtgg  420
cgcccgaaca gggacttgaa agcgaaaggg aaaccagagg agctctctcg acgcaggact  480
cggcttgctg aagcgcgcac ggcaagaggc gaggggcggc gactggtgag tacgccaaaa  540
attttgacta gcggaggcta gaaggagaga tgggtgcg agagcgtcag tattaagcgg  600
gggagaatta gatcgcgatg ggaaaaaatt cggttaaggc caggggaaa gaaaaaaatat  660
aaattaaaac atatagtatg ggcaagcagg gagctagaac gattcgcagt taatcctggc  720
ctgttagaaa catcagaagg ctgtagacaa atactgggac agctacaacc atcccttcag  780
acaggatcag aagaacttag atcattatat aatacagtag caaccctcta ttgtgtgcat  840
caaaggatag agataaaaga caccaaggaa gctttagaca gatagagga agagcaaaac  900
aaaagtaaga ccaccgcaca gcaagcggcc gctgatcttc agacctggag gaggagatat  960
gagggacaat tggagaagtg aattatataa atataaagta gtaaaaattg aaccattagg 1020
agtagcaccc accaaggcaa agagaagagt ggtgcagaga gaaaaaagag cagtgggaat 1080
aggagctttg ttccttgggt tcttgggagc agcaggaagc actatgggcg cagcctcaat 1140
gacgctgacg gtacaggcca gacaattatt gtctggtata gtgcagcagc agaacaattt 1200
gctgagggct attgaggcgc aacagcatct gttgcaactc acagtctggg gcatcaagca 1260
gctccaggca agaatcctgg ctgtggaaag atacctaaag gatcaacagc tcctgggaat 1320
ttggggttgc tctggaaaac tcatttgcac cactgctgtg ccttggaatg ctagttggag 1380
taataaatct ctggaacaga tttggaatca cacgacctgg atggagtggg acagagaaat 1440
taacaattac acaagcttaa tacactcctt aattgaagaa tcgcaaaacc agcaagaaaa 1500
gaatgaacaa gaattattgg aattagataa atgggcaagt ttgtggaatt ggtttaacat 1560
aacaaattgg ctgtggtata taaaattatt cataatgata gtaggaggct tggtaggttt 1620
aagaatagtt tttgctgtac tttctatagt gaatagagtt aggcaggat attcaccatt 1680
atcgtttcag accccctcc caaccccgag gggacccgac aggcccgaag gaatagaaga 1740
agaaggtgga gagagagaca gagacagatc cattcgatta gtgaacggat ctcgacggta 1800
tcggttaact tttaaaagaa aagggggat tgggggtac agtgcagggg aaagaatagt 1860
agacataata gcaacagaca tacaaactaa agaattacaa aaacaaatta caaaaattca 1920
```

-continued

```
aaattttatc gatcacgaga ctagcctcga gaagcttgat atcgaattcc cacgggggttg    1980
gacgcgtagg aacagagaaa caggagaata tgggccaaac aggatatctg tggtaagcag    2040
ttcctgcccc ggctcagggc caagaacagt tggaacagca gaatatgggc caaacaggat    2100
atctgtggta agcagttcct gccccggctc agggccaaga acagatggtc cccagatgcg    2160
gtcccgccct cagcagtttc tagagaacca tcagatgttt ccagggtgcc ccaaggacct    2220
gaaatgaccc tgtgccttat ttgaactaac caatcagttc gcttctcgct tctgttcgcg    2280
cgcttctgct ccccgagctc tatataagca gagctcgttt agtgaaccgt cagatcgcct    2340
ggagacgcca tccacgctgt tttgacttcc atagaaggat cccctgcagg taatacgact    2400
cactataggg tccactgccg ccaccatggc tctgcctgtg acagctctgc tgctgcctct    2460
ggccctgctg ctccatgccg ccagacccgg atccgatatc cagatgaccc agaccaccag    2520
cagcctgagc gccagcctgg gcgatagagt gaccatcagc tgcagagcca gccaggacat    2580
cagcaagtac ctgaactggt atcagcagaa acccgacggc accgtgaagc tgctgatcta    2640
ccacaccagc agactgcaca gcggcgtgcc cagcagattt tctggcagcg gctccggcac    2700
cgactacagc ctgaccatct ccaacctgga acaggaagat atcgctacct acttctgtca    2760
gcaaggcaac accctgccct acaccttcgg cggaggcacc aagctggaaa tcaccggcag    2820
cacaagcggc agcggcaagc ctggatctgg cgagggaagc accaagggcg aagtgaaact    2880
gcaggaaagc ggccctggac tggtggcccc aagccagtct ctgagcgtga cctgtaccgt    2940
gtccggcgtg tccctgcctg actatggcgt gtcctggatc agacagccac ccagaaaggg    3000
cctggaatgg ctgggagtga tctggggcag cgagacaacc tactacaaca gcgcccctgaa   3060
gtcccggctg accatcatca aggacaactc caagagccag gtgttcctga agatgaacag    3120
cctgcagacc gacgacaccg ccatctacta ctgcgccaag cactactact acggcggcag    3180
ctacggccatg gactactggg gccaggggcac aagcgtgacc gtgtccagcg ctagcgccaa    3240
gcccaccacg acgccagcgc cgcgaccacc aacaccggcg cccaccatcg cgtcgcagcc    3300
cctgtccctg cgcccagagg cgagccggcc agcggcgggg ggcgcagtgc acacgagggg    3360
gctggacttc gccagtgata tctacatctg ggcgcccctg gccgggactt gtggggtcctt    3420
tctcctgtca ctggttatca cccttttactg cagagtcagga ttcagcagga gcgcagacgc    3480
ccccgcgtac cagcagggcc agaaccagct ctataacgag ctcaatctag gacgaagaga    3540
ggagtacgat gttttggaca agagacgtgg ccgggaccct gagatggggg gaaagccgag    3600
aaggaagaac cctcaggaag gcctgtacaa tgaactgcag aaagataaga tggcggaggc    3660
ctacagtgag attgggatga aaggcgagcg ccggagggac aagggggcacg atggccttta    3720
ccagggtctc agtacagcca ccaaggacac ctacgacgcc cttcacatgc aggccctgcc    3780
ccctcgcggc agtggcgagg gcagaggaag tctgctaaca tgcggtgacg tggaggagaa    3840
tccgggcccc tctagaagcg agctgattaa ggagaacatg cacatgaagc tgtacatgga    3900
gggcaccgtg gacaaccatc acttcaagtg cacatccgag ggcgaaggca agccctacga    3960
gggcacccag accatgagaa tcaaggtggt cgagggcggc cctctcccct tcgccttcga    4020
catcctggct actagcttcc tctacggcag caagaccttc atcaaccaca cccagggcat    4080
ccccgacttc ttcaagcagt ccttccctga gggcttcaca tgggagagag tcaccacata    4140
cgaagacggg ggcgtgctga ccgctaccca ggacaccagc ctccaggacg gctgcctcat    4200
ctacaacgtc aagatcagag gggtgaactt cacatccaac ggccctgtga tgcagaagaa    4260
aacactcggc tgggaggcct tcaccgagac gctgtacccc gctgacggcg gcctggaagg    4320
cagaaacgac atggccctga gctcgtgggg cgggagccat ctgatcgcaa acatcaagac    4380
cacatataga tccaagaaac ccgctaagaa cctcaagatg cctggcgtct actatgtgga    4440
ctacagactg gaaagaatca aggaggccaa caacgagacc tacgtcgagg cacgagggt    4500
ggcagtggcc agatactgcg acctcccctag caaactgggg cacaagctta attgagtcga    4560
caatcaacct ctggattaca aaatttgtga aagattgact ggtattctta actatgttgc    4620
tccttttacg ctatgtggat acgctgcttt aatgcctttg tatcatgcta ttgcttcccg    4680
tatggctttc attttctcct ccttgtataa atcctggttg ctgtctcttt atgaggagtt    4740
gtggcccgtt gtcaggcaac gtggcgtggt gtgcactgtg tttgctgacg caaccccac    4800
tggttggggc attgccacca cctgtcagct cctttccggg actttcgctt tccccctccc    4860
tattgccacg gcggaactca tcgccgcctg ccttgcccgc tgctggacag gggctcggct    4920
gttggccgac gacaattccg tggtgttgtc ggggaagctg acgtcctttc catggctgct    4980
cgcctgtgtt gccacctgga ttctgcgcgg gacgtccttc tgctacgtcc cttcggccct    5040
caatccagcg gaccttcctt cccgcggcct gctgccggct ctgcggcctc ttccgcgtct    5100
tcgccttcgc cctcagacga gtcggatctc cctttgggcc gcctccccgc ctggaattcg    5160
agctcggtac ctttaagacc aatgacttac aaggcagctg tagatcttag ccactttta    5220
aaagaaaagg ggggactgga agggctaatt cactcccaac gaagacaaga tctgcttttt    5280
gcttgtactg ggtctctctg gttagaccag atctgagcct gggagctctc tggctaacta    5340
gggaacccac tgcttaagcc tcaataaagc ttgccttgag tgcttcaagt agtgtgtgcc    5400
cgtctgttgt gtgactctgg taactagaga tccctcagac cctttttagtc agtgtggaaa    5460
atctctagca gtagtagttc atgtcatctt attattcagt atttataact tgcaaagaaa    5520
tgaatatcag agagtgagag gaacttgttt attgcagctt ataatggtta caaataaagc    5580
aatagcatca caaatttcac aaataaagca ttttttttcac tgcattctag ttgtggtttg    5640
tccaaactca tcaatgtatc ttatcatgtc tggctctagc tatcccgccc ctaactccgc    5700
ccagttccgc ccattctccg ccccatggct gactaatttt ttttatttat gcagaggccg    5760
aggccgcctc ggcctctgag ctattccaga agtagtgagg aggctttttt ggaggcctag    5820
gcttttgcgt cgagacgtac ccaattcgcc ctatagtgag tcgtattacg cgcgctcact    5880
ggccgtcgtt ttacaacgtc gtgactggga aaaccctggc gttacccaac ttaatcgcct    5940
tgcagcacat cccccctttcg ccagctggcg taatagcgaa gaggcccgca ccgatcgccc    6000
ttcccaacag ttgcgcagcc tgaatggcga atggcgcgac gcgccctgta gcggcgcatt    6060
aagcgcggcg ggtgtggtgg ttacgcgcag cgtgaccgct acacttgcca gcgccctagc    6120
gcccgctcct ttcgctttct tcccttcctt tctcgccacg ttcgccggct ttccccgtca    6180
agctctaaat cggggggctcc ctttagggtt ccgatttagt gctttacggc acctcgaccc    6240
caaaaaactt gattagggtg atggttcacg tagtgggcca tcgccctgat agacggtttt    6300
tcgccctttg acgttggagt ccacgttctt taatagtgga ctcttgttcc aaactggaac    6360
aacactcaac cctatctcgg tctattcttt tgatttataa gggattttgc cgatttcggc    6420
ctattggtta aaaaatgagc tgatttaaca aaaatttaac gcgaatttta acaaaatatt    6480
aacgtttaca atttcccagg tggcactttt cggggaaatg tgcgcggaac ccctatttgt    6540
ttatttttct aaatacattc aaatatgtat ccgctcatga caataaacc ctgataaatg    6600
cttcaataat attgaaaaag gaagagtatg agtattcaac atttccgtgt cgcccttatt    6660
```

-continued

```
ccctttttttg cggcattttg ccttcctgtt tttgctcacc cagaaacgct ggtgaaagta   6720
aaagatgctg aagatcagtt gggtgcacga gtgggttaca tcgaactgga tctcaacagc   6780
ggtaagatcc ttgagagttt cgccccgaa gaacgttttc caatgatgag cacttttaaa    6840
gttctgctat gtggcgcggt attatcccgt attgacgccg ggcaagagca actcggtcgc   6900
cgcatacact attctcagaa tgacttggtt gagtactcac cagtcacaga aaagcatctt   6960
acggatggca tgacagtaag agaattatgc agtgctgcca taaccatgag tgataacact   7020
gcggccaact tacttctgac aacgatcgga ggaccgaagg agctaaccgc ttttttgcac   7080
aacatggggg atcatgtaac tcgccttgat cgttgggaac cggagctgaa tgaagccata   7140
ccaaacgacg agcgtgacac cacgatgcct gtagcaatgg caacaacgtt gcgcaaacta   7200
ttaactggcg aactacttac tctagcttcc cggcaacaat taatagactg gatggaggcg   7260
gataaagttg caggaccact tctgcgctcg gcccttccgg ctggctggtt tattgctgat   7320
aaatctggag ccggtgagcg tgggtctcgc ggtatcattg cagcactggg gccagatggt   7380
aagccctccc gtatcgtagt tatctacacg acggggagtc aggcaactat ggatgaacga   7440
aatagacaga tcgctgagat aggtgcctca ctgattaagc attggtaact gtcagaccaa   7500
gtttactcat atatacttta gattgattta aaacttcatt tttaatttaa aaggatctag   7560
gtgaagatcc tttttgataa tctcatgacc aaaatccctt aacgtgagtt ttcgttccac   7620
tgagcgtcag accccgtaga aaagatcaaa ggatcttctt gagatccttt ttttctgcgc   7680
gtaatctgct gcttgcaaac aaaaaaacca ccgctaccag cggtggtttg tttgccggat   7740
caagagctac caactctttt tccgaaggta actggcttca gcagagcgca gataccaaat   7800
actgtccttc tagtgtagcc gtagttaggc caccacttca agaactctgt agcaccgcct   7860
acatacctcg ctctgctaat cctgttacca gtggctgctg ccagtggcga taagtcgtgt   7920
cttaccgggt tggactcaag acgatagtta ccggataagg cgcagcggtc gggctgaacg   7980
ggggggttcgt gcacacagcc cagcttggag cgaacgacct acaccgaact gagatacta   8040
cagcgtgagc tatgagaaag cgccacgctt cccgaaggga gaaaggcgga caggtatccg   8100
gtaagcggca gggtcggaac aggagagcgc acgagggagc ttccaggggg aaacgcctgg   8160
tatctttata gtcctgtcgg gtttcgccac ctctgacttg agcgtcgatt tttgtgatgc   8220
tcgtcagggg ggcggagcct atggaaaaac gccagcaacg cggccttttt acggttcctg   8280
gccttttgct ggccttttgc tcacatgttc tttcctgcgt tatcccctga ttctgtggat   8340
aaccgtatta ccgcctttga gtgagctgat accgctcgcc gcagccgaac gaccgagcgc   8400
agcgagtcag tgagcgagga agcggaagag cgcccaatac gcaaaccgcc tctccccgcg   8460
cgttggccga ttcattaatg cagctggcac gacaggtttc ccgactggaa agcgggcagt   8520
gagcgcaacg caattaatgt gagttagctc actcattagg cacccaggc tttcacttt    8580
atgcttccgg ctcgtatgtt gtgtggaatt gtgagcggat aacaatttca cacaggaaac   8640
agctatgacc atgattacgc caagcgcgca attaaccctc actaaaggga acaaaagctg   8700
gagctgca                                                            8708
```

```
SEQ ID NO: 901              moltype = AA  length = 428
FEATURE                     Location/Qualifiers
REGION                      1..428
                            note = antiCD19 chimeric antigen receptor CAR-1
source                      1..428
                            mol_type = protein
                            organism = synthetic construct
SEQUENCE: 901
DIQMTQTTSS LSASLGDRVT ISCRASQDIS KYLNWYQQKP DGTVKLLIYH TSRLHSGVPS   60
RFSGSGSGTD YSLTISNLEQ EDIATYFCQQ GNTLPYTFGG GTKLEITGST SGSGKPGSGE   120
GSTKGEVKLQ ESGPGLVAPS QSLSVTCTVS GVSLPDYGVS WIRQPPRKGL EWLGVIWGSE   180
TTYYNSALKS RLTIIKDNSK SQVFLKMNSL QTDDTAIYYC AKHYYYGGSY AMDYWGQGTS   240
VTVSSASAKP TTTPAPRPPT PAPTIASQPL SLRPEACRPA AGGAVHTRGL DFACDIYIWA   300
PLAGTCGVLL LSLVITRVKF SRSADAPAYQ QGQNQLYNEL NLGRREEYDV LDKRRGRDPE   360
MGGKPRRKNP QEGLYNELQK DKMAEAYSEI GMKGERRRGK GHDGLYQGLS TATKDTYDAL   420
HMQALPPR                                                            428
```

```
SEQ ID NO: 902              moltype = AA  length = 706
FEATURE                     Location/Qualifiers
REGION                      1..706
                            note = antiCD19 chimeric antigen receptor CAR-1
source                      1..706
                            mol_type = protein
                            organism = synthetic construct
SEQUENCE: 902
MALPVTALLL PLALLLHAAR PGSDIQMTQT TSSLSASLGD RVTISCRASQ DISKYLNWYQ   60
QKPDGTVKLL IYHTSRLHSG VPSRFSGSGS GTDYSLTISN LEQEDIATYF CQQGNTLPYT   120
FGGGTKLEIT GSTSGSGKPG SGEGSTKGEV KLQESGPGLV APSQSLSVTC TVSGVSLPDY   180
GVSWIRQPPR KGLEWLGVIW GSETTYYNSA LKSRLTIIKD NSKSQVFLKM NSLQTDDTAI   240
YYCAKHYYYG GSYAMDYWGQ GTSVTVSSAS AKPTTTPAPR PPTPAPTIAS QPLSLRPEAC   300
RPAAGGAVHT RGLDFACDIY IWAPLAGTCG VLLLSLVITR VKFSRSADAP AYQQGQNQLY   360
NELNLGRREE YDVLDKRRGR DPEMGGKPRR KNPQEGLYNE LQKDKMAEAY SEIGMKGERR   420
RGKGHDGLYQ GLSTATKDTY DALHMQALPP RGGRSGEGRG SLLTCGDVEE NPGPSRSELI   480
KENMHMKLYM EGTVDNHHFK CTSEGEGKPY EGTQTMRIKV VEGGPLPFAF DILATSFLYG   540
SKTFINHTQG IPDFFKQSFP EGFTWERVTT YEDGGVLTAT QDTSLQDGCL IYNVKIRGVN   600
FTSNGPVMQK KTLWEAFTET LYPADGGLEG RNDMALKLVG GSHLIANIKT TYRSKKPAKN   660
LKMPGVYYVD YRLERIKEAN NETYVEQHEV AARYCDLPSK LGHKLN                  706
```

```
SEQ ID NO: 903              moltype = AA  length = 232
FEATURE                     Location/Qualifiers
REGION                      1..232
                            note = Blue fluorescent protein
source                      1..232
```

-continued

```
                            mol_type = protein
                            organism = synthetic construct
SEQUENCE: 903
SRSELIKENM HMKLYMEGTV DNHHFKCTSE GEGKPYEGTQ TMRIKVVEGG PLPFAFDILA      60
TSFLYGSKTF INHTQGIPDF FKQSPPEGFT WERVTTYEDG GVLTATQDTS LQDGCLIYNV     120
KIRGVNFTSN GPVMQKKTLW EAFTETLYPA DGGLEGRNDM ALKLVGGSHL IANIKTTYRS     180
KKPAKNLKMP GVYYVDYRLE RIKEANNETY VEQHEVAARY CDLPSKLGHK LN             232

SEQ ID NO: 904              moltype = AA   length = 400
FEATURE                     Location/Qualifiers
REGION                      1..400
                            note = PAS
source                      1..400
                            mol_type = protein
                            organism = synthetic construct
SEQUENCE: 904
ASPAAPAPAS PAAPAPSAPA ASPAAPAPAS PAAPAPSAPA ASPAAPAPAS PAAPAPSAPA      60
ASPAAPAPAS PAAPAPSAPA ASPAAPAPAS PAAPAPSAPA ASPAAPAPAS PAAPAPSAPA     120
ASPAAPAPAS PAAPAPSAPA ASPAAPAPAS PAAPAPSAPA ASPAAPAPAS PAAPAPSAPA     180
ASPAAPAPAS PAAPAPSAPA ASPAAPAPAS PAAPAPSAPA ASPAAPAPAS PAAPAPSAPA     240
ASPAAPAPAS PAAPAPSAPA ASPAAPAPAS PAAPAPSAPA ASPAAPAPAS PAAPAPSAPA     300
ASPAAPAPAS PAAPAPSAPA ASPAAPAPAS PAAPAPSAPA ASPAAPAPAS PAAPAPSAPA     360
ASPAAPAPAS PAAPAPSAPA ASPAAPAPAS PAAPAPSAPA                          400

SEQ ID NO: 905              moltype = AA   length = 238
FEATURE                     Location/Qualifiers
REGION                      1..238
                            note = ICOSL v228 ECD
source                      1..238
                            mol_type = protein
                            organism = synthetic construct
SEQUENCE: 905
DTQEKEVRAM VGSDVELSCA CPEGSRFDLN DVYVYWQTSE SKTVVTYHIP QNSFLENVDS      60
RYRNRALMSP AGMLRGDFSL RLFNVTPQDE QKFHCLVLSQ SLGFQEVLSV EVTLHVAANF     120
SVPVVSAPHS PSQDELTFTC TSINGYPRPN VYWINKTDNS LLDQALQNDT VFLNMRGLYD     180
VVSVLRIART PSANIGCCIE NVLLQQNLTV GSQTGNDIGE RDKITENPVS TGEKNAAT       238

SEQ ID NO: 906              moltype = AA   length = 111
FEATURE                     Location/Qualifiers
REGION                      1..111
                            note = ICOSL v228 IgV
source                      1..111
                            mol_type = protein
                            organism = synthetic construct
SEQUENCE: 906
DTQEKEVRAM VGSDVELSCA CPEGSRFDLN DVYVYWQTSE SKTVVTYHIP QNSFLENVDS      60
RYRNRALMSP AGMLRGDFSL RLFNVTPQDE QKFHCLVLSQ SLGFQEVLSV E             111

SEQ ID NO: 907              moltype = AA   length = 122
FEATURE                     Location/Qualifiers
REGION                      1..122
                            note = ICOSL v228 IgV
source                      1..122
                            mol_type = protein
                            organism = synthetic construct
SEQUENCE: 907
DTQEKEVRAM VGSDVELSCA CPEGSRFDLN DVYVYWQTSE SKTVVTYHIP QNSFLENVDS      60
RYRNRALMSP AGMLRGDFSL RLFNVTPQDE QKFHCLVLSQ SLGFQEVLSV EVTLHVAANF     120
SV                                                                   122

SEQ ID NO: 908              moltype = AA   length = 238
FEATURE                     Location/Qualifiers
REGION                      1..238
                            note = ICOSL v229 ECD
source                      1..238
                            mol_type = protein
                            organism = synthetic construct
SEQUENCE: 908
DTQEKEVRAM VGSDVELSCA CPEGSSFDLN DVYVYWQTSE SKTVVTYHIP QHSSLEYVDS      60
RYRNRALMSP AGMLRGDFSL RLFNVTPQDE QKFHCLVLSQ SLGFQEVLSD EVTLHVAANF     120
SVPVVSAPHS PSQDELAFTC TSINGYPRPN VYWINKTDNS LLDQALQNDT VFLNMRGLYD     180
VVSVLRIART PSVNIGCRIE NVLLQQNLTV GSQTGNDIGE RDKITENPVS TGEKNAAT       238

SEQ ID NO: 909              moltype = AA   length = 111
FEATURE                     Location/Qualifiers
REGION                      1..111
                            note = ICOSL v229 IgV
source                      1..111
                            mol_type = protein
```

```
                             organism = synthetic construct
SEQUENCE: 909
DTQEKEVRAM VGSDVELSCA CPEGSSFDLN DVYVYWQTSE SKTVVTYHIP QHSSLEYVDS  60
RYRNRALMSP AGMLRGDFSL RLFNVTPQDE QKFHCLVLSQ SLGFQEVLSD E          111

SEQ ID NO: 910           moltype = AA   length = 122
FEATURE                  Location/Qualifiers
REGION                   1..122
                         note = ICOSL v229 IgV
source                   1..122
                         mol_type = protein
                         organism = synthetic construct
SEQUENCE: 910
DTQEKEVRAM VGSDVELSCA CPEGSSFDLN DVYVYWQTSE SKTVVTYHIP QHSSLEYVDS  60
RYRNRALMSP AGMLRGDFSL RLFNVTPQDE QKFHCLVLSQ SLGFQEVLSD EVTLHVAANF  120
SV                                                                122

SEQ ID NO: 911           moltype = DNA   length = 1530
FEATURE                  Location/Qualifiers
misc_feature             1..1530
                         note = ICOSL/NKp30 Stack 1
source                   1..1530
                         mol_type = other DNA
                         organism = synthetic construct
SEQUENCE: 911
atggggtcaa ccgccatcct cgccctcctc ctggctgttc tccaaggagt cagcgctgat  60
actcaggaga aggaagtcag agcgatggta ggcagcgacg tggagctcag ctgcgcttgc  120
cctgaaggaa gccgttttga tttaaatgat gtttacgtat attggcaaac cagtgagtcg  180
aaaaccgtgg tgacctacca catcccacag gacagctcct tggaaaacgt ggacagccgc  240
taccggaacc gagccctgat gtcaccggcc ggcatgctgc gggacgactt ctccctgcgc  300
ttgttcaacg tcaccccca ggacgagcag aagtttcact gcctggtgtt gagccaatcc  360
ctgggattcc aggaggtttt gagcgttgag gttacactgc atgtggcagc aaacttcagc  420
gtgggaggtg gtggatcagg cggtggaggt tccggaggag gtggatctct ctgggtgtcc  480
cagcccctg agattcgtac cctggaagga tcctctgcct cctccttcaat  540
gccagccaag ggagagtggc cattggctcc gtcacgtggt tccgagatga ggtggttcca  600
gggaaggagg tgaggaatgg aaccccagag ttcaggggcc gcctggtccc acttgctccc  660
tcccgtttcc tccatgacca ccaggctgag ctgcacatcc gggacgtgcg aggccatgac  720
gccggtatct acgtgtgcag agtggaggtg ctgggccttg gtgtcgggac agggaatggg  780
actcggctgg tggtggagaa agaacatcct cagctaggat ccggtggagg agggtcagag  840
cccaaaagct ccgacaagac tcacacatgc ccccccttgtc cagcgcctga agctgagggt  900
gcgcccctg tcttcctttt cccccctaag ccgaaagata ccctgatgat ctcccgcact  960
cccgaagtca catgtgttgt tgtcgacgta tctcatgaag atcctgaggt gaaattcaac  1020
tggtatgtag acggggtcga agttcataat gctaagacta agccacgaga agagcaatac  1080
aactcaacgt atcgggtggt gagcgttctg acggttctgc accaagattg gcttaatgga  1140
aaagagtata agtgcaaggt gtccaacaag gctcttccgg cacccatcga aaagacgatt  1200
tccaaagcga aaggccaacc tagggaaccg caagtttaca ctttgccccc gtcaagagac  1260
gaacttacca agaatcaagt ttccctgacg tgccttgtga agggcttcta ccctagcgat  1320
atagcagttg agtgggaatc taacggccag cccgaaaata attataagac tactccgccc  1380
gtgctggaca gtgatggttc attttttcctg tattcaaaac tcactgtgga caaatctaga  1440
tggcagcagg gtaatgtgtt ctcttgttca gttatgcacg aggcattgca caatcactat  1500
acgcaaaaaa gtttgtctct ctctccgggg                                  1530

SEQ ID NO: 912           moltype = AA   length = 491
FEATURE                  Location/Qualifiers
REGION                   1..491
                         note = ICOSL/NKp30 Stack 1
source                   1..491
                         mol_type = protein
                         organism = synthetic construct
SEQUENCE: 912
DTQEKEVRAM VGSDVELSCA CPEGSRFDLN DVYVYWQTSE SKTVVTYHIP QDSSLENVDS  60
RYRNRALMSP AGMLRGDFSL RLFNVTPQDE QKFHCLVLSQ SLGFQEVLSV EVTLHVAANF  120
SVGGGGSGGG GSGGGGSLWV SQPPEIRTLE GSSAFLPCSF NASQGRVAIG SVTWFRDEVV  180
PGKEVRNGTP EFRGRLVPLA PSRFLHDHQA ELHIRDVRGH DAGIYVCRVE VLGLGVGTGN  240
GTRLVVEKEH PQLGSGGGGS EPKSSDKTHT CPPCPAPEAE GAPSVFLFPP KPKDTLMISR  300
TPEVTCVVVD VSHEDPEVKF NWYVDGVEVH NAKTKPREEQ YNSTYRVVSV LTVLHQDWLN  360
GKEYKCKVSN KALPAPIEKT ISKAKGQPRE PQVYTLPPSR DELTKNQVSL TCLVKGFYPS  420
DIAVEWESNG QPENNYKTTP PVLDSDGSFF LYSKLTVDKS RWQQGNVFSC SVMHEALHNH  480
YTQKSLSLSP G                                                      491

SEQ ID NO: 913           moltype = DNA   length = 1923
FEATURE                  Location/Qualifiers
misc_feature             1..1923
                         note = ICOSL/NKp30 Stack 2
source                   1..1923
                         mol_type = other DNA
                         organism = synthetic construct
SEQUENCE: 913
atggggtcaa ccgccatcct cgccctcctc ctggctgttc tccaaggagt cagcgctgat  60
```

-continued

```
actcaggaga aggaagtcag agcgatggta ggcagcgacg tggagctcag ctgcgcttgc   120
cctgaaggaa gccgttttga tttaaatgat gtttacgtat attggcaaac cagtgagtcg   180
aaaaccgtgg tgacctacca catcccacag gacagctcct tggaaaacgt ggacagccgc   240
taccggaacc gagccctgat gtcaccggcc ggcatgctgc ggggcgactt ctccctgcgc   300
ttgttcaacg tcaccccca ggacgagcag aagtttcact gcctggtgtt gagccaatcc   360
ctgggattcc aggaggtttt gagcgttgag gttacactgc atgtggcagc aaacttcagc   420
gtgggaggtg gtggatcagg cggtggaggt tccggaggag gtggatctct ctgggtgtcc   480
cagcccctg agattcgtac cctggaagga tcctctgcct cctgccctg ctccttcaat   540
gccagccaag ggagagtggc cattggctcc gtcacgtggt tccgagatga ggtggttcca   600
gggaaggagg tgaggaatgg aaccccagag ttcaggggcc gcctggtccc acttgctccc   660
tcccgtttcc tccatgacca ccaggctgag ctgcacatcc gggacgtgcg aggccatgac   720
gccggtatct acgtgtgcag agtggaggtg ctgggccttg gtgtcgggac agggaatggg   780
actcggctgg tggtggagaa agaacatcct cagctaggtg gaggaggtag cggggggagga   840
ggcagcggtg gtggcgggtc attgtgggtt tcacagcctc cagaaatacg gaccctgcag   900
ggttcctctg cttttctgcc ctgtagcttt aatgcttctc agggacgcgt ggctattggc   960
tccgttacgt ggtttcggga cgaggtggtc cctgggaagg aggtacggaa tggaacacct  1020
gagtttcggg gccgcctcgt tccgctcgct ccaagccgct tccttcacga ccaccaagcg  1080
gaacttcata taagggacgt gaggggcat gacgcgggta tatatgtctg ccgcgtcgag  1140
gtgctgggtc ttggggtggg tacgggcaat ggcaccgat tggtcgttga gaaagaaac  1200
cctcagctgg gatccggtgg aggagggtca gagcccaaaa gctccgacaa gactcacaca  1260
tgcccccctt gtccagcgcc tgaagctgag ggtgcgccct ctgtcttcct tttcccccct  1320
aagccgaaag ataccctgat gatctcccgc actcccgaag tcacatgtgt tgttgtcgac  1380
gtatctcatg aagatcctga ggtgaaattc aactggtatg tagacggggt cgaagttcat  1440
aatgctaaga ctaagccacg agaagagcaa tacaactcaa cgtatcgggt ggtgagcgtt  1500
ctgacggttc tgcaccaaga ttggcttaat ggaaaagagt ataagtgcaa ggtgtccaac  1560
aaggctcttc cggcacccat cgaaaagacg atttccaaag cccaaaggcca acctagggaa  1620
ccgcaagttt acactttgcc cccgtcaaga gacgaactta ccaagaatca agtttccctg  1680
acgtgccttg tgaagggctt ctaccctagc gatatagcag ttgagtggga atctaacggc  1740
cagcccgaaa ataattataa gactactccg cccgtgctgg acagtgatgg ttcatttttc  1800
ctgtattcaa aactcactgt ggacaaatct agatggcagc agggtaatgt gttctcttgt  1860
tcagttatgc acgaggcatt gcacaatcac tatacgcaaa aaagtttgtc tctctctccg  1920
ggg                                                                1923
```

```
SEQ ID NO: 914          moltype = AA  length = 622
FEATURE                 Location/Qualifiers
REGION                  1..622
                        note = ICOSL/NKp30 Stack 2
source                  1..622
                        mol_type = protein
                        organism = synthetic construct
SEQUENCE: 914
DTQEKEVRAM VGSDVELSCA CPEGSRFDLN DVYVYWQTSE SKTVVTYHIP QDSSLENVDS   60
RYRNRALMSP AGMLRGDFSL RLFNVTPQDE QKFHCLVLSQ SLGFQEVLSV EVTLHVAANF  120
SVGGGGSGGG GSGGGGSLWV SQPPEIRTLE GSSAFLPCSF NASQGRVAIG SVTWFRDEVV  180
PGKEVRNGTP EFRGRLVPLA PSRFLHDHQA ELHIRDVRGH DAGIYVCRVE VLGLGVGTGN  240
GTRLVVEKEH PQLGGGGSGG GGSGGGGSLW VSQPPEIRTL EGSSAFLPCS FNASQGRVAI  300
GSVTWFRDEV VPGKEVRNGT PEFRGRLVPL APSRFLHDHQ AELHIRDVRG HDAGIYVCRV  360
EVLGLGVGTG NGTRLVVEKE HPQLGSGGGG SEPKSSDKTH TCPPCPAPEA EGAPSVFLFP  420
PKPKDTLMIS RTPEVTCVVV DVSHEDPEVK FNWYVDGVEV HNAKTKPREE QYNSTYRVVS  480
VLTVLHQDWL NGKEYKCKVS NKALPAPIEK TISKAKGQPR EPQVYTLPPS RDELTKNQVS  540
LTCLVKGFYP SDIAVEWESN GQPENNYKTT PPVLDSDGSF FLYSKLTVDK SRWQQGNVFS  600
CSVMHEALHN HYTQKSLSLS PG                                           622
```

```
SEQ ID NO: 915          moltype = DNA  length = 1530
FEATURE                 Location/Qualifiers
misc_feature            1..1530
                        note = ICOSL/NKp30 Stack 3
source                  1..1530
                        mol_type = other DNA
                        organism = synthetic construct
SEQUENCE: 915
atggggtcaa ccgccatcct cgccctcctc ctggctgttc tccaaggagt cagcgctgat   60
actcaggaga aggaagtcag agcgatggta ggcagcgacg tggagctcag ctgcgcttgc   120
cctgaaggaa gccgttttga tttaaatgat gtttacgtat attggcaaac cagtgagtcg   180
aaaaccgtgg tgacctacca catcccacag cacagctcct tggaaaacgt ggacagccgc   240
taccggaacc gagccctgat gtcaccggcc ggcatgctgc ggggcgactt ctccctgcgc   300
ttgttcaacg tcaccccca ggacgagcag aagtttcact gcctggtgtt gagccgatcc   360
ctgggattcc aggaggtttt gagcgttgag gttacactgc atgtggcagc aaacttcagc   420
gtgggaggtg gtggatcagg cggtggaggt tccggaggag gtggatctct ctgggtgtcc   480
cagcccctg agattcgtac cctggaagga tcctctgcct cctgccctg ctccttcaat   540
gccagccaag ggagagtggc cattggctcc gtcacgtggt tccgagatga ggtggttcca   600
gggaaggagg tgaggaatgg aaccccagag ttcaggggcc gcctggtccc acttgctccc   660
tcccgtttcc tccatgacca ccaggctgag ctgcacatcc gggacgtgcg aggccatgac   720
gccggtatct acgtgtgcag agtggaggtg ctgggccttg gtgtcgggag agggaatggg   780
actcggctgg tggtggagaa agaacatcct cagctaggt ccggtggagg agggtcagag   840
cccaaaagct ccgacaagac tcacacatgc ccccccttgtc cagcgcctga gctgagggt   900
gcgcctctg tcttcctttt ccccctaag ccgaaagata ccctgatgat ctcccgcact   960
cccgaagtca catgtgttgt tgtcgacgta tctcatgaag atcctgaggt gaaattcaac  1020
tggtatgtag acggggtcga agttcataat gctaagacta gccacgaga gagcaatac  1080
```

-continued

```
aactcaacgt atcgggtggt gagcgttctg acggttctgc accaagattg gcttaatgga   1140
aaagagtata agtgcaaggt gtccaacaag gctcttccgg cacccatcga aaagacgatt   1200
tccaaagcga aaggccaacc tagggaaccg caagtttaca ctttgccccc gtcaagagac   1260
gaacttacca agaatcaagt ttccctgacg tgccttgtga agggcttcta ccctagcgat   1320
atagcagttg agtgggaatc taacggccag cccgaaaata attataagac tactccgccc   1380
gtgctggaca gtgatggttc attttcctg tattcaaaac tcactgtgga caaatctaga   1440
tggcagcagg gtaatgtgtt ctcttgttca gttatgcacg aggcattgca caatcactat   1500
acgcaaaaaa gtttgtctct ctctccgggg                                     1530
```

```
SEQ ID NO: 916           moltype = AA   length = 491
FEATURE                  Location/Qualifiers
REGION                   1..491
                         note = ICOSL/NKp30 Stack 3
source                   1..491
                         mol_type = protein
                         organism = synthetic construct
SEQUENCE: 916
DTQEKEVRAM VGSDVELSCA CPEGSRFDLN DVYVYWQTSE SKTVVTYHIP QHSSLENVDS   60
RYRNRALMSP AGMLRGDFSL RLFNVTPQDE QKFHCLVLSR SLGFQEVLSV EVTLHVAANF   120
SVGGGGSGGG GSGGGGSLWV SQPPEIRTLE GSSAFLPCSF NASQGRVAIG SVTWFRDEVV   180
PGKEVRNGTP EFRGRLVPLA PSRFLHDHQA ELHIRDVRGH DAGIYVCRVE VLGLGVGTGN   240
GTRLVVEKEH PQLGSGGGGS EPKSSDKTHT CPPCPAPEAE GAPSVFLFPP KPKDTLMISR   300
TPEVTCVVVD VSHEDPEVKF NWYVDGVEVH NAKTKPREEQ YNSTYRVVSV LTVLHQDWLN   360
GKEYKCKVSN KALPAPIEKT ISKAKGQPRE PQVYTLPPSR DELTKNQVSL TCLVKGFYPS   420
DIAVEWESNG QPENNYKTTP PVLDSDGSFF LYSKLTVDKS RWQQGNVFSC SVMHEALHNH   480
YTQKSLSLSP G                                                        491
```

```
SEQ ID NO: 917           moltype = DNA   length = 1923
FEATURE                  Location/Qualifiers
misc_feature             1..1923
                         note = ICOSL/NKp30 Stack 4
source                   1..1923
                         mol_type = other DNA
                         organism = synthetic construct
SEQUENCE: 917
atggggtcaa ccgccatcct cgccctcctc ctggctgttc tccaaggagt cagcgctgat   60
actcaggaga aggaagtcag agcgatggta ggcagcgacg tggagctcag ctgcgcttgc   120
cctgaaggaa gccgttttga tttaaatgat gtttacgtat attggcaaac cagtgagtcg   180
aaaaccgtgg tgacctacca tatcccacag cacagctcct tggaaaacgt ggacagccgc   240
taccggaacc gagccctgat gtcaccggcc ggcatgctgc ggggcgactt ctccctcgcg   300
ttgttcaacg tcacccccca ggacgagcag aagtttcact gcctggtgtt gagccgatcc   360
ctgggattcc aggaggtttt gagcgttgag gttacactgc atgtggcagc aaacttcagc   420
gtgggaggtg gtggatcagg cggtggaggt tccggaggag gtggatctct ctgggtgtcc   480
cagcccctg agattcgtac cctggaagga tcctctgcct tcctgccctg ctccttcaat   540
gccagccaag ggagagtggc cattggctcc gtcacgtggt tccagatga ggtgttcca   600
gggaaggagg tgaggaatgg aaccccagag ttcaggggcc gcctggtccc acttgctccc   660
tcccgtttcc tccatgacca ccaggctgag ctgcacatcc gggacgtgcg aggccatgac   720
gccggtatct acgtgtgcag agtggaggtg ctgggccttg gtgtcgggac agggaatggg   780
actcggctgg tggtggagaa agaacatcct cagctaggtg gaggaggtag cggggggagga   840
ggcagcggtg gtggcgggtc attgtgggtt tcacagcctc cagaaatacg gaccctcgag   900
ggttcctctg cttttctgcc ctgtagcttt aatgcttcc agggacgcgt ggctattggc   960
tccgttacgt ggtttcggga cgaggtggtc cctgggaagg aggtacggaa tggaacacct   1020
gagtttcggg gccgcctcgt tccgctcgct ccaagccgct tccttcacga ccaccaagcg   1080
gaacttcata taagggacgt gaggggggcat gacgcgggta tatatgtctg ccgcgtcgag   1140
gtgctgggtc ttggggtggg tacgggcaat ggcacccgat tggtcgttga gaaagaacac   1200
cctcagctgg gatccggtgg aggagggtca gagcccaaaa gctccgacaa gactcacaca   1260
tgccccccctt gtccagcgcc tgaagctgag ggtgcgccct ctgtcttcct ttttccccct   1320
aagccgaaag atacctgat gatctcccgc actcccgaag tcacatgtgt tgttgtcgac   1380
gtatctcatg aagatcctga ggtgaaattc aactggtatg tagacgggt cgaagttcat   1440
aatgctaaga ctaagccacg agaagagcaa tacaactcaa cgtatcgggt ggtgagcgtt   1500
ctgacggttc tgcaccaaga ttggcttaat ggaaaagagt ataagtgcaa ggtgtccaac   1560
aaggctcttc cggcacccat cgaaaagacg atttccaaag cgaaaggcca acctagggaa   1620
ccgcaagttt acactttgcc cccgtcaaga gacgaactta ccaagaatca gtttccctg   1680
acgtgccttg tgaagggctt ctaccctagc gatatagcag ttgagtggga atctaacggc   1740
cagcccgaaa ataattataa gactactccg cccgtgctgg acagtgatgg ttcatttttc   1800
ctgtattcaa aactcactgt ggacaaatct agatggcagc agggtaatgt gttctcttgt   1860
tcagttatgc acgaggcatt gcacaatcac tatacgcaaa aagtttgtc tctctctccg   1920
ggg                                                                 1923
```

```
SEQ ID NO: 918           moltype = AA   length = 622
FEATURE                  Location/Qualifiers
REGION                   1..622
                         note = ICOSL/NKp30 Stack 4
source                   1..622
                         mol_type = protein
                         organism = synthetic construct
SEQUENCE: 918
DTQEKEVRAM VGSDVELSCA CPEGSRFDLN DVYVYWQTSE SKTVVTYHIP QHSSLENVDS   60
RYRNRALMSP AGMLRGDFSL RLFNVTPQDE QKFHCLVLSR SLGFQEVLSV EVTLHVAANF   120
```

-continued

```
SVGGGGSGGG GSGGGGSLWV SQPPEIRTLE GSSAFLPCSF NASQGRVAIG SVTWFRDEVV  180
PGKEVRNGTP EFRGRLVPLA PSRFLHDHQA ELHIRDVRGH DAGIYVCRVE VLGLGVGTGN  240
GTRLVVEKEH PQLGGGGSGG GGSGGGGSLW VSQPPEIRTL EGSSAFLPCS FNASQGRVAI  300
GSVTWFRDEV VPGKEVRNGT PEFRGRLVPL APSRFLHDHQ AELHIRDVRG HDAGIYVCRV  360
EVLGLGVGTG NGTRLVVEKE HPQLGSGGGG SEPKSSDKTH TCPPCPAPEA EGAPSVFLFP  420
PKPKDTLMIS RTPEVTCVVV DVSHEDPEVK FNWYVDGVEV HNAKTKPREE QYNSTYRVVS  480
VLTVLHQDWL NGKEYKCKVS NKALPAPIEK TISKAKGQPR EPQVYTLPPS RDELTKNQVS  540
LTCLVKGFYP SDIAVEWESN GQPENNYKTT PPVLDSDGSF FLYSKLTVDK SRWQQGNVFS  600
CSVMHEALHN HYTQKSLSLS PG                                          622
```

SEQ ID NO: 919          moltype = DNA  length = 1530
FEATURE                 Location/Qualifiers
misc_feature            1..1530
                        note = ICOSL/NKp30 Stack 5
source                  1..1530
                        mol_type = other DNA
                        organism = synthetic construct
SEQUENCE: 919

```
atggggtcaa ccgccatcct cgccctcctc ctggctgttc tccaaggagt cagcgctgat   60
actcaggaga aggaagtcag agcgatggta ggcagcgacg tggagctcag ctgcgcttgc  120
cctgaaggaa gccgttttga tttaaatgat gtttacgtat attggcaaac cagtgagtcg  180
aagaccgtgg tgacctacca catcccacag cacagctcct tggaatacgt ggacagccgc  240
taccggaacc gagccctgat gtcaccggcc ggcatgctgc ggggcgactt ctccctgcgc  300
ttgttcaacg tcacccccca ggacgagcag aagtttcact gcctggtgtt gagccgatcc  360
ctgggattcc aggaggtttt gagcgttgag gttacactgc atgtggcagc aaacttcagc  420
gtgggaggtg gtggatcagg cggtggaggt tccggaggag gtggatctct ctgggtgtcc  480
cagccccctg agattcgtac cctggaagga tcctctgcct cctgccctg  ctccttcaat  540
gccagccaag gagagtggc  cattggctcc gtcacgtggt tccgagatga ggtggttcca  600
gggaaggagg tgaggaatgg aaccccagag ttcaggggcc gcctggtccc acttgctccc  660
tcccgtttcc tccatgacca ccaggctgag ctgcacatcc gggacgtgcg aggccatgac  720
gccggtatct acgtgtgcag agtggaggtg ctgggccttg gtgtcgggac agggaatggg  780
actcggctgg tggtggagaa agaacatcct cagctaggat ccggtggagg agggtcagag  840
cccaaaagct ccgacaagac tcacacatgc ccccccttgtc cagcgcctga gctgagggt   900
gcgccctctg tcttccttttt ccccccctaag ccgaaagata cctgatggt  ctcccgcact  960
cccgaagtca catgtgttgt tgtcgacgta tctcatgaag atcctgaggt gaaattcaac 1020
tggtatgtag acggggtcga agttcataat gctaagacta agccacgaga gagcaaatac 1080
aactcaacgt atcgggtggt gagcgttctg acggttctgc accaagattg gcttaatgga 1140
aaagagtata agtgcaaggt gtccaacaag gctcttccgg cacccatcga aaagacgatt 1200
tccaaagcga aaggccaacc tagggaaccg caagtttaca ctttgccccc gtcaagagac 1260
gaacttacca agaatcaagt ttccctgacg tgccttgtga agggcttcta ccctagcgat 1320
atagcagttg agtgggaatc taacggccag cccgaaaata attataagac tactccgccc 1380
gtgctggaca gtgatggttc attttttcctg tattcaaaac tcactgtgga caaatctaga 1440
tggcagcagg gtaatgtgtt ctcttgttca gttatgcacg aggcattgca caatcactat 1500
acgcaaaaaa gtttgtctct ctctccgggg                                  1530
```

SEQ ID NO: 920          moltype = AA  length = 491
FEATURE                 Location/Qualifiers
REGION                  1..491
                        note = ICOSL/NKp30 Stack 5
source                  1..491
                        mol_type = protein
                        organism = synthetic construct
SEQUENCE: 920

```
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSR SLGFQEVLSV EVTLHVAANF  120
SVGGGGSGGG GSGGGGSLWV SQPPEIRTLE GSSAFLPCSF NASQGRVAIG SVTWFRDEVV  180
PGKEVRNGTP EFRGRLVPLA PSRFLHDHQA ELHIRDVRGH DAGIYVCRVE VLGLGVGTGN  240
GTRLVVEKEH PQLGSGGGGS EPKSSDKTHT CPPCPAPEAE GAPSVFLFPP KPKDTLMISR  300
TPEVTCVVVD VSHEDPEVKF NWYVDGVEVH NAKTKPREEQ YNSTYRVVSV LTVLHQDWLN  360
GKEYKCKVSN KALPAPIEKT ISKAKGQPRE PQVYTLPPSR DELTKNQVSL TCLVKGFYPS  420
DIAVEWESNG QPENNYKTTP PVLDSDGSFF LYSKLTVDKS RWQQGNVFSC SVMHEALHNH  480
YTQKSLSLSP G                                                      491
```

SEQ ID NO: 921          moltype = DNA  length = 1923
FEATURE                 Location/Qualifiers
misc_feature            1..1923
                        note = ICOSL/NKp30 Stack 6
source                  1..1923
                        mol_type = other DNA
                        organism = synthetic construct
SEQUENCE: 921

```
atggggtcaa ccgccatcct cgccctcctc ctggctgttc tccaaggagt cagcgctgat   60
actcaggaga aggaagtcag agcgatggta ggcagcgacg tggagctcag ctgcgcttgc  120
cctgaaggaa gccgttttga tttaaatgat gtttacgtat attggcaaac cagtgagtcg  180
aagaccgtgg tgacctacca catcccacag cacagctcct tggaatacgt ggacagccgc  240
taccggaacc gagccctgat gtcaccggcc ggcatgctgc ggggcgactt ctccctgcgc  300
ttgttcaacg tcacccccca ggacgagcag aagtttcact gcctggtgtt gagccgatcc  360
ctgggattcc aggaggtttt gagcgttgag gttacactgc atgtggcagc aaacttcagc  420
gtgggaggtg gtggatcagg cggtggaggt tccggaggag gtggatctct ctgggtgtcc  480
```

```
cagccccctg agattcgtac cctggaagga tcctctgcct tcctgccctg ctccttcaat   540
gccagccaag ggagagtggc cattggctcc gtcacgtggt tccgagatga ggtggttcca   600
gggaaggagg tgaggaatgg aaccccagag ttcaggggcc gcctggtccc acttgctccc   660
tcccgtttcc tccatgacca ccaggctgag ctgcacatcc gggacgtgcg aggccatgac   720
gccggtatct acgtgtgcag agtggaggtg ctgggccttg gtgtcgggac agggaatggg   780
actcggctgg tggtggagaa agaacatcct cagctaggtg gaggaggtag cggggggagga   840
ggcagcggtg gtggcgggtc attgtggggtt tcacagcctc cagaaatacg gaccctcgag   900
ggttcctctg ctttttctgcc ctgtagcttt aatgcttctc agggacgcgt ggctattggc   960
tccgttacgt ggtttcggga cgaggtggtc cctgggaagg aggtacggaa tggaacacct   1020
gagtttcggg gccgcctcgt tccgctcgct ccaagccgct tccttcacga ccaccaagcg   1080
gaacttcata taagggacgt gaggggggcat gacgcgggta tatatgtctg ccgcgtcgag   1140
gtgctgggtc ttggggtggg tacgggcaat ggcaccgat tggtcgttga gaaagaaac   1200
cctcagctgg gatccggtgg aggagggtca gagcccaaaa gctccgacaa gactcacaca   1260
tgcccccctt gtccagcgcc tgaagctgag ggtgcgccct ctgtcttcct tttcccccct   1320
aagccgaaag ataccctgat gatctcccgc actcccgaag tcacatgtgt tgttgtcgac   1380
gtatctcatg aagatcctga ggtgaaattc aactggtatg tagacggggt cgaagttcat   1440
aatgctaaga ctaagccacg agaagagcaa tacaactaca cgtatcgggt ggtgagcgtt   1500
ctgacggttc tgcaccaaga ttggcttaat ggaaaagagt ataagtgcaa ggtgtccaac   1560
aaggctcttc cggcacccat cgaaaagacg atttccaaag cgaaaggcca acctaggggaa   1620
ccgcaagttt acactttgcc cccgtcaaga gacgaactta ccaagaatca agtttccctg   1680
acgtgccttg tgaagggctt ctaccctagc gatatagcag ttgagtggga atctaacggc   1740
cagcccgaaa ataattataa gactactccg cccgtgctgg acagtgatgg ttcattttc   1800
ctgtattcaa aactcactgt ggacaaatct agatggcagc agggtaatgt gttctcttgt   1860
tcagttatgc acgaggcatt gcacaatcac tatacgcaaa aaagtttgtc tctctctccg   1920
ggg                                                                 1923

SEQ ID NO: 922          moltype = AA  length = 622
FEATURE                 Location/Qualifiers
REGION                  1..622
                        note = ICOSL/NKp30 Stack 6
source                  1..622
                        mol_type = protein
                        organism = synthetic construct
SEQUENCE: 922
DTQEKEVRAM VGSDVELSCA CPEGSRFDLN DVYVYWQTSE SKTVVTYHIP QHSSLEYVDS   60
RYRNRALMSP AGMLRGDFSL RLFNVTPQDE QKFHCLVLSR SLGFQEVLSV EVTLHVAANF   120
SVGGGGSGGG GSGGGGSLWV SQPPEIRTLE GSSAFLPCSF NASQGRVAIG SVTWFRDEVV   180
PGKEVRNGTP EFRGRLVPLA PSRFLHDHQA ELHIRDVRGH DAGIYVCRVE VLGLGVGTGN   240
GTRLVVEKEH PQLGGGGSGG GGSGGGGSLW VSQPPEIRTL EGSSAFLPCS FNASQGRVAI   300
GSVTWFRDEV VPGKEVRNGT PEFRGRLVPL APSRFLHDHQ AELHIRDVRG HDAGIYVCRV   360
EVLGLGVGTG NGTRLVVEKE HPQLGSGGGG SEPKSSDKTH TCPPCPAPEA EGAPSVFLFP   420
PKPKDTLMIS RTPEVTCVVV DVSHEDPEVK FNWYVDGVEV HNAKTKPREE QYNSTYRVVS   480
VLTVLHQDWL NGKEYKCKVS NKALPAPIEK TISKAKGQPR EPQVYTLPPS RDELTKNQVS   540
LTCLVKGFYP SDIAVEWESN GQPENNYKTT PPVLDSDGSF FLYSKLTVDK SRWQQGNVFS   600
CSVMHEALHN HYTQKSLSLS PG                                            622

SEQ ID NO: 923          moltype = DNA  length = 1530
FEATURE                 Location/Qualifiers
misc_feature            1..1530
                        note = ICOSL/NKp30 Stack 7
source                  1..1530
                        mol_type = other DNA
                        organism = synthetic construct
SEQUENCE: 923
atggggtcaa ccgccatcct cgccctcctc ctggctgttc tccaaggagt cagcgctgat   60
actcaggaga aggaagtcag agcgatggta ggcagcgacg tggagctcag ctgcgcttgc   120
cctgaaggaa gccgttttga tttaaatgat gtttacgtat attggcaaac cagtgagtcg   180
aaaaccgtgg tgacctacca catcccacag ctgagctcct tggaacatgt ggacagccgc   240
taccggaacc gagccctgat gtcaccggcc ggcatgctgc ggggcgactt ctccctgcgc   300
ttgttcaacg tcacccccca ggacgagcag aagtttcact gcctggtgtt gagccggtcc   360
ctgggattcc aggaggtttt gagcgttgag gttacactgc atgtggcagc aaacttcagc   420
gtgggaggtg gtggatcagg cggtggaggt tccggaggag gtggatctct ctgggtgtcc   480
cagccccctg agattcgtac cctggaagga tcctctgcct tcctgccctg ctccttcaat   540
gccagccaag ggagagtggc cattggctcc gtcacgtggt tccgagatga ggtggttcca   600
gggaaggagg tgaggaatgg aaccccagag ttcaggggcc gcctggtccc acttgctccc   660
tcccgtttcc tccatgacca ccaggctgag ctgcacatcc gggacgtgcg aggccatgac   720
gccggtatct acgtgtgcag agtggaggtg ctgggccttg gtgtcgggac agggaatggg   780
actcggctgg tggtggagaa agaacatcct cagctaggt ccggtggagg agggtcagag   840
cccaaaagct ccgacaagac tcacatgtgc ccccttgtc cagcgcctga agctgaggt   900
gcgcctctg tcttcctttt ccccctaag ccgaaagata ccctgatgat ctcccgcact   960
cccgaagtca catgtgttgt gtcgacgta tctcatgaag atcctgaggt gaaattcaac   1020
tggtatgtag acgggtcga agttcataat gctaagacta gccacgaga gagcaatac   1080
aactcaacgt atcgggtggt gagcgttctg acggttctgc accaagattg gcttaatgga   1140
aaagagtata agtgcaaggt gtccaacaag gctcttccgg cacccatcga aaagacgatt   1200
tccaaagcga aaggccaacc tagggaaccg caagtttaca ctttgccccc gtcaagagac   1260
gaacttacca gaatcaagt ttccctgacg tgccttgtga agggcttcta ccctagcgat   1320
atagcagttg agtgggaatc taacggccag cccgaaaata ttataagac tactccgccc   1380
gtgctggaca gtgatggttc atttttcctg tattcaaaac tcactgtgga caaatctaga   1440
tggcagcagg gtaatgtgtt ctcttgttca gttatgcacg aggcattgca caatcactat   1500
```

```
acgcaaaaaa gtttgtctct ctctccgggg                                      1530

SEQ ID NO: 924          moltype = AA   length = 491
FEATURE                 Location/Qualifiers
REGION                  1..491
                        note = ICOSL/NKp30 Stack 7
source                  1..491
                        mol_type = protein
                        organism = synthetic construct
SEQUENCE: 924
DTQEKEVRAM VGSDVELSCA CPEGSRFDLN DVVYVWQTSE SKTVVTYHIP QLSSLEHVDS     60
RYRNRALMSP AGMLRGDFSL RLFNVTPQDE QKFHCLVLSR SLGFQEVLSV EVTLHVAANF    120
SVGGGGSGGG GSGGGGSLWV SQPPEIRTLE GSSAFLPCSF NASQGRVAIG SVTWFRDEVV    180
PGKEVRNGTP EFRGRLVPLA PSRFLHDHQA ELHIRDVRGH DAGIYVCRVE VLGLGVGTGN    240
GTRLVVEKEH PQLGSGGGGS EPKSSDKTHT CPPCPAPEAE GAPSVFLFPP KPKDTLMISR    300
TPEVTCVVVD VSHEDPEVKF NWYVDGVEVH NAKTKPREEQ YNSTYRVVSV LTVLHQDWLN    360
GKEYKCKVSN KALPAPIEKT ISKAKGQPRE PQVYTLPPSR DELTKNQVSL TCLVKGFYPS    420
DIAVEWESNG QPENNYKTTP PVLDSDGSFF LYSKLTVDKS RWQQGNVFSC SVMHEALHNH    480
YTQKSLSLSP G                                                        491

SEQ ID NO: 925          moltype = DNA   length = 1923
FEATURE                 Location/Qualifiers
misc_feature            1..1923
                        note = ICOSL/NKp30 Stack 8
source                  1..1923
                        mol_type = other DNA
                        organism = synthetic construct
SEQUENCE: 925
atgggggtcaa ccgccatcct cgccctcctc ctggctgttc tccaaggagt cagcgctgat    60
actcaggaga aggaagtcag agcgatggta ggcagcgacg tggagctcag ctgcgcttgc   120
cctgaaggaa gccgttttga tttaaatgat gtttacgtat attggcaaac cagtgagtcg   180
aaaaccgtgg tgacctacca catcccacag ctgagctcct tggaacatgt ggacagccgc   240
taccggaacc gagccctgat gtcaccggcc ggcatgctgc ggggcgactt ctccctgcgc   300
ttgttcaacg tcaccccccca ggacgagcag aagtttcact gcctggtgtt gagccggtcc   360
ctgggattcc aggaggtttt gagcgttgag gttacactgc atgtggcagc aaacttcagc   420
gtgggaggtg gtggatcagg cggtggaggt tccggaggag gtggatctct ctgggtgtcc   480
cagcccctg agattcgtac cctggaagga tcctctgcct cctgccctg ctccttcaat     540
gccagccaag ggagagtggc cattggctcc gtcacgtggt tccgagatga ggtggttcca   600
gggaaggagg tgaggaatgg aaccccagag ttcaggggcc gcctggtccc acttgctccc   660
tcccgtttcc tccatgacca ccaggctgag ctgcacatcc gggacgtgcg aggccatgac   720
gccggtatct acgtgtgcag agtggaggtg ctgggccttg gtgtcgggac agggaatggg   780
actcggctgg tggtggagaa agaacatcct cagctaggtg gaggaggtag cggggggagga  840
ggcagcggtg gtggcgggtc attgtgggtt tcacagcctc cagaaatacg gaccctcgag   900
ggttcctctg cttttctgcc ctgtagcttt aatgcttctc agggacgcgt ggctattggc   960
tccgttacgt ggtttcggga cgaggtggtc cctgggaagg aggtacggaa tggaacacct  1020
gagtttcggg gccgcctcgt tccgctcgct ccaagccgct ccttcacga ccaccaagcg   1080
gaacttcata taaggggacgt gagggggcat gacgcgggta tatatgtctg ccgcgtcgag  1140
gtgctgggtc ttggggtggg tacgggcaat ggcacccgat tggtcgttga gaaagaaaac  1200
cctcagctgg gatccggtgg aggagggtca gagcccaaaa gctccgacaa gactcacaca  1260
tgccccccctt gtccagcgcc tgaagctgag ggtgcgccct ctgtcttcct tttcccccct  1320
aagccgaaag atacccctgat gatctcccgc actcccgaag tcacatgtgt tgttgtcgac  1380
gtatctcatg aagatcctga ggtgaaattc aactggtatg tagacggggt cgaagttcat  1440
aatgctaaga ctaagccacg agaagagcaa tacaactcaa cgtatcgggt ggtgagcgtt  1500
ctgacggttc tgcaccaaga ttggcttaat ggaaaagagt ataagtgcaa ggtgtccaac  1560
aaggctcttc cggcacccat cgaaaagacg atttccaaag cgaaaggcca acctagggaa  1620
ccgcaagttt acactttgcc cccgtcaaga gacgaactta ccaagaatca agtttccctg  1680
acgtgccttg tgaagggctt ctaccctagc gatatagcag ttgagtggga atctaacggc  1740
cagcccgaaa ataattataa gactactccg cccgtgctgg acagtgatgg ttcattttc   1800
ctgtattcaa aactcactgt ggacaaatct agatggcagc agggtaatgt gttctcttgt  1860
tcagttatgc acgaggcatt gcacaatcac tatacgcaaa aaagtttgtc tctctctccg  1920
ggg                                                                1923

SEQ ID NO: 926          moltype = AA   length = 622
FEATURE                 Location/Qualifiers
REGION                  1..622
                        note = ICOSL/NKp30 Stack 8
source                  1..622
                        mol_type = protein
                        organism = synthetic construct
SEQUENCE: 926
DTQEKEVRAM VGSDVELSCA CPEGSRFDLN DVVYVWQTSE SKTVVTYHIP QLSSLEHVDS     60
RYRNRALMSP AGMLRGDFSL RLFNVTPQDE QKFHCLVLSR SLGFQEVLSV EVTLHVAANF    120
SVGGGGSGGG GSGGGGSLWV SQPPEIRTLE GSSAFLPCSF NASQGRVAIG SVTWFRDEVV    180
PGKEVRNGTP EFRGRLVPLA PSRFLHDHQA ELHIRDVRGH DAGIYVCRVE VLGLGVGTGN    240
GTRLVVEKEH PQLGGGGSGG GSGGGGSLW VSQPPEIRTL EGSSAFLPCS FNASQGRVAI    300
GSVTWFRDEV VPGKEVRNGT PEFRGRLVPL APSRFLHDHQ AELHIRDVRG HDAGIYVCRV    360
EVLGLGVGTG NGTRLVVEKE HPQLGSGGGG SEPKSSDKTH TCPPCPAPEA EGAPSVFLFP    420
PKPKDTLMIS RTPEVTCVVV DVSHEDPEVK FNWYVDGVEV HNAKTKPREE QYNSTYRVVS    480
VLTVLHQDWL NGKEYKCKVS NKALPAPIEK TISKAKGQPR EPQVYTLPPS RDELTKNQVS    540
```

```
LTCLVKGFYP SDIAVEWESN GQPENNYKTT PPVLDSDGSF FLYSKLTVDK SRWQQGNVFS    600
CSVMHEALHN HYTQKSLSLS PG                                             622

SEQ ID NO: 927            moltype = AA  length = 231
FEATURE                   Location/Qualifiers
REGION                    1..231
                          note = Fc with C220S/E356D/M358L/K447del
source                    1..231
                          mol_type = protein
                          organism = synthetic construct
SEQUENCE: 927
EPKSSDKTHT CPPCPAPELL GGPSVFLFPP KPKDTLMISR TPEVTCVVVD VSHEDPEVKF     60
NWYVDGVEVH NAKTKPREEQ YNSTYRVVSV LTVLHQDWLN GKEYKCKVSN KALPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP G            231

SEQ ID NO: 928            moltype = AA  length = 363
FEATURE                   Location/Qualifiers
REGION                    1..363
                          note = Variant ICOSL IgV-Fc
source                    1..363
                          mol_type = protein
                          organism = synthetic construct
SEQUENCE: 928
DTQEKEVRAM VGSDVELSCA CPEGSRFDLN DVYVYWQTSE SKTVVTYHIP QHSSLEYVDS     60
RYRNRALMSP AGMLRGDFSL RLFNVTPQDE QKFHCLVLSR SLGFQEVLSV EVTLHVAANF    120
SVGGGGSGGG GSEPKSSDKT HTCPPCPAPE AEGAPSVFLF PPKPKDTLMI SRTPEVTCVV    180
VDVSHEDPEV KFNWYVDGVE VHNAKTKPRE EQYNSTYRVV SVLTVLHQDW LNGKEYKCKV    240
SNKALPAPIE KTISKAKGQP REPQVYTLPP SRDELTKNQV SLTCLVKGFY PSDIAVEWES    300
NGQPENNYKT TPPVLDSDGS FFLYSKLTVD KSRWQQGNVF SCSVMHEALH NHYTQKSLSL    360
SPG                                                                 363

SEQ ID NO: 929            moltype = AA  length = 116
FEATURE                   Location/Qualifiers
REGION                    1..116
                          note = NKp30 WT IgV-like
source                    1..116
                          mol_type = protein
                          organism = synthetic construct
SEQUENCE: 929
LWVSQPPEIR TLEGSSAFLP CSFNASQGRL AIGSVTWFRD EVVPGKEVRN GTPEFRGRLA     60
PLASSRFLHD HQAELHIRDV RGHDASIYVC RVEVLGLGVG TGNGTRLVVE KEHPQL        116

SEQ ID NO: 930            moltype = AA  length = 116
FEATURE                   Location/Qualifiers
REGION                    1..116
                          note = NKp30 v2 IgV-like
source                    1..116
                          mol_type = protein
                          organism = synthetic construct
SEQUENCE: 930
LWVSQPPEIR TLEGSSAFLP CSFNASQGRV AIGSVTWFRD EVVPGKEVRN GTPEFRGRLA     60
PLASSRFLHD HQAELHIRDV RGHDASIYVC RVEVLGLGVG TGNGTRLVVE KEHPQL        116

SEQ ID NO: 931            moltype = AA  length = 116
FEATURE                   Location/Qualifiers
REGION                    1..116
                          note = NKp30 v3 IgV-like
source                    1..116
                          mol_type = protein
                          organism = synthetic construct
SEQUENCE: 931
LWVSQPPEIR TLEGSSAFLP CSFNASQGRL AIGSVTWFRD EVVPGKEVRN GTPEFRGRLV     60
PLASSRFLHD HQAELHIRDV RGHDASIYVC RVEVLGLGVG TGNGTRLVVE KEHPQL        116

SEQ ID NO: 932            moltype = AA  length = 116
FEATURE                   Location/Qualifiers
REGION                    1..116
                          note = NKp30 v4 IgV-like
source                    1..116
                          mol_type = protein
                          organism = synthetic construct
SEQUENCE: 932
LWVSQPPEIR TLEGSSAFLP CSFNASQGRL AIGSVTWFRD EVVPGKEVRN GTPEFRGRLA     60
PLAPSRFLHD HQAELHIRDV RGHDASIYVC RVEVLGLGVG TGNGTRLVVE KEHPQL        116

SEQ ID NO: 933            moltype = AA  length = 116
FEATURE                   Location/Qualifiers
REGION                    1..116
```

-continued

```
                      note = NKp30 v5 IgV-like
source                1..116
                      mol_type = protein
                      organism = synthetic construct
SEQUENCE: 933
LWVSQPPEIR TLEGSSAFLP CSFNASQGRL AIGSVTWFRD EVVPGKEVRN GTPEFRGRLA   60
PLASSRFLHD HQAELHIRDV RGHDAGIYVC RVEVLGLGVG TGNGTRLVVE KEHPQL       116
```

1

VARIANT ICOS LIGAND IMMUNOMODULATORY PROTEINS AND RELATED COMPOSITIONS AND METHODS

CROSS-REFERENCE TO RELATED APPLICATIONS

This application is a continuation of U.S. application Ser. No. 17/560,209 filed on Dec. 22, 2021, which is a continuation of U.S. application Ser. No. 16/757,344 filed on Apr. 17, 2020, which is a National Stage application under 35 U.S.C. § 371 of International Application No. PCT/US2018/056381, filed on Oct. 17, 2018, which claims priority from U.S. provisional patent application 62/574,161, filed Oct. 18, 2017, entitled "VARIANT ICOS LIGAND IMMUNO-MODULATORY PROTEINS AND RELATED COMPOSI-TIONS AND METHODS," the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 761612002202SeqList.xml, created Feb. 17, 2023, which is 1,365,337 bytes in size. The information in the electronic format of the Sequence Listing is incorporated by reference in its entirety.

FIELD

The present disclosure relates to therapeutic compositions for modulating immune response in the treatment of cancer and immunological diseases. In some aspects, the present disclosure relates to particular variants of ICOS Ligand (ICOSL) that exhibit improved binding, such as improved affinity or selectivity for one or both of the cognate binding partner proteins ICOS or CD28.

BACKGROUND

Modulation of the immune response by intervening in the processes that occur in the immunological synapse (IS) formed by and between antigen-presenting cells (APCs) or target cells and lymphocytes is of increasing medical interest. Mechanistically, cell surface proteins in the IS can involve the coordinated and often simultaneous interaction of multiple protein targets with a single protein to which they bind. IS interactions occur in close association with the junction of two cells, and a single protein in this structure can interact with both a protein on the same cell (cis) as well as a protein on the associated cell (trans), likely at the same time. Although therapeutics are known that can modulate the IS, improved therapeutics are needed. Provided are immunomodulatory proteins, including soluble proteins or trans-membrane immunomodulatory proteins capable of being expressed on cells, that meet such needs.

SUMMARY

Provided herein is a variant ICOS Ligand (ICOSL) polypeptide containing one or more amino acid modifications in an immunoglobulin superfamily (IgSF) domain of an ICOSL reference polypeptide, wherein the ICOSL reference polypeptide is a truncated extracellular domain comprising a contiguous sequence of amino acids comprising amino acids 1-112 and a C-terminal truncation of at least 25 amino acids with reference to the ICOSL extracellular domain sequence set forth in SEQ ID NO: 32. In some of any of the provided embodiments, the variant ICOSL polypeptide exhibits altered binding to the ectodomain(s) of ICOS or CD28 compared to the binding of the ICOSL reference polypeptide for the same ectodomain(s). In some of any of the provided embodiments, the variant ICOSL polypeptide exhibits increased binding to the ectodomain(s) of ICOS or CD28 compared to the binding of the ICOSL reference polypeptide for the same ectodomain(s).

In some of any such embodiments, the C-terminal truncation is of at least 30, at least 40, at least 50, at least 60, at least 70, at least 80, at least 90, at least 100, at least 125 amino acid residues. In some of any of the provided embodiments, the ICOSL reference polypeptide is altered in or lacks a protease cleavage site set forth as amino acids 204-209 of SEQ ID NO:32. In some examples, the ICOSL reference polypeptide contains the sequence of amino acids set forth in SEQ ID NO: 545. In some aspects, the ICOSL reference polypeptide consists of the sequence of amino acids set forth in SEQ ID NO: 545.

Provided herein is a variant ICOSL Ligand (ICOSL) polypeptide containing one or more amino acid modifications in an ICOSL reference polypeptide, wherein the ICOSL reference polypeptide consists of the sequence of amino acids set forth in SEQ ID NO: 545. Also provided herein is a variant ICOSL Ligand (ICOSL) polypeptide containing one or more amino acid modifications in an immunoglobulin superfamily (IgSF) domain of an ICOSL reference polypeptide, wherein the ICOSL reference polypeptide is altered in one or more amino acids corresponding to amino acids 204-209 with reference to SEQ ID NO: 32. In some of any of the provided embodiments, the variant ICOSL polypeptide exhibits altered binding to one or more of its binding partner(s) compared to the binding of the ICOSL reference polypeptide for the one or more binding partner(s). In some of any of the provided embodiments, the variant ICOSL polypeptide exhibits increased binding to one or more of its binding partner(s) compared to the binding of the ICOSL reference polypeptide for the one or more binding partner(s).

In some of any of the provided embodiments, the alteration (e.g., modification) includes a deletion of one or more contiguous amino acids corresponding to amino acids 204-209 with reference to SEQ ID NO: 32. In some cases, the ICOSL reference polypeptide comprises the sequence of amino acids set forth in any of SEQ ID NOS: 600-605. In some of any of the provided embodiments, the ICOSL reference polypeptide consists of the sequence of amino acids set forth in any of SEQ ID NOS: 600-605.

In some of any of the provided embodiments, the alteration (e.g., modification) includes at least one amino acid substitution at one or both of position 207 and 208 corresponding to positions set forth in SEQ ID NO: 32. In some examples, the at least one amino acid substitution is N207A, N207G or L208G, or a conservative amino acid substitution thereof.

In some of any of the provided embodiments, the reference ICOSL polypeptide contains the sequence of amino acids set forth in any of SEQ ID NOS: 623-628. In some of any of the provided embodiments, the reference ICOSL polypeptide consists of the sequence of amino acids set forth in any of SEQ ID NOS: 623-628.

In some of any of the provided embodiments, the variant ICOSL polypeptide exhibits reduced proteolytic cleavage when expressed from a cell. In some examples, the cell is a mammalian cell. In some cases, the cell is a Chinese Hamster Ovary (CHO) cell line or a derivative thereof.

In some of any such embodiments, the amino acid modification is an amino acid substitution, insertion or deletion. In some of any of the provided embodiments, the one or more amino acid modifications are in a position corresponding to position(s) selected from 10, 11, 13, 16, 18, 20, 25, 27, 30, 33, 37, 38, 42, 43, 47, 52, 54, 57, 61, 62, 67, 71, 72, 74, 75, 77, 78, 80, 84, 89, 90, 92, 93, 94, 96, 97, 98, 99, 100, 102, 103, 107, 109, 110, 111, 113, 115, 116, 117, 119, 120, 121, 122, 126, 129, 130, 132, 133, 135, 138, 139, 140, 142, 143, 144, 146, 148, 151, 152, 153, 154, 155, 156, 158, 161, 164, 166, 168, 172, 173, 175, 190, 192, 193, 194, 198, 201, 203, 207, 208, 210, 212, 217, 218, 220, 221, 224, 225, or 227 with reference to SEQ ID NO:32. In some of any of the provided embodiments, the one or more amino acid modifications are in a position corresponding to position(s) selected from 10, 11, 13, 16, 18, 20, 25, 26, 27, 30, 33, 37, 38, 42, 43, 47, 52, 54, 57, 61, 62, 67, 71, 72, 74, 75, 77, 78, 80, 84, 89, 90, 92, 93, 94, 96, 97, 98, 99, 100, 102, 103, 107, 109, 110, 111, 113, 115, 116, 117, 119, 120, 121, 122, 126, 129, 130, 132, 133, 135, 137, 138, 139, 140, 142, 143, 144, 146, 151, 152, 153, 154, 155, 156, 158, 161, 164, 166, 168, 172, 173, 175, 190, 192, 193, 194, 198, 201, 203, 207, 208, 210, 212, 217, 218, 220, 221, 224, 225, or 227 with reference to SEQ ID NO:32.

In some of any of the provided embodiments, the one or more amino acid modifications are selected from M10V, M10I, V11E, S13G, E16V, S18R, A20V, S25G, F27S, F27C, N30D, Y33del, Q37R, K42E, T43A, Y47H, N52A, N52C, N52D, N52G, N52H, N52K, N52L, N52M N52Q, N52R, N52S, N52T, N52V, N52Y, S54A, S54P, N57A, N57D, N57E, N57F, N57H, N57K, N57L, N57M, N57P, N57Q, N57S, N57T, N57V, N57Y, N57W, R61S, R61C, Y62F, L67P, A71T, G72R, L74Q, R75Q, D77G, F78L, L80P, N84Q, E90A, K92R, F93L, H94E, H94D, L96F, L96I, V97A, L98F, S99G, Q100A, Q100D, Q100G, Q100K, Q100L, Q100M, Q100N, Q100P, Q100R, Q100S, Q100T, Q100V, L102R, G103E, V107A, V107I, S109G, S109N, V110D, V110N, V110A, E111del, T113E, H115R, H115Q, V116A, A117T, N119Q, F120I, S121G, V122A, V122M, F120S, S126T, S126R, H129P, S130G, S132F, Q133H, E135K, F138L, T139S, C140del, C140D, S142F, I143V, I143T, N144D, Y146C, V151A, Y152C, Y152H, W153R, I154F, N155H, N155Q, K156M, D158G, L161P, L161M, L166Q, N168Q, F172S, L173S, M175T, T190A, T190S, S192G, V193M, N194D, C198R, N201S, L203P, L203F, N207Q, L208P, V210A, S212G, D217V, I218T, I218N, E220G, R221G, R221I, I224V, T225A, N227K, or a conservative amino acid substitution thereof.

In some of any of the provided embodiments, the one or more amino acid modifications are selected from M10V, M10I, V11E, S13G, E16V, S18R, A20T, A20V, S25G, R26S, F27C, F27S, N30D, Y33del, Q37R, T38P, K42E, T43A, Y47H, N52A, N52C, N52D, N52G, N52H, N52K, N52L, N52M, N52P, N52Q, N52R, N52S, N52T, N52V, N52Y, S54A, S54F, S54P, N57A, N57D, N57E, N57F, N57H, N57K, N57L, N57M, N57P, N57Q, N57S, N57T, N57V, N57W, N57Y, R61C, R61S, Y62F, L67P, A71T, G72R, L74Q, R75Q, D77G, F78L, L80P, N84Q, D89G, E90A, K92R, F93L, H94D, H94E, L96F, L96I, V97A, L98F, S99G, Q100A, Q100D, Q100E, Q100G, Q100K, Q100L, Q100M, Q100N, Q100P, Q100R, Q100S, Q100T, Q100V, L102R, G103E, V107A, V107I, S109G, S109N, V110A, V110D, V110N, E111del, T113E, H115Q, H115R, V116A, A117T, N119Q, F120I, F120S, S121G, V122A, V122M, S126R, S126T, H129P, S130G, S132F, Q133H, E135K, T137A, F138L, T139S, C140del, C140D, S142F, I143T, I143V, N144D, Y146C, V151A, Y152C, Y152H, W153R, I154F, N155H, N155Q, K156M, D158G, L161M, L161P, Q164L, L166Q, N168Q, F172S, L173S, M175T, T190A, T190S, S192G, V193A, V193M, N194D, C198R, N201S, L203F, L203P, N207Q, L208P, V210A, S212G, D217G, D217V, I218N, I218T, E220G, R221G, R221I, R221K, I224V, T225A, T225S, N227K, or a conservative amino acid substitution thereof.

In some of any of the provided embodiments, the one or more amino acid modifications are in a position corresponding to position(s) 52, 57 or 100. In some of any of the provided embodiments, the one or more amino acid modifications are selected from N52A, N52C, N52D, N52G, N52H, N52K, N52L, N52M, N52Q, N52R, N52S, N52T, N52V, N52Y, N57A, N57D, N57E, N57F, N57H, N57K, N57L, N57M, N57P, N57Q, N57S, N57T, N57V, N57Y, N57W, Q100A, Q100D, Q100G, Q100K, Q100L, Q100M, Q100N, Q100P, Q100R, Q100S, Q100T or Q100V. In some of any of the provided embodiments, the one or more amino acid modifications are selected from N52A, N52C, N52D, N52G, N52H, N52K, N52L, N52M, N52Q, N52R, N52S, N52T, N52V, N52Y, S54A, S54P, N57A, N57D, N57E, N57F, N57H, N57K, N57L, N57M, N57P, N57Q, N57S, N57T, N57V, N57Y, N57W, Q100A, Q100D, Q100G, Q100K, Q100L, Q100M, Q100N, Q100P, Q100R, Q100S, Q100T or Q100V. In some examples, the one or more amino acid modifications are selected from among N52Y/N57Y/ F138L/L203P, N52H/N57Y/Q100P, N52S/Y146C/Y152C, N52H/C198R, N52H/C140D/T225A, N52H/C198R/ T225A, N52H/K92R, N52H/S99G, N57Y/Q100P, N52S/ S130G/Y152C, N52S/Y152C, N52S/C198R, N52Y/N57Y/ Y152C, N52Y/N57Y/H129P/C198R, N52H/L161P/C198R, N52S/T113E, N52D/S54P, N52K/L208P, N52S/Y152H, N52D/V151A, N52H/I143T, N52S/L80P, N52S/R75Q/ L203P, N52S/D158G, N52D/Q133H, N52S/N57Y/H94D/ L96F/L98F/Q100R, N52S/N57Y/H94D/L96F/L98F/ Q100R/G103E/F120S, N52H/F78L/Q100R, N52H/N57Y/ Q100R/V110D, N52H/N57Y/R75Q/Q100R/V110D, N52H/ N57Y/Q100R, N52H/N57Y/L74Q/Q100R/V110D, N52H/ Q100R, N52H/S121G, A20V/N52H/N57Y/Q100R/S109G, N52H/N57Y/R61S/Q100R/V110D/L173S, N52H/N57Y/ Q100R/V122A, N57Y/N52H/N57Y/Q100R/F172S, N52H/N57Y, N52S/F120S, N52S/V97A, N52S/G72R, N52S/A71T/ A117T, N52S/E220G, Y47H/N52S/V107A/F120S, N52H/ N57Y/Q100R/V110D/S132F/M175T, E16V/N52H/N57Y/ Q100R/V110D/H115R/Y152C/K156M/C198R, Q37R/ N52H/N57Y/Q100R/V110N/S142F/C198R/D217V/ R221G, N52H/N57Y/Q100R/V110D/C198R, N52H/N57Y/ Q100R/V110D/V116A/L161M/F172S/S192G/C198R, F27S/N52H/N57Y/V110N, N52S/H94E/L96I/S109N/ L166Q, S18R/N52S/F93L/I143V/R221G, A20T/N52D/ Y146C/Q164L, V11E/N30D/N52H/N57Y/H94E/L96I/ L98F/N194D/V210A/I218T, N52S/H94E/L96I/V122M, N52H/N57Y/H94E/L96I/F120I/S126T/W153R/I218N, M10V/S18R/N30D/N52S/S126R/T139S/L203F, S25G/ N30D/N52S/F120S/N227K, N30D/N52S/L67P/Q100K/ D217G/R221K/T225S, N52H/N57Y/Q100R/V110D/ A117T/T190S/C198R, N52H/N57Y/Q100R/V110D/F172S/ C198R, S25G/F27C/N52H/N57Y/Q100R/V110D/E135K/ L173S/C198R, N52H/N57Y/V110A/C198R/R221I, M10I/ S13G/N52H/N57Y/D77G/V110A/H129P/I143V/F172S/ V193M/C198R, N52H/N57Y/R61C/Y62F/Q100R/V110N/ F120S/C198R, N52H/N57Y/Q100R/V110D/H115R/ C198R, N52H/N57Y/Q100R/V110D/N144D/F172S/ C198R, N52S/H94E/L98F/Q100R, N52S/E90A, N30D/ K42E/N52S, N52S/F120S/I143V/I224V, N52H/N57Y/

Q100R/V110D/C198R/S212G, N52H/N57Y/Q100R/
C198R, N52S/N194D, N52H/N57Y/Q100R/L102R/
V110D/H115R/C198R, N52H/N57Y/Q100R/V110D/
C198R/S212G, N52H/N57Y/Q100R/C198R, N52S/N194D,
N52H/N57Y/Q100R/L102R/V110D/H115R/C198R, N52S/
S54P, T38P/N52S/N57D, N52H/C140del/T225A, N52H/
F78L/Q100R/C198R, N52H/N57Y/R75Q/Q100P/V110D,
N52H/N57Y/L74Q/V110D/S192G, N52H/S121G/C198R,
N52S/F120S/N227K, N52S/A71T/A117T/T190A/C198R,
T43A/N52H/N57Y/L74Q/D89G/V110D/F172S, N52H/
N57Y/Q100R/V110D/S132F/M175T, N52D, N52H/N57Y/
Q100R/V107I/V110D/I154F/C198R/R221G, N52Q/
N207Q, N52Q/N168Q, N52Q/N84Q, N52Q/N119Q, N52Q/
N84Q/N168Q, N52Q/N84Q/N207Q, N52Q/N119Q/
N155Q, N52H/N84Q/N119Q, N52H/N84Q, N52H/N84Q/
N168Q/N207Q, N52Q/N84Q/N155Q/N168Q, N52Q/
N84Q/N119Q/N168Q, N52Q/N84Q/N119Q/N207Q,
N52Q/N84Q/N119Q/N155Q, N52Q/N84Q/N119Q/N155Q/
N207Q, N52Y/F138L/L203P, N57Y/Q100R/C198R, N57Y/
F138L/L203P, Q100R/F138L, N52H/N57Y/Q100R/H115R/
C198R, N52H/N57Y/Q100R/F172S/C198R, N52H/N57Y/
Q100R/H115R/F172S/C198R, N52H/N57Y/Q100R/
H115R/I143V/F172S/C198R, N52H/N57Y/Q100R/L102R/
H115R/F172S/C198R, N52H/V122A/F172S/C198R,
N52H/N57Y/Q100R/H115R/F172S/N194D, N52H/N57Y/
H115R/F172S/C198R, N52H/N57Y/Q100R/H115R/
C198R, N52H/N57Y/H115R, N52H/N57Y/Q100R/H115R,
N52H/N57Y/Q100R/H115R/F172S/I224V, N52H/N57Y/
Q100R/H115R/F172S, N52H/N57Y/Q100R/F172S, N52H/
Q100R/H115R/I143T/F172S, N52H/N57Y/Q100P/H115R/
F172S, N52Y/N57Y/Q100P/F172S, E16V/N52H/N57Y/
Q100R/V110D/H115R/C198R, E16V/N52H/N57Y/Q100R/
V110D/H115R/Y152C/K156M/F172S/C198R, N52S/
E90A/H115R, N30D/K42E N52S/H115R, N30D/K42E/
N52S/H115R/C198R/R221I, N30D/K42E/N52S/H115R/
C198R, N30D/K42E/N52S/H115R/F172S/N194D, N52S/
H115R/F120S/I143V/C198R, N52S/H115R/F172S/C198R,
N52H/N57Y/Q100P/C198R, N52H/N57Y/Q100P H115R/
F172S/C198R, N52H/N57Y/Q100P/F172S/C198R, N52H/
N57Y/Q100P/H115R, N52H/N57Y/Q100P/H115R/C198R,
N52H/Q100R/C198R, N52H/Q100R/H115R/F172S, N52H/
Q100R/F172S/C198R, N52H/Q100R/H115R/F172S/
C198R, N52H/N57Y/Q100R/F172S/C198R, N52A/N57F/
Q100S, N52A/N57H/Q100S, N52A/N57Y/Q100A, N52D/
N57A/Q100A, N52D/Q100S, N52G/Q100A, N52H/
Q100A, N52M/N57H/Q100S, N52M/N57W/Q100P, N52Q/
N57F, N52Q/N57S/Q100A, N52R/N57L/Q100A, N52R/
N57Y/Q100P, N52R/N57Y/Q100S, N52S/N57A/Q100A,
N52S/N57H/Q100E, N52S/N57L/Q100S, N52S/N57M/
Q100S, N52S/N57Y/Q100S, N52S/N57Y/Q100M, N52S/
N57Y/Q100V, N52T/N57H/Q100S, N52T/N57H/Q100A,
N52T/N57Y/Q100A, N52V/N57L/Q100A, N52H/N57Y/
Q100K, N52K/N57Y/Q100R, N52L/N57H/Q100R, N52R/
N57F/Q100N, N52R/N57F/Q100P, N52R/N57F/Q100R,
N52R/N57F/Q100T, N52R/N57H/Q100K, N52R/N57L/
Q100S, N52R/N57W/Q100K, N52R/N57W, N52R/N57Y/
Q100R, N52C/N57E/Q100S, N52G/N57P/Q100D, N52G/
N57V/Q100G, N52G/N57V, N52L/N57V, N52P/N57P,
N52P/N57S/Q100G, N52S/N57L/Q100G, N52T/N57K/
Q100P, N52V/N57T/Q100L or N57Q/Q100P.

In some of any of the provided embodiments, the one or
more amino acid modifications are selected from among
N52Y/N57Y/F138L/L203P, N52H/N57Y/Q100P, N52S/
Y146C/Y152C, N52H/C198R, N52H/C140D/T225A,
N52H/C198R/T225A, N52H/K92R, N52H/S99G, N57Y/
Q100P, N52S/S130G/Y152C, N52S/Y152C, N52S/C198R,
N52Y/N57Y/Y152C, N52Y/N57Y/H129P/C198R, N52H/

L161P/C198R, N52S/T113E, N52D/S54P, N52K/L208P,
N52S/Y152H, N52D/V151A, N52H/I143T, N52S/L80P,
F120S/Y152H/N201S, N52S/R75Q/L203P, N52S/D158G,
N52D/Q133H, N52S/N57Y/H94D/L96F/L98F/Q100R,
N52S/N57Y/H94D/L96F/L98F/Q100R/G103E/F120S,
N52S/G103E, N52H/F78L/Q100R, N52H/N57Y/Q100R/
V110D, N52H/N57Y/R75Q/Q100R/V110D, N52H/N57Y/
Q100R, N52H/N57Y/L74Q/Q100R/V110D, N52H/Q100R,
N52H/S121G, A20V/N52H/N57Y/Q100R/S109G, N52H/
N57Y/R61S/Q100R/V110D/L173S, N52H/N57Y/Q100R/
V122A, N52H/N57Y/Q100R/F172S, N52H/N57Y, N52S/
F120S, N52S/V97A, N52S/G72R, N52S/A71T/A117T,
N52S/E220G, Y47H/N52S/V107A/F120S, N52H/N57Y/
Q100R/V110D/S132F/M175T, E16V/N52H/N57Y/Q100R/
V110D/H115R/Y152C/K156M/C198R, Q37R/N52H/
N57Y/Q100R/V110N/S142F/C198R/D217V/R221G,
N52H/N57Y/Q100R/V110D/C198R, N52H/N57Y/Q100R/
V110D/V116A/L161M/F172S/S192G/C198R, F27S/N52H/
N57Y/V110N, N52S/H94E/L96I/S109N/L166Q, S18R/
N52S/F93L/I143V/R221G, A20T/N52D/Y146C/Q164L,
V11E/N30D/N52H/N57Y/H94E/L96I/L98F/N194D/
V210A/I218T, N52S/H94E/L96I/V122M, N52H/N57Y/
H94E/L96I/F120I/S126T/W153R/I218N, M10V/S18R/
N30D/N52S/S126R/T139S/L203F, S25G/N30D/N52S/
F120S/N227K, N30D/N52S/L67P/Q100K/D217G/R221K/
T225S, N52H/N57Y/Q100R/V110D/A117T/T190S/
C198R, N52H/N57Y/Q100R/V110D/F172S/C198R, S25G/
F27C/N52H/N57Y/Q100R/V110D/E135K/L173S/C198R,
N52H/N57Y/V110A/C198R/R221I, M10I/S13G/N52H/
N57Y/D77G/V110A/H129P/I143V/F172S/V193M,
C198R, N52H/N57Y/R61C/Y62F/Q100R/V110N/F120S/
C198R, N52H/N57Y/Q100R/V110D/H115R/C198R,
N52H/N57Y/Q100R/V110D/N144D/F172S/C198R, N52S/
H94E/L98F/Q100R, N52S/E90A, N30D/K42E/N52S,
N52S/F120S/I143V/I224V, N52H/N57Y/Q100R/V110D/
C198R/S212G, N52H/N57Y/Q100R/C198R, N52S/N194D,
N52H/N57Y/Q100R/L102R/V110D/H115R/C198R, N52H/
N57Y/Q100R/V110D/C198R/S212G, N52H/N57Y/
Q100R/C198R, N52S/N194D, N52H/N57Y/Q100R/
L102R/V110D/H115R/C198R, N52S/S54P, T38P/N52S/
N57D, N52H/C140del/T225A, N52H/F78L/Q100R/C198R,
N52H/N57Y/R75Q/Q100P/V110D, N52H/N57Y/L74Q/
V110D/S192G, N52H/S121G/C198R, N52S/F120S/
N227K, N52S/A71T/A117T/T190A/C198R, T43A/N52H/
N57Y/L74Q/D89G/V110D/F172S, N52H/N57Y/Q100R/
V110D/S132F/M175T, N52H/N57Y/Q100R/V107I/
V110D/I154F/C198R/R221G, N52Q/N207Q, N52Q/
N168Q, N52Q/N84Q, N52Q/N119Q, N52Q/N84Q/N168Q,
N52Q/N84Q/N207Q, N52Q/N119Q/N155Q, N52H/N84Q/
N119Q, N52H/N84Q, N52H/N84Q/N168Q/N207Q, N52Q/
N84Q/N155Q/N168Q, N52Q/N84Q/N119Q/N168Q,
N52Q/N84Q/N119Q/N207Q, N52Q/N84Q/N119Q/N155Q,
N52Q/N84Q/N119Q/N155Q/N207Q, N52Y/F138L/L203P,
N57Y/Q100R/C198R, N57Y/F138L/L203P, Q100R/F138L,
N52H/N57Y/Q100R/H115R/C198R, N52H/N57Y/Q100R/
F172S/C198R, N52H/N57Y/Q100R/H115R/F172S/C198R,
N52H/N57Y/Q100R/H115R/I143V/F172S/C198R, N52H/
N57Y/Q100R/L102R/H115R/F172S/C198R, N52H/
V122A/F172S/C198R, N52H/N57Y/Q100R/H115R/
F172S/N194D, N52H/N57Y/H115R/F172S/C198R, N52H/
N57Y/H115R, N52H/N57Y/Q100R/H115R, N52H/N57Y/
Q100R/H115R/F172S/I224V, N52H/N57Y/Q100R/H115R/
F172S, N52H/N57Y/Q100R/F172S, N52H/Q100R/H115R/
I143T/F172S, N52H/N57Y/Q100R/H115R/F172S, N52Y/
N57Y/Q100P/F172S, E16V/N52H/N57Y/Q100R/V110D/
H115R/C198R, E16V/N52H/N57Y/Q100R/V110D/H115R/
Y152C/K156M/F172S/C198R, N52S/E90A/H115R, N30D/

K42EN52S/H115R, N30D/K42E/N52S/H115R/C198R/ R221I, N30D/K42E/N52S/H115R/C198R, N30D/K42E/ N52S/H115R/F172S/N194D, N52S/H115R/F120S/I143V/ C198R, N52S/H115R/F172S/C198R, N52H/N57Y/Q100P/ C198R, N52H/N57Y/Q100P/H115R/F172S/C198R, N52H/ N57Y/Q100P/F172S/C198R, N52H/N57Y/Q100P/H115R, N52H/N57Y/Q100P/H115R/C198R, N52H/Q100R/C198R, N52H/Q100R/H115R/F172S, N52H/Q100R/F172S/C198R, N52H/Q100R/H115R/F172S/C198R, N52H/N57Y/Q100R/ F172S/C198R, N52A/N57F/Q100S, N52A/N57H/Q100S, N52A/N57Y/Q100A, N52D/N57A/Q100A, N52D/Q100S, N52G/Q100A, N52H/Q100A, N52M/N57H/Q100S, N52M/ N57W/Q100P, N52Q/N57F, N52Q/N57S/Q100A, N52R/ N57L/Q100A, N52R/N57Y/Q100P, N52R/N57Y/Q100S, N52S/N57A/Q100A, N52S/N57H/Q100E, N52S/N57L/ Q100S, N52S/N57M/Q100S, N52S/N57Y/Q100S, N52S/ N57Y/Q100M, N52S/N57Y/Q100V, N52T/N57H/Q100S, N52T/N57H/Q100A, N52T/N57Y/Q100A, N52V/N57L/ Q100A, N52H/N57Y/Q100K, N52K/N57Y/Q100R, N52L/ N57H/Q100R, N52R/N57F/Q100N, N52R/N57F/Q100P, N52R/N57F/Q100R, N52R/N57F/Q100T, N52R/N57H/ Q100K, N52R/N57L/Q100S, N52R/N57W/Q100K, N52R/ N57W, N52R/N57Y/Q100R, N52C/N57E/Q100S, N52G/ N57P/Q100D, N52G/N57V/Q100G, N52G/N57V, N52L/ N57V, N52P/N57P, N52P/N57S/Q100G, N52S/N57L/ Q100G, N52T/N57K/Q100P, N52V/N57T/Q100L, N57Q/ Q100P, or R26S/N52H/N57Y/V110D/T137A/C198R.

In some of any of the provided embodiments, the one or more amino acid modifications are N52H/Q100R. In some of any of the provided embodiments, the variant ICOSL polypeptide has the sequence set forth in SEQ ID NO:567.

In some of any of the provided embodiments, the one or more amino acid modifications are N52H/N57Y/Q100R. In some of any of the provided embodiments, the variant ICOSL polypeptide contains the sequence set forth in SEQ ID NO:565.

In some of any of the provided embodiments, the one or more amino acid modifications are N52L/N57H/Q100R. In some of any of the provided embodiments, the variant ICOSL polypeptide contains the sequence set forth in SEQ ID NO: 761.

In some of any of the provided embodiments, the one or more amino acid modifications is N52D. In some of any of the provided embodiments, the variant ICOSL polypeptide contains the sequence set forth in SEQ ID NO: 548.

In some of any of the provided embodiments, the one or more amino acid modifications is N52H/N57Y/Q100P. In some of any of the provided embodiments, the variant ICOSL polypeptide contains the sequence set forth in SEQ ID NO: 570.

In some of any of the provided embodiments, the one or more amino acid modifications are selected from among F120S/Y152H/N201S, E111del, Y33del, N168Q/N207Q, N84Q/N207Q, N155Q/N207Q, N119Q/N168Q, N119Q/ N207Q, N119Q/N155Q, N84Q/N119Q, N84Q/N155Q/ N168Q, N84Q/N168Q/N207Q, N84Q/N155H/N207Q, N155Q/N168Q/N207Q, N119Q N155Q/N168Q, N119Q/ N168Q/N207Q, N84Q/N119Q/N207Q, N119Q/N155H/ N207Q, N84Q/N119Q/N155Q, N84Q/N119Q/N155Q/ N168Q, N84Q/N155Q/N168Q/N207Q, N84Q/N119Q/ N155Q/N207Q, N84Q/N119Q/N155Q/N168Q/N207Q or F138L/L203P.

In some of any such embodiments, the one or more amino acid modifications are selected from C198R, D158G, E16V, E90A, F120S, F138L, F172S, H115R, H115X, I143T, I143V, I224V, K156M, K42E, K92R, L102R, L203P, L208P, N194D, N30D, N52A, N52D, N52G, N52H, N52K, N52L, N52M, N52Q, N52R, N52S, N52T, N52Y, N57F, N57H, N57K, N57L, N57M, N57P, N57S, N57V, N57W, N57Y, Q100A, Q100D, Q100E, Q100K, Q100M, Q100P, Q100R, Q100S, Q100T, Q133H, R221I, R75Q, S54A, S54P, T113E, T225A, V110D, V122A, Y146C, Y152C, A117T, A20V, A71T, A91G, A91G, AE88D, C140del, C198R, D158G, D77G, D90K, E117G, E135K, E16V, E81A, E88D, E90A, F120I, F120S, F138L, F172S, F27C, F92Y, G72R, H115R, H115X, H129P, H94E, I118V, I127T, I143T, I143V, I154F, I218N, I218T, I224V, K156M, K169E, K36G, K42E, K89R, K92R, K93R, L102R, L161P, L166Q, L173S, L203F, L203P, L208P, L209P, L40M, L70Q, L70R, L74Q, L80P, L96I, L98F, M10I, M10V, N115Q, N119Q, N122S, N144D, N155X, N168Q, N168X, N178S, N194D, N207Q, N207X, N227K, N25S, N30D, N52V, N57A, N57F, N57H, N57L, N57M, N57S, N57V, N57W, N57Y, N63S, N84Q, Q100G, Q100N, Q100V, R221G, S109G, S109N, S114T, S121G, S126R, S126T, S130G, S132F, S13G, S18R, S192G, S212G, S25G, S54A, S54P, S99G, T113E, 120S, T130A, T139S, T190A, T199S, T225A, T41I, V107I, V110A, V110D, V11E, V122A, V122M, V193M, V210A, W153R, Y146C, Y152C, or Y152H.

In some of any of the provided embodiments, the one or more amino acid modifications are selected from among N52S, N52H, N52D, N52H/N57Y/Q100P, N52S/Y146C/ Y152C, N52H/C198R, N52H/C198R/T225A, N52H/K92R, N57Y, N52S/C198R, N52S/T113E, S54A, N52D/S54P, N52K/L208P, N52H/I143T, N52S/R75Q/L203P, N52S/ D158G, N52D/Q133H, N52H/N57Y/Q100R/V122A, N52H/N57Y/Q100R/F172S, N52H/N57Y/Q100R, N52S/ N194D, N52H/N57Y/Q100R/L102R/V110D/H115R/ C198R, N52S/E90A, N52S/F120S/I143V/I224V, N52H/ N57Y/Q100R/F172S/C198R, N52H/N57Y/Q100R/H115R/ F172S/C198R, N52Y/N57Y/Q100P/F172S, E16V/N52H/ N57Y/Q100R/V110D/H115R/Y152C/K156M/F172S/ C198R, N52S/H115R/F120S/I143V/C198R, N52H/N57Y/ Q100P/C198R, N52H/N57Y/Q100P/H115R/F172S/C198R, N52H/N57Y/Q100P/F172S/C198R, N52H/N57Y/Q100P/ H115R, N52H/N57Y/Q100P/H115R/C198R, N52H/ Q100R/C198R, N52H/Q100R/H115X/F172S/C198R, N52H/Q100R/H115R/F172S/C198R, N52H/N57Y/Q100R/ H115R/F172S/C198R, N52H/N57Y/Q100R/H115R/F172S, N52H/N57Y/Q100R/H115R/F172S/C198R, Q100R, N52Y/ F138L/L203P, N57Y/Q100R/C198R, N57Y/F138L/L203P, N57Y/Q100P, Q100R/F138L, N52H/N57Y/Q100R/H115R, N52H/N57Y/Q100R/F172S, N52H/N57Y/Q100R/H115R/ F172S/I224V, N52H/N57Y/Q100R/H115R/F172S, N52H/ N57Y/Q100R/H115R/C198R, N52H/N57Y/Q100R/F172S/ C198R, N52H/N57Y/Q100R/H115R/F172S/C198R, N52H/ N57Y/Q100R/H115R/I143V/F172S/C198R, N52H/N57Y/ Q100R/L102R, H115R/F172S/C198R, N52H/N57Y/ Q100R/H115R F172S/N194D, N52H/N57Y/H115R/F172S/ C198R, N52H/N57Y/Q100R/H115R/C198R, N52H/N57Y/ H115R, N52H/Q100R/H115R/I143T F172S, N52H/N57Y/ Q100P/H115R/F172S, E16V/N52H/N57Y/Q100R/V110D/ H115R/C198R, N52S/E90A/H115R, N30D/K42E/N52S/ H115R/C198R/R221I, N30D/K42E/N52S/H115R/C198R, N30D/K42E/N52S/H115R/F172S/N194D, N30D/K42E/ N52S/H115R, N52S/E90A/H115R, N30D/K42E/N52S/ H115R, N52A/N57H/Q100S, N52A/N57Y/Q100A, N52D/ Q100S, N52G/Q100A, N52M/N57H/Q100S, N52M/ N57W/Q100P, N52Q/N57S/Q100A, N52R/N57L/Q100A, N52S/N57H/Q100E, N52S/N57L/Q100S, N52S/N57M/ Q100S, N52S/N57Y/Q100M, N52T/N57H/Q100S, N52R/ N57F/Q100P, N52R/N57F/Q100T, N52R/N57W/Q100K, N52R/N57W, N52G/N57P/Q100D, N52G/N57V/Q100G, N52G/N57V, N52L/N57V, N52S/N57L/Q100G or N52T/

N57K/Q100P; or N52S, N52H, N52D, N52Y/N57Y/F138L/ L203P, N52H/N57Y/Q100P, N52S/Y146C/Y152C, N52H/ C198R, N52H/C140del/T225A, N52H/C198R/T225A, N52H/K92R, N52H/S99G, N57Y, N57Y/Q100P, N52S/ S130G/Y152C, N52S/Y152C, N52S/C198R, N52Y/N57Y/ Y152C, N52Y/N57Y/H129P/C198R, N52H/L161P/C198R, N52S/T113E, S54A, N52D/S54P, N52K/L208P, N52S/ Y152H, N52H/I143T, N52S/L80P, N52S/D158G, N52D/ Q133H, L70Q/A91G/N144D, L70Q/A91G/E117G/I118V/ T120S/T130A, L70R/A91G/I118V/T120S/T130A/T199S, L70Q/E81A/A91G/I118V/T120S/I127T/T130A, N63S/ L70Q/A91G/S114T/I118V/T120S/T130A, T41I/A91G, E88D/K89R/D90K/A91G/F92Y/K93R/N122S/N178S, E88D/K89R/D90K/A91G/F92Y/K93R, AE88D/K89R/ D90K/A91G/F92Y/K93R, K36G/L40M, N52H/N57Y/ Q100R/V122A, N52H/N57Y/Q100R/F172S, N52H/N57Y/ Q100R, N52S/F120S/N227K, N52S/N194D, N52S/F120S, N52S/G72R, N52S/A71T/A117T/T190A/C198R, N52H/ N57Y/Q100R/V107I/V110D/S132F/I154F/C198R/R221G, E16V/N52H/N57Y/Q100R/V110D/H115R/Y152C/ K156M/C198R, N52H/N57Y/Q100R/V110D/C198R, V11E/N30D/N52H/N57Y/H94E/L96I/L98F/N194D/ V210A/I218T, N52S/H94E/L96I/V122M, N52H/N57Y/ H94E/L96I/F120I/S126T/W153R/I218N, M10V/S18R/ N30D/N52S/S126R/T139S/L203F, S25G/N30D/N52S/ F120S/N227K, N52H/N57Y/Q100R/V110D/F172S/ C198R, S25G/F27C/N52H/N57Y/Q100R/V110D/E135K/ L173S/C198R, N52H/N57Y/V110A/C198R/R221I, M10I/ S13G/N52H/N57Y/D77G/V110A/H129P/I143F/F172S/ V193M, C198R, N52H/N57Y/Q100R/L102R/V110D/ H115R/C198R, N52H/N57Y/Q100R/V110D/N144D/ F172S/C198R, N52S/H94E/L98F/Q100R, N52S/E90A, N52S/F120S/I143V/I224V, N52H/N57Y/Q100R/F172S/ C198R, N52H/N57Y/Q100R/H115R/F172S/C198R, N52Y/ N57Y/Q100P/F172S, E16V/N52H/N57Y/Q100R/V110D/ H115R/Y152C/K156M/F172S/C198R, N52S/H115R/ F120S/I143V/C198R, N52H/N57Y/Q100P/C198R, N52H/ N57Y/Q100P/H115R/F172S/C198R, N52H/N57Y/Q100P/ F172S/C198R, N52H/N57Y/Q100P/H115R, N52H/N57Y/ Q100P/H115R/C198R, N52H/Q100R/C198R, N52H/ Q100R/H115R/F172S, N52H/Q100R/H115X/F172S/ C198R, N52H/Q100R/H115R/F172S/C198R, N52H/N57Y/ Q100R/F172S/C198R, N52H/N57Y/Q100R/H115R/F172S/ C198R, N52H/N57Y/Q100R/H115R/F172S, N52H/N57Y/ Q100R/H115R/F172S/C198R, N52S/H94E/L96V/S109N/ L166Q/, N52H/N57Y/Q100R/C198R, N52H/N57Y/L74Q/ V110D/S192G, N52H/Q100R, N52H/S121G/C198R, A20V/N52H/N57Y/Q100R/S109G, N52H/N57Y/Q100P/ C198R, N52H/N57Y/Q100R/V110D/C198R/S212G, L70Q/A91G/I118A/T120S/T130A/K169E, Q100R, N52Y/ F138L/L203P, N57Y/Q100R/C198R, N57Y/F138L/L203P, N52H, N57Y, N57Y/Q100P, N52H/N57Y/Q100R/H115R, N52H/N57Y/Q100R/F172S, N52H/N57Y/Q100R/H115R/ F172S/I224V, N52H/N57Y/Q100R/H115R/F172S, N52H/ N57Y/Q100R/H115R/C198R, N52H/N57Y/Q100R/F172S/ C198R, N52H/N57Y/Q100R/H115R/F172S/C198R, N52H/ N57Y/Q100R/H115R/I143V/F172S/C198R, N52H/N57Y/ Q100R/L102R H115R/F172S/C198R, N52H/N57Y/ Q100R/H115R F172S/N194D, N52H/N57Y/H115R/F172S/ C198R, N52H/N57Y/Q100R/H115R/C198R, N52H/N57Y/ H115R, N52H/Q100R/H115R/I143T F172S, N52H/N57Y/ Q100P/H115R/F172S, E16V/N52H/N57Y/Q100R/V110D/ H115R/C198R, N30D/K42E/N52S/H115R/C198R R221I, N52S/E90A/H115R, N30D/K42E/N52S/H115R, N52S/ H115R/F172S/C198R, N119Q, N207Q, N52Q/N207X, N168X/N207X, N52Q/N168Q, N84Q/N207Q, N119Q N155X, N52Q/N119Q, N52Q/N84Q/N207Q, N119Q/

N155Q/N168Q, N52H/N84Q/N119Q, N52Q/N84Q/ N155X/N168X, N52A/N57F/Q100S, N52A/N57H/Q100S, N52A/N57Y/Q100A, N52D/N57A/Q100A, N52D/Q100S, N52G/Q100A, N52H/Q100A, N52M/N57H/Q100S, N52M/ N57W/Q100P, N52Q/N57F, N52Q/N57S/Q100A, N52R/ N57L/Q100A, N52R/N57Y/Q100P, N52R/N57Y/Q100S, N52S/N57A/Q100A, N52S/N57H/Q100E, N52S/N57L/ Q100S, N52S/N57M/Q100S, N52S/N57Y/Q100S, N52S/ N57Y/Q100M, N52S/N57Y/Q100V, N52T/N57H/Q100S, N52T/N57H/Q100A, N52T/N57Y/Q100A, N52V/N57L/ Q100A, N52H/N57Y/Q100K, N52K/N57Y/Q100R, N52L/ N57H/Q100R, N52R/N57F/Q100N, N52R/N57F/Q100P, N52R/N57F/Q100R, N52R/N57F/Q100T, N52R/N57L/ Q100S, N52R/N57W/Q100K, N52R/N57W, N52G/N57V, N52L/N57V, N52S/N57L/Q100G, or N52T/N57K/Q100P. In some of any of the provided embodiments, the variant ICOSL polypeptide exhibits increased binding to the ectodomain of ICOS or CD28 compared to the binding of the reference ICOSL polypeptide to the same ectodomain.

In some of any of the provided embodiments, the one or more amino acid modifications are selected from C198R, D158G, E16V, E90A, F120S, F138L, F172S, H115R, I143V, I224V, K156M, K42E, K92R, L102R, L203P, L208P, N194D, N30D, N52A, N52D, N52G, N52H, N52K, N52L, N52M, N52Q, N52R, N52S, N52T, N52Y, N57F, N57H, N57L, N57M, N57S, N57V, N57W, N57Y, Q100A, Q100E, Q100G, Q100K, Q100M, Q100P, Q100R, Q100S, Q133H, S212G, S54A, S54P, T113E, V110D, V122A, Y146C, Y152C, or T225A.

In some examples, the one or more amino acid modifications are selected from among N52A/N57Y/Q100A, N52D/Q100S, N52G/Q100A, N52M/N57H/Q100S, N52M/ N57W/Q100P, N52Q/N57S/Q100A, N52R/N57L/Q100A, N52S/N57H/Q100E, N52S/N57L/Q100S, N52S/N57M/ Q100S, N52S/N57Y/Q100M, N52T/N57H/Q100S, N52R/ N57F/Q100P, N52R/N57F/Q100T, N52R/N57W/Q100K, N52R/N57W, N52G/N57V, N52L/N57V, N52S/N57L/ Q100G, N52T/N57K/Q100P, N52S, N52H, N52D, N52Y/ N57Y/F138L/L203P, N52H/N57Y/Q100P, N52S/Y146C/ Y152C, N52H/C198R, N52H/C198R/T225A, N52H/K92R, N57Y, N52S/C198R, N52S/T113E, S54A, N52D/S54P, N52K/L208P, N52H/I143T, N52S/D158G, N52D/Q133H, N52H/N57Y/Q100R/V110D/C198R/S212G, N52H/N57Y/ Q100R/V122A, N52H/N57Y/Q100R/F172S, N52H/N57Y/ Q100R, N52S/N194D, N52H/N57Y/Q100R/L102R/ V110D/H115R/C198R, N52S/E90A, N52S/F120S/I143V/ I224V, N52H/N57Y/Q100R/F172S/C198R, N52H/N57Y/ Q100R/H115R/F172S/C198R, N52Y/N57Y/Q100P/F172S, E16V/N52H/N57Y/Q100R/V110D/H115R/Y152C/ K156M/F172S/C198R, N52S/H115R/F120S/I143V/ C198R, N52H/N57Y/Q100P/C198R, N52H/N57Y/Q100P/ H115R/F172S/C198R, N52H/N57Y/Q100P/F172S/C198R, N52H/N57Y/Q100P/H115R, N52H/N57Y/Q100P/H115R/ C198R, N52H/Q100R/C198R, N52H/Q100R/H115R/ F172S, N52H/Q100R/H115X/F172S/C198R, N52H/ Q100R/H115R/F172S/C198R, N52H/N57Y/Q100R/ H115R/F172S/C198R, N52H/N57Y/Q100R/H115R/F172S, N52H/N57Y/Q100R/H115R/F172S/C198R, Q100R, N52Y/ F138L/L203P, N57Y/Q100R/C198R, N57Y/F138L/L203P, N52H, N57Y, N57Y/Q100P, Q100R/F138L, N52H/N57Y/ Q100R/H115R, N52H/N57Y/Q100R/F172S, N52H/N57Y/ Q100R/H115R/F172S/I224V, N52H/N57Y/Q100R/H115R/ F172S, N52H/N57Y/Q100R/H115R/C198R, N52H/N57Y/ Q100R/F172S/C198R, N52H/N57Y/Q100R/H115R/F172S/ C198R, N52H/N57Y/Q100R/H115R/I143V/F172S/C198R, N52H/N57Y/Q100R/L102R H115R/F172S/C198R, N52H/ N57Y/Q100R/H115R F172S/N194D, N52H/N57Y/H115R/

F172S/C198R, N52H/N57Y/Q100R/H115R/C198R, N52H/ N57Y/H115R, N52H/Q100R/H115R/I143T/F172S, N52H/ N57Y/Q100P/H115R/F172S, E16V/N52H/N57Y/Q100R/ V110D/H115R/C198R, N52S/E90A/H115R, N52S/E90A/ H115R, or N30D/K42E/N52S/H115R. In some of any of the provided embodiments, the variant ICOSL polypeptide exhibits increased binding to the ectodomain of ICOS and CD28 compared to the binding of the reference ICOSL polypeptide to the same ectodomains.

In some of any of the provided embodiments, the variant ICOSL polypeptide contains the sequence of amino acids set forth in any one of SEQ ID NOS: 546-599, 734-781, 783, 786, 788, 792, 796, 798, 800, 802, 804, 806, 808, 811, 813, 815, 817, 818, 820, 822, 824, 826, 827, 829, 831, 833, 834, 836, 838, 840-843, 845, 847, 848, 850-853, 855, 857, 907, 910, or a sequence of amino acids that exhibits at least 90%, 91%%, 92%, 93%, 94%, 95%, 96%, 97%, 98%, or 99% sequence identity to any one of SEQ ID NOS: 546-599, 734-781, 783, 786, 788, 792, 796, 798, 800, 802, 804, 806, 808, 811, 813, 815, 817, 818, 820, 822, 824, 826, 827, 829, 831, 833, 834, 836, 838, 840-843, 845, 847, 848, 850-853, 855, 857, 907, 910. In some of any of the provided embodiments, the variant ICOSL polypeptide consists of the sequence of amino acids set forth in any one of SEQ ID NOS: 546-599, 734-781, 783, 786, 788, 792, 796, 798, 800, 802, 804, 806, 808, 811, 813, 815, 817, 818, 820, 822, 824, 826, 827, 829, 831, 833, 834, 836, 838, 840-843, 845, 847, 848, 850-853, 855, 857, 907, 910, or a sequence of amino acids that exhibits at least 90%, 91%%, 92%, 93%, 94%, 95%, 96%, 97%, 98%, or 99% sequence identity to any one of SEQ ID NOS: 546-599, 734-781, 783, 786, 788, 792, 796, 798, 800, 802, 804, 806, 808, 811, 813, 815, 817, 818, 820, 822, 824, 826, 827, 829, 831, 833, 834, 836, 838, 840-843, 845, 847, 848, 850-853, 855, 857, 907, 910.

In some of any of the provided embodiments of the variant ICOS Ligand (ICOSL) polypeptide containing an IgV domain or specific binding fragment thereof, an IgC domain or a specific binding fragment thereof, or both, the variant ICOSL polypeptide contains one or more amino acid modifications in an ICOSL reference polypeptide or a specific binding fragment thereof corresponding to amino acid modifications are selected from N52A, N52C, N52D, N52G, N52K, N52L, N52M, N52R, N52T, N52V, N57A, N57E, N57F, N57H, N57K, N57L, N57M, N57P, N57Q, N57S, N57T, N57V, N57W, Q100A, Q100D, Q100G, Q100L, Q100M, Q100N, Q100R, Q100S, Q100T or Q100V with reference to SEQ ID NO:32. In some of any of the provided embodiments, the one or more amino acid modifications are selected from among N52A/N57F/Q100S, N52A, /N57H/ Q100S, N52A/N57Y/Q100A, N52D/N57A/Q100A, N52D/ Q100S, N52G/Q100A, N52H/Q100A, N52M/N57H/ Q100S, N52M/N57W/Q100P, N52Q/N57F, N52Q/N57S/ Q100A, N52R/N57L/Q100A, N52R/N57Y/Q100P, N52R/ N57Y/Q100S, N52S/N57A/Q100A, N52S/N57H/Q100E, N52S/N57L/Q100S, N52S/N57M/Q100S, N52S/N57Y/ Q100S, N52S/N57Y/Q100M, N52S/N57Y/Q100V, N52T/ N57H/Q100S, N52T/N57H/Q100A, N52T/N57Y/Q100A, N52V/N57L/Q100A, N52H/N57Y/Q100K, N52K/N57Y/ Q100R, N52L/N57H/Q100R, N52R/N57F/Q100N, N52R/ N57F/Q100P, N52R/N57F/Q100R, N52R/N57F/Q100T, N52R/N57H/Q100K, N52R/N57L/Q100S, N52R/N57W/ Q100K, N52R/N57W, N52R/N57Y/Q100R, N52C/N57E/ Q100S, N52G/N57P/Q100D, N52G/N57V/Q100G, N52G/ N57V, N52L/N57V, N52P/N57P, N52P/N57S/Q100G, N52S/N57L/Q100G, N52T/N57K/Q100P, N52V/N57T/ Q100L or N57Q/Q100P.

In some of any of the provided embodiments, the ICOSL reference polypeptide is a mammalian ICOSL or a specific binding fragment thereof. In some examples, the ICOSL reference polypeptide is a human ICOSL or a specific binding fragment thereof.

In some of any of the provided embodiments, the ICOSL reference polypeptide contains (i) the sequence of amino acids set forth in SEQ ID NO:32, (ii) a sequence of amino acids that has at least 95% sequence identity to SEQ ID NO:32; or (iii) a portion of (i) or (ii) comprising an IgV domain or IgC domain or specific binding fragments thereof or both. In some of any of the provided embodiments, the specific binding fragment of the IgV domain or IgC domain has a length of at least 50, 60, 70, 80, 90, 100, 110 or more amino acids; or the specific binding fragment of the IgV domain contains a length that is at least 80% of the length of the IgV domain set for as amino acids 19-129 of SEQ ID NO:5 and/or the specific binding fragment of the IgC domain comprises a length that is at least 80% of the length of the IgC domain set forth as amino acids 141-227 of SEQ ID NO:5. In some of any of the provided embodiments, the variant ICOSL polypeptide comprises the IgV domain or a specific fragment thereof and the IgC domain or a specific fragment thereof.

In some of any of the provided embodiments, the variant ICOSL polypeptide contains the sequence of amino acids set forth in any one of SEQ ID NOS: 638-685, or a sequence of amino acids that exhibits at least 90%, 91%%, 92%, 93%, 94%, 95%, 96%, 97%, 98%, or 99% sequence identity to any one of SEQ ID NOS: 638-685. In some of any of the provided embodiments, the variant ICOSL polypeptide consists of the sequence of amino acids set forth in any one of SEQ ID NOS: 638-685, or a sequence of amino acids that exhibits at least 90%, 91%%, 92%, 93%, 94%, 95%, 96%, 97%, 98%, or 99% sequence identity to any one of SEQ ID NOS: 638-685.

In some of any of the provided embodiments, the variant ICOSL polypeptide contains the IgV domain or a specific binding fragment thereof. In some of any of the provided embodiments, the variant ICOSL polypeptide contains the sequence of amino acids set forth in any one of SEQ ID NOS: 686-781, or a sequence of amino acids that exhibits at least 90%, 91%%, 92%, 93%, 94%, 95%, 96%, 97%, 98%, or 99% sequence identity to any one of SEQ ID NOS: 686-781. In some of any of the provided embodiments, the variant ICOSL polypeptide consists of the sequence of amino acids set forth in any one of SEQ ID NOS: 686-781, or a sequence of amino acids that exhibits at least 90%, 91%%, 92%, 93%, 94%, 95%, 96%, 97%, 98%, or 99% sequence identity to any one of SEQ ID NOS: 686-781.

In some of any of the provided embodiments, the IgV domain or specific binding fragment thereof is the only ICOSL portion of the variant ICOSL polypeptide. In some examples, the IgC domain or specific binding fragment thereof is the only ICOSL portion of the variant ICOSL polypeptide.

In some of any of the provided embodiments, the variant ICOSL polypeptide exhibits altered binding to the ectodomain of ICOS or CD28 compared to the binding of the ICOSL reference polypeptide for the same ectodomain. In some aspects, the variant ICOSL polypeptide exhibits increased binding to the ectodomain(s) of ICOS or CD28 compared to the binding of the ICOSL reference polypeptide for the same ectodomain(s). In some examples, the binding is increased more than 1.2-fold, 1.5-fold, 2-fold, 3-fold, 4-fold, 5-fold, 6-fold, 7-fold, 8-fold, 9-fold, 10-fold, 20-fold, 30-fold, 40-fold, 50-fold or 60-fold.

In some of any such embodiments, the ICOS is a human ICOS. In some of any of the provided embodiments, the CD28 is a human CD28.

In some of any of the provided embodiments, the variant ICOSL polypeptide exhibits decreased binding to the ectodomain of CTLA-4 compared to the binding of the reference ICOSL polypeptide for the same ectodomain. In some examples, the binding is decreased more than 1.2-fold, 1.5-fold, 2-fold, 3-fold, 4-fold, 5-fold, 6-fold, 7-fold, 8-fold, 9-fold, 10-fold, 20-fold, 30-fold, 40-fold, 50-fold or 60-fold. In some of any of the provided embodiments, the CTLA-4 is a human CTLA-4.

In some of any of the provided embodiments, the altered (increased or decreased) binding is altered (increased or decreased) binding affinity. In some of any such embodiments, the variant ICOSL polypeptide comprises up to 1, 2, 3, 4, 5, 6, 7, 8, 9, 10, 11, 12, 13, 14, 15, 16, 17, 18, 19 or 20 amino acid modifications, optionally amino acid substitutions, insertions and/or deletions. In some cases, the variant ICOSL polypeptide exhibits at least or at least about 90%, 91%, 92%, 93%, 94%, 95%, 96%, 97%, 98% or 99% sequence identity to the ICOSL reference polypeptide.

In some of any of the provided embodiments, the variant ICOSL polypeptide is a soluble protein. In some of any of the provided embodiments, the variant ICOSL polypeptide lacks a transmembrane domain and intracellular signaling domain; and/or when expressed from a cell, the variant ICOSL polypeptide is not expressed on the surface of the cell.

In some of any of the provided embodiments, the variant ICOSL polypeptide further contains transmembrane domain. In some cases, the transmembrane domain contains the sequence of amino acids set forth as residues 257-277 of SEQ ID NO:5 or a functional variant thereof that exhibits at least 85% sequence identity to residues 257-277 of SEQ ID NO:5. In some of any of the provided embodiments, the variant ICOSL polypeptide further contains a cytoplasmic signaling domain linked to the transmembrane domain. In some cases, the cytoplasmic signaling domain contains the sequence of amino acids set forth as residues 278-302 of SEQ ID NO:5 or a functional variant thereof that exhibits at least 85% sequence identity to residues 278-302 of SEQ ID NO:5.

In some of any of the provided embodiments, the variant ICOSL polypeptide is deglycosylated or partially deglycosylated compared to the ICOSL reference sequence.

Provided herein is an immunomodulatory protein containing any of the provided variant ICOSL polypeptide and a half-life extending moiety. In some of any of the provided embodiments, the half-life extending moiety comprises a multimerization domain, albumin, an albumin-binding polypeptide, Pro/Ala/Ser (PAS), a C-terminal peptide (CTP) of the beta subunit of human chorionic gonadotropin, polyethylene glycol (PEG), long unstructured hydrophilic sequences of amino acids (XTEN), hydroxyethyl starch (HES), an albumin-binding small molecule, or a combination thereof. In some cases, the half-life extending moiety is or comprises Pro/Ala/Ser (PAS) and the variant ICOSL polypeptide is PASylated. In some of any of the provided embodiments, the half-life extending moiety contains the sequence set forth in SEQ ID NO: 904.

In some of any of the provided embodiments, the half-life extending moiety is or contains a multimerization domain. In some instances, the multimerization domain is selected from an Fc region of an immunoglobulin, a leucine zipper, an isoleucine zipper or a zinc finger. In some of any of the provided embodiments, the variant ICOSL polypeptide is linked, directly or indirectly via a linker, to the multimerization domain.

In some of any of the provided embodiments, the immunomodulatory protein is a multimer containing a first variant ICOSL polypeptide linked to a first multimerization domain and a second variant ICOSL polypeptide linked to a second multimerization domain, wherein the first and second multimerization domains interact to form a multimer comprising the first and second variant ICOSL polypeptide. In some cases, the multimer is a dimer.

In some of any of the provided embodiments, the first variant ICOSL polypeptide and the second variant ICOSL polypeptide are the same. In some of any of the provided embodiments, the dimer is a homodimer. In some instances, the dimer is a heterodimer.

In some of any of the provided embodiments, the multimerization domain is or contains an Fc region of an immunoglobulin. In some of any of the provided embodiments, the Fc region is of an immunoglobulin G1 (IgG1) or an immunoglobulin G2 (IgG2) protein. In some examples, the immunoglobulin protein is human and/or the Fc region is human. In some of any of the provided embodiments, the Fc region contains the sequence of amino acids set forth in SEQ ID NO: 227 or a variant thereof that exhibits at least 90%, 91%, 92%, 93%, 94%, 95%, 96%, 97%, 98% or 99% sequence identity to SEQ ID NO:227. In some aspects, the Fc region contains the sequence of amino acids set forth in SEQ ID NO: 226 or a variant thereof that exhibits at least 90%, 91%, 92%, 93%, 94%, 95%, 96%, 97%, 98% or 99% sequence identity to SEQ ID NO:226. In some of any of the provided embodiments, the Fc region exhibits one or more effector functions. In some of any of the provided embodiments, the Fc region exhibits one or more reduced effector function compared to a wildtype Fc region, optionally wherein the wildtype human Fc is of human IgG1.

In some of any of the provided embodiments, the one or more effector function is selected from among antibody dependent cellular cytotoxicity (ADCC), complement dependent cytotoxicity, programmed cell death and cellular phagocytosis. In some of any of the provided embodiments, the Fc region is a variant Fc region comprising one or more amino acid substitutions compared to the wildtype Fc region.

In some of any of the provided examples, the one or more amino acid substitutions of the variant Fc region are selected from N297G, E233P/L234V/L235A/G236del/S267K or L234A/L235E/G237A, wherein the residue is numbered according to the EU index of Kabat. In some of any of the provided embodiments, the variant Fc region further contains the amino acid substitution C220S, wherein the residues are numbered according to the EU index of Kabat. In some aspects, the Fc region contains the sequence of amino acid sequence set forth in any of SEQ ID NOS: 476-478 or a sequence of amino acids that exhibits at least 90%, 91%, 92%, 93%, 94%, 95%, 96%, 97%, 98%, 99% or more sequence identity to any of SEQ ID NOS: 476-478 and contains the amino acid substitutions. In some of any of the provided embodiments, the Fc region contains K447del, wherein the residue is numbered according to the EU index of Kabat.

In some of any of the provided embodiments, the Fc region contains the sequence of amino acid sequence set forth in any of SEQ ID NOS: 632-634 or a sequence of amino acids that exhibits at least 90%, 91%, 92%, 93%, 94%, 95%, 96%, 97%, 98%, 99% or more sequence identity to any of SEQ ID NOS: 632-634 and contains the amino acid substitutions.

In some of any of the provided embodiments, the Fc region contains the sequence of amino acid sequence set forth in SEQ ID NOS: 474 or 637, or a sequence of amino acids that exhibits at least 90%, 91%, 92%, 93%, 94%, 95%, 96%, 97%, 98%, 99% or more sequence identity to SEQ ID NOS: 474 or 637 and contains the amino acid substitutions.

In some of any of the provided embodiments, the Fc region contains the sequence of amino acids set forth in SEQ ID NO: 478 or SEQ ID NO: 634. In some of any of the provided embodiments, the Fc region contains the sequence of amino acids set forth in SEQ ID NO: 477. In some of any of the provided embodiments, the Fc region contains the sequence of amino acids set forth in SEQ ID NO: 633. In some of any of the provided embodiments, the Fc region contains the sequence of amino acids set forth in SEQ ID NO: 474. In some of any of the provided embodiments, the Fc region contains the sequence of amino acids set forth in SEQ ID NO: 637.

Provided herein is an immunomodulatory protein containing (a) a variant ICOSL polypeptide containing one or more amino acid modifications in an immunoglobulin superfamily (IgSF) domain of an ICOSL reference polypeptide, wherein the variant ICOSL polypeptide exhibits altered binding to the ectodomain(s) of ICOS or CD28 compared to the binding of the ICOSL reference polypeptide for the same ectodomain(s); and (b) a variant Fc region containing amino acid substitutions selected from N297G/K447del, E233P/L234V/L235A/G236del/S267K/K447del or L234A/L235E/G237A/K447del compared to wildtype human IgG1, wherein the residues are numbered according to the EU index of Kabat. In some cases, the immunomodulatory protein is a dimer. In some of any of the provided embodiments, the variant Fc region further contains the amino acid substitution C220S, wherein the residues are numbered according to the EU index of Kabat. In some examples, the Fc region contains the sequence of amino acid sequence set forth in any of SEQ ID NOS: 632-634 or a sequence of amino acids that exhibits at least 90%, 91%, 92%, 93%, 94%, 95%, 96%, 97%, 98%, 99% or more sequence identity to any of SEQ ID NOS: 632-634 and contains the amino acid substitutions. In some of any of the provided embodiments, the Fc region contains the sequence of amino acid sequence set forth in SEQ ID NOS: 474 or 637, or a sequence of amino acids that exhibits at least 90%, 91%, 92%, 93%, 94%, 95%, 96%, 97%, 98%, 99% or more sequence identity to SEQ ID NOS: 474 or 637 and contains the amino acid substitutions.

In some of any of the provided embodiments, the variant ICOSL polypeptide is linked, directly or indirectly via a linker, to the variant Fc region. In some examples, the linker contains 1 to 10 amino acids. In some of any of the provided embodiments, the linker is selected from AAA, G4S (SEQ ID NO: 636), (G₄S)₂ (SEQ ID NO: 229) or GSGGGGS linker (SEQ ID NO: 635). In some of any of the provided embodiments, the linker is (G₄S)₃ (SEQ ID NO: 228).

In some of any of the provided embodiments, the linker is AAA. In some of any of the provided embodiments, the linker is G₄S (SEQ ID NO:636). In some of any of the provided embodiments, the linker is (G₄S)₂ (SEQ ID NO:229). In some of any of the provided embodiments, the linker is GSGGGGS linker (SEQ ID NO: 635).

In some of any of the provided embodiments of a fusion protein, e.g. a variant ICOSL-Fc fusion protein, the variant ICOSL polypeptide is or comprise an IgV domain. In some of any of the provided embodiments, the variant ICOSL polypeptide contains amino acid modifications N52H/Q100R. In some of any of the provided embodiments, the variant ICOSL polypeptide has the sequence set forth in SEQ ID NO: 567. In some of any of the provided embodiments, the variant ICOSL polypeptide comprises amino acid modifications N52H/N57Y/Q100R. In some of any of the provided embodiments, the variant ICOSL polypeptide has the sequence set forth in SEQ ID NO: 565. In some of any of the provided embodiments, the variant ICOSL polypeptide comprises amino acid modifications are N52L/N57H/Q100R. In some of any of the provided embodiments, the variant ICOSL polypeptide has the sequence set forth in SEQ ID NO: 761. In some of any of the provided embodiments, the variant ICOSL polypeptide comprises amino acid modifications N52H/N57Y/Q100P. In some of any of the provided embodiments, the variant ICOSL polypeptide has the sequence set forth in SEQ ID NO: 570. In some of any of the provided embodiments, the variant ICOSL polypeptide comprises the amino acid modification is N52D. In some of any of the provided embodiments, the polypeptide has the sequence set forth in SEQ ID NO: 548.

In some of any of the provided embodiments, provided is a variant ICOSL-Fc fusion protein that has the sequence of amino acids set forth in SEQ ID NO: 928. In some of any of the provided embodiments, provided is a variant ICOSL-Fc fusion protein that has a sequence of amino acids that has at least 85%, 86%, 87%, 88%, 89%, 90%, 91%, 92%, 93%, 94%, 95%, 96%, 97%, 98%, 99% or more sequence identity to the sequence set forth in SEQ ID NO: 928.

In particular embodiments, the provided immunomodulatory proteins, such as fusion proteins, e.g. variant ICOSL-Fc fusion proteins, binds CD28 and ICOS. In some embodiments, the variant ICOSL-Fc fusion protein exhibits increased binding affinity to CD28 and/or ICOS compared to a human wild-type ICOSL-Fc fusion protein, e.g. containing an ICOSL IgV portion set forth in SEQ ID NO:545 linked via a linker, e.g. set forth in SEQ ID NO:229, to an Fc region. In such an example, the Fc region is an inert or effectorless Fc containing the mutations L234A, L235E and L235E in a human IgG1 Fc, e.g. set forth in SEQ ID NO:637, Provided herein is an immunomodulatory protein containing any of the variant ICOSL polypeptides linked to a second polypeptide comprising an immunoglobulin superfamily (IgSF) domain. In some cases, the IgSF domain is affinity modified and exhibits altered binding to one or more of its cognate binding partner(s) compared to the unmodified or wild-type IgSF domain. In some of any of the provided embodiments, the IgSF domain exhibits increased binding to one or more of its cognate binding partner(s) compared to the unmodified or wild-type IgSF domain.

In some of any of the provided embodiments, the variant ICOSL polypeptide is a first ICOSL variant polypeptide and the IgSF domain of the second polypeptide is an IgSF domain from a second variant ICOSL polypeptide provided herein, wherein the first and second ICOSL variant are the same or different.

In some of any of the provided embodiments, the variant ICOSL polypeptide is capable of specifically binding to CD28 or ICOS and the IgSF domain of the second polypeptide is capable of binding to a binding partner other than one specifically bound by the ICOSL variant polypeptide. In some of any of the provided embodiments, the IgSF domain is from a member of the B7 family.

In some of any of the provided embodiments, the IgSF domain is a tumor-localizing moiety that binds to a ligand expressed on a tumor or is an inflammatory-localizing moiety that binds to a ligand expressed on a cell or tissue of an inflammatory environment. In some cases, the ligand is B7H6. In some examples, the IgSF domain is from NKp30.

In some of any of the provided embodiments, the IgSF domain of the second polypeptide is or comprises an IgV domain. In some of any of the provided embodiments, the IgSF domain of the second polypeptide is a variant NKp30 molecule containing L30V/A60V/S64P/S86G. In some of any of the provided embodiments, the IgSF domain of the second polypeptide has the sequence set forth in SEQ ID NO: 504.

In some of any of the provided embodiments, the IgSF domain is or comprises an IgV domain. In some cases, the variant ICOSL polypeptide is or contains an IgV domain.

In some of any of the provided embodiments, the variant ICOSL polypeptide is or comprise an IgV domain. In some of any of the provided embodiments, the variant ICOSL polypeptide contains amino acid modifications N52H/Q100R. In some of any of the provided embodiments, the variant ICOSL polypeptide has the sequence set forth in SEQ ID NO: 567. In some of any of the provided embodiments, the variant ICOSL polypeptide comprises amino acid modifications N52H/N57Y/Q100R. In some of any of the provided embodiments, the variant ICOSL polypeptide has the sequence set forth in SEQ ID NO: 565. In some of any of the provided embodiments, the variant ICOSL polypeptide comprises amino acid modifications are N52L/N57H/Q100R. In some of any of the provided embodiments, the variant ICOSL polypeptide has the sequence set forth in SEQ ID NO: 761. In some of any of the provided embodiments, the variant ICOSL polypeptide comprises amino acid modifications N52H/N57Y/Q100P. In some of any of the provided embodiments, the variant ICOSL polypeptide has the sequence set forth in SEQ ID NO: 570. In some of any of the provided embodiments, the variant ICOSL polypeptide comprises the amino acid modification is N52D. In some of any of the provided embodiments, the polypeptide has the sequence set forth in SEQ ID NO: 548.

In some of any of the provided embodiments, the immunomodulatory protein comprises a multimerization domain linked to one or both of the variant ICOSL polypeptide or the second polypeptide comprising the IgSF domain. In some cases, the multimerization domain is an Fc domain or a variant thereof with reduced effector function.

In some of any of the provided embodiments, the immunomodulatory protein is dimeric. In some cases, the immunomodulatory protein is homodimeric. In some aspects, the immunomodulatory protein is heterodimeric.

Provided herein is a conjugate containing any of the provided variant ICOSL polypeptides or any of the provided immunomodulatory protein and a heterologous moiety. In some cases, the variant ICOSL polypeptide is linked, directly or indirectly via a linker, to the heterologous moiety. In some of any of the provided embodiments, the targeting moiety is a protein, a peptide, nucleic acid, small molecule or nanoparticle. In some examples, the target moiety is a protein or a peptide. In some of any of the provided embodiments, the conjugate is a fusion protein.

Provided is a fusion protein containing any of the provided variant ICOSL polypeptides or any of the provided immunomodulatory protein and a heterologous moiety. In some cases, the moiety is a targeting moiety that specifically binds to a molecule on the surface of a cell. In some examples, the targeting moiety specifically binds to a molecule on the surface of an immune cell. In some of any of the provided embodiments, the immune cell is an antigen presenting cell or a lymphocyte. In some cases, the targeting moiety is a tumor-localizing moiety that binds to a molecule on the surface of a tumor.

In some of any of the provided embodiments, the targeting moiety binds to a molecule HER1/EGFR, HER2/ERBB2, CD20, CD25 (IL-2Rα receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor (PDGFR; such as PDGF-R α), PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), VEGFR2, VEGF-A, integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, metalloproteinases, Ephrin receptor, Ephrin ligands, HGF receptor, CXCR4, CXCR4, Bombesin receptor, SK-1antigen, Bcr-abl, RET, MET, TRKB, TIE2, ALK, ROS, EMLA-ALK, ROS1, BRAFV600E, SRC, c-KIT, mTOR, TSC1, TSC2, BTK, KIT, BRCA, CDK 4/6, JAK1, JAK2, BRAF, FLT-3, MEK1, MEK2, SMO or B7-H6 (NCR3LG1). In some aspects, the targeting moiety binds to PD-L1.

In some of any of the provided embodiments, the targeting moiety is an antibody or antigen-binding fragment. In some of any of the provided embodiments, the antibody is selected from cetuximab, panitumumab, zalutumumab, nimotuzumab, trastuzumab, Ado-trastuzumab emtansine, Tositumomab (Bexxar®), Rituximab (Rituxan, Mabthera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Afatinib, Axitinib, Bosutinib, Cabozantinib, Ceritinib, Crizotinib, Dabrafenib, Dasatinib, Dinutuximab (Unituxin™), Erlotinib, Everolimus, Ibrutinib, Imatinib, Lapatinib, Lenvatinib, Nilotinib, Olaparib, Olaratumab (Lartruvo™), Palbociclib, Pazopanib, Pertuzumab (Perjeta®), Ramucirumab (Cyramza®), Regorafenib, Ruxolitinib, Sorafenib, Sunitinib, Temsirolimus, Trametinib, Vandetanib, Vemurafenib, Vismodegib, Basiliximab, Ipilimumab, Nivolumab, pembrolizumab, MPDL3280A, Pidilizumab (CT-011), AMP-224, MSB001078C, or MEDI4736, BMS-935559, LY3300054, atezolizumab, avelumab or durvalumab or is an antigen-binding fragment thereof.

In some of any of the provided embodiments, the variant ICOSL polypeptide is linked, directly or indirectly via a linker, to the N-terminus of the heavy and/or light chain of the antibody or antigen-binding fragment. In some cases, the variant ICOSL polypeptide is linked, directly or indirectly via a linker, to the C-terminus of the heavy and/or light chain of the antibody or antigen binding fragment.

In some of any of the provided embodiments, the conjugate is divalent, tetravalent, hexavalent or octavalent. In some of any of the provided embodiments, the heterologous moiety is or contains a label for detection or purification of the variant ICOSL polypeptide.

Provided herein is a monovalent fusion protein containing a variant ICOSL polypeptide containing one or more amino acid modifications in an immunoglobulin superfamily (IgSF) domain of an ICOSL reference polypeptide, wherein the variant ICOSL polypeptide exhibits altered binding to the ectodomain(s) of ICOS or CD28 compared to the binding of the ICOSL reference polypeptide for the same ectodomain(s); and a label for detection or purification of the variant ICOSL polypeptide. In some of any of the provided embodiments, the label for detection or purification is selected from a poly-histidine (His) tag, a FLAG-tag, a Myc-tag, or a fluorescent protein-tag.

In some of any of the provided embodiments, the variant ICOSL polypeptide contains one or more amino acid modifications in a position corresponding to position(s) selected from 10, 11, 13, 16, 18, 20, 25, 27, 30, 33, 37, 38, 42, 43, 47, 52, 54, 57, 61, 62, 67, 71, 72, 74, 75, 77, 78, 80, 84, 89, 90, 92, 93, 94, 96, 97, 98, 99, 100, 102, 103, 107, 109, 110, 111, 113, 115, 116, 117, 119, 120, 121, 122, 126, 129, 130, 132, 133, 135, 138, 139, 140, 142, 143, 144, 146, 148, 151, 152, 153, 154, 155, 156, 158, 161, 164, 166, 168, 172, 173, 175, 190, 192, 193, 194, 198, 201, 203, 207, 208, 210, 212, 217, 218, 220, 221, 224, 225, or 227 with reference to SEQ ID NO: 32. In some of any of the provided embodiments, the variant ICOSL polypeptide contains one or more amino acid modifications are in a position corresponding to position(s) selected from 10, 11, 13, 16, 18, 20, 25, 26, 27, 30, 33, 37, 38, 42, 43, 47, 52, 54, 57, 61, 62, 67, 71, 72, 74, 75, 77, 78, 80, 84, 89, 90, 92, 93, 94, 96, 97, 98, 99, 100, 102, 103, 107, 109, 110, 111, 113, 115, 116, 117, 119, 120, 121, 122, 126, 129, 130, 132, 133, 135, 137, 138, 139, 140, 142, 143, 144, 146, 151, 152, 153, 154, 155, 156, 158, 161, 164, 166, 168, 172, 173, 175, 190, 192, 193, 194, 198, 201, 203, 207, 208, 210, 212, 217, 218, 220, 221, 224, 225, or 227 with reference to SEQ ID NO: 32.

In some cases, the one or more amino acid modifications are selected from M10V, M10I, V11E, S13G, E16V, S18R, A20V, S25G, F27S, F27C, N30D, Y33del, Q37R, K42E, T43A, Y47H, N52A, N52C, N52D, N52G, N52H, N52K, N52L, N52M, N52Q, N52R, N52S, N52T, N52V, N52Y, N52K, S54A, S54P, N57A, N57D, N57E, N57F, N57H, N57K, N57L, N57M, N57P, N57Q, N57S, N57T, N57V, N57Y, N57W, R61S, R61C, Y62F, L67P, A71T, G72R, L74Q, R75Q, D77G, F78L, L80P, N84Q, E90A, K92R, F93L, H94E, H94D, L96F, L96I, V97A, L98F, S99G, Q100A, Q100D, Q100G, Q100K, Q100L, Q100M, Q100N, Q100P, Q100R, Q100S, Q100T, Q100V, L102R, G103E, V107A, V107I, S109G, S109N, V110D, V110N, V110A, E111del, T113E, H115R, H115Q, V116A, A117T, N119Q, F120I, S121G, V122A, V122M, F120S, S126T, S126R, H129P, S130G, S132F, Q133H, E135K, F138L, T139S, C140del, C140D, S142F, I143V, I143T, N144D, Y146C, V151A, Y152C, Y152H, W153R, I154F, N155H, N155Q, K156M, D158G, L161P, L161M, L166Q, N168Q, F172S, L173S, M175T, T190A, T190S, S192G, V193M, N194D, C198R, N201S, L203P, L203F, N207Q, L208P, V210A, S212G, D217V, I218T, I218N, E220G, R221G, R221I, I224V, T225A, N227K, or a conservative amino acid substitution thereof. In some cases, the one or more amino acid modifications are selected from M10V, M10I, V11E, S13G, E16V, S18R, A20T, A20V, S25G, R26S, F27C, F27S, N30D, Y33del, Q37R, T38P, K42E, T43A, Y47H, N52A, N52C, N52D, N52G, N52H, N52K, N52L, N52M, N52P, N52Q, N52R, N52S, N52T, N52V, N52Y, S54A, S54F, S54P, N57A, N57D, N57E, N57F, N57H, N57K, N57L, N57M, N57P, N57Q, N57S, N57T, N57V, N57W, N57Y, R61C, R61S, Y62F, L67P, A71T, G72R, L74Q, R75Q, D77G, F78L, L80P, N84Q, D89G, E90A, K92R, F93L, H94D, H94E, L96F, L96I, V97A, L98F, S99G, Q100A, Q100D, Q100E, Q100G, Q100K, Q100L, Q100M, Q100N, Q100P, Q100R, Q100S, Q100T, Q100V, L102R, G103E, V107A, V107I, S109G, S109N, V110A, V110D, V110N, E111del, T113E, H115Q, H115R, V116A, A117T, N119Q, F120I, F120S, S121G, V122A, V122M, S126R, S126T, H129P, S130G, S132F, Q133H, E135K, T137A, F138L, T139S, C140del, C140D, S142F, I143T, I143V, N144D, Y146C, V151A, Y152C, Y152H, W153R, I154F, N155H, N155Q, K156M, D158G, L161M, L161P, Q164L, L166Q, N168Q, F172S, L173S, M175T, T190A, T190S, S192G, V193A, V193M, N194D, C198R, N201S, L203F, L203P, N207Q, L208P, V210A, S212G, D217G, D217V, I218N, I218T, E220G, R221G, R221I, R221K, I224V, T225A, T225S, N227K, or a conservative amino acid substitution thereof.

In some of any of the provided embodiments, the ICOSL reference polypeptide contains (i) the sequence of amino acids set forth in SEQ ID NO:32, (ii) a sequence of amino acids that has at least 95% sequence identity to SEQ ID NO:32; or (iii) a portion of (i) or (ii) comprising an IgV domain or IgC domain or specific binding fragments thereof or both.

In some of any of the provided embodiments, the ICOSL reference polypeptide comprises the sequence of amino acids set forth in any of SEQ ID NOS: 196, 545, 600-605 and 623-628. In some aspects, the ICOSL reference polypeptide consists of the sequence of amino acids set forth in any of SEQ ID NOS: 32, 196, 545, 600-605 and 623-628.

Provided is a nucleic acid molecule(s) encoding any of the provided variant ICOSL polypeptides, immunomodulatory proteins, or fusion proteins. In some cases, the nucleic acid molecules(s) is synthetic nucleic acid. In some examples, the nucleic acid molecule(s) is cDNA.

Provided is a vector containing any of the provided the nucleic acid molecule(s). In some cases, the vector is an expression vector. In some of any of the provided embodiments, the vector is a mammalian expression vector or a viral vector.

Provided is a cell containing any of the provided vectors. In some cases, the cell is a mammalian cell. In some of any of the provided embodiments, the cell is a Chinese Hamster Ovary (CHO) cell or a derivative thereof.

Provided is a method of producing an immunomodulatory protein containing any of the variant ICOSL polypeptides, including introducing any of the provided nucleic acid molecules or vectors into a host cell under conditions to express the protein in the cell. In some examples, the host cell is a mammalian cell. In some instances, the mammalian cell is a Chinese Hamster Ovary cell or a derivative thereof. In some of any of the provided embodiments, the method further includes isolating or purifying the protein from the cell.

Provided is a protein produced by any of the provided methods.

Provided is a composition containing a protein containing any of the provided variant ICOSL polypeptides, or immunomodulatory proteins, wherein at least 95%, 96%, 97%, 98%, 99% of the individual sequences of the protein or the immunomodulatory protein in the composition have an identical sequence length, optionally wherein the composition is a pharmaceutical composition comprising a pharmaceutically acceptable carrier. In some of any of the provided embodiments, the protein or immunomodulatory protein is purified from Chinese Hamster Ovary Cells or a derivative thereof.

Provided is a polynucleotide containing a nucleic acid encoding a variant ICOSL polypeptide containing a provided transmembrane domain and one or more nucleic acid encoding one or more chain of a recombinant antigen receptor. In some cases, the recombinant antigen receptor is a chimeric antigen receptor (CAR) or an engineered T cell receptor (TCR). In some of any of the provided embodiments, each of the nucleic acid encoding the variant ICOSL polypeptide and the one or more nucleic acid encoding one or more chain of the recombinant receptor is separated by a nucleic acid encoding a self-cleaving peptide or a peptide that causes ribosome skipping.

In some examples, the polynucleotide contains the nucleic acid encoding the variant ICOSL polypeptide, a nucleic acid encoding a self-cleaving peptide or a peptide that causes ribosome skipping and a nucleic acid encoding a CAR. In some examples, the polynucleotide comprises the nucleic acid encoding the variant ICOSL polypeptide, a nucleic acid encoding a first self-cleaving peptide or a peptide that causes ribosome skipping, a nucleic acid encoding one of an engineered TCRalpha chain or an engineered TCRbeta chain, a nucleic acid encoding a second self-cleaving peptide or a peptide that causes ribosome skipping, and a nucleic acid encoding the other of the engineered TCRalpha chain or the engineered TCRbeta chain. In some aspects, the encoded first and second self-cleaving peptide is the same. In some of any of the provided embodiments, the self-cleaving peptide or the peptide that causes ribosome skipping is a T2A, a P2A, a E2A or a F2A.

Provided is a vector containing any of the provided polynucleotides. In some cases, the vector is a viral vector. In some of any of the provided embodiments, the viral vector is a retroviral vector or a lentiviral vector.

Provided is an engineered cell containing any of the provided polynucleotides or vectors. Also provided is an engineered cell containing any of the provided variant ICOSL polypeptides, immunomodulatory proteins, or fusion proteins.

Provided is an engineered cell containing any of the provided nucleic acid molecules or the vectors. In some cases, the nucleic acid encoding the variant ICOSL polypeptide, immunomodulatory protein or fusion protein encodes a signal peptide. In some of any of the provided embodiments, the variant ICOSL polypeptide, immunomodulatory protein or fusion protein does not contain a transmembrane domain and/or is not expressed on the surface of the cell. In some of any of the provided embodiments, the variant ICOSL polypeptide, immunomodulatory protein or fusion protein is secreted from the engineered cell. In some aspects, the engineered cell contains a variant ICOSL polypeptide containing a transmembrane domain. In some aspects, the variant ICOSL polypeptide is expressed on the surface of the cell.

In some of any of the provided embodiments, the cell is an immune cell. In some cases, the immune cell is an antigen presenting cell (APC) or a lymphocyte. In some examples, the engineered cell is primary cell. In some instances, the cell is a mammalian cell. In some cases, the cell is a human cell. In some of any of the provided embodiments, the lymphocyte is a T cell. In some examples, the engineered cell is an APC and the APC is an artificial APC.

In some of any of the provided embodiments, the engineered cell further contains a chimeric antigen receptor (CAR) or an engineered T-cell receptor.

Provided is an infectious agent containing a nucleic acid molecule encoding a provided variant ICOSL polypeptide or a provided immunomodulatory protein, a provided fusion protein. In some cases, the encoded variant ICOSL polypeptide, immunomodulatory protein or fusion protein does not contain a transmembrane domain and/or is not expressed on the surface of a cell in which it is expressed. In some of any of the provided embodiments, the encoded variant ICOSL polypeptide, immunomodulatory protein or fusion protein is secreted from the infectious agent when it is expressed. In some cases, the encoded variant ICOSL polypeptide comprises a transmembrane domain.

In some of any of the provided embodiments, the encoded variant ICOSL polypeptide is expressed on the surface of a cell in which it is expressed. In some cases, the infectious agent is a bacteria or a virus. In some of any of the provided embodiments, the virus is an oncolytic virus. In some examples, the oncolytic virus is an adenoviruses, adeno-associated viruses, herpes viruses, Herpes Simplex Virus, Vesticular Stomatic virus, Reovirus, Newcastle Disease virus, parvovirus, measles virus, vesticular stomatitis virus (VSV), Coxsackie virus or a Vaccinia virus.

In some of any of the provided embodiments, the virus specifically targets dendritic cells (DCs) and/or is dendritic cell-tropic. In some cases, the virus is a lentiviral vector that is pseudotyped with a modified Sindbis virus envelope product. In some of any of the provided embodiments, the infectious agent further contains a nucleic acid molecule encoding a further gene product that results in death of a target cell or that can augment or boost an immune response. In some of any of the provided embodiments, the further gene product is selected from an anticancer agent, anti-metastatic agent, an antiangiogenic agent, an immunomodulatory molecule, an immune checkpoint inhibitor, an anti-body, a cytokine, a growth factor, an antigen, a cytotoxic gene product, a pro-apoptotic gene product, an anti-apoptotic gene product, a cell matrix degradative gene, genes for tissue regeneration or a reprogramming human somatic cells to pluripotency.

Provided is a pharmaceutical composition containing any of the variant ICOSL polypeptides, immunomodulatory proteins, conjugates or fusion proteins or any of the provided engineered cells or infectious agents. In some of any of the provided embodiments, the pharmaceutical composition contains a pharmaceutically acceptable excipient. In some of any of the provided embodiments, the pharmaceutical composition is sterile.

In some of any of the provided embodiments, provided is an article of manufacture containing the pharmaceutical composition in a vial. In some cases, the vial is sealed.

Provided is a kit containing any of the provided compositions and instructions for use. Also provided is a kit containing any of the provided articles of manufacture and instructions for use.

Provided is a method of modulating an immune response in a subject, including administering the pharmaceutical composition to the subject. Also provided is a method of modulating an immune response in a subject including administering the engineered cells. In some cases, the engineered cells are autologous to the subject. In some of any of the provided embodiments, the engineered cells are allogenic to the subject.

In some of any of the provided embodiments, the modulating the immune response treats a disease or condition in the subject. In some aspects, the immune response is increased.

In some of any of the provided embodiments, an immunomodulatory protein or conjugate containing a variant ICOSL polypeptide linked to a tumor-localizing moiety is administered to the subject. In some cases, the tumor-localizing moiety is or comprises a binding molecule that recognizes a tumor antigen. In some of any of the provided embodiments, the binding molecule contains an antibody or an antigen-binding fragment thereof or comprises a wild-type IgSF domain or variant thereof. In some of any of the provided embodiments, the immunomodulatory protein or the conjugate or fusion protein is administered to the subject.

In some of any of the provided embodiments, a variant ICOSL polypeptide that is a transmembrane immunomodulatory protein is administered to the subject. In some cases, the engineered cell containing a variant ICOSL polypeptide that is a transmembrane immunomodulatory protein is administered to the subject. In some of any of the provided embodiments, the disease or condition is a tumor or cancer. In some examples, the disease or condition is selected from melanoma, lung cancer, bladder cancer, a hematological malignancy, liver cancer, brain cancer, renal cancer, breast cancer, pancreatic cancer, colorectal cancer, spleen cancer, prostate cancer, testicular cancer, ovarian cancer, uterine cancer, gastric carcinoma, a musculoskeletal cancer, a head and neck cancer, a gastrointestinal cancer, a germ cell cancer, or an endocrine and neuroendocrine cancer. In some of any of the provided embodiments, the immune response is decreased.

In some of any of the provided embodiments, a variant ICOSL polypeptide or immunomodulatory protein that is soluble is administered to the subject. In some of any of the provided embodiments, the soluble immunomodulatory protein is an immunomodulatory Fc fusion protein. In some of any of the provided embodiments, a provided variant ICOSL polypeptide, immunomodulatory protein, or fusion protein is administered to the subject. In some of any of the provided embodiments, an engineered cell containing a secretable variant ICOSL polypeptide is administered to the subject. In some of any of the provided embodiments, a provided engineered cell is administered to the subject. In some of any of the provided embodiments, an infectious agent encoding a variant ICOSL polypeptide that is a secretable immunomodulatory protein is administered to the subject, optionally under conditions in which the infectious agent infects a tumor cell or immune cell and the secretable immunomodulatory protein is secreted from the infected cell. In some of any of the provided embodiments, the disease or condition is an inflammatory or autoimmune disease or condition. In some examples, the disease or condition is an Antineutrophil cytoplasmic antibodies (ANCA)-associated vasculitis, a vasculitis, an autoimmune skin disease, transplantation, a Rheumatic disease, an inflammatory gastrointestinal disease, an inflammatory eye disease, an inflammatory neurological disease, an inflammatory pulmonary disease, an inflammatory endocrine disease, or an autoimmune hematological disease. In some cases, the disease or condition is selected from inflammatory bowel disease, transplant, Crohn's disease, ulcerative colitis, multiple sclerosis, asthma, rheumatoid arthritis, or psoriasis.

BRIEF DESCRIPTION OF THE DRAWINGS

FIG. 3A shows IFN-gamma and FIG. 3B shows IL-17 protein levels secreted from pan T-cells. Graphs are representative of typical IFN-gamma and IL-17 responses from pan T-cell costimulation.

FIG. 4A shows percent of total proliferating (arrows), $CD4^+$ (solid bar), and $CD8^+$ cells (hatched bar) T-cells following 40 nM ICOSL costimulation. FIG. 4B shows percent of total pan T-cell proliferation following 10 nM ICOSL costimulation. Graphs are representative of typical proliferative response from pan T-cell costimulation.

FIG. 6A-6D depicts the inhibition of soluble ICOSL Fc-fusion proteins on B and T cell responses in a B-T co-culture assay. FIG. 6A depicts soluble ICOSL Fc-fusion proteins inhibition of T cell-driven B cell proliferation. Purified CD4+ T cells and B cells from a single donor were CFSE-labeled and co-incubated at a 1:1 ration in the presence or absence of the indicated mitogens with or without the indicated ICOSL Fc-fusion proteins. Cells were stimulated with Staph enterotoxin B (SEB) at 100 ng/mL, Pokeweed mitogen (PWM) at 1 mg/mL, or both. ICOSL Fc-fusion proteins were included at a final concentration of 40 nM and cultures were incubated for 7 days and subjected to FACS analysis. The number of divided B cells was determined from the number of cells in the cultures that had diluted their CFSE. All of the ICOSL Fc-fusion proteins tested except for wild-type reduced B cell proliferation. FIG. 6B-6D show ICOSL Fc-fusion proteins inhibited cytokine T cell cytokine production in B-T co-cultures. Supernatants from the cultures described above were harvested on day 7 and analyzed for cytokine content using a LEGENDplex Human Th Cytokine Panel (Biolegend). T cell production of IL-5 (FIG. 6B), IL-13 (FIG. 6C) and IL-21 (FIG. 6D) is attenuated by inclusion of ICOSL Fc-fusion proteins.

FIG. 7A shows survival curves of the treated animals. Aggressive disease course and subsequent mortality was observed in the saline control animals, with similar survival observed in the animals treated with wild-type ICOSL-Fc, as well as the N52H/I143T ICOSL variant. Variant N52H/N57Y/Q100P had improved survival rates comparable to the clinical benchmark belatacept. FIG. 7B shows similar trends in body weight loss, with ICOSL variant N52H/N57Y/Q100P demonstrating similar weight maintenance as animals treated with belatacept, even though all other groups experienced rapid weight loss. FIG. 7C shows clinical scores from standardized GVHD Disease Activity Index (DAI) observations, again showing lower scores in animals treated with the ICOSL variant N52H/N57Y/Q100P that are comparable to the clinical benchmark belatacept while the other groups of animals experienced higher DAI scores. FIG. 7D depicts a flow cytometric measurement of CD4 and CD8 percentages in blood from experimental animals measured on day 14. The percentage of CD8 cells between experimental groups was largely the same, however, animals treated with ICOSL variant N52H/N57Y/Q100P and belatacept have lower percentages of CD4 cells compared to the other experimental groups.

FIG. 7E depicts survival curves from a similar experiment testing additional ICOSL variant molecules. FIG. 7F depicts clinical scores from a similar experiment testing additional ICOSL variant molecules.

PBS treated animals sensitized with ovalbumin and subsequently challenged in the car with the same protein, show the highest level of measured ear swelling. Mice treated with clinical benchmark Abatacept have slightly reduced ear swelling following ear challenge. All five ICOSL variant treatment groups demonstrated equal or improved reductions in ear swelling compared to Abatacept.

Figures 10A, 10B:
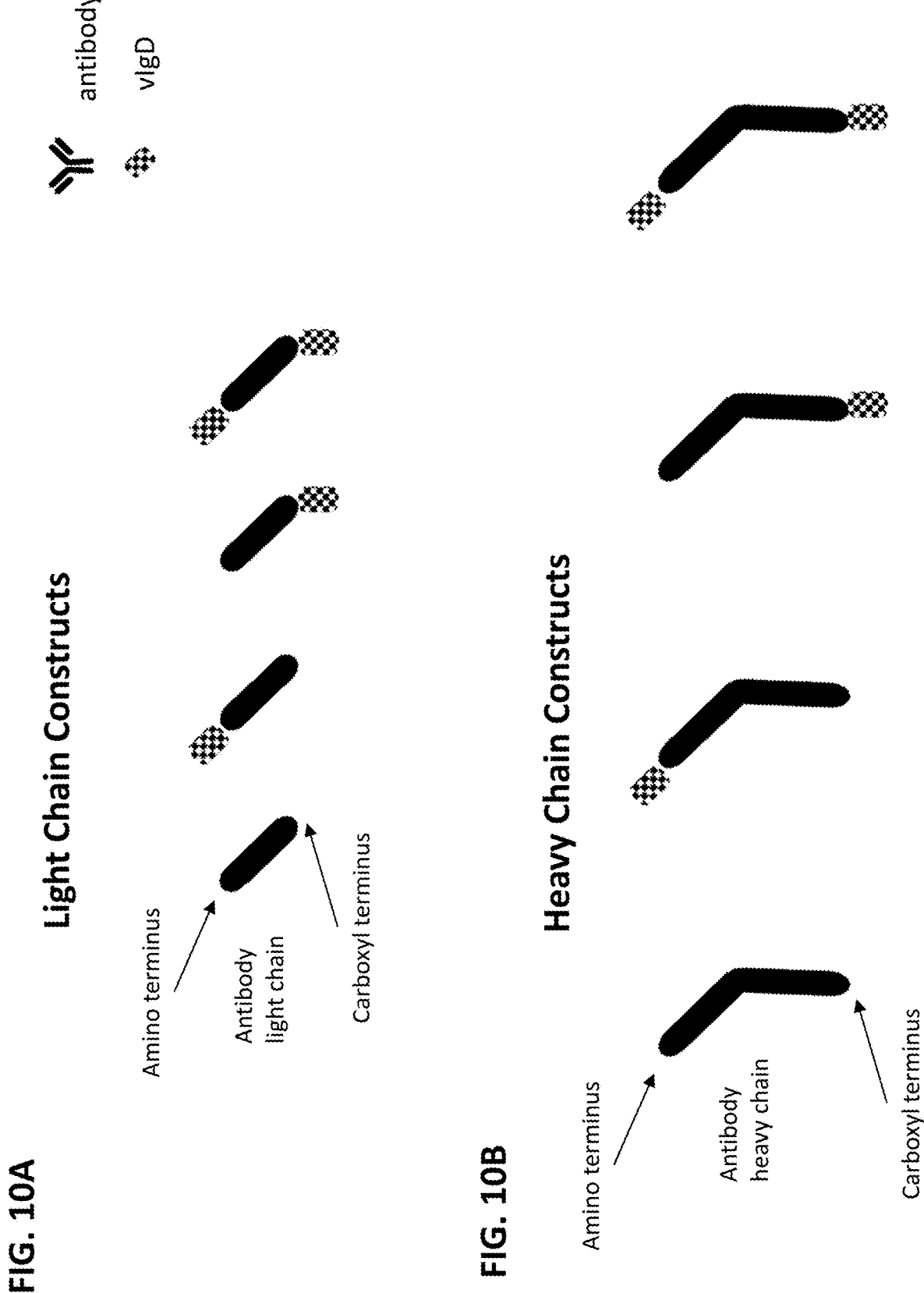
Figure 10C:
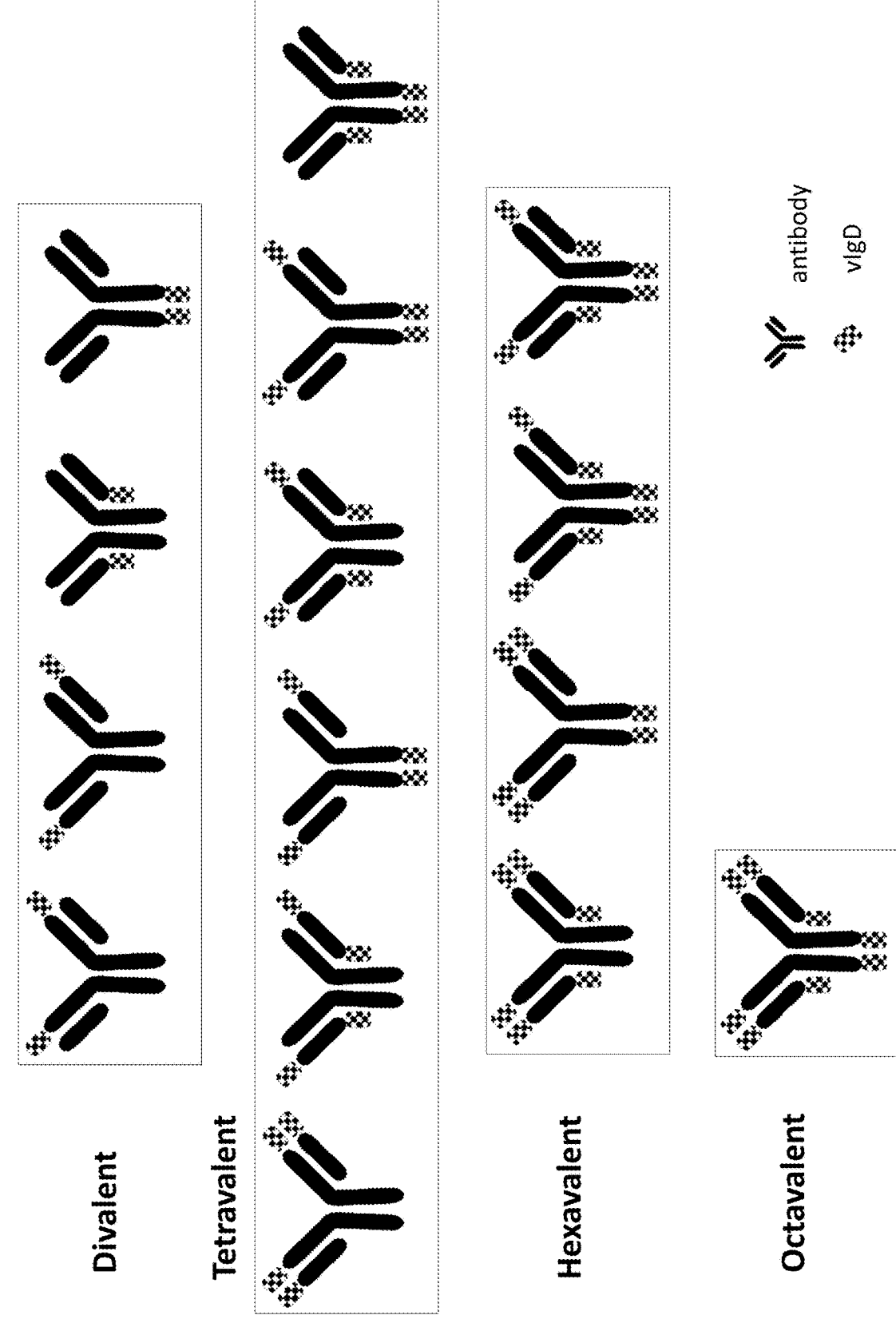

FIG. 10A-10C depicts various exemplary configurations of a variant IgSF domain (vIgD) conjugated to an antibody (V-Mab). FIG. 10A shows various configurations in which a vIgD is linked, directly or indirectly, to the N- and/or C-terminus of the light chain of an antibody. FIG. 10B shows various configurations in which a vIgD is linked, directly or indirectly, to the N- and/or C-terminus of the heavy chain of an antibody. FIG. 10C depicts the resulting V-Mab configurations when a light chain of FIG. 10A and a heavy chain of FIG. 10B are co-expressed in a cell.

Figure 11A:
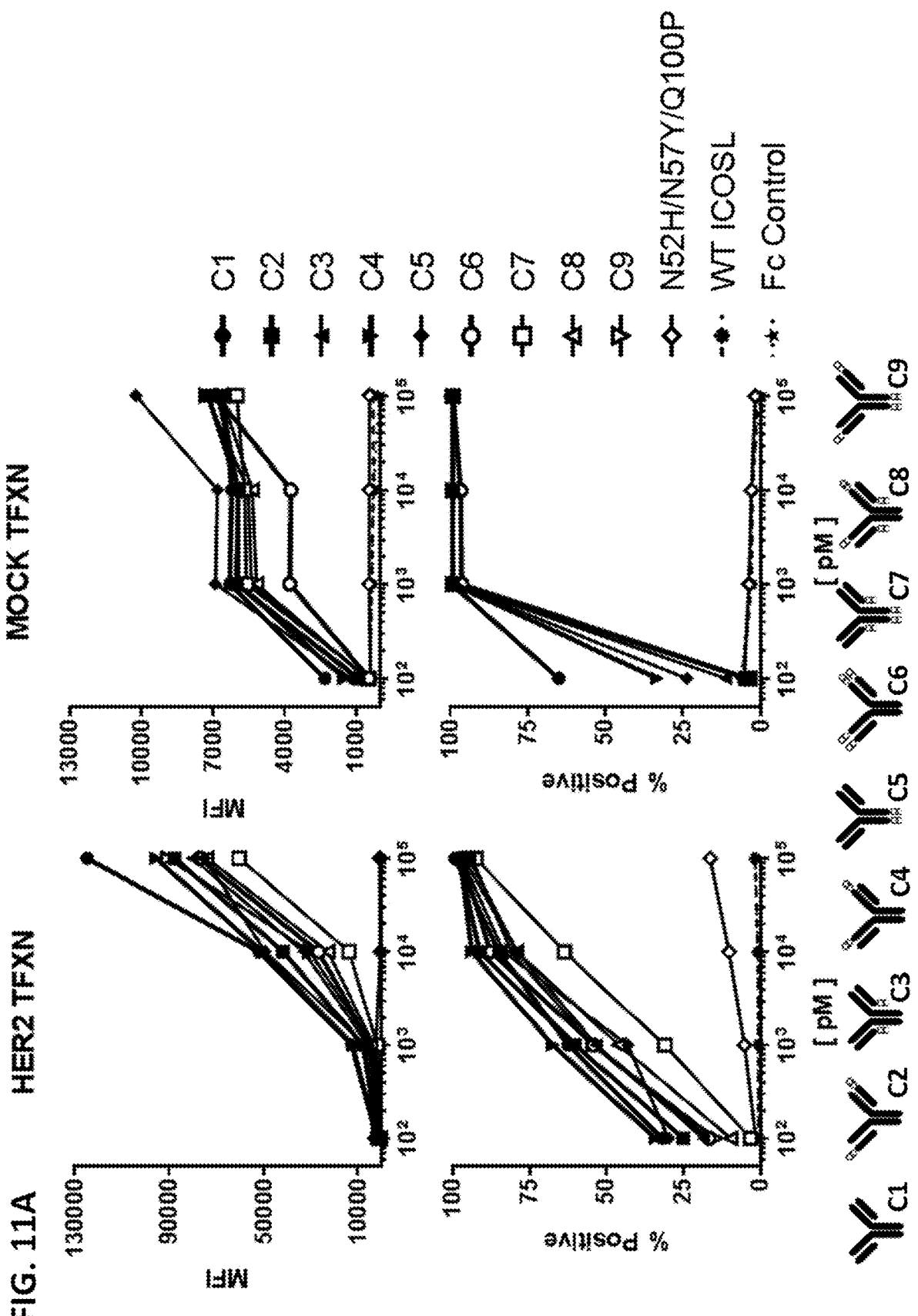
Figure 11B:
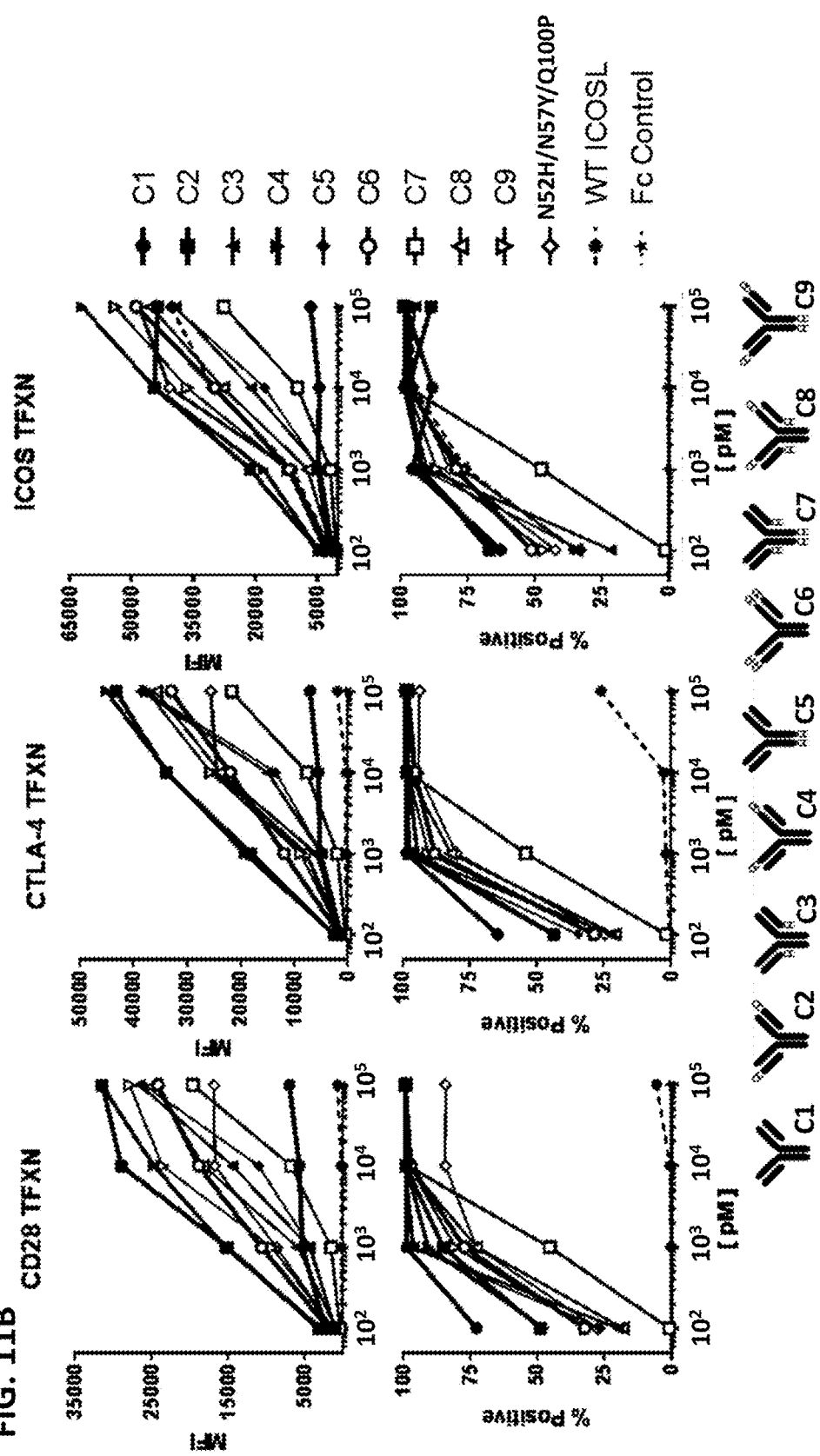

FIG. 11A-11B demonstrate V-Mab specificity for cognate binding partners. Binding assays were performed on Expi293 cells transiently transfected with DNA for mammalian surface expression of human HER2, CD28, CTLA-4, or ICOS. 200,000 transfected cells were incubated with 100,000 pM to 100 pM parental antibody (C1) or various V-Mabs (C2-9). Unbound antibody was removed, bound antibody detected with fluorescently conjugated anti-human IgG, and the cells were analyzed by flow cytometry for MFI and percentage positive based on Fc controls. FIG. 11A shows binding of the V-Mabs to HER2 transfectants at levels similar to the parental antibody. Binding to mock transfected cells is observed with all V-Mabs, though not WT ICOSL, due to low levels of endogenous HER2 expression on Expi293 parental cells. FIG. 11B shows binding of the parental IgSF-domain (N52H/N57Y/Q100P) to its cognate partners is maintained or increased (C2, C3, C4, C5, C6, C8, C9) by V-Mabs.

Figure 12:
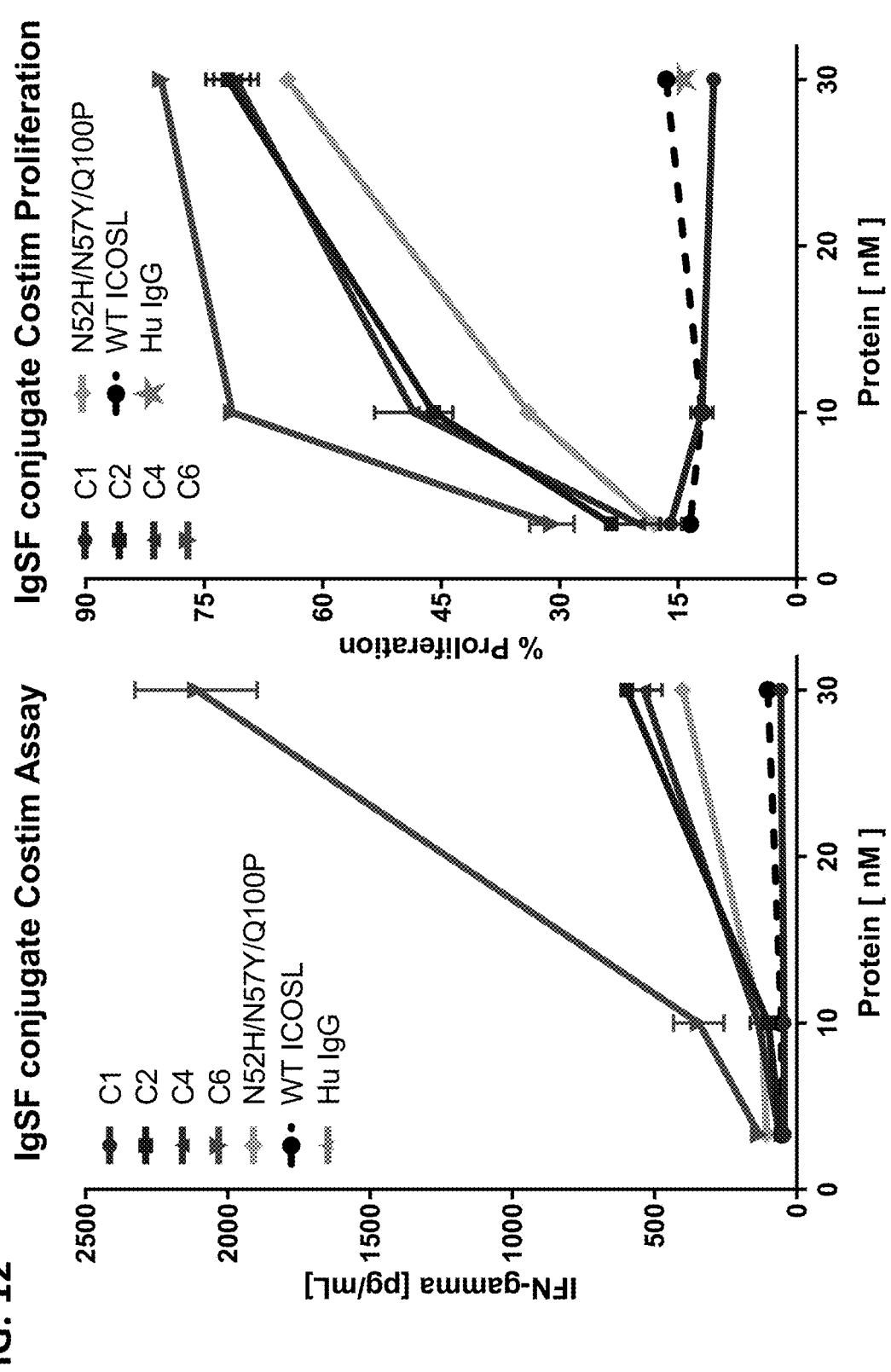

FIG. 12 demonstrates V-Mab costimulatory and proliferative capacity when coimmobilized with anti-CD3. 10 nM anti-CD3 was wet coated to the wells of 96-well flat bottomed polystyrene tissue culture plates with 30 nM to 3 nM parental antibody, V-Mabs, or Fc controls. CFSE-labeled pan T-cells were added for 72 hours. IFN-gamma secretion was measured by ELISA and total T-cell proliferation was measured by flow cytometric analysis of CFSE-dilution. IFN-gamma secretion and proliferation of IgSF-domain (N52H/N57Y/Q100P) is greater than WT ICOSL. V-Mabs demonstrate increased cytokine and proliferative costimulatory capacity over the parental IgSF.

Figure 13A:
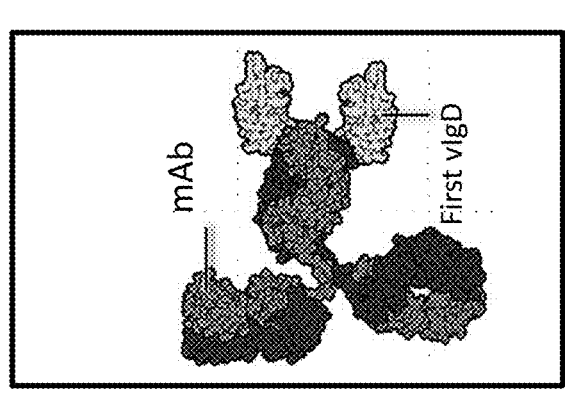
Figure 13A:
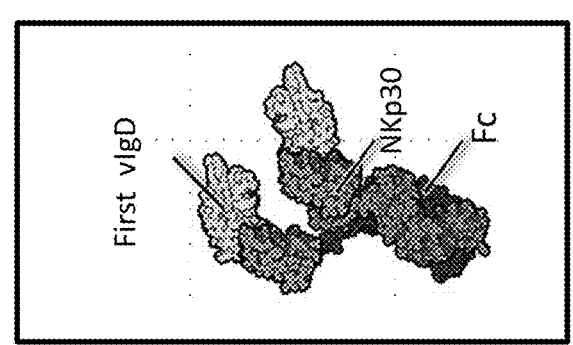
Figure 13A:
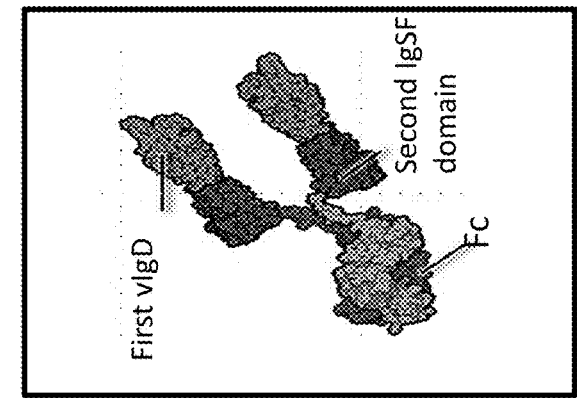
Figure 13B:
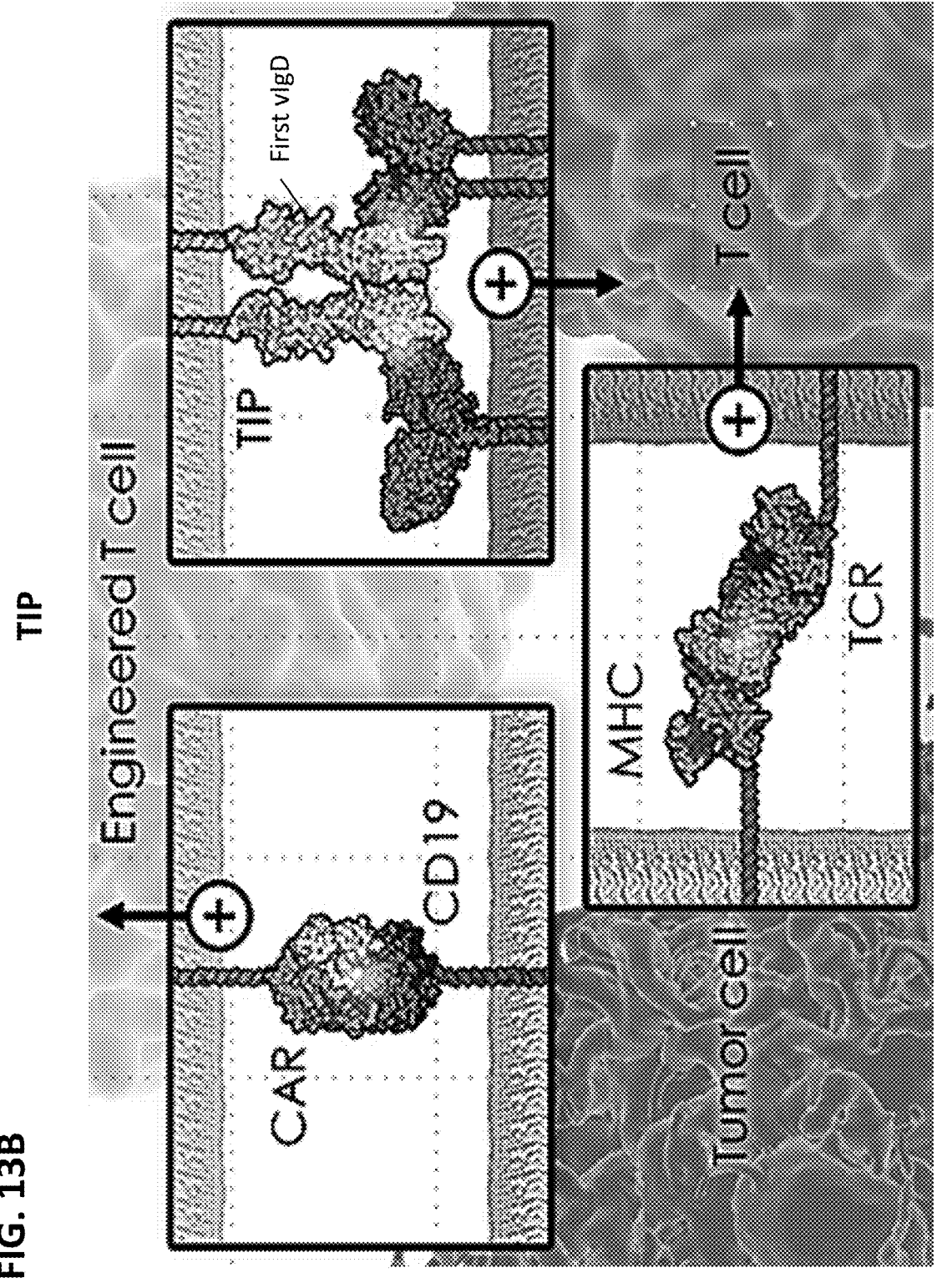
Figure 13C:
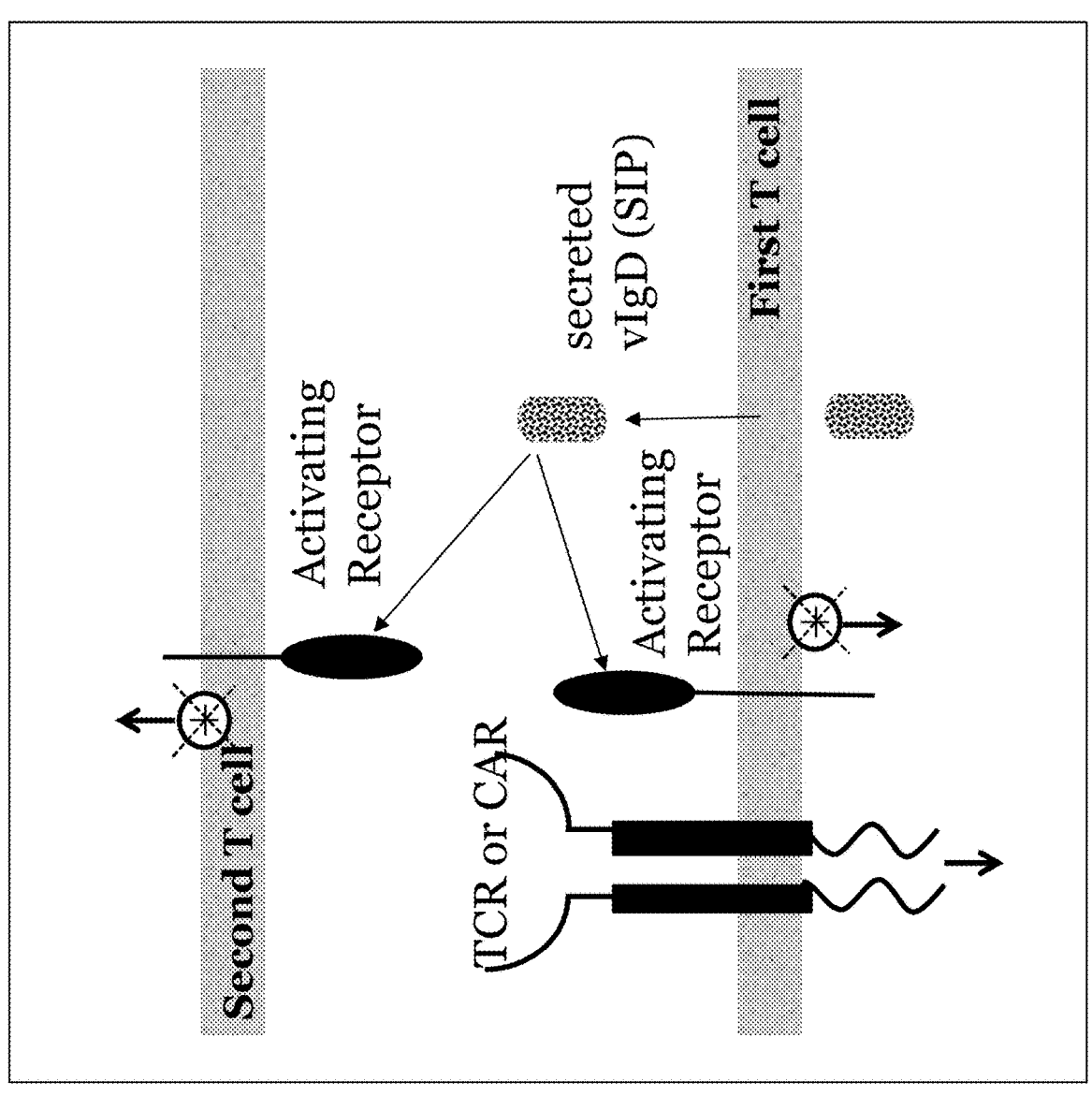

FIG. 13A-13C depicts various formats of the provided variant IgSF domain molecules. FIG. 13A depicts soluble molecules, including: (1) a variant IgSF domain (vIgD) fused to an Fc chain; (2) a stack molecule containing a first variant IgSF domain (first vIgD) and a second IgSF domain, such as a second variant IgSF domain (second vIgD); (3) a tumor targeting IgSF molecule containing a first variant IgSF domain (vIgD) and an IgSF domain that targets to a tumor antigen, such as an NKp30 IgSF domain; and (4) a variant IgSF domain (vIgD) linked to an antibody (V-Mab). FIG. 13B depicts a transmembrane immunomodulatory protein (TIP) containing a variant IgSF domain (vIgD), e.g., variant ICOSL, expressed on the surface of a cell. In an exemplary embodiment, the cognate binding partner of the transmembrane bound vIgD is a costimulatory receptor, e.g. CD28, and the TIP containing the vIgD (e.g. ICOSL vIgD) agonizes the costimulatory receptor such that the TIP induces a positive signal in the cell expressing the costimulatory receptor. FIG. 13C depicts a secreted immunomodulatory protein (SIP) in which a variant IgSF domain (vIgD), e.g., variant ICOSL, is secreted from a cell, such as a first T cell (e.g. CAR T cell). In an exemplary embodiment, the cognate binding partner of the secreted vIgD is an activating receptor, e.g., CD28, which can be expressed on the first cell (e.g., T cell, such as a CAR T cell) and/or on a second cell (e.g. T cell; either endogenous or engineered, such as a CAR T cell). Upon binding of the SIP with its cognate binding partner, signaling via the activating receptor is blocked. In all cases, the vIgD can be a V-domain (IgV) only, the combination of the V-domain (IgV) and C-domain (IgC), including the entire extracellular domain (ECD), or any combination of Ig domains of the IgSF superfamily member.

Figure 14:
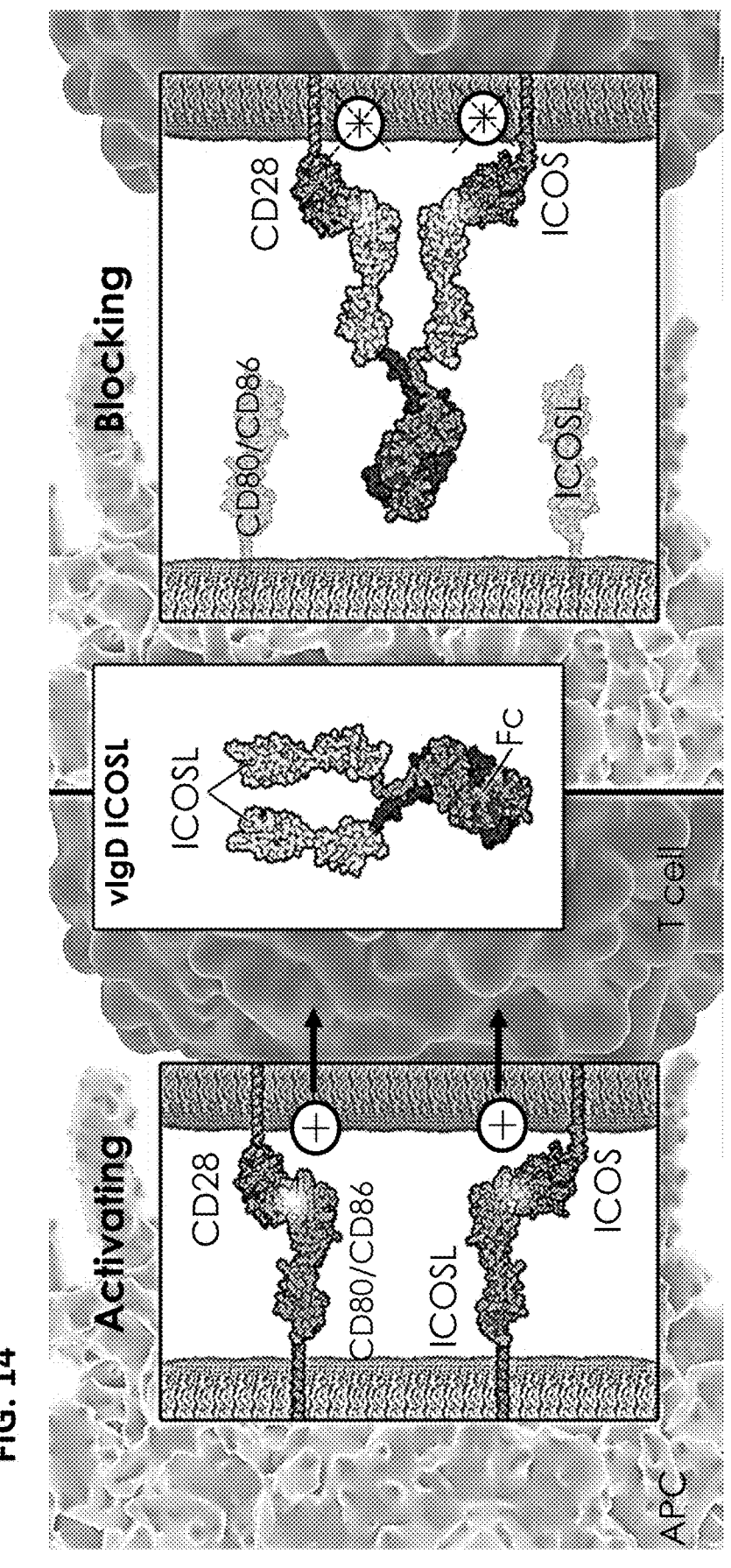

FIG. 14 depicts an exemplary schematic of the activity of a variant IgSF domain (vIgD) fused to an Fc (vIgD-Fc) in which the vIgD is a variant of an IgSF domain of ICOSL. As shown, a soluble vIgD of ICOSL interacts with its cognate binding partners to block interactions of CD80 (B7-1)/CD86 (B7-2) or ICOSL with CD28 or ICOS, respectively, thereby blocking costimulation by the CD28 and/or ICOS costimulatory receptors.

Figure 15:
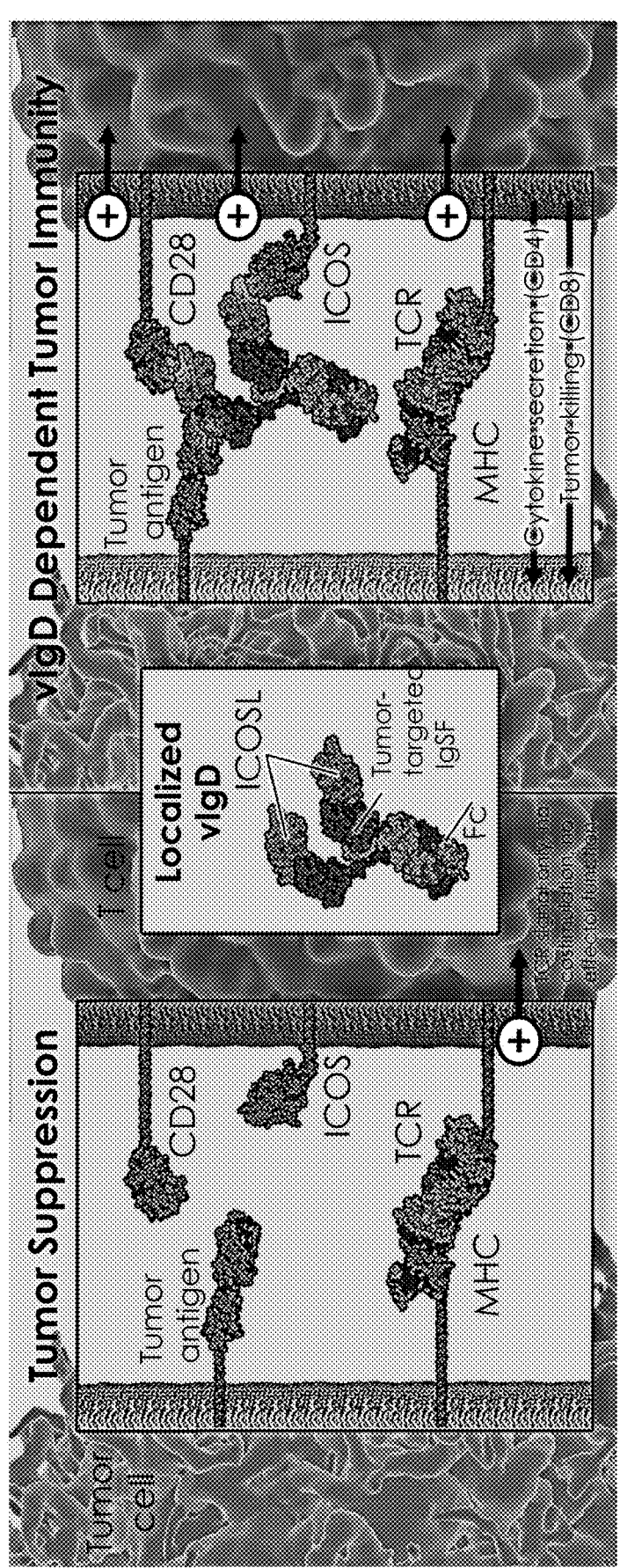

FIG. 15 depicts an exemplary schematic of a stack molecule for localizing the variant IgSF domain (vIgD) to a tumor cell. In this format, the stack molecule contains a first variant IgSF domain (first vIgD) and a second IgSF domain (e.g. a second vIgD) in which the second IgSF domain (e.g a second vIgD) is a tumor-targeted IgSF domain that binds to a tumor antigen. An exemplary tumor-targeted IgSF domain is an IgSF domain of NKp30, which binds to the tumor antigen B7-H6. In this depiction, the vIgD is a variant of an IgSF domain of ICOSL. As shown, binding of tumor-targeted IgSF domain to the surface of the tumor cell localizes the first vIgD on the tumor cell surface where it can interact with one or more of its cognate binding partners (e.g. CD28 or ICOS) expressed on the surface of an adjacent immune cell (e.g. T cell) to stimulate the costimulatory receptor.

Figure 16A:
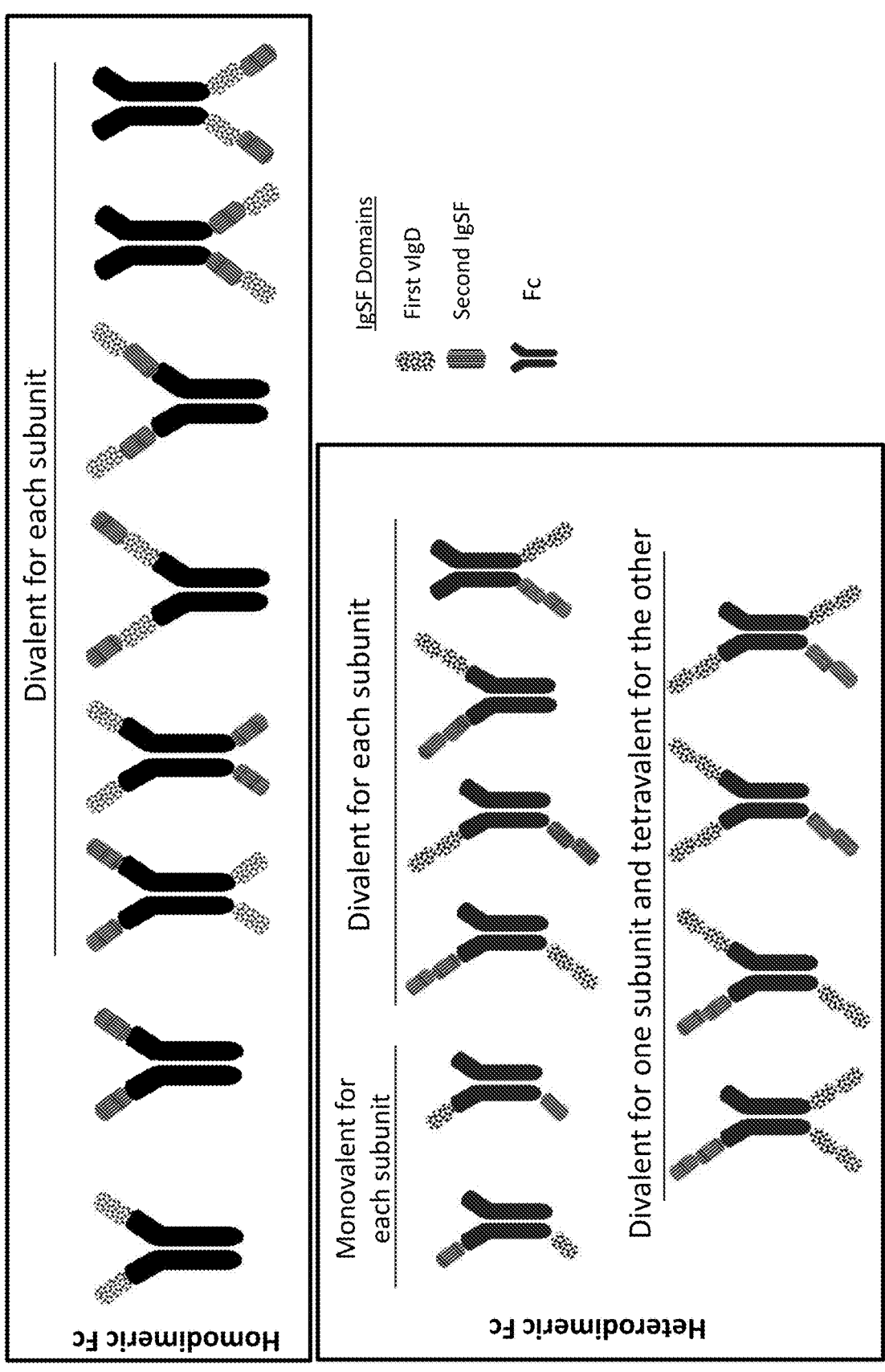

FIG. 16A depicts various exemplary configurations of a stack molecule containing a first variant IgSF domain (first vIgD), e.g. variant ICOSL, and a second IgSF domain, such as a second variant IgSF domain (second vIgD). As shown, the first vIgD and second IgSF domain are independently linked, directly or indirectly, to the N- or C-terminus of an Fc region. For generating a homodimeric Fc molecule, the Fc region is one that is capable of forming a homodimer with a matched Fc subunit by co-expression of the individual Fc regions in a cell. For generating a heterodimeric Fc molecule, the individual Fc regions contain mutations (e.g. "knob-into-hole" mutations in the CH3 domain), such that formation of the heterodimer is favored compared to homodimers when the individual Fc regions are co-expressed in a cell.

Figure 16B:
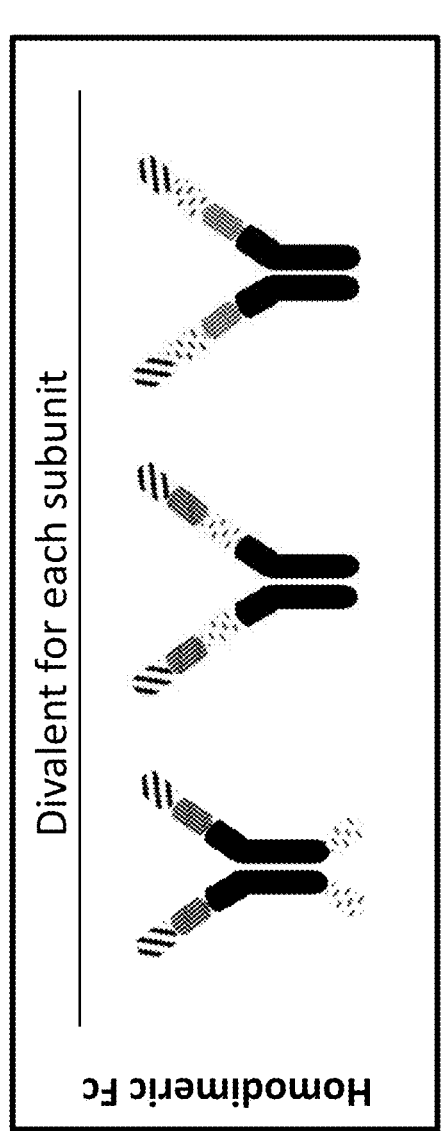

FIG. 16B depicts various exemplary configurations of a stack molecule containing a first variant IgSF domain (first vIgD), a second IgSF domain, such as a second variant IgSF domain (second vIgD), and a third IgSF domain, such as a third variant IgSF domain (third vIgD). As shown, the first vIgD, second IgSF, and third IgSF domains are independently linked, directly or indirectly, to the N- or C-terminus of an Fc region. For generating a homodimeric Fc molecule, the Fc region is one that is capable of forming a homodimer with a matched Fc region by co-expression of the individual Fc regions in a cell.

Figure 17:
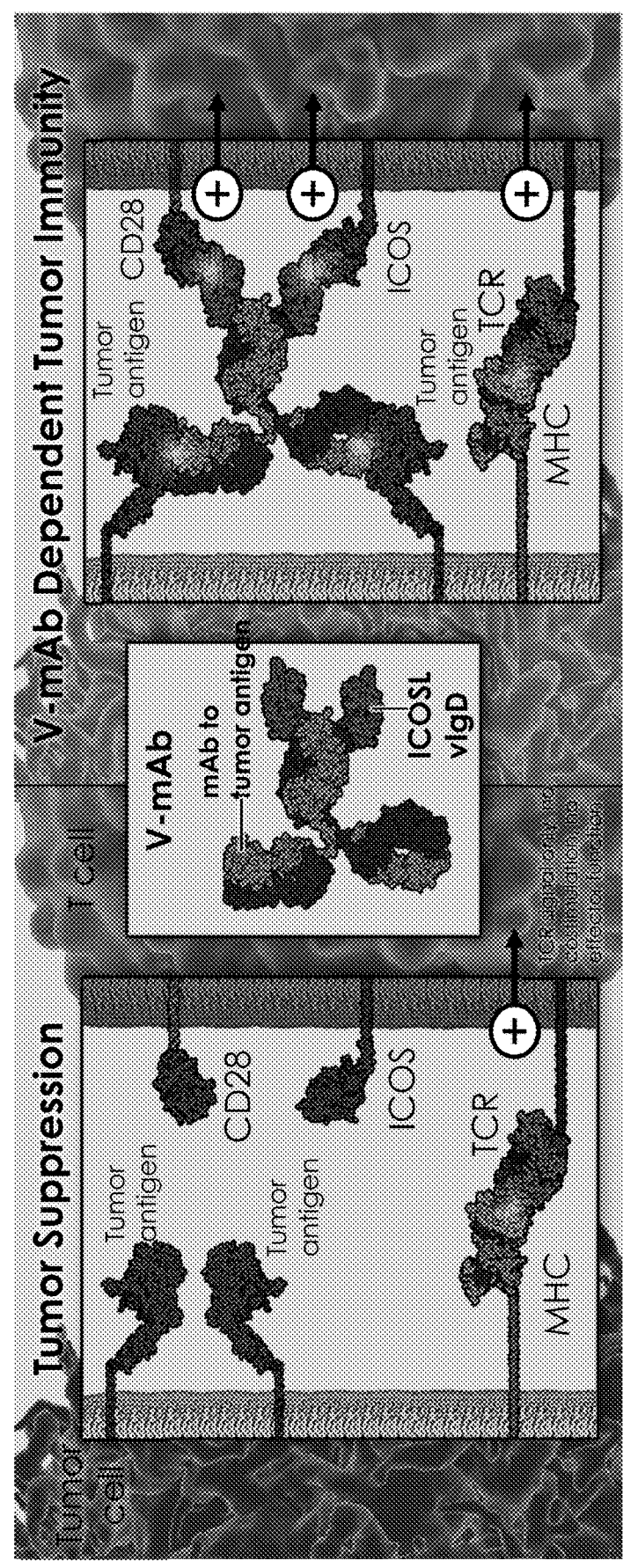

FIG. 17 depicts an exemplary schematic of the activity of a variant IgSF domain (vIgD) conjugated to an antibody (V-Mab) in which the antibody (e.g. anti-HER2 antibody) binds to an antigen on the surface of the tumor cell. In this depiction, the vIgD is a variant of an IgSF domain of ICOSL. As shown, binding of the antibody to the surface of the tumor cell localizes the vIgD on the tumor cell surface where it can interact with one or more of its cognate binding partners expressed on the surface of an adjacent immune cell (e.g. T cell) to agonize receptor signaling. In an exemplary embodiment as shown, the variant IgSF domain (vIgD) is a variant of an IgSF domain of ICOSL. Binding of the ICOSL vIgD to CD28 or ICOS costimulatory receptors provides an agonist or costimulatory signal.

Figure 18:
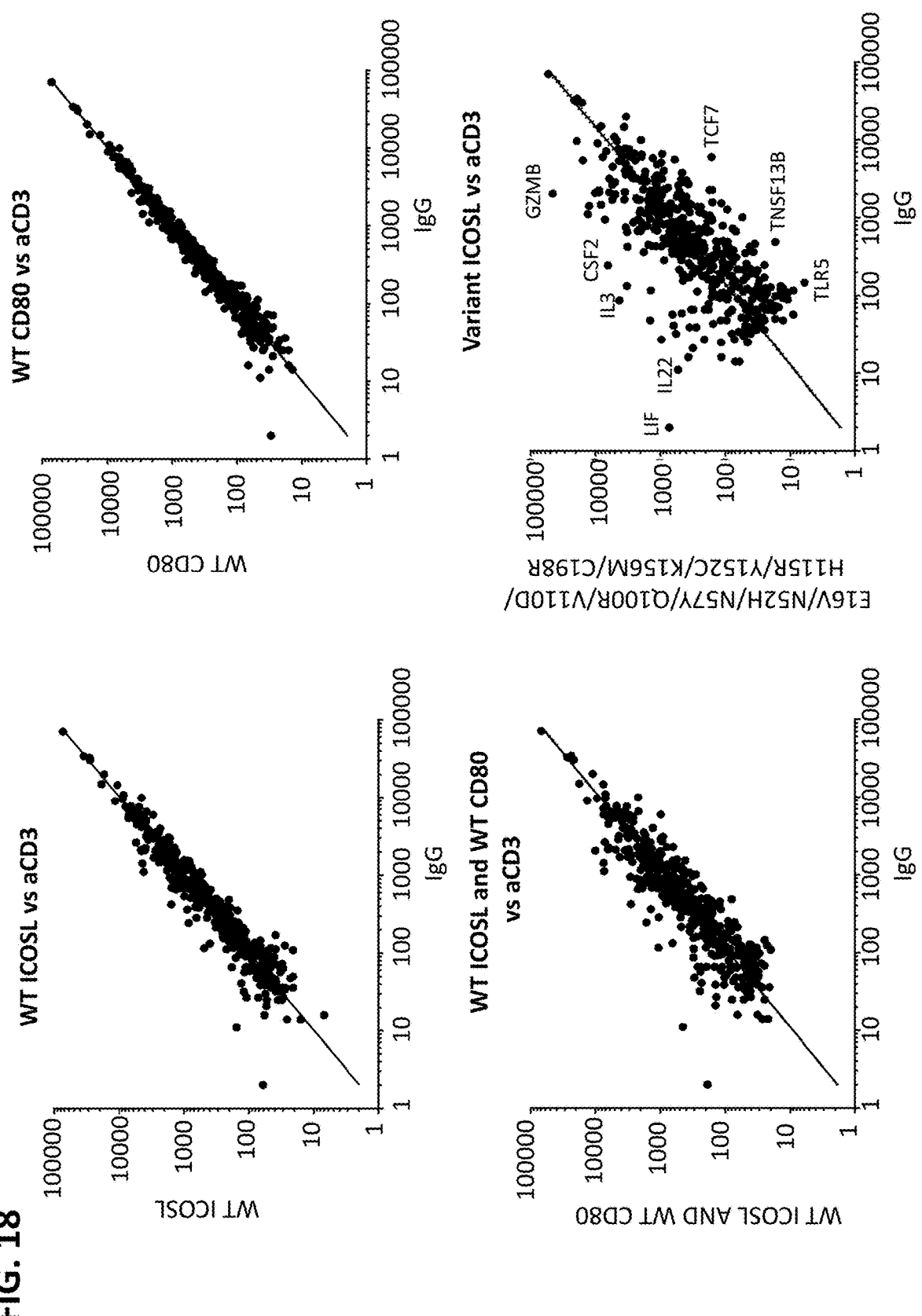

FIG. 18 depicts the Nanostring transcriptional signature of primary human T cells when incubated 10 nM anti-CD3 with 40 nM of an Fc-control protein, wild-type ICOSL-Fc, wild-type CD80-Fc, both of these proteins, or a variant ICOSL Fc-fusion proteins with mutations as indicated. Total RNA from samples was prepared from harvested cells and the RNA was transferred to Nanostring and a Cancer Immune chip was used to quantitate transcripts of 750 gene in each sample. Altered transcripts include those whose level is above or below the diagonal line, including the noted transcripts.

Figure 19:
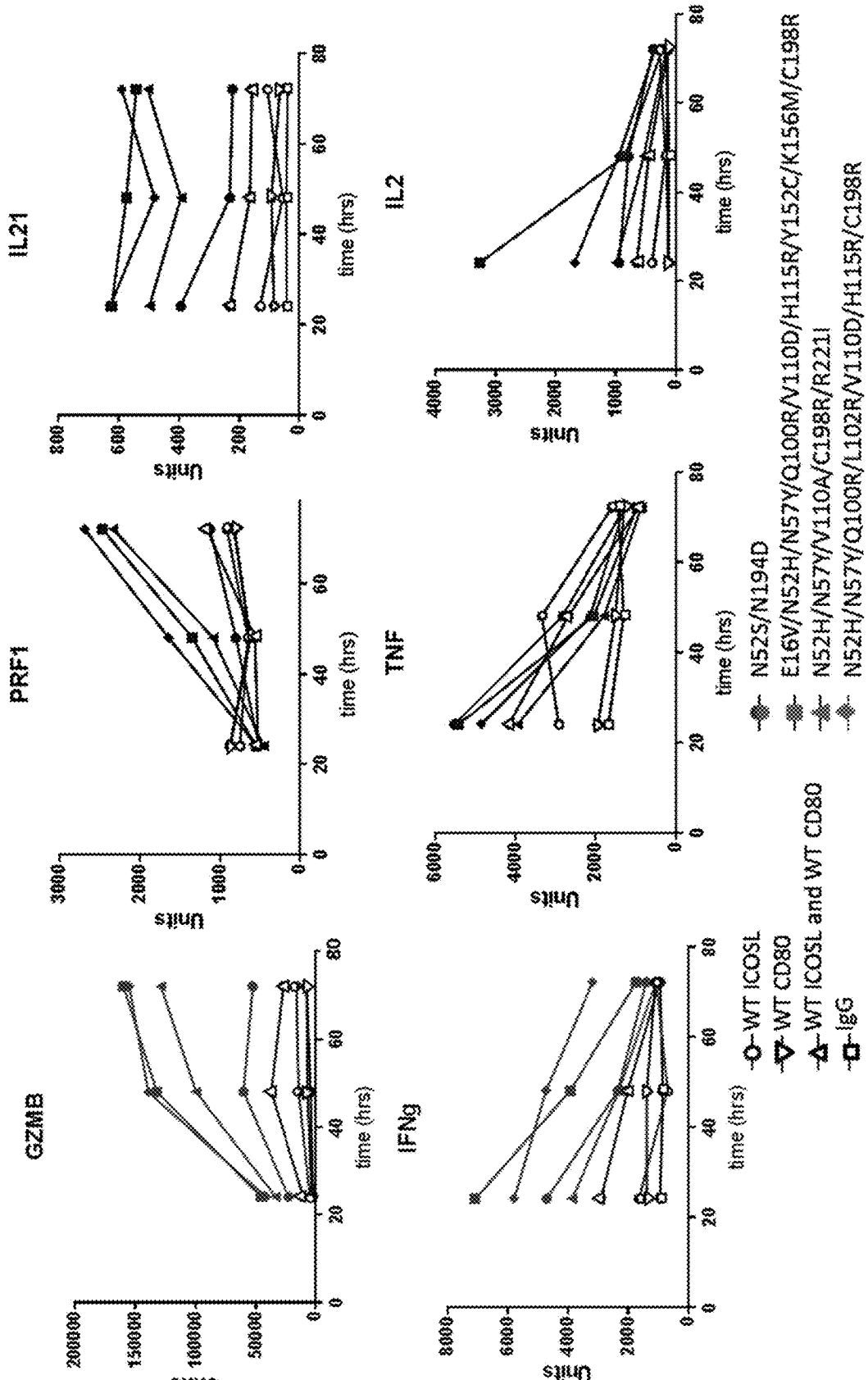

FIG. 19 depicts transcript levels of exemplary transcripts upon incubation as described in FIG. 18 for the indicated times in the presence of the various immunomodulatory proteins.

Figure 20A:
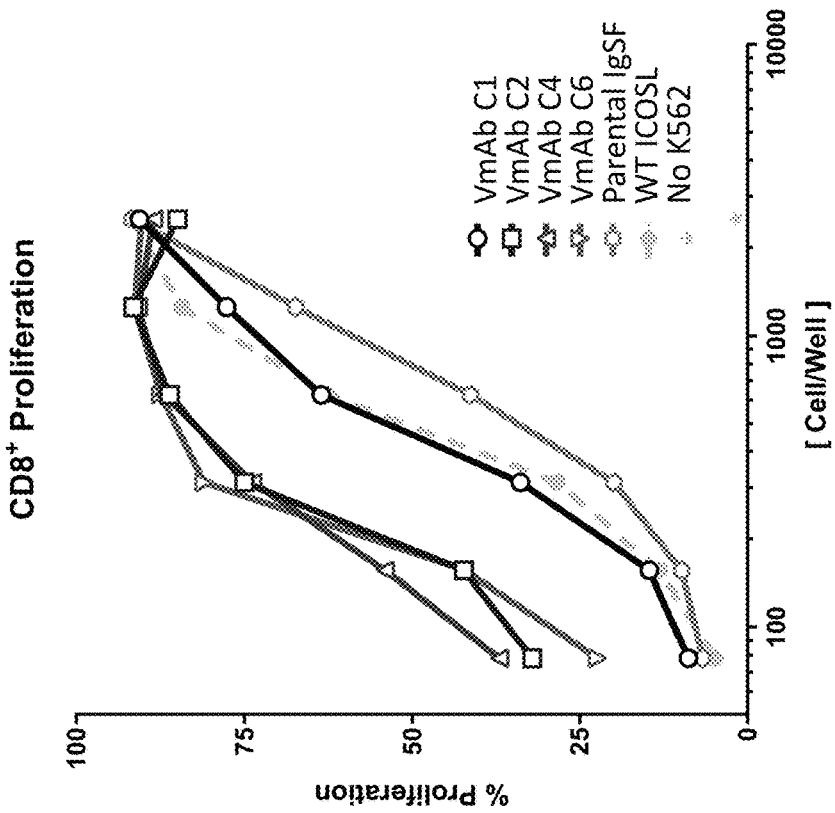
Figure 20A:
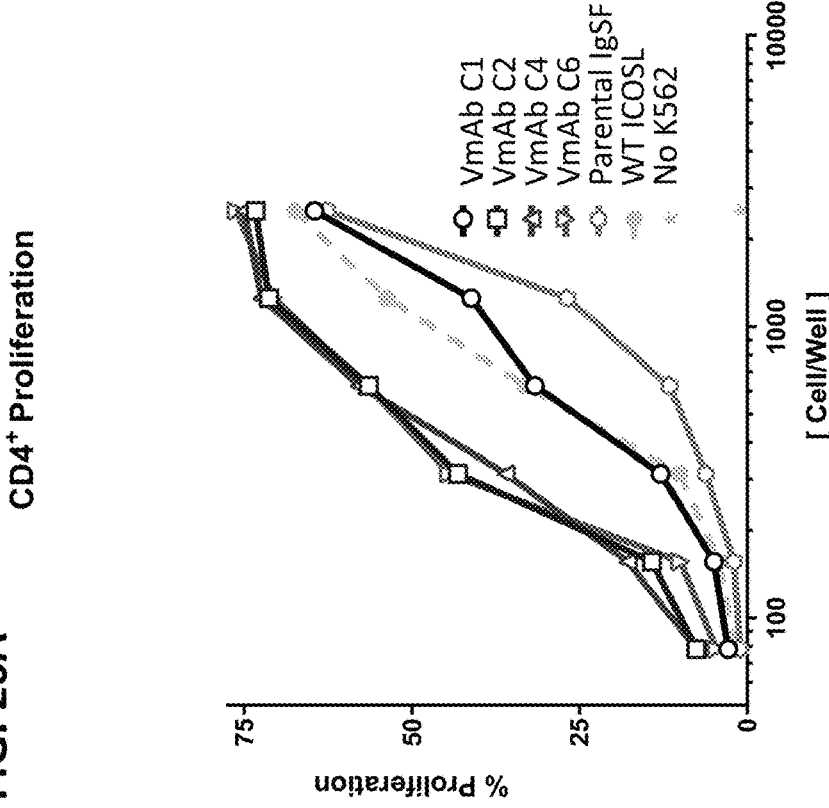
Figure 20B:
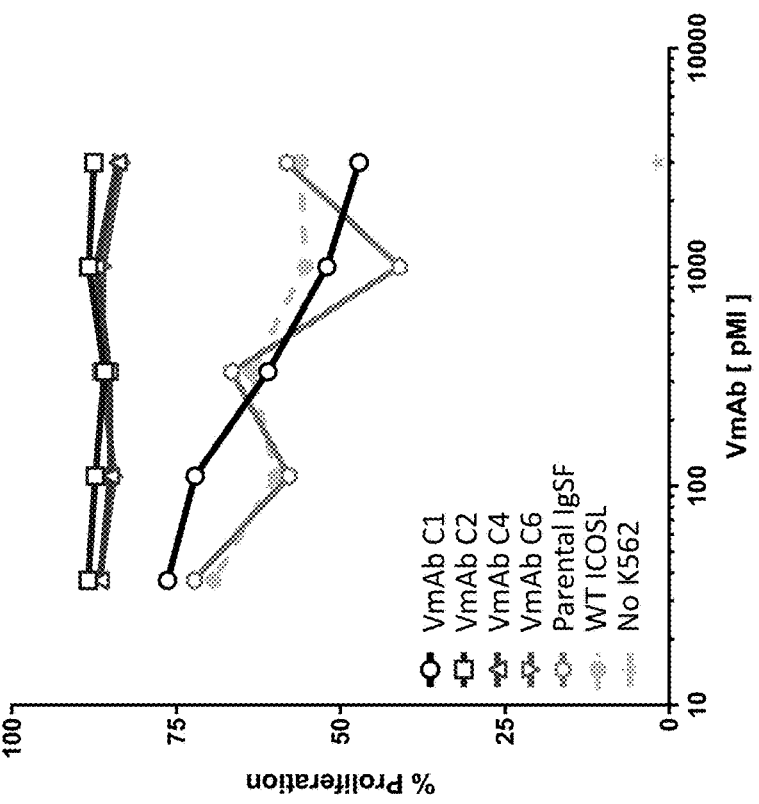
Figure 20B:
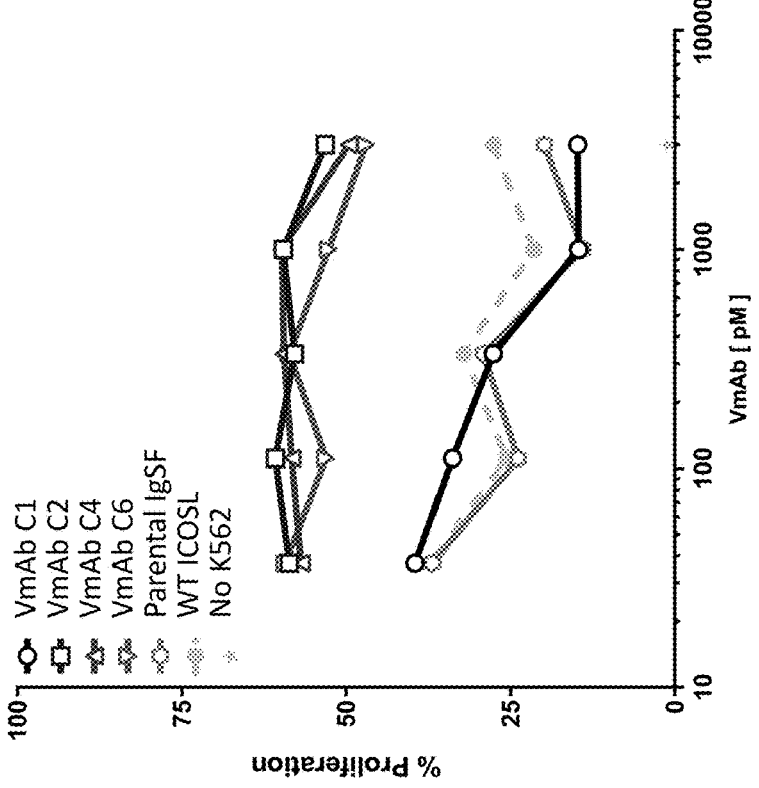

FIG. 20A-20B demonstrates VmAb mediated T-cell proliferation when co-cultured with HER2 expressing targets. CFSE-labeled pan T-cells were activated with K562-derived artificial target cells displaying cell surface anti-CD3 single chain Fv (OKT3) and HER2 in the presence of VmAbs or control proteins. Proliferation was measured by flow cytometric analysis of CFSE-dilution on CD4$^+$ (left panel) or CD8$^+$ (right panel) stained T-cells. In FIG. 20A, K562 cells were titrated and plated with T-cells for an effector:target (E:T) ratio of 40 to 1280:1. VmAbs, parental IgSF domain, or WT ICOSL were added at 1000 pM. In FIG. 20B, K562 cells were added to T-cells for an ET ratio of 160:1. VmAbs or control proteins were titrated and added at 3000 to 37 pM.

Figure 21:
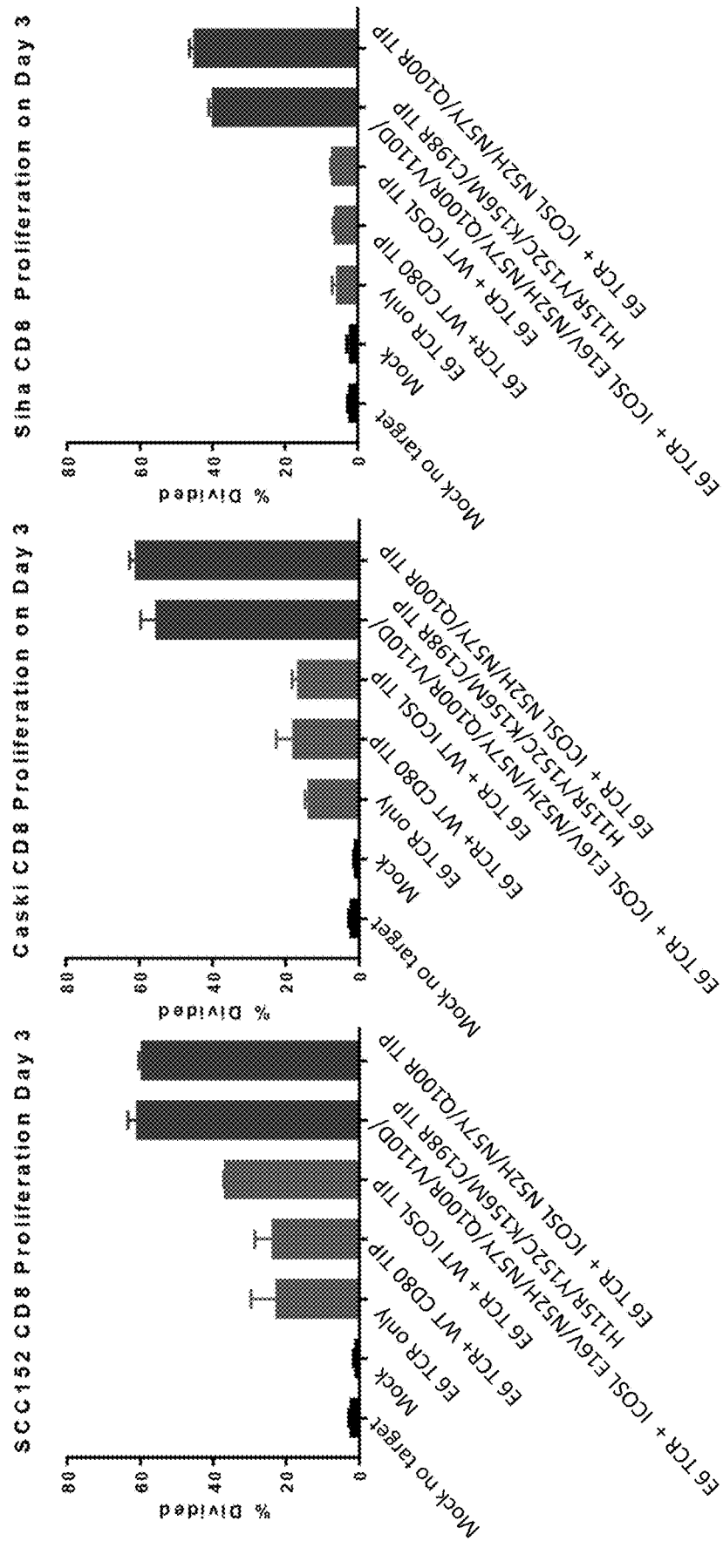

FIG. 21 depicts the proliferation studies for T cells transduced with various IgSF domain-containing transmembrane immunomodulatory proteins (TIPs) and an exemplary recombinant E6-specific TCRs in primary human T cells.

FIG. 22A-22G shows SEC analysis of proteolysis in variant ICOSL Fc-fusion molecules containing mutations N52H/N57Y/Q100R/F172S generated in various reference sequences, such as truncated ICOSL ECD Fc-fusion, an ICOSL IgV domain alone Fc-fusion, and/or ICOSL variant Fc fusion proteins with mutations at N207G/L208G with reference to the reference ICOSL extracellular domain (ECD) sequence set forth in SEQ ID NO:32. Molecules were expressed using ExpiCHO-S derived cells.

Figure 23A:
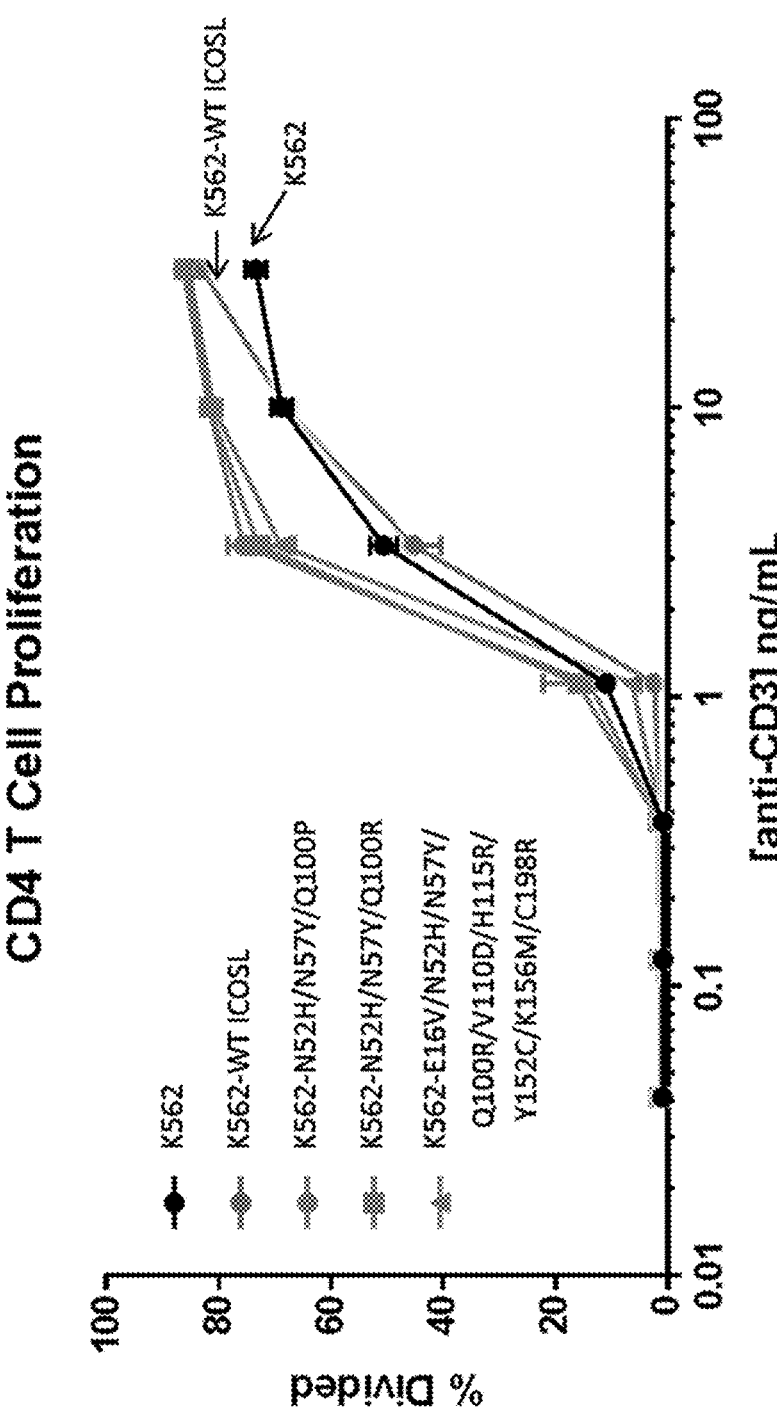
Figure 23B:
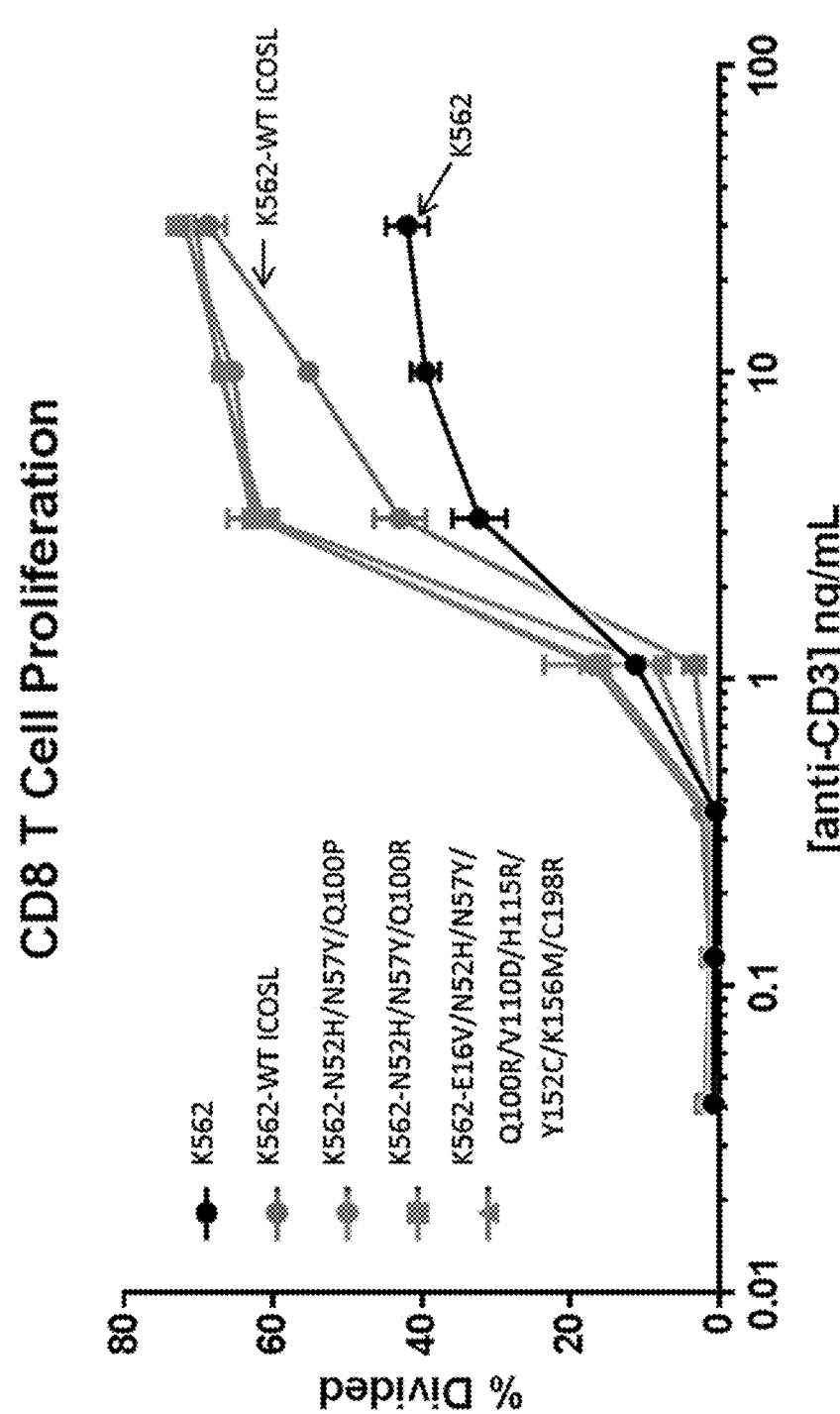

FIG. 23A-23B depicts the proliferation of CD4 and CD8 human T cells stimulated with K652 cells expressing variant ICOSL TIPs containing an ECD containing an affinity-modified IgSF with amino acid mutations corresponding to N52H/N57Y/Q100P (SEQ ID NO: 288), N52H/N57Y/Q100R (SEQ ID NO: 283), and E16V/N52H/N57Y/Q100R/V110D/H115R/Y152C/K156M/C198R (SEQ ID NO: 300).

Figure 24A:
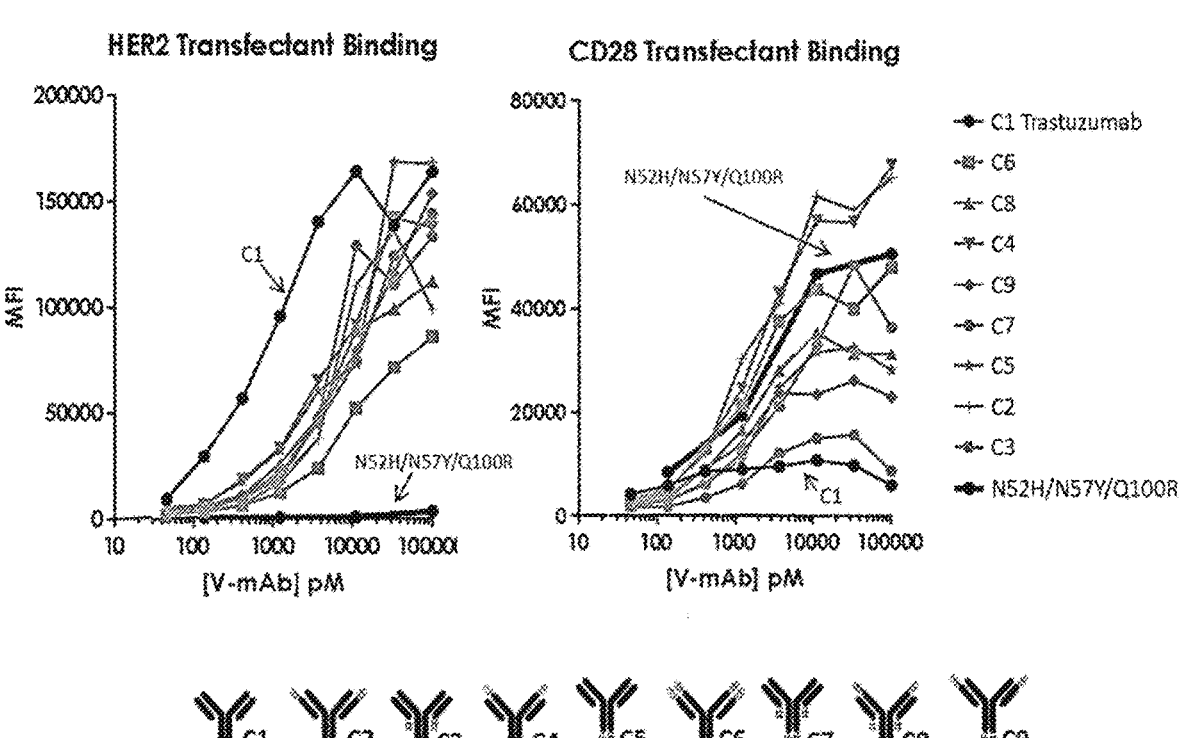

FIG. 24A depicts binding of V-mAbs to HER2 and CD28. FIG. 24B-24F depicts results of VmAb costimulation of T cells using a transfected cell system using Jurkat cells with an IL-2 promoter luciferase reporter, showing that V-mAbs provided a significant costimulatory signal in the presence of HER2+ K562/OKT3 cells.

Figure 25A:
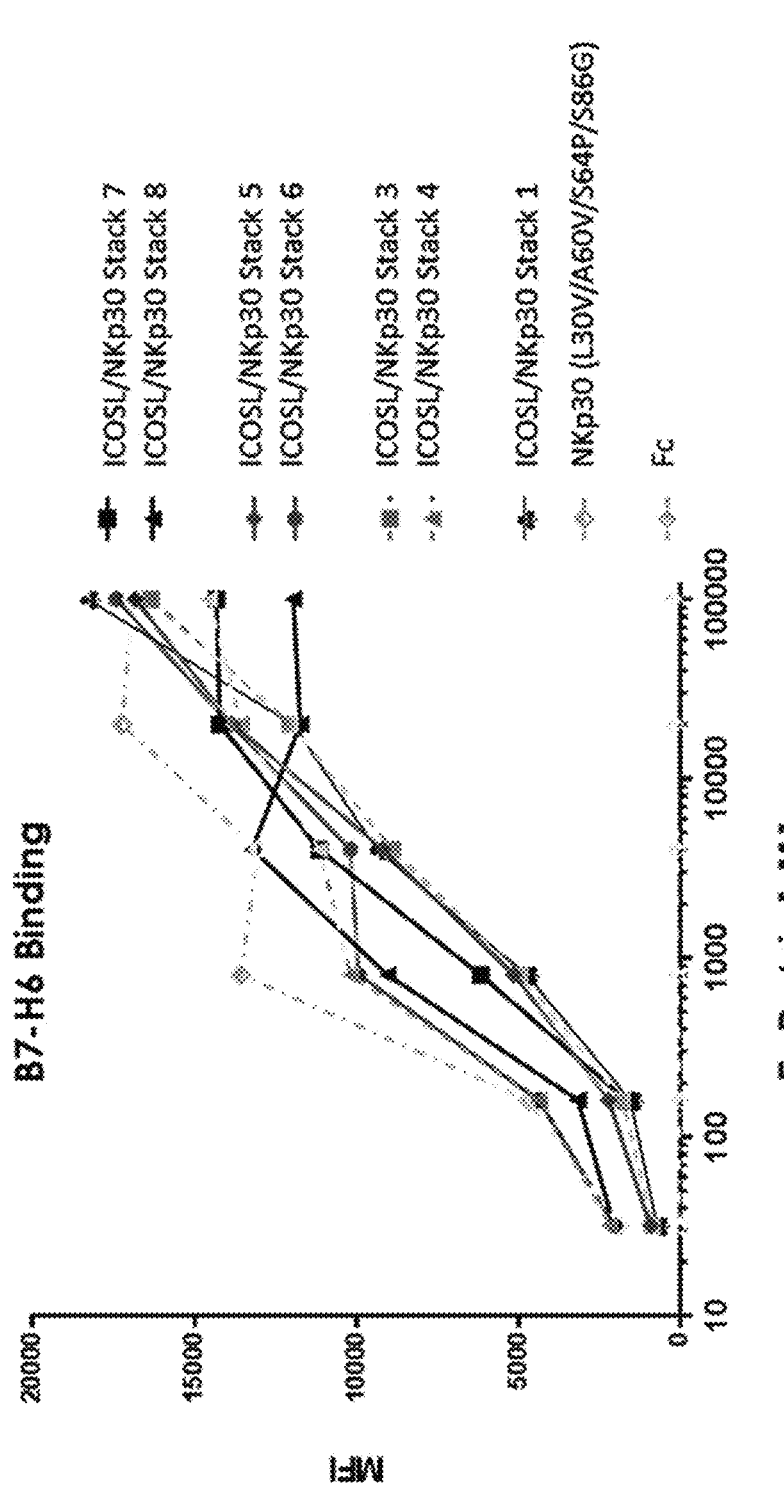
Figure 25B:
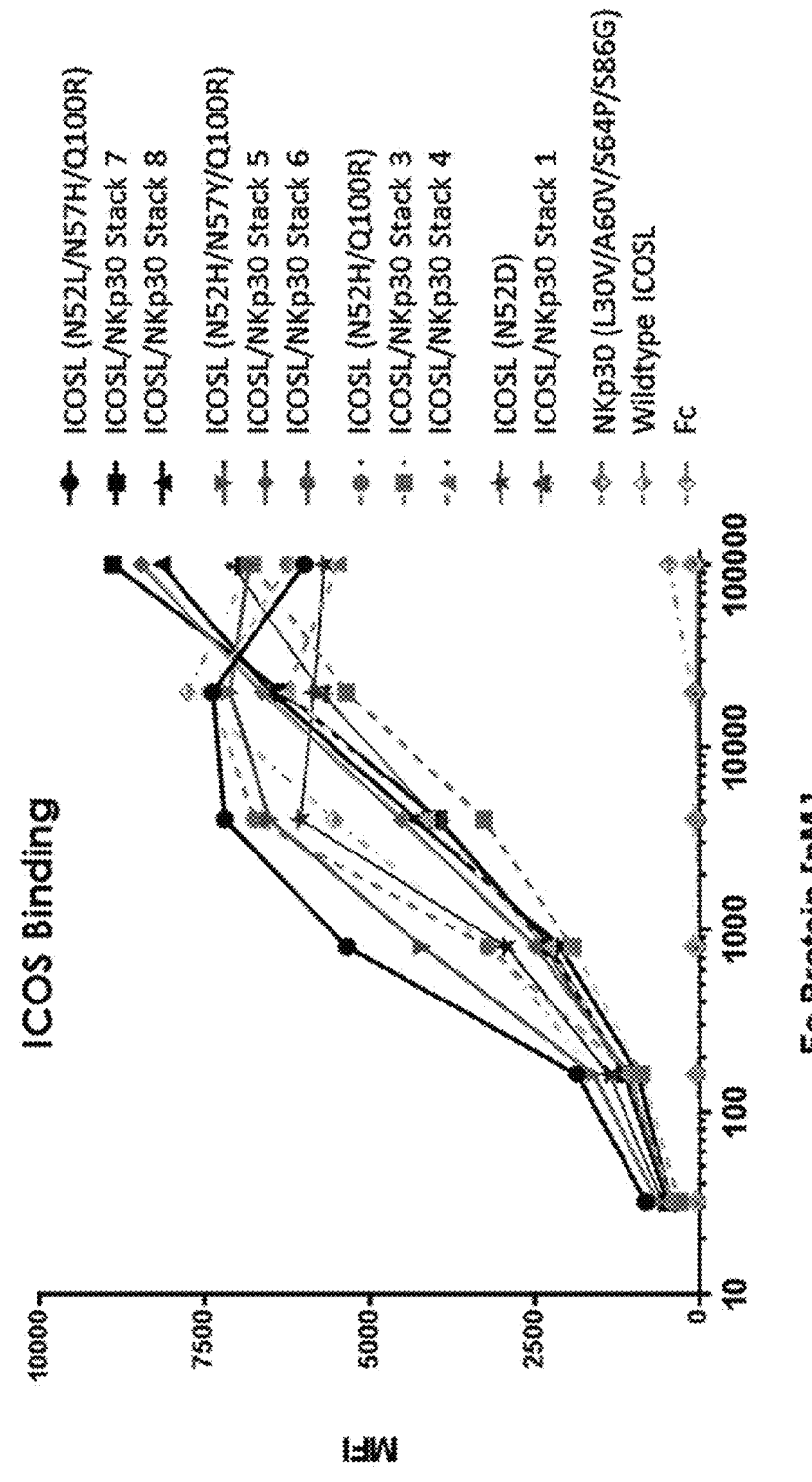
Figure 25C:
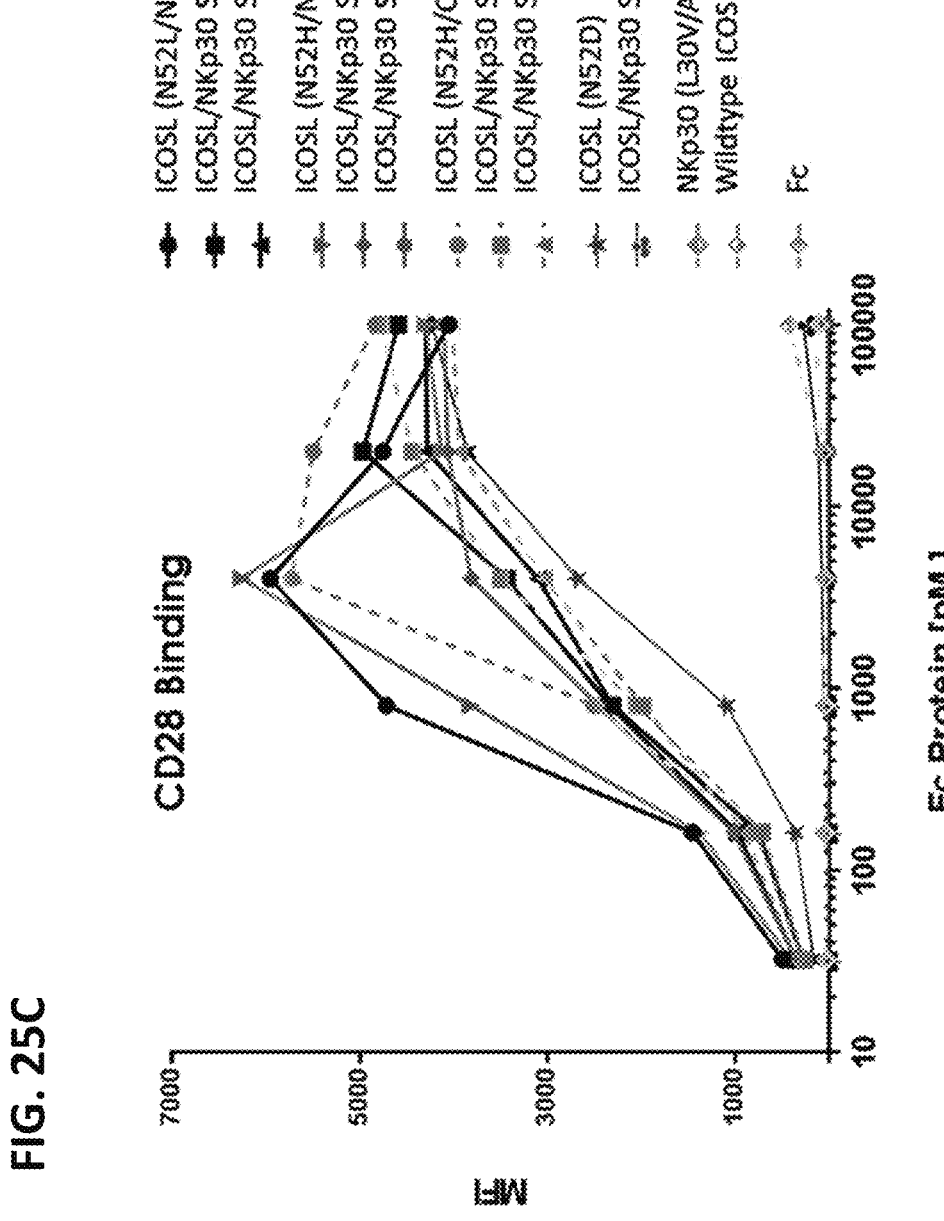
Figure 25D:
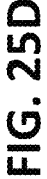
Figure 25D:
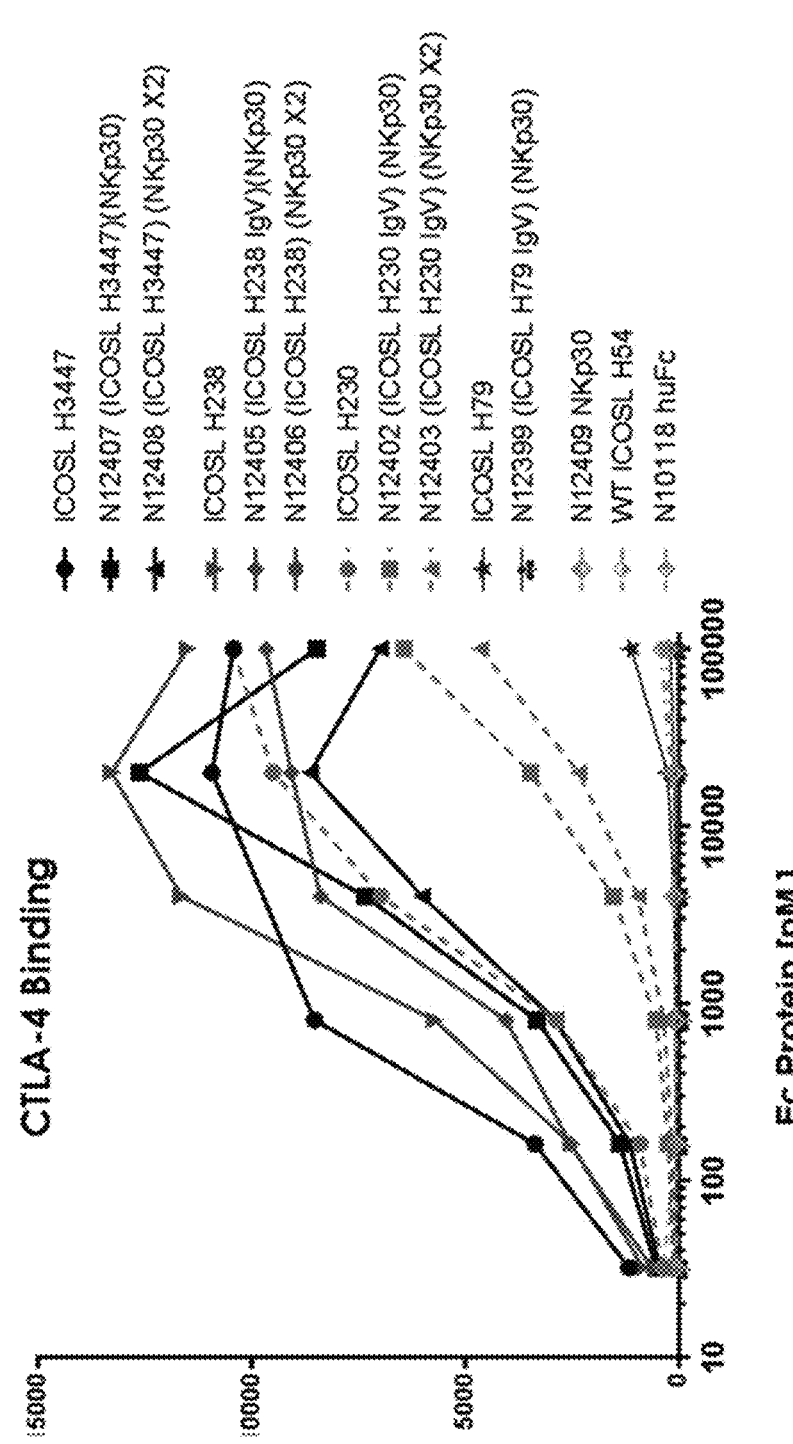

FIG. 25A-25D depicts binding of stack Fc-fusion molecules to cells expressing cognate binding partners B7H6 (FIG. 25A), ICOS (FIG. 25B), CD28 (FIG. 25C), and CTLA-4 (FIG. 25D).

Figure 26A:
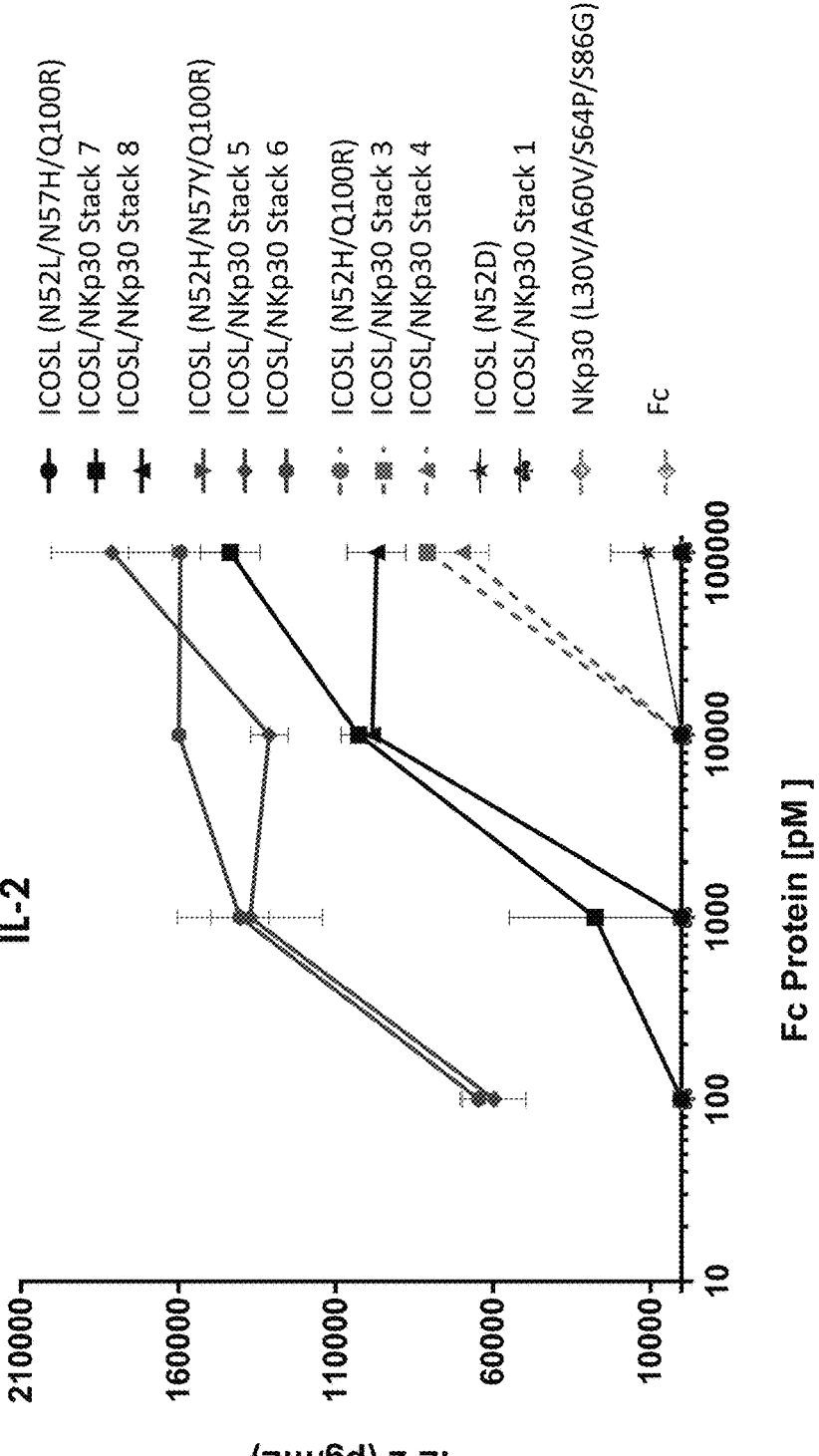
Figure 26B:
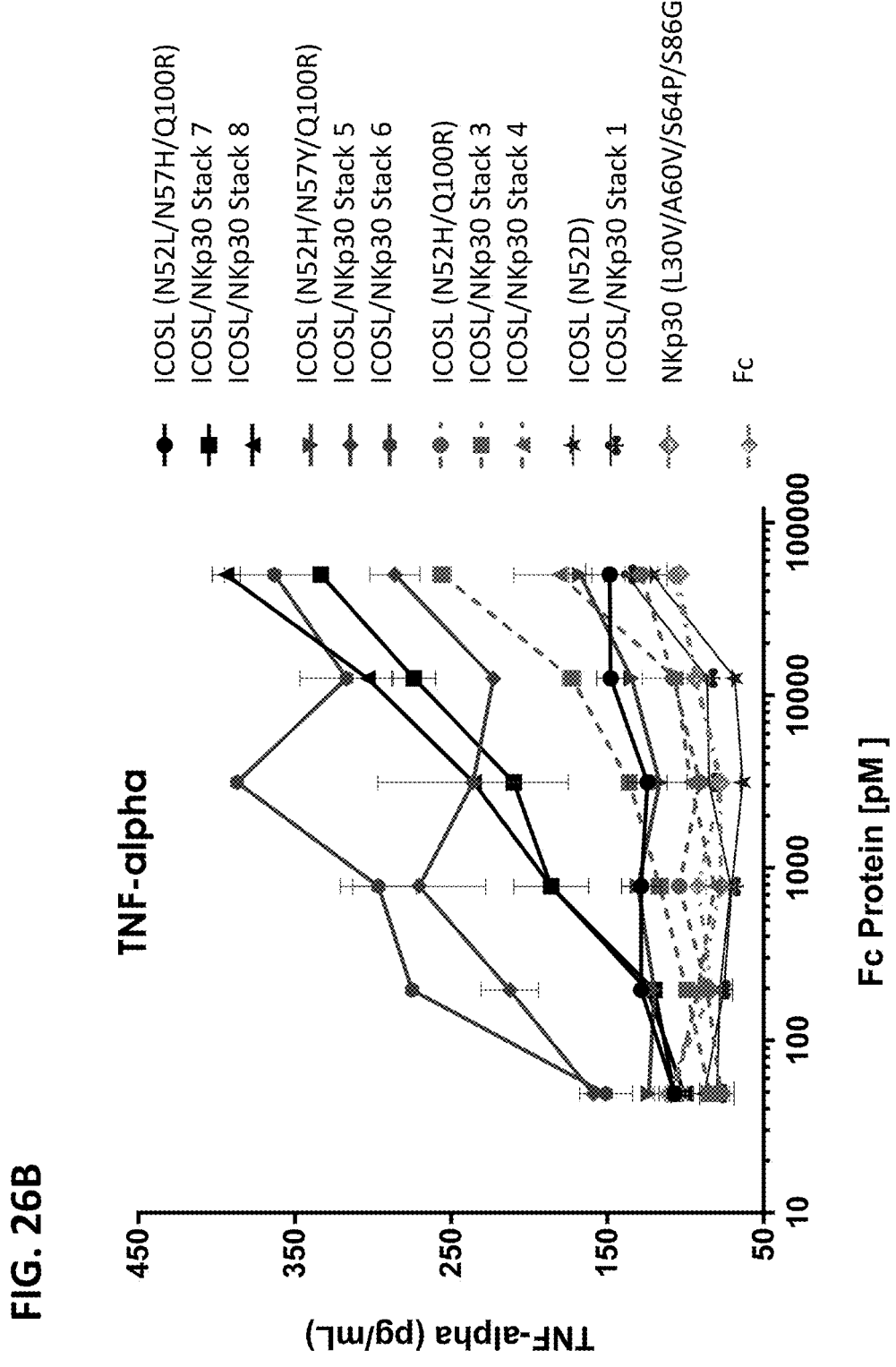

FIG. 26A-26B depicts bioactivity studies for exemplary tested ICOSL/NKp30 stack proteins.

Figure 27:
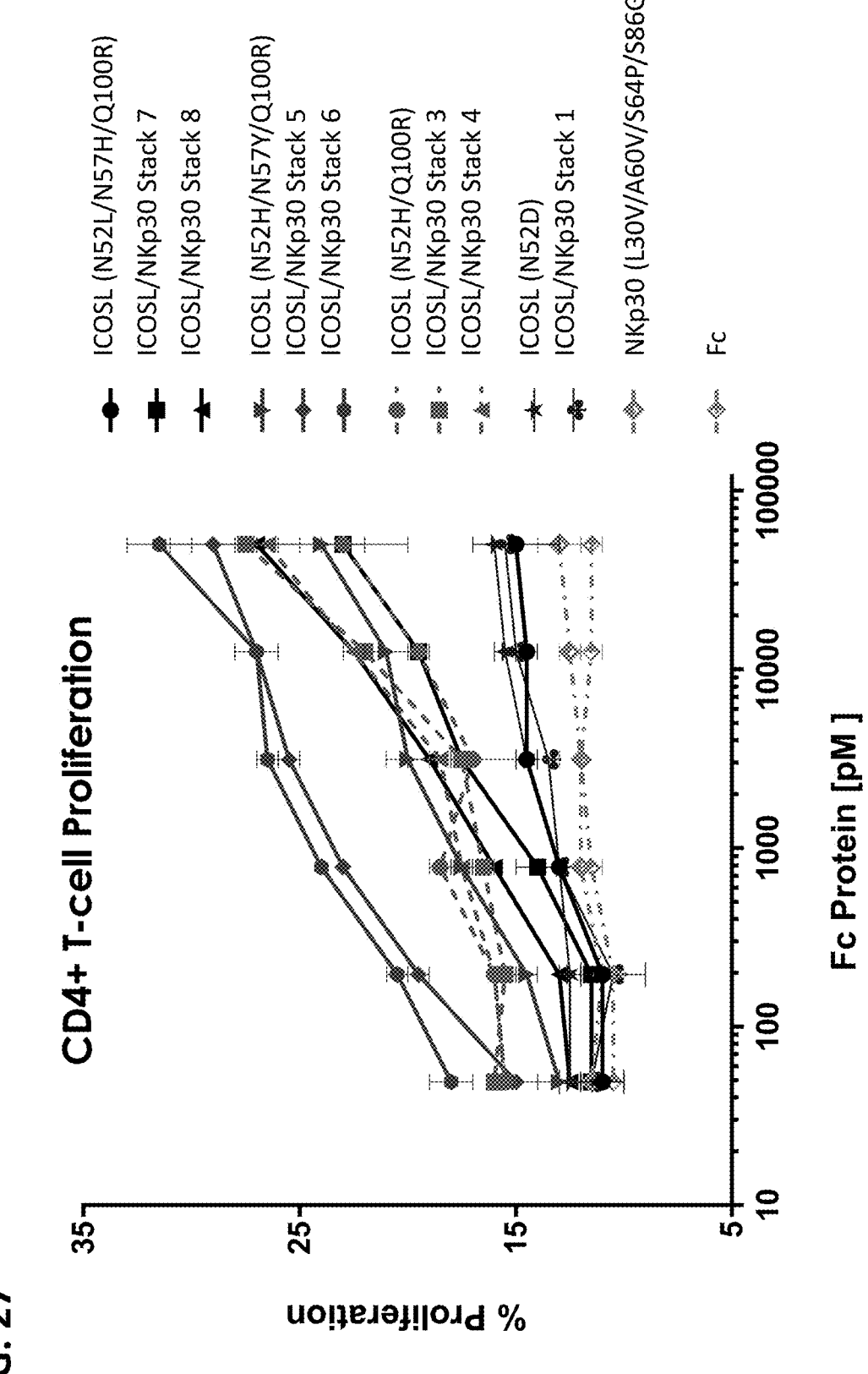

FIG. 27 depicts proliferation induced by ICOSL/NKp30 stack proteins as measured by flow cytometric analysis of CFSE-dilution on CD4+ or CD8+ stained T-cells.

Figure 28:
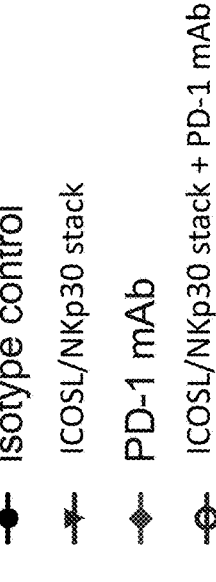
Figure 28:
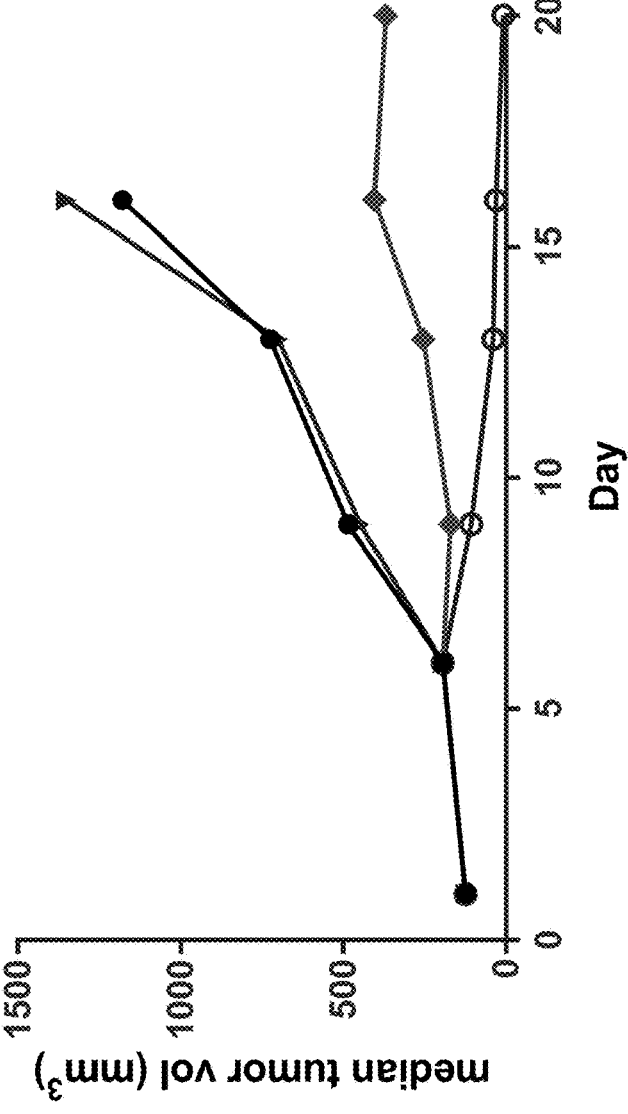

FIG. 28 depicts anti-tumor effects of the combination of the tested ICOSL/NKp30 stack protein and mPD-1 mAb.

Figure 29A:
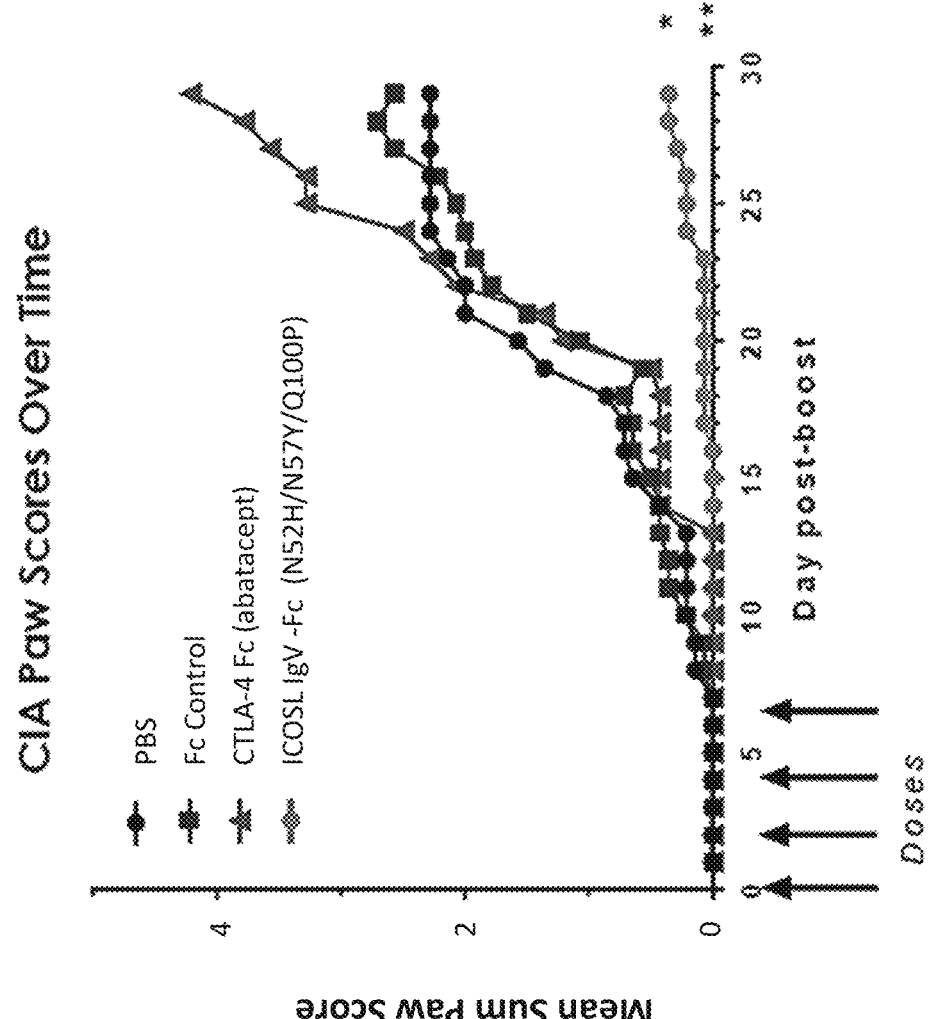
Figure 29B:
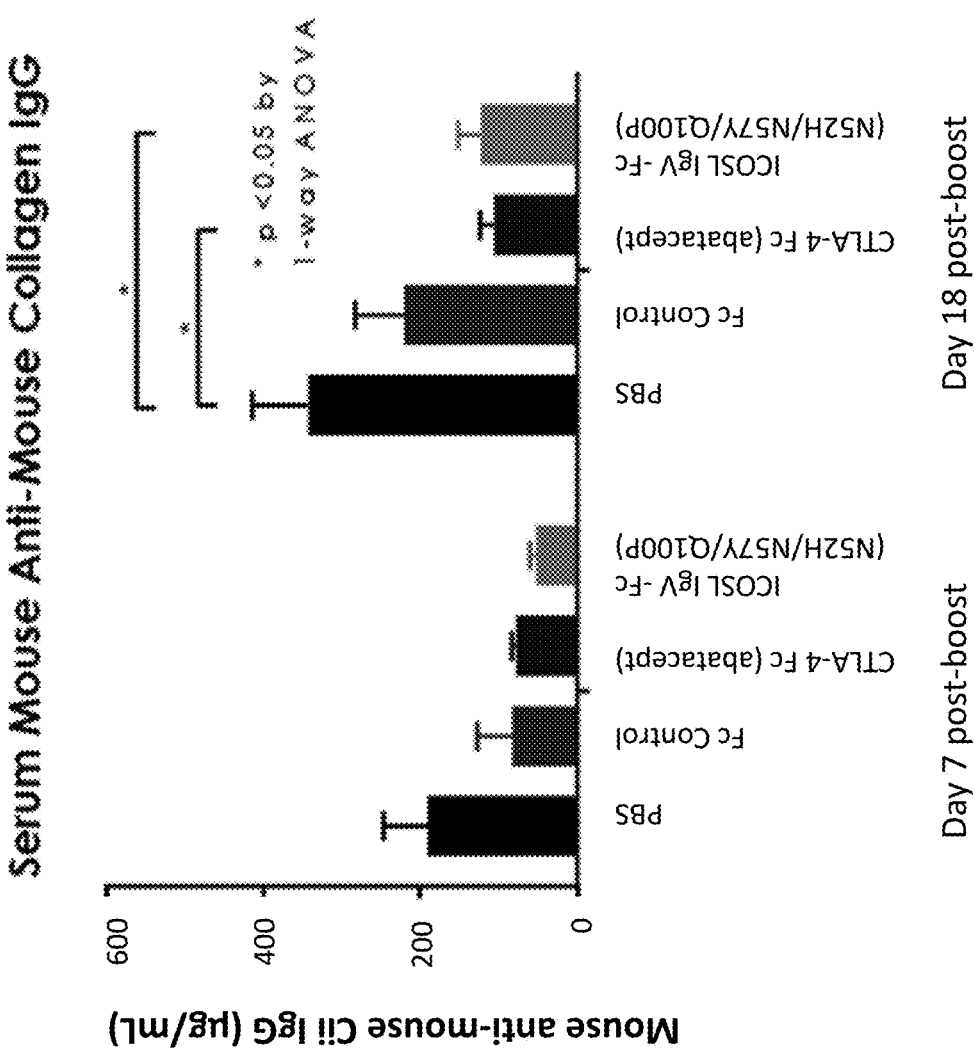
Figure 29C:
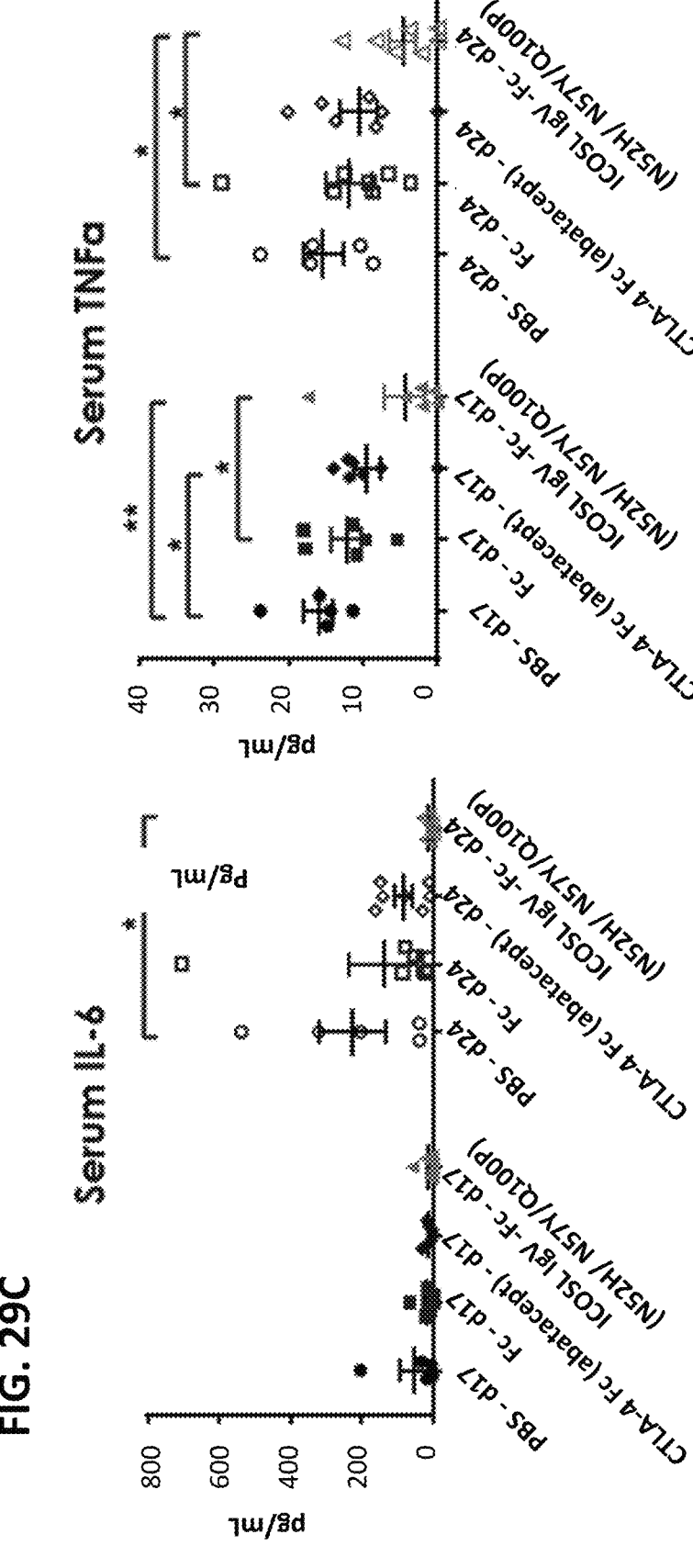
Figure 29D:
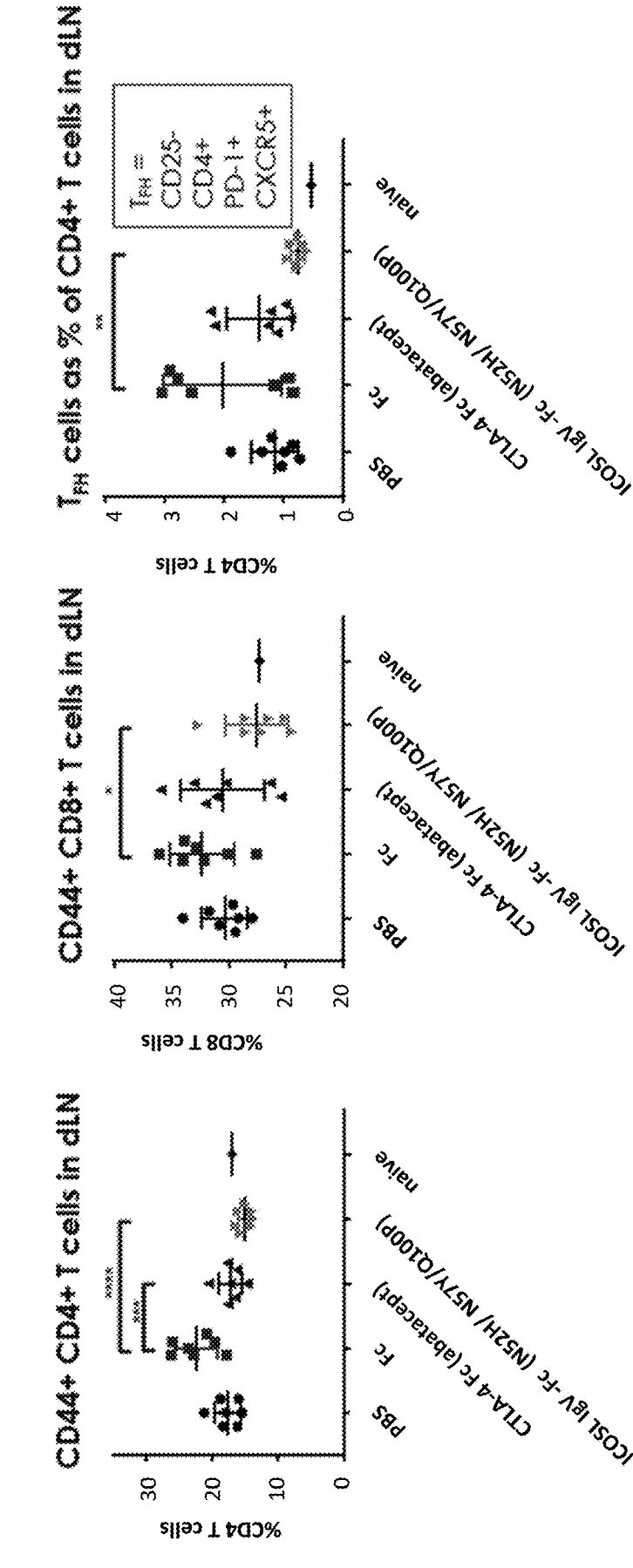
Figure 29E:
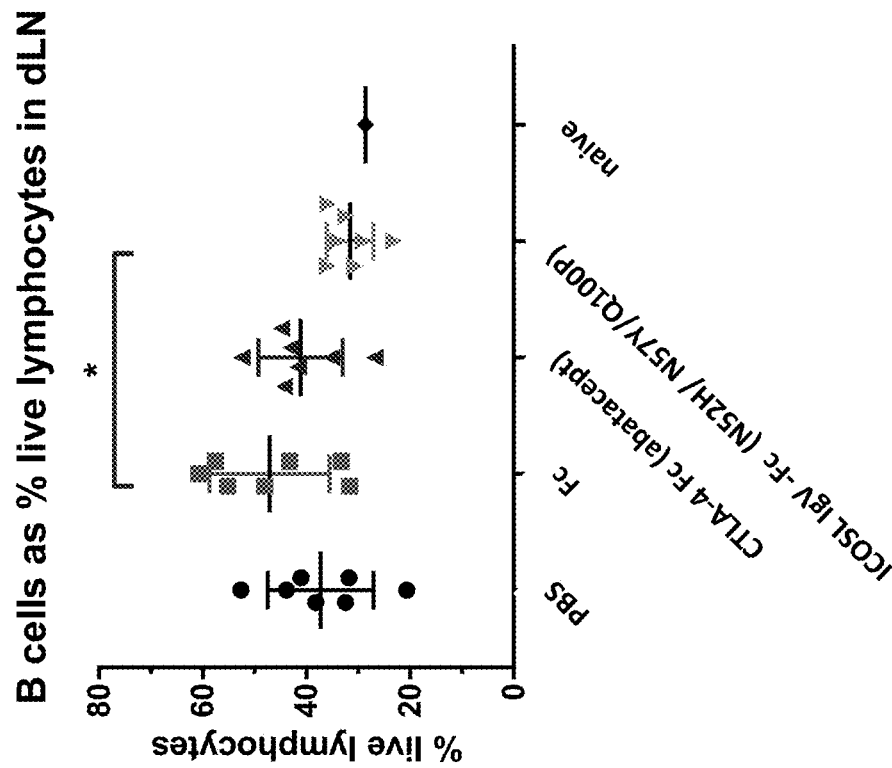

FIG. 29A-29E depicts anti-inflammatory activity of pro-phylactic dosing of the exemplary ICOSL IgV-Fc fusion molecule in the collagen-induced arthritis (CIA) model, including mean sum paw score (FIG. 29A), detected CII IgG (FIG. 29B), serum cytokine levels (FIG. 29C), CD44+ activated T cells or TFH cells (FIG. 29D), and fraction of B cells in the draining lymph node (FIG. 29E).

Figures 30A, 30B:
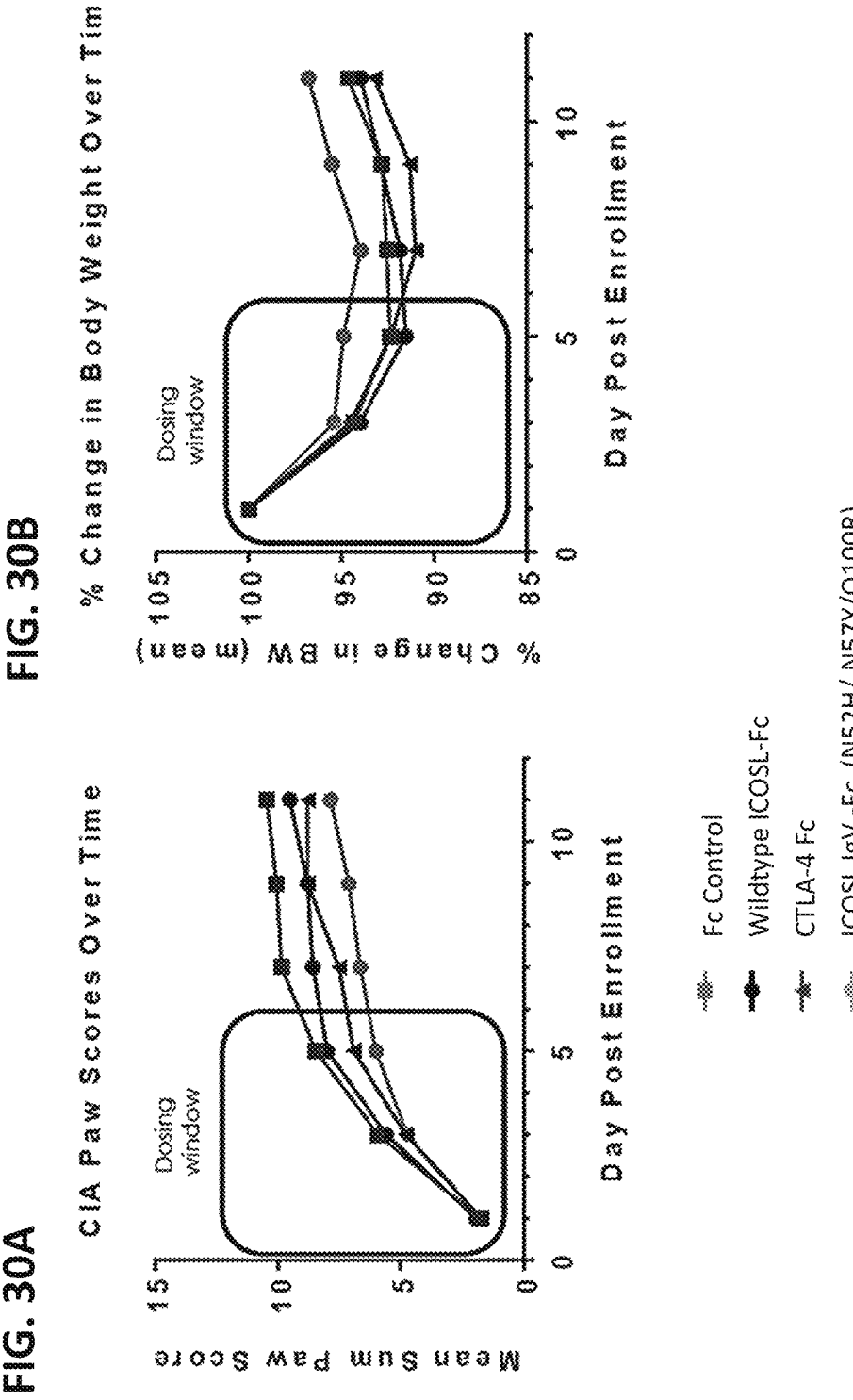
Figure 30C:
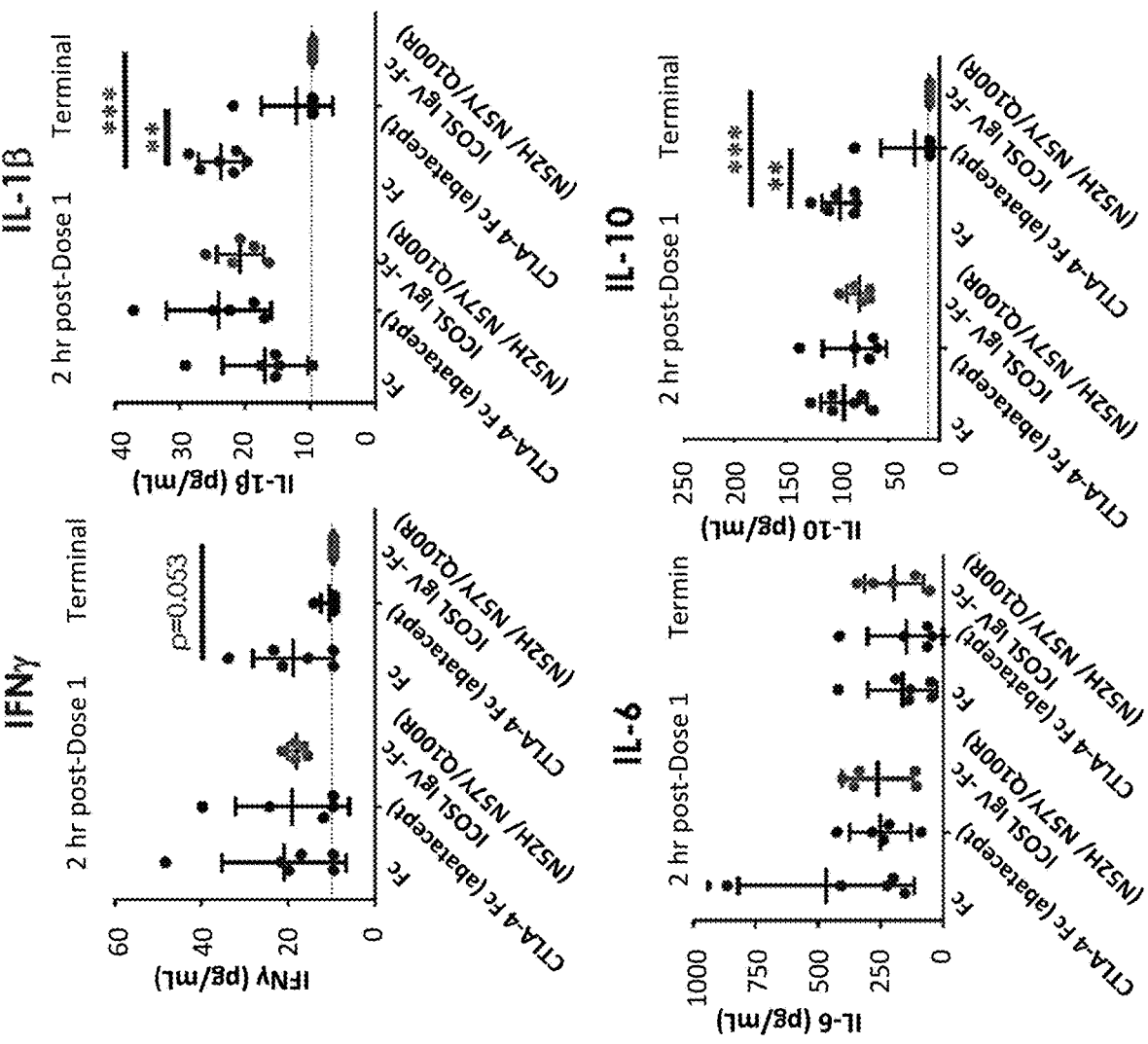
Figure 30D:
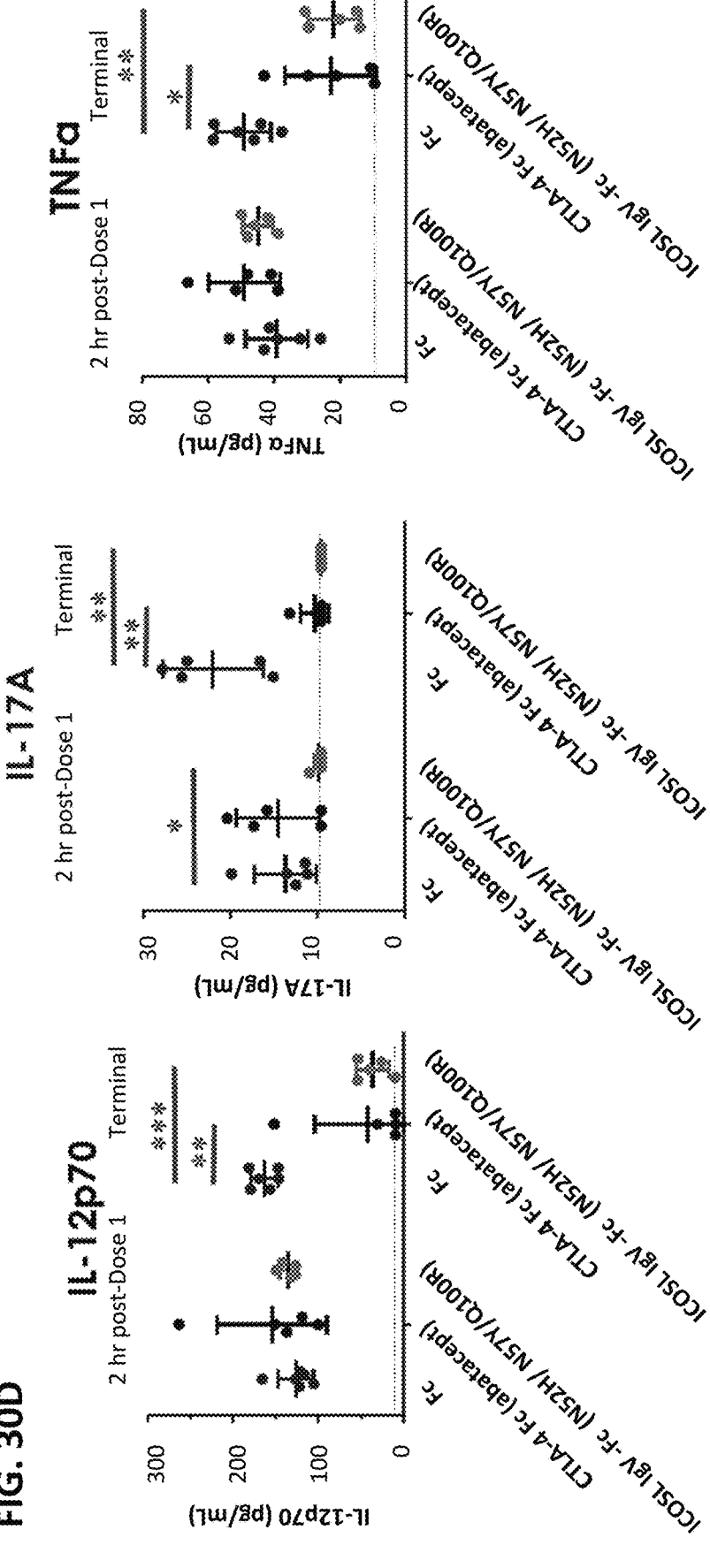

FIG. 30A-30D depicts anti-inflammatory activity of delayed dosing of the exemplary ICOSL IgV-Fc fusion molecule in the collagen-induced arthritis (CIA) model, including mean sum paw score (FIG. 30A) and serum cytokine levels (FIG. 30C-30D).

Figures 31A, 31B:
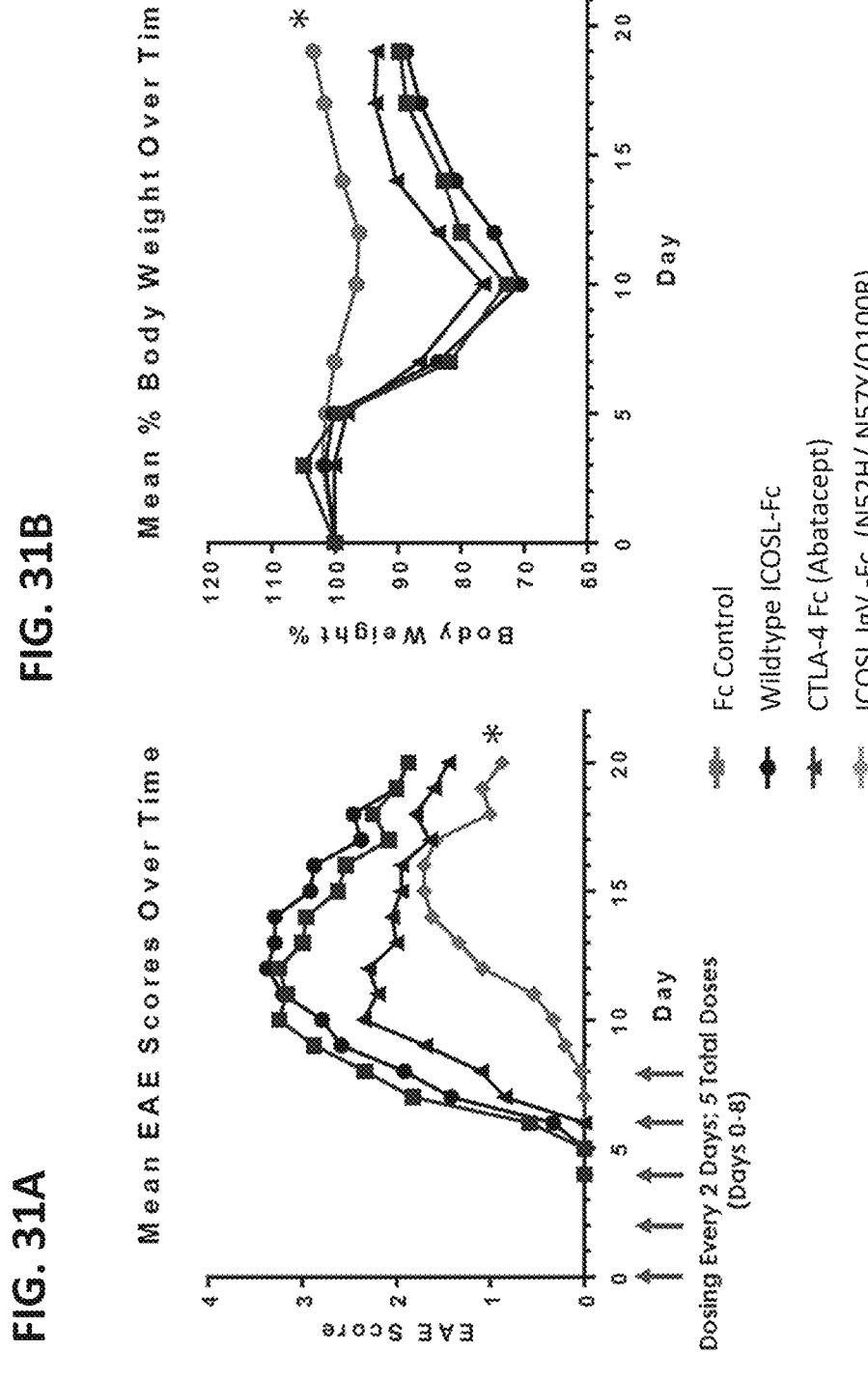
Figure 31C:
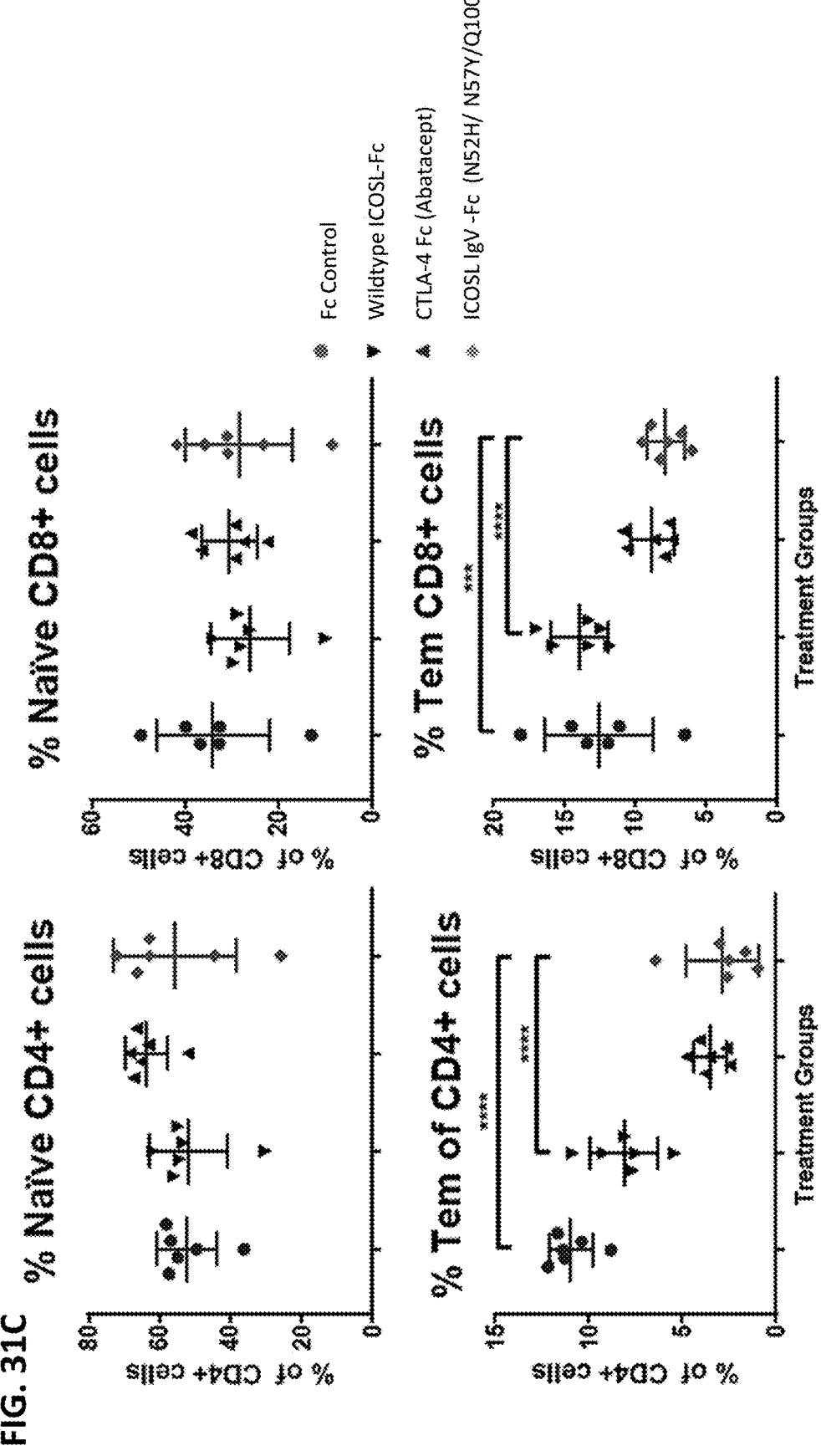
Figure 31D:
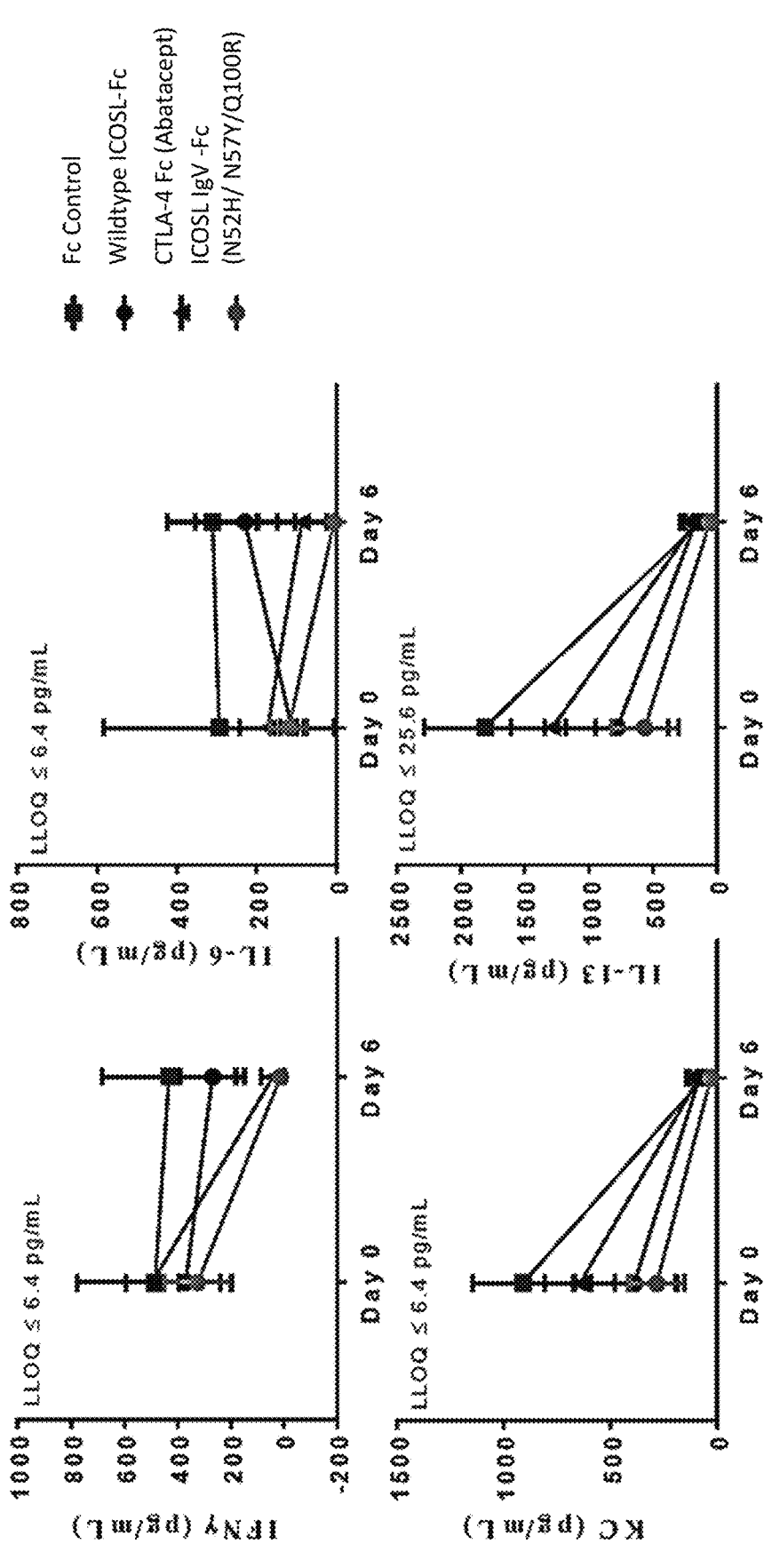

FIG. 31A-31D depicts anti-inflammatory activity of delayed dosing of the exemplary ICOSL IgV-Fc fusion molecule in the experimental autoimmune encephalomyeli-tis (EAE) model, including EAE score (FIG. 31A), flow cytometric analysis of inguinal lymph node T cells (FIG. 31C), and proinflammatory cytokines (FIG. 31D).

Figures 32A, 32B:
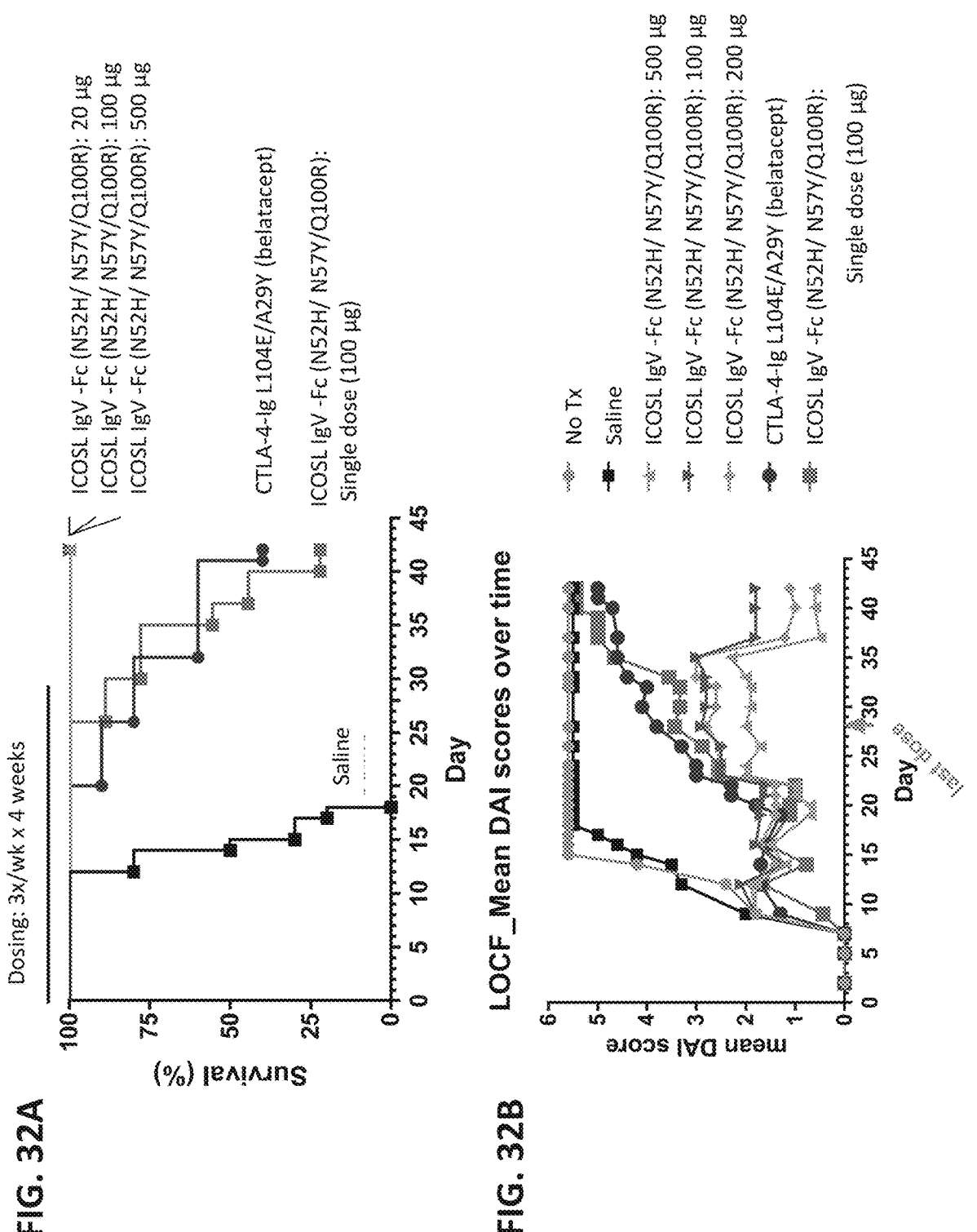

FIG. 32A-32B depicts survival and DAI score of Graft-versus-Host-Disease (GvHD) mice treated with various doses (20, 100, or 500 µg) of a variant ICOSL IgV-Fc molecule.

FIG. 33A-33F depicts results from flow cytometric analy-sis of Graft-versus-Host-Disease (GvHD) ratio of human cells/mouse cells in blood collected (FIG. 33A) or in total T cell count (FIG. 33B) at the end of the study, and assessment of ICOS+ CD4+ or CD8+ cells (FIG. 33C-33D), or CD28+ CD4+ or CD8+ cells (FIG. 33E-33F) from Graft-versus-Host-Disease (GvHD) mice treated with various doses (20, 100, or 500 µg) of a variant ICOSL IgV-Fc molecule.

Figure 34A:
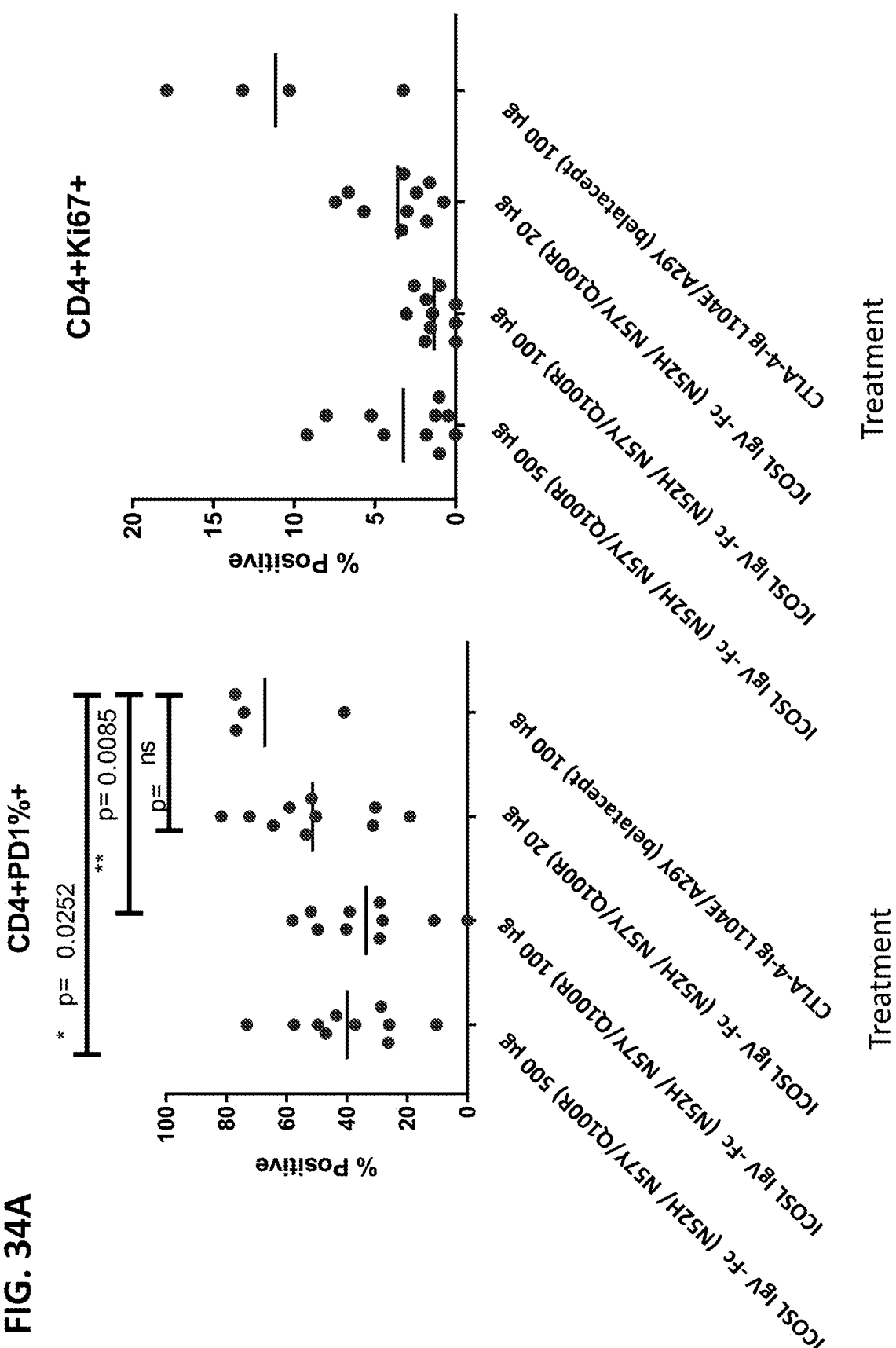
Figure 34B:
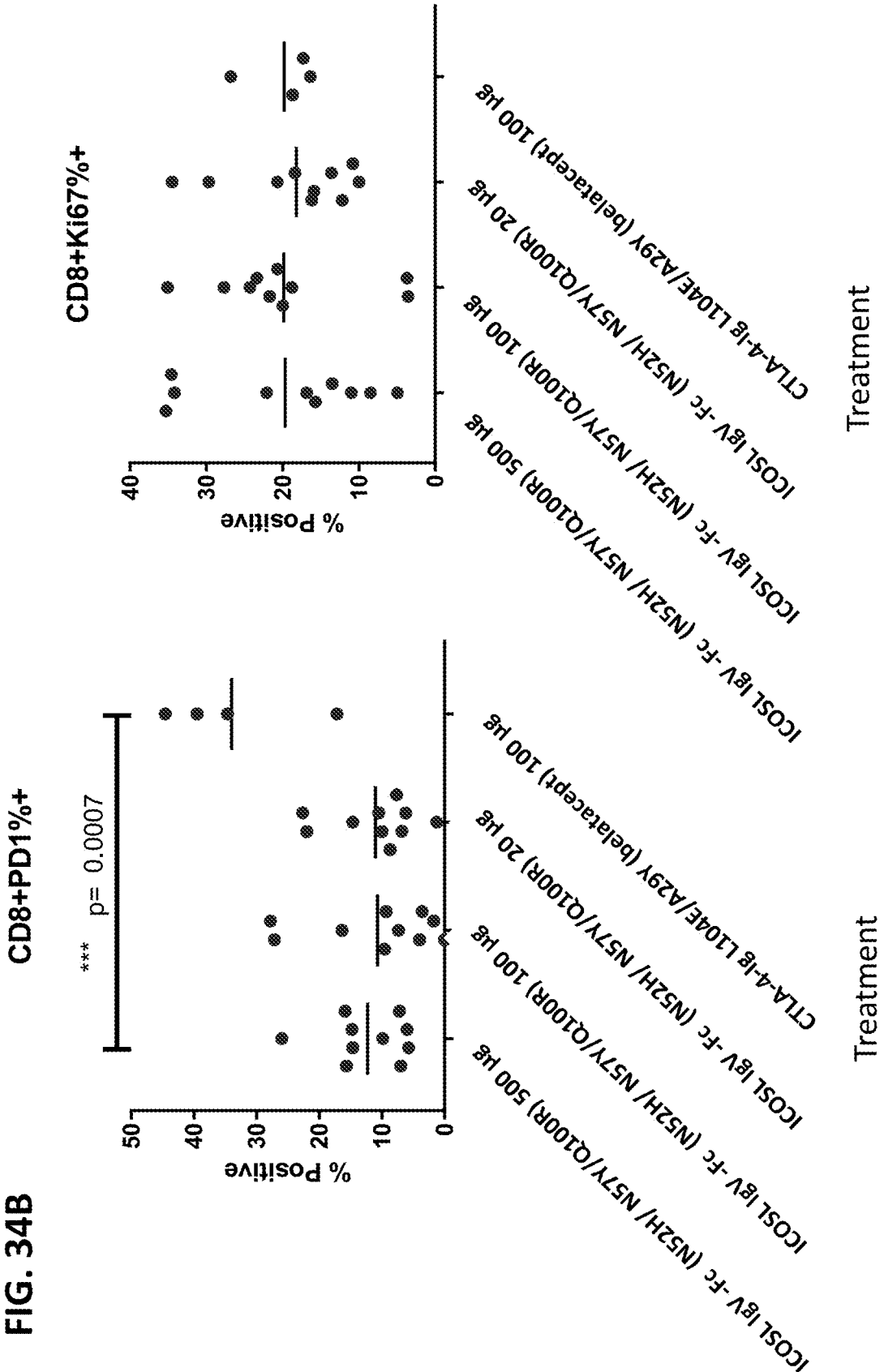

FIG. 34A-34B depicts expression of activation or exhaus-tion markers of T cells from Graft-versus-Host-Disease (GvHD) mice treated with various doses (20, 100, or 500 µg) of a variant ICOSL IgV-Fc molecule.

Figure 34C:
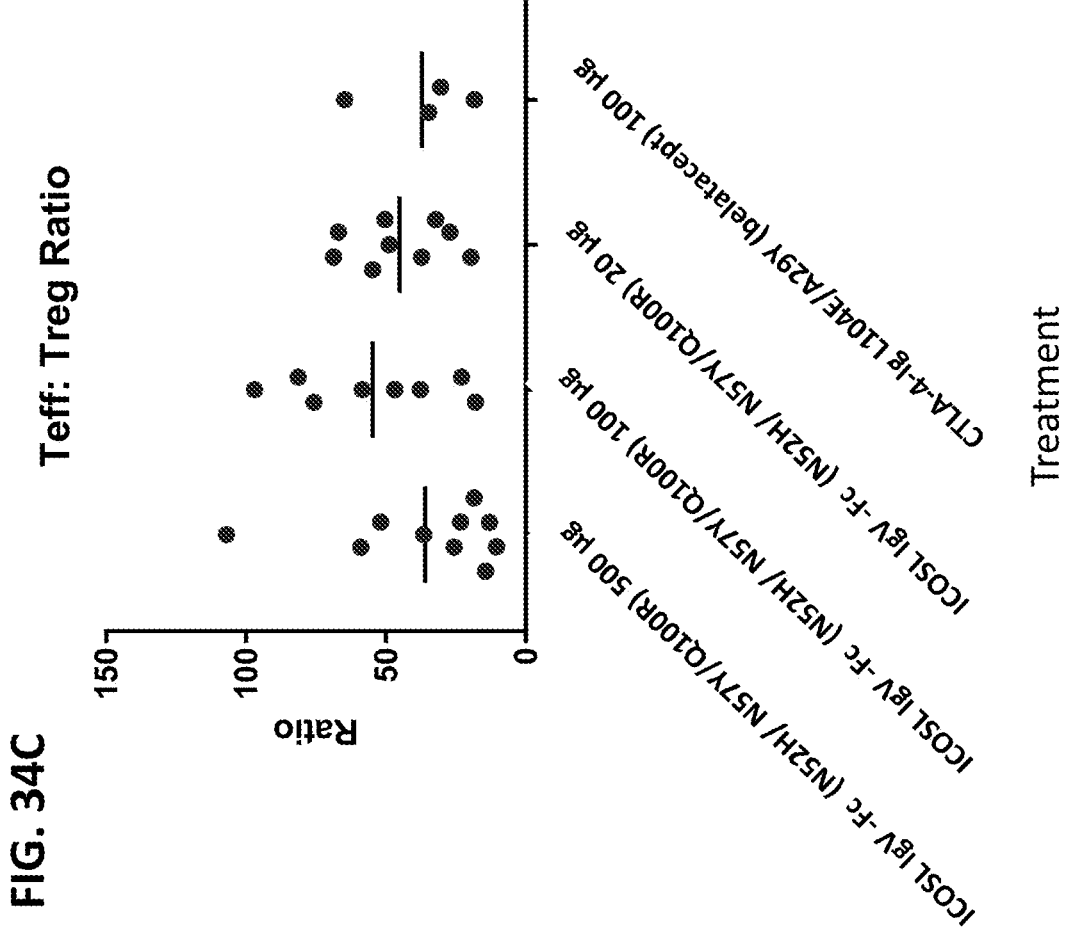

FIG. 34C depicts the ratio of T effector cells (Teff) to T regulatory cells (Treg) from Graft-versus-Host-Disease (GvHD) mice treated with various doses (20, 100, or 500 µg) of a variant ICOSL IgV-Fc molecule.

Figure 35A:
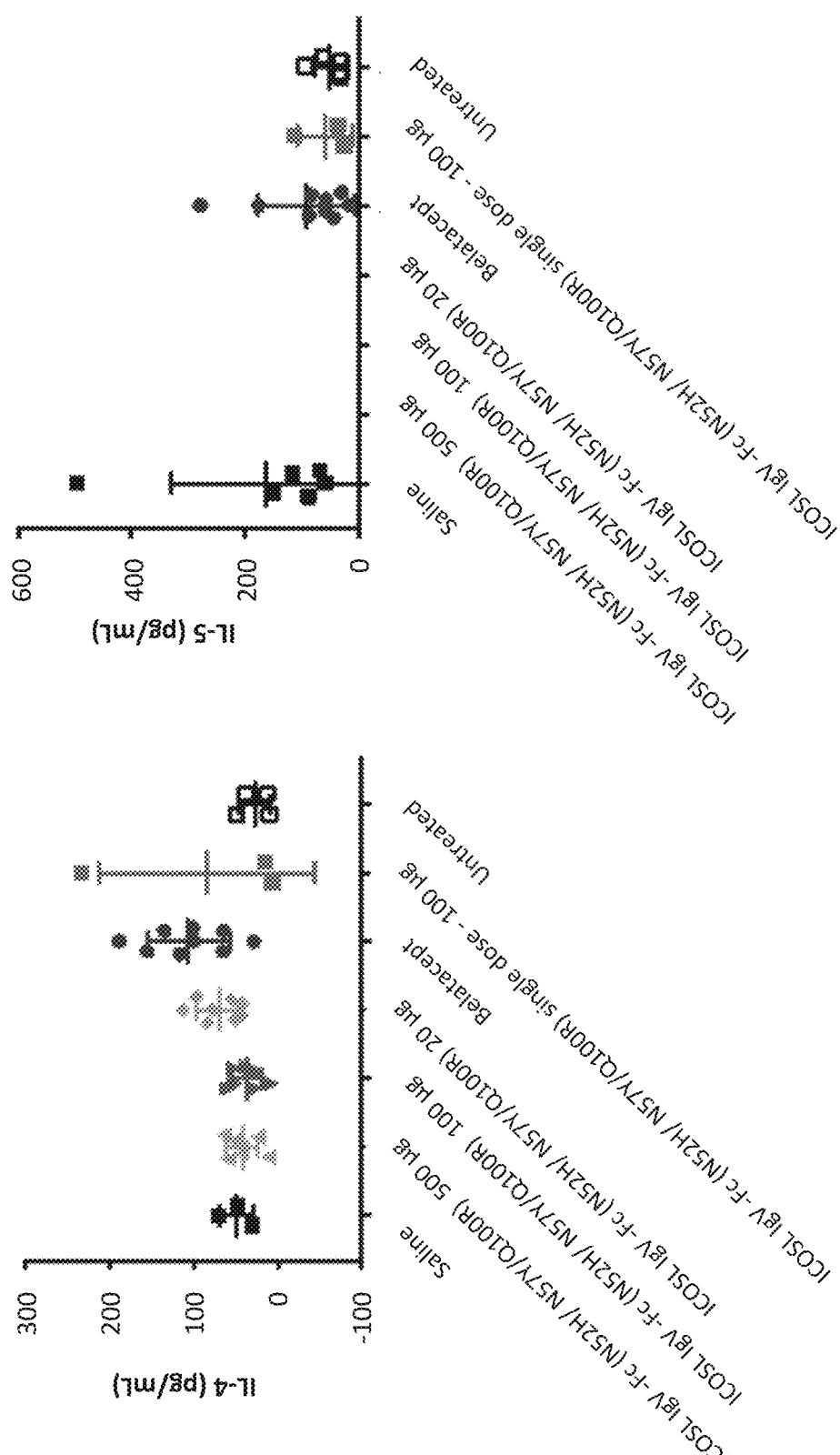
Figure 35B:
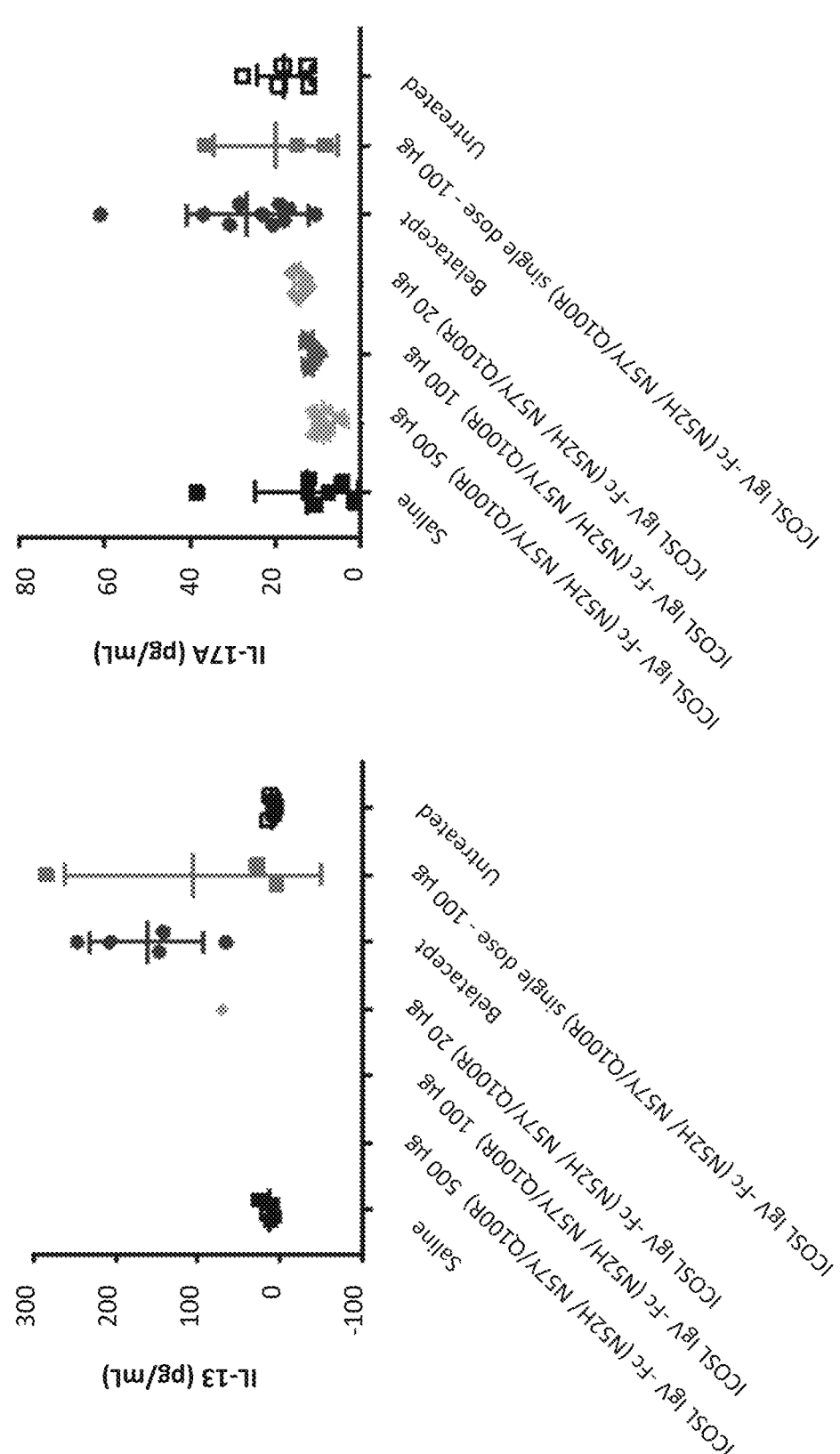
Figure 35C:
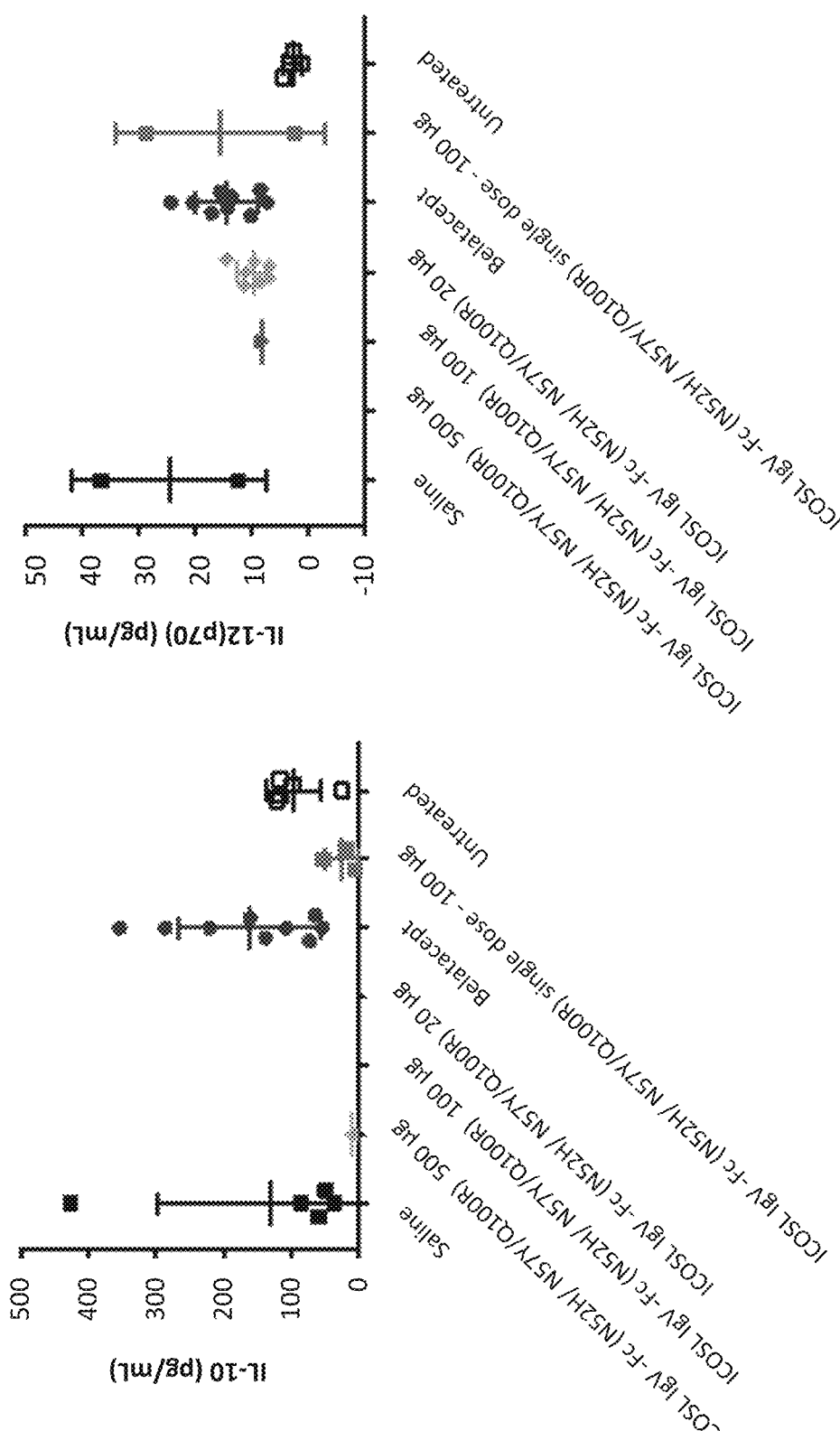
Figure 35D:
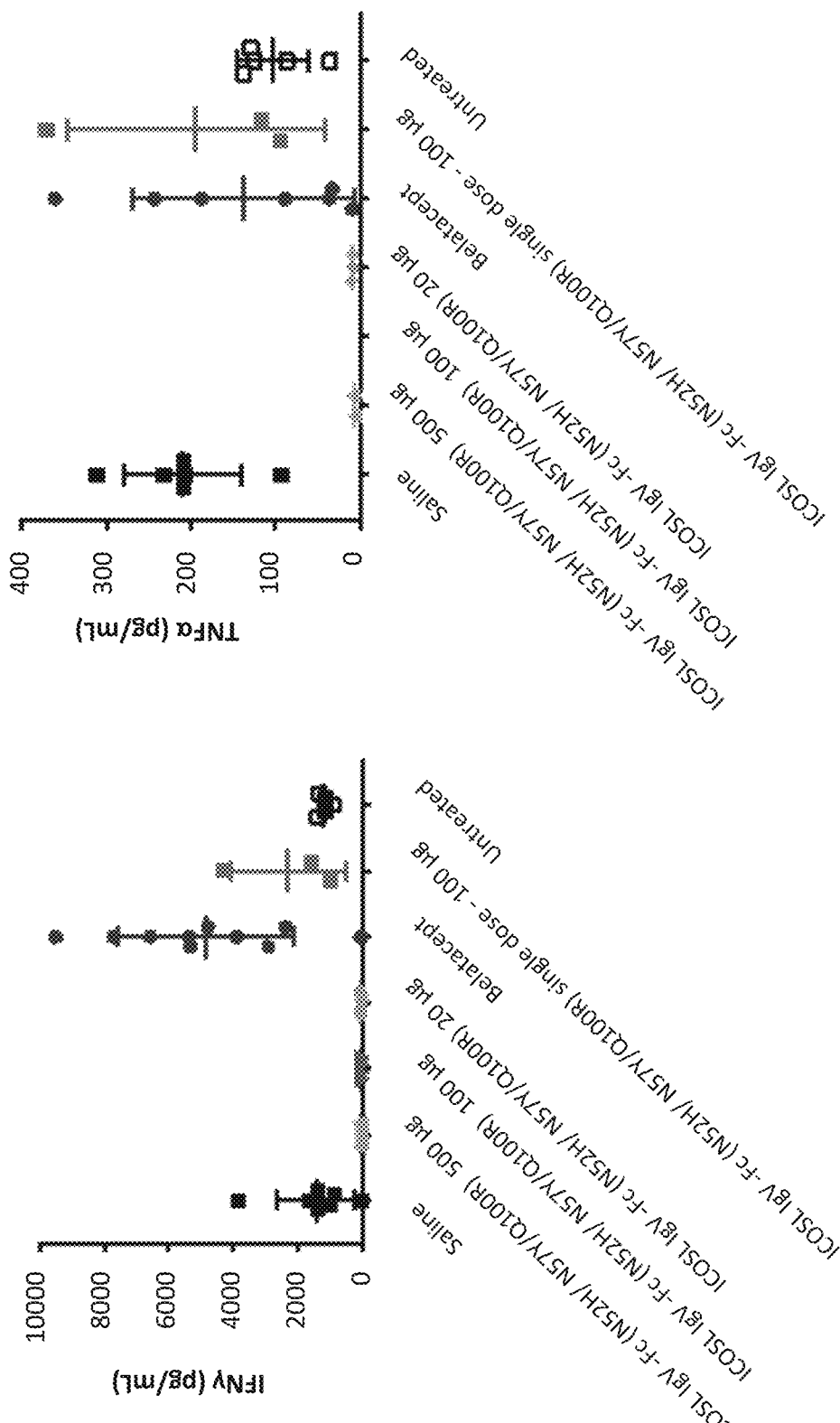
Figure 35E:
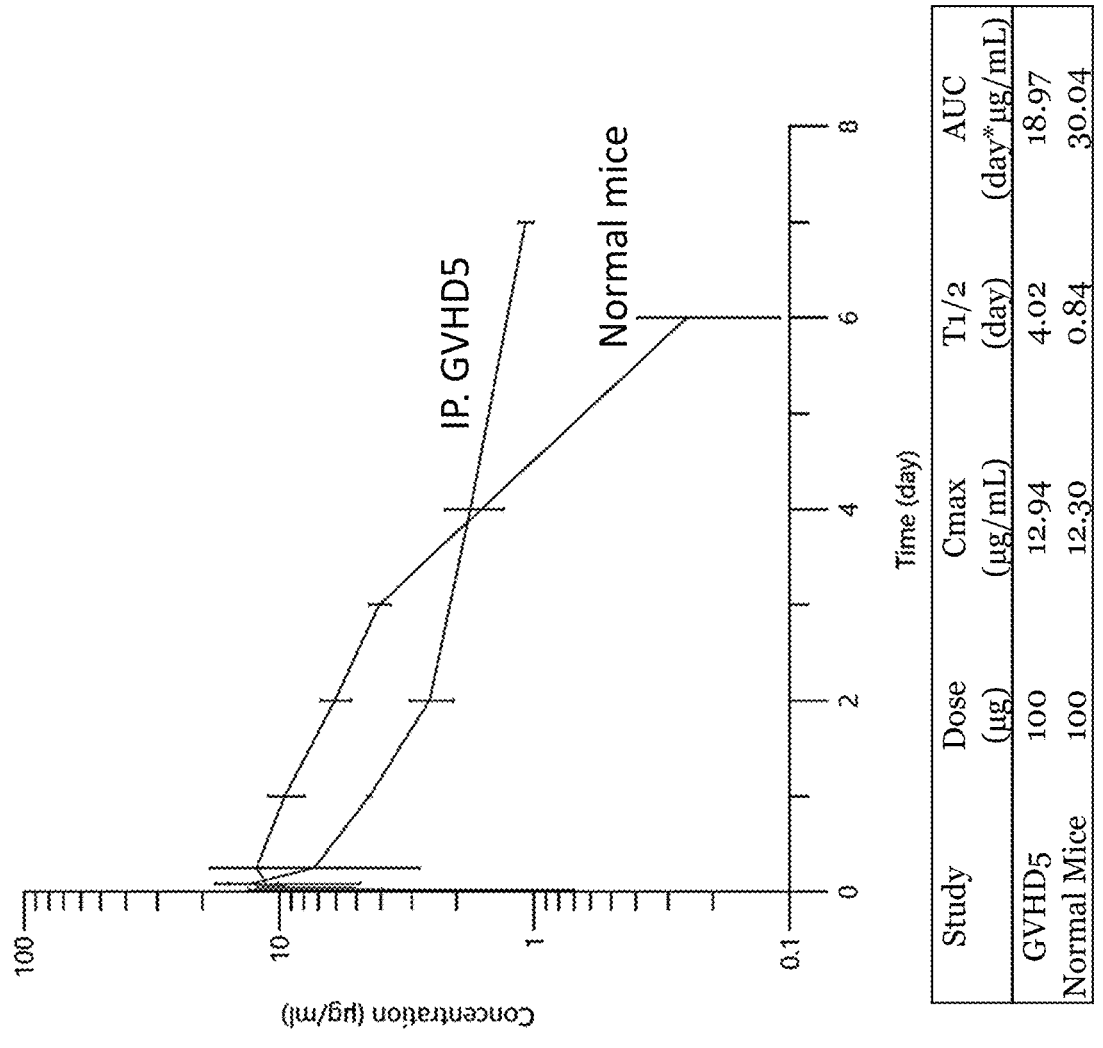

FIG. 35A-35D depicts serum proinflammatory cytokines from Graft-versus-Host-Disease (GvHD) mice treated with various doses (20, 100, or 500 µg) of a variant ICOSL IgV-Fc molecule. FIG. 35E depicts serum exposure of variant ICOSL IgV-Fc (N52H/N57Y/Q100R) in the GVHD model compared to normal mice.

Figure 36A:
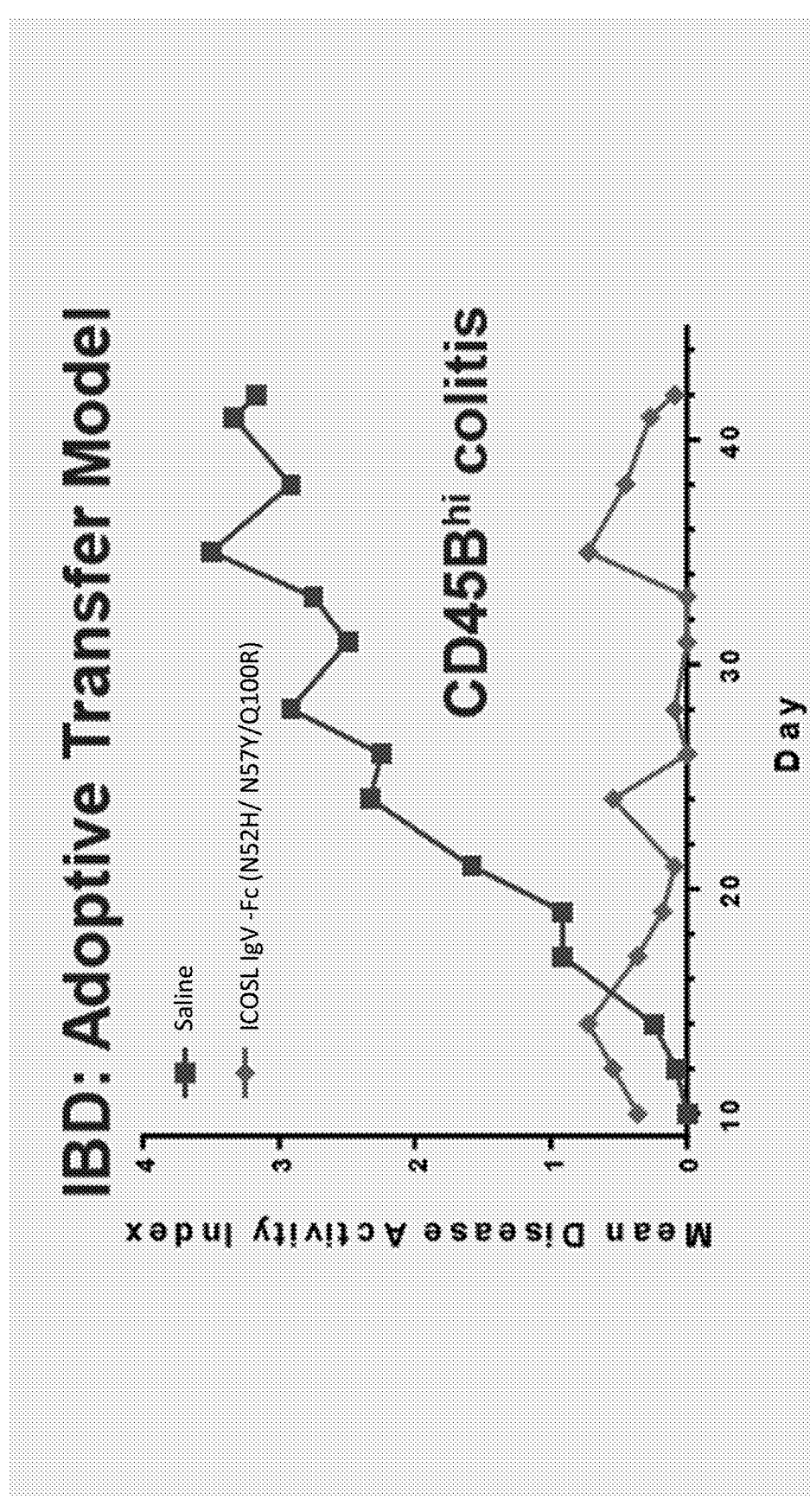
Figure 36B:
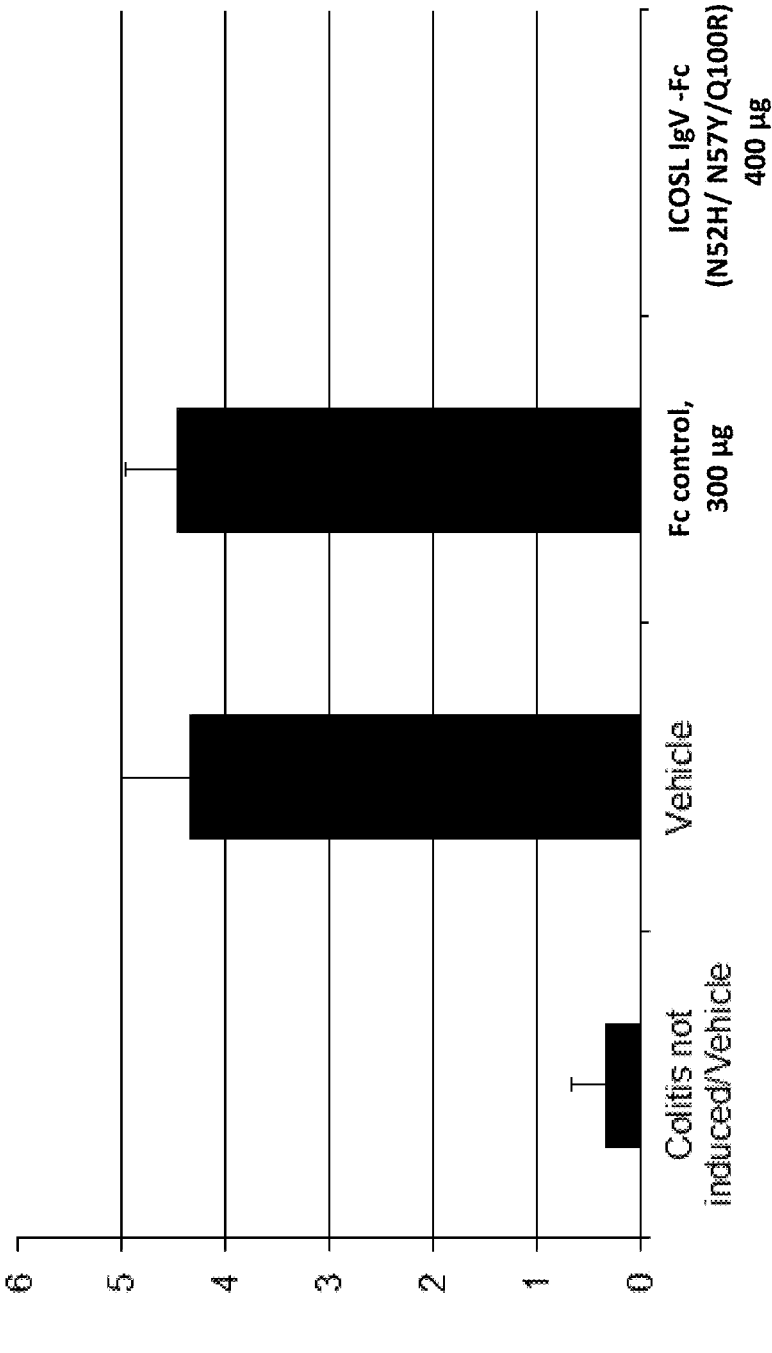

FIG. 36A depicts DAI results and FIG. 36B depicts histology results from treatment with an exemplary variant ICOSL IgV-Fc on disease activity index (DAI) calculated from body weight and stool scores in a CD4+CD45RBhigh-induced colitis model.

DETAILED DESCRIPTION

Provided herein are immunomodulatory proteins that are or comprise variants or mutants of ICOS ligand (ICOSL) or specific binding fragments thereof that exhibit activity to bind to at least one target ligand cognate binding partner (also called counter-structure protein). In some embodi-ments, the variant ICOSL polypeptides contain one or more amino acid modifications (e.g. amino acid substitutions, deletions or additions) compared to a reference (e.g., unmodified) or wild-type ICOSL polypeptide. In some embodiments, the one or more amino acid modifications (e.g. amino acid substitutions, deletions or additions) are in an immunoglobulin superfamily (IgSF) domain (e.g. IgV) of a reference (e.g., unmodified) or wild-type ICOSL polypep-tide. In some embodiments, the variant ICOSL polypeptide exhibits altered, such as increased or decreased, binding activity or affinity for at least one cognate binding partner, such as at least one of ICOS, CD28, or CTLA-4. In some embodiments, the immunomodulatory proteins are soluble. In some embodiments, the immunomodulatory proteins are transmembrane immunomodulatory proteins capable of being expressed on the surface of cells. In some embodi-ments, also provided herein are one or more other immu-nomodulatory proteins that are conjugates or fusions con-taining a variant ICOSL polypeptide provided herein and one or more other moiety or polypeptide.

In some embodiments, the variant ICOSL polypeptides and immunomodulatory proteins modulate an immunologi-cal immune response, such as an increased or decreased immune response. In some embodiments, the variant ICOSL polypeptides and immunomodulatory proteins provided herein can be used for the treatment of diseases or conditions that are associated with a dysregulated immune response.

In some embodiments, the provided variant ICOSL poly-peptides modulate T cell activation via interactions with costimulatory signaling molecules. In general, antigen spe-cific T-cell activation requires two distinct signals. The first signal is provided by the interaction of the T-cell receptor (TCR) with major histocompatibility complex (MHC) asso-ciated antigens present on antigen presenting cells (APCs). The second signal is costimulatory to TCR engagement and necessary to avoid T-cell apoptosis or anergy.

In some embodiments, under normal physiological con-ditions, the T cell-mediated immune response is initiated by antigen recognition by the T cell receptor (TCR) and is regulated by a balance of co-stimulatory and inhibitory signals (e.g., immune checkpoint receptors). The immune system relies on immune checkpoint receptors to prevent autoimmunity (i.e., self-tolerance) and to protect tissues from excessive damage during an immune response, for example during an attack against a pathogenic infection. In some cases, however, these immunomodulatory proteins can be dysregulated in diseases and conditions, including tumors, as a mechanism for evading the immune system.

In some embodiments, among known T-cell costimulatory receptors is CD28, which is the T-cell costimulatory receptor for the ligands B7-1 (CD80) and B7-2 (CD86) both of which are present on APCs. These same ligands can also bind to the inhibitory T-cell receptor CTLA4 (cytotoxic T-lymphocyte-associated protein 4) with greater affinity than for CD28; the binding to CTLA-4 acts to down-modulate the immune response. ICOS (inducible costimulator) is another T-cell costimulatory receptor which binds to ICOS ligand (ICOSL) on APCs. In some cases, CD28 and CTLA-4 also are known to interact with ICOSL at a binding site that overlaps with the binding of ICOSL to the T-cell costimulatory receptor ICOS (Yao et al. (2011) Immunity, 34:729-740). Although CD28 and ICOS are related CD28 family activating recep-tors and share some intracellular signaling motifs, costimu-latory effects between CD28 and ICOS differ. For example, CD28 is expressed on both unactivated and activated T cells and its signaling is important for IL-2 production and subsequent T cell effector function. ICOS is generally not expressed on the surface of T cells until after T cell activa-tion, and signaling through ICOS on activated T cells supports specialized T cell subset differentiation. Thus, in some cases, costimulation by CD28 and ICOS yields over-lapping and complementary effects.

In some aspects, T cells express the costimulatory molecules CD28 and ICOS, which interact with CD80/CD86 and ICOSL respectively, on antigen presenting cells (APC). In lymphoid organs, professional APC (i.e. dendritic cells, macrophages, and B cells) express CD80, CD86, and ICOSL and engage CD28+/ICOS+ T cells. In some embodiments, activated T cells can then differentiate into effector cells such as CD8+ cytotoxic T cells (CTL), IL-17A/F-secreting CD4+ Th17 cells, or CD4+ follicular helper (TPH) cells. TFH-expressing CD40L engage B cells in lymphoid follicles and release cytokines (e.g. IL-21) inducing differentiation of B cells to antibody (Ab)-secreting plasma cells. Plasma cells can produce tissue-damaging antibodies, e.g., rheumatoid factor (RF) and anti-citrullinated peptide antibodies (ACPA) in humans, and anti-collagen (CII) antibodies in mice, which can form immune complexes and deposits in the joints and other tissues. ICOSL can also be expressed on non-professional APCs, leading to T cell activation in non-lymphoid tissues and further damage to the tissues and joints.

In some aspects, CD4+Th1-, Th9- and Th17-cells, are implicated as key contributors to multiple sclerosis (MS) by increasing inflammation within the CNS in both multiple sclerosis and experimental autoimmune encephalomyelitis and CD4+ICOS+CXCR5+T follicular helper cells are increased in PBMC in relapsing-remitting and correlate with disease progression in secondary progressive MS. In some embodiments, there is significantly increased ICOS gene expression in cerebrospinal fluid cells, in secondary progressive MS, and an increased percentage of total monocytes and monocytes expressing ICOSL is observed. ICOSL also expressed on non-professional APCs, leading to T cell activation in non-lymphoid tissues and further tissue damage Among the provided variant ICOSL polypeptide are polypeptides that, when modified by one or more amino acid modifications of an IgSF domain of a reference ICOSL polypeptide, exhibit enhanced binding affinity for CD28 and/or ICOS. In some cases, the overall increase in ICOS binding in provided variants is less than the increase in CD28 binding because wild-type ICOSL already demonstrates substantially more binding affinity for ICOS than CD28. Also provided are various formats of the provided variant polypeptides. As shown herein, alternative formats can facilitate manipulation of the immune response, and hence the therapeutic application. For example, delivery of enhanced ICOSL proteins in soluble formats is shown herein to antagonize T cell activation by inhibiting CD28 and/or ICOS signaling. In other examples, tethering of the variant ICOSL molecules to a surface facilitates T cell activation by providing a costimulatory signal. Various tethering strategies are provided to localize delivery of a T cell costimulatory signal including, but not limited to, direct coating to plastic, use of another variant IgSF domain to localize to a plate-bound or cell surface expressed protein target, or fusion of the variant ICOSL to a tumor-specific monoclonal antibody.

In some embodiments, the modulation of immune signaling achieved by the provided variant ICOSL polypeptides and immunomodulatory polypeptides offers advantages for treatment of inflammatory and autoimmune disorders and other diseases and conditions compared to other treatments. In some cases, therapies to intervene and alter the costimulatory effects of both receptors are constrained by the spatial orientation requirements as well as size limitations imposed by the confines of the immunological synapse. In some aspects, existing therapeutic drugs, including antibody drugs, may not be able to interact simultaneously with the multiple target proteins involved in modulating these interactions. In addition, in some cases, existing therapeutic drugs may only have the ability to antagonize but not agonize an immune response. Additionally, pharmacokinetic differences between drugs that independently target one or the other of these two receptors can create difficulties in properly maintaining a desired blood concentration of such drug combinations throughout the course of treatment.

In some embodiments, the provided variant ICOSL polypeptides or immunomodulatory proteins modulate (e.g. increase or decrease) immunological activity induced by costimulatory receptors CD28 or ICOS. Thus, in some embodiments, the provided polypeptides overcome these constraints by providing variant ICOSL (inducible costimulator ligand) with altered (e.g. increased or decreased) binding affinities to both CD28 and ICOS, and, in some cases, CTLA-4, thereby agonizing or antagonizing the complementary effects of costimulation by receptors. Methods of making and using these variant ICOSL are also provided.

In some aspects, the provided molecules may also be more effective than other soluble therapeutic protein agents. For example, abatacept (CTLA-4-Fc) has been shown to interfere with T cell costimulation to attenuate T cell responses in autoimmune disease settings, such as for the treatment of rheumatoid arthritis, psoriatic arthritis and juvenile idiopathic arthritis, and belatacept, a variant CTLA-4-Fc molecule, for transplant rejection. These CTLA-4-Fc proteins, however, bind to CD80 and CD86 and prevent these costimulatory ligands from engaging and triggering only CD28. Variant ICOSL polypeptides provided herein, in some cases, exhibit binding affinity and enhanced activity for both CD28 and ICOS.

Furthermore, the ability to format the variant polypeptides in various configurations to, depending on the context, antagonize or agonize an immune response, offers flexibility in therapeutic applications based on the same increased binding and activity of a variant ICOSL for binding partners. In some embodiments, the particular format can be chosen for the desired therapeutic application. For example, as described, an immunomodulatory polypeptide comprising a variant ICOSL polypeptide is provided in a format, e.g. as an Fc-fusion protein, to antagonize or block activity of its cognate binding partner, e.g. ICOS and/or CD28. In some embodiments, blocking or inhibiting costimulatory signaling via CD28 or ICOS may be useful to suppresses an immune response, which can be useful in the treatment of inflammatory or autoimmune disorders (e.g., multiple sclerosis or brain inflammation), or organ transplantation. As an example, tethering variant ICOSL proteins to a surface can deliver a localized costimulatory signal, which, in some aspects, can be used to target tumor tissue to deliver localized costimulation to tumor infiltrating T cells. Most primary tumors lack expression of costimulatory molecules such as CD80, CD86 or ICOSL, and thus T cell anti-tumor responses can be compromised by a lack of costimulation (Yu et al. (1998) Int. Immunol. 10:791-797). By localizing costimulatory domains to tumor cells using a tumor-localizing moiety, such as Nkp30 localized to B7H6 tumor cells or a tumor-specific antibody, T cell responses can be enhanced in the absence of tumor-expressed costimulatory proteins.

All publications, including patents, patent applications scientific articles and databases, mentioned in this specification are herein incorporated by reference in their entirety for all purposes to the same extent as if each individual publication, including patent, patent application, scientific article or database, were specifically and individually indicated to be incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The terms used throughout this specification are defined as follows unless otherwise limited in specific instances. As used in the specification and the appended claims, the singular forms "a," "an," and "the" include plural referents unless the context clearly dictates otherwise. Unless defined otherwise, all technical and scientific terms, acronyms, and abbreviations used herein have the same meaning as commonly understood by one of ordinary skill in the art to which the invention pertains. Unless indicated otherwise, abbreviations and symbols for chemical and biochemical names is per IUPAC-IUB nomenclature. Unless indicated otherwise, all numerical ranges are inclusive of the values defining the range as well as all integer values in-between.

The term "affinity modified" as used in the context of an immunoglobulin superfamily domain, means a mammalian immunoglobulin superfamily (IgSF) domain having an altered amino acid sequence (relative to the corresponding wild-type parental or unmodified IgSF domain) such that it has an increased or decreased binding affinity or avidity to at least one of its cognate binding partners (alternatively "counter-structures") compared to the parental wild-type or unmodified (i.e., non-affinity modified) IgSF control domain. Included in this context is an affinity modified ICOSL IgSF domain. In some embodiments, the affinity-modified IgSF domain can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid differences, such as amino acid substitutions, in a reference (e.g., unmodified) or wild-type IgSF domain. An increase or decrease in binding affinity or avidity can be determined using well known binding assays such as flow cytometry. Larsen et al., American Journal of Transplantation, Vol 5:443-453 (2005). See also, Linsley et al., Immunity, Vol 1:793-801 (1994). An increase in a protein's binding affinity or avidity to its cognate binding partner(s) is to a value at least 10% greater than that of the wild-type IgSF domain control and in some embodiments, at least 20%, 30%, 40%, 50%, 100%, 200%, 300%, 500%, 1000%, 5000%, or 10000% greater than that of the wild-type IgSF domain control value. A decrease in a protein's binding affinity or avidity to at least one of its cognate binding partner is to a value no greater than 90% of the control but no less than 10% of the wild-type IgSF domain control value, and in some embodiments no greater than 80%, 70% 60%, 50%, 40%, 30%, or 20% but no less than 10% of the wild-type IgSF domain control value. An affinity-modified protein is altered in primary amino acid sequence by substitution, addition, or deletion of amino acid residues. The term "affinity modified IgSF domain" is not be construed as imposing any condition for any particular starting composition or method by which the affinity-modified IgSF domain was created. Thus, the affinity modified IgSF domains of the present invention are not limited to wild type IgSF domains that are then transformed to an affinity modified IgSF domain by any particular process of affinity modification. An affinity modified IgSF domain polypeptide can, for example, be generated starting from wild type mammalian IgSF domain sequence information, then modeled in silico for binding to its cognate binding partner, and finally recombinantly or chemically synthesized to yield the affinity modified IgSF domain composition of matter. In but one alternative example, an affinity modified IgSF domain can be created by site-directed mutagenesis of a wild-type IgSF domain. Thus, affinity modified IgSF domain denotes a product and not necessarily a product produced by any given process. A variety of techniques including recombinant methods, chemical synthesis, or combinations thereof, may be employed.

The term "allogeneic" as used herein means a cell or tissue that is removed from one organism and then infused or adoptively transferred into a genetically dissimilar organism of the same species. In some embodiments of the invention, the species is murine or human.

The term "autologous" as used herein means a cell or tissue that is removed from the same organism to which it is later infused or adoptively transferred. An autologous cell or tissue can be altered by, for example, recombinant DNA methodologies, such that it is no longer genetically identical to the native cell or native tissue which is removed from the organism. For example, a native autologous T-cell can be genetically engineered by recombinant DNA techniques to become an autologous engineered cell expressing a transmembrane immunomodulatory protein and/or chimeric antigen receptor (CAR), which in some cases involves engineering a T-cell or TIL (tumor infiltrating lymphocyte). The engineered cells are then infused into a patient from which the native T-cell was isolated. In some embodiments, the organism is human or murine.

The terms "binding affinity," and "binding avidity" as used herein means the specific binding affinity and specific binding avidity, respectively, of a protein for its counter-structure under specific binding conditions. In biochemical kinetics avidity refers to the accumulated strength of multiple affinities of individual non-covalent binding interactions, such as between ICOSL and its counter-structures ICOS and/or CD28. As such, avidity is distinct from affinity, which describes the strength of a single interaction. An increase or attenuation in binding affinity of a variant ICOSL containing an affinity modified ICOSL IgSF domain to its counter-structure is determined relative to the binding affinity of the unmodified ICOSL, such as an unmodified ICOSL containing the native or wild-type IgSF domain, such as IgV domain. Methods for determining binding affinity or avidity are known in art. See, for example, Larsen et al., American Journal of Transplantation, Vol 5:443-453 (2005). In some embodiments, a variant ICOSL of the invention (i.e. a ICOSL protein containing an affinity modified IgSF domain) specifically binds to CD28 and/or ICOS measured by flow cytometry with a binding affinity that yields a Mean Fluorescence Intensity (MFI) value at least 10%, 20%, 30%, 40%, 50%, 60%, 70%, 80%, 90%, or 100% greater than a wild-type ICOSL control in a binding assay such as described in Example 6.

The term "biological half-life" refers to the amount of time it takes for a substance, such as an immunomodulatory polypeptide comprising a variant ICOSL of the present invention, to lose half of its pharmacologic or physiologic activity or concentration. Biological half-life can be affected by elimination, excretion, degradation (e.g., enzymatic) of the substance, or absorption and concentration in certain organs or tissues of the body. In some embodiments, biological half-life can be assessed by determining the time it takes for the blood plasma concentration of the substance to reach half its steady state level ("plasma half-life"). Conjugates that can be used to derivatize and increase the biological half-life of polypeptides of the invention are known in the art and include, but are not limited to, polyethylene glycol (PEG), hydroxyethyl starch (HES), XTEN (extended recombinant peptides; see, WO2013130683), human serum albumin (HSA), bovine serum albumin (BSA), lipids (acylation), and poly-Pro-Ala-Ser (PAS), polyglutamic acid (glutamylation).

The term "chimeric antigen receptor" or "CAR" as used herein refers to an artificial (i.e., man-made) transmembrane protein expressed on a mammalian cell comprising at least an ectodomain, a transmembrane, and an endodomain. Optionally, the CAR protein includes a "spacer" which covalently links the ectodomain to the transmembrane domain. A spacer is often a polypeptide linking the ectodomain to the transmembrane domain via peptide bonds. The CAR is typically expressed on a mammalian lymphocyte. In some embodiments, the CAR is expressed on a mammalian cell such as a T-cell or a tumor infiltrating lymphocyte (TIL). A CAR expressed on a T-cell is referred to herein as a "CAR T-cell" or "CAR-T." In some embodiments the CAR-T is a T helper cell, a cytotoxic T-cell, a natural killer T-cell, a memory T-cell, a regulatory T-cell, or a gamma delta T-cell. When used clinically in, e.g. adoptive cell transfer, a CAR-T with antigen binding specificity to the patient's tumor is typically engineered to express on a native T-cell obtained from the patient. The engineered T-cell expressing the CAR is then infused back into the patient. The CAR-T is thus often an autologous CAR-T although allogeneic CAR-T are included within the scope of the invention. The ectodomain of a CAR comprises an antigen binding region, such as an antibody or antigen binding fragment thereof (e.g. scFv), that specifically binds under physiological conditions with a target antigen, such as a tumor specific antigen. Upon specific binding a biochemical chain of events (i.e., signal transduction) results in modulation of the immunological activity of the CAR-T. Thus, for example, upon specific binding by the antigen binding region of the CAR-T to its target antigen can lead to changes in the immunological activity of the T-cell activity as reflected by changes in cytotoxicity, proliferation or cytokine production. Signal transduction upon CAR-T activation is achieved in some embodiments by the CD3-zeta chain ("CD3-z") which is involved in signal transduction in native mammalian T-cells. CAR-Ts can further comprise multiple signaling domains such as CD28, 41BB or OX40, to further modulate immunomodulatory response of the T-cell. CD3-z comprises a conserved motif known as an immunoreceptor tyrosine-based activation motif (ITAM) which is involved in T-cell receptor signal transduction.

The term "collectively" or "collective" when used in reference to cytokine production induced by the presence of two or more variant ICOSL of the invention in an in vitro assay, means the overall cytokine expression level irrespective of the cytokine production induced by individual variant ICOSL. In some embodiments, the cytokine being assayed is IFN-gamma in an in vitro primary T-cell assay such as described in Example 6 and Example 7.

The term "cognate binding partner" (used interchangeably with "counter-structure") in reference to a polypeptide, such as in reference to an IgSF domain of a variant ICOSL, refers to at least one molecule (typically a native mammalian protein) to which the referenced polypeptide specifically binds under specific binding conditions. In some aspects, a variant ICOSL containing an affinity modified IgSF domain specifically binds to the counter-structure of the corresponding native or wild-type ICOSL but with increased or attenuated affinity. A species of ligand recognized and specifically binding to its cognate receptor under specific binding conditions is an example of a counter-structure or cognate binding partner of that receptor. A "cognate cell surface binding partner" is a cognate binding partner expressed on a mammalian cell surface. A "cell surface molecular species" is a cognate binding partner of ligands of the immunological synapse (IS), expressed on and by cells, such as mammalian cells, forming the immunological synapse.

As used herein, "conjugate," "conjugation" or grammatical variations thereof refers the joining or linking together of two or more compounds resulting in the formation of another compound, by any joining or linking methods known in the art. It can also refer to a compound which is generated by the joining or linking together two or more compounds. For example, a variant ICOSL polypeptide linked directly or indirectly to one or more chemical moieties or polypeptide is an exemplary conjugate. Such conjugates include fusion proteins, those produced by chemical conjugates and those produced by any other methods.

The term "competitive binding" as used herein means that a protein is capable of specifically binding to at least two cognate binding partners but that specific binding of one cognate binding partner inhibits, such as prevents or precludes, simultaneous binding of the second cognate binding partner. Thus, in some cases, it is not possible for a protein to bind the two cognate binding partners at the same time. Generally, competitive binders contain the same or overlapping binding site for specific binding but this is not a requirement. In some embodiments, competitive binding causes a measurable inhibition (partial or complete) of specific binding of a protein to one of its cognate binding partner due to specific binding of a second cognate binding partner. A variety of methods are known to quantify competitive binding such as ELISA (enzyme linked immunosorbent assay) assays.

The term "conservative amino acid substitution" as used herein means an amino acid substitution in which an amino acid residue is substituted by another amino acid residue having a side chain R group with similar chemical properties (e.g., charge or hydrophobicity). Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups are: valine-leucine-isoleucine, phenylalanine-tyrosine, lysine-arginine, alanine-valine, glutamate-aspartate, and asparagine-glutamine.

The term, "corresponding to" with reference to positions of a protein, such as recitation that nucleotides or amino acid positions "correspond to" nucleotides or amino acid positions in a disclosed sequence, such as set forth in the Sequence listing, refers to nucleotides or amino acid positions identified upon alignment with the disclosed sequence based on structural sequence alignment or using a standard alignment algorithm, such as the GAP algorithm. For example, corresponding residues can be determined by alignment of a reference sequence with the sequence set forth in SEQ ID NO: 32 (ECD domain) or set forth in SEQ ID NOs: 196 or 545 (IgV domain) by structural alignment methods as described herein. By aligning the sequences, one skilled in the art can identify corresponding residues, for example, using conserved and identical amino acid residues as guides.

The terms "decrease" or "attenuate" "or suppress" as used herein means to decrease by a statistically significant amount. A decrease can be at least 10%, 20%, 30%, 40%, 50%, 60%, 70%, 80%, 90%, or 100% of a control value, such as a non-zero control value.

The terms "decreased" or "reduced" as used herein in the context of decreasing immunological activity of a mammalian lymphocyte means to decrease one or more activities of the lymphocyte, as compared to a control, such as an untreated control or a control in which a treatment using an unmodified or non-variant control was employed under the same conditions. A decreased activity can refer to one or more of cell cycle inhibition, reduced cell survival, reduced cell proliferation, reduced cytokine production, or reduced T-cell cytotoxicity, such as by a statistically significant amount. In some embodiments, reference to reduced immunological activity means to reduce interferon gamma (IFN-gamma) production compared to in the absence of treatment, such as by a statistically significant amount. In some embodiments, the immunological activity can be assessed in a mixed lymphocyte reaction (MLR) assay. Methods of conducting MLR assays are known in the art. Wang et al., Cancer Immunol Res. 2014 September: 2(9):846-56. Other methods of assessing activities of lymphocytes are known in the art, including any assay as described herein. In some embodiments an enhancement can be a decrease by at least 5%, 10%, 15%, 20%, 25%, 30%, 35%, 40%, 45%, 50%, 60%, 70%, 80%, 90%, or 100%, as compared to a control value, such as an untreated control value or a non-zero control value.

The terms "derivatives" or "derivatized" refer to modification of a protein by covalently linking it, directly or indirectly, to a composition so as to alter such characteristics as biological half-life, bioavailability, immunogenicity, solubility, toxicity, potency, or efficacy while retaining or enhancing its therapeutic benefit. Derivatives of immunomodulatory polypeptides of the invention are within the scope of the invention and can be made by, for example, glycosylation, pegylation, lipidation, or Fc-fusion.

As used herein, domain (typically a sequence of three or more, generally 5 or 7 or more amino acids, such as 10 to 200 amino acid residues) refers to a portion of a molecule, such as a protein or encoding nucleic acid, that is structurally and/or functionally distinct from other portions of the molecule and is identifiable. For example, domains include those portions of a polypeptide chain that can form an independently folded structure within a protein made up of one or more structural motifs and/or that is recognized by virtue of a functional activity, such as binding activity. A protein can have one, or more than one, distinct domains. For example, a domain can be identified, defined or distin-guished by homology of the primary sequence or structure to related family members, such as homology to motifs. In another example, a domain can be distinguished by its function, such as an ability to interact with a biomolecule, such as a cognate binding partner. A domain independently can exhibit a biological function or activity such that the domain independently or fused to another molecule can perform an activity, such as, for example binding. A domain can be a linear sequence of amino acids or a non-linear sequence of amino acids. Many polypeptides contain a plurality of domains. Such domains are known, and can be identified by those of skill in the art. For exemplification herein, definitions are provided, but it is understood that it is well within the skill in the art to recognize particular domains by name. If needed appropriate software can be employed to identify domains.

The term "ectodomain" as used herein refers to the region of a membrane protein, such as a transmembrane protein, that lies outside the vesicular membrane. Ectodomains often comprise binding domains that specifically bind to ligands or cell surface receptors, such as via a binding domain that specifically binds to the ligand or cell surface receptor. The ectodomain of a cellular transmembrane protein is alternately referred to as an extracellular domain.

The terms "effective amount" or "therapeutically effective amount" refer to a quantity and/or concentration of a therapeutic composition of the invention, including a protein composition or cell composition, that when administered ex vivo (by contact with a cell from a patient) or in vivo (by administration into a patient) either alone (i.e., as a monotherapy) or in combination with additional therapeutic agents, yields a statistically significant decrease in disease progression as, for example, by ameliorating or eliminating symptoms and/or the cause of the disease. An effective amount may be an amount that relieves, lessens, or alleviates at least one symptom or biological response or effect associated with a disease or disorder, prevents progression of the disease or disorder, or improves physical functioning of the patient. In the case of cell therapy, the effective amount is an effective dose or number of cells administered to a patient by adoptive cell therapy. In some embodiments the patient is a mammal such as a non-human primate or human patient.

The term "endodomain" as used herein refers to the region found in some membrane proteins, such as transmembrane proteins, that extends into the interior space defined by the cell surface membrane. In mammalian cells, the endodomain is the cytoplasmic region of the membrane protein. In cells, the endodomain interacts with intracellular constituents and can be play a role in signal transduction and thus, in some cases, can be an intracellular signaling domain. The endodomain of a cellular transmembrane protein is alternately referred to as a cytoplasmic domain, which, in some cases, can be a cytoplasmic signaling domain.

The terms "enhanced" or "increased" as used herein in the context of increasing immunological activity of a mammalian lymphocyte means to increase one or more activities the lymphocyte, as compared to a control, such as an untreated control or a control in which a treatment using an unmodified or non-variant control was employed under the same conditions. An increased activity can be one or more of increase cell survival, cell proliferation, cytokine production, or T-cell cytotoxicity, such as by a statistically significant amount. In some embodiments, reference to increased immunological activity means to increase interferon gamma (IFN-gamma) production, such as by a statistically significant amount. In some embodiments, the immunological activity can be assessed in a mixed lymphocyte reaction (MLR) assay. Methods of conducting MLR assays are known in the art. Wang et al., Cancer Immunol Res. 2014 September: 2(9):846-56. Other methods of assessing activities of lymphocytes are known in the art, including any assay as described herein. In some embodiments an enhancement can be an increase of at least 10%, 20%, 30%, 40%, 50%, 75%, 100%, 200%, 300%, 400%, or 500% greater than a non-zero control value.

The term "engineered cell" as used herein refers to a mammalian cell that has been genetically modified by human intervention such as by recombinant DNA methods or viral transduction. In some embodiments, the cell is an immune cell, such as a lymphocyte (e.g. T cell, B cell, NK cell) or an antigen presenting cell (e.g. dendritic cell). The cell can be a primary cell from a patient or can be a cell line. In some embodiments, an engineered cell of the invention comprises a variant ICOSL provided herein. In some embodiments, the variant ICOSL is a transmembrane immunomodulatory protein (hereinafter referred to as "TIP") that is expressed on the engineered cell. In some embodiments, the TIP contains the extracellular domain or a portion thereof containing the IgV domain linked to a transmembrane domain (e.g., a ICOSL transmembrane domain) and, optionally, an intracellular signaling domain. In some cases, the TIP is formatted as a chimeric receptor containing a heterologous cytoplasmic signaling domain or endodomain. In some embodiments, an engineered cell is capable of expressing and secreting a immunomodulatory protein as described herein. Among provided engineered cells also are cells further containing an engineered T-cell receptor (TCR) or chimeric antigen receptor (CAR).

The term "engineered T-cell" as used herein refers to a T-cell such as a T helper cell, cytotoxic T-cell (alternatively, cytotoxic T lymphocyte or CTL), natural killer T-cell, regulatory T-cell, memory T-cell, or gamma delta T-cell, that has been genetically modified by human intervention such as by recombinant DNA methods or viral transduction methods. An engineered T-cell comprises a variant ICOSL transmembrane immunomodulatory protein (TIP) or secreted immunomodulatory protein (SIP) of the present invention that is expressed on the T-cell and is engineered to modulate immunological activity of the engineered T-cell itself, or a mammalian cell to which the variant ICOSL expressed on the T-cell specifically binds. An engineered T-cell can comprise a variant ICOSL secreted immunomodulatory protein (SIP) of the present invention that is expressed by and/or secreted by the T-cell and is engineered to modulate immunological activity of the engineered T-cell itself, or a mammalian cell to which the variant ICOSL when secreted by the T-cell, specifically binds.

The term "engineered T-cell receptor" or "engineered TCR" refers to a T-cell receptor (TCR) engineered to specifically bind with a desired affinity to a major histocompatibility complex (MHC)/peptide target antigen that is selected, cloned, and/or subsequently introduced into a population of T-cells, often used for adoptive immunotherapy. In contrast to engineered TCRs, CARs are engineered to bind target antigens in a MHC independent manner.

The term "expressed on" as used herein is used in reference to a protein expressed on the surface of a cell, such as a mammalian cell. Thus, the protein is expressed as a membrane protein. In some embodiments, the expressed protein is a transmembrane protein. In some embodiments, the protein is conjugated to a small molecule moiety such as a drug or detectable label. Proteins expressed on the surface of a cell can include cell-surface proteins such as cell surface receptors that are expressed on mammalian cells.

The term "half-life extending moiety" refers to a moiety of a polypeptide fusion or chemical conjugate that extends the half-life of a protein circulating in mammalian blood serum compared to the half-life of the protein that is not so conjugated to the moiety. In some embodiments, half-life is extended by greater than or greater than about 1.2-fold, 1.5-fold, 2.0-fold, 3.0-fold, 4.0-fold, 5.0-fold, or 6.0-fold. In some embodiments, half-life is extended by more than 6 hours, more than 12 hours, more than 24 hours, more than 48 hours, more than 72 hours, more than 96 hours or more than 1 week after in vivo administration compared to the protein without the half-life extending moiety. The half-life refers to the amount of time it takes for the protein to lose half of its concentration, amount, or activity. Half-life can be determined for example, by using an ELISA assay or an activity assay. Exemplary half-life extending moieties include an Fc domain, a multimerization domain, polyethylene glycol (PEG), hydroxyethyl starch (HES), XTEN (extended recombinant peptides; see, WO2013130683), human serum albumin (HSA), bovine serum albumin (BSA), lipids (acylation), and poly-Pro-Ala-Ser (PAS), and polyglutamic acid (glutamylation).

The term "immunological synapse" or "immune synapse" as used herein means the interface between a mammalian cell that expresses MHC I (major histocompatibility complex) or MHC II, such as an antigen-presenting cell or tumor cell, and a mammalian lymphocyte such as an effector T cell or Natural Killer (NK) cell.

An Fc (fragment crystallizable) region or domain of an immunoglobulin molecule (also termed an Fc polypeptide) corresponds largely to the constant region of the immunoglobulin heavy chain, and is responsible for various functions, including the antibody's effector function(s). The Fc domain contains part or all of a hinge domain of an immunoglobulin molecule plus a CH2 and a CH3 domain. The Fc domain can form a dimer of two polypeptide chains joined by one or more disulfide bonds. In some embodiments, the Fc is a variant Fc that exhibits reduced (e.g. reduced greater than 30%, 40%, 50%, 60%, 70%, 80%, 90% or more) activity to facilitate an effector function. In some embodiments, reference to amino acid substitutions in an Fc region is by EU numbering system unless described with reference to a specific SEQ ID NO. EU numbering is known and is according to the most recently updated IMGT Scientific Chart (IMGT®, the international ImMunoGeneTics Information System® http://www.imgt.org/IMGTScientific-Chart/Numbering/Hu_IGHGnber.html (created: 17 May 2001, last updated: 10 Jan. 2013) and the EU index as reported in Kabat, E. A. et al. Sequences of Proteins of Immunological interest. 5th ed. US Department of Health and Human Services, NIH publication No. 91-3242 (1991).

An immunoglobulin Fc fusion ("Fc-fusion"), such as an immunomodulatory Fc fusion protein, is a molecule comprising one or more polypeptides (or one or more small molecules) operably linked to an Fc region of an immunoglobulin. An Fc-fusion may comprise, for example, the Fc region of an antibody (which facilitates effector functions and pharmacokinetics) and a variant ICOSL. An immunoglobulin Fc region may be linked indirectly or directly to one or more variant ICOSL or small molecules (fusion partners). Various linkers are known in the art and can optionally be used to link an Fc to a fusion partner to generate an Fc-fusion. Fc-fusions of identical species can be dimerized to form Fc-fusion homodimers, or using non-identical species to form Fc-fusion heterodimers. In some embodiments, the Fc is a mammalian Fc such as a murine or human Fc.

The term "host cell" refers to a cell that can be used to express a protein encoded by a recombinant expression vector. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include Chinese hamster ovary (CHO) cells or their derivatives such as Veggie CHO and related cell lines which grow in serum-free media or CHO strain DX-B11, which is deficient in DHFR. In some embodiments, a host cell is a mammalian cell (e.g., a human cell, a monkey cell, a hamster cell, a rat cell, a mouse cell, or an insect cell).

The term "immunoglobulin" (abbreviated "Ig") as used herein refers to a mammalian immunoglobulin protein including any of the five human classes of antibody: IgA (which includes subclasses IgA1 and IgA2), IgD, IgE, IgG (which includes subclasses IgG1, IgG2, IgG3, and IgG4), and IgM. The term is also inclusive of immunoglobulins that are less than full-length, whether wholly or partially synthetic (e.g., recombinant or chemical synthesis) or naturally produced, such as antigen binding fragment (Fab), variable fragment (Fv) containing $V_H$ and $V_L$, the single chain variable fragment (scFv) containing $V_H$ and $V_L$ linked together in one chain, as well as other antibody V region fragments, such as Fab', F (ab)$_2$, F(ab')$_2$, dsFv diabody, Fc, and Fd polypeptide fragments. Bispecific antibodies, homo-bispecific and heterobispecific, are included within the meaning of the term.

The term "immunoglobulin superfamily" or "IgSF" as used herein means the group of cell surface and soluble proteins that are involved in the recognition, binding, or adhesion processes of cells. Molecules are categorized as members of this superfamily based on shared structural features with immunoglobulins (i.e., antibodies); they all possess a domain known as an immunoglobulin domain or fold. Members of the IgSF include cell surface antigen receptors, co-receptors and co-stimulatory molecules of the immune system, molecules involved in antigen presentation to lymphocytes, cell adhesion molecules, certain cytokine receptors and intracellular muscle proteins. They are commonly associated with roles in the immune system. Proteins in the immunological synapse are often members of the IgSF. IgSF can also be classified into "subfamilies" based on shared properties such as function. Such subfamilies typically consist of from 4 to 30 IgSF members.

The terms "IgSF domain" or "immunoglobulin domain" or "Ig domain" as used herein refers to a structural domain of IgSF proteins. Ig domains are named after the immunoglobulin molecules. They contain about 70-110 amino acids and are categorized according to their size and function. Ig-domains possess a characteristic Ig-fold, which has a sandwich-like structure formed by two sheets of antiparallel beta strands. Interactions between hydrophobic amino acids on the inner side of the sandwich and highly conserved disulfide bonds formed between cysteine residues in the B and F strands, stabilize the Ig-fold. One end of the Ig domain has a section called the complementarity determining region that is important for the specificity of antibodies for their ligands. The Ig like domains can be classified (into classes) as: IgV, IgC1, IgC2, or IgI. Most Ig domains are either variable (IgV) or constant (IgC). IgV domains with 9 beta strands are generally longer than IgC domains with 7 beta strands. Ig domains of some members of the IgSF resemble IgV domains in the amino acid sequence, yet are similar in size to IgC domains. These are called IgC2 domains, while standard IgC domains are called IgC1 domains. T-cell receptor (TCR) chains contain two Ig domains in the extracellular portion; one IgV domain at the N-terminus and one IgC1 domain adjacent to the cell membrane. ICOSL contains two Ig domains: IgV and IgC.

The term "IgSF species" as used herein means an ensemble of IgSF member proteins with identical or substantially identical primary amino acid sequence. Each mammalian immunoglobulin superfamily (IgSF) member defines a unique identity of all IgSF species that belong to that IgSF member. Thus, each IgSF family member is unique from other IgSF family members and, accordingly, each species of a particular IgSF family member is unique from the species of another IgSF family member. Nevertheless, variation between molecules that are of the same IgSF species may occur owing to differences in post-translational modification such as glycosylation, phosphorylation, ubiquitination, nitrosylation, methylation, acetylation, and lipidation. Additionally, minor sequence differences within a single IgSF species owing to gene polymorphisms constitute another form of variation within a single IgSF species as do wild type truncated forms of IgSF species owing to, for example, proteolytic cleavage. A "cell surface IgSF species" is an IgSF species expressed on the surface of a cell, generally a mammalian cell.

The term "immunological activity" as used herein in the context of mammalian lymphocytes such as T-cells refers to one or more cell survival, cell proliferation, cytokine production (e.g. interferon-gamma), or T-cell cytotoxicity activities. In some cases, an immunological activity can mean the cell expression of cytokines, such as chemokines or interleukins. Assays for determining enhancement or suppression of immunological activity include the MLR (mixed lymphocyte reaction) assays measuring interferon-gamma cytokine levels in culture supernatants (Wang et al., Cancer Immunol Res. 2014 September: 2(9):846-56), SEB (staphylococcal enterotoxin B) T cell stimulation assay (Wang et al., Cancer Immunol Res. 2014 September: 2(9): 846-56), and anti-CD3 T cell stimulation assays (Li and Kurlander, J Transl Med. 2010:8: 104). Since T cell activation is associated with secretion of IFN-gamma cytokine, detecting IFN-gamma levels in culture supernatants from these in vitro human T cell assays can be assayed using commercial ELISA kits (Wu et al, Immunol Lett 2008 Apr. 15; 117(1): 57-62). Induction of an immune response results in an increase in immunological activity relative to quiescent lymphocytes. An immunomodulatory protein, such as a variant ICOSL polypeptide containing an affinity modified IgSF domain, as provided herein can in some embodiments increase or, in alternative embodiments, decrease IFN-gamma (interferon-gamma) expression in a primary T-cell assay relative to a wild-type IgSF member or IgSF domain control. Those of skill will recognize that the format of the primary T-cell assay used to determine an increase in IFN-gamma expression will differ from that employed to assay for a decrease in IFN-gamma expression. In assaying for the ability of an immunomodulatory protein or affinity modified IgSF domain of the invention to decrease IFN-gamma expression in a primary T-cell assay, a Mixed Lymphocyte Reaction (MLR) assay can be used as described in Example 6. Conveniently, a soluble form of an affinity modified IgSF domain of the invention can be employed to determine its ability to antagonize and thereby decrease the IFN-gamma expression in a MLR as likewise described in Example 6. Alternatively, in assaying for the ability of an immunomodulatory protein or affinity modified IgSF domain of the invention to increase IFN-gamma expression in a primary T-cell assay, a co-immobilization assay can be used. In a co-immobilization assay, a T-cell receptor signal, provided in some embodiments by anti-CD3 antibody, is used in conjunction with a co-immobilized affinity modified IgSF domain, such as variant ICOSL, to determine the ability to increase IFN-gamma expression relative to a wild-type IgSF domain control. Methods to assay the immunological activity of engineered cells, including to evaluate the activity of a variant ICOSL transmembrane immunomodulatory protein, are known in the art and include, but are not limited to, the ability to expand T cells following antigen stimulation, sustain T cell expansion in the absence of re-stimulation, and anti-cancer activities in appropriate animal models. Assays also include assays to assess cytotoxicity, including a standard $^{51}$Cr-release assay (see e.g. Milone et al., (2009) Molecular Therapy 17:1453-1464) or flow based cytotoxicity assays, or an impedance based cytotoxicity assay (Peper et al. (2014) Journal of Immunological Methods, 405:192-198).

An "immunomodulatory polypeptide" or "immunomodulatory protein" is a polypeptide or protein molecule that modulates immunological activity. By "modulation" or "modulating" an immune response is meant that immunological activity is either increased or decreased. An immunomodulatory protein can be a single polypeptide chain or a multimer (dimers or higher order multimers) of at least two polypeptide chains covalently bonded to each other by, for example, interchain disulfide bonds. Thus, monomeric, dimeric, and higher order multimeric polypeptides are within the scope of the defined term. Multimeric polypeptides can be homomultimeric (of identical polypeptide chains) or heteromultimeric (of non-identical polypeptide chains). An immunomodulatory protein of the invention comprises a variant ICOSL.

The term "increase" as used herein means to increase by a statistically significant amount. An increase can be at least 5%, 10%, 20%, 30%, 40%, 50%, 75%, 100%, or greater than a non-zero control value.

An "isoform" of ICOSL (inducible costimulator ligand; CD275) is one of a plurality of naturally occurring ICOSL polypeptides that differ in amino acid sequence. Isoforms can be the product of splice variants of an RNA transcript expressed by a single gene, or the expression product of highly similar but different genes yielding a functionally similar protein such as may occur from gene duplication. As used herein, the term "isoform" of ICOSL also refers to the product of different alleles of an ICOSL gene (e.g., ICOSLG).

The term "lymphocyte" as used herein means any of three subtypes of white blood cell in a mammalian immune system. They include natural killer cells (NK cells) (which function in cell-mediated, cytotoxic innate immunity), T cells (for cell-mediated, cytotoxic adaptive immunity), and B cells (for humoral, antibody-driven adaptive immunity). T cells include: T helper cells, cytotoxic T-cells, natural killer T-cells, memory T-cells, regulatory T-cells, or gamma delta T-cells. Innate lymphoid cells (ILC) are also included within the definition of lymphocyte.

The terms "mammal," or "patient" specifically includes reference to at least one of a: human, chimpanzee, rhesus monkey, cynomolgus monkey, dog, cat, mouse, or rat.

The term "membrane protein" as used herein means a protein that, under physiological conditions, is attached directly or indirectly to a lipid bilayer. A lipid bilayer that forms a membrane can be a biological membrane such as a eukaryotic (e.g., mammalian) cell membrane or an artificial (i.e., man-made) membrane such as that found on a liposome. Attachment of a membrane protein to the lipid bilayer can be by way of covalent attachment, or by way of non-covalent interactions such as hydrophobic or electrostatic interactions. A membrane protein can be an integral membrane protein or a peripheral membrane protein. Membrane proteins that are peripheral membrane proteins are non-covalently attached to the lipid bilayer or non-covalently attached to an integral membrane protein. A peripheral membrane protein forms a temporary attachment to the lipid bilayer such that under the range of conditions that are physiological in a mammal, peripheral membrane protein can associate and/or disassociate from the lipid bilayer. In contrast to peripheral membrane proteins, integral membrane proteins form a substantially permanent attachment to the membrane's lipid bilayer such that under the range of conditions that are physiological in a mammal, integral membrane proteins do not disassociate from their attachment to the lipid bilayer. A membrane protein can form an attachment to the membrane by way of one layer of the lipid bilayer (monotopic), or attached by way of both layers of the membrane (polytopic). An integral membrane protein that interacts with only one lipid bilayer is an "integral monotopic protein". An integral membrane protein that interacts with both lipid bilayers is an "integral polytopic protein" alternatively referred to herein as a "transmembrane protein".

The terms "modulating" or "modulate" as used herein in the context of an immune response, such as a mammalian immune response, refer to any alteration, such as an increase or a decrease, of existing or potential immune responses that occurs as a result of administration of an immunomodulatory polypeptide comprising a variant ICOSL of the present invention or as a result of administration of engineered cells expresses an immunomodulatory protein, such as a variant ICOSL transmembrane immunomodulatory protein of the present invention. Thus, it refers to an alteration, such as an increase or decrease, of an immune response as compared to the immune response that occurs or is present in the absence of the administration of the immunomodulatory protein comprising the variant ICOSL or cells expressing such an immunomodulatory polypeptide. Such modulation includes any induction, activation, suppression or alteration in degree or extent of immunological activity of an immune cell. Immune cells include B cells, T cells, NK (natural killer) cells, NK T cells, professional antigen-presenting cells (APCs), and non-professional antigen-presenting cells, and inflammatory cells (neutrophils, macrophages, monocytes, eosinophils, and basophils). Modulation includes any change imparted on an existing immune response, a developing immune response, a potential immune response, or the capacity to induce, regulate, influence, or respond to an immune response. Modulation includes any alteration in the expression and/or function of genes, proteins and/or other molecules in immune cells as part of an immune response. Modulation of an immune response or modulation of immunological activity includes, for example, the following: elimination, deletion, or sequestration of immune cells; induction or generation of immune cells that can modulate the functional capacity of other cells such as autoreactive lymphocytes, antigen presenting cells, or inflammatory cells; induction of an unresponsive state in immune cells (i.e., anergy); enhancing or suppressing the activity or function of immune cells, including but not limited to altering the pattern of proteins expressed by these cells. Examples include altered production and/or secretion of certain classes of molecules such as cytokines, chemokines, growth factors, transcription factors, kinases, costimulatory molecules, or other cell surface receptors or any combination of these modulatory events. Modulation can be assessed, for example, by an alteration in IFN-gamma (interferon gamma) expression relative to the wild-type ICOSL control in a primary T cell assay (see, Zhao and Ji, Exp Cell Res. 2016 Jan. 1; 340(1) 132-138). Modulation can be assessed, for example, by an alteration of an immunological activity of engineered cells, such as an alteration in in cytotoxic activity of engineered cells or an alteration in cytokine secretion of engineered cells relative to cells engineered with a wild-type ICOSL transmembrane protein.

The term "molecular species" as used herein means an ensemble of proteins with identical or substantially identical primary amino acid sequence. Each mammalian immunoglobulin superfamily (IgSF) member defines a collection of identical or substantially identical molecular species. Thus, for example, human ICOSL is an IgSF member and each human ICOSL molecule is a molecule species of ICOS. Variation between molecules that are of the same molecular species may occur owing to differences in post-translational modification such as glycosylation, phosphorylation, ubiquitination, nitrosylation, methylation, acetylation, and lipidation. Additionally, minor sequence differences within a single molecular species owing to gene polymorphisms constitute another form of variation within a single molecular species as do wild type truncated forms of a single molecular species owing to, for example, proteolytic cleavage. A "cell surface molecular species" is a molecular species expressed on the surface of a mammalian cell. Two or more different species of protein, each of which is present exclusively on one or exclusively the other (but not both) of the two mammalian cells forming the IS, are said to be in "cis" or "cis configuration" with each other. Two different species of protein, the first of which is exclusively present on one of the two mammalian cells forming the IS and the second of which is present exclusively on the second of the two mammalian cells forming the IS, are said to be in "trans" or "trans configuration." Two different species of protein each of which is present on both of the two mammalian cells forming the IS are in both cis and trans configurations on these cells.

The term, a "multimerization domain" refers to a sequence of amino acids that promotes stable interaction of a polypeptide molecule with one or more additional polypeptide molecules, each containing a complementary multimerization domain (e.g. a first multimerization domain and a second multimerization domain), which can be the same or a different multimerization domain. The interactions between complementary multimerization domains, e.g. interaction between a first multimerization domain and a second multimerization domain, form a stable protein-protein interaction to produce a multimer of the polypeptide molecule with the additional polypeptide molecule. In some cases, the multimerization domain is the same and interacts with itself to form a stable protein-protein interaction between two polypeptide chains. Generally, a polypeptide is joined directly or indirectly to the multimerization domain. Exemplary multimerization domains include the immunoglobulin sequences or portions thereof, leucine zippers, hydrophobic regions, hydrophilic regions, and compatible protein-protein interaction domains. The multimerization domain, for example, can be an immunoglobulin constant region or domain, such as, for example, the Fc domain or portions thereof from IgG, including IgG1, IgG2, IgG3 or IgG4 subtypes, IgA, IgE, IgD and IgM and modified forms thereof.

The terms "nucleic acid" and "polynucleotide" are used interchangeably to refer to a polymer of nucleic acid residues (e.g., deoxyribonucleotides or ribonucleotides) in either single- or double-stranded form. Unless specifically limited, the terms encompass nucleic acids containing known analogues of natural nucleotides and that have similar binding properties to it and are metabolized in a manner similar to naturally-occurring nucleotides. Unless otherwise indicated, a particular nucleic acid sequence also implicitly encompasses conservatively modified variants thereof (e.g., degenerate codon substitutions) and complementary nucleotide sequences as well as the sequence explicitly indicated (a "reference sequence"). Specifically, degenerate codon substitutions may be achieved by generating sequences in which the third position of one or more selected (or all) codons is substituted with mixed-base and/or deoxyinosine residues. The term nucleic acid or polynucleotide encompasses cDNA or mRNA encoded by a gene.

The term "non-competitive binding" as used herein means the ability of a protein to specifically bind simultaneously to at least two cognate binding partners. Thus, the protein is able to bind to at least two different cognate binding partners at the same time, although the binding interaction need not be for the same duration such that, in some cases, the protein is specifically bound to only one of the cognate binding partners. In some embodiments, the binding occurs under specific binding conditions. In some embodiments, the simultaneous binding is such that binding of one cognate binding partner does not substantially inhibit simultaneous binding to a second cognate binding partner. In some embodiments, non-competitive binding means that binding a second cognate binding partner to its binding site on the protein does not displace the binding of a first cognate binding partner to its binding site on the protein. Methods of assessing non-competitive binding are well known in the art such as the method described in Perez de La Lastra et al., Immunology, 1999 April: 96(4): 663-670. In some cases, in non-competitive interactions, the first cognate binding partner specifically binds at an interaction site that does not overlap with the interaction site of the second cognate binding partner such that binding of the second cognate binding partner does not directly interfere with the binding of the first cognate binding partner. Thus, any effect on binding of the cognate binding partner by the binding of the second cognate binding partner is through a mechanism other than direct interference with the binding of the first cognate binding partner. For example, in the context of enzyme-substrate interactions, a non-competitive inhibitor binds to a site other than the active site of the enzyme. Non-competitive binding encompasses uncompetitive binding interactions in which a second cognate binding partner specifically binds at an interaction site that does not overlap with the binding of the first cognate binding partner but binds to the second interaction site only when the first interaction site is occupied by the first cognate binding partner.

The term "pharmaceutical composition" refers to a composition suitable for pharmaceutical use in a mammalian subject, often a human. A pharmaceutical composition typically comprises an effective amount of an active agent (e.g., an immunomodulatory polypeptide comprising a variant ICOSL or engineered cells expressing a variant ICOSL transmembrane immunomodulatory protein) and a carrier, excipient, or diluent. The carrier, excipient, or diluent is typically a pharmaceutically acceptable carrier, excipient or diluent, respectively.

The terms "polypeptide" and "protein" are used interchangeably herein and refer to a molecular chain of two or more amino acids linked through peptide bonds. The terms do not refer to a specific length of the product. Thus, "peptides," and "oligopeptides," are included within the definition of polypeptide. The terms include post-translational modifications of the polypeptide, for example, glycosylations, acetylations, phosphorylations and the like. The terms also include molecules in which one or more amino acid analogs or non-canonical or unnatural amino acids are included as can be synthesized, or expressed recombinantly using known protein engineering techniques. In addition, proteins can be derivatized.

The term "primary T-cell assay" as used herein refers to an in vitro assay to measure interferon-gamma ("IFN-gamma") expression. A variety of such primary T-cell assays are known in the art such as that described in Example 7. In a preferred embodiment, the assay used is an anti-CD3 coimmobilizaton assay. In this assay, primary T cells are stimulated by anti-CD3 immobilized with or without additional recombinant proteins. Culture supernatants are harvested at timepoints, usually 24-72 hours. In another embodiment, the assay used is the MLR. In this assay, primary T cells are stimulated with allogeneic APC. Culture supernatants are harvested at timepoints, usually 24-72 hours. Human IFN-gamma levels are measured in culture supernatants by standard ELISA techniques. Commercial kits are available from vendors and the assay is performed according to manufacturer's recommendation.

The term "purified" as applied to nucleic acids, such as encoding immunomodulatory proteins of the invention, generally denotes a nucleic acid or polypeptide that is substantially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or protein of the invention is at least about 50% pure, usually at least about 75%, 80%, 85%, 90%, 95%, 96%, 99% or more pure (e.g., percent by weight or on a molar basis).

The term "recombinant" indicates that the material (e.g., a nucleic acid or a polypeptide) has been artificially (i.e., non-naturally) altered by human intervention. The alteration can be performed on the material within, or removed from, its natural environment or state. For example, a "recombinant nucleic acid" is one that is made by recombining nucleic acids, e.g., during cloning, affinity modification, DNA shuffling or other well-known molecular biological procedures. A "recombinant DNA molecule," is comprised of segments of DNA joined together by means of such molecular biological techniques. The term "recombinant protein" or "recombinant polypeptide" as used herein refers to a protein molecule which is expressed using a recombinant DNA molecule. A "recombinant host cell" is a cell that contains and/or expresses a recombinant nucleic acid or that is otherwise altered by genetic engineering, such as by introducing into the cell a nucleic acid molecule encoding a recombinant protein, such as a transmembrane immunomodulatory protein provided herein. Transcriptional control signals in eukaryotes comprise "promoter" and "enhancer" elements. Promoters and enhancers consist of short arrays of DNA sequences that interact specifically with cellular proteins involved in transcription. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. The terms "in operable combination," "in operable order" and "operably linked" as used herein refer to the linkage of nucleic acid sequences in such a manner or orientation that a nucleic acid molecule capable of directing the transcription of a given gene and/or the synthesis of a desired protein molecule is produced.

The term "recombinant expression vector" as used herein refers to a DNA molecule containing a desired coding sequence and appropriate nucleic acid sequences necessary for the expression of the operably linked coding sequence in a particular host cell. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the recombinant expression vector, operably linked to the coding sequence for the recombinant protein, such as a recombinant fusion protein, so that the expressed fusion protein can be secreted by the recombinant host cell, for easier isolation of the fusion protein from the cell, if desired. The term includes the vector as a self-replicating nucleic acid structure as well as the vector incorporated into the genome of a host cell into which it has been introduced. Among the vectors are viral vectors, such as lentiviral vectors.

The term "selectivity" refers to the preference of a subject protein, or polypeptide, for specific binding of one substrate, such as one cognate binding partner, compared to specific binding for another substrate, such as a different cognate binding partner of the subject protein. Selectivity can be reflected as a ratio of the binding activity (e.g. binding affinity) of a subject protein and a first substrate, such as a first cognate binding partner, (e.g., $K_{d1}$) and the binding activity (e.g. binding affinity) of the same subject protein with a second cognate binding partner (e.g., $K_{d2}$).

The term "sequence identity" as used herein refers to the sequence identity between genes or proteins at the nucleotide or amino acid level, respectively. "Sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned. Methods for the alignment of sequences for comparison are well known in the art, such methods include GAP, BESTFIT, BLAST, FASTA and TFASTA. The BLAST algorithm calculates percent sequence identity and performs a statistical analysis of the similarity between the two sequences. The software for performing BLAST analysis is publicly available through the National Center for Biotechnology Information (NCBI) website.

The term "soluble" as used herein in reference to proteins, means that the protein is not a membrane protein. In general, a soluble protein contains only the extracellular domain of an IgSF family member receptor, or a portion thereof containing an IgSF domain or domains or specific-binding fragments thereof, but does not contain the transmembrane domain and/or is not capable of being expressed on the surface of a cell. In some cases, solubility of a protein can be improved by linkage or attachment, directly or indirectly via a linker, to an Fc domain, which, in some cases, also can improve the stability and/or half-life of the protein. In some aspects, a soluble protein is an Fc fusion protein.

The term "species" as used herein with respect to poly-peptides or nucleic acids means an ensemble of molecules with identical or substantially identical sequences. Variation between polypeptides that are of the same species may occur owing to differences in post-translational modification such as glycosylation, phosphorylation, ubiquitination, nitrosy-lation, methylation, acetylation, and lipidation. Slightly truncated sequences of polypeptides that differ (or encode a difference) from the full length species at the amino-termi-nus or carboxy-terminus by no more than 1, 2, or 3 amino acid residues are considered to be of a single species. Such microheterogeneities are a common feature of manufactured proteins.

The term "specific binding fragment" as used herein in reference to a full-length wild-type mammalian ICOSL polypeptide or an IgV or an IgC domain thereof, means a polypeptide having a subsequence of an IgV and/or IgC domain and that specifically binds in vitro and/or in vivo to a mammalian ICOS and/or mammalian CD28 such as a human or murine ICOS or CD28. In some embodiments, the specific binding fragment of ICOSL IgV or ICOSL IgC is at at least 60%, 70%, 75%, 80%, 85%, 90%, 95%, 96%, 97%, 98%, or 99% the sequence length of the full-length wild-type sequence. The specific binding fragment can be altered in sequence to form a variant ICOSL of the invention.

The term "specifically binds" as used herein means the ability of a protein, under specific binding conditions, to bind to a target protein such that its affinity or avidity is at least 5 times as great, but optionally at least 10, 20, 30, 40, 50, 100, 250 or 500 times as great, or even at least 1000 times as great as the average affinity or avidity of the same protein to a collection of random peptides or polypeptides of sufficient statistical size. A specifically binding protein need not bind exclusively to a single target molecule but may specifically bind to a non-target molecule due to similarity in structural conformation between the target and non-target (e.g., paralogs or orthologs). Those of skill will recognize that specific binding to a molecule having the same function in a different species of animal (i.e., ortholog) or to a non-target molecule having a substantially similar epitope as the target molecule (e.g., paralog) is possible and does not detract from the specificity of binding which is determined relative to a statistically valid collection of unique non-targets (e.g., random polypeptides). Thus, a polypeptide of the invention may specifically bind to more than one distinct species of target molecule due to cross-reactivity. Solid-phase ELISA immunoassays or Biacore measurements can be used to determine specific binding between two proteins. Generally, interactions between two binding proteins have dissociation constants ($K_d$) less than $1\times10^{-5}$ M, and often as low as $1\times10^{-12}$ M. In certain embodiments of the present disclosure, interactions between two binding proteins have dissociation constants of $1\times10^{-6}$ M, $1\times10^{-7}$ M, $1\times10^{-8}$ M, $1\times10^{-9}$ M, $1\times10^{-10}$ M or $1\times10^{-11}$ M.

The terms "surface expresses", "surface expression" or "expressed on the surface" in reference to a mammalian cell expressing a polypeptide means that the polypeptide is expressed as a membrane protein. In some embodiments, the membrane protein is a transmembrane protein.

As used herein, "synthetic," with reference to, for example, a synthetic nucleic acid molecule or a synthetic gene or a synthetic peptide refers to a nucleic acid molecule or polypeptide molecule that is produced by recombinant methods and/or by chemical synthesis methods.

The term "targeting moiety" as used herein refers to a composition that is covalently or non-covalently attached to, or physically encapsulates, a polypeptide comprising a vari-ant ICOSL of the present invention. In some embodiments, the targeting moiety has specific binding affinity for a target molecule such as a target molecule expressed on a cell. Typically, the target molecule is localized on a specific tissue or cell-type. Targeting moieties include: antibodies, antigen binding fragment (Fab), variable fragment (Fv) containing $V_H$ and $V_L$, the single chain variable fragment (scFv) con-taining $V_H$ and $V_L$ linked together in one chain, as well as other antibody V region fragments, such as Fab', F (ab)$_2$, F(ab')$_2$, dsFv diabody, nanobodies, soluble receptors, recep-tor ligands, affinity matured receptors or ligands, as well as small molecule (<500 dalton) compositions (e.g., specific binding receptor compositions). Targeting moieties can also be attached covalently or non-covalently to the lipid mem-brane of liposomes that encapsulate a polypeptide of the present invention.

The term "transmembrane protein" as used herein means a membrane protein that substantially or completely spans a lipid bilayer such as those lipid bilayers found in a biological membrane such as a mammalian cell, or in an artificial construct such as a liposome. The transmembrane protein comprises a transmembrane domain ("transmembrane domain") by which it is integrated into the lipid bilayer and by which the integration is thermodynamically stable under physiological conditions. Transmembrane domains are gen-erally predictable from their amino acid sequence via any number of commercially available bioinformatics software applications on the basis of their elevated hydrophobicity relative to regions of the protein that interact with aqueous environments (e.g., cytosol, extracellular fluid). A trans-membrane domain is often a hydrophobic alpha helix that spans the membrane. A transmembrane protein can pass through the both layers of the lipid bilayer once or multiple times. A transmembrane protein includes the provided trans-membrane immunomodulatory proteins described herein. In addition to the transmembrane domain, a transmembrane immunomodulatory protein of the invention further com-prises an ectodomain and, in some embodiments, an endodo-main.

The terms "treating," "treatment," or "therapy" of a disease or disorder as used herein mean slowing, stopping or reversing the disease or disorders progression, as evidenced by decreasing, cessation or elimination of either clinical or diagnostic symptoms, by administration of a therapeutic composition (e.g. containing an immunomodulatory protein or engineered cells) of the invention either alone or in combination with another compound as described herein. "Treating," "treatment," or "therapy" also means a decrease in the severity of symptoms in an acute or chronic disease or disorder or a decrease in the relapse rate as for example in the case of a relapsing or remitting autoimmune disease course or a decrease in inflammation in the case of an inflammatory aspect of an autoimmune disease. As used herein in the context of cancer, the terms "treatment" or, "inhibit," "inhibiting" or "inhibition" of cancer refers to at least one of: a statistically significant decrease in the rate of tumor growth, a cessation of tumor growth, or a reduction in the size, mass, metabolic activity, or volume of the tumor, as measured by standard criteria such as, but not limited to, the Response Evaluation Criteria for Solid Tumors (RECIST), or a statistically significant increase in progression free survival (PFS) or overall survival (OS). "Preventing," "prophylaxis," or "prevention" of a disease or disorder as used in the context of this invention refers to the administration of an immunomodulatory polypeptide or engineered cells of the invention, either alone or in combination with another compound, to prevent the occurrence or onset of a disease or disorder or some or all of the symptoms of a disease or disorder or to lessen the likelihood of the onset of a disease or disorder.

The term "tumor specific antigen" or "TSA" as used herein refers to a counter-structure that is present primarily on tumor cells of a mammalian subject but generally not found on normal cells of the mammalian subject. A tumor specific antigen need not be exclusive to tumor cells but the percentage of cells of a particular mammal that have the tumor specific antigen is sufficiently high or the levels of the tumor specific antigen on the surface of the tumor are sufficiently high such that it can be targeted by anti-tumor therapeutics, such as immunomodulatory polypeptides of the invention, and provide prevention or treatment of the mammal from the effects of the tumor. In some embodiments, in a random statistical sample of cells from a mammal with a tumor, at least 50% of the cells displaying a TSA are cancerous. In other embodiments, at least 60%, 70%, 80%, 85%, 90%, 95%, or 99% of the cells displaying a TSA are cancerous.

The term "variant" (also "modified" or mutant") as used in reference to a variant ICOSL means an ICOSL, such as a mammalian (e.g., human or murine) ICOSL created by human intervention. The variant ICOSL is a polypeptide having an altered amino acid sequence, relative to a reference (e.g. unmodified) or wild-type ICOSL. The variant ICOSL is a polypeptide which differs from a reference ICOSL, such as a wild-type ICOSL isoform sequence, by one or more modifications, such as one or more amino acid substitutions, deletions, additions, or combinations thereof. For purposes herein, the variant ICOSL contains at least one affinity modified domain, whereby one or more of the amino acid differences occurs in an IgSF domain (e.g. IgV domain). A variant ICOSL can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid differences, such as amino acid substitutions. A variant ICOSL polypeptide generally exhibits at least 50%, 60%, 70%, 80%, 85%, 86%, 87%, 88%, 89%, 90%, 91%, 92%, 93%, 94%, 95%, 96%, 97%, 98%, 99% or more sequence identity to a corresponding reference (e.g. unmodified ICOSL) or wild-type, such as to the sequence of SEQ ID NO:5, a mature sequence thereof or a portion thereof containing the extracellular domain or an IgSF domain thereof. In some embodiments, a variant ICOSL polypeptide exhibits at least 50%, 60%, 70%, 80%, 85%, 86%, 87%, 88%, 89%, 90%, 91%, 92%, 93%, 94%, 95%, 96%, 97%, 98%, 99% or more sequence identity to a corresponding reference (e.g. unmodified) or wild-type ICOSL, such as a reference ICOSL set forth in SEQ ID NO:32 or SEQ ID NOs: 196 or 545. Non-naturally occurring amino acids as well as naturally occurring amino acids are included within the scope of permissible substitutions or additions. A variant ICOSL is not limited to any particular method of making and includes, for example, de novo chemical synthesis, de novo recombinant DNA techniques, or combinations thereof. A variant ICOSL of the invention specifically binds to CD28, ICOS, and/or CTLA-4 of a mammalian species. In some embodiments, the altered amino acid sequence results in an altered (i.e., increased or decreased) binding affinity or avidity to ICOS and/or CD28 compared to the reference (e.g. unmodified) or wild-type ICOSL protein. An increase or decrease in binding affinity or avidity can be determined using well known binding assays such as flow cytometry. Larsen et al., American Journal of Transplantation, Vol 5:443-453 (2005). See also, Linsley et al., Immunity, Vol. 1(9): 793-801 (1994). An increase in variant ICOSL binding affinity or avidity to ICOS and/or CD28 is to a value at least 5% greater than that of the reference (e.g. unmodified) or wild-type ICOSL and in some embodiments, at least 10%, 15%, 20%, 30%, 40%, 50%, 100% greater than that of the reference (e.g. unmodified) or wild-type ICOSL control value. A decrease in ICOSL binding affinity or avidity to ICOS and/or CD28 is to a value no greater than 95% of the of the wild-type control values, and in some embodiments no greater than 80%, 70% 60%, 50%, 40%, 30%, 20%, 10%, 5%, or no detectable binding affinity or avidity of the wild-type ICOS and/or CD28 control values. A variant ICOSL is altered in primary amino acid sequence by substitution, addition, or deletion of amino acid residues. The term "variant" in the context of variant ICOSL is not be construed as imposing any condition for any particular starting composition or method by which the variant ICOSL is created. A variant ICOSL can, for example, be generated starting from a reference ICOSL or wild type mammalian ICOSL sequence information, then modeled in silico for binding to ICOS and/or CD28, and finally recombinantly or chemically synthesized to yield a variant ICOSL of the present invention. In but one alternative example, a variant ICOSL can be created by site-directed mutagenesis of a reference (e.g. unmodified) or wild-type ICOSL. Thus, variant ICOSL denotes a composition and not necessarily a product produced by any given process. A variety of techniques including recombinant methods, chemical synthesis, or combinations thereof, may be employed.

The term "wild-type" or "natural" or "native" as used herein is used in connection with biological materials such as nucleic acid molecules, proteins (e.g., ICOSL), IgSF members, host cells, and the like, refers to those which are found in nature and not modified by human intervention.

II. VARIANT ICOSL POLYPEPTIDES

Provided herein are variant ICOSL polypeptides that exhibit altered (increased or decreased) binding activity or affinity for one or more of an ICOSL cognate binding partner. In some embodiments, the ICOSL cognate binding partner is one or more of CD28, ICOS, or CTLA-4. In some embodiments, the variant ICOSL polypeptide contains one or more amino acids modifications, such as one or more substitutions (alternatively, "mutations" or "replacements"), deletions or addition, in an immunoglobulin superfamily (IgSF) domain (IgD) relative to a wild-type or unmodified ICOSL polypeptide or a portion of a wild-type or unmodified ICOSL containing an immunoglobulin superfamily (IgSF) domain or a specific binding fragment thereof. Thus, a provided variant ICOSL polypeptide is or comprises a variant IgD (hereinafter called "vIgD") in which the one or more amino acid modifications (e.g. substitutions) is in an IgD.

In some embodiments, the IgD comprises an IgV domain or an IgC (e.g. IgC2) domain or specific binding fragment of the IgV domain or the IgC (e.g. IgC2) domain, or combinations thereof. In some embodiments, the IgD can be an IgV only, the combination of the IgV and IgC, including the entire extracellular domain (ECD), or any combination of Ig domains of ICOSL. Table 2 provides exemplary residues that correspond to IgV or IgC regions of ICOSL. In some embodiments, the variant ICOSL polypeptide contains an IgV domain or an IgC domain or specific binding fragments thereof in which the at least one of the amino acid modifications (e.g. substitutions) is in the IgV domain or IgC domain or a specific binding fragment thereof. In some embodiments, by virtue of the altered binding activity or affinity, the IgV domain or IgC domain is an affinity-modified IgSF domain.

In some embodiments, the variant is modified in one more IgSF domains relative to the sequence of a reference (e.g., unmodified) ICOSL sequence. In some embodiments, the reference (e.g., unmodified) ICOSL sequence is a wild-type ICOSL. In some embodiments, the reference (e.g., unmodified) or wild-type ICOSL has the sequence of a native ICOSL or an ortholog thereof. In some embodiments, the reference (e.g., unmodified) or wild-type ICOSL is or comprises the extracellular domain (ECD) of ICOSL or a portion thereof containing one or more IgSF domain (see Table 2). In some embodiments, the extracellular domain of a reference (e.g., unmodified) or wild-type ICOSL polypeptide comprises an IgV domain and an IgC domain or domains. However, the variant ICOSL polypeptide need not comprise both the IgV domain and the IgC domain or domains. In some embodiments, the variant ICOSL polypeptide comprises or consists essentially of the IgV domain or a specific binding fragment thereof. In some embodiments, the variant ICOSL polypeptide comprises or consists essentially of the IgC domain or specific binding fragments thereof. In some embodiments, the variant ICOSL is soluble and lacks a transmembrane domain. In some embodiments, the variant ICOSL further comprises a transmembrane domain and, in some cases, also a cytoplasmic domain.

In some embodiments, the reference (e.g., unmodified) or wild-type ICOSL sequence is a mammalian ICOSL sequence. In some embodiments, the reference (e.g., unmodified) or wild-type ICOSL sequence can be a mammalian ICOSL that includes, but is not limited to, human, mouse, cynomolgus monkey, or rat. In some embodiments, the reference (e.g., unmodified) or wildtype ICOSL sequence is human.

In some embodiments, the reference (e.g., unmodified) or wild-type ICOSL sequence has (i) the sequence of amino acids set forth in SEQ ID NO:5 or a mature form thereof lacking the signal sequence, (ii) a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:5 or the mature form thereof, or (iii) is a portion of (i) or (ii) containing an IgV domain or IgC domain or specific binding fragments thereof.

In some embodiments, the reference ICOSL sequence is or comprises an extracellular domain of the ICOSL or a portion thereof. In some embodiments, the reference or wild-type ICOSL polypeptide comprises the amino acid sequence set forth in SEQ ID NO:32, or an ortholog thereof.

```
                                         (SEQ ID NO: 32)
DTQEKEVRAMVGSDVELSCACPEGSRFDLNDVYVYWQTSESKTVVTYHIPQ

NSSLENVDSRYRNRALMSPAGMLRGDFSLRLFNVTPQDEQKFHCLVLSQSL

GFQEVLSVEVTLHVAANFSVPVVSAPHSPSQDELTFTCTSINGYPRPNVYW

INKTDNSLLDQALQNDTVFLNMRGLYDVVSVLRIARTPSVNIGCCIENVLL

QQNLTVGSQTGNDIGERDKITENPVSTGEKNAAT
```

In some cases, the reference (e.g., unmodified) or wild-type ICOSL polypeptide can comprise (i) the sequence of amino acids set forth in SEQ ID NO:32, (ii) a sequence of amino acids that has at least about 85%, 86%, 87%, 88%, 89%, 90%, 91%, 92%, 93%, 94%, 95%, 96%, 97%, 98%, 99% sequence identity to SEQ ID NO: 32, or (iii) is a specific binding fragment of the sequence of (i) or (ii) comprising an IgV domain or an IgC domain.

In some embodiments, the reference ICOSL polypeptide comprises a truncated extracellular domain comprising a C-terminal truncation with reference to the reference ICOSL extracellular domain sequence set forth in SEQ ID NO:32. In some embodiments, the C-terminal truncation is of at least 10, at least 20, at least 30, at least 40, at least 50, at least 60, at least 70, at least 80, at least 90, at least 100, at least 125 amino acid residues. In some embodiments, the C-terminal truncation is of at least 1, at least 5 at least 10, at least 15, at least 20, at least 25, at least 30, at least 35 amino acid residues. In some embodiments, the ICOSL polypeptide comprising a C-terminal truncation does not contain, beyond the C-terminus of the truncation point, contiguous amino acid residues of a wild-type ICOSL. Hence, among provided ICOSL reference sequences are those that are shorter than the full extracellular domain of a wild-type ICOSL, e.g. set forth in SEQ ID NO: 32. In some embodiments, the ICOSL polypeptide comprising a C-terminal truncation does not contain or is not fused to amino acid residues of an ICOSL domain beyond the extracellular domain.

In some embodiments, the ICOSL reference polypeptide is altered, such as mutated or deleted, in one or more protease cleavage site. As found herein, wild-type ICOSL polypeptide contains a protease cleavage site that, in some cases, results in cleavage of the protein upon expression in cells, e.g. Chinese Hamster Ovary cells, thereby resulting in a heterogeneous product of multiple species, including species of different lengths or sizes. For example, cleavage of the ICOSL polypeptide may occur at the LQQN/LT protease cleavage site between residues 207 and 208 of SEQ ID NO: 32 ("/" indicates potential cleavage site). In some embodiments, the ICOSL reference polypeptide is altered in or lacks a protease cleavage site set forth as amino acids 204-209 of SEQ ID NO:32. In some embodiments, a truncated ICOSL polypeptide is more resistant to protease cleavage compared to a wild-type or non-truncated ICOSL polypeptide. Exemplary truncated ICOSL polypeptide ECD truncations lacking all or a portion of the LQQN/LT protease cleavage site (designated Truncations #2, #3, #4, #5, #6, #7, or #8) are provided in SEQ ID NOs: 600-606.

```
Truncation #2:
                                         (SEQ ID NO: 600)
DTQEKEVRAMVGSDVELSCACPEGSRFDLNDVYVYWQTSESKTVVTYHIPQNSSLENVDSRY

RNRALMSPAGMLRGDFSLRLFNVTPQDEQKFHCLVLSQSLGFQEVLSVEVTLHVAANFSVPV

VSAPHSPSQDELTFTCTSINGYPRPNVYWINKTDNSLLDQALQNDTVFLNMRGLYDVVSVLRI

ARTPSVNIGCCIENVLLQQNL
```

-continued

Truncation #3:
(SEQ ID NO: 601)
DTQEKEVRAMVGSDVELSCACPEGSRFDLNDVYVYWQTSESKTVVTYHIPQNSSLENVDSRY

RNRALMSPAGMLRGDFSLRLFNVTPQDEQKFHCLVLSQSLGFQEVLSVEVTLHVAANFSVPV

VSAPHSPSQDELTFTCTSINGYPRPNVYWINKTDNSLLDQALQNDTVFLNMRGLYDVVSVLRI

ARTPSVNIGCCIENVLLQQNLTVGSQ

Truncation #4:
(SEQ ID NO: 602)
DTQEKEVRAMVGSDVELSCACPEGSRFDLNDVYVYWQTSESKTVVTYHIPQNSSLENVDSRY

RNRALMSPAGMLRGDFSLRLFNVTPQDEQKFHCLVLSQSLGFQEVLSVEVTLHVAANFSVPV

VSAPHSPSQDELTFTCTSINGYPRPNVYWINKTDNSLLDQALQNDTVFLNMRGLYDVVSVLRI

ARTPSVNIGCCIENVLLQQN

Truncation #5:
(SEQ ID NO: 603)
DTQEKEVRAMVGSDVELSCACPEGSRFDLNDVYVYWQTSESKTVVTYHIPQNSSLENVDSRY

RNRALMSPAGMLRGDFSLRLFNVTPQDEQKFHCLVLSQSLGFQEVLSVEVTLHVAANFSVPV

VSAPHSPSQDELTFTCTSINGYPRPNVYWINKTDNSLLDQALQNDTVFLNMRGLYDVVSVLRI

ARTPSVNIGCCIENVLLQQ

Truncation #6:
(SEQ ID NO: 604)
DTQEKEVRAMVGSDVELSCACPEGSRFDLNDVYVYWQTSESKTVVTYHIPQNSSLENVDSRY

RNRALMSPAGMLRGDFSLRLFNVTPQDEQKFHCLVLSQSLGFQEVLSVEVTLHVAANFSVPV

VSAPHSPSQDELTFTCTSINGYPRPNVYWINKTDNSLLDQALQNDTVFLNMRGLYDVVSVLRI

ARTPSVNIGCCIENVLL

Truncation #7:
(SEQ ID NO: 605)
DTQEKEVRAMVGSDVELSCACPEGSRFDLNDVYVYWQTSESKTVVTYHIPQNSSLENVDSRY

RNRALMSPAGMLRGDFSLRLFNVTPQDEQKFHCLVLSQSLGFQEVLSVEVTLHVAANFSVPV

VSAPHSPSQDELTFTCTSINGYPRPNVYWINKTDNSLLDQALQNDTVFLNMRGLYDVVSVLRI

ARTPSVNIGCCIEN

Truncation #8:
(SEQ ID NO: 606)
DTQEKEVRAMVGSDVELSCACPEGSRFDLNDVYVYWQTSESKTVVTYHIPQNSSLENVDSRY

RNRALMSPAGMLRGDFSLRLFNVTPQDEQKFHCLVLSQSLGFQEVLSVEVTLHVAANFSVPV

VSAPHSPSQDELTFTCTSINGYPRPNVYWINKTDNSLLDQALQNDTVFLNMRGLYDVVSVLRI

ARTPSVNIGCCIENVLLQQNLT

In some embodiments, the ICOSL reference polypeptide is altered in one or more amino acids corresponding to amino acids 204-209 with reference to SEQ ID NO:32. In some embodiments, the variant ICOSL polypeptide has one or more amino acid modification, e.g., substitution in a reference ICOSL or specific binding fragment thereof corresponding to position(s) 207 and/or 208 with reference to numbering of SEQ ID NO:32. In some embodiments, the variant ICOSL polypeptide has one or more amino acid modification, e.g., substitution, selected from N207A, N207G, L208G, or a conservative amino acid modification, e.g., substitution thereof. In some embodiments, the one or more amino acid modification, e.g., substitution is N207A/ L208G or N207G/L208G. In some embodiments, the full length reference ECDs or truncated reference ECDs of the variant ICOSL polypeptide are modified to contain one or more amino acid modifications, e.g., substitutions, selected from N207A, N207G, L208G, or a conservative amino acid modification. Exemplary full length or truncated reference ECDs with one or more modifications are set forth in SEQ ID NOs: 607-628. Exemplary reference sequences containing mutations at cleavage site N207 and/or L208 with reference to positions are set forth in SEQ ID NO: 32 are set forth in SEQ ID NOs: 624-628. In some cases, the provided modifications may reduce protease cleavage of the ICOSL polypeptide, such as cleavage that may occur at the LQQN/ LT protease cleavage site.

In some embodiments, combinations of the above truncation and modification strategies can be employed in a reference ICOSL ECD sequence. In some embodiments, the modifications e.g., substitutions, are made in a truncated reference ICOSL polypeptide such as exemplary reference ICOSL sequence set forth in SEQ ID NOs: 600-606. Exemplary variant ICOSL polypeptide sequences with modifications at the potential protease cleavage site(s) N207 and/or L208 are set forth in SEQ ID NOs: 607-628. In some embodiments, the variant ICOSL polypeptide exhibits decreased protease cleavage compared to wild-type ICOSL polypeptide, such as containing the ECD sequence set forth in SEQ ID NO:32.

In some embodiments, the reference (e.g., unmodified) or wildtype ICOSL polypeptide comprises an IgV domain or an IgC domain, or a specific binding fragment thereof. In some embodiments, an ICOSL reference polypeptide containing an IgV domain comprises the amino acid sequence set forth in SEQ ID NO: 196 (corresponding to amino acid residues 19-129 of SEQ ID NO:5), or an ortholog thereof.

```
                              (SEQ ID NO: 196)
DTQEKEVRAMVGSDVELSCACPEGSRFDLNDVYVYWQTSESKTVVTYHI
PQNSSLENVDSRYRNRALMSPAGMLRGDFSLRLFNVTPQDEQKFHCLVL
SQSLGFQEVLSVE
```

In some embodiments, the reference ICOSL polypeptide containing the IgV domain contains at least amino acids 1-112, 1-113, 1-114, 1-115, 1-116, 1-117, 1-118, 1-119, 1-120, 1-121, 1-122, with reference to numbering set forth in SEQ ID NO:32. In some embodiments, an ICOSL reference polypeptide containing an IgV domain comprises the amino acid sequence set forth in SEQ ID NO: 545 (corresponding to amino acid residues 19-140 of SEQ ID NO:5), or an ortholog thereof. In some embodiments, the IgV domain is the only IgSF domain of the ICOSL reference polypeptide.

```
                              (SEQ ID NO: 545)
DTQEKEVRAMVGSDVELSCACPEGSRFDLNDVYVYWQTSESKTVVTYHI
PQNSSLENVDSRYRNRALMSPAGMLRGDFSLRLFNVTPQDEQKFHCLVL
SQSLGFQEVLSVEVTLHVAANFSV
```

In some embodiments, the IgV domain of the reference (e.g., unmodified) or wild-type ICOSL polypeptide can contain (i) the sequence of amino acids set forth in SEQ ID NO: 196 or 545, (ii) a sequence of amino acids that has at least about 85%, 86%, 87%, 88%, 89%, 90%, 91%, 92%, 93%, 94%, 95%, 96%, 97%, 98%, 99% sequence identity to SEQ ID NO: 196 or 545, or (iii) a specific binding fragment of the sequence of amino acids set forth in SEQ ID NO: 196 or 545 or a specific binding fragment of a sequence of (i) or (ii). In some embodiments, the reference (e.g., unmodified) IgV domain is capable of binding one or more ICOSL cognate binding proteins, such as one or more of CD28, ICOS, or CTLA-4.

In some embodiments, the IgC domain of the reference (e.g., unmodified) or wild-type ICOSL polypeptide comprises the amino acid sequence set forth as residues 141-227 of SEQ ID NO: 5, or an ortholog thereof. For example, the IgC domain of the reference (e.g., unmodified) or wild-type ICOSL polypeptide can contain (i) the sequence of amino acids set forth residues 141-227 of SEQ ID NO: 5, (ii) a sequence of amino acids that has at least about 85%, 86%, 87%, 88%, 89%, 90%, 91%, 92%, 93%, 94%, 95%, 96%, 97%, 98%, 99% sequence identity to residues 141-227 of SEQ ID NO: 5, or (iii) (i) or (ii). In some embodiments, the reference IgV domain is capable of binding one or more ICOSL cognate binding proteins.

In some embodiments, the reference (e.g., unmodified) or wild-type ICOSL polypeptide contains a specific binding fragment of ICOSL, such as a specific binding fragment of the IgV domain or the IgC domain. In some embodiments the specific binding fragment can bind CD28, ICOS, and/or CTLA-4. The specific binding fragment can have an amino acid length of at least 50 amino acids, such as at least 60, 70, 80, 90, 100, or 110 amino acids. In some embodiments, the specific binding fragment of the IgV domain contains an amino acid sequence that is at least about 85%, 86%, 87%, 88%, 89%, 90%, 91%, 92%, 93%, 94%, 95%, 96%, 97%, 98%, 99% of the length of the IgV domain set forth as amino acids 19-129 of SEQ ID NO: 5. In some embodiments, the specific binding fragment of the IgC domain comprises an amino acid sequence that is at least about 85%, 86%, 87%, 88%, 89%, 90%, 91%, 92%, 93%, 94%, 95%, 96%, 97%, 98%, 99% of the length of the IgC domain set forth as amino acids 141-227 of SEQ ID NO: 5.

In some embodiments, the variant ICOSL polypeptide comprises the ECD domain, a truncated ECD domain, or a portion thereof comprising one or more affinity modified IgSF domains. In some embodiments, the variant ICOSL polypeptides can comprise an IgV domain or an IgC domain, in which one or more of the IgSF domains (IgV or IgC) or a specific binding fragment of the IgV domain or a specific binding fragment of the IgC domain contains the one or more amino acid modifications (e.g. substitutions). In some embodiments, the variant ICOSL polypeptides can comprise an IgV domain and an IgC domain, or a specific binding fragment of the IgV domain and a specific binding fragment of the IgC domain. In some embodiments, the variant ICOSL polypeptide comprises a full-length IgV domain. In some embodiments, the variant ICOSL polypeptide comprises a full-length IgC domain. In some embodiments, the variant ICOSL polypeptide comprises a specific binding fragment of the IgV domain. In some embodiments, the variant ICOSL polypeptide comprises a specific binding fragment of the IgC domain. In some embodiments, the variant ICOSL polypeptide comprises a full-length IgV domain and a full-length IgC domain. In some embodiments, the variant ICOSL polypeptide comprises a full-length IgV domain and a specific binding fragment of an IgC domain. In some embodiments, the variant ICOSL polypeptide comprises a specific binding fragment of an IgV domain and a full-length IgC domain. In some embodiments, the variant ICOSL polypeptide comprises a specific binding fragment of an IgV domain and a specific binding fragment of an IgC domain.

In any of such embodiments, the one or more amino acid modifications (e.g., substitutions) of the variant ICOSL polypeptides can be located in any one or more of the ICOSL polypeptide domains. For example, in some embodiments, one or more amino acid substitutions are located in the extracellular domain (ECD) of the variant ICOSL polypeptide, such as set forth in SEQ ID NO: 32. In some embodiments, one or more amino acid substitutions are located in the IgV domain or specific binding fragment of the IgV domain. In some embodiments, one or more amino acid modifications (e.g. substitutions) are located in the IgC domain or specific binding fragment of the IgC domain.

Generally, each of the various attributes of polypeptides are separately disclosed below (e.g., soluble, secretable and membrane bound polypeptides, affinity of ICOSL for CD28, ICOS, and CTLA-4, number of variations per polypeptide chain, number of linked polypeptide chains, the number and nature of amino acid alterations per variant ICOSL, etc.). However, as will be clear to the skilled artisan, any particular polypeptide can comprise a combination of these independent attributes. It is understood that reference to amino acids, including to a specific sequence set forth as a SEQ ID NO used to describe domain organization of an IgSF domain are for illustrative purposes and are not meant to limit the scope of the embodiments provided. It is understood that polypeptides and the description of domains thereof are theoretically derived based on homology analysis and alignments with similar molecules. Thus, the exact locus can vary, and is not necessarily the same for each protein. Hence, the specific IgSF domain, such as specific IgV domain or IgC domain, can be several amino acids (such as one, two, three or four) longer or shorter.

Further, various embodiments of the invention as discussed below are frequently provided within the meaning of a defined term as disclosed above. The embodiments described in a particular definition are therefore to be interpreted as being incorporated by reference when the defined term is utilized in discussing the various aspects and attributes described herein. Thus, the headings, the order of presentation of the various aspects and embodiments, and the separate disclosure of each independent attribute is not meant to be a limitation to the scope of the present disclosure.

A. Exemplary Modifications

Provided herein are variant ICOSL polypeptides containing at least one affinity-modified IgSF domain (e.g., IgV or IgC) or a specific binding fragment thereof in an IgSF domain contained in a reference (e.g., unmodified) or wild-type ICOSL polypeptide such that the variant ICOSL polypeptide exhibits altered (increased or decreased) binding activity or affinity for one or more ligands ICOS, CD28, or CTLA-4 compared to a reference (e.g., unmodified) or wild-type ICOSL polypeptide. In some embodiments, a variant ICOSL polypeptide has a binding affinity for CD28, ICOS, and/or CTLA-4 that differs from that of a reference (e.g., unmodified) or wild-type ICOSL polypeptide control sequence as determined by, for example, solid-phase ELISA immunoassays, flow cytometry or Biacore assays. In some embodiments, the variant ICOSL polypeptide has an increased binding affinity for CD28, ICOS, and/or CTLA-4. In some embodiments, the variant ICOSL polypeptide has a decreased binding affinity for CD28, ICOS, and/or CTLA-4, relative to a reference (unmodified) or wild-type ICOSL polypeptide. The CD28, ICOS and/or the CTLA-4 can be a mammalian protein, such as a human protein or a murine protein.

Binding affinities for each of the cognate binding partners are independent; that is, in some embodiments, a variant ICOSL polypeptide has an increased binding affinity for one, two or three of CD28, ICOS, and/or CTLA-4, and a decreased binding affinity for one, two or three of CD28, ICOS, and CTLA-4, relative to a reference (e.g., unmodified) or wild-type ICOSL polypeptide.

In some embodiments, the variant ICOSL polypeptide has an increased binding affinity for CD28, relative to a reference (e.g., unmodified) or wildtype ICOSL polypeptide. In some embodiments, the variant ICOSL polypeptide has an increased binding affinity for ICOS, relative to a reference (e.g., unmodified) or wild-type ICOSL polypeptide. In some embodiments, the variant ICOSL polypeptide has an increased binding affinity for CTLA-4, relative to a reference (e.g., unmodified) or wild-type ICOSL polypeptide. In some embodiments, the variant ICOSL polypeptide has a decreased binding affinity for CD28, relative to a reference (e.g., unmodified) or wild-type ICOSL polypeptide. In some embodiments, the variant ICOSL polypeptide has a decreased binding affinity for ICOS, relative to a reference (e.g., unmodified) or wild-type ICOSL polypeptide. In some embodiments, the variant ICOSL polypeptide has a decreased binding affinity for CTLA-4, relative to a reference (e.g., unmodified) or wild-type ICOSL polypeptide.

In some embodiments, the variant ICOSL polypeptide has an increased binding affinity for CD28 and ICOS, relative to a reference (e.g., unmodified) or wild-type ICOSL polypeptide. In some embodiments, the variant ICOSL polypeptide has an increased binding affinity for CD28 and a decreased binding affinity for ICOS, relative to a reference (e.g., unmodified) or wild-type ICOSL polypeptide. In some embodiments, the variant ICOSL polypeptide has a decreased binding affinity for CD28 and ICOS, relative to a reference (e.g., unmodified) or wild-type ICOSL polypeptide. In some embodiments, the variant ICOSL polypeptide has a decreased binding affinity for CD28 and an increased binding affinity for ICOS, relative to a reference (e.g., unmodified) or wild-type ICOSL polypeptide.

In some embodiments, the variant ICOSL polypeptide has an increased binding affinity for CD28 and CTLA-4, relative to a reference (e.g., unmodified) or wild-type ICOSL polypeptide. In some embodiments, the variant ICOSL polypeptide has an increased binding affinity for CD28 and a decreased binding affinity for CTLA-4, relative to a reference (e.g., unmodified) or wild-type ICOSL polypeptide. In some embodiments, the variant ICOSL polypeptide has a decreased binding affinity for CD28 and CTLA-4, relative to a reference (e.g., unmodified) or wild-type ICOSL polypeptide. In some embodiments, the variant ICOSL polypeptide has a decreased binding affinity for CD28 and an increased binding affinity for CTLA-4, relative to a reference (e.g., unmodified) or wild-type ICOSL polypeptide.

In some embodiments, the variant ICOSL polypeptide has an increased binding affinity for ICOS and CTLA-4, relative to a reference (e.g., unmodified) or wild-type ICOS polypeptide. In some embodiments, the variant ICOSL polypeptide has an increased binding affinity for ICOS and a decreased binding affinity for CTLA-4, relative to a reference (e.g., unmodified) or wild-type ICOSL polypeptide. In some embodiments, the variant ICOSL polypeptide has a decreased binding affinity for ICOS and CTLA-4, relative to a reference (e.g., unmodified) or wild-type ICOSL polypeptide. In some embodiments, the variant ICOSL polypeptide has a decreased binding affinity for ICOS and an increased binding affinity for CTLA-4, relative to a reference (e.g., unmodified) or wild-type ICOSL polypeptide.

In some embodiments, the variant ICOSL polypeptide has an increased binding affinity for CD28, ICOS, and CTLA-4, relative to a reference (e.g., unmodified) or wild-type ICOSL polypeptide. In some embodiments, the variant ICOSL polypeptide has an increased binding affinity for CD28 and ICOS, and a decreased binding affinity for CTLA-4, relative to a reference (e.g., unmodified) or wild-type ICOSL polypeptide. In some embodiments, the variant ICOSL polypeptide has an increased binding affinity for CD28 and CTLA-4, and a decreased binding affinity for ICOS, relative to a reference (e.g., unmodified) or wild-type ICOSL polypeptide. In some embodiments, the variant ICOSL polypeptide has a decreased binding affinity for CD28 and ICOS, and an increased binding affinity for CTLA-4, relative to a reference (e.g., unmodified) or wild-type ICOSL polypeptide. In some embodiments, the variant ICOSL polypeptide has a decreased binding affinity for CD28 and an increased binding affinity for ICOS and CTLA-4, relative to a reference (e.g., unmodified) or wild-type ICOSL polypeptide. In some embodiments, the variant ICOSL polypeptide has an increased binding affinity for CD28, and a decreased binding affinity for ICOS and CTLA-4, relative to a reference (e.g., unmodified) or wild-type ICOSL polypeptide. In some embodiments, the variant ICOSL polypeptide has a decreased binding affinity for CD28, CTLA-4, and ICOS, relative to a reference (e.g., unmodified) or wild-type ICOSL polypeptide. In some embodiments, the variant ICOSL polypeptide has a decreased binding affinity for CD28, and an increased binding affinity for ICOS and CTLA-4, relative to a reference (e.g., unmodified) or wild-type ICOSL polypeptide.

In some embodiments, a variant ICOSL polypeptide with increased or greater binding affinity to CD28, ICOS, and/or CTLA-4 will have an increase in binding affinity relative to the reference (e.g., unmodified) or wild-type ICOSL polypeptide control of at least about 5%, such as at least about 10%, 15%, 20%, 25%, 35%, or 50% for the CD28, ICOS, and/or CTLA-4. In some embodiments, the increase in binding affinity relative to the reference (e.g., unmodified) or wild-type ICOSL polypeptide is more than 1.2-fold, 1.5-fold, 2-fold, 3-fold, 4-fold, 5-fold, 6-fold, 7-fold, 8-fold, 9-fold, 10-fold, 20-fold, 30-fold 40-fold or 50-fold. In such examples, the reference (e.g., unmodified) or wild-type ICOSL polypeptide has the same sequence as the variant ICOSL polypeptide except that it does not contain the one or more amino acid modifications (e.g., substitutions).

In some embodiments, a variant ICOSL polypeptide with reduced or decreased binding affinity to CD28, ICOS, and/or CTLA-4 will have decrease in binding affinity relative to the reference (e.g., unmodified) or wild-type ICOSL polypeptide control of at least 5%, such as at least about 10%, 15%, 20%, 30%, 40%, 50%, 60%, 70%, 80%, 90% or more for the CD28, ICOSL, and/or CTLA-4. In some embodiments, the decrease in binding affinity relative to the reference (e.g., unmodified) or wild-type ICOSL polypeptide is more than 1.2-fold, 1.5-fold, 2-fold, 3-fold, 4-fold, 5-fold, 6-fold, 7-fold, 8-fold, 9-fold, 10-fold, 20-fold, 30-fold 40-fold or 50-fold. In such examples, the reference (e.g., unmodified) or wild-type ICOSL polypeptide has the same sequence as the variant ICOSL polypeptide except that it does not contain the one or more amino acid modifications, e.g. substitutions.

In some embodiments, the equilibrium dissociation constant ($K_d$) of any of the foregoing embodiments to CD28, ICOS, and/or CTLA-4 can be less than $1\times10^{-5}$ M, $1\times10^{-6}$ M, $1\times10^{-7}$ M, $1\times10^{-8}$ M, $1\times10^{-9}$ M, $1\times10^{-10}$ M or $1\times10^{-11}$M, or $1\times10^{-12}$ M.

In some embodiments, a variant ICOSL polypeptide has an increased or greater binding affinity to CD28. In some embodiments, a variant ICOSL polypeptide with increased or greater binding affinity to CD28 will have an increase in binding affinity relative to the reference (e.g., unmodified) or wild-type ICOSL polypeptide control of at least about 25%, such as at least about 30%, 40%, 50%, or 60% for CD28. In some embodiments, a variant ICOSL polypeptide with increased or greater binding affinity to CD28 has an equilibrium dissociation constant ($K_d$) of less than 200 pM, 300 pM, 400 pM, 500 pM, or 600 pM for CD28. In some embodiments, the variant polypeptide specifically binds to the ectodomain of one of ICOS, CD28 or CTLA4 with increased selectivity compared to the reference (e.g., unmodified) or wild-type ICOSL. In some embodiments, the increased selectivity is for CD28. In some embodiments, the increased selectivity comprises a greater ratio of binding of the variant ICOSL polypeptide for one cognate binding partner selected from among ICOS, CD28 and CTLA4 versus another of the cognate binding partner compared to the ratio of binding of the reference (e.g., unmodified) or wild-type ICOSL polypeptide for the one cognate binding partner versus the another of the cognate binding partner. In some embodiments, the ratio is greater by at least or at least about 1.5-fold, 2.0-fold, 3.0-fold, 4.0-fold, 5-fold, 10-fold, 15-fold, 20-fold, 30-fold, 40-fold, 50-fold or more.

The reference (e.g., unmodified) or wild-type ICOSL sequence does not necessarily have to be used as a starting composition to generate variant ICOSL polypeptides described herein. Therefore, use of the term "modification", such as "substitution" does not imply that the present embodiments are limited to a particular method of making variant ICOSL polypeptides. Variant ICOSL polypeptides can be made, for example, by de novo peptide synthesis and thus does not necessarily require a modification, such as a "substitution", in the sense of altering a codon to encode for the modification, e.g. substitution. This principle also extends to the terms "addition" and "deletion" of an amino acid residue which likewise do not imply a particular method of making. The means by which the variant ICOSL polypeptides are designed or created is not limited to any particular method. In some embodiments, however, a reference (e.g., unmodified) or wild-type ICOSL encoding nucleic acid is mutagenized from reference (e.g., unmodified) or wild-type ICOSL genetic material and screened for desired specific binding affinity and/or induction of IFN-gamma expression or other functional activity. In some embodiments, a variant ICOSL polypeptide is synthesized de novo utilizing protein or nucleic acid sequences available at any number of publicly available databases and then subsequently screened. The National Center for Biotechnology Information provides such information and its website is publicly accessible via the internet as is the UniProtKB database as discussed previously.

Unless stated otherwise, as indicated throughout the present disclosure, the amino acid modification(s) are designated by amino acid position number corresponding to the numbering of positions of the reference ECD sequence set forth in SEQ ID NO:32. It is within the level of a skilled artisan to identify the corresponding position of a modification, e.g. amino acid substitution, in an ICOSL polypeptide, including portion thereof containing an IgSF domain (e.g. IgV) thereof, such as by alignment of a reference sequence (e.g. SEQ ID NO:196, 545, 600-628) with SEQ ID NO:32. In the listing of modifications throughout this disclosure, the amino acid position is indicated in the middle, with the corresponding reference (e.g. unmodified or wild-type) amino acid listed before the number and the identified variant amino acid substitution listed after the number. If the modification is a deletion of the position a "del" is indicated and if the modification is an insertion at the position an "ins" is indicated. In some cases, an insertion is listed with the amino acid position indicated in the middle, with the corresponding reference amino acid listed before and after the number and the identified variant amino acid insertion listed after the unmodified (e.g. wild-type) amino acid.

In some embodiments, the variant ICOSL polypeptide has one or more amino acid modification, e.g. substitution in a reference (e.g., unmodified) or wild-type ICOSL sequence. The one or more amino acid modification, e.g. substitution, can be in the ectodomain (extracellular domain) of the reference (e.g., unmodified) or wild-type ICOSL sequence. In some embodiments, the one or more amino acid modi-fication, e.g. substitution is in the IgV domain or specific binding fragment thereof. In some embodiments, the one or more amino acid modification, e.g. substitution is in the IgC domain or specific binding fragment thereof. In some embodiments of the variant ICOSL polypeptide, some of the one or more amino acid modification, e.g. substitution is in the IgV domain or a specific binding fragment thereof, and some of the one or more amino acid modification, e.g. substitution are in the IgC domain or a specific binding fragment thereof.

In some embodiments, the variant ICOSL polypeptide has up to 1, 2, 3, 4, 5, 6, 7, 8, 9, 10, 11, 12, 13, 14, 15, 16, 17, 18, 19, or 20 amino acid modification(s), e.g. substitution. The modification, e.g. substitution can be in the IgV domain or the IgC domain. In some embodiments, the variant ICOSL polypeptide has up to 1, 2, 3, 4, 5, 6, 7, 8, 9, 10, 11, 12, 13, 14, 15, 16, 17, 18, 19, or 20 amino acid substitutions in the IgV domain or specific binding fragment thereof. In some embodiments, the variant ICOSL polypeptide has up to 1, 2, 3, 4, 5, 6, 7, 8, 9, 10, 11, 12, 13, 14, 15, 16, 17, 18, 19, or 20 amino acid substitutions in the IgC domain or specific binding fragment thereof. In some embodiments, the variant ICOSL polypeptide has at least about 85%, 86%, 86%, 88%, 89%, 90%, 91%, 92%, 93%, 94%, 95%, 96%, 97%, 98%, or 99% sequence identity with the reference (e.g., unmodified) or wild-type ICOSL polypeptide or specific binding fragment thereof, such as with the amino acid sequence of SEQ ID NO: 32, 196 or 545.

In some embodiments, the variant ICOSL polypeptide has one or more amino acid modification, e.g. substitution in a reference ICOSL or specific binding fragment there of corresponding to position(s) 10, 11, 13, 16, 18, 20, 25, 27, 30, 33, 37, 42, 43, 47, 52, 54, 57, 61, 62, 67, 71, 72, 74, 77, 78, 75, 80, 84, 89, 90, 92, 93, 94, 96, 97, 98, 99, 100, 102, 103, 107, 109, 110, 111, 113, 115, 116, 117, 119, 120, 121, 122, 126, 129, 130, 132, 133, 135, 138, 139, 140, 142, 143, 144, 146, 151, 152, 153, 154, 155, 156, 158, 161, 166, 168, 172, 173, 175, 190, 192, 193, 194, 198, 201, 203, 207, 208, 210, 212, 217, 218, 220, 221, 224, 225, or 227 with reference to numbering of SEQ ID NO:32. In some embodiments, the variant ICOSL polypeptide has one or more amino acid modification, e.g. substitution in a reference ICOSL or specific binding fragment there of corresponding to position(s) 10, 11, 13, 16, 18, 20, 25, 26, 27, 30, 33, 37, 38, 42, 43, 47, 52, 54, 57, 61, 62, 67, 71, 72, 74, 75, 77, 78, 80, 84, 89, 90, 92, 93, 94, 96, 97, 98, 99, 100, 102, 103, 107, 109, 110, 111, 113, 115, 116, 117, 119, 120, 121, 122, 126, 129, 130, 132, 133, 135, 137, 138, 139, 140, 142, 143, 144, 146, 151, 152, 153, 154, 155, 156, 158, 161, 164, 166, 168, 172, 173, 175, 190, 192, 193, 194, 198, 201, 203, 207, 208, 210, 212, 217, 218, 220, 221, 224, 225, or 227 with reference to numbering of SEQ ID NO:32.

In some embodiments, such variant ICOSL polypeptides exhibit altered binding affinity to one or more of CD28, ICOS, and/or CTLA-4 compared to the reference (e.g., unmodified) or wild-type ICOSL polypeptide. For example, in some embodiments, the variant ICOSL polypeptide exhibits increased binding affinity to CD28, ICOS, and/or CTLA-4 compared to a reference (e.g., unmodified) or wild-type ICOSL polypeptide. In some embodiments, the variant ICOSL polypeptide exhibits decreased binding affinity to CD28, ICOS, or CTLA-4 compared to a reference (e.g., unmodified) or wild-type ICOSL polypeptide.

In some embodiments, the variant ICOSL polypeptide has one or more amino acid modification, e.g. substitution selected from M10V, M10I, V11E, S13G, E16V, S18R, A20V, S25G, F27S, F27C, N30D, Y33del, Q37R, K42E, Y47H, T43A, N52A, N52C, N52D, N52G, N52H, N52L, N52K, N52M, N52P, N52Q, N52R, N52S, N52T, N52V, N52Y, S54A, S54P, N57A, N57E, N57F, N57H, N57K, N57L, N57M, N57P, N57Q, N57S, N57T, N57V, N57W, N57Y, R61S, R61C, Y62F, L67P, A71T, G72R, L74Q, R75Q, D77G, F78L, L80P, N84Q, D89G, E90A, K92R, F93L, H94E, H94D, L96F, L96I, V97A, L98F, S99G, Q100A, Q100D, Q100E, Q100G, Q100K, Q100L, Q100M, Q100N, Q100R, Q100P, Q100S, Q100T, Q100V, L102R, G103E, V107A, V107I, S109G, S109N, V110D, V110N, V110A, E111del, T113E, H115R, H115Q, V116A, A117T, N119Q, F120I, F120S, S121G, V122A, V122M, S126T, S126R, H129P, S130G, S132F, Q133H, E135K, F138L, T139S, C140D, C140del, S142F, I143V, I143T, N144D, Y146C, V151A, Y152C, Y152H, W153R, I154F, N155H, N155Q, K156M, D158G, L161P, L161M, L166Q, N168Q, F172S, L173S, M175T, T190S, T190A, S192G, V193M, N194D, C198R, N201S, L203P, L203F, N207Q, L208P, V210A, S212G, D217V, I218T, I218N, E220G, R221G, R221I, I224V, T225A, N227K or a conservative amino acid modification, e.g. substitution thereof. In some embodiments, the variant ICOSL polypeptide has one or more amino acid modification, e.g. substitution selected from M10V, M10I, V11E, S13G, E16V, S18R, A20T, A20V, S25G, R26S, F27C, F27S, N30D, Y33del, Q37R, T38P, K42E, T43A, Y47H, N52A, N52C, N52D, N52G, N52H, N52K, N52L, N52M, N52P, N52Q, N52R, N52S, N52T, N52V, N52Y, S54A, S54F, S54P, N57A, N57D, N57E, N57F, N57H, N57K, N57L, N57M, N57P, N57Q, N57S, N57T, N57V, N57W, N57Y, R61C, R61S, Y62F, L67P, A71T, G72R, L74Q, R75Q, D77G, F78L, L80P, N84Q, D89G, E90A, K92R, F93L, H94D, H94E, L96F, L96I, V97A, L98F, S99G, Q100A, Q100D, Q100E, Q100G, Q100K, Q100L, Q100M, Q100N, Q100P, Q100R, Q100S, Q100T, Q100V, L102R, G103E, V107A, V107I, S109G, S109N, V110A, V110D, V110N, E111del, T113E, H115Q, H115R, V116A, A117T, N119Q, F120I, F120S, S121G, V122A, V122M, S126R, S126T, H129P, S130G, S132F, Q133H, E135K, T137A, F138L, T139S, C140del, C140D, S142F, I143T, I143V, N144D, Y146C, V151A, Y152C, Y152H, W153R, I154F, N155H, N155Q, K156M, D158G, L161M, L161P, Q164L, L166Q, N168Q, F172S, L173S, M175T, T190A, T190S, S192G, V193A, V193M, N194D, C198R, N201S, L203F, L203P, N207Q, L208P, V210A, S212G, D217G, D217V, I218N, I218T, E220G, R221G, R221I, R221K, I224V, T225A, T225S, N227K, or a conservative amino acid substitution thereof.

A conservative amino acid modification, e.g. substitution is any amino acid that falls in the same class of amino acids as the substituted amino acids, other than the reference (e.g., unmodified) or wild-type amino acid. The classes of amino acids are aliphatic (glycine, alanine, valine, leucine, and isoleucine), hydroxyl or sulfur-containing (serine, cysteine, threonine, and methionine), cyclic (proline), aromatic (phenylalanine, tyrosine, tryptophan), basic (histidine, lysine, and arginine), and acidic/amide (aspartate, glutamate, asparagine, and glutamine).

In some embodiments, the variant ICOSL polypeptide has one or more amino acid modification, e.g. substitution selected from M10V, M10I, V11E, S13G, E16V, S18R, A20V, S25G, F27S, F27C, N30D, Y33del, Q37R, K42E, T43A, Y47H, N52A, N52C, N52D, N52G, N52H, N52L, N52K, N52M, N52P, N52Q, N52R, N52S, N52T, N52V, N52Y, S54A, S54P, N57A, N57E, N57F, N57H, N57K, N57L, N57M, N57P, N57Q, N57S, N57T, N57V, N57W, N57Y, R61S, R61C, Y62F, L67P, A71T, G72R, L74Q, R75Q, D77G, F78L, L80P, N84Q, D89G, E90A, K92R, F93L, H94E, H94D, L96F, L96I, V97A, L98F, S99G, Q100A, Q100D, Q100E, Q100G, Q100K, Q100L, Q100M, Q100N, Q100R, Q100P, Q100S, Q100T, Q100V, G103E, L102R, V107A, V107I, S109G, S109N, V110D, V110N, V110A, E111del, T113E, H115R, H115Q, V116A, A117T, N119Q, F120I, F120S, S121G, V122A, V122M, S126T, S126R, H129P, S130G, S132F, Q133H, E135K, F138L, T139S, C140D, C140del, S142F, I143V, I143T, N144D, Y146C, V151A, Y152C, Y152H, W153R, I154F, N155H, N155Q, K156M, D158G, L161P, L161M, L166Q, N168Q, F172S, L173S, M175T, T190A, T190S, S192G, V193M, N194D, C198R, N201S, L203P, L203F, N207Q, L208P, V210A, S212G, D217V, I218T, I218N, E220G, R221G, R221I, I224V, T225A, or N227K. In some embodiments, the variant ICOSL polypeptide has one or more amino acid modification, e.g. substitution selected from M10V, M10I, V11E, S13G, E16V, S18R, A20T, A20V, S25G, R26S, F27C, F27S, N30D, Y33del, Q37R, T38P, K42E, T43A, Y47H, N52A, N52C, N52D, N52G, N52H, N52K, N52L, N52M, N52P, N52Q, N52R, N52S, N52T, N52V, N52Y, S54A, S54F, S54P, N57A, N57D, N57E, N57F, N57H, N57K, N57L, N57M, N57P, N57Q, N57S, N57T, N57V, N57W, N57Y, R61C, R61S, Y62F, L67P, A71T, G72R, L74Q, R75Q, D77G, F78L, L80P, N84Q, D89G, E90A, K92R, F93L, H94D, H94E, L96F, L96I, V97A, L98F, S99G, Q100A, Q100D, Q100E, Q100G, Q100K, Q100L, Q100M, Q100N, Q100P, Q100R, Q100S, Q100T, Q100V, L102R, G103E, V107A, V107I, S109G, S109N, V110A, V110D, V110N, E111del, T113E, H115Q, H115R, V116A, A117T, N119Q, F120I, F120S, S121G, V122A, V122M, S126R, S126T, H129P, S130G, S132F, Q133H, E135K, T137A, F138L, T139S, C140del, C140D, S142F, I143T, I143V, N144D, Y146C, V151A, Y152C, Y152H, W153R, I154F, N155H, N155Q, K156M, D158G, L161M, L161P, Q164L, L166Q, N168Q, F172S, L173S, M175T, T190A, T190S, S192G, V193A, V193M, N194D, C198R, N201S, L203F, L203P, N207Q, L208P, V210A, S212G, D217G, D217V, I218N, I218T, E220G, R221G, R221I, R221K, I224V, T225A, T225S, N227K, or a conservative amino acid substitution thereof.

In some embodiments, the one or more amino acid modification, e.g. substitution is N52Y/N57Y/F138L/ L203P, N52H/N57Y/Q100P, N52S/Y146C/Y152C, N52H/ C198R, N52H/C140D/T225A, N52H/C198R/T225A, N52H/K92R, N52H/S99G, N57Y/Q100P, N52S/G103E, N52S/S130G/Y152C, N52S/Y152C, N52S/C198R, N52Y/ N57Y/Y152C, N52Y/N57Y/H129P/C198R, N52H/L161P/ C198R, N52S/T113E, N52D/S54P, N52K/L208P, N52S/ Y152H, N52D/V151A, N52H/I143T, N52S/L80P, F120S/ Y152H/N201S, N52S/R75Q/L203P, N52S/D158G, N52D/ Q133H, N52S/N57Y/H94D/L96F/L98F/Q100R, N52S/ N57Y/H94D/L96F/L98F/Q100R/G103E/F120S, N52H/ F78L/Q100R, N52H/N57Y/Q100R/V110D, N52H/N57Y/ R75Q/Q100R/V110D, N52H/N57Y/Q100R, N52H/N57Y/ L74Q/Q100R/V110D, N52H/Q100R, N52H/S121G, A20V/ N52H/N57Y/Q100R/S109G, N52H/N57Y/Q100P, N52H/ N57Y/R61S/Q100R/V110D/L173S, N52H/N57Y/Q100R/ V122A, N52H/N57Y/Q100R/F172S, N52H/N57Y, N52S/ F120S, N52S/V97A, N52S/G72R, N52S/A71T/A117T, N52S/E220G, Y47H/N52S/V107A/F120S, N52H/N57Y/ Q100R/V110D/S132F/M175T, E16V/N52H/N57Y/Q100R/ V110D/H115R/Y152C/K156M/C198R, Q37R/N52H/ N57Y/Q100R/V110N/S142F/C198R/D217V/R221G, N52H/N57Y/Q100R/V110D/C198R, N52H/N57Y/Q100R/ V110D/V116A/L161M/F172S/S192G/C198R, F27S/N52H/ N57Y/V110N, N52S/H94E/L96I/S109N/L166Q, S18R/ N52S/F93L/I143V/R221G, A20T/N52D/Y146C/Q164L, V11E/N30D/N52H/N57Y/H94E/L96I/L98F/N194D/ V210A/I218T, N52S/H94E/L96I/V122M, N52H/N57Y/ H94E/L96I/F120I/S126T/W153R/I218N, M10V/S18R/ N30D/N52S/S126R/T139S/L203F, S25G/N30D/N52S/ F120S/N227K, N30D/N52S/L67P/Q100K/D217G/R221K/

T225S, N52H/N57Y/Q100R/V110D/A117T/T190S/ C198R, N52H/N57Y/Q100R/V110D/F172S/C198R, S25G/ F27C/N52H/N57Y/Q100R/V110D/E135K/L173S/C198R, N52H/N57Y/V110A/C198R/R221I, M10I/S13G/N52H/ N57Y/D77G/V110A/H129P/I143V/F172S/V193M, C198R, N52H/N57Y/R61C/Y62F/Q100R/V110N/F120S/ C198R, N52H/N57Y/Q100R/V110D/H115R/C198R, N52H/N57Y/Q100R/V110D/N144D/F172S/C198R, N52S/ H94E/L98F/Q100R, N52S/E90A, N30D/K42E/N52S, N52S/F120S/I143V/I224V, N52H/N57Y/Q100R/V110D/ C198R/S212G, N52H/N57Y/Q100R/C198R, N52S/N194D, N52H/N57Y/Q100R/L102R/V110D/H115R/C198R, N52S/ S54P, T38P/N52S/N57D, N52H/C140del/T225A, N52H/ F78L/Q100R/C198R, N52H/N57Y/R75Q/Q100P/V110D, N52H/N57Y/L74Q/V110D/S192G, N52H/S121G/C198R, N52S/F120S/N227K, N52S/A71T/A117T/T190A/C198R, T43A/N52H/N57Y/L74Q/D89G/V110D/F172S, N52H/ N57Y/Q100R/V110D/S132F/M175T, N52H/N57Y/Q100R/ V107I/V110D/I154F/C198R/R221G, Q100R, F138L/ L203P, N57Y/F138L/L203P, N57Y/Q100R/C198R, N57Y/ F138L/L203P, Q100R/F138L, L203P, N52H/N57Y/Q100R/ H115R/C198R, N52H/N57Y/Q100R/F172S/C198R, N52H/ N57Y/Q100R/H115R/F172S/C198R, N52H/N57Y/Q100R/ H115R/I143V/F172S/C198R, N52H/N57Y/Q100R/L102R/ H115R/F172S/C198R, N52H/V122A/F172S/C198R, N52H/N57Y/Q100R/H115R/F172S/N194D, N52H/N57Y/ H115R/F172S/C198R, N52H/N57Y/Q100R/H115R/ C198R, N52H/N57Y/H115R, N52H/N57Y/Q100R/H115R, N52H/N57Y/Q100R/H115R/F172S/I224V, N52H/N57Y/ Q100R/H115R/F172S, N52H/N57Y/Q100R/F172S, N52H/ Q100R/H115R/I143T/F172S, N52H/N57Y/Q100P/H115R/ F172S, N52Y/N57Y/Q100P/F172S, E16V/N52H/N57Y/ Q100R/V110D/H115R/C198R, E16V/N52H/N57Y/Q100R/ V110D/H115R/Y152C/K156M/F172S/C198R, N52S/ E90A/H115R, N30D/K42E N52S/H115R, N30D/K42E/ N52S/H115R/C198R/R221I, N30D/K42E/N52S/H115R/ C198R, N30D/K42E/N52S/H115R/F172S/N194D, N52S/ H115R/F120S/I143V/C198R, N52S/H115R/F172S/C198R, N52H/N57Y/Q100P/C198R, N52H/N57Y/Q100P H115R/ F172S/C198R, N52H/N57Y/Q100P/F172S/C198R, N52H/ N57Y/Q100P/H115R, N52H/N57Y/Q100P/H115R/C198R, N52H/Q100R/C198R, N52H/Q100R/H115R/F172S, N52H/ Q100R/F172S/C198R, N52H/Q100R/H115Q/F172S/ C198R, N52H/N57Y/Q100R/F172S/C198R, N52Q/N207Q, N168Q/N207Q, N52Q/N168Q, N84Q/N207Q, N155Q/ N207Q, N119Q/N168Q, N119Q/N207Q, N119Q/N155Q, N52Q/N84Q, N52Q/N119Q, N84Q/N119Q, N52Q/N84Q/ N168Q, N52Q/N84Q/N207Q, N84Q/N155Q/N168Q, N84Q/N168Q/N207Q, N84Q/N155H/N207Q, N155Q/ N168Q/N207Q, N119Q/N155Q/N168Q, N119Q/N168Q/ N207Q, N84Q/N119Q/N207Q, N119Q/N155H/N207Q, N84Q/N119Q/N155Q, N52Q/N119Q/N155Q, N52H/ N84Q/N119Q, N52H/N84Q, N52H/N84Q/N168Q, N52H/ N84Q/N207Q, N52H/N84Q/N168Q/N207Q, N52Q/N84Q/ N155Q, N52Q/N84Q/N168Q, N52Q/N84Q/N155Q/ N168Q, N52Q/N84Q/N119Q/N168Q, N84Q/N119Q/ N155Q/N168Q, N84Q/N155Q/N168Q/N207Q, N84Q/ N119Q/N155Q/N207Q, N52Q/N84Q/N119Q/N207Q, N52Q/N84Q/N119Q/N155Q, N52Q/N84Q/N119Q/N155Q/ N207Q, N84Q/N119Q/N155Q/N168Q/N207Q, N52A/ N57F/Q100S, N52A/N57H/Q100S, N52A/N57Y/Q100A, N52D/N57A/Q100A, N52D/Q100S, N52G/Q100A, N52H/ Q100A, N52M/N57H/Q100S, N52M/N57W/Q100P, N52Q/ N57F, N52Q/N57S/Q100A, N52R/N57L/Q100A, N52R/ N57Y/Q100P, N52R/N57Y/Q100S, N52S/N57A/Q100A, N52S/N57H/Q100E, N52S/N57L/Q100S, N52S/N57M/ Q100S, N52S/N57Y/Q100S, N52S/N57Y/Q100M, N52S/

N57Y/Q100V, N52T/N57H/Q100S, N52T/N57H/Q100A, N52T/N57Y/Q100A, N52V/N57L/Q100A, N52H/N57Y/Q100K, N52K/N57Y/Q100R, N52L/N57H/Q100R, N52R/N57F/Q100N, N52R/N57F/Q100P, N52R/N57F/Q100R, N52R/N57F/Q100T, N52R/N57H/Q100K, N52R/N57L/Q100S, N52R/N57W/Q100K, N52R/N57W, N52R/N57Y/Q100R, N52C/N57E/Q100S, N52G/N57P/Q100D, N52G/N57V/Q100G, N52G/N57V, N52L/N57V, N52P/N57P, N52P/N57S/Q100G, N52S/N57L/Q100G, N52T/N57K/Q100P, N52V/N57T/Q100L, or N57Q/Q100P.

In some embodiments, the one or more amino acid modifications are selected from among N52Y/N57Y/F138L/L203P, N52H/N57Y/Q100P, N52S/Y146C/Y152C, N52H/C198R, N52H/C140D/T225A, N52H/C198R/T225A, N52H/K92R, N52H/S99G, N57Y/Q100P, N52S/S130G/Y152C, N52S/Y152C, N52S/C198R, N52Y/N57Y/Y152C, N52Y/N57Y/H129P/C198R, N52H/L161P/C198R, N52S/T113E, N52D/S54P, N52K/L208P, N52S/Y152H, N52D/V151A, N52H/I143T, N52S/L80P, F120S/Y152H/N201S, N52S/R75Q/L203P, N52S/D158G, N52D/Q133H, N52S/N57Y/H94D/L96F/L98F/Q100R, N52S/N57Y/H94D/L96F/L98F/Q100R/G103E/F120S, N52S/G103E, N52H/F78L/Q100R, N52H/N57Y/Q100R/V110D, N52H/N57Y/R75Q/Q100R/V110D, N52H/N57Y/Q100R, N52H/N57Y/L74Q/Q100R/V110D, N52H/Q100R, N52H/S121G, A20V/N52H/N57Y/Q100R/S109G, N52H/N57Y/R61S/Q100R/V110D/L173S, N52H/N57Y/Q100R/V122A, N52H/N57Y/Q100R/F172S, N52H/N57Y, N52S/F120S, N52S/V97A, N52S/G72R, N52S/A71T/A117T, N52S/E220G, Y47H/N52S/V107A/F120S, N52H/N57Y/Q100R/V110D/S132F/M175T, E16V/N52H/N57Y/Q100R/V110D/H115R/Y152C/K156M/C198R, Q37R/N52H/N57Y/Q100R/V110N/S142F/C198R/D217V/R221G, N52H/N57Y/Q100R/V110D/C198R, N52H/N57Y/Q100R/V110D/V116A/L161M/F172S/S192G/C198R, F27S/N52H/N57Y/V110N, N52S/H94E/L96I/S109N/L166Q, S18R/N52S/F93L/I143V/R221G, A20T/N52D/Y146C/Q164L, V11E/N30D/N52H/N57Y/H94E/L96I/L98F/N194D/V210A/I218T, N52S/H94E/L96I/V122M, N52H/N57Y/H94E/L96I/F120I/S126T/W153R/I218N, M10V/S18R/N30D/N52S/S126R/T139S/L203F, S25G/N30D/N52S/F120S/N227K, N30D/N52S/L67P/Q100K/D217G/R221K/T225S, N52H/N57Y/Q100R/V110D/A117T/T190S/C198R, N52H/N57Y/Q100R/V110D/F172S/C198R, S25G/F27C/N52H/N57Y/Q100R/V110D/E135K/L173S/C198R, N52H/N57Y/V110A/C198R/R221I, M10I/S13G/N52H/N57Y/D77G/V110A/H129P/I143V/F172S/V193M, C198R, N52H/N57Y/R61C/Y62F/Q100R/V110N/F120S/C198R, N52H/N57Y/Q100R/V110D/H115R/C198R, N52H/N57Y/Q100R/V110D/N144D/F172S/C198R, N52S/H94E/L98F/Q100R, N52S/E90A, N30D/K42E/N52S, N52S/F120S/I143V/I224V, N52H/N57Y/Q100R/V110D/C198R/S212G, N52H/N57Y/Q100R/C198R, N52S/N194D, N52H/N57Y/Q100R/L102R/V110D/H115R/C198R, N52H/N57Y/Q100R/V110D/C198R/S212G, N52H/N57Y/Q100R/C198R, N52S/N194D, N52H/N57Y/Q100R/L102R/V110D/H115R/C198R, N52S/S54P, T38P/N52S/N57D, N52H/C140del/T225A, N52H/F78L/Q100R/C198R, N52H/N57Y/R75Q/Q100P/V110D, N52H/N57Y/L74Q/V110D/S192G, N52H/S121G/C198R, N52S/F120S/N227K, N52S/A71T/A117T/T190A/C198R, T43A/N52H/N57Y/L74Q/D89G/V110D/F172S, N52H/N57Y/Q100R/V110D/S132F/M175T, N52H/N57Y/Q100R/V107I/V110D/I154F/C198R/R221G, N52Q/N207Q, N52Q/N168Q, N84Q/N207Q, N155Q/N207Q, N119Q/N168Q, N119Q/N207Q, N119Q/N155Q, N52Q/N84Q, N52Q/N119Q, N84Q/N119Q, N52Q/N84Q/N168Q, N52Q/N84Q/N207Q, N84Q/N155Q/N168Q, N84Q/N168Q/N207Q, N84Q/N155H/N207Q, N155Q/N168Q/N207Q, N119Q N155Q/N168Q, N119Q/N168Q/N207Q, N84Q/N119Q/N207Q, N119Q/N155H/N207Q, N84Q/N119Q/N155Q, N52Q/N119Q/N155Q, N52H/N84Q/N119Q, N52H/N84Q, N52H/N84Q/N168Q/N207Q, N52Q/N84Q/N155Q/N168Q, N52Q/N84Q/N119Q/N168Q, N84Q/N119Q/N155Q/N168Q, N84Q/N155Q/N168Q/N207Q, N84Q/N119Q/N155Q/N207Q, N52Q/N84Q/N119Q/N207Q, N52Q/N84Q/N119Q/N155Q, N52Q/N84Q/N119Q/N155Q/N207Q, N84Q/N119Q/N155Q/N168Q/N207Q, F138L/L203P, N52Y/F138L/L203P, N57Y/Q100R/C198R, N57Y/F138L/L203P, Q100R/F138L, N52H/N57Y/Q100R/H115R/C198R, N52H/N57Y/Q100R/F172S/C198R, N52H/N57Y/Q100R/H115R/F172S/C198R, N52H/N57Y/Q100R/H115R/I143V/F172S/C198R, N52H/N57Y/Q100R/L102R/H115R/F172S/C198R, N52H/V122A/F172S/C198R, N52H/N57Y/Q100R/H115R/F172S/N194D, N52H/N57Y/H115R/F172S/C198R, N52H/N57Y/H115R, N52H/N57Y/Q100R/H115R, N52H/N57Y/Q100R/H115R/F172S/I224V, N52H/N57Y/Q100R/H115R/F172S, N52H/N57Y/Q100R/F172S, N52H/Q100R/H115R/I143T/F172S, N52H/N57Y/Q100P/H115R/F172S, N52Y/N57Y/Q100R/F172S, E16V/N52H/N57Y/Q100R/V110D/H115R/C198R, E16V/N52H/N57Y/Q100R/V110D/H115R/Y152C/K156M/F172S/C198R, N52S/E90A/H115R, N30D/K42EN52S/H115R, N30D/K42E/N52S/H115R/C198R/R221I, N30D/K42E/N52S/H115R/C198R, N30D/K42E/N52S/H115R/F172S/N194D, N52S/H115R/F120S/I143V/C198R, N52S/H115R/F172S/C198R, N52H/N57Y/Q100P/C198R, N52H/N57Y/Q100P/H115R/F172S/C198R, N52H/N57Y/Q100P/F172S/C198R, N52H/N57Y/Q100P/H115R, N52H/N57Y/Q100P/H115R/C198R, N52H/Q100R/C198R, N52H/Q100R/H115R/F172S, N52H/Q100R/F172S/C198R, N52H/Q100R/H115R/F172S/C198R, N52H/N57Y/Q100R/F172S/C198R, N52A/N57F/Q100S, N52A/N57H/Q100S, N52A/N57Y/Q100A, N52D/N57A/Q100A, N52D/Q100S, N52G/Q100A, N52H/Q100A, N52M/N57H/Q100S, N52M/N57W/Q100P, N52Q/N57F, N52Q/N57S/Q100A, N52R/N57L/Q100A, N52R/N57Y/Q100P, N52R/N57Y/Q100S, N52S/N57A/Q100A, N52S/N57H/Q100E, N52S/N57L/Q100S, N52S/N57M/Q100S, N52S/N57Y/Q100S, N52S/N57Y/Q100M, N52S/N57Y/Q100V, N52T/N57H/Q100S, N52T/N57H/Q100A, N52T/N57Y/Q100A, N52V/N57L/Q100A, N52H/N57Y/Q100K, N52K/N57Y/Q100R, N52L/N57H/Q100R, N52R/N57F/Q100N, N52R/N57F/Q100P, N52R/N57F/Q100R, N52R/N57F/Q100T, N52R/N57H/Q100K, N52R/N57L/Q100S, N52R/N57W/Q100K, N52R/N57W, N52R/N57Y/Q100R, N52C/N57E/Q100S, N52G/N57P/Q100D, N52G/N57V/Q100G, N52G/N57V, N52L/N57V, N52P/N57P, N52P/N57S/Q100G, N52S/N57L/Q100G, N52T/N57K/Q100P, N52V/N57T/Q100L, N57Q/Q100P, S54F/V193A or R26S/N52H/N57Y/V110D/T137A/C198R.

In some embodiments, the variant ICOSL polypeptide comprises any of the mutations listed in Table 1. Table 1 also provides exemplary sequences by reference to SEQ ID NO for the extracellular domain (ECD) or IgV domain of the reference (e.g., unmodified) or wild-type ICOSL or exemplary variant ICOSL polypeptides. As indicated, the exact locus or residues corresponding to a given domain can vary, such as depending on the methods used to identify or classify the domain. Also, in some cases, adjacent N- and/or C-terminal amino acids of a given domain (e.g. IgV) also can be included in a sequence of a variant IgSF polypeptide, such as to ensure proper folding of the domain when expressed. Thus, it is understood that the exemplification of the SEQ ID NOSs in Table 1 is not to be construed as limiting. For example, the particular domain, such as the ECD domain, of a variant ICOSL polypeptide can be several amino acids longer or shorter, such as 1-10, e.g., 1, 2, 3, 4, 5, 6 or 7 amino acids longer or shorter, than the sequence of amino acids set forth in the respective SEQ ID NO.

In some embodiments, the variant ICOSL polypeptide comprises any of the mutations listed in Table 1. In some examples, the mutations are made in a reference ICOSL containing the sequence of amino acids set forth in SEQ ID NO: 32, a reference ICOSL that contains the IgV domain of ICOSL set forth in SEQ ID NOs: 196 or 545, or a reference ICOSL that is truncated and/or modified containing the sequence of amino acids set forth in any of SEQ ID NOs: 600-628. In some embodiments, the variant ICOSL polypeptide comprises any of the extracellular domain (ECD) sequences listed in Table 1 (i.e., any one of SEQ ID NOS: 109-142, 239, 280-325, 364-381, 387-424, 427-433, 435-470, 638-685). In some embodiments, the variant ICOSL polypeptide comprises a polypeptide sequence that exhibits at least 90% identity, at least 91% identity, at least 92% identity, at least 93% identity, at least 94% identity, at least 95% identity, such as at least 96% identity, 97% identity, 98% identity, or 99% identity to any of the extracellular domain (ECD) sequences listed in Table 1 (i.e., any one of SEQ ID NOS: 109-142, 239, 280-325, 364-381, 387-424, 427-433, 435-470, 638-685) and contains the amino acid modification(s), e.g. substitution(s) not present in the reference (e.g., unmodified) or wild-type ICOSL. In some embodiments, the variant ICOSL polypeptide comprises a specific binding fragment of any of the extracellular domain (ECD) sequences listed in Table 1 (i.e., any one of SEQ ID NOS: 109-142, 239, 280-325, 364-381, 387-424, 427-433, 435-470, 638-685) and contains the amino acid modification (s), e.g. substitution(s) not present in the reference (e.g., unmodified) or wild-type ICOSL.

In some embodiments, the variant ICOSL polypeptide comprises any of the extracellular domain (ECD) sequences listed in Table 1 (i.e., any one of SEQ ID NOS: 109-142, 239, 280-325, 364-381, 387-424, 427-433, 435-470, 638-685, 905, 908). In some embodiments, the variant ICOSL polypeptide comprises a polypeptide sequence that exhibits at least 90% identity, at least 91% identity, at least 92% identity, at least 93% identity, at least 94% identity, at least 95% identity, such as at least 96% identity, 97% identity, 98% identity, or 99% identity to any of the extracellular domain (ECD) sequences listed in Table 1 (i.e., any one of SEQ ID NOS: 109-142, 239, 280-325, 364-381, 387-424, 427-433, 435-470, 638-685, 905, 908) and contains the amino acid modification(s), e.g. substitution(s) not present in the reference (e.g., unmodified) or wild-type ICOSL. In some embodiments, the variant ICOSL polypeptide comprises a specific binding fragment of any of the extracellular domain (ECD) sequences listed in Table 1 (i.e., any one of SEQ ID NOS: 109-142, 239, 280-325, 364-381, 387-424, 427-433, 435-470, 638-685, 905, 908) and contains the amino acid modification(s), e.g. substitution(s) not present in the reference (e.g., unmodified) or wild-type ICOSL.

In some embodiments, the variant ICOSL polypeptide comprises any of the IgV sequences listed in Table 1 (i.e., any one of SEQ ID NOS: 197-199, 201-208, 210, 212, 240, 326-340, 382-386, 425-426, 434, 546-599, 686-857). In some embodiments, the variant ICOSL polypeptide comprises a polypeptide sequence that exhibits at least 90% identity, at least 91% identity, at least 92% identity, at least 93% identity, at least 94% identity, at least 95% identity, such as at least 96% identity, 97% identity, 98% identity, or 99% identity to any of the IgV sequences listed in Table 1 (i.e., any one of SEQ ID NOS: 197-199, 201-208, 210, 212, 240, 326-340, 382-386, 425-426, 434, 546-599, 686-857) and contains the amino acid modification(s), e.g. substitution(s) not present in the reference (e.g., unmodified) or wild-type ICOSL. In some embodiments, the variant ICOSL polypeptide comprises a specific binding fragment of any of the IgV sequences listed in Table 1 (i.e., any one of SEQ ID NOS: 197-199, 201-208, 210, 212, 240, 326-340, 382-386, 425-426, 434, 546-599, 686-857) and contains the amino acid substitution(s) not present in the reference (e.g., unmodified) or wild-type ICOSL.

In some embodiments, the variant ICOSL polypeptide comprises any of the IgV sequences listed in Table 1 (i.e., any one of SEQ ID NOS: 197-199, 201-208, 210, 212, 240, 326-340, 382-386, 425-426, 434, 546-599, 686-857, 906-907, 909-910). In some embodiments, the variant ICOSL polypeptide comprises a polypeptide sequence that exhibits at least 90% identity, at least 91% identity, at least 92% identity, at least 93% identity, at least 94% identity, at least 95% identity, such as at least 96% identity, 97% identity, 98% identity, or 99% identity to any of the IgV sequences listed in Table 1 (i.e., any one of SEQ ID NOS: 197-199, 201-208, 210, 212, 240, 326-340, 382-386, 425-426, 434, 546-599, 686-857, 906-907, 909-910) and contains the amino acid modification(s), e.g. substitution(s) not present in the reference (e.g., unmodified) or wild-type ICOSL. In some embodiments, the variant ICOSL polypeptide comprises a specific binding fragment of any of the IgV sequences listed in Table 1 (i.e., any one of SEQ ID NOS: 197-199, 201-208, 210, 212, 240, 326-340, 382-386, 425-426, 434, 546-599, 686-857, 906-907, 909-910) and contains the amino acid substitution(s) not present in the reference (e.g., unmodified) or wild-type ICOSL.

Mutations designated with an "X" indicate the designated position contains a Q or the wild-type residue set forth in the corresponding position of SEQ ID NO: 32.

TABLE 1

| Exemplary variant ICOSL polypeptides | | |
| --- | --- | --- |
| Mutation(s) | ECD SEQ ID NO | IgV SEQ ID NO |
| Wild-type | 32 | 196, 545 |
| N52S | 109 | 197, 546 |
| N52H | 110 | 198, 547 |
| N52D | 111 | 199, 548 |
| N52Y/N57Y/F138L/L203P | 112 | 782, 783 |
| N52H/N57Y/Q100P | 113 | 201, 549 |
| N52S/Y146C/Y152C | 114 | 197, 546 |
| N52H/C198R | 115 | 198, 547 |

TABLE 1-continued

| | | |
|---|---|---|
| | | Exemplary variant ICOSL polypeptides |

| Mutation(s) | ECD SEQ ID NO | IgV SEQ ID NO |
|---|---|---|
| N52H/C140D/T225A | 116 | 198, 547 |
| N52H/C198R/T225A | 117 | 198, 547 |
| N52H/K92R | 118 | 202, 550 |
| N52H/S99G | 119 | 203, 551 |
| N52Y | 120 | 204, 552 |
| N57Y | 121 | 205, 553 |
| N57Y/Q100P | 122 | 206, 554 |
| N52S/S130G/Y152C | 123 | 197, 546 |
| N52S/Y152C | 124 | 197, 546 |
| N52S/C198R | 125 | 197, 546 |
| N52Y/N57Y/Y152C | 126 | 782, 783 |
| N52Y/N57Y/H129P/C198R | 127 | 782, 783 |
| N52H/L161P/C198R | 128 | 198, 547 |
| N52S/T113E | 129 | 197, 555 |
| S54A | 130 | 207, 556 |
| N52D/S54P | 131 | 208, 557 |
| N52K/L208P | 132 | 785, 786 |
| N52S/Y152H | 133 | 197, 546 |
| N52D/V151A | 134 | 199, 548 |
| N52H/I143T | 135 | 198, 547 |
| N52S/L80P | 136 | 210, 558 |
| F120S/Y152H/N201S | 137 | 196, 545 |
| N52S/R75Q/L203P | 138 | 787, 788 |
| N52S/D158G | 139 | 197, 546 |
| N52D/Q133H | 140 | 199, 548 |
| N52S/N57Y/H94D/L96F/L98F/Q100R | 141 | 212, 559 |
| N52S/N57Y/H94D/L96F/L98F/Q100R/G103E/F120S | 142 | 789, 560 |
| N52S/G103E | 239 | 240, 561 |
| N52H/F78L/Q100R | 280 | 326, 562 |
| N52H/N57Y/Q100R/V110D | 281 | 327, 563 |
| N52H/N57Y/R75Q/Q100R/V110D | 282 | 328, 564 |
| N52H/N57Y/Q100R | 283 | 329, 565 |
| N52H/N57Y/L74Q/Q100R/V110D | 284 | 330, 566 |
| N52H/Q100R | 285 | 331, 567 |
| N52H/S121G | 286 | 198, 568 |
| A20V/N52H/N57Y/Q100R/S109G | 287 | 332, 569 |
| N52H/N57Y/Q100P | 288 | 333, 570 |
| N52H/N57Y/R61S/Q100R/V110D/L173S | 289 | 791, 792 |
| N52H/N57Y/Q100R/V122A | 290 | 329, 571 |
| N52H/N57Y/Q100R/F172S | 291 | 329, 565 |
| N52H/N57Y | 292 | 334, 572 |
| N52S/F120S | 293 | 197, 573 |
| N52S/V97A | 294 | 335, 574 |
| N52S/G72R | 295 | 336, 575 |
| N52S/A71T/A117T | 296 | 793, 576 |
| N52S/E220G | 297 | 197, 546 |
| Y47H/N52S/V107A/F120S | 298 | 794, 577 |
| N52H/N57Y/Q100R/V110D/S132F/M175T | 299 | 327, 563 |
| E16V/N52H/N57Y/Q100R/V110D/H115R/Y152C/K156M/C198R | 300 | 795, 796 |
| Q37R/N52H/N57Y/Q100R/V110N/S142F/C198R/D217V/R221G | 301 | 797, 798 |
| N52H/N57Y/Q100R/V110D/C198R | 302 | 327, 563 |
| N52H/N57Y/Q100R/V110D/V116A/L161M/F172S/S192G/C198R | 303 | 799, 800 |
| F27S/N52H/N57Y/V110N | 304 | 337, 578 |
| N52S/H94E/L96I/S109N/L166Q | 305 | 801, 802 |
| S18R/N52S/F93L/I143V/R221G | 306 | 803, 804 |
| A20T/N52D/YI46C/Q164L | 307 | 805, 806 |
| V11E/N30D/N52H/N57Y/H94E/L96I/L98F/N194D/V210A/I218T | 308 | 807, 808 |
| N52S/H94E/L96I/V122M | 309 | 809, 579 |
| N52H/N57Y/H94E/L96I/F120I/S126T/W153R/I218N | 310 | 810, 811 |
| M10V/S18R/N30D/N52S/S126R/T139S/L203F | 311 | 812, 813 |
| S25G/N30D/N52S/F120S/N227K | 312 | 814, 815 |
| N30D/N52S/L67P/Q100K/D217G/R221K/T225S | 313 | 816, 817 |
| N52H/N57Y/Q100R/V110D/A117T/T190S/C198R | 314 | 327, 818 |
| N52H/N57Y/Q100R/V110D/F172S/C198R | 315 | 327, 563 |
| S25G/F27C/N52H/N57Y/Q100R/V110D/E135K/L173S/C198R | 316 | 819, 820 |
| N52H/N57Y/V110A/C198R/R221I | 317 | 821, 822 |
| M10I/S13G/N52H/N57Y/D77G/V110A/H129P/I143V/F172S/V193M/C198R | 318 | 823, 824 |
| N52H/N57Y/R61C/Y62F/Q100R/V110N/F120S/C198R | 319 | 825, 826 |
| N52H/N57Y/Q100R/V110D/H115R/C198R | 320 | 327, 827 |
| N52H/N57Y/Q100R/V110D/N144D/F172S/C198R | 321 | 327, 563 |
| N52S/H94E/L98F/Q100R | 322 | 338, 580 |
| N52S/E90A | 323 | 339, 581 |
| N30D/K42E/N52S | 324 | 340, 582 |
| N52S/F120S/I143V/I224V | 325 | 197, 573 |

TABLE 1-continued

| Exemplary variant ICOSL polypeptides | | |
|---|---|---|
| Mutation(s) | ECD SEQ ID NO | IgV SEQ ID NO |
| N52H/N57Y/Q100R/V110D/C198R/S212G | 364 | 828, 829 |
| N52H/N57Y/Q100R/C198R | 365 | 329, 565 |
| N52S/N194D | 366 | 197, 546 |
| N52H/N57Y/Q100R/L102R/V110D/H115R/C198R | 367 | 830, 831 |
| N52S/S54P | 368 | 382, 583 |
| T38P/N52S/N57D | 369 | 383, 584 |
| E111del | 370 | 384, 585 |
| Y33del | 371 | 385, 586 |
| N52H/C140del/T225A | 372 | 198, 547 |
| N52H/F78L/Q100R/C198R | 373 | 326, 562 |
| N52H/N57Y/R75Q/Q100P/V110D | 374 | 386, 587 |
| N52H/N57Y/L74Q/V110D/S192G | 375 | 832, 833 |
| N52H/S121G/C198R | 376 | 198, 568 |
| N52S/F120S/N227K | 377 | 197, 573 |
| N52S/A71T/A117T/T190A/C198R | 378 | 793, 576 |
| T43A/N52H/N57Y/L74Q/D89G/V110D/F172S | 379 | 790, 834 |
| N52H/N57Y/Q100R/V110D/S132F/M175T | 380 | 327, 563 |
| N52H/N57Y/Q100R/V107I/V110D/I154F/C198R/R221G | 381 | 835, 836 |
| N84Q | 387 | 425, 588 |
| N119Q | 388 | 196, 842 |
| N168Q | 389 | 196, 545 |
| N207Q | 390 | 196, 545 |
| N52Q/N207X | 391 | 837, 838 |
| N168X/N207X | 392 | 196, 545 |
| N52Q/N168Q | 393 | 837, 838 |
| N84Q/N207Q | 394 | 425, 840 |
| N155Q/N207Q | 395 | 196, 545 |
| N119Q/N168Q | 396 | 196, 842 |
| N119Q/N207Q | 397 | 196, 842 |
| N119Q/N155X | 398 | 196, 842 |
| N52Q/N84Q | 399 | 426, 590 |
| N52Q/N119Q | 400 | 837, 591 |
| N84Q/N119Q | 401 | 425, 592 |
| N52Q/N84Q/N168Q | 402 | 426, 590 |
| N52Q/N84Q/N207Q | 403 | 426, 590 |
| N84Q/N155Q/N168Q | 404 | 425, 588 |
| N84Q/N168Q/N207Q | 405 | 425, 588 |
| N84Q/N155H/N207Q | 406 | 425, 588 |
| N155Q/N168Q/N207Q | 407 | 196, 545 |
| N119Q N155Q/N168Q | 408 | 196, 842 |
| N119Q/N168Q/N207Q | 409 | 196, 842 |
| N84Q/N119Q/N207Q | 410 | 425, 592 |
| N119Q/N155H/N207Q | 411 | 196, 842 |
| N84Q/N119Q/N155Q | 412 | 425, 592 |
| N52Q/N119Q/N155Q | 413 | 837, 591 |
| N52H/N84Q/N119Q | 414 | 839, 593 |
| N52H/N84Q/N168X/N207X | 415 | 839, 841 |
| N52Q/N84Q/N155X/N168X | 416 | 426, 590 |
| N52Q/N84Q/N119Q/N168Q | 417 | 426, 843 |
| N84Q/N119Q/N155Q/N168Q | 418 | 425, 592 |
| N84Q/N155Q/N168Q/N207Q | 419 | 425, 588 |
| N84Q/N119Q/N155Q/N207Q | 420 | 425, 592 |
| N52Q/N84Q/N119Q/N207Q | 421 | 426, 843 |
| N52Q/N84Q/N119Q/N155Q | 422 | 426, 843 |
| N52Q/N84Q/N119Q/N155Q/N207Q | 423 | 426, 843 |
| N84Q/N119Q/N155Q/N168Q/N207Q | 424 | 425, 592 |
| Q100R | 427 | 434, 594 |
| F138L/L203P | 428 | 196, 545 |
| N52Y/F138L/L203P | 429 | 204, 552 |
| N57Y/Q100R/C198R | 430 | 844, 845 |
| N57Y/F138L/L203P | 431 | 205, 553 |
| Q100R/F138L | 432 | 846, 847 |
| L203P | 433 | 196, 545 |
| N52H/N57Y/Q100R/H115R/C198R | 435 | 329, 596 |
| N52H/N57Y/Q100R/F172S/C198R | 436 | 329, 565 |
| N52H/N57Y/Q100R/H115R/F172S/C198R | 437 | 329, 596 |
| N52H/N57Y/Q100R/H115R/I143V/F172S/C198R | 438 | 329, 596 |
| N52H/N57Y/Q100R/L102R/H115R/F172S/C198R | 439 | 849, 850 |
| N52H/V122A/F172S/C198R | 440 | 198, 851 |
| N52H/N57Y/Q100R/H115R/F172S/N194D | 441 | 329, 596 |
| N52H/N57Y/H115R/F172S/C198R | 442 | 334, 595 |
| N52H/N57Y/Q100R/H115R/C198R | 443 | 329, 596 |
| N52H/N57Y/H115R | 444 | 334, 595 |
| N52H/N57Y/Q100R/H115R | 445 | 329, 596 |

TABLE 1-continued

| | | |
|---|---|---|
| Exemplary variant ICOSL polypeptides | | |
| Mutation(s) | ECD SEQ ID NO | IgV SEQ ID NO |
| N52H/N57Y/Q100R/H115R/F172S/I224V | 446 | 329, 596 |
| N52H/N57Y/Q100R/H115R/F172S | 447 | 329, 596 |
| N52H/N57Y/Q100R/F172S | 448 | 329, 565 |
| N52H/Q100R/H115R/I143T/F172S | 449 | 331, 852 |
| N52H/N57Y/Q100P/H115R/F172S | 450 | 333, 853 |
| N52Y/N57Y/Q100P/F172S | 451 | 854, 855 |
| E16V/N52H/N57Y/Q100R/V110D/H115R/C198R | 452 | 795, 796 |
| E16V/N52H/N57Y/Q100R/V110D/H115R/Y152C/K156M/F172S/C198R | 453 | 795, 796 |
| N52S/E90A/H115R | 454 | 339, 597 |
| N30D/K42E/N52S/H115R | 455 | 856, 598 |
| N30D/K42E/N52S/H115R/C198R/R221I | 456 | 856, 598 |
| N30D/K42E/N52S/H115R/C198R | 457 | 856, 598 |
| N30D/K42E/N52S/H115R/F172S/N194D | 458 | 856, 598 |
| N52S/H115R/F120S/I143V/C198R | 459 | 197, 857 |
| N52S/H115R/F172S/C198R | 460 | 197, 853 |
| N52H/N57Y/Q100P/C198R | 461 | 333, 570 |
| N52H/N57Y/Q100P/H115R/F172S/C198R | 462 | 333, 599 |
| N52H/N57Y/Q100P/F172S/C198R | 463 | 333, 570 |
| N52H/N57Y/Q100P/H115R | 464 | 333, 599 |
| N52H/N57Y/Q100P/H115R/C198R | 465 | 333, 599 |
| N52H/Q100R/C198R | 466 | 331, 567 |
| N52H/Q100R/H115R/F172S | 467 | 331, 852 |
| N52H/Q100R/H115X/F172S/C198R | 468 | 331, 848 |
| N52H/Q100R/H115R/F172S/C198R | 469 | 331, 852 |
| N52H/N57Y/Q100R/F172S/C198R | 470 | 329, 565 |
| N52A/N57F/Q100S | 638 | 686, 734 |
| N52A/N57H/Q100S | 639 | 687, 735 |
| N52A/N57Y/Q100A | 640 | 688, 736 |
| N52D/N57A/Q100A | 641 | 689, 737 |
| N52D/Q100S | 642 | 690, 738 |
| N52G/Q100A | 643 | 691, 739 |
| N52H/Q100A | 644 | 692, 740 |
| N52M/N57H/Q100S | 645 | 693, 741 |
| N52M/N57W/Q100P | 646 | 694, 742 |
| N52Q/N57F | 647 | 695, 743 |
| N52Q/N57S/Q100A | 648 | 696, 744 |
| N52R/N57L/Q100A | 649 | 697, 745 |
| N52R/N57Y/Q100P | 650 | 698, 746 |
| N52R/N57Y/Q100S | 651 | 699, 747 |
| N52S/N57A/Q100A | 652 | 700, 748 |
| N52S/N57H/Q100E | 653 | 701, 749 |
| N52S/N57L/Q100S | 654 | 702, 750 |
| N52S/N57M/Q100S | 655 | 703, 751 |
| N52S/N57Y/Q100S | 656 | 704, 752 |
| N52S/N57Y/Q100M | 657 | 705, 753 |
| N52S/N57Y/Q100V | 658 | 706, 754 |
| N52T/N57H/Q100S | 659 | 707, 755 |
| N52T/N57H/Q100A | 660 | 708, 756 |
| N52T/N57Y/Q100A | 661 | 709, 757 |
| N52V/N57L/Q100A | 662 | 710, 758 |
| N52H/N57Y/Q100K | 663 | 711, 759 |
| N52K/N57Y/Q100R | 664 | 712, 760 |
| N52L/N57H/Q100R | 665 | 713, 761 |
| N52R/N57F/Q100N | 666 | 714, 762 |
| N52R/N57F/Q100P | 667 | 715, 763 |
| N52R/N57F/Q100R | 668 | 716, 764 |
| N52R/N57F/Q100T | 669 | 717, 765 |
| N52R/N57H/Q100K | 670 | 718, 766 |
| N52R/N57L/Q100S | 671 | 719, 767 |
| N52R/N57W/Q100K | 672 | 720, 768 |
| N52R/N57W | 673 | 721, 769 |
| N52R/N57Y/Q100R | 674 | 722, 770 |
| N52C/N57E/Q100S | 675 | 723, 771 |
| N52G/N57P/Q100D | 676 | 724, 772 |
| N52G/N57V/Q100G | 677 | 725, 773 |
| N52G/N57V | 678 | 726, 774 |
| N52L/N57V | 679 | 727, 775 |
| N52P/N57P | 680 | 728, 776 |
| N52P/N57S/Q100G | 681 | 729, 777 |
| N52S/N57L/Q100G | 682 | 730, 778 |
| N52T/N57K/Q100P | 683 | 731, 779 |
| N52V/N57T/Q100L | 684 | 732, 780 |

TABLE 1-continued

| | ECD SEQ ID NO | IgV SEQ ID NO |
|---|---|---|
| Mutation(s) | | |
| N57Q/Q100P | 685 | 733, 781 |
| S54F/V193A | 905 | 906, 907 |
| R26S/N52H/N57Y/V110D/T137A/C198R | 908 | 909, 910 |

Exemplary variant ICOSL polypeptides

In some embodiments, the variant ICOSL polypeptide exhibits increased affinity for the ectodomain of CD28 compared to the reference (e.g., unmodified) or wild-type ICOSL polypeptide, such as comprising the sequence set forth in SEQ ID NO: 32, 196, or 545. In some embodiments, the ICOSL polypeptide exhibits increased affinity for the ectodomain of ICOS compared to the reference (e.g., unmodified) or wild-type ICOSL, such as comprising the sequence set forth in SEQ ID NO: 32, 196, or 545. In some embodiments, the ICOSL polypeptide exhibits increased affinity for the ectodomain of CD28 and the ectodomain of ICOS compared to the reference (e.g., unmodified) or wild-type ICOSL, such as comprising the sequence set forth in SEQ ID NO: 32, 196, or 545.

In some embodiments, the variant ICOSL polypeptide has one or more amino acid modification, e.g. substitution corresponding to position(s) 52, 54 or 57. In some embodiments, the variant ICOSL polypeptide has one or more amino acid modification, e.g. substitution selected from N52H, N52D, N52Q, N52S, N52Y, N52K, S54A, S54P, or N57Y or a conservative amino acid modification, e.g. substitution thereof. In some embodiments, the variant ICOSL polypeptide has one or more amino acid modification, e.g. substitution selected from N52H, N52D, N52S, N52K or N57Y or a conservative amino acid modification, e.g. substitution thereof.

In some embodiments, the variant ICOSL polypeptide can contain one or more further amino acid modification, e.g. substitution in addition to an amino acid modification, e.g. substitution at a position corresponding to position 52, 54 or 57. In some embodiments, the one or more further amino acid modification, e.g. substitution is at a position corresponding to 10, 11, 13, 16, 18, 20, 25, 27, 30, 37, 42, 43, 47, 52, 54, 57, 61, 62, 67, 71, 72, 74, 75, 77, 78, 80, 84, 89, 90, 92, 93, 94, 96, 97, 98, 99, 100, 102, 103, 107, 109, 110, 113, 115, 116, 117, 119, 120, 121, 122, 126, 129, 130, 132, 133, 135, 138, 139, 140, 142, 143, 144, 146, 151, 152, 153, 154, 155, 156, 158, 161, 166, 168, 172, 173, 175, 190, 192, 193, 194, 198, 201, 203, 207, 208, 210, 212, 217, 218, 220, 221, 224, 225 or 227. In some embodiments, the one or more further amino acid modification, e.g. substitution is at a position corresponding to 10, 11, 13, 16, 18, 20, 25, 26, 27, 30, 33, 37, 38, 42, 43, 47, 52, 54, 57, 61, 62, 67, 71, 72, 74, 75, 77, 78, 80, 84, 89, 90, 92, 93, 94, 96, 97, 98, 99, 100, 102, 103, 107, 109, 110, 111, 113, 115, 116, 117, 119, 120, 121, 122, 126, 129, 130, 132, 133, 135, 137, 138, 139, 140, 142, 143, 144, 146, 151, 152, 153, 154, 155, 156, 158, 161, 164, 166, 168, 172, 173, 175, 190, 192, 193, 194, 198, 201, 203, 207, 208, 210, 212, 217, 218, 220, 221, 224, 225, or 227 with reference to SEQ ID NO:32.

In some embodiments, the variant ICOSL contains one or more further amino acid modification, e.g. substitution selected from M10V, M10I, V11E, S13G, E16V, S18R, A20V, S25G, F27S, F27C, N30D, Y33del, Q37R, K42E, T43A, Y47H, N52H, N52D, N52S, N52Y, N52K, N52Q, S54A, S54P, N57D, N57Y, R61S, R61C, Y62F, L67P, A71T, G72R, L74Q, R75Q, D77G, F78L, L80P, N84Q, D89G, E90A, K92R, F93L, H94E, H94D, L96F, L96I, V97A, L98F, S99G, Q100R, Q100K, Q100P, L102R, G103E, V107A, V107I, S109G, S109N, V110D, V110N, V110A, E111del, T113E, H115R, H115Q, V116A, A117T, N119Q, F120I, F120S, S121G, V122A, V122M, S126T, S126R, H129P, S130G, S132F, Q133H, E135K, F138L, T139S, C140del, S142F, I143V, I143T, N144D, Y146C, V151A, Y152C, Y152H, W153R, I154F, K156M, D158G, L161P, L161M, L166Q, N168Q, F172S, L173S, M175T, T190A, T190S, S192G, V193M, N194D, C198R, N201S, L203P, L203F, N207Q, L208P, V210A, S212G, D217V, I218T, I218N, E220G, R221G, R221I, I224V, T225A, N227K, or a conservative amino acid substitution thereof. In some embodiments, the variant ICOSL contains one or more further amino acid modification, e.g. substitution selected from M10V, M10I, V11E, S13G, E16V, S18R, A20T, A20V, S25G, R26S, F27C, F27S, N30D, Y33del, Q37R, T38P, K42E, T43A, Y47H, N52A, N52C, N52D, N52G, N52H, N52K, N52L, N52M, N52P, N52Q, N52R, N52S, N52T, N52V, N52Y, S54A, S54F, S54P, N57A, N57D, N57E, N57F, N57H, N57K, N57L, N57M, N57P, N57Q, N57S, N57T, N57V, N57W, N57Y, R61C, R61S, Y62F, L67P, A71T, G72R, L74Q, R75Q, D77G, F78L, L80P, N84Q, D89G, E90A, K92R, F93L, H94D, H94E, L96F, L96I, V97A, L98F, S99G, Q100A, Q100D, Q100E, Q100G, Q100K, Q100L, Q100M, Q100N, Q100P, Q100R, Q100S, Q100T, Q100V, L102R, G103E, V107A, V107I, S109G, S109N, V110A, V110D, V110N, E111del, T113E, H115Q, H115R, V116A, A117T, N119Q, F120I, F120S, S121G, V122A, V122M, S126T, S126R, H129P, S130G, S132F, Q133H, E135K, T137A, F138L, T139S, C140del, C140D, S142F, I143T, I143V, N144D, Y146C, V151A, Y152C, Y152H, W153R, I154F, N155H, N155Q, K156M, D158G, L161M, L161P, Q164L, L166Q, N168Q, F172S, L173S, M175T, T190A, T190S, S192G, V193A, V193M, N194D, C198R, N201S, L203F, L203P, N207Q, L208P, V210A, S212G, D217G, D217V, I218N, I218T, E220G, R221G, R221I, R221K, I224V, T225A, T225S, N227K, or a conservative amino acid substitution thereof.

In some embodiments of any one of the variant ICOSL polypeptides described above, the variant ICOSL polypeptide further comprises one or more amino acid deletions corresponding to positions 140 of SEQ ID NO: 32.

In some embodiments, the variant ICOSL polypeptide has one or more amino acid modification, e.g. substitution selected from N52Y/N57Y/F138L/L203P, N52H/N57Y/Q100P, N52S/Y146C/Y152C, N52H/C198R, N52H/C140del/T225A, N52H/C198R/T225A, N52H/K92R, N57Y/Q100P, N52S/C198R, N52Y/N57Y/Y152C, N52Y/N57Y/H129P/C198R, N52H/L161P/C198R, N52S/T113E, N52S/S54P, N52K/L208P, N52S/Y152H, N52H/I143T, N52S/R75Q/L203P, N52S/D158G, N52D/Q133H, N52H/N57Y/Q100R/V110D/C198R/S212G, N52H/N57Y/

Q100R/C198R, N52S/N194D, N52H/N57Y/Q100R/ L102R/V110D/H115R/C198R, N52S/S54P, T38P/N52S/ N57D, N52H/C140del/T225A, N52H/F78L/Q100R/C198R, N52H/N57Y/R75Q/Q100P/V110D, N52H/N57Y/L74Q/ V110D/S192G, N52H/S121G/C198R, N52S/F120S/ N227K, N52S/A71T/A117T/T190A/C198R, T43A/N52H/ N57Y/L74Q/D89G/V110D/F172S, N52H/N57Y/Q100R/ V110D/S132F/M175T, N52H/N57Y/Q100R/V107/V110D/ I154F/C198R/R221G, N52Q/N207Q, N52Q/N168Q, N52Q/N84Q, N52Q/N119Q, N52Q/N84Q/N168Q, N52Q/ N84Q/N207Q, N52Q/N119Q/N155Q, N52H/N84Q/ N119Q, N52H/N84Q, N52H/N84Q/N168Q, N52H/N84Q/ N207Q, N52H/N84Q/N168Q/N207Q, N52Q/N84Q/ N155Q, N52Q/N84Q/N168Q, N52Q/N84Q/N155Q/ N168Q, N52Q/N84Q/N119Q/N168Q, N52Q/N84Q/ N119Q/N207Q, N52Q/N84Q/N119Q/N155Q, N52Q/ N84Q/N119Q/N155Q/N207Q, N52Y/F138L/L203P, N57Y/ Q100R/C198R, N57Y/F138L/L203P, N52H/N57Y/Q100R/ H115R/C198R, N52H/N57Y/Q100R/F172S/C198R, N52H/ N57Y/Q100R/H115R/F172S/C198R, N52H/N57Y/Q100R/ H115R/I143V/F172S/C198R, N52H/N57Y/Q100R/L102R/ H115R/F172S/C198R, N52H/V122A/F172S/C198R, N52H/N57Y/Q100R/H115R/F172S/N194D, N52H/N57Y/ H115R/F172S/C198R, N52H/N57Y/Q100R/H115R/ C198R, N52H/N57Y/H115R, N52H/N57Y/Q100R/H115R, N52H/N57Y/Q100R/H115R/F172S/I224V, N52H/N57Y/ Q100R/H115R/F172S, N52H/N57Y/Q100R/F172S, N52H/ Q100R/H115R/I143T/F172S, N52H/N57Y/Q100P/H115R/ F172S, N52Y/N57Y/Q100P/F172S, E16V/N52H/N57Y/ Q100R/V110D/H115R/C198R, E16V/N52H/N57Y/Q100R/ V110D/H115R/Y152C/K156M/F172S/C198R, N52S/ E90A/H115R, N30D/K42E/N52S/H115R, N30D/K42E/ N52S/H115R/C198R/R221I, N30D/K42E/N52S/H115R/ C198R, N30D/K42E/N52S/H115R/F172S/N194D, N52S/ H115R/F120S/I143V/C198R, N52S/H115R/F172S/C198R, N52H/N57Y/Q100P/C198R, N52H/N57Y/Q100P H115R/ F172S/C198R, N52H/N57Y/Q100P/F172S/C198R, N52H/ N57Y/Q100P/H115R, N52H/N57Y/Q100P/H115R/C198R, N52H/Q100R/C198R, N52H/Q100R/H115R/F172S, N52H/ Q100R/F172S/C198R, N52H/Q100R/H115R/F172S/ C198R, or N52H/N57Y/Q100R/F172S/C198R.

In some embodiments, the variant ICOSL polypeptide has one or more amino acid modification, e.g. substitution in an reference ICOSL or specific binding fragment there of corresponding to position(s) 52, 57, or 100 with reference to numbering of SEQ ID NO:32. In some embodiments, the variant ICOSL polypeptide has one or more amino acid modification, e.g. substitution selected from N52A, N52C, N52D, N52G, N52H, N52L, N52K, N52M, N52P, N52Q, N52R, N52S, N52T, N52V, N52Y, N57A, N57E, N57F, N57H, N57K, N57L, N57M, N57P, N57Q, N57S, N57T, N57V, N57W, N57Y, Q100A, Q100D, Q100E, Q100G, Q100K, Q100L, Q100M, Q100N, Q100R, Q100P, Q100S, Q100T, or Q100V. In some embodiments, the one or more amino acid modification, e.g. substitution is N52Y/N57Y/ F138L/L203P, N52H/N57Y/Q100P, N52S/Y146C/Y152C, N52H/C198R, N52H/C140D/T225A, N52H/C198R/ T225A, N52H/K92R, N52H/S99G, N57Y/Q100P, N52S/ S130G/Y152C, N52S/Y152C, N52S/C198R, N52Y/N57Y/ Y152C, N52Y/N57Y/H129P/C198R, N52H/L161P/C198R, N52S/T113E, N52D/S54P, N52K/L208P, N52S/Y152H, N52D/V151A, N52H/I143T, N52S/L80P, N52S/R75Q/ L203P, N52S/D158G, N52D/Q133H, N52S/N57Y/H94D/ L96F/L98F/Q100R, N52S/N57Y/H94D/L96F/L98F/ Q100R/G103E/F120S, N52H/F78L/Q100R, N52H/N57Y/ Q100R/V110D, N52H/N57Y/R75Q/Q100R/V110D, N52H/ N57Y/Q100R, N52H/N57Y/L74Q/Q100R/V110D, N52H/

Q100R, N52H/S121G, A20V/N52H/N57Y/Q100R/S109G, N52H/N57Y/R61S/Q100R/V110D/L173S, N52H/N57Y/ Q100R/V122A, N52H/N57Y/Q100R/F172S, N52H/N57Y, N52S/F120S, N52S/V97A, N52S/G72R, N52S/A71T/ A117T, N52S/E220G, Y47H/N52S/V107A/F120S, N52H/ N57Y/Q100R/V110D/S132F/M175T, E16V/N52H/N57Y/ Q100R/V110D/H115R/Y152C/K156M/C198R, Q37R/ N52H/N57Y/Q100R/V110N/S142F/C198R/D217V/ R221G, N52H/N57Y/Q100R/V110D/C198R, N52H/N57Y/ Q100R/V110D/V116A/L161M/F172S/S192G/C198R, F27S/N52H/N57Y/V110N, N52S/H94E/L96I/S109N/ L166Q, S18R/N52S/F93L/I143V/R221G, A20T/N52D/ Y146C/Q164L, V11E/N30D/N52H/N57Y/H94E/L96I/ L98F/N194D/V210A/I218T, N52S/H94E/L96I/V122M, N52H/N57Y/H94E/L96I/F120I/S126T/W153R/I218N, M10V/S18R/N30D/N52S/S126R/T139S/L203F, S25G/ N30D/N52S/F120S/N227K, N30D/N52S/L67P/Q100K/ D217G/R221K/T225S, N52H/N57Y/Q100R/V110D/ A117T/T190S/C198R, N52H/N57Y/Q100R/V110D/F172S/ C198R, S25G/F27C/N52H/N57Y/Q100R/V110D/E135K/ L173S/C198R, N52H/N57Y/V110A/C198R/R221I, M10I/ S13G/N52H/N57Y/D77G/V110A/H129P/I143V/F172S/ V193M, C198R, N52H/N57Y/R61C/Y62F/Q100R/V110N/ F120S/C198R, N52H/N57Y/Q100R/V110D/H115R/ C198R, N52H/N57Y/Q100R/V110D/N144D/F172S/ C198R, N52S/H94E/L98F/Q100R, N52S/E90A, N30D/ K42E/N52S, N52S/F120S/I143V/I224V, N52H/N57Y/ Q100R/V110D/C198R/S212G, N52H/N57Y/Q100R/ C198R, N52S/N194D, N52H/N57Y/Q100R/L102R/ V110D/H115R/C198R, N52H/N57Y/Q100R/V110D/ C198R/S212G, N52H/N57Y/Q100R/C198R, N52S/N194D, N52H/N57Y/Q100R/L102R/V110D/H115R/C198R, N52S/ S54P, T38P/N52S/N57D, N52H/C140del/T225A, N52H/ F78L/Q100R/C198R, N52H/N57Y/R75Q/Q100P/V110D, N52H/N57Y/L74Q/V110D/S192G, N52H/S121G/C198R, N52S/F120S/N227K, N52S/A71T/A117T/T190A/C198R, T43A/N52H/N57Y/L74Q/D89G/V110D/F172S, N52H/ N57Y/Q100R/V110D/S132F/M175T, N52D, N52H/N57Y/ Q100R/V107I/V110D/I154F/C198R/R221G, N52Q/ N207Q, N168Q/N207Q, N52Q/N168Q, N52Q/N84Q, N52Q/N119Q, N52Q/N84Q/N168Q, N52Q/N84Q/N207Q, N52Q/N119Q/N155Q, N52H/N84Q/N119Q, N52H/N84Q, N52H/N84Q/N168Q/N207Q, N52Q/N84Q/N155Q/N168Q, N52Q/N84Q/N119Q/N168Q, N52Q/N84Q/N119Q/N207Q, N52Q/N84Q/N119Q/N155Q, N52Q/N84Q/N119Q/N155Q/ N207Q, N52Y/F138L/L203P, N57Y/Q100R/C198R, N57Y/ F138L/L203P, Q100R/F138L, N52H/N57Y/Q100R/H115R/ C198R, N52H/N57Y/Q100R/F172S/C198R, N52H/N57Y/ Q100R/H115R/F172S/C198R, N52H/N57Y/Q100R/ H115R/I143V/F172S/C198R, N52H/N57Y/Q100R/L102R/ H115R/F172S/C198R, N52H/V122A/F172S/C198R, N52H/N57Y/Q100R/H115R/F172S/N194D, N52H/N57Y/ H115R/F172S/C198R, N52H/N57Y/Q100R/H115R/ C198R, N52H/N57Y/H115R, N52H/N57Y/Q100R/H115R, N52H/N57Y/Q100R/H115R/F172S/I224V, N52H/N57Y/ Q100R/H115R/F172S, N52H/N57Y/Q100R/F172S, N52H/ Q100R/H115R/I143T/F172S, N52H/N57Y/Q100P/H115R/ F172S, N52Y/N57Y/Q100P/F172S, E16V/N52H/N57Y/ Q100R/V110D/H115R/C198R, E16V/N52H/N57Y/Q100R/ V110D/H115R/Y152C/K156M/F172S/C198R, N52S/ E90A/H115R, N30D/K42EN52S/H115R, N30D/K42E/ N52S/H115R/C198R/R221I, N30D/K42E/N52S/H115R/ C198R, N30D/K42E/N52S/H115R/F172S/N194D, N52S/ H115R/F120S/I143V/C198R, N52S/H115R/F172S/C198R, N52H/N57Y/Q100R/C198R, N52H/N57Y/Q100P H115R/ F172S/C198R, N52H/N57Y/Q100P/F172S/C198R, N52H/ N57Y/Q100P/H115R, N52H/N57Y/Q100P/H115R/C198R, N52H/Q100R/C198R, N52H/Q100R/H115R/F172S, N52H/ Q100R/F172S/C198R, N52H/Q100R/H115R/F172S/ C198R, N52H/N57Y/Q100R/F172S/C198R, N52A/N57F/ Q100S, N52A/N57H/Q100S, N52A/N57Y/Q100A, N52D/ N57A/Q100A, N52D/Q100S, N52G/Q100A, N52H/ Q100A, N52M/N57H/Q100S, N52M/N57W/Q100P, N52Q/ N57F, N52Q/N57S/Q100A, N52R/N57L/Q100A, N52R/ N57Y/Q100P, N52R/N57Y/Q100S, N52S/N57A/Q100A, N52S/N57H/Q100E, N52S/N57L/Q100S, N52S/N57M/ Q100S, N52S/N57Y/Q100S, N52S/N57Y/Q100M, N52S/ N57Y/Q100V, N52T/N57H/Q100S, N52T/N57H/Q100A, N52T/N57Y/Q100A, N52V/N57L/Q100A, N52H/N57Y/ Q100K, N52K/N57Y/Q100R, N52L/N57H/Q100R, N52R/ N57F/Q100N, N52R/N57F/Q100P, N52R/N57F/Q100R, N52R/N57F/Q100T, N52R/N57H/Q100K, N52R/N57L/ Q100S, N52R/N57W/Q100K, N52R/N57W, N52R/N57Y/ Q100R, N52C/N57E/Q100S, N52G/N57P/Q100D, N52G/ N57V/Q100G, N52G/N57V, N52L/N57V, N52P/N57P, N52P/N57S/Q100G, N52S/N57L/Q100G, N52T/N57K/ Q100P, N52V/N57T/Q100L, or N57Q/Q100P.

In some embodiments, the one or more amino acid modifications are selected from among N52Y/N57Y/F138L/ L203P, N52H/N57Y/Q100P, N52S/Y146C/Y152C, N52H/ C198R, N52H/C140D/T225A, N52H/C198R/T225A, N52H/K92R, N52H/S99G, N57Y/Q100P, N52S/S130G/ Y152C, N52S/Y152C, N52S/C198R, N52Y/N57Y/Y152C, N52Y/N57Y/H129P/C198R, N52H/L161P/C198R, N52S/ T113E, N52D/S54P, N52K/L208P, N52S/Y152H, N52D/ V151A, N52H/I143T, N52S/L80P, F120S/Y152H/N201S, N52S/R75Q/L203P, N52S/D158G, N52D/Q133H, N52S/ N57Y/H94D/L96F/L98F/Q100R, N52S/N57Y/H94D/ L96F/L98F/Q100R/G103E/F120S, N52S/G103E, N52H/ F78L/Q100R, N52H/N57Y/Q100R/V110D, N52H/N57Y/ R75Q/Q100R/V110D, N52H/N57Y/Q100R, N52H/N57Y/ L74Q/Q100R/V110D, N52H/Q100R, N52H/S121G, A20V/ N52H/N57Y/Q100R/S109G, N52H/N57Y/R61S/Q100R/ V110D/L173S, N52H/N57Y/Q100R/V122A, N52H/N57Y/ Q100R/F172S, N52H/N57Y, N52S/F120S, N52S/V97A, N52S/G72R, N52S/A71T/A117T, N52S/E220G, Y47H/ N52S/V107A/F120S, N52H/N57Y/Q100R/V110D/S132F/ M175T, E16V/N52H/N57Y/Q100R/V110D/H115R/ Y152C/K156M/C198R, Q37R/N52H/N57Y/Q100R/ V110N/S142F/C198R/D217V/R221G, N52H/N57Y/ Q100R/V110D/C198R, N52H/N57Y/Q100R/V110D/ V116A/L161M/F172S/S192G/C198R, F27S/N52H/N57Y/ V110N, N52S/H94E/L96I/S109N/L166Q, S18R/N52S/ F93L/I143V/R221G, A20T/N52D/Y146C/Q164L, V11E/ N30D/N52H/N57Y/H94E/L96I/L98F/N194D/V210A/ I218T, N52S/H94E/L96I/V122M, N52H/N57Y/H94E/ L96I/F120I/S126T/W153R/I218N, M10V/S18R/N30D/ N52S/S126R/T139S/L203F, S25G/N30D/N52S/F120S/ N227K, N30D/N52S/L67P/Q100K/D217G/R221K/T225S, N52H/N57Y/Q100R/V110D/A117T/T190S/C198R, N52H/ N57Y/Q100R/V110D/F172S/C198R, S25G/F27C/N52H/ N57Y/Q100R/V110D/E135K/L173S/C198R, N52H/N57Y/ V110A/C198R/R221I, M10V/S13G/N52H/N57Y/D77G/ V110A/H129P/I143V/F172S/V193M, C198R, N52H/ N57Y/R61C/Y62F/Q100R/V110N/F120S/C198R, N52H/ N57Y/Q100R/V110D/H115R/C198R, N52H/N57Y/ Q100R/V110D/N144D/F172S/C198R, N52S/H94E/L98F/ Q100R, N52S/E90A, N30D/K42E/N52S, N52S/F120S/ I143V/I224V, N52H/N57Y/Q100R/V110D/C198R/S212G, N52H/N57Y/Q100R/C198R, N52S/N194D, N52H/N57Y/ Q100R/L102R/V110D/H115R/C198R, N52H/N57Y/ Q100R/V110D/C198R/S212G, N52H/N57Y/Q100R/ C198R, N52S/N194D, N52H/N57Y/Q100R/L102R/ V110D/H115R/C198R, N52S/S54P, T38P/N52S/N57D, N52H/C140del/T225A, N52H/F78L/Q100R/C198R, N52H/N57Y/R75Q/Q100P/V110D, N52H/N57Y/L74Q/ V110D/S192G, N52H/S121G/C198R, N52S/F120S/ N227K, N52S/A71T/A117T/T190A/C198R, T43A/N52H/ N57Y/L74Q/D89G/V110D/F172S, N52H/N57Y/Q100R/ V110D/S132F/M175T, N52H/N57Y/Q100R/V107I/ V110D/I154F/C198R/R221G, N52Q/N207Q, N52Q/ N168Q, N52Q/N84Q, N52Q/N119Q, N52Q/N84Q/N168Q, N52Q/N84Q/N207Q, N52Q/N119Q/N155Q, N52H/N84Q/ N119Q, N52H/N84Q, N52H/N84Q/N168Q/N207Q, N52Q/ N84Q/N155Q/N168Q, N52Q/N84Q/N119Q/N168Q, N52Q/N84Q/N119Q/N207Q, N52Q/N84Q/N119Q/N155Q, N52Q/N84Q/N119Q/N155Q/N207Q, N52Y/F138L/L203P, N57Y/Q100R/C198R, N57Y/F138L/L203P, Q100R/F138L, N52H/N57Y/Q100R/H115R/C198R, N52H/N57Y/Q100R/ F172S/C198R, N52H/N57Y/Q100R/H115R/F172S/C198R, N52H/N57Y/Q100R/H115R/I143V/F172S/C198R, N52H/ N57Y/Q100R/L102R/H115R/F172S/C198R, N52H/ V122A/F172S/C198R, N52H/N57Y/Q100R/H115R/ F172S/N194D, N52H/N57Y/H115R/F172S/C198R, N52H/ N57Y/H115R, N52H/N57Y/Q100R/H115R, N52H/N57Y/ Q100R/H115R/F172S/I224V, N52H/N57Y/Q100R/H115R/ F172S, N52H/N57Y/Q100R/F172S, N52H/Q100R/H115R/ I143T/F172S, N52H/N57Y/Q100P/H115R/F172S, N52Y/ N57Y/Q100P/F172S, E16V/N52H/N57Y/Q100R/V110D/ H115R/C198R, E16V/N52H/N57Y/Q100R/V110D/H115R/ Y152C/K156M/F172S/C198R, N52S/E90A/H115R, N30D/ K42EN52S/H115R, N30D/K42E/N52S/H115R/C198R/ R221I, N30D/K42E/N52S/H115R/C198R, N30D/K42E/ N52S/H115R/F172S/N194D, N52S/H115R/F120S/I143V/ C198R, N52S/H115R/F172S/C198R, N52H/N57Y/Q100P/ C198R, N52H/N57Y/Q100P/H115R/F172S/C198R, N52H/ N57Y/Q100P/F172S/C198R, N52H/N57Y/Q100P/H115R, N52H/N57Y/Q100P/H115R/C198R, N52H/Q100R/C198R, N52H/Q100R/H115R/F172S, N52H/Q100R/F172S/C198R, N52H/Q100R/H115R/F172S/C198R, N52H/N57Y/Q100R/ F172S/C198R, N52A/N57F/Q100S, N52A/N57H/Q100S, N52A/N57Y/Q100A, N52D/N57A/Q100A, N52D/Q100S, N52G/Q100A, N52H/Q100A, N52M/N57H/Q100S, N52M/ N57W/Q100P, N52Q/N57F, N52Q/N57S/Q100A, N52R/ N57L/Q100A, N52R/N57Y/Q100P, N52R/N57Y/Q100S, N52S/N57A/Q100A, N52S/N57H/Q100E, N52S/N57L/ Q100S, N52S/N57M/Q100S, N52S/N57Y/Q100S, N52S/ N57Y/Q100M, N52S/N57Y/Q100V, N52T/N57H/Q100S, N52T/N57H/Q100A, N52T/N57Y/Q100A, N52V/N57L/ Q100A, N52H/N57Y/Q100K, N52K/N57Y/Q100R, N52L/ N57H/Q100R, N52R/N57F/Q100N, N52R/N57F/Q100P, N52R/N57F/Q100R, N52R/N57F/Q100T, N52R/N57H/ Q100K, N52R/N57L/Q100S, N52R/N57W/Q100K, N52R/ N57W, N52R/N57Y/Q100R, N52C/N57E/Q100S, N52G/ N57P/Q100D, N52G/N57V/Q100G, N52G/N57V, N52L/ N57V, N52P/N57P, N52P/N57S/Q100G, N52S/N57L/ Q100G, N52T/N57K/Q100P, N52V/N57T/Q100L, N57Q/ Q100P, or R26S/N52H/N57Y/V110D/T137A/C198R.

In some embodiments, the variant ICOSL polypeptide has one or more amino acid modification, e.g. substitution selected from N52A, N52C, N52D, N52G, N52K, N52L, N52M, N52R, N52T, N52V, N57A, N57E, N57F, N57H, N57K, N57L, N57M, N57P, N57Q, N57S, N57T, N57V, N57W, Q100A, Q100D, Q100G, Q100L, Q100M, Q100N, Q100R, Q100S, Q100T or Q100V. with reference to SEQ ID NO:32. In some embodiments, the one or more amino acid modifications are selected from among N52A/N57F/Q100S, N52A/N57H/Q100S, N52A/N57Y/Q100A, N52D/N57A/ Q100A, N52D/Q100S, N52G/Q100A, N52H/Q100A, N52M/N57H/Q100S, N52M/N57W/Q100P, N52Q/N57F, N52Q/N57S/Q100A, N52R/N57L/Q100A, N52R/N57Y/

Q100P, N52R/N57Y/Q100S, N52S/N57A/Q100A, N52S/ N57H/Q100E, N52S/N57L/Q100S, N52S/N57M/Q100S, N52S/N57Y/Q100S, N52S/N57Y/Q100M, N52S/N57Y/ Q100V, N52T/N57H/Q100S, N52T/N57H/Q100A, N52T/ N57Y/Q100A, N52V/N57L/Q100A, N52H/N57Y/Q100K, N52K/N57Y/Q100R, N52L/N57H/Q100R, N52R/N57F/ Q100N, N52R/N57F/Q100P, N52R/N57F/Q100R, N52R/ N57F/Q100T, N52R/N57H/Q100K, N52R/N57L/Q100S, N52R/N57W/Q100K, N52R/N57W, N52R/N57Y/Q100R, N52C/N57E/Q100S, N52G/N57P/Q100D, N52G/N57V/ Q100G, N52G/N57V, N52L/N57V, N52P/N57P, N52P/ N57S/Q100G, N52S/N57L/Q100G, N52T/N57K/Q100P, N52V/N57T/Q100L or N57Q/Q100P.

In some embodiments, the variant ICOSL polypeptide has one or more amino acid modification, e.g. substitution selected from N52H/N57Y/Q100R/C198R, N52H/N57Y/ Q100R/V122A, N52H/N57Y/Q100R/F172S, N52Y/N57Y/ F138L/L203P, V11E/N30D/N52H/N57Y/H94E/L96I/L98F/ N194D/V210A/I218T, N52H/N57Y/Q100R/L102R/ V110D/H115R/C198R, N52H/N57Y/Q100R, N52H/ Q100R, N52H/N57Y/Q100R/V110D/C198R/S212G, N52H/N57Y/Q100R/L102R/V110D/H115R/C198R, E16V/ N52H/N57Y/Q100R/V110D/H115R/V152C/K156M/ C198R, N30D/K42E/N52S, N52S/F120S/I143V/I224V, N52S/E90A, N52H/N57Y/V110A/C198R/R221I, N52H/ N57Y/Q100P, or N52S/N194D.

In some embodiments, the variant ICOSL polypeptide has one or more amino acid modification, e.g. substitution selected from N52H/N57Y/Q100R/F172S, N52H/Q100R, or N52H/N57Y/Q100R/C198R. In some embodiments, the variant ICOSL polypeptide has one or more amino acid modification, e.g. substitution selected from E16V/N52H/ N57Y/Q100R/V110D/H115R/Y152C/K156M/C198R, N52H/N57Y/Q100R, and N52H/N57Y/Q100P.

In some embodiments, the variant ICOSL polypeptide has one or more amino acid modification, e.g. substitution selected from N52H/N57Y/F138L/L203P, N52H/N57Y/ Q100P, N52H/K92R, N52H/C140del/T225A, N52H/ C198R/T225A, N52H/K92R, N57Y/Q100P, N52Y/N57Y/ H129P/C198R, N52H/L161P/C198R, N52K/L208P or N52H/I143T.

In some embodiments, the one or more amino acid modifications are selected from among F120S/Y152H/ N201S, E111del, Y33del, N168Q/N207Q, N84Q/N207Q, N155Q/N207Q, N119Q/N168Q, N119Q/N207Q, N119Q/ N155Q, N84Q/N119Q, N84Q/N155Q/N168Q, N84Q/ N168Q/N207Q, N84Q/N155H/N207Q, N155Q/N168Q/ N207Q, N119Q N155Q/N168Q, N119Q/N168Q/N207Q, N84Q/N119Q/N207Q, N119Q/N155H/N207Q, N84Q/ N119Q/N155Q, N84Q/N119Q/N155Q/N168Q, N84Q/ N155Q/N168Q/N207Q, N84Q/N119Q/N155Q/N207Q, N84Q/N119Q/N155Q/N168Q/N207Q or F138L/L203P.

In some embodiments, the variant ICOSL polypeptide exhibits increased binding affinity for binding one of the ectodomains of CD28 or ICOS and exhibits decreased binding affinity for binding to the other of the ectodomains of CD28 or ICOS compared to the reference (e.g., unmodified) or wild-type ICOSL polypeptide, such as comprising the sequence set forth in SEQ ID NO: 32, 196, or 545.

In some embodiments, the variant ICOSL polypeptide exhibits increased binding affinity for ICOS. In some embodiments, the one or more amino acid substitution is at a position corresponding to 16, 30, 42, 52, 54, 57, 75, 90, 92, 100, 102, 110, 113, 115, 120, 122, 133, 138, 143, 146, 152, 156, 158, 172, 194, 198, 203, 208, 221, 224, or 225. In some embodiments, the variant ICOSL contains one or more amino acid substitutions selected from C198R, D158G, E16V, E90A, F120S, F138L, F172S, H115R, H115X, I143T, I143V, I224V, K156M, K42E, K92R, L102R, L203P, L208P, N194D, N30D, N52A, N52D, N52G, N52H, N52K, N52L, N52M, N52Q, N52R, N52S, N52T, N52Y, N57F, N57H, N57K, N57L, N57M, N57P, N57S, N57V, N57W, N57Y, Q100A, Q100D, Q100E, Q100K, Q100M, Q100P, Q100P, Q100R, Q100S, Q100T, Q133H, R221I, R75Q, S54A, S54P, T113E, T225A, V110D, V122A, Y146C, Y152C, or a conservative amino acid substitution thereof. In some embodiments, the variant ICOSL polypeptide has one or more amino acid substitutions selected from N52S, N52H, N52D, N52H/N57Y/Q100P, N52S/Y146C/Y152C, N52H/C198R, N52H/C198R/T225A, N52H/K92R, N57Y, N52S/C198R, N52S/T113E, S54A, N52D/S54P, N52K/L208P, N52H/ I143T, N52S/R75Q/L203P, N52S/D158G, N52D/Q133H, N52H/N57Y/Q100R/V122A, N52H/N57Y/Q100R/F172S, N52H/N57Y/Q100R, N52S/N194D, N52H/N57Y/Q100R/ L102R/V110D/H115R/C198R, N52S/E90A, N52S/F120S/ I143V/I224V, N52H/N57Y/Q100R/F172S/C198R, N52H/ N57Y/Q100R/H115R/F172S/C198R, N52Y/N57Y/Q100P/ F172S, E16V/N52H/N57Y/Q100R/V110D/H115R/Y152C/ K156M/F172S/C198R, N52S/H115R/F120S/I143V/ C198R, N52H/N57Y/Q100P/C198R, N52H/N57Y/Q100P/ H115R/F172S/C198R, N52H/N57Y/Q100P/F172S/C198R, N52H/N57Y/Q100P/H115R, N52H/N57Y/Q100P/H115R/ C198R, N52H/Q100R/C198R, N52H/Q100R/H115X/ F172S/C198R, N52H/Q100R/H115R/F172S/C198R, N52H/N57Y/Q100R/H115R/F172S/C198R, N52H/N57Y/ Q100R/H115R/F172S, N52H/N57Y/Q100R/H115R/F172S/ C198R, Q100R, N52Y/F138L/L203P, N57Y/Q100R/ C198R, N57Y/F138L/L203P, N57Y/Q100P, Q100R/F138L, N52H/N57Y/Q100R/H115R, N52H/N57Y/Q100R/F172S, N52H/N57Y/Q100R/H115R/F172S/I224V, N52H/N57Y/ Q100R/H115R/F172S, N52H/N57Y/Q100R/H115R/ C198R, N52H/N57Y/Q100R/F172S/C198R, N52H/N57Y/ Q100R/H115R/F172S/C198R, N52H/N57Y/Q100R/ H115R/I143V/F172S/C198R, N52H/N57Y/Q100R/L102R, H115R/F172S/C198R, N52H/N57Y/Q100R/H115R F172S/ N194D, N52H/N57Y/H115R/F172S/C198R, N52H/N57Y/ Q100R/H115R/C198R, N52H/N57Y/H115R, N52H/ Q100R/H115R/I143T F172S, N52H/N57Y/Q100P/H115R/ F172S, E16V/N52H/N57Y/Q100R/V110D/H115R/C198R, N52S/E90A/H115R, N30D/K42E/N52S/H115R/C198R/ R221I, N30D/K42E/N52S/H115R/C198R, N30D/K42E/ N52S/H115R/F172S/N194D, N30D/K42E/N52S/H115R, N52S/E90A/H115R, N30D/K42E/N52S/H115R, N52A/ N57H/Q100S, N52A/N57Y/Q100A, N52D/Q100S, N52G/ Q100A, N52M/N57H/Q100S, N52M/N57W/Q100P, N52Q/ N57S/Q100A, N52R/N57L/Q100A, N52S/N57H/Q100E, N52S/N57L/Q100S, N52S/N57M/Q100S, N52S/N57Y/ Q100M, N52T/N57H/Q100S, N52R/N57F/Q100P, N52R/ N57F/Q100T, N52R/N57W/Q100K, N52R/N57W, N52G/ N57P/Q100D, N52G/N57V/Q100G, N52G/N57V, N52L/ N57V, N52S/N57L/Q100G or N52T/N57K/Q100P.

In some embodiments, the variant ICOSL polypeptide exhibits increased binding affinity for ICOS and exhibits decreased binding affinity for CD28. In some embodiments, the one or more further amino acid substitution is at a position corresponding to 52, 57, 80 100, 130, 152, 161 or 198. In some embodiments, the variant ICOSL contains one or more amino acid substitutions selected from N52S, N52H, N52Y, N52H, N57Y, L80P, Q100P Q100R, Q100K, V110D, S130G, Y152C, L161P, L161M, C198R, R221G, or a conservative amino acid substitution thereof. In some embodiments, the variant ICOSL polypeptide has one or more amino acid substitutions selected from N57Y/Q100P, N52S/S130G/Y152C, N52S/Y152C, N52Y/N57Y/Y152C, N52H/L161P/C198R, N52H/L161P/C198R, N52S/L80P, A20V/N52H/N57Y/Q100R/S109G, N52H/N57Y/R61S/ Q100R/V110D/L173S, N52H/N57Y/Q100R/V107I/ V110D/S132F/I154F/C198R/R221G, Q37R/N52H/N57Y/ Q100R/V110N/S142F/C198R/D217V/R221G, N52H/ N57Y/Q100R/V110D/C198R, F27S/N52H/N57Y/V110N, S18R/N52S/F93L/I143V/R221G, A20T/N52D/Y146C/ Q164L, N52H/N57Y/H94E/L96I/F120I/S126T/W153R/ I218N, N52H/N57Y/Q100R/V110D/F172S/C198R, S25G/ F27C/N52H/N57Y/Q100R/V110D/E135K/L173S/C198R, M10I/S13G/N52H/N57Y/D77G/V110A/H129P/I143V/ F172S/V193M/C198R.

In some embodiments, the variant ICOSL polypeptide exhibits increased binding affinity for CD28. In some embodiments, the one or more amino acid substitution is at a position corresponding to 10, 11, 13, 16, 18, 20, 25, 27, 30, 36, 40, 41, 42, 52, 54, 57, 63, 70, 71, 72, 74, 77, 80, 81, 84, 88, 89, 90, 91, 92, 93, 94, 96, 98, 99, 100, 102, 107, 109, 110, 113, 114, 115, 117, 118, 119, 120, 121, 122, 126, 127, 129, 130, 132, 133, 135, 138, 139, 140, 143, 144, 146, 152, 153, 154, 155, 156, 158, 161, 166, 168, 169, 172, 173, 178, 190, 192, 193, 194, 198, 199, 201, 203, 207, 208, 209, 212, 218, 221, 224, 225, or 227.

In some embodiments, the variant ICOSL contains one or more amino acid substitutions selected from A117T, A20V, A71T, A91G, A91G, AE88D, C140del, C198R, D158G, D77G, D90K, E117G, E135K, E16V, E81A, E88D, E90A, F120I, F120S, F138L, F172S, F27C, F92Y, G72R, H115R, H115X, H129P, H94E, I118V, I127T, I143T, I143V, I154F, I218N, I218T, I224V, K156M, K169E, K36G, K42E, K89R, K92R, K93R, L102R, L161P, L166Q, L173S, L203F, L203P, L208P, L209P, L40M, L70Q, L70R, L74Q, L80P, L96I, L98F, M10I, M10V, N115Q, N119Q, N122S, N144D, N155X, N168Q, N168X, N178S, N194D, N207Q, N207X, N227K, N25S, N30D, N52A, N52D, N52G, N52H, N52K, N52L, N52M, N52Q, N52R, N52S, N52T, N52V, N52Y, N57A, N57F, N57H, N57L, N57M, N57S, N57V, N57W, N57Y, N63S, N84Q, Q100A, Q100E, Q100G, Q100K, Q100M, Q100N, Q100P, Q100R, Q100S, Q100T, Q100V, Q133H, R221G, R221I, S109G, S109N, S114T, S121G, S126R, S126T, S130G, S132F, S13G, S18R, S192G, S212G, S25G, S54A, S54P, S99G, T113E, T120S, T130A, T139S, T190A, T199S, T225A, T41I, V107I, V110A, V110D, V11E, V122A, V122M, V193M, V210A, W153R, Y146C, Y152C, Y152H, or a conservative amino acid substitution thereof. In some embodiments, the variant ICOSL polypeptide has one or more amino acid substitutions selected from N52S, N52H, N52D, N52Y/N57Y/ F138L/L203P, N52H/N57Y/Q100P, N52S/Y146C/Y152C, N52H/C198R, N52H/C140del/T225A, N52H/C198R/ T225A, N52H/K92R, N52H/S99G, N57Y, N57Y/Q100P, N52S/S130G/Y152C, N52S/Y152C, N52S/C198R, N52Y/ N57Y/Y152C, N52Y/N57Y/H129P/C198R, N52H/L161P/ C198R, N52S/T113E, S54A, N52D/S54P, N52K/L208P, N52S/Y152H, N52H/I143T, N52S/L80P, N52S/D158G, N52D/Q133H, L70Q/A91G/N144D, L70Q/A91G/E117G/ I118V/T120S/T130A, L70R/A91G/I118V/T120S/T130A/ T199S, L70Q/E81A/A91G/I118V/T120S/I127T/T130A, N63S/L70Q/A91G/S114T/I118V/T120S/T130A, T41I/ A91G, E88D/K89R/D90K/A91G/F92Y/K93R/N122S/ N178S, E88D/K89R/D90K/A91G/F92Y/K93R, AE88D/ K89R/D90K/A91G/F92Y/K93R, K36G/L40M, N52H/ N57Y/Q100R/V122A, N52H/N57Y/Q100R/F172S, N52H/ N57Y/Q100R, N52S/F120S/N227K, N52S/N194D, N52S/ F120S, N52S/G72R, N52S/A71T/A117T/T190A/C198R, N52H/N57Y/Q100R/V107I/V110D/S132F/I154F/C198R/ R221G, E16V/N52H/N57Y/Q100R/V110D/H115R/

Y152C/K156M/C198R, N52H/N57Y/Q100R/V110D/ C198R, V11E/N30D/N52H/N57Y/H94E/L96I/L98F/ N194D/V210A/I218T, N52S/H94E/L96I/V122M, N52H/ N57Y/H94E/L96I/F120I/S126T/W153R/I218N, M10V/ S18R/N30D/N52S/S126R/T139S/L203F, S25G/N30D/ N52S/F120S/N227K, N52H/N57Y/Q100R/V110D/F172S/ C198R, S25G/F27C/N52H/N57Y/Q100R/V110D/E135K/ L173S/C198R, N52H/N57Y/V110A/C198R/R221I, M10I/ S13G/N52H/N57Y/D77G/V110A/H129P/I143V/F172S/ V193M, C198R, N52H/N57Y/Q100R/L102R/V110D/ H115R/C198R, N52H/N57Y/Q100R/V110D/N144D/ F172S/C198R, N52S/H94E/L98F/Q100R, N52S/E90A, N52S/F120S/I143V/I224V, N52H/N57Y/Q100R/F172S/ C198R, N52H/N57Y/Q100R/H115R/F172S/C198R, N52Y/ N57Y/Q100P/F172S, E16V/N52H/N57Y/Q100R/V110D/ H115R/Y152C/K156M/F172S/C198R, N52S/H115R/ F120S/I143V/C198R, N52H/N57Y/Q100P/C198R, N52H/ N57Y/Q100P/H115R/F172S/C198R, N52H/N57Y/Q100P/ F172S/C198R, N52H/N57Y/Q100P/H115R, N52H/N57Y/ Q100P/H115R/C198R, N52H/Q100R/C198R, N52H/ Q100R/H115R/F172S, N52H/Q100R/H115X/F172S/ C198R, N52H/Q100R/H115R/F172S/C198R, N52H/N57Y/ Q100R/F172S/C198R, N52H/N57Y/Q100R/H115R/F172S/ C198R, N52H/N57Y/Q100R/H115R/F172S, N52H/N57Y/ Q100R/H115R/F172S/C198R, N52S/H94E/L96I/S109N/ L166Q/, N52H/N57Y/Q100R/C198R, N52H/N57Y/L74Q/ V110D/S192G, N52H/Q100R, N52H/S121G/C198R, A20V/N52H/N57Y/Q100R/S109G, N52H/N57Y/Q100P/ C198R, N52H/N57Y/Q100R/V110D/C198R/S212G, L70Q/A91G/I118A/T120S/T130A/K169E, Q100R, N52Y/ F138L/L203P, N57Y/Q100R/C198R, N57Y/F138L/L203P, N52H, N57Y, N57Y/Q100P, N52H/N57Y/Q100R/H115R, N52H/N57Y/Q100R/F172S, N52H/N57Y/Q100R/H115R/ F172S/I224V, N52H/N57Y/Q100R/H115R/F172S, N52H/ N57Y/Q100R/H115R/C198R, N52H/N57Y/Q100R/F172S/ C198R, N52H/N57Y/Q100R/H115R/F172S/C198R, N52H/ N57Y/Q100R/H115R/I143V/F172S/C198R, N52H/N57Y/ Q100R/L102R H115R/F172S/C198R, N52H/N57Y/ Q100R/H115R F172S/N194D, N52H/N57Y/H115R/F172S/ C198R, N52H/N57Y/Q100R/H115R/C198R, N52H/N57Y/ H115R, N52H/Q100R/H115R/I143T F172S, N52H/N57Y/ Q100P/H115R/F172S, E16V/N52H/N57Y/Q100R/V110D/ H115R/C198R, N30D/K42E/N52S/H115R/C198R R221I, N52S/E90A/H115R, N30D/K42E/N52S/H115R, N52S/ H115R/F172S/C198R, N119Q, N207Q, N52Q/N207X, N168X/N207X, N52Q/N168Q, N84Q/N207Q, N119Q N155X, N52Q/N119Q, N52Q/N84Q/N207Q, N119Q/ N155Q/N168Q, N52H/N84Q/N119Q, N52Q/N84Q/ N155X/N168X, N52A/N57F/Q100S, N52A/N57H/Q100S, N52A/N57Y/Q100A, N52D/N57A/Q100A, N52D/Q100S, N52G/Q100A, N52H/Q100A, N52M/N57H/Q100S, N52M/ N57W/Q100P, N52Q/N57F, N52Q/N57S/Q100A, N52R/ N57L/Q100A, N52R/N57Y/Q100P, N52R/N57Y/Q100S, N52S/N57A/Q100A, N52S/N57H/Q100E, N52S/N57L/ Q100S, N52S/N57M/Q100S, N52S/N57Y/Q100S, N52S/ N57Y/Q100M, N52S/N57Y/Q100V, N52T/N57H/Q100S, N52T/N57H/Q100A, N52T/N57Y/Q100A, N52V/N57L/ Q100A, N52H/N57Y/Q100K, N52K/N57Y/Q100R, N52L/ N57H/Q100R, N52R/N57F/Q100N, N52R/N57F/Q100P, N52R/N57F/Q100R, N52R/N57F/Q100T, N52R/N57L/ Q100S, N52R/N57W/Q100K, N52R/N57W, N52G/N57V, N52L/N57V, N52S/N57L/Q100G, or N52T/N57K/Q100P.

In some embodiments, the variant ICOSL polypeptide exhibits increased binding affinity for CD28 and exhibits decreased binding affinity for ICOS. In some embodiments, the one or more amino acid substitution is at a position corresponding to 52, 75 or 203. In some embodiments, the variant ICOSL contains one or more amino acid substitution selected from N52S, R75Q, L203F, or L203P. In some embodiments, the variant ICOSL polypeptide has amino acid substitutions N52S/R75Q/L203P.

In some embodiments, the variant ICOSL polypeptide has one or more amino acid modification, e.g. substitution in an reference ICOSL or specific binding fragment there of corresponding to position(s) 16, 30, 42, 52, 57, 90, 100, 102, 110, 115, 120, 122, 138, 143, 152, 156, 172, 194, 198, 203, 221, or 224 with reference to numbering of SEQ ID NO: 32. In some embodiments, the variant ICOSL polypeptide has one or more amino acid modification, e.g. substitution selected from E16V, N30D, K42E, N52H, N52Y, N52S, N57Y, E90A, Q100R, Q100P, L102R, V110D, H115R, F120S, V122A, F138L, I143V, I143T, H152C, K156M, F172S, N194D, C198R, L203P, R221I, or I224V. In some embodiments, the variant ICOSL polypeptide has one or more amino acid modification, e.g. substitution in an reference ICOSL or specific binding fragment there of corresponding to position(s) 115, 172, or 198 with reference to numbering of SEQ ID NO:32. In some embodiments, the variant ICOSL polypeptide has one or more amino acid modification, e.g. substitution selected from H115R, F172S or C198R. In some embodiments, the one or more amino acid modification, e.g. substitution is N52H/N57Y/Q100R/ H115R/C198R, N52H/N57Y/Q100R/F172S/C198R, N52H/ N57Y/Q100R/H115R/F172S/C198R, N52H/N57Y/Q100R/ H115R/I143V/F172S/C198R, N52H/N57Y/Q100R/L102R/ H115R/F172S/C198R, N52H/V122A/F172S/C198R, N52H/N57Y/Q100R/H115R/F172S/N194D, N52H/N57Y/ H115R/F172S/C198R, N52H/N57Y/Q100R/H115R/ C198R, N52H/N57Y/H115R, N52H/N57Y/Q100R/H115R, N52H/N57Y/Q100R/H115R/F172S/I224V, N52H/N57Y/ Q100R/H115R/F172S, N52H/N57Y/Q100R/F172S, N52H/ Q100R/H115R/I143T/F172S, N52H/N57Y/Q100P/H115R/ F172S, N52Y/N57Y/Q100P/F172S, E16V/N52H/N57Y/ Q100R/V110D/H115R/C198R, E16V/N52H/N57Y/Q100R/ V110D/H115R/Y152C/K156M/F172S/C198R, N52S/ E90A/H115R, N30D/K42EN52S/H115R, N30D/K42E/ N52S/H115R/C198R/R221I, N30D/K42E/N52S/H115R/ C198R, N30D/K42E/N52S/H115R/F172S/N194D, N52S/ H115R/F120S/I143V/C198R, N52S/H115R/F172S/C198R, N52H/N57Y/Q100P/C198R, N52H/N57Y/Q100P H115R/ F172S/C198R, N52H/N57Y/Q100P/F172S/C198R, N52H/ N57Y/Q100P/H115R, N52H/N57Y/Q100P/H115R/C198R, N52H/Q100R/C198R, N52H/Q100R/H115R/F172S, N52H/ Q100R/F172S/C198R, N52H/Q100R/H115R/F172S/ C198R or N52H/N57Y/Q100R/F172S/C198R. In some embodiments, the variant ICOSL polypeptides exhibit potentially enhanced protein solubility or enhanced protein expression ('solubility mutations') compared to the reference (e.g., unmodified) or wild-type ICOSL polypeptide.

In some embodiments, the variant ICOSL polypeptide comprises any of the extracellular domain (ECD) sequences set forth in SEQ ID NOS: 435-470. In some embodiments, the variant ICOSL polypeptide comprises a polypeptide sequence that exhibits at least 90% identity, at least 91% identity, at least 92% identity, at least 93% identity, at least 94% identity, at least 95% identity, such as at least 96% identity, 97% identity, 98% identity, or 99% identity to any of the extracellular domain (ECD) set forth in SEQ ID NOS: 435-470 and contains the amino acid modification(s), e.g. substitution(s) not present in the reference (e.g., unmodified) or wild-type ICOSL. In some embodiments, the variant ICOSL polypeptide comprises a specific binding fragment of any of the extracellular domain (ECD) sequences set forth in SEQ ID NOS: 435-470 and contains the amino acid modification(s), e.g. substitution(s) not present in the reference (e.g., unmodified) or wild-type ICOSL.

In some embodiments, the variant ICOSL polypeptide exhibits increased binding affinity for CD28 and exhibits increased binding affinity for ICOS. In some embodiments, the one or more amino acid substitution is at a position corresponding to 16, 30, 42, 52, 54, 57, 90, 92, 100, 102, 110, 113, 115, 120, 122, 133, 138, 143, 146, 152, 156, 158, 172, 194, 198, 203, 208, 212, 224, or 225. In some embodiments, the variant ICOSL contains one or more amino acid substitutions selected from C198R, D158G, E16V, E90A, F120S, F138L, F172S, H115R, I143V, I224V, K156M, K42E, K92R, L102R, L203P, L208P, N194D, N30D, N52A, N52D, N52G, N52H, N52K, N52L, N52M, N52Q, N52R, N52S, N52T, N52Y, N57F, N57H, N57L, N57M, N57S, N57V, N57W, N57Y, Q100A, Q100E, Q100G, Q100K, Q100M, Q100P, Q100R, Q100S, Q133H, S212G, S54A, S54P, T113E, T225A, V110D, V122A, Y146C, Y152C, or a conservative amino acid substitution thereof. In some embodiments, the variant ICOSL polypeptide has one or more amino acid substitutions selected from N52A/N57Y/ Q100A, N52D/Q100S, N52G/Q100A, N52M/N57H/ Q100S, N52M/N57W/Q100P, N52Q/N57S/Q100A, N52R/ N57L/Q100A, N52S/N57H/Q100E, N52S/N57L/Q100S, N52S/N57M/Q100S, N52S/N57Y/Q100M, N52T/N57H/ Q100S, N52R/N57F/Q100P, N52R/N57F/Q100T, N52R/ N57W/Q100K, N52R/N57W, N52G/N57V, N52L/N57V, N52S/N57L/Q100G, N52T/N57K/Q100P, N52S, N52H, N52D, N52Y/N57Y/F138L/L203P, N52H/N57Y/Q100P, N52S/Y146C/Y152C, N52H/C198R, N52H/C198R/T225A, N52H/K92R, N57Y, N52S/C198R, N52S/T113E, S54A, N52D/S54P, N52K/L208P, N52H/I143T, N52S/D158G, N52D/Q133H, N52H/N57Y/Q100R/V110D/C198R/ S212G, N52H/N57Y/Q100R/V122A, N52H/N57Y/Q100R/ F172S, N52H/N57Y/Q100R, N52S/N194D, N52H/N57Y/ Q100R/L102R/V110D/H115R/C198R, N52S/E90A, N52S/ F120S/I143V/I224V, N52H/N57Y/Q100R/F172S/C198R, N52H/N57Y/Q100R/H115R/F172S/C198R, N52Y/N57Y/ Q100P/F172S, E16V/N52H/N57Y/Q100R/V110D/H115R/ Y152C/K156M/F172S/C198R, N52S/H115R/F120S/ I143V/C198R, N52H/N57Y/Q100P/C198R, N52H/N57Y/ Q100P/H115R/F172S/C198R, N52H/N57Y/Q100P/F172S/ C198R, N52H/N57Y/Q100P/H115R, N52H/N57Y/Q100P/ H115R/C198R, N52H/Q100R/C198R, N52H/Q100R/ H115R/F172S, N52H/Q100R/H115X/F172S/C198R, N52H/Q100R/H115R/F172S/C198R, N52H/N57Y/Q100R/ H115R/F172S/C198R, N52H/N57Y/Q100R/H115R/F172S, N52H/N57Y/Q100R/H115R/F172S/C198R, Q100R, N52Y/ F138L/L203P, N57Y/Q100R/C198R, N57Y/F138L/L203P, N52H, N57Y, N57Y/Q100P, Q100R/F138L, N52H/N57Y/ Q100R/H115R, N52H/N57Y/Q100R/F172S, N52H/N57Y/ Q100R/H115R/F172S/I224V, N52H/N57Y/Q100R/H115R/ F172S, N52H/N57Y/Q100R/H115R/C198R, N52H/N57Y/ Q100R/F172S/C198R, N52H/N57Y/Q100R/H115R/F172S/ C198R, N52H/N57Y/Q100R/H115R/I143V/F172S/C198R, N52H/N57Y/Q100R/L102R H115R/F172S/C198R, N52H/ N57Y/Q100R/H115R F172S/N194D, N52H/N57Y/H115R/ F172S/C198R, N52H/N57Y/Q100R/H115R/C198R, N52H/ N57Y/H115R, N52H/Q100R/H115R/I143T/F172S, N52H/ N57Y/Q100P/H115R/F172S, E16V/N52H/N57Y/Q100R/ V110D/H115R/C198R, N52S/E90A/H115R, N52S/E90A/ H115R, N30D/K42E/N52S/H115R.

In some embodiments, the variant ICOSL polypeptide has one or more amino acid modification, e.g. substitution in a reference ICOSL or specific binding fragment there of corresponding to position(s) 52, 57, 100, 138, 198, or 203 with reference to numbering of SEQ ID NO: 32. In some embodiments, the variant ICOSL polypeptide has one or more amino acid modification, e.g. substitution selected from N52H, N52Y, N57Y, Q100R, Q100P, F138L, C198R, or L203P. In some embodiments, the one or more amino acid modification, e.g. substitution is Q100R, F138L/L203P, N52Y/F138L/L203P, N57Y/Q100R/C198R, N57Y/F138L/L203P, N52H, N57Y, N57Y/Q100P, Q100R/F138L, or L203P.

In some embodiments, the variant ICOSL polypeptide comprises any of the extracellular domain (ECD) sequences set forth in SEQ ID NOS: 427-433. In some embodiments, the variant ICOSL polypeptide comprises a polypeptide sequence that exhibits at least 90% identity, at least 91% identity, at least 92% identity, at least 93% identity, at least 94% identity, at least 95% identity, such as at least 96% identity, 97% identity, 98% identity, or 99% identity to any of the extracellular domain (ECD) set forth in SEQ ID NOS: 427-433 and contains the amino acid modification(s), e.g. substitution(s) not present in the reference (e.g., unmodified) or wild-type ICOSL. In some embodiments, the variant ICOSL polypeptide comprises a specific binding fragment of any of the extracellular domain (ECD) sequences set forth in SEQ ID NOS: 427-433 and contains the amino acid modification(s), e.g. substitution(s) not present in the reference (e.g., unmodified) or wild-type ICOSL. In some embodiments, the variant ICOSL polypeptide comprises the IgV sequence set forth in SEQ ID NO: 434. In some embodiments, the variant ICOSL polypeptide comprises a polypeptide sequence that exhibits at least 90% identity, at least 91% identity, at least 92% identity, at least 93% identity, at least 94% identity, at least 95% identity, such as at least 96% identity, 97% identity, 98% identity, or 99% identity to the IgV sequence set forth in SEQ ID NO: 434 and contains the amino acid modification(s), e.g. substitution(s) not present in the reference (e.g., unmodified) or wild-type ICOSL. In some embodiments, the variant ICOSL polypeptide comprises a specific binding fragment of the IgV sequence set forth in SEQ ID NO: 434 and contains the amino acid substitution(s) not present in the reference (e.g., unmodified) or wild-type ICOSL.

In some embodiments, the variant ICOSL polypeptide has one or more amino acid modification, e.g. substitution in a reference ICOSL or specific binding fragment there of corresponding to position(s) 52, 84, 91, 119, 155, 168, 207 with reference to numbering of SEQ ID NO: 32. In some embodiments, the variant ICOSL polypeptide has one or more amino acid modification, e.g. substitution selected from A91S, N52H, N52Q, N84Q, N119Q, N155H, N155Q, N168Q, N207Q. In some embodiments, the one or more amino acid modification, e.g. substitution is N84Q, N119Q, N168Q, N207Q, N52Q, N52Q/N207Q, N168Q/N207Q, N52Q/N168Q, N84Q/N207Q, N155Q/N207Q, N119Q/N168Q, N119Q/N207Q, N119Q/N155Q, N52Q/N84Q, N52Q/N119Q, N84Q/N119Q, N52Q/N84Q/N168Q, N52Q/N84Q/N207Q, N84Q/N155Q/N168Q, N84Q/N168Q/N207Q, N84Q/N155H/N207Q, N155Q/N168Q/N207Q, N119Q N155Q/N168Q, N119Q/N168Q/N207Q, N84Q/N119Q/N207Q, N119Q/N155H/N207Q, N84Q/N119Q/N155Q, N52Q/N119Q/N155Q, N52H/N84Q/N119Q, N52H/N84Q, N52H/N84Q/N168Q, N52H/N84Q/N207Q, N52H/N84Q/N168Q/N207Q, N52Q/N84Q/N155Q, N52Q/N84Q/N168Q, N52Q/N84Q/N155Q/N168Q, N52Q/N84Q/N119Q/N168Q, N84Q/N119Q/N155Q/N168Q, N84Q/N155Q/N168Q/N207Q, N84Q/N119Q/N155Q/N207Q, N52Q/N84Q/N119Q/N207Q, N52Q/N84Q/N119Q/N155Q, N52Q/N84Q/N119Q/N155Q/N207Q, N84Q/N119Q/N155Q/N168Q/N207Q or A91S/N119Q/N168Q/N207Q. In some embodiments, the variant ICOSL polypeptides exhibit potentially reduced glycosylation compared to the reference (e.g., unmodified) or wild-type ICOSL polypeptide.

In some embodiments, the variant ICOSL polypeptide comprises any of the extracellular domain (ECD) sequences set forth in SEQ ID NOS: 387-424, 427-433, 435-470. In some embodiments, the variant ICOSL polypeptide comprises a polypeptide sequence that exhibits at least 90% identity, at least 91% identity, at least 92% identity, at least 93% identity, at least 94% identity, at least 95% identity, such as at least 96% identity, 97% identity, 98% identity, or 99% identity to any of the extracellular domain (ECD) set forth in SEQ ID NOS: 387-424, 427-433, 435-470 and contains the amino acid modification(s), e.g. substitution(s) not present in the reference (e.g., unmodified) or wild-type ICOSL. In some embodiments, the variant ICOSL polypeptide comprises a specific binding fragment of any of the extracellular domain (ECD) sequences set forth in SEQ ID NOS: 387-424, 427-433, 435-470 and contains the amino acid modification(s), e.g. substitution(s) not present in the reference (e.g., unmodified) or wild-type ICOSL. In some embodiments, the variant ICOSL polypeptide comprises any of the IgV sequences set forth in SEQ ID NOS: 425-426. In some embodiments, the variant ICOSL polypeptide comprises a polypeptide sequence that exhibits at least 90% identity, at least 91% identity, at least 92% identity, at least 93% identity, at least 94% identity, at least 95% identity, such as at least 96% identity, 97% identity, 98% identity, or 99% identity to any of the IgV sequences set forth in SEQ ID NO: 425-426 and contains the amino acid modification(s), e.g. substitution(s) not present in the reference (e.g., unmodified) or wild-type ICOSL. In some embodiments, the variant ICOSL polypeptide comprises a specific binding fragment of any of the IgV sequences set forth in SEQ ID NO: 425-426 and contains the amino acid substitution(s) not present in the reference (e.g., unmodified) or wild-type ICOSL.

III. FORMAT OF VARIANT POLYPEPTIDES

The immunomodulatory polypeptide comprising a variant ICOSL provided herein can be formatted in a variety of ways, including as a soluble protein, a membrane bound protein, secreted protein, conjugate or fusion or for expression by an engineered cell or infectious agent as described elsewhere herein. In some aspects, both immunomodulatory polypeptides comprising one or more vIgD of ICOSL or immunomodulatory polypeptides comprising multiple IgSF domains can be formatted in a variety of ways.

In some embodiments, the particular format can be chosen for the desired therapeutic application. In some cases, an immunomodulatory polypeptide comprising a variant ICOSL polypeptide is provided in a format to antagonize or block activity of its cognate binding partner, e.g. CD28. In some embodiments, antagonism of CD28 may be useful to treat inflammation or autoimmunity. In some cases, an immunomodulatory polypeptide comprising a variant ICOSL polypeptide is provided in a format to agonize or stimulate activity of its cognate binding partner, e.g. CD28. In some embodiments, agonism of CD28 may be useful for treating oncology indications. A skilled artisan can readily determine the activity of a particular format, such as for antagonizing or agonizing one or more specific cognate binding partner. Exemplary methods for assessing such activities are provided herein, including in the examples.

In some embodiments, a soluble immunomodulatory polypeptide, such as a variant ICOSL containing a vIgD, can be encapsulated within a liposome which itself can be conjugated to any one of or any combination of the provided conjugates (e.g., a targeting moiety). In some embodiments, the soluble or membrane bound immunomodulatory polypeptides of the invention are deglycosylated. In more specific embodiments, the variant ICOSL sequence is deglycosylated. In even more specific embodiments, the IgV and/or IgC (e.g. IgC2) domain or domains of the variant ICOSL is deglycosylated.

Non-limiting examples of provided formats are described in FIGS. 13A-13C and further described below.

A. Soluble Polypeptides

In some aspects, provided are immunomodulatory polypeptides comprising a vIgD of ICOSL. In some embodiments, the immunomodulatory protein containing a variant ICOSL polypeptide is a soluble protein. Those of skill will appreciate that cell surface proteins typically have an intracellular, transmembrane, and extracellular domain (ECD) and that a soluble form of such proteins can be made using the extracellular domain or an immunologically active subsequence thereof. Thus, in some embodiments, the immunomodulatory protein containing a variant ICOSL polypeptide lacks a transmembrane domain or a portion of the transmembrane domain. In some embodiments, the immunomodulatory protein containing a variant ICOSL lacks the intracellular (cytoplasmic) domain or a portion of the intracellular domain. In some embodiments, the immunomodulatory protein containing the variant ICOSL polypeptide only contains the vIgD portion containing the ECD domain or a portion thereof containing an IgV domain and/or IgC (e.g. IgC2) domain or domains or specific binding fragments thereof containing the amino acid modification(s).

In some embodiments, an immunomodulatory polypeptide comprising a variant ICOSL can include one or more variant ICOSL polypeptides. In some aspects, one or more additional IgSF domain, such as one or more additional vIgD, may be linked to a vIgD of ICOSL as provided herein. In some aspects, both immunomodulatory polypeptides comprising one or more vIgD of ICOSL or immunomodulatory polypeptides comprising multiple IgSF domains can be formatted in a variety of ways, such as described in subsection C of Section III.

In some embodiments, an immunomodulatory polypeptide comprising a variant ICOSL can include one or more variant ICOSL polypeptides of the invention. In some embodiments a polypeptide of the invention will comprise exactly 1, 2, 3, 4, 5 variant ICOSL sequences. In some embodiments, at least two of the variant ICOSL sequences are identical variant ICOSL sequences.

In some embodiments, the provided immunomodulatory polypeptide comprises two or more vIgD sequences of ICOSL. Multiple variant ICOSL polypeptides within the polypeptide chain can be identical (i.e., the same species) to each other or be non-identical (i.e., different species) variant ICOSL sequences. In addition to single polypeptide chain embodiments, in some embodiments two, three, four, or more of the polypeptides of the invention can be covalently or non-covalently attached to each other. Thus, monomeric, dimeric, and higher order (e.g., 3, 4, 5, or more) multimeric proteins are provided herein. For example, in some embodiments exactly two polypeptides of the invention can be covalently or non-covalently attached to each other to form a dimer. In some embodiments, attachment is made via interchain cysteine disulfide bonds. Compositions comprising two or more polypeptides of the invention can be of an identical species or substantially identical species of polypeptide (e.g., a homodimer) or of non-identical species of polypeptides (e.g., a heterodimer). A composition having a plurality of linked polypeptides of the invention can, as noted above, have one or more identical or non-identical variant ICOSL polypeptides of the invention in each polypeptide chain.

In some aspects, one or more additional IgSF domain, such as one or more additional vIgD, may be linked to a vIgD of ICOSL as provided herein (hereinafter called a "stack" or "stacked" immunomodulatory protein). In some embodiments, the modular format of the provided immunomodulatory proteins provides flexibility for engineering or generating immunomodulatory proteins for modulating activity of multiple counterstrucutres (multiple cognate binding partners). In some embodiments, such "stack" molecules can be provided in a soluble format or, in some cases, may be provided as membrane bound or secreted proteins.

In some embodiments, the immunomodulatory proteins can contain any of the variant ICOSL polypeptides provided herein linked, directly or indirectly, to one or more other immunoglobulin superfamily (IgSF) domain ("stacked" immunomodulatory protein construct and also called a "Type II" immunomodulatory protein). In some aspects, this can create unique multi-domain immunomodulatory proteins that bind two or more, such as three or more, cognate binding partners, thereby providing a multi-targeting modulation of the immune synapse.

In some embodiments, an immunomodulatory protein comprises a combination (a "non-wild-type combination") and/or arrangement (a "non-wild type arrangement" or "non-wild-type permutation") of a variant ICOSL domain with one or more other affinity modified and/or non-affinity modified IgSF domain sequences of another IgSF family member (e.g. a mammalian IgSF family member) that are not found in wild-type IgSF family members. In some embodiments, the immunomodulatory protein contains 2, 3, 4, 5 or 6 immunoglobulin superfamily (IgSF) domains, where at least one of the IgSF domain is a variant ICOSL IgSF domain (vIgD of ICOSL) according to the provided description.

In some embodiments, the sequences of the additional IgSF domains can be a modified IgSF domain that contains one or more amino acid modifications, e.g. substitutions, compared to a reference (e.g., unmodified) or wild-type IgSF domain. In some embodiments, the IgSF domain can be non-affinity modified (e.g., wild-type) or have been affinity modified. In some embodiments, the reference (e.g., unmodified) or wild-type IgSF domain can be from mouse, rat, cynomolgus monkey, or human origin, or combinations thereof. In some embodiments, the additional IgSF domains can be an IgSF domain of an IgSF family member set forth in Table 2. In some embodiments, the additional IgSF domain can be an affinity-modified IgSF domain containing one or more amino acid modifications, e.g. substitutions, compared to an IgSF domain contained in an IgSF family member set forth in Table 2.

In some embodiments, the additional IgSF domain is an affinity or non-affinity modified IgSF domain contained in an IgSF family member of a family selected from Signal-Regulatory Protein (SIRP) Family, Triggering Receptor Expressed On Myeloid Cells Like (TREML) Family, Carcinoembryonic Antigen-related Cell Adhesion Molecule (CEACAM) Family, Sialic Acid Binding Ig-Like Lectin (SIGLEC) Family, Butyrophilin Family, B7 family, CD28 family, V-set and Immunoglobulin Domain Containing (VSIG) family, V-set transmembrane Domain (VSTM) family, Major Histocompatibility Complex (MHC) family, Signaling lymphocytic activation molecule (SLAM) family, Leukocyte immunoglobulin-like receptor (LIR), Nectin (Nec) family, Nectin-like (NECL) family, Poliovirus receptor related (PVR) family, Natural cytotoxicity triggering receptor (NCR) family, T cell immunoglobulin and mucin (TIM) family or Killer-cell immunoglobulin-like receptors (KIR) family. In some embodiments, the additional IgSF domains are independently derived from an IgSF protein selected from the group consisting of CD80(B7-1), CD86 (B7-2), CD274 (PD-L1, B7-H1), PDCD1LG2(PD-L2, CD273), ICOSLG(B7RP1, CD275, ICOSL, B7-H2), CD276(B7-H3), VTCN1(B7-H4), CD28, CTLA4, PDCD1 (PD-1), ICOS, BTLA(CD272), CD4, CD8A(CD8-alpha), CD8B(CD8-beta), LAG3, HAVCR2(TIM-3), CEACAM1, TIGIT, PVR(CD155), PVRL2(CD112), CD226, CD2, CD160, CD200, CD200R1(CD200R), and NCR3 (NKp30).

The first column of Table 2 provides the name and, optionally, the name of some possible synonyms for that particular IgSF member. The second column provides the protein identifier of the UniProtKB database, a publicly available database accessible via the internet at uniprot.org or, in some cases, the GenBank Number. The Universal Protein Resource (UniProt) is a comprehensive resource for protein sequence and annotation data. The UniProt databases include the UniProt Knowledgebase (UniProtKB). UniProt is a collaboration between the European Bioinformatics Institute (EMBL-EBI), the SIB Swiss Institute of Bioinformatics and the Protein Information Resource (PIR) and supported mainly by a grant from the U.S. National Institutes of Health (NIH). GenBank is the NIH genetic sequence database, an annotated collection of all publicly available DNA sequences (Nucleic Acids Research, 2013 January; 41 (D1):D36-42). The third column provides the region where the indicated IgSF domain is located. The region is specified as a range where the domain is inclusive of the residues defining the range. Column 3 also indicates the IgSF domain class for the specified IgSF region. Colum 4 provides the region where the indicated additional domains are located (signal peptide, S; extracellular domain, E; transmembrane domain, T; cytoplasmic domain, C). It is understood that description of domains can vary depending on the methods used to identify or classify the domain, and may be identified differently from different sources. The description of residues corresponding to a domain in Table 2 is for exemplification only and can be several amino acids (such as one, two, three or four) longer or shorter. Column 5 indicates for some of the listed IgSF members, some of its cognate cell surface binding partners.

TABLE 2

| IgSF members according to the present disclosure. | | | | | | | |
|---|---|---|---|---|---|---|---|
| IgSF Member (Synonyms) | NCBI Protein Accession Number/ UniProtKB Protein Identifier | IgSF Region & Domain Class | Other Domains | Cognate Cell Surface Binding Partners | IgSF Member Amino Acid Sequence (SEQ ID NO) | | |
| | | | | | Precursor (mature residues) | Mature | ECD |
| CD80 (B7-1) | NP_005182.1 P33681 | 35-135, 35-138 or 35-141, 37-138 IgV, 145-230 or 154-232 IgC | S: 1-34, E: 35-242, T: 243-263, C: 264-288 | CD28, CTLA4, PD-L1 | SEQ ID NO: 1 (35-288) | SEQ ID NO: 253 | SEQ ID NO: 28 |
| CD86 (B7-2) | P42081.2 | 33-131 IgV, 150-225 IgC2 | S: 1-23, E: 24-247, T: 248-268, C: 269-329 | CD28, CTLA4 | SEQ ID NO: 2 (24-329) | SEQ ID NO: 254 | SEQ ID NO: 29 |
| CD274 (PD-L1, B7-H1) | Q9NZQ7.1 | 24-130, 19-127, IgV, 133-225 IgC2 | S: 1-18, E: 19-238, T: 239-259, C: 260-290 | PD-1, B7-1 | SEQ ID NO: 3 (19-290) | SEQ ID NO: 255 | SEQ ID NO: 30 |
| PDCD1LG2 (PD-L2, CD273) | Q9BQ51.2 | 21-118 IgV, 122-203 IgC2 | S: 1-19, E: 20-220, T: 221-241, C: 242-273 | PD-1, RGMb | SEQ ID NO: 4 (20-273) | SEQ ID NO: 256 | SEQ ID NO: 31 |
| ICOSLG (B7RP1, CD275, ICOSL, B7-H2) | O75144.2 | 19-129 IgV, 141-227 IgC2 | S: 1-18, E: 19-256, T: 257-277, C: 278-302 | ICOS, CD28, CTLA4 | SEQ ID NO: 5 (19-302) | SEQ ID NO: 257 | SEQ ID NO: 32 |
| CD276 (B7-H3) | Q5ZPR3.1 | 29-139 IgV, 145-238 IgC2, 243-357 IgV2, 367-453, 363-456 IgC2 | S: 1-28, E: 29-466, T: 467-487, C: 488-534 | | SEQ ID NO: 6 (29-534) | SEQ ID NO: 258 | SEQ ID NO: 33 |
| VTCN1 (B7-H4) | Q7Z7D3.1 | 35-146 IgV, 153-241 IgV | S: 1-24, E: 25-259, T: 260-280, C: 281-282 | | SEQ ID NO: 7 (25-282) | SEQ ID NO: 259 | SEQ ID NO: 34 |
| CD28 | P10747.1 | 28-137 IgV | S: 1-18, E: 19-152, T: 153-179, C: 180-220 | B7-1, B7-2, B7RP1 | SEQ ID NO: 8 (19-220) | SEQ ID NO: 260 | SEQ ID NO: 35 |

TABLE 2-continued

IgSF members according to the present disclosure.

| IgSF Member (Synonyms) | NCBI Protein Accession Number/ UniProtKB Protein Identifier | IgSF Region & Domain Class | Other Domains | Cognate Cell Surface Binding Partners | IgSF Member Amino Acid Sequence (SEQ ID NO) | | |
|---|---|---|---|---|---|---|---|
| | | | | | Precursor (mature residues) | Mature | ECD |
| CTLA4 | AAL07473.1 P16410.3 | 39-152 IgV, 39-140 IgV | S: 1-35, E: 36-161, T: 162-182, C: 183-223 | B7-1, B7-2, B7RP1 | SEQ ID NO: 9 (36-223) | SEQ ID NO: 261 | SEQ ID NO: 36 |
| PDCD1 (PD-1) | Q15116.3 | 35-145 IgV | S: 1-20, E: 21-170, T: 171-191, C: 192-288 | PD-L1, PD-L2 | SEQ ID NO: 10 (21-288) | SEQ ID NO: 262 | SEQ ID NO: 37 |
| ICOS | Q9Y6W8.1 | 30-132 IgV | S: 1-20, E: 21-140, T: 141-161, C: 162-199 | B7RP1 | SEQ ID NO: 11 (21-199) | SEQ ID NO: 263 | SEQ ID NO: 38 |
| BTLA (CD272) | Q7Z6A9.3 | 31-132 IgV | S: 1-30, E: 31-157, T: 158-178, C: 179-289 | HVEM | SEQ ID NO: 12 (31-289) | SEQ ID NO: 264 | SEQ ID NO: 39 |
| CD4 | P01730.1 | 26-125 IgV, 126-203 IgC2, 204-317 IgC2, 317-389, 318-374 IgC2 | S: 1-25, E: 26-396, T: 397-418, C: 419-458 | MHC class II | SEQ ID NO: 13 (26-458) | SEQ ID NO: 265 | SEQ ID NO: 40 |
| CD8A (CD8-alpha) | P01732.1 | 22-135 IgV | S: 1-21, E: 22-182, T: 183-203, C: 204-235 | MHC class I | SEQ ID NO: 14 (22-235) | SEQ ID NO: 266 | SEQ ID NO: 41 |
| CD8B (CD8-beta) | P10966.1 | 22-132 IgV | S: 1-21, E: 22-170, T: 171-191, C: 192-210 | MHC class I | SEQ ID NO: 15 (22-210) | SEQ ID NO: 267 | SEQ ID NO: 42 |
| LAG3 | P18627.5 | 37-167 IgV, 168-252 IgC2, 265-343 IgC2, 349-419 IgC2 | S: 1-28, E: 29-450, T: 451-471, C: 472-525 | MHC class II | SEQ ID NO: 16 (29-525) | SEQ ID NO: 268 | SEQ ID NO: 43 |
| HAVCR2 (TIM-3) | Q8TDQ0.3 | 22-124 IgV | S: 1-21, E: 22-202, T: 203-223, C: 224-301 | CEACAM-1, phosphatidylserine, Galectin-9, HMGB1 | SEQ ID NO: 17 (22-301) | SEQ ID NO: 269 | SEQ ID NO: 44 |
| CEACAM1 | P13688.2 | 35-142 IgV, 145-232 IgC2, 237-317 IgC2, 323-413 IgC2 | S: 1-34, E: 35-428, T: 429-452, C: 453-526 | TIM-3 | SEQ ID NO: 18 (35-526) | SEQ ID NO: 270 | SEQ ID NO: 45 |
| TIGIT | Q495A1.1 | 22-124 IgV | S: 1-21, E: 22-141, T: 142-162, C: 163-244 | CD155, CD112 | SEQ ID NO: 19 (22-244) | SEQ ID NO: 271 | SEQ ID NO: 46 |
| PVR (CD155) | P15151.2 | 24-139 IgV, 145-237 IgC2, 244-328 IgC2 | S: 1-20, E: 21-343, T: 344-367, C: 368-417 | TIGIT, CD226, CD96, poliovirus | SEQ ID NO: 20 (21-417) | SEQ ID NO: 272 | SEQ ID NO: 47 |
| PVRL2 (CD112) | Q92692.1 | 32-156 IgV, 162-256 IgC2, 261-345 IgC2 | S: 1-31, E: 32-360, T: 361-381, C: 382-538 | TIGIT, CD226, CD112R | SEQ ID NO: 21 (32-538) | SEQ ID NO: 273 | SEQ ID NO: 48 |
| CD226 | Q15762.2 | 19-126 IgC2, 135-239 IgC2 | S: 1-18, E: 19-254, T: 255-275, C: 276-336 | CD155, CD112 | SEQ ID NO: 22 (19-336) | SEQ ID NO: 274 | SEQ ID NO: 49 |
| CD2 | P06729.2 | 25-128 IgV, 129-209 IgC2 | S: 1-24, E: 25-209, T: 210-235, C: 236-351 | CD58 | SEQ ID NO: 23 (25-351) | SEQ ID NO: 275 | SEQ ID NO: 50 |
| CD160 | O95971.1 | 27-122 IgV | S: 1-26 E: 27-122 | HVEM, MHC family of proteins | SEQ ID NO: 24 (27-159) | SEQ ID NO: 276 | SEQ ID NO: 51 |
| CD200 | P41217.4 | 31-141 IgV, 142-232 IgC2 | S: 1-30, E: 31-232, T: 233-259, C: 260-278 | CD200R | SEQ ID NO: 25 (31-278) | SEQ ID NO: 277 | SEQ ID NO: 52 |

TABLE 2-continued

IgSF members according to the present disclosure.

| IgSF Member (Synonyms) | NCBI Protein Accession Number/ UniProtKB Protein Identifier | IgSF Region & Domain Class | Other Domains | Cognate Cell Surface Binding Partners | IgSF Member Amino Acid Sequence (SEQ ID NO) | | |
|---|---|---|---|---|---|---|---|
| | | | | | Precursor (mature residues) | Mature | ECD |
| CD200R1 (CD200R) | Q8TD46.2 | 53-139 IgV, 140-228 IgC2 | S: 1-28, E: 29-243, T: 244-264, C: 265-325 | CD200 | SEQ ID NO: 26 (29-325) | SEQ ID NO: 278 | SEQ ID NO: 53 |
| NCR3 (NKp30) | O14931.1 | 19-126 IgC-like | S: 1-18, E: 19-135, T: 136-156, C:157-201 | B7-H6 | SEQ ID NO: 27 (19-201) | SEQ ID NO: 279 | SEQ ID NO: 54 |
| VSIG8 | Q5VU13 | 22-141 IgV1 146-257 IgV2 | S: 1-21 E: 22-263 T: 264-284 C: 285-414 | VISTA | SEQ ID NO: 341 (22-414) | SEQ ID NO: 342 | SEQ ID NO: 343 |

In some embodiments, the provided immunomodulatory proteins, in addition to containing a variant ICOSL polypeptide, also contains at least 1, 2, 3, 4, 5 or 6 additional immunoglobulin superfamily (IgSF) domains, such as an IgD domain of an IgSF family member set forth in Table 2.

In some embodiments, the provided immunomodulatory protein contains at least one additional IgSF domain (e.g. second IgSF domain). In some embodiments, the provided immunomodulatory protein contains at least two additional IgSF domains (e.g. second and third IgSF domain). In some embodiments, the provided immunomodulatory protein contains at least three additional IgSF domains (e.g. second, third and fourth). In some embodiments, the provided immunomodulatory protein contains at least four additional IgSF domains (e.g. second, third, fourth and fifth). In some embodiments, the provided immunomodulatory protein contains at least five additional IgSF domains (e.g. second, third, fourth, fifth and sixth). In some embodiments, the provided immunomodulatory protein contains at least six additional IgSF domains (e.g. second, third, fourth, fifth, sixth and seventh). In some embodiments, each of the IgSF domains in the immunomodulatory protein are different. In some embodiments, at least one of the additional IgSF domain is the same as at least one other IgSF domain in the immunomodulatory protein. In some embodiments, each of the IgSF domains is from or derived from a different IgSF family member. In some embodiments, at least two of the IgSF domains is from or derived from the same IgSF family member.

In some embodiments, the additional IgSF domain comprises an IgV domain or an IgC (e.g., IgC2) domain or domains, or a specific binding fragment of the IgV domain or a specific binding fragment of the IgC (e.g., IgC2) domain or domains. In some embodiments, the additional IgSF domain is or comprises a full-length IgV domain. In some embodiments, the additional IgSF domain is or comprises a full-length IgC (e.g., IgC2) domain or domains. In some embodiments, the additional IgSF domain is or comprises a specific binding fragment of the IgV domain. In some embodiments, the additional IgSF domain is or comprises a specific binding fragment of the IgC (e.g., IgC2) domain or domains. In some embodiments, the immunomodulatory protein contains at least two additional IgSF domains from a single (same) IgSF member. For example, in some aspects, the immunomodulatory protein contains an ECD or portion thereof of an IgSF member containing a full-length IgV domain and a full-length IgC (e.g., IgC2) domain or domains or specific binding fragments thereof.

In some embodiments, the provided immunomodulatory proteins contain at least one additional IgSF domain (e.g. a second or, in some cases, also a third IgSF domain) in which at least one additional, e.g., second or third IgSF domain, is an IgSF domain set forth in a reference (e.g., unmodified) or wild-type IgSF domain or a specific binding fragment thereof contained in the sequence of amino acids set forth in any of SEQ ID NOS: 1-27 and 341. In some embodiments, the reference (e.g., unmodified) or wild-type IgSF domain is an IgV domain or an IgC domain, such as an IgC1 or IgC2 domain.

In some embodiments, the provided immunomodulatory proteins, in addition to containing a variant ICOSL polypeptide, also contains at least one additional IgSF domain (e.g. a or, in some cases, also a third affinity-modified IgSF domain and so on) in which at least one additional IgSF domain is a vIgD that contains one or more amino acid modifications (e.g. substitution, deletion or mutation) compared to an IgSF domain in a reference (e.g., unmodified) or wild-type IgSF domain, such as an IgSF domain in an IgSF family member set forth in Table 2. In some embodiments, the additional, e.g., second or third affinity-modified IgSF domain comprises at least 85%, 86%, 87%, 88%, 89%, 90%, 91%, 92%, 93%, 94%, 95%, 96%, 97%, 98%, 99% or more sequence identity to a reference (e.g., unmodified) or wild-type IgSF domain or a specific binding fragment thereof contained in the sequence of amino acids set forth in any of SEQ ID NOS: 1-27 and 341. In some embodiments, the reference (e.g., unmodified) or wild-type IgSF domain is an IgV domain or an IgC domain, such as an IgC1 or IgC2 domain. In some embodiments, the additional, e.g., second or third IgSF domain is an affinity-modified IgV domain and/or IgC domain. In some embodiments, the one or more additional IgSF domain is an affinity-modified IgSF domain that contains an IgV domain and/or an IgC (e.g., IgC2) domain or domains, or a specific binding fragment of the IgV domain and/or a specific binding fragment of the IgC (e.g., IgC2) domain or domains, in which the IgV and/or IgC domain contains the amino acid modification(s) (e.g., substitution(s)). In some embodiments, the one or more additional affinity-modified IgSF domain contains an IgV domain containing the amino acid modification(s) (e.g.

substitution(s)). In some embodiments, the one or more additional affinity-modified IgSF domain include IgSF domains present in the ECD or a portion of the ECD of the corresponding reference IgSF family member, such as a full-length IgV domain and a full-length IgC (e.g., IgC2) domain or domains, or specific binding fragments thereof, in which one or both of the IgV and IgC contain the amino acid modification(s) (e.g. substitution(s)). In some embodiments, the particular domain or each of the particular domains (e.g. additional, e.g., second or third IgSF domain) of a variant IgSF domain polypeptide can be several amino acids longer or shorter, such as 1-10, e.g., 1, 2, 3, 4, 5, 6 or 7 amino acids longer or shorter, than the sequence of amino acids set forth in the respective SEQ ID NO.

In some embodiments, the provided immunomodulatory protein contains at least one additional, (e.g., second or, in some cases, also a third IgSF domain and so on) or second IgSF domain that is a vIgD that contains one or more amino acid substitutions compared to an IgSF domain (e.g., IgV) of a reference (e.g., unmodified) or wild-type IgSF domain other than ICOSL.

In some embodiments, the additional or second IgSF domain contains one or more amino acid substitutions compared to an IgSF domain in a reference (e.g., unmodified) or wild-type IgSF domain, such as an IgSF domain in an IgSF family member set forth in Table 2. In some embodiments, the additional or second affinity-modified IgSF domain comprises at least 85%, 86%, 87%, 88%, 89%, 90%, 91%, 92%, 93%, 94%, 95%, 96%, 97%, 98%, 99% or more sequence identity to a reference (e.g., unmodified) or wild-type IgSF domain or a specific binding fragment thereof contained in the sequence of amino acids set forth in any of SEQ ID NOS: 1-27. In some embodiments, the reference (e.g., unmodified) or wild-type IgSF domain is an IgV domain or an IgC domain, such as an IgC1 or IgC2 domain. In some embodiments, the additional or second IgSF domain is an affinity-modified IgV domain or IgC domain. Tables 3-5 provide exemplary polypeptides containing one or more affinity-modified IgSF domains that can be used in stack constructs provided herein.

In some embodiments, the one or more additional IgSF domain (e.g. second IgSF) domain is an IgSF domain (e.g. IgV) of another IgSF family member that binds or recognizes a tumor antigen. In such embodiments, the IgSF family member serves as a tumor-localizing moiety, thereby bringing the vIgD of ICOSL in close proximity to immune cells in the tumor microenvironment. In some embodiments, the additional IgSF domain (e.g. second IgSF) domain is an IgSF domain of NKp30, which binds or recognizes B7-H6 expressed on a tumor cell. In some embodiments, the at least one additional (e.g. second) IgSF domain, e.g. NKp30, is a vIgD that contains one or more amino acid modifications (e.g. substitutions, deletions or additions). In some embodiments, the one or more amino acid modifications increase binding affinity and/or selectivity to B7-H6 compared to reference IgSF domain, e.g. NKp30, such as by at least or at least about 1.2-fold, 1.5-fold, 2-fold, 3-fold, 4-fold, 5-fold, 6-fold, 7-fold, 8-fold, 9-fold, 10-fold, 20-fold, 30-fold 40-fold or 50-fold.

TABLE 3

| | | |
|---|---|---|
| Exemplary variant CD80 polypeptides | | |
| Mutation(s) | ECD SEQ ID NO | IgV SEQ ID NO |
| Wild-type | 28 | 152 |
| L70Q/A91G | 55 | 153 |
| L70Q/A91G/T130A | 56 | |
| L70Q/A91G/I118A/T120S/T130A | 57 | |
| V4M/L70Q/A91G/T120S/T130A | 58 | 154 |
| L70Q/A91G/T120S/T130A | 59 | |
| V20L/L70Q/A91S/T120S/T130A | 60 | 155 |
| S44P/L70Q/A91G/T130A | 61 | 156 |
| L70Q/A91G/E117G/T120S/T130A | 62 | |
| A91G/T120S/T130A | 63 | 157 |
| L70R/A91G/T120S/T130A | 64 | 158 |
| L70Q/E81A/A91G/T120S/I127T/T130A | 65 | 159 |
| L70Q/Y87N/A91G/T130A | 66 | 160 |
| T28S/L70Q/A91G/E95K/T120S/T130A | 67 | 161 |
| N63S/L70Q/A91G/T120S/T130A | 68 | 162 |
| K36E/I67T/L70Q/A91G/T120S/T130A/N152T | 69 | 163 |
| E52G/L70Q/A91G/T120S/T130A | 70 | 164 |
| K37E/F59S/L70Q/A91G/T120S/T130A | 71 | 165 |
| A91G/S103P | 72 | |
| K89E/T130A | 73 | 166 |
| A91G | 74 | |
| D60V/A91G/T120S/T130A | 75 | 167 |
| K54M/A91G/T120S | 76 | 168 |
| M38T/L70Q/E77G/A91G/T120S/T130A/N152T | 77 | 169 |
| R29H/E52G/L70R/E88G/A91G/T130A | 78 | 170 |
| Y31H/T41G/L70Q/A91G/T120S/T130A | 79 | 171 |
| V68A/T110A | 80 | 172 |
| S66H/D90G/T110A/F116L | 81 | 173 |
| R29H/E52G/T120S/T130A | 82 | 174 |
| A91G/L102S | 83 | |
| I67T/L70Q/A91G/T120S | 84 | 175 |
| L70Q/A91G/T110A/T120S/T130A | 85 | |
| M38V/T41D/M43I/W50G/D76G/V83A/K89E/T120S/T130A | 86 | 176 |
| V22A/L70Q/S121P | 87 | 177 |
| A12V/S15F/Y31H/T41G/T130A/P137L/N152T | 88 | 178 |
| I67F/L70R/E88G/A91G/T120S/T130A | 89 | 179 |

TABLE 3-continued

| | | |
|---|---|---|
| Exemplary variant CD80 polypeptides | | |
| Mutation(s) | ECD SEQ ID NO | IgV SEQ ID NO |
| E24G/L25P/L70Q/T120S | 90 | 180 |
| A91G/F92L/F108L/T120S | 91 | 181 |
| R29D/Y31L/Q33H/K36G/M38I/T41A/M43R/M47T/E81V/ L85R/K89N/A91T/F92P/K93V/R94L/I118T/N149S | 92 | 182 |
| R29D/Y31L/Q33H/K36G/M38I/T41A/M43R/M47T/E81V/ L85R/K89N/A91T/F92P/K93V/R94L/N144S/N149S | 93 | |
| R29D/Y31L/Q33H/K36G/M38I/T41A/M42T/M43R/M47T/ E81V/L85R/K89N/A91T/F92P/K93V/R94L/L148S/N149S | 94 | 183 |
| E24G/R29D/Y31L/Q33H/K36G/M38I/T4IA/M43R/M47T/ F59L/E81V/L85R/K89N/A91T/F92P/K93V/R94L/H96R/ N149S/C182S | 95 | 184 |
| R29D/Y31L/Q33H/K36G/M38I/T41A/M43R/M47T/E81V/ L85R/K89N/A91T/F92P/K93V/R94L/N149S | 96 | |
| R29V/M43Q/E81R/L85I/K89R/D90L/A91E/F92N/K93Q/R94G | 97 | 185 |
| T41I/A91G | 98 | 186 |
| K89R/D90K/A91G/F92Y/K93R/N122S/N177S | 99 | 187 |
| K89R/D90K/A91G/F92Y/K93R | 100 | |
| K36G/K37Q/M38I/F59L/E81V/L85R/K89N/A91T/F92P/ K93V/R94L/E99G/T130A/N149S | 101 | 188 |
| E88D/K89R/D90K/A91G/F92Y/K93R | 102 | 189, 543 |
| K36G/K37Q/M38I/L40M | 103 | 190 |
| K36G | 104 | 191 |
| R29H/Y31H/T41G/Y87N/E88G/K89E/D90N/A91G/P109S | 105 | 192 |
| A12T/H18L/M43V/F59L/E77K/P109S/I118T | 106 | 193 |
| R29V/Y31F/K36G/M38L/M43Q/E81R/V83I/L85I/K89R/ D90L/A91E/F92N/K93Q/R94G | 107 | 194 |
| V68M/L70P/L72P/K86E | 108 | 195 |
| L70Q/A91G/N144D | 508 | |
| L70Q/A91G/I118A/T120S/T130A/K169E | 509 | |
| V4M/L70Q/A91G/I118V/T120S/T130A/K169E | 510 | |
| L70Q/A91G/I118V/T120S/T130A/K169E | 511 | |
| L70Q/A91G/I118V/T120S/T130A | 512 | |
| V20L/L70Q/A91S/I118V/T120S/T130A | 513 | |
| L70Q/A91G/E117G/I118V/T120S/T130A | 514 | |
| A91G/I118V/T120S/T130A | 515 | |
| L70R/A91G/I118V/T120S/T130A/T199S | 516 | |
| L70Q/E81A/A91G/I118V/T120S/I127T/T130A | 517 | |
| T28S/L70Q/A91G/E95K/I118V/T120S/I126V/T130A/K169E | 518 | |
| N63S/L70Q/A91G/S114T/I118V/T120S/T130A | 519 | |
| K36E/I67T/L70Q/A91G/I118V/T120S/T130A/N152T | 520 | |
| E52G/L70Q/A91G/D107N/I118V/T120S/T130A/K169E | 521 | |
| K37E/F59S/L70Q/A91G/I118V/T120S/T130A/K185E | 522 | |
| D60V/A91G/I118V/T120S/T130AK169E | 523 | |
| K54M/L70Q/A91G/Y164H/T120S | 524 | |
| M38T/L70Q/E77G/A91G/I118V/T120S/T130A/N152T | 525 | |
| Y31H/T41G/M43L/L70Q/A91G/I118V/T120S/I126V/T130A | 526 | |
| LS656H/D90G/T110A/F116L | 527 | |
| R29D/E52G/D90N/I118V/T120S/T130A | 528 | |
| R29H/E52G/D90N/I118V/T120S/T130A | 529 | |
| I67T/L70Q/A91G/I118V/T120S | 530 | |
| L70Q/A91G/T110A/I118V/T120S/T130A | 531 | |
| M38V/T41D/M43I/W50G/D76G/V83A/K89E/I118V/T120S/I126V/T130A | 532 | |
| A12V/S15F/Y31H/M38L/T41G/M43L/D90N/T130A/P137L/N149D/N152T | 533 | |
| I67F/L70R/E88G/A91G/I118V/T120S/T130A | 534 | |
| E24G/L25P/L70Q/A91G/I118VT120S/N152T | 535 | |
| A91G/F92L/F108L/I118V/T120S | 536 | |
| E88D/K89R/D90K/A91G/F92Y/K93R/N122S/N177S | 537 | |
| K36G/K37Q/M38I/L40M/F59L/E81V/L85R/K89N/A91T/ F92P/K93V/R94L/E99G/T130A/N149S | 539 | |
| K36G/L40M | 540 | 542, 544 |

TABLE 4

| | | IgC-like | IgV-like |
| | ECD | domain | domain |
| | SEQ ID | SEQ ID | SEQ ID |
| Mutation(s) | NO | NO | NO |
|---|---|---|---|
| Wild-type | 54 | 214 | 929 |
| L30V/A60V/S64P/S86G | 143 | 215 | 504 |
| L30V | 144 | 216 | 930 |
| A60V | 145 | 217 | 931 |
| S64P | 146 | 218 | 932 |
| S86G | 147 | 219 | 933 |

_Exemplary variant NKp30 polypeptides_

TABLE 5

| | ECD | IgV |
| | SEQ ID | SEQ ID |
| Mutation(s) | NO | NO |
|---|---|---|
| Wild-type | 29 | 220 |
| Q35H/H90L/Q102H | 148 | 221 |
| Q35H | 149 | 222 |
| H90L | 150 | 223 |
| Q102H | 151 | 224 |

_Exemplary variant CD86 polypeptides_

The number of such non-affinity modified or affinity modified IgSF domains present in a "stacked" immunomodulatory protein construct (whether non-wild type combinations or non-wild type arrangements) is at least 2, 3, 4, or 5 and in some embodiments exactly 2, 3, 4, or 5 IgSF domains (whereby determination of the number of affinity modified IgSF domains disregards any non-specific binding fractional sequences thereof and/or substantially immunologically inactive fractional sequences thereof).

In some embodiments of a stacked immunomodulatory protein provided herein, the number of IgSF domains is at least 2 wherein the number of affinity modified and the number of non-affinity modified IgSF domains is each independently at least: 0, 1, 2, 3, 4, 5, or 6. Thus, the number of affinity modified IgSF domains and the number of non-affinity modified IgSF domains, respectively, (affinity modified IgSF domain: non-affinity modified IgSF domain), can be exactly or at least: 2:0 (affinity modified: wild-type), 0:2, 2:1, 1:2, 2:2, 2:3, 3:2, 2:4, 4:2, 1:1, 1:3, 3:1, 1:4, 4:1, 1:5, or 5:1.

In some embodiments of a stacked immunomodulatory protein, at least two of the non-affinity modified and/or affinity modified IgSF domains are identical IgSF domains.

In some embodiments, a stacked immunomodulatory protein provided herein comprises at least two affinity modified and/or non-affinity modified IgSF domains from a single IgSF member but in a non-wild-type arrangement (alternatively, "permutation"). One illustrative example of a non-wild type arrangement or permutation is an immunomodulatory protein comprising a non-wild-type order of affinity modified and/or non-affinity modified IgSF domain sequences relative to those found in the wild-type ICOSL whose IgSF domain sequences served as the source of the variant IgSF domains as provided herein. Thus, in one example, the immunomodulatory protein can comprise an IgV proximal and an IgC distal to the transmembrane domain albeit in a non-affinity modified and/or affinity modified form. The presence, in an immunomodulatory protein provided herein, of both non-wild-type combinations and non-wild-type arrangements of non-affinity modified and/or affinity modified IgSF domains is also within the scope of the provided subject matter.

In some embodiments of a stacked immunomodulatory protein, the non-affinity modified and/or affinity modified IgSF domains are non-identical (i.e., different) IgSF domains. Non-identical affinity modified IgSF domains specifically bind, under specific binding conditions, different cognate binding partners and are "non-identical" irrespective of whether or not the reference (e.g., unmodified) or wild-type IgSF domains from which they are engineered was the same. Thus, for example, a non-wild-type combination of at least two non-identical IgSF domains in an immunomodulatory protein can comprise at least one IgSF domain sequence whose origin is from and unique to one ICOSL, and at least one of a second IgSF domain sequence whose origin is from and unique to another IgSF family member that is not ICOSL, wherein the IgSF domains of the immunomodulatory protein are in non-affinity modified and/or affinity modified form. However, in alternative embodiments, the two non-identical IgSF domains originate from the same IgSF domain sequence but at least one is affinity modified such that they specifically bind to different cognate binding partners.

A plurality of non-affinity modified and/or affinity modified IgSF domains in a stacked immunomodulatory protein polypeptide chain need not be covalently linked directly to one another. In some embodiments, an intervening span of one or more amino acid residues indirectly covalently bonds the non-affinity modified and/or affinity modified IgSF domains to each other. The linkage can be via the N-terminal to C-terminal residues.

In some embodiments, the linkage can be made via side chains of amino acid residues that are not located at the N-terminus or C-terminus of the non-affinity modified and/or affinity modified IgSF domain. Thus, linkages can be made via terminal or internal amino acid residues or combinations thereof.

In some embodiments, the two or more IgSF domain, including a vIgD of ICOSL and one or more additional IgSF domain (e.g. second or third variant IgSF domain) from another IgSF family member, are covalently or non-covalently linked. In some embodiments, the two or more IgSF domains are linked directly or indirectly, such as via a linker. In some embodiments, an intervening span of one or more amino acid residues indirectly covalently bonds IgSF domains to each other. The linkage can be via the N-terminal to C-terminal residues. In some embodiments, the linkage can be made via side chains of amino acid residues that are not located at the N-terminus or C-terminus of the IgSF domain(s). Thus, linkages can be made via terminal or internal amino acid residues or combinations thereof.

In some embodiments, the immunomodulatory protein contains at least two IgSF domains, each linked directly or indirectly via a linker. In some embodiments, the immunomodulatory protein contains at least three immunomodulatory proteins, each linked directly or indirectly via a linker. Various configurations are shown in FIGS. 16A and 16B.

In some embodiments, one or more "peptide linkers" link the vIgD of ICOSL and one or more additional IgSF domain (e.g. second or third variant IgSF domain). In some embodiments, a peptide linker can be a single amino acid residue or greater in length. In some embodiments, the peptide linker has at least one amino acid residue but is no more than 20, 19, 18, 17, 16, 15, 14, 13, 12, 11, 10, 9, 8, 7, 6, 5, 4, 3, 2, or 1 amino acid residues in length. In some embodiments, the linker is a flexible linker. In some embodiments, the linker is (in one-letter amino acid code): GGGGS ("4GS";

SEQ ID NO: 636) or multimers of the 4GS linker, such as repeats of 2, 3, 4, or 5 4GS linkers. In some embodiments, the peptide linker is (GGGGS)$_2$ or (GGGGS)$_3$ as set forth in SEQ ID NOs: 229 and 228, respectively. In some embodiments, the linker also can include a series of alanine residues alone or in addition to another peptide linker (such as a 4GS linker or multimer thereof). In some embodiments, the number of alanine residues in each series is: 2, 3, 4, 5, or 6 alanines. In some embodiments, the linker is a rigid linker. For example, the linker is an α-helical linker. In some embodiments, the linker is (in one-letter amino acid code): EAAAK or multimers of the EAAAK linker, such as repeats of 2, 3, 4, or 5 EAAAK linkers, such as set forth in SEQ ID NO: 629 (1×EAAAK), SEQ ID NO: 630 (3×EAAAK) or SEQ ID NO: 631 (5×EAAAK). In some embodiments, the linker can further include amino acids introduced by cloning and/or from a restriction site, for example the linker can include the amino acids GS (in one-letter amino acid code) as introduced by use of the restriction site BAMHI. In some embodiments, the linker (in one-letter amino acid code) is GSGGGGS (SEQ ID NO: 635). In some examples, the linker is a 2×GGGGS followed by three alanines (GGGGSGGGGSAAA; SEQ ID NO: 230).

In some embodiments, the non-affinity modified and/or affinity modified IgSF domains are linked by "wild-type peptide linkers" inserted at the N-terminus and/or C-terminus of a second non-affinity modified and/or affinity modified IgSF domains. In some embodiments, there is present a leading peptide linker inserted at the N-terminus of the first IgSF domain and/or a first trailing sequence inserted at the C-terminus of the first non-affinity modified and/or affinity modified IgSF domain. In some embodiments, there is present a second leading peptide linker inserted at the N-terminus of the second IgSF domain and/or a second trailing sequence inserted at the C-terminus of the second non-affinity modified and/or affinity modified IgSF domain. When the first and second non-affinity modified and/or affinity modified IgSF domains are derived from the same parental protein and are connected in the same orientation, wild-type peptide linkers between the first and second non-affinity modified and/or affinity modified IgSF domains are not duplicated. For example, when the first trailing wild-type peptide linker and the second leading wild-type peptide linker are the same, the Type II immunomodulatory protein does not comprise either the first trailing wild-type peptide linker or the second leading wild-type peptide linker.

In some embodiments, the Type II immunomodulatory protein comprises a first leading wild-type peptide linker inserted at the N-terminus of the first non-affinity modified and/or affinity modified IgSF domain, wherein the first leading wild-type peptide linker comprises at least 5 (such as at least about any of 6, 7, 8, 9, 10, 11, 12, 13, 14, 15, or more) consecutive amino acids from the intervening sequence in the wild-type protein from which the first non-affinity modified and/or affinity modified IgSF domain is derived between the parental IgSF domain and the immediately preceding domain (such as a signal peptide or an IgSF domain). In some embodiments, the first leading wild-type peptide linker comprises the entire intervening sequence in the wild-type protein from which the first non-affinity modified and/or affinity modified IgSF domain is derived between the parental IgSF domain and the immediately preceding domain (such as a signal peptide or an IgSF domain).

In some embodiments, the Type II immunomodulatory protein further comprises a first trailing wild-type peptide linker inserted at the C-terminus of the first non-affinity modified and/or affinity modified IgSF domain, wherein the first trailing wild-type peptide linker comprises at least 5 (such as at least about any of 6, 7, 8, 9, 10, 11, 12, 13, 14, 15, or more) consecutive amino acids from the intervening sequence in the wild-type protein from which the first non-affinity modified and/or affinity modified IgSF domain is derived between the parental IgSF domain and the immediately following domain (such as an IgSF domain or a transmembrane domain). In some embodiments, the first trailing wild-type peptide linker comprises the entire intervening sequence in the wild-type protein from which the first non-affinity modified and/or affinity modified IgSF domain is derived between the parental IgSF domain and the immediately following domain (such as an IgSF domain or a transmembrane domain).

In some embodiments, the Type II immunomodulatory protein further comprises a second leading wild-type peptide linker inserted at the N-terminus of the second non-affinity modified and/or affinity modified IgSF domain, wherein the second leading wild-type peptide linker comprises at least 5 (such as at least about any of 6, 7, 8, 9, 10, 11, 12, 13, 14, 15, or more) consecutive amino acids from the intervening sequence in the wild-type protein from which the second non-affinity modified and/or affinity modified IgSF domain is derived between the parental IgSF domain and the immediately preceding domain (such as a signal peptide or an IgSF domain). In some embodiments, the second leading wild-type peptide linker comprises the entire intervening sequence in the wild-type protein from which the second non-affinity modified and/or affinity modified IgSF domain is derived between the parental IgSF domain and the immediately preceding domain (such as a signal peptide or an IgSF domain).

In some embodiments, the Type II immunomodulatory protein further comprises a second trailing wild-type peptide linker inserted at the C-terminus of the second non-affinity modified and/or affinity modified IgSF domain, wherein the second trailing wild-type peptide linker comprises at least 5 (such as at least about any of 6, 7, 8, 9, 10, 11, 12, 13, 14, 15, or more) consecutive amino acids from the intervening sequence in the wild-type protein from which the second non-affinity modified and/or affinity modified IgSF domain is derived between the parental IgSF domain and the immediately following domain (such as an IgSF domain or a transmembrane domain). In some embodiments, the second trailing wild-type peptide linker comprises the entire intervening sequence in the wild-type protein from which the second non-affinity modified and/or affinity modified IgSF domain is derived between the parental IgSF domain and the immediately following domain (such as an IgSF domain or a transmembrane domain).

Exemplary of a leading sequence and trailing sequence for a Type II protein containing a CD80 IgSF domain is set forth in SEQ ID NO:231 and SEQ ID NO:232. Exemplary of a leading sequence and trailing sequence for a Type II protein containing an ICOSL IgSF domain is set forth in SEQ ID NO: 233 and 234. Exemplary of a leading sequence and a trailing sequence for a Type II protein containing a CD86 IgSF domain is set forth in any of SEQ ID NOS: 236-238. Exemplary of a wild-type linker sequence for a Type II protein containing an NKp30 IgSF domain is set forth in SEQ ID NO: 235.

1. Monovalent

Provided herein are immunomodulatory proteins containing a variant ICOSL polypeptide that is monovalent. In some embodiments, the variant ICOSL polypeptide of the monovalent immunomodulatory protein is linked, directly or indirectly, to a further moiety. In some embodiments, the further moiety is a protein, peptide, small molecule or nucleic acid. In some embodiments, the monovalent immunomodulatory protein is a fusion protein.

In some embodiments, the moiety is a half-life extending molecule. Exemplary of such half-life extending molecules include, but are not limited to, albumin, an albumin-binding polypeptide, Pro/Ala/Ser (PAS), a C-terminal peptide (CTP) of the beta subunit of human chorionic gonadotropin, polyethylene glycol (PEG), long unstructured hydrophilic sequences of amino acids (XTEN), hydroxyethyl starch (HES), an albumin-binding small molecule, or a combination thereof.

In some embodiments, the immunomodulatory polypeptide comprising a variant ICOSL can include conformationally disordered polypeptide sequences composed of the amino acids Pro, Ala, and Ser (See e.g., WO2008/155134; SEQ ID NO: 904). In some cases, the amino acid repeat is at least 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid residues, wherein each repeat comprises (an) Ala, Ser, and Pro residue(s). Thus, provided herein is an immunomodulatory protein is a PASylated protein wherein the variant ICOSL polypeptide is linked, directly or indirectly via a linker, to Pro/Ala/Ser (PAS). In some embodiments, one or more additional linker structures may be used.

In some embodiments, the moiety facilitates detection or purification of the variant ICOSL polypeptide. In some cases, the immunomodulatory polypeptide comprises a tag or fusion domain, e.g. affinity or purification tag, linked, directly or indirectly, to the N- and/or c-terminus of the ICOSL polypeptide. Various suitable polypeptide tags and/or fusion domains are known, and include but are not limited to, a poly-histidine (His) tag, a FLAG-tag (SEQ ID NO: 865), a Myc-tag, and fluorescent protein-tags (e.g., EGFP, set forth in SEQ ID NOs: 858, 859, or 896). In some cases, the immunomodulatory polypeptide comprising a variant ICOSL comprises at least six histidine residues (set forth in SEQ ID NO: 864). In some cases, the immunomodulatory polypeptide comprising a variant ICOSL further comprises various combinations of moieties. For example, the immunomodulatory polypeptide comprising a variant ICOSL further comprises one or more polyhistidine-tag and FLAG tag.

In some embodiments, the ICOSL polypeptide is linked to a modified immunoglobulin heavy chain constant region (Fc) that remains in monovalent form such as set forth in SEQ ID NO: 472.

2. Bivalent

In some embodiments, the immunomodulatory protein containing a variant ICOSL is multivalent, such as bivalent. In aspects, the immunomodulatory protein is linked, directly or indirectly via a linker, to a multimerization domain. In some aspects, the mutlimerization domain increase half-life of the molecule.

Interaction of two or more variant ICOSL polypeptides can be facilitated by their linkage, either directly or indirectly, to any moiety or other polypeptide that are themselves able to interact to form a stable structure. For example, separate encoded variant ICOSL polypeptide chains can be joined by multimerization, whereby multimerization of the polypeptides is mediated by a multimerization domain. Typically, the multimerization domain provides for the formation of a stable protein-protein interaction between a first variant ICOSL polypeptide and a second variant ICOSL polypeptide. Homo- or heteromultimeric polypeptides can be generated from co-expression of separate variant ICOSL polypeptides. The first and second variant ICOSL polypeptides can be the same or different.

In some embodiments, a multimerization domain includes any capable of forming a stable protein-protein interaction. The multimerization domains can interact via an immunoglobulin sequence (e.g. Fc domain; see e.g., International Patent Pub. Nos. WO 93/10151 and WO 2005/063816 US; U.S. Pub. No. 2006/0024298; U.S. Pat. No. 5,457,035); leucine zipper (e.g. from nuclear transforming proteins fos and jun or the proto-oncogene c-myc or from General Control of Nitrogen (GCN4)) (ee e.g., Busch and Sassone-Corsi (1990) Trends Genetics, 6:36-40; Gentz et al., (1989) Science, 243:1695-1699); a hydrophobic region; a hydrophilic region; or a free thiol which forms an intermolecular disulfide bond between the chimeric molecules of a homo- or heteromultimer. In addition, a multimerization domain can include an amino acid sequence comprising a protuberance complementary to an amino acid sequence comprising a hole, such as is described, for example, in U.S. Pat. No. 5,731,168; International Patent Pub. Nos. WO 98/50431 and WO 2005/063816; Ridgway et al. (1996) Protein Engineering, 9:617-621. Such a multimerization region can be engineered such that steric interactions not only promote stable interaction, but further promote the formation of heterodimers over homodimers from a mixture of chimeric monomers. Generally, protuberances are constructed by replacing small amino acid side chains from the interface of the first polypeptide with larger side chains (e.g., tyrosine or tryptophan). Compensatory cavities of identical or similar size to the protuberances are optionally created on the interface of the second polypeptide by replacing large amino acid side chains with smaller ones (e.g., alanine or threonine). Exemplary multimerization domains are described below.

The variant ICOSL polypeptide can be joined anywhere, but typically via its N- or C-terminus, to the N- or C-terminus of a multimerization domain to form a chimeric polypeptide. The linkage can be direct or indirect via a linker. Also, the chimeric polypeptide can be a fusion protein or can be formed by chemical linkage, such as through covalent or non-covalent interactions. For example, when preparing a chimeric polypeptide containing a multimerization domain, nucleic acid encoding all or part of a variant ICOSL polypeptide can be operably linked to nucleic acid encoding the multimerization domain sequence, directly or indirectly or optionally via a linker domain. In some cases, the construct encodes a chimeric protein where the C-terminus of the variant ICOSL polypeptide is joined to the N-terminus of the multimerization domain. In some instances, a construct can encode a chimeric protein where the N-terminus of the variant ICOSL polypeptide is joined to the N- or C-terminus of the multimerization domain.

A polypeptide multimer contains two chimeric proteins created by linking, directly or indirectly, two of the same or different variant ICOSL polypeptides directly or indirectly to a multimerization domain. In some examples, where the multimerization domain is a polypeptide, a gene fusion encoding the variant ICOSL polypeptide and multimerization domain is inserted into an appropriate expression vector. The resulting chimeric or fusion protein can be expressed in host cells transformed with the recombinant expression vector, and allowed to assemble into multimers, where the multimerization domains interact to form multivalent polypeptides. Chemical linkage of multimerization domains to variant ICOSL polypeptides can be effected using heterobifunctional linkers.

The resulting chimeric polypeptides, such as fusion proteins, and multimers formed therefrom, can be purified by any suitable method such as, for example, by affinity chromatography over Protein A or Protein G columns. Where two nucleic acid molecules encoding different polypeptides are transformed into cells, formation of homo- and heterodimers will occur. Conditions for expression can be adjusted so that heterodimer formation is favored over homodimer formation.

Immunoglobulin Domain

In some embodiments, the immunomodulatory protein comprises a variant ICOSL polypeptide attached to an Fc region of an immunoglobulin (yielding an "immunomodulatory Fc fusion," such as an "ICOSL-Fc variant fusion," also termed a ICOSL vIgD-Fc fusion). In some embodiments, the ICOSL-Fc variant fusion also comprises one or more additional IgSF domain(s), such as one or more additional vIgD linked to a vIgD of ICOSL. In some embodiments, the attachment of the variant ICOSL polypeptide or additional IgSF domain is at the N-terminus of the Fc. In some embodiments, the attachment of the variant ICOSL or additional IgSF domain polypeptide is at the C-terminus of the Fc. In some embodiments, two or more ICOSL or additional IgSF domain variant polypeptides (the same or different) are independently attached at the N-terminus and at the C-terminus.

In some embodiments, the Fc is murine or human Fc. In some embodiments, the Fc is a mammalian or human IgG1, IgG2, IgG3, or IgG4 Fc regions. In some embodiments, the Fc is derived from IgG1, such as human IgG1. In some embodiments, the Fc comprises the amino acid sequence set forth in SEQ ID NO: 226 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 226.

In some embodiments, the Fc region contains one more modifications to alter (e.g. reduce) one or more of its normal functions. In general, the Fc region is responsible for effector functions, such as complement-dependent cytotoxicity (CDC) and antibody-dependent cell cytotoxicity (ADCC), in addition to the antigen-binding capacity, which is the main function of immunoglobulins. Additionally, the FcRn sequence present in the Fc region plays the role of regulating the IgG level in serum by increasing the in vivo half-life by conjugation to an in vivo FcRn receptor. In some embodiments, such functions can be reduced or altered in an Fc for use with the provided Fc fusion proteins.

In some embodiments, one or more amino acid modifications may be introduced into the Fc region of an ICOSL-Fc variant fusion provided herein, thereby generating an Fc region variant. In some embodiments, the Fc region variant has decreased effector function. There are many examples of changes or mutations to Fc sequences that can alter effector function. For example, WO 2000/42072, WO2006/019447, WO2012/125850, WO2015/107026, US2016/0017041 and Shields et al. *J Biol. Chem.* 9(2): 6591-6604 (2001) describe exemplary Fc variants with improved or diminished binding to FcRs. The contents of those publications are specifically incorporated herein by reference.

In some embodiments, the provided variant ICOSL-Fc fusions comprise an Fc region that exhibits reduced effector functions (also called inert Fc or effectorless Fc), which makes it a desirable candidate for applications in which the half-life of the ICOSL-Fc variant fusion in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the ICOSL-Fc variant fusion lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821, 337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the ICOSL-Fc variant fusion is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

ICOSL-Fc variant fusions with reduced effector function include those with substitution of one or more of Fc region residues 238, 265, 269, 270, 297, 327 and 329 by EU numbering (U.S. Pat. No. 6,737,056). Such Fc mutants include Fc mutants with substitutions at two or more of amino acid positions 265, 269, 270, 297 and 327 by EU numbering, including the so-called "DANA" Fc mutant with substitution of residues 265 and 297 to alanine (U.S. Pat. No. 7,332,581).

In some embodiments, the Fc region of ICOSL-Fc variant fusions has an Fc region in which any one or more of amino acids at positions 234, 235, 236, 237, 238, 239, 270, 297, 298, 325, and 329 (indicated by EU numbering) are substituted with different amino acids compared to the native Fc region. Such alterations of Fc region are not limited to the above-described alterations, and include, for example, alterations such as deglycosylated chains (N297A and N297Q), IgG1-N297G, IgG1-L234A/L235A, IgG1-L234A/L235E/G237A, IgG1-A325A/A330S/P331S, IgG1-C226S/C229S, IgG1-C226S/C229S/E233P/L234V/L235A, IgG1-E233P/L234V/L235A/G236del/S267K, IgG1-L234F/L235E/P331S, IgG1-S267E/L328F, IgG2-V234A/G237A, IgG2-H268Q/V309L/A330S/A331S, IgG4-L235A/G237A/E318A, and IgG4-L236E described in Current Opinion in Biotechnology (2009) 20 (6), 685-691; alterations such as G236R/L328R, L235G/G236R, N325A/L328R, and N325L/L328R described in WO 2008/092117; amino acid insertions at positions 233, 234, 235, and 237 (indicated by EU numbering); and alterations at the sites described in WO 2000/042072.

Certain Fc variants with improved or diminished binding to FcRs are described. (See, e.g., U.S. Pat. No. 6,737,056; WO 2004/056312, WO2006/019447 and Shields et al., *J. Biol. Chem.* 9(2): 6591-6604 (2001).)

In some embodiments, there is provided a ICOSL-Fc variant fusion comprising a variant Fc region comprising one or more amino acid substitutions which increase half-life and/or improve binding to the neonatal Fc receptor (FcRn). Antibodies with increased half-lives and improved binding to FcRn are described in US2005/0014934A1 (Hinton et al.) or WO2015107026. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434 by EU numbering, e.g., substitution of Fc region residue 434 (U.S. Pat. No. 7,371,826).

In some embodiments, the Fc region of a ICOSL-Fc variant fusion comprises one or more amino acid substitution E356D and M358L by EU numbering. In some embodiments, the Fc region of a ICOSL-Fc variant fusion comprises one or more amino acid substitutions C220S, C226S, and/or C229S by EU numbering. In some embodiments, the Fc region of a ICOSL variant fusion comprises one or more amino acid substitutions R292C and V302C. See also Duncan & Winter, Nature 322:738-40 (1988); U.S. Pat. Nos. 5,648,260; 5,624,821; and WO 94/29351 concerning other examples of Fc region variants.

In some embodiments, the wild-type IgG1 Fc can be the Fc set forth in SEQ ID NO: 226 having an allotype containing residues Glu (E) and Met (M) at positions 356 and 358 by EU numbering (e.g., f allotype). In other embodiments, the wild-type IgG1 Fc contains amino acids of the human G1m1 allotype, such as residues containing Asp (D) and Leu (L) at positions 356 and 358, e.g. as set forth in SEQ ID NO: 927. Thus, in some cases, an Fc provided herein can contain amino acid substitutions E356D and M358L to reconstitute residues of allotype G1 m1 (e.g., alpha allotype). In some aspects, a wild-type Fc is modified by one or more amino acid substitutions to reduce effector activity or to render the Fc inert for Fc effector function. Exemplary effectorless or inert mutations include those described herein. Among effectorless mutations that can be included in an Fc of constructs provided herein are L234A, L235E and G237A by EU numbering. In some embodiments, a wild-type Fc is further modified by the removal of one or more cysteine residue, such as by replacement of the cysteine residues to a serine residue at position 220 (C220S) by EU numbering. Exemplary inert Fc regions having reduced effector function are set forth in SEQ ID NO: 633 or 477 and SEQ ID NO: 474 or 637, which are based on allotypes set forth in SEQ ID NO: 226 or SEQ ID NO: 927, respectively. In some embodiments, an Fc region used in a construct provided herein can further lack a C-terminal lysine residue.

In some embodiments, alterations are made in the Fc region that result in diminished C1q binding and/or Complement Dependent Cytotoxicity (CDC), e.g., as described in U.S. Pat. No. 6,194,551, WO 99/51642, and Idusogie et al., *J. Immunol.* 164:4178-4184 (2000).

In some embodiments, there is provided a ICOSL-Fc variant fusion comprising a variant Fc region comprising one or more amino acid modifications, wherein the variant Fc region is derived from IgG1, such as human IgG1. In some embodiments, the variant Fc region is derived from the amino acid sequence set forth in SEQ ID NO: 226. In some embodiments, the Fc exhibits reduced effector function. In some embodiments, the Fc contains at least one amino acid substitution that is N82G by numbering of SEQ ID NO: 226 (corresponding to N297G by EU numbering). In some embodiments, the Fc further contains at least one amino acid substitution that is R77C or V87C by numbering of SEQ ID NO: 226 (corresponding to R292C or V302C by EU numbering). In some embodiments, the variant Fc region further comprises a C5S amino acid modification by numbering of SEQ ID NO: 226 (corresponding to C220S by EU numbering). For example, in some embodiments, the variant Fc region comprises the following amino acid modifications: V297G and one or more of the following amino acid modifications C220S, R292C or V302C by EU numbering (corresponding to N82G and one or more of the following amino acid modifications C5S, R77C or V87C with reference to SEQ ID NO:226), e.g. the Fc region comprises the sequence set forth in SEQ ID NO:476. In some embodiments, the variant Fc region comprises one or more of the amino acid modifications C220S, L234A, L235E or G237A, e.g. the Fc region comprises the sequence set forth in SEQ ID NO:477. In some embodiments, the variant Fc region comprises one or more of the amino acid modifications C220S, E233P, L234V, L235A, G236del or S267K, e.g. the Fc region comprises the sequence set forth in SEQ ID NO:478. In some embodiments, the variant Fc comprises one or more of the amino acid modifications C220S, L234A, L235E, G237A, E356D or M358L, e.g. the Fc region comprises the sequence set forth in SEQ ID NO:474.

In some embodiments, the Fc region lacks the C-terminal lysine corresponding to position 232 of the reference (e.g., unmodified) or wild-type Fc set forth in SEQ ID NO: 56 (corresponding to K447del by EU numbering). In some embodiments, because the C-terminal lysine may be differentially removed during biosynthesis, removal of the C-terminal lysine residue results in a more homogenous product when the protein is expressed in cells. In some aspects, such an Fc region can additionally include one or more additional modifications, e.g. amino acid substitutions, such as any as described. Exemplary of such an Fc region is set forth in SEQ ID NO: 632, 633, 634, or 637.

In some embodiments, there is provided a ICOSL-Fc variant fusion comprising a variant Fc region in which the variant Fc comprises the sequence of amino acids set forth in any of SEQ ID NOS: 474, 476, 477, 478, 507, 632, 633, 634, or 637 or a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 474, 476, 477, 478, 507, 632, 633, 634, or 637. In some embodiments, the Fc exhibits reduced effector function.

In some embodiments, the Fc is derived from IgG2, such as human IgG2. In some embodiments, the Fc comprises the amino acid sequence set forth in SEQ ID NO: 227 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 227.

In some embodiments, the Fc comprises the amino acid sequence set forth in SEQ ID NO: 505 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 505. In some embodiments, the IgG4 Fc is a stabilized Fc in which the CH3 domain of human IgG4 is substituted with the CH3 domain of human IgG1 and which exhibits inhibited aggregate formation, an antibody in which the CH3 and CH2 domains of human IgG4 are substituted with the CH3 and CH2 domains of human IgG1, respectively, or an antibody in which arginine at position 409 indicated in the EU index proposed by Kabat et al. of human IgG4 is substituted with lysine and which exhibits inhibited aggregate formation (see e.g. U.S. Pat. No. 8,911,726). In some embodiments, the Fc is an IgG4 containing the S228P mutation, which has been shown to prevent recombination between a therapeutic antibody and an endogenous IgG4 by Fab-arm exchange (see e.g. Labrijin et al. (2009) Nat. Biotechnol., 27(8)767-71.) In some embodiments, the Fc comprises the amino acid sequence set forth in SEQ ID NO: 506 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 506.

In some embodiments, the variant ICOSL polypeptide is directly linked to the Fc sequence. In some embodiments, the variant ICOSL polypeptide is indirectly linked to the Fc sequence, such as via a linker. In some embodiments, one or more "peptide linkers" link the variant ICOSL polypeptide and the Fc domain. In some embodiments, a peptide linker can be a single amino acid residue or greater in length. In some embodiments, the peptide linker has at least one amino acid residue but is no more than 20, 19, 18, 17, 16, 15, 14, 13, 12, 11, 10, 9, 8, 7, 6, 5, 4, 3, 2, or 1 amino acid residues in length. In some embodiments, the linker is three alanines (AAA). In some embodiments, the linker is (in one-letter amino acid code): GGGGS ("4GS"; SEQ ID NO:636) or multimers of the 4GS linker, such as repeats of 2, 3, 4, 5 or 6 4GS linkers, such as set forth in SEQ ID NO: 229 (2×GGGGS) or SEQ ID NO: 228 (3×GGGGS). In some embodiments, the linker is a rigid linker. For example, the linker is an α-helical linker. In some embodiments, the linker is (in one-letter amino acid code): EAAAK or multimers of the EAAAK linker, such as repeats of 2, 3, 4, or 5 4GS linkers, such as set forth in SEQ ID NO: 629 (EAAAK) or SEQ ID NO: 630 (3×EAAAK) or SEQ ID NO: 631 (5×EAAAK). In some embodiments, linkers start with one or more EAAAK units and can be lengthened by addition of A, AA, AAA, AAAA, EAAAA and EAAAK sequences. In some embodiments, the linker can further include amino acids introduced by cloning and/or from a restriction site, for example the linker can include the amino acids GS (in one-letter amino acid code) as introduced by use of the restriction site BAMHI. In some embodiments, the linker (in one-letter amino acid code) is GSGGGGS (SEQ ID NO: 635). In some examples, the linker is a 2×GGGGS followed by three alanines (GGGGSGGGGSAAA; SEQ ID NO: 230).

In some embodiments, the variant ICOSL-Fc fusion protein is a dimer formed by two variant ICOSL Fc polypeptides linked to an Fc domain. In some specific embodiments, identical or substantially identical species (allowing for 3 or fewer N-terminus or C-terminus amino acid sequence differences) of ICOSL-Fc variant fusion polypeptides will be dimerized to create a homodimer. In some embodiments, the dimer is a homodimer in which the two variant ICOSL Fc polypeptides are the same. Alternatively, different species of ICOSL-Fc variant fusion polypeptides can be dimerized to yield a heterodimer. Thus, in some embodiments, the dimer is a heterodimer in which the two variant ICOSL Fc polypeptides are different.

In some embodiments, provided is a variant ICOSL-Fc fusion protein containing a variant ICOSL polypeptide that includes one or more amino acid modifications in a reference ICOSL as described in Section II that is linked, directly or indirectly, to an Fc region. In some cases, the C-terminus of the variant ICOSL polypeptide is joined to the N-terminus of the Fc region. In some embodiments, the variant ICOSL of an ICOSL-Fc fusion contains one or more amino acid modifications in the sequence of amino acids the reference IgV domain set forth in SEQ ID NO:545. In particular cases, such an immunomodulatory protein contains variant ICOSL polypeptide containing an IgV domain, such as an IgV domain set forth in any one of SEQ ID NOS: 197-199, 201-208, 210, 212, 240, 326-340, 382-386, 425-426, 434, 546-599, 686-857, 906-907, 909-910, or an IgV domain that has at least 85%, 86%, 87%, 88%, 89%, 90%, 91%, 92%, 93%, 94%, 95%, 96%, 97%, 98%, 99% to any of SEQ ID NOS: 197-199, 201-208, 210, 212, 240, 326-340, 382-386, 425-426, 434, 546-599, 686-857, 906-907, 909-910 and contains the one or more amino acid modifications of the respective SEQ ID NO. In some embodiments, the variant ICOSL polypeptide has an IgSF domain (e.g. IgV domain) that exhibits increased binding affinity to CD28 or ICOS, such as any of the amino acid modifications described herein. In some embodiments, the variant ICOSL polypeptide has an IgSF domain (e.g. IgV domain) containing one or more amino acid modification, e.g. substitution in an reference ICOSL or specific binding fragment, corresponding to position(s) 52, 57, or 100 with reference to numbering of SEQ ID NO: 32. In some embodiments, the variant ICOSL polypeptide has one or more amino acid modification, e.g. substitution selected from N52A, N52C, N52D, N52G, N52H, N52L, N52K, N52M, N52P, N52Q, N52R, N52S, N52T, N52V, N52Y, N57A, N57E, N57F, N57H, N57K, N57L, N57M, N57P, N57Q, N57S, N57T, N57V, N57W, N57Y, Q100A, Q100D, Q100E, Q100G, Q100K, Q100L, Q100M, Q100N, Q100R, Q100P, Q100S, Q100T, or Q100V. Exemplary of such variant molecules include any as described herein. In some embodiments, the variant ICOSL polypeptide contains the amino acid modifications N52H/N57Y/Q100R (e.g. is or includes an IgV domain set forth in SEQ ID NO: 565). In some embodiments, the variant ICOSL polypeptide contains the amino acid modifications N52D (e.g. is or includes an IgV domain set forth in SEQ ID NO: 548). In some embodiments, the variant ICOSL polypeptide contains the amino acid modifications N52H/Q100R (e.g. is or includes an IgV domain set forth in SEQ ID NO: 567). In some embodiments, the variant ICOSL polypeptide contains the amino acid modifications N52L/N57H/Q100R (e.g. is or includes an IgV domain set forth in SEQ ID NO: 761). In some embodiments, the variant ICOSL polypeptide contains the amino acid modifications N52H/N57Y/Q100P (e.g. is or includes an IgV domain set forth in SEQ ID NO: 570).

In particular embodiments of such variant ICOSL-Fc fusion proteins, the Fc polypeptide is a variant of a human IgG1 Fc region that exhibits reduced effector functions, such as any as described. In some embodiments, the Fc region is a human IgG1 that contains the amino acid modifications N297G, E233P/L234V/L235A/G236del/S267K or L234A/L235E/G237A, wherein the residue is numbered according to the EU index of Kabat. In some embodiments, the variant IgG1 Fc region further contains the amino acid substitution C220S, wherein the residues are numbered according to the EU index of Kabat. In some embodiments, the Fc region contains K447del, wherein the residue is numbered according to the EU index of Kabat. In some aspects, the Fc region contains the sequence of amino acid sequence set forth in any of SEQ ID NOS: 474, 476, 477, 478, 633 or 637 or a sequence of amino acids that exhibits at least 85%, 90%, 91%, 92%, 93%, 94%, 95%, 96%, 97%, 98%, 99% or more sequence identity to any of SEQ ID NOS: 474, 476, 477, 478, 633 or 637 and contains the amino acid substitutions of the respective SEQ ID NO. The linkage between the variant ICOSL IgSF (e.g. IgV) polypeptide and the Fc can be via a peptide linker, such as any as described. In some embodiments, the linker is GGGGS ("4GS"; SEQ ID NO: 636), SEQ ID NO: 229 (2×GGGGS) or SEQ ID NO: 228 (3×GGGGS). In particular examples, the C-terminus of the variant ICOSL polypeptide is joined to the N-terminus of the Fc region, such that the order of components is variant ICOSL-linker-Fc.

In some embodiments, there is provided a variant ICOSL-Fc fusion protein, e.g. variant ICOSL-linker-Fc, containing a variant ICOSL IgV domain set forth in SEQ ID NO:565, a linker set forth in SEQ ID NO:636 and an Fc polypeptide set forth in SEQ ID NO: 637. In some embodiments, there is provided a variant ICOSL-Fc fusion protein, e.g. variant ICOSL-linker-Fc, containing a variant ICOSL IgV domain set forth in SEQ ID NO:565, a linker set forth in SEQ ID NO: 636 and an Fc polypeptide set forth in SEQ ID NO: 474. In some embodiments, there is provided a variant ICOSL-Fc fusion protein, e.g. variant ICOSL-linker-Fc, containing a variant ICOSL IgV domain set forth in SEQ ID NO:565, a linker set forth in SEQ ID NO:636 and an Fc polypeptide set forth in SEQ ID NO: 477. In some embodiments, there is provided a variant ICOSL-Fc fusion protein, e.g. variant ICOSL-linker-Fc, containing a variant ICOSL IgV domain set forth in SEQ ID NO:565, a linker set forth in SEQ ID NO:636 and an Fc polypeptide set forth in SEQ ID NO: 633.

In some embodiments, there is provided a variant ICOSL-Fc fusion protein, e.g. variant ICOSL-linker-Fc, containing a variant ICOSL IgV domain set forth in SEQ ID NO:565, a linker set forth in SEQ ID NO: 229 and an Fc polypeptide set forth in SEQ ID NO: 637. In some embodiments, there is provided a variant ICOSL-Fc fusion protein, e.g. variant ICOSL-linker-Fc, containing a variant ICOSL IgV domain set forth in SEQ ID NO:565, a linker set forth in SEQ ID NO:229 and an Fc polypeptide set forth in SEQ ID NO: 474. In some embodiments, there is provided a variant ICOSL-Fc fusion protein, e.g. variant ICOSL-linker-Fc, containing a variant ICOSL IgV domain set forth in SEQ ID NO:565, a linker set forth in SEQ ID NO: 229 and an Fc polypeptide set forth in SEQ ID NO: 477. In some embodiments, there is provided a variant ICOSL-Fc fusion protein, e.g. variant ICOSL-linker-Fc, containing a variant ICOSL IgV domain set forth in SEQ ID NO:565, a linker set forth in SEQ ID NO:229 and an Fc polypeptide set forth in SEQ ID NO: 633.

In some embodiments, there is provided a variant ICOSL-Fc fusion protein, e.g. variant ICOSL-linker-Fc, containing a variant ICOSL IgV domain set forth in SEQ ID NO:565, a linker set forth in SEQ ID NO:228 and an Fc polypeptide set forth in SEQ ID NO: 637. In some embodiments, there is provided a variant ICOSL-Fc fusion protein, e.g. variant ICOSL-linker-Fc, containing a variant ICOSL IgV domain set forth in SEQ ID NO:565, a linker set forth in SEQ ID NO: 228 and an Fc polypeptide set forth in SEQ ID NO: 474. In some embodiments, there is provided a variant ICOSL-Fc fusion protein, e.g. variant ICOSL-linker-Fc, containing a variant ICOSL IgV domain set forth in SEQ ID NO:565, a linker set forth in SEQ ID NO: 228 and an Fc polypeptide set forth in SEQ ID NO: 477. In some embodiments, there is provided a variant ICOSL-Fc fusion protein, e.g. variant ICOSL-linker-Fc, containing a variant ICOSL IgV domain set forth in SEQ ID NO: 565, a linker set forth in SEQ ID NO:228 and an Fc polypeptide set forth in SEQ ID NO: 633.

In some embodiments, there is provided a variant ICOSL IgSF Fc fusion protein that has the sequence of amino acids set forth in SEQ ID NO: 928, or a sequence of amino acids that exhibits at least 85%, 90%, 91%, 92%, 93%, 94%, 95%, 96%, 97%, 98%, 99% to SEQ ID NO: 928. In some embodiments, the variant ICOSL IgSF Fc fusion protein binds to CD28 and ICOS, such as with increased binding affinity compared to reference (wild-type) ICOSL-Fc fusion protein. In some embodiments, the variant ICOSL IgSF Fc fusion exhibits reduced Fc effector function compared to fusion with an Fc of a wild-type human IgG1.

In some embodiments, there is provided a multi-domain stack immunomodulatory protein in which two or more IgSF domain, including a vIgD of ICOSL and one or more additional IgSF domain (e.g. second variant IgSF domain) from another IgSF family member, are linked or attached to an Fc to form an Fc fusion, which, upon expression in a cell can, in some aspects, produce a dimeric multi-domain stack immunomodulatory protein. Thus, also provided are dimeric multi-domain immunomodulatory proteins.

In some embodiments, the variant ICOSL polypeptide and one or more additional IgSF domain are independently linked, directly or indirectly, to the N- or C-terminus of an Fc region. In some embodiments, the variant ICOSL polypeptide and at least one of the one or more additional IgSF domain are linked, directly or indirectly, and one of the variant ICOSL or and one of the one or more additional IgSF domain is also linked, directly or indirectly, to the N- or C-terminus of an Fc region. In some embodiments, the N- or C-terminus of the Fc region is linked to the variant ICOSL polypeptide or the one or more additional IgSF domain and the other of the N- or C-terminus of the Fc region is linked to the other of the ICOSL variant or another of the one or more additional IgSF domain. In some embodiments, linkage to the Fc is via a peptide linker, e.g. a peptide linker, such as described above. In some embodiments, linkage between the variant ICOSL and second IgSF domain is via a peptide linker, e.g. a peptide linker, such as described above. In some embodiments, linkage between the variant ICOSL and the one or more additional IgSF domain is via a peptide linker, e.g., a peptide linker, such as described above. In some embodiments, the vIgD of ICOSL, the one or more additional IgSF domains, and the Fc domain can be linked together in any of numerous configurations as depicted in FIGS. 16A and 16B. In some embodiments, the ICOSL-Fc variant fusion can further contain a signal peptide, such as an exemplary signal peptide as contained in the sequence of amino acids set forth in SEQ ID NO: 59 or 225. Exemplary configurations are described in the Examples.

In some embodiments, the stacked immunomodulatory protein is a dimer formed by two immunomodulatory Fc fusion polypeptides. Also provided are nucleic acid molecules encoding any of the stacked immunomodulatory proteins. In some embodiments, the dimeric multi-domain stack immunomodulatory protein can be produced in cells by expression, or in some cases co-expression, of stack immunomodulatory Fc region polypeptides, such as described further below.

In some embodiments, the dimeric multi-domain stack immunomodulatory protein is divalent for each Fc subunit, monovalent for each subunit, or divalent for one subunit and tetravalent for the other.

In some embodiments, the dimeric multi-domain stack immunomodulatory protein is a homodimeric multi-domain stack Fc protein. In some embodiments, the dimeric multi-domain stack immunomodulatory protein comprises a first stack immunomodulatory Fc fusion polypeptide and a second stack immunomodulatory Fc fusion polypeptide in which the first and second polypeptide are the same. In some embodiments, the Fc portion of the polypeptide can be any Fc as described above.

In some embodiments, the multi-domain stack molecule contains a first Fc fusion polypeptide containing a variant ICOSL and a second fusion IgSF domain and a second Fc polypeptide containing the variant ICOSL and the second IgSF domain. In some embodiments, the multi-domain stack molecule contains a first Fc fusion polypeptide containing a variant ICOSL and a second IgSF domain, and a third IgSF domain and a second Fc fusion polypeptide containing the variant ICOSL, the second IgSF domain, and the third IgSF domain. In some embodiments, the Fc portion of the first and/or second fusion polypeptide can be any Fc as described above. In some embodiments, the Fc portion or region of the first and second fusion polypeptide is the same.

In some embodiments, there is provided an immuno-modulatory protein that is a ICOSL-NKp30 multi-domain stack containing any of the variant ICOSL polypeptides and one or more IgF domains of NKp30, e.g. wild-type or unmodified NKp30, such as an IgV domain set forth in SEQ ID NO: 929 or an ECD or a binding portion thereof set forth in SEQ ID NO: 215 or a binding portion thereof. In some embodiments, there is provided an immunomodulatory protein containing any of the variant ICOSL polypeptide and one or more IgSF domains of a variant NKp30 containing one or more amino acid modifications in the wild-type or unmodified sequence set forth in SEQ ID NO: 215 or 929. In some embodiments, the one or more amino acid modifications (e.g. substitutions) include one or more of L30V, A60V, S64P, S86G, such as 1, 2, 3 or 4 of such amino acid modifications. In some aspects, a variant NKp30 of the multi-domain stack polypeptides is or includes a variant IgV domain, such as a variant IgV domain set forth in any of SEQ ID NOS: 504, 930, 931, 932 or 933, or an IgV domain that has at least 85%, 86%, 87%, 88%, 89%, 90%, 91%, 92%, 93%, 94%, 95%, 96%, 97%, 98%, 99% to any of SEQ ID NOS: 504, 930, 931, 932 or 933 and contains the one or more amino acid modifications of the respective SEQ ID NO. In some aspects, a variant NKp30 of the multi-domain stack polypeptides is or includes a variant ECD domain, such as a variant ECD set forth in any of SEQ ID NOS: 215, 216, 217, 218 or 219, or an ECD domain that has at least 85%, 86%, 87%, 88%, 89%, 90%, 91%, 92%, 93%, 94%, 95%, 96%, 97%, 98%, 99% to any of SEQ ID NOS: 215, 216, 217, 218 or 219 and contains the one or more amino acid modifications of the respective SEQ ID NO.

In any of such embodiments of an ICOSL-NKp30 multi-domain stack, the variant ICOSL polypeptide can include any described in Section II containing a variant IgSF domain (e.g. IgV or ECD), such as including any of the amino acid modifications set forth in a Table 1. In some cases, such an immunomodulatory protein contains a variant ICOSL polypeptide containing an ECD domain, such as an ECD domain set forth in any one of SEQ ID NOS: 109-142, 239, 280-325, 364-381, 387-424, 427-433, 435-470, 638-685, 905, 908, or an ECD domain that has at least 85%, 86%, 87%, 88%, 89%, 90%, 91%, 92%, 93%, 94%, 95%, 96%, 97%, 98%, 99% to any of SEQ ID NOS: 109-142, 239, 280-325, 364-381, 387-424, 427-433, 435-470, 638-685, 905, 908 and contains the one or more amino acid modifications of the respective SEQ ID NO. In particular cases, such an immunomodulatory protein contains a variant ICOSL polypeptide containing an IgV domain, such as an IgV domain set forth in any one of SEQ ID NOS: 197-199, 201-208, 210, 212, 240, 326-340, 382-386, 425-426, 434, 546-599, 686-857, 906-907, 909-910, or an IgV domain that has at least 85%, 86%, 87%, 88%, 89%, 90%, 91%, 92%, 93%, 94%, 95%, 96%, 97%, 98%, 99% to any of SEQ ID NOS: 197-199, 201-208, 210, 212, 240, 326-340, 382-386, 425-426, 434, 546-599, 686-857, 906-907, 909-910 and contains the one or more amino acid modifications of the respective SEQ ID NO. In some embodiments, the variant ICOSL polypeptide has an IgSF domain (e.g. IgV domain) exhibits increased binding affinity to CD28 or ICOS, such as any described herein. In some embodiments, the variant ICOSL polypeptide has an IgSF domain (e.g. IgV domain) containing one or more amino acid modification, e.g. substitution in an reference ICOSL or specific binding fragment, corresponding to position(s) 52, 57, or 100 with reference to numbering of SEQ ID NO:32. In some embodiments, the variant ICOSL polypeptide has one or more amino acid modification, e.g. substitution selected from N52A, N52C, N52D, N52G, N52H, N52L, N52K, N52M, N52P, N52Q, N52R, N52S, N52T, N52V, N52Y, N57A, N57E, N57F, N57H, N57K, N57L, N57M, N57P, N57Q, N57S, N57T, N57V, N57W, N57Y, Q100A, Q100D, Q100E, Q100G, Q100K, Q100L, Q100M, Q100N, Q100R, Q100P, Q100S, Q100T, or Q100V. Exemplary of such variant molecules include any as described herein. In some embodiments, the variant ICOSL polypeptide contains the amino acid modifications N52D (e.g. is or includes an IgV domain set forth in SEQ ID NO: 548), N52H/Q100R (e.g. is or includes an IgV domain set forth in SEQ ID NO:567), N52H/N57Y/Q100R (e.g. is or includes an IgV domain set forth in SEQ ID NO:565), or N52L/N57H/Q100R (e.g. is or includes an IgV domain set forth in SEQ ID NO:761).

In some embodiments, the provided multi-domain stack immunomodulatory proteins, such as an ICOSL-NKp30 multi-domain stack immunomodulatory protein, are fused to an Fc polypeptide. In particular embodiments, the Fc polypeptide is a variant of a human IgG1 Fc region that exhibits reduced effector functions, such as any as described. In some embodiments, the Fc region is a human IgG1 that contains the amino acid modifications N297G, E233P/L234V/L235A/G236del/S267K or L234A/L235E/G237A, wherein the residue is numbered according to the EU index of Kabat. In some embodiments, the variant IgG1 Fc region further contains the amino acid substitution C220S, wherein the residues are numbered according to the EU index of Kabat. In some embodiments, the Fc region contains K447del, wherein the residue is numbered according to the EU index of Kabat. In some aspects, the Fc region contains the sequence of amino acid sequence set forth in any of SEQ ID NOS: 474, 476, 477, 478, 633 or 637 or a sequence of amino acids that exhibits at least 90%, 91%, 92%, 93%, 94%, 95%, 96%, 97%, 98%, 99% or more sequence identity to any of SEQ ID NOS: 474, 476, 477, 478, 633 or 637 and contains the amino acid substitutions of the respective SEQ ID NO.

Exemplary of such configurations are set forth in FIGS. 16A-16B and described herein. In some embodiments, any of the provided ICOSL-NKp30 multi-domain stack immunomodulatory polypeptides can contain two copies of a polypeptide having the structure: variant ICOSL IgSF (e.g. IgV, such as set forth in SEQ ID NO: 548, 565, 567 or 761)-linker 1-variant NKp30 IgSF (e.g. IgV, such as set forth in SEQ ID NO: 504)-linker 2-Fc. In some embodiments, any of the provided ICOSL-NKp30 multi-domain stack immunomodulatory polypeptides can contain two copies of a polypeptide having the structure: variant ICOSL IgSF (e.g. IgV, such as set forth in SEQ ID NO: 548, 565, 567 or 761)-linker 1-variant NKp30 IgSF (e.g. IgV, such as set forth in SEQ ID NO:504)-linker 1-variant NKp30 IgSF (e.g. IgV, such as set forth in SEQ ID NO:504)-linker 2-Fc. In some embodiments, linker 1 and linker 2 are peptide linkers, such as any as described. In some embodiments, linker 1 and linker 2 are the same. In some embodiments, linker 1 and linker 2 are different. In some embodiments, linker 1 is 3×GGGGS (SEQ ID NO: 228). In some embodiments, linker 2 is GSGGGS (SEQ ID NO: 635).

Exemplary ICOSL-NKp30 multidomain stacks have the sequence of amino acids set forth in any of SEQ ID NOS: 912, 914, 916, 918, 920, 922, 924 or 926, or a sequence of amino acids that exhibits at least 85%, 86%, 87%, 88%, 89%, 90%, 91%, 92%, 93%, 94%, 95%, 96%, 97%, 98%, 99% to any of SEQ ID NOS: 912, 914, 916, 918, 920, 922, 924 or 926.

In some embodiments, any of the provided ICOSL-NKp30 multi-domain stack immunomodulatory proteins bind to ICOS and/or CD28 and bind to B7-H6. In some embodiments, the provided ICOSL-NKp30 multi-domain stack immunomodulatory proteins provide for a binding molecule capable of tumor localization adjacent to an immune cell that expresses ICOS and/or CD28 (e.g. a T cell). In some embodiments, such ICOSL-NKp30 multi-domain stack immunomodulatory proteins can be used to increase an immune response by engagement of ICOS and/or CD28 costimulatory receptors on T cells in a tumor microenvironment. In some cases, such ICOSL-NKp30 multi-domain stack immunomodulatory proteins, or pharmaceutical compositions thereof, can be used to treat a tumor or cancer.

In some embodiments, the multi-domain stack molecule is heterodimeric, comprising two different Fc fusion polypeptides, e.g. a first and a second Fc polypeptide, wherein at least one is an Fc fusion polypeptide containing at least one variant ICOSL polypeptide and/or at least one is an Fc polypeptide containing a second IgSF domain (e.g. second variant IgSF domain). In some embodiments, the first or second Fc fusion polypeptide further contains a third IgSF domain (e.g. third variant IgSF domain). In some embodiments, the mult-domain stack molecule contains a first Fc fusion polypeptide containing a variant ICOSL and a second Fc fusion polypeptide containing at a second IgSF domain, in which, in some cases, the first or second Fc fusion polypeptide additionally contains a third IgSF domain. In some embodiments, the multi-domain stack molecule contains a first Fc fusion polypeptide containing a variant ICOSL, a second IgSF domain, and in some cases, a third IgSF domain and a second Fc fusion polypeptide that is not linked to either a variant ICOSL polypeptide or an additional IgSF domain. In some embodiments, the Fc portion or region of the first and second fusion polypeptide is the same. In some embodiments, the Fc portion or region of the first and second fusion polypeptide is different. In some embodiments, the multi-domain stack molecule contains a first fusion Fc polypeptide containing 1, 2, 3, 4 or more variant ICOSL polypeptides and/or 1, 2, 3, 4 or more additional IgSF domains, wherein the total number of IgSF domains in the first stack Fc fusion polypeptide is greater than 2, 3, 4, 5, 6 or more. In one example of such an embodiment, the second stack Fc fusion polypeptide contains 1, 2, 3, 4 or more variant ICOSL polypeptides and/or 1, 2, 3, 4 or more second IgSF domains, wherein the total number of IgSF domains in the second stack Fc fusion polypeptide is greater than 2, 3, 4, 5, 6 or more. In another example of such an embodiment, the second Fc fusion polypeptide is not linked to either a variant ICOSL polypeptide or additional IgSF domain.

In some embodiments, the heterodimeric stack molecule contains a first stack immunomodulatory Fc fusion polypeptide and a second stack immunomodulatory Fc fusion polypeptide in which the first and second polypeptide are different. In some embodiments, a heterodimeric stack molecule contains a first Fc polypeptide fusion containing an Fc region and a first variant ICOSL polypeptide and/or second IgSF domain (e.g. second variant IgSF domain) and a second Fc polypeptide fusion containing an Fc region and the other of the first variant ICOSL polypeptide or the second IgSF domain. In some embodiments, a heterodimeric stack molecule contains a first Fc polypeptide fusion containing an Fc region and a first variant ICOSL polypeptide and/or second IgSF domain (e.g. second variant IgSF domain) and a second Fc polypeptide fusion containing both the first variant ICOSL polypeptide and second IgSF domain (e.g. second variant IgSF domain) but in a different orientation or configuration from the first Fc region. In some embodiments, the first and/or second Fc fusion polypeptide also contains a third IgSF domain (e.g. third variant IgSF domain).

In some embodiments, the Fc domain of one or both of the first and second stacked immunomodulatory Fc fusion polypeptide comprises a modification (e.g. substitution) such that the interface of the Fc molecule is modified to facilitate and/or promote heterodimerization. In some embodiments, modifications include introduction of a protuberance (knob) into a first Fc polypeptide and a cavity (hole) into a second Fc polypeptide such that the protuberance is positionable in the cavity to promote complexing of the first and second Fc-containing polypeptides. Amino acids targeted for replacement and/or modification to create protuberances or cavities in a polypeptide are typically interface amino acids that interact or contact with one or more amino acids in the interface of a second polypeptide.

In some embodiments, a sequence of amino acids is added preceding the Fc sequence for constructs in which the Fc sequence is the N-terminal portion of the sequence. In some cases, the sequence of amino acids HMSSVSAQ (SEQ ID NO:475) is added immediately preceding the Fc sequence for constructs in which the Fc sequence is the N-terminal portion of the sequence. In some embodiments, a heterodimeric stack molecule contains a first Fc polypeptide fusion containing an Fc region (knob) and a first variant ICOSL polypeptide and/or second IgSF domain (e.g. second variant IgSF domain) and a second Fc polypeptide fusion containing an Fc region (hole) and a stuffer sequence HMSSVSAQ (SEQ ID NO:475) added immediately preceding both Fc regions of the first and second Fc polypeptide fusion.

In some embodiments, a first polypeptide that is modified to contain protuberance (hole) amino acids include replacement of a native or original amino acid with an amino acid that has at least one side chain which projects from the interface of the first polypeptide and is therefore positionable in a compensatory cavity (hole) in an adjacent interface of a second polypeptide. Most often, the replacement amino acid is one which has a larger side chain volume than the original amino acid residue. One of skill in the art knows how to determine and/or assess the properties of amino acid residues to identify those that are ideal replacement amino acids to create a protuberance. In some embodiments, the replacement residues for the formation of a protuberance are naturally occurring amino acid residues and include, for example, arginine (R), phenylalanine (F), tyrosine (Y), or tryptophan (W). In some examples, the original residue identified for replacement is an amino acid residue that has a small side chain such as, for example, alanine, asparagine, aspartic acid, glycine, serine, threonine, or valine.

In some embodiments, a second polypeptide that is modified to contain a cavity (hole) is one that includes replacement of a native or original amino acid with an amino acid that has at least one side chain that is recessed from the interface of the second polypeptide and thus is able to accommodate a corresponding protuberance from the interface of a first polypeptide. Most often, the replacement amino acid is one which has a smaller side chain volume than the original amino acid residue. One of skill in the art knows how to determine and/or assess the properties of amino acid residues to identify those that are ideal replacement residues for the formation of a cavity. Generally, the replacement residues for the formation of a cavity are naturally occurring amino acids and include, for example, alanine (A), serine(S), threonine (T) and valine (V). In some examples, the original amino acid identified for replacement is an amino acid that has a large side chain such as, for example, tyrosine, arginine, phenylalanine, or typtophan.

The CH3 interface of human IgG1, for example, involves sixteen residues on each domain located on four anti-parallel β-strands which buries 1090 Å2 from each surface (see e.g., Deisenhofer et al. (1981) Biochemistry, 20:2361-2370; Miller et al., (1990) J Mol. Biol., 216, 965-973; Ridgway et al., (1996) Prot. Engin., 9:617-621; U.S. Pat. No. 5,731, 168). Modifications of a CH3 domain to create protuberances or cavities are described, for example, in U.S. Pat. No. 5,731,168; International Patent Applications WO98/50431 and WO 2005/063816; and Ridgway et al., (1996) Prot. Engin., 9:617-621. In some examples, modifications of a CH3 domain to create protuberances or cavities are typically targeted to residues located on the two central anti-parallel β-strands. The aim is to minimize the risk that the protuberances which are created can be accommodated by protruding into the surrounding solvent rather than being accommodated by a compensatory cavity in the partner CH3 domain.

In some embodiments, the heterodimeric molecule contains a T366W mutation in the CH3 domain of the "knobs chain" and T366S, L368A, Y407V mutations in the CH3 domain of the "hole chain". In some cases, an additional interchain disulfide bridge between the CH3 domains can also be used (Merchant, A. M., et al., Nature Biotech. 16 (1998) 677-681) e.g. by introducing a Y349C mutation into the CH3 domain of the "knobs" or "hole" chain and a E356C mutation or a S354C mutation into the CH3 domain of the other chain. In some embodiments, the heterodimeric molecule contains S354C, T366W mutations in one of the two CH3 domains and Y349C, T366S, L368A, Y407V mutations in the other of the two CH3 domains. In some embodiments, the heterodimeric molecule comprises E356C, T366W mutations in one of the two CH3 domains and Y349C, T366S, L368A, Y407V mutations in the other of the two CH3 domains. In some embodiments, the heterodimeric molecule comprises Y349C, T366W mutations in one of the two CH3 domains and E356C, T366S, L368A, Y407V mutations in the other of the two CH3 domains. In some embodiments, the heterodimeric molecule comprises Y349C, T366W mutations in one of the two CH3 domains and S354C, T366S, L368A, Y407V mutations in the other of the two CH3 domains. Examples of other knobs-in-holes technologies are known in the art, e.g. as described by EP 1 870 459 A1.

In some embodiments, the Fc regions of the heterodimeric molecule additionally can contain one or more other Fc mutation, such as any described above. In some embodiments, the heterodimer molecule contains an Fc region with a mutation that reduces effector function.

In some embodiments, an Fc variant containing CH3 protuberance (knob) or cavity (hole) modifications can be joined to a stacked immunomodulatory polypeptide anywhere, but typically via its N- or C-terminus, to the N- or C-terminus of a first and/or second stacked immunomodulatory polypeptide, such as to form a fusion polypeptide. The linkage can be direct or indirect via a linker. Typically, a knob and hole molecule is generated by co-expression of a first stacked immunomodulatory polypeptide linked to an Fc variant containing CH3 protuberance modification(s) with a second stacked immunomodulatory polypeptide linked to an Fc variant containing CH3 cavity modification(s).

Also provided are nucleic acid molecules encoding the variant ICOSL-Fc fusion protein. In some embodiments, for production of an Fc fusion protein, a nucleic acid molecule encoding a variant ICOSL-Fc fusion protein is inserted into an appropriate expression vector. The resulting variant ICOSL-Fc fusion protein can be expressed in host cells transformed with the expression where assembly between Fc domains occurs by interchain disulfide bonds formed between the Fc moieties to yield dimeric, such as divalent, variant ICOSL-Fc fusion proteins.

The resulting Fc fusion proteins can be easily purified by affinity chromatography over Protein A or Protein G columns. For the generation of heterodimers, additional steps for purification can be necessary. For example, where two nucleic acids encoding different variant ICOSL polypeptides are transformed into cells, the formation of heterodimers must be biochemically achieved since variant ICOSL molecules carrying the Fc-domain will be expressed as disulfide-linked homodimers as well. Thus, homodimers can be reduced under conditions that favor the disruption of interchain disulfides, but do no effect intra-chain disulfides. In some cases, different variant-ICOSL Fc monomers are mixed in equimolar amounts and oxidized to form a mixture of homo- and heterodimers. The components of this mixture are separated by chromatographic techniques. Alternatively, the formation of this type of heterodimer can be biased by genetically engineering and expressing Fc fusion molecules that contain a variant-ICOSL polypeptide using knob-into-hole methods described below.

B. Conjugates and Fusions of Variant Polypeptides and Immunomodulatory Proteins

In some embodiments, the variant polypeptides provided herein, which are immunomodulatory proteins comprising variants of an Ig domain of the IgSF family (vIgD), can be conjugated with, such as fused directly or indirectly, to, a moiety, such as an effector moiety, such as another protein, directly or indirectly, to form a conjugate ("IgSF conjugate"). In some embodiments, a variant ICOSL immunomodulatory protein is provided as a conjugate in which is contained a vIgD of ICOSL linked, directly or indirectly, to a targeting agent or moiety, e.g. to an antibody or other binding molecules that specifically binds to a ligand, e.g. an antigen, for example, for targeting or localizing the vIgD to a specific environment or cell, such as when administered to a subject. In some embodiments, the targeting agent, e.g. antibody or other binding molecule, binds to a tumor antigen, thereby localizing the variant ICOSL containing the vIgD to the tumor microenvironment, for example, to modulate activity of tumor infiltrating lymphocytes (TILs) specific to the tumor microenvironment. In some embodiments, the attachment can be covalent or non-covalent, e.g., via a biotin-streptavidin non-covalent interaction. In some embodiments, the conjugate is a fusion protein of a variant ICOSL polypeptide linked, directly or via a linker, to another protein or polypeptide moiety.

In some embodiments the fusion protein is an ICOSL-Fc variant fusion, in which any two or more of the foregoing variant polypeptides can be attached to an Fc.

In some embodiments, the IgSF conjugate, such as fusion protein, comprises the ECD of a wildtype (full length or truncated) or a variant ICOSL polypeptide. In some embodiments, the IgSF conjugate, such as fusion protein, comprises an IgV domain or an IgC (e.g., IgC2) domain or domains, or a specific binding fragment of the IgV domain or a specific binding fragment of the IgC (e.g., IgC2) domain or domains. In some embodiments, the IgSF conjugate, such as fusion protein, comprises an IgV domain of ICOSL as set forth in SEQ ID NOs: 196 or 545.

In some embodiments, the moiety can be a targeting moiety, a small molecule drug (non-polypeptide drug of less than 500 daltons molar mass), a toxin, a cytostatic agent, a cytotoxic agent, an immunosuppressive agent, a radioactive agent suitable for diagnostic purposes, a radioactive metal ion for therapeutic purposes, a prodrug-activating enzyme, an agent that increases biological half-life, or a diagnostic or detectable agent.

In some embodiments the effector moiety is a therapeutic agent, such as a cancer therapeutic agent, which is either cytotoxic, cytostatic or otherwise provides some therapeutic benefit. In some embodiments, the effector moiety is a targeting moiety or agent, such as an agent that targets a cell surface antigen, e.g., an antigen on the surface of a tumor cell. In some embodiments, the effector moiety is a label, which can generate a detectable signal, either directly or indirectly. In some embodiments, the effector moiety is a toxin. In some embodiments, the effector moiety is a protein, peptide, nucleic acid, small molecule or nanoparticle.

In some embodiments, 1, 2, 3, 4, 5 or more effector moieties, which can be the same or different, are conjugated, linked or fused to the variant polypeptide or protein to form an IgSF conjugate. In some embodiments, such effector moieties can be attached to the variant polypeptide or immunomodulatory protein using various molecular biological or chemical conjugation and linkage methods known in the art and described below. In some embodiments, linkers such as peptide linkers, cleavable linkers, non-cleavable linkers or linkers that aid in the conjugation reaction, can be used to link or conjugate the effector moieties to the variant polypeptide or immunomodulatory protein.

In some embodiments, the IgSF conjugate comprises the following components: (protein or polypeptide), (L) q and (effector moiety) m, wherein the protein or polypeptide is any of the described variant polypeptides or immunomodulatory proteins capable of binding one or more cognate counter structure ligands as described; L is a linker for linking the protein or polypeptide to the moiety; m is at least 1; q is 0 or more; and the resulting IgSF conjugate binds to the one or more counter structure ligands. In particular embodiments, m is 1 to 4 and q is 0 to 8. In some embodiments, the linker is a peptide. In some embodiments, the effector moiety is a protein or polypeptide.

In some embodiments, there is provided an IgSF conjugate comprising a variant polypeptide or immunomodulatory protein provided herein conjugated with a targeting agent that binds to a cell surface molecule, for example, for targeted delivery of the variant polypeptide or immunomodulatory protein to a specific cell. In some embodiments, the targeting agent is a molecule(s) that has the ability to localize and bind to a molecule present on a normal cell/tissue and/or tumor cell/tumor in a subject. In other words, IgSF conjugates comprising a targeting agent can bind to a ligand (directly or indirectly), which is present on a cell, such as a tumor cell. The targeting agents of the invention contemplated for use include antibodies, polypeptides, peptides, aptamers, other ligands, or any combination thereof, that can bind a component of a target cell or molecule.

In some embodiments, the targeting agent binds a tumor cell(s) or can bind in the vicinity of a tumor cell(s) (e.g., tumor vasculature or tumor microenvironment) following administration to the subject. The targeting agent may bind to a receptor or ligand on the surface of the cancer cell. In another aspect of the invention, a targeting agent is selected which is specific for a noncancerous cells or tissue. For example, a targeting agent can be specific for a molecule present normally on a particular cell or tissue. Furthermore, in some embodiments, the same molecule can be present on normal and cancer cells. Various cellular components and molecules are known. For example, if a targeting agent is specific for EGFR, the resulting IgSF conjugate can target cancer cells expressing EGFR as well as normal skin epidermal cells expressing EGFR. Therefore, in some embodiments, an IgSF conjugate of the invention can operate by two separate mechanisms (targeting cancer and non-cancer cells).

In various aspects of the invention disclosed herein an IgSF conjugate of the invention comprises a targeting agent which can bind/target a cellular component, such as a tumor antigen, a bacterial antigen, a viral antigen, a mycoplasm antigen, a fungal antigen, a prion antigen, an antigen from a parasite. In some aspects, a cellular component, antigen or molecule can each be used to mean, a desired target for a targeting agent. For example, in various embodiments, a targeting agent is specific for or binds to a component, which includes but is not limited to, epidermal growth factor receptor (EGFR, ErbB-1, HER1), ErbB-2 (HER2/neu), ErbB-3/HER3, ErbB-4/HER4, EGFR ligand family; insulin-like growth factor receptor (IGFR) family, IGF-binding proteins (IGFBPs), IGFR ligand family; platelet derived growth factor receptor (PDGFR) family, PDGFR ligand family; fibroblast growth factor receptor (FGFR) family, FGFR ligand family, vascular endothelial growth factor receptor (VEGFR) family, VEGF family; HGF receptor family; TRK receptor family; ephrin (EPH) receptor family; AXL receptor family; leukocyte tyrosine kinase (LTK) receptor family; TIE receptor family, angiopoietin 1,2; receptor tyrosine kinase-like orphan receptor (ROR) receptor family, e.g. ROR1; CD171 (L1CAM); B7-H6 (NCR3LG1); PD-L1, tumor glycosylation antigen, e.g. sTn or Tn, such as sTn Ag of MUC1; LHR (LHCGR); phosphatidylserine, discoidin domain receptor (DDR) family; RET receptor family; KLG receptor family; RYK receptor family; MuSK receptor family; Transforming growth factor-α (TGF-α) receptors, TGF-β; Cytokine receptors, Class I (hematopoietin family) and Class II (interferon/IL-10 family) receptors, tumor necrosis factor (TNF) receptor superfamily (TNFRSF), death receptor family; cancer-testis (CT) antigens, lineage-specific antigens, differentiation antigens, alpha-actinin-4, ARTCl, breakpoint cluster region-Abelson (Bcr-abl) fusion products, B-RAF, caspase-5 (CASP-5), caspase-8 (CASP-8), β-catenin (CTNNB1), cell division cycle 27 (CDC27), cyclin-dependent kinase 4 (CDK4), CDKN2A, COA-I, dek-can fusion protein, EFTUD-2, Elongation factor 2 (ELF2), Ets variant gene 6/acute myeloid leukemia 1 gene ETS (ETC6-AML1) fusion protein, fibronectin (FN), e.g. the extradomain A (EDA) of fibronectin, GPNMB, low density lipid receptor/GDP-L fucose: β-D-galactose 2-α-L-fucosyltransferase (LDLR/FUT) fusion protein, HLA-A2. arginine to isoleucine exchange at residue 170 of the α-helix of the α2-domain in the HLA-A2gene (HLA-A*201-R170I), HLA-A1 1, heat shock protein 70-2 mutated (HSP70-2M), K1AA0205, MART2, melanoma ubiquitous mutated 1, 2, 3 (MUM-I, 2, 3), prostatic acid phosphatase (PAP), neo-PAP, Myosin class I, NFYC, OGT, OS-9, pml-RARα fusion protein, PRDX5, PTPRK, K-ras (KRAS2), N-ras (NRAS), HRAS, RBAF600, SIRT2, SNRPD1, SYT-SSX1 or -SSX2 fusion protein, Tri-osephosphate Isomerase, BAGE, BAGK-1, BAGE-2,3,4,5, GAGE-1,2,3,4,5,6,7,8, GnT-V (aberrant N-acetyl glu-cosaminyl transferase V, MGAT5), HERV-K-MEL, KK-LC, KM-HN-I, LAGE, LAGE-I, CTL-recognized antigen on melanoma (CAMEL), MAGE-A1 (MAGE-I), MAGE-A2, MAGE-A3, MAGE-A4, MAGE-A5, MAGE-A6, MAGE-A8, MAGE-A9, MAGE-A10, MAGE-AI1, MAGE-A12, MAGE-3, MAGE-B1, MAGE-B2, MAGE-B5, MAGE-B6, MAGE-C1, MAGE-C2, mucin 1 (MUC1), MART-1/ Melan-A (MLANA), gp100, gp100/Pmell7 (SILV), tyrosi-nase (TYR), TRP-I, HAGE, NA-88, NY-ESO-I, NY-ESO-I/LAGE-2, SAGE, Spl7, SSX-1,2,3,4, TRP2-INT2, carcino-embryonic antigen (CEA), Kallikrein 4, mammaglobin-A, OA1, prostate specific antigen (PSA), TRP-1/gp75, TRP-2, adipophilin, interferon inducible protein absent in melanoma 2 (AIM-2), BING-4, CPSF, cyclin D1, epithelial cell adhe-sion molecule (Ep-CAM), EphA3, fibroblast growth fac-tor-5 (FGF-5), glycoprotein 250 (gp250), EGFR (ERBB1), HER-2/neu (ERBB2), interleukin 13 receptor α2 chain (IL13Rα2), IL-6 receptor, intestinal carboxyl esterase (ICE), alpha-feto protein (AFP), M-CSF, mdm-2, MUC1, p53 (TP53), PBF, PRAME, PSMA, RAGE-I, RNF43, RU2AS, SOX1O, STEAP1, survivin (BIRC5), human telomerase reverse transcriptase (hTERT), telomerase, Wilms' tumor gene (WTI), SYCP1, BRDT, SPANX, XAGE, ADAM2, PAGE-5, LIP1, CTAGE-I, CSAGE, MMA1, CAGE, BORIS, HOM-TES-85, AF15q14, HCA661, LDHC, MORC, SGY-I, SPO1 1, TPX1, NY-SAR-35, FTHL17, NXF2, TDRD1, TEX15, FATE, TPTE, immunoglobulin idiotypes, Bence-Jones protein, estrogen receptors (ER), androgen receptors (AR), CD40, CD30, CD20, CD19, CD33, cancer antigen 72-4 (CA 72-4), cancer antigen 15-3 (CA 15-3), cancer antigen 27-29 (CA 27-29), cancer antigen 125 (CA 125), cancer antigen 19-9 (CA 19-9), β-human chorionic gonadotropin, β-2 microglobulin, squamous cell carcinoma antigen, neuron-specific enolase, heat shock pro-tein gp96, GM2, sargramostim, CTLA-4, 707 alanine pro-line (707-AP), adenocarcinoma antigen recognized by T cells 4 (ART-4), carcinoembryogenic antigen peptide-1 (CAP-I), calcium-activated chloride channel-2 (CLCA2), cyclophilin B (Cyp-B), human signet ring tumor-2 (HST-2), Human papilloma virus (HPV) proteins (HPV-E6, HPV-E7, major or minor capsid antigens, others), Epstein-Barr virus (EBV) proteins (EBV latent membrane proteins-LMP1, LMP2; others), Hepatitis B or C virus proteins, and HIV proteins.

In some embodiments, a targeting agent is specific for or binds to a component, which includes, but is not limited to, HER1/EGFR, HER2/ERBB2, CD20, CD25 (IL-2Rα recep-tor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Cap-rin-1, mesothelin, PDGF receptor (PDGFR; such as PDGF-R α), PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), VEGFR2, VEGF-A, integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, metalloproteinases, Ephrin receptor, Ephrin ligands, HGF receptor, CXCR4, CXCR4, Bombesin receptor, SK-1anti-gen, Bcr-abl, RET, MET, TRKB, TIE2, ALK, ROS, EML4-ALK, ROS1, BRAFV600E, SRC, c-KIT, mTOR, TSC1, TSC2, BTK, KIT, BRCA, CDK 4/6, JAK1, JAK2, BRAF, FLT-3, MEK1, MEK2, SMO or B7-H6 (NCR3LG1).

In some embodiments, an IgSF conjugate, through its targeting agent, will bind a cellular component of a tumor cell, tumor vasculature or tumor microenvironment, thereby promoting killing of targeted cells via modulation of the immune response, (e.g., by activation of co-stimulatory molecules or inhibition of negative regulatory molecules of immune cell activation), inhibition of survival signals (e.g., growth factor or cytokine or hormone receptor antagonists), activation of death signals, and/or immune-mediated cyto-toxicity, such as through antibody dependent cellular cyto-toxicity. Such IgSF conjugates can function through several mechanisms to prevent, reduce or eliminate tumor cells, such as to facilitate delivery of conjugated effector moieties to the tumor target, such as through receptor-mediated endocytosis of the IgSF conjugate; or such conjugates can recruit, bind, and/or activate immune cells (e.g. NK cells, monocytes/macrophages, dendritic cells, T cells, B cells). Moreover, in some instances one or more of the foregoing pathways may operate upon administration of one or more IgSF conjugates of the invention.

In some embodiments, an IgSF conjugate, through its targeting agent, will be localized to, such as bind to, a cellular component of a tumor cell, tumor vasculature or tumor microenvironment, thereby modulating cells of the immune response in the vicinity of the tumor. In some embodiments, the targeting agent facilitates delivery of the conjugated IgSF (e.g. vIgD) to the tumor target, such as to interact with its cognate binding partner to alter signaling of immune cells (e.g. NK cells, monocytes/macrophages, den-dritic cells, T cells, B cells) bearing the cognate binding partner. In some embodiments, localized delivery agonizes or stimulates the costimulatory receptor.

In some embodiments, the targeting agent is an immuno-globulin. As used herein, the term "immunoglobulin" includes natural or artificial mono- or polyvalent antibodies including, but not limited to, polyclonal, monoclonal, mul-tispecific, human, humanized or chimeric antibodies, single chain antibodies, Fab fragments, F(ab') fragments, frag-ments produced by a Fab expression library, single chain Fv (scFv); anti-idiotypic (anti-Id) antibodies (including, e.g., anti-Id antibodies to antibodies of the invention), and epitope-binding fragments of any of the above. The term "antibody," as used herein, refers to immunoglobulin mol-ecules and immunologically active portions of immuno-globulin molecules, e.g., molecules that contain an antigen binding site that immunospecifically binds an antigen. The immunoglobulin molecules of the invention can be of any type (e.g., IgG, IgE, IgM, IgD, IgA, and IgY), class (e.g., IgG1, IgG2, IgG3, IgG4, IgA1, and IgA2) or subclass of immunoglobulin molecule.

In some embodiments, an IgSF conjugate, through its antibody targeting moiety, will bind a cellular component of a tumor cell, tumor vasculature or tumor microenvironment, thereby promoting apoptosis of targeted cells via modulation of the immune response, (e.g., by activation of co-stimula-tory molecules or inhibition of negative regulatory mol-ecules of immune cell activation), inhibition of survival signals (e.g., growth factor or cytokine or hormone receptor antagonists), activation of death signals, and/or immune-mediated cytotoxicity, such as through antibody dependent cellular cytotoxicity. Such IgSF conjugates can function through several mechanisms to prevent, reduce or eliminate tumor cells, such as to facilitate delivery of conjugated effector moieties to the tumor target, such as through recep-tor-mediated endocytosis of the IgSF conjugate; or such conjugates can recruit, bind, and/or activate immune cells (e.g. NK cells, monocytes/macrophages, dendritic cells, T cells, B cells).

In some embodiments, an IgSF conjugate, through its antibody targeting moiety, will bind a cellular component of a tumor cell, tumor vasculature or tumor microenvironment, thereby modulating the immune response (e.g., by activation of co-stimulatory molecules or inhibition of negative regulatory molecules of immune cell activation). In some embodiments, such conjugates can recognize, bind, and/or modulate (e.g. inhibit or activate) immune cells (e.g. NK cells, monocytes/macrophages, dendritic cells, T cells, B cells).

Antibody targeting moieties of the invention include antibody fragments that include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. Also included in the invention are Fc fragments, antigen-Fc fusion proteins, and Fc-targeting moiety conjugates or fusion products (Fc-peptide, Fc-aptamer). The antibody targeting moieties of the invention may be from any animal origin including birds and mammals. In one aspect, the antibody targeting moieties are human, murine (e.g., mouse and rat), donkey, sheep, rabbit, goat, guinea pig, camel, horse, or chicken. Further, such antibodies may be humanized versions of animal antibodies. The antibody targeting moieties of the invention may be monospecific, bispecific, trispecific, or of greater multispecificity.

In various embodiments, an antibody/targeting moiety recruits, binds, and/or activates immune cells (e.g. NK cells, monocytes/macrophages, dendritic cells) via interactions between Fc (in antibodies) and Fc receptors (on immune cells) and via the conjugated variant polypeptides or immunomodulatory proteins provided herein. In some embodiments, an antibody/targeting moiety recognizes or binds a tumor agent via and localizes to the tumor cell the conjugated variant polypeptides or immunomodulatory proteins provided herein to facilitate modulation of immune cells in the vicinity of the tumor.

Examples of antibodies which can be incorporated into IgSF conjugates include but are not limited to antibodies such as Cetuximab (IMC-C225; Erbitux®), Trastuzumab (Herceptin®), Rituximab (Rituxan®; MabThera®), Bevacizumab (Avastin®), Alemtuzumab (Campath®; Campath-1H®; Mabcampath®), Pertuzumab (Perjeta®), Panitumumab (ABX-EGF; Vectibix®), Ranibizumab (Lucentis®), Ibritumomab, Ibritumomab tiuxetan, (Zevalin®), Tositumomab, Iodine I 131 Tositumomab (BEXXAR®), Catumaxomab (Removab®), Dinutuximab (Unituxin™), Gemtuzumab, Gemtuzumab ozogamicine (Mylotarg®), Abatacept (CTLA4-Ig; Orencia®), Belatacept (L104EA29YIg; LEA29Y; LEA), Ipilimumab (MDX-010; MDX-101), Tremelimumab (ticilimumab; CP-675,206), PRS-010, PRS-050, Aflibercept (VEGF Trap, AVE005), Volociximab (M200), F200, MORAb-009, SS1P (CAT-5001), Cixutumumab (IMC-A12), Matuzumab (EMD72000), Nimotuzumab (h-R3), Zalutumumab (HuMax-EGFR), Necitumumab IMC-11F8, mAb806/ch806, Sym004, mAb-425, Panorex @ (17-1A) (murine monoclonal antibody); Panorex @ (17-1A) (chimeric murine monoclonal antibody); IDEC-Y2B8 (murine, anti-CD20 MAb); BEC2 (anti-idiotypic MAb, mimics the GD epitope) (with BCG); Olaratumab (Lartruvo™); Oncolym (Lym-1 monoclonal antibody); SMART MI95 Ab, humanized 13' ILYM-I (Oncolym), Ovarex (B43.13, anti-idiotypic mouse MAb); Ramucirumab (Cyramza®); MDX-210 (humanized anti-HER-2 bispecific antibody); 3622W94 MAb that binds to EGP40 (17-1A) pancarcinoma antigen on adenocarcinomas; Anti-VEGF, Zenapax (SMART Anti-Tac (IL-2 receptor); SMART MI95 Ab, humanized Ab, humanized); MDX-210 (humanized anti-HER-2 bispecific antibody); MDX-447 (humanized anti-EGF receptor bispecific antibody); NovoMAb-G2 (pancarcinoma specific Ab); TNT (chimeric MAb to histone antigens); TNT (chimeric MAb to histone antigens); Gliomab-H (Monoclon s-Humanized Abs); GNI-250 Mab; EMD-72000 (chimeric-EGF antagonist); LymphoCide (humanized LL2 antibody); and MDX-260 bispecific, targets GD-2, ANA Ab, SMART ID1O Ab, SMART ABL 364 Ab or ImmuRAIT-CEA. As illustrated by the forgoing list, it is conventional to make antibodies to a particular target epitope.

In some embodiments, the antibody or antigen-binding fragment of the provided conjugates, including fusion molecules, is cetuximab, panitumumab, zalutumumab, nimotuzumab, trastuzumab, Ado-trastuzumab emtansine, Tositumomab (Bexxar®), Rituximab (Rituxan, Mabthera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Afatinib, Axitinib, Bosutinib, Cabozantinib, Ceritinib, Crizotinib, Dabrafenib, Dasatinib, Dinutuximab (Unituxin™), Erlotinib, Everolimus, Ibrutinib, Imatinib, Lapatinib, Lenvatinib, Nilotinib, Olaparib, Olaratumab (Lartruvo™), Palbociclib, Pazopanib, Pertuzumab (Perjeta®), Ramucirumab (Cyramza®), Regorafenib, Ruxolitinib, Sorafenib, Sunitinib, Temsirolimus, Trametinib, Vandetanib, Vemurafenib, Vismodegib, Basiliximab, Ipilimumab, Nivolumab, pembrolizumab, MPDL3280A, Pidilizumab (CT-011), AMP-224, MSB001078C, or MEDI4736, BMS-935559, LY3300054, atezolizumab, avelumab or durvalumab or is an antigen-binding fragment thereof.

In some embodiments, PD-L1 antibodies or antigen binding fragments thereof can be incorporated into the IgSF conjugates. Examples of PD-L1 antibodies which can be incorporated. into IgSF conjugates include but are not limited to antibodies such as BMS-936559, 12A4, LY3300054, Atezolizumab (Tecentriq®), Avelumab (Bavencio®), Durvalumab (Imfinzi®). See, e.g., WO2007/005874, WO2017/034916, WO2010/077634, WO2013/079174, WO2011/066389, these references are incorporated by reference in their entirety. In some embodiments, the vIgD is linked, directly or indirectly, to the N- or C-terminus of the light and/or heavy chain of an anti-PD-L1 antibody. In some embodiments, the anti-PD-L1 antibody is BMS-936559, LY3300054, atezolizumab, avelumab or durvalumab. Exemplary light chain and heavy chain of an anti-PD-L1 antibody atezolizumab are set forth in SEQ ID NO: 866 and 867, respectively. Exemplary IgSF conjugates that include the anti-PD-L1 antibody Atezolizumab is set forth in SEQ ID NOs: 868-895.

In some embodiments, the antibody targeting moiety is a full length antibody, or antigen-binding fragment thereof, containing an Fc domain. In some embodiments, the variant polypeptide or immunomodulatory protein is conjugated to the Fc portion of the antibody targeting moiety, such as by conjugation to the N-terminus of the Fc portion of the antibody.

In some embodiments, the vIgD is linked, directly or indirectly, to the N- or C-terminus of the light and/or heavy chain of the antibody. In some embodiments, linkage can be via a peptide linker, such as any described above. In some embodiments, the linker can further include amino acids introduced by cloning and/or from a restriction site. In some embodiments, the linker may include additional amino acids on either end introduced by a restriction site. For example, the linker can include additional amino acids such as SA (in one-letter amino acid code) as introduced by use of the restriction site AFEI. Various configurations can be constructed. FIG. 10A-10C depict exemplary configurations. In some embodiments, the antibody conjugate can be produced by co-expression of the heavy and light chain of the antibody in a cell.

In one aspect of the invention, the targeting agent is an aptamer molecule. For example, in some embodiments, the aptamer is comprised of nucleic acids that function as a targeting agent. In various embodiments, an IgSF conjugate of the invention comprises an aptamer that is specific for a molecule on a tumor cell, tumor vasculature, and/or a tumor microenvironment. In some embodiments, the aptamer itself can comprise a biologically active sequence, in addition to the targeting module (sequence), wherein the biologically active sequence can induce an immune response to the target cell. In other words, such an aptamer molecule is a dual use agent. In some embodiments, an IgSF conjugate of the invention comprises conjugation of an aptamer to an antibody, wherein the aptamer and the antibody are specific for binding to separate molecules on a tumor cell, tumor vasculature, tumor microenvironment, and/or immune cells.

The term "aptamer" includes DNA, RNA or peptides that are selected based on specific binding properties to a particular molecule. For example, an aptamer(s) can be selected for binding a particular gene or gene product in a tumor cell, tumor vasculature, tumor microenvironment, and/or an immune cell, as disclosed herein, where selection is made by methods known in the art and familiar to one of skill in the art.

In some aspects of the invention the targeting agent is a peptide. For example, the variant polypeptides or immunomodulatory proteins provided herein can be conjugated to a peptide which can bind with a component of a cancer or tumor cells. Therefore, such IgSF conjugates of the invention comprise peptide targeting agents which binds to a cellular component of a tumor cell, tumor vasculature, and/or a component of a tumor microenvironment. In some embodiments, targeting agent peptides can be an antagonist or agonist of an integrin. Integrins, which comprise an alpha and a beta subunit, include numerous types well known to a skilled artisan.

In one embodiment, the targeting agent is Vvβ3. Integrin Vvβ3 is expressed on a variety of cells and has been shown to mediate several biologically relevant processes, including adhesion of osteoclasts to bone matrix, migration of vascular smooth muscle cells, and angiogenesis. Suitable targeting molecules for integrins include RGD peptides or peptidomimetics as well as non-RGD peptides or peptidomimetics (see, e.g., U.S. Pat. Nos. 5,767,071 and 5,780,426) for other integrins such as V4.βi (VLA-4), V4-P7 (see, e.g., U.S. Pat. No. 6,365,619; Chang et al, Bioorganic & Medicinal Chem Lett, 12:159-163 (2002); Lin et al., Bioorganic & Medicinal Chem Lett, 12:133-136 (2002)), and the like.

In some embodiments, there is provided an IgSF conjugate comprising a variant polypeptide or immunomodulatory protein provided herein conjugated with a therapeutic agent. In some embodiments, the therapeutic agent includes, for example, daunomycin, doxorubicin, methotrexate, and vindesine (Rowland et al., Cancer Immunol. Immunother. 21:183-187, 1986). In some embodiments, the therapeutic agent has an intracellular activity. In some embodiments, the IgSF conjugate is internalized and the therapeutic agent is a cytotoxin that blocks the protein synthesis of the cell, therein leading to cell death. In some embodiments, the therapeutic agent is a cytotoxin comprising a polypeptide having ribosome-inactivating activity including, for example, gelonin, bouganin, saporin, ricin, ricin A chain, bryodin, diphtheria toxin, restrictocin, Pseudomonas exotoxin A and variants thereof. In some embodiments, where the therapeutic agent is a cytotoxin comprising a polypeptide having a ribosome-inactivating activity, the IgSF conjugate must be internalized upon binding to the target cell in order for the protein to be cytotoxic to the cells.

In some embodiments, there is provided an IgSF conjugate comprising a variant polypeptide or immunomodulatory protein provided herein conjugated with a toxin. In some embodiments, the toxin includes, for example, bacterial toxins such as diphtheria toxin, plant toxins such as ricin, small molecule toxins such as geldanamycin (Mandler et al., J. Nat. Cancer Inst. 92(19):1573-1581 (2000); Mandler et al., Bioorganic & Med. Chem. Letters 10:1025-1028 (2000); Mandler et al., Bioconjugate Chem. 13:786-791 (2002)), maytansinoids (EP 1391213; Liu et al., Proc. Natl. Acad. Sci. USA 93:8618-8623 (1996)), and calicheamicin (Lode et al., Cancer Res. 58:2928 (1998); Hinman et al., Cancer Res. 53:3336-3342 (1993)). The toxins may exert their cytotoxic and cytostatic effects by mechanisms including tubulin binding, DNA binding, or topoisomerase inhibition.

In some embodiments, there is provided an IgSF conjugate comprising a variant polypeptide or immunomodulatory protein provided herein conjugated with a label, which can generate a detectable signal, indirectly or directly. These IgSF conjugates can be used for research or diagnostic applications, such as for the in vivo detection of cancer. The label is preferably capable of producing, either directly or indirectly, a detectable signal. For example, the label may be radio-opaque or a radioisotope, such as 3H, 14C, 32P, 35S, 1231, 1251, 1311; a fluorescent (fluorophore) or chemiluminescent (chromophore) compound, such as fluorescein isothiocyanate, rhodamine or luciferin; an enzyme, such as alkaline phosphatase,β-galactosidase or horseradish peroxidase; an imaging agent; or a metal ion. In some embodiments, the label is a radioactive atom for scintigraphic studies, for example 99Tc or 1231, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983). In some embodiments, the IgSF conjugate is detectable indirectly. For example, a secondary antibody that is specific for the IgSF conjugate and contains a detectable label can be used to detect the IgSF conjugate.

The IgSF conjugates may be prepared using any methods known in the art. See, e.g., WO 2009/067800, WO 2011/133886, and U.S. Patent Application Publication No. 2014322129, incorporated by reference herein in their entirety.

The variant polypeptides or immunomodulatory proteins of an IgSF conjugate may be "attached to" the effector moiety by any means by which the variant polypeptides or immunomodulatory proteins can be associated with, or linked to, the effector moiety. For example, the variant polypeptides or immunomodulatory proteins of an IgSF conjugate may be attached to the effector moiety by chemical or recombinant means. Chemical means for preparing fusions or conjugates are known in the art and can be used to prepare the IgSF conjugate. The method used to conjugate the variant polypeptides or immunomodulatory proteins and effector moiety must be capable of joining the variant polypeptides or immunomodulatory proteins with the effector moiety without interfering with the ability of the variant polypeptides or immunomodulatory proteins to bind to their one or more counter structure ligands.

The variant polypeptides or immunomodulatory proteins of an IgSF conjugate may be linked indirectly to the effector moiety. For example, the variant polypeptides or immunomodulatory proteins of an IgSF conjugate may be directly linked to a liposome containing the effector moiety of one of several types. The effector moiety(s) and/or the variant polypeptides or immunomodulatory proteins may also be bound to a solid surface.

In some embodiments, the variant polypeptides or immunomodulatory proteins of an IgSF conjugate and the effector moiety are both proteins and can be conjugated using techniques well known in the art. There are several hundred crosslinkers available that can conjugate two proteins. (See for example "Chemistry of Protein Conjugation and Cross-linking," 1991, Shans Wong, CRC Press, Ann Arbor). The crosslinker is generally chosen based on the reactive functional groups available or inserted on the variant polypeptides or immunomodulatory proteins and/or effector moiety. In addition, if there are no reactive groups, a photoactivatible crosslinker can be used. In certain instances, it may be desirable to include a spacer between the variant polypeptides or immunomodulatory proteins and the effector moiety. Crosslinking agents known to the art include the homobifunctional agents: glutaraldehyde, dimethyladipimidate and Bis(diazobenzidine) and the heterobifunctional agents: m Maleimidobenzoyl-N-Hydroxysuccinimide and Sulfo-m Malcimidobenzoyl-N-Hydroxysuccinimide.

In some embodiments, the variant polypeptides or immunomodulatory proteins of an IgSF conjugate may be engineered with specific residues for chemical attachment of the effector moiety. Specific residues used for chemical attachment of molecule known to the art include lysine and cysteine. The crosslinker is chosen based on the reactive functional groups inserted on the variant polypeptides or immunomodulatory proteins, and available on the effector moiety.

An IgSF conjugate may also be prepared using recombinant DNA techniques. In such a case a DNA sequence encoding the variant polypeptides or immunomodulatory proteins is fused to a DNA sequence encoding the effector moiety, resulting in a chimeric DNA molecule. The chimeric DNA sequence is transfected into a host cell that expresses the fusion protein. The fusion protein can be recovered from the cell culture and purified using techniques known in the art.

Examples of attaching an effector moiety, which is a label, to the variant polypeptides or immunomodulatory proteins include the methods described in Hunter, et al., Nature 144:945 (1962); David, et al., Biochemistry 13:1014 (1974); Pain, et al., J. Immunol. Meth. 40:219 (1981); Nygren, J. Histochem. and Cytochem. 30:407 (1982); Wensel and Meares, Radioimmunoimaging and Radioimmunotherapy, Elsevier, N.Y. (1983); and Colcher et al., "Use Of Monoclonal Antibodies as Radiopharmaceuticals For The Localization Of Human Carcinoma Xenografts In Athymic Mice", Meth. Enzymol., 121:802-16 (1986).

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as 99Tc or 123I, 186Re, 188Re and 111 In can be attached via a cysteine residue in the peptide. Yttrium-90 can be attached via a lysine residue. The IODOGEN method (Fraker et al., Biochem. Biophys. Res. Commun. 80:49-57 (1978)) can be used to incorporate iodine-123. "Monoclonal Antibodies in Immunoscintigraphy" (Chatal, CRC Press 1989) describes other methods in detail.

Conjugates of the variant polypeptides or immunomodulatory proteins and a cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-p-isothiocyanatobenzyl-3-methyldiethylenetriaminepentaacetic acid (MX-DTPA) is an exemplary chelating agent for conjugation of radionucleotide to the antibody. See, e.g., WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The IgSF conjugates of the invention expressly contemplate, but are not limited to, drug conjugates prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A). See pages 467-498, 2003-2004 Applications Handbook and Catalog.

C. Transmembrane and Secretable Immunomodulatory Proteins and Engineered Cells

Provided herein are engineered cells which express the immunomodulatory variant ICOSL polypeptides (alternatively, "engineered cells"). In some embodiments, the variant ICOSL polypeptide is expressed on a cell, such as an immune cell (e.g. T cell or antigen presenting cell), in membrane-bound form, thereby providing a transmembrane immunomodulatory protein (hereinafter also called a "TIP"). In some aspects, the variant ICOSL polypeptide is expressed in a cell, such as an immune cell (e.g. T cell or antigen presenting cell), in secretable form to thereby produce a secreted or soluble form of the variant ICOSL polypeptide (hereinafter also called a "SIP"), such as when the cells are administered to a subject. In some aspects, a SIP can antagonize a cognate binding partner in the environment (e.g. tumor microenvironment) in which it is secreted.

1. Transmembrane Immunomodulatory Proteins

In some embodiments, an immunomodulatory polypeptide comprising a variant ICOSL can be a membrane bound protein. As described in more detail below, the immunomodulatory polypeptide can be a transmembrane immuno-modulatory polypeptide comprising a variant ICOSL in which is contained: an ectodomain containing at least one affinity modified IgSF domain (IgV or IgC), a transmembrane domain and, optionally, a cytoplasmic domain. In some embodiments, the transmembrane immunomodulatory protein can be expressed on the surface of an immune cell, such as a mammalian cell, including on the surface of a lymphocyte (e.g. T cell or NK cell) or antigen presenting cell. In some embodiments, the transmembrane immuno-modulatory protein is expressed on the surface of a mammalian T-cell, including such T-cells as: a T helper cell, a cytotoxic T-cell (alternatively, cytotoxic T lymphocyte or CTL), a natural killer T-cell, a regulatory T-cell, a memory T-cell, or a gamma delta T-cell. In some embodiments, the mammalian cell is an antigen presenting cell (APC). Typically, but not exclusively, the ectodomain (alternatively, "extracellular domain") of comprises the one or more amino acid variations (e.g. amino acid substitutions) of the variant ICOSL of the invention. Thus, for example, in some embodiments a transmembrane protein will comprise an ectodomain that comprises one or more amino acid substitutions of a variant ICOSL of the invention.

In some embodiments, the engineered cells express variant ICOSL polypeptides that are transmembrane immuno-modulatory polypeptides (TIPs) that can be a membrane protein such as a transmembrane protein. In typical embodiments, the ectodomain of a membrane protein comprises an extracellular domain or IgSF domain thereof of a variant ICOSL provided herein in which is contained one or more amino acid substitutions in at least one IgSF domain as described. The transmembrane immunomodulatory proteins provided herein further contain a transmembrane domain linked to the ectodomain. In some embodiments, the trans-membrane domain results in an encoded protein for cell surface expression on a cell. In some embodiments, the transmembrane domain is linked directly to the ectodomain. In some embodiments, the transmembrane domain is linked indirectly to the ectodomain via one or more linkers or spacers. In some embodiments, the transmembrane domain contains predominantly hydrophobic amino acid residues, such as leucine and valine.

In some embodiments, a full length transmembrane anchor domain can be used to ensure that the TIPs will be expressed on the surface of the engineered cell, such as engineered T cell. Conveniently, this could be from a particular native protein that is being affinity modified (e.g. ICOSL or other native IgSF protein), and simply fused to the sequence of the first membrane proximal domain in a similar fashion as the native IgSF protein (e.g. ICOSL). In some embodiments, the transmembrane immunomodulatory pro-tein comprises a transmembrane domain of the correspond-ing reference (e.g., unmodified) or wild-type IgSF member, such as a transmembrane domain contained in the sequence of amino acids set forth in SEQ ID NO:5 (Table 2). In some embodiments, the membrane bound form comprises a trans-membrane domain of the corresponding reference (e.g., unmodified) or wild-type polypeptide, such as correspond-ing to residues 257-277 of SEQ ID NO:5.

In some embodiments, the transmembrane domain is a non-native transmembrane domain that is not the transmem-brane domain of native ICOSL. In some embodiments, the transmembrane domain is derived from a transmembrane domain from another non-ICOSL family member polypep-tide that is a membrane-bound or is a transmembrane protein. In some embodiments, a transmembrane anchor domain from another protein on T cells can be used. In some embodiments, the transmembrane domain is derived from CD8. In some embodiments, the transmembrane domain can further contain an extracellular portion of CD8 that serves as a spacer domain. An exemplary CD8 derived transmem-brane domain is set forth in SEQ ID NO: 246 or 483 or a portion thereof containing the CD8 transmembrane domain. In some embodiments, the transmembrane domain is a synthetic transmembrane domain.

In some embodiments, the transmembrane immunomodu-latory protein further contains an endodomain, such as a cytoplasmic signaling domain, linked to the transmembrane domain. In some embodiments, the cytoplasmic signaling domain induces cell signaling. In some embodiments, the endodomain of the transmembrane immunomodulatory pro-tein comprises the cytoplasmic domain of the corresponding reference (e.g., unmodified) or wild-type polypeptide, such as a cytoplasmic domain contained in the sequence of amino acids set forth in SEQ ID NO:5 (see Table 2).

In some embodiments, a provided transmembrane immu-nomodulatory protein that is or comprises a variant ICOSL comprises a sequence of amino acids that exhibits at least 85%, 86%, 87%, 88%, 89%, 90%, 91%, 92%, 93%, 94%, 95%, 96%, 97%, 98% or 99% sequence identity to SEQ ID NO: 257 and contains an ectodomain comprising at least one affinity-modified ICOSL IgSF domain as described and a transmembrane domain. In some embodiments, the trans-membrane immunomodulatory protein contains any one or more amino acid substitutions in an IgSF domain (e.g. IgV domain) as described, including any set forth in Table 1. In some embodiments, the transmembrane immunomodulatory protein can further comprise a cytoplasmic domain as described. In some embodiments, the transmembrane immu-nomodulatory protein can further contain a signal peptide. In some embodiments, the signal peptide is the native signal peptide of wild-type IgSF member, such as contained in the sequence of amino acids set forth in SEQ ID NO: 5 (see e.g. Table 2).

In some embodiments, provided are transmembrane immunomodulatory proteins comprising the amino acid substitutions E16V/N52H/N57Y/Q100R/V110D/H115R/Y152C/K156M/C198R, N52H/N57Y/Q100R, or N52H/N57Y/Q100P. In some embodiments, the provided trans-membrane immunomodulatory protein is or comprises a variant ICOSL comprising the sequence of amino acids set forth in SEQ ID NO: 257, but in which is contained amino substitutions E16V/N52H/N57Y/Q100R/V110D/H115R/Y152C/K156M/C198R, N52H/N57Y/Q100R, or N52H/N57Y/Q100P at corresponding positions in SEQ ID NO:257, or a sequence of amino acids that exhibits at least 85%, 86%, 87%, 88%, 89%, 90%, 91%, 92%, 93%, 94%, 95%, 96%, 97%, 98% or 99% sequence identity to SEQ ID NO: 257 and contains the amino acid substitutions E16V/N52H/N57Y/Q100R/V110D/H115R/Y152C/K156M/C198R, N52H/N57Y/Q100R, or N52H/N57Y/Q100P.

In some embodiments, provided are transmembrane immunomodulatory proteins comprising the sequence of amino acids set forth in SEQ ID NOS: 496 or 497 (each containing the amino acid substitution N52D), SEQ ID NOS: 498 or 499 (each containing the amino acid substitu-tions N52H/N57Y/Q100P), SEQ ID NOS: 500 or 501 (each containing the amino acid substitutions E16V/N52H/N57Y/Q100R/V110D/H115R/Y152C/K156M/C198R) or SEQ ID NOS: 502 or 503 (each containing the amino acid substitu-tions N52H/N57Y/Q100R), or a sequence of amino acids that comprises at least 85%, 86%, 87%, 88%, 89%, 90%, 91%, 92%, 93%, 94%, 95%, 96%, 97%, 98% or 99% sequence identity to any of SEQ ID NOS: 495-503 and that contains the indicated amino acid substitutions. In some embodiments, when expressed in an engineered cell, such transmembrane immunomodulatory proteins are expressed on the surface of the cell.

Also provided is a nucleic acid molecule encoding such transmembrane immunomodulatory proteins. In some embodiments, a nucleic acid molecule encoding a transmembrane immunomodulatory protein comprises a nucleotide sequence that encodes a sequence of amino acids that exhibits at least 85%, 86%, 87%, 88%, 89%, 90%, 91%, 92%, 93%, 94%, 95%, 96%, 97%, 98% or 99% sequence identity to SEQ ID NO: 257 and contains an ectodomain comprising at least one affinity-modified IgSF domain as described, a transmembrane domain and, optionally, a cytoplasmic domain. In some embodiments, the nucleic acid molecule can further comprise a sequence of nucleotides encoding a signal peptide. In some embodiments, the signal peptide is the native signal peptide of the corresponding wild-type IgSF member (see e.g. Table 2).

Exemplary of a transmembrane immunomodulatory protein is a ICOSL TIP comprising i) the sequence of amino acids set forth in SEQ ID NO:383 or ii) a sequence of amino acids that exhibits at least 85%, 86%, 87%, 88%, 89%, 90%, 91%, 92%, 93%, 94%, 95%, 96%, 97%, 98% or 99% sequence identity to SEQ ID NO: 243 and that comprises the affinity-modified domain contained in SEQ ID NO: 243 or the amino acid substitutions therein. Also provided is i) a sequence of nucleotides set forth in SEQ ID NO: 244, ii) a sequence that exhibits at least 85%, 86%, 87%, 88%, 89%, 90%, 91%, 92%, 93%, 94%, 95%, 96%, 97%, 98% or 99% sequence identity to SEQ ID NO: 244 and that encodes a TIP that comprises the affinity-modified domain of SEQ ID NO: 243, or iii) a sequence of i) or ii) having degenerate codons.

In some embodiments, provided are CAR-related transmembrane immunomodulatory proteins in which the endodomain of a transmembrane immunomodulatory protein comprises a cytoplasmic signaling domain that comprises at least one ITAM (immunoreceptor tyrosine-based activation motif)-containing signaling domain. ITAM is a conserved motif found in a number of protein signaling domains involved in signal transduction of immune cells, including in the CD3-zeta chain ("CD3-z") involved in T-cell receptor signal transduction. In some embodiments, the endodomain comprises at CD3-zeta signaling domain. In some embodiments, the CD3-zeta signaling domain comprises the sequence of amino acids set forth in SEQ ID NO: 243 or a sequence of amino acids that exhibits at least 85%, 86%, 87%, 88%, 89%, 90%, 91%, 92%, 93%, 94%, 95%, 96%, 97%, 98% or 99% to SEQ ID NO:247 and retains the activity of T cell signaling. In some embodiments, the endodomain of a CAR-related transmembrane immunomodulatory protein can further comprise a costimulatory signaling domain to further modulate immunomodulatory responses of the T-cell. In some embodiments, the costimulatory signaling domain is CD28, ICOS, 41BB or OX40. In some embodiments, the costimulatory signaling domain is a derived from CD28 or 4-1BB and comprises the sequence of amino acids set forth in any of SEQ ID NOS: 484-487 or a sequence of amino acids that exhibits at least 85%, 86%, 87%, 88%, 89%, 90%, 91%, 92%, 93%, 94%, 95%, 96%, 97%, 98% or 99% to SEQ ID NO: 484-487 and retains the activity of T cell costimulatory signaling. In some embodiments, the provided CAR-related transmembrane immunomodulatory proteins have features of CARs to stimulate T cell signaling upon binding of an affinity modified IgSF domain to a cognate binding partner or counter structure. In some embodiments, upon specific binding by the affinity-modified IgSF domain to its counter structure can lead to changes in the immunological activity of the T-cell activity as reflected by changes in cytotoxicity, proliferation or cytokine production.

In some embodiments, the transmembrane immunomodulatory protein does not contain an endodomain capable of mediating cytoplasmic signaling. In some embodiments, the transmembrane immunomodulatory protein lacks the signal transduction mechanism of the wild-type or unmodified polypeptide and therefore does not itself induce cell signaling. In some embodiments, the transmembrane immunomodulatory protein lacks an intracellular (cytoplasmic) domain or a portion of the intracellular domain of the corresponding reference (e.g., unmodified) or wild-type polypeptide, such as a cytoplasmic signaling domain contained in the sequence of amino acids set forth in SEQ ID NO:5 (see Table 2). In some embodiments, the transmembrane immunomodulatory protein does not contain an ITIM (immunoreceptor tyrosine-based inhibition motif), such as contained in certain inhibitory receptors, including inhibitory receptors of the IgSF family (e.g. PD-1 or TIGIT). Thus, in some embodiments, the transmembrane immunomodulatory protein only contains the ectodomain and the transmembrane domain, such as any as described.

2. Secreted Immunomodulatory Proteins and Engineered Cells

In some embodiments, the ICOSL variant immunomodulatory polypeptide containing any one or more of the amino acid mutations as described herein, is secretable, such as when expressed from a cell. Such a variant ICOSL immunomodulatory protein does not comprise a transmembrane domain. In some embodiments, the variant ICOSL immunomodulatory protein is not conjugated to a half-life extending moiety (such as an Fc domain or a multimerization domain). In some embodiments, the variant ICOSL immunomodulatory protein comprises a signal peptide, e.g. an antibody signal peptide or other efficient signal sequence to get domains outside of cell. When the immunomodulatory protein comprises a signal peptide and is expressed by an engineered cell, the signal peptide causes the immunomodulatory protein to be secreted by the engineered cell. Generally, the signal peptide, or a portion of the signal peptide, is cleaved from the immunomodulatory protein with secretion. The immunomodulatory protein can be encoded by a nucleic acid (which can be part of an expression vector). In some embodiments, the immunomodulatory protein is expressed and secreted by a cell (such as an immune cell, for example a primary immune cell).

Thus, in some embodiments, there are provided variant ICOSL immunomodulatory proteins that further comprise a signal peptide. In some embodiments, provided herein is a nucleic acid molecule encoding the variant ICOSL immunomodulatory protein operably connected to a secretion sequence encoding the signal peptide.

A signal peptide is a sequence on the N-terminus of an immunomodulatory protein that signals secretion of the immunomodulatory protein from a cell. In some embodiments, the signal peptide is about 5 to about 40 amino acids in length (such as about 5 to about 7, about 7 to about 10, about 10 to about 15, about 15 to about 20, about 20 to about 25, or about 25 to about 30, about 30 to about 35, or about 35 to about 40 amino acids in length).

In some embodiments, the signal peptide is a native signal peptide from the corresponding wild-type ICOSL (see Table 6). In some embodiments, the signal peptide is a non-native signal peptide. For example, in some embodiments, the non-native signal peptide is a mutant native signal peptide from the corresponding wild-type ICOSL, and can include one or more (such as 2, 3, 4, 5, 6, 7, 8, 9, or 10 or more) substitutions insertions or deletions. In some embodiments, the non-native signal peptide is a signal peptide or mutant thereof of a family member from the same IgSF family as the wild-type IgSF family member. In some embodiments, the non-native signal peptide is a signal peptide or mutant thereof from an IgSF family member from a different IgSF family than the wild-type IgSF family member. In some embodiments, the signal peptide is a signal peptide or mutant thereof from a non-IgSF protein family, such as a signal peptide from an immunoglobulin (such as IgG heavy chain or IgG-kappa light chain), a cytokine (such as interleukin-2 (IL-2), or CD33), a serum albumin protein (e.g. HSA or albumin), a human azurocidin preprotein signal sequence, a luciferase, a trypsinogen (e.g. chymotrypsinogen or trypsinogen) or other signal peptide able to efficiently secrete a protein from a cell. Exemplary signal peptides include any described in the Table 6.

modulatory protein under the operable control of a signal sequence for secretion. In some embodiments, the encoded immunomodulatory protein is secreted when expressed from a cell. In some embodiments, the immunomodulatory protein encoded by the nucleic acid molecule does not comprise a transmembrane domain. In some embodiments, the immunomodulatory protein encoded by the nucleic acid molecule does not comprise a half-life extending moiety (such as an Fc domain or a multimerization domain). In some embodiments, the immunomodulatory protein encoded by the nucleic acid molecule comprises a signal peptide. In some embodiments, a nucleic acid of the invention further comprises nucleotide sequence that encodes a secretory or signal peptide operably linked to the nucleic acid encoding the immunomodulatory protein, thereby allowing for secretion of the immunomodulatory protein

3. Cells and Engineering Cells

Provided herein are engineered cells expressing any of the provided immunomodulatory polypeptides. In some

TABLE 6

Exemplary Signal Peptides

| SEQ ID NO | Signal Peptide | Peptide Sequence |
|---|---|---|
| SEQ ID NO: 346 | HSA signal peptide | MKWVTFISLLFLFSSAYS |
| SEQ ID NO: 347 | Ig kappa light chain | MDMRAPAGIFGFLLVLFPGYRS |
| SEQ ID NO: 348 | human azurocidin preprotein signal sequence | MTRLTVLALLAGLLASSRA |
| SEQ ID NO: 349 | IgG heavy chain signal peptide | MELGLSWIFLLAILKGVQC |
| SEQ ID NO: 350 | IgG heavy chain signal peptide | MELGLRWVFLVAILEGVQC |
| SEQ ID NO: 351 | IgG heavy chain signal peptide | MKHLWFFLLLVAAPRWVLS |
| SEQ ID NO: 352 | IgG heavy chain signal peptide | MDWTWRILFLVAAATGAHS |
| SEQ ID NO: 353 | IgG heavy chain signal peptide | MDWTWRFLFVVAAATGVQS |
| SEQ ID NO: 354 | IgG heavy chain signal peptide | MEFGLSWLFLVAILKGVQC |
| SEQ ID NO: 355 | IgG heavy chain signal peptide | MEFGLSWVFLVALFRGVQC |
| SEQ ID NO: 356 | IgG heavy chain signal peptide | MDLLHKNMKHLWFFLLLVAAPRWVLS |
| SEQ ID NO: 357 | IgG Kappa light chain signal sequence | MDMRVPAQLLGLLLLWLSGARC |
| SEQ ID NO: 358 | IgG Kappa light chain signal sequence | MKYLLPTAAAGLLLLAAQPAMA |
| SEQ ID NO: 359 | Gaussia luciferase | MGVKVLFALICIAVAEA |
| SEQ ID NO: 360 | Human albumin | MKWVTFISLLFLFSSAYS |
| SEQ ID NO: 361 | Human chymotrypsinogen | MAFLWLLSCWALLGTTFG |
| SEQ ID NO: 362 | Human interleukin-2 | MQLLSCIALILALV |
| SEQ ID NO: 363 | Human trypsinogen-2 | MNLLLILTFVAAAVA |

In some embodiments of a secretable variant ICOSL immunomodulatory protein, the immunomodulatory protein comprises a signal peptide when expressed, and the signal peptide (or a portion thereof) is cleaved from the immunomodulatory protein upon secretion.

In some embodiments, the engineered cells express a variant ICOSL polypeptide that is secreted from the cell. In some embodiments, such a variant ICOSL polypeptide is encoded by a nucleic acid molecule encoding an immunoembodiments, the engineered cells express on their surface any of the provided transmembrane immunomodulatory polypeptides. In some embodiments, the engineered cells express and are capable of or are able to secrete the immunomodulatory protein from the cells under conditions suitable for secretion of the protein. In some embodiments, the immunomodulatory protein is expressed on or in a lymphocyte such as a tumor infiltrating lymphocyte (TIL), T-cell or NK cell, or on a myeloid cell. In some embodiments, the engineered cells are antigen presenting cells (APCs). In some embodiments, the engineered cells are engineered mammalian T-cells or engineered mammalian antigen presenting cells (APCs). In some embodiments, the engineered T-cells or APCs are human or murine cells.

In some embodiments, engineered T-cells include, but are not limited to, T helper cell, cytotoxic T-cell (alternatively, cytotoxic T lymphocyte or CTL), natural killer T-cell, regulatory T-cell, memory T-cell, or gamma delta T-cell. In some embodiments, the engineered T cells are CD4+ or CD8+. In addition to the signal of the MHC, engineered T-cells also require a co-stimulatory signal which in some embodiments is provided by a variant ICOSL transmembrane immunomodulatory polypeptide expressed in membrane bound form as discussed previously.

In some embodiments, the engineered APCs include, for example, MHC II expressing APCs such as macrophages, B cells, and dendritic cells, as well as artificial APCs (aAPCs) including both cellular and acellular (e.g., biodegradable polymeric microparticles) aAPCs. Artificial APCs (aAPCs) are synthetic versions of APCs that can act in a similar manner to APCs in that they present antigens to T-cells as well as activate them. Antigen presentation is performed by the MHC (Class I or Class II). In some embodiments, in engineered APCs such as aAPCs, the antigen that is loaded onto the MHC is, in some embodiments, a tumor specific antigen or a tumor associated antigen. The antigen loaded onto the MHC is recognized by a T-cell receptor (TCR) of a T cell, which, in some cases, can express ICOS, CD28, or other molecule recognized by the variant ICOSL polypeptides provided herein. Materials which can be used to engineer an aAPC include: poly (glycolic acid), poly(lactic-co-glycolic acid), iron-oxide, liposomes, lipid bilayers, sepharose, and polystyrene.

In some embodiments a cellular aAPC can be engineered to contain a TIP and TCR agonist which is used in adoptive cellular therapy. In some embodiments, a cellular aAPC can be engineered to contain a TIP and TCR agonist which is used in ex vivo expansion of human T cells, such as prior to administration, e.g., for reintroduction into the patient. In some aspects, the aAPC may include expression of at least one anti-CD3 antibody clone, e.g. such as, for example, OKT3 and/or UCHT1. In some aspects, the aAPCs may be inactivated (e.g. irradiated). In some embodiment, the TIP can include any variant IgSF domain that exhibits binding affinity for a cognate binding partner on a T cell.

In some embodiments, an immunomodulatory protein provided herein, such as a transmembrane immunomodulatory protein or a secretable immunomodulatory protein, is co-expressed or engineered into a cell that expresses an antigen-binding receptor, such as a recombinant receptor, such as a chimeric antigen receptor (CAR) or T cell receptor (TCR). In some embodiments, the engineered cell, such as an engineered T cell, recognizes a desired antigen associated with cancer, inflammatory and autoimmune disorders, or a viral infection. In specific embodiments, the antigen-binding receptor contains an antigen-binding moiety that specifically binds a tumor specific antigen or a tumor associated antigen. In some embodiments, the engineered T-cell is a CAR (chimeric antigen receptor) T-cell that contains an antigen-binding domain (e.g. scFv) that specifically binds to an antigen, such as a tumor specific antigen or tumor associated antigen. In some embodiments, the antigen-binding domain (e.g. scFv) is specific for a particular antigen, e.g., CD19. Exemplary of a CAR is an anti-CD19 CAR, such as a CAR containing an anti-CD19 scFv set forth in SEQ ID NO:482 or SEQ ID NO:245. In some embodiments, the TIP protein is expressed in an engineered T-cell receptor cell or an engineered chimeric antigen receptor cell. In such embodiments, the engineered cell co-expresses the TIP and the CAR or TCR. In some embodiments, the SIP protein is expressed in an engineered T-cell receptor cell or an engineered chimeric antigen receptor cell. In such embodiments, the engineered cell co-expresses the SIP and the CAR or TCR.

Chimeric antigen receptors (CARs) are recombinant receptors that include an antigen-binding domain (ectodomain), a transmembrane domain and an intracellular signaling region (endodomain) that is capable of inducing or mediating an activation signal to the T cell after the antigen is bound. In some example, CAR-expressing cells are engineered to express an extracellular single chain variable fragment (scFv) with specificity for a particular tumor antigen linked to an intracellular signaling part comprising an activating domain and, in some cases, a costimulatory domain. The costimulatory domain can be derived from, e.g., CD28, OX-40, 4-1BB/CD137 or inducible T cell costimulator (ICOS). The activating domain can be derived from, e.g., CD3, such as CD3 zeta, epsilon, delta, gamma, or the like. In certain embodiments, the CAR is designed to have two, three, four, or more costimulatory domains. The CAR scFv can be designed to target an antigen expressed on a cell associated with a disease or condition, e.g. a tumor antigen, such as, for example, CD19, which is a transmembrane protein expressed by cells in the B cell lineage, including all normal B cells and B cell malignances, including but not limited to NHL, CLL, and non-T cell ALL. Example CAR+ T cell therapies and constructs are described in U.S. Patent Publication Nos. 2013/0287748, 2014/0227237, 2014/0099309, and 2014/0050708, and these references are incorporated by reference in their entirety.

In some aspects, the antigen-binding domain is an antibody or antigen-binding fragment thereof, such as a single chain fragment (scFv). In some embodiments, the antigen is expressed on a tumor or cancer cell. Exemplary of an antigen is CD19. Exemplary of a CAR is an anti-CD19 CAR, such as a CAR containing an anti-CD19 scFv set forth in SEQ ID NO: 245. In some embodiments, the CAR further contains a spacer, a transmembrane domain, and an intracellular signaling domain or region comprising an ITAM signaling domain, such as a CD3zeta signaling domain. In some embodiments, the CAR further includes a costimulatory signaling domain.

In some embodiments, the CAR further contains a spacer or hinge, a transmembrane domain, and an intracellular signaling domain (endodomain) comprising an ITAM signaling domain, such as a CD3zeta signaling domain. In some embodiments, the CAR further includes a costimulatory signaling domain. The costimulatory domain can be derived from, e.g., CD28, OX-40, 4-1BB/CD137 or inducible T cell costimulator (ICOS). In certain embodiments, the CAR is designed to have two, three, four, or more costimulatory domains. The CAR scFv can be designed to target an antigen expressed on a cell associated with a disease or condition, e.g. a tumor antigen, such as, for example, CD19, which is a transmembrane protein expressed by cells in the B cell lineage, including all normal B cells and B cell malignances, including but not limited to NHL, CLL, and non-T cell ALL. Example CAR+ T cell therapies and constructs are described in U.S. Patent Publication Nos. 2013/0287748, 2014/0227237, 2014/0099309, and 2014/0050708, and these references are incorporated by reference in their entirety. In some embodiments, the spacer or hinge is present between the antigen-binding domain and the transmembrane domain, such as is between the antigen-binding domain and plasma membrane when expressed on a cell. In some embodiments, the spacer or hinge is derived from IgG subclass (such as IgG1 and IgG4, IgD or CD8 (see e.g., Qin et al. (2017) J. Hematol. Oncol., 10:68). In some embodiments, the spacer or hinge is derived from IgG1.

In some embodiments, the spacer and transmembrane domain are the hinge and transmembrane domain derived from CD8, such as having an exemplary sequence set forth in SEQ ID NO: 246, 483, or 897 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:246, 483, or 897. In some embodiments, the endodomain comprises at CD3-zeta signaling domain. In some embodiments, the CD3-zeta signaling domain comprises the sequence of amino acids set forth in SEQ ID NO: 243 or a sequence of amino acids that exhibits at least 85%, 86%, 87%, 88%, 89%, 90%, 91%, 92%, 93%, 94%, 95%, 96%, 97%, 98% or 99% or more sequence identity to SEQ ID NO: 247 and retains the activity of T cell signaling. In some embodiments, the endodomain of a CAR can further comprise a costimulatory signaling domain or region to further modulate immunomodulatory responses of the T-cell. In some embodiments, the costimulatory signaling domain is or comprises a costimulatory region, or is derived from a costimulatory region, of CD28, ICOS, 41BB or OX40. In some embodiments, the costimulatory signaling domain is a derived from CD28 or 4-1BB and comprises the sequence of amino acids set forth in any of SEQ ID NOS: 484-487 or a sequence of amino acids that exhibits at least 85%, 86%, 87%, 88%, 89%, 90%, 91%, 92%, 93%, 94%, 95%, 96%, 97%, 98% or 99% or more sequence identity to SEQ ID NO:484-487 and retains the activity of T cell costimulatory signaling.

Provided herein is a polynucleotide encoding an ICOSL polypeptide and encoding one or more proteins, such as a recombinant antigen receptor (e.g., chimeric antigen receptor (CAR) or engineered T cell receptor (TCR)), a marker, and one or more self-cleaving peptides. In some embodiments, the construct encoding the CAR further encodes a second protein, such as a marker, e.g. detectable protein, separated from the CAR by a self-cleaving peptide sequence. In some examples, the nucleic acid encoding the variant ICOSL polypeptide is separated from the one or more sequence(s) that is a nucleic acid encoding a protein, wherein the protein encodes a recombinant antigen receptor (e.g., CAR or TCR), a marker, a cytokine, or a chemokine. Any of the nucleotide sequences can be in a vector, such as viral vector. In some examples, the viral vector is a lentiviral vector or retroviral vector.

In some embodiments, the self-cleaving peptide sequence is an F2A, T2A, E2A or P2A self-cleaving peptide. Exemplary sequences of a T2A self-cleaving peptide are set for the in any one of SEQ ID NOS: 250, 488, 860-862 or a sequence of amino acids that exhibits at least 85%, 86%, 87%, 88%, 89%, 90%, 91%, 92%, 93%, 94%, 95%, 96%, 97%, 98% or 99% or more sequence identity to any of SEQ ID NOS: 250, 488, 860-862. In some embodiments, the T2A is encoded by the sequence of nucleotides set forth in SEQ ID NO:249 or a sequence that exhibits at least 85%, 86%, 87%, 88%, 89%, 90%, 91%, 92%, 93%, 94%, 95%, 96%, 97%, 98% or 99% or more sequence identity to any of SEQ ID NO: 249. An exemplary sequence of a P2A self-cleaving peptide is set in SEQ ID NO: 863 or a sequence of amino acids that exhibits at least 85%, 86%, 87%, 88%, 89%, 90%, 91%, 92%, 93%, 94%, 95%, 96%, 97%, 98% or 99% or more sequence identity to SEQ ID NOS: 863. In some cases, a nucleic acid construct that encodes more than one P2A self-cleaving peptide (such as a P2A1 and P2A2), in which the nucleotide sequence P2A1 and P2A2 each encode the P2A set forth in SEQ ID NO:863, the nucleotide sequence may be different to avoid recombination between sequences.

In some embodiments, the marker is a detectable protein, such as a fluorescent protein, e.g., a green fluorescent protein (GFP) or blue fluorescent protein (BFP). Exemplary sequences of a fluorescent protein marker are set forth in SEQ ID NO:489, 858, 859, 903 or a sequence of amino acids that exhibits at least 85%, 86%, 87%, 88%, 89%, 90%, 91%, 92%, 93%, 94%, 95%, 96%, 97%, 98% or 99% or more sequence identity to SEQ ID NO: 489, 858, 859, 903.

In some embodiments, the CAR is an anti-CD19 CAR that has the sequence of amino acids set forth in any of SEQ ID NOS: 479, 490, 491, 492, 898, 899, 901, or 902 or a sequence of amino acids that exhibits at least 85%, 86%, 87%, 88%, 89%, 90%, 91%, 92%, 93%, 94%, 95%, 96%, 97%, 98% or 99% or more sequence identity to any one of SEQ ID NOS: 479, 490, 491, 492, 898, 899, 901, or 902. In some embodiments, the CAR is encoded by a sequence of nucleotides set forth in SEQ ID NO: 248 or 900 or a sequence of amino acids that exhibits at least 85%, 86%, 87%, 88%, 89%, 90%, 91%, 92%, 93%, 94%, 95%, 96%, 97%, 98% or 99% or more sequence identity to any one of SEQ ID NO: 248 or 900.

In another embodiment, the engineered T-cell possesses a TCR, including a recombinant or engineered TCR. In some embodiments, the TCR can be a native TCR. Those of skill in the art will recognize that generally native mammalian T-cell receptors comprise an alpha and a beta chain (or a gamma and a delta chain) involved in antigen specific recognition and binding. In some embodiments, the TCR is an engineered TCR that is modified. In some embodiments, the TCR of an engineered T-cell specifically binds to a tumor associated or tumor specific antigen presented by an APC.

In some embodiments, the immunomodulatory polypeptides, such as transmembrane immunomodulatory polypeptides or secretable immunomodulatory polypeptides, can be incorporated into engineered cells, such as engineered T cells or engineered APCs, by a variety of strategies such as those employed for recombinant host cells. A variety of methods to introduce a DNA construct into primary T cells are known in the art. In some embodiments, viral transduction or plasmid electroporation are employed. In typical embodiments, the nucleic acid molecule encoding the immunomodulatory protein, or the expression vector, comprises a signal peptide that localizes the expressed transmembrane immunomodulatory proteins to the cellular membrane or for secretion. In some embodiments, a nucleic acid encoding a transmembrane immunomodulatory proteins of the invention is sub-cloned into a viral vector, such as a retroviral vector, which allows expression in the host mammalian cell. The expression vector can be introduced into a mammalian host cell and, under host cell culture conditions, the immunomodulatory protein is expressed on the surface or is secreted.

In an exemplary example, primary T-cells can be purified ex vivo (CD4 cells or CD8 cells or both) and stimulated with an activation protocol consisting of various TCR/CD28 agonists, such as anti-CD3/anti-CD28 coated beads. After a 2 or 3 day activation process, a recombinant expression vector containing an immunomodulatory polypeptide can be stably introduced into the primary T cells through art standard lentiviral or retroviral transduction protocols or plasmid electroporation strategies. Cells can be monitored for immunomodulatory polypeptide expression by, for example, flow cytometry using anti-epitope tag or antibodies that cross-react with native parental molecule and polypeptides comprising variant ICOSL. T-cells that express the immunomodulatory polypeptide can be enriched through sorting with anti-epitope tag antibodies or enriched for high or low expression depending on the application.

Upon immunomodulatory polypeptide expression the engineered T-cell can be assayed for appropriate function by a variety of means. The engineered CAR or TCR co-expression can be validated to show that this part of the engineered T cell was not significantly impacted by the expression of the immunomodulatory protein. Once validated, standard in vitro cytotoxicity, proliferation, or cytokine assays (e.g., IFN-gamma expression) can be used to assess the function of engineered T-cells. Exemplary standard endpoints are percent lysis of the tumor line, proliferation of the engineered T-cell, or IFN-gamma protein expression in culture supernatants. An engineered construct which results in statistically significant increased lysis of tumor line, increased proliferation of the engineered T-cell, or increased IFN-gamma expression over the control construct can be selected for. Additionally, non-engineered, such as native primary or endogenous T-cells could also be incorporated into the same in vitro assay to measure the ability of the immunomodulatory polypeptide construct expressed on the engineered cells, such as engineered T-cells, to modulate activity, including, in some cases, to activate and generate effector function in bystander, native T-cells. Increased expression of activation markers such as CD69, CD44, or CD62L could be monitored on endogenous T cells, and increased proliferation and/or cytokine production could indicate desired activity of the immunomodulatory protein expressed on the engineered T cells.

In some embodiments, the similar assays can be used to compare the function of engineered T cells containing the CAR or TCR alone to those containing the CAR or TCR and a TIP construct. Typically, these in vitro assays are performed by plating various ratios of the engineered T cell and a "tumor" cell line containing the cognate CAR or TCR antigen together in culture. Standard endpoints are percent lysis of the tumor line, proliferation of the engineered T cell, or IFN-gamma production in culture supernatants. An engineered immunomodulatory protein which resulted in statistically significant increased lysis of tumor line, increased proliferation of the engineered T cell, or increased IFN-gamma production over the same TCR or CAR construct alone can be selected for.

Engineered human T cells can be analyzed in immunocompromised mice, like the NSG strain, which lacks mouse T, NK and B cells. Engineered human T cells in which the CAR or TCR binds a target counter-structure on the xenograft and is co-expressed with the TIP affinity modified IgSF domain can be adoptively transferred in vivo at different cell numbers and ratios compared to the xenograft. For example, engraftment of CD19+ leukemia tumor lines containing a luciferase/GFP vector can be monitored through bioluminescence or ex vivo by flow cytometry. In a common embodiment, the xenograft is introduced into the murine model, followed by the engineered T cells several days later. Engineered T cells containing the immunomodulatory protein can be assayed for increased survival, tumor clearance, or expanded engineered T cells numbers relative to engineered T cells containing the CAR or TCR alone. As in the in vitro assay, endogenous, native (i.e., non-engineered) human T cells could be co-adoptively transferred to look for successful epitope spreading in that population, resulting in better survival or tumor clearance.

D. Infectious Agents Expressing Variant Polypeptides and Immunomodulatory Proteins Also provided are infectious agents that contain nucleic acids encoding any of the variant polypeptides, such as ICOSL vIgD polypeptides, including secretable or transmembrane immunomodulatory proteins described herein. In some embodiments, such infectious agents can deliver the nucleic acids encoding the variant immunomodulatory polypeptides described herein, such as ICOSL vIgD polypeptides, to a target cell in a subject, e.g., immune cell and/or antigen-presenting cell (APC) or tumor cell in a subject. Also provided are nucleic acids contained in such infectious agents, and/or nucleic acids for generation or modification of such infectious agents, such as vectors and/or plasmids, and compositions containing such infectious agents. In some embodiments, a variant ICOSL polypeptide is expressed in an infectious agent (e.g. viral or bacterial agent) which, upon administration to a subject, is able to infect a cell in vivo, such as an immune cell (e.g. T cell or antigen presenting cell) or tumor, for delivery or expression of the variant polypeptide as a TIP or a SIP in the cell.

In some embodiments, the infectious agent is a microorganism or a microbe. In some embodiments, the infectious agent is a virus or a bacterium. In some embodiments, the infectious agent is a virus. In some embodiments, the infectious agent is a bacterium. In some embodiments, such infectious agents can deliver nucleic acid sequences encoding any of the variant polypeptides, such as ICOSL vIgD polypeptides, including secretable or transmembrane immunomodulatory proteins, described herein. Thus, in some embodiments, the cell in a subject that is infected or contacted by the infectious agents can be rendered to express on the cell surface or secrete, the variant immunomodulatory polypeptides. In some embodiments, the infectious agent can also deliver one or more other therapeutics or nucleic acids encoding other therapeutics to the cell and/or to an environment within the subject. In some embodiments, other therapeutics that can be delivered by the infectious agents include cytokines or other immunomodulatory molecules.

In some embodiments, the infectious agent, e.g., virus or bacteria, contains nucleic acid sequences that encode any of the variant polypeptides, such as ICOSL vIgD polypeptides, including secretable or transmembrane immunomodulatory proteins, described herein, and by virtue of contact and/or infection of a cell in the subject, the cell expresses the variant polypeptides, such as ICOSL vIgD polypeptides, including secretable or transmembrane immunomodulatory proteins, encoded by the nucleic acid sequences contained in the infectious agent. In some embodiments, the infectious agent can be administered to the subject. In some embodiments, the infectious agent can be introduced to cells from the subject ex vivo.

In some embodiments, the variant polypeptides, such as ICOSL vIgD polypeptides, including transmembrane immunomodulatory proteins, expressed by the cell infected by the infectious agent is a transmembrane protein and is surface expressed. In some embodiments, the variant polypeptides, such as ICOSL vIgD polypeptides, including secretable immunomodulatory proteins, expressed by the cell infected by the infectious agent is expressed and secreted from the cell. The transmembrane immunomodulatory protein or secreted immunomodulatory protein can be any described herein.

In some embodiments, the cells in the subject that are targeted by the infectious agent include a tumor cell, an immune cell, and/or an antigen-presenting cell (APC). In some embodiments, the infectious agent targets a cell in the tumor microenvironment (TME). In some embodiments, the infectious agent delivers the nucleic acids encoding the variant polypeptides, such as ICOSL vIgD polypeptides, including secretable or transmembrane immunomodulatory proteins, to an appropriate cell (for example, an APC, such as a cell that displays a peptide/MHC complex on its cell surface, such as a dendritic cell) or tissue (e.g., lymphoid tissue) that modulate an immune response and/or a specific cell-medicated immune response, e.g., CD4 and/or CD8 T cell response, which CD8 T cell response may include a cytotoxic T cell (CTL) response. In some embodiments, the infectious agent targets an APC, such as a dendritic cell (DC). In some embodiments, the nucleic acid molecule delivered by the infectious agents described herein include appropriate nucleic acid sequences necessary for the expression of the operably linked coding sequences encoding the variant immunomodulatory polypeptides, in a particular target cell, e.g., regulatory elements such as promoters.

In some embodiments, the infectious agent that contains nucleic acid sequences encoding the immunomodulatory polypeptides can also contain nucleic acid sequences that encode one or more additional gene products, e.g., cytokines, prodrug converting enzymes, cytotoxins and/or detectable gene products. For example, in some embodiments, the infectious agent is an oncolytic virus and the virus can include nucleic acid sequences encoding additional therapeutic gene products (see, e.g., Kirn et al., (2009) Nat Rev Cancer 9:64-71; Garcia-Aragoncillo et al., (2010) Curr Opin Mol Ther 12:403-411; see U.S. Pat. Nos. 7,588,767, 7,588, 771, 7,662,398 and 7,754,221 and U.S. Pat. Publ. Nos. 2007/0202572, 2007/0212727, 2010/0062016, 2009/ 0098529, 2009/0053244, 2009/0155287, 2009/0117034, 2010/0233078, 2009/0162288, 2010/0196325, 2009/ 0136917 and 2011/0064650. In some embodiments, the additional gene product can be a therapeutic gene product that can result in death of the target cell (e.g., tumor cell) or gene products that can augment or boost or regulate an immune response (e.g., cytokine). Exemplary gene products also include among an anticancer agent, an anti-metastatic agent, an antiangiogenic agent, an immunomodulatory molecule, an immune checkpoint inhibitor, an antibody, a cytokine, a growth factor, an antigen, a cytotoxic gene product, a pro-apoptotic gene product, an anti-apoptotic gene product, a cell matrix degradative gene, genes for tissue regeneration and reprogramming human somatic cells to pluripotency, and other genes described herein or known to one of skill in the art. In some embodiments, the additional gene product is Granulocyte-macrophage colony-stimulating factor (GM-CSF).

1. Viruses

In some embodiments, the infectious agent is a virus. In some embodiments, the infectious agent is an oncolytic virus, or a virus that targets particular cells, e.g., immune cells. In some embodiments, the infectious agent targets a tumor cell and/or cancer cell in the subject. In some embodiments, the infectious agent targets an immune cell or an antigen-presenting cell (APC).

In some embodiments, the infectious agent is an oncolytic virus. Oncolytic viruses are viruses that accumulate in tumor cells and replicate in tumor cells. By virtue of replication in the tumor cells, and optional delivery of nucleic acids encoding variant ICOSL polypeptides or immunomodulatory polypeptides described herein, tumor cells are lysed, and the tumor shrinks and can be eliminated. Oncolytic viruses can also have a broad host and cell type range. For example, oncolytic viruses can accumulate in immunoprivileged cells or immunoprivileged tissues, including tumors and/or metastases, and also including wounded tissues and cells, thus allowing the delivery and expression of nucleic acids encoding the variant immunomodulatory polypeptides described herein in a broad range of cell types. Oncolytic viruses can also replicate in a tumor cell specific manner, resulting in tumor cell lysis and efficient tumor regression.

Exemplary oncolytic viruses include adenoviruses, adeno-associated viruses, herpes viruses, Herpes Simplex Virus, vesticular stomatic virus, Reovirus, Newcastle Disease virus, parvovirus, measles virus, vesticular stomatitis virus (VSV), Coxsackie virus and Vaccinia virus. In some embodiments, oncolytic viruses can specifically colonize solid tumors, while not infecting other organs, and can be used as an infectious agent to deliver the nucleic acids encoding the variant immunomodulatory polypeptides described herein to such solid tumors.

Oncolytic viruses for use in delivering the nucleic acids encoding variant ICOSL polypeptides or immunomodulatory polypeptides described herein, can be any of those known to one of skill in the art and include, for example, vesicular stomatitis virus, see, e.g., U.S. Pat. Nos. 7,731,974, 7,153,510, 6,653,103 and U.S. Pat. Pub. Nos. 2010/ 0178684, 2010/0172877, 2010/0113567, 2007/0098743, 20050260601, 20050220818 and EP Pat. Nos. 1385466, 1606411 and 1520175; herpes simplex virus, see, e.g., U.S. Pat. Nos. 7,897,146, 7,731,952, 7,550,296, 7,537,924, 6,723,316, 6,428,968 and U.S. Pat. Pub. Nos., 2014/ 0154216, 2011/0177032, 2011/0158948, 2010/0092515, 2009/0274728, 2009/0285860, 2009/0215147, 2009/ 0010889, 2007/0110720, 2006/0039894, 2004/0009604, 2004/0063094, International Patent Pub. Nos., WO 2007/ 052029, WO 1999/038955; retroviruses, see, e.g., U.S. Pat. Nos. 6,689,871, 6,635,472, 5,851,529, 5,716,826, 5,716,613 and U.S. Pat. Pub. No. 20110212530; vaccinia viruses, see, e.g., 2016/0339066, and adeno-associated viruses, see, e.g., U.S. Pat. Nos. 8,007,780, 7,968,340, 7,943,374, 7,906,111, 7,927,585, 7,811,814, 7,662,627, 7,241,447, 7,238,526, 7,172,893, 7,033,826, 7,001,765, 6,897,045, and 6,632,670.

Oncolytic viruses also include viruses that have been genetically altered to attenuate their virulence, to improve their safety profile, enhance their tumor specificity, and they have also been equipped with additional genes, for example cytotoxins, cytokines, prodrug converting enzymes to improve the overall efficacy of the viruses (see, e.g., Kirn et al., (2009) Nat Rev Cancer 9:64-71; Garcia-Aragoncillo et al., (2010) Curr Opin Mol Ther 12:403-411; see U.S. Pat. Nos. 7,588,767, 7,588,771, 7,662,398 and 7,754,221 and U.S. Pat. Publ. Nos. 2007/0202572, 2007/0212727, 2010/ 0062016, 2009/0098529, 2009/0053244, 2009/0155287, 2009/0117034, 2010/0233078, 2009/0162288, 2010/ 0196325, 2009/0136917 and 2011/0064650). In some embodiments, the oncolytic viruses can be those that have been modified so that they selectively replicate in cancerous cells, and, thus, are oncolytic. For example, the oncolytic virus is an adenovirus that has been engineered to have modified tropism for tumor therapy and also as gene therapy vectors. Exemplary of such is ONYX-015, H101 and AdSΔCR (Hallden and Portella (2012) Expert Opin Ther Targets, 16:945-58) and TNFerade (McLoughlin et al. (2005) Ann. Surg. Oncol., 12:825-30), or a conditionally replicative adenovirus Oncorine®.

In some embodiments, the infectious agent is a modified herpes simplex virus. In some embodiments, the infectious agent is a modified version of Talimogene laherparepvec (also known as T-Vec, Imlygic or OncoVex GM-CSF), that is modified to contain nucleic acids encoding any of the variant ICOSL polypeptides or immunomodulatory polypeptides described herein. In some embodiments, the infectious agent is a modified herpes simplex virus that is described, e.g., in WO 2007/052029, WO 1999/038955, US 2004/0063094, US 2014/0154216, or, variants thereof.

In some embodiments, the infectious agent is a virus that targets a particular type of cells in a subject that is administered the virus, e.g., a virus that targets immune cells or antigen-presenting cells (APCs). Dendritic cells (DCs) are essential APCs for the initiation and control of immune responses. DCs can capture and process antigens, migrate from the periphery to a lymphoid organ, and present the antigens to resting T cells in a major histocompatibility complex (MHC)-restricted fashion. In some embodiments, the infectious agent is a virus that specifically can target DCs to deliver nucleic acids encoding the variant ICOSL polypeptide or immunomodulatory polypeptides for expression in DCs. In some embodiments, the virus is a lentivirus or a variant or derivative thereof, such as an integration-deficient lentiviral vector. In some embodiments, the virus is a lentivirus that is pseudotyped to efficiently bind to and productively infect cells expressing the cell surface marker dendritic cell-specific intercellular adhesion molecule-3-grabbing non-integrin (DC-SIGN), such as DCs. In some embodiments, the virus is a lentivirus pseudotyped with a Sindbis virus E2 glycoprotein or modified form thereof, such as those described in WO 2013/149167. In some embodiments, the virus allows for delivery and expression of a sequence of interest (e.g., a nucleic acid encoding any of the variant ICOSL polypeptides or immunomodulatory polypeptides described herein) to a DC. In some embodiments, the virus includes those described in WO 2008/011636, US 2011/0064763, Tareen et al. (2014) Mol. Ther., 22:575-587, or variants thereof. Exemplary of a dendritic cell-tropic vector platform is ZVex™.

2. Bacteria

In some embodiments, the infectious agent is a bacterium. For example, in some embodiments, the bacteria can deliver nucleic acids encoding any of the variant immunomodulatory polypeptides described herein, e.g., variant ICOSL polypeptide or immunomodulatory polypeptide, to a target cell in the subject, such as a tumor cell, an immune cell, an antigen-presenting cell and/or a phagocytic cell. In some embodiments, the bacterium can be preferentially targeted to a specific environment within a subject, such as a tumor microenvironment (TME), for expression and/or secretion of the variant immunomodulatory polypeptides and/or to target specific cells in the environment for expression of the variant immunomodulatory polypeptides.

In some embodiments, the bacterium delivers the nucleic acids to the cells via bacterial-mediated transfer of plasmid DNA to mammalian cells (also referred to as "bactofection"). For example, in some embodiments, delivery of genetic material is achieved through entry of the entire bacterium into target cells. In some embodiments, spontaneous or induced bacterial lysis can lead to the release of plasmid for subsequent eukaryotic cell expression. In some embodiments, the bacterium can deliver nucleic acids to non-phagocytic mammalian cells (e.g., tumor cells) and/or to phagocytic cells, e.g., certain immune cells and/or APCs. In some embodiments, the nucleic acids delivered by the bacterium can be transferred to the nucleus of the cell in the subject for expression. In some embodiments, the nucleic acids also include appropriate nucleic acid sequences necessary for the expression of the operably linked sequences encoding the variant immunomodulatory polypeptides in a particular host cell, e.g., regulatory elements such as promoters or enhancers. In some embodiments, the infectious agent that is a bacterium can deliver nucleic acids encoding the immunomodulatory proteins in the form of an RNA, such as a pre-made translation-competent RNA delivered to the cytoplasm of the target cell for translation by the target cell's machinery.

In some embodiments, the bacterium can replicate and lyse the target cells, e.g., tumor cells. In some embodiments, the bacterium can contain and/or release nucleic acid sequences and/or gene products in the cytoplasm of the target cells, thereby killing the target cell, e.g., tumor cell. In some embodiments, the infectious agent is bacterium that can replicate specifically in a particular environment in the subject, e.g., tumor microenvironment (TME). For example, in some embodiments, the bacterium can replicate specifically in anaerobic or hypoxic microenvironments. In some embodiments, conditions or factors present in particular environments, e.g., aspartate, serine, citrate, ribose or galactose produced by cells in the TME, can act as chemoattractants to attract the bacterium to the environment. In some embodiments, the bacterium can express and/or secrete the immunomodulatory proteins described herein in the environment, e.g., TME.

In some embodiments, the infectious agent is a bacterium that is a *Listeria* sp., a *Bifidobacterium* sp., an *Escherichia* sp., a *Clostridium* sp., a *Salmonella* sp., a *Shigella* sp., a *Vibrio* sp. or a *Yersinia* sp. In some embodiments, the bacterium is selected from among one or more of *Listeria monocytogenes, Salmonella typhimurium, Salmonella choleraesuis, Escherichia coli, Vibrio cholera, Clostridium perfringens, Clostridium butyricum, Clostridium novyi, Clostridium acetobutylicum, Bifidobacterium infantis, Bifidobacterium longum* and *Bifidobacterium adolescentis*. In some embodiments, the bacterium is an engineered bacterium. In some embodiments, the bacterium is an engineered bacterium such as those described in, e.g., Seow and Wood (2009) Molecular Therapy 17(5):767-777; Baban et al. (2010) Bioengineered Bugs 1:6, 385-394; Patyar et al. (2010) J Biomed Sci 17:21; Tangney et al. (2010) Bioengineered Bugs 1:4, 284-287; van Pijkeren et al. (2010) Hum Gene Ther. 21(4):405-416; WO 2012/149364; WO 2014/198002; U.S. Pat. Nos. 9,103,831; 9,453,227; US 2014/0186401; US 2004/0146488; US 2011/0293705; US 2015/0359909 and EP 3020816. The bacterium can be modified to deliver nucleic acid sequences encoding any of the variant immunomodulatory polypeptides, conjugates and/or fusions provided herein, and/or to express such variant immunomodulatory polypeptides in the subject.

IV. NUCLEIC ACIDS, VECTORS AND METHODS FOR PRODUCING THE POLYPEPTIDES OR CELLS

Provided herein are isolated or recombinant nucleic acids collectively referred to as "nucleic acids" which encode any of the various provided embodiments of the variant ICOSL polypeptides or immunomodulatory polypeptides provided herein. In some embodiments, nucleic acids provided herein, including all described below, are useful in recombinant production (e.g., expression) of variant ICOSL polypeptides or immunomodulatory polypeptides provided herein. In some embodiments, nucleic acids provided herein, including all described below, are useful in expression of variant ICOSL polypeptides or immunomodulatory polypeptides provided herein in cells, such as in engineered cells, e.g. immune cells, or infectious agent cells. The nucleic acids provided herein can be in the form of RNA or in the form of DNA, and include mRNA, CRNA, recombinant or synthetic RNA and DNA, and cDNA. The nucleic acids provided herein are typically DNA molecules, and usually double-stranded DNA molecules. However, single-stranded DNA, single-stranded RNA, double-stranded RNA, and hybrid DNA/RNA nucleic acids or combinations thereof comprising any of the nucleotide sequences of the invention also are provided.

Also provided herein are recombinant expression vectors and recombinant host cells useful in producing the variant ICOSL polypeptides or immunomodulatory polypeptides provided herein.

Also provided herein are engineered cells, such as engineered immune cells, containing any of the provided nucleic acid molecules or any of the variant ICOSL polypeptides or immunomodulatory polypeptides, such as any of the transmembrane immunomodulatory polypeptides or secretable immunomodulatory polypeptides.

Also provided herein are infectious agents, such as bacterial or viral cells, containing any of the provided nucleic acid molecules or any of the variant ICOSL polypeptides or immunomodulatory polypeptides, such as any of the transmembrane immunomodulatory polypeptides or secretable immunomodulatory polypeptides.

In any of the above provided embodiments, the nucleic acids encoding the variant polypeptides or immunomodulatory polypeptides provided herein can be introduced into cells using recombinant DNA and cloning techniques. To do so, a recombinant DNA molecule encoding an immunomodulatory polypeptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidite method. Also, a combination of these techniques could be used. In some instances, a recombinant or synthetic nucleic acid may be generated through polymerase chain reaction (PCR). In some embodiments, a DNA insert can be generated encoding one or more variant ICOSL polypeptides containing at least one affinity-modified IgSF domain and, in some embodiments, a signal peptide, a transmembrane domain and/or an endodomain in accord with the provided description. This DNA insert can be cloned into an appropriate transduction/transfection vector as is known to those of skill in the art. Also provided are expression vectors containing the nucleic acid molecules.

In some embodiments, the expression vectors are capable of expressing the immunomodulatory proteins in an appropriate cell under conditions suited to expression of the protein. In some aspects, nucleic acid molecule or an expression vector comprises the DNA molecule that encodes the immunomodulatory protein operatively linked to appropriate expression control sequences. Methods of effecting this operative linking, either before or after the DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

In some embodiments, expression of the immunomodulatory protein is controlled by a promoter or enhancer to control or regulate expression. The promoter is operably linked to the portion of the nucleic acid molecule encoding the variant polypeptide or immunomodulatory protein. In some embodiments, the promotor is a constitutively active promotor (such as a tissue-specific constitutively active promotor or other constitutive promotor). In some embodiments, the promotor is an inducible promotor, which may be responsive to an inducing agent (such as a T cell activation signal).

In some embodiments, a constitutive promoter is operatively linked to the nucleic acid molecule encoding the variant polypeptide or immunomodulatory protein. Exemplary constitutive promoters include the Simian vacuolating virus 40 (SV40) promoter, the cytomegalovirus (CMV) promoter, the ubiquitin C (UbC) promoter, and the EF-1 alpha (EF1a) promoter. In some embodiments, the constitutive promoter is tissue specific. For example, in some embodiments, the promoter allows for constitutive expression of the immunomodulatory protein in specific tissues, such as immune cells, lymphocytes, or T cells. Exemplary tissue-specific promoters are described in U.S. Pat. No. 5,998,205, including, for example, a fetoprotein, DF3, tyrosinase, CEA, surfactant protein, and ErbB2 promoters.

In some embodiments, an inducible promoter is operatively linked to the nucleic acid molecule encoding the variant polypeptide or immunomodulatory protein such that expression of the nucleic acid is controllable by controlling the presence or absence of the appropriate inducer of transcription. For example, the promoter can be a regulated promoter and transcription factor expression system, such as the published tetracycline-regulated systems or other regulatable systems (see, e.g. published International PCT Appl. No. WO 01/30843), to allow regulated expression of the encoded polypeptide. An exemplary regulatable promoter system is the Tet-On (and Tet-Off) system available, for example, from Clontech (Palo Alto, CA). This promoter system allows the regulated expression of the transgene controlled by tetracycline or tetracycline derivatives, such as doxycycline. Other regulatable promoter systems are known (see e.g., published U.S. Application No. 2002-0168714, entitled "Regulation of Gene Expression Using Single-Chain, Monomeric, Ligand Dependent Polypeptide Switches," which describes gene switches that contain ligand binding domains and transcriptional regulating domains, such as those from hormone receptors).

In some embodiments, the promotor is responsive to an element responsive to T-cell activation signaling. Solely by way of example, in some embodiments, an engineered T cell comprises an expression vector encoding the immunomodulatory protein and a promotor operatively linked to control expression of the immunomodulatory protein. The engineered T cell can be activated, for example by signaling through an engineered T cell receptor (TCR) or a chimeric antigen rector (CAR), and thereby triggering expression and secretion of the immunomodulatory protein through the responsive promotor.

In some embodiments, an inducible promoter is operatively linked to the nucleic acid molecule encoding the immunomodulatory protein such that the immunomodulatory protein is expressed in response to a nuclear factor of activated T-cells (NFAT) or nuclear factor kappa-light-chain enhancer of activated B cells (NF-κB). For example, in some embodiments, the inducible promoter comprises a binding site for NFAT or NF-κB. For example, in some embodiments, the promoter is an NFAT or NF-κB promoter or a functional variant thereof. Thus, in some embodiments, the nucleic acids make it possible to control the expression of immunomodulatory protein while also reducing or eliminating the toxicity of the immunomodulatory protein. In particular, engineered immune cells comprising the nucleic acids of the invention express and secrete the immunomodulatory protein only when the cell (e.g., a T-cell receptor (TCR) or a chimeric antigen receptor (CAR) expressed by the cell) is specifically stimulated by an antigen and/or the cell (e.g., the calcium signaling pathway of the cell) is non-specifically stimulated by, e.g., phorbol myristate acetate (PMA)/Ionomycin. Accordingly, the expression and, in some cases, secretion, of immunomodulatory protein can be controlled to occur only when and where it is needed (e.g., in the presence of an infectious disease-causing agent, cancer, or at a tumor site), which can decrease or avoid undesired immunomodulatory protein interactions.

In some embodiments, the nucleic acid encoding an immunomodulatory protein described herein comprises a suitable nucleotide sequence that encodes a NFAT promoter, NF-κB promoter, or a functional variant thereof. "NFAT promoter" as used herein means one or more NFAT responsive elements linked to a minimal promoter. "NF-κB promoter" refers to one or more NF-κB responsive elements linked to a minimal promoter. In some embodiments, the minimal promoter of a gene is a minimal human IL-2 promoter or a CMV promoter. The NFAT responsive elements may comprise, e.g., NFAT1, NFAT2, NFAT3, and/or NFAT4 responsive elements. The NFAT promoter, NF-κB promoter, or a functional variant thereof may comprise any number of binding motifs, e.g., at least two, at least three, at least four, at least five, or at least six, at least seven, at least eight, at least nine, at least ten, at least eleven, or up to twelve binding motifs.

The resulting recombinant expression vector having the DNA molecule thereon is used to transform an appropriate host. This transformation can be performed using methods well known in the art. In some embodiments, a nucleic acid provided herein further comprises nucleotide sequence that encodes a secretory or signal peptide operably linked to the nucleic acid encoding an immunomodulatory polypeptide such that a resultant soluble immunomodulatory polypeptide is recovered from the culture medium, host cell, or host cell periplasm. In other embodiments, the appropriate expression control signals are chosen to allow for membrane expression of an immunomodulatory polypeptide. Furthermore, commercially available kits as well as contract manufacturing companies can also be utilized to make engineered cells or recombinant host cells provided herein.

In some embodiments, the resulting expression vector having the DNA molecule thereon is used to transform, such as transduce, an appropriate cell. The introduction can be performed using methods well known in the art. Exemplary methods include those for transfer of nucleic acids encoding the receptors, including via viral, e.g., retroviral or lentiviral, transduction, transposons, and electroporation. In some embodiments, the expression vector is a viral vector. In some embodiments, the nucleic acid is transferred into cells by lentiviral or retroviral transduction methods.

Any of a large number of publicly available and well-known mammalian host cells, including mammalian T-cells or APCs, can be used in the preparing the polypeptides or engineered cells. The selection of a cell is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all cells can be equally effective for the expression of a particular DNA sequence.

In some embodiments, the host cells can be a variety of eukaryotic cells, such as in yeast cells, or with mammalian cells such as Chinese hamster ovary (CHO) or HEK293 cells. In some embodiments, the host cell is a suspension cell and the polypeptide is engineered or produced in cultured suspension, such as in cultured suspension CHO cells, e.g. CHO-S cells. In some examples, the cell line is a CHO cell line that is deficient in DHFR (DHFR−), such as DG44 and DUXB11. In some embodiments, the cell is deficient in glutamine synthase (GS), e.g. CHO-S cells, CHOK1 SV cells, and CHOZN((R)) GS−/− cells. In some embodiments, the CHO cells, such as suspension CHO cells, may be CHO-S-2H2 cells, CHO-S-clone 14 cells, or ExpiCHO-S cells.

In some embodiments, expressing the provided ICOSL polypeptides from CHO cells results in a more homogenous composition of produced proteins. In some embodiments, the provided ICOSL polypeptides results in a more homogenous product when the proteins are expressed from CHO cells compared to ICOSL polypeptides containing the full ECD reference sequence and/or containing the protease cleavage site (e.g., LQQN/LT). In some embodiments, at least 91%, 92%, 93%, 94%, 95%, 96%, 97%, 98%, or 99% of the composition of produced proteins containing an ICOSL variant polypeptide produced herein, have the same amino acid length or are the same size. Techniques to assess homogeneity of size include high performance liquid chromatography (HPLC), size exclusion chromatography, SDS page, or sequencing.

In some embodiments, host cells can also be prokaryotic cells, such as with E. coli. The transformed recombinant host is cultured under polypeptide expressing conditions, and then purified to obtain a soluble protein. Recombinant host cells can be cultured under conventional fermentation conditions so that the desired polypeptides are expressed. Such fermentation conditions are well known in the art. Finally, the polypeptides provided herein can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, and affinity chromatography. Protein refolding steps can be used, as desired, in completing configuration of the mature protein. Finally, high performance liquid chromatography (HPLC) can be employed in the final purification steps.

In some embodiments, the cell is an immune cell, such as any described above in connection with preparing engineered cells. In some embodiments, such engineered cells are primary cells. In some embodiments, the engineered cells are autologous to the subject. In some embodiment, the engineered cells are allogeneic to the subject. In some embodiments, the engineered cells are obtained from a subject, such as by leukapheresis, and transformed ex vivo for expression of the immunomodulatory polypeptide, e.g. transmembrane immunomodulatory polypeptide or secretable immunomodulatory polypeptide.

Also provided are nucleic acids encoding any of the variant immunomodulatory polypeptides contained in infectious agents described herein. In some embodiments, the infectious agents deliver the nucleic acids to a cell in the subject, and/or permit expression of the encoded variant polypeptides in the cell. Also provided are nucleic acids that are used to generate, produce or modify such infectious agents. For example, in some embodiments, provided are vectors and/or plasmids that contain nucleic acids encoding the variant immunomodulatory polypeptides, for generation of the infectious agents, delivery to the cells in a subject and/or expression of the variant immunomodulatory polypeptides in the cells in the subject.

In some embodiments, the provided nucleic acids are recombinant viral or bacterial vectors containing nucleic acid sequences encoding the variant immunomodulatory polypeptides. In some embodiments, the recombinant vectors can be used to produce an infectious agent that contains nucleic acid sequences encoding the variant immunomodulatory polypeptides and/or to be delivered to a target cell in the subject for expression by the target cell. In some embodiments, the recombinant vector is an expression vector. In some embodiments, the recombinant vector includes appropriate sequences necessary for generation and/or production of the infectious agent and expression in the target cell.

In some embodiments, the recombinant vector is a plasmid or cosmid. Plasmid or cosmid containing nucleic acid sequences encoding the variant immunomodulatory polypeptides, as described herein, is readily constructed using standard techniques well known in the art. For generation of the infectious agent, the vector or genome can be constructed in a plasmid form that can then be transfected into a packaging or producer cell line or a host bacterium. The recombinant vectors can be generated using any of the recombinant techniques known in the art. In some embodiments, the vectors can include a prokaryotic origin of replication and/or a gene whose expression confers a detectable or selectable marker such as a drug resistance for propagation and/or selection in prokaryotic systems.

In some embodiments, the recombinant vector is a viral vector. Exemplary recombinant viral vectors include a lentiviral vector genome, poxvirus vector genome, vaccinia virus vector genome, adenovirus vector genome, adenovirus-associated virus vector genome, herpes virus vector genome, and alpha virus vector genome. Viral vectors can be live, attenuated, replication conditional or replication deficient, non-pathogenic (defective), replication competent viral vector, and/or is modified to express a heterologous gene product, e.g., the variant immunomodulatory polypeptides provided herein. Vectors for generation of viruses also can be modified to alter attenuation of the virus, which includes any method of increasing or decreasing the transcriptional or translational load.

Exemplary viral vectors that can be used include modified vaccinia virus vectors (see, e.g., Guerra et al., J. Virol. 80:985-98 (2006); Tartaglia et al., AIDS Research and Human Retroviruses 8:1445-47 (1992); Gheradi et al., J. Gen. Virol. 86:2925-36 (2005); Mayr et al., Infection 3:6-14 (1975); Hu et al., J. Virol. 75:10300-308 (2001); U.S. Pat. Nos. 5,698,530, 6,998,252, 5,443,964, 7,247,615 and 7,368, 116); adenovirus vector or adenovirus-associated virus vectors (see, e.g., Molin et al., J. Virol. 72:8358-61 (1998); Narumi et al., Am J. Respir. Cell Mol. Biol. 19:936-41 (1998); Mercier et al., Proc. Natl. Acad. Sci. USA 101:6188-93 (2004); U.S. Pat. Nos. 6,143,290; 6,596,535; 6,855,317; 6,936,257; 7,125,717; 7,378,087; 7,550,296); retroviral vectors including those based upon murine leukemia virus (MuLV), gibbon ape leukemia virus (GaLV), ecotropic retroviruses, simian immunodeficiency virus (SIV), human immunodeficiency virus (HIV), and combinations (see, e.g., Buchscher et al., J. Virol. 66:2731-39 (1992); Johann et al., J. Virol. 66:1635-40 (1992); Sommerfelt et al., Virology 176:58-59 (1990); Wilson et al., J. Virol. 63:2374-78 (1989); Miller et al., J. Virol. 65:2220-24 (1991); Miller et al., Mol. Cell Biol. 10:4239 (1990); Kolberg, NIH Res. 4:43 1992; Cornetta et al., Hum. Gene Ther. 2:215 (1991)); lentiviral vectors including those based upon Human Immunodeficiency Virus (HIV-1), HIV-2, feline immunodeficiency virus (FIV), equine infectious anemia virus, Simian Immunodeficiency Virus (SIV), and maedi/visna virus (see, e.g., Pfeifer et al., Annu. Rev. Genomics Hum. Genet. 2:177-211 (2001); Zufferey et al., J. Virol. 72:9873, 1998; Miyoshi et al., J. Virol. 72:8150, 1998; Philpott and Thrasher, Human Gene Therapy 18:483, 2007; Engelman et al., J. Virol. 69:2729, 1995; Nightingale et al., Mol. Therapy, 13:1121, 2006; Brown et al., J. Virol. 73:9011 (1999); WO 2009/076524; WO 2012/141984; WO 2016/011083; McWilliams et al., J. Virol. 77:11150, 2003; Powell et al., J. Virol. 70:5288, 1996) or any, variants thereof, and/or vectors that can be used to generate any of the viruses described above. In some embodiments, the recombinant vector can include regulatory sequences, such as promoter or enhancer sequences, that can regulate the expression of the viral genome, such as in the case for RNA viruses, in the packaging cell line (see, e.g., U.S. Pat. Nos. 5,385,839 and 5,168,062).

In some embodiments, the recombinant vector is an expression vector, e.g., an expression vector that permits expression of the encoded gene product when delivered into the target cell, e.g., a cell in the subject, e.g., a tumor cell, an immune cell and/or an APC. In some embodiments, the recombinant expression vectors contained in the infectious agent are capable of expressing the immunomodulatory proteins in the target cell in the subject, under conditions suited to expression of the protein.

In some aspects, nucleic acids or an expression vector comprises a nucleic acid sequence that encodes the immunomodulatory protein operatively linked to appropriate expression control sequences. Methods of affecting this operative linking, either before or after the nucleic acid sequence encoding the immunomodulatory protein is inserted into the vector, are well known. Expression control sequences include promoters, activators, enhancers, operators, ribosomal binding sites, start signals, stop signals, cap signals, polyadenylation signals, and other signals involved with the control of transcription or translation. The promoter can be operably linked to the portion of the nucleic acid sequence encoding the immunomodulatory protein. In some embodiments, the promotor is a constitutively active promotor in the target cell (such as a tissue-specific constitutively active promotor or other constitutive promotor). For example, the recombinant expression vector may also include, lymphoid tissue-specific transcriptional regulatory elements (TRE) such as a B lymphocyte, T lymphocyte, or dendritic cell specific TRE. Lymphoid tissue specific TRE are known in the art (see, e.g., Thompson et al., Mol. Cell. Biol. 12:1043-53 (1992); Todd et al., J. Exp. Med. 177: 1663-74 (1993); Penix et al., J. Exp. Med. 178:1483-96 (1993)). In some embodiments, the promotor is an inducible promotor, which may be responsive to an inducing agent (such as a T cell activation signal). In some embodiments, nucleic acids delivered to the target cell in the subject, e.g., tumor cell, immune cell and/or APC, can be operably linked to any of the regulatory elements described above.

In some embodiments, the vector is a bacterial vector, e.g., a bacterial plasmid or cosmid. In some embodiments, the bacterial vector is delivered to the target cell, e.g., tumor cells, immune cells and/or APCs, via bacterial-mediated transfer of plasmid DNA to mammalian cells (also referred to as "bactofection"). In some embodiments, the delivered bacterial vector also contains appropriate expression control sequences for expression in the target cells, such as a promoter sequence and/or enhancer sequences, or any regulatory or control sequences described above. In some embodiments, the bacterial vector contains appropriate expression control sequences for expression and/or secretion of the encoded variant polypeptides in the infectious agent, e.g., the bacterium.

In some embodiments, polypeptides provided herein can also be made by synthetic methods. Solid phase synthesis is the preferred technique of making individual peptides since it is the most cost-effective method of making small peptides. For example, well known solid phase synthesis techniques include the use of protecting groups, linkers, and solid phase supports, as well as specific protection and deprotection reaction conditions, linker cleavage conditions, use of scavengers, and other aspects of solid phase peptide synthesis. Peptides can then be assembled into the polypeptides as provided herein.

V. METHODS OF ASSESSING ACTIVITY IMMUNE MODULATION OF VARIANT ICOSL POLYPEPTIDES AND IMMUNOMODULATORY PROTEINS

In some embodiments, the variant ICOSL polypeptides provided herein (e.g. full-length and/or specific binding fragments or conjugates, stack constructs or fusion thereof) exhibit immunomodulatory activity to modulate T cell activation. In some embodiments, ICOSL polypeptides modulate IFN-gamma expression in a primary T cell assay relative to a reference (e.g., unmodified) or wild-type ICOSL control. In some cases, modulation of IFN-gamma expression can increase or decrease IFN-gamma expression relative to the control. Assays to determine specific binding and IFN-gamma expression are well-known in the art and include the MLR (mixed lymphocyte reaction) assays measuring interferon-gamma cytokine levels in culture supernatants (Wang et al., Cancer Immunol Res. 2014 September: 2(9):846-56), SEB (staphylococcal enterotoxin B) T cell stimulation assay (Wang et al., Cancer Immunol Res. 2014 September: 2(9): 846-56), and anti-CD3 T cell stimulation assays (Li and Kurlander, J Transl Med. 2010:8: 104).

In some embodiments, a variant ICOSL polypeptide can in some embodiments increase or, in alternative embodiments, decrease IFN-gamma (interferon-gamma) expression in a primary T-cell assay relative to a wild-type ICOSL control. In some embodiments of the provided polypeptides containing a soluble variant ICOSL sequence, the polypeptide can increase IFN-gamma expression and, in alternative embodiments, decrease IFN-gamma expression in a primary T-cell assay relative to a wild-type ICOSL control. In some embodiments of the provided polypeptides containing multiple variant ICOSL sequences, the polypeptide can increase IFN-gamma expression and, in alternative embodiments, decrease IFN-gamma expression in a primary T-cell assay relative to a wild-type ICOSL control.

Those of skill will recognize that the format of the primary T-cell assay used to determine an increase in IFN-gamma expression can differ from that employed to assay for a decrease in IFN-gamma expression. In assaying for the ability of a variant ICOSL to decrease IFN-gamma expression in a primary T-cell assay, a Mixed Lymphocyte Reaction (MLR) assay can be used as described in Example 6. In some cases, a soluble form of a variant ICOSL can be employed to determine the ability of the variant ICOSL to antagonize and thereby decrease the IFN-gamma expression in a MLR as likewise described in Example 6.

Alternatively, in assaying for the ability of a variant ICOSL to increase IFN-gamma expression in a primary T-cell assay, a co-immobilization assay can be used as described in Example 6. In a co-immobilization assay, a TCR signal, provided in some embodiments by anti-CD3 antibody, is used in conjunction with a co-immobilized variant ICOSL to determine the ability to increase IFN-gamma expression relative to an ICOSL control. In some cases, a soluble form of a variant ICOSL that is multimerized to a degree to provide multivalent binding can be employed to determine the ability of the variant ICOSL to agonize and thereby increase the IFN-gamma expression in a MLR as likewise described in Example 6.

In some embodiments, in assaying for the ability of a variant ICOSL to modulate an increase or decrease IFN-gamma expression a T cell reporter assay can be used. In some embodiments, the T cell is a Jurkat T cell line or is derived from Jurkat T cell lines. In reporter assays, the reporter cell line (e.g. Jurkat reporter cell) also is generated to overexpress an inhibitory receptor that is the cognate binding partner of the variant IgSF domain polypeptide. In some embodiments, the reporter T cells also contain a reporter construct containing an inducible promoter responsive to T cell activation operably linked to a reporter. In some embodiments, the reporter is a fluorescent or luminescent reporter. In some embodiments, the reporter is luciferase. In some embodiments, the promoter is responsive to CD3 signaling. In some embodiments, the promoter is an NFAT promoter. In some embodiments, the promoter is responsive to costimulatory signaling, e.g. CD28 costimulatory signaling. In some embodiments, the promoter is an IL-2 promoter.

In aspects of a reporter assay, a reporter cell line is stimulated, such as by co-incubation with antigen presenting cells (APCs) expressing the wild-type ligand of the inhibitory receptor, e.g. ICOSL. In some embodiments, the APCs are artificial APCs. Artificial APCs are well known to a skilled artisan. In some embodiments, artificial APCs are derived from one or more mammalian cell line, such as K562, CHO or 293 cells.

In some embodiments, the Jurkat reporter cells are co-incubated with artificial APCs overexpressing the inhibitory ligand in the presence of the variant IgSF domain molecule or immunomodulatory protein, e.g., variant ICOSL polypeptide or immunomodulatory protein. In some embodiments, reporter expression is monitored, such as by determining the luminescence or fluorescence of the cells. In some embodiments, normal interactions between its inhibitory receptor and ligand result in a repression of or decrease in the reporter signal, such as compared to control, e.g. reporter expression by co-incubation of control T cells and APCs in which the inhibitory receptor and ligand interaction is not present, e.g. APCs that do not overexpress ICOSL. In some embodiments, a variant ICOSL polypeptide or immunomodulatory protein provided herein antagonizes the interaction, e.g. when provided in soluble form as a variant ICOSL-Fc or when expressed from the APC as a secretable immunomodulatory protein, thereby resulting in an increase in the reporter signal compared to the absence of the variant ICOSL polypeptide or immunomodulatory protein. In some cases, certain formats of a variant ICOSL polypeptide or immunomodulatory protein as provided herein may provide an agonist activity, thereby decreasing reporter expression compared to the absence of the variant ICOSL polypeptide or immunomodulatory protein.

Use of proper controls is known to those of skill in the art, however, in the aforementioned embodiments, the control typically involves use of the reference ICOSL, such as a wild-type of native ICOSL isoform from the same mammalian species from which the variant ICOSL was derived or developed. Irrespective of whether the binding affinity to either one or both of ICOS and CD28 is increased or decreased, a variant ICOSL in some embodiments will increase IFN-gamma expression and, in alternative embodiments, decrease IFN-gamma expression in a primary T-cell assay relative to a wild-type ICOSL control.

In some embodiments, a variant ICOSL increases IFN-gamma expression (i.e., protein expression) relative to a reference (e.g., unmodified) or wild-type ICOSL control by at least: 5%, 10%, 20%, 30%, 40%, 50%, 60%, 70%, 80%, 90%, or higher. In other embodiments, a variant ICOSL decreases IFN-gamma expression (i.e. protein expression) relative to a wild-type or unmodified ICOSL control by at least: 5%, 10%, 20%, 30%, 40%, 50%, 60%, 70%, 80%, 90%, or higher. In some embodiments, the wild-type ICOSL control is murine ICOSL, such as would typically be used for a variant ICOSL altered in sequence from that of a wild-type murine ICOSL sequence. In some embodiments, the wild-type ICOSL control is human ICOSL, such as would typically be used for a variant ICOSL altered in sequence from that of a wild-type human ICOSL sequence such as an ICOSL sequence comprising the sequence of amino acids of SEQ ID NO: 32 or SEQ ID NO:196 or 545.

VI. PHARMACEUTICAL FORMULATIONS

Provided herein are compositions containing any of the variant ICOSL polypeptides, immunodulatory proteins, conjugates, engineered cells or infectious agents described herein. The pharmaceutical composition can further comprise a pharmaceutically acceptable excipient. For example, the pharmaceutical composition can contain one or more excipients for modifying, maintaining or preserving, for example, the pH, osmolarity, viscosity, clarity, color, isotonicity, odor, sterility, stability, rate of dissolution or release, adsorption, or penetration of the composition. In some aspects, a skilled artisan understands that a pharmaceutical composition containing cells may differ from a pharmaceutical composition containing a protein.

In some embodiments, the pharmaceutical composition is a solid, such as a powder, capsule, or tablet. For example, the components of the pharmaceutical composition can be lyophilized. In some embodiments, the solid pharmaceutical composition is reconstituted or dissolved in a liquid prior to administration.

In some embodiments, the pharmaceutical composition is a liquid, for example variant ICOSL polypeptides dissolved in an aqueous solution (such as physiological saline or Ringer's solution). In some embodiments, the pH of the pharmaceutical composition is between about 4.0 and about 8.5 (such as between about 4.0 and about 5.0, between about 4.5 and about 5.5, between about 5.0 and about 6.0, between about 5.5 and about 6.5, between about 6.0 and about 7.0, between about 6.5 and about 7.5, between about 7.0 and about 8.0, or between about 7.5 and about 8.5).

In some embodiments, the pharmaceutical composition comprises a pharmaceutically-acceptable excipient, for example a filler, binder, coating, preservative, lubricant, flavoring agent, sweetening agent, coloring agent, a solvent, a buffering agent, a chelating agent, or stabilizer. Examples of pharmaceutically-acceptable fillers include cellulose, dibasic calcium phosphate, calcium carbonate, microcrystalline cellulose, sucrose, lactose, glucose, mannitol, sorbitol, maltol, pregelatinized starch, corn starch, or potato starch. Examples of pharmaceutically-acceptable binders include polyvinylpyrrolidone, starch, lactose, xylitol, sorbitol, maltitol, gelatin, sucrose, polyethylene glycol, methyl cellulose, or cellulose. Examples of pharmaceutically-acceptable coatings include hydroxypropyl methylcellulose (HPMC), shellac, corn protein zein, or gelatin. Examples of pharmaceutically-acceptable disintegrants include polyvinylpyrrolidone, carboxymethyl cellulose, or sodium starch glycolate. Examples of pharmaceutically-acceptable lubricants include polyethylene glycol, magnesium stearate, or stearic acid. Examples of pharmaceutically-acceptable preservatives include methyl parabens, ethyl parabens, propyl paraben, benzoic acid, or sorbic acid. Examples of pharmaceutically-acceptable sweetening agents include sucrose, saccharine, aspartame, or sorbitol. Examples of pharmaceutically-acceptable buffering agents include carbonates, citrates, gluconates, acetates, phosphates, or tartrates.

In some embodiments, the pharmaceutical composition further comprises an agent for the controlled or sustained release of the product, such as injectable microspheres, bio-erodible particles, polymeric compounds (polylactic acid, polyglycolic acid), beads, or liposomes.

In some embodiments, the pharmaceutical composition is sterile. Sterilization may be accomplished by filtration through sterile filtration membranes or radiation. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

In some embodiments, provided are pharmaceutical compositions containing the transmembrane immunomodulatory proteins, including engineered cells expressing such transmembrane immunomodulatory proteins. In some embodiments, the pharmaceutical compositions and formulations include one or more optional pharmaceutically acceptable carrier or excipient. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

In some embodiments, the pharmaceutical composition contains infectious agents containing nucleic acid sequences encoding the immunomodulatory variant polypeptides. In some embodiments, the pharmaceutical composition contains a dose of infectious agents suitable for administration to a subject that is suitable for treatment. In some embodiments, the pharmaceutical composition contains an infectious agent that is a virus, at a single or multiple dosage amount, of between about between or between about $1 \times 10^5$ and about $1 \times 10^{12}$ plaque-forming units (pfu), $1 \times 10^6$ and $1 \times 10^{10}$ pfu, or $1 \times 10^7$ and $1 \times 10^{10}$ pfu, each inclusive, such as at least or at least about or at about $1 \times 10^6$, $1 \times 10^7$, $1 \times 10^8$, $1 \times 10^9$, $2 \times 10^9$, $3 \times 10^9$, $4 \times 10^9$, $5 \times 10^9$ pfu or about $1 \times 10^{10}$ pfu. In some embodiments, the pharmaceutical composition can contain a virus concentration of from or from about $10^5$ to about $10^{10}$ pfu/mL, for example, $5 \times 10^6$ to $5 \times 10^9$ or $1 \times 10^7$ to $1 \times 10^9$ pfu/mL, such as at least or at least about or at about $10^6$ pfu/mL, $10^7$ pfu/mL, $10^8$ pfu/mL or $10^9$ pfu/mL. In some embodiments, the pharmaceutical composition contains an infectious agent that is a bacterium, at a single or multiple dosage amount, of between about between or between about $1 \times 10^3$ and about $1 \times 10^9$ colony-forming units (cfu), $1 \times 10^4$ and $1 \times 10^9$ cfu, or $1 \times 10^5$ and $1 \times 10^7$ cfu, each inclusive, such as at least or at least about or at about $1\times10^4$, $1\times10^5$, $1\times10^6$, $1\times10^7$, $1\times10^8$ or $1\times10^9$ cfu. In some embodiments, the pharmaceutical composition can contain a bacterial concentration of from or from about $10^3$ to about $10^8$ cfu/mL, for example, $5\times10^5$ to $5\times10^7$ or $1\times10^6$ to $1\times10^7$ cfu/mL, such as at least or at least about or at about $10^5$ cfu/mL, $10^6$ cfu/mL, $10^7$ cfu/mL or $10^8$ cfu/mL Such a formulation may, for example, be in a form suitable for intravenous infusion. A pharmaceutically acceptable carrier may be a pharmaceutically acceptable material, composition, or vehicle that is involved in carrying or transporting cells of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

In some embodiments, the pharmaceutical composition is administered to a subject. Generally, dosages and routes of administration of the pharmaceutical composition are determined according to the size and condition of the subject, according to standard pharmaceutical practice. For example, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans. The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy.

Long-acting pharmaceutical compositions may be administered every 3 to 4 days, every week, or biweekly depending on the half-life and clearance rate of the particular formulation. The frequency of dosing will depend upon the pharmacokinetic parameters of the molecule in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data. A number of biomarkers or physiological markers for therapeutic effect can be monitored including T cell activation or proliferation, cytokine synthesis or production (e.g., production of TNF-$\alpha$, IFN-$\gamma$, IL-2), induction of various activation markers (e.g., CD25, IL-2 receptor), inflammation, joint swelling or tenderness, serum level of C-reactive protein, anti-collagen antibody production, and/or T cell-dependent antibody response(s).

In some embodiments, the pharmaceutical composition is administered to a subject through any route, including orally, transdermally, by inhalation, intravenously, intra-arterially, intramuscularly, direct application to a wound site, application to a surgical site, intraperitoneally, by suppository, subcutaneously, intradermally, transcutaneously, by nebulization, intrapleurally, intraventricularly, intra-articularly, intraocularly, or intraspinally.

In some embodiments, the dosage of the pharmaceutical composition is a single dose or a repeated dose. In some embodiments, the doses are given to a subject once per day, twice per day, three times per day, or four or more times per day. In some embodiments, about 1 or more (such as about 2 or more, about 3 or more, about 4 or more, about 5 or more, about 6 or more, or about 7 or more) doses are given in a week. In some embodiments, multiple doses are given over the course of days, weeks, months, or years. In some embodiments, a course of treatment is about 1 or more doses (such as about 2 or more does, about 3 or more doses, about 4 or more doses, about 5 or more doses, about 7 or more doses, about 10 or more doses, about 15 or more doses, about 25 or more doses, about 40 or more doses, about 50 or more doses, or about 100 or more doses).

In some embodiments, an administered dose of the pharmaceutical composition is about 1 µg of protein per kg subject body mass or more (such as about 2 µg of protein per kg subject body mass or more, about 5 µg of protein per kg subject body mass or more, about 10 µg of protein per kg subject body mass or more, about 25 µg of protein per kg subject body mass or more, about 50 µg of protein per kg subject body mass or more, about 100 µg of protein per kg subject body mass or more, about 250 µg of protein per kg subject body mass or more, about 500 µg of protein per kg subject body mass or more, about 1 mg of protein per kg subject body mass or more, about 2 mg of protein per kg subject body mass or more, or about 5 mg of protein per kg subject body mass or more).

In some embodiments, a therapeutic amount of a cell composition is administered. Typically, precise amount of the compositions of the present invention to be administered can be determined by a physician with consideration of individual differences in age, weight, tumor size, extent of infection or metastasis, and condition of the patient (subject). It can generally be stated that a pharmaceutical composition comprising engineered cells, e.g. T cells, as described herein may be administered at a dosage of $10^4$ to $10^9$ cells/kg body weight, such as $10^5$ to $10^6$ cells/kg body weight, including all integer values within those ranges. Engineered cell compositions, such as T cell compositions, may also be administered multiple times at these dosages. The cells can be administered by using infusion techniques that are commonly known in immunotherapy (see, e.g., Rosenberg et al, New Eng. J. of Med. 319:1676, 1988). The optimal dosage and treatment regime for a particular patient can readily be determined by one skilled in the art of medicine by monitoring the patient for signs of disease and adjusting the treatment accordingly.

A variety of means are known for determining if administration of a therapeutic composition of the invention sufficiently modulates immunological activity by eliminating, sequestering, or inactivating immune cells mediating or capable of mediating an undesired immune response; inducing, generating, or turning on immune cells that mediate or are capable of mediating a protective immune response; changing the physical or functional properties of immune cells; or a combination of these effects. Examples of measurements of the modulation of immunological activity include, but are not limited to, examination of the presence or absence of immune cell populations (using flow cytometry, immunohistochemistry, histology, electron microscopy, polymerase chain reaction (PCR)); measurement of the functional capacity of immune cells including ability or resistance to proliferate or divide in response to a signal (such as using T-cell proliferation assays and pepscan analysis based on 3H-thymidine incorporation following stimulation with anti-CD3 antibody, anti-T-cell receptor antibody, anti-CD28 antibody, calcium ionophores, PMA (phorbol 12-myristate 13-acetate) antigen presenting cells loaded with a peptide or protein antigen; B cell proliferation assays); measurement of the ability to kill or lyse other cells (such as cytotoxic T cell assays); measurements of the cytokines, chemokines, cell surface molecules, antibodies and other products of the cells (e.g., by flow cytometry, enzyme-linked immunosorbent assays, Western blot analysis, protein microarray analysis, immunoprecipitation analysis); measurement of biochemical markers of activation of immune cells or signaling pathways within immune cells (e.g., Western blot and immunoprecipitation analysis of tyrosine, serine or threonine phosphorylation, polypeptide cleavage, and formation or dissociation of protein complexes; protein array analysis; DNA transcriptional, profiling using DNA arrays or subtractive hybridization); measurements of cell death by apoptosis, necrosis, or other mechanisms (e.g., annexin V staining, TUNEL assays, gel electrophoresis to measure DNA laddering, histology; fluorogenic caspase assays, Western blot analysis of caspase substrates); measurement of the genes, proteins, and other molecules produced by immune cells (e.g., Northern blot analysis, polymerase chain reaction, DNA microarrays, protein microarrays, 2-dimensional gel electrophoresis, Western blot analysis, enzyme linked immunosorbent assays, flow cytometry); and measurement of clinical symptoms or outcomes such as improvement of autoimmune, neurodegenerative, and other diseases involving self-proteins or self-polypeptides (clinical scores, requirements for use of additional therapies, functional status, imaging studies) for example, by measuring relapse rate or disease severity (using clinical scores known to the ordinarily skilled artisan) in the case of multiple sclerosis, measuring blood glucose in the case of type I diabetes, or joint inflammation in the case of rheumatoid arthritis.

VII. ARTICLES OF MANUFACTURE AND KITS

Also provided herein are articles of manufacture comprising the pharmaceutical compositions described herein in suitable packaging. Suitable packaging for compositions (such as ophthalmic compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

Further provided are kits comprising the pharmaceutical compositions (or articles of manufacture) described herein, which may further comprise instruction(s) on methods of using the composition, such as uses described herein. The kits described herein may also include other materials desirable from a commercial and user standpoint, including other buffers, diluents, filters, needles, syringes, and package inserts with instructions for performing any methods described herein.

VIII. THERAPEUTIC APPLICATIONS

The pharmaceutical compositions described herein (including pharmaceutical composition comprising the variant ICOSL polypeptides, the immunomodulatory proteins, the conjugates, the engineered cells and infectious agents described herein) can be used in a variety of therapeutic applications, such as the treatment of a disease. For example, in some embodiments the pharmaceutical composition is used to treat inflammatory or autoimmune disorders, cancer, organ transplantation, viral infections, and/or bacterial infections in a mammal. The pharmaceutical composition can modulate (e.g. increase or decrease) an immune response to treat the disease.

Such methods and uses include therapeutic methods and uses, for example, involving administration of the molecules or engineered cells, or compositions containing the same, to a subject having a disease, condition, or disorder. In some cases, such as described, the disease or disorder is an autoimmune or inflammatory disease or disorder. In some cases, such as described, the disease or disorder is a tumor or cancer. In some embodiments, the molecule or engineered cell is administered in an effective amount to effect treatment of the disease or disorder. Uses include uses of molecules containing a variant ICOSL polypeptide, immunomodulatory protein, conjugate, engineered cell and infectious agents in such methods and treatments, and in the preparation of a medicament in order to carry out such therapeutic methods. In some embodiments, the methods are carried out by administering a variant ICOSL polypeptide, immunomodulatory protein, conjugate, engineered cell, and infectious agent, or compositions comprising the same, to the subject having or suspected of having the disease or condition. In some embodiments, the methods thereby treat the disease or condition or disorder in the subject.

In some embodiments, the provided methods are applicable to therapeutic administration of variant ICOSL polypeptides, the immunomodulatory proteins, the conjugates, the engineered cells and infectious agents described herein. It is within the level of a skilled artisan, in view of the provided disclosure, to choose a format for the indication depending on the type of modulation of the immune response, e.g. increase or decrease that is desired.

In some embodiments, a pharmaceutical composition provided herein that stimulates the immune response is administered, which can be useful, for example, in the treatment of cancer, viral infections, or bacterial infections. In some embodiments, the pharmaceutical composition contains a variant ICOSL polypeptide in a format that exhibits agonist activity of its cognate binding partner CD28 or ICOS and/or that stimulates or initiates costimulatory signaling via CD28 or ICOS. Exemplary formats of an ICOSL polypeptide for use in connection with such therapeutic applications include, for example, an immunomodulatory protein or "stack" of a variant ICOSL polypeptide and an IgSF domain or variant thereof that binds to a tumor antigen (e.g. Nkp30 or affinity-modified variant) (also called a "tumor-localizing IgSF domain), a conjugate containing a variant ICOSL polypeptide linked to a tumor-targeting moiety (also called a tumor-localizing moiety), an engineered cell expressing a transmembrane immunomodulatory protein or an infectious agent comprising a nucleic acid molecule encoding a transmembrane immunomodulatory protein, such as for expression of the transmembrane immunomodulatory protein in an infected cell (e.g. tumor cell or APC, e.g. dendritic cell).

Pharmaceutical compositions comprising engineered cells and the methods described herein can be used in adoptive cell transfer applications. In some embodiments, cell compositions comprising engineered cells can be used in associated methods to, for example, modulate immunological activity in an immunotherapy approach to the treatment of, for example, a mammalian cancer or, in other embodiments the treatment of autoimmune disorders. The methods employed generally comprise a method of contacting a TIP of the present invention with a mammalian cell under conditions that are permissive to specific binding of the affinity modified IgSF domain and modulation of the immunological activity of the mammalian cell. In some embodiments, immune cells (such as tumor infiltrating lymphocytes (TILs), T-cells (including CD8+ or CD4+ T-cells), or APCs) are engineered to express as a membrane protein and/or as a soluble variant ICOSL polypeptide, immunomodulatory protein, or conjugate as described herein. The engineered cells can then contact a mammalian cell, such as an APC, a second lymphocyte or tumor cell in which modulation of immunological activity is desired under conditions that are permissive of specific binding of the affinity modified IgSF domain to a counter-structure on the mammalian cell such that immunological activity can be modulated in the mammalian cell. Cells can be contacted in vivo or ex vivo.

In some embodiments, the engineered cells are autologous cells. In other embodiments, the cells are allogeneic. In some embodiments, the cells are autologous engineered cells reinfused into the mammal from which it was isolated. In some embodiments, the cells are allogenic engineered cells infused into the mammal. In some embodiments, the cells are harvested from a patient's blood or tumor, engineered to express a polypeptide (such as the variant ICOSL polypeptide, immunomodulatory protein, or conjugate as described herein), expanded in an in vitro culture system (for example, by stimulating the cells), and reinfused into the patient to mediate tumor destruction. In some embodiments, the methods are conducted by adoptive cell transfer wherein cells expressing the TIP (e.g., a T-cell) are infused back into the patient. In some embodiments, the therapeutic compositions and methods of the invention are used in the treatment of a mammalian patient of cancers such as lymphoma, lymphoid leukemia, myeloid leukemia, cervical cancer, neuroblastoma, or multiple myeloma.

In some embodiments, the pharmaceutical composition can be used to inhibit growth of mammalian cancer cells (such as human cancer cells). A method of treating cancer can include administering an effective amount of any of the pharmaceutical compositions described herein to a subject with cancer. The effective amount of the pharmaceutical composition can be administered to inhibit, halt, or reverse progression of cancers.

The cancers that can be treated by the pharmaceutical compositions and the treatment methods described herein include, but are not limited to, melanoma, bladder cancer, hematological malignancies (leukemia, lymphoma, myeloma), liver cancer, brain cancer, renal cancer, breast cancer, pancreatic cancer (adenocarcinoma), colorectal cancer, lung cancer (small cell lung cancer and non-small-cell lung cancer), spleen cancer, cancer of the thymus or blood cells (i.e., leukemia), prostate cancer, testicular cancer, ovarian cancer, uterine cancer, gastric carcinoma, a musculoskeletal cancer, a head and neck cancer, a gastrointestinal cancer, a germ cell cancer, or an endocrine and neuroendocrine cancer. In some embodiments, the cancer is Ewing's sarcoma. In some embodiments, the cancer is selected from melanoma, lung cancer, bladder cancer, and a hematological malignancy. In some embodiments, the cancer is a lymphoma, lymphoid leukemia, myeloid leukemia, cervical cancer, neuroblastoma, or multiple myeloma.

Human cancer cells can be treated in vivo, or ex vivo. In ex vivo treatment of a human patient, tissue or fluids containing cancer cells are treated outside the body and then the tissue or fluids are reintroduced back into the patient. In some embodiments, the cancer is treated in a human patient in vivo by administration of the therapeutic composition into the patient.

In some embodiments, the pharmaceutical composition is administered as a monotherapy (i.e., as a single agent) or as a combination therapy (i.e., in combination with one or more additional anticancer agents, such as a chemotherapeutic drug, a cancer vaccine, or an immune checkpoint inhibitor. In some embodiments, the pharmaceutical composition can also be administered with radiation therapy.

In some embodiments, the pharmaceutical composition is administered as a monotherapy (i.e., as a single agent) or as a combination therapy (i.e., in combination with one or more additional anticancer agents, such as a chemotherapeutic drug, a cancer vaccine, or an immune checkpoint inhibitor. In some embodiments, the pharmaceutical composition can also be administered with radiation therapy. In some aspects, the immune checkpoint inhibitor blocks PD-1 interactions with PD-L1 and/or PD-L2. In some cases, the immune checkpoint inhibitor is an antibody or antigen binding fragment thereof that specifically binds PD-1, PD-L1 or PD-L2. In some cases, the immune checkpoint inhibitor is an anti-PD-1 antibody, such as nivolumab or pembrolizumab or an antigen binding fragment thereof. In some cases, the immune checkpoint inhibitor blocks or is an antagonist of CTLA-4, such as is an anti-CTLA-4 antibody or antigen binding fragment thereof. In some aspects of the present disclosure, the immune checkpoint inhibitor is tremelimumab or ipilimumab.

In some embodiments, the pharmaceutical composition suppresses an immune response, which can be useful in the treatment of inflammatory or autoimmune disorders, or organ transplantation. In some embodiments, the pharmaceutical composition contains a variant ICOSL polypeptide in a format that exhibits antagonist activity of its cognate binding partner CD28 or ICOS and/or that blocks or inhibits costimulatory signaling via CD28 or ICOS. Exemplary formats of an ICOSL polypeptide for use in connection with such therapeutic applications include, for example, a variant ICOSL polypeptide that is soluble (e.g. variant ICOSL-Fc fusion protein), an immunomodulatory protein or "stack" of a variant ICOSL polypeptide and another IgSF domain, including soluble forms thereof that are Fc fusions, an engineered cell expressing a secretable immunomodulatory protein, or an infectious agent comprising a nucleic acid molecule encoding a secretable immunomodulatory protein, such as for expression and secretion of the secretable immunomodulatory protein in an infected cell (e.g. tumor cell or APC, e.g. dendritic cell).

In some embodiments, the inflammatory or autoimmune disorder is antineutrophil cytoplasmic antibodies (ANCA)-associated vasculitis, a vasculitis, an autoimmune skin disease, transplantation, a Rheumatic disease, an inflammatory gastrointestinal disease, an inflammatory eye disease, an inflammatory neurological disease, an inflammatory pulmonary disease, an inflammatory endocrine disease, or an autoimmune hematological disease.

In some embodiments, the inflammatory and autoimmune disorders that can be treated by the pharmaceutical composition described herein is Addison's Disease, allergies, alopecia areata, Alzheimer's, antineutrophil cytoplasmic antibodies (ANCA)-associated vasculitis, ankylosing spondylitis, antiphospholipid syndrome (Hughes Syndrome), asthma, atherosclerosis, rheumatoid arthritis, autoimmune hemolytic anemia, autoimmune hepatitis, autoimmune inner ear disease, autoimmune lymphoproliferative syndrome, autoimmune myocarditis, autoimmune oophoritis, autoimmune orchitis, azoospermia, Behcet's Disease, Berger's Disease, bullous pemphigoid, cardiomyopathy, cardiovascular disease, celiac Sprue/coeliac disease, chronic fatigue immune dysfunction syndrome (CFIDS), chronic idiopathic polyneuritis, chronic inflammatory demyelinating, polyradicalneuropathy (CIDP), chronic relapsing polyneuropathy (Guillain-Barré syndrome), Churg-Strauss Syndrome (CSS), cicatricial pemphigoid, cold agglutinin disease (CAD), COPD (chronic obstructive pulmonary disease), CREST syndrome, Crohn's disease, dermatitis, herpetiformus, dermatomyositis, diabetes, discoid lupus, eczema, epidermolysis bullosa acquisita, essential mixed cryoglobulinemia, Evan's Syndrome, exopthalmos, fibromyalgia, Goodpasture's Syndrome, Graves' Disease, Hashimoto's thyroiditis, idiopathic pulmonary fibrosis, idiopathic thrombocytopenia purpura (ITP), IgA nephropathy, immunoproliferative disease or disorder, inflammatory bowel disease (IBD), interstitial lung disease, juvenile arthritis, juvenile idiopathic arthritis (JIA), Kawasaki's Disease, Lambert-Eaton Myasthenic Syndrome, lichen planus, lupus nephritis, lymphocytic hypophysitis, Ménière's Disease, Miller Fish Syndrome/acute disseminated encephalomyeloradiculopathy, mixed connective tissue disease, multiple sclerosis (MS), muscular rheumatism, myalgic encephalomyelitis (ME), myasthenia gravis, ocular inflammation, pemphigus foliaceus, pemphigus vulgaris, pernicious anaemia, polyarteritis nodosa, polychondritis, polyglandular syndromes (Whitaker's syndrome), polymyalgia rheumatica, polymyositis, primary agammaglobulinemia, primary biliary cirrhosis/autoimmune cholangiopathy, psoriasis, psoriatic arthritis, Raynaud's Phenomenon, Reiter's Syndrome/reactive arthritis, restenosis, rheumatic fever, rheumatic disease, sarcoidosis, Schmidt's syndrome, scleroderma, Sjörgen's Syndrome, stiff-man syndrome, systemic lupus erythematosus (SLE), systemic scleroderma, Takayasu arteritis, temporal arteritis/giant cell arteritis, thyroiditis, Type 1 diabetes, ulcerative colitis, uveitis, vasculitis, vitiligo, interstitial bowel disease or Wegener's Granulomatosis. In some embodiments, the inflammatory or autoimmune disorder is selected from interstitial bowel disease, transplant, Crohn's disease, ulcerative colitis, multiple sclerosis, asthma, rheumatoid arthritis, and psoriasis.

In some embodiments, the inflammatory or autoimmune disorder is a chronic autoimmune disease. In some embodiments, the inflammatory or autoimmune disorder is Sjogren's Syndrome (pSS) or Systemic Lupus Erythematosus (SLE). In some embodiments, the inflammatory or autoimmune disorder is an inflammatory bowel disease (IBD). In some examples, the inflammatory or autoimmune disorder is Crohn's Disease. In some embodiments, the inflammatory or autoimmune disorder is an IBD-related disease or disorder, e.g. interstitial lung disease (ILD). In some embodiments, the inflammatory or autoimmune disorder is psoriatic arthritis or rheumatoid arthritis. In some embodiments, the pharmaceutical composition is administered to modulate an autoimmune condition. For example, suppressing an immune response can be beneficial in methods for inhibiting rejection of a tissue, cell, or organ transplant from a donor by a recipient. Accordingly, in some embodiments, the pharmaceutical compositions described herein are used to limit or prevent graft-related or transplant related diseases or disorders, such as graft versus host disease (GvHD). In some embodiments, the pharmaceutical compositions are used to suppress autoimmune rejection of transplanted or grafted bone marrow, organs, skin, muscle, neurons, islets, or parenchymal cells.

In some embodiments, a pharmaceutical composition provided herein, such as a variant ICOSL IgSF (e.g. IgV) Fc fusion protein provided herein, is used to treat psoriatic arthritis (PsA). In some cases, the PsA affects one or more joints, such as fingers, toes, arms or legs, including elbows, wrists, hands and feet, or sacroliliac joint. In some cases, the PsA is mild and/or affects four or less joints. In some cases the PsA is moderate and/or affects four or more joints. In some cases, a subject with PsA may exhibit pain, stiffness or inflammation in the spine or neck, or in the one more joints.

In some embodiments, a pharmaceutical composition provided herein, such as a variant ICOSL IgSF (e.g. IgV) Fc fusion protein provided herein, is used to treat rheumatoid arthritis (RA). In some cases, RA affects joints, lining of joints, and/or non-joint structures in the body (e.g., skin, eyes, lungs, heart, kidneys, salivary glands, nerve tissue, bone marrow or blood vessels). In some embodiments, RA or RA symptoms are chronic.

In some embodiments, a pharmaceutical composition provided herein, such as a variant ICOSL IgSF (e.g. IgV) Fc fusion protein provided herein, is used to treat GVHD. In some embodiments, the GVHD is acute GVHD (aGVHD). In some cases, aGVHD occurs after allogeneic hematopoietic stem cell transplant (HSCT) and/or a reaction of donor immune cells against host tissues. In some case, the aGVHD manifests in the skin, liver or gastrointestinal tract.

In some embodiments, a pharmaceutical composition provided herein, such as a variant ICOSL IgSF (e.g. IgV) Fc fusion protein provided herein, is used to treat an autoimmune condition associated with an organ transplant. In some cases, treating the autoimmune condition associated with an organ transplant may prolong the survival of the host and transplanted organ. In some embodiments, treating the autoimmune condition associated with an organ transplant includes prophylaxis of or inhibiting or preventing transplant rejections by a subject that is the recipient of the organ transplant.

In some embodiments, a pharmaceutical composition provided herein, such as a variant ICOSL IgSF (e.g. IgV) Fc fusion protein provided herein, is used to treat an inflammatory bowel disease (IBD). In some embodiments, a pharmaceutical composition provided herein, such as a variant ICOSL IgSF (e.g. IgV) Fc fusion protein provided herein, is used to treat Crohn's disease. In some embodiments, the Crohn's disease can include a subtype from Crohn's colitis, Crohn's enteritis, Crohn's iletis or Crohn's enterocolitis.

In some embodiments, a pharmaceutical composition provided herein, such as a variant ICOSL IgSF (e.g. IgV) Fc fusion protein provided herein, is used to treat systemic lupus erythematosus (SLE). In some embodiments, a pharmaceutical composition provided herein, such as a variant ICOSL IgSF (e.g. IgV) Fc fusion protein provided herein, is used to treat Sjogren's Syndrome.

IX. EXEMPLARY EMBODIMENTS

Among the provided embodiments are:

1. A variant ICOS Ligand (ICOSL) polypeptide, comprising one or more amino acid modifications in an immunoglobulin superfamily (IgSF) domain of an ICOSL reference polypeptide, wherein the ICOSL reference polypeptide is a truncated extracellular domain comprising a contiguous sequence of amino acids comprising amino acids 1-112 and a C-terminal truncation of at least 25 amino acids with reference to the ICOSL extracellular domain sequence set forth in SEQ ID NO: 32.

2. The variant ICOSL polypeptide of embodiment 1, wherein the variant ICOSL polypeptide exhibits altered binding to the ectodomain(s) of ICOS or CD28 compared to the binding of the ICOSL reference polypeptide for the same ectodomain(s).

3. The variant ICOSL polypeptide of embodiment 1 or embodiment 2, wherein the variant ICOSL polypeptide exhibits increased binding to the ectodomain(s) of ICOS or CD28 compared to the binding of the ICOSL reference polypeptide for the same ectodomain(s).

4. The variant ICOSL polypeptide of any of embodiments 1-3, wherein the C-terminal truncation is of at least 30, at least 40, at least 50, at least 60, at least 70, at least 80, at least 90, at least 100, at least 125 amino acid residues.

5. The variant ICOSL polypeptide of any of embodiments 1-4, wherein the ICOSL reference polypeptide is altered in or lacks a protease cleavage site set forth as amino acids 204-209 of SEQ ID NO: 32.

6. The variant ICOSL polypeptide of any of embodiments 1-5, wherein the ICOSL reference polypeptide comprises the sequence of amino acids set forth in SEQ ID NO: 545.

7. The variant ICOSL polypeptide of any of embodiments 1-5, wherein the ICOSL reference polypeptide consists of the sequence of amino acids set forth in SEQ ID NO: 545.

8. A variant ICOSL Ligand (ICOSL) polypeptide, comprising one or more amino acid modifications in an ICOSL reference polypeptide, wherein the ICOSL reference polypeptide consists of the sequence of amino acids set forth in SEQ ID NO: 545.

9. A variant ICOS Ligand (ICOSL) polypeptide, comprising one or more amino acid modifications in an immunoglobulin superfamily (IgSF) domain of an ICOSL reference polypeptide, wherein the ICOSL reference polypeptide is altered in one or more amino acids corresponding to amino acids 204-209 with reference to SEQ ID NO: 32.

10. The variant ICOSL polypeptide of embodiment 8 or embodiment 9, wherein the variant ICOSL polypeptide exhibits altered binding to one or more of its binding partner(s) compared to the binding of the ICOSL reference polypeptide for the one or more binding partner(s).

11. The variant ICOSL polypeptide of embodiment 8 or embodiment 9, wherein the variant ICOSL polypeptide exhibits increased binding to one or more of its binding partner(s) compared to the binding of the ICOSL reference polypeptide for the one or more binding partner(s).

12. The variant ICOSL polypeptide of any of embodiments 9-11, wherein the alteration comprises a deletion of one or more contiguous amino acids corresponding to amino acids 204-209 with reference to SEQ ID NO: 32.

13. The variant ICOSL polypeptide of any of embodiments 1-6 and 9-12, wherein the ICOSL reference polypeptide comprises the sequence of amino acids set forth in any of SEQ ID NOS: 600-605.

14. The variant ICOSL polypeptide of any of embodiments 1-6 and 9-12, wherein the ICOSL reference polypeptide consists of the sequence of amino acids set forth in any of SEQ ID NOS: 600-605.

15. The variant ICOSL polypeptide of any of embodiments 1-6 and 9-14, wherein the alteration comprises at least one amino acid substitution at one or both of position 207 and 208 corresponding to positions set forth in SEQ ID NO: 32.

16. The variant ICOSL polypeptide of embodiment 15, wherein the at least one amino acid substitution is N207A, N207G or L208G, or a conservative amino acid substitution thereof.

17. The variant ICOSL polypeptide of any of embodiments 9-16, wherein the reference ICOSL polypeptide comprises the sequence of amino acids set forth in any of SEQ ID NOS: 623-628.

18. The variant ICOSL polypeptide of any of embodiments 9-17, wherein the reference ICOSL polypeptide consists of the sequence of amino acids set forth in any of SEQ ID NOS: 623-628.

19. The variant ICOSL polypeptide of any of embodiments 5-7 and 9-18, wherein the variant ICOSL polypeptide exhibits reduced proteolytic cleavage when expressed from a cell, optionally compared to a full-length extracellular domain of the variant ICOSL polypeptide when expressed from the same cell.

20. The variant ICOSL polypeptide of embodiment 19, wherein the cell is a mammalian cell.

21. The variant ICOSL polypeptide of embodiment 19 or embodiment 20, wherein the cell is a Chinese Hamster Ovary (CHO) cell line or a derivative thereof.

22. The variant ICOSL polypeptide of any of embodiments 1-21, wherein the amino acid modification is an amino acid substitution, insertion or deletion.

23. The variant of any of embodiments 1-22, wherein the one or more amino acid modifications are in a position corresponding to position(s) selected from 10, 11, 13, 16, 18, 20, 25, 26, 27, 30, 33, 37, 38, 42, 43, 47, 52, 54, 57, 61, 62, 67, 71, 72, 74, 75, 77, 78, 80, 84, 89, 90, 92, 93, 94, 96, 97, 98, 99, 100, 102, 103, 107, 109, 110, 111, 113, 115, 116, 117, 119, 120, 121, 122, 126, 129, 130, 132, 133, 135, 137, 138, 139, 140, 142, 143, 144, 146, 151, 152, 153, 154, 155, 156, 158, 161, 164, 166, 168, 172, 173, 175, 190, 192, 193, 194, 198, 201, 203, 207, 208, 210, 212, 217, 218, 220, 221, 224, 225, or 227 with reference to SEQ ID NO:32.

24. The variant of any of embodiments 1-23, wherein the one or more amino acid modifications are selected from M10V, M10I, V11E, S13G, E16V, S18R, A20T, A20V, S25G, R26S, F27C, F27S, N30D, Y33del, Q37R, T38P, K42E, T43A, Y47H, N52A, N52C, N52D, N52G, N52H, N52K, N52L, N52M, N52P, N52Q, N52R, N52S, N52T, N52V, N52Y, S54A, S54F, S54P, N57A, N57D, N57E, N57F, N57H, N57K, N57L, N57M, N57P, N57Q, N57S, N57T, N57V, N57W, N57Y, R61C, R61S, Y62F, L67P, A71T, G72R, L74Q, R75Q, D77G, F78L, L80P, N84Q, D89G, E90A, K92R, F93L, H94D, H94E, L96F, L96I, V97A, L98F, S99G, Q100A, Q100D, Q100E, Q100G, Q100K, Q100L, Q100M, Q100N, Q100P, Q100R, Q100S, Q100T, Q100V, L102R, G103E, V107A, V107I, S109G, S109N, V110A, V110D, V110N, E111del, T113E, H115Q, H115R, V116A, A117T, N119Q, F120I, F120S, S121G, V122A, V122M, S126R, S126T, H129P, S130G, S132F, Q133H, E135K, T137A, F138L, T139S, C140del, C140D, S142F, I143T, I143V, N144D, Y146C, V151A, Y152C, Y152H, W153R, I154F, N155H, N155Q, K156M, D158G, L161M, L161P, Q164L, L166Q, N168Q, F172S, L173S, M175T, T190A, T190S, S192G, V193A, V193M, N194D, C198R, N201S, L203F, L203P, N207Q, L208P, V210A, S212G, D217G, D217V, I218N, I218T, E220G, R221G, R221I, R221K, I224V, T225A, T225S, N227K, or a conservative amino acid substitution thereof.

25. The variant ICOSL polypeptide of any of embodiments 1-24, wherein the one or more amino acid modifications are in a position corresponding to position(s) 52, 57 or 100.

26. The variant ICOSL polypeptide of any of embodiments 1-25, wherein the one or more amino acid modifications are selected from N52A, N52C, N52D, N52G, N52H, N52K, N52L, N52M, N52Q, N52R, N52S, N52T, N52V, N52Y, N52K, S54A, S54P, N57A, N57D, N57E, N57F, N57H, N57K, N57L, N57M, N57P, N57Q, N57S, N57T, N57V, N57Y, N57W, Q100A, Q100D, Q100G, Q100K, Q100L, Q100M, Q100N, Q100P, Q100R, Q100S, Q100T or Q100V.

27. The variant ICOSL polypeptide of any of embodiments 1-26, wherein the one or more amino acid modifications are selected from among N52Y/N57Y/F138L/L203P, N52H/N57Y/Q100P, N52S/Y146C/Y152C, N52H/C198R, N52H/C140D/T225A, N52H/C198R/T225A, N52H/K92R, N52H/S99G, N57Y/Q100P, N52S/S130G/Y152C, N52S/ Y152C, N52S/C198R, N52Y/N57Y/Y152C, N52Y/N57Y/ H129P/C198R, N52H/L161P/C198R, N52S/T113E, N52D/ S54P, N52K/L208P, N52S/Y152H, N52D/V151A, N52H/ I143T, N52S/L80P, N52S/R75Q/L203P, N52S/D158G, N52D/Q133H, N52S/N57Y/H94D/L96F/L98F/Q100R, N52S/N57Y/H94D/L96F/L98F/Q100R/G103E/F120S, N52S/G103E, N52H/F78L/Q100R, N52H/N57Y/Q100R/ V110D, N52H/N57Y/R75Q/Q100R/V110D, N52H/N57Y/ Q100R, N52H/N57Y/L74Q/Q100R/V110D, N52H/Q100R, N52H/S121G, A20V/N52H/N57Y/Q100R/S109G, N52H/ N57Y/R61S/Q100R/V110D/L173S, N52H/N57Y/Q100R/ V122A, N52H/N57Y/Q100R/F172S, N52H/N57Y, N52S/ F120S, N52S/V97A, N52S/G72R, N52S/A71T/A117T, N52S/E220G, Y47H/N52S/V107A/F120S, N52H/N57Y/ Q100R/V110D/S132F/M175T, E16V/N52H/N57Y/Q100R/ V110D/H115R/Y152C/K156M/C198R,      Q37R/N52H/ N57Y/Q100R/V110N/S142F/C198R/D217V/R221G, N52H/N57Y/Q100R/V110D/C198R, N52H/N57Y/Q100R/ V110D/V116A/L161M/F172S/S192G/C198R, F27S/N52H/ N57Y/V110N, N52S/H94E/L96I/S109N/L166Q, S18R/ N52S/F93L/I143V/R221G,      A20T/N52D/Y146C/Q164L, V11E/N30D/N52H/N57Y/H94E/L96I/L98F/N194D/ V210A/I218T, N52S/H94E/L96I/V122M, N52H/N57Y/ H94E/L96I/F120I/S126T/W153R/I218N,      M10V/S18R/ N30D/N52S/S126R/T139S/L203F,      S25G/N30D/N52S/ F120S/N227K, N30D/N52S/L67P/Q100K/D217G/R221K/ T225S,      N52H/N57Y/Q100R/V110D/A117T/T190S/ C198R, N52H/N57Y/Q100R/V110D/F172S/C198R, S25G/ F27C/N52H/N57Y/Q100R/V110D/E135K/L173S/C198R, N52H/N57Y/V110A/C198R/R221I,      M10I/S13G/N52H/ N57Y/D77G/V110A/H129P/I143V/F172S/V193M, C198R,      N52H/N57Y/R61C/Y62F/Q100R/V110N/F120S/ C198R,      N52H/N57Y/Q100R/V110D/H115R/C198R, N52H/N57Y/Q100R/V110D/N144D/F172S/C198R, N52S/ H94E/L98F/Q100R,      N52S/E90A,      N30D/K42E/N52S, N52S/F120S/I143V/I224V, N52H/N57Y/Q100R/V110D/ C198R/S212G, N52H/N57Y/Q100R/C198R, N52S/N194D, N52H/N57Y/Q100R/L102R/V110D/H115R/C198R, N52H/ N57Y/Q100R/V110D/C198R/S212G,      N52H/N57Y/ Q100R/C198R,      N52S/N194D,      N52H/N57Y/Q100R/ L102R/V110D/H115R/C198R, N52S/S54P, T38P/N52S/ N57D, N52H/C140del/T225A, N52H/F78L/Q100R/C198R, N52H/N57Y/R75Q/Q100P/V110D,      N52H/N57Y/L74Q/ V110D/S192G,      N52H/S121G/C198R,      N52S/F120S/ N227K, N52S/A71T/A117T/T190A/C198R, T43A/N52H/ N57Y/L74Q/D89G/V110D/F172S,      N52H/N57Y/Q100R/ V110D/S132F/M175T, N52D, N52H/N57Y/Q100R/V107/ V110D/I154F/C198R/R221G,      N52Q/N207Q,      N168Q/ N207Q, N52Q/N168Q, N52Q/N84Q, N52Q/N119Q, N52Q/ N84Q/N168Q,      N52Q/N84Q/N207Q,      N52Q/N119Q/ N155Q, N52H/N84Q/N119Q, N52H/N84Q, N52H/N84Q/ N168Q/N207Q,      N52Q/N84Q/N155Q/N168Q,      N52Q/ N84Q/N119Q/N168Q,      N52Q/N84Q/N119Q/N207Q, N52Q/N84Q/N119Q/N155Q, N52Q/N84Q/N119Q/N155Q/ N207Q, N52Y/F138L/L203P, N57Y/Q100R/C198R, N57Y/ F138L/L203P, Q100R/F138L, N52H/N57Y/Q100R/H115R/

C198R, N52H/N57Y/Q100R/F172S/C198R, N52H/N57Y/ Q100R/H115R/F172S/C198R,      N52H/N57Y/Q100R/ H115R/I143V/F172S/C198R, N52H/N57Y/Q100R/L102R/ H115R/F172S/C198R,      N52H/V122A/F172S/C198R, N52H/N57Y/Q100R/H115R/F172S/N194D, N52H/N57Y/ H115R/F172S/C198R,      N52H/N57Y/Q100R/H115R/ C198R, N52H/N57Y/H115R, N52H/N57Y/Q100R/H115R, N52H/N57Y/Q100R/H115R/F172S/I224V,      N52H/N57Y/ Q100R/H115R/F172S, N52H/N57Y/Q100R/F172S, N52H/ Q100R/H115R/I143T/F172S, N52H/N57Y/Q100P/H115R/ F172S, N52Y/N57Y/Q100P/F172S, E16V/N52H/N57Y/ Q100R/V110D/H115R/C198R, E16V/N52H/N57Y/Q100R/ V110D/H115R/Y152C/K156M/F172S/C198R,      N52S/ E90A/H115R, N30D/K42EN52S/H115R, N30D/K42E/ N52S/H115R/C198R/R221I,      N30D/K42E/N52S/H115R/ C198R, N30D/K42E/N52S/H115R/F172S/N194D, N52S/ H115R/F120S/I143V/C198R, N52S/H115R/F172S/C198R, N52H/N57Y/Q100P/C198R, N52H/N57Y/Q100P H115R/ F172S/C198R, N52H/N57Y/Q100P/F172S/C198R, N52H/ N57Y/Q100P/H115R, N52H/N57Y/Q100P/H115R/C198R, N52H/Q100R/C198R, N52H/Q100R/H115R/F172S, N52H/ Q100R/F172S/C198R,      N52H/Q100R/H115R/F172S/ C198R, N52H/N57Y/Q100R/F172S/C198R, N52A/N57F/ Q100S, N52A/N57H/Q100S, N52A/N57Y/Q100A, N52D/ N57A/Q100A, N52D/Q100S, N52G/Q100A, N52H/ Q100A, N52M/N57H/Q100S, N52M/N57W/Q100P, N52Q/ N57F, N52Q/N57S/Q100A, N52R/N57L/Q100A, N52R/ N57Y/Q100P, N52R/N57Y/Q100S, N52S/N57A/Q100A, N52S/N57H/Q100E, N52S/N57L/Q100S, N52S/N57M/ Q100S, N52S/N57Y/Q100S, N52S/N57Y/Q100M, N52S/ N57Y/Q100V, N52T/N57H/Q100S, N52T/N57H/Q100A, N52T/N57Y/Q100A, N52V/N57L/Q100A, N52H/N57Y/ Q100K, N52K/N57Y/Q100R, N52L/N57H/Q100R, N52R/ N57F/Q100N, N52R/N57F/Q100P, N52R/N57F/Q100R, N52R/N57F/Q100T, N52R/N57H/Q100K, N52R/N57L/ Q100S, N52R/N57W/Q100K, N52R/N57W, N52R/N57Y/ Q100R, N52C/N57E/Q100S, N52G/N57P/Q100D, N52G/ N57V/Q100G, N52G/N57V, N52L/N57V, N52P/N57P, N52P/N57S/Q100G, N52S/N57L/Q100G, N52T/N57K/ Q100P, N52V/N57T/Q100L, N57Q/Q100P, or R26S/N52H/ N57Y/V110D/T137A/C198R.

28. The variant ICOSL polypeptide of any of embodiments 1-24, wherein the one or more amino acid modifications are selected from among F120S/Y152H/N201S, E111del, Y33del, N168Q/N207Q, N84Q/N207Q, N155Q/ N207Q, N119Q/N168Q, N119Q/N207Q, N119Q/N155Q, N84Q/N119Q,      N84Q/N155Q/N168Q,      N84Q/N168Q/ N207Q, N84Q/N155H/N207Q, N155Q/N168Q/N207Q, N119Q N155Q/N168Q, N119Q/N168Q/N207Q, N84Q/ N119Q/N207Q, N119Q/N155H/N207Q, N84Q/N119Q/ N155Q, N84Q/N119Q/N155Q/N168Q, N84Q/N155Q/ N168Q/N207Q, N84Q/N119Q/N155Q/N207Q, N84Q/ N119Q/N155Q/N168Q/N207Q or F138L/L203P.

29. The variant ICOSL polypeptide of any of embodiments 1-28, wherein the one or more amino acid modifications are selected from C198R, D158G, E16V, E90A, F120S, F138L, F172S, H115R, H115X, I143T, I143V, I224V, K156M, K42E, K92R, L102R, L203P, L208P, N194D, N30D, N52A, N52D, N52G, N52H, N52K, N52L, N52M, N52Q, N52R, N52S, N52T, N52Y, N57F, N57H, N57K, N57L, N57M, N57P, N57S, N57V, N57W, N57Y, Q100A, Q100D, Q100E, Q100K, Q100M, Q100P, Q100P, Q100R, Q100S, Q100T, Q133H, R221I, R75Q, S54A, S54P, T113E, T225A, V110D, V122A, Y146C, or Y152C; or A117T, A20V, A71T, A91G, A91G, AE88D, C140del, C198R, D158G, D77G, D90K, E117G, E135K, E16V, E81A, E88D, E90A, F120I, F120S, F138L, F172S, F27C, F92Y, G72R, H115R, H115X, H129P, H94E, I118V, I127T, I143T, I143V, I154F, I218N, I218T, I224V, K156M, K169E, K36G, K42E, K89R, K92R, K93R, L102R, L161P, L166Q, L173S, L203F, L203P, L208P, L209P, L40M, L70Q, L70R, L74Q, L80P, L96I, L98F, M10I, M10V, N115Q, N119Q, N122S, N144D, N155X, N168Q, N168X, N178S, N194D, N207Q, N207X, N227K, N25S, N30D, N52A, N52D, N52G, N52H, N52K, N52L, N52M, N52Q, N52R, N52S, N52T, N52V, N52Y, N57A, N57F, N57H, N57L, N57M, N57S, N57V, N57W, N57Y, N63S, N84Q, Q100A, Q100E, Q100G, Q100K, Q100M, Q100N, Q100P, Q100R, Q100S, Q100T, Q100V, Q133H, R221G, R221I, S109G, S109N, S114T, S121G, S126R, S126T, S130G, S132F, S13G, S18R, S192G, S212G, S25G, S54A, S54P, S99G, T113E, T120S, T130A, T139S, T190A, T199S, T225A, T41I, V107I, V110A, V110D, V11E, V122A, V122M, V193M, V210A, W153R, Y146C, Y152C, or Y152H.

30. The variant ICOSL polypeptide of any of embodiments 1-29, wherein the one or more amino acid modifications are selected from among N52S, N52H, N52D, N52H/N57Y/Q100P, N52S/Y146C/Y152C, N52H/C198R, N52H/C198R/T225A, N52H/K92R, N57Y, N52S/C198R, N52S/T113E, S54A, N52D/S54P, N52K/L208P, N52H/I143T, N52S/R75Q/L203P, N52S/D158G, N52D/Q133H, N52H/N57Y/Q100R/V122A, N52H/N57Y/Q100R/F172S, N52H/N57Y/Q100R, N52S/N194D, N52H/N57Y/Q100R/L102R/V110D/H115R/C198R, N52S/E90A, N52S/F120S/I143V/I224V, N52H/N57Y/Q100R/F172S/C198R, N52H/N57Y/Q100R/H115R/F172S/C198R, N52Y/N57Y/Q100P/F172S, E16V/N52H/N57Y/Q100R/V110D/H115R/Y152C/K156M/F172S/C198R, N52S/H115R/F120S/I143V/C198R, N52H/N57Y/Q100P/C198R, N52H/N57Y/Q100P/H115R/F172S/C198R, N52H/N57Y/Q100P/F172S/C198R, N52H/N57Y/Q100P/H115R, N52H/N57Y/Q100P/H115R/C198R, N52H/Q100R/C198R, N52H/Q100R/H115X/F172S/C198R, N52H/Q100R/H115R/F172S/C198R, N52H/N57Y/Q100R/H115R/F172S/C198R, N52H/N57Y/Q100R/H115R/F172S, N52H/N57Y/Q100R/H115R/F172S/C198R, Q100R, N52Y/F138L/L203P, N57Y/Q100R/C198R, N57Y/F138L/L203P, N57Y/Q100P, Q100R/F138L, N52H/N57Y/Q100R/H115R, N52H/N57Y/Q100R/F172S, N52H/N57Y/Q100R/H115R/F172S/I224V, N52H/N57Y/Q100R/H115R/F172S, N52H/N57Y/Q100R/H115R/C198R, N52H/N57Y/Q100R/F172S/C198R, N52H/N57Y/Q100R/H115R/F172S/C198R, N52H/N57Y/Q100R/H115R/I143V/F172S/C198R, N52H/N57Y/Q100R/L102R, H115R/F172S/C198R, N52H/N57Y/Q100R/H115R F172S/N194D, N52H/N57Y/H115R/F172S/C198R, N52H/N57Y/Q100R/H115R/C198R, N52H/N57Y/H115R, N52H/Q100R/H115R/I143T F172S, N52H/N57Y/Q100P/H115R/F172S, E16V/N52H/N57Y/Q100R/V110D/H115R/C198R, N52S/E90A/H115R, N30D/K42E/N52S/H115R/C198R/R221I, N30D/K42E/N52S/H115R/C198R, N30D/K42E/N52S/H115R/F172S/N194D, N30D/K42E/N52S/H115R, N52S/E90A/H115R, N30D/K42E/N52S/H115R, N52A/N57H/Q100S, N52A/N57Y/Q100A, N52D/Q100S, N52G/Q100A, N52M/N57H/Q100S, N52M/N57W/Q100P, N52Q/N57S/Q100A, N52R/N57L/Q100A, N52S/N57H/Q100E, N52S/N57L/Q100S, N52S/N57M/Q100S, N52S/N57Y/Q100M, N52T/N57H/Q100S, N52R/N57F/Q100P, N52R/N57F/Q100T, N52R/N57W/Q100K, N52R/N57W, N52P/Q100D, N52G/N57V/Q100G, N52G/N57V, N52L/N57V, N52S/N57L/Q100G or N52T/N57K/Q100P; or N52S, N52H, N52D, N52Y/N57Y/F138L/L203P, N52H/N57Y/Q100P, N52S/Y146C/Y152C, N52H/C198R, N52H/C140del/T225A, N52H/C198R/T225A, N52H/K92R, N52H/S99G, N57Y, N57Y/Q100P, N52S/S130G/Y152C, N52S/Y152C, N52S/C198R, N52Y/N57Y/Y152C, N52Y/N57Y/H129P/C198R, N52H/L161P/C198R, N52S/T113E, S54A, N52D/S54P, N52K/L208P, N52S/Y152H, N52H/I143T, N52S/L80P, N52S/D158G, N52D/Q133H, L70Q/A91G/N144D, L70Q/A91G/E117G/I118V/T120S/T130A, L70R/A91G/I118V/T120S/T130A/T199S, L70Q/E81A/A91G/I118V/T120S/I127T/T130A, N63S/L70Q/A91G/S114T/I118V/T120S/T130A, T41I/A91G, E88D/K89R/D90K/A91G/F92Y/K93R/N122S/N178S, E88D/K89R/D90K/A91G/F92Y/K93R, AE88D/K89R/D90K/A91G/F92Y/K93R, K36G/L40M, N52H/N57Y/Q100R/V122A, N52H/N57Y/Q100R/F172S, N52H/N57Y/Q100R, N52S/F120S/N227K, N52S/N194D, N52S/F120S, N52S/G72R, N52S/A71T/A117T/T190A/C198R, N52H/N57Y/Q100R/V107I/V110D/S132F/I154F/C198R/R221G, E16V/N52H/N57Y/Q100R/V110D/H115R/Y152C/K156M/C198R, N52H/N57Y/Q100R/V110D/C198R, V11E/N30D/N52H/N57Y/H94E/L96I/L98F/N194D/V210A/I218T, N52S/H94E/L96I/V122M, N52H/N57Y/H94E/L96I/F120I/S126T/W153R/I218N, M10V/S18R/N30D/N52S/S126R/T139S/L203F, S25G/N30D/N52S/F120S/N227K, N52H/N57Y/Q100R/V110D/F172S/C198R, S25G/F27C/N52H/N57Y/Q100R/V110D/E135K/L173S/C198R, N52H/N57Y/V110A/C198R/R221I, M10I/S13G/N52H/N57Y/D77G/V110A/H129P/I143V/F172S/V193M, C198R, N52H/N57Y/Q100R/L102R/V110D/H115R/C198R, N52H/N57Y/Q100R/V110D/N144D/F172S/C198R, N52S/H94E/L98F/Q100R, N52S/E90A, N52S/F120S/I143V/I224V, N52H/N57Y/Q100R/F172S/C198R, N52H/N57Y/Q100R/H115R/F172S/C198R, N52Y/N57Y/Q100P/F172S, E16V/N52H/N57Y/Q100R/V110D/H115R/Y152C/K156M/F172S/C198R, N52S/H115R/F120S/I143V/C198R, N52H/N57Y/Q100P/C198R, N52H/N57Y/Q100P/H115R/F172S/C198R, N52H/N57Y/Q100P/F172S/C198R, N52H/N57Y/Q100P/H115R, N52H/N57Y/Q100P/H115R/C198R, N52H/Q100R/C198R, N52H/Q100R/H115R/F172S, N52H/Q100R/H115X/F172S/C198R, N52H/Q100R/H115R/F172S/C198R, N52H/N57Y/Q100R/F172S/C198R, N52H/N57Y/Q100R/H115R/F172S/C198R, N52H/N57Y/Q100R/H115R/F172S, N52H/N57Y/Q100R/H115R/F172S/C198R, N52S/H94E/L96I/S109N/L166Q/, N52H/N57Y/Q100R/C198R, N52H/N57Y/L74Q/V110D/S192G, N52H/Q100R, N52H/S121G/C198R, A20V/N52H/N57Y/Q100R/S109G, N52H/N57Y/Q100P/C198R, N52H/N57Y/Q100R/V110D/C198R/S212G, L70Q/A91G/I118A/T120S/T130A/K169E, Q100R, N52Y/F138L/L203P, N57Y/Q100R/C198R, N57Y/F138L/L203P, N52H, N57Y, N57Y/Q100P, N52H/N57Y/Q100R/H115R, N52H/N57Y/Q100R/F172S, N52H/N57Y/Q100R/H115R/F172S/I224V, N52H/N57Y/Q100R/H115R/F172S, N52H/N57Y/Q100R/H115R/C198R, N52H/N57Y/Q100R/F172S/C198R, N52H/N57Y/Q100R/H115R/F172S/C198R, N52H/N57Y/Q100R/H115R/I143V/F172S/C198R, N52H/N57Y/Q100R/L102R H115R/F172S/C198R, N52H/N57Y/Q100R/H115R F172S/N194D, N52H/N57Y/H115R/F172S/C198R, N52H/N57Y/Q100R/H115R/C198R, N52H/N57Y/H115R, N52H/Q100R/H115R/I143T F172S, N52H/N57Y/Q100P/H115R/F172S, E16V/N52H/N57Y/Q100R/V110D/H115R/C198R, N30D/K42E/

N52S/H115R/C198R R221I, N52S/E90A/H115R, N30D/K42E/N52S/H115R, N52S/H115R/F172S/C198R, N119Q, N207Q, N52Q/N207X, N168X/N207X, N52Q/N168Q, N84Q/N207Q, N119Q N155X, N52Q/N119Q, N52Q/N84Q/N207Q, N119Q/N155Q/N168Q, N52H/N84Q/N119Q, N52Q/N84Q/N155X/N168X, N52A/N57F/Q100S, N52A/N57H/Q100S, N52A/N57Y/Q100A, N52D/N57A/Q100A, N52D/Q100S, N52G/Q100A, N52H/Q100A, N52M/N57H/Q100S, N52M/N57W/Q100P, N52Q/N57F, N52Q/N57S/Q100A, N52R/N57L/Q100A, N52R/N57Y/Q100P, N52R/N57Y/Q100S, N52S/N57A/Q100A, N52S/N57H/Q100E, N52S/N57L/Q100S, N52S/N57M/Q100S, N52S/N57Y/Q100S, N52S/N57Y/Q100M, N52S/N57Y/Q100V, N52T/N57H/Q100S, N52T/N57H/Q100A, N52T/N57Y/Q100A, N52V/N57L/Q100A, N52H/N57Y/Q100K, N52K/N57Y/Q100R, N52L/N57H/Q100R, N52R/N57F/Q100N, N52R/N57F/Q100P, N52R/N57F/Q100R, N52R/N57F/Q100T, N52R/N57L/Q100S, N52R/N57W/Q100K, N52R/N57W, N52G/N57V, N52L/N57V, N52S/N57L/Q100G, or N52T/N57K/Q100P.

31. The variant ICOSL polypeptide of any of embodiments 1-30, wherein the variant ICOSL polypeptide exhibits increased binding to the ectodomain of ICOS or CD28 compared to the binding of the reference ICOSL polypeptide to the same ectodomain.

32. The variant ICOSL polypeptide of any of embodiments 1-31, wherein the one or more amino acid modifications are selected from C198R, D158G, E16V, E90A, F120S, F138L, F172S, H115R, I143V, I224V, K156M, K42E, K92R, L102R, L203P, L208P, N194D, N30D, N52A, N52D, N52G, N52H, N52K, N52L, N52M, N52Q, N52R, N52S, N52T, N52Y, N57F, N57H, N57L, N57M, N57S, N57V, N57W, N57Y, Q100A, Q100E, Q100G, Q100K, Q100M, Q100P, Q100R, Q100S, Q133H, S212G, S54A, S54P, T113E, V110D, V122A, Y146C, Y152C, or T225A.

33. The variant ICOSL polypeptide of any of embodiments 1-33, wherein the one or more amino acid modifications are selected from among N52A/N57Y/Q100A, N52D/Q100S, N52G/Q100A, N52M/N57H/Q100S, N52M/N57W/Q100P, N52Q/N57S/Q100A, N52R/N57L/Q100A, N52S/N57H/Q100E, N52S/N57L/Q100S, N52S/N57M/Q100S, N52S/N57Y/Q100M, N52T/N57H/Q100S, N52R/N57F/Q100P, N52R/N57F/Q100T, N52R/N57W/Q100K, N52R/N57W, N52G/N57V, N52L/N57V, N52S/N57L/Q100G, N52T/N57K/Q100P, N52S, N52H, N52D, N52Y/N57Y/F138L/L203P, N52H/N57Y/Q100P, N52S/Y146C/Y152C, N52H/C198R, N52H/C198R/T225A, N52H/K92R, N57Y, N52S/C198R, N52S/T113E, S54A, N52D/S54P, N52K/L208P, N52H/I143T, N52S/D158G, N52D/Q133H, N52H/N57Y/Q100R/V110D/C198R/S212G, N52H/N57Y/Q100R/V122A, N52H/N57Y/Q100R/F172S, N52H/N57Y/Q100R, N52S/N194D, N52H/N57Y/Q100R/L102R/V110D/H115R/C198R, N52S/E90A, N52S/F120S/I143V/I224V, N52H/N57Y/Q100R/F172S/C198R, N52H/N57Y/Q100R/H115R/F172S/C198R, N52Y/N57Y/Q100P/F172S, E16V/N52H/N57Y/Q100R/V110D/H115R/Y152C/K156M/F172S/C198R, N52S/H115R/F120S/I143V/C198R, N52H/N57Y/Q100P/C198R, N52H/N57Y/Q100P/H115R/F172S/C198R, N52H/N57Y/Q100P/F172S/C198R, N52H/N57Y/Q100P/H115R, N52H/N57Y/Q100P/H115R/C198R, N52H/Q100R/C198R, N52H/Q100R/H115R/F172S, N52H/Q100R/H115X/F172S/C198R, N52H/Q100R/H115R/F172S/C198R, N52H/N57Y/Q100R/H115R/F172S/C198R, N52H/N57Y/Q100R/H115R/F172S/C198R, Q100R, N52Y/

F138L/L203P, N57Y/Q100R/C198R, N57Y/F138L/L203P, N52H, N57Y, N57Y/Q100P, Q100R/F138L, N52H/N57Y/Q100R/H115R, N52H/N57Y/Q100R/F172S, N52H/N57Y/Q100R/H115R/F172S/I224V, N52H/N57Y/Q100R/H115R/F172S, N52H/N57Y/Q100R/H115R/C198R, N52H/N57Y/Q100R/F172S/C198R, N52H/N57Y/Q100R/H115R/F172S/C198R, N52H/N57Y/Q100R/H115R/I143V/F172S/C198R, N52H/N57Y/Q100R/L102R H115R/F172S/C198R, N52H/N57Y/Q100R/H115R F172S/N194D, N52H/N57Y/H115R/F172S/C198R, N52H/N57Y/Q100R/H115R/C198R, N52H/N57Y/H115R, N52H/Q100R/H115R/I143T/F172S, N52H/N57Y/Q100P/H115R/F172S, E16V/N52H/N57Y/Q100R/V110D/H115R/C198R, N52S/E90A/H115R, N52S/E90A/H115R, or N30D/K42E/N52S/H115R.

34. The variant ICOSL polypeptide of any of embodiments 1-33, wherein the variant ICOSL polypeptide exhibits increased binding to the ectodomain of ICOS and CD28 compared to the binding of the reference ICOSL polypeptide to the same ectodomains.

35. The variant ICOSL polypeptide of any of embodiments 1-34, wherein the variant ICOSL polypeptide comprises the sequence of amino acids set forth in any one of SEQ ID NOS: 546-599, 734-781, 783, 786, 788, 792, 796, 798, 800, 802, 804, 806, 808, 811, 813, 815, 817, 818, 820, 822, 824, 826, 827, 829, 831, 833, 834, 836, 838, 840-843, 845, 847, 848, 850-853, 855, 857, 907, 910, or a sequence of amino acids that exhibits at least 90%, 91%%, 92%, 93%, 94%, 95%, 96%, 97%, 98%, or 99% sequence identity to any one of SEQ ID NOS: 546-599, 734-781, 783, 786, 788, 792, 796, 798, 800, 802, 804, 806, 808, 811, 813, 815, 817, 818, 820, 822, 824, 826, 827, 829, 831, 833, 834, 836, 838, 840-843, 845, 847, 848, 850-853, 855, 857, 907, 910.

36. The variant ICOSL polypeptide of any of embodiments 1-34, wherein the variant ICOSL polypeptide consists of the sequence of amino acids set forth in any one of SEQ ID NOS: 546-599, 734-781, 783, 786, 788, 792, 796, 798, 800, 802, 804, 806, 808, 811, 813, 815, 817, 818, 820, 822, 824, 826, 827, 829, 831, 833, 834, 836, 838, 840-843, 845, 847, 848, 850-853, 855, 857, 907, 910, or a sequence of amino acids that exhibits at least 90%, 91%%, 92%, 93%, 94%, 95%, 96%, 97%, 98%, or 99% sequence identity to any one of SEQ ID NOS: 546-599, 734-781, 783, 786, 788, 792, 796, 798, 800, 802, 804, 806, 808, 811, 813, 815, 817, 818, 820, 822, 824, 826, 827, 829, 831, 833, 834, 836, 838, 840-843, 845, 847, 848, 850-853, 855, 857, 907, or 910.

37. A variant ICOS Ligand (ICOSL) polypeptide, comprising an IgV domain or specific binding fragment thereof, an IgC domain or a specific binding fragment thereof, or both, wherein the variant ICOSL polypeptide comprises one or more amino acid modifications in an ICOSL reference polypeptide or a specific binding fragment thereof corresponding to amino acid modifications are selected from N52A, N52C, N52D, N52G, N52K, N52L, N52M, N52R, N52T, N52V, N57A, N57E, N57F, N57H, N57K, N57L, N57M, N57P, N57Q, N57S, N57T, N57V, N57W, Q100A, Q100D, Q100G, Q100L, Q100M, Q100N, Q100R, Q100S, Q100T or Q100V. with reference to SEQ ID NO:32.

38. The variant ICOSL polypeptide of embodiment 37, wherein the one or more amino acid modifications are selected from among N52A/N57F/Q100S, N52A, /N57H/Q100S, N52A/N57Y/Q100A, N52D/N57A/Q100A, N52D/Q100S, N52G/Q100A, N52H/Q100A, N52M/N57H/Q100S, N52M/N57W/Q100P, N52Q/N57F, N52Q/N57S/Q100A, N52R/N57L/Q100A, N52R/N57Y/Q100P, N52R/N57Y/Q100S, N52S/N57A/Q100A, N52S/N57H/Q100E, N52S/N57L/Q100S, N52S/N57M/Q100S, N52S/N57Y/Q100S, N52S/N57Y/Q100M, N52S/N57Y/Q100V, N52T/

N57H/Q100S, N52T/N57H/Q100A, N52T/N57Y/Q100A, N52V/N57L/Q100A, N52H/N57Y/Q100K, N52K/N57Y/Q100R, N52L/N57H/Q100R, N52R/N57F/Q100N, N52R/N57F/Q100P, N52R/N57F/Q100R, N52R/N57F/Q100T, N52R/N57H/Q100K, N52R/N57L/Q100S, N52R/N57W/Q100K, N52R/N57W, N52R/N57Y/Q100R, N52C/N57E/Q100S, N52G/N57P/Q100D, N52G/N57V/Q100G, N52G/N57V, N52L/N57V, N52P/N57P, N52P/N57S/Q100G, N52S/N57L/Q100G, N52T/N57K/Q100P, N52V/N57T/Q100L or N57Q/Q100P.

39. The variant ICOSL polypeptide of embodiment 37 or embodiment 38, wherein the ICOSL reference polypeptide is a mammalian ICOSL or a specific binding fragment thereof.

40. The variant ICOSL polypeptide of any of embodiments 37-39, wherein the ICOSL reference polypeptide is a human ICOSL or a specific binding fragment thereof.

41. The variant ICOSL polypeptide of any one of embodiments 37-40, wherein the ICOSL reference polypeptide comprises (i) the sequence of amino acids set forth in SEQ ID NO: 32, (ii) a sequence of amino acids that has at least 95% sequence identity to SEQ ID NO:32; or (iii) a portion of (i) or (ii) comprising an IgV domain or IgC domain or specific binding fragments thereof or both.

42. The variant ICOSL polypeptide of any one of embodiments 37-41, wherein:
the specific binding fragment of the IgV domain or IgC domain has a length of at least 50, 60, 70, 80, 90, 100, 110 or more amino acids; or
the specific binding fragment of the IgV domain comprises a length that is at least 80% of the length of the IgV domain set for as amino acids 19-129 of SEQ ID NO:5 and/or the specific binding fragment of the IgC domain comprises a length that is at least 80% of the length of the IgC domain set forth as amino acids 141-227 of SEQ ID NO:5.

43. The variant ICOSL polypeptide of any of embodiments 37-42, wherein the variant ICOSL polypeptide comprises the IgV domain or a specific fragment thereof and the IgC domain or a specific fragment thereof.

44. The variant ICOSL polypeptide of any of embodiments 37-43, wherein the variant ICOSL polypeptide comprises the sequence of amino acids set forth in any one of SEQ ID NOS: 638-685, 905, 908, or a sequence of amino acids that exhibits at least 90%, 91%%, 92%, 93%, 94%, 95%, 96%, 97%, 98%, or 99% sequence identity to any one of SEQ ID NOS: 638-685, 905, 908.

45. The variant ICOSL polypeptide of any of embodiments 37-43, wherein the variant ICOSL polypeptide consists of the sequence of amino acids set forth in any one of SEQ ID NOS: 638-685, 905, 908, or a sequence of amino acids that exhibits at least 90%, 91%%, 92%, 93%, 94%, 95%, 96%, 97%, 98%, or 99% sequence identity to any one of SEQ ID NOS: 638-685, 905, 908.

46. The variant ICOSL polypeptide of any of embodiments 37-43, wherein the variant ICOSL polypeptide comprises the IgV domain or a specific binding fragment thereof.

47. The variant ICOSL polypeptide of any of embodiments 37-43 and 46, wherein the variant ICOSL polypeptide comprises the sequence of amino acids set forth in any one of SEQ ID NOS: 686-781, 907, 910, or a sequence of amino acids that exhibits at least 90%, 91%%, 92%, 93%, 94%, 95%, 96%, 97%, 98%, or 99% sequence identity to any one of SEQ ID NOS: 686-781, 907, 910.

48. The variant ICOSL polypeptide of any of embodiments 37-43 and 46, wherein the variant ICOSL polypeptide consists of the sequence of amino acids set forth in any one of SEQ ID NOS: 686-781, 907, 910, or a sequence of amino acids that exhibits at least 90%, 91%%, 92%, 93%, 94%, 95%, 96%, 97%, 98%, or 99% sequence identity to any one of SEQ ID NOS: 686-781, 907, 910.

49. The variant ICOSL polypeptide of any of embodiments 37-43 and 46-48, wherein the IgV domain or specific binding fragment thereof is the only ICOSL portion of the variant ICOSL polypeptide.

50. The variant ICOSL polypeptide of any of embodiments 37-42, wherein the IgC domain or specific binding fragment thereof is the only ICOSL portion of the variant ICOSL polypeptide.

51. The variant ICOSL polypeptide of any of embodiments 37-50, wherein the variant ICOSL polypeptide exhibits altered binding to the ectodomain of ICOS or CD28 compared to the binding of the ICOSL reference polypeptide for the same ectodomain.

52. The variant ICOSL polypeptide of any of embodiments 37-51, wherein the variant ICOSL polypeptide exhibits increased binding to the ectodomain(s) of ICOS or CD28 compared to the binding of the ICOSL reference polypeptide for the same ectodomain(s).

53. The variant ICOSL polypeptide of any of embodiments 1-52, wherein the binding is increased more than 1.2-fold, 1.5-fold, 2-fold, 3-fold, 4-fold, 5-fold, 6-fold, 7-fold, 8-fold, 9-fold, 10-fold, 20-fold, 30-fold, 40-fold, 50-fold or 60-fold.

54. The variant ICOSL polypeptide of any of embodiments 1-53, wherein the ICOS is a human ICOS.

55. The variant ICOSL polypeptide of any of embodiments 1-54, wherein the CD28 is a human CD28.

56. The variant ICOSL polypeptide of any of embodiments 1-55, wherein the variant ICOSL polypeptide exhibits decreased binding to the ectodomain of CTLA-4 compared to the binding of the reference ICOSL polypeptide for the same ectodomain.

57. The variant ICOSL polypeptide of embodiment 56, wherein the binding is decreased more than 1.2-fold, 1.5-fold, 2-fold, 3-fold, 4-fold, 5-fold, 6-fold, 7-fold, 8-fold, 9-fold, 10-fold, 20-fold, 30-fold, 40-fold, 50-fold or 60-fold.

58. The variant ICOSL polypeptide of any of embodiments 1-57, wherein the CTLA-4 is a human CTLA-4.

59. The variant ICOSL polypeptide of any of embodiments 1-58, wherein the altered (increased or decreased) binding is altered (increased or decreased) binding affinity.

60. The variant ICOSL polypeptide of any of embodiments 1-59, wherein the variant ICOSL polypeptide comprises up to 1, 2, 3, 4, 5, 6, 7, 8, 9, 10, 11, 12, 13, 14, 15, 16, 17, 18, 19 or 20 amino acid modifications, optionally amino acid substitutions, insertions and/or deletions.

61. The variant ICOSL polypeptide of any of embodiments 1-60, wherein the variant ICOSL polypeptide exhibits at least or at least about 90%, 91%, 92%, 93%, 94%, 95%, 96%, 97%, 98% or 99% sequence identity to the ICOSL reference polypeptide.

62. The variant ICOSL polypeptide of any of embodiments 1-61 that is a soluble protein.

63. The variant ICOSL polypeptide of any of embodiments 1-62, wherein:
the variant ICOSL polypeptide lacks a transmembrane domain and intracellular signaling domain; and/or
when expressed from a cell, the variant ICOSL polypeptide is not expressed on the surface of the cell.

64. The variant ICOSL polypeptide of any of embodiments 1-61, wherein the variant ICOSL polypeptide further comprises a transmembrane domain.

65. The variant ICOSL polypeptide of embodiment 64, wherein the transmembrane domain comprises the sequence of amino acids set forth as residues 257-277 of SEQ ID NO:5 or a functional variant thereof that exhibits at least 85% sequence identity to residues 257-277 of SEQ ID NO:5.

66. The variant ICOSL polypeptide of embodiment 64 or embodiment 65, further comprising a cytoplasmic signaling domain linked to the transmembrane domain.

67. The variant ICOSL polypeptide of embodiment 66, wherein the cytoplasmic signaling domain comprises the sequence of amino acids set forth as residues 278-302 of SEQ ID NO: 5 or a functional variant thereof that exhibits at least 85% sequence identity to residues 278-302 of SEQ ID NO:5.

68. The variant ICOSL polypeptide of any of embodiments 1-67 that is deglycosylated or partially deglycosylated compared to the ICOSL reference sequence.

69. An immunomodulatory protein, comprising the variant ICOSL polypeptide of any of embodiments 1-68 and a half-life extending moiety.

70. The immunomodulatory protein of embodiment 69, wherein the half-life extending moiety comprises a multimerization domain, albumin, an albumin-binding polypeptide, Pro/Ala/Ser (PAS), a C-terminal peptide (CTP) of the beta subunit of human chorionic gonadotropin, polyethylene glycol (PEG), long unstructured hydrophilic sequences of amino acids (XTEN), hydroxyethyl starch (HES), an albumin-binding small molecule, or a combination thereof.

71. The immunomodulatory protein of embodiment 69 or embodiment 70, wherein the half-life extending moiety is or comprises Pro/Ala/Ser (PAS) and the variant ICOSL polypeptide is PASylated.

72. The immunomodulatory protein of embodiment 71, wherein the half-life extending moiety comprises the sequence set forth in SEQ ID NO: 904.

73. The immunomodulatory protein of embodiment 69 or embodiment 70, wherein the half-life extending moiety is or comprises a multimerization domain.

74. The immunomodulatory protein of embodiment 73, wherein the multimerization domain is selected from an Fc region of an immunoglobulin, a leucine zipper, an isoleucine zipper or a zinc finger.

75. The immunomodulatory protein of embodiment 73 or embodiment 74, wherein the variant ICOSL polypeptide is linked, directly or indirectly via a linker, to the multimerization domain.

76. The immunomodulatory protein of any of embodiments 73-75, wherein the immunomodulatory protein is a multimer comprising a first variant ICOSL polypeptide linked to a first multimerization domain and a second variant ICOSL polypeptide linked to a second multimerization domain, wherein the first and second multimerization domains interact to form a multimer comprising the first and second variant ICOSL polypeptide. 77. The immunomodulatory protein of embodiment 76, wherein the multimer is a dimer.

78. The immunomodulatory protein of embodiment 76 or embodiment 77, wherein the first variant ICOSL polypeptide and the second variant ICOSL polypeptide are the same.

79. The immunomodulatory protein of embodiment 77 or embodiment 78, wherein the dimer is a homodimer.

80. The immunomodulatory protein of embodiment 77, wherein the dimer is a heterodimer.

81. The immunomodulatory protein of any of embodiments 73-80, wherein the multimerization domain is or comprises an Fc region of an immunoglobulin.

82. The immunomodulatory protein of embodiment 81, wherein the Fc region is of an immunoglobulin G1 (IgG1) or an immunoglobulin G2 (IgG2) protein.

83. The immunomodulatory protein of embodiment 81 or embodiment 82, wherein the immunoglobulin protein is human and/or the Fc region is human.

84. The immunomodulatory protein of any of embodiments 81-83, wherein the Fc region comprises the sequence of amino acids set forth in SEQ ID NO: 227 or a variant thereof that exhibits at least 90%, 91%, 92%, 93%, 94%, 95%, 96%, 97%, 98% or 99% sequence identity to SEQ ID NO:227.

85. The immunomodulatory protein of any of embodiments 81-84, wherein the Fc region comprises the sequence of amino acids set forth in SEQ ID NO: 226 or a variant thereof that exhibits at least 90%, 91%, 92%, 93%, 94%, 95%, 96%, 97%, 98% or 99% sequence identity to SEQ ID NO:226.

86. The immunomodulatory protein of any of embodiments 81-85, wherein the Fc region exhibits one or more effector functions.

87. The immunomodulatory protein of any of embodiments 81-86, wherein the Fc region exhibits one or more reduced effector function compared to a wildtype Fc region, optionally wherein the wildtype human Fc is of human IgG1.

88. The immunomodulatory protein of embodiment 86 or embodiment 87, wherein the one or more effector function is selected from among antibody dependent cellular cytotoxicity (ADCC), complement dependent cytotoxicity, programmed cell death and cellular phagocytosis.

89. The immunomodulatory protein of embodiment 87 or embodiment 88, wherein the Fc region is a variant Fc region comprising one or more amino acid substitutions compared to the wildtype Fc region.

90. The immunomodulatory protein of embodiment 89, wherein the one or more amino acid substitutions of the variant Fc region are selected from N297G, E233P/L234V/L235A/G236del/S267K or L234A/L235E/G237A, wherein the residue is numbered according to the EU index of Kabat.

91. The immunomodulatory protein of embodiment 90, wherein the variant Fc region further comprises the amino acid substitution C220S, wherein the residues are numbered according to the EU index of Kabat.

92. The immunomodulatory protein of any of embodiments 87-91, wherein the Fc region comprises the sequence of amino acid sequence set forth in any of SEQ ID NOS: 476-478 or a sequence of amino acids that exhibits at least 90%, 91%, 92%, 93%, 94%, 95%, 96%, 97%, 98%, 99% or more sequence identity to any of SEQ ID NOS: 476-478 and contains the amino acid substitutions.

93. The immunomodulatory protein of any of embodiments 87-92, wherein the Fc region comprises K447del, wherein the residue is numbered according to the EU index of Kabat.

94. The immunomodulatory protein of any of embodiments 87-92 and 93, wherein the Fc region comprises the sequence of amino acid sequence set forth in any of SEQ ID NOS: 632-634 or a sequence of amino acids that exhibits at least 90%, 91%, 92%, 93%, 94%, 95%, 96%, 97%, 98%, 99% or more sequence identity to any of SEQ ID NOS: 632-634 and contains the amino acid substitutions.

95. An immunomodulatory protein, comprising:

(a) a variant ICOSL polypeptide comprising one or more amino acid modifications in an immunoglobulin superfamily (IgSF) domain of an ICOSL reference polypeptide, wherein the variant ICOSL polypeptide exhibits altered binding to the ectodomain(s) of ICOS or CD28 compared to the binding of the ICOSL reference polypeptide for the same ectodomain(s); and (b) a variant Fc region comprising amino acid substitutions selected from N297G/K447del, E233P/L234V/ L235A/G236del/S267K/K447del or L234A/L235E/ G237A/K447del compared to wildtype human IgG1, wherein the residues are numbered according to the EU index of Kabat.

96. The immunomodulatory protein of embodiment 95 that is a dimer.

97. The immunomodulatory protein of embodiment 95 or embodiment 96, wherein the variant Fc region further comprises the amino acid substitution C220S, wherein the residues are numbered according to the EU index of Kabat.

98. The immunomodulatory protein of any of embodiments 95-97, wherein the Fc region comprises the sequence of amino acid sequence set forth in any of SEQ ID NOS: 632-634 or a sequence of amino acids that exhibits at least 90%, 91%, 92%, 93%, 94%, 95%, 96%, 97%, 98%, 99% or more sequence identity to any of SEQ ID NOS: 632-634 and contains the amino acid substitutions.

99. The immunomodulatory protein of any of embodiments 95-98, wherein the variant ICOSL polypeptide is linked, directly or indirectly via a linker, to the variant Fc region.

100. The immunomodulatory protein of embodiment 75 and embodiment 99, wherein the linker comprises 1 to 10 amino acids.

101. The immunomodulatory protein of embodiment 100, wherein the linker is selected from AAA, G4S (SEQ ID NO:636), (G$_4$S)$_2$ (SEQ ID NO:229) or GSGGGGS linker (SEQ ID NO: 635).

102. An immunomodulatory protein, comprising the variant ICOSL polypeptide of any of embodiments 1-68 linked to a second polypeptide comprising an immunoglobulin superfamily (IgSF) domain.

103. The immunomodulatory protein of embodiment 102, wherein the IgSF domain is affinity modified and exhibits altered binding to one or more of its cognate binding partner(s) compared to the unmodified or wild-type IgSF domain.

104. The immunomodulatory polypeptide of embodiment 103, wherein the IgSF domain exhibits increased binding to one or more of its cognate binding partner(s) compared to the unmodified or wild-type IgSF domain.

105. The immunomodulatory polypeptide of any one of embodiments 102-104, wherein the variant ICOSL polypeptide is a first ICOSL variant polypeptide and the IgSF domain of the second polypeptide is an IgSF domain from a second variant ICOSL polypeptide of any of embodiments 1-68, wherein the first and second ICOSL variant are the same or different.

106. The immunomodulatory protein of any one of embodiments 102-105, wherein the variant ICOSL polypeptide is capable of specifically binding to CD28 or ICOS and the IgSF domain of the second polypeptide is capable of binding to a binding partner other than one specifically bound by the ICOSL variant polypeptide.

107. The immunomodulatory polypeptide of embodiment 106, wherein the IgSF domain is from a member of the B7 family.

108. The immunomodulatory polypeptide of any of embodiments 102-104 and 106, wherein the IgSF domain is a tumor-localizing moiety that binds to a ligand expressed on a tumor or is an inflammatory-localizing moiety that binds to a ligand expressed on a cell or tissue of an inflammatory environment.

109. The immunomodulatory polypeptide of embodiment 108, wherein the ligand is B7H6.

110. The immunomodulatory polypeptide of embodiment 108 or embodiment 109, wherein the IgSF domain is from NKp30.

111. The immunomodulatory polypeptide of any of embodiments 102-110, wherein the IgSF domain is or comprises an IgV domain.

112. The immunomodulatory polypeptide of any of embodiments 102-111, wherein the variant ICOSL polypeptide is or comprise an IgV domain.

113. The immunomodulatory protein of any of embodiments 102-112, wherein the immunomodulatory protein comprises a multimerization domain linked to one or both of the variant ICOSL polypeptide or the second polypeptide comprising the IgSF domain.

114. The immunomodulatory protein of embodiment 113, wherein the multimerization domain is an Fc domain or a variant thereof with reduced effector function.

115. The immunomodulatory protein of any of embodiments 102-114 that is dimeric.

116. The immunomodulatory protein of embodiment 115 that is homodimeric.

117. The immunomodulatory protein of embodiment 116 that is heterodimeric.

118. A conjugate comprising the variant ICOSL polypeptide of any of embodiments 1-68 or immunomodulatory protein of any of embodiments 69-117 and a heterologous moiety.

119. The conjugate of embodiment 118, wherein the variant ICOSL polypeptide is linked, directly or indirectly via a linker, to the heterologous moiety.

120. The conjugate of any of embodiments 118 or embodiment 119, wherein the targeting moiety is a protein, a peptide, nucleic acid, small molecule or nanoparticle.

121. The conjugate of any of embodiments 118-120, wherein the target moiety is a protein or a peptide.

122. The conjugate of embodiment 121, wherein the conjugate is a fusion protein.

123. A fusion protein, comprising a variant ICOSL polypeptide of any of embodiments 1-68 or immunomodulatory protein of any of embodiments 69-117 and a heterologous moiety.

124. The conjugate or fusion protein of any of embodiments 118-123, wherein the moiety is a targeting moiety that specifically binds to a molecule on the surface of a cell.

125. The conjugate or fusion protein of embodiment 124, wherein the targeting moiety specifically binds to a molecule on the surface of an immune cell.

126. The conjugate or fusion protein of embodiment 125, wherein the immune cell is an antigen presenting cell or a lymphocyte.

127. The conjugate or fusion protein of embodiment 124, wherein the targeting moiety is a tumor-localizing moiety that binds to a molecule on the surface of a tumor.

128. The conjugate or fusion protein of any of embodiments 124-127, wherein the targeting moiety binds to a molecule HER1/EGFR, HER2/ERBB2, CD20, CD25 (IL-2Rα receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor (PDGFR), PDGF-R α, PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), VEGFR2, VEGF-A, integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, metalloproteinases, Ephrin receptor, Ephrin ligands, HGF receptor, CXCR4, CXCR4, Bombesin receptor, SK-1anti-gen, Bcr-abl, RET, MET, TRKB, TIE2, ALK, ROS, EMLA-ALK, ROS1, BRAFV600E, SRC, c-KIT, mTOR, TSC1, TSC2, BTK, KIT, BRCA, CDK 4/6, JAK1, JAK2, BRAF, FLT-3, MEK1, MEK2, SMO or B7-H6 (NCR3LG1).

129. The conjugate or fusion protein of any of embodiments 124-128, wherein the targeting moiety binds to PD-L1.

130. The conjugate or fusion protein of any of embodiments 124-129, wherein the targeting moiety is an antibody or antigen-binding fragment.

131. The conjugate or fusion protein of embodiment 130, wherein the antibody is selected from cetuximab, panitumumab, zalutumumab, nimotuzumab, trastuzumab, Ado-trastuzumab emtansine, Tositumomab (Bexxar®), Rituximab (Rituxan, Mabthera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Afatinib, Axitinib, Bosutinib, Cabozantinib, Ceritinib, Crizotinib, Dabrafenib, Dasatinib, Dinutuximab, Erlotinib, Everolimus, Ibrutinib, Imatinib, Lapatinib, Lenvatinib, Nilotinib, Olaparib, Olaratumab, Palbociclib, Pazopanib, Pertuzumab, Ramucirumab, Regorafenib, Ruxolitinib, Sorafenib, Sunitinib, Temsirolimus, Trametinib, Vandetanib, Vemurafenib, Vismodegib, Basiliximab, Ipilimumab, Nivolumab, pembrolizumab, MPDL3280A, Pidilizumab (CT-011), AMP-224, MSB001078C, or MEDI4736, BMS-935559, LY3300054, atezolizumab, avelumab or durvalumab or is an antigen-binding fragment thereof.

132. The conjugate or fusion protein of embodiment 130 or embodiment 131, wherein the variant ICOSL polypeptide is linked, directly or indirectly via a linker, to the N-terminus of the heavy and/or light chain of the antibody or antigen-binding fragment.

133. The conjugate or fusion protein of embodiment 130 or embodiment 131, wherein the variant ICOSL polypeptide is linked, directly or indirectly via a linker, to the C-terminus of the heavy and/or light chain of the antibody or antigen binding fragment.

134. The conjugate or fusion protein of any of embodiments 118-133, wherein the conjugate is divalent, tetravalent, hexavalent or octavalent.

135. The conjugate or fusion protein of any of embodiments 118-123, wherein the heterologous moiety is or comprises a label for detection or purification of the variant ICOSL polypeptide.

136. A monovalent fusion protein comprising:
(a) a variant ICOSL polypeptide comprising one or more amino acid modifications in an immunoglobulin superfamily (IgSF) domain of an ICOSL reference polypeptide, wherein the variant ICOSL polypeptide exhibits altered binding to the ectodomain(s) of ICOS or CD28 compared to the binding of the ICOSL reference polypeptide for the same ectodomain(s); and
(b) a label for detection or purification of the variant ICOSL polypeptide.

137. The conjugate or fusion protein of embodiment 135 or embodiment 136, wherein the label for detection or purification is selected from a poly-histidine (His) tag, a FLAG-tag, a Myc-tag, or a fluorescent protein-tag.

138. The immunomodulatory protein of any of embodiments 95-101 or the fusion protein of embodiment 136 or embodiment 137, wherein the variant ICOSL polypeptide comprises one or more amino acid modifications are in a position corresponding to position(s) selected from 10, 11, 13, 16, 18, 20, 25, 26, 27, 30, 33, 37, 38, 42, 43, 47, 52, 54, 57, 61, 62, 67, 71, 72, 74, 75, 77, 78, 80, 84, 89, 90, 92, 93, 94, 96, 97, 98, 99, 100, 102, 103, 107, 109, 110, 111, 113, 115, 116, 117, 119, 120, 121, 122, 126, 129, 130, 132, 133, 135, 137, 138, 139, 140, 142, 143, 144, 146, 151, 152, 153, 154, 155, 156, 158, 161, 164, 166, 168, 172, 173, 175, 190, 192, 193, 194, 198, 201, 203, 207, 208, 210, 212, 217, 218, 220, 221, 224, 225, or 227 with reference to SEQ ID NO:32.

139. The immunomodulatory protein or fusion protein of embodiment 138, wherein the one or more amino acid modifications are selected from M10V, M10I, V11E, S13G, E16V, S18R, A20T, A20V, S25G, R26S, F27C, F27S, N30D, Y33del, Q37R, T38P, K42E, T43A, Y47H, N52A, N52C, N52D, N52G, N52H, N52K, N52L, N52M, N52P, N52Q, N52R, N52S, N52T, N52V, N52Y, S54A, S54F, S54P, N57A, N57D, N57E, N57F, N57H, N57K, N57L, N57M, N57P, N57Q, N57S, N57T, N57V, N57W, N57Y, R61C, R61S, Y62F, L67P, A71T, G72R, L74Q, R75Q, D77G, F78L, L80P, N84Q, D89G, E90A, K92R, F93L, H94D, H94E, L96F, L96I, V97A, L98F, S99G, Q100A, Q100D, Q100E, Q100G, Q100K, Q100L, Q100M, Q100N, Q100P, Q100R, Q100S, Q100T, Q100V, L102R, G103E, V107A, V107I, S109G, S109N, V110A, V110D, V110N, E111del, T113E, H115Q, H115R, V116A, A117T, N119Q, F120I, F120S, S121G, V122A, V122M, S126R, S126T, H129P, S130G, S132F, Q133H, E135K, T137A, F138L, T139S, C140del, C140D, S142F, I143T, I143V, N144D, Y146C, V151A, Y152C, Y152H, W153R, I154F, N155H, N155Q, K156M, D158G, L161M, L161P, Q164L, L166Q, N168Q, F172S, L173S, M175T, T190A, T190S, S192G, V193A, V193M, N194D, C198R, N201S, L203F, L203P, N207Q, L208P, V210A, S212G, D217G, D217V, I218N, I218T, E220G, R221G, R221I, R221K, I224V, T225A, T225S, N227K, or a conservative amino acid substitution thereof.

140. The immunomodulatory protein or fusion protein of embodiment 138 or embodiment 139, wherein the ICOSL reference polypeptide comprises (i) the sequence of amino acids set forth in SEQ ID NO:32, (ii) a sequence of amino acids that has at least 95% sequence identity to SEQ ID NO:32; or (iii) a portion of (i) or (ii) comprising an IgV domain or IgC domain or specific binding fragments thereof or both.

141. The immunomodulatory protein or fusion protein of any of embodiments 138-140, wherein the ICOSL reference polypeptide comprises the sequence of amino acids set forth in any of SEQ ID NOS: 196, 545, 600-605 and 623-628.

142. The immunomodulatory protein or fusion protein of any of embodiments 138-141, wherein the ICOSL reference polypeptide consists of the sequence of amino acids set forth in any of SEQ ID NOS: 32, 196, 545, 600-605 and 623-628.

143. A nucleic acid molecule(s), encoding a variant ICOSL polypeptide of any of embodiments 1-68, an immunomodulatory protein of any of embodiments 69-117 and 118-142 or a fusion protein of any of embodiments 123-142.

144. The nucleic acid molecule(s) of embodiment 143 that is synthetic nucleic acid.

145. The nucleic acid molecule(s) of embodiment 143 or embodiment 144 that is CDNA. 146. A vector, comprising the nucleic acid molecule(s) of any of embodiments 143-145.

147. The vector of embodiment 146 that is an expression vector.

148. The vector of embodiment 146 or embodiment 147, wherein the vector is a mammalian expression vector or a viral vector.

149. A cell, comprising the vector of any of embodiments 146-148.

150. The cell of embodiment 149 that is a mammalian cell.

151. The cell of embodiment 149 or embodiment 150 that is a Chinese Hamster Ovary (CHO) cell or a derivative thereof.

152. A method of producing an immunomodulatory protein comprising a variant ICOSL polypeptide, comprising introducing the nucleic acid molecule of any of embodiments 143-145 or vector of any of embodiments 146-148 into a host cell under conditions to express the protein in the cell.

153. The method of embodiment 152, wherein the host cell is a mammalian cell.

154. The method of embodiment 153, wherein the mammalian cell is a Chinese Hamster Ovary cell or a derivative thereof.

155. The method of any of embodiments 152-154, further comprising isolating or purifying the protein from the cell.

156. A protein produced by the method of any of embodiments 152-155.

157. A composition comprising a protein comprising a variant ICOSL polypeptide of any of embodiments 1-68 or an immunomodulatory protein of any of embodiments 69-117, wherein at least 95%, 96%, 97%, 98%, 99% of the individual sequences of the protein or the immunomodulatory protein in the composition have an identical sequence length, optionally wherein the composition is a pharmaceutical composition comprising a pharmaceutically acceptable carrier.

158. The composition of embodiment 157, wherein the protein or immunomodulatory protein is purified from Chinese Hamster Ovary Cells or a derivative thereof.

159. A polynucleotide comprising a nucleic acid encoding a variant ICOSL polypeptide comprising a transmembrane domain of any of embodiments 64-68 and one or more nucleic acid encoding one or more chain of a recombinant antigen receptor.

160. The polynucleotide of embodiment 159, wherein the recombinant antigen receptor is a chimeric antigen receptor (CAR) or an engineered T cell receptor (TCR).

161. The polynucleotide of embodiment 159 or embodiment 160, wherein each of the nucleic acid encoding the variant ICOSL polypeptide and the one or more nucleic acid encoding one or more chain of the recombinant receptor is separated by a nucleic acid encoding a self-cleaving peptide or a peptide that causes ribosome skipping.

162. The polynucleotide of embodiment 161, wherein the polynucleotide comprises the nucleic acid encoding the variant ICOSL polypeptide, a nucleic acid encoding a self-cleaving peptide or a peptide that causes ribosome skipping and a nucleic acid encoding a CAR.

163. The polynucleotide of embodiment 161, wherein the polynucleotide comprises the nucleic acid encoding the variant ICOSL polypeptide, a nucleic acid encoding a first self-cleaving peptide or a peptide that causes ribosome skipping, a nucleic acid encoding one of an engineered TCRalpha chain or an engineered TCRbeta chain, a nucleic acid encoding a second self-cleaving peptide or a peptide that causes ribosome skipping, and a nucleic acid encoding the other of the engineered TCRalpha chain or the engineered TCRbeta chain.

164. The polynucleotide of embodiment 163, wherein the encoded first and second self-cleaving peptide is the same.

165. The polynucleotide of any of embodiments 160-163, wherein the self-cleaving peptide or the peptide that causes ribosome skipping is a T2A, a P2A, a E2A or a F2A.

166. A vector comprising the polynucleotide of any of embodiments 159-165.

167. The vector of embodiment 166, wherein the vector is a viral vector.

168. The vector of embodiment 167, wherein the viral vector is a retroviral vector or a lentiviral vector.

169. An engineered cell comprising the polynucleotide of any of embodiments 159-165 or the vector of any of embodiments 166-168.

170. An engineered cell comprising the variant ICOSL polypeptide of any of embodiments 1-68, the immunomodulatory protein of any of embodiments 69-117, or the fusion protein of any of embodiments 123-142.

171. An engineered cell comprising the nucleic acid molecule of any of embodiments 143-145 or the vector of any of embodiments 146-148.

172. The engineered cell of any of embodiments 169-171, wherein the nucleic acid encoding the variant ICOSL polypeptide, immunomodulatory protein or fusion protein encodes a signal peptide.

173. The engineered cell of any of embodiments 169-172, wherein the variant ICOSL polypeptide, immunomodulatory protein or fusion protein does not comprise a transmembrane domain and/or is not expressed on the surface of the cell.

174. The engineered cell of any of embodiments 169-173, wherein the variant ICOSL polypeptide, immunomodulatory protein or fusion protein is secreted from the engineered cell.

175. The engineered cell of any of embodiments 169-171, wherein the engineered cell comprises a variant ICOSL polypeptide comprising a transmembrane domain of any of embodiments 64-68.

176. The engineered cell of any of embodiments 169-171 and 175, wherein the variant ICOSL polypeptide is expressed on the surface of the cell.

177. The engineered cell of any of embodiments 169-176, wherein the cell is an immune cell.

178. The engineered cell of embodiment 177, wherein the immune cell is an antigen presenting cell (APC) or a lymphocyte.

179. The engineered cell of any of embodiments 169-178 that is a primary cell.

180. The engineered cell of any of embodiments 169-179, wherein the cell is a mammalian cell.

181. The engineered cell of any of embodiments 169-180, wherein the cell is a human cell.

182. The engineered cell of any of embodiments 169-181, wherein the lymphocyte is a T cell.

183. The engineered cell of embodiment 178, wherein the engineered cell is an APC and the APC is an artificial APC.

184. The engineered cell of any of embodiments 169-183, further comprising a chimeric antigen receptor (CAR) or an engineered T-cell receptor.

185. A pharmaceutical composition, comprising the variant ICOSL polypeptide of any of embodiments 1-68, the immunomodulatory protein of any of embodiments 69-117, a conjugate or fusion protein of any of embodiments 118-

142 or an engineered cell of any of embodiments 169-184 or an infectious agent of an of embodiments 216-227.

186. The pharmaceutical composition of embodiment 185, comprising a pharmaceutically acceptable excipient.

187. The pharmaceutical composition of embodiment 185 or 186, wherein the pharmaceutical composition is sterile.

188. An article of manufacture comprising the pharmaceutical composition of any of embodiments 185-187 in a vial.

189. The article of manufacture of embodiment 188, wherein the vial is sealed.

190. A kit comprising the composition of any of embodiments 157-158 and 185-187, and instructions for use.

191. A kit comprising the article of manufacture according to embodiment 189 and 190, and instructions for use.

192. A method of modulating an immune response in a subject, comprising administering the pharmaceutical composition of any of embodiments 157-158 and 185-187 to the subject.

193. A method of modulating an immune response in a subject, comprising administering the engineered cells of any of embodiments 169-184.

194. The method of embodiment 193, wherein the engineered cells are autologous to the subject.

195. The method of embodiment 193, wherein the engineered cells are allogenic to the subject.

196. The method of any of embodiments 193-195, wherein modulating the immune response treats a disease or condition in the subject.

197. The method of any of embodiments 193-196, wherein the immune response is increased.

198. The method of any of embodiments 192, 196 and 197, wherein an immunomodulatory protein or conjugate comprising a variant ICOSL polypeptide linked to a tumor-localizing moiety is administered to the subject.

199. The method of embodiment 198, wherein the tumor-localizing moiety is or comprises a binding molecule that recognizes a tumor antigen.

200. The method of embodiment 199, wherein the binding molecule comprises an antibody or an antigen-binding fragment thereof or comprises a wild-type IgSF domain or variant thereof.

201. The method of any of embodiments 192 and 196-200, wherein the immunomodulatory protein of any of embodiments 102-117 or the conjugate or fusion protein of any of embodiments 118-142 is administered to the subject.

202. The method of any of embodiments 193-197, wherein a variant ICOSL polypeptide that is a transmembrane immunomodulatory protein is administered to the subject.

203. The method of any of embodiments 193-197 and 202, wherein the engineered cell comprising a variant ICOSL polypeptide that is a transmembrane immunomodulatory protein of any of embodiments 64-68 is administered to the subject.

204. The method of embodiment 192-203, wherein the disease or condition is a tumor or cancer.

205. The method of any one of embodiments 192-204, wherein the disease or condition is selected from melanoma, lung cancer, bladder cancer, a hematological malignancy, liver cancer, brain cancer, renal cancer, breast cancer, pancreatic cancer, colorectal cancer, spleen cancer, prostate cancer, testicular cancer, ovarian cancer, uterine cancer, gastric carcinoma, a musculoskeletal cancer, a head and neck cancer, a gastrointestinal cancer, a germ cell cancer, or an endocrine and neuroendocrine cancer.

206. The method of any of embodiments 192-196, wherein the immune response is decreased.

207. The method of any of embodiments 192-196 and 206, wherein a variant ICOSL polypeptide or immunomodulatory protein that is soluble is administered to the subject.

208. The method of embodiment 207, wherein the soluble immunomodulatory protein is an immunomodulatory Fc fusion protein.

209. The method of any of embodiments 192-196 and 206-208, wherein a variant ICOSL polypeptide of any of embodiments 1-63 and 68, the immunomodulatory protein of any of embodiments 70-101 or the fusion protein of embodiment 136 and 137 is administered to the subject.

210. The method of any of embodiments 192-196 and 206-208, wherein an engineered cell comprising a secretable variant ICOSL polypeptide is administered to the subject.

211. The method of any of embodiments 192-196, 206-208 and 210, wherein an engineered cell of any of embodiments 169-174 and 177-184 is administered to the subject.

212. The method of any of embodiments 192-196, 206-208 and 210, wherein an infectious agent encoding a variant ICOSL polypeptide that is a secretable immunomodulatory protein is administered to the subject, optionally under conditions in which the infectious agent infects a tumor cell or immune cell and the secretable immunomodulatory protein is secreted from the infected cell.

213. The method of any of embodiments 192-196 and 206-212, wherein the disease or condition is an inflammatory or autoimmune disease or condition.

214. The method of any of embodiments 192-196 and 206-213, wherein the disease or condition is an Antineutrophil cytoplasmic antibodies (ANCA)-associated vasculitis, a vasculitis, an autoimmune skin disease, transplantation, a Rheumatic disease, an inflammatory gastrointestinal disease, an inflammatory eye disease, an inflammatory neurological disease, an inflammatory pulmonary disease, an inflammatory endocrine disease, or an autoimmune hematological disease.

215. The method of embodiment 213 or embodiment 214, wherein the disease or condition is selected from inflammatory bowel disease, transplant, Crohn's disease, ulcerative colitis, multiple sclerosis, asthma, rheumatoid arthritis, or psoriasis.

216. An infectious agent, comprising a nucleic acid molecule encoding a variant ICOSL polypeptide of any of embodiments 1-68 or an immunomodulatory protein of any of embodiments the immunomodulatory protein of any of embodiments 69-117, or the fusion protein of any of embodiments 123-142.

217. The infectious agent of embodiment 216, wherein the encoded variant ICOSL polypeptide, immunomodulatory protein or fusion protein does not comprise a transmembrane domain and/or is not expressed on the surface of a cell in which it is expressed.

218. The infectious agent of embodiment 216 or embodiment 217, wherein the encoded variant ICOSL polypeptide, immunomodulatory protein or fusion protein is secreted from the infectious agent when it is expressed.

219. The infectious agent of embodiment 218, wherein the encoded variant ICOSL polypeptide comprises a transmembrane domain.

220. The infectious agent of embodiment 216, embodiment 217 or embodiment 219, wherein the encoded variant ICOSL polypeptide is expressed on the surface of a cell in which it is expressed.

221. The infectious agent of any of embodiments 216-220, wherein the infectious agent is a bacteria or a virus.

222. The infectious agent of embodiment 221, wherein the virus is an oncolytic virus.

223. The infectious agent of embodiment 222, wherein the oncolytic virus is an adenoviruses, adeno-associated viruses, herpes viruses, Herpes Simplex Virus, Vesticular Stomatic virus, Reovirus, Newcastle Disease virus, parvovirus, measles virus, vesticular stomatitis virus (VSV), Coxsackie virus or a Vaccinia virus.

224. The infectious agent of embodiment 222, wherein the virus specifically targets dendritic cells (DCs) and/or is dendritic cell-tropic.

225. The infectious agent of embodiment 224, wherein the virus is a lentiviral vector that is pseudotyped with a modified Sindbis virus envelope product.

226. The infectious agent of any of embodiments 216-225, further comprising a nucleic acid molecule encoding a further gene product that results in death of a target cell or that can augment or boost an immune response.

227. The infectious agent of embodiment 226, wherein the further gene product is selected from an anticancer agent, anti-metastatic agent, an antiangiogenic agent, an immuno-modulatory molecule, an immune checkpoint inhibitor, an antibody, a cytokine, a growth factor, an antigen, a cytotoxic gene product, a pro-apoptotic gene product, an anti-apoptotic gene product, a cell matrix degradative gene, genes for tissue regeneration or a reprogramming human somatic cells to pluripotency.

X. EXAMPLES

The following examples are included for illustrative purposes only and are not intended to limit the scope of the invention.

Example 1

Example 1 Generation of Mutant DNA Constructs of IgSF Domains

Example 1 describes the generation of mutant DNA constructs of human ICOSL IgSF domains for translation and expression on the surface of yeast as yeast display libraries.

A. Degenerate Libraries

Mutant DNA constructs encoding a variant of the ECD domain of ICOSL were generated. Constructs were generated based on a wildtype human ICOSL sequence set forth in SEQ ID NO:32 containing the ECD domain as follows:

DTQEKEVRAMVGSDVELSCACPEGSRFDLNDVYVYWQTSESKTVVTYHI

PQNSSLENVDSRYRNRALMSPAGMLRGDFSLRLFNVTPQDEQKFHCLVL

SQSLGFQEVLSVEVTLHVAANFSVPVVSAPHSPSQDELTFTCTSINGYP

RPNVYWINKTDNSLLDQALQNDTVFLNMRGLYDVVSVLRIARTPSVNIG

CCIENVLLQQNLTVGSQTGNDIGERDKITENPVSTGEKNAAT

For libraries that target specific residues for complete or partial randomization with degenerate codons, the DNA encoding SEQ ID NO:32 was ordered from Integrated DNA Technologies (Coralville, IA) as a set of overlapping oligonucleotides of up to 80 base pairs (bp) in length. To generate a library of diverse variants of the ECD, the oligonucleotides contained desired degenerate codons, such as specific mixed base sets to code for various amino acid substitutions, at desired amino acid positions. Degenerate codons were generated using an algorithm at the URL: rosettadesign.med.unc.edu/SwiftLib/.

In general, positions to mutate and degenerate codons were chosen from homology models (ICOSL) of the target-ligand pairs of interest to identify ligand contact residues, such as target side chain residues that interact with the ligand, as well as residues that are at the protein interaction interface. This analysis was performed using a structure viewer available at the URL: spdbv.vital-it.ch).

The next step in library design was the alignment of human, mouse, rat and monkey ICOSL sequences to identify conserved residues. Based on this analysis, conserved target residues were mutated with degenerate codons that only specified conservative amino acid changes plus the wild-type residue. Residues that were not conserved, were mutated more aggressively, but also included the wild-type residue. Degenerate codons that also encoded the wild-type residue were deployed to avoid excessive mutagenesis of target protein. For the same reason, only up to 20 positions were targeted for mutagenesis at a time. These residues were a combination of contact residues and non-contact interface residues.

The oligonucleotides were dissolved in sterile water, mixed in equimolar ratios, heated to 95° C. for five minutes and slowly cooled to room temperature for annealing. ECD-specific oligonucleotide primers that anneal to the start and end of the ECDs, respectively, were then used to generate PCR product. ECD-specific oligonucleotides which overlap by 40-50 bp with a modified version of pBYDS03 cloning vector (Life Technologies USA), beyond and including the BamH1 and Kpn1 cloning sites, were then used to amplify 100 ng of PCR product from the prior step to generate a total of 5 µg of DNA. Both PCR's were by polymerase chain reaction (PCR) using OneTaq 2×PCR master mix (New England Biolabs, USA). The second PCR products were purified using a PCR purification kit (Qiagen, Germany) and resuspended in sterile deionized water.

To prepare for library insertion, a modified yeast display version of vector pBYDS03 was digested with BamHI and KpnI restriction enzymes (New England Biolabs, USA) and the large vector fragment was gel-purified and dissolved in sterile, deionized water. Electroporation-ready DNA for the next step was generated by mixing 12 µg of library DNA for every electroporation with 4 µg of linearized vector in a total volume of 50 µl deionized and sterile water. An alternative way to generate targeted libraries, was to carry out site-directed mutagenesis (Multisite kit, Agilent, USA) of the target ECD with oligonucleotides containing degenerate codons. This approach was used to generate sublibraries that only target specific stretches of target protein for mutagenesis. In these cases, sublibraries were mixed before proceeding to the selection steps. In general, library sizes were in the range of 10E7 to 10E8 clones, except that sublibraries were only in the range of 10E4 to 10E5. Large libraries and sublibraries are generated for ICOSL.

B. Random Libraries

Random libraries were also constructed to identify variants of the ECD of ICOSL set forth in SEQ ID NO:32 containing the ECD domain. DNA encoding the wild-type ECD was cloned between the BamHI and KpnI restriction sites of modified yeast display vector pBYDS03. The DNA was then mutagenized with the Genemorph II Kit (Agilent, USA) to generate an average of three to five amino acid changes per library variant. Mutagenized DNA was then amplified by the two-step PCR and further processed as described above for targeted libraries.

Example 2

Introduction of DNA Libraries into Yeast

Example 2 describes the introduction of ICOSL DNA libraries into yeast.

To introduce degenerate and random library DNA into yeast, electroporation-competent cells of yeast strain BJ5464 (ATCC.org; ATCC number 208288) were prepared and electroporated on a Gene Pulser II (Biorad, USA) with the electroporation-ready DNA from the step above essentially as described (Colby, D. W. et al. 2004 Methods Enzymology 388, 348-358). The only exception is that transformed cells were grown in non-inducing minimal selective SCD-Leu medium to accommodate the LEU2 selectable marker carried by modified plasmid pBYDS03. One liter of SCD-Leu media consists of 14.7 grams sodium citrate, 4.29 grams citric acid monohydrate, 20 grams dextrose, 6.7 grams yeast nitrogen base, and 1.6 grams yeast synthetic drop-out media supplement without leucine. The Medium was filter sterilized before use using a 0.22 µm vacuum filter device.

Library size was determined by plating serial dilutions of freshly recovered cells on SCD-Leu agar plates and then extrapolating library size from the number of single colonies from plating that generated at least 50 colonies per plate. In general, library sizes ranged from 10E8 to 10E9 transformants based on this dilution assay. The remainder of the electroporated culture was grown to saturation in SCD-Leu and cells from this culture were subcultured (e.g. 1/100) into fresh SCD-Leu once more to minimize the fraction of untransformed cells. To maintain library diversity, this subculturing step was carried out using an inoculum that contained at least 10× more cells than the calculated library size. Cells from the second saturated culture were resuspended in fresh medium containing sterile 25% (weight/volume) glycerol to a density of 10E10/mL and frozen and stored at −80° C. (frozen library stock).

Library size was determined by plating dilutions of freshly recovered cells on SCD-Leu agar plates and then extrapolating library size from the number of single colonies from a plating that generate at least 50 colonies per plate.

To segregate plasmid from cells that contain two or more different library clones, a number of cells corresponding to 10 times the library size, were taken from the overnight SCD-Leu culture and subcultured 1/100 into fresh SCD-Leu medium and grown overnight. Cells from this overnight culture were resuspended in sterile 25% (weight/volume) glycerol to a density of 10E10/mL and frozen and stored at −80° C. (frozen library stock).

Example 3

Yeast Selection

Example 3 describes the selection of yeast expressing affinity modified variants of ICOSL.

A number of cells equal to at least 10 times the library size were thawed from individual library stocks, suspended to 0.1×10E6 cells/mL in non-inducing SCD-Leu medium, and grown overnight. The next day, a number of cells equal to 10 times the library size were centrifuged at 2000 RPM for two minutes and resuspended to 0.5×10E6 cells/mL in inducing SCDG-Leu media. One liter of the SCDG-Leu induction media consists of 5.4 grams $Na_2HPO_4$, 8.56 grams $NaH_2PO_4 \cdot H_2O$, 20 grams galactose, 2.0 grams dextrose, 6.7 grams Difco yeast nitrogen base, and 1.6 grams of yeast synthetic drop out media supplement without leucine dissolved in water and sterilized through a 0.22 µm membrane filter device. The culture was grown for two days at 20° C. to induce expression of library proteins on the yeast cell surface.

Cells were processed with magnetic beads to reduce non-binders and enrich for all ICOSL variants with the ability to bind their exogenous recombinant counter-structure proteins. This was then followed by two to three rounds of flow cytometry sorting using exogenous counter-structure protein staining to enrich the fraction of yeast cells that displays improved binders. Magnetic bead enrichment and selections by flow cytometry are essentially as described in Miller, K. D. Current Protocols in Cytometry 4.7.1-4.7.30, July 2008.

With ICOSL libraries, target ligand proteins were sourced from R&D Systems (USA) as follows: human rCD28.Fc (i.e., recombinant CD28-Fc fusion protein), rCTLA4.Fc and rICOS.Fc. Magnetic streptavidin beads were obtained from New England Biolabs, USA. For biotinylation of counter-structure protein, biotinylation kit cat #21955, Life Technologies, USA, was used. For two-color, flow cytometric sorting, a Becton Dickinson FACS Aria II sorter was used. ICOSL display levels were monitored with an anti-hemagglutinin antibody labeled with Alexafluor 488 (Life Technologies, USA). Ligand binding Fc fusion proteins rCD28.Fc, rCTLA4.Fc, or rICOS.Fc were detected with PE conjugated human Ig specific goat Fab (Jackson ImmunoResearch, USA). Doublet yeast were gated out using forward scatter (FSC)/side scatter (SSC) parameters, and sort gates were based upon higher ligand binding detected in FL4 that possessed more limited tag expression binding in FL1.

Yeast outputs from the flow cytometric sorts were assayed for higher specific binding affinity. Sort output yeast were expanded and re-induced to express the particular IgSF affinity modified domain variants they encode. This population then can be compared to the parental, wild-type yeast strain, or any other selected outputs, such as the bead output yeast population, by flow cytometry.

For ICOSL, the second sort outputs (F2) were compared to parental ICOSL yeast for binding of each rICOS.Fc, rCD28.Fc, and rCTLA4.Fc by double staining each population with anti-HA (hemagglutinin) tag expression and the anti-human Fc secondary to detect ligand binding.

In the case of ICOSL yeast variants selected for binding to ICOS, the F2 sort outputs gave Mean Fluorescence Intensity (MFI) values of 997, when stained with 5.6 nM rICOS.Fc, whereas the parental ICOSL strain MFI was measured at 397 when stained with the same concentration of rICOS.Fc. This represents a roughly three-fold improvement of the average binding in this F2 selected pool of clones, and it is predicted that individual clones from that pool will have much better improved MFI/affinity when individually tested.

In the case of ICOSL yeast variants selected for binding to CD28, the F2 sort outputs gave MFI values of 640 when stained with 100 nM rCD28.Fc, whereas the parental ICOSL strain MFI was measured at 29 when stained with the same concentration of rCD28.Fc (22-fold improvement). In the case of ICOSL yeast variants selected for binding to CTLA4, the F2 sort outputs gave MFI values of 949 when stained with 100 nM rCTLA4.Fc, whereas the parental ICOSL strain MFI was measured at 29 when stained with the same concentration of rCTLA4.Fc (32-fold improvement).

Importantly, the MFIs of all F2 outputs described above when measured with the anti-HA tag antibody on FL1 did not increase and sometimes went down compared to wild-type strains, indicating that increased binding was not a function of increased expression of the selected variants on the surface of yeast, and validated gating strategies of only selecting mid to low expressors with high ligand binding.

Selected variant ICOSL ECD domains were further formatted as fusion proteins and tested for binding and functional activity as described below.

Example 4

Reformatting Selection Outputs as Fc-Fusions and in Various Immunomodulatory Protein Types Example 4 describes reformatting of selection outputs identified in Example 3 as immunomodulatory proteins containing an affinity modified (variant) extracellular domain (ECD) of ICOSL fused to an Fc molecule (variant ECD-Fc fusion molecules).

Output cells from final flow cytometric ICOSL sorts were grown to terminal density in SCD-Leu medium. Plasmid DNA from each output was isolated using a yeast plasmid DNA isolation kit (Zymo Research, USA). For Fc fusions, PCR primers with added restriction sites suitable for cloning into the Fc fusion vector of choice were used to batch-amplify from the plasmid DNA preps the coding DNA's for the mutant target ECD's. After restriction digestion, the PCR products were ligated into an appropriate Fc fusion vector followed by chemical transformation into strain *E. coli* XL1 Blue (Agilent, USA) or NEB5alpha (New England Biolabs, USA) as directed by supplier. Exemplary of an Fc fusion vector is pFUSE-hIgG1-Fc2 (InvivoGen, USA).

Dilutions of transformation reactions were plated on LB-agar containing 100 μg/mL carbenicillin (Teknova, USA) to generate single colonies. Up to 96 colonies from each transformation were then grown in 96 well plates to saturation overnight at 37° C. in LB-broth (Teknova cat #L8112) and a small aliquot from each well was submitted for DNA sequencing of the ECD insert in order to identify the mutation(s) in all clones. Sample preparation for DNA sequencing was carried out using protocols provided by the service provider (Genewiz; South Plainfield, NJ). After removal of sample for DNA sequencing, glycerol was then added to the remaining cultures for a final glycerol content of 25% and plates were stored at –20° C. for future use as master plates (see below). Alternatively, samples for DNA sequencing were generated by replica plating from grown liquid cultures onto solid agar plates using a disposable 96 well replicator (VWR, USA). These plates were incubated overnight to generate growth patches and the plates were submitted to Genewiz for DNA sequencing following their specifications. In some instances, resequencing was performed to verify mutations.

After analysis of the Genewiz-generated DNA sequencing data, clones of interest were recovered from master plates and individually grown to saturation in 5 mL liquid LB-broth containing 100 μg/mL carbenicillin (Teknova, USA) and 2 mL of each culture were then used for preparation of approximately 10 μg of miniprep plasmid DNA of each clone using a standard kit such as the Pureyield kit (Promega, USA). Identification of clones of interest generally involved the following steps. First, DNA sequence data files were downloaded from the Genewiz website. All sequences were then manually curated so that they start at the beginning of the ECD coding region. The curated sequences were then batch-translated using a suitable program available at the URL: www.ebi.ac.uk/Tools/st/emboss_transeq/. The translated sequences were then aligned using a suitable program available at the URL: multalin.toulouse.inra.fr/ multalin/multalin.html. Alternatively, Genewiz sequences were processed to generate alignments using Ugene software (http://ugene.net).

Clones of interest were then identified using the following criteria: 1.) identical clone occurs at least two times in the alignment and 2.) a mutation occurs at least two times in the alignment and preferably in distinct clones. Clones that meet at least one of these criteria were clones that have been enriched by the sorting process most likely due to improved binding.

To generate recombinant immunomodulatory proteins that are Fc fusion proteins containing an ECD of ICOSL with at least one affinity-modified domain (e.g. variant ICOSL ECD-Fc), the encoding nucleic acid molecule was generated to encode a protein designed as follows: signal peptide followed by variant (mutant) ICOSL ECD followed by a linker of three alanines (AAA) followed by a human IgG1 Fc containing the mutation N82G with reference to wild-type human IgG1 Fc set forth in SEQ ID NO: 226 (corresponding to N297G by EU numbering). This exemplary Fc also contained stabilizing cysteine mutations R77C and V87C and replacement of the cysteine residue to a serine residue at position 220 (C220S) by EU numbering (corresponding to position 5 (C5S) with reference with reference to wild-type human IgG1 Fc set forth in SEQ ID NO:226 (corresponding to R292C, V302C and C220S, respectively, by EU numbering). In some cases, the NotI cloning site which contributes to the AAA linker sequence was deleted to generate a direct fusion of the ICOSL ECD and the beginning of the Fc. Since the construct does not include any antibody light chains that can form a covalent bond with a cysteine, the human IgG1 Fc also contains replacement of the cysteine residues to a serine residue at position 5 (C5S) compared to the wild-type or unmodified Fc set forth in SEQ ID NO: 226.

Example 5

Expression and Purification of Fc-Fusions

Example 5 describes the high throughput expression and purification of Fc-fusion proteins containing variant ECD ICOSL as described in the above Examples.

Recombinant variant Fc fusion proteins were produced from suspension-adapted human embryonic kidney (HEK) 293 cells using the Expi293 expression system (Invitrogen, USA). 4 μg of each plasmid DNA from the previous step was added to 200 μL Opti MEM (Invitrogen, USA) at the same time as 10.8 μL ExpiFectamine was separately added to another 200 μL Opti-MEM. After 5 minutes, the 200 μL of plasmid DNA was mixed with the 200 μL of ExpiFectamine and was further incubated for an additional 20 minutes before adding this mixture to cells. Ten million Expi293 cells were dispensed into separate wells of a sterile 10 ml, conical bottom, deep 24 well growth plate (Thomson Instrument Company, USA) in a volume 3.4 ml Expi293 media (Invitrogen, USA). Plates were shaken for 5 days at 120 RPM in a mammalian cell culture incubator set to 95% humidity and 8% $CO_2$. Following a 5 day incubation, cells were pelleted and culture supernatants were retained.

Proteins were purified from supernatants using a high throughput 96 well Protein A purification kit using the manufacturer's protocol (Catalog number 45202, Life Technologies, USA). Resulting elution fractions were buffer exchanged into PBS using Zeba 96 well spin desalting plate (Catalog number 89807, Life Technologies, USA) using the manufacturer's protocol. Purified protein was quantitated using 280 nm absorbance measured by Nanodrop instrument (Thermo Fisher Scientific, USA), and protein purity was assessed by loading 5 μg of protein on NUPAGE pre-cast, polyacrylamide gels (Life Technologies, USA) under denaturing and reducing conditions and subsequent gel electrophoresis. Proteins were visualized in gel using standard Coomassie staining.

Example 6

Assessment of Binding and Activity of Affinity-Matured IgSF Domain-Containing Molecules
A. Binding to Cell-Expressed Counter Structures
   This Example describes Fc-fusion binding studies of purified proteins from the above Examples to assess specificity and affinity of ICOSL domain variant immunomodulatory proteins for cognate binding partners.
   To produce cells expressing cognate binding partners, full-length mammalian surface expression constructs for each of human CD28 and ICOS were designed in pcDNA3.1 expression vector (Life Technologies) and sourced from Genscript, USA. Binding studies were carried out on transfected HEK293 cells generated to express the full-length mammalian surface ligands using the transient transfection system (Life Technologies, USA) described above. As a control, binding to mock (non-transfected) cells also was assessed. The number of cells needed for the experiment was determined, and the appropriate 30 mL scale of transfection was performed using the manufacturer's suggested protocol. For each CD28, ICOS or mock 30 mL transfection, 75 million Expi293F cells were incubated with 30 μg expression construct DNA and 1.5 ml diluted ExpiFectamine 293 reagent for 48 hours, at which point cells were harvested for staining.
   For staining by flow cytometry, 200,000 cells of appropriate transient transfection or negative control (mock) were plated in 96 well round bottom plates. Cells were spun down and resuspended in staining buffer (PBS (phosphate buffered saline), 1% BSA (bovine serum albumin), and 0.1% sodium azide) for 20 minutes to block non-specific binding. Afterwards, cells were centrifuged again and resuspended in staining buffer containing 100 nM to 1 nM variant immunomodulatory protein, depending on the experiment of each candidate CD80 variant Fc, ICOSL variant Fc, or stacked IgSF variant Fc fusion protein in 50 μL. Primary staining was performed on ice for 45 minutes, before washing cells in staining buffer twice. PE-conjugated anti-human Fc (Jackson ImmunoResearch, USA) was diluted 1:150 in 50 μL staining buffer and added to cells and incubated another 30 minutes on ice. Secondary antibody was washed out twice, cells were fixed in 4% formaldehyde/PBS, and samples were analyzed on FACScan flow cytometer (Becton Dickinson, USA) or a Hypercyt flow cytometer (Intellicyte, USA).
   Mean Fluorescence Intensity (MFI) was calculated for each transfectant and negative parental line with Cell Quest Pro software (Becton Dickinson, USA) or a Hypercyt flow cytometer (Intellicyte, USA).
B. Bioactivity Characterization
   This Example further describes Fc-fusion variant protein bioactivity characterization in human primary T cell in vitro assays.
1. Mixed Lymphocyte Reaction (MLR)
   Soluble rICOSL.Fc bioactivity was tested in a human Mixed Lymphocyte Reaction (MLR). Human primary dendritic cells (DC) were generated by culturing monocytes isolated from PBMC (BenTech Bio, USA) in vitro for 7 days with 500 U/mL rIL-4 (R&D Systems, USA) and 250 U/mL rGM-CSF (R&D Systems, USA) in Ex-Vivo 15 media (Lonza, Switzerland). 10,000 matured DC and 100,000 purified allogeneic CD4+ T cells (BenTech Bio, USA) were co-cultured with ICOSL variant Fc fusion proteins and controls in 96 well round bottom plates in 200 μl final volume of Ex-Vivo 15 media. On day 5, IFN-gamma secretion in culture supernatants was analyzed using the Human IFN-gamma Duoset ELISA kit (R&D Systems, USA). Optical density was measured by VMax ELISA Microplate Reader (Molecular Devices, USA) and quantitated against titrated rIFN-gamma standard included in the IFN-gamma Duo-set kit (R&D Systems, USA). A second MLR protocol consisted of human primary dendritic cells (DC) generated by culturing monocytes isolated from PBMC (BenTech Bio, USA) in vitro for 7 days with 50 ng/mL rIL-4 (R&D Systems, USA) and 80 ng/mL rGM-CSF (R&D Systems, USA) in Ex-Vivo 15 media (Lonza, Switzerland). On days 3 and 5, half of the media was removed and replaced with fresh media containing 50 ng/ml rIL-4 and 80 ng/mL rGM-CSF. To fully induce DC maturation, lipopolysaccharide (LPS) (InvivoGen Corp., USA) was added at 100 ng/mL to the DC cultures on day 6 and cells were incubated for an additional 24 hours. Approximately, 10,000 matured DC and 100,000 purified allogeneic CD3+ T cells (BenTech Bio, USA) were co-cultured with ICOSL variant Fc fusion proteins and controls in 96 well round bottom plates in 200 μl final volume of Ex-Vivo 15 media. On day 4-5, IFN-gamma secretion in culture supernatants was analyzed using the Human IFN-gamma Duoset ELISA kit (R&D Systems, USA). Optical density was measured on a BioTek Cytation Multimode Microplate Reader (BioTek Corp., USA) and quantitated against titrated rIFN-gamma standard included in the IFN-gamma Duo-set kit (R&D Systems, USA).
2. Anti-CD3 Coimmobilization Assay
   Costimulatory bioactivity of ICOSL fusion variants was determined in anti-CD3 coimmobilization assays. 1 nM or 10 nM mouse anti-human CD3 (OKT3, Biolegends, USA) was diluted in PBS with 1 nM to 80 nM rICOSL.Fc variant proteins. This mixture was added to tissue culture treated flat bottom 96 well plates (Corning, USA) overnight to facilitate adherence of the stimulatory proteins to the wells of the plate. The next day, unbound protein was washed off the plates and 100,000 purified human pan T cells (BenTech Bio, US) or human T cell clone BC3 (Astarte Biologics, USA) were added to each well in a final volume of 200 μl of Ex-Vivo 15 media (Lonza, Switzerland). In some instances, human pan T cells were labeled with 0.25 uM carboxyfluorescein succinimidyl ester (CFSE, ThermoFisher Scientific, USA). Cells were cultured 3 days before harvesting culture supernatants and measuring human IFN-gamma levels with Duoset ELISA kit (R&D Systems, USA) as mentioned above. Cellular proliferation was determined by the percent of input cells that entered division as measured by CFSE dilution on cells stained with fluorescently-conjugated anti-CD4, anti-CD8 antibodies (BD, USA) or total T cells via flow cytometric analysis on an LSR II (BD, USA),
C. Results
   Results for the binding and activity studies for exemplary tested variants are shown in Table 7 which indicates exemplary IgSF domain amino acid substitutions (replacements) in the ECD of ICOSL selected in the screen for affinity-maturation against the respective cognate structures ICOS and CD28. In the Tables, the exemplary amino acid substitutions are designated by amino acid position number corresponding to the respective reference (e.g., unmodified)

ECD sequence as follows. For example, the reference (e.g., unmodified) ECD sequence in Table 7 (WT ICOSL) is the (e.g., unmodified) ICOSL ECD sequence set forth in SEQ ID NO: 32. The amino acid position is indicated in the middle, with the corresponding reference (e.g. unmodified or wild-type) amino acid listed before the number and the identified variant amino acid substitution listed after the number. Column 2 sets forth the SEQ ID NO identifier for the variant ECD for each variant ECD-Fc fusion molecule.

Also shown is the binding activity as measured by the Mean Fluorescence Intensity (MFI) value for binding of each variant Fc-fusion molecule to cells transfected to express the cognate ligand and the ratio of the MFI compared to the binding of the corresponding reference (e.g., unmodified) ECD-Fc fusion molecule not containing the amino acid substitution(s) to the same cell-expressed counter structure ligand. The functional activity of the variant Fc-fusion molecules to modulate the activity of T cells also is shown based on the calculated levels of IFN-gamma in culture supernatants (pg/mL) generated either i) with the indicated variant ECD-Fc fusion molecule coimmoblized with anti-CD3 or ii) with the indicated variant ECD-Fc fusion molecule in an MLR assay. The Table also depicts the ratio of IFN-gamma produced by each variant ECD-Fc compared to the corresponding reference (e.g., unmodified or wild-type) ECD-Fc in both functional assays.

As shown, the selections resulted in the identification of a number of ICOSL IgSF domain variants that were affinity-modified to exhibit increased binding for at least one, and in some cases more than one, cognate counter structure ligand. In addition, the results showed that affinity modification of the variant molecules also exhibited improved activities to both increase and/or decrease immunological activity depending on the format of the molecule. For example, coimmobilization of the ligand likely provides a multivalent interaction with the cell to cluster or increase the avidity to favor agonist activity and increase T cell activation compared to the reference (e.g. unmodified or wildtype) ECD-Fc molecule not containing the amino acid replacement(s). However, when the molconle is provided as a bivalent Fe molecule in solution, the same IgSF domain variants exhibited an antagonist activity to decrease T cell activation compared to the reference (e.g., unmodified or wildtype) ECD-Fv molecule not containing the amino acid replacement(s).

TABLE 7

| ICOSL variants selected against CD28 or ICOS. Molecule sequences, binding data, and costimulatory bioactivity data. | | | | | |
|---|---|---|---|---|---|
| | | Binding | | Coimmobilization with anti-CD3 IFN-gamma | MLR IFN-gamma |
| ICOSL mutation(s) | SEQ ID NO (ECD) | ICOS OD (parental ratio) | CD28 MFI (parental ratio) | pg/mL (parental ratio) | levels pg/mL (parental ratio) |
| N52S | 109 | 1.33 (1.55) | 162 (9.00) | 1334 (1.93) | 300 (0.44) |
| N52H | 110 | 1.30 (1.51) | 368 (20.44) | 1268 (1.83) | 39 (0.06) |
| N52D | 111 | 1.59 (1.85) | 130 (7.22) | 1943 (2.80) | 190 (0.28) |
| N52Y/N57Y/ F138L/L203P | 112 | 1.02 (1.19) | 398 (22.11) | 510* (1.47*) | 18 (0.03) |
| N52H/N57Y/Q100P | 113 | 1.57 (1.83) | 447 (24.83) | 2199 (3.18) | 25 (0.04) |
| N52S/Y146C/Y152C | 114 | 1.26 (1.47) | 39 (2.17) | 1647 (2.38) | 152 (0.22) |
| N52H/C198R | 115 | 1.16 (1.35) | 363 (20.17) | 744* (2.15*) | ND (ND) |
| N52H/C140del/ T225A | 372 | ND (ND) | 154 (8.56) | 522* (1.51*) | ND (ND) |
| N52H/C198R/T225A | 117 | 1.41 (1.64) | 344 (19.11) | 778* (2.25*) | 0 (0) |
| N52H/K92R | 118 | 1.48 (1.72) | 347 (19.28) | 288* (0.83*) | 89 (0.13) |
| N52H/S99G | 119 | 0.09 (0.10) | 29 (1.61) | 184* (0.53*) | 421 (0.61) |
| N52Y | 120 | 0.08 (0.09) | 18 (1.00) | 184* (0.53*) | 568 (0.83) |
| N57Y | 121 | 1.40 (1.63) | 101 (5.61) | 580* (1.68*) | 176 (0.26) |
| N57Y/Q100P | 122 | 0.62 (0.72) | 285 (15.83) | 301* (0.87*) | 177 (0.26) |
| N52S/S130G/Y152C | 123 | 0.16 (0.19) | 24 (1.33) | 266* (0.77*) | 1617 (2.35) |
| N52S/Y152C | 124 | 0.18 (0.21) | 29 (1.61) | 238* (0.69*) | 363 (0.53) |
| N52S/C198R | 125 | 1.80 (2.09) | 82 (4.56) | 1427 (2.06) | 201 (0.29) |
| N52Y/N57Y/Y152C | 126 | 0.08 (0.09) | 56 (3.11) | 377* (1.09*) | 439 (0.64) |
| N52Y/N57Y/ H129P/C198R | 127 | ND (ND) | 449 (24.94) | 1192 (1.72) | ND (ND) |
| N52H/L161P/C198R | 128 | 0.18 (0.21) | 343 (19.05) | 643* (1.86*) | 447 (0.65) |

TABLE 7-continued

ICOSL variants selected against CD28 or ICOS. Molecule sequences,
binding data, and costimulatory bioactivity data.

| ICOSL mutation(s) | SEQ ID NO (ECD) | Binding | | Coimmobilization with anti-CD3 IFN-gamma | MLR IFN-gamma |
| | | ICOS OD (parental ratio) | CD28 MFI (parental ratio) | pg/mL (parental ratio) | levels pg/mL (parental ratio) |
|---|---|---|---|---|---|
| N52S/T113E | 129 | 1.51 (1.76) | 54 (3.00) | 451* (1.30*) | 345 (0.50) |
| S54A | 130 | 1.62 (1.88) | 48 (2.67) | 386* (1.12*) | 771 (1.12) |
| N52D/S54P | 368 | 1.50 (1.74) | 38 (2.11) | 476* (1.38*) | 227 (0.33) |
| S54F/V193A | 905 | 0.51 (0.59) | 16 (0.87) | 294 (0.85) | 262 (0.38) |
| N52K/L208P | 132 | 1.91 (2.22) | 291 (16.17) | 1509 (2.18) | 137 (0.20) |
| N52S/Y152H | 133 | 0.85 (0.99) | 68 (3.78) | 2158 (3.12) | 221 (0.32) |
| N52D/V151A | 134 | 0.90 (1.05) | 19 (1.06) | 341* (0.99*) | 450 (0.66) |
| N52H/I143T | 135 | 1.83 (2.13) | 350 (19.44) | 2216 (3.20) | 112 (0.16) |
| N52S/L80P | 136 | 0.09 (0.10) | 22 (1.22) | 192* (0.55*) | 340 (0.49) |
| F120S/Y152H/N201S | 137 | 0.63 (0.73) | 16 (0.89) | 351* (1.01*) | 712 (1.04) |
| N52S/R75Q/L203P | 138 | 1.71 (1.99) | 12 (0.67) | 1996 (2.88) | 136 (0.20) |
| N52S/D158G | 139 | 1.33 (1.55) | 39 (2.17) | 325* (0.94*) | 277 (0.40) |
| N52D/Q133H | 140 | 1.53 (1.78) | 104 (5.78) | 365* (1.05*) | 178 (0.26) |
| WT ICOSL | 32 | 0.86 (1.00) | 18 (1.00) | 692/346* (1.00) | 687 (1.00) |

*Parental ratio calculated using 346 pg/mL IFN-gamma for WT ICOSL

Binding assays were repeated substantially as described above, except that binding also was assessed against cells expressing full-length human CTLA4. ICOSL variant Fc fusion proteins also were further assessed in an anti-CD3 coimmobilization assay substantially as described above. The results confirmed identification of a number of ICOSL IgSF domain variants that exhibited increased binding affinity for at least one, and in some cases more than one, cognate ligand. In addition, the results showed that affinity modification of the variant molecules also exhibited improved activities in the coimmobilization assay.

Example 7

Additional Affinity Modified IgSF Domains

This examples describe the design, creation, and screening of additional affinity modified CD80 (B7-1), CD86 (B7-2) and NKp30 immunomodulatory proteins, which are other components of the immune synapse (IS) that have a demonstrated dual role in both immune activation and inhibition. These examples demonstrate that affinity modification of IgSF domains yields proteins that can act to both increase and decrease immunological activity. This work also describes the various combinations of those domains fused in pairs (i.e., stacked) with a variant affinity modified ICOSL to form a Type II immunomodulatory protein to achieve immunomodulatory activity.

Mutant DNA constructs of human CD80, CD86 and NKp30 IgSF domains for translation and expression as yeast display libraries were generated substantially as described in Example 1. For libraries that target specific residues of target protein for complete or partial randomization with degenerate codons, the coding DNA's for the extracellular domains (ECD) of human CD80 (SEQ ID NO:28), and NKp30 (SEQ ID NO:54) were ordered from Integrated DNA Technologies (Coralville, IA) as a set of overlapping oligonucleotides of up to 80 base pairs (bp) in length. Alternatively, residues were mutated by site-directed targeted mutagenesis substantially as described in Example 1. Alternatively, random libraries were constructed to identify variants of the ECD of CD80 (SEQ ID NO:28), CD86 (SEQ ID NO: 29) and NKp30 (SEQ ID NO:54) substantially as described in Example 1.

The targeted and random library DNA was introduced into yeast substantially as described in Example 2 to generate yeast libraries. The libraries were used to select yeast expressing affinity modified variants of CD80, CD86 and NKp30 substantially as described in Example 3. Cells were processed to reduce non-binders and to enrich for CD80, CD86 or NKp30 variants with the ability to bind their exogenous recombinant counter-structure proteins substantially as described in Example 3. For example, yeast displayed targeted or random CD80 libraries were selected against each of CD28, CTL-4, and PD-L1, separately. This was then followed by two to three rounds of flow cytometry sorting using exogenous counter-structure protein staining to enrich the fraction of yeast cells that displays improved binders. Magnetic bead enrichment and selections by flow cytometry are essentially as described in Keith D. Miller, 1 Noah B. Pefaur, 2 and Cheryl L. Baird1 Current Protocols in Cytometry 4.7.1-4.7.30, July 2008.

With CD80, CD86 and NKp30 libraries, target ligand proteins were sourced from R&D Systems (USA) as follows: human rCD28.Fc (i.e., recombinant CD28-Fc fusion protein), rPDL1.Fc, rCTLA4.Fc, and rB7H6.Fc. Two-color flow cytometry was performed substantially as described in Example 3. Yeast outputs from the flow cytometric sorts were assayed for higher specific binding affinity. Sort output yeast were expanded and re-induced to express the particular IgSF affinity modified domain variants they encode. This population then can be compared to the parental, wild-type yeast strain, or any other selected outputs, such as the bead output yeast population, by flow cytometry.

In the case of NKp30 yeast variants selected for binding to B7-H6, the F2 sort outputs gave MFI values of 533 when stained with 16.6 nM rB7H6.Fc, whereas the parental NKp30 strain MFI was measured at 90 when stained with the same concentration of rB7H6.Fc (6-fold improvement).

Among the NKp30 variants that were identified, was a variant that contained mutations L30V/A60V/S64P/S86G with reference to positions in the NKp30 extracellular domain corresponding to positions set forth in SEQ ID NO:54. Among the CD86 variants that were identified, was a variant that contained mutations Q35H/H90L/Q102H with reference to positions in the CD86 extracellular domain corresponding to positions set forth in SEQ ID NO: 29. Among the CD80 variants that were identified, were variants set forth in Table 8 and described further below.

As with ICOSL, the MFIs of all F2 outputs described above when measured with the anti-HA tag antibody on FL1 did not increase and sometimes went down compared to wild-type strains, indicating that increased binding was not a function of increased expression of the selected variants on the surface of yeast, and validated gating strategies of only selecting mid to low expressors with high ligand binding.

Exemplary selection outputs were reformatted as immunomodulatory proteins containing an affinity modified (variant) extracellular domain (ECD) of CD80 fused to an Fc molecule (variant ECD-Fc fusion molecules) substantially as described in Example 4 and the Fc-fusion protein was expressed and purified substantially as described in Example 5.

Binding of exemplary CD80 Fc-fusion variants to cell-expressed counter structures was then assessed substantially as described in Example 6. To produce cells expressing cognate binding partners, full-length mammalian surface expression constructs for each of human CD28, CTLA4 and PD-L1 were produced substantially as described in Example 6. Binding studies and flow cytometry were carried out substantially as described in Example 6. In addition, the bioactivity of the Fc-fusion variant protein was characterized by either mixed lymphocyte reaction (MLR) or anti-CD3 coimmobilization assay substantially as described in Example 6.

Results for the binding and activity studies for exemplary tested variants are shown in Tables 8 and 9. In particular, Table 8 indicates exemplary IgSF domain amino acid substitutions (replacements) in the ECD of CD80 selected in the screen for affinity-maturation against the respective cognate structure CD28. Table 9 indicates exemplary IgSF domain amino acid substitutions (replacements) in the ECD of CD80 selected in the screen for affinity-maturation against the respective cognate structure PD-L1. As above, for each Table, the exemplary amino acid substitutions are designated by amino acid position number corresponding to the respective reference (e.g., unmodified) ECD sequence as follows. For example, the reference (e.g., unmodified) ECD sequence in Tables 8 and 9 is the unmodified CD80 ECD sequence set forth in SEQ ID NO:28. The amino acid position is indicated in the middle, with the corresponding reference (e.g., unmodified) amino acid listed before the number and the identified variant amino acid substitution listed after the number. Column 2 sets forth the SEQ ID NO identifier for the variant ECD for each variant ECD-Fc fusion molecule.

Also shown is the binding activity as measured by the Mean Fluorescence Intensity (MFI) value for binding of each variant Fc-fusion molecule to cells engineered to express the cognate counter structure ligand and the ratio of the MFI compared to the binding of the corresponding reference (e.g., unmodified) ECD-Fc fusion molecule not containing the amino acid substitution(s) to the same cell-expressed counter structure ligand. The functional activity of the variant Fc-fusion molecules to modulate the activity of T cells also is shown based on the calculated levels of IFN-gamma in culture supernatants (pg/mL) generated either i) with the indicated variant ECD-Fc fusion molecule coimmoblized with anti-CD3 or ii) with the indicated variant ECD-Fc fusion molecule in an MLR assay. The Tables also depict the ratio of IFN-gamma produced by each variant ECD-Fc compared to the corresponding reference (e.g., unmodified) ECD-Fc in both functional assays.

As shown, the selections resulted in the identification of a number of CD80 IgSF domain variants that were affinity-modified to exhibit increased binding for at least one, and in some cases more than one, cognate counter structure ligand. In addition, the results showed that affinity modification of the variant molecules also exhibited improved activities to both increase and decrease immunological activity depending on the format of the molecule. For example, coimmobilization of the ligand likely provides a multivalent interaction with the cell to cluster or increase the avidity to favor agonist activity and increase T cell activation compared to the reference (e.g. unmodified or wildtype) ECD-Fc molecule not containing the amino acid replacement(s). However, when the molecule is provided as a bivalent Fc molecule in solution, the same IgSF domain variants exhibited an antagonist activity to decrease T cell activation compared to the reference (e.g. unmodified or wildtype) ECD-Fc molecule not containing the amino acid replacement(s).

TABLE 8

| CD80 variants selected against CD28. Molecule sequences, binding data, and costimulatory bioactivity data. | | | | | | |
|---|---|---|---|---|---|---|
| | | | Binding | | Coimmobilization with anti-CD3 | MLR IFN-gamma |
| CD80 mutation(s) | SEQ ID NO (ECD) | CD28 MFI (parental ratio) | CTLA-4 MFI (parental ratio) | PD-L1 MFI (parental ratio) | IFN-gamma pg/mL (parental ratio) | levels pg/mL (parental ratio) |
| L70Q/A91G/N144D | 508 | 125 (1.31) | 283 (1.36) | 6 (0.08) | 93 (1.12) | 716 (0.83) |
| L70Q/A91G/T130A | 56 | 96 (1.01) | 234 (1.13) | 7 (0.10) | 99 (1.19) | 752 (0.87) |
| L70Q/A91G/I118A/T120S/T130A/K169E | 59 | 123 (1.29) | 226 (1.09) | 7 (0.10) | 86 (1.03) | 741 (0.86) |

TABLE 8-continued

CD80 variants selected against CD28. Molecule sequences, binding data, and costimulatory bioactivity data.

| CD80 mutation(s) | SEQ ID NO (ECD) | Binding CD28 MFI (parental ratio) | Binding CTLA-4 MFI (parental ratio) | Binding PD-L1 MFI (parental ratio) | Coimmobilization with anti-CD3 IFN-gamma pg/mL (parental ratio) | MLR IFN-gamma levels pg/mL (parental ratio) |
|---|---|---|---|---|---|---|
| V4M/L70Q/A91G/I118V/T20S/T130A/ K169E | 510 | 89 (0.94) | 263 (1.26) | 6 (0.09) | 139 (1.67) | 991 (1.14) |
| L70Q/A91G/I118V/T120S/T130A/K169E | 59 | 106 (1.12) | 263 (1.26) | 6 (0.09) | 104 (1.25) | 741 (0.86) |
| V20L/L70Q/A91S/I118V/T120S/T130A | 513 | 105 (1.11) | 200 (0.96) | 9 (0.13) | 195 (2.34) | 710 (0.82) |
| S44P/L70Q/A91G/T130A | 61 | 88 (0.92) | 134 (0.64) | 5 (0.07) | 142 (1.71) | 854 (0.99) |
| L70Q/A91G/E117G/I118V/T120S/T130A | 514 | 120 (1.27) | 193 (0.93) | 6 (0.08) | 98 (1.05) | 736 (0.85) |
| A91G/I118V/T120S/T130A | 515 | 84 (0.89) | 231 (1.11) | 44 (0.62) | 276 (3.33) | 714 (0.82) |
| L70R/A91G/I118V/T120S/T130A/T199S | 516 | 125 (1.32) | 227 (1.09) | 6 (0.09) | 105 (1.26) | 702 (0.81) |
| L70Q/E81A/A91G/I118V/T120S/I127T/ T130A | 517 | 140 (1.48) | 185 (0.89) | 18 (0.25) | 98 (1.18) | 772 (0.89) |
| L70Q/Y87N/A91G/T130A | 66 | 108 (1.13) | 181 (0.87) | 6 (0.08) | 136 (1.63) | 769 (0.89) |
| T28S/L70Q/A91G/I118V/E95K/T120S/ I126V/T130A/K169E | 518 | 32 (0.34) | 65 (0.31) | 6 (0.08) | 120 (1.44) | 834 (0.96) |
| N63S/L70Q/A91G/S114T/I118V/ T120S/T130A | 519 | 124 (1.30) | 165 (0.79) | 6 (0.08) | 116 (1.39) | 705 (0.81) |
| K36E/I67T/L70Q/A91G/I118V/ T120S/T130A/N152T | 520 | 8 (0.09) | 21 (0.10) | 5 (0.08) | 53 (0.63) | 852 (0.98) |
| E52G/L70Q/A91G/D107N/I118V/ T120S/T130A K169E | 521 | 113 (1.19) | 245 (1.18) | 6 (0.08) | 94 (1.13) | 874 (1.01) |
| K37E/F59S/L70Q/A91G/I118V/T120S/ T130A/K185E | 522 | 20 (0.21) | 74 (0.36) | 6 (0.08) | 109 (1.31) | 863 (1.00) |
| A91G/S103P | 72 | 39 (0.41) | 56 (0.27) | 9 (0.13) | 124 (1.49) | 670 (0.77) |
| K89E/T130A | 73 | 90 (0.95) | 148 (0.71) | 75 (1.07) | 204 (2.45) | 761 (0.88) |
| A91G | 74 | 96 (1.01) | 200 (0.96) | 85 (1.21) | 220 (2.65) | 877 (1.01) |
| D60V/A91G/I118V/T120S/T130A/K169E | 523 | 111 (1.17) | 222 (1.07) | 12 (0.18) | 120 (1.44) | 744 (0.86) |
| K54M/L70Q/A91G/Y164H | 524 | 68 (0.71) | 131 (0.63) | 5 (0.08) | 152 (1.83) | 685 (0.79) |
| M38T/L70Q/E77G/A91G/I118V/T120S/ T130A/N152T | 525 | 61 (0.64) | 102 (0.49) | 5 (0.07) | 119 (1.43) | 796 (0.92) |
| R29H/E52G/L70R/E88G/A91G/T130A | 78 | 100 (1.05) | 119 (0.57) | 5 (0.08) | 200 (2.41) | 740 (0.85) |
| Y31H/T41G/M43L/L70Q/A91G/ I118V/T120S/I126V/T130A | 526 | 85 (0.89) | 85 (0.41) | 6 (0.08) | 288 (3.47) | 782 (0.90) |
| V68A/T110A | 80 | 103 (1.08) | 233 (1.12) | 48 (0.68) | 163 (1.96) | 861 (0.99) |
| L65H/D90G/T110A/F116L | 527 | 33 (0.35) | 121 (0.58) | 11 (0.15) | 129 (1.55) | 758 (0.88) |
| R29H/E52G/D90N/I118V/T120S/T130A | 82 | 66 (0.69) | 141 (0.68) | 11 (0.15) | 124 (1.49) | 800 (0.92) |
| A91G/L102S | 83 | 6 (0.06) | 6 (0.03) | 5 (0.08) | 75 (0.90) | 698 (0.81) |
| I67T/L70Q/A91G/I118V T120S | 530 | 98 (1.03) | 160 (0.77) | 5 (0.08) | 1751 (21.1) | 794 (0.92) |
| L70Q/A91G/T110A/I118V/T120S/T130A | 531 | 8 (0.09) | 14 (0.07) | 5 (0.07) | 77 (0.93) | 656 (0.76) |
| M38T/T41D/M43I/W50G/D76G/V83A/ K89E/I118V/T120S/I126V/T130A | 532 | 5 (0.06) | 8 (0.04) | 8 (0.11) | 82 (0.99) | 671 (0.78) |
| V22A/L70Q/S121P | 87 | 5 (0.06) | 7 (0.04) | 5 (0.07) | 105 (1.27) | 976 (1.13) |
| A12V/S15F/Y31H/M38L/T41G/M43L/ D90N/T130A/P137L/N149D N152T | 533 | 6 (0.06) | 6 (0.03) | 5 (0.08) | 104 (1.25) | 711 (0.82) |
| I67F/L70R/E88G/A91G/I118V/T120S/ T130A | 534 | 5 (0.05) | 6 (0.03) | 6 (0.08) | 62 (0.74) | 1003 (1.16) |
| E24G/L25P/L70Q/A91G/I118V/T120S/ N152T | 535 | 26 (0.27) | 38 (0.18) | 8 (0.11) | 101 (1.21) | 969 (1.12) |
| A91G/F92L/F108L/I118V/T120S | 536 | 50 (0.53) | 128 (0.61) | 16 (0.11) | 59 (0.71) | 665 (0.77) |
| WT CD80 | 28 | 95 (1.00) | 208 (1.00) | 70 (1.00) | 83 (1.00) | 866 (1.00) |

TABLE 9

CD80 variants selected against PD-L1. Molecule sequences, binding data, and costimulatory bioactivity data.

| CD80 mutation(s) | SEQ ID NO (ECD) | Binding CD28 MFI (parental ratio) | Binding CTLA-4 MFI (parental ratio) | Binding PD-L1 MFI (parental ratio) | Coimmobilization with anti-CD3 IFN-gamma pg/mL (parental ratio) | MLR IFN-gamma levels pg/mL (parental ratio) |
|---|---|---|---|---|---|---|
| R29D/Y31L/Q33H/ K36G/M38I/T41A/ M43R/M47T/E81V/ L85R/K89N/A91T/ F92P/K93V/ R94L/ I118T/N149S | 92 | 1071 (0.08) | 1089 (0.02) | 37245 (2.09) | 387 (0.76) | 5028 (0.26) |

TABLE 9-continued

CD80 variants selected against PD-L1. Molecule sequences, binding data, and costimulatory bioactivity data.

| CD80 mutation(s) | SEQ ID NO (ECD) | Binding | | | Coimmobilization with anti-CD3 | MLR IFN-gamma |
|---|---|---|---|---|---|---|
| | | CD28 MFI (parental ratio) | CTLA-4 MFI (parental ratio) | PD-L1 MFI (parental ratio) | IFN-gamma pg/mL (parental ratio) | levels pg/mL (parental ratio) |
| R29D/Y31L/Q33H/ K36G/M38I/T41A/ M43R/M47T/E81V/ L85R/K89N/A91T/ F92P/K93V/R94L/ N144S/N149S | 93 | 1065 (0.08) | 956 (0.02) | 30713 (1.72) | 400 (0.79) | 7943 (0.41) |
| R29D/Y31L/Q33H/ K36G/M38I/T41A/ M42T/M43R/M47T/ E81V/L85R/K89N/ A91T/F92P/K93V/ R94L/L148S/N149S | 94 | 926 (0.07) | 954 (0.02) | 47072 (2.64) | 464 (0.91) | 17387 (0.91) |
| E24G/R29D/Y31L/ Q33H/K36G/M38I/ T41A/M43R/M47T/ F59L/E81V/L85R/ K89N/A91T/F92P/ K93V/R94L/H96R | 95 | 1074 (0.08) | 1022 (0.02) | 1121 (0.06) | 406 (0.80) | 13146 (0.69) |
| R29D/Y31L/Q33H/ K36G/M38I/T41A/ M43R/M47T/E81V/ L85R/K89N/A91T/ F92P/K93V/R94L/N149S | 96 | 1018 (0.08) | 974 (0.02) | 25434 (1.43) | 405 (0.80) | 24029 (1.25) |
| R29V/M43Q/E81R/ L85I/K89R/D90L/ A91E/F92N/K93Q/R94G | 97 | 1029 (0.08) | 996 (0.02) | 1575 (0.09) | 342 (0.67) | 11695 (0.61) |
| T41I/A91G | 98 | 17890 (1.35) | 50624 (1.01) | 12562 (0.70) | 433 (0.85) | 26052 (1.36) |
| E88D/K89R/D90K/A91G/ F92Y/K93R/N122S/ N178S | 537 | 41687 (3.15) | 49429 (0.99) | 20140 (1.13) | 773 (1.52) | 6345 (0.33) |
| E88D/K89R/D90K/A91G/ F92Y/K93R | 538 | 51663 (3.91) | 72214 (1.44) | 26405 (1.48) | 1125 (2.21) | 9356 (0.49) |
| K36G/K37Q/M38I/ L40M/F59L/E81V/L85R/ K89N/A91T/F92P/ K93V/R94L/E99G/ T130A/N149S | 539 | 1298 (0.10) | 1271 (0.03) | 3126 (0.18) | 507 (1.00) | 3095 (0.16) |
| AE88D/K89R/D90K/ A91G/F92Y/K93R | 102 | 31535 (2.38) | 50868 (1.02) | 29077 (1.63) | 944 (1.85) | 5922 (0.31) |
| K36G/K37Q/M38I/L40M | 103 | 1170 (0.09) | 1405 (0.03) | 959 (0.05) | 427 (0.84) | 811 (0.04) |
| K36G/L40M | 540 | 29766 (2.25) | 58889 (1.18) | 20143 (1.13) | 699 (1.37) | 30558 (1.59) |
| WTCD80 | 28 | 13224 (1.00) | 50101 (1.00) | 17846 (1.00) | 509 (1.00) | 19211 (1.00) |

Example 8

Generation and Assessment of Stacked Molecules Containing Different Affinity-Modified Domains This Example describes further immunomodulatory proteins that were generated as stack constructs containing at least two different affinity modified domains from identified variant ICOSL polypeptides and one more additional variant CD80, CD86, ICOSL, and NKp30 molecules linked together and fused to an Fc.

Selected variant molecules described above that were affinity-modified for one or more counter structure ligand were used to generate "stack" molecule (i.e., Type II immunomodulatory protein) containing two or more affinity-modified IgSF domains. Stack constructs were obtained as geneblocks (Integrated DNA Technologies, Coralville, IA) that encode the stack in a format that enables its fusion to Fc by standard Gibson assembly using a Gibson assembly kit (New England Biolabs, USA).

The encoding nucleic acid molecule of all stacks was generated to encode a protein designed as follows: Signal peptide, followed by the first variant IgV of interest, followed by a 15 amino acid linker which is composed of three GGGGS (G4S) motifs (SEQ ID NO:228), followed by the second IgV of interest, followed by two GGGGS linkers (SEQ ID NO: 229) followed by three alanines (AAA), followed by a human IgG1 Fc as described above. To maximize the chance for correct folding of the IgV domains in each stack, the first IgV was preceded by all residues that normally occur in the wild-type protein between this IgV and the signal peptide (leading sequence). Similarly, the first IgV was followed by all residues that normally connect it in the wild-type protein to either the next Ig domain (typically an IgC domain) or if such a second IgV domain is absent, the residues that connect it to the transmembrane domain (trailing sequence). The same design principle was applied to the second IgV domain except that when both IgV domains were derived from same parental protein (e.g. a ICOSL IgV stacked with another ICOSL IgV), the linker between both was not duplicated.

Table 10 sets forth the design for exemplary stacked constructs. The exemplary stack molecules shown in Table 10 contains the Ig domains (e.g. IgV domain) as indicated and additionally trailing sequences as described above. In the Table, the following components are present in order:

signal peptide (SP; SEQ ID NO:225), Ig domain 1 (e.g. Ig1), trailing sequence 1 (TS1), linker 1 (LR1; SEQ ID NO:228), Ig domain 2 (Ig2), trailing sequence 2 (TS2), linker 2 (LR2; SEQ ID NO:230) and Fc domain (SEQ ID NO:226 containing C5S/R77C/N82G/V87C amino acid substitution). In some cases, a leading sequence 1 (LS1) is present between the signal peptide and IgV1 and in some cases a leading sequence 2 (LS2) is present between the linker and IgV2.

TABLE 10

| Amino acid sequence (SEQ ID NO) of components of exemplary stacked constructs | | | | | | | | | | |
|---|---|---|---|---|---|---|---|---|---|---|
| | First domain | | | | | Second domain | | | | |
| | SP | LS1 | Ig1 | TS1 | LR1 | LS2 | Ig2 | TS2 | LR2 | Fc |
| Domain 1: NKp30 WT<br>Domain 2: ICOSL WT | + | – | 214 | 235 | + | – | 196 | 233 | + | + |
| Domain 1: NKp30 L30V/A60V/S64P/ S86G<br>Domain 2: ICOSL N52S/N57Y/H94D/ L96F/L98F/Q100R | + | – | 215 | 235 | + | – | 212 | 233 | + | + |
| Domain 1: NKp30 L30V/A60V/S64P/ S86G)<br>Domain 2: ICOSL N52D | + | – | 215 | 235 | + | – | 199 | 233 | + | + |
| Domain 1: NKp30 L30V/A60V/S64P/ S86G<br>Domain 2: ICOSL N52H/N57Y/Q100P | + | – | 215 | 235 | + | – | 201 | 233 | + | + |
| Domain 1: ICOSL WT<br>Domain 2: Nkp30 WT | + | – | 196 | 233 | + | – | 214 | 235 | + | + |
| Domain 1: ICOSL N52D<br>Domain 2: NKp30 L30V/A60V/S64P/ S86G | + | – | 199 | 233 | + | – | 215 | 235 | + | + |
| Domain 1: ICOSL N52H/N57Y/Q100P Domain 2: NKp30 L30V/A60V/S64P/ S86G | + | – | 201 | 233 | + | – | 215 | 235 | + | + |
| Domain 1: CD80 WT<br>Domain 2: ICOSL WT | + | – | 152 | 471 | + | – | 196 | 233 | + | + |
| Domain 1: CD80 E88D/K89R/D90K/ A91G/F92Y/K93R Domain 2: ICOSL N52S/N57Y/H94D/ L96F/L98F/Q100R/ G103E/F120S | + | – | 189 | 471 | + | – | 213 | 233 | + | + |
| Domain 1: CD80 A12T/H18L/M43V/ F59L/E77K/P109S/ I118T Domain 2: ICOSL N52S/N57Y/H94D/ L96F/L98F/Q100R/ G103E/F120S | + | – | 193 | 471 | + | – | 213 | 233 | + | + |
| Domain 1: CD80 A12T/H18L/M43V/ F59L/E77K/P109S/ I118T Domain 2: ICOSL N52D | + | – | 193 | 471 | + | – | 199 | 233 | + | + |

TABLE 10-continued

Amino acid sequence (SEQ ID NO) of components
of exemplary stacked constructs

| | | First domain | | | | Second domain | | | |
|---|---|---|---|---|---|---|---|---|---|
| | SP | LS1 | Ig1 | TS1 | LR1 | LS2 | Ig2 | TS2 | LR2 | Fc |
| Domain 1: CD80 E88D/K89R/D90K/ A91G/F92Y/K93R Domain 2: ICOSL N52H/N57Y/Q100P | + | – | 189 | 471 | + | – | 201 | 233 | + | + |
| Domain 1: CD80 A12T/H18L/M43V/ F59L/E77K/P109S/ I118T Domain 2: ICOSL N52H/N57Y/Q100P | + | – | 193 | 471 | + | – | 201 | 233 | + | + |
| Domain 1: ICOSL WT Domain 2: CD80 WT | + | – | 196 | 233 | + | – | 152 | 471 | + | + |
| Domain 1: ICOSL N52S/N57Y/H94D/ L96F/L98F/Q100R/ G103E/F120S Domain 2: CD80 E88D/K89R/D90K/ A91G/F92Y/K93R | + | – | 213 | 233 | + | – | 189 | 471 | + | + |
| Domain 1: ICOSL N52S/N57Y/H94D/ L96F/L98F/Q100R/ G103E/F120S Domain 2: CD80 A12T/H18L/M43V/ F59L/E77K/P109S/ I118T | + | – | 213 | 233 | + | – | 193 | 471 | + | + |
| Domain 1: ICOSL N52D Domain 2: CD80 E88D/K89R/D90K/ A91G/F92Y/K93R | + | – | 199 | 233 | + | – | 189 | 471 | + | + |
| Domain 1: ICOSL N52D Domain 2: CD80 A12T/H18L/M43V/ F59L/E77K/P109S/ I118T | + | – | 199 | 233 | + | – | 193 | 471 | + | + |
| Domain 1: ICOSL N52H/N57Y/Q100P Domain 2: CD80 E88D/K89R/D90K/ A91G/F92Y/K93R | + | – | 201 | 233 | + | – | 189 | 471 | + | + |
| Domain 1: ICOSL N52H/N57Y/Q100P Domain 2: CD80 A12T/H18L/M43V/ F59L/E77K/P109S/ I118T | + | – | 201 | 233 | + | – | 193 | 471 | + | + |
| Domain 1: CD86 WT Domain 2: ICOSL WT | + | 236 | 220 | 237 | + | – | 196 | 233 | + | + |
| Domain 1: CD80 R29H/Y31H/T41G/ Y87N/E88G/K89E/ D90N/A91G/P109S Domain 2: ICOSL N52S/N57Y/H94D/ L96F/L98F/Q100R/ G103E/F120S | + | – | 192 | 471 | + | – | 213 | 233 | + | + |
| Domain 1: CD80 I67T/L70Q/A91G/ T120S Domain 2: ICOSL N52S/N57Y/H94D/ L96F/L98F/Q100R/ G103E/F120S | + | – | 175 | 471 | + | – | 213 | 233 | + | + |

TABLE 10-continued

| | SP | LS1 | Ig1 | TS1 | LR1 | LS2 | Ig2 | TS2 | LR2 | Fc |
|---|---|---|---|---|---|---|---|---|---|---|
| Amino acid sequence (SEQ ID NO) of components of exemplary stacked constructs | | | | | | | | | | |
| | | First domain | | | | Second domain | | | | |
| Domain 1: CD80 R29H/Y31H/T41G/ Y87N/E88G/K89E/ D90N/A91G/P109S Domain 2: ICOSL N52D | + | − | 192 | 471 | + | − | 199 | 233 | + | + |
| Domain 1: CD80 I67T/L70Q/A91G/ T120S Domain 2: ICOSL N52D | + | − | 175 | 471 | + | − | 199 | 233 | + | + |
| Domain 1: CD80 R29H/Y31H/T41G/ Y87N/E88G/K89E/ D90N/A91G/P109S Domain 2: ICOSL N52H/N57Y/Q100P | + | − | 192 | 471 | + | − | 201 | 233 | + | + |
| Domain 1: CD80 I67T/L70Q/A91G/ T120S Domain 2: ICOSL N52H/N57Y/Q100P | + | − | 175 | 471 | + | − | 201 | 233 | + | + |
| Domain 1: CD86 Q35H/H90L/Q102H Domain 2: ICOSL N52S/N57Y/H94D/ L96F/L98F/Q100R/ G103E/F120S | + | 236 | 221 | 237 | + | − | 213 | 233 | + | + |
| Domain 1: CD86 Q35H/H90L/Q102H Domain 2: ICOSL N52D | + | 236 | 221 | 237 | + | − | 199 | 233 | + | + |
| Domain 1: CD86 Q35H/H90L/Q102H Domain 2: ICOSL N52H/N57Y/Q100P | + | 236 | 221 | 237 | + | − | 201 | 233 | + | + |
| Domain 1: ICOSL WT Domain 2: CD86 WT | + | − | 196 | 233 | + | 236 | 220 | 237 | + | + |
| Domain 1: ICOSL N52S/N57Y/H94D/ L96F/L98F/Q100R/ G103E/F120S Domain 2: CD80 R29H/Y31H/T41G/ Y87N/E88G/K89E/ D90N/A91G/P109S | + | − | 213 | 233 | + | − | 192 | 471 | + | + |
| Domain 1: ICOSL N52S/N57Y/H94D/ L96F/L98F/Q100R/ G103E/F120S Domain 2: CD80 I67T/L70Q/A91G/ T120S | + | − | 213 | 233 | + | − | 175 | 471 | + | + |
| Domain 1: ICOSL N52D Domain 2: CD80 R29H/Y31H/T41G/ Y87N/E88G/K89E/ D90N/A91G/P109S | + | − | 199 | 233 | + | − | 192 | 471 | + | + |
| Domain 1: ICOSL N52D Domain 2: CD80 I67T/L70Q/A91G/ T120S | + | − | 199 | 233 | + | − | 175 | 471 | + | + |
| Domain 1: ICOSL N52H/N57Y/Q100P Domain 2: CD80 R29H/Y31H/T41G/ Y87N/E88G/K89E/ D90N/A91G/P109S | + | − | 201 | 233 | + | − | 192 | 471 | + | + |

TABLE 10-continued

Amino acid sequence (SEQ ID NO) of components
of exemplary stacked constructs

| | | First domain | | | | Second domain | | | |
|---|---|---|---|---|---|---|---|---|---|---|
| | SP | LS1 | Ig1 | TS1 | LR1 | LS2 | Ig2 | TS2 | LR2 | Fc |
| Domain 1: ICOSL N52S/N57Y/H94D/ L96F/L98F/Q100R/ G103E/F120S Domain 2: CD86 Q35H/H90L/Q102H | + | – | 213 | 233 | + | 236 | 221 | 237 | + | + |
| Domain 1: ICOSL N52D Domain 2: CD86 Q35H/H90L/Q102H | + | – | 199 | 233 | + | 236 | 221 | 237 | + | + |
| Domain 1: ICOSL N52H/N57Y/Q100P Domain 2: CD86 Q35H/H90L/Q102H | + | – | 201 | 233 | + | 236 | 221 | 237 | + | + |

High throughput expression and purification of the variant IgV-stacked-Fc fusion molecules containing various combinations of variant IgV domains from CD80, CD86, ICOSL or Nkp30 containing at least one affinity-modified IgV domain were generated substantially as described in Example 5. Binding of the variant IgV-stacked-Fc fusion molecules to respective counter structures and functional activity by anti-CD3 coimmobilization assay also were assessed substantially as described in Example 6. For example, costimulatory bioactivity of the stacked IgSF Fc fusion proteins was determined in a similar immobilized anti-CD3 assay as above. In this case, 4 nM of anti-CD3 (OKT3, Biolegend, USA) was coimmobilized with 4 nM to 120 nM of human rB7-H6.Fc (R&D Systems, USA) or human rPD-L1.Fc (R&D Systems, USA) overnight on tissue-culture treated 96-well plates (Corning, USA). The following day unbound protein was washed off with PBS and 100,000 purified pan T cells were added to each well in 100 μl Ex-Vivo 15 media (Lonza, Switzerland). The stacked IgSF domains were subsequently added at concentrations ranging from 8 nM to 40 nM in a volume of 100 μl for 200 μl volume total. Cells were cultured 3 days before harvesting culture supernatants and measuring human IFN-gamma levels with Duoset ELISA kit (R&D Systems, USA) as mentioned above.

The results are set forth in Tables 11-13. Specifically, Table 11 sets forth binding and functional activity results for variant IgV-stacked-Fc fusion molecules containing an NKp30 IgV domain and an ICOSL IgV domain. Table 12 and 13 sets forth binding and functional activity results for variant IgV-stacked-Fc fusion molecules containing a variant ICOSL IgV domain and a variant CD80 IgV or CD86 IgV domain.

For each of Tables 11-13, Column 1 indicates the structural organization and orientation of the stacked, affinity modified or wild-type (WT) domains beginning with the amino terminal (N terminal) domain, followed by the middle WT or affinity modified domain located before the C terminal human IgG1 Fc domains. Column 2 sets forth the SEQ ID NO identifier for the sequence of each IgV domain contained in a respective "stack" molecule. Column 3 shows the binding partners which the indicated affinity modified stacked domains from column 1 were selected against.

Also shown is the binding activity as measured by the Mean Fluorescence Intensity (MFI) value for binding of each stack molecule to cells transfected to express various counter structure ligands and the ratio of the MFI compared to the binding of the corresponding stack molecule containing reference (e.g., unmodified) IgV domains not containing the amino acid substitution(s) to the same cell-expressed counter structure ligand. The functional activity of the variant stack molecules to modulate the activity of T cells also is shown based on the calculated levels of IFN-gamma in culture supernatants (pg/mL) generated with the indicated variant stack molecule in solution and the appropriate ligand coimmoblized with anti-CD3 as described in Example 6. The Table also depicts the ratio of IFN-gamma produced by each variant stack molecule compared to the corresponding reference (e.g., unmodified) stack molecule in the coimmobilization assay.

As shown, the results showed that it was possible to generate stack molecules containing at least one variant IgSF domains that exhibited affinity-modified activity of increased binding for at least one cognate counter structure ligand compared to a corresponding stack molecule containing the respective reference (e.g. wild-type or unmodified) IgV domain. In some cases, the stack molecule, either from one or a combination of both variant IgSF domains in the molecule, exhibited increased binding for more than one cognate counter structure ligand. The results also showed that the order of the IgV domains in the stacked molecules could, in some cases, alter the degree of improved binding activity. In some cases, functional T cell activity also was altered when assessed in the targeted coimmobilization assay.

TABLE 11

Stacked variant IgV Fc fusion proteins containing an NKp30 IgV domain and an ICOSL IgV domain

| Domain Structure | SEQ | Counter | Binding Activity | | | Anti-CD3 coimmobilization |
|---|---|---|---|---|---|---|
| N terminal to C terminal: domain 1/domain 2/Fc | ID NO (Ig domain) | structure selected against | B7H6 MFI (WT parental MFI ratio) | ICOS MFI (WT parental MFI ratio) | CD28 MFI (WT parental MFI ratio) | assay pg/mL IFN-gamma (WT parental IFN-gamma ratio) |
| Domain 1: NKp30 WT | 214 | — | 64538 (1.00) | 26235 (1.00) | 6337 (1.00) | 235 (1.00) |
| Domain 2: ICOSL WT | 196 | | | | | |
| Domain 1: NKp30 L30V/A60V/S64P/S86G | 215 | B7-H6 | 59684 (0.92) | 12762 (0.49) | 9775 (1.54) | 214 (0.91) |
| Domain 2: ICOSL N52S N57Y H94D L96F L98F Q100R | 212 | ICOS-CD28 | | | | |
| Domain 1: NKp30 L30V/A60V/S64P/S86G | 215 | B7-H6 | 65470 (1.01) | 30272 (1.15) | 9505 (1.50) | 219 (0.93) |
| Domain 2: ICOSL N52D | 199 | ICOS-CD28 | | | | |
| Domain 1: NKp30 L30V/A60V/S64P/S86G | 215 | B7-H6 | 38153 (0.59) | 27903 (1.06) | 11300 (1.78) | 189 (0.80) |
| Domain 2: ICOSL N52H N57Y Q100P | 201 | ICOS-CD28 | | | | |
| Domain 1: ICOSL WT | 196 | — | 117853 (1.0) | 70320 (1.0) | 7916 (1.0) | 231 (1.0) |
| Domain 2: Nkp30 WT | 214 | | | | | |
| Domain 1: ICOSL N52D | 199 | ICOS-CD28 | 100396 (0.85) | 83912 (1.19) | 20778 (2.62) | 228 (0.98) |
| Domain 2: NKp30 L30V/A60V/S64P/S86G | 215 | B7-H6 | | | | |
| Domain 1: ICOSL N52H/N57Y/Q100P | 201 | ICOS-CD28 | 82792 (0.70) | 68874 (0.98) | 72269 (9.12) | 561 (2.43) |
| Domain 2: NKp30 L30V/A60V/S64P/S86G | 215 | B7-H6 | | | | |

TABLE 12

Stacked variant IgV Fc fusion proteins containing a CD80 IgV domain and a ICOSL IgV domain

| Domain Structure | SEQ | Counter | Binding Activity | | | Anti-CD3 coimmobilization |
|---|---|---|---|---|---|---|
| N terminal to C terminal: domain 1/domain 2/Fc | ID NO (Ig domain) | structure selected against | CD28 MFI (WT parental MFI ratio) | PD-L1 MFI (WT parental MFI ratio) | ICOS MFI (WT parental MFI ratio) | assay pg/mL IFN-gamma (WT parental IFN-gamma ratio) |
| Domain 1: CD80 WT | 152 | | 1230 (1.00) | 2657 (1.00) | 11122 (1.00) | 69 (1.00) |
| Domain 2: ICOSL WT | 196 | | | | | |
| Domain 1: CD80 E88D/K89R/D90K/A91G/F92Y/K93R | 189 | PD-L1 | 3383 (2.75) | 4515 (1.70) | 5158 (0.46) | 90 (1.30) |
| Domain 2: ICOSL N52S/N57Y/H94D/L96F/L98F/Q100R/G103E/F120S | 213 | ICOS/CD28 | | | | |
| Domain 1: CD80 A12T/H18L/M43V/F59L/E77K/P109S/I118T | 193 | PD-L1 | 2230 (1.81) | 2148 (0.81) | 3860 (0.35) | 112 (1.62) |
| Domain 2: ICOSL N52S/N57Y/H94D/L96F/L98F/Q100R/G103E/F120S | 213 | ICOS/CD28 | | | | |
| Domain 1: CD80 A12T/H18L/M43V/F59L/E77K/P109S/I118T | 193 | PD-L1 | 5665 (4.61) | 6446 (2.43) | 15730 (1.41) | 126 (1.83) |
| Domain 2: ICOSL N52D | 199 | ICOS/CD28 | | | | |
| Domain 1: CD80 E88D/K89R/D90K/A91G/F92Y/K93R | 189 | PD-L1 | 6260 (5.09) | 4543 (1.71) | 11995 (1.08) | 269 (3.90) |
| Domain 2: ICOSL N52H/N57Y/Q100P | 201 | ICOS/CD28 | | | | |
| Domain 1: CD80 A12T/H18L/M43V/F59L/E77K/P109S/I118T | 193 | PD-L1 | 3359 (2.73) | 3874 (1.46) | 8541 (0.77) | 97 (1.41) |
| Domain 2: ICOSL N52H/N57Y/Q100P | 201 | ICOS/CD28 | | | | |
| Domain 1: ICOSL WT | 196 | | 3000 (1.00) | 2966 (1.00) | 14366 (1.00) | 101 (1.00) |
| Domain 2: CD80 WT | 152 | | | | | |

TABLE 12-continued

Stacked variant IgV Fc fusion proteins containing a CD80 IgV domain and a ICOSL IgV domain

| Domain Structure N terminal to C terminal: domain 1/domain 2/Fc | SEQ ID NO (Ig domain) | Counter structure selected against | Binding Activity | | | Anti-CD3 coimmobilization assay pg/mL IFN-gamma (WT parental IFN-gamma ratio) |
|---|---|---|---|---|---|---|
| | | | CD28 MFI (WT parental MFI ratio) | PD-L1 MFI (WT parental MFI ratio) | ICOS MFI (WT parental MFI ratio) | |
| Domain 1: ICOSL N52S/N57Y/H94D/L96F/L98F/Q100R/G103E/F120S | 213 | ICOS/CD28 | 3634 (1.21) | 4893 (1.65) | 6403 (0.45) | 123 (1.22) |
| Domain 2: CD80 E88D/K89R/D90K/A91G/F92Y/K93R | 189 | PD-L1 | | | | |
| Domain 1: ICOSL N52S/N57Y/H94D/L96F/L98F/Q100R/G103E/F120S | 213 | ICOS/CD28 | 1095 (0.37) | 5929 (2.0) | 7923 (0.55) | 127 (1.26) |
| Domain 2: CD80 A12T/H18L/M43V/F59L/E77K/P109S/I118T | 193 | PD-L1 | | | | |
| Domain 1: ICOSL N52D | 199 | ICOS/CD28 | 2023 (0.67) | 5093 (1.72) | 16987 (1.18) | 125 (1.24) |
| Domain 2: CD80 E88D/K89R/D90K/A91G/F92Y/K93R | 189 | PD-L1 | | | | |
| Domain 1: ICOSL N52D | 199 | ICOS/CD28 | 3441 (1.15) | 3414 (1.15) | 20889 (1.45) | 165 (1.63) |
| Domain 2: CD80 A12T/H18L/M43V/F59L/E77K/P109S/I118T | 193 | PD-L1 | | | | |
| Domain 1: ICOSL N52H/N57Y/Q100P | 201 | ICOS/CD28 | 7835 (2.61) | 6634 (2.24) | 20779 (1.45) | 95 (0.94) |
| Domain 2: CD80 E88D/K89R/D90K/A91G/F92Y/K93R | 189 | PD-L1 | | | | |
| Domain 1: ICOSL N52H/N57Y/Q100P | 201 | ICOS/CD28 | 8472 (2.82) | 3789 (1.28) | 13974 (0.97) | 106 (1.05) |
| Domain 2: CD80 A12T/H18L/M43V/F59L/E77K/P109S/I118T | 193 | PD-L1 | | | | |

TABLE 13

Stacked variant IgV Fc fusion proteins containing a CD80 or CD86 IgV domain and an ICOSL IgV domain

| Domain Structure N terminal to C terminal: domain 1/domain 2/Fc | SEQ ID NO (Ig domain) | Counter structure selected against | Binding Activity | | Functional Activity MLR IFN-gamma pg/mL |
|---|---|---|---|---|---|
| | | | PD-L1 MFI (WT parental MFI ratio) | CTLA-4 MFI (WT parental MFI ratio) | |
| Domain 1: CD80 WT | 152 | | 1230 (1.00) | 11122 (1.00) | 1756 (1.00) |
| Domain 2: ICOSL WT | 196 | | | | |
| Domain 1: CD86 WT | 220 | | 29343 (1.00) | 55193 (1.00) | 6305 (1.00) |
| Domain 2: ICOSL WT | 196 | | | | |
| Domain 1: CD80 R29H/Y31H/T41G/Y87N/E88G/K89E/D90N/A91G/P109S | 192 | CD28 | 2280 (1.85) | 3181 (0.29) | 2281 (1.30) |
| Domain 2: ICOSL N52S/N57Y/H94D/L96F/L98F/Q100R/G103E/F120S | 213 | ICOS/CD28 | | | |
| Domain 1: CD80 I67T/L70Q/A91G/T120S | 175 | CD28 | 2309 (1.88) | 26982 (2.43) | 1561 (0.89) |
| Domain 2: ICOSL N52S/N57Y/H94D/L96F/L98F/Q100R/G103E/F120S | 213 | ICOS/CD28 | | | |
| Domain 1: CD80 R29H/Y31H/T41G/Y87N/E88G/K89E/D90N/A91G/P109S | 192 | CD28 | 4285 (3.48) | 22744 (2.04) | 1612 (0.92) |
| Domain 2: ICOSL N52D | 199 | ICOS/CD28 | | | |
| Domain 1: CD80 I67T/L70Q/A91G/T120S | 175 | CD28 | 3024 (2.46) | 16916 (1.52) | 3857 (2.20) |

TABLE 13-continued

Stacked variant IgV Fc fusion proteins containing
a CD80 or CD86 IgV domain and an ICOSL IgV domain

| Domain Structure N terminal to C terminal: domain 1/domain 2/Fc | SEQ ID NO (Ig domain) | Counter structure selected against | Binding Activity | | Functional Activity MLR IFN-gamma pg/mL |
|---|---|---|---|---|---|
| | | | PD-L1 MFI (WT parental MFI ratio) | CTLA-4 MFI (WT parental MFI ratio) | |
| Domain 2: ICOSL N52D | 199 | ICOS/CD28 | | | |
| Domain 1: CD80 R29H/Y31H/T41G/Y87N/ E88G/K89E/D90N/A91G/ P109S | 192 | CD28 | 6503 (5.29) | 7240 (0.65) | 6886 (3.92) |
| Domain 2: ICOSL N52H/N57Y/Q100P | 201 | ICOS/CD28 | | | |
| Domain 1: CD80 I67T/L70Q/A91G/T120S | 175 | CD28 | 3110 (2.53) | 4848 (0.44) | 3393 (1.93) |
| Domain 2: ICOSL N52H/N57Y/Q100P | 201 | ICOS/CD28 | | | |
| Domain 1: CD86 Q35H/H90L/Q102H | 221 | CD28 | 11662 (0.40) | 21165 (0.38) | 880 (0.14) |
| Domain 2: ICOSL N52S/N57Y/H94D/L96F/ L98F/Q100R/G103E/F120S | 213 | ICOS/CD28 | | | |
| Domain 1: CD86 Q35H/H90L/Q102H | 221 | CD28 | 24230 (0.83) | 73287 (1.33) | 1110 (0.18) |
| Domain 2: ICOSL N52D | 199 | ICOS/CD28 | | | |
| Domain 1: CD86 Q35H/H90L/Q102H | 221 | CD28 | 1962 (0.07) | 1630 (0.03) | 587 (0.09) |
| Domain 2: ICOSL N52H/N57Y/Q100P | 201 | ICOS/CD28 | | | |
| Domain 1: ICOSL WT | 196 | | 3000 | 14366 | 4113 |
| Domain 2: CD80 WT | 152 | | (1.00) | (1.00) | (1.00) |
| Domain 1: ICOSL WT | 196 | | 18005 | 53602 | 18393 |
| Domain 2: CD86 WT | 220 | | (1.00) | (1.00) | (1.00) |
| Domain 1: ICOSL N52S/N57Y/H94D/L96F/ L98F/Q100R/G103E/F120S | 213 | ICOS/CD28 | 10426 (3.48) | 51286 (3.57) | 18680 (4.54) |
| Domain 2: CD80 R29H/Y31H/T41G/Y87N/ E88G/K89E/D90N/A91G/ P109S | 192 | CD28 | | | |
| Domain 1: ICOSL N52S/N57Y/H94D/L9617 L98F/Q100R/G103E/F120S | 213 | ICOS/CD28 | 17751 (5.92) | 29790 (2.07) | 10637 (2.59) |
| Domain 2: CD80 I67T/L70Q/A91G/T120S | 175 | CD28 | | | |
| Domain 1: ICOSL N52D | 199 | ICOS/CD28 | 2788 (0.93) | 25870 (1.80) | 6205 (1.51) |
| Domain 2: CD80 R29H/Y3IH/T41G/Y87N/ E88G/K89E/D90N/A91G/ P109S | 192 | CD28 | | | |
| Domain 1: ICOSL N52D | 199 | ICOS/CD28 | 2522 (0.84) | 13569 (0.94) | 5447 (1.32) |
| Domain 2: CD80 I67T/L70Q/A91G/T120S | 175 | CD28 | | | |
| Domain 1: ICOSL N52H/N57Y/Q100P | 201 | ICOS/CD28 | 9701 (3.23) | 9187 (0.64) | 5690 (1.38) |
| Domain 2: CD80 R29H/Y31H/T41G/Y87N/ E88G/K89E/D90N/A91G/ P109S | 192 | CD28 | | | |
| Domain 1: ICOSL N52S/N57Y/H94D/L96F/ L98F/Q100R/G103E/F120S | 213 | ICOS/CD28 | 27050 (1.50) | 21257 (0.40) | 8131 (0.44) |
| Domain 2: CD86 Q35H/H90L/Q102H | 221 | CD28 | | | |
| Domain 1: ICOSL N52D | 199 | ICOS/CD28 | 34803 (1.93) | 80210 (1.50) | 6747 (0.37) |
| Domain 2: CD86 Q35H/H90L/Q102H | 221 | CD28 | | | |
| Domain 1: ICOSL N52H/N57Y/Q100P | 201 | ICOS/CD28 | 5948 (0.33) | 4268 (0.08) | 26219 (1.43) |
| Domain 2: CD86 Q35H/H90L/Q102H | 221 | CD28 | | | |

Example 9

Generation and Assessment of Engineered Cells Expressing a Transmembrane Immunomodulatory Protein Engineered T cells were generated in which a transmembrane immunomodulatory protein (TIP) containing an extracellular domain (ECD) containing either a variant CD80 as described above or an ICOSL affinity-modified IgSF domain was co-expressed with a chimeric antigen receptor (CAR). The TIP also contained a transmembrane domain and a cytoplasmic domain of the corresponding wild-type CD80 or ICOSL transmembrane protein sequence. The immunomodulatory activity of the engineered cells was compared to cells that only expressed the CAR or cells that co-expressed the corresponding wild-type CD80 or ICOSL transmembrane protein with the CAR.

The exemplary CD80-TIP was a variant CD80 having an affinity-modified IgSF domain containing amino acid mutations in the IgV and IgC domains corresponding to I67T/L70Q/A91G/T120S with reference to positions in the CD80 extracellular domain set forth in SEQ ID NO:28 and a transmembrane and cytoplasmic domain corresponding to residues 243-288 of SEQ ID NO:1. The amino acid sequence of the exemplary CD80-TIP is set forth in SEQ ID NO: 241 and is encoded by the sequence of nucleotides set forth in SEQ ID NO:242. The corresponding wild-type CD80 transmembrane protein had the sequence of amino acids set forth as amino acid residues 35-288 of SEQ ID NO:1 and encoded by the sequence of amino acids set forth in SEQ ID NO: 251.

The exemplary ICOSL-TIP was a variant ICOSL having an affinity-modified IgSF domain containing amino acid mutations in the IgV domain corresponding to N52H/I143T with reference to positions in the ICOSL extracellular domain set forth in SEQ ID NO:32 and a transmembrane and cytoplasmic domain corresponding to residues 257-302 of SEQ ID NO:5. The amino acid sequence of the exemplary ICOSL-TIP is set forth in SEQ ID NO:243 and is encoded by the sequence of nucleotides set forth in SEQ ID NO:244. The corresponding wild-type ICOSL transmembrane protein had the sequence of amino acids set forth as amino acid residues 19-302 of SEQ ID NO:5 and encoded by the sequence of amino acids set forth in SEQ ID NO: 252.

The TIP containing the affinity-modified domain or the wild-type transmembrane protein containing a corresponding non-affinity modified IgSF domain were co-expressed in T cells with a 1$^{st}$ generation chimeric antigen receptor (CAR) containing a CD3zeta intracellular signaling domain. The 1$^{st}$ generation CAR included an scFv specific for CD19 (SEQ ID NO: 245), a hinge and transmembrane domain derived from CD8 (SEQ ID NO:246) and an intracellular signaling domain derived from CD3zeta (set forth in SEQ ID NO:47). The nucleotide sequence encoding the CD19 scFv-CD3zeta CAR is set forth in SEQ ID NO: 248 and the amino acid sequence of the CD19 scFv-CD3zeta CAR is set forth in SEQ ID NO: 479.

Nucleic acid molecules encoding the CAR alone or also encoding one of the exemplary TIPs or wild-type transmembrane proteins separated from the CAR by a self-cleaving T2A sequence (SEQ ID NO:250 and encoded by the sequence of nucleotides set forth in SEQ ID NO: 249) were generated. Exemplary constructs contained nucleic acid sequences set forth in Table 14. As a control, a nucleic acid construct encoding a 2$^{nd}$ generation CAR additionally containing a CD28 costimulatory domain also was generated (CD19 scFv-CD28-CD3zeta).

TABLE 14

| Nucleic Acid Constructs | | | |
| --- | --- | --- | --- |
| | CAR (SEQ ID NO) | T2A Linker (SEQ ID NO) | TIP (SEQ ID NO) |
| CD19 scFv - CD3zeta | + (248) | – | – |
| CD19 scFv - CD3zeta - T2A - B7-1 | + (248) | + (249) | Wildtype CD80 (251) |
| CD19 scFv - CD3zeta - T2A - B7-1_TIP | + (248) | + (249) | CD80 TIP (242) |
| CD19 scFv - CD3zeta - T2A - ICOSL | + (248) | + (249) | Wildtype ICOSL (252) |
| CD19 scFv - CD3zeta - T2A - ICOSL_TIP | + (248) | + (249) | ICOSL TIP (244) |

The nucleic acid molecules were individually cloned into a lentiviral vector, which was used to transduce T cells isolated from human PBMC samples obtained from three different healthy donors. Lentivirus particles containing the nucleic acid sequences were produced after co-transfection of HEK293 cells with the vectors and lentivirus packaging constructs. The lentivirus particles were collected from the culture medium by ultracentrifugation and titered by qRT-PCR. Human peripheral blood mononuclear cells (PBMC) were isolated from three normal blood donors using density sedimentation. The PBMC were cultured overnight with anti-CD3 and anti-CD28 antibodies and IL-2, then transduced with the lentivirus preparations at a multiplicity of infection of 5:1. The lentiviral vectors encoding the control 2$^{nd}$ generation CAR was only used to transduce cells from one donor.

After two weeks (14 days) of culture, the cells were analyzed for cytotoxicity following co-culture with target antigen-expressing cells using the Acea Real-Time Cell Analyzer (RTCA), which measures the impedance variations in the culture media of a 96-well microelectronic plate (E-plate), and shows the changes in cell number and morphology in a real-time plot. CD19-expressing HeLa target cells (HeLa-CD19) were seeded into a 96-well E-plate and the impedance of each monolayer was monitored for 24 hours using the RTCA system. The engineered T cells were added to the wells at an effector:target ratio of 10:1 and the wells were monitored for another 48 hours. The results were displayed and recorded as Cell Index (CI) value derived from the change in measured electrical impedance and were then ratio transformed by dividing the CI readouts of all wells at all time points over the CI value of individual wells at a same time (base-time) to obtain a normalized cell index value representing the percentage of the value at the base-time (see Zhang et al. "Introduction to the Data Analysis of the Roche xCELLigence®System with RTCA Package." Bioconductor. May 3, 2016, bioconductor.org/packages/devel/bioc/vignettes/RTCA/inst/doc/aboutRTCA.pdf. Accessed Sep. 9, 2016). In this assay, a decrease in the impedance of a monolayer reflects killing of the target cells by the transduced cells.

The results showed that decreased impedance was observed in cells expressing the 1$^{st}$ generation CAR compared to non-transduced T cells, although the degree of decreased impedance for cells expressing the 1$^{st}$ generation CAR was less than cells expressing the 2$^{nd}$ generation CAR. The decreased impedance in cells expressing the 1$^{st}$ generation CAR continued generally for up to the first 8 hours of the assay, while only the 2nd generation CAR-expressing cells continued to decrease the impedance thereafter.

Figure 1:
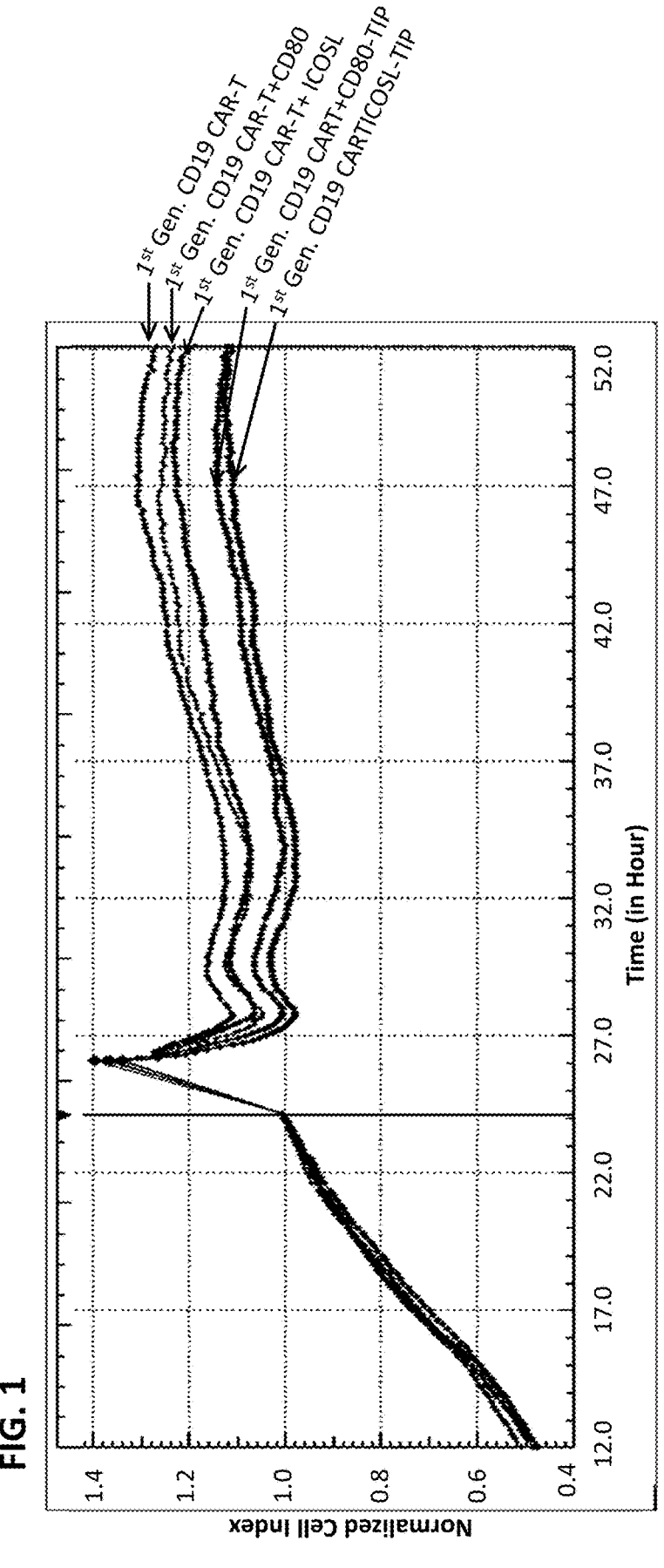
FIG. 1 depicts impedance results reflecting cytotoxic killing activity of cells engineered with an anti-CD19 chimeric antigen receptor (CAR) alone or with an exemplary transmembrane immunomodulatory TIP (CD80-TIP or ICOSL-TIP) or the corresponding CD80 or ICOSL wild-type transmembrane protein following co-culture with target antigen-expressing cells. Impedance was assessed using the Acea Real-Time Cell Analyzer (RTCA), which measures the impedance variations in the culture media of a 96-well microelectronic plate (E-plate).

As shown in FIG. 1, in one donor, each of the cells co-expressing the TIP or corresponding wild-type transmembrane protein with the 1st generation CAR exhibited a greater decrease in impedance, indicating greater cytotoxic activity, compared to cells only expressing the 1st generation CAR. Further, the results showed that the cytotoxic activity was greater in CAR-expressing cells that co-expressed the CD80-TIP or ICOSL-TIP relative to CAR-expressing cells that co-expressed the corresponding wild-type CD80 or ICOSL transmembrane proteins containing a non-affinity modified IgSF domain. The observed results of these TIP-engineered cells showed that cytotoxic activity in cells co-expressing the CD80-TIP or ICOSL-TIP with the CAR exhibit increased activity to modulate the cytotoxic immune response of antigen-specific T cells, such as the CAR-expressing T cells.

In the other two donors, the cells expressing the CD80-TIP did not result in a greater decreased impedance compared to cells expressing the corresponding wild-type CD80 transmembrane protein. In one donor, there were not enough cells to transduce with the wild-type transmembrane protein construct, although in this donor the ICOS-L TIP gave the best cytotoxicity compared to the other constructs tested. In the other donor, the cells expressing the ICOS-L-TIP did not result in a greater decreased impedance compared to cells expressing the corresponding wild-type ICOS-L transmembrane protein. In the tested cells, all cells co-expressing either a CD80-TIP, ICOSL-TIP or corresponding wild type transmembrane protein with the CAR exhibited greater cytotoxic activity than cells only expressing the 1st generation CAR. The differences in the results observed among donors may be related to the differences in the T cells among the donors, differences in expression levels of the various engineered proteins on the surface of the cells, the particular conditions used in this exemplary assay for assessing killing in cells (e.g. assessing Day 14 transduced cells, assessing a single effector:target cell ratio) or other factors.

Example 10

Assessment of Binding and Activity of ICOSL IgSF Domain Variants

Additional ECD ICOSL variants were identified by the yeast selection method substantially as described above and were used to produce ECD-Fc fusion proteins as described in Example 5. Binding studies were performed to assess specificity and affinity of ICOSL domain variant immunomodulatory proteins for cognate binding partners substantially as described in Example 6.

A. Binding and Functional Characterization

Binding was assessed to cells expressed full-length cognate binding partners CD28, ICOS and CTLA-4 substantially as described in Example 6. Bioactivity of the ECD ICOSL variants also was assessed in an anti-CD3 coimmobilization assay or human Mixed Lymphocyte Reaction (MLR) substantially as described in Example 6, except that for the coimmobilization assay, costimulatory activity was determined by culture of human T cells with a mixture of 10 nM plate-bound anti-CD3 and 40 nM ICOSL Fc variant proteins.

Table 15 depicts exemplary results for the additional ICOSL IgSF domain variants for binding to cell-expressed counter structures and bioactivity in the anti-CD3 coimmobilization assay or MLR assay. The exemplary amino acid substitutions depicted in Table 15 are designated by amino acid position number corresponding to the respective reference (e.g., unmodified) ICOSL ECD sequence set forth in SEQ ID NO:32. The amino acid position is indicated in the middle, with the corresponding unmodified (e.g. wild-type) amino acid listed before the number and the identified variant amino acid substitution listed after the number. Column 2 sets forth the SEQ ID NO identifier for the variant ECD for each variant ECD-Fc fusion molecule.

The results in Table 15 depict binding activity as measured by the Mean Fluorescence Intensity (MFI) value for binding of each variant Fc-fusion molecule to cells engineered to express the cognate counter structure ligand and the ratio of the MFI compared to the binding of the corresponding reference (e.g., unmodified) ECD-Fc fusion molecule not containing the amino acid substitution(s) to the same cell-expressed counter structure ligand. The functional activity of the variant Fc-fusion molecules to modulate the activity of T cells also is shown based on the calculated levels of IFN-gamma in culture supernatants (pg/mL) generated either i) with the indicated variant ECD-Fc fusion molecule coimmoblized with anti-CD3 or ii) with the indicated variant ECD-Fc fusion molecule in an MLR assay. The Table also depicts the ratio of IFN-gamma produced by each variant ECD-Fc compared to the corresponding unmodified (parental) ECD-Fc in both functional assays.

The results show altered, including increased, binding affinity of affinity-modified ICOSL IgSF domain variants for at least one cognate counter structure ligand and/or improved immunological activity. Specifically, similar to the initial hits identified in Example 6, the selections resulted in the identification of a number of additional ICOSL IgSF domain variants that were affinity-modified to exhibit increased binding for at least one, and in some cases more than one, cognate counter structure ligand. In addition, the results showed that affinity modification of the variant molecules also exhibited improved activities to both increase and/or decrease immunological activity depending on the format of the molecule as described in Example 6.

TABLE 15

| | | | | | Anti-CD3 | MLR |
| ICOSL mutation(s) | SEQ ID NO (ECD) | ICOS tfxn MFI (parental ratio) | CD28 tfxn MFI (parental ratio) | CTLA-4 tfxn MFI (parental ratio) | IFN-gamma Coimmobilization Assay pg/mL (parental ratio) | IFN-gamma pg/mL (parental ratio) |
|---|---|---|---|---|---|---|
| | | | ICOSL variants: binding data and costimulatory bioactivity data. | | | |
| N52H, F78L, Q100R, C198R | 373 | 9568 (0.12) | 1966 (0.24) | 1454 (0.12) | 130 (0.31) | 5927 (1.84) |
| N52H, N57Y, Q100R, V110D, C198R, S212G | 364 | 9418 (1.16) | 136665 (16.55) | 115352 (9.59) | 944 (2.21) | 821 (0.25) |
| N52H, N57Y, R75Q, Q100P, V110D | 374 | 5558 (0.07) | 7465 (0.90) | 4689 (0.39) | 122 (0.28) | 1136 (0.35) |

TABLE 15-continued

ICOSL variants: binding data and costimulatory bioactivity data.

| ICOSL mutation(s) | SEQ ID NO (ECD) | ICOS tfxn MFI (parental ratio) | CD28 tfxn MFI (parental ratio) | CTLA-4 tfxn MFI (parental ratio) | Anti-CD3 IFN-gamma Coimmobilization Assay pg/mL (parental ratio) | MLR IFN-gamma pg/mL (parental ratio) |
|---|---|---|---|---|---|---|
| N52H, N57Y, Q100R, C198R | 365 | 9148 (1.13) | 134923 (16.33) | 83241 (6.92) | 1060 (2.48) | 375 (0.12) |
| N52H, N57Y, L74Q, V110D, S192G | 375 | 9448 (1.17) | 128342 (15.54) | 123510 (10.26) | 1137 (2.66) | 889 (0.28) |
| N52H, Q100R | 285 | 9478 (1.17) | 151977 (18.40) | 133929 (11.13) | 972 (2.28) | 794 (0.25) |
| N52H, S121G, C198R | 376 | 9128 (1.13) | 124732 (15.10) | 182607 (15.18) | 827 (1.94) | 1257 (0.39) |
| A20V, N52H, N57Y, Q100R, S109G | 287 | 5828 (0.72) | 76973 (9.32) | 73640 (6.12) | 447 (1.05) | 2283 (0.71) |
| N52H, N57Y, Q100P, C198R | 461 | 9548 (1.18) | 130676 (15.82) | 81966 (6.81) | 1125 (2.64) | 643 (0.20) |
| N52H, N57Y, R61S, Q100R, V110D, L173S | 289 | 1018 (0.13) | 9129 (1.11) | 5790 (0.48) | 109 (0.25) | 5094 (1.58) |
| N52H, N57Y, Q100R, V122A | 290 | 9978 (1.23) | 137372 (16.63) | 70764 (5.88) | 1316 (3.08) | 473 (0.15) |
| N52H, N57Y, Q100R, F172S | 291 | 1028 (1.27) | 135821 (16.44) | 73320 (6.09) | 1561 (3.66) | 486 (0.15) |
| N52H, N57Y, Q100R | 283 | 9858 (1.22) | 140612 (17.02) | 75106 (6.24) | 1648 (3.86) | 778 (0.24) |
| N52S, F120S, N227K | 377 | 9438 (1.17) | 67796 (8.21) | 82370 (6.85) | 1157 (2.71) | 1626 (0.50) |
| N52S, N194D | 366 | 9798 (1.21) | 59431 (7.19) | 74502 (6.19) | 1671 (3.91) | 1690 (0.52) |
| N52S, V97A | 294 | 3138 (0.04) | 1733 (0.21) | 1541 (0.13) | 84 (0.20) | 3858 (1.20) |
| N52S, F120S | 293 | 9068 (1.12) | 67233 (8.14) | 97880 (8.13) | 1178 (2.76) | 2814 (0.87) |
| N52S, G72R | 295 | 9288 (1.15) | 51638 (6.25) | 62339 (5.18) | 1161 (2.72) | 2947 (0.91) |
| N52S, A71T, A117T, T190A, C198R | 378 | 8918 (1.10) | 44044 (5.33) | 56646 (4.71) | 1076 (2.52) | 4031 (1.25) |
| N52S, E220G | 297 | 3878 (0.05) | 2047 (0.25) | 1796 (0.15) | 122 (0.29) | 1927 (0.60) |
| Y47H, N52S, V107A, F120S | 298 | 3268 (0.04) | 2562 (0.31) | 2104 (0.17) | 334 (0.78) | 4390 (1.36) |
| WT ICOSL | 32 | 8088 (1.00) | 8260 (1.00) | 12033 (1.00) | 427 (1.00) | 3226 (1.00) |
| T43A, N52H, N57Y, L74Q, D89G, V110D, F172S | 379 | 2821 (0.02) | 2180 (0.49) | 2051 (0.12) | 184 (0.75) | |
| N52H, N57Y, Q100R, V1071, V110D, S132F, I154F, C198R, R221G | 381 | 174586 (0.97) | 122383 (27.24) | 76202 (4.31) | 985 (4.01) | 1037 (0.36) |
| E16V, N52H, N57Y, Q100R, V110D, H115R, Y152C, K156M, C198R | 300 | 190765 (1.05) | 129070 (28.73) | 68488 (3.87) | 4288 (17.46) | 1225 (0.43) |
| Q37R, N52H, N57Y, Q100R, V110N, S142F, C198R, D217V, R221G | 301 | 148638 (0.82) | 91104 (20.28) | 13498 (0.76) | 62 (0.25) | 7643 (2.68) |
| N52H, N57Y, Q100R, V110D, C198R | 302 | 179194 (0.99) | 123312 (27.45) | 84136 (4.76) | 762 (3.10) | 1342 (0.47) |
| N52H, N57Y, Q100R, V110D, V116A, L161M, F172S, S192G, C198R | 303 | 5236 (0.03) | 4160 (0.93) | 3305 (0.19) | 49 (0.20) | 2039 (0.72) |
| F27S, N52H, N57Y, V110N | 304 | 20154 (0.11) | 8613 (1.92) | 3903 (0.22) | 83 (0.34) | 7522 (2.64) |
| F27S, N52H, N57Y, V110N | 304 | 5236 (0.03) | 4160 (0.93) | 2957 (0.17) | 40 (0.16) | — |
| N52S, H94E, L96I, S109N, L166Q, | 305 | 198604 (1.10) | 100361 (22.34) | 102892 (5.82) | 1253 (5.10) | 5645 (1.98) |
| S18R, N52S, F93L, I143V, R221G | 306 | 154561 (0.85) | 7625 (1.70) | 4254 (0.24) | 203 (0.83) | 5239 (1.84) |
| A20T, N52D, Y146C, Q164L | 307 | 149661 (0.83) | 9073 (2.02) | 6901 (0.39) | 287 (1.17) | 4829 (1.69) |
| V11E, N30D, N52H, N57Y, H94E, L96I, L98F, N194D, V210A, I218T | 308 | 180016 (1.00) | 120230 (26.76) | 62809 (3.55) | 2218 (9.03) | 7283 (2.56) |
| N52S, H94E, L96I, V122M | 309 | 198717 (1.10) | 88901 (19.79) | 94231 (5.33) | 590 (2.40) | 618 (0.22) |
| N52H, N57Y, H94E, L96I, F120I, S126T, W153R, I218N | 310 | 87711 (0.48) | 42035 (9.36) | 31798 (1.80) | 67 (0.27) | 2500 (0.88) |
| M10V, S18R, N30D, N52S, S126R, T139S, L203F | 311 | 180665 (1.00) | 64929 (14.45) | 48362 (2.73) | 1193 (4.86) | 13647 (4.79) |
| S25G, N30D, N52S, F120S, N227K | 312 | 178834 (0.99) | 66127 (14.72) | 46631 (2.64) | 1246 (5.07) | 2202 (0.77) |
| N30D, N52S, L67P, Q100K, D217G, R221K, T225S | 313 | 18630 (0.10) | 1986 (0.44) | 1940 (0.11) | 54 (0.22) | 2752 (0.97) |
| WT ICOSL | 32 | 180900 (1.00) | 4493 (1.00) | 17685 (1.00) | 246 (1.00) | 2850 (1.00) |
| R26S, N52H, N57Y, V110D, T137A, C198R | 908 | N/A | N/A | N/A | N/A | N/A |
| N52H, N57Y, Q100R, V110D, A117T, T190S, C198R | 314 | 2831 (0.04) | 2881 (0.57) | 2464 (0.23) | 59 (0.08) | — |
| N52H, N57Y, Q100R, V110D, F172S, C198R | 315 | 58478 (0.79) | 74031 (14.75) | 56850 (5.33) | 712 (0.96) | 1093 (0.23) |
| S25G, F27C, N52H, N57Y, Q100R, V110D, E135K, L173S, C198R | 316 | 22514 (0.30) | 21320 (4.25) | 20450 (1.92) | 353 (0.48) | 5765 (1.21) |

TABLE 15-continued

| | | | | | Anti-CD3 IFN-gamma | |
| | | | | | Coimmobilization | MLR |
| | SEQ | ICOS | CD28 | CTLA-4 | Assay pg/mL | IFN-gamma |
| | ID NO | tfxn MFI | tfxn MFI | tfxn MFI | pg/mL |
| ICOSL mutation(s) | (ECD) | (parental ratio) | (parental ratio) | (parental ratio) | (parental ratio) | (parental ratio) |
|---|---|---|---|---|---|---|
| N52H, N57Y, V110A, C198R, R221I | 317 | 84236 (1.14) | 81842 (16.31) | 121519 (11.39) | 4593 (6.18) | 1137 (0.24) |
| M10I, S13G, N52H, N57Y, D77G, V110A, H129P, I143V, F172S, V193M, C198R | 318 | 6362 (0.09) | 6001 (1.20) | 4834 (0.45) | 141 (0.19) | 4326 (0.91) |
| N52H, N57Y, R61C, Y62F, Q100R, V110N, F120S, C198R | 319 | 4355 (0.06) | 4316 (0.86) | 3430 (0.32) | 110 (0.15) | 6854 (1.44) |
| N52H, N57Y, Q100R, L102R, V110D, H115R, C198R | 367 | 96736 (1.31) | 77881 (15.52) | 148012 (13.88) | 8765 (11.79) | 630 (0.13) |
| N52H, N57Y, Q100R, V110D, N144D, F172S, C198R | 321 | 67578 (0.91) | 64953 (12.94) | 95731 (8.98) | 1672 (2.52) | 1490 (0.31) |
| N52S, H94E, L98F, Q100R, | 322 | 80690 (1.09) | 78750 (15.69) | 148160 (13.89) | 3564 (4.80) | 1497 (0.32) |
| N52S, E90A | 323 | 108908 (1.47) | 31086 (6.19) | 108866 (10.21) | 4564 (6.14) | 3927 (0.83) |
| N30D, K42E, N52S | 324 | 85726 (1.16) | 4293 (0.86) | 10755 (1.01) | 5211 (7.01) | 5656 (1.19) |
| N52S, F120S, I143V, I224V | 325 | 90862 (1.23) | 28443 (5.67) | 105229 (9.87) | 4803 (6.46) | 4357 (0.92) |
| WT ICOSL | 32 | 73964 (1.00) | 5018 (1.00) | 10665 (1.00) | 743 (1.00) | 4748 (1.00) |

B. Cytokine Production in Anti-CD3 Costimulation Assays

Exemplary variant ECD ICOSL Fc-fusion molecules described above were further assessed for stimulation of cytokines IL-17 in the anti-CD3 costimulatory (coimmobilization) bioactivity assay described above. A mixture of 10 nM plate-bound anti-CD3 and 40 nM ICOSL Fc variant proteins were cultured with human T cells. Supernatants were collected and IL-17 levels were determined by ELISA. The amount of IL-17 in culture supernatants (pg/mL) generated with the indicated variant ECD-Fc fusion molecule and corresponding unmodified (parental) ECD-Fc coimmobilized with anti-CD3 was measured. For comparison, also shown in this Table are the results for production of IFN-gamma in the same assay as depicted in Table 15 for the exemplary variants.

Results are shown in Table 16, which depict the pg/mL of IL-17 measured in the supernatant as well as the ratio (fold increase) of IL-17 produced by each variant ECD-Fc compared to the corresponding unmodified (wild-type) ECD-Fc. Similar results are shown for IFN-gamma. Also shown is the % of total IL-17 or IFN-gamma cytokine produced by cells. The results showed that affinity modification of the variant molecules exhibited altered functional T cell activity to increase IL-17 in addition to IFN-gamma in the costimulation assay.

TABLE 16

| | | | | | | | % of Total Cytokine Produced | | % Total |
| | SEQ | | IL-17A | | IFN-g | Total | | | |
| | ID NO | IL-17A | Fold | IFN-g | Fold | Fold | % | % | IL-17 + |
| ICOSL mutation(s) | (ECD) | [pg/mL] | ↑WT | [pg/mL] | ↑WT | ↑WT | IL-17 | IFN-g | IFN-g |
|---|---|---|---|---|---|---|---|---|---|
| N52H, N57Y, Q100R, C198R | 365 | 617 | 7.93 | 1060 | 2.48 | 10.42 | 5.51 | 0.77 | 6.28 |
| N52H, N57Y, Q100R, V122A | 290 | 647 | 8.33 | 1316 | 3.08 | 11.41 | 5.79 | 0.96 | 6.75 |
| N52H, N57Y, Q100R, F172S | 291 | 549 | 7.06 | 1561 | 3.66 | 10.72 | 4.91 | 1.14 | 6.05 |
| N52Y, N57Y, F138L, L203P | 112 | 90 | 1.05 | 1999 | 2.69 | 3.74 | 0.81 | 2.91 | 3.72 |
| V11E, N30D, N52H, N57Y, H94E, L96I, L98F, N194D, V210A, I218T | 308 | 319 | 3.16 | 2218 | 9.03 | 12.19 | 2.85 | 3.23 | 6.08 |
| N52H, N57Y, Q100R, L102R, V110D, H115R, C198R | 367 | 510 | 5.90 | 8765 | 11.79 | 17.70 | 4.56 | 12.78 | 17.33 |
| N52H, N57Y, Q100R | 283 | 473 | 6.08 | 1648 | 3.86 | 9.94 | 4.23 | 1.20 | 5.43 |
| N52H, Q100R | 285 | 358 | 4.60 | 972 | 7.01 | 11.62 | 3.20 | 0.71 | 3.91 |
| N52H, N57Y, Q100R, V110D, C198R, S212G | 364 | 124 | 1.60 | 944 | 2.21 | 3.81 | 1.11 | 0.69 | 1.80 |

TABLE 16-continued

| | | | | | | | % of Total Cytokine Produced | | % Total |
|---|---|---|---|---|---|---|---|---|---|
| | SEQ | | IL-17A | | IFN-g | Total | | | |
| ICOSL mutation(s) | ID NO (ECD) | IL-17A [pg/mL] | Fold ↑WT | IFN-g [pg/mL] | Fold ↑WT | Fold ↑WT | % IL-17 | % IFN-g | IL-17 + IFN-g |
| N52H, N57Y, Q100P | 113 | 127 | 1.47 | 4922 | 6.62 | 8.09 | 1.14 | 7.17 | 8.31 |
| E16V, N52H, N57Y, Q100R, V110D, H115R, Y152C, K156M, C198R | 300 | 22 | 7.11 | 130 | 17.46 | 24.57 | 6.41 | 6.25 | 12.66 |
| N30D, K42E, N52S | 324 | 349 | 4.04 | 5211 | 7.01 | 11.05 | 3.12 | 7.60 | 10.71 |
| N52S, F120S, I143V, I224V | 325 | 292 | 3.39 | 4803 | 6.46 | 9.85 | 2.61 | 7.00 | 9.62 |
| N52S, E90A | 323 | 306 | 3.54 | 4564 | 6.14 | 9.68 | 2.73 | 6.65 | 9.39 |
| N52H, N57Y, V110A, C198R, R221I | 317 | 290 | 3.35 | 4593 | 6.18 | 9.53 | 2.59 | 6.69 | 9.28 |
| N52S, N194D | 366 | 428 | 5.50 | 1671 | 3.90 | 9.4 | 1.52 | 5.19 | 5.40 |
| N52H, I143T | 135 | 84 | — | 1727 | — | 3.30 | 0.75 | 2.52 | 3.27 |
| N52D | 111 | 126 | — | 1447 | — | 3.41 | 1.13 | 2.11 | 3.23 |

Example 11

Generation of Additional Engineered T cell Expressing a Transmembrane Immunomodulatory Protein and Assessment of Proliferation This Example describes the generation of additional engineered T cells in which a transmembrane immunomodulatory protein (TIP) containing an extracellular domain (ECD) containing ICOSL affinity-modified IgSF domain was co-expressed with a chimeric antigen receptor (CAR). Specifically, the TIP was generated to include the ECD of exemplary variant ICOSL containing amino acid mutations N52D, N52H/N57Y/Q100P, E16V/N52H/N57Y/Q100R/ V110D/H115R/Y152C/K156M/C198R or N52H/N57Y/ Q100R with reference to positions in the ICOSL extracellular domain set forth in SEQ ID NO:32. The TIP also contained a transmembrane domain and a cytoplasmic domain of the corresponding wild-type ICOSL transmembrane protein sequence corresponding to residues 257-302 of SEQ ID NO: 5. The sequence of the TIP with and without its signal peptide are as follows: N52D (SEQ ID NO: 496 and 497); N52H/N57Y/Q100P (SEQ ID NO: 498 and 499); E16V/N52H/N57Y/Q100R/V110D/H115R/Y152C/ K156M/C198R (SEQ ID NO: 500 and 501) and N52H/ N57Y/Q100R (SEQ ID NO: 502 and 503). For comparison, the full-length transmembrane wild-type ICOSL (amino acid residues 19-302 of SEQ ID NO:5) also was expressed in cells. The sequence of the wildtype TIP with and without its signal peptide is set forth in SEQ ID NO: 494 and 495. The nucleic acid encoding the TIP also included a sequence encoding a green fluorescent protein (GFP) separated from the TIP by a self-cleaving T2A sequence.

The TIP containing the affinity-modified domain or the wild-type transmembrane protein containing a corresponding non-affinity modified IgSF domain were co-expressed in T cells with a chimeric antigen receptor (CAR). The nucleotide sequence encoding the CAR encodes, in order: a CD8 signal sequence (SEQ ID NO: 481), an anti-CD19 scFv (SEQ ID NO: 482), a hinge/transmembrane region derived from CD8 (SEQ ID NO: 483), a costimulatory signaling domain derived from 4-1BB (SEQ ID NO: 484), and a CD3zeta signaling domain (SEQ ID NO: 247). The resulting anti-CD19 CAR has the sequence of amino acids set forth in SEQ ID NO: 490. The nucleic acid encoding the CAR also included a sequence encoding a blue fluorescent protein (BFP; SEQ ID NO: 489) separated from the CAR by a self-cleaving T2A sequence (set forth in SEQ ID NO: 488).

Figure 2A:
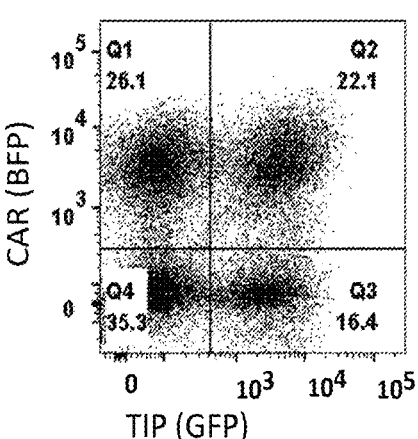
FIG. 2A depicts that primary T cells are effectively transduced with viruses encoding both the CAR and TIP proteins. Primary human T cells activated 48 hours with anti-CD3 plus anti-CD28 beads and were then tranduced with a Lenti-virus encoding an anti-CD19 CAR with a BFP reporter, plus a second Lenti-virus encoding and ICOSL TIP with a GFP reporter. The FACs plot shows BFP expression on the y-axis and GFP expression on the x-axis and the percentage of T cells that fall into each quadrant are indicated. Results show that the cultures include CAR only transduced cells (upper left quadrant), TIP only transduced cells (lower right quadrant), cells transduced with both viruses (upper right quadrant) and cells that were not transduced with either (lower left).

Viral vector constructs were separately generated into which was cloned either the nucleic acid molecule encoding the CAR alone or a nucleic acid molecule encoding one of the exemplary TIPs or wild-type ICOSL. The viral vector encoding the CAR and the viral vector encoding the TIP or wild-type ICOSL were co-transduced into T cells. For transduction, primary T cells were activated with anti-CD3 and anti-CD28 beads (Dynal) at 1:1 bead:cell ratio and incubated in the presence of 100 IU/mL of IL-2 at 37° C. for 2 days. T cells were then harvested and transduced with 400 µL of CAR viral supernatant and 400 µL of TIP viral supernatant in the presence of 8 µg/mL of polybrene. The cells were spinoculated at 1000g for 30 minutes at 30° C. The cells were then transferred and incubated overnight at 37° C. After the incubation, cells were collected and viral supernatant was removed. The cells were resuspended with complete media and 50 IU/mL of IL-2. Cells were expanded, replenished with IL-2 and media every two days for a total of 6 days. Beads were removed from the cells using a magnet and counted before being assessed in a proliferation assay. An exemplary expression profile of a TIP and CAR in an exemplary transduced T cells is shown in FIG. 2A.

To assess proliferation of CAR T cells and CAR-TIP T cells in response to antigen, cells were labeled with cell trace far red dye. CD19-expressing Nalm6 target cells were titrated starting from 1.5:1 target:T cell ratio and by 1:2 dilutions with 8-point dilution. Labeled CAR T cells or CAR-TIP T cells were added to Nalm6 cells and the culture was incubated for 4 days before cells were analyzed by flow cytometry. The supernatant was collected and further assessed in a cytokine release assay.

Figure 2B:
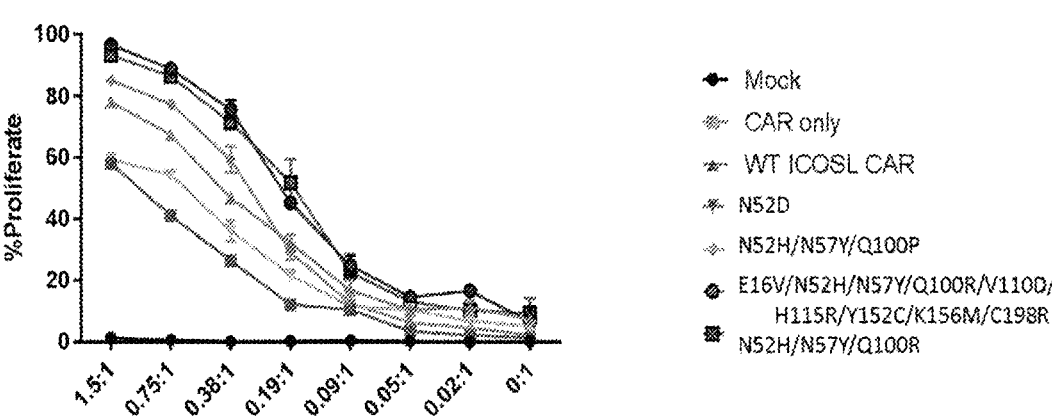
In FIG. 2B, TIPs expressed on CAR-T cells provide co-stimulation to the CAR-T cells. CAR-T cells with or without TIP co-transduction were labeled with Cell-Trace Far Red and incubated with the CD19+ NALM6 cell line to engage the CAR. Proliferation was assessed by the percentage of CAR-expressing cells that had diluted out the fluorescent dye. Cells transduced with mutated TIPs showed an increase proliferation of CAR+ T cells compared to those without TIPs or those transduced with wild-type ICOSL. Mock transduced cells that lacked CAR expression failed to proliferate in this assay.

As shown in FIG. 2B, CAR+ primary T cells proliferate in a dose dependent manner to CD19+ NALM6 cells. Compared to a CAR only T cells, T cells coexpressing the CAR and either wild-type ICOSL or one of the exemplary ICOSL TIP exhibited enhanced proliferation compared to CAR only expressing T cells. Co-expression of a CAR and a TIP containing either the N52H/N57Y/Q100P, E16V/ N52H/N57Y/Q100R/V110D/H115R/Y152C/K156M/ C198R or N52H/N57Y/Q100R variant ICOSLECD exhibited greater proliferation than T cells co-expressing the CAR and wildtype ICOSL, indicating that TIPs expressed on primary T cells provide an improved costimulatory signal to enhance T cell proliferation.

Example 12

Purification and Assessment of Purified of ICOSL IgSF Domain Variants

A purification strategy was employed for exemplary candidate hits described in Example 6 and 10. Human cells derived from the 293 cell line (Expi293) were transiently transfected with expression construct and the ECD ICOSL Fc fusion molecule was expressed in the cells. The Fc fusion proteins were then purified from supernatants with Protein A by affinity chromatography (MabSelect SuRe). This initial purification step was then followed by a preparative size exclusion chromatography (SEC) step to further purify the proteins (Superdex200 16×60). Samples from both purification steps were retained and compared by analytic SEC. The concentration of the protein was determined after Protein A purification. The resulting purified proteins also were analyzed by analytic SEC on a high performance liquid chromatography (HPLC) to assess purity.

The percent main peak in the purified samples was determined and compared to protein purified in the initial Protein A step (% Main Peak Prot A pool) versus protein purified with Protein A followed by preparative SEC (% Main Peak SEC pool T=D0). As shown in Table 17, the additional SEC step substantially increased protein purity of purified proteins. To further assess stability of the proteins, proteins purified by preparative SEC were left at room temperature for 24 hours and then % Main Peak by HPLC (% Main Peak SEC pool T=D24) was assessed and compared to DO sample. The change in % Main Peak at DO versus D24 was determined (▲ % Main Peak SEC pool). As shown in Table 17, most of the tested exemplary variant ECD ICOSL Fc fusion molecules exhibited little change in % Main Peak at this time, indicating minimal aggregation of the protein variants had occurred.

TABLE 17

Purification of ICOSL Protein Variants

| ICOSL mutation(s) | SEQ ID NO (ECD) | Expi293 Prod. Prot A mg/L | % Main Peak Prot A pool | % Main Peak SEC pool T = D 0 | % Main Peak SEC pool T = D 24 | ▲ % Main Peak SEC pool |
|---|---|---|---|---|---|---|
| N52S, N194D | 366 | 120 | 87.9 | 93.5 | 92 | 1.5 |
| N52H, N57Y, Q100R, F172S | 291 | 217 | 86.9 | 97.4 | 95.6 | 1.8 |
| N52S, E90A | 323 | 128 | 86.5 | 89.5 | 88.3 | 1.2 |
| N52H, Q100R | 285 | 176 | 85.9 | 97.5 | 96.1 | 1.4 |
| N52H, N57Y, Q100R | 283 | 186 | 85.1 | 97.6 | 95.7 | 1.9 |
| N52S, F120S, I143V, I224V | 325 | 87 | 83.2 | 88.9 | 88.3 | 0.6 |
| N52H, N57Y, Q100R, C198R | 365 | 204 | 82.9 | 95.8 | 92.3 | 3.5 |
| N52H, N57Y, Q100P | 113 | 63 | 80.5 | 94.5 | 88.5 | 6 |
| N30D, K42E, N52S | 324 | 81 | 80 | 95.4 | 91.3 | 4.1 |
| N52H, N57Y, Q100R, L102R, V110D, H115R, C198R | 367 | 141 | 78.9 | 96 | 92.9 | 3.1 |
| N52H, N57Y, Q100R, V122A | 290 | 260 | 77.6 | 96.4 | 95.2 | 1.2 |
| N52Y/N57Y/F138L/L203P | 112 | 40 | 75.6 | 96.8 | 94.8 | 2 |
| E16V, N52H, N57Y, Q100R, V110D, H115R, Y152C, K156M, C198R | 300 | 60 | 73.8 | 97.1 | 95.8 | 1.3 |
| N52H, N57Y, V110A, C198R, R221I | 317 | 95 | 65.4 | 90.9 | 86 | 4.9 |
| N52H, N57Y, Q100R, V110D, C198R, S212G | 364 | 73 | 50.6 | 87.9 | 78.6 | 9.3 |
| V11E, N30D, N52H, N57Y, H94E, L96I, L98F, N194D, V210A, I218T | 308 | 58 | — | — | — | — |
| N52H, I143T | 135 | 134 | 93.2 | 96 | 92.7 | 3.3 |
| N52D | 111 | 136 | 90.4 | 95.5 | 93.3 | 2.2 |

Example 13

Assessment of Costimulatory Bioactivity of Purified ICOSL IgSF Domain Variant Hits Exemplary ECD ICOSL Fc fusion molecules purified as described in Example 12 were assessed for bioactivity by MLR substantially as described in Example 6. A mixture of 10 nM or 40 nM ICOSL Fc variant proteins was bound overnight to 96-well plates in the presence of 10 nM anti-CD3. The plates were washed and 100,000 CFSE labelled pan T cells were added for 96 hours. Supernatants were collected, and IFN-gamma and IL-17 levels were measured by ELISA.

Figure 3A:
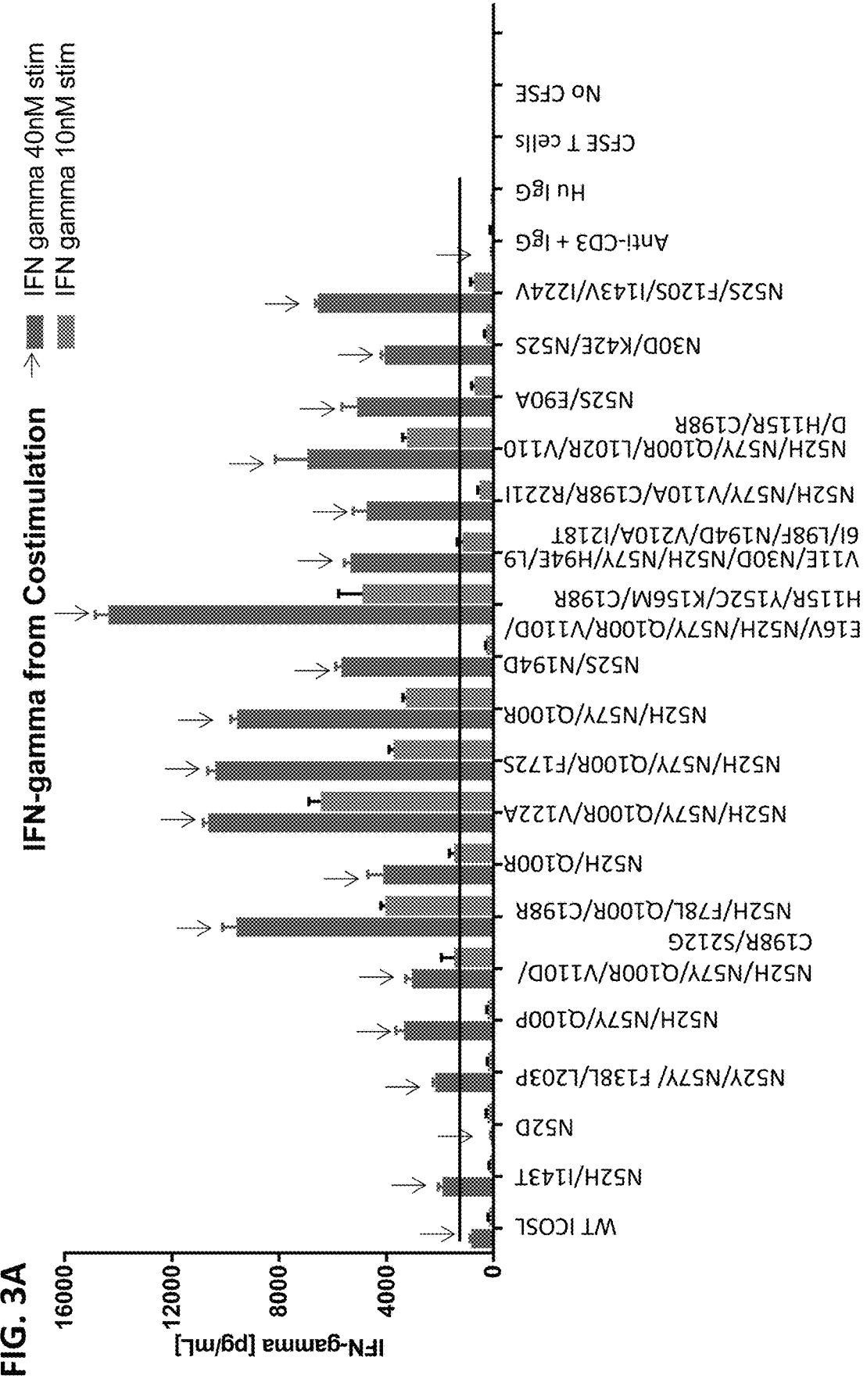
FIG. 3A-3B demonstrate, via cytokine release, the costimulatory capacity of wild-type (WT) or variant ICOSL when coimmobilized with anti-CD3. 10 nM anti-CD3 was wet coated to the wells of 96-well flat bottomed polystyrene tissue culture plates with 40 nM (arrows) or 10 nM WT or variant ICOSL. 100,000 purified $CD4^+$ and $CD8^+$ (pan) T-cells cells were added and supernatant was harvested 72 hours later for ELISA analysis for cytokine release.
Figure 3B:
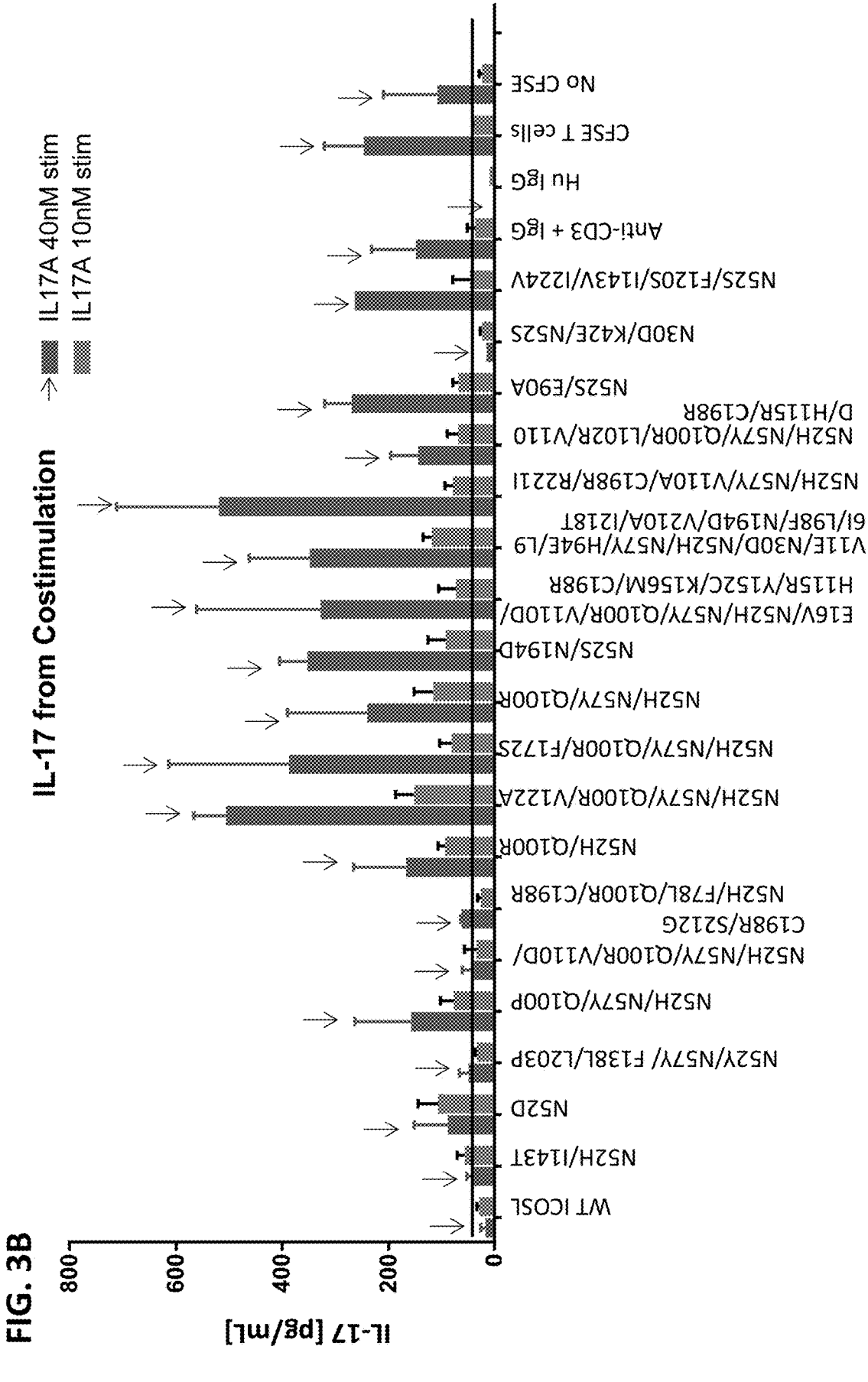

Results for the cytokine secretion induced by anti-CD3 costimulation with exemplary tested variants (10 nM and 40 nM ICOSL Fc) are shown in FIGS. 3A and 3B, which indicates exemplary IgSF domain amino acid substitutions (replacements) in the ECD of ICOSL. The bar graphs in FIGS. 3A and 3B depict the amount of secreted IFN-gamma and IL-17, respectively, by ELISA in the supernatants (pg/mL). The level of cytokine release induced by anti-CD3 costimulation with the tested variants compared to the level induced by anti-CD3 costimulation with WT ICOSL is indicated by the horizontal line. The results showed that affinity modification of the variant molecules exhibited activity to modulate functional T cell activity, including to substantially increase IFN-gamma and IL-17 secretion in the costimulation assay. Increased immunological activity was observed with some variants.

Example 14

Assessment of Proliferation of Purified ICOSL IgSF Domain Variant Hits

Exemplary variant ECD ICOSL Fc fusion molecules purified as described in Example 12 were assessed for ability to costimulate anti-CD3-induced proliferation of T cells. Primary T cells were labeled with carboxyfluorescein succinimidyl ester (CFSE). A mixture of 10 nM or 40 nM variant ECD ICOSL Fc or wild-type ECD ICOSL proteins were bound overnight to 96-well plates in the presence of 10 nM anti-CD3, and then labeled T cells were added and incubated for 3 days. As a control, proliferation also was assessed in the presence of bound anti-CD3 and IgG or IgG alone. Cells were stained for CD4 or CD8 surface markers and proliferation of total T cells, CD4+ T cells or CD8+ T cells was determined by assessing CFSE dilution by flow cytometry.

Figure 4A:
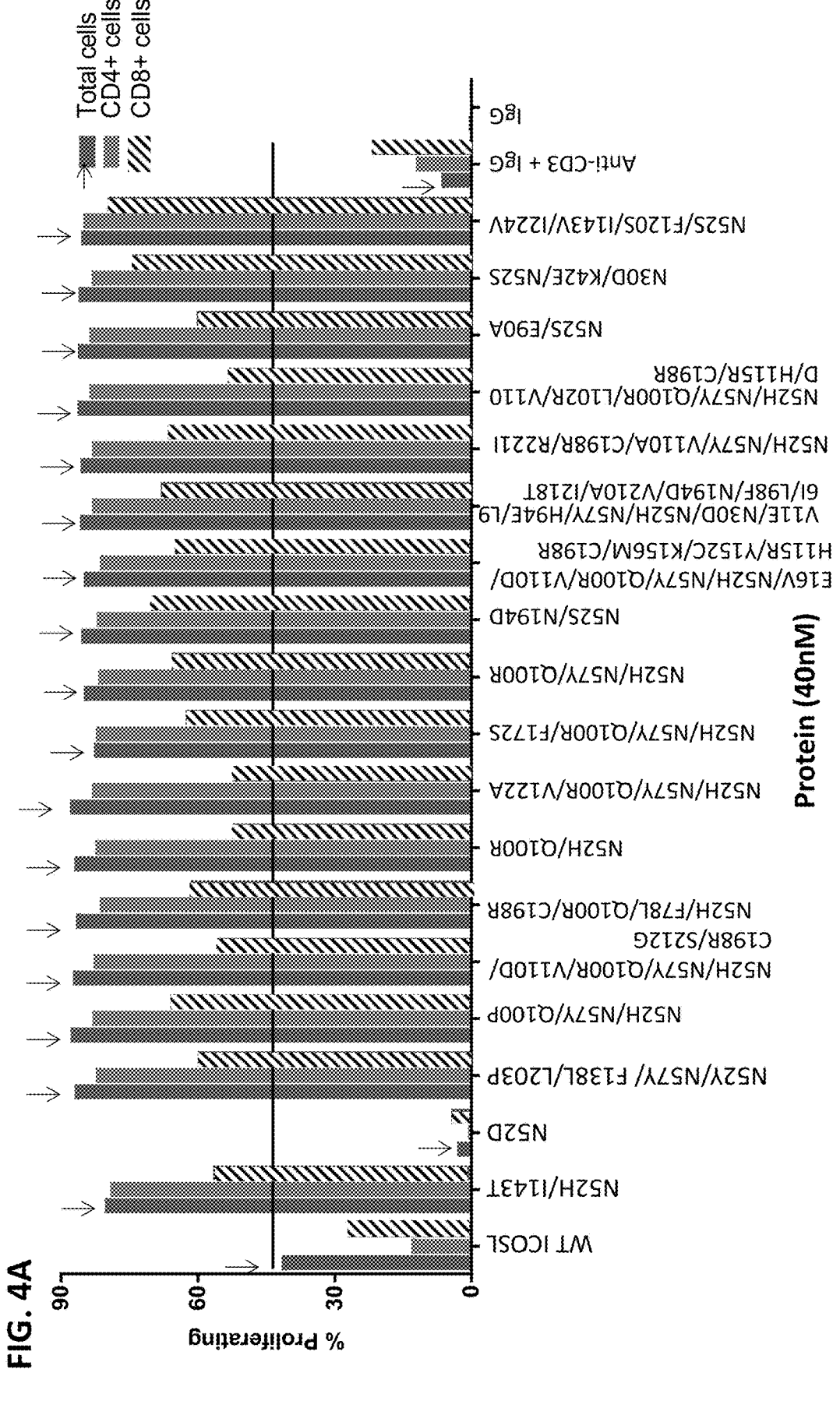
FIG. 4A-4B demonstrate, via proliferation, the costimulatory capacity of wild-type (WT) or variant ICOSL when coimmobilized with anti-CD3. CFSE-labeled pan T-cells were incubated in anti-CD3 and ICOSL coated plates as previously described for 72 hours. Cells were harvested, washed, stained with fluorescently conjugated anti-CD4 or anti-CD8 antibodies, and analyzed by flow cytometry. Gates and cytometer voltages were set using non-stimulated control CFSE-labeled T-cells. Proliferation was determined by CFSE dilution from control.
Figure 4B:
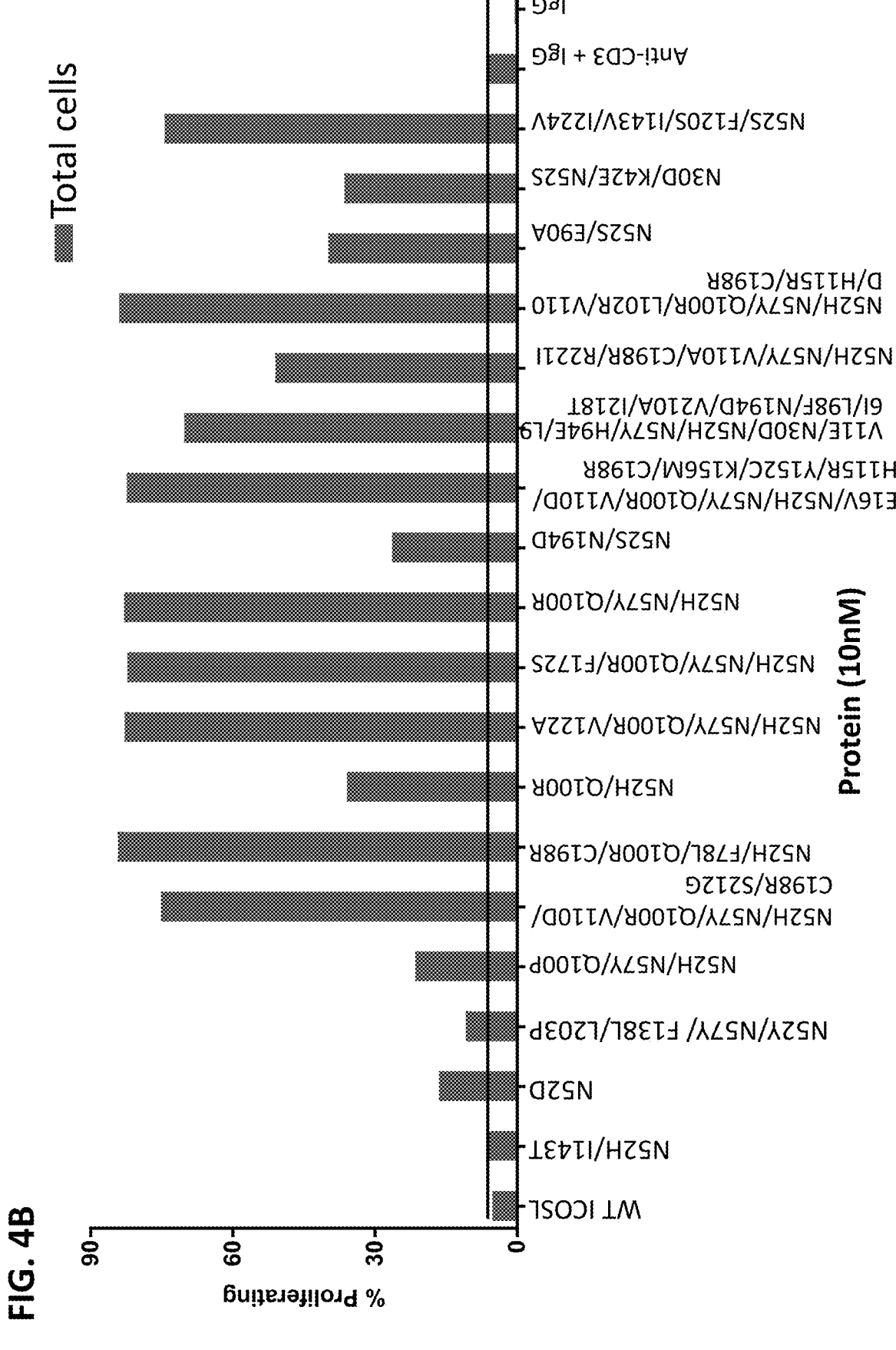

The results are set forth in FIG. 4A and FIG. 4B for exemplary variants tested at 40 nM and 10 nM ICOSL, respectively. As shown in FIG. 4A, nearly all tested variant ECD ICOSL Fc fusion molecules induced proliferation greater than WT control. As shown in FIG. 4B, differences in proliferation were more apparent at 10 nM with certain variants providing maximal proliferation even at this lower concentration.

Example 15

Assessment of Binding and Activity of Purified ICOSL IgSF Domain Variant Hits

Exemplary variant ECD ICOSL Fc fusion molecules purified as described in Example 12 were assessed for binding and functional activities using methods substantially as described in Example 6 or Example 10.

A. Flow Cytometric Binding Assays

Human cells derived from the 293 cell line (Expi293) were transfected with CD28, CTLA-4, ICOS or mock transfected. Cells were then incubated with ECD ICOSL Fc fusion molecules or wild-type ECD ICOSL-Fc that were titrated from 100,000 pM to 46 PM, and binding was observed using a PE-conjugated anti-human Fc as described in Example 6. Binding was assessed by flow cytometry and mean fluorescence intensity (MFI) and percent (%) of cells positive for signal was determined using Cell Quest Pro software (Becton Dickinson, USA). The concentration of ICOSL-Fc that gave a half-maximal MFI response (MFI EC50) or % positive cells (% (+) EC50) was determined.

Table 18 sets forth the results. The ICOSL amino acid substitutions depicted in Table 18 are designated by amino acid position number corresponding to the respective reference (e.g., unmodified) ICOSL ECD sequence set forth in SEQ ID NO:32. For some values (e.g. WT binding to CD28) it was not possible to obtain an EC50, therefore 1000000 pM was arbitrarily piced for data formatting purposes. Similar to results obtained from previous binding assays as described in Example 10 above, altered binding affinity of variant ICOSL ECD-Fc fusion molecule for at least one cognate counter structure ligand was observed.

TABLE 18

| | | CD28 | CD28 | CTLA-4 | CTLA-4 | ICOS | ICOS |
|---|---|---|---|---|---|---|---|
| ICOSL mutation(s) | SEQ ID NO (ECD) | MFI EC50 [pM] | % (+) EC50 [pM] | MFI EC50 [pM] | % (+) EC50 [pM] | MFI EC50 [pM] | % (+) EC50 [pM] |
| WT ICOSL | 32 | 1000000 | 1000000 | 1000000 | 1000000 | 10543 | 762 |
| N52H, I143T | 135 | 19147 | 567 | 20259 | 1891 | 2666 | 286 |
| N52H, N57Y, Q100R, C198R | 365 | 950 | 159 | 73548 | 422 | 1032 | 179 |
| N52H, N57Y, Q100R, V122A | 290 | 29701 | 152 | 1008 | 293 | 302 | 64 |
| N52H, N57Y, Q100R, F172S | 291 | 1006 | 231 | 1332 | 396 | 779 | 130 |
| N52Y/N57Y/F138L/L203P | 112 | 7844 | 386 | 7457 | 994 | 3104 | 408 |
| V11E, N30D, N52H, N57Y, H94E, L96I, L98F, N194D, V210A, I218T | 308 | 5961 | 595 | 6909 | 1026 | 5514 | 852 |
| N52H, N57Y, Q100R, L102R, V110D, H115R, C198R | 367 | 1034 | 307 | 23328 | 579 | 3172 | 347 |
| N52H, N57Y, Q100R | 283 | 1665 | 238 | 11002 | 533 | 383 | 131 |
| N52H, Q100R | 285 | 1305 | 274 | 8593 | 1997 | 702 | 167 |
| N52H, N57Y, Q100R, V110D, C198R, S212G | 364 | 4987 | 594 | 30382 | 922 | 50219 | 814 |
| N52H, N57Y, Q100P | 113 | 21137 | 402 | 22651 | 758 | 4090 | 320 |
| E16V, N52H, N57Y, Q100R, | 300 | 2508 | 387 | 5399 | 806 | 2381 | 421 |

Flow Cytometric EC50s for ICOSL variants

TABLE 18-continued

| | | CD28 | CD28 | CTLA-4 | CTLA-4 | ICOS | ICOS |
|---|---|---|---|---|---|---|---|
| | SEQ ID NO (ECD) | MFI EC50 [pM] | % (+) EC50 [pM] | MFI EC50 [pM] | % (+) EC50 [pM] | MFI EC50 [pM] | % (+) EC50 [pM] |
| ICOSL mutation(s) | | | | | | | |
| V110D, H115R, Y152C, K156M, C198R | | | | | | | |
| N30D, K42E, N52S | 324 | — | 3683800 | 8593 | 1997 | 3251 | 558 |
| N52S, F120S, I143V, I224V | 325 | 902400 | 9060 | 28126 | 2948 | 4366 | 245 |
| N52S, E90A | 323 | 1339700 | 31302 | 31419 | 5828 | 5225 | 473 |
| N52H, N57Y, V110A, C198R, R221I | 317 | 1809 | 426 | 7201 | 841 | 1293 | 433 |
| N52S, N194D | 366 | 944669 | 11876 | 1254880 | 5170 | 473 | 206 |
| N52D | 111 | 288617 | 17793 | 396841 | 3891 | 2642 | 137 |

Flow Cytometric EC50s for ICOSL variants

B. ForteBio Binding Assay

Protein-protein interactions between the receptors and ICOSL domain variant immunomodulatory proteins were further assessed using Fortebio binding assays. ICOS, CD28, and CTLA-4 receptors were loaded individually onto anti-human capture sensors (ForteBio Octet AHC) and wildtype unmodified ICOSL ECD-Fc fusion molecule, wildtype PD-L2 ED-Fc fusion molecule or variant ICOSL Fc-fusion molecules were bound to the receptors in 4 point titrations. Each titration was globally fit to calculate the associate ($k_{on}$) and dissociation ($K_{dis}$) of each protein. Loading response of anti-human capture sensors of each receptor being tested with the variant ICOSL ECD-Fc fusion molecule was determined. The dissociation constant (KD) was calculated and compared to wildtype to determine a fold improvement value (fold imp.).

Binding results to ICOS are set forth in Table 19, to CD28 are set forth in Table 20 and to CTLA-4 are set forth in Table 21. The exemplary amino acid substitutions depicted in Table 19-21 are designated by amino acid position number corresponding to the respective reference unmodified ICOSL ECD sequence set forth in SEQ ID NO:32.

TABLE 19

ICOS ForteBio Binding Assay

| ICOSL mutation(s) | SEQ ID NO (ECD) | Response | KD (M) | $K_{on}$ (1/Ms) | $K_{dis}$ (1/s) | Full $R^2$ | Fold Imp. |
|---|---|---|---|---|---|---|---|
| WT ICOSL | 32 | 0.73 | 8.83E−10 | 1.78E+05 | 1.58E−04 | 0.9908 | — |
| N52H, I143T | 135 | 0.87 | 3.32E−10 | 3.13E+05 | 1.04E−04 | 0.9683 | 2.7 |
| N52H, N57Y, Q100R, C198R | 365 | 0.74 | 4.92E−10 | 3.85E+05 | 1.89E−04 | 0.9882 | 1.8 |
| N52H, N57Y, Q100R, V122A | 290 | 0.67 | 4.72E−10 | 3.77E+05 | 1.78E−04 | 0.9775 | 1.9 |
| N52H, N57Y, Q100R, F172S | 291 | 0.68 | 4.20E−10 | 4.34E+05 | 1.82E−04 | 0.9545 | 2.1 |
| N52Y/N57Y/F138L/L203P | 112 | 0.64 | 7.69E−10 | 2.22E+05 | 1.71E−04 | 0.9782 | 1.1 |
| V11E, N30D, N52H, N57Y, H94E, L96I, L98F, N194D, V210A, I218T | 308 | 0.67 | 3.62E−10 | 3.55E+05 | 1.29E−04 | 0.9687 | 2.4 |
| N52H, N57Y, Q100R, L102R, V110D, H115R, C198R | 367 | 0.76 | 4.77E−10 | 3.29E+05 | 1.57E−04 | 0.9616 | 1.9 |
| N52H, N57Y, Q100R | 283 | 0.74 | 3.69E−10 | 2.87E+05 | 1.06E−04 | 0.9817 | 2.4 |
| N52H, Q100R | 285 | 0.79 | 3.73E−10 | 4.45E+05 | 1.66E−04 | 0.968 | 2.4 |
| N52H, N57Y, Q100R, V110D, C198R, S212G | 364 | 0.60 | 1.29E−09 | 1.66E+05 | 2.15E−04 | 0.9846 | 0.7 |
| N52H, N57Y, Q100P | 113 | 0.73 | 3.82E−10 | 3.71E+05 | 1.42E−04 | 0.9729 | 2.3 |
| E16V, N52H, N57Y, Q100R, V110D, H115R, Y152C, K156M, C198R | 300 | 0.75 | 5.43E−10 | 2.65E+05 | 1.44E−04 | 0.9848 | 1.6 |
| N30D, K42E, N52S | 324 | 0.80 | 3.71E−10 | 4.48E+05 | 1.66E−04 | 0.9651 | 2.4 |
| N52S, F120S, I143V, I224V | 325 | 0.80 | 3.11E−10 | 5.03E+05 | 1.56E−04 | 0.9673 | 2.8 |
| N52S, E90A | 323 | 0.88 | 3.40E−10 | 4.85E+05 | 1.65E−04 | 0.9792 | 2.6 |
| N52H, N57Y, V110A, C198R, R221I | 317 | 0.68 | 4.77E−10 | 3.15E+05 | 1.50E−04 | 0.976 | 1.9 |
| N52S, N194D | 366 | 0.88 | 3.37E−10 | 3.38E+05 | 1.14E−04 | 0.9723 | 2.6 |
| N52D | 111 | 0.87 | 3.38E−10 | 3.91E+05 | 1.32E−04 | 0.9792 | 2.6 |
| Wildtype PD-L2 ED-Fc | — | 0.03 | | | | | |

TABLE 20

| ICOSL mutation(s) | SEQ ID NO (ECD) | Response | KD (M) | $K_{on}$ (1/Ms) | $K_{dis}$ (1/s) | Full $R^2$ | Fold Imp. |
|---|---|---|---|---|---|---|---|
| | | | CD28 ForteBio Binding Assay | | | | |
| WT ICOSL | 32 | 0.33 | 1.39E−08 | 6.69E+04 | 9.29E−04 | 0.9715 | — |
| N52H, I143T | 135 | 0.95 | 5.25E−10 | 4.27E+05 | 2.24E−04 | 0.9877 | 26.5 |
| N52H, N57Y, Q100R, C198R | 365 | 1.14 | 4.47E−10 | 4.12E+05 | 1.84E−04 | 0.9877 | 31.0 |
| N52H, N57Y, Q100R, V122A | 290 | 1.04 | 3.90E−10 | 4.07E+05 | 1.59E−04 | 0.9878 | 35.6 |
| N52H, N57Y, Q100R, F172S | 291 | 1.06 | 2.93E−10 | 4.26E+05 | 1.25E−04 | 0.9836 | 47.3 |
| N52Y/N57Y/F138L/L203P | 112 | 0.86 | 7.83E−10 | 1.79E+05 | 1.40E−04 | 0.993 | 17.7 |
| V11E, N30D, N52H, N57Y, H94E, L96I, L98F, N194D, V210A, I218T | 308 | 0.92 | 5.53E−10 | 2.54E+05 | 1.40E−04 | 0.9906 | 25.1 |
| N52H, N57Y, Q100R, L102R, V110D, H115R, C198R | 367 | 1.10 | 3.66E−10 | 3.41E+05 | 1.25E−04 | 0.986 | 37.9 |
| N52H, N57Y, Q100R | 283 | 1.04 | 3.68E−10 | 3.72E+05 | 1.37E−04 | 0.983 | 37.7 |
| N52H, Q100R | 285 | 1.09 | 4.01E−10 | 5.0SE+05 | 2.02E−04 | 0.9938 | 34.7 |
| N52H, N57Y, Q100R, V110D, C198R, S212G | 364 | 0.94 | 8.96E−10 | 1.78E+05 | 1.60E−04 | 0.9961 | 15.5 |
| N52H, N57Y, Q100P | 113 | 0.99 | 4.36E−10 | 3.29E+05 | 1.43E−04 | 0.9835 | 31.8 |
| E16V, N52H, N57Y, Q100R, V110D, H115R, Y152C, K156M, C198R | 300 | 1.06 | 5.03E−10 | 3.06E+05 | 1.54E−04 | 0.9872 | 27.6 |
| N30D, K42E, N52S | 324 | 0.54 | 1.95E−09 | 2.74E+05 | 5.33E−04 | 0.9772 | 7.1 |
| N52S, F120S, I143V, I224V | 325 | 0.84 | 9.10E−10 | 4.51E+05 | 4.10E−04 | 0.9742 | 15.3 |
| N52S, E90A | 323 | 0.94 | 9.69E−10 | 4.74E+05 | 4.59E−04 | 0.978 | 14.3 |
| N52H, N57Y, V110A, C198R, R221I | 317 | 0.94 | 5.63E−10 | 2.63E+05 | 1.48E−04 | 0.9781 | 24.7 |
| N52S, N194D | 366 | 0.82 | 1.04E−09 | 3.53E+05 | 3.68E−04 | 0.9887 | 13.3 |
| N52D | 111 | 0.86 | 1.16E−09 | 3.36E+05 | 3.90E−04 | 0.989 | 11.9 |
| wildtype PD-L2 ED-Fc | — | −0.04 | | | | | |

TABLE 21

| ICOSL mutation(s) | SEQ ID NO (ECD) | Response | KD (M) | $K_{on}$ (1/Ms) | $K_{dis}$ (1/s) | Full $R^2$ | Fold Imp. |
|---|---|---|---|---|---|---|---|
| | | | CTLA-4 ForteBio Binding Assay | | | | |
| WT ICOSL | 32 | 0.21 | 7.71E−08 | 1.92E+04 | 1.48E−03 | 0.8919 | — |
| N52H, I143T | 135 | 0.96 | 6.78E−10 | 7.26E+05 | 4.92E−04 | 0.9641 | 113.8 |
| N52H, N57Y, Q100R, C198R | 365 | 1.57 | 6.45E−10 | 4.79E+05 | 3.09E−04 | 0.9875 | 119.6 |
| N52H, N57Y, Q100R, V122A | 290 | 1.43 | 5.76E−10 | 4.73E+05 | 2.72E−04 | 0.9926 | 133.9 |
| N52H, N57Y, Q100R, F172S | 291 | 1.47 | 5.36E−10 | 5.13E+05 | 2.75E−04 | 0.9924 | 144.0 |
| N52Y/N57Y/F138L/L203P | 112 | 1.33 | 8.33E−10 | 3.45E+05 | 2.87E−04 | 0.9943 | 92.6 |
| V11E, N30D, N52H, N57Y, H94E, L96I, L98F, N194D, V210A, I218T | 308 | 1.50 | 6.48E−10 | 3.12E+05 | 2.02E−04 | 0.9943 | 119.0 |
| N52H, N57Y, Q100R, L102R, V110D, H115R, C198R | 367 | 1.60 | 8.64E−10 | 4.79E+05 | 4.14E−04 | 0.9825 | 89.2 |
| N52H, N57Y, Q100R | 283 | 1.65 | 7.19E−10 | 4.28E+05 | 3.08E−04 | 0.9895 | 107.2 |
| N52H, Q100R | 285 | 1.17 | 5.92E−10 | 8.37E+05 | 4.96E−04 | 0.9629 | 130.3 |
| N52H, N57Y, Q100R, V110D, C198R, S212G | 364 | 1.32 | 1.47E−09 | 2.34E+05 | 3.44E−04 | 0.9937 | 52.6 |
| N52H, N57Y, Q100P | 113 | 1.51 | 6.47E−10 | 3.61E+05 | 2.33E−04 | 0.9911 | 119.2 |
| E16V, N52H, N57Y, Q100R, V110D, H115R, Y152C, K156M, C198R | 300 | 1.58 | 1.06E−09 | 4.24E+05 | 4.49E−04 | 0.9779 | 72.8 |
| N30D, K42E, N52S | 324 | 0.42 | 2.81E−09 | 2.42E+05 | 6.81E−04 | 0.9676 | 27.4 |
| N52S, F120S, I143V, I224V | 325 | 0.58 | 1.20E−09 | 3.10E+05 | 3.72E−04 | 0.9283 | 64.3 |
| N52S, E90A | 323 | 0.64 | 1.12E−09 | 3.28E+05 | 3.68E−04 | 0.9184 | 68.7 |
| N52H, N57Y, V110A, C198R, R221I | 317 | 1.44 | 1.07E−09 | 4.0SE+05 | 4.32E−04 | 0.9811 | 72.3 |
| N52S, N194D | 366 | 0.59 | 2.52E−09 | 2.66E+05 | 6.69E−04 | 0.9643 | 30.6 |
| N52D | 111 | 0.62 | 1.52E−09 | 4.16E+05 | 6.32E−04 | 0.9234 | 50.7 |
| wildtype PD-L2 ED-Fc | — | 0.00 | | | | | |

C. Coimmobilization Assay

Costimulatory bioactivity of ICOSL fusion variants was determined in anti-CD3 coimmobilization assays substantially as described in Example 6. Approximately 0.37 nM, 1.3 nM or 10 nM mouse anti-human CD3 (OKT3, Biolegends, USA) was diluted in PBS with 10 nM or 40 nM variant ICOSL ECD Fc or wild-type ICOSL ECD-Fc. This mixture was added to tissue culture treated flat bottom 96 well plates overnight to facilitate adherence of the stimulatory proteins to the wells of the plate. The next day, unbound protein was washed off the plates and 100,000 purified human pan T cells were added to each well. Cells were cultured 3 days before harvesting culture supernatants and measuring human IFN-gamma levels with an ELISA kit.

Table 22 sets fort the amount of IFN-gamma (pg/mL) produced by cells under the various conditions in the anti-CD3 coimmobilization assay. In the Table, the amino acid substitutions of exemplary variant ECD ICOSL-Fc fusions are designated by amino acid position number corresponding to the unmodified ICOSL ECD sequence set forth in SEQ ID NO: 32 and the corresponding SEQ ID NO identifier for the variant ECD for each variant ICOSL ECD-Fc fusion molecule is set forth. The ratio of IFN-gamma produced in the presence of each variant ICOSL ECD-Fc in the functional assay compared to in the presence of the corresponding unmodified (wildtype) ECD-Fc is shown (Fold ↑ WT). As shown, costimulatory signaling of the variant ICOSL-ECD-Fc molecules were substantially greater compared to wildtype ICOSL.

TABLE 22

| Assessment of IFN-gamma Responses in Co-stimulation Assay | | | | | | | |
|---|---|---|---|---|---|---|---|
| | | IFN-gamma [pg/mL] | | | | | |
| | SEQ | 40 nM Ligand | | 10 nM Ligand | | 40 nM Ligand | | |
| ICOSL mutation(s) | ID NO (ECD) | 10 mM OKT3 | Fold ↑WT | 10 mM OKT3 | Fold ↑WT | 10 mM OKT3 | 1.1 nM OKT3 | 0.37 nM OKT3 |
| E16V, N52H, N57Y, Q100R, V110D, H115R, Y152C, K156M, C198R | 300 | 14372 | 17.3 | 4903 | 29.9 | 8379.2 | 7422.8 | 2893.7 |
| N52H, N57Y, Q100R, VI22A | 290 | 10640 | 12.8 | 6456 | 39.4 | 5636.2 | 4724.2 | 2246.3 |
| N52H, N57Y, Q100R, F172S | 291 | 10379 | 12.5 | 3741 | 22.8 | 3979.7 | 4067.7 | 1415.5 |
| N52H, N57Y, Q100R, C198R | 365 | 9590 | 11.5 | 4048 | 24.7 | 4215.8 | 2787.1 | 1072.4 |
| N52H, N57Y, Q100R | 283 | 9568 | 11.5 | 3270 | 19.9 | 4412.3 | 3862.0 | 1820.0 |
| N52H, N57Y, Q100R, L102R, V110D, H115R, C198R | 367 | 6939 | 8.4 | 3234 | 19.7 | 5495.2 | 4081.6 | 1442.8 |
| N52S, F120S, I143V, I224V | 325 | 6567 | 7.9 | 717 | 4.4 | 2145.4 | 2185.7 | 646.1 |
| N52S, N194D | 366 | 5690 | 6.8 | 272 | 1.7 | 2315.1 | 1485.0 | 1140.6 |
| V11E, N30D, N52H, N57Y, H94E, L96I, L98F, N194D, V210A, I218T | 308 | 5345 | 6.4 | 1152 | 7.0 | 2747.0 | 3383.4 | 1701.2 |
| N52S, E90A | 323 | 5097 | 6.1 | 706 | 4.3 | 5019.8 | 3036.4 | 1482.4 |
| N52H, N57Y, V110A, C198R, R221I | 317 | 4737 | 5.7 | 520 | 3.2 | 2501.5 | 1632.1 | 937.5 |
| N52H, Q100R | 285 | 4122 | 5.0 | 1466 | 8.9 | 5782.1 | 2861.4 | 967.5 |
| N30D, K42E, N52S | 324 | 4080 | 4.9 | 273 | 1.7 | 1336.8 | 1260.7 | 541.1 |
| N52H, N57Y, Q100P | 113 | 3344 | 4.0 | 229 | 1.4 | 2525.4 | 2439.5 | 1233.9 |
| N52H, N57Y, Q100R, V110D, C198R, S212G | 364 | 3064 | 3.7 | 1471 | 9.0 | 2699.5 | 2629.9 | 678.2 |
| N52Y, N57Y, F138L, L203P | 112 | 2177 | 2.6 | 200 | 1.2 | 1889.5 | 1757.9 | 808.8 |
| N52H, I143T | 135 | 1906 | 2.3 | 138 | 0.8 | 1417.1 | 1367.9 | 275.2 |
| WT ICOSL | 32 | 831 | 1.0 | 164 | 1.0 | 558.8 | 377.7 | 152.0 |
| N52D | 111 | 88 | 0.1 | 231 | 1.4 | 1288.9 | 1737.9 | 289.0 |

D. Mixed Lymphocyte Reaction for Assessment of Bioreactivity Suppression

Modulation of T cell activity by fusion variants was determined in a mixed lymphocyte reaction (MLR) substantially as described in Example 6. Human monocytes were incubated for 6 days in the presence of IL-4 and GM-CSF and matured to dendritic cells with the additional of LPS for the final 24 hours. $1 \times 10^4$ dendritic cells and $1 \times 10^5$ human CFSE-labeled T cells were plated per well and incubated for 4 days in the presence of three different concentrations (40 nM, 13.3 nM or 4.4 nM) of wildtype or recombinant variant ICOSL ECD-Fc molecules diluted in PBS. The same concentrations of human IgG, PD-L2-Fc or Belatacept (CTLA4-Fc containing L104E and A29Y mutations) were used as controls. Supernatants were harvested and IFN-gamma responses were characterized by ELISA.

Figure 5:
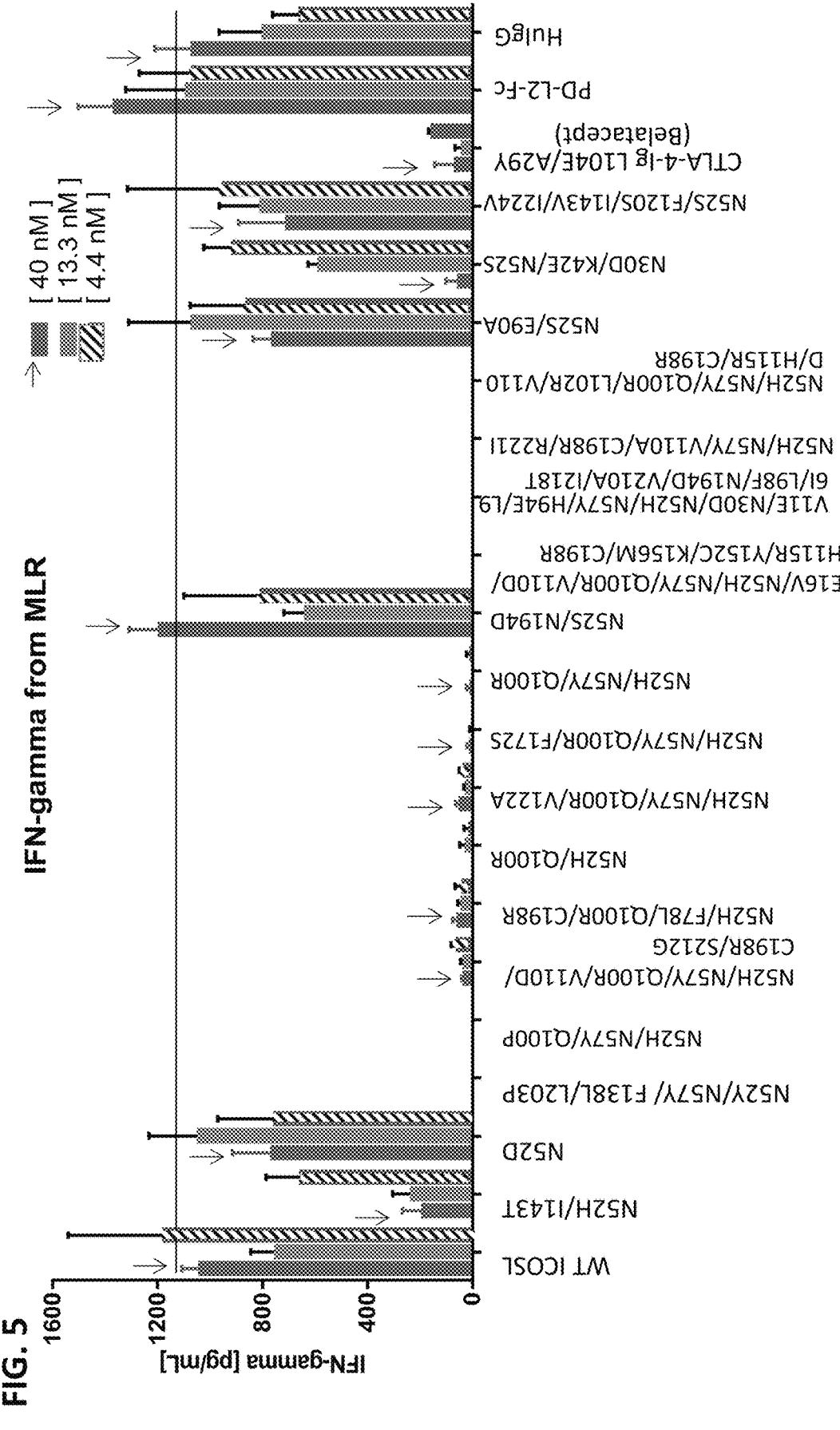
FIG. 5 depicts ICOSL vIgD candidate function in a human Mixed-Lymphocyte-Reaction (MLR). ICOSL variants and their mutations are listed on the x-axis, along with wild-type ICOSL, negative controls PDL2-Fc and human IgG, as well as the positive control benchmark molecule CTLA-Ig Belatacept. The line across the graph represents the baseline amount of IFN-gamma detected in the supernatants of negative control cultures. For each ICOSL variant candidate or control, three different concentrations were tested with arrows indicating the highest concentration of protein in cultures at 40 nM. The majority of ICOSL variant candidates show superior antagonistic activity at all three concentrations tested compared to belatacept as reflected by the lower concentration of IFN-gamma in those cultures.

FIG. 5 depicts the IFN-gamma production under the various conditions. The levels of IFN-gamma produced by cells in the presence of wild-type ICOSL is set forth by the horizontal line. No suppression of IFN-gamma production was observed in the presence of negative control protein PD-L2-Fc. In contrast, most of the tested ICOSL variants exhibited some degree of inhibition of IFN-gamma production in the MLR. Certain variants exhibited substantial inhibition of IFN-gamma with very low to no detectable IFN-gamma produced in the cultures, even at the lowest concentration of 4.4 nM tested. The percent MLR suppression in the presence of 4.4 nM of variant of variant ECD ICOSL-Fc is set forth in Table 23. In the Table, the negative values indicate an inflammatory effect in the assay.

TABLE 23

Costimulatory bioactivity data for ICOSL in MLR

| ICOSL mutation(s) | SEQ ID NO (ECD) | % MLR Suppresion (4.4 nM) |
|---|---|---|
| N52H, N57Y, Q100R, C198R | 365 | 93.6 |
| N52H, N57Y, Q100R, V122A | 290 | 94.4 |
| N52H, N57Y, Q100R, F172S | 291 | 100.0 |
| N52Y/N57Y/F138L/L203P | 112 | 100.0 |
| V11E, N30D, N52H, N57Y, H94E, L96I, L98F, N194D, V210A, I218T | 308 | 100.0 |
| N52H, N57Y, Q100R, L102R, V110D, H115R, C198R | 367 | 100.0 |
| N52H, N57Y, Q100R | 283 | 98.2 |

TABLE 23-continued

Costimulatory bioactivity data for ICOSL in MLR

| ICOSL mutation(s) | SEQ ID NO (ECD) | % MLR Suppresion (4.4 nM) |
|---|---|---|
| N52H, Q100R | 285 | 97.5 |
| N52H, N57Y, Q100R, V110D, C198R, S212G | 364 | 90.4 |
| N52H, N57Y, Q100P | 113 | 100.0 |
| E16V, N52H, N57Y, Q100R, V110D, H115R, Y152C, K156M, C198R | 300 | 100.0 |
| N30D, K42E, N52S | 324 | −38.8 |
| N52S, F120S, I143V, I224V | 325 | −44.2 |
| N52S, E90A | 323 | −30.4 |
| N52H, N57Y, V110A, C198R, R221I | 317 | 100.0 |
| N52S, N194D | 366 | −22.3 |
| N52H, I143T | 135 | −78.0 |
| N52D | 111 | 0.5 |

E. Assessment of Proliferation and Intracellular Cytokine Markers by Flow Cytometry Carboxyfluorescein succinmidyl ester (CFSE) labeled pan T cells from MLR studies as described above that had been incubated for 4 days in the presence of wildtype or recombinant variant ICOSL ECD-Fc molecules were further tested for cytokine levels by restimulation with phorbol myristate acetate (PMA)/Ionomycin for 6 hours in the presence of golgi inhibitor (Golgi/Block/Plug). T cells from the MLR study that had been incubated with human IgG, anti-CD28, anti-ICOSL, PD-L2-Fc, or Belatacept (CTLA4-Fc containing L104E and A29Y mutations) also were restimulated. T cells were stained for CD4 or CD8 surface markers, fixed, permeabilized, and intracellularly stained for various cytokines as set forth in Table 24 and 25.

The percent (%) of CD4+ and CD8+ T cells that were positive for specific intracellular cytokines are shown in Table 24, respectively. The results showed that a number of the variant ICOSL ECD-Fc molecules were able to suppress one or more cytokines, including, in some cases, a majority of cytokines. A total score and mean score are calculated to assess the sum effects of individual molecules tested over the parameters examined in this assay. Proliferation was also assessed and a percentage of cells that have divided as determined by CFSE dilution is also shown in Table 24 and 25. Among the provided results, the results show that certain variants show comparable or better activity than Belatacept, particularly from the CD8+ cells.

TABLE 24

Assessment of Proliferation and Intracellular Cytokine levels of CD4+ T cells

| Variant SEQ ID NO (ECD) or Protein | Prolif | % Cytokine+ | | | | | | | | Total Score | Mean Score |
|---|---|---|---|---|---|---|---|---|---|---|---|
| | | % IFNg+ | % IL4+ | % IL21+ | % IL22+ | % TNF+ | % IL2+ | % IL10+ | % IL17A+ | | |
| 308 | 3.0 | 9.9 | 3.0 | 1.0 | 1.3 | 34.9 | 31.3 | 0.1 | 0.2 | 41.0 | 4.6 |
| 300 | 2.7 | 11.1 | 3.4 | 1.1 | 1.4 | 38.0 | 35.0 | 0.0 | 0.1 | 63.0 | 7.0 |
| 317 | 2.9 | 10.9 | 3.3 | 1.1 | 1.5 | 37.3 | 34.1 | 0.1 | 0.2 | 65.0 | 7.2 |
| 291 | 3.2 | 8.1 | 2.5 | 0.6 | 1.1 | 27.9 | 24.1 | 0.9 | 1.3 | 66.0 | 7.3 |
| 283 | 3.3 | 9.2 | 3.0 | 0.8 | 1.4 | 31.1 | 26.3 | 0.8 | 1.3 | 70.0 | 7.8 |
| 364 | 3.4 | 10.9 | 3.3 | 1.0 | 1.6 | 36.5 | 32.3 | 0.5 | 0.9 | 89.0 | 9.9 |
| 390 | 3.6 | 9.5 | 3.1 | 0.9 | 1.5 | 33.8 | 29.4 | 0.8 | 1.4 | 92.0 | 10.2 |
| 367 | 2.8 | 12.0 | 3.5 | 1.1 | 1.6 | 40.9 | 38.5 | 0.1 | 0.3 | 92.0 | 10.2 |
| CTLA-4-Ig: L104E, A29Y (Belatacept) | 10.7 | 10.5 | 2.7 | 2.4 | 2.0 | 24.5 | 19.6 | 0.6 | 1.4 | 99.0 | 11.0 |
| 112 | 3.5 | 12.0 | 3.8 | 1.3 | 1.6 | 41.3 | 36.7 | 0.2 | 0.4 | 109.0 | 12.1 |
| 285 | 4.4 | 9.8 | 3.2 | 1.2 | 1.7 | 32.7 | 29.3 | 0.9 | 1.4 | 114.0 | 12.7 |
| 113 | 3.0 | 13.2 | 4.1 | 1.2 | 1.8 | 43.2 | 39.8 | 0.1 | 0.2 | 115.0 | 12.8 |

TABLE 24-continued

Assessment of Proliferation and Intracellular Cytokine levels of CD4+ T cells

| Variant SEQ ID NO (ECD) or Protein | Prolif | % Cytokine+ | | | | | | | | Total Score | Mean Score |
|---|---|---|---|---|---|---|---|---|---|---|---|
| | | % IFNg+ | % IL4+ | % IL21+ | % IL22+ | % TNF+ | % IL2+ | % IL10+ | % IL17A+ | | |
| 365 | 3.6 | 11.3 | 3.9 | 1.0 | 2.0 | 39.1 | 34.6 | 0.8 | 1.3 | 118.0 | 13.1 |
| WT ICOSL | 12.7 | 16.7 | 5.8 | 4.9 | 4.7 | 36.2 | 29.2 | 0.2 | 0.4 | 127.0 | 14.1 |
| 113 | 3.5 | 12.3 | 3.9 | 1.1 | 1.8 | 39.2 | 37.5 | 0.4 | 0.6 | 127.0 | 14.1 |
| 366 | 10.9 | 16.0 | 7.2 | 4.9 | 5.4 | 40.6 | 33.0 | 0.1 | 0.2 | 135.0 | 15.0 |
| 321 | 10.6 | 16.7 | 6.0 | 4.3 | 5.0 | 41.3 | 37.3 | 0.2 | 0.3 | 146.0 | 16.2 |
| mIgG ctl | 15.5 | 15.6 | 5.9 | 5.2 | 4.6 | 31.7 | 26.0 | 0.4 | 1.7 | 146.0 | 16.2 |
| PDL2 | 12.3 | 17.9 | 5.7 | 4.7 | 5.2 | 41.4 | 36.0 | 0.3 | 0.6 | 163.0 | 18.1 |
| 323 | 11.9 | 17.7 | 6.2 | 5.2 | 5.3 | 42.4 | 37.5 | 0.2 | 0.4 | 167.0 | 18.6 |
| WT ICOSL | 12.8 | 17.4 | 6.3 | 5.4 | 5.6 | 38.9 | 32.1 | 0.3 | 0.6 | 167.0 | 18.6 |
| Anti-ICOSL | 15.5 | 16.3 | 6.5 | 5.2 | 5.5 | 35.1 | 29.1 | 0.7 | 2.0 | 168.0 | 18.7 |
| 135 | 12.6 | 17.4 | 6.5 | 5.4 | 4.9 | 44.3 | 37.2 | 0.4 | 0.5 | 179.0 | 19.9 |
| HuIgG | 12.7 | 17.1 | 6.3 | 5.9 | 4.9 | 41.1 | 32.4 | 0.7 | 1.3 | 181.0 | 20.1 |
| Anti-CD28 | 88.2 | 42.9 | 5.0 | 5.8 | 5.4 | 43.5 | 25.5 | 0.4 | 1.4 | 183.0 | 20.3 |
| 325 | 12.7 | 18.7 | 6.5 | 5.4 | 5.6 | 44.2 | 40.0 | 0.1 | 0.3 | 186.0 | 20.7 |
| 111 | 13.7 | 18.3 | 6.8 | 5.9 | 6.1 | 42.1 | 35.2 | 0.3 | 0.5 | 194.0 | 21.6 |

TABLE 25

Assessment of Proliferation andIntracellular Cytokine levels of CD8+ T cells

| Variant SEQ ID NO (ECD) or Protein | Prolif | % Cytokine+ | | | | | | | | Total Score | Mean Score |
|---|---|---|---|---|---|---|---|---|---|---|---|
| | | % IFNg+ | % IL4+ | % IL21+ | % IL22+ | % TNF+ | % IL2+ | % IL10+ | % IL17A+ | | |
| 308 | 4.2 | 8.4 | 1.6 | 2.2 | 47.2 | 7.6 | 8.0 | 0.2 | 0.1 | 67.0 | 7.4 |
| 300 | 3.8 | 8.5 | 2.0 | 2.2 | 47.2 | 8.1 | 9.1 | 0.1 | 0.0 | 69.0 | 7.7 |
| 317 | 3.9 | 8.8 | 2.0 | 1.7 | 45.6 | 8.4 | 9.0 | 0.1 | 0.1 | 64.0 | 7.1 |
| 291 | 3.8 | 7.0 | 1.4 | 1.8 | 46.6 | 5.9 | 5.9 | 1.1 | 1.1 | 78.0 | 8.7 |
| 283 | 4.3 | 8.4 | 1.9 | 1.7 | 50.2 | 7.1 | 6.6 | 1.1 | 1.1 | 98.0 | 10.9 |
| 364 | 4.1 | 9.0 | 1.8 | 1.8 | 46.4 | 8.2 | 8.5 | 0.7 | 0.8 | 87.0 | 9.7 |
| 390 | 4.1 | 7.9 | 1.8 | 1.8 | 49.8 | 7.3 | 7.2 | 1.0 | 1.2 | 93.0 | 10.3 |
| 367 | 3.5 | 9.0 | 1.7 | 2.0 | 47.3 | 8.6 | 10.4 | 0.2 | 0.2 | 78.0 | 8.7 |
| CTLA-4-Ig: L104E, A29Y (Belatacept) | 12.3 | 14.5 | 2.0 | 3.2 | 38.1 | 11.2 | 8.8 | 0.9 | 1.6 | 121.0 | 13.4 |
| 112 | 4.2 | 9.6 | 1.9 | 1.8 | 40.4 | 9.4 | 9.9 | 0.3 | 0.3 | 81.0 | 9.0 |
| 285 | 5.4 | 9.5 | 2.0 | 2.7 | 44.2 | 7.8 | 8.4 | 1.2 | 1.3 | 112.0 | 12.4 |
| 113 | 3.7 | 9.5 | 1.9 | 1.3 | 44.4 | 9.4 | 10.5 | 0.1 | 0.1 | 62.0 | 6.9 |
| 365 | 4.1 | 9.6 | 2.3 | 1.8 | 46.8 | 9.0 | 9.3 | 0.9 | 1.0 | 122.0 | 13.6 |
| ICOSL | 17.2 | 22.3 | 4.9 | 6.4 | 46.4 | 22.0 | 15.7 | 0.4 | 0.7 | 181.0 | 20.1 |
| 113 | 4.2 | 9.5 | 2.0 | 2.1 | 45.6 | 8.9 | 10.7 | 0.5 | 0.5 | 110.0 | 12.2 |
| 366 | 14.5 | 19.4 | 5.6 | 4.8 | 48.4 | 19.2 | 13.8 | 0.1 | 0.2 | 142.0 | 15.8 |
| 321 | 13.4 | 18.9 | 4.3 | 5.0 | 46.3 | 18.4 | 15.4 | 0.3 | 0.6 | 138.0 | 15.3 |
| mIgG ctl | 20.2 | 25.0 | 4.4 | 4.1 | 35.5 | 24.6 | 15.8 | 0.7 | 1.8 | 174.0 | 19.3 |
| PDL2 | 15.6 | 21.2 | 4.1 | 4.8 | 44.1 | 20.7 | 15.6 | 0.5 | 0.8 | 147.0 | 16.3 |
| 323 | 15.4 | 20.8 | 4.7 | 5.6 | 44.9 | 20.6 | 17.1 | 0.2 | 0.5 | 149.0 | 16.6 |
| WT ICOSL | 17.5 | 22.1 | 5.5 | 4.6 | 45.0 | 21.0 | 12.8 | 0.2 | 0.4 | 148.0 | 16.4 |
| Anti-ICOSL | 21.5 | 26.4 | 4.8 | 5.3 | 33.4 | 26.9 | 19.0 | 1.0 | 2.3 | 198.0 | 22.0 |
| 135 | 17.2 | 22.2 | 4.7 | 6.7 | 39.4 | 22.5 | 18.1 | 0.8 | 0.9 | 178.0 | 19.8 |
| HuIgG | 15.9 | 21.5 | 4.4 | 6.4 | 41.6 | 21.4 | 15.1 | 1.4 | 1.7 | 179.0 | 19.9 |
| Anti-CD28 | 60.6 | 44.3 | 3.5 | 2.1 | 38.6 | 32.5 | 16.0 | 1.2 | 1.6 | 182.0 | 20.2 |
| 325 | 16.5 | 22.0 | 4.9 | 5.4 | 44.0 | 21.9 | 18.5 | 0.2 | 0.6 | 161.0 | 17.9 |
| 111 | 17.7 | 22.8 | 5.3 | 6.1 | 45.4 | 22.9 | 16.7 | 0.4 | 0.6 | 183.0 | 20.3 |

Example 16

Assessment of Cytokine Production in B-T Cell Co-Culture

B cells and CD4+ T cells were purified from the same donor and labeled with CSFE and plated in 96 well plates in 1:1 cellular ratios at 5×10⁴ cells of each per well. Variant ICOSL ECD-Fc fusion molecules or Belatacept were added at a final concentration of 40 nM per well. Cells were either unstimulated or incubated with 100 ng/ml of Staphylococcus enterotoxin B (SEB), 1 µg/mL of Pokeweed Mitogen (PWM) or both for 7 days at 37° C. in a final volume of 200 µl/well.

Cells were harvested and surface stained for the following B and T cell lineage markers (IgM, IgD, CD38, CD138, CD27, CD19, CD4, CD3). Proliferation was assessed by flow cytometry and culture supernatants were analyzed for IL-5, IL-13 or IL-21 cytokines using a LEGENDplex human Th cytokine detection kit (Biolegend, USA).

Figures 6A, 6B:
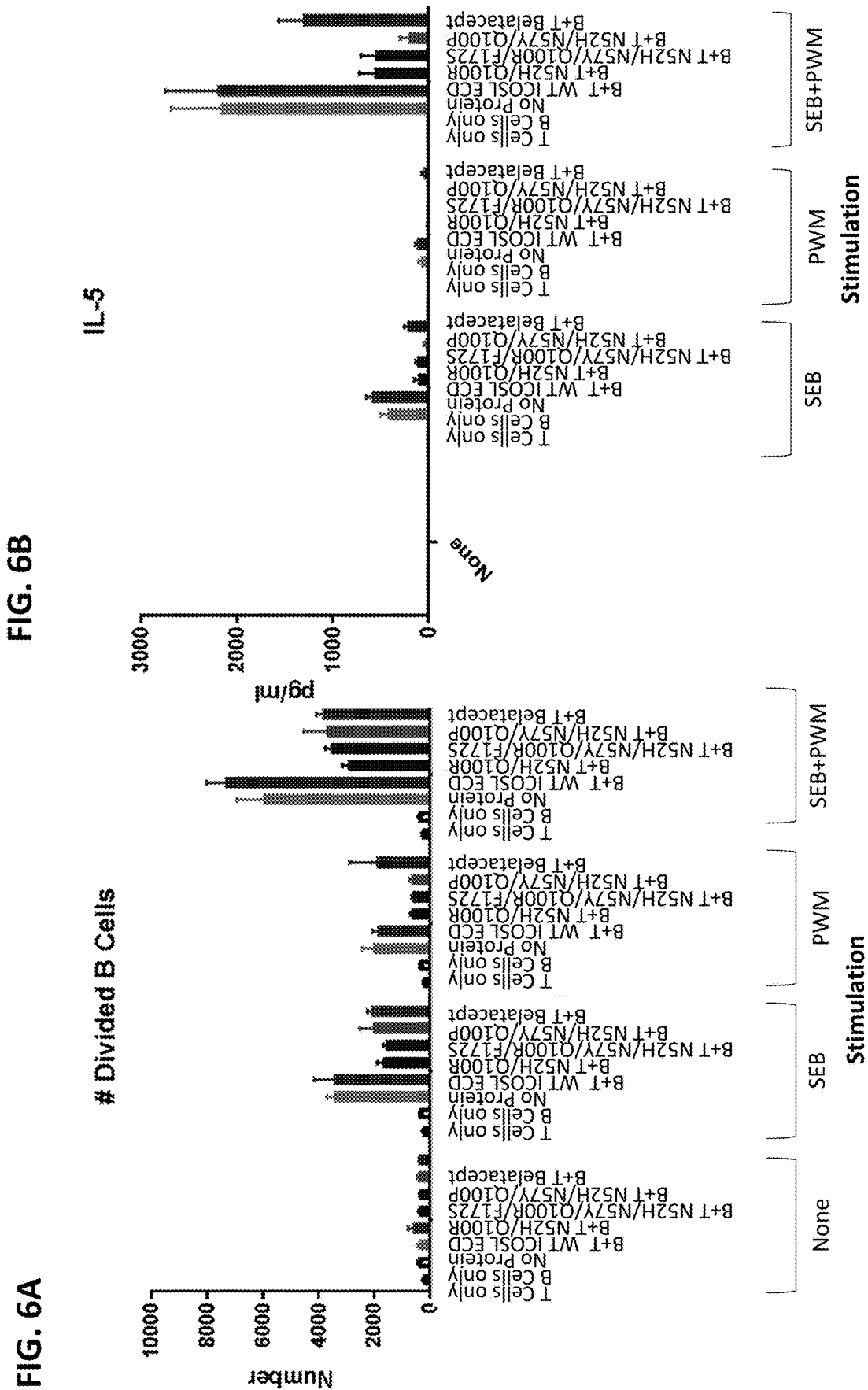

As shown in FIG. 6A, the number of dividing B cells was reduced in B/T cell co-cultures when incubated in the presence of variant ICOSL ECD Fc-fusion molecules compared to no protein controls. The degree of antagonistic effect for the tested exemplary variants was similar to CTLA-4-Ig Belatacept (L104E, A29Y). Likewise, as shown in FIGS. 6B-6D, variant ICOSL ECD Fc-fusion molecules inhibited cytokine production in primary human B cell/T cell coculture in vitro compared to no protein controls as well as cultures containing wild-type ICOSL control. Compared to Belatacept, exemplary tested variant ICOSL ECD Fc-fusion molecules were more effective in blocking cytokine production in some cases.

Example 17

Assessment of Survival and Disease Activity in Graft-Versus-Host-Disease (GvHD) Model Exemplary ICOSL variant ECD-Fc protein, were assessed for activity in a graft-versus-host-disease (GvHD) model. Female NSG mice (n=10 per group) were irradiated (100 rad) and administered 10 mg of gamma globulin subcutaneously on Day-1. On Day 0, the mice received 10 million human peripheral blood mononuclear cells (PBMCs) and intraperitoneal injection dosing of either 100 μg of WT-ICOSL ECD Fc, a variant ICOSL ECD Fc molecule N52H/I143T (ECD set forth in SEQ ID NO: 135), a variant ICOSL ECD Fc molecule N52H/N57Y/Q100P (ECD set forth in SEQ ID NO: 113), 75 μg of Belatacept (CTLA-4-Ig L104E/A29Y; U.S. Patent Application Publication Number US20160271218) or saline as control. On Day 15, engrafted human CD45+ cells were phenotyped by flow cytometry. After the study was terminated on Day 35, endpoint measurements of survival, body weight loss, and disease activity were evaluated.

Figure 7A:
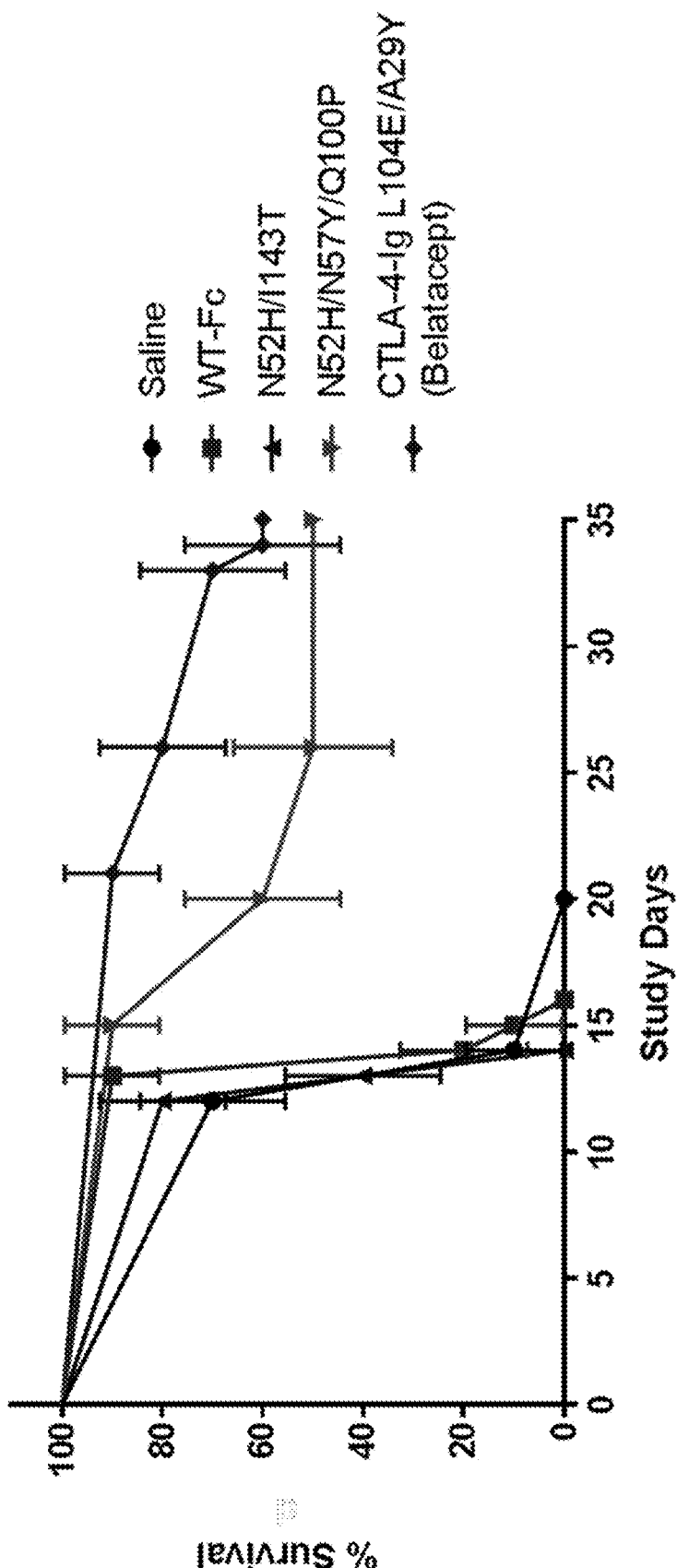
FIG. 7A-7F depicts different endpoints in a mouse model of Graft Verse Host Disease (GVHD) where human PBMC cells were adoptively transferred into immunodeficient NSG murine hosts.
Figure 7B:
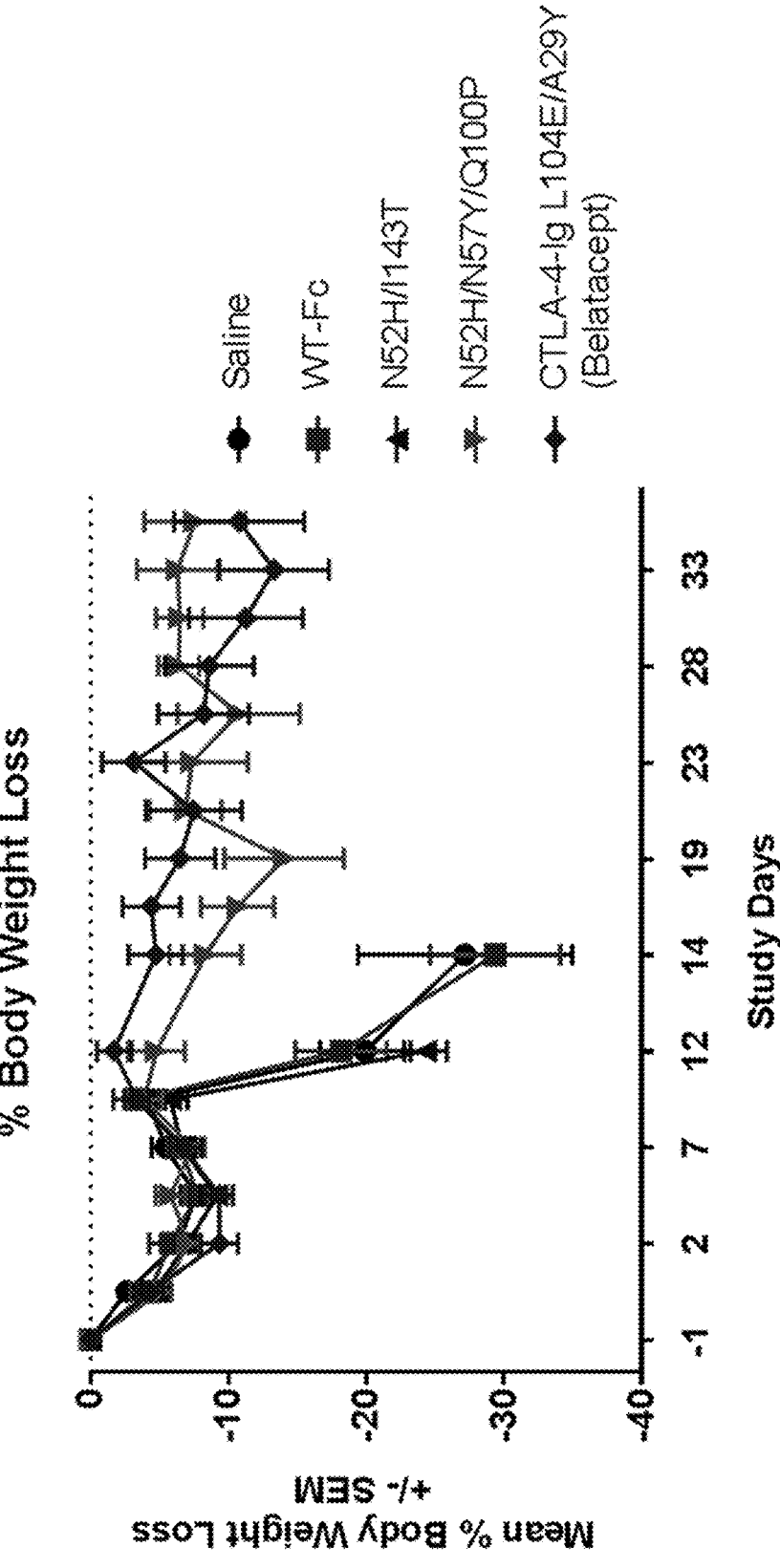

FIG. 7A shows the survival of GVHD mice treated with saline, WT ICOSL-ECD Fc, the variant ICOSL ECD-Fc molecules, or Belatacept. A significant difference in the survival of mice administered variant ICOSL ECD-Fc N52H/N57Y/Q100P (ECD set forth in SEQ ID NO: 113) compared to mice administered saline or WT ICSOL ECD-Fc was observed (p<0.0001 by Mantel-Cox and Gehan-Breslow-Wilcoxon tests). FIG. 7B shows similar differences between the body weight loss of mice treated with saline, WT ICOSL ECD-Fc, the variant ICOSL ECD-Fc molecules, or Belatacept over the course of the study.

Figure 7C:
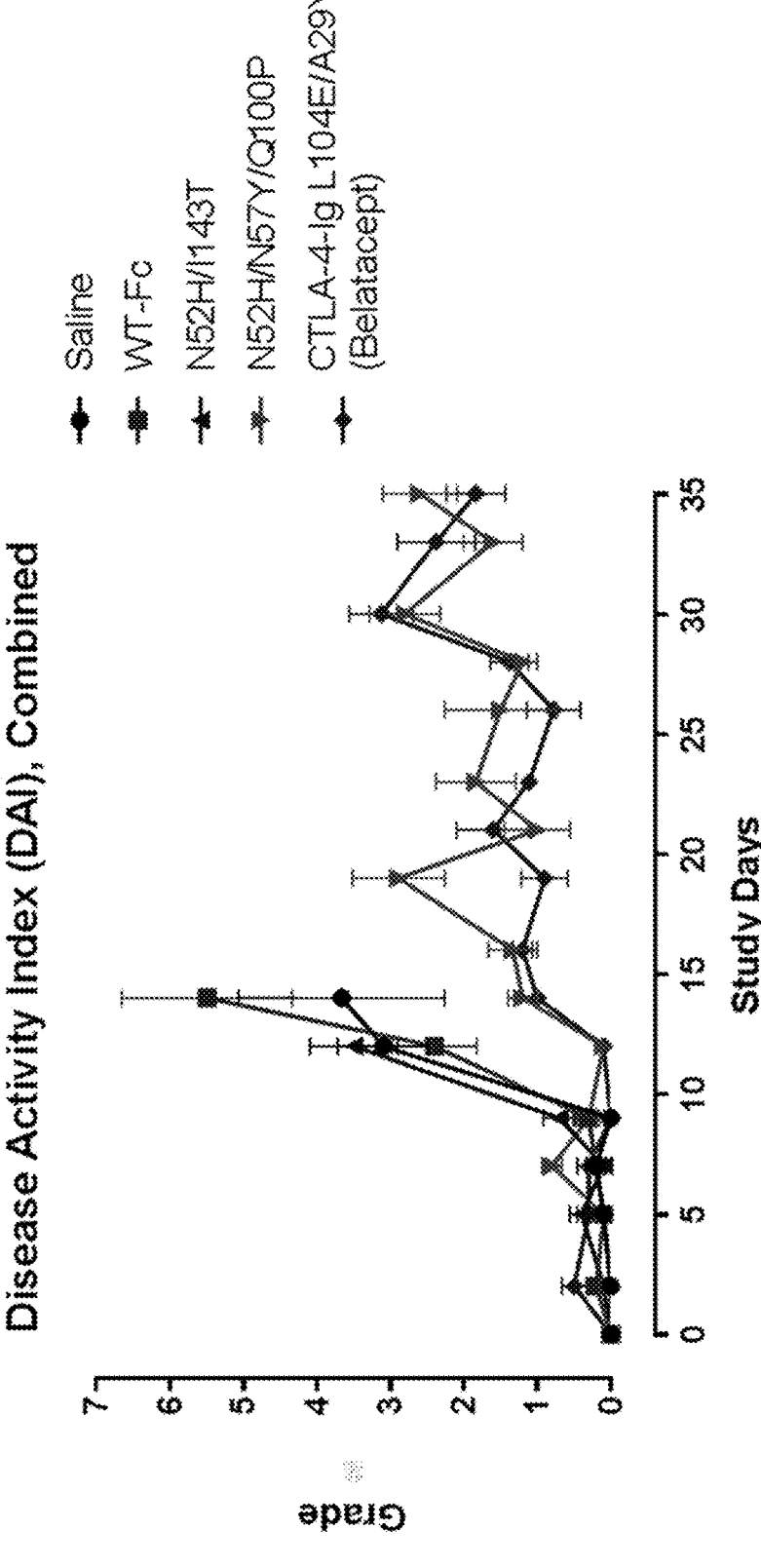
Figure 7D:
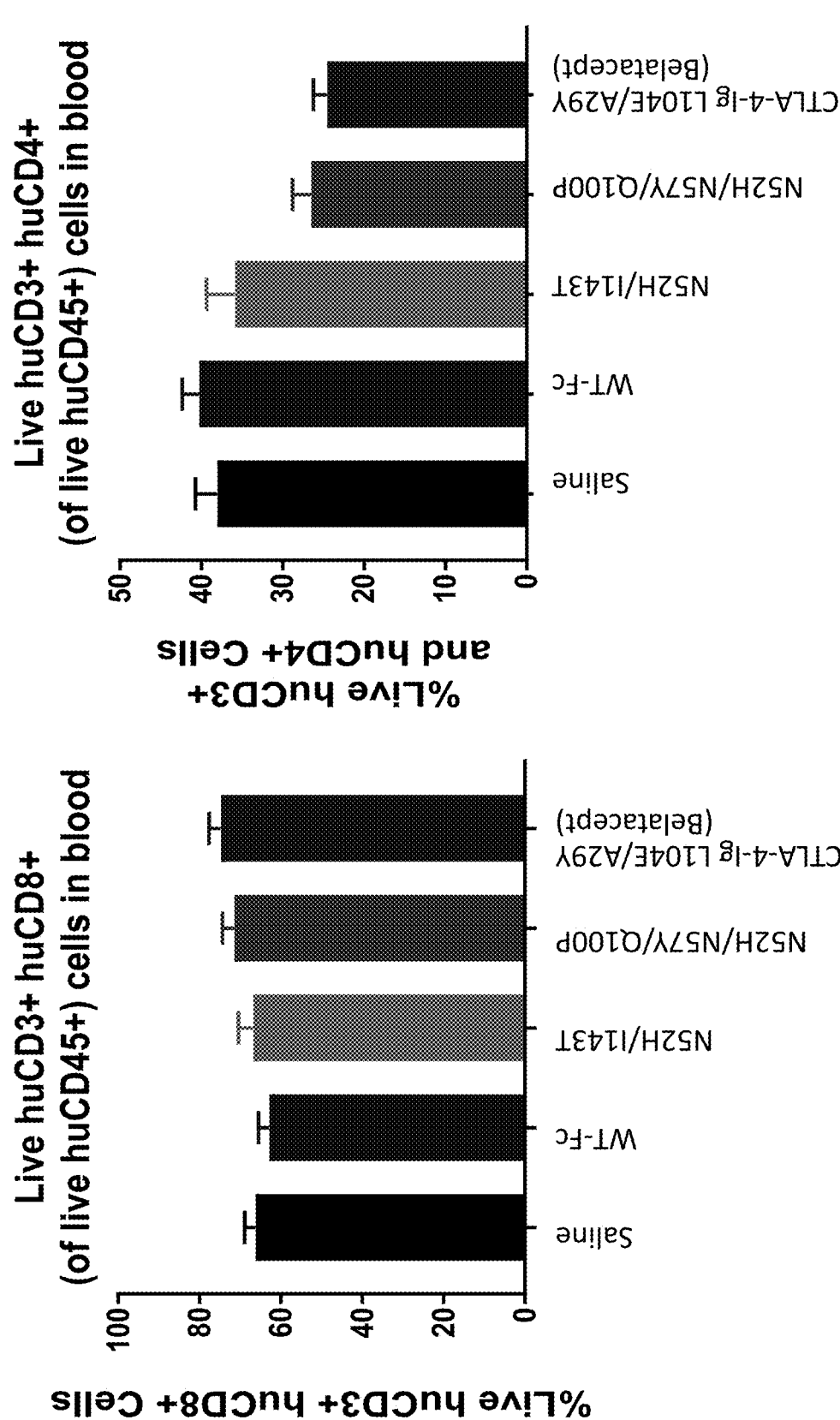

A disease activity index (DAI) was determined three times a week during the study and evaluated the scoring of weight loss, posture, activity, appearance of the hair coat and skin of the mice. The grade of disease over the course of the study is shown in FIG. 7C. Treatment groups that received ICOSL Fc variant N52H/N57Y/Q100P (ECD set forth SEQ ID NO: 113) or Belatacept showed significantly improved DAI scores. The percentage of human T cells in the peripheral blood on day 14 of the study was also assessed by flow cytometry. Measurements were averaged by treatment group and error bars represent standard error of the mean (SEM). FIG. 7D shows the percent of live CD3+/CD4+ or CD3+/CD8+ cells in the blood. Treatment groups that received variant ICOSL ECD Fc with N52H/N57Y/Q100P (ECD set forth SEQ ID NO: 113) or Belatacept showed significantly different levels of CD4+ T cells compared to saline treatment group (p=0.008 and 0.006, respectively, by unpaired t-test). This study demonstrates the therapeutic effect of the variant ICOSL Fc variant protein on human primary T cells and GVHD during in vivo modeling.

A similar study with additional variant ICOSL ECD-Fc fusion molecules was carried out including variant ICOSL ECD-Fc N52H/N57Y/Q100R/C198R (ECD set forth in

244

Figure 7E:
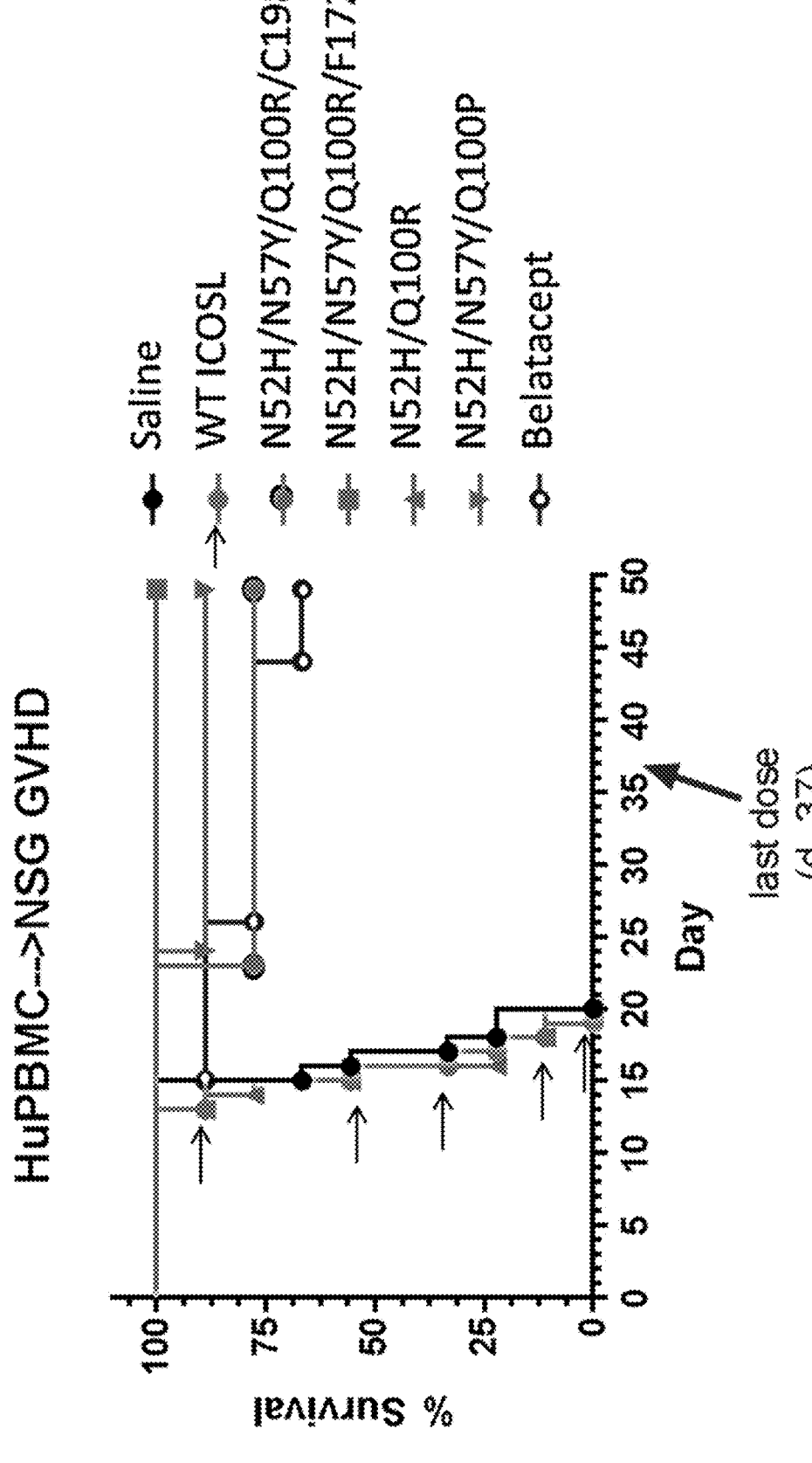
Figure 7F:

SEQ ID NO: 365), N52H/N57Y/Q100R/F172S (ECD set forth in SEQ ID NO: 291), and N52H/N57Y/Q100P (ECD set forth in SEQ ID NO: 288). N52H/Q100R (ECD set forth in SEQ ID NO: 285), which had reduced activity in the in vitro MLR studies as shown above, also was tested. NSG mice (n=9/group) were treated as described above. In this study, dosing with the ICOSL-Fc or Belatacept continued 3 times per week from day 0 through day 37 and surviving mice were terminated on day 49. To determine statistical differences in survival proportions among groups, data were analyzed using the Mantel-Cox (log-rank) test. The resulting survival curves are shown in FIG. 7E. Belatacept and ICOSL-Fc variants N52H/N57Y/Q100R/C198R (ECD set forth in SEQ ID NO: 365), N52H/N57Y/Q100R/F172S (ECD set forth in SEQ ID NO: 291), and N52H/N57Y/Q100P (ECD set forth in SEQ ID NO: 288) significantly prolonged survival as compared to saline and WT ICOSL-Fc (p<0.001). The mean DAI scores were plotted for the time course of the experiment, with the last observation (i.e. mean scores collected on days of termination) carried forward on the graph for those groups terminated prior to the last planned study day (Day 49). Significant differences among groups for data over time (i.e. DAI scores) were determined using 2-way repeated measures ANOVA for 'treatment' effects. The resulting DAI scores are shown in FIG. 7F. Belatacept and ICOSL-Fc variants N52H/N57Y/Q100R/C198R (ECD set forth in SEQ ID NO: 365), N52H/N57Y/Q100R/F172S (ECD set forth in SEQ ID NO: 291), and N52H/N57Y/Q100P (ECD set forth in SEQ ID NO: 288) significantly reduced DAI scores as compared to saline and WT ICOSL-Fc (p<0.001), and between Belatacept and ICOSL-Fc variant with N52H/N57Y/Q100R/C198R by 2-way ANOVA for DAI scores (p=0.035).

The activity of the variant ICOSL-Fc, in some cases, was improved compared to treatment with belatacept. Administration of ICOSL-Fc variants protected from effects of GVHD, as evidenced by enhanced survival and attenuated disease development, at levels comparable to or better than belatacept. The activity in this model correlated with in vitro activity, since WT ICOSL-Fc and variant ICOSL-Fc with mutations N52H/Q100R (ECD set forth in SEQ ID NO: 285) were not as effective in this model.

Example 18

Assessment of Activation by Stacked Molecules

Stacked variant IgV Fc fusion proteins containing an NKp30 IgV domain as a localizing domain (designated "L") and an ICOSL IgV domain as a costimulatory domain (designated "C") were generated and assessed substantially as described in Example 8. Specifically, the constructs tested in this experiment include: (1) a stacked construct with variant IgV Fc fusion protein (vIgD C-L) containing an NKp30 composed of Ig of consensus NKp30 variant (SEQ ID NO:143) with the IgV domain of ICOSL variant N52H/N57Y/Q100P (ECD set forth in SEQ ID NO: 113 and IgV set forth in SEQ ID NO:201); (2) a stacked construct with the NKp30 wildtype domain Ig domain (SEQ ID NO:214) and V domain of wildtype ICOSL (WT C-L) (SEQ ID NO:196); (3) a construct with wild-type ICOSL IgV domain (WT C domain; SEQ ID NO: 196), and (3) a construct with the wildtype NKp30 domain (WT L domain; SEQ ID NO: 214).

CD32+ K562 cells were engineered to stably express B7-H6 on the cell surface. The cells were then treated with mitomycin and plated with pan T-cells in the presence of absence of 10 nM anti-CD3 and stacked variants or control domains at 100, 33, 11, or 3.7 nM. Cells were cultured 3 days before harvesting culture supernatants and measuring human IFN-gamma levels using an ELISA.

Figure 8:
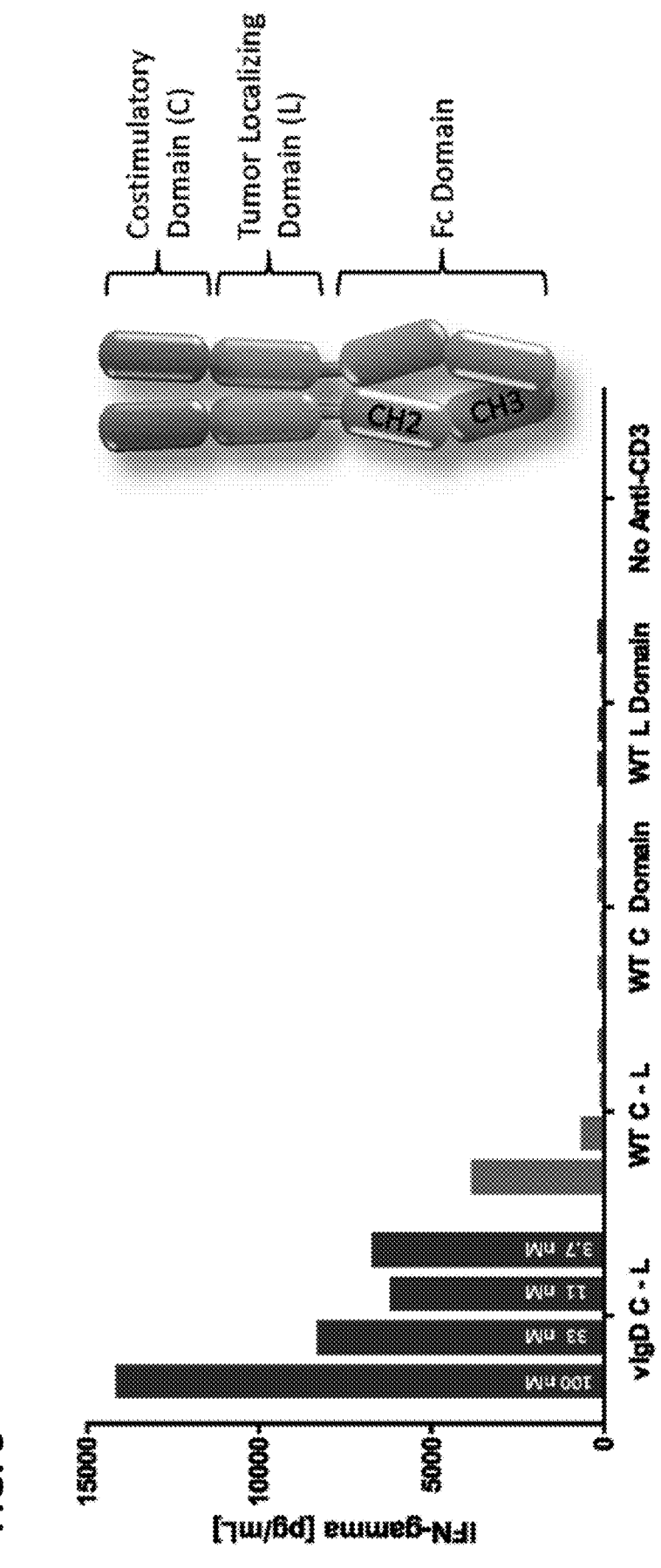
FIG. 8 shows localized costimulatory activity conveyed by the indicated variant stack molecule vIgD C-L, where C represents an ICOSL costimulatory domain and L represents a NKp30 localizing domain. In this assay, target K562 cells expressing the localizing surface protein, B7-H6, were cultured in the presence of anti-CD3 with human T cells and T cell activation was assessed by IFN-gamma levels in culture supernatants. Including anti-CD3 alone or no stack variant Fc molecules did not induce T cell activation. Similarly, cells cultured with only the wild-type localizing NKp30 domain alone or the wild-type costimulatory ICOSL domain alone as Fc fusion proteins did not result in T cell activation. A stacked domain containing the wild-type version of both the costimulatory domain and localizing domain induced measurable IFN-gamma at the highest concentration tested, however, the variant localizing costimulatory stack induced greater than two fold higher IFN-gamma levels at the highest concentration, and IFN-gamma levels that were still observed as the concentrations were titrated down.

As shown in FIG. 8A, both variant and wildtype costimulatory-localizing domain stacks were able to localize to the engineered K562 cells and deliver a co-stimulatory signal to the pan-T-cells to induce IFN-gamma secretion. The stacked construct with variant IgV Fc fusion protein (vIgD C-L) showed increased functional activity results at all concentrations tested, while the individual domain components had no effect when not combined with each other.

Example 19

Assessment of Delayed Type Hypersensitivity In Vivo

Variant ICOSL ECD-Fc fusion molecules were assessed for anti-inflammatory activity in vivo in the mouse delayed-type hypersensitivity (DTH) model. Delayed-type hypersensitivity immune reactions were elicited in ovalbumin (OVA)-sensitized mice and response after challenge was assessed. The variant ICOSL ECD-Fc fusion molecules tested contained a variant ECD with the following amino acid substitutions: N52H/N57Y/Q100P (ECD set forth in SEQ ID NO: 113), N52H/Q100R (ECD set forth in SEQ ID NO: 285), or N52H/N57Y/Q100R/F172S (ECD set forth in SEQ ID NO: 291). The variants were fused to either an Fc backbone containing mutations C220S/L234A/L235E/G237A by EU numbering (designated Fc #1) set forth in SEQ ID NO: 477) or an Fc backbone containing mutations C220S/E233P/L234V/L235A/G236del/S267K by EU numbering (designated Fc #2) set forth in SEQ ID NO:478) either with or without a G4S (GGGGS; SEQ ID NO: 636) linker. Table 26 sets forth the tested constructs:

TABLE 26

| ICOSL ECD-Fc Fusion Constructs | | |
|---|---|---|
| ICOSL ECD (SEQ ID NO) | G4S Linker | Fc (SEQ ID NO) |
| N52H/N57Y/Q100P (G4S)-Fc #1 | 113 | + | 477 |
| N52H/Q100R (G4S)-Fc #1 | 285 | + | 477 |
| N52H/N57Y/Q100R/ F172S (G4S)-Fc | 291 | + | 478 |
| N52H/N57Y/Q100R/ F172S (G4S)-Fc | 291 | + | 477 |
| N52H/N57Y/Q100R/ F172S-Fc | 291 | − | 477 |

For sensitization, 8-week old female BALB/c mice were injected subcutaneously with 100 µg of OVA emulsified in Sigma Adjuvant (100 µL; catalog number S6322-1VL) at the base of the tail on day 0. On days 1 and 4, the mice were administered variant ICOSL ECD-Fc fusion proteins, 75 µg of CTLA-4 Fc (abatacept), or PBS as negative control by intraperitoneal injection. On day 7 at two to three hours prior to OVA challenge, the mice were further administered PBS as a control, 75 µg of CTLA-4 Fc (abatacept from Orencia), or the indicated variant ICOSL polypeptide by intraperitoneal injection. Abatacept and variant ICOSL-Fc fusion molecules were dosed at molar equivalents.

For OVA challenge, an intradermal injection of 10 µg OVA in the left ear pinnae in a 10 µL volume of PBS was delivered under gas isoflurane anesthesia 2-3 hours following therapeutic treatment. Baseline ear thickness was measured prior to OVA challenge.

Figure 9:
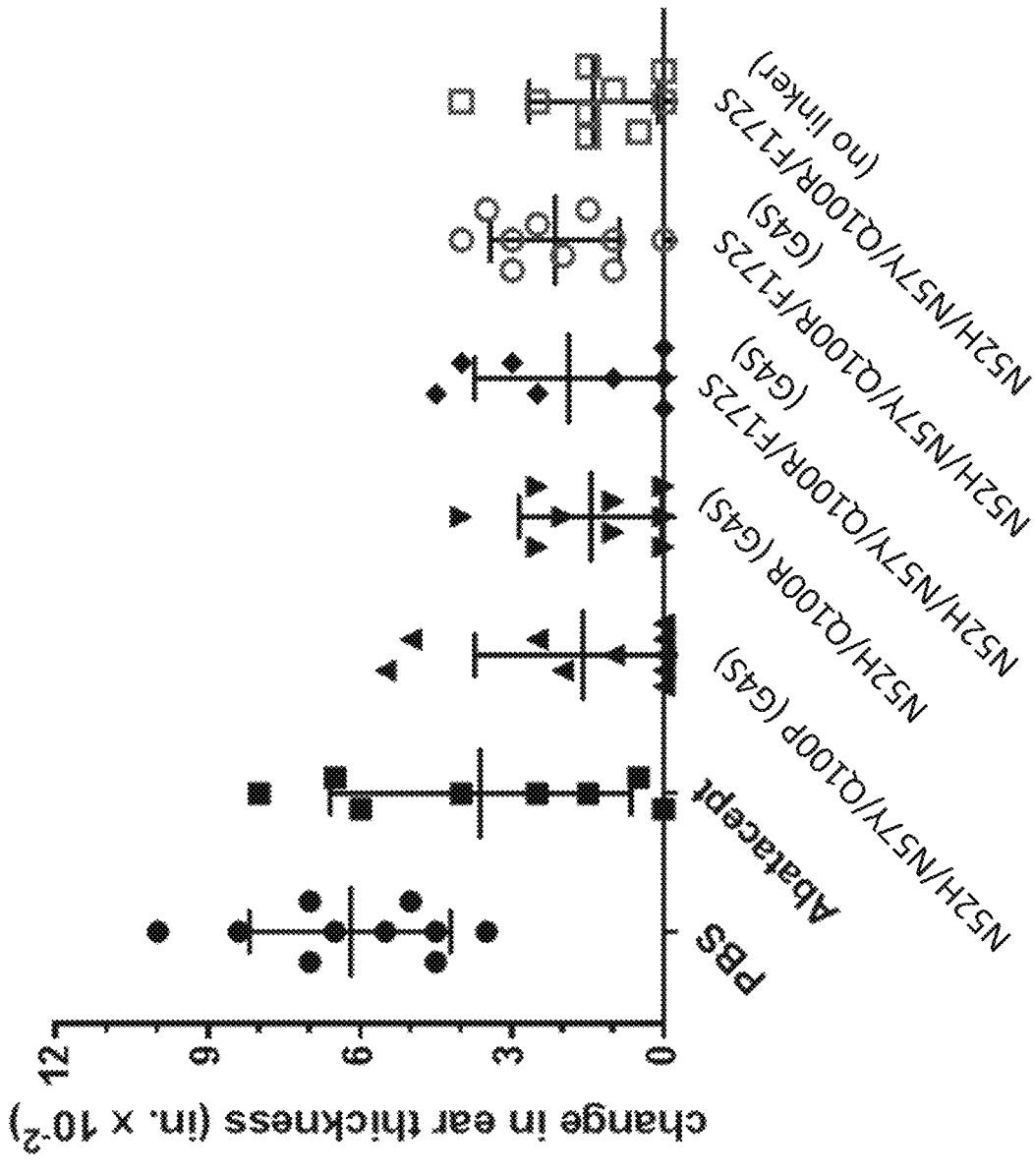
FIG. 9 summarizes changes in ear thickness in mice from a standard model of Delayed-Type Hypersensitivity (DTH).

On day 8, ear thickness was measured under isoflurane anesthesia using Mitutoyo calipers and the change in ear thickness before and after OVA challenge was determined. As shown in FIG. 9, mice treated with the indicated variant ICOSL ECD-Fc fusion molecules showed significantly less OVA-induced ear swelling as compared to PBS control (<0.0001 by 1-way ANOVA). There were no significant differences between ear thickness for mice treated with abatacept compared to any of the indicated variant ICOSL ECD-Fc fusion molecules tested or between the variant ICOSL treatments. These results demonstrate that variant ICOSL molecules can reduce immune responses in vivo.

Example 20

Generation and Assessment of Binding and Activity of Variant ICOSL IgSF Domain-Containing Molecules Additional variant ICOSL IgSF (e.g. ECD) domain-containing molecules were generated, as described below. In each of the Tables below, the Table indicates amino acid substitutions in the ECD of the variant ICOSL as designated by amino acid position number corresponding to amino acid positions in the respective reference (e.g., unmodified) ICOSL extracellular domain (ECD) sequence set forth in SEQ ID NO:32. In some cases, the removal of the AAA linker sequence of the variant ICOSL ECD-Fc is indicated by "AAAA". Column 2 sets forth the SEQ ID NO identifier for each variant ECD domain contained in the variant ECD-Fc fusion molecule.

A. Generation of Additional Variants
1. Solubility Variants

From a collection of mutants containing the following mutations including E16V, N30D, K42E, N52H, N52Y, N52S, N57Y, E90A, Q100R, Q100P, L102R, V110D, H115R, F120S, V122A, F138L, I143V, I143T, H152C, K156M, F172S, N194D, C198R, L203P, R221I, I224V, the mutations H115R, F172S and C198R were identified as mutations that may potentially enhance protein solubility or enhance protein expression ('solubility mutations'). These three mutations (H115R, F172S and C198R) were randomly introduced by site directed mutagenesis into the same set of clones to generate a collection of derivatives that contain one or more of these solubility mutations. Because site directed mutagenesis reaction was carried out with pooled mutagenic oligos reacted with pooled parental clones in a single reaction, some of the clones also contain some mutations from other parental clones. The generated variants contained between 3 to 10 different amino acid mutations in various combinations, as summarized in Table 27A.

TABLE 27A

| Exemplary variant ICOSL polypeptides | |
|---|---|
| Mutation(s) | ECD SEQ ID NO |
| Wild-type | 32 |
| N52H/N57Y/Q100R/H115R/C198R | 435 |
| N52H/N57Y/Q100R/F172S/C198R | 436 |
| N52H/N57Y/Q100R/H115R/F172S/C198R | 437 |
| N52H/N57Y/Q100R/H115R/I143V/F172S/C198R | 438 |
| N52H/N57Y/Q100R/L102R/H115R/F172S/C198R | 439 |
| N52H/V122A/F172S/C198R | 440 |
| N52H/N57Y/Q100R/H115R/F172S/N194D | 441 |
| N52H/N57Y/H115R/F172S/C198R | 442 |
| N52H/N57Y/Q100R/H115R/C198R | 443 |
| N52H/N57Y/H115R | 444 |
| N52H/N57Y/Q100R/H115R | 445 |

TABLE 27A-continued

Exemplary variant ICOSL polypeptides

| Mutation(s) | ECD SEQ ID NO |
|---|---|
| N52H/N57Y/Q100R/H115R/F172S/I224V | 446 |
| N52H/N57Y/Q100R/H115R/F172S | 447 |
| N52H/N57Y/Q100R/F172S | 448 |
| N52H/Q100R/H115R/I143T/F172S | 449 |
| N52H/N57Y/Q100P/H115R/F172S | 450 |
| N52Y/N57Y/Q100P/F172S | 451 |
| E16V/N52H/N57Y/Q100R/V110D/H115R/C198R | 452 |
| E16V/N52H/N57Y/Q100R/V110D/H115R/Y152C/K156M/F172S/C198R | 453 |
| N52S/E90A/H115R | 454 |
| N30D/K42E N52S/H115R | 455 |
| N30D/K42E/N52S/H115R/C198R/R221I | 456 |
| N30D/K42E/N52S/H115R/C198R | 457 |
| N30D/K42E/N52S/H115R/F172S/N194D | 458 |
| N52S/H115R/F120S/I143V/C198R | 459 |
| N52S/H115R/F172S/C198R | 460 |
| N52H/N57Y/Q100P/C198R | 461 |
| N52H/N57Y/Q100P H115R/F172S/C198R | 462 |
| N52H/N57Y/Q100P/F172S/C198R | 463 |
| N52H/N57Y/Q100P/H115R | 464 |
| N52H/N57Y/Q100P/H115R/C198R | 465 |
| N52H/Q100R/C198R | 466 |
| N52H/Q100R/H115R/F172S | 467 |
| N52H/Q100R/H115X/F172S/C198R | 468 |
| N52H/Q100R/H115R/F172S/C198R | 469 |
| N52H/N57Y/Q100R/F172S/C198R | 470 |

2. Back Variants

Particular exemplary mutations including N52H, N52Y, N57Y, Q100R, Q100P, F138L, C198R, L203P identified in select variants described in Example 6 were further combined in the ECD of the reference (e.g., wild-type) ICOSL with reference to positions set forth in SEQ ID NO:32 to generate additional combination variants. The generated variants contained between 1 to 3 different amino acid mutations in various combinations as set forth in Table 27B.

TABLE 27B

Exemplary variant ICOSL polypeptides

| Mutation(s) | ECD SEQ ID NO |
|---|---|
| Wild-type | 32 |
| Q100R | 427 |
| F138L/L203P | 428 |
| N52Y/F138L/L203P | 429 |
| N57Y/Q100R/C198R | 430 |
| N57Y/F138L/L203P | 431 |
| N52H | 110 |
| N57Y | 121 |
| N57Y/Q100P | 122 |
| Q100R/F138L | 432 |
| L203P | 433 |

3. Glycosylation Variants

Exemplary glycosylation mutations selected from N52H, N52Q, N84Q, N119Q, N155H, N155Q, N168Q, N207Q were combined in various permutations in the ECD of the reference (e.g., wild-type) ICOSL with reference to positions set forth in SEQ ID NO:32 to generate additional combination variants. The generated variants contained between 1 to 5 different amino acid mutations in various combinations as set forth in Table 27C. Mutations designated with an "X" indicate either an N or Q at the indicated position.

TABLE 27C (glyc): Exemplary variant ICOSL polypeptides

| Mutation(s) | ECD SEQ ID NO |
|---|---|
| Wild-type | 32 |
| N84Q | 387 |
| N119Q | 388 |
| N168Q | 389 |
| N207Q | 390 |
| N52Q/N207X | 391 |
| N168X/N207X | 392 |
| N52Q/N168Q | 393 |
| N84Q/N207Q | 394 |
| N155Q/N207Q | 395 |
| N119Q/N168Q | 396 |
| N119Q/N207Q | 397 |
| N119Q/N155X | 398 |
| N52Q/N84Q | 399 |
| N52Q/N119Q | 400 |
| N84Q/N119Q | 401 |
| N52Q/N84Q/N168Q | 402 |
| N52Q/N84Q/N207Q | 403 |
| N84Q/N155Q/N168Q | 404 |
| N84Q/N168Q/N207Q | 405 |
| N84Q/N155H/N207Q | 406 |
| N155Q/N168Q/N207Q | 407 |
| N119Q N155Q/N168Q | 408 |
| N119Q/N168Q/N207Q | 409 |
| N84Q/N119Q/N207Q | 410 |
| N119Q/N155H/N207Q | 411 |
| N84Q/N119Q/N155Q | 412 |
| N52Q/N119Q/N155Q | 413 |
| N52H/N84Q/N119Q | 414 |
| N52H/N84Q/N168X/N207X | 415 |
| N52Q/N84Q/N155X/N168X | 416 |
| N52Q/N84Q/N119Q/N168Q | 417 |
| N84Q/N119Q/N155Q/N168Q | 418 |
| N84Q/N155Q/N168Q/N207Q | 419 |
| N84Q/N119Q/N155Q/N207Q | 420 |
| N52Q/N84Q/N119Q/N207Q | 421 |
| N52Q/N84Q/N119Q/N155Q | 422 |
| N52Q/N84Q/N119Q/N155Q/N207Q | 423 |
| N84Q/N119Q/N155Q/N168Q/N207Q | 424 |

B. Binding to Cell-Expressed Counter Structures

The additional variants were formatted as Fc-fusion proteins as described in Example 4. The variant Fc-fusion molecules were assessed in binding studies to assess specificity and affinity of ICOSL domain variant immunomodulatory proteins for cognate binding partners. Expi293 cells transfected with cognate binding partners, human CD28, ICOS and CTLA4, were used in binding studies as described in Example 6. MFI was determined for each transfectant and compared to the corresponding unmodified (parental) ECD-Fc.

Results for the binding for exemplary variant ICOSL ECD-Fc fusion molecules are shown in Tables 28A-C. As shown in Table 28A-C, ICOSL IgSF (e.g. ECD) domain variants generated with the various combinations of specific mutations exhibited increased binding for at least one, and in some cases more than one, cognate counter structure ligand.

C. Bioactivity Characterization with Anti-CD3 Coimmobilization Assay

The costimulatory bioactivity of generated variant Fc-fusion molecules was also assessed in anti-CD3 coimmobilization assays as described in Example 6. Table 28A-C depicts the ratio of IFN-gamma produced by each variant ECD-Fc compared to the corresponding unmodified (wild-type) ICOSL ECD-Fc in the assay. Mutations designated with an "X" indicate a Q or the wildtype residue corresponding to the indicated position of SEQ ID NO: 32 at the indicated position. As shown, variant Fc-fusion molecules generated exhibited improved activities to increase immunological activity.

TABLE 28A

Molecule sequences, binding data, and costimulatory bioactivity data
of variant ICOSL ECD-Fc molecules containing select mutations

| | | Binding | | | Coimmobilization with anti-CD3 |
|---|---|---|---|---|---|
| ICOSL Mutations | SEQ ID NO (ECD) | ICOS MFI (parental ratio) | CD28 MFI (parental ratio) | CTLA-4 MFI (parental ratio) | IFN-gamma pg/mL (parental ratio) |
| N52H, N57Y, Q100R, F172S, C198R | 436 | 118145 (1.33) | 59651 (29.60) | 178790 (41.12) | 5059 (37.90) |
| N52H, N57Y, Q100R, H115R, F172S, C198R | 437 | 125341 (1.41) | 51604 (25.60) | 211000 (48.53) | 8218 (61.57) |
| N52Y, N57Y, Q100P, F172S | 451 | 121280 (1.37) | 63663 (31.59) | 174224 (40.07) | 8123 (60.86) |
| E16V, N52H, N57Y, Q100R, V110D, H115R, Y152C, K156M, F172S, C198R | 453 | 107819 (1.22) | 68883 (34.18) | 170080 (39.12) | 8936 (66.95) |
| N52S, H115R, F120S, I143V, C198R | 459 | 116235 (1.31) | 25582 (12.69) | 22483 (5.17) | 125 (0.93) |
| N52H, N57Y, Q100P, C198R | 461 | 107164 (1.21) | 56103 (27.84) | 172319 (39.63) | 1258 (9.43) |
| N52H, N57Y, Q100P, H115R, F172S, C198R | 462 | 120864 (1.36) | 54586 (27.08) | 176637 (40.63) | 5507 (41.26) |
| N52H, N57Y, Q100P, F172S, C198R | 463 | 117954 (1.33) | 59376 (29.46) | 151265 (34.79) | 3884 (29.10) |
| N52H, N57Y, Q100P, H115R | 464 | 126221 (1.42) | 53321 (26.46) | 178812 (41.13) | 4154 (31.13) |
| N52H, N57Y, Q100P, H115R, C198R | 465 | 137004 (1.55) | 55454 (27.51) | 148417 (34.14) | 5069 (37.98) |
| N52H, Q100R, C198R | 466 | 111428 (1.26) | 58608 (29.08) | 116111 (26.71) | 3729 (27.94) |
| N52H, Q100R, H115R, F172S | 467 | 105532 (1.19) | 58287 (28.92) | 106295 (24.45) | 5294 (39.67) |
| N52H, Q100R, H115X, F172S, C198R | 468 | 106555 (1.20) | 73397 (36.42) | 171815 (39.52) | 6961 (52.16) |
| N52H, Q100R, H115R, F172S, C198R | 469 | 114223 (1.29) | 66686 (33.09) | 157154 (36.15) | 7592 (56.88) |
| N52H, N57Y, Q100R, F172S, C198R | 470 | 99350 (1.12) | 61292 (30.41) | 182288 (41.93) | 9167 (68.68) |
| N52H, N57Y, Q100R, H115R, F172S, C198R | 437 | 114057 (1.29) | 52011 (25.81) | 146471 (33.69) | 6545 (49.04) |
| N52H, N57Y, Q100R, H115R, F172S | 447 | 136143 (1.54) | 66516 (33.00) | 177376 (40.80) | 8527 (63.89) |
| N52H, N57Y, Q100R, H115R, F172S, C198R | 437 | 132970 (1.50) | 59633 (29.59) | 133247 (30.65) | 5999 (44.95) |
| Q100R | 427 | 62064 (8.31) | 16740 (8.31) | 29654 (8.31) | 35 (0.26) |
| Q100R ΔAAA | 427 | 1594 (8.20) | 16535 (8.20) | 33457 (8.20) | 87 (0.65) |
| F138L, L203P | 428 | 53804 (0.75) | 1510 (0.75) | 2151 (0.75) | 35 (0.26) |
| F138L, L203P ΔAAA | 428 | 53044 (0.93) | 1882 (0.93) | 1623 (0.93) | 35 (0.26) |
| N52Y, F138L, L203P | 429 | 99761 (23.50) | 47369 (23.50) | 67300 (23.50) | 1489 (11.16) |
| N52Y, F138L, L203P ΔAAA | 429 | 59576 (26.23) | 52865 (26.23) | 66553 (26.23) | 997 (7.47) |
| N57Y, Q100R, C198R | 430 | 58706 (28.65) | 57739 (28.65) | 99426 (28.65) | 9962 (74.64) |
| N57Y, Q100R, C198R ΔAAA | 430 | 98514 (28.63) | 57694 (28.63) | 131458 (28.63) | 6763 (50.67) |
| N57Y, F138L, L203P | 431 | 109472 (20.98) | 42276 (20.98) | 64477 (20.98) | 4979 (37.30) |
| N57Y, F138L, L203P ΔAAA | 431 | 97777 (22.29) | 44924 (22.29) | 64742 (22.29) | 6507 (48.75) |
| N52H | 110 | 91598 (28.91) | 58264 (28.91) | 103025 (28.91) | 3393 (25.42) |
| N57Y | 121 | 109031 (21.71) | 43754 (21.71) | 50683 (21.71) | 4881 (36.57) |
| N57Y, Q100P | 122 | 72480 (29.85) | 60161 (29.85) | 109522 (29.85) | 2797 (20.95) |
| Q100R, F138L | 432 | 65974 (2.23) | 4485 (2.23) | 8136 (2.23) | 685 (5.13) |

TABLE 28A-continued

Molecule sequences, binding data, and costimulatory bioactivity data
of variant ICOSL ECD-Fc molecules containing select mutations

| ICOSL Mutations | SEQ ID NO (ECD) | Binding | | | Coimmobilization with anti-CD3 |
|---|---|---|---|---|---|
| | | ICOS MFI (parental ratio) | CD28 MFI (parental ratio) | CTLA-4 MFI (parental ratio) | IFN-gamma pg/mL (parental ratio) |
| L203P | 433 | 61554 (0.76) | 1533 (0.76) | 2031 (0.76) | 2434 (18.24) |
| Wildtype ICOSL ECD | 32 | 88625 (1.00) | 2015 (1.00) | 4348 (1.00) | 133 (1.00) |

TABLE 28B

Molecule sequences, binding data, and costimulatory bioactivity data
of variant ICOSL ECD-Fc molecules containing select mutations

| ICOSL Mutations | SEQ ID NO (ECD) | Binding | | | Coimmobilization with anti-CD3 |
|---|---|---|---|---|---|
| | | ICOS MFI (parental ratio) | CD28 MFI (parental ratio) | CTLA-4 MFI (parental ratio) | IFN-gamma pg/mL (parental ratio) |
| N52H, N57Y, Q100R, H115R | 445 | 165027 (1.97) | 51666 (9.89) | 287581 (60.27) | 5858 (20.36) |
| N52H, N57Y, Q100R, F172S | 448 | 184449 (2.20) | 51394 (9.84) | 182109 (38.16) | 3449 (11.99) |
| N52H, N57Y, Q100R, H115R, F172S, I224V | 446 | 165120 (1.97) | 46636 (8.93) | 274026 (57.43) | 2053 (7.13) |
| N52H, N57Y, Q100R, H115R, F172S | 447 | 164750 (1.97) | 40046 (7.67) | 259351 (54.35) | 3722 (12.93) |
| N52H, N57Y, Q100R, H115R, C198R | 435 | 186017 (2.22) | 39073 (7.48) | 200505 (42.02) | 3909 (13.58) |
| N52H, N57Y, Q100R, F172S, C198R | 436 | 181118 (2.16) | 38233 (7.32) | 210709 (44.16) | 1199 (4.17) |
| N52H, N57Y, Q100R, H115R, F172S, C198R | 437 | 155392 (1.85) | 28828 (5.52) | 169736 (35.57) | 3449 (11.99) |
| N52H, N57Y, Q100R, H115R, I143V, F172S, C198R | 438 | 139977 (1.67) | 31459 (6.02) | 179089 (37.53) | 1620 (5.63) |
| N52H, N57Y, Q100R, L102R H115R, F172S, C198R | 439 | 146799 (1.75) | 29636 (5.68) | 200000 (41.91) | 2712 (9.43) |
| N52H, N57Y, Q100R, H115R F172S, N194D | 441 | 150863 (1.80) | 31304 (5.99) | 167783 (35.16) | 15607 (54.24) |
| N52H, N57Y, H115R, F172S, C198R | 442 | 126909 (1.51) | 35803 (6.86) | 152858 (32.03) | 5374 (18.67) |
| N52H, N57Y, Q100R, H115R, C198R | 443 | 131730 (1.57) | 37595 (7.20) | 139041 (29.14) | 9306 (32.34) |
| N52H, N57Y, H115R | 444 | 162632 (1.94) | 49847 (9.55) | 266878 (55.93) | 2918 (10.14) |
| N52H, Q100R, H115R, I143T F172S | 449 | 132873 (1.59) | 52058 (9.97) | 186366 (39.06) | 3086 (10.72) |
| N52H, N57Y, Q100P, H115R, F172S | 450 | 148160 (1.77) | 46851 (8.97) | 246636 (51.69) | 4987 (17.33) |
| E16V, N52H, N57Y, Q100R, V110D, H115R, C198R | 452 | 154036 (1.84) | 48674 (9.32) | 212905 (44.62) | 5095 (17.71) |
| N52S, E90A, H115R | 454 | 142963 (1.71) | 3597 (0.69) | 3772 (0.79) | 2241 (7.79) |
| N30D, K42E, N52S, H115R, C198R R221I | 456 | 124095 (1.48) | 8066 (1.54) | 7751 (1.62) | 417 (1.45) |
| N30D, K42E, N52S, H115R, C198R | 457 | 161734 (1.93) | 2791 (0.53) | 2919 (0.61) | 841 (2.92) |
| N30D, K42E, N52S, H115R, F172S, N194D | 458 | 117880 (1.41) | 4395 (0.84) | 4941 (1.04) | 2904 (10.09) |
| N30D, K42E, N52S, H115R, | 455 | 114107 (1.36) | 2935 (0.56) | 2748 (0.58) | 549 (1.91) |
| N52S, E90A, H115R, | 454 | 120450 (1.44) | 12768 (2.45) | 23282 (4.88) | 2890 (10.04) |
| N30D, K42E, N52S, H115R | 455 | 115273 (1.38) | 11964 (2.29) | 22779 (4.77) | 2241 (7.79) |
| N52S, H15R, F172S, C198R | 460 | 95537 (1.14) | 7614 (1.46) | 21701 (4.55) | 1458 (5.07) |

TABLE 28B-continued

Molecule sequences, binding data, and costimulatory bioactivity data
of variant ICOSL ECD-Fc molecules containing select mutations

| ICOSL Mutations | SEQ ID NO (ECD) | Binding | | | Coimmobilization with anti-CD3 |
| | | ICOS MFI (parental ratio) | CD28 MFI (parental ratio) | CTLA-4 MFI (parental ratio) | IFN-gamma pg/mL (parental ratio) |
| --- | --- | --- | --- | --- | --- |
| Wildtype | 32 | 83813 (1.00) | 5222 (1.00) | 4772 (1.00) | 288 (1.00) |

TABLE 28C

Molecule sequences, binding data, and costimulatory bioactivity data
of variant ICOSL ECD-Fc molecules containing glycosylation mutations

| ICOSL Mutation(s) | SSEQ ID NO (ECD) | Binding | | | Coimmobilization with anti-CD3 |
| | | ICOS MFI (parental ratio) | CD28 MFI (parental ratio) | CTLA-4 MFI (parental ratio) | IFN-gamma pg/mL (parental ratio) |
| --- | --- | --- | --- | --- | --- |
| N84Q | 387 | 34426 (0.94) | 1755 (1.16) | 5757 (1.51) | 100 (2.03) |
| N119Q | 388 | 30806 (0.84) | 4102 (2.70) | 19836 (5.21) | 81 (1.66) |
| N168Q | 389 | 27041 (0.74) | 1410 (0.93) | 18641 (4.90) | 67 (1.36) |
| N207Q | 390 | 36516 (1.00) | 11923 (7.86) | 25701 (6.76) | 206 (4.20) |
| N52Q, N207X | 391 | 30216 (0.83) | 12086 (7.97) | 27952 (7.35) | 77 (1.56) |
| N168X, N207X | 392 | 37191 (1.02) | 5787 (3.81) | 12280 (3.23) | 104 (2.12) |
| N52Q, N168Q | 393 | 32576 (0.89) | 12638 (8.33) | 27167 (7.14) | 101 (2.06) |
| N84Q, N207Q | 394 | 37176 (1.02) | 5292 (3.49) | 3153 (0.83) | 31 (0.63) |
| N155Q, N207Q | 395 | 34884 (0.95) | 1489 (0.98) | 987 (0.26) | 73 (1.48) |
| N119Q, N168Q | 396 | 29099 (0.80) | 2534 (1.67) | 11289 (2.97) | 51 (1.05) |
| N119Q, N207Q | 397 | 32603 (0.89) | 1861 (1.23) | 6795 (1.79) | 153 (3.12) |
| N119Q, N155X | 398 | 38516 (1.05) | 15318 (10.10) | 27498 (7.23) | 173 (3.52) |
| N52Q, N84Q | 399 | 33988 (0.93) | 1675 (1.10) | 3525 (0.93) | 39 (0.80) |
| N52Q, N119Q | 400 | 35729 (0.98) | 11040 (7.28) | 26139 (6.87) | 51 (1.03) |
| N84Q, NH9Q | 401 | 34777 (0.95) | 1493 (0.98) | 2877 (0.76) | 39 (0.80) |
| N52Q, N84Q, N168Q | 402 | 27021 (0.74) | 1584 (1.04) | 958 (0.25) | 38 (0.78) |
| N52Q, N84Q, N207Q | 403 | 39942 (1.09) | 13396 (8.83) | 26360 (6.93) | 37 (0.76) |
| N84Q, N155Q, N168Q | 404 | 27812 (0.76) | 357 (0.24) | 466 (0.12) | 30 (0.61) |
| N84Q, N168Q, N207Q | 405 | 30659 (0.84) | 737 (0.49) | 861 (0.23) | 25 (0.52) |
| N84Q, N155H, N207Q | 406 | 13557 (0.37) | 685 (0.45) | 607 (0.16) | 29 (0.59) |
| N155Q, NI68Q, N207Q | 407 | 13999 (0.38) | 277 (0.18) | 317 (0.08) | 40 (0.82) |
| N119Q, N155Q, N168Q | 408 | 36896 (1.01) | 4094 (2.70) | 2179 (0.57) | 50 (1.02) |
| N119Q, N168Q, N207Q | 409 | 29543 (0.81) | 921 (0.61) | 3744 (0.98) | 72 (1.47) |
| N84Q, N119Q, N207Q | 410 | 21357 (0.58) | 569 (0.38) | 640 (0.17) | 59 (1.20) |
| N119Q, N155H, N207Q | 411 | 37310 (1.02) | 614 (0.40) | 931 (0.24) | 86 (1.75) |

TABLE 28C-continued

Molecule sequences, binding data, and costimulatory bioactivity data
of variant ICOSL ECD-Fc molecules containing glycosylation mutations

| | | Binding | | | Coimmobilization with anti-CD3 |
|---|---|---|---|---|---|
| ICOSL Mutation(s) | SSEQ ID NO (ECD) | ICOS MFI (parental ratio) | CD28 MFI (parental ratio) | CTLA-4 MFI (parental ratio) | IFN-gamma pg/mL (parental ratio) |
| N84Q, N119Q, N155Q | 412 | 2675 (0.07) | 262 (0.17) | 291 (0.08) | 34 (0.70) |
| N52Q, N119Q, N155Q | 413 | 27853 (0.76) | 552 (0.36) | 772 (0.20) | 42 (0.87) |
| N52H, N84Q, N119Q | 414 | 40700 (1.11) | 4580 (3.02) | 4601 (1.21) | 39 (0.80) |
| N52H, N84Q, N168X, N207X | 415 | 8796 (0.24) | 587 (0.39) | 481 (0.13) | 32 (0.66) |
| N52Q, N84Q, N155X, N168X | 416 | 43521 (1.19) | 6605 (4.35) | 4811 (1.26) | 32 (0.66) |
| N52Q, N84Q, N119Q, N168Q | 417 | 39342 (1.07) | 4519 (2.98) | 3300 (0.87) | 37 (0.76) |
| N52Q, N84Q, N119Q, N207Q | 421 | 7011 (0.19) | 602 (0.40) | 433 (0.11) | 37 (0.75) |
| Wildtype ICOSL ECD | 32 | 36602 (1.00) | 1517 (1.00) | 3804 (1.00) | 49 (1.00) |

Example 21

Generation and Assessment of Fusion Molecules with HER2-Targeting Antibody

This Example describes the generation and assessment of variant ICOSL ECD-Fc fusion molecules conjugated with a tumor targeting agent to form a conjugate ("vIgD conjugate").

The V-domain only of the ICOSL vIgD (N52H/N57Y/Q100P; set forth in SEQ ID NO: 201) was fused to the amino and carboxyl termini of the light chain (FIG. 10A) and heavy chain (FIG. 10B) of a HER2 targeting antibody with intervening GGGSGGGS linkers. Exemplary configurations of vIgD conjugates are shown in FIG. 10C.

To assess HER2 binding, HER2 DNA or mock Expi293 transfectants were stained with titrated amounts of a HER2 targeting antibody containing the variant ICOSL conjugate (vIgD N52H/N57Y/Q100P conjugate) at a concentration of 100 pM to 100 nM. Control proteins, including wildtype ICOSL ECD-Fc fusion, wildtype PD-L2 IgV-Fc fusion, and variant ICOSL ECD-Fc fusion molecule with mutations at N52H/N57Y/Q100P, were also tested. Mean Fluorescence Intensity (MFI) or percent positive cells was determined for each transfectant as described in Example 6. All IgSF conjugates generated as shown in FIG. 11A-11B retained binding to HER2 compared to the endogenous level of HER2 expression observed in Expi293 cells. Similarly, vIgD conjugates also showed binding to cognate binding partners of ICOSL including CD28, CTLA-4, and ICOS.

Protein bioactivity and proliferation of human primary T cell in vitro assays were also characterized as described in Example 6. vIgD conjugates were bound overnight to 96-well plates at 30-0.1 nM in the presence of 10 nM anti-CD3. The plates were washed and 100,000 CFSE-labeled pan T cells were added to the plates and incubated for 72 hours. IFN gamma levels in supernatant were assayed by ELISA. As shown in FIG. 12, vIgD conjugates with the indicated configurations showed greater IFN gamma secretion and proliferation compared to parental wild-type ICOSL ECD-Fc fusion molecule conjugate.

Example 22

Nanostring Transcriptional Signature of Primary Human T Cells

Tissue culture plates were coated with 10 nM anti-CD3 with 40 nM of an Fc-control protein, wild-type ICOSL-Fc, wild-type CD80-Fc, both of these proteins, or variant ICOSL Fc-fusion proteins with mutations as indicated. Purified human T cells were then plated on the protein coated plates and incubated at 37° C. Cultures from each treatment group described above were harvested at 24, 48 and 72 hours and total RNA was prepared from each cell sample. The RNA was transferred to Nanostring and a Cancer Immune chip was used to quantitate transcripts of 750 gene in each sample. Transcript values were normalized using Nanostring's proprietary software allowing comparison of transcript levels between treatment groups and over the various time points. As shown in FIG. 18 and FIG. 19, the variant ICOSL ECD-Fc polypeptides tested show altered inflammatory activity compared to wildtype CD80 ECD-Fc, wild-type ICOSL ECD-Fc, or a combination of both.

Example 23

Generation and Assessment of Fusion Molecules with HER2-Targeting Antibody

Proliferation of human T-cells co-cultured with VmAbs and HER2 expressing target cells was also characterized. CFSE-labeled pan T-cells were stimulated for 72 hours with K562-derived artificial target cells displaying cell surface anti-CD3 single chain Fv (OKT3) and HER2 in the presence of VmAbs or control proteins. Proliferation was measured by flow cytometric analysis of CFSE-dilution on CD4+ or CD8+ stained T-cells. Vmabs were assayed varying either target cell number or the concentration of the VmAb utilized. In the first assay, K562 target cells were titrated from 2500 to 78 cells/well and added to 100,000 T-cells for an effector:target (E:T) range of 40 to 1280:1. VmAbs, parental IgSF domain, or WT ICOSL were added at 1000 pM. In the second assay, K562 target cells were added at 625 cells/well to 100,000 T-cells for an effector:target ratio of 160:1.

VmAbs or control proteins were titrated and added at 3000 to 37 pM. As shown in FIGS. 20A and 20B, both configurations of the assay demonstrate VmAbs containing the vIgD-conjugate provide superior proliferation compared to the parental antibody, parental IgSF domain, or WT ICOSL. Additionally, vIgD-conjugates mediated proliferation at low E:T ratios (1280:1) or at low protein concentrations (37 pM).

Example 24

Generation and Assessment of Engineered Cells Expressing a Transmembrane Immunomodulatory Protein and a T Cell Receptor This Example describes the expression of various variant ICOSL IgSF domain-containing transmembrane immunomodulatory proteins (TIPs) with an exemplary recombinant E6-specific T cell receptor (TCR) in human T cells and assessment of T cell proliferation.

Human HLA-A2+ T cells were activated on Day 0 with anti-CD3/anti-CD28 activation beads (ThermoFisher Scientific, USA) and transduced, on day 1, with a TCR specific to HPV E6 (described in WO 2015/009606) and various transmembrane immunomodulatory proteins (TIPs) containing a variant ICOSL IgSF domain. The exemplary ICOSL-TIPs had an affinity-modified IgSF domain containing amino acid mutations corresponding to cither E16V/N52H/N57Y/Q100R/V110D/H115R/Y152C/K156M/C198R or N52H/N57Y/Q100R with reference to positions in the ICOSL extracellular domain set forth in SEQ ID NO: 32. The ICOSL TIPs also included a transmembrane and cytoplasmic domain corresponding to residues 257-302 of SEQ ID NO: 5. For comparison, T cells also were co-transduced with the HPV E6 TCR and either a WT CD80-TIP (set forth as amino acids 35-288 of SEQ ID NO: 1 and encoded by the sequence of nucleotides set forth in SEQ ID NO:251) or a WT ICOSL-TIP (set forth as amino acids 19-302 of SEQ ID NO:5 and encoded by the sequence of nucleotides set forth in SEQ ID NO:252). For transduction, cells were transduced with a viral vector construct in which was inserted a polynucleotide encoding the TIP and the TCRα and TCRβ chain sequences, each separated from each other by a sequence encoding a P2A ribosome skip sequence (SEQ ID NO: 863), for co-expression of the TIP and the TCR containing the TCRα and TCRβ chain in the engineered cells. Specifically, the nucleic acid construct had the following structure: ICOSL-P2A1-TCRβ-P2A2-TCRα, in which the nucleotide sequence P2A1 and P2A2 each encoded the P2A set forth in SEQ ID NO: 863 but differed in the nucleotide sequence to avoid recombination between sequences.

As a control, T cells were mock transduced or transduced with the exemplary E6 TCR only.

The T cell activation beads were removed on day 3 and cytokines IL-2, IL-7, and IL-15 were added to the culture. On day 6 after transduction, cell surface expression of the TIP and TCR was assessed by flow cytometry, with 35-65% of engineered cells double positive for the TCR and TIP. The TCR-expressing cells were expanded in the presence of HPV E6 peptide to result in a population of cells that were >90% double positive for the TCR/TIP as assessed at day 14. On day 14, the engineered cells were incubated with HPV-infected cells, either a squamous cell carcinoma cell line UPCI:SCC152 (ATCC® CRL-3240™; HPV+, HLA-A2+), epidermoid carcinoma CaSki cells (ATCC® No. CRL-1550™; HPV+, HLA-A2+), or squamous cell carcinoma SiHa cells (ATCC® HTB-35™; HPV+, HLA-A2−). Proliferation of the engineered cells was assessed on day 3 after initiation of co-culture with target cells. As shown in FIG. 21, increased proliferation of T cells engineered with E6 TCR was observed in the two HPV+ cell lines, but not significantly in the HPV-SiHa line. Engineered cells that co-expressed variant ICOSL TIPS had increased proliferation in response to the HLA-A2+HPV+target SCC152 and Caski cell lines.

Example 25

Generation and Assessment of Fc-Fusion Immunomodulatory Proteins

Variant ICOSL IgSF (e.g. ECD) domain-containing molecules were formatted as Fc-fusion proteins substantially as described in Example 4, except using various linkers and Fc molecules. To generate immunomodulatory proteins that are Fc fusion proteins containing an ECD of ICOSL with at least one affinity-modified domain (e.g. variant ICOSL ECD-Fc), the encoding nucleic acid molecule was generated to encode a protein designed as follows: variant (mutant) ECD linked directly or indirectly via a linker to an inert human IgG1 Fc. Specifically, the generated immunomodulatory proteins either did not contain a linker (none) or contained a AAA or a G4S (SEQ ID NO: 636) linker. The inert human IgG1 Fc contained mutations, by EU numbering, as follows: C220S/R292C/N297G/V302C (SEQ ID NO: 476), C220S/E233P/L234V/L235A/G236del/S267K (SEQ ID NO: 478), C220S/L234A/L235E/G237A (SEQ ID NO: 477), or allotypes thereof. The replacement C220S was included because the resulting proteins do not include an antibody light chain that can form a covalent bond with a cysteine. The recombinant variant Fc fusion proteins were produced in 293 cells and purified with Protein A substantially as described in Example 5.

The variant ICOSL Fc-fusion immunomodulatory proteins were assessed in binding studies to assess binding for cognate binding partners. Expi293 cells transfected with cognate binding partners, human CD28, ICOS and CTLA4, were used as target cells in binding studies as described in Example 6. MFI of binding of variant ICOSL Fc fusion immunomodulatory proteins for target cell expressing each binding partner was determined and compared to the binding of the corresponding unmodified (wildtype) ICOSL ECD-Fc to the same target cells. Modulation of T cell activity by the variant ICOSL Fc-fusion immunomodulatory proteins was also determined using a mixed lymphocyte reaction (MLR) substantially as described in Example 6.

Results for the binding of exemplary variant ICOSL ECD-Fc fusion immunomodulatory proteins containing various linkers and Fc regions are shown in Table 29. The Table indicates amino acid substitutions in the ECD of the variant ICOSL as designated by amino acid position number corresponding to amino acid positions in the respective reference (e.g., unmodified) ICOSL extracellular domain (ECD) sequence set forth in SEQ ID NO:32. Column 1 also sets forth the SEQ ID NO identifier for each variant ECD domain contained in the variant ICOSL Fc fusion. Column 2 indicates the linker used in the Fc fusion protein and the SEQ ID NO identifier for the linker. Column 3 sets forth the mutations in the Fc by EU numbering and the SEQ ID NO identifier for the Fc contained in the variant ICOSL Fe fusion protein.

As shown in Table 29, similar results were observed for binding to cognate binding partners among the tested variant ICOSL Fc fusion proteins. These results indicate that the format of the Fc fusion with different Fc molecules or different linkers did not impact the binding of the ICOSL IgSF domain variants for their cognate binding partner. In addition, all Fc fusion formats, when provided as bivalent Fc molecules in solution in an MLR reaction, exhibited an antagonist activity to decrease T cell activation compared to the reference (e.g. unmodified or wildtype) ECD-Fc molecule not containing the amino acid substitution. In some cases, no detectable IFN-gamma was measured in the supernatant consistent with complete blocking of interactions of costimulatory ligand cognate binding partners with their ligands to induce IFN-gamma secretion.

TABLE 29

| Molecule sequences, binding data, and costimulatory bioactivity data of variant ICOSL ECD-Fc molecules | | | | | | |
|---|---|---|---|---|---|---|
| | | | Binding | | | MLR |
| ICOSL Mutation (s) (SEQ ID NO) | Linker (SEQ ID NO) | Fc Mutations (SEQ ID NO) | CD28 MFI (ΔWT) | CTLA-4 MFI (ΔWT) | ICOS MFI (ΔWT) | IFN-gamma pg/mL (ΔWT) |
| N52H/N57Y/Q100R/F172S (291) | AAA | C220S/R292C/N297G/V302C (476) | 67870 (13.0) | 213333 (22.7) | 120042 (1.5) | 3 (0.02) |
| N52H/N57Y/Q100R/F172S (291) | AAA | C220S/E233P/L234V/L235A/ G236del/S267K (478) | 57272 (10.9) | 192595 (20.5) | 103983 (1.3) | 0 (0.00) |
| N52H/N57Y/Q100R/F172S (291) | AAA | C220S/L234A/L235E/G237A (477) | 65506 (12.5) | 193704 (20.6) | 105432 (1.3) | 0 (0.00) |
| N52H/N57Y/Q100R/F172S (291) | G4S (636) | C220S/E233P/L234V/L235A/ G236del/S267K (478) | | | | |
| N52H/N57Y/Q100R/F172S (291) | G4S (636) | C220S/L234A/L235E/G237A (477) | 67596 (12.9) | 212875 (22.7) | 106576 (1.4) | 0 (0.00) |
| N52H/N57Y/Q100R/F172S (291) | none | C220S/E233P/L234V/L235A/ G236del/S267K (478) | — | — | — | — |
| N52H/N57Y/Q100R/F172S (291) | none | C220S/L234A/L235E/G237A (477) | 59987 (11.5) | 210061 (22.4) | 106405 (1.4) | 0 (0.00) |
| N52H/Q100R (285) | AAA | C220S/R292C/N297G/V302C (476) | 57419 (11.0) | 190012 (20.2) | 86522 (1.1) | 30 (0.26) |
| N52H/Q100R (285) | AAA | C220S/E233P/L234V/L235A/ G236del/S267K (478) | | | | |
| N52H/Q100R (285) | AAA | C220S/L234A/L235E/G237A (477) | 58772 (11.2) | 211494 (22.5) | 88969 (1.1) | 25 (0.22) |
| N52H/Q100R (285) | G4S (636) | C220S/E233P/L234V/L235A/ G236del/S267K (478) | 62331 (11.9) | 207285 (22.1) | 110512 (1.4) | 31 (0.28) |
| N52H/Q100R (285) | G4S (636) | C220S/L234A/L235E/G237A (477) | 70142 (13.4) | 187699 (20.0) | 125505 (1.6) | 49 (0.44) |
| N52H/Q100R (285) | none | C220S/E233P/L234V/L235A/ G236del/S267K (478) | 58726 (11.2) | 206110 (21.9) | 110721 (1.4) | 54 (0.48) |
| N52H/Q100R (285) | none | C220S/L234A/L235E/G237A (477) | 62746 (12.0) | 198281 (21.1) | 96948 (1.2) | 16 (0.14) |
| N52H/N57Y/Q100P (113) | AAA | C220S/R292C/N297G/V302C (476) | 79792 (15.3) | 193633 (20.6) | 91384 (1.2) | 1 (0.01) |
| N52H/N57Y/Q100P (113) | AAA | C220S/E233P/L234V/L235A/ G236del/S267K (478) | 69603 (13.3) | 314593 (33.5) | 103387 (1.3) | 0 (0.00) |
| N52H/N57Y/Q100P (113) | AAA | C220S/L234A/L235E/G237A (477) | 68729 (13.1) | 171223 (18.2) | 97068 (1.2) | 0 (0.00) |
| N52H/N57Y/Q100P (113) | G4S (636) | C220S/E233P/L234V/L235A/ G236del/S267K (478) | 67753 (13.0) | 188192 (20.0) | 93424 (1.2) | 1 (0.01) |
| N52H/N57Y/Q100P (113) | G4S (636) | C220S/L234A/L235E/G237A (477) | 69887 (13.4) | 160705 (17.1) | 104124 (1.3) | 0 (0.00) |
| N52H/N57Y/Q100P (113) | None | C220S/E233P/L234V/L235A/ G236del/S267K (478) | 68979 (13.2) | 184726 (19.7) | 98512 (1.3) | 0 (0.00) |
| N52H/N57Y/Q100P (113) | none | C220S/L234A/L235E/G237A (477) | 67863 (13.0) | 154563 (16.5) | 97714 (1.2) | 0 (0.00) |
| WT (32) | AAA | C220S/R292C/N297G/V302C (476) | 5232 (1.0) | 9394 (1.0) | 78795 (1.0) | 113 (1.00) |

Example 26

Expression of Variant ICOSL Molecules in CHO Cells

As an alternative to expressing variant ICOSL Fc fusion proteins in Expi293 cells as described in Example 5, suspension Chinese hamster ovary cells (ExpiCHO-S) cells were used to produce various ICOSL molecules. A DNA construct encoding the exemplary variant ICOSL IgSF (e.g. ECD) Fc-fusion proteins containing the variant (mutant) ECD N52H/N57Y/Q100R/F172S (SEQ ID NO:291) linked to an inert Fc containing mutations C220S/L234A/L235E/ G237A by EU numbering set forth in SEQ ID NO: 477 or an allotype thereof set forth in SEQ ID NO: 637, with a GSGGGGS linker (SEQ ID NO: 635) was used to transfect cells.

ExpiCHO-S cells, and reagents for transfection using the ExpiCHO™ Expression System, were purchased from ThermoFisher Scientific (Cat #A29133). The cells were thawed and expanded per manufacture's recommended protocol. After at least 2 passages, the cells were split 24 hours pre-transfection and allowed to expand to high density. Cells were then diluted to the number of cells for transfection, DNA complex was formed with the ExpiFectamine™ CHO reagent and added to the cells. One day post DNA complex addition the ExpiCHO™ feed and ExpiFectamine™ CHO Enhancer were added to the culture, which was then placed in a 32 degree C. incubator. The cell viability and cell mass were monitored and the culture was harvested when the viability fell below 80%. The culture was then centrifuged at low speed to remove the cell pellet, and the cleared supernatant was 0.2 μm sterile filtered. Protein was purified as described in Example 5.

A. Protein Analysis

The purified variant ICOSL Fc fusion protein was run on SDS-PAGE and analyzed by protein staining. Multiple bands were observed in cells produced from CHO cells but not from 293 cells, which is consistent with an observation that proteolysis clipping of the ICOSL was occurring when expressed in CHO cells. Table 30A depicts the molecular weight of intact, single-clipped, and double clipped proteins calculated based on amino acid sequences and potential carbohydrates as observed by SDS-PAGE. Proteolysis of the ICOSL Fc-fusion proteins expressed in ExpiCHO-S derived cells was observed, as indicated by the presence of both reduced/non-reduced clipped species with lower molecular weight (single and double clipping). Based on the size of the observed bands and Mass Spectrometry analysis, these results are consistent with a potential cleavage site in ICOSL ECD corresponding to the sequence LQQN/LT ("/" indicates potential cleavage site), thereby resulting in cleavage before the stalk region of the ECD and removal of the Fc portion of the sequence in one or both chains of the Fc fusion protein. The observed protease cleavage may result in a heterogenous protein product when produced in CHO cells. Also, for formats expressed as transmembrane immunomodulatory proteins, protease cleavage, occurring in certain cells, could lead to release of soluble protein from cells, thereby reducing cell surface-expressed forms of the variant protein on engineered cells.

TABLE 30A

Reduced/Non-Reduced Species Detected After Capture and Elution from Protein A Column Chromatography Using SDS-PAGE to Assay Proteolysis

| | Calculated MW | | Observed (Apparent) MW[1] | |
| | Non Reduced | Reduced | Non Reduced | Reduced |
|---|---|---|---|---|
| Intact | 105.6 kD aa ~29 kD carb | 52.8 kD aa ~14.5 kD carb | 150 kD | 80 kD |
| | 135 kD total | 67.3 kD total | | |
| Single Clip | 78.8 kD aa ~16.5 kD carb | 52.8 kD aa ~14.5 kD carb | 100 kD | 80 kD 37 kD |
| | 95.3 kD total | 67.3 kD total 26 kD aa ~2 kd carb | | |
| Double Clip | 52.1 kD aa ~4 kD carb | 28 kD total 26 kD aa ~2 kd carb | 65 Kd | 37 kD |
| | 56.1 kdD total | 28 kd total | | |

[1]Estimated MW from SDS-PAGE relative to Protein MW Markers

Example 27

Generation of Proteolysis-Resistant Variants of ICOSL IgSF Domain-Containing Molecules To render variant ICOSL polypeptides resistant to proteolysis upon expression in cells, such as in CHO cells, various additional forms of variant ICOSL polypeptides were generated. The following additional modified reference sequences of the ICOSL ECD were generated: (1) various ECD truncations lacking all or a portion of the LQQN/LT protease cleavage site (designated Trunc #4, #5, #6, #7, or #8); (2) ICOSL variant reference sequences containing mutations at cleavage site N207 and/or L208 with reference to positions set forth in SEQ ID NO:32; or an ICOSL alone IgV reference sequence containing the IgV domain as the only IgSF domain of the molecule (set forth in SEQ ID NO: 545, corresponding to amino acids 1-122 of SEQ ID NO:32). In some cases, combinations of the above strategies were employed in a ICOSL ECD reference sequence. Table 30B below sets forth various generated reference sequences.

The exemplary mutations N52H/N57Y/Q100R/F172S, with reference to numbering set forth in SEQ ID NO: 32, were introduced into the various reference sequences. Because the reference ICOSL IgV set forth in SEQ ID NO: 545 does not contain a position corresponding to F172S, the variant ICOSL IgV did not contain the mutation F172S. The generated variant ICOSL polypeptides were formatted as an Fc fusion protein containing the generated reference ICOSL IgSF domain linked via a (G$_4$S)2 linker (SEQ ID NO:229) to an inert Fc containing mutations C220S/L234A/L235E/ G237A/K447del by EU numbering set forth in SEQ ID NO: 633, or an allotype thereof set forth in SEQ ID NO:637.

TABLE 30B

Exemplary ICOSL IgSF-containing domain reference sequences

```
Reference ICOSL      ...----------ECD1Stalk----------------|
Sequence             --------Stalk-------------------------------
```

TABLE 30B-continued

| Exemplary ICOSL IgSF-containing domain reference sequences | |
|---|---|
| Full ECD (32) | ...VNIGCCIENVLLQQNLT_VGSQTGNDIGERDKITENPVSTGEKNAAT_ |
| Truncation #2 (600) | ...VNIGCCIENVLLQQNL |
| Truncation #3 (601) | ...VNIGCCIENVLLQQNL_TVGSQ_ |
| Truncation #4 (602) | ...VNIGCCIENVLLQQN |
| Truncation #5 (603) | ...VNIGCCIENVLLQQ |
| Truncation #6 (604) | ...VNIGCCIENVLL |
| Truncation #7 (605) | ...VNIGCCIEN |
| Truncation #8 with N207G/L208G (623) | ...VNIGCCIENVLLQQGGT |
| ECD with N207A (624) | ...VNIGCCIENVLLQQALTVGSQTGNDIGERDKITENPVSTGEKNAAT |
| ECD with N207G/L208G (628) | ...VNIGCCIENVLLQQGGTVGSQTGNDIGERDKITENPVSTGEKNAAT |
| IgV (545) | ...HVAANFSV |

A. Proteolysis Assessment

DNA constructs encoding the variant ICOSL Fc-fusion molecules described above were transfected into Chinese hamster ovary cells (ExpiCHO-S). The ICOSL Fc-fusion proteins were then purified from supernatants with Protein A by affinity chromatography as described in Example 5. Purified protein was analyzed by analytical SEC.

Figure 22A:
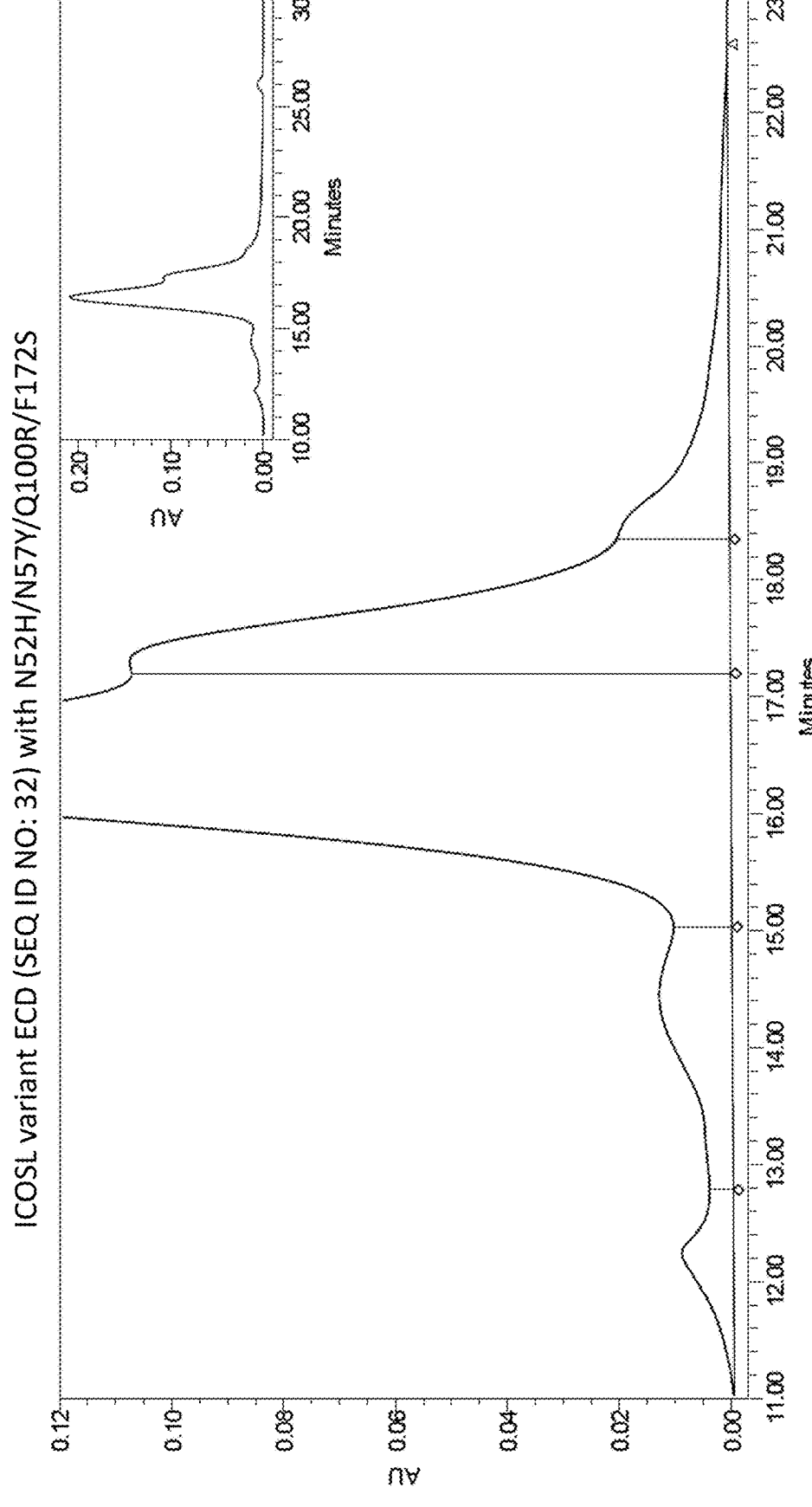
Figure 22B:
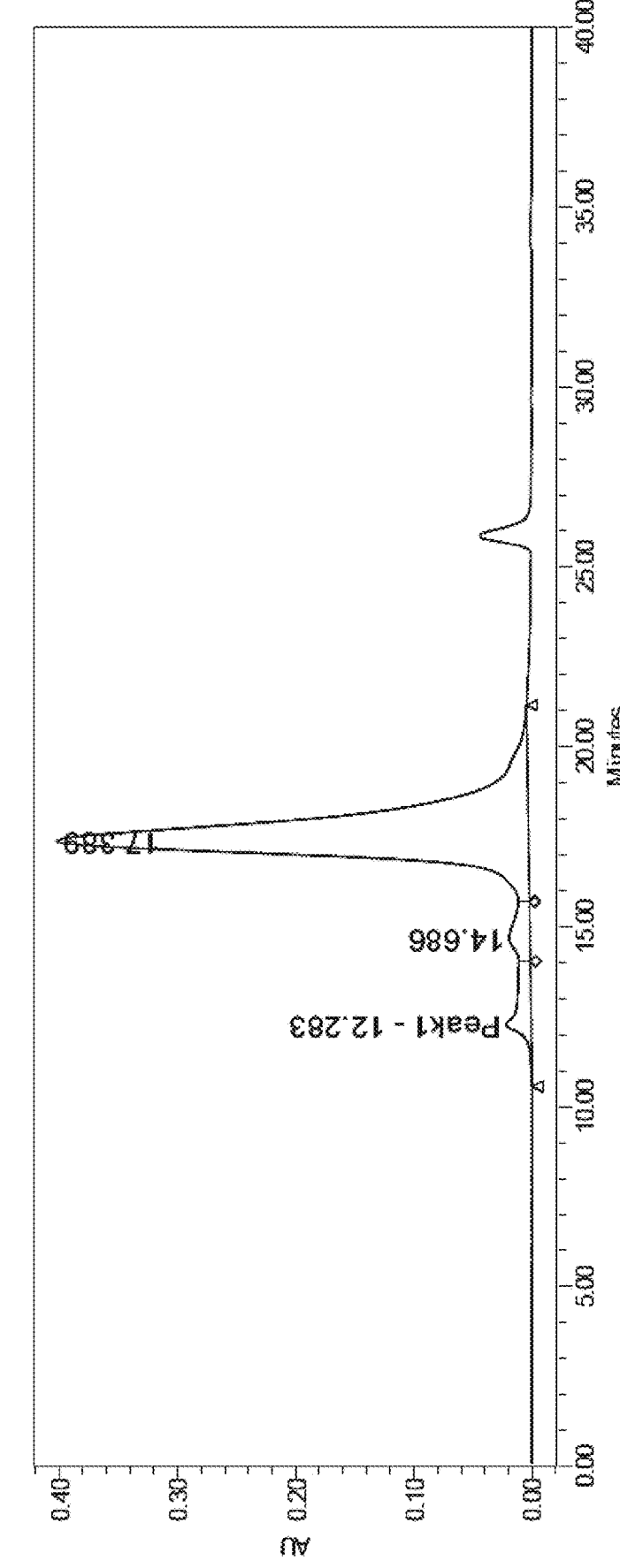
Figure 22C:
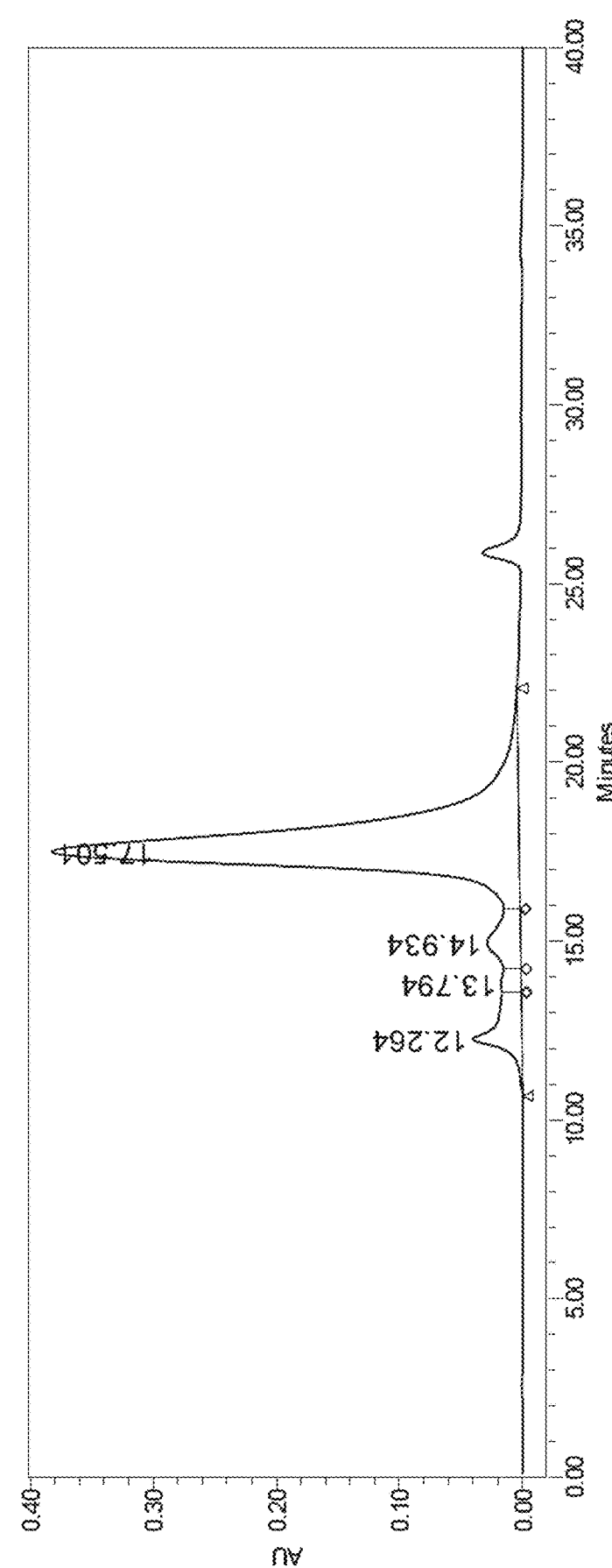
Figure 22D:
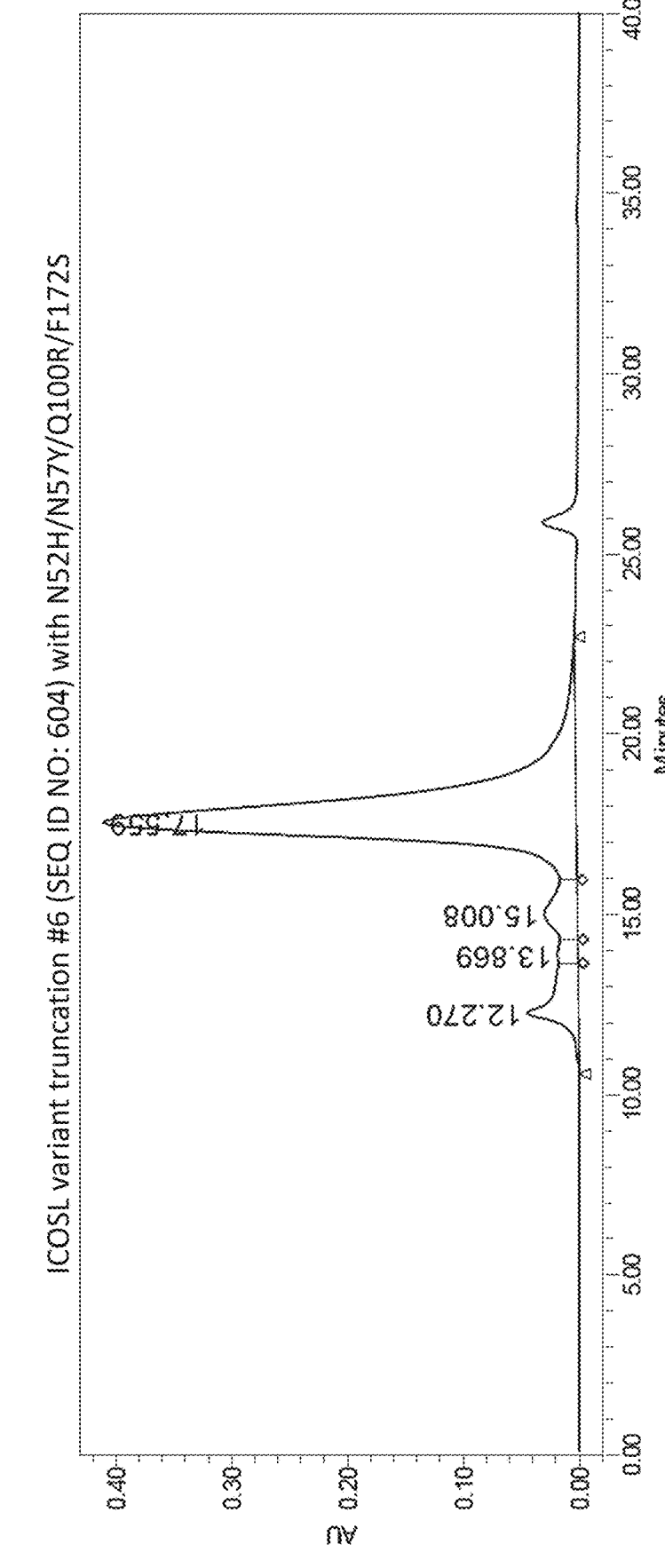
Figure 22E:
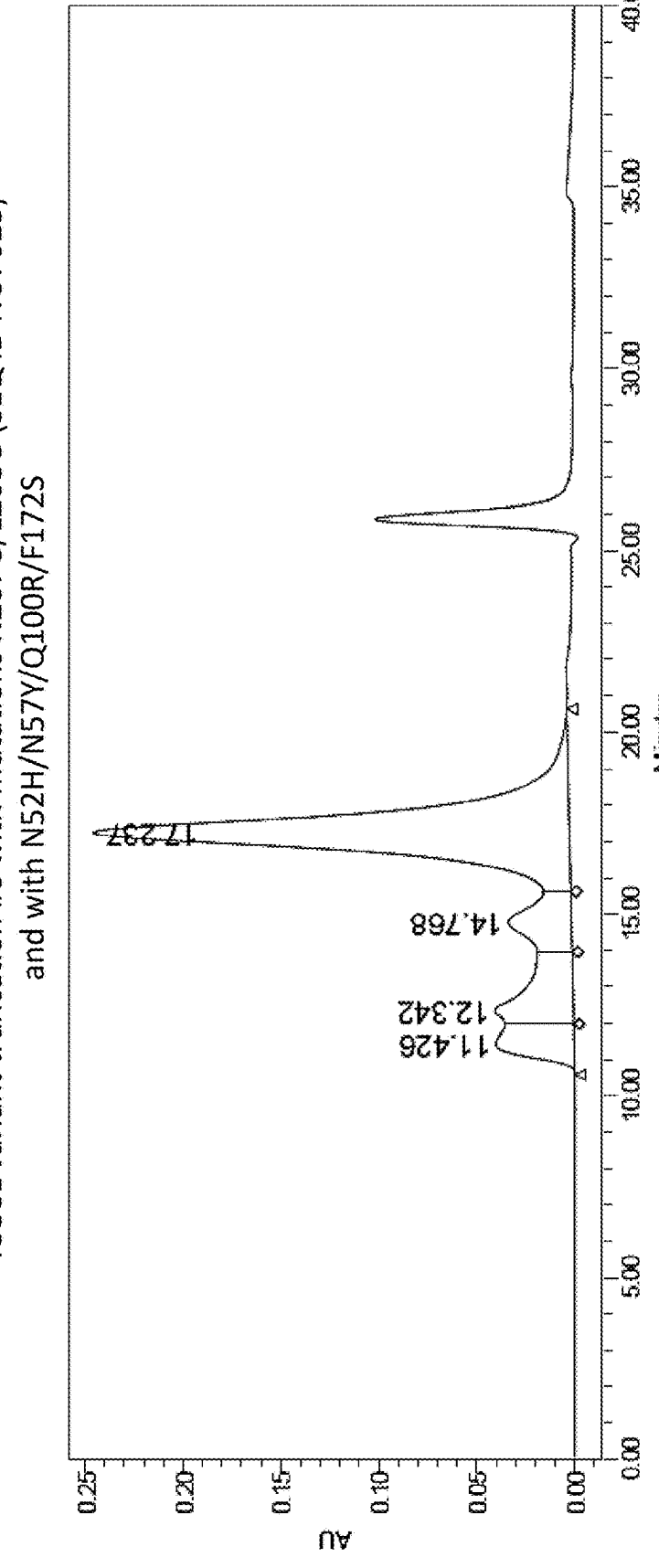
Figure 22F:
Figure 22G:
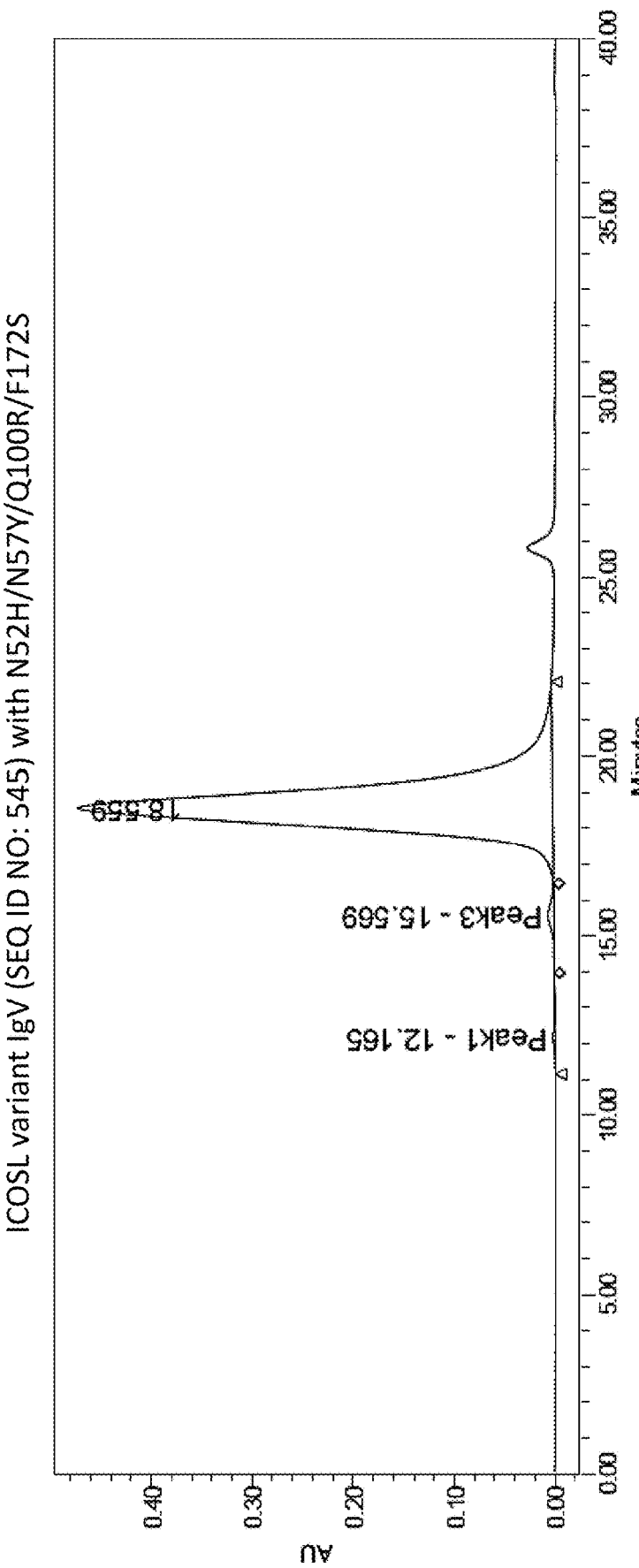

By SEC, intact protein displayed as a single peak while clipped protein displayed as multiple peaks, including lower molecular weight species. Consistent with the SDS-PAGE results described in Example 26, proteolysis as assessed by SEC was observed when variant ICOSL ECD Fc-fusion protein was expressed in ExpiCHO-S derived cells, as indicated by the multiple peaks shown in FIG. 22A. As shown in FIGS. 22B-22G, single peaks were observed by SEC analysis of the variant ICOSL Fc fusion proteins generated using modified reference ICOSL polypeptides in which the putative ECD protease cleavage site was removed or mutated, indicating reduced cleavage of the proteins occurred. In one purification lot, however, lower molecular weight species were observed by SEC analysis of the variant ICOSL Fc fusion protein generated using the reference ICOSL polypeptide set forth in SEQ ID NO: 604 (Trunc. #5), although it was not clear the reason for the presence of these species in this lot. As shown in FIG. 22G, the generation of lower molecular weight species, and hence proteolysis, also was not observed by SEC analysis of the variant ICOSL Fc-fusion proteins generated using the ICOSL IgV alone reference sequence.

B. Binding and Activity

Binding and activity of protein produced and purified following transfection of DNA constructs encoding the variant ICOSL Fc-fusion immunomodulatory proteins in various reference sequences described above in CHO cells was compared. In some cases, purified clones as assessed below were later found to contain additional mutations beyond those described above, which were not believed to impact the immunomodulatory activity of the tested proteins.

The resulting purified variant ICOSL Fc-fusion immunomodulatory proteins were assessed for binding to cognate binding partners and for modulation of T cell activity using a mixed lymphocyte reaction (MLR) substantially as described above. Table 30C indicates amino acid substitutions in the ICOSL reference sequence as designated by amino acid position number corresponding to amino acid positions in the respective reference (e.g., unmodified) ICOSL extracellular domain (ECD) sequence set forth in SEQ ID NO: 32, and sets forth the SEQ ID NO identifier for each ICOSL reference sequence. As shown, the binding and MLR antagonist activity was generally similar for all tested formats.

TABLE 30C

Molecule sequences, binding data, and costimulatory
bioactivity data of variant ICOSL molecules

| Description | Reference Sequence SEQ ID NO | Binding | | | MLR IFN- |
|---|---|---|---|---|---|
| | | CD28 MFI (ΔWT) | CTLA-4 MFI (ΔWT) | ICOS MFI (ΔWT) | gamma pg/mL (ΔWT) |
| ICOSL ECD Truncation #7 with N52H/N57Y/Q100R/F172S and F83S | 605 | 88329 (51.1) | 206566 (27.3) | 106493 (1.1) | 12 (0.02) |
| ICOSL ECD Truncation #6 with N52H/N57Y/Q100R/F172S | 604 | 91273 (52.8) | 239746 (31.6) | 90074 (0.9) | 14 (0.02) |
| ICOSL ECD Truncation #4 with | 602 | 80555 | 320229 | 107957 | 9 |

TABLE 30C-continued

| | | Binding | | | MLR IFN- |
|---|---|---|---|---|---|
| Description | Reference Sequence SEQ ID NO | CD28 MFI (ΔWT) | CTLA-4 MFI (ΔWT) | ICOS MFI (ΔWT) | gamma pg/mL (ΔWT) |
| N52H/N57Y/Q100R/F172S and E200G | | (46.6) | (42.3) | (1.1) | (0.01) |
| ICOSL ECD Truncation #4 with N52H/N57Y/Q100R/F172S | 602 | 68599 (39.7) | 377254 (49.8) | 132880 (1.3) | 2 (0.00) |
| ICOSL ECD Truncation #8 with N207G/L208G and N52H/N57Y/Q100R/F172S | 606 | 107837 (62.4) | 308427 (40.7) | 132654 (1.3) | 8 (0.01) |
| ICOSL IgV with N52H/N57Y/Q100R and H48R/S54P | 545 | 75304 (43.6) | 321613 (42.4) | 143141 (1.4) | 995 (1.31) |
| ICOSL ECD with N52H/N57Y/Q100R/F172S | 32 | 110407 (63.9) | 323219 (42.6) | 136060 (1.4) | 0 (0.00) |
| ICOSL ECD Truncation #7 with N52H/N57Y/Q100R/C198R and E90K/E111G | 605 | 38876 (22.5) | 83695 (11.0) | 54596 (0.5) | 761 (1.00) |
| ICOSL ECD Truncation #6 with N52H/N57Y/Q100R/C198R | 604 | 84566 (49.0) | 236011 (31.1) | 91357 (0.9) | 7 (0.01) |
| ICOSL ECD Truncation #5 with N52H/N57Y/Q100R/C198R | 603 | 86289 (50.0) | 216071 (28.5) | 110188 (1.1) | 9 (0.01) |
| ICOSL ECD Truncation #8 with N207G/L208G and N52H/N57Y/Q100R/C198R and Y151H | 606 | 94156 (54.5) | 368471 (48.6) | 142900 (1.4) | 2 (0.00) |
| ICOSL IgV with N52H/N57Y/Q100R | 545 | 84594 (49.0) | 204840 (27.0) | 117707 (1.2) | 0 (0.00) |
| ICOSL ECD with N52H/N57Y/Q100R/C198R | 32 | 59179 (34.3) | 132894 (17.5) | 138555 (1.4) | 0 (0.00) |
| Wildtype ICOSL ECD | 32 | 1727 (1.0) | 7579 (1.0) | 100466 (1.0) | 757 (1.00) |

C. Binding and Activity of Proteins Expressed in 293 (Expi293) or CHO cells

The variant ICOSL Fc fusion proteins, generated based on ICOSL reference sequences described above, were assessed for binding and activity following expression in 293 (Expi293) or CHO cells. In addition, a DNA construct encoding exemplary IgSF domain ICOSL variants N52H/N57Y/Q100R/C198R or N52H/Q100R, in exemplary ICOSL reference sequences as set forth in Table 30D, also were linked to an inert Fc containing mutations C220S/L234A/L235E/G237A by EU numbering set forth in SEQ ID NO: 477, and were produced and purified following transfection of 293 or CHO cells with the DNA constructs. In addition, an exemplary variant immunomodulatory protein was generated as a monomer in which cells were transfected with a DNA construct encoding the variant in the variant ICOSL ECD reference sequence but without fusion with an Fc sequence.

The resulting purified variant ICOSL Fc-fusion proteins or variant ICOSL monomer were assessed for binding to cognate binding partners and for modulation of T cell activity using a mixed lymphocyte reaction (MLR) substantially as described above. Table 30D indicates amino acid substitutions in the reference sequence of the variant ICOSL as designated by amino acid position number corresponding to amino acid positions in the respective reference (e.g., unmodified) ICOSL extracellular domain (ECD) sequence set forth in SEQ ID NO:32, and sets forth the SEQ ID NO identifier for each reference ICOSL sequence. Column 3 indicates the cell type (ExpiCHO-S or Expi293) used to produce the ICOSL protein. As shown in Table 30D, the results indicate substantially similar binding and activity, whether or not the variant ICOSL immunomodulatory protein was produced in CHO or 293 cells.

TABLE 30D

Molecule sequences, binding data, and costimulatory bioactivity data of variant ICOSL ECD Fc-fusion molecules produced using various cells

| Description | Reference Sequence SEQ ID NO | CHO or 293 Material | Binding | | | MLR |
|---|---|---|---|---|---|---|
| | | | CD28 MFI (ΔWT) | CTLA-4 MFI (ΔWT) | ICOS MFI (ΔWT) | IFN-gamma pg/mL (ΔWT) |
| ICOSL ECD with N52H/N57Y/Q100R/C198R | 32 | 293 | 13710 (3.9) | 8715 (0.7) | 16746 (1.4) | 20 (0.02) |
| ICOSL ECD with N52H/N57Y/Q100R/C198R | 32 | CHO | 12876 (3.6) | 8750 (0.7) | 7700 (0.7) | 16 (0.02) |
| ICOSCL ECD with N52H/Q100R | 32 | 293 | 11664 (3.3) | 13429 (1.1) | 10284 (0.9) | 168 (0.19) |
| ICOSCL ECD with N52H/N57Y/Q100R/F172S | 32 | 293 | 12900 (3.6) | 8179 (0.7) | 15956 (1.4) | 14 (0.02) |

TABLE 30D-continued

Molecule sequences, binding data, and costimulatory bioactivity data
of variant ICOSL ECD Fc-fusion molecules produced using various cells

| Description | Reference Sequence SEQ ID NO | CHO or 293 Material | Binding | | | MLR |
| | | | CD28 MFI (ΔWT) | CTLA-4 MFI (ΔWT) | ICOS MFI (ΔWT) | IFN-gamma pg/mL (ΔWT) |
| --- | --- | --- | --- | --- | --- | --- |
| ICOSCL ECD with N52H/N57Y/Q100R/F172S | 32 | CHO | 14437 (4.1) | 8708 (0.7) | 12610 (1.1) | 21 (0.02) |
| ICOSCL IgV with N52H/N57Y/Q100R | 545 | 293 | 16618 (4.7) | 9674 (0.8) | 9377 (0.8) | 10 (0.01) |
| ICOSCL IgV with N52H/N57Y/Q100R | 545 | CHO | 17343 (4.9) | 9039 (0.7) | 8673 (0.7) | 14 (0.01) |
| ICOSL ECD Truncation #4 with N52H/N57Y/Q100R/F172S | 602 | 293 | 14710 (4.1) | 8841 (0.7) | 6893 (0.6) | 21 (0.02) |
| ICOSL ECD Truncation #4 with N52H/N57Y/Q100R/F172S | 602 | CHO | 12743 (3.6) | 9000 (0.7) | 7606 (0.7) | 21 (0.02) |
| ICOSL ECD Truncation #7 with N52H/N57Y/Q100R/F172S | 605 | 293 | 12017 (3.4) | 9674 (0.8) | 7599 (0.7) | 15 (0.02) |
| ICOSL ECD Truncation #7 with N52H/N57Y/Q100R/F172S | 605 | CHO | 13043 (3.7) | 9039 (0.7) | 8077 (0.7) | 7 (0.01) |
| ICOSL ECD Monomer with N52H/N57Y/Q100R no Fc | 32 | 293 | 20575 (5.8) | 19978 (1.6) | 11989 (1.0) | 133 (0.15) |
| ICOSL ECD Dimer with N52H/N57Y/Q100R no Fc | 32 | 293 | 18477 (5.2) | 22361 (1.8) | 12913 (1.1) | 119 (0.13) |
| Wildtype ICOSL ECD | 32 | 293 | 3556 (1.0) | 12121 (1.0) | 11690 (1.0) | 905 (1.00) |

Example 28

Generation of NNK Variant Library of ICOSL IgSF Domain Variants and Assessment of Binding and Activity Additional variant ICOSL IgSF domain-containing molecules were generated with mutations at position 52, 57, and 100 with reference to positions set forth in SEQ ID NO:32. The variants were generated from an NNK library, where K=T or G, such that the encoding codons encode all potential amino acids, but prevent the encoding of two stop residues TAA and TGA. The NNK library DNA was introduced into yeast substantially as described in Example 2 to generate yeast libraries. The libraries were used to select yeast expressing affinity modified variants of ICOSL substantially as described in Example 3.

The selected variant ICOSL IgSF domain-containing molecules were further formatted as an Fc-fusion protein substantially as described in Example 4 except containing the generated ICOSL IgSF domain linked via a GSGGGGS linker (SEQ ID NO:635) to an inert Fc containing mutations C220S/L234A/L235E/G237A/K447del by EU numbering set forth in SEQ ID NO: 633, or an allotype thereof set forth in SEQ ID NO:637.

The variant ICOSL Fc-fusion immunomodulatory proteins were assessed in binding studies to assess binding for cognate binding partners. Expi293 cells transfected with cognate binding partners, human CD28, ICOS and CTLA4, were used as target cells in binding studies as described in Example 6. MFI of binding of 100 nM of variant ICOSL Fc fusion immunomodulatory proteins for target cells expressing each binding partner was determined and compared for binding of the corresponding reference (e.g., unmodified or wildtype) ICOSL IgV-Fc for the same target cell. The costimulatory bioactivity of generated ICOSL variant Fc-fusion molecules was also assessed in anti-CD3 (10 mM) coimmobilization assays as described in Example 6. Modulation of T cell activity by the variant ICOSL Fc-fusion immunomodulatory proteins was also determined using a mixed lymphocyte reaction (MLR) with 1 nM ICOSL-Fc substantially as described in Example 6. IFN-gamma secretion from triplicate wells was determined.

Results for binding and functional activity, based on costimulatory bioactivity or activity in an MLR assay, for exemplary variant ICOSL IgV-Fc fusion molecules are shown in Table 31. The Table below indicates amino acid substitutions in the variant ICOSL as designated by amino acid position number corresponding to amino acid positions in the respective reference (e.g., unmodified) ICOSL extracellular domain (ECD) sequence set forth in SEQ ID NO:32. Column 2 sets forth the SEQ ID NO identifier for each variant IgV domain contained in the variant IgV-Fc fusion molecule. As shown, the ICOSL IgSF (e.g. IgV) domain variants generated with the various combinations of specific mutations at positions 52, 57, and 100, exhibited altered binding for at least one, and in some cases more than one, cognate binding partner. The last two columns of the Table also depict the functional activity of the variant Fc-fusion molecules to modulate the activity of T cells based on the calculated levels of IFN-gamma in culture supernatants (pg/mL) generated either i) with the indicated variant IgV-Fc fusion soluble molecule coimmoblized with anti-CD3 or ii) with the indicated variant IgV-Fc fusion molecule in an MLR assay. The Table also depicts the ratio of IFN-gamma produced by each variant ECD-Fc compared to the corresponding reference (e.g., unmodified or wild-type) ECD-Fc in both functional assays. Variant Fc-fusion proteins also exhibited altered immunological activity. Costimulatory signaling of some variant molecules was substantially greater compared to wild-type ICOSL. Certain variants exhibited substantial inhibition of IFN-gamma with very low to no detectable IFN-gamma produced in the cultures in the MLR assay.

TABLE 31

Additional exemplary variant ICOSL polypeptides

| Mutations | SEQ ID NO (IgV) | Binding CD28 MFI (ΔWT) | CTLA-4 MFI (ΔWT) | ICOS MFI (ΔWT) | Costim IFN-gamma pg/mL (ΔWT) | MLR IFN-gamma pg/mL (ΔWT) |
|---|---|---|---|---|---|---|
| N52A/N57F/Q100S | 734 | 156589 (7.00) | 255078 (0.77) | 241891 (1.14) | 1119 (0.68) | 0 (0.00) |
| N52A/N57H/Q100S | 735 | 159363 (7.10) | 321437 (0.97) | 304600 (1.44) | 2972 (1.80) | 0 (0.00) |
| N52A/N57Y/Q100A | 736 | 147258 (6.60) | 319745 (0.97) | 260713 (1.23) | 2978 (1.81) | 0 (0.00) |
| N52D/N57A/Q100A | 737 | 137882 (6.20) | 340186 (1.03) | 248975 (1.17) | 477 (0.29) | 134 (0.60) |
| N52D/Q100S | 738 | 95731 (4.30) | 332743 (1.01) | 275097 (1.30) | 957 (0.58) | 110 (0.49) |
| N52G/Q100A | 739 | 98652 (4.40) | 97118 (0.29) | 303229 (1.43) | 296 (0.18) | 96 (0.43) |
| N52H/Q100A | 740 | 145762 (6.50) | 361334 (1.09) | 213008 (1.01) | 784 (0.48) | 37 (0.17) |
| N52M/N57H/Q100S | 741 | 114743 (5.10) | 463404 (1.40) | 265637 (1.25) | 1333 (0.81) | 0 (0.00) |
| N52M/N57W/Q100P | 742 | 168057 (7.50) | 342659 (1.04) | 322277 (1.52) | 1865 (1.13) | 0 (0.00) |
| N52Q/N57F | 743 | 131301 (5.90) | 366714 (1.11) | 192206 (0.91) | 1403 (0.85) | 0 (0.00) |
| N52Q/N57S/Q100A | 744 | 91306 (4.10) | 315021 (0.95) | 262735 (1.24) | 290 (0.18) | 123 (0.55) |
| N52R/N57L/Q100A | 745 | 118803 (5.30) | 402961 (1.22) | 307965 (1.45) | 709 (0.43) | 0 (0.00) |
| N52R/N57Y/Q100P | 746 | 133283 (6.00) | 502179 (1.52) | 251264 (1.19) | 7380 (4.48) | 0 (0.00) |
| N52R/N57Y/Q100S | 747 | 133454 (6.00) | 504037 (1.53) | 229271 (1.08) | 5841 (3.54) | 0 (0.00) |
| N52S/N57A/Q100A | 748 | 98153 (4.40) | 233184 (0.71) | 181297 (0.86) | 442 (0.27) | 52 (0.23) |
| N52S/N57H/Q100E | 749 | 116821 (5.20) | 302383 (0.92) | 257518 (1.22) | 8412 (5.11) | 132 (0.59) |
| N52S/N57L/Q100S | 750 | 108133 (4.80) | 197064 (0.60) | 268940 (1.27) | 3120 (1.89) | 0 (0.00) |
| N52S/N57M/Q100S | 751 | 133604 (6.00) | 227615 (0.69) | 312088 (1.47) | 349 (0.21) | 199 (0.89) |
| N52S/N57Y/Q100S | 752 | 161330 (7.20) | 204577 (0.62) | 223684 (1.06) | 7411 (4.50) | 0 (0.00) |
| N52S/N57Y/Q100M | 753 | 156869 (7.00) | 395350 (1.20) | 302569 (1.43) | 2954 (1.79) | 0 (0.00) |
| N52S/N57Y/Q100V | 754 | 126281 (5.70) | 304795 (0.92) | 218925 (1.03) | 1304 (0.79) | 0 (0.00) |
| N52T/N57H/Q100S | 755 | 143441 (6.40) | 377542 (1.14) | 258634 (1.22) | 6312 (3.83) | 0 (0.00) |
| N52T/N57H/Q100A | 756 | 112637 (5.00) | 350453 (1.06) | 220339 (1.04) | 2874 (1.74) | 0 (0.00) |
| N52T/N57Y/Q100A | 757 | 161333 (7.20) | 340845 (1.03) | 239136 (1.13) | 442 (0.27) | 0 (0.00) |
| N52V/N57L/Q100A | 758 | 132144 (5.90) | 252148 (0.76) | 181344 (0.86) | 518 (0.31) | 159 (0.71) |
| N52H/N57Y/Q100K | 759 | 141720 (6.30) | 393476 (1.19) | 214270 (1.01) | 12919 (7.84) | 0 (0.00) |
| N52K/N57Y/Q100R | 760 | 140729 (6.30) | 233283 (0.71) | 198941 (0.94) | 12515 (7.60) | 0 (0.00) |
| N52L/N57H/Q100R | 761 | 140807 (6.30) | 352518 (1.07) | 250052 (1.18) | 12544 (7.61) | 0 (0.00) |
| N52R/N57F/Q100N | 762 | 161029 (7.20) | 233254 (0.71) | 252904 (1.19) | 448 (0.27) | 106 (0.47) |
| N52R/N57F/Q100P | 763 | 153850 (6.90) | 503696 (1.52) | 296566 (1.40) | 1718 (1.04) | 0 (0.00) |
| N52R/N57F/Q100R | 764 | 185231 (8.30) | 463873 (1.40) | 234248 (1.11) | 11402 (6.92) | 0 (0.00) |
| N52R/N57F/Q100T | 765 | 126875 (5.70) | 357505 (1.08) | 270134 (1.27) | 272 (0.17) | 0 (0.00) |
| N52R/N57H/Q100K | 766 | — | — | — | — | — |
| N52R/N57L/Q100S | 767 | 111704 (5.00) | 289326 (0.88) | 230617 (1.09) | 1292 (0.78) | 0 (0.00) |
| N52R/N57W/Q100K | 768 | 130875 (5.90) | 477268 (1.44) | 349316 (1.65) | 10056 (6.10) | 0 (0.00) |
| N52R/N57W | 769 | 136967 (6.10) | 318199 (0.96) | 298850 (1.41) | 12652 (7.68) | 0 (0.00) |
| N52R/N57Y/Q100R | 770 | 3285 (0.10) | 4266 (0.01) | 6104 (0.03) | 349 (0.21) | 347 (1.54) |
| N52C/N57E/Q100S | 771 | 13361 (0.60) | 10616 (0.03) | 125274 (0.59) | 296 (0.18) | 372 (1.65) |
| N52G/N57P/Q100D | 772 | 5715 (0.30) | 10181 (0.03) | 274629 (1.30) | 254 (0.15) | 343 (1.53) |
| N52G/N57V/Q100G | 773 | 23658 (1.10) | 14727 (0.04) | 260057 (1.23) | 325 (0.20) | 245 (1.09) |
| N52G/N57V | 774 | 69117 (3.10) | 52498 (0.16) | 332068 (1.57) | 847 (0.51) | 327 (1.45) |
| N52L/N57V | 775 | 54775 (2.50) | 150970 (0.46) | 256730 (1.21) | 986 (0.60) | 270 (1.20) |
| N52P/N57P | 776 | 21008 (0.90) | 27043 (0.08) | 222171 (1.05) | 260 (0.16) | 478 (2.13) |
| N52P/N57S/Q100G | 777 | 6803 (0.30) | 5054 (0.02) | 143255 (0.68) | 110 (0.07) | 481 (2.14) |
| N52S/N57L/Q100G | 778 | 71895 (3.20) | 79432 (0.24) | 275602 (1.30) | 726 (0.44) | 513 (2.28) |
| N52T/N57K/Q100P | 779 | 88653 (4.00) | 78299 (0.24) | 312905 (1.48) | 116 (0.07) | 395 (1.76) |
| N52V/N57T/Q100L | 780 | 6205 (0.30) | 11458 (0.03) | 29167 (0.14) | 85 (0.05) | 562 (2.50) |
| N57Q/Q100P | 781 | 15195 (0.70) | 69058 (0.21) | 204533 (0.97) | 159 (0.10) | 432 (1.92) |
| WT ICOSL | 545 | 22340 (1.00) | 330437 (1.00) | 211945 (1.00) | 1648 (1.00) | 225 (1.00) |
| Full length N52H/N57Y/Q100R/F172S | 291 | 138141 (6.20) | 605794 (1.83) | 237653 (1.12) | — | 0 (0.00) |
| N52H/N57Y/Q100R | 565 | 142274 (6.40) | 817010 (2.47) | 199528 (0.94) | — | 0 (0.00) |
| N52H/N57Y/Q100R | 283 | — | — | — | 10362 (6.29) | — |

Example 29

Assessment of K562 Cells Expressing a Transmembrane Immunomodulatory Protein (TIP)

K562 cells were engineered to express a Transmembrane Immunomodulatory Protein (TIP) that contained the ECD of the vIgD ICOSL domains fused to the native transmembrane and intracellular domain of WT human ICOSL set forth in SEQ ID NO: 5. The exemplary variant ICOSL-TIP had an affinity-modified IgSF domain containing amino acid mutations corresponding to N52H/N57Y/Q100P (SEQ ID NO: 288), N52H/N57Y/Q100R (SEQ ID NO: 283), or E16V/N52H/N57Y/Q100R/V110D/H115R/Y152C/K156M/C198R (SEQ ID NO: 300) with reference to positions in the ICOSL extracellular domain set forth in SEQ ID NO:32.

K562 cells (ATCC) were labeled with CFSE to better distinguish them from T cells in co-culture assays. Purified primary human T cells were labeled with Cell Trace Far Red (both from Thermo-Fisher) and co-plated in a 96 well round bottom tissue culture plates with anti-CD3 antibody. To provide a TCR signal for T cells, anti-CD3 antibody was included in soluble format over a range of concentrations that allowed K562 presentation of this stimulating antibody through the Fc-receptor CD32 expressed by the cells. Cells were incubated 72 hours and proliferation of CD4+ (FIG. 23A) and CD8+ (FIG. 23B) was monitored and reported as percent of cells divided versus anti-CD3 concentration. Each point represents the mean of triplicate weels with error bars showing standard deviation.

Wild type K562 cells stimulated T cells to proliferate when co-incubated with soluble anti-CD3 antibody in a dose-dependent manner, whereas K562 cells in the absence of anti-CD3 did not. As shown in FIGS. 23A and 23B, expression of WT ICOSL TIP on the surface enhanced responses, but the effects were greater when K562 cells expressed the variant ICOSL TIPs, indicating that these molecules expressed on the surface of cells provided superior costimulation for T cells.

Example 30

Assessment of Binding and Costimulatory Function of Fusion Molecules with HER2-Targeting Antibody An exemplary variant ICOSL ECD, containing mutations N52H/N57Y/Q100R was fused to either the N- or C-terminal ends of the heavy or light chain of the exemplary anti-HER2 antibody, trastuzumab, as depicted in the various configurations shown in FIG. 24A-24F. VmAbs DNA encoding each of the constructs diagrammed in FIG. 24A-24F was transfected into HEK-293 cells and secreted proteins were purified by Protein A and size exclusion chromatography. The resultant V-mAb proteins were next assessed for retention of appropriate binding properties. HEK-293 cells were transiently transfected with HER2, CD28, or ICOS expression vectors and each transfectant was then incubated with individual V-mAb proteins plus a secondary antibody for detection of bound reagents. As shown in FIG. 24A, HER2 binding was retained by all V-mAbs although the magnitude of the binding was reduced somewhat. Moreover, binding of V-mAbs to CD28 transfected cells was largely intact, although a few forms showed some reduction in binding (FIG. 24A). This data indicated that the ICOSL variants fused to antibody heavy and/or light chains to form fusion proteins largely retained counter-structure and antibody binding activity.

To test whether VmAbs could drive target-specific costimulation of T cells, a transfected cell system including a T cell reporter line for measuring costimulation was used. Jurkat cells with an IL-2 promoter luciferase reporter were used to evaluate costimulatory function. To stimulate the cells, K562 cells were engineered for use as an artificial antigen presenting cell. Specifically, K562 cells were transduced with a lentivirus encoding a single-chain Fv version of the anti-CD3 antibody OKT3 with or without transduction with a separate lentivirus directing HER2 expression. K562 cells displaying cell surface anti-CD3 single chain Fv (OKT3) with or without surface HER2 expression were plated in Jurkat Assay Buffer (RPMI1640+5% FBS) at $2\times10^4$ cell/well. Target cells were incubated with V-mAbs titrated from 20,000 pM to 6 pM or control proteins for 20 minutes at room temperature. Jurkat effector cells expressing an IL-2-luciferase reporter gene (Promega) were added at $1\times10^5$ cell/well to bring the final volume/well to 100 µl. Target and Jurkat cells were incubated for 5 hours at 37° C. Plates were removed from the incubator and acclimated to room temperature for 15 minutes. 100 µL of cell lysis and luciferase substrate solution (BioGlo luciferase reagent, Promega) was added to each well and the plates were incubated on an orbital shaker for 10 minutes. Luminescence was measured with a 1 second per well integration time using a Cytation 3 imaging reader (BioTek Instruments). Relative luminescence values (RLU) were determined for each test sample and reported.

Figure 24B:
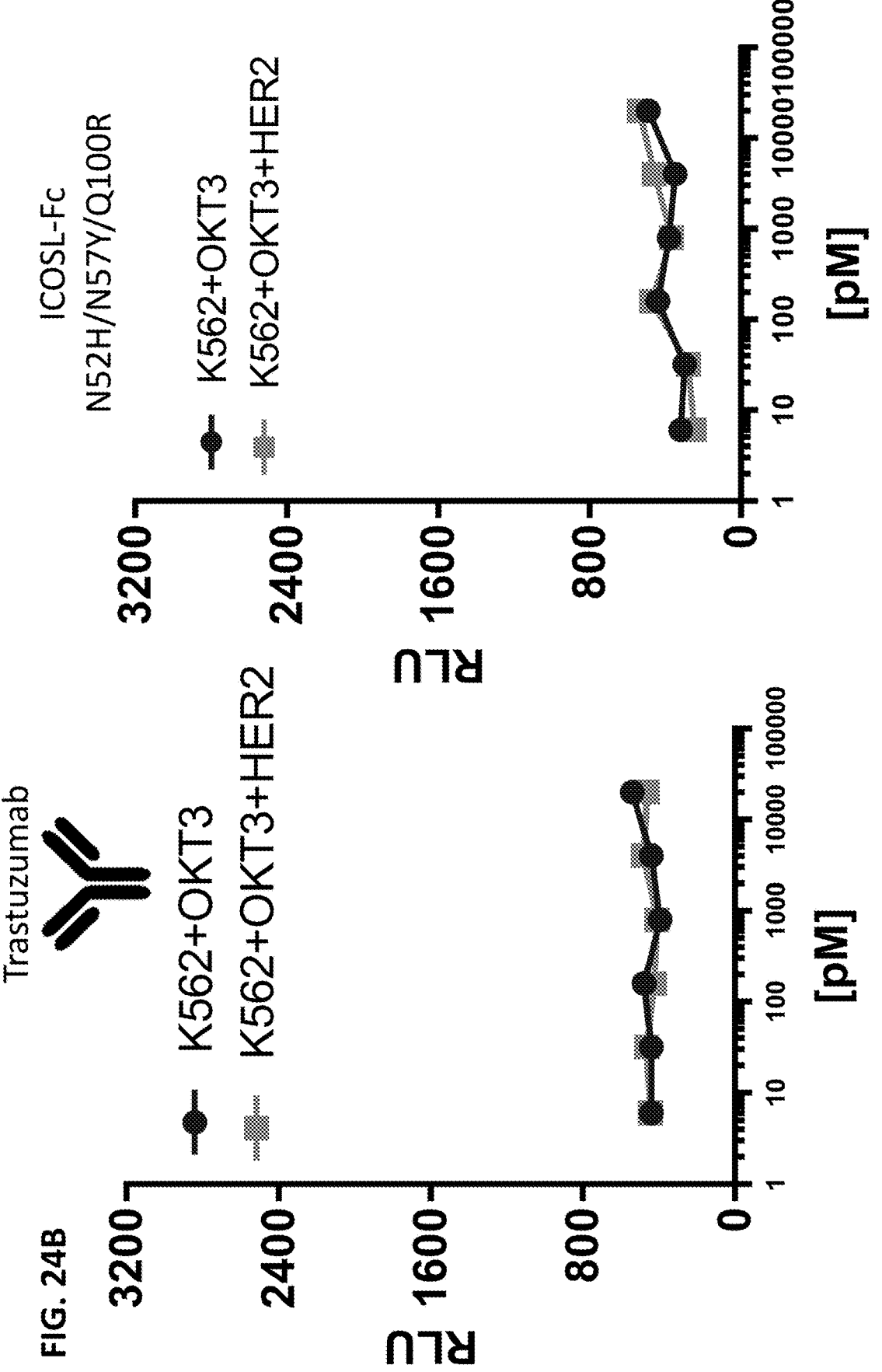
Figure 24C:
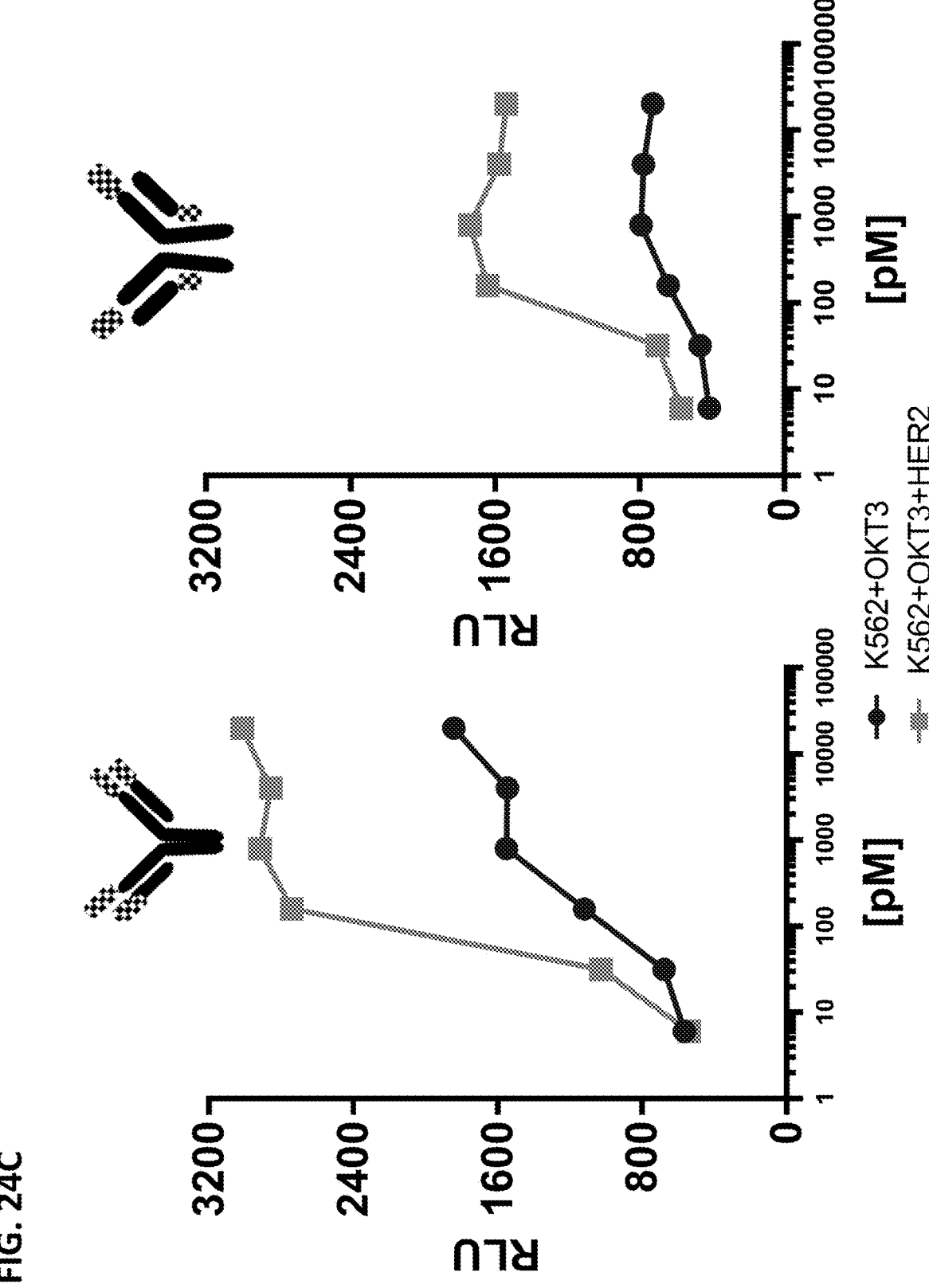
Figure 24D:
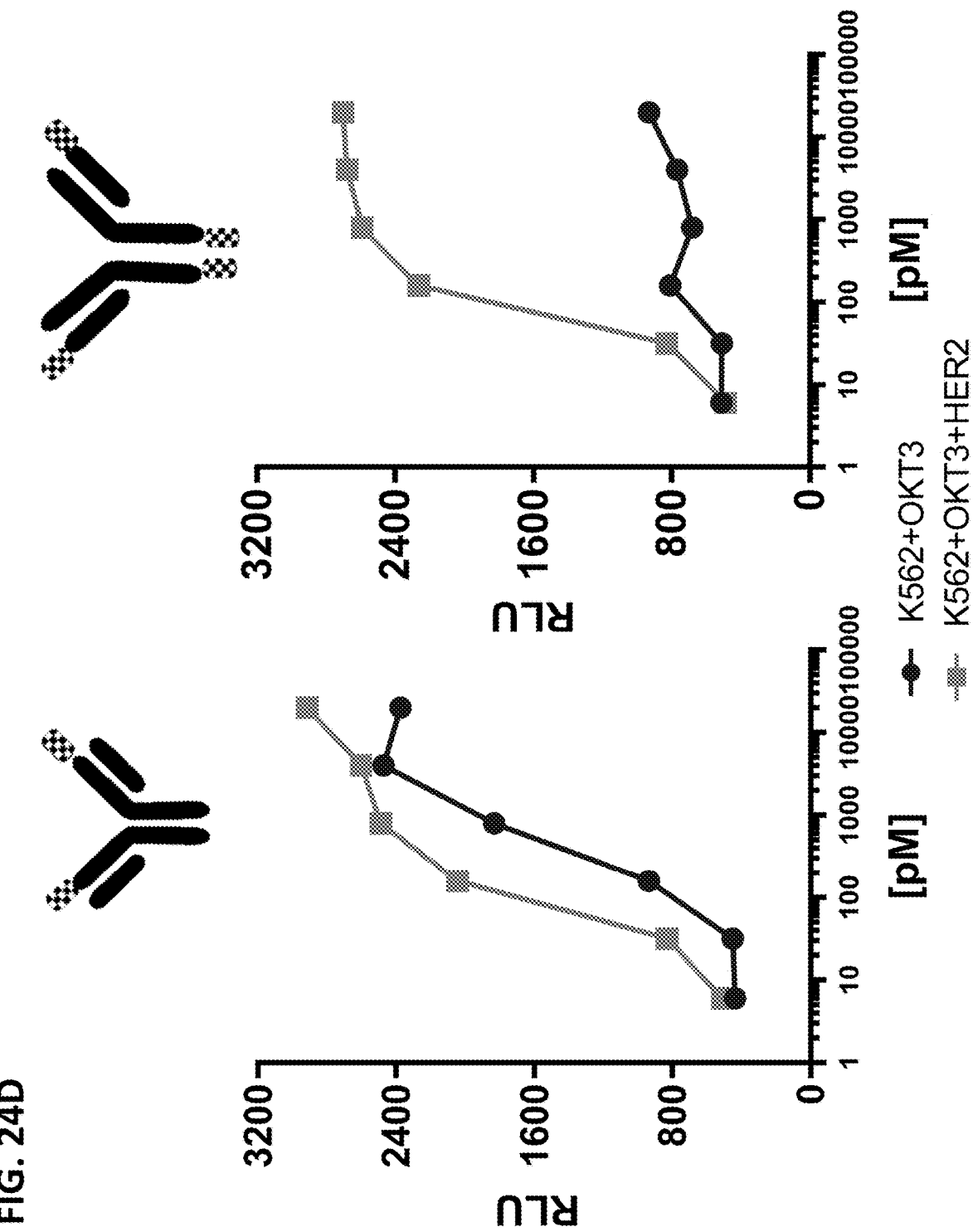
Figure 24E:
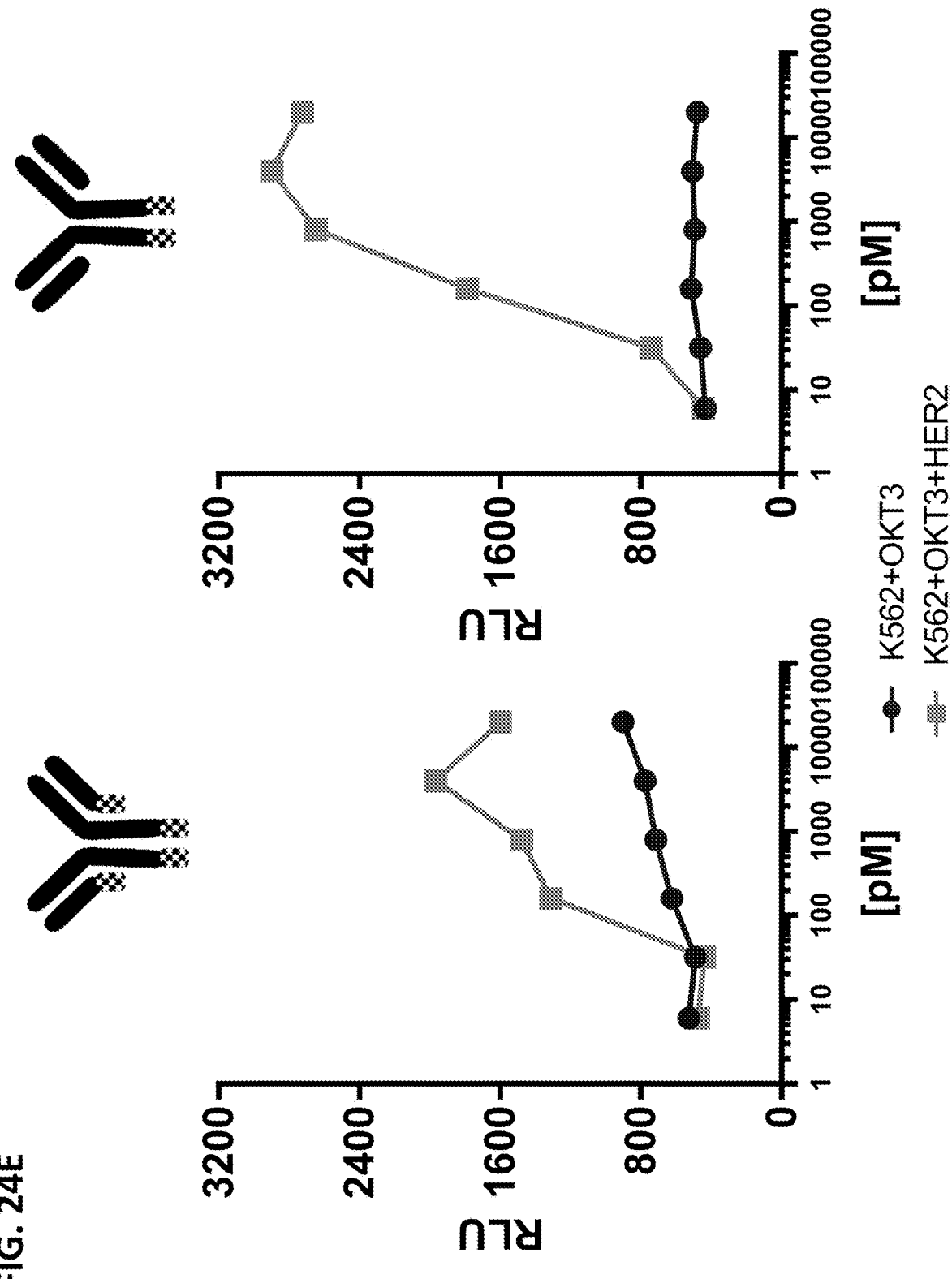
Figure 24F:
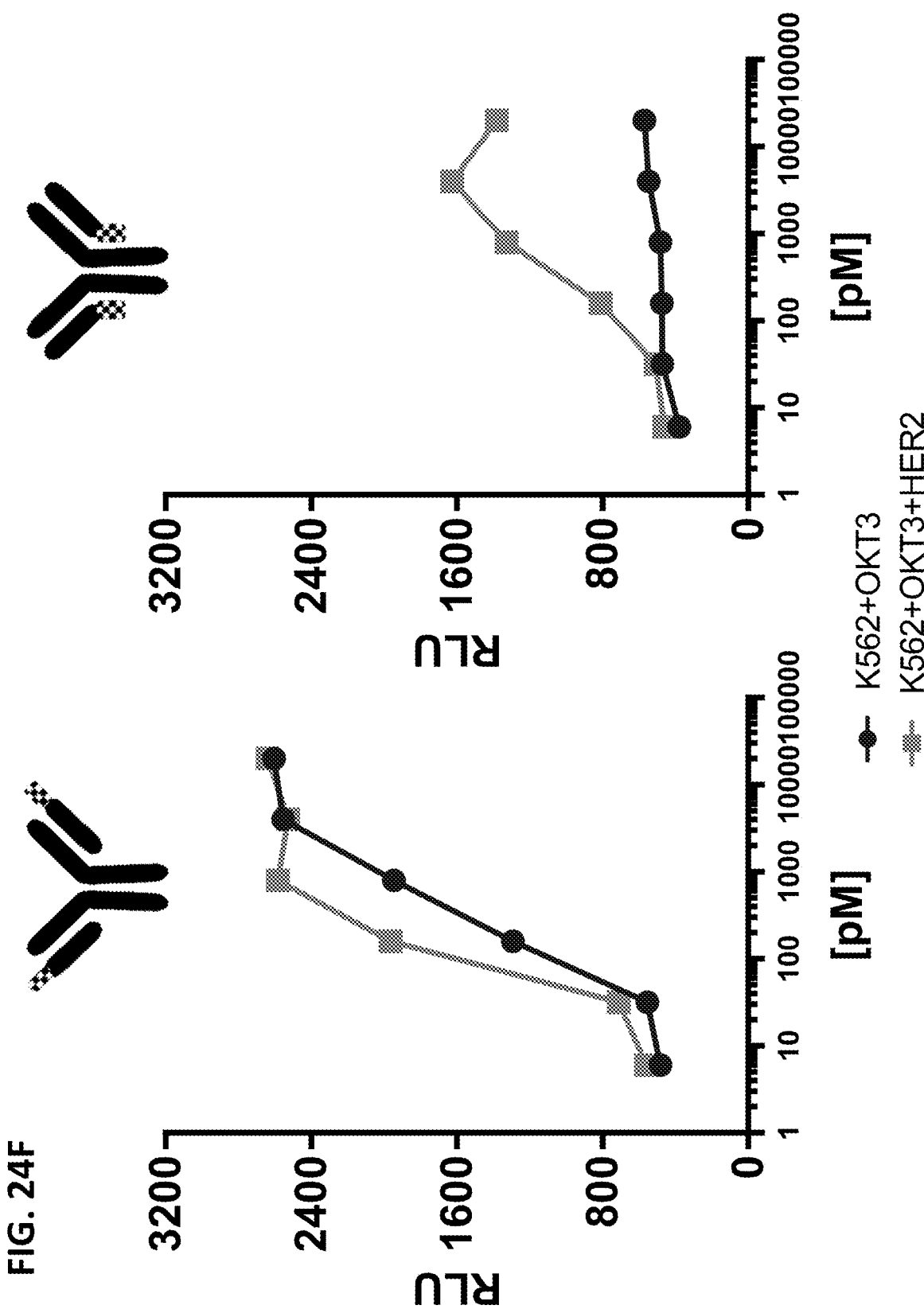

As shown in FIG. 24B, inclusion of native trastuzumab had no effect on luciferase induction. Similarly, inclusion of the variant ICOSL-Fc protein N52H/N57Y/Q100R (not fused to trastuzumab) did not affect responses (FIG. 24B). However, inclusion of multiple V-mAbs provided a significant costimulatory signal in the presence of HER2+ K562/OKT3 cells that was much more robust than with K562/OKT3 that lacked HER2 expression (FIG. 24C-24F). In some cases, signal was induced in K562/OKT3 cells lacking HER2, but this was most likely due to the Fc domain of the V-mAbs allowing CD32-mediated presentation of the V-mAbs. The results indicate that fusing a variant ICOSL polypeptide to an antibody can be used to deliver a localized T cell costimulatory signal.

Example 31

Generation of Stacked Molecules Containing ICOSL and NKp30 Affinity-Modified Domains This Example describes immunomodulatory proteins that were generated as multi-domain stack constructs containing an affinity modified IgV domain from identified variant ICOSL polypeptides and identified variant NKp30 polypeptides described above. Specifically, an exemplary variant ICOSL IgV (N52D as set forth in SEQ ID NO:548; N52H/Q100R as set forth in SEQ ID NO:567; N52H/N57Y/Q100R as set forth in SEQ ID NO: 565; N52L/N57H/Q100R as set forth in SEQ ID NO: 761), and the exemplary variant NKp30 IgV molecule L30V/A60V/S64P/S86G (SEQ ID NO: 504) were linked together and fused to an inert Fc (containing mutations L234A, L235E and L235E in a human IgG1 Fc, e.g. set forth in SEQ ID NO: 637) in various configurations. Homodimeric stack constructs were generated containing identical Fc subunits in which the variant ICOSL IgV and variant NKp30 IgV were variously linked to the N- or C-terminus of the Fc region via a GSGGGS (SEQ ID NO: 635) and/or 3×GGGGS (SEQ ID NO: 228) peptide linker. Other linkers and Fc regions also are suitable for generation of stack molecules. Exemplary generated stacks are set forth below.

Nucleic acid molecule encoding the immunomodulatory proteins also contained residues encoding the exemplary signal peptide MGSTAILALLLAVLQGVSA (set forth in SEQ ID NO: 225). Expression constructs encoding Fc fusion proteins of interest were transiently expressed in Expi293 HEK293 cells from Invitrogen using the manufacturer's commercial Expifectamine reagents and media. Supernatants were harvested and protein was captured and eluted from a Protein A column using an AKTA protein purification system.

The encoding nucleic acid molecule was designed to produce homodimeric stacks in various configurations of sequences in the order shown in Table 32.

TABLE 32

Description of ICOSL/NKp30 Immunomodulatory Proteins

| Stack | Protein SEQ ID NO (DNA SEQ ID NO) | Description |
|---|---|---|
| ICOSL/NKp3Q Stack 1 | 912 (911) | ICOSL variant (SEQ ID NO: 548) - 3x GGGGS (SEQ ID NO: 228) - NKp30 variant (SEQ ID NO: 504) - GSGGGGS (SEQ ID NO: 635) - Fc (SEQ ID NO: 637) |
| ICOSL/NKp30 Stack 2 | 914 (913) | ICOSL variant (SEQ ID NO: 548) - 3x GGGGS (SEQ ID NO: 228) - NKp30 variant (SEQ ID NO: 504) - 3x GGGGS (SEQ ID NO: 228) - NKp30 variant (SEQ ID NO: 504) - GSGGGGS (SEQ ID NO: 635) - Fc (SEQ ID NO: 637) |
| ICOSL/NKp30 Stack 3 | 916 (915) | ICOSL variant (SEQ ID NO: 567) - 3x GGGGS (SEQ ID NO: 228) - NKp30 variant (SEQ ID NO: 504) - GSGGGGS (SEQ ID NO: 635) - Fc (SEQ ID NO: 637) |
| ICOSL/NKp30 Stack 4 | 918 (917) | ICOSL variant (SEQ ID NO: 567) - 3x GGGGS (SEQ ID NO: 228) - NKp30 variant (SEQ ID NO: 504) - 3x GGGGS (SEQ ID NO: 228) - NKp30 variant (SEQ ID NO: 504) - GSGGGGS (SEQ ID NO: 635) - Fc (SEQ ID NO: 637) |
| ICOSL/NKp30 Stack 5 | 920 (919) | ICOSL variant (SEQ ID NO: 565) - 3x GGGGS (SEQ ID NO: 228) - NKp30 variant (SEQ ID NO: 504) - GSGGGGS (SEQ ID NO: 635) - Fc (SEQ ID NO: 637) |
| ICOSL/NKp30 Stack 6 | 922 (921) | ICOSL variant (SEQ ID NO: 565) - 3x GGGGS (SEQ ID NO: 228) - NKp30 variant (SEQ ID NO: 504) - 3x GGGGS (SEQ ID NO: 228) - NKp30 variant (SEQ ID NO: 504) - GSGGGGS (SEQ ID NO: 635) - Fc (SEQ ID NO: 637) |
| ICOSL/NKp30 Stack 7 | 924 (923) | ICOSL variant (SEQ ID NO: 761) - 3x GGGGS (SEQ ID NO: 228) - NKp30 variant (SEQ ID NO: 504) - GSGGGGS (SEQ ID NO: 635) - Fc (SEQ ID NO: 637) |
| ICOSL/NKp30 Stack 8 | 926 (925) | ICOSL variant (SEQ ID NO: 761) - 3x GGGGS (SEQ ID NO: 228) - NKp30 variant (SEQ ID NO: 504) - 3x GGGGS (SEQ ID NO: 228) - NKp30 variant (SEQ ID NO: 504) - GSGGGGS (SEQ ID NO: 635) - Fc (SEQ ID NO: 637) |

Example 32

Assessment of Binding to Cell-Expressed Counter Structures and Bioactivity of ICOSL and NKp30 Domain-Containing Stack Molecules This Example describes binding studies to show specificity and affinity of exemplary ICOSL/NKp30 stack immunomodulatory proteins generated in Example 31 for cognate binding partners. The exemplary ICOSL/NKp30 stack immunomodulatory proteins generated in Example 31 also were assessed for bioactivity characterization in a human primary T cell in vitro assay.

A. Binding to Cell-Expressed Counter Structure

ICOSL/NKp30 stack binding studies were performed on cells with stable or transient cell surface expression of cognate binding partners specific for ICOSL domain variant immunomodulatory proteins or NKp30-Fc.

For assessing binding to a binding partner of variant ICOSL domains, Chinese hamster ovarian cells (CHO) were used which had been transduced with lentivirus for surface expression of full-length human CD28, CTLA-4, or ICOS.

To produce cells expressing the cognate binding partner of NKp30, a full-length mammalian surface expression construct containing human B7-H6 was cloned into a pcDNA3.1 expression vector (Life Technologies). Binding studies were carried out using the Expi293F transient transfection system (Life Technologies, USA). Briefly, for a 30 mL transfection, approximately 75 million Expi293F cells were incubated with 30 µg of expression construct DNA and 1.5 mL diluted ExpiFectamine 293 reagent for 48 hours, at which point cells were harvested for staining.

For flow cytometric analysis, 200,000 cells of a given stable cell line, transient transfection or appropriate negative control were plated in 96 well round bottom plates. Cells were spun down and suspended in staining buffer (PBS (phosphate buffered saline), 1% BSA (bovine serum albumin), and 0.1% sodium azide) for 20 minutes to block non-specific binding. Afterwards, cells were centrifuged again and suspended in staining buffer containing 100 nM to 32 PM of ICOSL/NKp30 stack or control protein in 50 µL. Primary staining was performed for 45 minutes, before washing cells in staining buffer twice. Bound protein was detected with PE-conjugated anti-human IgG (Jackson ImmunoResearch, USA) diluted 1:150 in 50 µL staining buffer and incubated for 30 minutes. After final incubation, cells were washed twice to remove unbound conjugated antibodies, fixed in 2% formaldehyde/PBS, and analyzed on a LSRII (Becton Dickinson, USA) flow cytometer. Mean Fluorescence Intensity (MFI) was calculated for each sample with FlowJo Version 10 software (FlowJo LLC, USA).

Binding activity as measured by MFI was assessed for all ICOSL-NKp30 Fc fusion proteins or controls. As shown in FIG. 25A-25D, exemplary stack proteins bound cognate proteins of both ICOSL and NKp30 with high affinity.

B. Assessment of Bioactivity of Affinity-Matured IgSF Domain-Containing Molecules Soluble ICOSL/NKp30 stack protein bioactivity was tested in a co-culture with B7-H6+ cells for induction of cytokine production in primary human T cells. K562 cells which endogenously express B7-H6 were transduced with lentivirus to express cell surface anti-human CD3 single chain Fv (OKT3) yielding K562/OTK3 targets. Human primary T cells were co-cultured at an effector to target (E:T) ratio of 2.5 or 10:1 with ICOSL/Nkp30 stack or control proteins titrated from 100 nM to 49 pM in 200 μL final volume of Ex-Vivo 15 media. On day 3-5, the assay was terminated and the culture supernatants were tested using IL-2 and TNF-alpha ELISA MAX kits (Biolegend, USA). Optical density was measured on a BioTek Cytation Multi-mode Microplate Reader (BioTek Corp., USA) and quantitated against titrated rIL-2 and rTNF-alpha standards included in the ELISA kits.

Results for the bioactivity studies for exemplary tested ICOSL/NKp30 stack proteins are shown in FIGS. 26A and 26B, which sets forth the calculated levels of IL-2 or IFN-gamma in culture supernatants (pg/mL). The sequence identifier (SEQ ID NO) for each stack proteins is set forth in in FIGS. 26A and 26B. Incubation in the presence of exemplary ICOSL/NKp30 stack proteins in this assay resulted in increased levels of B7-H6-dependent cytokine induction in primary human T cells demonstrated by an increase in cytokine production with the ICOSL/NKp30 stacks compared to the parental ICOSL or NKp30 only proteins.

C. Assessment of Proliferation

Proliferation of human T-cells co-cultured with ICOSL/NKp30 stack proteins and B7-H6+ cells was also characterized. CFSE-labeled human primary T-cells were stimulated for 3-5 days with K562/OKT3 at an E:T ratio of 2.5 to 10:1 in the presence of ICOSL/NKp30 stack proteins or control proteins. Exemplary ICOSL/NKp30 stack proteins were titrated from 100 nM to 49 PM in 200 μL final volume of Ex-Vivo 15 media. Proliferation was measured by flow cytometric analysis of CFSE-dilution on CD4+ or CD8+ stained T-cells using LSRII flow cytometer and Flowjo software as described above.

As shown in in FIG. 27, exemplary tested ICOSL/NKp30 stack proteins costimulated proliferation of primary human CD4+ T cells in a B7H6-dependent manner demonstrated by an increase in proliferation of the ICOSL/NKp30 stack compared to the parental ICOSL or NKp30 only proteins.

Example 33

Assessment of ICOSL and NKp30 Domain-Containing Stack Molecules in Combination and Anti-PD-1 Antibody in Tumor Model This Example describes the assessment of anti-tumor activity of an exemplary ICOSL/NKp30 stack proteins, generated as described in Example 31, evaluated alone or in combination with an anti-mouse PD-1 monoclonal antibody (mPD-1 mAb) in mice bearing B7-H6+ CT26 colon carcinoma cells.

Mice were implanted subcutaneously with approximately $0.3 \times 10^5$ B7-H6+ CT26 tumor cells. Tumors were grown to day 13 and mice were staged and measured for mean tumor volumes (80 to 120 mm³). Tumors were measured with electronic calipers two-dimensionally beginning on day 6 post-tumor cell implant. Tumor volume was measured, and median tumor volume was determined. Three mice/group with smallest starting tumors (~75 mm³) were excluded from the analysis.

As shown in FIG. 28, the combination of the tested ICOSL/NKp30 stack protein and mPD-1 mAb significantly reduced tumor growth (median tumor volumes) over time compared to groups treated with Fc control, either ICOSL or NKp30 alone, ICOSL/NKp30 stack alone, or anti-mouse PD-1 mAb alone. No differences in outgrowth of any treatment group with parental CT26 (B7-H6-negative) tumors was observed. The anti-tumor activity of the combination as shown in FIG. 28 is consistent with a finding that the combination of the tested ICOSL/NKp30 stack protein and anti-PD-1 antibody is better than individual reagents alone.

Example 34

Assessment of Dosing and in vivo Effects of ICOSL IgV-Fc Fusion Molecules in a CIA Model Variant ICOSL IgV-Fc fusion molecules were assessed for anti-inflammatory activity in the collagen-induced arthritis (CIA) model with either prophylactic or therapeutic dosing. The variant ICOSL IgV-Fc fusion molecule was dosed a maximum of 4 times either prior to or just after disease onset. The tested variant ICOSL IgV-Fc fusion molecule contained a variant ICOSL IgV with N52H/N57Y/Q100P as set forth in SEQ ID NO: 570 or N52H/N57Y/Q100R as set forth in SEQ ID NO: 565, fused to an inert Fc (containing mutations L234A, L235E and L235E in a human IgG1 Fc, e.g. set forth in SEQ ID NO:637).

For induction of joint inflammation, mice were injected on day −18 or −21 with a chick or bovine collagen II/CFA emulsion in the tail and with a chick or bovine collagen II/IFA emulsion ('boost') on day 0. For prophylactic dosing, mice were dosed with the variant ICOSL IgV-Fc fusion molecule (N52H/N57Y/Q100P) with four doses beginning on the day of the boost, before the onset of disease. For therapeutic/delayed treatment, mice were dosed with the variant ICOSL IgV-Fc fusion molecule (N52H/N57Y/Q100R) started when the observed paw score was greater than one, and dosing occurred every two days for a total of four doses. As a control, Fc only molecules and a CTLA-4-Fc (abatacept) molecule were also tested. Paw score based on redness or swelling was determined. Serum also was collected to measure anti-collagen (CII IgG) antibodies and IL-6 and TNFα proinflammatory cytokines. Cells from draining lymph nodes were collected, stained for CD4, CD8, CD44 or markers of T follicular helper (TFH) cells (CD25− CD4+PD−1+CXCR5+). FIG. 29A-29D show results for prophylactic dosing. Mice treated with the variant ICOSL IgV-Fc fusion molecule on the prophylactic dosing treatment showed suppressed disease in the CIA mouse model of rheumatoid arthritis as shown by a lower mean sum paw score (FIG. 29A), and decreased detected CII IgG (FIG. 29B). *p<0.05 for ICOSL IgV-Fc vs. abatacept p<0.001 for ICOSL IgV-Fc vs. PBS (by 2-way repeated-measures ANOVA). Lower levels of serum cytokines (FIG. 29C) and CD44+ activated T cells or TFH cells (FIG. 29D**) were also observed in mice treated with the variant ICOSL IgV-Fc fusion molecule compared to Fc control; *p<0.05, p<0.01, *p<0.001, **p<0.0001 (by 1-way ANOVA). The fraction of B cells in the draining lymph node was also significantly reduced in the ICOSL IgV-Fc treated group vs. the Fc control group (p<0.05) (FIG. 29E**).

FIG. 30A-30D show results for delayed dosing. The variant ICOSL-IgV Fc resulted in the lowest mean sum paw score (FIG. 30A) and greatest percent change in body weight (FIG. 30B) compared to other groups, including the abatacept control. As shown in FIG. 30C and FIG. 30D, serum cytokines also were suppressed in the therapeutic CIA model in mice treated with the variant ICOS IgV-Fc. Statistical significance between groups: *p<0.05; p<0.01; *p<0.001 by Student's unpaired t-test. In FIG. 30C and FIG. 30D, the dotted horizontal lines indicate the assay lower limit of quantification (LLOQ) for each cytokine.

Together, these data evidence that the CD28 and ICOS pathways play important roles in inflammatory arthritis. In particular, the superior activity of the variant ICOSL dual CD28/ICOS antagonist is consistent with an observation that blockade of both pathways is necessary and that only partial benefit is achieved by a single pathway blockade.

Example 35

Assessment of in vivo Effects of ICOSL IgV-Fc Fusion Molecules in a EAE Model

A variant ICOSL IgV-Fc fusion molecule was assessed for anti-inflammatory activity in an adoptive transfer experimental autoimmune encephalomyelitis (EAE) model. The tested variant ICOSL IgV-Fc fusion molecule containing a variant ICOSL IgV (N52H/N57Y/Q100R; SEQ ID NO: 565) fused to an inert Fc (containing mutations L234A, L235E and L235E in a human IgG1 Fc).

Female C57BL/6 mice were subcutaneously injected with a MOG$_{35-55}$/CFA emulsion. After 11 days, spleen cells were obtained and cultured with MOG$_{35-55}$ peptide, IL-12, and anti-IFNγ. Three days post culture, encephalitogenic T cells were delivered via intraperitoneal injection (Day 0). Mice were dosed with variant ICOSL IgV-Fc fusion molecule every other day starting on Day 0 for a total of five doses. As a control, Fc only molecules and a CTLA-4-Fc molecule (abatacept) were also tested. For 20 days post injection of the T cells, mice were weighed, monitored and assessed for EAE score as described in Table 33. At end of study, serum was collected for analysis of pro-inflammatory cytokines, and cells from draining lymph nodes were collected for flow cytometric analysis.

TABLE 33

EAE Scoring

| Score | Clinical Observations |
|---|---|
| 0 | No obvious changes in motor functions |
| 1 | Limp tail |
| 2 | Limp tail and weakness of hind legs |
| 3 | Limp tail and complete paralysis of hind legs, OR Limp tail with paralysis of one front and one hind leg, OR ALL of: 1) Severe head tilting, 2) Walking only along the edges of the cage, 3) Pushing against the cage wall, 4) Spinning when picked up by the tail. |
| 4 | Limp tail, complete hind leg and partial front leg paralysis |
| 5 | Complete hind and complete front leg paralysis, no movement; OR Mouse is spontaneously rolling in the cage; OR Mouse found dead due to paralysis. |

278

As shown in FIG. 31A, mice treated with the variant ICOSL IgV-Fc fusion molecule suppressed disease in the EAE mouse model as shown by a lower EAE score, *p<0.0001 by 1-way ANOVA Area Under the Curve (AUC); variant ICOSL IgV-Fc fusion molecule compared to controls.

For flow cytometric analysis of inguinal lymph node T cells, the cells were stained with viability dye & analyzed with anti-CD44, anti-CD62L, anti-CD4, anti-CD8 and assessed for percentage of viable naïve (CD62L+CD44−) and T effector memory (Tem) (CD62L−CD44+) CD4+ and CD8+ T cells. As shown in FIG. 31C, CD4+ and CD8+ Tem cells were reduced with treatment with the variant ICOSL IgV-Fc fusion molecule (**p<0.0001; *p<0.001 by 1-way ANOVA).

Serum cytokines were assessed on Day 0 (2 hours post 1$^{st}$ dose) and on Day 6 (1 hour before 4th dose). As shown in FIG. 31D, the tested variant ICOSL IgV-Fc fusion molecule resulted in reduction of pro-inflammatory cytokines in serum on Day 0, including IL-5, IL-10, IL-12p70 and TNFα. At day 6, serum levels of IFN-gamma and IL-6 were reduced by treatment with the variant ICOSL IgV-Fc fusion molecule compared to Fc control.

Example 36

Dose Ranging Study of Variant ICOSL-IgV Fc in Graft-Versus-Host-Disease (GvHD) Model A dose ranging study was conducted with 20, 100, or 500 μg of a variant ICOSL IgV-Fc molecule, containing a variant ICOSL IgV (N52H/N57Y/Q100R; SEQ ID NO: 565) fused to an inert Fc (containing mutations L234A, L235E and L235E in a human IgG1 Fc, e.g. set forth in SEQ ID NO:637), in a mouse model of graft-versus-host-disease (GVHD). The activity of the variant ICOSL IgV-Fc molecule was compared to belatacept (CTLA-4-FcL104E/A29Y; U.S. Patent Application Publication Number US2016/0271218).

Female NSG mice (n=5 per group for Group 1, no treatment; n=10 per group for treatment Groups 2-7) were administered 10 mg of gamma globulin subcutaneously and then irradiated (100 cGy/rad) on Day-1. On Day 0 (within 24 hours post-irradiation), the mice in Groups 2-7 were dosed with test articles as set forth in Table 34, and then all mice received 1×10$^7$ human PBMCs injected IV via tail vein post-dosing.

A disease activity index (DAI) was determined by evaluating the mice three times a week during the study and scoring disease based on body weight loss, posture, activity, appearance of the fur and skin of the mice. After the study was terminated on Day 42, endpoint measurements of survival, body weight loss, and disease activity were evaluated. Kaplan-Meier survival plots representing the percentage of animals surviving to the study endpoint were generated and survival curve comparisons were analyzed by the Mantel-Cox and Gehan-Breslow-Wilcox tests (95% CI). Blood/serum samples were collected from surviving mice at the end of the study (Day 42) and cells were assessed by flow cytometry for markers of T cells, including mouse or human markers, CD4, CD8, CD28, ICOS, activation or exhaustion markers (PD-1, Ki67) and FoxP3 (a marker of Tregs). The levels of serum pro-inflammatory cytokines (e.g. IFN-gamma, IL-10, IL-12 (p70), IL-17A, IL-4, IL-5 and TNFα) also were assessed.

TABLE 34

Dosing Schedule

| Group | N | Test Articles | Dose (µg) | Dose Volume (µl) | Route | Schedule | Start of Dosing |
|-------|---|---------------|-----------|------------------|-------|----------|-----------------|
| 1 | 5 | No treatment | n/a | n/a | n/a | n/a | n/a |
| | | | | | | Survival/DAI | |
| 2 | 10 | Saline | n/a | 100 | IP | 3x weekly 4 weeks | Day 0 |
| 3 | 10 | variant ICOSL IgV-Fc | 500 | 100 | IP | 3x weekly 4 weeks | Day 0 |
| 4 | 10 | variant ICOSL IgV-Fc | 100 | 100 | IP | 3x weekly 4 weeks | Day 0 |
| 5 | 10 | variant ICOSL IgV-Fc | 20 | 100 | IP | 3x weekly 4 weeks | Day 0 |
| 6 | 10 | Belatacept | 100 | 100 | IP | 3x weekly 4 weeks | Day 0 |
| | | | | | | PK/Survival//DAI | |
| 7 | 9 | variant ICOSL IgV-Fc | 100 | 100 | IP | Single Day 1 | Day 1 |

FIG. 32A-32B show the survival and DAI scores of GVHD mice treated in accord with each dosing schedule. As shown, the tested variant ICOSL IgV-Fc (N52H/N57Y/Q100R) at all dose levels tested significantly enhanced survival (FIG. 32A) and reduced disease scores (FIG. 32B) compared to mice treated with belatacept (i.e. 100% vs. 40% survival at Day 42, respectively; $p<0.01$ by Mantel-Cox log rank test). Notably, single dose (100 µg) administration of variant ICOSL IgV-Fc (N52H/N57Y/Q100R) resulted in similar protection from disease as repeat dosing of 100 µg belatacept.

Figures 33A, 33B:
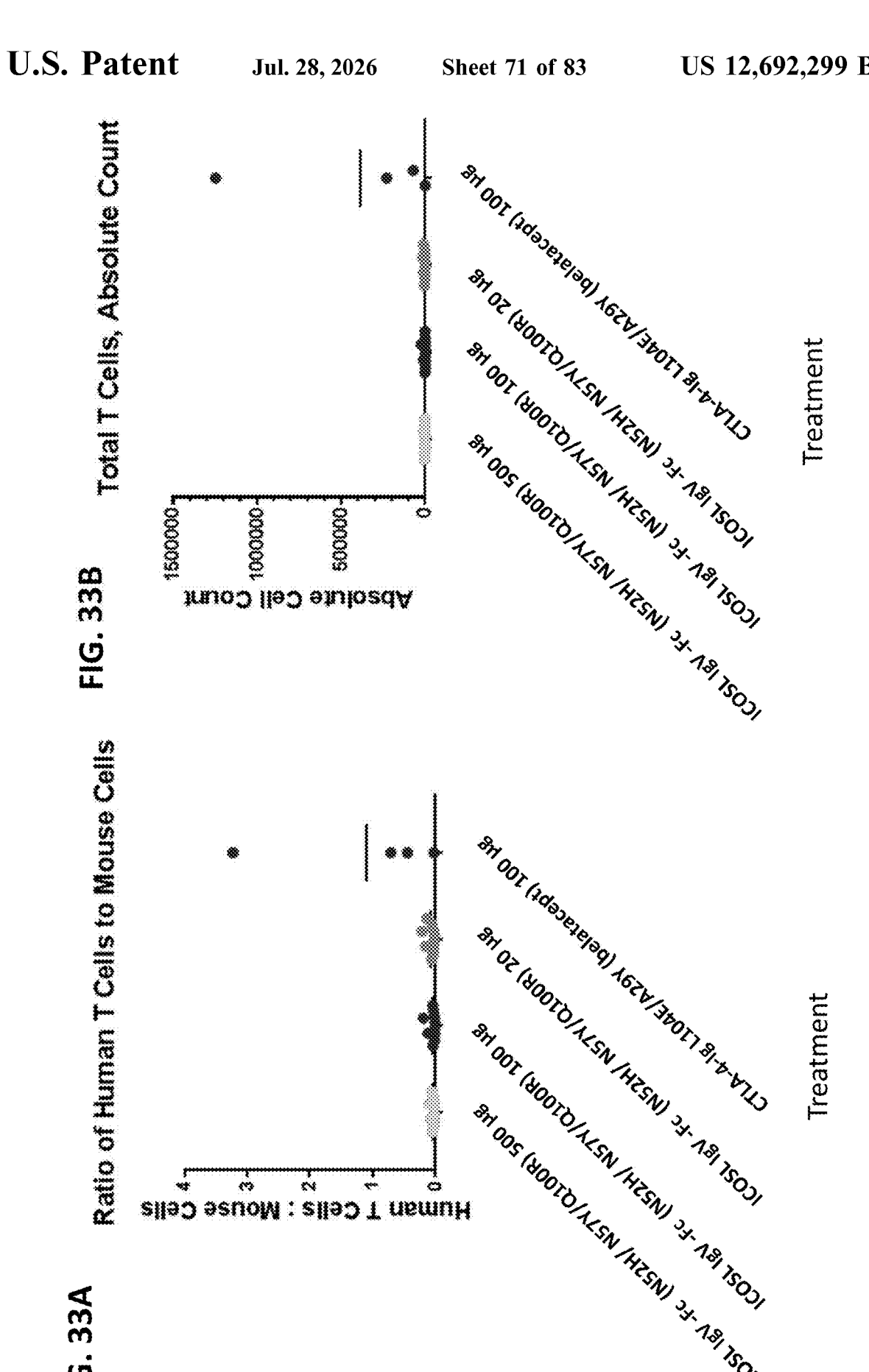
Figures 33C, 33D:
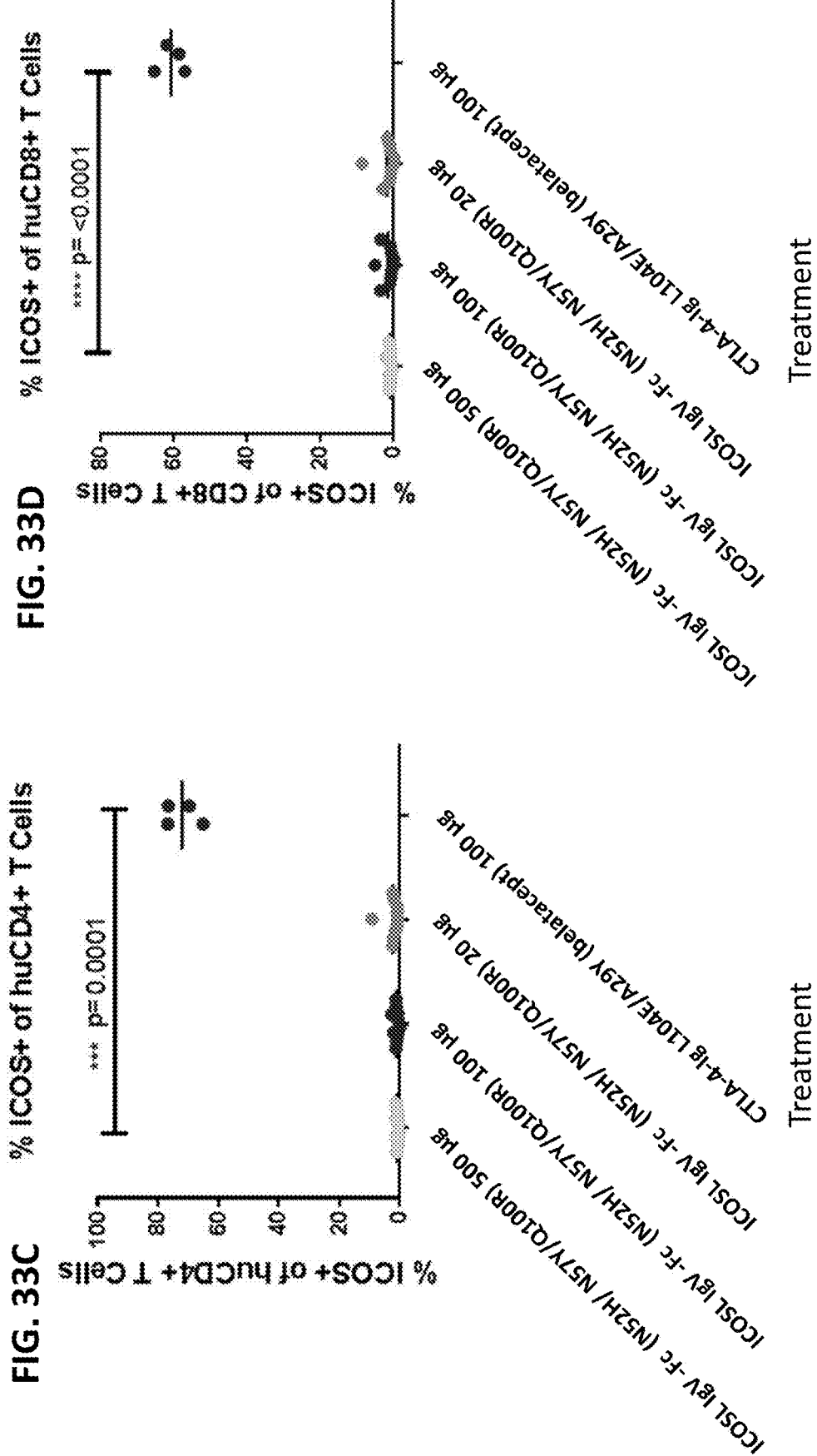
Figures 33E, 33F:
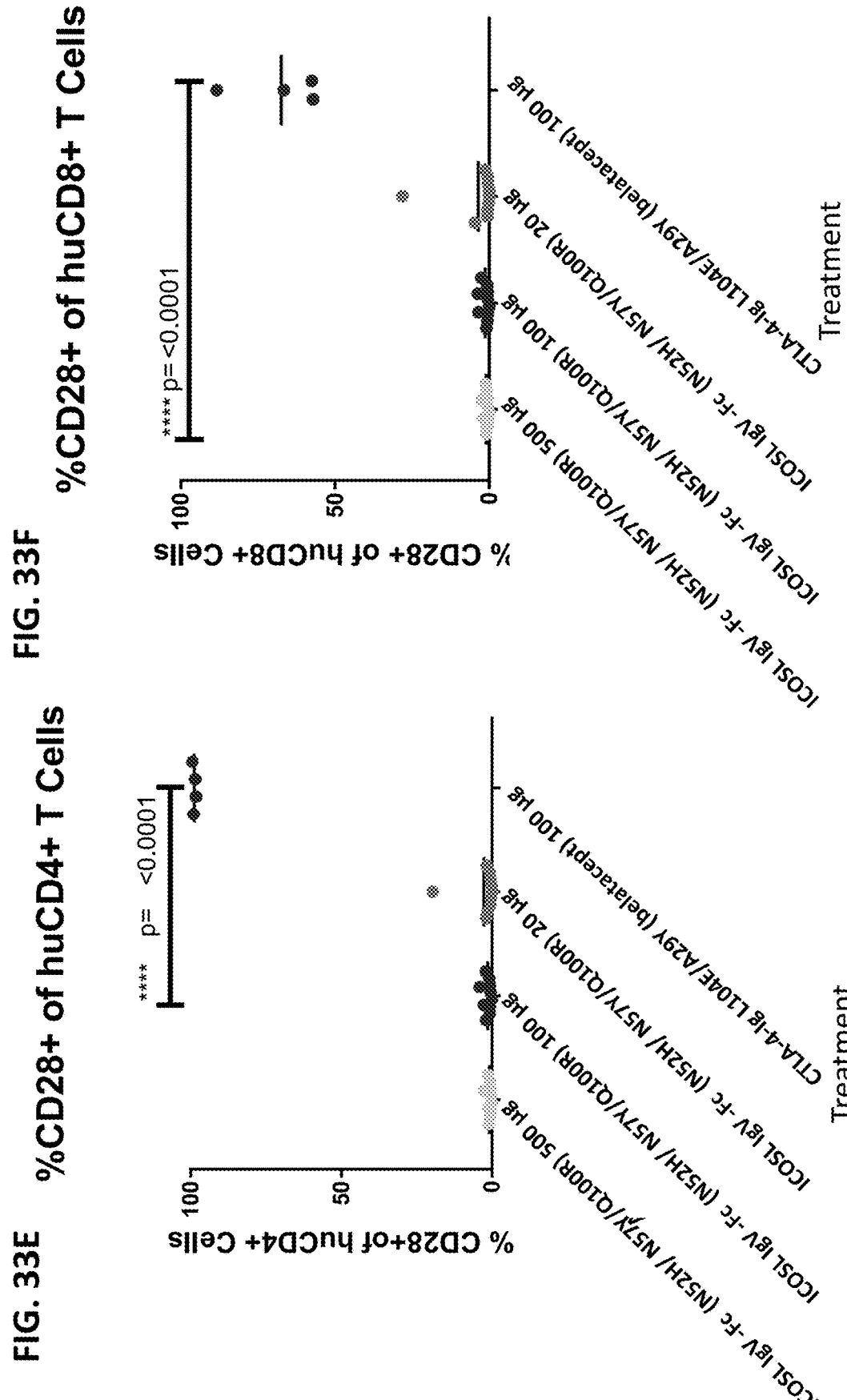

Flow cytometric analysis of blood collected at the end of the study demonstrated that the tested variant ICOSL IgV-Fc (N52H/N57Y/Q100R) effectively suppressed expansion of transferred human T cells as observed by a reduced ratio of human cells/mouse cells (FIG. 33A) and the greatly reduced total T cell counts (FIG. 33B). As shown in FIGS. 33C-33F, flow cytometry staining of blood collected at end of the study of CD4+ and CD8+ T cells co-stained for ICOS (FIGS. 33C-33D) and CD28 (FIGS. 33E-33F) demonstrated essentially no staining in groups treated with variant ICOSL IgV-Fc (N52H/N57Y/Q100R), although CD4+ and CD8+ T cells expressing ICOS were readily detectable in belatacept-treated mice. These results are consistent with the lack of T cells remaining in the ICOSL IgV-Fc-treated mice, and also with the ability of the variant ICOSL IgV-Fc (N52H/N57Y/Q100R) to bind its target molecules CD28 and ICOS and block their detection by the flow cytometry antibodies. Binding of variant ICOSL IgV-Fc (N52H/N57Y/Q100R) on the few remaining human T cells was confirmed by detection using anti-Human IgG Fc. Notably, while most of the transferred human T cells initially expressed CD28 and just 10-20% were ICOS+, the activated T cells remaining in the saline- or belatacept-treated mice at termination/end of study were >80% ICOS+.

The presence of activation or exhaustion markers of T cells also was suppressed in groups treated with variant ICOSL IgV-Fc (N52H/N57Y/Q100R), as evidenced by lower expression of PD1 in CD4+ and CD8+ T cells and decreased Ki67 expression in CD4+ T cells, (FIG. 34A-3B). The ratio of effector T cells to Tregs remained stable in groups treated with variant ICOSL IgV-Fc (N52H/N57Y/Q100R) compared to belatacept (FIG. 34C). Serum proinflammatory cytokines also were suppressed in groups treated with variant ICOSL IgV-Fc (N52H/N57Y/Q100R) compared to belatacept (FIG. 35A-35D).

Pharmacokinetic (PK) analysis also was carried out to monitor serum exposure of variant ICOSL IgV-Fc (N52H/N57Y/Q100R). Test article concentrations were measured in mouse serum samples using a quantitative PK ELISA using an anti-human ICOSL mAb capture antibody and an Fc-specific mouse anti-human IgG as the detection reagent.

The observed serum exposure of variant ICOSL IgV-Fc (N52H/N57Y/Q100R) in the GVHD model was 45% lower than that of normal mice, determined in a separate study (FIG. 35E). The longer terminal half-life of variant ICOSL IgV-Fc (N52H/N57Y/Q100R) in the GvHD model may due to reduced target (CD28, ICOS) at later time points in GvHD (as the human T cells disappear), and/or to anti-drug antibody (ADA) formation in normal mice, which can interfere with drug exposure. The observation that variant ICOSL IgV-Fc (N52H/N57Y/Q100R) had lower serum exposure compared to normal mice may be due to target mediated drug disposition (TMDD) in the GvHD model (i.e. its higher affinity for human CD28 and ICOS as compared to the mouse orthologues), and/or to lack of FcRn in the NOD/SCID (NSG) mice used in this model.

Together, these results are consistent with an observation that variant ICOSL IgV-Fc (N52H/N57Y/Q100R) exhibits potent antagonist activity, even with only a single dose, and superior activity to belatacept. This observation may be attributable to the variant ICOSL IgV-Fc (N52H/N57Y/Q100R) exhibiting superior control of ICOS+ T cells, which otherwise escape single ICOS or CD28 pathway blockade, such as that achieved with the CD28 pathway antagonist belatacept.

Example 37

Assessment of Variant ICOSL-IgV Fc in CD4+ CD45RBhigh-induced Colitis Model The effect of the exemplary variant ICOSL IgV-Fc containing a variant ICOSL IgV (N52H/N57Y/Q100R; SEQ ID NO: 565) fused to an inert Fc (containing mutations L234A, L235E and L235E in a human IgG1 Fc, e.g. set forth in SEQ ID NO:637) on disease development in CD4+CD45RBhigh-induced colitis model was evaluated.

CD4+CD45RBhigh donor cells were enriched by negative selection from spleen cell suspensions obtained from 15 male BALB/C donor mice. On Day 0, 0.3 million CD4+ CD25− CD45RBhigh (Treg depleted) donor cells were injected intravenously into immunodeficient C.B17 (SCID) mice (n=12 or 21 per group) to induce colitis. As a control, 0.3 million CD4+ cells (containing Treg cells), which do not induce development of colitis in this model, were injected into SCID mice recipients (n=12). On the day of cell transfer, mice in each group were dosed with variant ICOSL-IgV Fc or Fc only or vehicle controls. Table 35 summarizes the treatment regimen for tested groups.

TABLE 35

| | | | Treatment Regimens | | | |
|---|---|---|---|---|---|---|
| Group | # mice | Cells injected | Treatment | Dose | Route | Frequency |
| 1 | 12 | CD4+ | PBS (sterile) | — | i.p. | 3x/week (M, W, F) |
| 2 | 12 | CD4 + CD45RBhigh | PBS (sterile) | — | i.p. | 3x/week (M, W, F) |
| 3 | 21 | CD4 + CD45RBhigh | Fc control | 300 μg | i.p. | 3x/week (M, W, F) |
| 5 | 12 | CD4 + CD45RBhigh | Variant ICOSL IgV-Fc | 400 μg | i.p. | 3x/week (M, W, F) |

Body weight (taken starting on Day 0) and stool consistency score (taken starting on Day 10), were evaluated three times per week. Daily disease activity index (DAI) was calculated from body weight and stool scores. After the study was terminated on Day 42, colon was collected for determination of length and weight and histological analysis. Statistical analysis of end body weight and end colon weight and length of variant ICOSL-IgV Fc treated group to vehicle group was assessed using two-tailed Student's t-test. Stool scores and DAI scores were compared using Wilcoxon's non-parametric T test.

DAI results are shown in Tables 36 (DAI) and FIG. 36A, colon measurements are shown in Table 37, and colon histology results are shown in Table 38 and FIG. 36B. As shown tested variant ICOSL IgV-Fc (N52H/N57Y/Q100R) exhibited significantly reduced development of colitis in this model, which is consistent with the utility of this dual CD28/ICOS antagonist to effectively treat inflammatory bowel disease (IBD).

TABLE 36

| | | | Disease Activity Score | | | |
|---|---|---|---|---|---|---|
| Treatment | End % body weight +/− SD | p value | End stool score +/− SD | p value | End DAI score +/− SD | p value |
| Colitis not induced/Vehicle | 112.3% +/− 3.9% | | 0.3 +/− 0.5 | | 0.3 +/− 0.5 | |
| Vehicle | 92.7% +/− 11.7% | <0.0001^ | 1.3 +/− 1.3 | 0.0016^ | 3.2 +/− 2.6 | 0.0003^ |
| Fc control, 300 μg | 96.2% +/− 5.4% | 0.2656* | 1.4 +/− 1.4 | 0.8836* | 2.5 +/− 1.7 | 0.6948* |
| ICOSL IgV-Fc (N52H/N57Y/Q100R), 400 μg | 109.6% +/− 4.0% | <0.0001~ | 0.1 +/− 0.3 | 0.0014~ | 0.1 +/− 0.3 | <0.0001~ |

^Compared to Colitis not induced/Vehicle
*Compared to Vehicle
~Compared to Fc control, 300 μg

TABLE 37

| | | | Colon Measurements | | | |
|---|---|---|---|---|---|---|
| Treatment | End colon weight (mg) +/− SD | p value | End colon length (mm) +/− SD | p value | End Colon weight/ length +/− SD | p value |
| Colitis not induced/Vehicle | 175.3 +/− 16.9 | | 82.8 +/− 5.2 | | 2.1 +/− 0.2 | |
| Vehicle | 323.1 +/− 78.0 | <0.0001^ | 77.7 +/− 7.5 | 0.0668^ | 4.2 +/− 1.2 | <0.0001^ |
| Fc control, 300 μg | 276.7 +/− 92.4 | 0.1602* | 77.6 +/− 8.9 | 0.9911* | 3.6 +/− 1.2 | 0.1843* |

TABLE 37-continued

| | Colon Measurements | | | | | |
|---|---|---|---|---|---|---|
| Treatment | End colon weight (mg) +/− SD | p value | End colon length (mm) +/− SD | p value | End Colon weight/ length +/− SD | p value |
| ICOSL IgV-Fc (N52H/N57Y/Q100R), 400 µg | 160.8 +/− 24.4 | 0.0004~ | 79.4 +/− 6.1 | 0.5738~ | 2.0 +/− 0.3 | 0.0003~ |

^Compared to Colitis not induced/Vehicle

*Compared to Vehicle

~Compared to Fc control, 300 µg

TABLE 38

| | | | | Histology Results | | | |
|---|---|---|---|---|---|---|---|
| | Cage | Mouse | Mouse | Colon (swiss roll) | | | |
| Group | # | # | ID# | Mucosa | Submucosa | Muscularis | Total score |
| Colitis not | 1 | 1 | 1-1 | 0 | 0 | 0 | 0.0 |
| induced/Vehicle | | 2 | 1-2 | 0 | 0 | 0 | 0.0 |
| | | 3 | 1-3 | 0 | 0 | 0 | 0.0 |
| | | 4 | 1-4 | 0 | 0 | 0 | 0.0 |
| | 2 | 1 | 2-1 | 1 | 1 | 0 | 2.0 |
| | | 2 | 2-2 | 0 | 0 | 0 | 0.0 |
| | | 3 | 2-3 | | | | |
| | | 4 | 2-4 | | | | |
| | 3 | 1 | 3-1 | | | | |
| | | 2 | 3-2 | | | | |
| | | 3 | 3-3 | | | | |
| | | 4 | 3-4 | | | | |
| | Average | | | 0.2 | 0.2 | 0.0 | 0.3 |
| | Std Dev | | | 0.4 | 0.4 | 0.0 | 0.8 |
| | SEM | | | 0.2 | 0.2 | 0.0 | 0.3 |
| Vehicle | 4 | 1 | 4-1 | 3 | 3 | 1 | 7.0 |
| | | 2 | 4-2 | 1 | 1 | 0 | 2.0 |
| | | 3 | 4-3 | 2 | 2 | 0 | 4.0 |
| | | 4 | 4-4 | 2 | 2 | 0 | 4.0 |
| | 5 | 1 | 5-1 | 2 | 3 | 0 | 5.0 |
| | | 2 | 5-2 | 2 | 2 | 0 | 4.0 |
| | | 3 | 5-3 | | | | |
| | | 4 | 5-4 | | | | |
| | 6a | 1 | 6a-1 | | | | |
| | | 2 | 6a-2 | | | | |
| | | 3 | 6a-3 | | | | |
| | 6b | 1 | 6b-1 | | | | |
| | Average | | | 2.0 | 2.2 | 0.2 | 4.3 |
| | Std Dev | | | 0.6 | 0.8 | 0.4 | 1.6 |
| | SEM | | | 0.3 | 0.3 | 0.2 | 0.7 |
| | T-test vs colitis not induced/Vehicle | | | 0.0001 | 0.0002 | 0.3409 | 0.0003 |
| Fc control, | 6b | 2 | 6b-2 | 2 | 1 | 0 | 3.0 |
| 300 µg | | 3 | 6b-3 | 3 | 3 | 1 | 7.0 |
| | 6c | 1 | 6c-1 | 3 | 3 | 0 | 6.0 |
| | | 2 | 6c-2 | 2 | 2 | 2 | 6.0 |
| | | 3 | 6c-3 | 3 | 2 | 1 | 6.0 |
| | 7 | 1 | 7-1 | | | | |
| | | 2 | 7-2 | 2 | 2 | 1 | 5.0 |
| | | 3 | 7-3 | 2 | 1 | 0 | 3.0 |
| | | 4 | 7-4 | 2 | 3 | 0 | 5.0 |
| | 8 | 1 | 8-1 | 2 | 1 | 0 | 3.0 |
| | | 2 | 8-2 | 2 | 1 | 0 | 3.0 |
| | | 3 | 8-3 | | | | |
| | | 4 | 8-4 | 1 | 1 | 0 | 2.0 |
| | 9 | 1 | 9-1 | | | | |
| | | 2 | 9-2 | | | | |
| | | 3 | 9-3 | | | | |
| | | 4 | 9-4 | | | | |
| | 10 | 1 | 10-1 | | | | |
| | | 2 | 10-2 | | | | |
| | | 3 | 10-3 | | | | |
| | | 4 | 10-4 | | | | |

TABLE 38-continued

| | | | | Colon (swiss roll) | | | |
|---|---|---|---|---|---|---|---|
| | | | | | | | |
| | Cage | Mouse | Mouse | | | | |
| Group | # | # | ID# | Mucosa | Submucosa | Muscularis | Total score |
| | Average | | | 2.2 | 1.8 | 0.5 | 4.5 |
| | Std Dev | | | 0.6 | 0.9 | 0.7 | 1.7 |
| | SEM | | | 0.2 | 0.3 | 0.2 | 0.5 |
| | T-test vs Vehicle | | | 0.5676 | 0.4240 | 0.3663 | 0.8885 |
| ICOSL IgV -Fc | 14 | 1 | 14-1 | 0 | 0 | 0 | 0.0 |
| (N52H/N57Y/Q100R), | | 2 | 14-2 | 0 | 0 | 0 | 0.0 |
| 400 µg | | 3 | 14-3 | 0 | 0 | 0 | 0.0 |
| | | 4 | 14-4 | 0 | 0 | 0 | 0.0 |
| | 15 | 1 | 15-1 | 0 | 0 | 0 | 0.0 |
| | | 2 | 15-2 | 0 | 0 | 0 | 0.0 |
| | | 3 | 15-3 | | | | |
| | | 4 | 15-4 | | | | |
| | 16 | 1 | 16-1 | | | | |
| | | 2 | 16-2 | | | | |
| | | 3 | 16-3 | | | | |
| | | 4 | 16-4 | | | | |
| | Average | | | 0.0 | 0.0 | 0.0 | 0.0 |
| | Std Dev | | | 0.0 | 0.0 | 0.0 | 0.0 |
| | SEM | | | 0.0 | 0.0 | 0.0 | 0.0 |
| | T-test vs Fc control | | | 0.0000 | 0.0002 | 0.1315 | 0.0000 |

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

What is claimed:

1. A nucleic acid molecule encoding a variant ICOSL-Fc fusion protein comprising a variant ICOSL polypeptide linked via a linker to an Fc region, wherein the variant ICOSL polypeptide is set forth in SEQ ID NO:565, the linker is set forth in SEQ ID NO:229, and the Fc region is set forth in SEQ ID NO:637.

2. An expression vector comprising the nucleic acid molecule of claim 1.

3. A cell comprising the nucleic acid molecule of claim 1.

4. A method of producing a variant ICOSL-Fc fusion protein, the method comprising introducing the nucleic acid molecule of claim 1 into a host cell under conditions to express the protein in the cell, and purifying the expressed protein.

5. The method of claim 4, wherein the cell is a CHO cell or a derivative thereof.

6. The method of claim 5, wherein the CHO cell or derivative thereof is a CHO DG44 cell.

* * * * *